US011078542B2

United States Patent

(12) United States Patent
Davicioni et al.

(10) Patent No.: US 11,078,542 B2
(45) Date of Patent: Aug. 3, 2021

(54) GENETIC SIGNATURES TO PREDICT PROSTATE CANCER METASTASIS AND IDENTIFY TUMOR AGGRESSIVENESS

(71) Applicant: DECIPHER BIOSCIENCES, INC., San Diego, CA (US)

(72) Inventors: Elai Davicioni, La Jolla, CA (US); Nicholas Erho, Vancouver (CA); Hussam Al-Deen Ashab, Vancouver (CA); Mohammed Alshalalfa, New Westminster (CA)

(73) Assignee: DECIPHER BIOSCIENCES, INC., San Diego, CA (US)

( * ) Notice: Subject to any disclaimer, the term of this patent is extended or adjusted under 35 U.S.C. 154(b) by 0 days.

(21) Appl. No.: 15/977,249

(22) Filed: May 11, 2018

(65) Prior Publication Data

US 2019/0017123 A1 Jan. 17, 2019

Related U.S. Application Data

(60) Provisional application No. 62/505,665, filed on May 12, 2017.

(51) Int. Cl.
*C12Q 1/6886* (2018.01)
*G01N 33/574* (2006.01)

(52) U.S. Cl.
CPC ..... *C12Q 1/6886* (2013.01); *G01N 33/57434* (2013.01); *C12Q 2600/112* (2013.01); *C12Q 2600/118* (2013.01); *C12Q 2600/158* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 3,645,691 | A | 2/1972 | Guenter et al. |
| 3,687,808 | A | 8/1972 | Thomas, Jr. et al. |
| 4,323,546 | A | 4/1982 | Crockfor et al. |
| 4,683,195 | A | 7/1987 | Mullis et al. |
| 4,683,202 | A | 7/1987 | Mullis et al. |
| 4,800,159 | A | 1/1989 | Mullis et al. |
| 4,965,188 | A | 10/1990 | Mullis et al. |
| 5,130,238 | A | 7/1992 | Malek et al. |
| 5,143,854 | A | 9/1992 | Pinung et al. |
| 5,225,326 | A | 7/1993 | Bresser et al. |
| 5,270,184 | A | 12/1993 | Walker et al. |
| 5,283,174 | A | 2/1994 | Arnold et al. |
| 5,288,514 | A | 2/1994 | Ellman |
| 5,384,261 | A | 1/1995 | Winkle et al. |
| 5,399,491 | A | 3/1995 | Kacian et al. |
| 5,455,166 | A | 10/1995 | Walker |
| 5,480,784 | A | 1/1996 | Kacian et al. |
| 5,494,810 | A | 2/1996 | Barany et al. |
| 5,538,848 | A | 7/1996 | Livak et al. |
| 5,545,524 | A | 8/1996 | Trent et al. |
| 5,677,195 | A | 10/1997 | Winkler et al. |
| 5,705,365 | A | 1/1998 | Ryder et al. |
| 5,710,029 | A | 1/1998 | Ryder et al. |
| 5,711,029 | A | 1/1998 | Ryder et al. |
| 5,744,305 | A | 4/1998 | Fodor et al. |
| 5,814,447 | A | 9/1998 | Ishiguro et al. |
| 5,824,518 | A | 10/1998 | Kacian et al. |
| 5,830,711 | A | 11/1998 | Barany et al. |
| 5,846,717 | A | 12/1998 | Brow et al. |
| 5,854,033 | A | 12/1998 | Lizardi |
| 5,854,206 | A | 12/1998 | Twardzik et al. |
| 5,888,779 | A | 3/1999 | Kacian et al. |
| 5,925,517 | A | 7/1999 | Tyagi et al. |
| 5,928,862 | A | 7/1999 | Morrison |
| 5,965,360 | A | 10/1999 | Zain et al. |
| 5,985,557 | A | 11/1999 | Prudent et al. |
| 5,989,815 | A | 11/1999 | Skolnick et al. |
| 5,994,069 | A | 11/1999 | Hall et al. |
| 6,001,567 | A | 12/1999 | Brow et al. |
| 6,022,692 | A | 2/2000 | Coulie et al. |
| 6,027,887 | A | 2/2000 | Zavada et al. |
| 6,034,218 | A | 3/2000 | Reed et al. |
| 6,090,543 | A | 7/2000 | Prudent et al. |
| 6,121,489 | A | 9/2000 | Dorner et al. |
| 6,136,182 | A | 10/2000 | Dolan et al. |
| 6,150,097 | A | 11/2000 | Tyagi et al. |
| 6,198,107 | B1 | 3/2001 | Seville |
| 6,218,523 | B1 | 4/2001 | French |
| 6,225,051 | B1 | 5/2001 | Sugiyama et al. |
| 6,251,639 | B1 | 6/2001 | Kurn |
| 6,262,245 | B1 | 7/2001 | Xu et al. |
| 6,268,142 | B1 | 7/2001 | Duff et al. |
| 6,303,305 | B1 | 10/2001 | Wittwer et al. |
| 6,410,278 | B1 | 6/2002 | Notomi et al. |
| 6,436,642 | B1 | 8/2002 | Gould-Rothberg et al. |

(Continued)

FOREIGN PATENT DOCUMENTS

| | | |
|---|---|---|
| EP | 0 684 315 | 11/1995 |
| EP | 1 409 727 | 11/2005 |

(Continued)

OTHER PUBLICATIONS

US 5,962,233 A, 10/1999, Livak et al. (withdrawn)

(Continued)

*Primary Examiner* — Carla J Myers
(74) *Attorney, Agent, or Firm* — Knobbe, Martens, Olson & Bear, LLP

(57) ABSTRACT

The present invention relates to methods, systems and kits for the diagnosis, prognosis and the determination of cancer progression of prostate cancer in a subject. The invention also provides clinically useful genomic classifiers for predicting prostate cancer metastasis and identifying tumor aggressiveness. The methods, systems and kits can provide expression-based analysis of biomarkers for purposes of predicting metastatic disease and lethal prostate cancer in a subject. Further disclosed herein, in certain instances, are probe sets for use in predicting prostate cancer metastasis in a subject. Classifiers for predicting prostate cancer metastasis are provided. Methods of treating cancer based on tumor aggressiveness are also provided. The methods and classifiers of the present invention are also useful for predicting early prostate cancer metastasis.

3 Claims, 8 Drawing Sheets

Specification includes a Sequence Listing.

(56) References Cited

U.S. PATENT DOCUMENTS 6,541,205 B1 4/2003 Yokoyama et al.
6,573,043 B1 6/2003 Cohen et al.
6,630,358 B1 10/2003 Wagner et al.
6,723,506 B2 4/2004 Fletcher et al.
6,828,429 B1 12/2004 Srivastava et al.
7,008,765 B1 3/2006 Bussemakers et al.
7,186,514 B2 3/2007 Zavada et al.
7,211,390 B2 5/2007 Rothberg et al.
7,244,559 B2 7/2007 Rothberg et al.
7,264,929 B2 9/2007 Rothberg et al.
7,280,922 B2 10/2007 Mei et al.
7,300,788 B2 11/2007 Matsuzaki et al.
7,319,011 B2 1/2008 Riggins et al.
7,323,305 B2 1/2008 Leamon et al.
7,335,762 B2 2/2008 Rothberg et al.
7,358,061 B2 4/2008 Yamamoto et al.
7,361,488 B2 4/2008 Fan et al.
7,378,233 B2 5/2008 Sidransky et al.
7,407,755 B2 8/2008 Lubinski et al.
7,541,169 B2 6/2009 Freimuth et al.
7,598,052 B2 10/2009 Giordano et al.
7,662,553 B2 2/2010 Lenz et al.
7,767,391 B2 8/2010 Scott et al.
7,901,881 B2 3/2011 Libutti et al.
7,901,888 B2 3/2011 Kebebew
7,914,988 B1 3/2011 Chudin et al.
7,927,826 B2 4/2011 Riggins et al.
8,008,009 B2 8/2011 Choquet-Kastylevsky et al.
8,202,692 B2 6/2012 Giordano et al.
8,273,539 B2 9/2012 Klee et al.
8,293,880 B2 10/2012 Cote et al.
8,299,233 B2 10/2012 Andre et al.
8,338,109 B2 12/2012 Vasmatzis et al.
8,354,228 B2 1/2013 Ron
8,465,914 B2 6/2013 Brown et al.
8,541,170 B2 9/2013 Kennedy et al.
8,568,971 B2 10/2013 Brown et al.
8,669,057 B2 3/2014 Kennedy et al.
8,802,599 B2 8/2014 Aharonov et al.
8,828,656 B2 9/2014 Bullerdiek et al.
8,877,445 B2 11/2014 Shackney
8,945,829 B2 2/2015 Keutgen et al.
9,040,286 B2 5/2015 Zon et al.
9,074,258 B2 7/2015 Davicion et al.
9,096,906 B2 8/2015 Aharonov et al.
9,157,123 B2 10/2015 Xing
9,175,352 B2 11/2015 Keutgen et al.
9,206,481 B2 12/2015 Srivastava et al.
9,206,482 B2 12/2015 Davicioni et al.
9,234,244 B2 1/2016 Zeiger et al.
9,435,812 B2 9/2016 Pestano et al.
9,495,515 B1 11/2016 Giulia et al.
9,534,249 B2 1/2017 Vasmatzis et al.
9,587,279 B2 3/2017 Fahey, III et al.
9,617,604 B2 4/2017 Davicion et al.
9,708,667 B2 7/2017 Yanai et al.
9,714,452 B2 7/2017 Davicioni et al.
9,856,537 B2 1/2018 Kennedy et al.
9,994,907 B2 6/2018 Davicioni et al.
10,114,924 B2 10/2018 Kennedy et al.
10,407,731 B2 9/2019 Klee et al.
10,407,735 B2 9/2019 Chinnaiyan et al.
10,422,009 B2 9/2019 Davicioni et al.
10,494,677 B2 12/2019 Vasmatzis et al.
10,513,737 B2 12/2019 Davicioni et al.
10,865,452 B2 12/2020 Davicioni
2001/0051344 A1 12/2001 Shalon et al.
2002/0076735 A1 6/2002 Williams et al.
2002/0090633 A1 7/2002 Becker et al.
2002/0119463 A1 8/2002 Fads
2002/0168638 A1 11/2002 Schlegel et al.
2002/0169137 A1 11/2002 Reiner et al.
2002/0182586 A1 12/2002 Morris et al.
2003/0119168 A1 6/2003 Madison et al.
2003/0152980 A1 8/2003 Golub et al.
2003/0175736 A1 9/2003 Chinnaiyan et al.
2003/0185830 A1 10/2003 Xu et al.
2003/0186248 A1 10/2003 Erlander et al.
2003/0190602 A1 10/2003 Pressman et al.
2003/0194734 A1 10/2003 Jatkoe
2003/0224399 A1 12/2003 Reed et al.
2003/0235820 A1 12/2003 Mack et al.
2004/0009481 A1 1/2004 Schlegel et al.
2004/0018493 A1 1/2004 Anastasio et al.
2004/0019466 A1 1/2004 Minor et al.
2004/0029114 A1 2/2004 Mack et al.
2004/0058378 A1 3/2004 Kong et al.
2004/0259086 A1 12/2004 Schlegel et al.
2005/0042222 A1 2/2005 Yamamoto et al.
2005/0042638 A1 2/2005 Arnold et al.
2005/0048533 A1 3/2005 Sidransky et al.
2005/0064455 A1 3/2005 Baker et al.
2005/0118625 A1 6/2005 Mounts
2005/0137805 A1 6/2005 Lewin et al.
2005/0202442 A1 9/2005 Morris et al.
2005/0227917 A1 10/2005 Williams et al.
2005/0240357 A1 10/2005 Minor
2005/0250125 A1 11/2005 Novakoff
2005/0260646 A1 11/2005 Baker et al.
2005/0266443 A1 12/2005 Croce et al.
2005/0266459 A1 12/2005 Poulsen
2006/0019256 A1 1/2006 Clarke et al.
2006/0019615 A1 1/2006 Ditmer
2006/0035244 A1 2/2006 Riggins et al.
2006/0046253 A1 3/2006 Nakao
2006/0046265 A1 3/2006 Becker et al.
2006/0083744 A1 4/2006 Chen et al.
2006/0088851 A1 4/2006 Erlander et al.
2006/0094061 A1 5/2006 Brys et al.
2006/0105360 A1 5/2006 Croce et al.
2006/0127907 A1 6/2006 Matsubara et al.
2006/0134663 A1 6/2006 Harkin et al.
2006/0204989 A1 9/2006 Kopreski
2006/0211017 A1 9/2006 Chinnaiyan et al.
2007/0010469 A1 1/2007 Chan
2007/0020657 A1 1/2007 Grebe et al.
2007/0031873 A1 2/2007 Wang et al.
2007/0037165 A1 2/2007 Venter et al.
2007/0037186 A1 2/2007 Jiang et al.
2007/0048738 A1 3/2007 Donkena et al.
2007/0065827 A1 3/2007 Pauloski et al.
2007/0065833 A1 3/2007 Gupta
2007/0083334 A1 4/2007 Mintz et al.
2007/0099197 A1 5/2007 Afar et al.
2007/0099209 A1 5/2007 Clarke et al.
2007/0105133 A1 5/2007 Clarke et al.
2007/0148667 A1 6/2007 Williams et al.
2007/0148687 A1 6/2007 Bedingham et al.
2007/0161004 A1 7/2007 Brown et al.
2007/0172841 A1 7/2007 Wang
2007/0172844 A1 7/2007 Lancaster et al.
2007/0212702 A1 9/2007 Tomlins et al.
2007/0220621 A1 9/2007 Clarke et al.
2007/0238119 A1 10/2007 Yu et al.
2007/0259352 A1 11/2007 Bentwich et al.
2007/0275915 A1 11/2007 Hallenbeck et al.
2008/0009001 A1 1/2008 Bettuzzi et al.
2008/0028302 A1 1/2008 Meschkat
2008/0044824 A1 2/2008 Giordano et al.
2008/0076674 A1 3/2008 Litman et al.
2008/0124344 A1 5/2008 Combs et al.
2008/0131892 A1 6/2008 Becker et al.
2008/0145841 A1 6/2008 Libutti et al.
2008/0254470 A1 10/2008 Berlkin
2008/0269157 A1 10/2008 Srivastava et al.
2008/0274457 A1 11/2008 Eng et al.
2008/0281568 A1 11/2008 Kao et al.
2009/0020433 A1 1/2009 Cohen et al.
2009/0036415 A1 2/2009 Rubin et al.
2009/0062144 A1 3/2009 Guo
2009/0075921 A1 3/2009 Ikegawa
2009/0149333 A1 6/2009 Knudsen et al.
2009/0191535 A1 7/2009 Connelly et al.
2009/0204333 A1 8/2009 Friend et al.

(56) References Cited

U.S. PATENT DOCUMENTS

2009/0239221 A1 9/2009 Chinnaiyan et al.
2009/0280490 A1 11/2009 Baker et al.
2009/0298082 A1 12/2009 Klee et al.
2010/0021538 A1 1/2010 Byun et al.
2010/0055704 A1 3/2010 Giordano et al.
2010/0075384 A1 3/2010 Kong et al.
2010/0099093 A1 4/2010 Weaver et al.
2010/0131286 A1 5/2010 Houlgatte et al.
2010/0131432 A1 5/2010 Kennedy et al.
2010/0178653 A1 7/2010 Aharonov et al.
2010/0215638 A1 8/2010 Ijin et al.
2010/0257617 A1 10/2010 Ami et al.
2010/0279327 A1 11/2010 Ossovskaya
2010/0285979 A1 11/2010 Zeiger et al.
2011/0009286 A1 1/2011 Andre et al.
2011/0045462 A1 2/2011 Fu et al.
2011/0092375 A1 4/2011 Zamore et al.
2011/0136683 A1 6/2011 Davicioni
2011/0152110 A1 6/2011 Vierlinger et al.
2011/0178163 A1 7/2011 Chowdhury
2011/0212855 A1 9/2011 Rafnar et al.
2011/0229894 A1 9/2011 Levy et al.
2011/0230372 A1 9/2011 Willman et al.
2011/0236903 A1 9/2011 McClelland
2011/0287946 A1 11/2011 Gudmundsson et al.
2011/0294123 A1 12/2011 Nakamura et al.
2011/0312520 A1 12/2011 Kennedy et al.
2012/0015839 A1 1/2012 Chinnaiyan
2012/0015843 A1 1/2012 Von et al.
2012/0041274 A1 2/2012 Stone et al.
2012/0108453 A1 5/2012 Smit et al.
2012/0115743 A1 5/2012 Davicioni et al.
2012/0122698 A1 5/2012 Stacey et al.
2012/0122718 A1 5/2012 Reisman
2012/0157334 A1 6/2012 Beaudenon-Huibregtse et al.
2012/0172243 A1 7/2012 Davicioni et al.
2012/0214165 A1 8/2012 Walfish et al.
2012/0220474 A1 8/2012 Kennedy et al.
2012/0304318 A1 11/2012 Ohnuma et al.
2013/0004974 A1 1/2013 Klee et al.
2013/0023434 A1 1/2013 Van Laar
2013/0142728 A1 6/2013 Beaudenon-Huibregtse et al.
2013/0150257 A1 6/2013 Abdueva et al.
2013/0172203 A1 7/2013 Yeatman et al.
2013/0184999 A1 7/2013 Ding
2013/0196866 A1 8/2013 Pestano et al.
2013/0225662 A1 8/2013 Kennedy et al.
2013/0231258 A1 9/2013 Wilde et al.
2013/0273543 A1 10/2013 Gudmundsson et al.
2013/0302808 A1 11/2013 Vasmatzis
2013/0302810 A1 11/2013 Latham et al.
2013/0303826 A1 11/2013 Jurisica et al.
2014/0030714 A1 1/2014 Paschke et al.
2014/0066323 A1 3/2014 Buerki et al.
2014/0080731 A1 3/2014 Davicioni et al.
2014/0087961 A1 3/2014 Sulem et al.
2014/0099261 A1 4/2014 Keutgen et al.
2014/0121126 A1 5/2014 Bivona et al.
2014/0143188 A1 5/2014 Mackey et al.
2014/0228237 A1 8/2014 Kennedy et al.
2014/0243240 A1 8/2014 Soldin et al.
2014/0302042 A1 10/2014 Chin et al.
2014/0315199 A1 10/2014 Rhodes et al.
2014/0315739 A1 10/2014 Aharonov et al.
2014/0349856 A1 11/2014 Schnabel et al.
2014/0349864 A1 11/2014 Kennedy et al.
2014/0371096 A1 12/2014 Umbright et al.
2015/0038376 A1 2/2015 Tian et al.
2015/0099665 A1 4/2015 Rosenfeld et al.
2015/0141470 A1 5/2015 Garraway et al.
2015/0275306 A1 10/2015 Bernards et al.
2015/0292030 A1 10/2015 McConkey
2015/0299808 A1 10/2015 Gonzalez et al.
2015/0307947 A1 10/2015 Basu et al.
2015/0329915 A1 11/2015 Davicioni et al.
2015/0368724 A1 12/2015 Aharonov et al.
2016/0024586 A1 1/2016 Delfour et al.
2016/0032395 A1* 2/2016 Davicioni ............ C12Q 1/6886
506/8
2016/0032400 A1 2/2016 Gomis et al.
2016/0068915 A1 3/2016 Kennedy et al.
2016/0076108 A1 3/2016 Davicioni et al.
2016/0115546 A1 4/2016 Rosenfeld et al.
2016/0120832 A1 5/2016 Rabinowitz et al.
2016/0251729 A1 9/2016 Chinnaiyan et al.
2016/0312305 A1 10/2016 Kennedy et al.
2016/0312306 A1 10/2016 Kennedy et al.
2016/0312307 A1 10/2016 Kennedy et al.
2016/0312308 A1 10/2016 Kennedy et al.
2017/0016076 A1 1/2017 Barnett-Itzhaki et al.
2017/0145513 A1 5/2017 Kennedy et al.
2017/0166980 A1 6/2017 Fahey, III et al.
2017/0329894 A1 11/2017 Kennedy et al.
2018/0016642 A1 1/2018 Kennedy et al.
2018/0216197 A1 1/2018 Davicioni et al.
2018/0030540 A1 2/2018 Davicioni et al.
2018/0068058 A1 3/2018 Abdueva et al.
2018/0112275 A1 4/2018 Davicioni et al.
2018/0122508 A1 5/2018 Wilde et al.
2018/0127832 A1 5/2018 Kennedy et al.
2018/0291459 A1 10/2018 Al-Deen Ashab et al.
2019/0017123 A1 1/2019 Davicioni et al.
2019/0191133 A1 6/2019 Ostrow
2019/0204322 A1 7/2019 Alshalalfa et al.
2019/0218621 A1 7/2019 Davicioni
2020/0165682 A1 5/2020 Chinnaiyan et al.
2020/0224276 A1 7/2020 Chinnaiyan et al.

FOREIGN PATENT DOCUMENTS

EP 2 366 800 9/2011
WO WO 90/015070 12/1990
WO WO 92/010092 6/1992
WO WO 93/009668 5/1993
WO WO 93/022684 11/1993
WO WO 98/045420 10/1998
WO WO 01/060860 8/2001
WO WO 01/066753 9/2001
WO WO 02/000929 1/2002
WO WO 02/083921 10/2002
WO WO 03/012067 2/2003
WO WO 04/037972 5/2004
WO WO 05/040396 5/2005
WO WO 05/085471 9/2005
WO WO 05/100608 10/2005
WO WO 06/047484 5/2006
WO WO 06/091776 8/2006
WO WO 06/110264 10/2006
WO WO 06/127537 11/2006
WO WO 06/135596 12/2006
WO WO 07/056049 5/2007
WO WO 07/070621 6/2007
WO WO 07/081720 7/2007
WO WO 07/081740 7/2007
WO WO 08/023087 2/2008
WO WO 08/046911 4/2008
WO WO 08/086478 7/2008
WO WO 08/112283 9/2008
WO WO 09/009432 1/2009
WO WO 09/020521 2/2009
WO WO 09/020905 2/2009
WO WO 09029266 3/2009
WO WO 09/045115 4/2009
WO WO 09/074968 6/2009
WO WO 09/143603 12/2009
WO WO 10/018601 2/2010
WO WO 10/056374 5/2010
WO WO 10/073248 7/2010
WO WO 10/099598 9/2010
WO WO 10/123626 10/2010
WO WO 10/124372 11/2010
WO WO 11/150453 12/2011
WO WO 12/031008 3/2012
WO WO 12/068383 5/2012

(56) References Cited

FOREIGN PATENT DOCUMENTS

| | | |
|---|---|---|
| WO | WO 12/135008 | 10/2012 |
| WO | WO 13/006495 | 1/2013 |
| WO | WO 13/088457 | 6/2013 |
| WO | WO 13/116742 | 8/2013 |
| WO | WO 14/028884 | 2/2014 |
| WO | WO 14/043803 | 3/2014 |
| WO | WO 14/085666 | 5/2014 |
| WO | WO 14/151764 | 9/2014 |
| WO | WO 15/071876 | 5/2015 |
| WO | WO 15/073949 | 5/2015 |
| WO | WO 16/141127 | 9/2016 |
| WO | WO 17/059549 | 4/2017 |
| WO | WO 17/062505 | 4/2017 |
| WO | WO 18/165600 | 9/2018 |
| WO | WO 19/023517 | 1/2019 |

OTHER PUBLICATIONS

Leyten et al. Clinical Cancer Research. AACR. Mar. 18, 2015, p. 1-10, available via URL: <clincancerres.aacrjournals.org/content/clincanres/early/2015/05/06/1078-0432.CCR-14-3334.full.pdf> (Year: 2015).*

Schmidt et al. Blood. 1998. 91: 22-29 (Year: 1998).*

Garber et al. PNAS. 2001. 98: 13784-13789 (Year: 2001).*

Ito et al AntiCancer Research. 2002. 22(4):2385-2389 (Year: 2002).*

Agell et al. Am J Pathology. Nov. 2012. 181: 1585-1593 (Year: 2012).*

Abdueva et al., "Quantitative Expression Profiting in Formalin-Fixed Paraffin-Embedded Samples by Affymetrix Microarrays," Journal of Molecular Diagnostics (Jul. 2010) vol. 12, No. 4, pp. 409-417.

Adamo and Ladomery, "The Oncogene ERG: A Key Factor in Prostate Cancer," *Oncogene*(2016), 35:403-414.

Affymetrix GeneChip Human Genome U133 Array Set HG-U133A, Geo, Mar. 11, 2002, retrieved on Mar. 11, 2002.

Affymetrix: Data Sheet, "GeneChip® Exon Array System for Human, Mouse, and Rat," Internet Citation, [Online] Jan. 25, 2012 [Retrieved from the Internet] Intp://www.biainformatics.atickland.aciaz/workshops/1O_March_2011 1Exon_EOST_Datash eet.pdf, 8 pages.

Agell et al., "A 12-Gene Expression Signature Is Associated with Aggressive Histological in Prostate Cancer: SEC14L1 and TCEB1 Genes Are Potential Markers of Progression," Am J Pathol (2012) vol. 181 (5), pp. 1585-1594.

Alberts et al., "Vesicular traffic in the secretory and endocytic pathways," Molecular Biology of the Cell (1994) 3rd Ed., p. 465.

Aldred et al., "Papillary and follicular thyroid carcinomas show distinctly different microarray expression profiles and can be distinguished by a minimum of five genes," J Clin Oncol. (2004) 22(17):3531-9.

Amling et al.: "Long-term hazard of progression after radical prostatectomy for clinically EB localized prostate cancer continued risk of biochemical failure after 5 years," J Urol. (2000) 164:101-105.

Amundadottir et al., "A common variant associated with prostate cancer in European and African populations," Nat Genet. (2006) 38:652-658.

Amundson et al., "Integrating global gene expression and radiation survival parameters across the 60 cell lines of the National Cancer Institute Anticancer Drug Screen," Cancer Research (2008) 68(2):415-424.

Ausubel, et al. Current Protocols in Molecular Biology. Wiley & Sons, New York (1995) Table of Contents.

Baetke et al., "Molecular Pathways Involved in Prostate Carcinogenesis: Insights from Public Microarray Datasets," PLoS One (2012) 7(11):e49831, 1-11.

Baggerly et al., "Deriving Chemosensitivity from Cell Lines: Forensic Bioinformatics and Reproducible Research in High-Throughput Biology," The Annals of Applied Sciences (2009) vol. 3, No. 4, pp. 1309-1334.

Ballman et al., "Faster cyclic loess: normalizing RNA arrays via linear models," Bioinformatics, 2004, 20 :2778-2786.

Bannert et al., "Retroelements and the human genome: new perspectives on an old relation." PNAS (Oct. 5, 2004) vol. 101, Suppl. 2, pp. 14572-14579.

Barlow et al., "Analysis of Case-Cohort Designs," J Clin Epidemiol (1999) vol. 52 (12), 1165-1172.

Bauer et al., "Identification of Markers of Taxane Sensitivity Using Proteomic and Genomic Analyses of Breast Tumor from Patients Receiving Neoadjuvant Paclitaxel and Radiation," Clin. Cancer Res. (2010) 16(2):681-690, American Association for Cancer Research.

Benner et al., "Evolution, language and analogy in functional genomics," Trends in Genetics, (Jul. 2001) vol. 17, pp. 414-418.

Bergstralh et al., "Software for optimal matching in observation al studies," Epidemiology (1996) 7(3):331-332.

Best et al., "Molecular differentiation of high- and moderate-grade human prostate cancer by cDNA microarray analysis", Diagn Mol Pathol. (2003) 12(2):63-70.

Bibikova et al., "Expression signatures that correlated with Gleason score and relapse in prostate cancer," Genomics (2007) 89(6):666-672.

Bibikova et al., "Gene expression profiles in formalin-fixed, paraffin-embedded tissues obtained with a novel assay for microarray analysis," Clin Chem., 2004, 50:2384-2386.

Bibikova et al., "Quantitative gene expression profiling in formalin-fixed, paraffin-embedded tissues using universal bead arrays," Am J Pathol. (2004) 165:1799-1807.

Birney et al., "Identification and analysis of functional elements in 1% of the human genome by the ENCODE pilot project." Nature Jun. 14, 2007; 447(7146):799-816.

Bismar et al., "ERG Protein Expression Reflects Hormonal Treatment Response and is Associated with Gleason Score and Prostate Cancer Specific Mortality," *Eur. J. Cancer* (2012), 48:538-546,Elsevier Ltd.

Biton et al., Nov. 20, 2014, Independent component analysis uncovers the landscape of the bladder tumor transcriptome and reveals insights into luminal and basal subtypes, Cell Reports, 9(4):1235-1245.

Blute et al., "Use of Gleason score, prostate specific antigen, seminal vesicle and margin status to predict biochemical failure after radical prostatectomy," J Urol (2001) 165: 119-125.

Boorjian et al., "Long-term risk of clinical progression after biochemical recurrence following radical prostatectomy: the mpact of time from surgery to recurrence." Eur Urol. (Jun. 2011) 59(6):893-9.

Boormans et al., "Identification of TDRD1 as a direct target gene of ERG in primary prostate cancer," Int J Cancer (2013) vol. 133 (2), pp. 335-345.

Bostwick et al., "Prognostic factors in prostate cancer: College of American Pathologists consensus statement," Arch Pathol Lab Med (2000) 124(7):995-1000.

Bott et al., "Prostate cancer management: (2) an update on locally advanced and metastatic disease", Postgrad Med J, Dec. 3, 2003, 79(937), 643-645.

Brase et al., "TMPRSS2-ERG—specific transcriptional modulation is associated with prostate cancer biomarkers and TGF-β signaling," BMC Cancer (2011) 11(507):1-8.

Breiman, "Random Forests," Machine Learning (2001)45:5-32.

Brouha et al., "Hot L1s account for the bulk of retrotransposition in the human population." PNAS USA (Apr. 29, 2003) 100(9):5280-5.

Bueno et al., "A diagnostic test for prostate cancer from gene expression profiling data," J Urol, Feb. 2004; 171(2 Pt 1):903-6.

Bull et al., "Identification of potential diagnostic markers of prostate cancer and prostatic intraepithelial neoplasia using cDNA microarrav," British J Cancer (Jun. 1, 2001) 84(11):1512-1519.

Bussemakers et al., "DD3: a new prostate-specific gene, highly overexpressed in prostate cancer." Cancer Res. (Dec. 1, 1999) 59(23):5975-9.

Carninci et al., "The transcriptional landscape of the mammalian genome," Science (Sep. 2, 2005) 09(5740):1559-63.

Cerutti et al. "Diagnosis of suspicious thyroid nodules using four protein biomarkers," Clin Cancer Res. (2006) 12(11 Pt 1):3311-8.

(56) References Cited

OTHER PUBLICATIONS

Chalitchagorn et al., "Distinctive pattern of LINE-1 methylation level in normal tissues and the association with carcinogenesis." Oncogene (Nov. 18, 2004) 23(54):8841-6.
Che et al.: "Prognostic Value of Abnormal p53 Expression in Locally Advanced Prostate Cancer Treated With Androgen Deprivation and Radiotherapy: A Study Based on RTOG 9202"; International Journal of Radiation: Oncology Biology Physics (Nov. 15, 2007) vol. 69, No. 4, pp. 1117-1123.
Chen et al., "Deregulation of a Hox Protein Regulatory Network Spanning Prostate Cancer Initiation and Progression," Clin Cancer Res (Jun. 2012) 18(16):4291-4302.
Chen et al., "Hepsin and maspin are inversely expressed in laser capture microdissectioned prostate cancer," J Urol. (Apr. 2003) 169(4):1316-1319.
Chen et al., "Significance of noninvasive diagnosis of prostate cancer with cytologic examination of prostatic fluid," J Nippon Med Sch. (Jun. 2006) 73(3)129-135.
Chen et al.: "Molecular determinants of resistance to antiandrogen therapy"; Nature Medicine, Nature Publishing Group, New York, NY (Jan. 1, 2004) vol. 10, No. 1, pp. 33-39.
Cheng et al. "Cell Proliferation in Prostate Cancer Patients with Lymph Node Metastasis", Clin Cancer Res (Oct. 1999) 5(10): 2820-2823.
Cheung et al., "Natural variation in human gene expression assessed in lymphoblastoid cells," Nature Genetics (2003) vol. 33, pp. 422-425.
Cheville et at., "Gene Panel Model Predictive of Outcome in Men at High-Risk of Systemic Progression and Death From Prostate Cancer After Radical Retropubic Prostatectomy," Journal of Clinical Oncology (Aug. 20, 2008) vol. 26 , No. 24.
Chifman et al., "Conservation of immune gene signatures in solid tumors and prognostic implications," BMC Cancer (2016) 16:911, pp. 1-17. DOI 10.1186/S12885-016-2948-Z.
Cho et al., "Hypermethylation of CpG island loci and hypomethylation of LINE-1 and Alu repeats in prostate denocarcinoma and their relationship to clinicopathological features", J Pathol (Feb. 2007) 211(3):269-77.
Choi et al., Feb. 2014, Identification of distinct basal and luminal subtypes of muscle-invasive bladder cancer with different sensitivities to frontline chemotherapy, Cancer Cell, 25(2):152-165.
Chow et al., "LINE-1 activity in facultative heterochromatin formation during X chromosome inactivation," Cell (Jun. 11, 2010) 141(6):956-69.
Cibas, et al. "The Bethesda System for Reporting Thyroid Cytopathology," Am J Clin Pathol. (Nov. 2009) 132(5):658-65. doi: 10.1309/AJCPPHLWMI3JV4LA.
Clancy et al., "Profiling networks of distinct immune-cells in tumors," BMC Bioinformatics (2016) 17:263, pp. 1-15. DOI 10.1186/s12859-016-1141-3.
Clark-Langone et al. "Riomarker discovery for colon cancer using a 761 gene RT-PCR assay 2007," BMC Genomics (2007) 8:279 pp. 1-18.
Cologne et al., "Optimal Case-Control Matching in Practice," Epidemiology Resources Inc. (1995) 6(3):271-275.
Cooper et al., "Mechanisms of Disease: biormarkers and molecular targets from microarray gene expression studies in prostate cancer ," Nat Clin Pract Urol. (2007) Dee:4(12):677-87.
Cooperberg et al., "The CAPRA-S score: A straightforward tool for improved prediction of outcomes after radical prostatectomy," Cancer (2011) vol. 117 (22), pp. 5039-5046.
Cordaux et al., "The impact of retrotransposons on human genome evolution." Nat Rev Genet. (Oct. 2009) 10(10):691-703.
Cordon-Cardo et al., "Improved prediction of prostate cancer recurrence through systems pathology," The Journal of Clinical Investigation (Jul. 2007) vol. 117, No. 7, pp. 1876-1883.
Couzin-Frankel, Jennifer, "As Questions Grow, Duke Halts Trials, Launches Investigation," Science (Aug. 6, 2010) vol. 329, pp. 614-615.
Cuzik et al., "Prognostic value of an RNA expression signature derived from cell cycle proliferation genes in patients with prostate cancer: a restrospective study," thelancet.com/oncology (Mar. 2011) vol. 12, pp. 245-255.
Dahlman et al., "Effect of androgen deprivation therapy on the expression of prostate cancer biomarkets MSMB and MSMB-binding protein CRISP3," Prostate Cancer and Prostatic Diseases (2010) 13:369-375.
Dalela et al., "Contemporary Role of the Decipher Test in Prostate Cancer Management: Current Practice and Future Perspectives," Rev. Urol. (2016), 18(1):1-9, MedReviews®, LLC.
Dalsgaard Sorensen et al.: "Discovery of prostate cancer biomarkers by microarray gene expression profiling"; Expert Review of Molecular Diagnostics, vol. 10, No. 1, Jan. 1, 2010, pp. 49-64.
D'Amico et al., "Cancer-specific mortality after surgery or radiation for patients with clinically localized prostate cancer managed during the prostate-specific antigen era," J Clin Oncol. (2003) 21:2163-2172.
D'Amico et al., "Determinants of prostate cancer-specific survival after radiation therapy for patients with clinically localized prostate cancer," J Clin Oncol. (2002) 20:4567-4573.
Dawood, Shaheenah, "Novel Biomarkers of Metastatic Cancer," Expert Rev. Mo/. Diagn. (2010) 10(5):581-590, Expert Reviews Ltd.
Day et al., "Estimating enrichment of repetitive elements from high-throughput sequence data." Genome Biol. (2010) 11 (6):R69.
De Klein et al., "A cellular oncogene is translocated to the Philadelphia chromosome in chronic myelocytic leukaemia." Nature (Dec. 23, 1982) 300(5894):765-7.
De Marzo et al., "Pathological and molecular mechanisms of prostate carcinogenesis: implications for diagnosis, detection, prevention, and treatment," J Cell Biochem. (Feb. 15, 2004) 91(3):459-477.
Dechassa et al., "Architecture of the SWI/SNF-nucleosome complex," Mol Cell Biol. (Oct. 2008) vol. 28, No. 19, pp. 6010-6021.
Demichelis et al., "TMPRSS2:ERG gene fusion associated with lethal prostate cancer in a watchful waiting cohort," Oncogene (2007) 26:4596-4599.
Den et al., Mar. 10, 2015, Genomic classifier indentifies men with adverse pathology after racial prostatectomy who benefit from adjuvant radiation therapy, Journal of Clinical Oncology, 33(8):944-951.
Dhanasekaran et al., "Delineation of prognostic biomarkers in prostate cancer," Nature (2001) 412: 822-826.
Dougherty, "The fundamental role of pattern recognition for gene-expression/microarray data in bioinformatics," Pattern recognition (2005) 38:2226-2228.
Eder et al., "Genes differentially expressed in prostate cancer," BJU Int. (May 2004) 93(8): 1151-1155.
Edwards et al., "Expression analysis onto microarrays of randomly selected cDNA clones highlights HOXB13 as a marker of human prostate cancer," Br J Cancer. (Jan. 31, 2005) 92(2):376-381.
Edwards et al.: "MicroRNAs and Ultraconserved Genes as Diagnostic Markers and Therapeutic Targets in Cancer and Cardiovascular Diseases", Journal of Cardiovascular Translational Research (May 5, 2010) vol. 3, No. 3, pp. 271-279.
Englisch, et al., "Chemically Modified Oligonucleotides as Probes and Inhibitors," Angew. Chem. Int. Ed. Eng. (1991) 30:613-629.
Epstein et al., "Prognostic factors and reporting of prostate carcinoma in radical AU prostatectomy and pelvic lymphadenectomy specimens," Scand. J. Urol. Nephrol. Suppl. (2005) 216:34-63.
Erho et al., "Discovery and Validation of a Prostate Cancer Genomic Classifier that Predicts Early Metastasis Following Radical Prostatectomy," PLoS One (2013) 8(6):e66855, 1-12.
Ernst et al., "Decrease and gain of gene expression are equally discriminatory markers for prostate carcinoma: a gene expression analysis on total and microdissected prostate tissue," Am J Pathol. (Jun. 2002) 160(6):2169-2180.
Etzioni et al. "The case for early detection", Nature Reviews | Cancer (Apr. 2003) vol. 3, pp. 1-10.
Fan et al., "Concordance among gene-expression-based predictors for breast cancer," N Engl J Med. (2006) 355:560-569.

(56) References Cited

OTHER PUBLICATIONS

Feng et al., "Luminal and basal subtyping of prostate cancer," *J Clin Oncol* (Feb. 20, 2017) vol. 35, No. 6, p. 3, Abstract.
Feroze-Merzoug et al., "Molecular profiling in prostate cancer," Cancer Metastasis Rev. 1 (2001) 20(3-4):165-71.
Fine et al., "A Proportional Hazards Model for the Subdistribution of a Competing Risk," Journal of the American Statistical Association (1999) vol. 94 (446), pp. 496-509.
Finley et al., "Advancing the molecular diagnosis of thyroid nodules: defining benign lesions by molecular profiling," Thyroid (2005) 15(6):562-8.
Finley et al., "Discrimination of benign and malignant thyroid nodules by molecular profiling," Ann Surg. (2004) 240(3):425-36; discussion 436-7.
Fodor et al., "Light-directed, spatially addressable parallel chemical synthesis," Science (Feb. 15, 1991) 251(4995):767-773.
Foley et al., "Molecular pathology of prostate cancer: the key to identifying new biomarkers of disease," Endocrine-Related Cancer (2004) 11:477-488.
Fontaine, et al., "Increasing the number of thyroid lesions classes in microarray analysis improves the relevance of diagnostic markers," PLoS One (Oct. 29, 2009) 4(10):e7632. doi: 10.1371/journal.pone.0007632.
Fryknas et al., "Molecular markers for discrimination of benign and malignant follicular thyroid tumors," Tumour Biol. (2006) 27(4):211-20.
Fu et al., "Regulation of apoptosis by a prostate-specific and prostate cancer-associated noncoding gene, PCGEM1." DNA Cell Biol. (Mar. 2006) 25(3): 135-41.
Fujarewicz et al., "A multi-gene approach to differentiate papillary thyroid carcinoma from benign lesions: gene selection using support vector machines with bootstrapping," Endocr Relat Cancer (Sep. 2007) 14(3):809-26.
Gait. Chapter 16: Oligoribonucleotides. Antisense Research and Applications, Crookeand Lebleu Eds., CRC Press (1993) pp. 289-302.
Galamb et al., "Diagnostic mRNA Expression Patterns of Inflamed, Benign, and Malignant Colorectal Biopsy Specimen and their Correlation with Peripheral Blood Results," Cancer Epidemiology, Biomarkers & Prevention (Oct. 2008) 17(10):2835-2845.
Galavotti et al., Apr. 2012, The autophagy-associated factors DRAM1 and p62 regulate cell migration and invasion in glioblastoma stem cells, Oncogene, 32:699-712.
Gao et al., "VISTA is an inhibitory immune checkpoint that is increased after ipilimumab therapy in patients with prostate cancer," Nat Med. (May 2017) 23(5):551-555.
Garber et al., "Diversity of gene expression in adenocarcinoma of the lung," PNAS (Nov. 20, 2001) vol. 98, No. 24, pp. 13784-13789.
Genevieve de Saint Basile et al., "Severe Combined Immunodeficiency Caused by Deficiency in Either the Ii or the E Subunit of CD3," Journal of Clinical Investigation (2004) vol. 114, No. 10. p. 1512-1517.
Gibb et al., "The functional role of long non-coding RNA in human carcinomas", Molecular Cancer, Biomed Central, London, GB (Apr. 13, 2011) vol. 10, No. 1, p. 38.
Giordano et al., "Organ-Specific Molecular Classification of Primary Lung, Colon, and Ovarian Adenocarcinomas Using Gene Expression Profiles," Am J Pathol (2001) 159(4):1231-1238.
Gleason: "Histologic grading and clinical staging of prostatic carcinoma", Urologic pathology: the prostate, (Tannenbaum, ed.) (1977) Lea & Febiger, Philadelphia, PA, pp. 171-197.
Gleason: "Histologic grading of prostate cancer: a perspective"; Hum. Pathol. (1992) 23(3):273-279.
Gleave et al., "Randomized comparative study of 3 versus 8-month neoadjuvant hormonal therapy before radical orostatectomy : biochemical and pathological effects," J Urol. (2001) 166:500-507.
Glinsky et al., "Gene expression profiling predicts clinical outcome of prostate cancer," J Clin Investigation (2004) 113(6):913-923.
Glinsky et al., "Microarray analysis identifies a death-from-cancer signature predicting therapy i failure in patients with multiple types of cancer," J Clin Invest. (2005) 115: 1503-1521.
Gonzalgo et al: "Molecular pathways to prostate cancer"; J Urol. (2003) 170(6 Pt 1):2444-2452.
Grambsch et al., "Proportional Hazards Tests and Diagnostics Based on Weighted Residuals," Biometrika (2013) vol. 81 (3), pp. 515-526.
Greenbaum et al.: "Comparing protein abundance and mRNA expression levels on a genomic scale"; Genome Biology (2003) 4(9):117.1-117.8.
Griffith et al., "Meta-analysis and meta-review of thyroid cancer gene expression profiling studies identifies important diagnostic biomarkers," J Clin Oncol. (2006) 24(31):5043-51.
Griffith, et al. Biomarker panel diagnosis of thyroid cancer: a critical review. Expert Rev Anticancer Ther. (Sep. 2008) 8(9):1399-413. doi: 10.1586/14737140.8.9.1399.
Gupta et al., "Long non-coding RNA HOTAIR reprograms chromatin state to promote cancer metastasis," Nature (Apr. 15, 2010) 464(7291): 1071-6.
Guttman et al., "Ab initio reconstruction of transcriptomes of pluripotent and lineage committed cells reveals gene structures of thousands of lincRNAs," Nat Biotechnol. (May 2010) 28(5):503-10.
Guttman et al., "Chromatin signature reveals over a thousand highly conserved large non-coding RNAs in mammals", Nature (Mar. 12, 2009) 458(7235):223-7.
Haiman et al.: "Multiple regions within 8q24 independently affect risk for prostate cancer"; Nat Genet. (2007) 39:638-644.
Hamada et al., "Diagnostic usefulness of PCR profiling of the differentially expressed marker genes in thyroid papillary carcinomas," Cancer Lett. (Jun. 28, 2005) 224(2):289-301. Epub Nov. 18, 2004.
He et al., "The antisense transcriptomes of human cells", Science (Dec. 19, 2008) 322(5909): 1855-7.
Heagerty et al., "Time-Dependent ROC Curves for Censored Survival Data and a Diagnostic Marker," Biometrics (2000) vol. 56 (2), pp. 337-344.
Heemers, H. V. et al.: "Identification of a Clinically Relevant Androgen-Dependent Gene Signature in Prostate Cancer"; Cancer Research, vol. 71, No. 5 (2011) pp. 1978-1988.
Heidenreich et al., "EAU Guidelines on Prostate Cancer. Part 1: Screening, Diagnosis, and Treatment of Clinically Localised Disease," European Urology (2011) vol. 59, pp. 61-71.
Henrotin et al.: "Type II collagen peptides for measuring cartilage degradation," Biotheology (2004) 41 (3-4): Abstract.
Henshall et al., "Survival Analysis of Genome-Wide Gene Expression Profiles of Prostate ancers Identifies New Prognostic Targets of Disease Relapse," Cancer Research (Jul. 15, 2003) 63, 14196-4203.
Holzbeierlein et al., "Gene expression analysis of human prostate carcinoma during hormonal therapy identifies androgen-responsive genes and mechanisms of therapy resistance," Am. J . Pathol. (Jan. 2004) 164(1):217-227.
Hornberger et al., "A Multigene Prognostic Assay for Selection of Adjuvant Chemotherapy in Patients with T3, Stage II Colon Cancer: Impact on Quality-Adjusted Life Expectancy and Costs," Value in Health 15 (2012) pp. 1014-1021.
Huarte et al., "Large non-coding RNAs: missing links in cancer?" Human Molecular Genetics (Oct. 15, 2010) 19(2): R152-R161.
Hughes et al., "Molecular pathology of prostate cancer," J Clin Pathol. (Jul. 2005) 58(7):673-684.
Hughes et al., "Topoisomerase II—a expression increases with increasing Gleason score and with hormone insensitivity in prostate carcinoma," J Clin Pathol. (Jul. 2006) 59(7): 721-724.
Humphrey et al: "Histologic grade, DNA ploidy, and intraglandular tumor extent as indicators of tumor progression of clinical Stage B prostatic carcinoma"; Am J Surg Pathol (1991) 15(12):1165-1170.
Ida et al., "Topoisomerase II alpha protein expression Is predictive of outcome in Gleason score 7 prostate cancer patients treated surgically and is dependent on ERG status." Mod Pathol. (Feb. 2010) Abstract 1895, 23 : 424A-425A.
Ito et al., "Linkage of elevated ets-2 expression to hepatocarcinogenesis," Anticancer Research (2002) 22(4):2385-2389.

(56) References Cited

OTHER PUBLICATIONS

Jemal et al.: "Cancer statistics," CA Cancer J Clin. (2005) 55:10-30.
Jenkins et al., "Prognostic significance of ailetic imbalance of chromosome arms 71, 8p, 16q, and 18q in stage T3NOMO prostate cancer," Genes, Chromosomes & Cancer (1998) 21:131-143.
Jhavar et al., "Integration of ERG gene mapping and gene-expression profiling identifies distinct categories of human prostate cancer," BJUI (2008) vol. 103 (9), pp. 1256-1269.
Jhavar et al., "Technical Advance: Detection of TMPRSS2-ERG Translocations in Human Prostate Cancer by Expression Profiling Using GeneChip Human Exon 1.0 ST Arrays," J Mol. Diag (Jan. 2008) vol. 10, No. 1, pp. 50-57.
Jones et al., "Frequent mutations of chromatin remodeling gene ARID1A in ovarian clear cell carcinoma" Science (Oct. 8, 2010) 330(6001):228-31.
Kanehisa, "Use of statistical criteria for screening potential homologies in nucleic acid sequences," Nucleic Acids Res. (Jan. 11, 1984) 12(1 Pt 1):203-13.
Karan et al., "Current status of the molecular genetics of human prostatic adenocarcinomas," Int J Cancer, 2003, 103(3):285-293.
Karayi et al., "Molecular biology of prostate cancer," Prostate Cancer Prostatic Dis. (2004) 7(1):6-20.
Karnes et al., "Radical prostatectomy for high-risk prostate cancer," Jpn. J. Clin. Oneal. (Oct. 19, 2009) 40 (1): 3-9, Epub.
Karnes et al., "The ability of biomarkers to predict systemic progression in men with high-risk prostate cancer treated surgically is dependent on ERG status," Cancer Res. (Nov. 9, 2010) 70(22):8994-9002, Epub.
Kasraeian, et al. , "A comparison of fine-needle aspiration, core biopsy, and surgical biopsy in the diagnosis of extremity soft tissue masses," Clin Orthop Relat Res. (Nov. 2010) 468(11):2992-3002.
Kawamorita et al., "Radical prostatectomy for high-risk prostate cancer: Biochemical outcome," International Journal of Urology (2009) 16:733-738.
Kebebew et al., "Diagnostic and extent of disease multigene assay for malignant thyroid neoplasms," Cancer (2006) 106(12):2592-7.
Kestin, "Potential survival advantage with early androgen deprivation for biochemical failure after external beam radiotherapy: the importance of accurately defining biochemical disease status," Int J Rad Oncol Biol Phys. (2004) 60:453-62.
Khor et al.: "Bcl-2 and Bax Expression Predict Prostate Cancer Outcome in Men Treated with Androgen Deprivation and Radiotherapy on Radiation Therapy Oncology Group Protocol 92-02"; Clinical Cancer Research (Jun. 15, 2007) vol. 13, No. 12, pp. 3585-3590.
Kiessling, et al., "D-TMPP: A novel androgen-regulated gene preferentially expressed in prostate and prostate cancer that is the first characterized member of an eukaryotic gene family," The Prostate (2005) 64:387-400.
Kikuchi et al., "Expression profiles of non-small cell lung cancers on cDNA microarrays: identification of genes for prediction of lymph-node metastasis and sensitivity to anti-cancer drugs," Oncogene (2003) 22, pp. 2192-2205.
Kishi et al., "Expression of the survivin gene in prostate cancer: correlation with clinicopathological characteristics, proliferative activity and apoptosis," J Urol. (May 2004) 171(5): 1855-1860.
Klee et al., "Candidate Serum Biomarkers for Prostate Adenocarcinoma identified by mRNA Differences in Prostate Tissue and Verified with Protein Measurements in Tissue and Blood," Clinical Chemistry (2012) 58(3):599-609.
Kosari et al., "Identification of biomarkers for prostate cancer," Clin. Cancer Res. (2008) 1734-1743.
Koshkin et al., "LNA (locked nucleic acids): An RNA mimic forming exceedingly stable LNA," LNA duplexes. J Am Chem Soc (1998) 120:13252-13253.
Koshkin et al., "LNA (locked nucleic acids): synthesis of the adenine, cytosine, guanine 5-methylcytosine, thymine and uracil bicyclonucleoside monomers, oligomerisation, and unprecedented nucleic acid recognition," Tetrahedron (1998) 54(14):3607-3630.

Kroschwitz The Concise Encyclopedia of Polymer Science and Engineering (1990) (pp. 858-859).
Kube et al., "Optimization of laser capture microdissection and RNA amplification for gene expression profiling of prostate cancer," BMC Mol. Biol. (2007) 8:25.
Kumar, et al., "The first analogues of LNA (locked nucleic acids): phosphorothioate-LNA and 2'-thio-LNA," Bioorg Med Chem Lett. (Aug. 18, 1998) 8(16):2219-22.
Kumar-Sinha et al., "Molecular markers to identify patients al risk for recurrence after primary treatment for prostate cancer," Urology, 62 Suppl 1:19-35, Dec. 29, 2003.
Kunarso et al., "Transposable elements have rewired the core regulatory network of human embryonic stem cells," Nat Genet (Jul. 2010) 42(7):631-4.
Landers et al.: "Use of multiple biomarkers for a molecular diagnosis of prostate cancer"; Int. J. Cancer (May 10, 2005) 114 pp. 950-956.
Lapointe et al., "Gene expression profiling identifies clinically relevant subtypes of prostate cancer," PNAS USA (2004) 101:811-816.
Latulippe et al., "Comprehensive Gene Expression Analysis of Prostate Cancer Reveals Distinct Transcriptional Programs Associated with Metastatic Disease," Cancer Res. (2002) 62:4499-4506.
Lawton et al., "Updated results of the phase III Radiation Therapy Oncology Group (RTOG) trial 85-31 evaluating the potential benefit of androgen suppression following standard radiation therapy for unfavorable prognosis carcinoma of the prostate," Int J Rad Oncol Biol Phvs. (2001) 49:937-946.
Leyten et al., "Identification of a Candidate Gene Panel for the Early Diagnosis of Prostate Cancer," Clinical Cancer Research (2015) 21(13):3061-3070.
Lin et al., "Cox Regression with Incomplete Covariate Measurements," Journal of the American Statistical Association (1993) vol. 88 (424), pp. 1341-1349.
Lin et al., "Nuclear receptor-induced chromosomal proximity and DNA breaks underlie specific translocations in cancer," Cell (Dec. 11, 2009) 139(6):1069-83.
Liong et al., "Blood-Based Biomarkers of Aggressive Prostate Cancer," PLoS One (Sep. 2012) vol. 7, Issue 7, e45802, pp. 1-7.
Liu et al., 2014, Synergistic killing of lung cancer cells by cisplatin and radiation via autophagy and apoptosis, Oncology Letters, 7:1903-1910.
Livingston et al., "*Homo sapiens* CDC20 Cell Division Cycle 20 Homolog (CDC20)," Gene (Apr. 24, 2006).
Lockstone, "Exon array data analysis using Affymetrix power tools and R statistical software," Briefings in bioinformatics (2011) vol. 12 (6), pp. 634-644.
Lunardi et al., "A co-clinical approach identified mechanisms and potential therapies for androgen deprivation resistance in prostate cancer," Nature Genetics (Jul. 2013) vol. 45, No. 7, pp. 747-757.
Luo et al., "Gene expression analysis of prostate cancers," Molecular Carcinogenesis (Jan. 2002) 33(1):25-35.
Luo et al., "Human Prostate Cancer and Benign Prostatic Hyperplasia : Molecular Dissection by Gene Expression Profiling," Cancer Res. (2001) 61:4683-4688.
Magee et al., "Expression Profiling Reveals Hepsin Overexpression in Prostate Cancer," Cancer Res. (2001) 61:5692-5696.
Martens-Uzunova, E. S. et al.: "Diagnostic and prognostic signatures from the small non-coding RNA transcriptome in prostate cancer", Oncogene (Jul. 18, 2011) vol. 31, No. 8, pp. 978-991.
Martin, "A New Access to 2'-O-Alkylated Ribonucleosides and Properties of 2'-O-Alkylated Oligoribonucleotides," Helv. Chim. Acta. (1995) 78:486-504. (in German with English abstract).
Mazzanti, et al., "Using gene expression profiling to differentiate benign versus malignant thyroid tumors," Cancer Res. (Apr. 15, 2004) 64(8):2898-903.
McCall et al., "Frozen robust multiarray analysis (fRMA)", Biostatistics (2010) vol. 11 (2), 242-253.
McConkey et al., Apr. 2015, Therapeutic opportunities in the intrinsic subtypes of muscle-invasive bladder cancer, Hematology/Oncology Clinics of North America, 29(2):377-394.
McConkey et al., May 2016, A prognostic gene expression signature in the molecular classification of chemotherapy-naïve urothelical

(56) References Cited

OTHER PUBLICATIONS cancer is predictive of clinical outcomes from neoadjuvant chemotherapy: a phase 2 trial of dose-dense methotrexate, vinblastine, doxorubicin, and cisplatin with bevacizumab in urothelial cancer, European Urology, 69(5):855-862.
Mendiratta et al., "Genomic signatures associated with the development, progression, rand outcome of prostate cancer," Molecular diagnosis & therapy (2007) 11(6):345-54.
Mercer, DW, "Use of multiple markers to enhance clinical utility", Immunol Ser. (1990) 53: 39-54.
Mineva et al., "Differential expression of alphaB-crystallin and Hsp27-1 in anaplastic thyroid carcinomas because of tumor-specific alphaB-crystallin gene (CRYAB) silencing," Cell Stress Chaperones (Autumn 2005) 10(3):171-84.
Mitelman, "Recurrent chromosome aberrations in cancer," Mutation Research (2000) 462: 247-253.
Montironi et al., "Carcinoma of the prostate: inherited susceptibility, somatic gene defects and androgen receptors," Virchows Arch. (Jun. 2004) 444(6):503-508.
Moul et al., "Early versus delayed hormonal therapy for prostate specific antigen only recurrence of prostate cancer after radical prostatectomy," J Urol. (2004) 171:1141-1147.
Moul, "Prostate specific antigen only progression of prostate cancer," J Urol. (2000) 163:1632-42.
Mühlenbruch et al., "Multiple imputation was a valid approach to estimate absolute risk from a prediction model based on case—cohort data," Journal of Clinical Epidemiology (2017) 84:130-141.
Nakagawa et al., "A Tissue Biomarker Panel Predicting Systemic Progression after PSA Recurrence Post-Definitive Prostate Cancer Therapy," PLos One (2008) 3(5):e2318, 14 pages.
Nelson, "Predicting prostate cancer behavior using transcript profiles," J Urol. (Nov. 2004) 172(5 Pt 2):S28-32; discussion S33.
Newson, Roger, "Confidence intervals for rank statistics: Somers' D and extensions," The Stata Journal (Sep. 2006) 6(3):309-334.
Nielsen et al., "Sequence-selective recognition of DNA by strand displacement with a thymine-substituted polyamide," Science (1991) 254: 1497-1500.
Noordzij et al. "The prognostic value of CD44 isoforms in prostate cancer patients treated by radical prostatectomy", Clin Cancer Res (May 1997) 3(5): 805-815.
Norman, James, "Thyroid Nodule Ultrasound", Endocrine website (Updated Oct. 13, 2010) http://www.endocrineweb.com/noduleus.html.
Ohl et al., "Gene expression studies in prostate cancer tissue: which reference gene should be selected for normalization?," J. Mol. Med . (2005) 83(12):1014-1024.
Ong et al., "Expression Profiling Identifies a Novel-Methylacyl-CoA Racemase Exon with Fumarate Hydratase Homology," Cancer Research (Jun. 15, 2003) 63:3296-3301.
Oosumi et al., "Mariner transposons in humans", Nature (Dec. 14, 1995) 378 (6558): 672.
Ozen et al., Sep. 24, 2007, Widespread deregulation of microRNA expression in human prostate cancer, Oncogene, 27:1788-1793.
Parker et al., "High expression levels of surviving protein independently predict a poor outcome for patients who undergo surgery for clear cell renal cell carcinoma," Cancer (2006) 107:37-45.
Pascal et al., "Correlation of mRNA and protein levels: Cell type-specific gene expression of cluster designation antigens in the prostate," BMC Genomics (2008) 9:246 (13 pages).
Patel et al., "Preoperative PSA velocity is an independent prognostic factor for relapse after radical prostatectomy," J Clin Oncol. (2005) 23:6157-6162.
Paulo et al., "Molecular Subtyping of Primary Prostate Cancer Reveals Specific and Shared Target Genes of Different ETS Rearrangements," *Neoplasia* (Jul. 2012) 14(7):600-611.
Penney et al., "mRNA Expression Signature of Gleason Grade Predicts Lethal Prostate Cancer," J Clin Oncol (Jun. 10, 2011) vol. 29, No. 17, pp. 2391-2396, and Appendix.
Pereira et al, "Coagulation factor V and VIIIN ratio as predictors of outcome in paracetamol induced fulminant hepatic failure: relation to other prognostic indicators," Gut (1992) 33:98-102.
Perez et al., "Long, abundantly expressed non-coding transcripts are altered in cancer," Human Molecular Genetics (2008) vol. 17, No. 5, pp. 642-655. Published online Nov. 15, 207.
Pienta et al. "The current state of preclinical prostate cancer animal models"; Prostate (2008) 69: 629-639.
Pilepich et al., "Phase III radiation therapy oncology group (RTOG) trial 86-10 of androgen deprivation adjuvant to definitive radiotherapy in locally advanced carcinoma of the prostate," Int. J. Radiation Oncology Biol. Phys. (2001) vol. 50, No. 5, pp. 1243-1252.
Pinover et al., "Validation of a treatment policy for patients with prostate specific antigen failure after three-dimensional conformal prostate radiation therapy," Cancer (Feb. 15, 2003) vol. 97, No. 4, pp. 1127-1133.
Pittoni et al., "The Dark Side of Mast Cell-Targeted Therapy in Prostate Cancer," Cancer Res. (2012) 72(4):831-835.
Porkka et al., "RAD21 and KIAA0196 at 8q24 are amplified and overexpressed in prostate cancer," Genes Chromosomes Cancer (2007) 39:1-10.
Porkka et al: Molecular mechanisms of prostate cancer; Eur Urol. (2004) 45(6):683-691.
Pound et al., "Natural history of progression after PSA elevation following radical prostatectomy," JAMA (1999) 281:1591-1597.
Prasad et al., "Identification of genes differentially expressed in benign versus malignant thyroid tumors," Clin Cancer Res. (2008) 14(11):3327-37.
Prensner et al., "Transcriptome Sequencing Identifies PCAT-1, a Novel lincRNA Implicated in Prostate Cancer Progression," (2012) 29 (8): 742-749.
Probe Set Listing for the Affymetrix Human Genome U133 Plus 2.0 array (Accessed from https://www.affymetrix.com/analysis/index.affx on Jul. 1, 2015) (Year: 2015).
Puskas, et al., "Gene profiling identifies genes specific for well-differentiated epithelial thyroid tumors," Cell Mol Biol (Noisy-le-grand) (Sep. 5, 2005) 51(2):177-86.
Rabbits, "Chromosomal translocations in human cancer", Nature (Nov. 10, 1994) 372: 143-149.
Reddy et al., "Clinical utility of microarray-derived genetic signatures in predicting outcomes in prostate cancer," Clinical Genitourinary Cancer (2006) 5(3):187-189.
Reis et al., "Antisense intronic non-coding RNA levels correlate to the degree of tumor differentiation in prostate cancer," Oncogene (2004) 23(39):6684-6692.
Rhodes et al., "Large-scale meta-analysis of cancer microarray data identifies common transcriptional profiles of neoplastic transformation and progression," Proc Nat Acad Sci USA (2004) 101:9309-9314.
Rhodes et al., "Multiplex biomarker approach for determining risk of prostate specific antigen-defined recurrence of prostate cancer," J Nat Cancer Inst. (May 7, 2003) vol. 95, No. 9. pp. 661-668.
Rhodes et al., "ONCOMINE: A Cancer Microarray Database and Integrated Data-Mining Platform," Neoplasia (2004) 6:1-6.
Rinn et al., "Functional demarcation of active and silent chromatin domains in human HOX loci by noncoding RNAs," Cell (Jun. 29, 2007) 129(7):1311-23.
Roberts et al., "The SWI/SNF complex-chromatin and cancer." Nat Rev Cancer (Feb. 2004) 4(2):133-42.
Robertson et al., "DNA in radical prostatectomy specimens. Prognostic value of tumor ploidy," Acta Oncologica (1991) 30(2):205-207.
Robertson et al., "Reconstructing the ancient mariners of humans." Nat Genet. (Apr. 1996) 12(4):360-1.
Robinson et al., "A dynamic programming approach for the alignment of signal peaks in multiple gas chromatography-mass spectrometry experiments," BMC Bioinformatics (2007) 8.1:419.
Robinson, et al., "A comparison of Affymetrix gene expression arrays," BMC Bioinformatics (Nov. 15, 2007) 8:449.
Romanuik et al., "LNCaP Atlas: Gene expression associated with in vivo progression to castration-recurrent prostate cancer," GMB Medical Genomics (2010) 3:43, pp. 1-19.

(56) References Cited

OTHER PUBLICATIONS

Ross et al., "Tissue-based Genomics Augments Post-prostatectomy Risk Stratification in a Natural History Cohort of Intermediate- and High-Risk Men," European Urology 69 (2016) pp. 157-165.
Rotblat et al., "A Possible Role for Long Non-Coding RNA in Modulating Signaling Pathways," Med. Hvnotheses (2011) 77:962-965, Elsevier.
Rotunno et al., "A Gene Expression Signature from Peripheral Whole Blood for Stage I Lung Adenocarcinoma," Cancer Prevention Research (Jul. 8, 2011) 4(10) 1599-1607.
Rowley, "A new Consistent Chromosomal Abnormal ity in Chronic Myelogenous Leukaemia Identified by Quinacrine rluorescence and Giemsa Staining," Nature (Jun. 1, 1973) 243:290-293.
Rowley, "Chromosome translocations: dangerous liaisons revisited," Nature Reviews: Cancer (Dec. 2001) 1):245-250.
Rubin et al., "Molecular genetics of human prostate cancer," Modern Pathol. (2004) 17(3):380-388.
Saito-Hisaminato et al., "Genome-Wide Profiling of Gene Expression in 29 Normal Human Tissues with a cDNA Microarray," DNA Research (2002) vol. 9, pp. 35-45.
Saligan et al., "Supervised Classification by Filter Methods and Recursive Feature Elimination Predicts Rick of Radiotherapy-Related Fatigue in Patients with Prosate Cancer," Cancer Informatics (2014) 13: 141-152.
Sandler et al., "Overall survival after prostate-specific-antigen-detected recurrence following conformal radiation therapy," Int J Rad Oncol Biol Phvs. (2000) 48:629-633.
Sanghvi, "Heterocyclic base modifications in nucleic acids and their applications in antisense oligonucleotides in Antisense Research and Applications," Crooke, S. T. and Lebleu, B., ed., CRC Press. (1993) Ch 15 274-285.
Saramaki et al., "Amplification of EIF3S3 gene is associated with advanced stage in prostate cancer," Am J Pathol. (2001) 159:2089-2094.
Sato et al., "Clinical significance of alterations of chromosome 8 in high-grade, advanced, nonmetastatic prostate carcinoma," J Natl Cancer Inst. (1999) 91:1574-1580.
Savinainen et al., "Expression and copy number analysis of TRPS 1, EIF3S3 and MYC genes in breast and prostate cancer," Br J Cancer (2004) 90: 1041-1046.
Savinainen et al., "Over expression of EIF3S3 promotes cancer cell growth," The Prostate (2006) 66: 1144-1150.
Schlomm et al., "Molecular staging of prostate cancer in the year 2007," World .J. Urol. (Mar. 2007) 25(1):19-30.
Schmidt et al., "Lack of interferon consensus sequence binding protein (ICSBP) transcripts in human myeloid leukemias," Blood (1998) 91:22-29.
Schumacher et al., "A Common 8q24 Variant in Prostate and Breast Cancer from a Large Nested Case-Control Study," Cancer Res. (2007) 67:2951-2956.
Seiler et al., Oct. 2017, Impact of molecular subtypes in muscle-invasive bladder cancer on predicting response and survival after neoadjuvant chemotherapy, European Urology, 72(4):544-554.
Severi et al., "The Common Variant rs1447295 on Chromosome 8q24 and Prostate Cancer Risk: Results from an Australian Population-based Case-Control Study", Cancer Epidemiology, Biomarkers & Prevention (2007) 16:610-611.
Shariat et al., "An updated catalog of prostate cancer predictive tools," Cancer (2008) 113(11):3062-6.
Shariat et al., "Survivin expression is associated with features of biologically aggressive prostate carcinoma," Cancer (2004) 100(4): 751-757.
Shen et al., "The SWI/SNF ATPase Brm is a gatekeeper of proliferative control in prostate cancer," Cancer Res. (Dec. 15, 2008) 68(24):10154-62.
Shibru et al., "Does the 3-gene diagnostic assay accurately distinguish benign from malignant thyroid neoplasms?" Cancer (Sep. 1, 2008) 113(5):930-5. doi: 10.1002/cncr.23703.
Shipley et al., "Radiation therapy for clinically localized prostate cancer: a multi-institutional pooled analysis," JAMA (1999) 281:1598-1604.
Simmons et al.. "Natural history of biochemical recurrence after radical prostatectomy: risk assessment for secondary herapy," Eur Urol. (May 2007) 51(5):1175-84.
Singh et al., "Gene expression correlates of clinical prostate cancer behavior." Cancer Cell (Mar. 2002) vol. 1, pp. 1203-1209.
Singh et al., "LNA (locked nucleic acids): synthesis and high-affinity nucleic acid recognition," Chem Commun (1998) 4:455-456.
Singh et al., "Synthesis of 2'-amino-LNA: A novel conformationally restricted high-affinity oligonucleotide analogues with a handle," J Org Chem (1998) 63:10035-10039.
Slotkin et al., "Transposable elements and the epigenetic regulation of the genome." Nat Rev Genet. (Apr. 2007) 8(4):272-85.
Smit et al., "High-Resolution ERG-Expression Profiling on GeneChip Exon 1.0 ST Arrays in Primaryand Castration-Resistant Prostate Cancer," *BJU International* (2013), 111(5):836-842, BJU International.
Solo et al., "Prevalence of prostate cancer (PC) clinical states (CS) in the United States: Estimates using a dynamic progression model," ASCO Annual Meeting, Journal of Clinical Oncology (May 20, 2011) vol. 29, No. 15, Abstract 4637.
Srikantan et al., "PCGEM1, a prostate-specific gene, is overexpressed in prostate cancer," PNAS (Oct. 24, 2000) 97(22): 12216-12221.
Stamey et al., "Molecular genetic profiling of Gleason grade 415 prostate cancers compared to benign prostatichyperplasia," J Urol. (2001) 166(6):2171-2177.
Stanbrough et al., "Increased Expression of Genes Converting Adrenal Androgens to Testosterone in Androgen-Independent Prostate Cancer," Cancer Res (Mar. 1, 2006) 66(5):2815-2825.
Stavenhagen et al.. "An ancient provirus has imposed androgen regulation on the adjacent mouse sex-limited protein Jene." Cell (Oct. 21, 1988) 55(2):247-54.
Stephenson et al., "Integration of gene expression profiling and clinical variables to predict prostate carcinoma recurrence after radical prostatectomy," Cancer (Jul. 15, 2005) 104(2):290-298.
Stephenson et al., "Postoperative Nomogram Predicting the 10-Year Probability of Prostate Cancer Recurrence After Radical Prostatectomy," J Clin Oncol (2008) vol. 23 (28), pp. 7005-7012.
Subramanian et al., "Gene set enrichment analysis: A knowledge-based approach for interpreting genome-wide expression profiles," PNAS USA (2005) 102:15545-15550.
Sun et al., "Aberrant expression of SWI/SNF catalytic subunits BRG1/BRM is associated with tumor development and ncreased invasiveness in prostate cancers," Prostate (Feb. 1, 2007) 67(2):203-13.
Taft et al., "Non-coding RNAs: regulators of disease," J Pathol. (Jan. 2010) 220(2):126-39.
Takayama et al., "TACC2 Is an Androgen-Responsive Cell Cycle Regulator Promoting Androgen-Mediatged and Castration-Resistant Growth of Prostate Cancer," Mol Endocrinol (May 2012) 26(5):748-761.
Talantov et al., "Gene Based Prediction of Clinically Localized Prostate Cancer Progression After Radical Prostatectomy," The Journal of Urology (Oct. 2010) vol. 184, 1521-1528.
Taylor et al., "Integrative genomic profiling of human prostate cancer," Cancer Cell (Jul. 13, 2010) vol. 18 (1), pp. 11-22.
Thompson et al., "Adjuvant and Salvage Radiotherapy After Prostatectomy: AUA/ASTRO Guideline," J Urol. (2013) 190(2):441-449.
Thompson et al., "Is the GPSM scoring algorithm for patients with prostate cancer valid in the contemporary era?" J Urol. (Aug. 2007) vol. 178 (2), 459-463.
Thorsen et al., "Alternative Splicing in Colon, Bladder, and Prostate Cancer Identified by Exon Array Analysis," Molecular & Cellular Proteomics (Mar. 18, 2008) vol. 7, No. 7, pp. 1214-1224.
Tockman et al., "Considerations in bringing a cancer biomarker to clinical application," Cancer Research (1992) 52:2711-2718.
Tollefson et al., "Stratification of Patient Risk Based on Prostate-Specific Antigen Doubling Time After Radical Retropubic Prostatectomy," Mayo Clin Proc. (2007) 82:422-427.

(56) References Cited

OTHER PUBLICATIONS

Tomlins et al., "Distinct classes of chromosomal rearrangements create oncogenic ETS gene fusions in prostate cancer," Nature (Aug. 2, 2007) 448(7153):595-9.
Tomlins et al., "Integrative molecular concept modeling of prostate cancer progression," Nat Genet. (2007) 39:41-51.
Tomlins et al., "Recurrent Fusion of TMPRSS2 and ETS Transcription Factor Genes in Prostate Cancer," Science (2005) 310(5748):644-648.
Tomlins et al., "TMPRSS2:ETV4 Gene Fusions Define a Third Molecular Subtype of Prostate Cancer," Cancer Res. (2006) 66:3396-3400.
Tricoli et al.. "Detection of prostate cancer and predicting progression: current and future diagnostic markers," Clinical Cancer Research (Jun. 15, 2004) 10:3943-3953.
True et al., "A molecular correlate to the Gleason grading system for prostate adenocarcinoma," PNAS (Jul. 18, 2006) vol. 103, No. 29, pp. 10991-10996.
Tsuchiya et al., "Clinical significance in situ hybridization analysis in pathologic of alterations of chromosome 8 detected by fluorescence organ-confined prostate cancer," Genes Chromosomes Cancer (2002) 34:363-371.
Tsuchiya et al., "Mapping and gene expression profile of the minimally overrepresented 8q24 region in prostate cancer," Am J Pathol. (May 2002) 160(5):1799-1806.
Vanaja et al., "PDLIM4 Represseion by Hypermethylation as a Potential Biomarker for Prostate Cancer," Clin. Cancer Res. (2006) 12(4):1128-1136.
Vanaja et al., "Transcriptional Silencing of Zinc Finger Protein 185 Identified Profiling Is Associated with Prostate Cancer Progression," Cancer Research (Jul. 15, 2003) 63:3877-3882.
Varambally et al., "Integrative Genomic and Proteomic Analysis of Prostate Cancer Reveals Signatures of Metastatic Progression," Cancer Cell (Nov. 2005) 8(5):393-406.
Varela et al., "Exome sequencing identifies frequent mutation of the SWI/SNF complex gene PBRM1 in renal carcinoma," Nature (Jan. 27, 2011) 469(7331):539-42.
Varricchi et al., "Are Mast Cells MASTers in Cancer?" Front Immunol. ePub (Apr. 12, 2017) 8:424.
Versteege et al., "Truncating mutations of hSNF5/INI1 in aggressive paediatric cancer." Nature (Jul. 9, 1998) 394 6689):203-6.
Vickers et al., "Extensions to decision curve analysis, a novel method for evaluating diagnostic tests, prediction models and molecular markers," BMC Medical Informatics and Decision Making, (2008) 8(53):1-17.
Visakorpi, "The molecular genetics of prostate cancer," Urology (2003) 62(5 Suppl 1):3-10.
Wang et al., "RNA-Seq: a revolutionary tool for transcriptomics," Nature Reviews/Genetics (Jan. 2009) vol. 10, pp. 57-63.
Wang et al., "Two common chromosome 8q24 variants are associated with increased risk for prostate cancer," Cancer Res. (2007) 67:2944-2950.
Watson et al., "Future opportunities for the diagnosis and treatment of prostate cancer," Prostate Cancer Prostatic Dis. (2004) 7:S8-S13.
Weber et al., "The prognostic value of expression of HIF1 [alpha], EGFR and VEGF-A, in localized prostate cancer for intermediate- and high-risk patients treated with radiation therapy with or without androgen deprivation therapy," Radiation Oncology (Apr. 30, 2012) vol. 7, No. 66, 8 pages.
Welsh et al., "Analysis of Gene Expression Identifies Candidate Markers and Pharmacological Targets in Prostate Cancer," Cancer Res. (Aug. 15, 2001) 61:5974-5978.
Wiegand et al., "ARID1A mutations in endometriosis-associated ovarian carcinomas," N Engl J Med. (Oct. 14, 2010) 363 (16):1532-43.
Willman et al., "Immunohistochemical staining for DNA topoisomerase II-alpha in benign, premalignant, and malignant lesions of the prostate," Prostate (Mar. 1, 2000) 42(4):280-286.
Winkler et al.: "Stage D1 prostatic adenocarcinoma: significance of nuclear DNA ploidy patterns studied by flow cytometry," Mayo Clin Proc. (1988) 63(2): 103-112.
Wyatt et al., "Heterogeneity in the inter-tumor transcriptome of high risk prostate cancer," *Genome Biology* (Aug. 26, 2014) vol. 15, No. 8, pp. 2-14.
Yap et al., "Molecular interplay of the noncoding RNA ANRIL and methylated histone H3 lysine 27 by polycomb CBX7 n transcriptional silencing of INK4a," Mol Cell. (Jun. 11, 2010) 38(5):662-74.
Yates et al., "X:Map: annotation and visualization of genome structure for Affymetrix exon array analysis," Nucleic Acids Res. (2008) vol. 36:D780-D786.
Yeager et al., "Genome-wide association study of prostate cancer identifies a second risk locus at 8q24," Nat Genet (2007) 39:645-649.
Yegnasubramanian et al., "DNA hypomethylation arises later in prostate cancer progression than CpG island hypermethylation and contributes to metastatic tumor heterogeneity," Cancer Res. (Nov. 1, 2008) 68(21): pp. 8954-8967.
Yeliin et al., "Widespread occurrence of antisense transcription in the human genome," Nat Biotechnol. (2003) 21(4):379-86.
Yu et al., "An integrated network of androgen receptor, polycomb, and TMPRSS2-ERG gene fusions in prostate cancer progression," Cancer Cell. (May 18, 2010) 17(5):443-54.
Yu et al., "Gene expression alterations in prostate cancer predicting tumor aggression and preceding development of malignancy," J Clin Oncol. (Jul. 15, 2004) 22(14):2790-2799.
Yukinawa et al., "A multi-class predictor based on a probabilistic model: application to gene expression profiling-based diagnosis of thyroid tumors," BMC Genomics (Jul. 27, 2006) 7:190.
Zanetta et al., "Flow-cytometric analysis of deoxyribonucleic acid content in advanced ovarian carcinoma: its importance in long-term survival," Am J Obstet Gynecol (1996) 175(5): 1217-1225.
Zelefsky et al., "High dose radiation delivered by intensity modulated conformal radiotherapy improves the outcome of localized prostate cancer," The Journal of Urology (Sep. 2001) 166(3):876-881.
Zelefsky et al., "Neoadjuvant hormonal therapy improves the therapeutic ratio in patients with bulky prostatic cancer treated with three-dimensional conformal radiation therapy," Int J Radiat Oncol Biol Phvs. (1994) 29:755-761.
Zhao et al., "Development and validation of a 24-gene predictor of response to postoperative radiotherapy in prostate cancer: a matched, retrospective analysis," Lancet Oncol (2016) 17, pp. 1612-1620.
GenBank Accession No. AA462934 dated Jun. 10, 1997, 2 pages.
GenBank Accession No. AA920095 dated Apr. 20, 1998, 2 pages.
GenBank Accession No. AB028840 dated Jan. 12, 2000, 2 pages.
GenBank Accession No. AB030836 dated Oct. 23, 1999, 2 pages.
GenBank Accession No. AB036741 dated Dec. 22, 2000, 3 pages.
GenBank Accession No. AF077349 dated Dec. 14, 2000, 2 pages.
GenBank Accession No. AF077351 dated Dec. 20, 2000, 3 pages.
GenBank Accession No. AF115517 dated Nov. 23, 2005, 4 pages.
GenBank Accession No. AI413910 dated Feb. 9, 1999, 2 pages.
GenBank Accession No. AI414999 dated Feb. 9, 1999, 2 pages.
GenBank Accession No. AI425960 dated Mar. 9, 1999, 2 pages.
GenBank Accession No. AI851940 dated Jul. 15, 1999, 2 pages.
GenBank Accession No. AK018022 dated Sep. 19, 2008, 4 pages.
GenBank Accession No. AK019341 dated Sep. 19, 2008, 3 pages.
GenBank Accession No. AK019342 dated Sep. 19, 2008, 3 pages.
GenBank Accession No. AK034387 dated Sep. 19, 2008, 4 pages.
GenBank Accession No. AK038229 dated Sep. 19, 2008, 4 pages.
GenBank Accession No. AK038434 dated Sep. 19, 2008, 4 pages.
GenBank Accession No. AK041534 dated Sep. 19, 2008, 4 pages.
GenBank Accession No. AK042683 dated Sep. 19, 2008, 4 pages.
GenBank Accession No. AK136096 dated Sep. 19, 2008, 4 pages.
GenBank Accession No. AK136101 dated Sep. 19, 2008, 4 pages.
GenBank Accession No. AK142768 dated Sep. 19, 2008, 3 pages.
GenBank Accession No. AL591433 dated Jan. 15, 2009, 56 pages.
GenBank Accession No. BC004702 dated Jul. 15, 2006, 3 pages.
GenBank Accession No. BC055737 dated Jul. 15, 2006, 2 pages.
GenBank Accession No. BC086799 dated Sep. 21, 2006, 3 pages.
GenBank Accession No. BF449664 dated Dec. 1, 2000, 1 page.
GenBank Accession No. BG063957 dated Jan. 26, 2001, 2 pages.

(56) References Cited

OTHER PUBLICATIONS

GenBank Accession No. BG077309 dated Dec. 17, 2003, 2 pages.
GenBank Accession No. BM114282 dated Jan. 30, 2002, 2 pages.
GenBank Accession No. BY023910 dated Dec. 6, 2002, 2 pages.
GenBank Accession No. CN724527 dated May 18, 2004, 2 pages.
GenBank Accession No. NM_000130 dated Oct. 18, 2009, 6 pages.
GenBank Accession No. NM_000493 dated Mar. 15, 2009, 4 pages.
GenBank Accession No. NM_000598, GI No. 62243067 , dated Jun. 6, 2010, 5 pages.
GenBank Accession No. NM_000688, GI No. 40316942, dated Apr. 11, 2010, 5 pages.
GenBank Accession No. NM_001013398; GI No. 62243247, dated Jun. 6, 2010, 5 pages.
GenBank Accession No. NM_001034 dated Oct. 5, 2009, 5 pages.
GenBank Accession No. NM_001039573, GI No. 221316683, dated Mar. 4, 2010, 5 pages.
GenBank Accession No. NM_001049 dated Jun. 21, 2009, 4 pages.
GenBank Accession No. NM_001067 dated Oct. 18, 2009, 5 pages.
GenBank Accession No. NM_001098533, GI No. 237858579, dated May 7, 2010, 5 pages.
GenBank Accession No. NM_001130851; GI No. 195927024, dated Mar. 5, 2010, 4 pages.
GenBank Accession No. NM_001136154 dated Jan. 8, 2012, 6 pages.
GenBank Accession No. NM_001136155 dated Jan. 8, 2012, 6 pages.
GenBank Accession No. NM_001143998, GI No. 221316675, dated Mar. 4, 2010, 5 pages.
GenBank Accession No. NM_001143999, GI No. 221316679, dated Mar. 5, 2010, 5 pages.
GenBank Accession No. NM_001144001, GI No. 221316686, dated Mar. 4, 2010, 5 pages.
GenBank Accession No. NM_001160367, GI No. 237858581, dated May 7, 2010, 5 pages.
GenBank Accession No. NM_001786 dated Nov. 1, 2009, 4 pages.
GenBank Accession No. NM_001844 dated Sep. 28, 2009, 7 pages.
GenBank Accession No. NM_003003, GI No. 221316681, dated Mar. 4, 2010, 5 pages.
GenBank Accession No. NM_003014; GI No. 170784837, dated Mar. 13, 2010, 5 pages.
GenBank Accession No. NM_003184; GI No. 115527086, dated Mar. 4, 2010, 7 pages.
GenBank Accession No. NM_003873.3 dated Oct. 18, 2009, 4 pages.
GenBank Accession No. NM_004336; GI No. 211938448, dated Mar. 14, 2010, 6 pages.
GenBank Accession No. NM_004449 dated Jan. 8, 2012, 6 pages.
GenBank Accession No. NM_005025.2 dated Jul. 12, 2009, 4 pages.
GenBank Accession No. NM_005192, GI No. 195927023, dated Mar. 4, 2010, 4 pages.
GenBank Accession No. NM_005651.1 dated Oct. 27, 2009, 3 pages.
GenBank Accession No. NM_006265, GI No. 208879448, dated Apr. 11, 2010, 6 pages.
GenBank Accession No. NM_006558 dated 812109, 3 pages.
GenBank Accession No. NM_006727 dated Oct. 18, 2009, 3 pages.
GenBank Accession No. NM_006819; GI No. 110225356, dated May 17, 2010, 5 pages.
GenBank Accession No. NM_012152; GI No. 183396778, dated Apr. 5, 2010, 5 pages.
GenBank Accession No. NM_014846; GI No. 120952850, dated Mar. 4, 2010, 6 pages.
GenBank Accession No. NM_016623; GI No. 42734437, dated Mar. 29, 2009, 4 pages.
GenBank Accession No. NM_018930 dated Feb. 10, 2008, ___ pages.
GenBank Accession No. NM_031966 GI No. 34304372, dated Jun. 6, 2010, 5 pages.
GenBank Accession No. NM_032334; GI No. 223468686, dated Mar. 5, 2010, 3 pages.
GenBank Accession No. NM_052987, GI No. 237858574, dated May 17, 2010, 5 pages.
GenBank Accession No. NM_052988, GI No. 237858573, dated May 17, 2010, 5 pages.
GenBank Accession No. NM_080546; GI No. 112363101, dated May 17, 2010, 6 pages.
GenBank Accession No. NM_080607 dated Sep. 3, 2009, 2 pages.
GenBank Accession No. NM_133445 dated Sep. 20, 2009, 5 pages.
GenBank Accession No. NM_138455; GI No. 34147546, dated May 7, 2010, 3 pages.
GenBank Accession No. NM_182918 dated Jan. 8, 2012, 6 pages.
GenBank Accession No. NM_199166, GI No. 40316938, dated Apr. 11, 2010, 5 pages.
GenBank Accession No. NP_001058 dated Dec. 25, 2011, 9 pages.
GenBank Accession No. W34764 dated May 13, 1996, 2 pages.
Supplemental Table 1 of U.S. Appl. No. 61/057,698, filed May 30, 2008, 13 pages.
Supplemental Table 2 of U.S. Appl. No. 61/057,698, filed May 30, 2008, 15 pages.
Supplemental Table 3 of U.S. Appl. No. 61/057,698, filed May 30, 2008, 21 pages.
Supplemental Table 4 of U.S. Appl. No. 61/057,698, filed May 30, 12008, 1 page.
Supplemental Table 5 of U.S. Appl. No. 61/057,698, filed May 30, 12008, 2 pages.
Supplemental Table 6 of U.S. Appl. No. 61/057,698, filed May 30, 2008, 1 page.
International Search Report and Written Opinion of PCT/CA2018/050563 dated Aug. 13, 2018.
Anonymous, UCSC Genome Browser on Human Mar. 2006, NCBI36/hg18) Assembly, Mar. 2006, XP055587638, Retrieved from the Internet: URL:https://genome-euro.ucsc.edu/cgi-bin/hgTracks?db=hg18&lastVirtModeType=default&lastVirtModeExtraState=& virtModeType=default&virtMode=0&nonVirtPosition=&position=chr5%3A14025126%2D14062770&hgsid=232148223_IYIy9VS0Lh0jhldEBQ3nViBrQuB5 [retrieved on May 10, 2019].
Choi et al., Jun. 24, 2014, Intrinsic basal and luminal subtypes of muscle-invasive bladder cancer, Nature Reviews Urology, 11(7):400-410.
Damrauer et al., Feb. 25, 2014, Intrinsic subtypes of high-grade bladder cancer reflect the hallmarks of breast cancer biology, Proc Natl Acad Sci USA, 111(8):3110-3115.
Dhani et al., 2011, Phase II study of cytarabine in men with docetaxel-refractory, castration-resistnt prostate cancer with evaluation of TMPRSS2-ERG and SPINK1 as serum biomarkers, BJUI, 110:840-845.
Ha et al., Nov. 12, 2009, Comparison of affymetrix gene array with the exon array shows potential application for detection of transcript isoform variation, BMC Genomics, 19(1):519.
Knowles et al., Dec. 23, 2014, Molecular biology of bladder cancer: new insights into pathogenesis and clinical diversity, Nature Reviews Cancer, 15(1):25-41.
Warrick et al., 2016, FOXA1, GATA3 and PPARγ cooperate to drive luminal subtype in bladder cancer: a molecular analysis of established human cell lines, Scientific Reports, 6:38531, DOI: 10.1038, 15 pp.

* cited by examiner

GENETIC SIGNATURES TO PREDICT PROSTATE CANCER METASTASIS AND IDENTIFY TUMOR AGGRESSIVENESS

CROSS-REFERENCE TO RELATED APPLICATIONS

This application claims priority to the U.S. Provisional Patent Application Ser. No. 62/505,665, filed on May 12, 2017, which is hereby incorporated by reference herein in its entirety.

INCORPORATION OF SEQUENCE LISTING

The material in the accompanying sequence listing is hereby incorporated by reference into this application. The accompanying sequence listing text file, name GP715_Sequence_Listing.txt, was created on May 10, 2018, and is 531 kb. The file can be assessed using Microsoft Word on a computer that uses Windows OS.

FIELD OF THE INVENTION

The present invention relates to methods, systems and kits for the diagnosis, prognosis and the determination of cancer progression of prostate cancer in a subject. The invention also provides clinically useful genomic classifiers for predicting prostate cancer metastasis and identifying tumor aggressiveness. The methods, systems and kits can provide expression-based analysis of biomarkers for purposes of predicting metastatic disease and lethal prostate cancer in a subject. Further disclosed herein, in certain instances, are probe sets for use in predicting prostate cancer metastasis in a subject. Classifiers for predicting prostate cancer metastasis are provided. Methods of treating cancer based on tumor aggressiveness are also provided. The methods and classifiers of the present invention are also useful for predicting early prostate cancer metastasis.

BACKGROUND OF THE INVENTION

Cancer is the uncontrolled growth of abnormal cells anywhere in a body. The abnormal cells are termed cancer cells, malignant cells, or tumor cells. Many cancers and the abnormal cells that compose the cancer tissue are further identified by the name of the tissue that the abnormal cells originated from (for example, prostate cancer). Cancer cells can proliferate uncontrollably and form a mass of cancer cells. Cancer cells can break away from this original mass of cells, travel through the blood and lymph systems, and lodge in other organs where they can again repeat the uncontrolled growth cycle. This process of cancer cells leaving an area and growing in another body area is often termed metastatic spread or metastatic disease. For example, if prostate cancer cells spread to a bone (or anywhere else), it can mean that the individual has metastatic prostate cancer.

Standard clinical parameters such as tumor size, grade, lymph node involvement and tumor-node-metastasis (TNM) staging (American Joint Committee on Cancer http://www.cancerstaging.org) may correlate with outcome and serve to stratify patients with respect to (neo)adjuvant chemotherapy, immunotherapy, antibody therapy and/or radiotherapy regimens. Incorporation of molecular markers in clinical practice may define tumor subtypes that are more likely to respond to targeted therapy. However, stage-matched tumors grouped by histological or molecular subtypes may respond differently to the same treatment regimen. Additional key genetic and epigenetic alterations may exist with important etiological contributions. A more detailed understanding of the molecular mechanisms and regulatory pathways at work in cancer cells and the tumor microenvironment (TME) could dramatically improve the design of novel anti-tumor drugs and inform the selection of optimal therapeutic strategies. For example, methods that enable the identification of aggressive tumors would ensure that those patients are adequately treated for their cancer, while patients with low risk tumors could avoid unnecessary cancer treatment. The development and implementation of diagnostic, prognostic and therapeutic biomarkers to characterize the biology of each tumor may assist clinicians in making important decisions with regard to individual patient care and treatment. Thus, provided herein are methods, systems and kits for the diagnosis, prognosis and the determination of cancer progression of cancer in a subject. The invention also provides biomarkers that identify aggressive prostate cancer, clinically useful classifiers for predicting prostate cancer metastasis, bioinformatic methods for determining clinically useful classifiers, and methods of use of each of the foregoing. The methods, systems and kits can provide expression-based analysis of biomarkers for purposes of predicting prostate cancer metastasis in a subject. Further disclosed herein, in certain instances, are probe sets for use in predicting prostate cancer metastasis in a subject. Classifiers for predicting prostate cancer metastasis are provided. Methods of treating cancer based on tumor aggressiveness are also provided. The methods and classifiers of the present invention are also useful for predicting early prostate cancer metastasis.

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

The present invention relates to methods, systems and kits for the diagnosis, prognosis and the determination of cancer progression of cancer in a subject. The invention also provides biomarkers that define subgroups of prostate cancer, clinically useful classifiers for predicting prostate cancer aggressiveness and metastasis, bioinformatic methods for determining clinically useful classifiers, and methods of use of each of the foregoing. The methods, systems and kits can provide expression-based analysis of biomarkers for purposes of prognosing and diagnosing prostate cancer in a subject. Further disclosed herein, in certain instances, are probe sets for use in prognosing and diagnosing prostate cancer in a subject. Classifiers for prognosing and diagnosing a prostate cancer are provided. Methods of treating cancer based on prognosis and/or diagnosis according to the present invention are also provided.

In one embodiment, the present invention provides a method comprising: obtaining a biological sample from a subject; and detecting the presence or assaying an expression level in the sample from the subject for a plurality of target sequences, wherein the plurality of target sequences is selected from Table 1 or SEQ ID NOs: 1-1815. In some embodiments, the plurality of target sequences comprises a coding and/or non-coding target. In other embodiments, the coding target is an exonic sequence. In yet other embodiments, non-coding target comprises an intronic sequence, partially overlaps an intronic sequence, a sequence within the UTR or partially overlaps with a UTR sequence. In other embodiments, the plurality of target sequences comprises a nucleic acid sequence. In still other embodiments, the nucleic acid sequence is a DNA sequence or an RNA sequence. In some embodiments, the plurality of target sequences comprises at least 5, 10, 15, 20, 25, 30, 35, 40, 45, 50, 55 or 60 target sequences selected from Table 1 or SEQ ID NOs: 1-1815. In some embodiments, the subject has cancer. In other embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In yet other embodiments, the cancer is prostate cancer. In still other embodiments, the methods further comprise administering a treatment to the subject. In some embodiments, the treatment is selected from the group consisting of surgery, chemotherapy, radiation therapy, immunotherapy/biological therapy, and photodynamic therapy. In other embodiments, the biological sample is a biopsy. In yet other embodiments, the biological sample is a urine sample, a blood sample or a prostate tumor sample. In certain embodiments, the blood sample is plasma, serum, or whole blood. In other embodiments, the subject is a human.

In another embodiment, the present invention provides methods of diagnosing, prognosing and determining cancer progression of cancer in a subject comprising obtaining a biological sample from a subject; and detecting the presence or assaying an expression level in the sample from the subject for a plurality of target sequences, wherein the plurality of target sequences is selected from Table 1 or SEQ ID NOs: 1-1815, thereby diagnosing, prognosing and determining cancer progression of cancer in the subject. In some embodiments, the plurality of target sequences comprises a coding and/or non-coding target. In other embodiments, the coding target is an exonic sequence. In yet other embodiments, non-coding target comprises an intronic sequence, partially overlaps an intronic sequence, a sequence within the UTR or partially overlaps with a UTR sequence. In other embodiments, the plurality of target sequences comprises a nucleic acid sequence. In still other embodiments, the nucleic acid sequence is a DNA sequence or an RNA sequence. In some embodiments, the plurality of target sequences comprises at least 5, 10, 15, 20, 25, 30, 35, 40, 45, 50, 55 or 60 target sequences selected from Table 1 or SEQ ID NOs: 1-1815. In some embodiments, the subject has cancer. In other embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In yet other embodiments, the cancer is prostate cancer. In still other embodiments, the methods further comprise administering a treatment to the subject. In some embodiments, the treatment is selected from the group consisting of surgery, chemotherapy, radiation therapy, immunotherapy/biological therapy, and photodynamic therapy. In other embodiments, the biological sample is a biopsy. In yet other embodiments, the biological sample is a urine sample, a blood sample or a prostate tumor sample. In certain embodiments, the blood sample is plasma, serum, or whole blood. In other embodiments, the subject is a human.

In other embodiments, the present invention provides methods of determining a treatment regimen for a subject having cancer comprising: obtaining a biological sample from a subject having cancer; assaying an expression level in a sample from the subject for a plurality of target sequences, wherein the plurality of target sequences is selected from Table 1 or SEQ ID NOs: 1-1815; and determining the treatment regimen for the subject. In other embodiments, the expression level is increased or reduced compared to a control. In still other embodiments, the assaying an expression level comprises performing in situ hybridization, a PCR-based method, an array-based method, an immunohistochemical method, an RNA assay method, or an immunoassay method. In other embodiments, the assaying an expression level comprises using a reagent selected from the group consisting of a nucleic acid probe, one or more nucleic acid primers, and an antibody. In yet other embodiments, the assaying an expression level comprises assaying the level of an RNA transcript. In other embodiments, the method further comprises administering at least one cancer treatment selected from the group consisting of surgery, radiation therapy, immunotherapy, biological therapy, neoadjuvant chemotherapy, and photodynamic therapy after androgen deprivation therapy.

In other embodiments, the present invention provides kits for predicting cancer aggressiveness or risk of metastasis, the kit comprising agents for assaying an expression level of a plurality of genes, wherein said plurality of genes comprises one or more genes selected from Table 1 or SEQ ID NOs: 1-1815. In certain embodiments, the kit comprises agents for assaying an expression level of the genes listed in Table 1. In certain aspects, the agents comprise reagents for performing in situ hybridization, a PCR-based method, an array-based method, an immunohistochemical method, an RNA assay method, or an immunoassay method. In other aspects, the agents comprise one or more of a microarray, a nucleic acid probe, a nucleic acid primer, or an antibody. In certain embodiments, the kit comprises at least one set of PCR primers capable of amplifying a nucleic acid comprising a sequence of a gene selected from Table 1 or its complement. In other embodiments, the kit comprises at least one probe capable of hybridizing to a nucleic acid comprising a sequence of a gene selected from Table 1 or its complement. In yet other embodiments, the kits further comprise one or more control reference samples.

In one embodiment, the present invention provides a probe set for prognosing or diagnosing cancer in a subject, the probe set comprising a plurality of probes for detecting a plurality of target nucleic acids, wherein the plurality of target nucleic acids comprises one or more gene sequences, or complements thereof, of genes selected from Table 1. In one aspect, at least one probe is detectably labeled.

In other embodiments, the present invention provides methods for treating a subject with cancer, the method comprising: a) obtaining a biological sample from a subject having cancer; b) detecting the presence or assaying the expression level in the biological sample for a plurality of targets selected from Table 1 or SEQ ID NOs: 1-1815; and c) administering a treatment to the subject. In some embodiments, the treatment is selected from the group consisting of surgery, chemotherapy, radiation therapy, immunotherapy, biological therapy, hormonal therapy, and photodynamic therapy. In other embodiments, the cancer is prostate cancer.

In one embodiment, the present invention provides a method comprising: a) obtaining a biological sample from a subject; and b) detecting the presence or assaying the expression level in the biological sample for a plurality of targets selected from the group consisting of AC020571.3, ANO7, ARL6IP1P2, ASPN, AZGP1, AZGP1P1, DEGS1, ERO1LB, FBXL8, FMO5, FTH1P2, FTH1P8, GLB1L2, GLB1L3, GLYATL1P3, GMNN, HIF3A, INHBA, KIAA1210, KRT15, LIPH, LPAR3, LPGAT1, MIR4435-1HG, MKI67, MLLT11, MYBPC1, NADK2, NR4A1, NUSAP1, OR51A6P, PABPC1, PART1, PCAT14, PGM5P4-AS1, PICK1, PTTG1, R3HDM1, RNA5SP121, RP11-121G22.3 RP11-159H20.3, RP11-755O11.2, RP11-770G2.5, RP11-923I11.3, RP13-753N3.3, RPL31P57, SCIN, SESN3, SETP14, SLC22A3, SMC4, TIPARP, TMEM100, TNFRSF19, TOP2A, TPX2, TRIQK, VBP1, WFDC2, and XPO6. In one aspect, the plurality of target sequences comprises a coding and/or non-coding target. In some embodiments, the plurality of target sequences comprises a coding and/or non-coding target. In other embodiments, the coding target is an exonic sequence. In yet other embodiments, non-coding target comprises an intronic sequence, partially overlaps an intronic sequence, a sequence within the UTR or partially overlaps with a UTR sequence. In other embodiments, the plurality of target sequences comprises a nucleic acid sequence. In still other embodiments, the nucleic acid sequence is a DNA sequence or an RNA sequence. In some embodiments, the plurality of target sequences comprises at least 5, 10, 15, 20, 25, 30, 35, 40, 45, 50, 55 or 60 target sequences selected from Table 1 or SEQ ID NOs: 1-1815. In some embodiments, the subject has cancer. In other embodiments, the cancer is selected from the group consisting of skin cancer, lung cancer, colon cancer, pancreatic cancer, prostate cancer, liver cancer, thyroid cancer, ovarian cancer, uterine cancer, breast cancer, cervical cancer, kidney cancer, epithelial carcinoma, squamous carcinoma, basal cell carcinoma, melanoma, papilloma, and adenomas. In yet other embodiments, the cancer is prostate cancer. In still other embodiments, the methods further comprise administering a treatment to the subject. In some embodiments, the treatment is selected from the group consisting of surgery, chemotherapy, radiation therapy, immunotherapy/biological therapy, and photodynamic therapy. In other embodiments, the biological sample is a biopsy. In yet other embodiments, the biological sample is a urine sample, a blood sample or a prostate tumor sample. In certain embodiments, the blood sample is plasma, serum, or whole blood. In other embodiments, the subject is a human.

The plurality of targets may comprise one or more targets selected from AC020571.3, ANO7, ARL6IP1P2, ASPN, AZGP1, AZGP1P1, DEGS1, ERO1LB, FBXL8, FMO5, FTH1P2, FTH1P8, GLB1L2, GLB1L3, GLYATL1P3, GMNN, HIF3A, INHBA, KIAA1210, KRT15, LIPH, LPAR3, LPGAT1, MIR4435-1HG, MKI67, MLLT11, MYBPC1, NADK2, NR4A1, NUSAP1, OR51A6P, PABPC1, PART1, PCAT14, PGM5P4-AS1, PICK1, PTTG1, R3HDM1, RNA5SP121, RP11-121G22.3 RP11-159H20.3, RP11-755O11.2, RP11-770G2.5, RP11-923I11.3, RP13-753N3.3, RPL31P57, SCIN, SESN3, SETP14, SLC22A3, SMC4, TIPARP, TMEM100, TNFRSF19, TOP2A, TPX2, TRIQK, VBP1, WFDC2, and XPO6; TIPARP and TMEM100; SETP14, MLLT11, and INHBA; ANO7, NR4A1, PART1, PCAT-14, SLC22A3, and TIPARP; FBXL8, MKI67, NUSAP1, PTTG1, TOP2A, and TPX2; ASPN, AZGP1, KRT15, MYBPC1, PICK1, TRIQK, and WFDC2; DEGS1, ERO1LB, FMO5, GLB1L2, GLB1L3, GLYATL1P3, LIPH, LPGAT1, NADK2, and XPO6; GMNN, SESN3, SMC4, and VBP1; HIF3A; INHBA, R3HDM1, and TNFRSF19; LPAR3 and SCIN; LOC101927482, ARL6IP1P2, AZGP1P1, FTH1P2, FTH1P8, KIAA1210, MIR4435-1HG, OR51A6P, PGM5P4-AS1, RNA5SP121, RP11-121G22.3, RP11-159H20.3, RP11-755O11.2, RP11-77062.5, RP11-923I11.3, and RP13-753N3.3; ANO7, NR4A1, and PART1; PCAT-14, SLC22A3, and TIPARP; FBXL8, MKI67, and NUSAP1; PTTG1, TOP2A, and TPX2; ASPN, AZGP1, and KRT15; MYBPC1, PICK1, TRIQK, and WFDC2; DEGS1, ERO1LB, and FMO5; GLB1L2, GLB1L3, and GLYATL1P3; LIPH, LPGAT1, NADK2, and XPO6; GMNN and SESN3; SMC4 and VBP1; INHBA and R3HDM1; INHBA and TNFRSF19; LPAR3 and SCIN; LOC101927482 and ARL6IP1P2; AZGP1P1 and FTH1P2; FTH1P8 and KIAA1210; MIR4435-1HG and OR51A6P; PGM5P4-AS1 and RNA5SP121; RP11-121G22.3 and RP11-159H20.3; RP11-755O11.2 and RP11-77062.5; RP11-923I11.3 and RP13-753N3.3; AC020571.3 and ANO7; ARL6IP1P2 and ASPN; AZGP1 and AZGP1P1; DEGS1 and ERO1LB; FBXL8 and FMO5; FTH1P2 and FTH1P8; GLB1L2 and GLB1L3; GLYATL1P3 and GMNN; HIF3A and INHBA; KIAA1210 and KRT15; LIPH and LPAR3; LPGAT1 and MIR4435-1HG; MKI67 and MLLT11; MYBPC1 and NADK2; NR4A1 and NUSAP1; OR51A6P and PABPC1; PART1 and PCAT14; PGM5P4-AS1 and PICK1; PTTG1 and R3HDM1; RNA5SP121 and RP11-121G22.3; RP11-159H20.3 and RP11-755O11.2; RP11-770G2.5 and RP11-923I11.3; RP13-753N3.3 and RPL31P57; SCIN and SESN3; SETP14 and SLC22A3; SMC4 and TIPARP; TMEM100 and TNFRSF19; TOP2A and TPX2; TRIQK and VBP1; WFDC2 and XPO6; TIPARP and TMEM100.

In one embodiment, the present invention provides a method comprising: a) obtaining a biological sample from a subject having prostate cancer and b) detecting the presence or expression level in the biological sample for a plurality of targets selected from Table 1 or SEQ ID NOs: 1-1815. In some embodiments, the method further comprises treating the prostate cancer in the subject according to a genomic classifier score based on the presence or expression levels of the plurality of targets.

In some embodiments, the present invention also provides a method of diagnosing, prognosing, assessing the risk of recurrence or predicting benefit from therapy in a subject with prostate cancer, comprising: providing a biological sample comprising prostate cancer cells from the subject; assaying an expression level in the biological sample from the subject for a plurality of targets using at least one reagent that specifically binds to said targets, wherein the plurality of targets comprises one or more targets selected from Table 1 or SEQ ID NOs: 1-1815; and diagnosing, prognosing, assessing the risk of recurrence or predicting benefit from therapy in the subject based on the expression levels of the plurality of targets. In some embodiments, the expression level of the target is reduced expression of the target. In other embodiments, the expression level of said target is increased expression of said target. In yet other embodiments, the level of expression of said target is determined by using a method selected from the group consisting of in situ hybridization, a PCR-based method, an array-based method, an immunohistochemical method, an RNA assay method and an immunoassay method. In other embodiments, the reagent is selected from the group consisting of a nucleic acid probe, one or more nucleic acid primers, and an antibody. In other embodiments, the target comprises a nucleic acid sequence.

In some embodiments, the present invention provides a system for analyzing a cancer, comprising, a probe set comprising a plurality of target sequences, wherein the plurality of target sequences hybridizes to one or more targets selected from Table 1 or SEQ ID NOs: 1-1815; or the plurality of target sequences comprises one or more targets selected from Table 1 or SEQ ID NOs: 1-1815; and a computer model or algorithm for analyzing an expression level and/or expression profile of the target hybridized to the probe in a sample from a subject suffering from prostate cancer. In some embodiments, the method further comprises a label that specifically binds to the target, the probe, or a combination thereof.

In some embodiments, the present invention provides a method comprising: (a) providing a biological sample from a subject with prostate cancer; (b) detecting the presence or expression level in the biological sample for a plurality of targets, wherein the plurality of targets comprises one or more targets selected from Table 1 or SEQ ID NOs: 1-1815; (c) generating a genomic classifier score based on the presence or expression levels of the plurality of targets; and (d) administering a treatment to the subject, wherein the treatment is selected from the group consisting of surgery, chemotherapy, radiation therapy, immunotherapy/biological therapy, hormonal therapy, and photodynamic therapy. In some embodiments, the present invention provides a method of treating a subject with prostate cancer, comprising: providing a biological sample comprising prostate cancer cells from the subject; determining the level of expression or amplification of at least one or more targets selected from Table 1 or SEQ ID NOs: 1-1815 using at least one reagent that specifically binds to said targets; generating a genomic classifier score based on the level of expression or amplification of the at least one or more targets; and prescribing a treatment regimen based on the genomic classifier score.

In some embodiments, the present invention provides a kit for analyzing a prostate cancer, comprising, a probe set comprising a plurality of target sequences, wherein the plurality of target sequences comprises at least one target sequence listed in Table 1 or SEQ ID NOs: 1-1815; and a computer model or algorithm for analyzing an expression level and/or expression profile of the target sequences in a sample. In some embodiments, the method further comprises a computer model or algorithm for correlating the expression level or expression profile with disease state or outcome. In other embodiments, the method further comprises a computer model or algorithm for designating a treatment modality for the individual. In yet other embodiments, the method further comprises a computer model or algorithm for normalizing expression level or expression profile of the target sequences. In some embodiments, the method further comprises sequencing the plurality of targets. In some embodiments, the method further comprises hybridizing the plurality of targets to a solid support. In some embodiments, the solid support is a bead or array. In some embodiments, assaying the expression level of a plurality of targets may comprise the use of a probe set. In some embodiments, assaying the expression level may comprise the use of a classifier. The classifier may comprise a probe selection region (PSR). In some embodiments, the classifier may comprise the use of an algorithm. The algorithm may comprise a machine learning algorithm. In some embodiments, assaying the expression level may also comprise sequencing the plurality of targets.

Further disclosed herein methods for using genomic classifiers for prognosing and/or diagnosing prostate cancer, wherein the genomic classifier has an AUC value of at least about 0.40 to predict patient outcomes. In some embodiments, patient outcomes are selected from the group consisting of biochemical recurrence (BCR), metastasis (MET) and prostate cancer death (PCSM) after radical prostatectomy. The AUC of the genomic classifier may be at least about 0.40, 0.45, 0.50, 0.55, 0.60, 0.61, 0.62, 0.63, 0.64, 0.65, 0.66, 0.67, 0.68, 0.69, 0.70 or more.

Further disclosed herein is a method for using genomic classifiers for prognosing and/or diagnosing prostate cancer, comprising determining the level of expression or amplification of at least one or more targets of the present invention, wherein the significance of the expression level of the one or more targets is based on one or more metrics selected from the group comprising T-test, P-value, KS (Kolmogorov Smirnov) P-value, accuracy, accuracy P-value, positive predictive value (PPV), negative predictive value (NPV), sensitivity, specificity, AUC, AUC P-value (Auc.pvalue), Wilcoxon Test P-value, Median Fold Difference (MFD), Kaplan Meier (KM) curves, survival AUC (survAUC), Kaplan Meier P-value (KM P-value), Univariable Analysis Odds Ratio P-value (uvaORPval), multivariable analysis Odds Ratio P-value (mvaORPval), Univariable Analysis Hazard Ratio P-value (uvaHRPval) and Multivariable Analysis Hazard Ratio P-value (mvaHRPval). The significance of the expression level of the one or more targets may be based on two or more metrics selected from the group comprising AUC, AUC P-value (Auc.pvalue), Wilcoxon Test P-value, Median Fold Difference (MFD), Kaplan Meier (KM) curves, survival AUC (survAUC), Univariable Analysis Odds Ratio P-value (uvaORPval), multivariable analysis Odds Ratio P-value (mvaORPval), Kaplan Meier P-value (KM P-value), Univariable Analysis Hazard Ratio P-value (uvaHRPval) and Multivariable Analysis Hazard Ratio P-value (mvaHRPval). The molecular subtypes of the present invention are useful for predicting clinical characteristics of subjects with prostate cancer. In some embodiments, the clinical characteristics are selected from the group consisting of seminal vesical invasion (SVI), lymph node invasion (LNI), prostate-specific antigen (PSA), and gleason score (GS).

INCORPORATION BY REFERENCE

All publications, patents, and patent applications mentioned in this specification are herein incorporated by reference in their entireties to the same extent as if each individual publication, patent, or patent application was specifically and individually indicated to be incorporated by reference.

DETAILED DESCRIPTION OF THE INVENTION

Figure 1A:
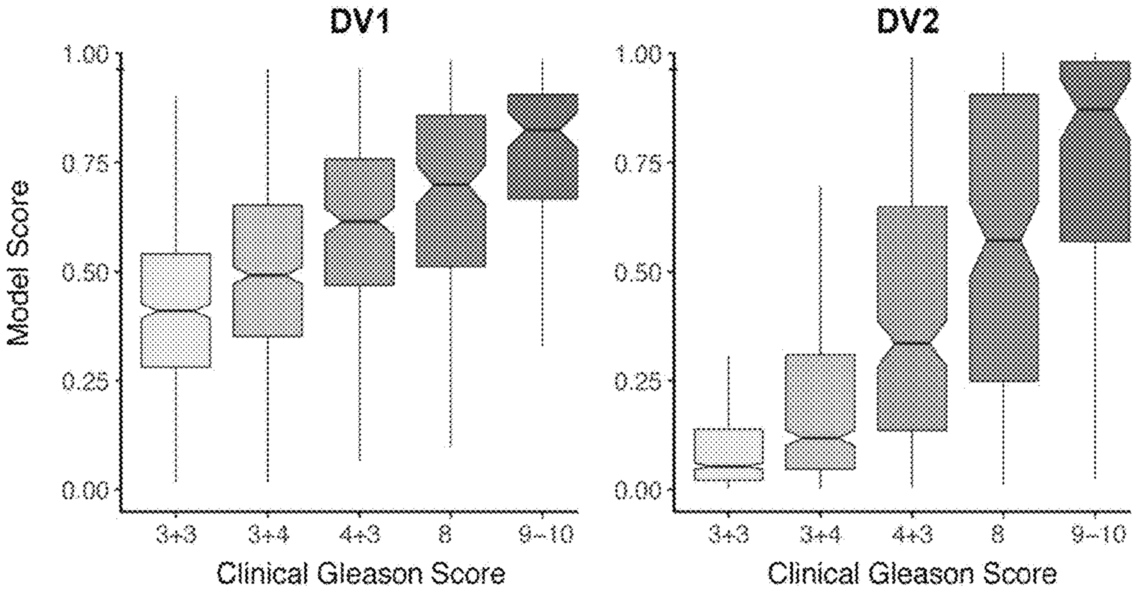
FIGS. 1A-B set forth data showing correlation of genomic classifiers with biopsy Grade Groups and NCCN risk categories.

The present invention discloses systems and methods for diagnosing, predicting, and/or monitoring the status or outcome of a prostate cancer in a subject using expression-based analysis of a plurality of targets. Generally, the method comprises (a) optionally obtaining a sample from a subject; (b) assaying the expression level for a plurality of targets in the sample; and (c) diagnosing, predicting and/or monitoring the status or outcome of a prostate cancer based on the expression level of the plurality of targets.

Assaying the expression level for a plurality of targets in the sample may comprise applying the sample to a microarray. In some instances, assaying the expression level may comprise the use of an algorithm. The algorithm may be used to produce a classifier and subsequently a classifier score. Alternatively, the classifier may comprise a probe selection region. In some instances, assaying the expression level for a plurality of targets comprises detecting and/or quantifying the plurality of targets. In some embodiments, assaying the expression level for a plurality of targets comprises sequencing the plurality of targets. In some embodiments, assaying the expression level for a plurality of targets comprises amplifying the plurality of targets. In some embodiments, assaying the expression level for a plurality of targets comprises quantifying the plurality of targets. In some embodiments, assaying the expression level for a plurality of targets comprises conducting a multiplexed reaction on the plurality of targets.

In some instances, the plurality of targets comprises one or more targets selected from Table 1 or SEQ ID NOs: 1-1815. In some instances, the plurality of targets comprises at least about 2, at least about 3, at least about 4, at least about 5, at least about 6, at least about 7, at least about 8, at least about 9, at least about 10, at least about 20, at least about 30, at least about 40, at least about 50, or at least about 60 targets selected from Table 1 or SEQ ID NOs: 1-1815.

Further disclosed herein are methods for prognosing or diagnosing prostate cancer. Generally, the method comprises: (a) obtaining a sample comprising prostate cancer cells from a subject; (b) assaying the expression level for a plurality of targets in the sample; and (c) prognosing or diagnosing the cancer based on the expression level of the plurality of targets. In some instances, the plurality of targets comprises one or more targets selected from Table 1 or SEQ ID NOs: 1-1815. In some instances, the plurality of targets comprises at least about 2, at least about 3, at least about 4, at least about 5, at least about 6, at least about 7, at least about 8, at least about 9, at least about 10, at least about 20, at least about 30, at least about 40, at least about 50, or at least about 60 targets selected from Table 1 or SEQ ID NOs: 1-1815.

In some instances, prognosing or diagnosing the prostate cancer comprises determining whether the cancer is aggressive or will metastasize. Alternatively, prognosing or diagnosing the prostate cancer comprises identifying the cancer as non-responsive to an anti-cancer therapy. Optionally, prognosing or diagnosing the prostate cancer comprises identifying the cancer as responsive to an anti-cancer therapy.

Before the present invention is described in further detail, it is to be understood that this invention is not limited to the particular methodology, compositions, articles or machines described, as such methods, compositions, articles or machines can, of course, vary. It is also to be understood that the terminology used herein is for the purpose of describing particular embodiments only, and is not intended to limit the scope of the present invention.

Targets

The methods disclosed herein often comprise assaying the expression level of a plurality of targets. The plurality of targets may comprise coding targets and/or non-coding targets of a protein-coding gene or a non protein-coding gene. A protein-coding gene structure may comprise an exon and an intron. The exon may further comprise a coding sequence (CDS) and an untranslated region (UTR). The protein-coding gene may be transcribed to produce a pre-mRNA and the pre-mRNA may be processed to produce a mature mRNA. The mature mRNA may be translated to produce a protein.

A non protein-coding gene structure may comprise an exon and intron. Usually, the exon region of a non protein-coding gene primarily contains a UTR. The non protein-coding gene may be transcribed to produce a pre-mRNA and the pre-mRNA may be processed to produce a non-coding RNA (ncRNA).

A coding target may comprise a coding sequence of an exon. A non-coding target may comprise a UTR sequence of an exon, intron sequence, intergenic sequence, promoter sequence, non-coding transcript, CDS antisense, intronic antisense, UTR antisense, or non-coding transcript antisense. A non-coding transcript may comprise a non-coding RNA (ncRNA).

In some instances, the plurality of targets may be differentially expressed. In some instances, a plurality of probe selection regions (PSRs) is differentially expressed.

In some instances, the plurality of targets comprises one or more targets selected from at least about 10, at least about 20, at least about 30, at least about 40, at least about 50, or at least about 60 targets selected from Table 1 or SEQ ID NOs: 1-1815. In some instances, the plurality of targets comprises at least about 2, at least about 3, at least about 4, at least about 5, at least about 6, at least about 7, at least about 8, at least about 9, at least about 10, at least about 20, at least about 30, at least about 40, at least about 50, or at least about 60 targets selected from Table 1 or SEQ ID NOs: 1-1815.

In some instances, the plurality of targets comprises a coding target, non-coding target, or any combination thereof. In some instances, the coding target comprises an exonic sequence. In other instances, the non-coding target comprises a non-exonic or exonic sequence. Alternatively, a non-coding target comprises a UTR sequence, an intronic sequence, antisense, or a non-coding RNA transcript. In some instances, a non-coding target comprises sequences which partially overlap with a UTR sequence or an intronic sequence. A non-coding target also includes non-exonic and/or exonic transcripts. Exonic sequences may comprise regions on a protein-coding gene, such as an exon, UTR, or a portion thereof. Non-exonic sequences may comprise regions on a protein-coding, non protein-coding gene, or a portion thereof. For example, non-exonic sequences may comprise intronic regions, promoter regions, intergenic regions, a non-coding transcript, an exon anti-sense region, an intronic anti-sense region, UTR anti-sense region, non-coding transcript anti-sense region, or a portion thereof. In other instances, the plurality of targets comprises a non-coding RNA transcript.

The plurality of targets may comprise one or more targets selected from a classifier disclosed herein. The classifier may be generated from one or more models or algorithms. The one or more models or algorithms may be Naïve Bayes (NB), recursive Partitioning (Rpart), random forest (RF), support vector machine (SVM), k-nearest neighbor (KNN), high dimensional discriminate analysis (HDDA), or a combination thereof. The classifier may have an AUC of equal to or greater than 0.60. The classifier may have an AUC of equal to or greater than 0.61. The classifier may have an AUC of equal to or greater than 0.62. The classifier may have an AUC of equal to or greater than 0.63. The classifier may have an AUC of equal to or greater than 0.64. The classifier may have an AUC of equal to or greater than 0.65. The classifier may have an AUC of equal to or greater than 0.66. The classifier may have an AUC of equal to or greater than 0.67. The classifier may have an AUC of equal to or greater than 0.68. The classifier may have an AUC of equal to or greater than 0.69. The classifier may have an AUC of equal to or greater than 0.70. The classifier may have an AUC of equal to or greater than 0.75. The classifier may have an AUC of equal to or greater than 0.77. The classifier may have an AUC of equal to or greater than 0.78. The classifier may have an AUC of equal to or greater than 0.79. The classifier may have an AUC of equal to or greater than 0.80. The AUC may be clinically significant based on its 95% confidence interval (CI). The accuracy of the classifier may be at least about 70%. The accuracy of the classifier may be at least about 73%. The accuracy of the classifier may be at least about 75%. The accuracy of the classifier may be at least about 77%. The accuracy of the classifier may be at least about 80%. The accuracy of the classifier may be at least about 83%. The accuracy of the classifier may be at least about 84%. The accuracy of the classifier may be at least about 86%. The accuracy of the classifier may be at least about 88%. The accuracy of the classifier may be at least about 90%. The p-value of the classifier may be less than or equal to 0.05. The p-value of the classifier may be less than or equal to 0.04. The p-value of the classifier may be less than or equal to 0.03. The p-value of the classifier may be less than or equal to 0.02. The p-value of the classifier may be less than or equal to 0.01. The p-value of the classifier may be less than or equal to 0.008. The p-value of the classifier may be less than or equal to 0.006. The p-value of the classifier may be less than or equal to 0.004. The p-value of the classifier may be less than or equal to 0.002. The p-value of the classifier may be less than or equal to 0.001.

The plurality of targets may comprise one or more targets selected from a Random Forest (RF) classifier. The plurality of targets may comprise two or more targets selected from a Random Forest (RF) classifier. The plurality of targets may comprise three or more targets selected from a Random Forest (RF) classifier. The plurality of targets may comprise 2, 3, 4, 5, 6, 7, 8, 9, 10, 11, 12, 13, 14, 15, 20, 25, 30, 40, 50, 60 or more targets selected from a Random Forest (RF) classifier. The RF classifier may be an RF2, and RF3, or an RF4 classifier. The RF classifier may be an RF60 classifier (e.g., a Random Forest classifier with 50 targets).

A RF classifier of the present invention may comprise two or more targets comprising two or more targets selected from Table 1 or SEQ ID NOs: 1-1815.

The plurality of targets may comprise one or more targets selected from an SVM classifier. The plurality of targets may comprise 2, 3, 4, 5, 6, 7, 8, 9, 10, 11, 12, 13, 14, 15, 20, 25, 30, 40, 50, 60 or more targets selected from an SVM classifier. The plurality of targets may comprise 12, 13, 14, 15, 17, 20, 22, 25, 27, 30, 40, 50, 60 or more targets selected from an SVM classifier. The plurality of targets may comprise 32, 35, 37, 40, 43, 45, 47, 50, 60 or more targets selected from an SVM classifier. The SVM classifier may be an SVM2 classifier.

A SVM classifier of the present invention may comprise two or more targets comprising two or more targets selected from Table 1 or SEQ ID NOs: 1-1815.

The plurality of targets may comprise one or more targets selected from a KNN classifier. The plurality of targets may comprise 2, 3, 4, 5, 6, 7, 8, 9, 10 or more targets selected from a KNN classifier. The plurality of targets may comprise 12, 13, 14, 15, 17, 20, 22, 25, 27, 30 or more targets selected from a KNN classifier. The plurality of targets may comprise 32, 35, 37, 40, 43, 45, 47, 50, 60 or more targets selected from a KNN classifier.

The KNN classifier may be a KNN50 classifier. A KNN classifier of the present invention may comprise sixty or more targets comprising sixty or more targets selected from Table 1 or SEQ ID NOs: 1-1815.

The plurality of targets may comprise one or more targets selected from a Naïve Bayes (NB) classifier. The plurality of targets may comprise 2, 3, 4, 5, 6, 7, 8, 9, 10 or more targets selected from an NB classifier. The plurality of targets may comprise 12, 13, 14, 15, 17, 20, 22, 25, 27, 30 or more targets selected from an NB classifier. The plurality of targets may comprise 32, 35, 37, 40, 43, 45, 47, 50, 60 or more targets selected from a NB classifier.

The NB classifier may be a NB2 classifier. An NB classifier of the present invention may comprise two or more targets comprising two or more targets selected from Table 1 or SEQ ID NOs: 1-1815.

The plurality of targets may comprise one or more targets selected from a recursive Partitioning (Rpart) classifier. The plurality of targets may comprise 2, 3, 4, 5, 6, 7, 8, 9, 10 or more targets selected from an Rpart classifier. The plurality of targets may comprise 12, 13, 14, 15, 17, 20, 22, 25, 27, 30 or more targets selected from an Rpart classifier. The plurality of targets may comprise 32, 35, 37, 40, 43, 45, 47, 50, 60 or more targets selected from an Rpart classifier.

The Rpart classifier may be an Rpart2 classifier. An Rpart classifier of the present invention may comprise two or more targets comprising two or more targets selected from Table 1 or SEQ ID NOs: 1-1815.

The plurality of targets may comprise one or more targets selected from a high dimensional discriminate analysis (HDDA) classifier. The plurality of targets may comprise two or more targets selected from a high dimensional discriminate analysis (HDDA) classifier. The plurality of targets may comprise three or more targets selected from a high dimensional discriminate analysis (HDDA) classifier. The plurality of targets may comprise 5, 6, 7, 8, 9, 10, 11, 12, 13, 14, 15, 20, 30, 40, 50, 60 or more targets selected from a high dimensional discriminate analysis (HDDA) classifier.

Probes/Primers

The present invention provides for a probe set for diagnosing, monitoring and/or predicting a status or outcome of a prostate cancer in a subject comprising a plurality of probes, wherein (i) the probes in the set are capable of detecting an expression level of at least one target selected from Table 1 or SEQ ID NOs: 1-1815; and (ii) the expression level determines the cancer status of the subject with at least about 40% specificity.

The probe set may comprise one or more polynucleotide probes. Individual polynucleotide probes comprise a nucleotide sequence derived from the nucleotide sequence of the target sequences or complementary sequences thereof. The nucleotide sequence of the polynucleotide probe is designed such that it corresponds to, or is complementary to the target sequences. The polynucleotide probe can specifically hybridize under either stringent or lowered stringency hybridization conditions to a region of the target sequences, to the complement thereof, or to a nucleic acid sequence (such as a cDNA) derived therefrom.

The selection of the polynucleotide probe sequences and determination of their uniqueness may be carried out in silico using techniques known in the art, for example, based on a BLASTN search of the polynucleotide sequence in question against gene sequence databases, such as the Human Genome Sequence, UniGene, dbEST or the non-redundant database at NCBI. In one embodiment of the invention, the polynucleotide probe is complementary to a region of a target mRNA derived from a target sequence in the probe set. Computer programs can also be employed to select probe sequences that may not cross hybridize or may not hybridize non-specifically.

In some instances, microarray hybridization of RNA, extracted from prostate cancer tissue samples and amplified, may yield a dataset that is then summarized and normalized by the fRMA technique. After removal (or filtration) of cross-hybridizing PSRs, and PSRs containing less than 4 probes, the remaining PSRs can be used in further analysis. Following fRMA and filtration, the data can be decomposed into its principal components and an analysis of variance model is used to determine the extent to which a batch effect remains present in the first 10 principal components.

These remaining PSRs can then be subjected to filtration by a T-test between CR (clinical recurrence) and non-CR samples. Using a p-value cut-off of 0.01, the remaining features (e.g., PSRs) can be further refined. Feature selection can be performed by regularized logistic regression using the elastic-net penalty. The regularized regression may be bootstrapped over 1000 times using all training data; with each iteration of bootstrapping, features that have non-zero co-efficient following 3-fold cross validation can be tabulated. In some instances, features that were selected in at least 25% of the total runs were used for model building.

The polynucleotide probes of the present invention may range in length from about 15 nucleotides to the full length of the coding target or non-coding target. In one embodiment of the invention, the polynucleotide probes are at least about 15 nucleotides in length. In another embodiment, the polynucleotide probes are at least about 20 nucleotides in length. In a further embodiment, the polynucleotide probes are at least about 25 nucleotides in length. In another embodiment, the polynucleotide probes are between about 15 nucleotides and about 500 nucleotides in length. In other embodiments, the polynucleotide probes are between about 15 nucleotides and about 450 nucleotides, about 15 nucleotides and about 400 nucleotides, about 15 nucleotides and about 350 nucleotides, about 15 nucleotides and about 300 nucleotides, about 15 nucleotides and about 250 nucleotides, about 15 nucleotides and about 200 nucleotides in length. In some embodiments, the probes are at least 15 nucleotides in length. In some embodiments, the probes are at least 15 nucleotides in length. In some embodiments, the probes are at least 20 nucleotides, at least 25 nucleotides, at least 50 nucleotides, at least 75 nucleotides, at least 100 nucleotides, at least 125 nucleotides, at least 150 nucleotides, at least 200 nucleotides, at least 225 nucleotides, at least 250 nucleotides, at least 275 nucleotides, at least 300 nucleotides, at least 325 nucleotides, at least 350 nucleotides, at least 375 nucleotides in length.

The polynucleotide probes of a probe set can comprise RNA, DNA, RNA or DNA mimetics, or combinations thereof, and can be single-stranded or double-stranded. Thus the polynucleotide probes can be composed of naturally-occurring nucleobases, sugars and covalent internucleoside (backbone) linkages as well as polynucleotide probes having non-naturally-occurring portions which function similarly. Such modified or substituted polynucleotide probes may provide desirable properties such as, for example, enhanced affinity for a target gene and increased stability. The probe set may comprise a coding target and/or a non-coding target. Preferably, the probe set comprises a combination of a coding target and non-coding target.

In some embodiments, the probe set comprise a plurality of target sequences that hybridize to at least about 5 coding targets and/or non-coding targets selected from Table 1 or SEQ ID NOs: 1-1815. Alternatively, the probe set comprise a plurality of target sequences that hybridize to at least about 10 coding targets and/or non-coding targets selected from Table 1 or SEQ ID NOs: 1-1815. In some embodiments, the probe set comprise a plurality of target sequences that hybridize to at least about 15 coding targets and/or non-coding targets selected from Table 1 or SEQ ID NOs: 1-1815. In some embodiments, the probe set comprise a plurality of target sequences that hybridize to at least about 20 coding targets and/or non-coding targets selected from Table 1 or SEQ ID NOs: 1-1815. In some embodiments, the probe set comprise a plurality of target sequences that hybridize to at least about 30 coding targets and/or non-coding targets selected from Table 1 or SEQ ID NOs: 1-1815. In some embodiments, the probe set comprise a plurality of target sequences that hybridize to at least about 40 coding targets and/or non-coding targets selected from Table 1 or SEQ ID NOs: 1-1815. In some embodiments, the probe set comprise a plurality of target sequences that hybridize to at least about 50 coding targets and/or non-coding targets selected from Table 1 or SEQ ID NOs: 1-1815. In some embodiments, the probe set comprise a plurality of target sequences that hybridize to at least about 60 coding targets and/or non-coding targets selected from Table 1 or SEQ ID NOs: 1-1815.

The system of the present invention further provides for primers and primer pairs capable of amplifying target sequences defined by the probe set, or fragments or subsequences or complements thereof. The nucleotide sequences of the probe set may be provided in computer-readable media for in silico applications and as a basis for the design of appropriate primers for amplification of one or more target sequences of the probe set.

Primers based on the nucleotide sequences of target sequences can be designed for use in amplification of the target sequences. For use in amplification reactions such as PCR, a pair of primers can be used. The exact composition of the primer sequences is not critical to the invention, but for most applications the primers may hybridize to specific sequences of the probe set under stringent conditions, particularly under conditions of high stringency, as known in the art. The pairs of primers are usually chosen so as to generate an amplification product of at least about 50 nucleotides, more usually at least about 100 nucleotides. Algorithms for the selection of primer sequences are generally known, and are available in commercial software packages. These primers may be used in standard quantitative or qualitative PCR-based assays to assess transcript expression levels of RNAs defined by the probe set. Alternatively, these primers may be used in combination with probes, such as molecular beacons in amplifications using real-time PCR.

In one embodiment, the primers or primer pairs, when used in an amplification reaction, specifically amplify at least a portion of a nucleic acid sequence of a target selected from Table 1 or SEQ ID NOs: 1-1815 (or subgroups thereof as set forth herein), an RNA form thereof, or a complement to either thereof.

A label can optionally be attached to or incorporated into a probe or primer polynucleotide to allow detection and/or quantitation of a target polynucleotide representing the target sequence of interest. The target polynucleotide may be the expressed target sequence RNA itself, a cDNA copy thereof, or an amplification product derived therefrom, and may be the positive or negative strand, so long as it can be specifically detected in the assay being used. Similarly, an antibody may be labeled.

In certain multiplex formats, labels used for detecting different targets may be distinguishable. The label can be attached directly (e.g., via covalent linkage) or indirectly, e.g., via a bridging molecule or series of molecules (e.g., a molecule or complex that can bind to an assay component, or via members of a binding pair that can be incorporated into assay components, e.g. biotin-avidin or streptavidin). Many labels are commercially available in activated forms which can readily be used for such conjugation (for example through amine acylation), or labels may be attached through known or determinable conjugation schemes, many of which are known in the art.

Labels useful in the invention described herein include any substance which can be detected when bound to or incorporated into the biomolecule of interest. Any effective detection method can be used, including optical, spectroscopic, electrical, piezoelectrical, magnetic, Raman scattering, surface plasmon resonance, colorimetric, calorimetric, etc. A label is typically selected from a chromophore, a lumiphore, a fluorophore, one member of a quenching system, a chromogen, a hapten, an antigen, a magnetic particle, a material exhibiting nonlinear optics, a semiconductor nanocrystal, a metal nanoparticle, an enzyme, an antibody or binding portion or equivalent thereof, an aptamer, and one member of a binding pair, and combinations thereof. Quenching schemes may be used, wherein a quencher and a fluorophore as members of a quenching pair may be used on a probe, such that a change in optical parameters occurs upon binding to the target introduce or quench the signal from the fluorophore. One example of such a system is a molecular beacon. Suitable quencher/fluorophore systems are known in the art. The label may be bound through a variety of intermediate linkages. For example, a polynucleotide may comprise a biotin-binding species, and an optically detectable label may be conjugated to biotin and then bound to the labeled polynucleotide. Similarly, a polynucleotide sensor may comprise an immunological species such as an antibody or fragment, and a secondary antibody containing an optically detectable label may be added.

Chromophores useful in the methods described herein include any substance which can absorb energy and emit light. For multiplexed assays, a plurality of different signaling chromophores can be used with detectably different emission spectra. The chromophore can be a lumophore or a fluorophore. Typical fluorophores include fluorescent dyes, semiconductor nanocrystals, lanthanide chelates, polynucleotide-specific dyes and green fluorescent protein.

In some embodiments, polynucleotides of the invention comprise at least 20 consecutive bases of the nucleic acid sequence of a target selected from Table 1 or SEQ ID NOs: 1-1815 or a complement thereto. The polynucleotides may comprise at least 21, 22, 23, 24, 25, 27, 30, 32, 35 or more consecutive bases of the nucleic acids sequence of a target selected from Table 1 or SEQ ID NOs: 1-1815, as applicable.

The polynucleotides may be provided in a variety of formats, including as solids, in solution, or in an array. The polynucleotides may optionally comprise one or more labels, which may be chemically and/or enzymatically incorporated into the polynucleotide.

In some embodiments, one or more polynucleotides provided herein can be provided on a substrate. The substrate can comprise a wide range of material, either biological, nonbiological, organic, inorganic, or a combination of any of these. For example, the substrate may be a polymerized Langmuir Blodgett film, functionalized glass, Si, Ge, GaAs, GaP, $SiO_2$, $SiN_4$, modified silicon, or any one of a wide variety of gels or polymers such as (poly)tetrafluoroethylene, (poly)vinylidenedifluoride, polystyrene, cross-linked polystyrene, polyacrylic, polylactic acid, polyglycolic acid, poly(lactide coglycolide), polyanhydrides, poly(methyl methacrylate), poly(ethylene-co-vinyl acetate), polysiloxanes, polymeric silica, latexes, dextran polymers, epoxies, polycarbonates, or combinations thereof. Conducting polymers and photoconductive materials can be used.

The substrate can take the form of an array, a photodiode, an optoelectronic sensor such as an optoelectronic semiconductor chip or optoelectronic thin-film semiconductor, or a biochip. The location(s) of probe(s) on the substrate can be addressable; this can be done in highly dense formats, and the location(s) can be microaddressable or nanoaddressable.

Diagnostic Samples

Diagnostic samples for use with the systems and in the methods of the present invention comprise nucleic acids suitable for providing RNAs expression information. In principle, the biological sample from which the expressed RNA is obtained and analyzed for target sequence expression can be any material suspected of comprising prostate cancer tissue or cells. The diagnostic sample can be a biological sample used directly in a method of the invention. Alternatively, the diagnostic sample can be a sample prepared from a biological sample.

In one embodiment, the sample or portion of the sample comprising or suspected of comprising cancer tissue or cells can be any source of biological material, including cells, tissue or fluid, including bodily fluids. Non-limiting examples of the source of the sample include an aspirate, a needle biopsy, a cytology pellet, a bulk tissue preparation or a section thereof obtained for example by surgery or autopsy, lymph fluid, blood, plasma, serum, tumors, and organs. In some embodiments, the sample is from urine. Alternatively, the sample is from blood, plasma or serum. In some embodiments, the sample is from saliva.

The samples may be archival samples, having a known and documented medical outcome, or may be samples from current patients whose ultimate medical outcome is not yet known.

In some embodiments, the sample may be dissected prior to molecular analysis. The sample may be prepared via macrodissection of a bulk tumor specimen or portion thereof, or may be treated via microdissection, for example via Laser Capture Microdissection (LCM).

The sample may initially be provided in a variety of states, as fresh tissue, fresh frozen tissue, fine needle aspirates, and may be fixed or unfixed. Frequently, medical laboratories routinely prepare medical samples in a fixed state, which facilitates tissue storage. A variety of fixatives can be used to fix tissue to stabilize the morphology of cells, and may be used alone or in combination with other agents.

Exemplary fixatives include crosslinking agents, alcohols, acetone, Bouin's solution, Zenker solution, Hely solution, osmic acid solution and Carnoy solution.

Crosslinking fixatives can comprise any agent suitable for forming two or more covalent bonds, for example an aldehyde. Sources of aldehydes typically used for fixation include formaldehyde, paraformaldehyde, glutaraldehyde or formalin. Preferably, the crosslinking agent comprises formaldehyde, which may be included in its native form or in the form of paraformaldehyde or formalin. One of skill in the art would appreciate that for samples in which crosslinking fixatives have been used special preparatory steps may be necessary including for example heating steps and proteinase-k digestion; see methods.

One or more alcohols may be used to fix tissue, alone or in combination with other fixatives. Exemplary alcohols used for fixation include methanol, ethanol and isopropanol.

Formalin fixation is frequently used in medical laboratories. Formalin comprises both an alcohol, typically methanol, and formaldehyde, both of which can act to fix a biological sample.

Whether fixed or unfixed, the biological sample may optionally be embedded in an embedding medium. Exemplary embedding media used in histology including paraffin, Tissue-Tek® V.I.P.™, Paramat, Paramat Extra, Paraplast, Paraplast X-tra, Paraplast Plus, Peel Away Paraffin Embedding Wax, Polyester Wax, Carbowax Polyethylene Glycol, Polyfin™, Tissue Freezing Medium TFMFM, Cryo-Gef™, and OCT Compound (Electron Microscopy Sciences, Hatfield, Pa.). Prior to molecular analysis, the embedding material may be removed via any suitable techniques, as known in the art. For example, where the sample is embedded in wax, the embedding material may be removed by extraction with organic solvent(s), for example xylenes. Kits are commercially available for removing embedding media from tissues. Samples or sections thereof may be subjected to further processing steps as needed, for example serial hydration or dehydration steps.

In some embodiments, the sample is a fixed, wax-embedded biological sample. Frequently, samples from medical laboratories are provided as fixed, wax-embedded samples, most commonly as formalin-fixed, paraffin embedded (FFPE) tissues.

Whatever the source of the biological sample, the target polynucleotide that is ultimately assayed can be prepared synthetically (in the case of control sequences), but typically is purified from the biological source and subjected to one or more preparative steps. The RNA may be purified to remove or diminish one or more undesired components from the biological sample or to concentrate it. Conversely, where the RNA is too concentrated for the particular assay, it may be diluted.

RNA Extraction

RNA can be extracted and purified from biological samples using any suitable technique. A number of techniques are known in the art, and several are commercially available (e.g., FormaPure nucleic acid extraction kit, Agencourt Biosciences, Beverly Mass., High Pure FFPE RNA Micro Kit, Roche Applied Science, Indianapolis, Ind.). RNA can be extracted from frozen tissue sections using TRIzol (Invitrogen, Carlsbad, Calif.) and purified using RNeasy Protect kit (Qiagen, Valencia, Calif.). RNA can be further purified using DNAse I treatment (Ambion, Austin, Tex.) to eliminate any contaminating DNA. RNA concentrations can be made using a Nanodrop ND-1000 spectrophotometer (Nanodrop Technologies, Rockland, Del.). RNA can be further purified to eliminate contaminants that interfere with cDNA synthesis by cold sodium acetate precipitation. RNA integrity can be evaluated by running electropherograms, and RNA integrity number (RIN, a correlative measure that indicates intactness of mRNA) can be determined using the RNA 6000 PicoAssay for the Bioanalyzer 2100 (Agilent Technologies, Santa Clara, Calif.).

Kits

Kits for performing the desired method(s) are also provided, and comprise a container or housing for holding the components of the kit, one or more vessels containing one or more nucleic acid(s), and optionally one or more vessels containing one or more reagents. The reagents include those described in the composition of matter section above, and those reagents useful for performing the methods described, including amplification reagents, and may include one or more probes, primers or primer pairs, enzymes (including polymerases and ligases), intercalating dyes, labeled probes, and labels that can be incorporated into amplification products.

In some embodiments, the kit comprises primers or primer pairs specific for those subsets and combinations of target sequences described herein. The primers or pairs of primers suitable for selectively amplifying the target sequences. The kit may comprise at least two, three, four or five primers or pairs of primers suitable for selectively amplifying one or more targets. The kit may comprise at least 5, 10, 15, 20, 30, 40, 50, 60, 70, 80, 90, 100 or more primers or pairs of primers suitable for selectively amplifying one or more targets.

In some embodiments, the primers or primer pairs of the kit, when used in an amplification reaction, specifically amplify a non-coding target, coding target, exonic, or non-exonic target described herein, a nucleic acid sequence corresponding to a target selected from Table 1 or SEQ ID NOs: 1-1815, an RNA form thereof, or a complement to either thereof. The kit may include a plurality of such primers or primer pairs which can specifically amplify a corresponding plurality of different amplify a non-coding target, coding target, exonic, or non-exonic transcript described herein, a nucleic acid sequence corresponding to a target selected from Table 1 or SEQ ID NOs: 1-1815, RNA forms thereof, or complements thereto. At least two, three, four or five primers or pairs of primers suitable for selectively amplifying the one or more targets can be provided in kit form. In some embodiments, the kit comprises from five to fifty primers or pairs of primers suitable for amplifying the one or more targets.

The reagents may independently be in liquid or solid form. The reagents may be provided in mixtures. Control samples and/or nucleic acids may optionally be provided in the kit. Control samples may include tissue and/or nucleic acids obtained from or representative of tumor samples from patients showing no evidence of disease, as well as tissue and/or nucleic acids obtained from or representative of tumor samples from patients that develop systemic cancer.

The nucleic acids may be provided in an array format, and thus an array or microarray may be included in the kit. The kit optionally may be certified by a government agency for use in prognosing the disease outcome of cancer patients and/or for designating a treatment modality.

Instructions for using the kit to perform one or more methods of the invention can be provided with the container, and can be provided in any fixed medium. The instructions may be located inside or outside the container or housing, and/or may be printed on the interior or exterior of any surface thereof. A kit may be in multiplex form for concurrently detecting and/or quantitating one or more different target polynucleotides representing the expressed target sequences.

Amplification and Hybridization

Following sample collection and nucleic acid extraction, the nucleic acid portion of the sample comprising RNA that is or can be used to prepare the target polynucleotide(s) of interest can be subjected to one or more preparative reactions. These preparative reactions can include in vitro transcription (IVT), labeling, fragmentation, amplification and other reactions. mRNA can first be treated with reverse transcriptase and a primer to create cDNA prior to detection, quantitation and/or amplification; this can be done in vitro with purified mRNA or in situ, e.g., in cells or tissues affixed to a slide.

By "amplification" is meant any process of producing at least one copy of a nucleic acid, in this case an expressed RNA, and in many cases produces multiple copies. An amplification product can be RNA or DNA, and may include a complementary strand to the expressed target sequence. DNA amplification products can be produced initially through reverse translation and then optionally from further amplification reactions. The amplification product may include all or a portion of a target sequence, and may optionally be labeled. A variety of amplification methods are suitable for use, including polymerase-based methods and ligation-based methods. Exemplary amplification techniques include the polymerase chain reaction method (PCR), the lipase chain reaction (LCR), ribozyme-based methods, self-sustained sequence replication (3SR), nucleic acid sequence-based amplification (NASBA), the use of Q Beta replicase, reverse transcription, nick translation, and the like.

Asymmetric amplification reactions may be used to preferentially amplify one strand representing the target sequence that is used for detection as the target polynucleotide. In some cases, the presence and/or amount of the amplification product itself may be used to determine the expression level of a given target sequence. In other instances, the amplification product may be used to hybridize to an array or other substrate comprising sensor polynucleotides which are used to detect and/or quantitate target sequence expression.

The first cycle of amplification in polymerase-based methods typically forms a primer extension product complementary to the template strand. If the template is single-stranded RNA, a polymerase with reverse transcriptase activity is used in the first amplification to reverse transcribe the RNA to DNA, and additional amplification cycles can be performed to copy the primer extension products. The primers for a PCR must, of course, be designed to hybridize to regions in their corresponding template that can produce an amplifiable segment; thus, each primer must hybridize so that its 3' nucleotide is paired to a nucleotide in its complementary template strand that is located 3' from the 3' nucleotide of the primer used to replicate that complementary template strand in the PCR.

The target polynucleotide can be amplified by contacting one or more strands of the target polynucleotide with a primer and a polymerase having suitable activity to extend the primer and copy the target polynucleotide to produce a full-length complementary polynucleotide or a smaller portion thereof. Any enzyme having a polymerase activity that can copy the target polynucleotide can be used, including DNA polymerases, RNA polymerases, reverse transcriptases, enzymes having more than one type of polymerase or enzyme activity. The enzyme can be thermolabile or thermostable. Mixtures of enzymes can also be used. Exemplary enzymes include: DNA polymerases such as DNA Polymerase I ("Pol I"), the Klenow fragment of Pol I, T4, T7, Sequenase® T7, Sequenase® Version 2.0 T7, Tub, Taq, Tth, Pfic, Pfu, Tsp, Tfl, Tli and *Pyrococcus* sp GB-D DNA polymerases; RNA polymerases such as *E. coli*, SP6, T3 and T7 RNA polymerases; and reverse transcriptases such as AMV, M-MuLV, MMLV, RNAse H MMLV (SuperScript®), SuperScript® II, ThermoScript®, HIV-1, and RAV2 reverse transcriptases. All of these enzymes are commercially available. Exemplary polymerases with multiple specificities include RAV2 and Tli (exo-) polymerases. Exemplary thermostable polymerases include Tub, Taq, Tth, Pfic, Pfu, Tsp, Tfl, Tli and *Pyrococcus* sp. GB-D DNA polymerases.

Suitable reaction conditions are chosen to permit amplification of the target polynucleotide, including pH, buffer, ionic strength, presence and concentration of one or more salts, presence and concentration of reactants and cofactors such as nucleotides and magnesium and/or other metal ions (e g, manganese), optional cosolvents, temperature, thermal cycling profile for amplification schemes comprising a polymerase chain reaction, and may depend in part on the polymerase being used as well as the nature of the sample. Cosolvents include formamide (typically at from about 2 to about 10%), glycerol (typically at from about 5 to about 10%), and DMSO (typically at from about 0.9 to about 10%). Techniques may be used in the amplification scheme in order to minimize the production of false positives or artifacts produced during amplification. These include "touchdown" PCR, hot-start techniques, use of nested primers, or designing PCR primers so that they form stem-loop structures in the event of primer-dimer formation and thus are not amplified. Techniques to accelerate PCR can be used, for example centrifugal PCR, which allows for greater convection within the sample, and comprising infrared heating steps for rapid heating and cooling of the sample. One or more cycles of amplification can be performed. An excess of one primer can be used to produce an excess of one primer extension product during PCR; preferably, the primer extension product produced in excess is the amplification product to be detected. A plurality of different primers may be used to amplify different target polynucleotides or different regions of a particular target polynucleotide within the sample.

An amplification reaction can be performed under conditions which allow an optionally labeled sensor polynucleotide to hybridize to the amplification product during at least part of an amplification cycle. When the assay is performed in this manner, real-time detection of this hybridization event can take place by monitoring for light emission or fluorescence during amplification, as known in the art.

Where the amplification product is to be used for hybridization to an array or microarray, a number of suitable commercially available amplification products are available. These include amplification kits available from NuGEN, Inc. (San Carlos, Calif.), including the WT-Ovation™ System, WT-Ovation™ System v2, WT-Ovation™ Pico System, WT-Ovation™ FFPE Exon Module, WT-Ovation™ FFPE Exon Module RiboAmp and RiboAmp$^{Plus}$ RNA Amplification Kits (MDS Analytical Technologies (formerly Arcturus) (Mountain View, Calif.), Genisphere, Inc. (Hatfield, Pa.), including the RampUp Plus™ and SenseAmp™ RNA Amplification kits, alone or in combination Amplified nucleic acids may be subjected to one or more purification reactions after amplification and labeling, for example using magnetic beads (e.g., RNAC1ean magnetic beads, Agencourt Biosciences).

Multiple RNA biomarkers can be analyzed using real-time quantitative multiplex RT-PCR platforms and other multiplexing technologies such as GenomeLab GeXP Genetic Analysis System (Beckman Coulter, Foster City, Calif.), SmartCycler® 9600 or GeneXpert® Systems (Cepheid, Sunnyvale, Calif.), ABI 7900 HT Fast Real Time PCR system (Applied Biosystems, Foster City, Calif.), LightCycler® 480 System (Roche Molecular Systems, Pleasanton, Calif.), xMAP 100 System (Luminex, Austin, Tex.) Solexa Genome Analysis System (Illumina, Hayward, Calif.), OpenArray Real Time qPCR (BioTrove, Woburn, Mass.) and BeadXpress System (Illumina, Hayward, Calif.).

Detection and/or Quantification of Target Sequences

Any method of detecting and/or quantitating the expression of the encoded target sequences can in principle be used in the invention. The expressed target sequences can be directly detected and/or quantitated, or may be copied and/or amplified to allow detection of amplified copies of the expressed target sequences or its complement.

Methods for detecting and/or quantifying a target can include Northern blotting, sequencing, array or microarray hybridization, by enzymatic cleavage of specific structures (e.g., an Invader® assay, Third Wave Technologies, e.g. as described in U.S. Pat. Nos. 5,846,717, 6,090,543; 6,001,567; 5,985,557; and 5,994,069) and amplification methods, e.g. RT-PCR, including in a TaqMan® assay (PE Biosystems, Foster City, Calif., e.g. as described in U.S. Pat. Nos. 5,962,233 and 5,538,848), and may be quantitative or semi-quantitative, and may vary depending on the origin, amount and condition of the available biological sample. Combinations of these methods may also be used. For example, nucleic acids may be amplified, labeled and subjected to microarray analysis.

In some instances, target sequences may be detected by sequencing. Sequencing methods may comprise whole genome sequencing or exome sequencing. Sequencing methods such as Maxim-Gilbert, chain-termination, or high-throughput systems may also be used. Additional, suitable sequencing techniques include classic dideoxy sequencing reactions (Sanger method) using labeled terminators or primers and gel separation in slab or capillary, sequencing by synthesis using reversibly terminated labeled nucleotides, pyrosequencing, 454 sequencing, allele specific hybridization to a library of labeled oligonucleotide probes, sequencing by synthesis using allele specific hybridization to a library of labeled clones that is followed by ligation, real time monitoring of the incorporation of labeled nucleotides during a polymerization step, and SOLiD sequencing.

Additional methods for detecting and/or quantifying a target include single-molecule sequencing (e.g., Helicos, PacBio), sequencing by synthesis (e.g., Illumina, Ion Torrent), sequencing by ligation (e.g., ABI SOLID), sequencing by hybridization (e.g., Complete Genomics), in situ hybridization, bead-array technologies (e.g., Luminex xMAP, Illumina BeadChips), branched DNA technology (e.g., Panomics, Genisphere). Sequencing methods may use fluorescent (e.g., Illumina) or electronic (e.g., Ion Torrent, Oxford Nanopore) methods of detecting nucleotides.

Reverse Transcription for ORT-PCR Analysis

Reverse transcription can be performed by any method known in the art. For example, reverse transcription may be performed using the Omniscript kit (Qiagen, Valencia, Calif.), Superscript III kit (Invitrogen, Carlsbad, Calif.), for RT-PCR. Target-specific priming can be performed in order to increase the sensitivity of detection of target sequences and generate target-specific cDNA.

TaqMan® Gene Expression Analysis

TaqMan® RT-PCR can be performed using Applied Biosystems Prism (ABI) 7900 HT instruments in a 5 1.11 volume with target sequence-specific cDNA equivalent to 1 ng total RNA.

Primers and probes concentrations for TaqMan analysis are added to amplify fluorescent amplicons using PCR cycling conditions such as 95° C. for 10 minutes for one cycle, 95° C. for 20 seconds, and 60° C. for 45 seconds for 40 cycles. A reference sample can be assayed to ensure reagent and process stability. Negative controls (e.g., no template) should be assayed to monitor any exogenous nucleic acid contamination.

Classification Arrays

The present invention contemplates that a probe set or probes derived therefrom may be provided in an array format. In the context of the present invention, an "array" is a spatially or logically organized collection of polynucleotide probes. An array comprising probes specific for a coding target, non-coding target, or a combination thereof may be used. Alternatively, an array comprising probes specific for two or more of transcripts of a target selected from Table 1 or SEQ ID NOs: 1-1815 or a product derived thereof can be used. Desirably, an array may be specific for 5, 10, 15, 20, 25, 30, 40, 50 or more of transcripts of a target selected from Table 1 or SEQ ID NOs: 1-1815. Expression of these sequences may be detected alone or in combination with other transcripts. In some embodiments, an array is used which comprises a wide range of sensor probes for prostate-specific expression products, along with appropriate control sequences. In some instances, the array may comprise the Human Exon 1.0 ST Array (HuEx 1.0 ST, Affymetrix, Inc., Santa Clara, Calif.).

Typically the polynucleotide probes are attached to a solid substrate and are ordered so that the location (on the substrate) and the identity of each are known. The polynucleotide probes can be attached to one of a variety of solid substrates capable of withstanding the reagents and conditions necessary for use of the array. Examples include, but are not limited to, polymers, such as (poly)tetrafluoroethylene, (poly)vinylidenedifluoride, polystyrene, polycarbonate, polypropylene and polystyrene; ceramic; silicon; silicon dioxide; modified silicon; (fused) silica, quartz or glass; functionalized glass; paper, such as filter paper; diazotized cellulose; nitrocellulose filter; nylon membrane; and polyacrylamide gel pad. Substrates that are transparent to light are useful for arrays that may be used in an assay that involves optical detection.

Examples of array formats include membrane or filter arrays (for example, nitrocellulose, nylon arrays), plate arrays (for example, multiwell, such as a 24-, 96-, 256-, 384-, 864- or 1536-well, microtitre plate arrays), pin arrays, and bead arrays (for example, in a liquid "slurry"). Arrays on substrates such as glass or ceramic slides are often referred to as chip arrays or "chips." Such arrays are well known in the art. In one embodiment of the present invention, the Cancer Prognosticarray is a chip.

Data Analysis

In some embodiments, one or more pattern recognition methods can be used in analyzing the expression level of target sequences. The pattern recognition method can comprise a linear combination of expression levels, or a nonlinear combination of expression levels. In some embodiments, expression measurements for RNA transcripts or combinations of RNA transcript levels are formulated into linear or non-linear models or algorithms (e.g., an 'expression signature') and converted into a likelihood score. This likelihood score indicates the probability that a biological sample is from a patient who may exhibit no evidence of disease, who may exhibit systemic cancer, or who may exhibit biochemical recurrence. The likelihood score can be used to distinguish these disease states. The models and/or algorithms can be provided in machine readable format, and may be used to correlate expression levels or an expression profile with a disease state, and/or to designate a treatment modality for a patient or class of patients.

Assaying the expression level for a plurality of targets may comprise the use of an algorithm or classifier. Array data can be managed, classified, and analyzed using techniques known in the art. Assaying the expression level for a plurality of targets may comprise probe set modeling and data pre-processing. Probe set modeling and data pre-processing can be derived using the Robust Multi-Array (RMA) algorithm or variants GC-RMA, IRMA, Probe Logarithmic Intensity Error (PLIER) algorithm or variant iterPLIER. Variance or intensity filters can be applied to pre-process data using the RMA algorithm, for example by removing target sequences with a standard deviation of <10 or a mean intensity of <100 intensity units of a normalized data range, respectively.

Alternatively, assaying the expression level for a plurality of targets may comprise the use of a machine learning algorithm. The machine learning algorithm may comprise a supervised learning algorithm. Examples of supervised learning algorithms may include Average One-Dependence Estimators (AODE), Artificial neural network (e.g., Backpropagation), Bayesian statistics (e.g., Naive Bayes classifier, Bayesian network, Bayesian knowledge base), Case-based reasoning, Decision trees, Inductive logic programming, Gaussian process regression, Group method of data handling (GMDH), Learning Automata, Learning Vector Quantization, Minimum message length (decision trees, decision graphs, etc.), Lazy learning, Instance-based learning Nearest Neighbor Algorithm, Analogical modeling, Probably approximately correct learning (PAC) learning, Ripple down rules, a knowledge acquisition methodology, Symbolic machine learning algorithms, Subsymbolic machine learning algorithms, Support vector machines, Random Forests, Ensembles of classifiers, Bootstrap aggregating (bagging), and Boosting. Supervised learning may comprise ordinal classification such as regression analysis and Information fuzzy networks (IFN). Alternatively, supervised learning methods may comprise statistical classification, such as AODE, Linear classifiers (e.g., Fisher's linear discriminant, Logistic regression, Naive Bayes classifier, Perceptron, and Support vector machine), quadratic classifiers, k-nearest neighbor, Boosting, Decision trees (e.g., C4.5, Random forests), Bayesian networks, and Hidden Markov models.

The machine learning algorithms may also comprise an unsupervised learning algorithm. Examples of unsupervised learning algorithms may include artificial neural network, Data clustering, Expectation-maximization algorithm, Self-organizing map, Radial basis function network, Vector Quantization, Generative topographic map, Information bottleneck method, and IBSEAD. Unsupervised learning may also comprise association rule learning algorithms such as Apriori algorithm, Eclat algorithm and FP-growth algorithm. Hierarchical clustering, such as Single-linkage clustering and Conceptual clustering, may also be used. Alternatively, unsupervised learning may comprise partitional clustering such as K-means algorithm and Fuzzy clustering.

In some instances, the machine learning algorithms comprise a reinforcement learning algorithm. Examples of reinforcement learning algorithms include, but are not limited to, temporal difference learning, Q-learning and Learning Automata. Alternatively, the machine learning algorithm may comprise Data Pre-processing.

Preferably, the machine learning algorithms may include, but are not limited to, Average One-Dependence Estimators (AODE), Fisher's linear discriminant, Logistic regression, Perceptron, Multilayer Perceptron, Artificial Neural Networks, Support vector machines, Quadratic classifiers, Boosting, Decision trees, C4.5, Bayesian networks, Hidden Markov models, High-Dimensional Discriminant Analysis, and Gaussian Mixture Models. The machine learning algorithm may comprise support vector machines, Naïve Bayes classifier, k-nearest neighbor, high-dimensional discriminant analysis, or Gaussian mixture models. In some instances, the machine learning algorithm comprises Random Forests.

Cancer

The systems, compositions and methods disclosed herein may be used to diagnosis, monitor and/or predict the status or outcome of a cancer. Generally, a cancer is characterized by the uncontrolled growth of abnormal cells anywhere in a body. The abnormal cells may be termed cancer cells, malignant cells, or tumor cells. Cancer is not confined to humans; animals and other living organisms can get cancer.

In some instances, the cancer may be malignant. Alternatively, the cancer may be benign. The cancer may be a recurrent and/or refractory cancer. Most cancers can be classified as a carcinoma, sarcoma, leukemia, lymphoma, myeloma, or a central nervous system cancer.

The cancer may be a sarcoma. Sarcomas are cancers of the bone, cartilage, fat, muscle, blood vessels, or other connective or supportive tissue. Sarcomas include, but are not limited to, bone cancer, fibrosarcoma, chondrosarcoma, Ewing's sarcoma, malignant hemangioendothelioma, malignant schwannoma, bilateral vestibular schwannoma, osteosarcoma, soft tissue sarcomas (e.g. alveolar soft part sarcoma, angiosarcoma, cystosarcoma phylloides, dermatofibrosarcoma, desmoid tumor, epithelioid sarcoma, extraskeletal osteosarcoma, fibrosarcoma, hemangiopericytoma, hemangiosarcoma, Kaposi's sarcoma, leiomyosarcoma, liposarcoma, lymphangiosarcoma, lymphosarcoma, malignant fibrous histiocytoma, neurofibrosarcoma, rhabdomyosarcoma, and synovial sarcoma).

Alternatively, the cancer may be a carcinoma. Carcinomas are cancers that begin in the epithelial cells, which are cells that cover the surface of the body, produce hormones, and make up glands. By way of non-limiting example, carcinomas include breast cancer, pancreatic cancer, lung cancer, colon cancer, colorectal cancer, rectal cancer, kidney cancer, bladder cancer, stomach cancer, prostate cancer, liver cancer, ovarian cancer, brain cancer, vaginal cancer, vulvar cancer, uterine cancer, oral cancer, penic cancer, testicular cancer, esophageal cancer, skin cancer, cancer of the fallopian tubes, head and neck cancer, gastrointestinal stromal cancer, adenocarcinoma, cutaneous or intraocular melanoma, cancer of the anal region, cancer of the small intestine, cancer of the endocrine system, cancer of the thyroid gland, cancer of the parathyroid gland, cancer of the adrenal gland, cancer of the urethra, cancer of the renal pelvis, cancer of the ureter, cancer of the endometrium, cancer of the cervix, cancer of the pituitary gland, neoplasms of the central nervous system (CNS), primary CNS lymphoma, brain stem glioma, and spinal axis tumors. In some instances, the cancer is a skin cancer, such as a basal cell carcinoma, squamous, melanoma, nonmelanoma, or actinic (solar) keratosis. Preferably, the cancer is a prostate cancer. Alternatively, the cancer may be a thyroid cancer, bladder cancer, or pancreatic cancer.

In some instances, the cancer is a lung cancer. Lung cancer can start in the airways that branch off the trachea to supply the lungs (bronchi) or the small air sacs of the lung (the alveoli). Lung cancers include non-small cell lung carcinoma (NSCLC), small cell lung carcinoma, and mesothelioma. Examples of NSCLC include squamous cell carcinoma, adenocarcinoma, and large cell carcinoma. The mesothelioma may be a cancerous tumor of the lining of the lung and chest cavity (pleura) or lining of the abdomen (peritoneum). The mesothelioma may be due to asbestos exposure. The cancer may be a brain cancer, such as a glioblastoma.

Alternatively, the cancer may be a central nervous system (CNS) tumor. CNS tumors may be classified as gliomas or nongliomas. The glioma may be malignant glioma, high grade glioma, diffuse intrinsic pontine glioma. Examples of gliomas include astrocytomas, oligodendrogliomas (or mixtures of oligodendroglioma and astocytoma elements), and ependymomas. Astrocytomas include, but are not limited to, low-grade astrocytomas, anaplastic astrocytomas, glioblastoma multiforme, pilocytic astrocytoma, pleomorphic xanthoastrocytoma, and subependymal giant cell astrocytoma. Oligodendrogliomas include low-grade oligodendrogliomas (or oligoastrocytomas) and anaplastic oligodendriogliomas. Nongliomas include meningiomas, pituitary adenomas, primary CNS lymphomas, and medulloblastomas. In some instances, the cancer is a meningioma.

The cancer may be a leukemia. The leukemia may be an acute lymphocytic leukemia, acute myelocytic leukemia, chronic lymphocytic leukemia, or chronic myelocytic leukemia. Additional types of leukemias include hairy cell leukemia, chronic myelomonocytic leukemia, and juvenile myelomonocytic-leukemia.

In some instances, the cancer is a lymphoma. Lymphomas are cancers of the lymphocytes and may develop from either B or T lymphocytes. The two major types of lymphoma are Hodgkin's lymphoma, previously known as Hodgkin's disease, and non-Hodgkin's lymphoma. Hodgkin's lymphoma is marked by the presence of the Reed-Sternberg cell. Non-Hodgkin's lymphomas are all lymphomas which are not Hodgkin's lymphoma. Non-Hodgkin lymphomas may be indolent lymphomas and aggressive lymphomas. Non-Hodgkin's lymphomas include, but are not limited to, diffuse large B cell lymphoma, follicular lymphoma, mucosa-associated lymphatic tissue lymphoma (MALT), small cell lymphocytic lymphoma, mantle cell lymphoma, Burkitt's lymphoma, mediastinal large B cell lymphoma, Waldenström macroglobulinemia, nodal marginal zone B cell lymphoma (NMZL), splenic marginal zone lymphoma (SMZL), extranodal marginal zone B cell lymphoma, intravascular large B cell lymphoma, primary effusion lymphoma, and lymphomatoid granulomatosis.

Cancer Staging

Diagnosing, predicting, or monitoring a status or outcome of a cancer may comprise determining the stage of the cancer. Generally, the stage of a cancer is a description (usually numbers I to IV with IV having more progression) of the extent the cancer has spread. The stage often takes into account the size of a tumor, how deeply it has penetrated, whether it has invaded adjacent organs, how many lymph nodes it has metastasized to (if any), and whether it has spread to distant organs. Staging of cancer can be used as a predictor of survival, and cancer treatment may be determined by staging. Determining the stage of the cancer may occur before, during, or after treatment. The stage of the cancer may also be determined at the time of diagnosis.

Cancer staging can be divided into a clinical stage and a pathologic stage. Cancer staging may comprise the TNM classification. Generally, the TNM Classification of Malignant Tumours (TNM) is a cancer staging system that describes the extent of cancer in a patient's body. T may describe the size of the tumor and whether it has invaded nearby tissue, N may describe regional lymph nodes that are involved, and M may describe distant metastasis (spread of cancer from one body part to another). In the TNM (Tumor, Node, Metastasis) system, clinical stage and pathologic stage are denoted by a small "c" or "p" before the stage (e.g., cT3N1M0 or pT2N0).

Often, clinical stage and pathologic stage may differ. Clinical stage may be based on all of the available information obtained before a surgery to remove the tumor. Thus, it may include information about the tumor obtained by physical examination, radiologic examination, and endoscopy. Pathologic stage can add additional information gained by examination of the tumor microscopically by a pathologist. Pathologic staging can allow direct examination of the tumor and its spread, contrasted with clinical staging which may be limited by the fact that the information is obtained by making indirect observations at a tumor which is still in the body. The TNM staging system can be used for most forms of cancer.

Alternatively, staging may comprise Ann Arbor staging. Generally, Ann Arbor staging is the staging system for lymphomas, both in Hodgkin's lymphoma (previously called Hodgkin's disease) and Non-Hodgkin lymphoma (abbreviated NHL). The stage may depend on both the place where the malignant tissue is located (as located with biopsy, CT scanning and increasingly positron emission tomography) and on systemic symptoms due to the lymphoma ("B symptoms": night sweats, weight loss of >10% or fevers). The principal stage may be determined by location of the tumor. Stage I may indicate that the cancer is located in a single region, usually one lymph node and the surrounding area. Stage I often may not have outward symptoms. Stage II can indicate that the cancer is located in two separate regions, an affected lymph node or organ and a second affected area, and that both affected areas are confined to one side of the diaphragm—that is, both are above the diaphragm, or both are below the diaphragm. Stage III often indicates that the cancer has spread to both sides of the diaphragm, including one organ or area near the lymph nodes or the spleen. Stage IV may indicate diffuse or disseminated involvement of one or more extralymphatic organs, including any involvement of the liver, bone marrow, or nodular involvement of the lungs.

Modifiers may also be appended to some stages. For example, the letters A, B, E, X, or S can be appended to some stages. Generally, A or B may indicate the absence of constitutional (B-type) symptoms is denoted by adding an "A" to the stage; the presence is denoted by adding a "B" to the stage. E can be used if the disease is "extranodal" (not in the lymph nodes) or has spread from lymph nodes to adjacent tissue. X is often used if the largest deposit is >10 cm large ("bulky disease"), or whether the mediastinum is wider than ⅓ of the chest on a chest X-ray. S may be used if the disease has spread to the spleen.

The nature of the staging may be expressed with CS or PS. CS may denote that the clinical stage as obtained by doctor's examinations and tests. PS may denote that the pathological stage as obtained by exploratory laparotomy (surgery performed through an abdominal incision) with splenectomy (surgical removal of the spleen).

Therapeutic Regimens

Diagnosing, predicting, or monitoring a status or outcome of a cancer may comprise treating a cancer or preventing a cancer progression. In addition, diagnosing, predicting, or monitoring a status or outcome of a cancer may comprise identifying or predicting responders to an anti-cancer therapy. In some instances, diagnosing, predicting, or monitoring may comprise determining a therapeutic regimen. Determining a therapeutic regimen may comprise administering an anti-cancer therapy. Alternatively, determining a therapeutic regimen may comprise modifying, recommending, continuing or discontinuing an anti-cancer regimen. In some instances, if the sample expression patterns are consistent with the expression pattern for a known disease or disease outcome, the expression patterns can be used to designate one or more treatment modalities (e.g., therapeutic regimens, anti-cancer regimen). An anti-cancer regimen may comprise one or more anti-cancer therapies. Examples of anti-cancer therapies include surgery, chemotherapy, radiation therapy, immunotherapy/biological therapy, photodynamic therapy.

Surgical oncology uses surgical methods to diagnose, stage, and treat cancer, and to relieve certain cancer-related symptoms. Surgery may be used to remove the tumor (e.g., excisions, resections, debulking surgery), reconstruct a part of the body (e.g., restorative surgery), and/or to relieve symptoms such as pain (e.g., palliative surgery). Surgery may also include cryosurgery. Cryosurgery (also called cryotherapy) may use extreme cold produced by liquid nitrogen (or argon gas) to destroy abnormal tissue. Cryosurgery can be used to treat external tumors, such as those on the skin. For external tumors, liquid nitrogen can be applied directly to the cancer cells with a cotton swab or spraying device. Cryosurgery may also be used to treat tumors inside the body (internal tumors and tumors in the bone). For internal tumors, liquid nitrogen or argon gas may be circulated through a hollow instrument called a cryoprobe, which is placed in contact with the tumor. An ultrasound or MRI may be used to guide the cryoprobe and monitor the freezing of the cells, thus limiting damage to nearby healthy tissue. A ball of ice crystals may form around the probe, freezing nearby cells. Sometimes more than one probe is used to deliver the liquid nitrogen to various parts of the tumor. The probes may be put into the tumor during surgery or through the skin (percutaneously). After cryosurgery, the frozen tissue thaws and may be naturally absorbed by the body (for internal tumors), or may dissolve and form a scab (for external tumors).

Chemotherapeutic agents may also be used for the treatment of cancer. Examples of chemotherapeutic agents include alkylating agents, anti-metabolites, plant alkaloids and terpenoids, vinca alkaloids, podophyllotoxin, taxanes, topoisomerase inhibitors, and cytotoxic antibiotics. Cisplatin, carboplatin, and oxaliplatin are examples of alkylating agents. Other alkylating agents include mechlorethamine, cyclophosphamide, chlorambucil, ifosfamide. Alkylating agents may impair cell function by forming covalent bonds with the amino, carboxyl, sulfhydryl, and phosphate groups in biologically important molecules. Alternatively, alkylating agents may chemically modify a cell's DNA.

Anti-metabolites are another example of chemotherapeutic agents. Anti-metabolites may masquerade as purines or pyrimidines and may prevent purines and pyrimidines from becoming incorporated in to DNA during the "S" phase (of the cell cycle), thereby stopping normal development and division. Antimetabolites may also affect RNA synthesis. Examples of metabolites include azathioprine and mercaptopurine.

Alkaloids may be derived from plants and block cell division may also be used for the treatment of cancer. Alkyloids may prevent microtubule function. Examples of alkaloids are vinca alkaloids and taxanes. Vinca alkaloids may bind to specific sites on tubulin and inhibit the assembly of tubulin into microtubules (M phase of the cell cycle). The vinca alkaloids may be derived from the Madagascar periwinkle, *Catharanthus roseus* (formerly known as *Vinca rosea*). Examples of vinca alkaloids include, but are not limited to, vincristine, vinblastine, vinorelbine, or vindesine. Taxanes are diterpenes produced by the plants of the genus *Taxus* (yews). Taxanes may be derived from natural sources or synthesized artificially. Taxanes include paclitaxel (Taxol) and docetaxel (Taxotere). Taxanes may disrupt microtubule function. Microtubules are essential to cell division, and taxanes may stabilize GDP-bound tubulin in the microtubule, thereby inhibiting the process of cell division. Thus, in essence, taxanes may be mitotic inhibitors. Taxanes may also be radiosensitizing and often contain numerous chiral centers.

Alternative chemotherapeutic agents include podophyllotoxin. Podophyllotoxin is a plant-derived compound that may help with digestion and may be used to produce cytostatic drugs such as etoposide and teniposide. They may prevent the cell from entering the G1 phase (the start of DNA replication) and the replication of DNA (the S phase).

Topoisomerases are essential enzymes that maintain the topology of DNA. Inhibition of type I or type II topoisomerases may interfere with both transcription and replication of DNA by upsetting proper DNA supercoiling. Some chemotherapeutic agents may inhibit topoisomerases. For example, some type I topoisomerase inhibitors include camptothecins: irinotecan and topotecan. Examples of type II inhibitors include amsacrine, etoposide, etoposide phosphate, and teniposide.

Another example of chemotherapeutic agents is cytotoxic antibiotics. Cytotoxic antibiotics are a group of antibiotics that are used for the treatment of cancer because they may interfere with DNA replication and/or protein synthesis. Cytotoxic antibiotics include, but are not limited to, actinomycin, anthracyclines, doxorubicin, daunorubicin, valrubicin, idarubicin, epirubicin, bleomycin, plicamycin, and mitomycin.

In some instances, the anti-cancer treatment may comprise radiation therapy. Radiation can come from a machine outside the body (external-beam radiation therapy) or from radioactive material placed in the body near cancer cells (internal radiation therapy, more commonly called brachytherapy). Systemic radiation therapy uses a radioactive substance, given by mouth or into a vein that travels in the blood to tissues throughout the body.

External-beam radiation therapy may be delivered in the form of photon beams (either x-rays or gamma rays). A photon is the basic unit of light and other forms of electromagnetic radiation. An example of external-beam radiation therapy is called 3-dimensional conformal radiation therapy (3D-CRT). 3D-CRT may use computer software and advanced treatment machines to deliver radiation to very precisely shaped target areas. Many other methods of external-beam radiation therapy are currently being tested and used in cancer treatment. These methods include, but are not limited to, intensity-modulated radiation therapy (IMRT), image-guided radiation therapy (IGRT), Stereotactic radiosurgery (SRS), Stereotactic body radiation therapy (SBRT), and proton therapy.

Intensity-modulated radiation therapy (IMRT) is an example of external-beam radiation and may use hundreds of tiny radiation beam-shaping devices, called collimators, to deliver a single dose of radiation. The collimators can be stationary or can move during treatment, allowing the intensity of the radiation beams to change during treatment sessions. This kind of dose modulation allows different areas of a tumor or nearby tissues to receive different doses of radiation. IMRT is planned in reverse (called inverse treatment planning). In inverse treatment planning, the radiation doses to different areas of the tumor and surrounding tissue are planned in advance, and then a high-powered computer program calculates the required number of beams and angles of the radiation treatment. In contrast, during traditional (forward) treatment planning, the number and angles of the radiation beams are chosen in advance and computers calculate how much dose may be delivered from each of the planned beams. The goal of IMRT is to increase the radiation dose to the areas that need it and reduce radiation exposure to specific sensitive areas of surrounding normal tissue.

Another example of external-beam radiation is image-guided radiation therapy (IGRT). In IGRT, repeated imaging scans (CT, MRI, or PET) may be performed during treatment. These imaging scans may be processed by computers to identify changes in a tumor's size and location due to treatment and to allow the position of the patient or the planned radiation dose to be adjusted during treatment as needed. Repeated imaging can increase the accuracy of radiation treatment and may allow reductions in the planned volume of tissue to be treated, thereby decreasing the total radiation dose to normal tissue.

Tomotherapy is a type of image-guided IMRT. A tomotherapy machine is a hybrid between a CT imaging scanner and an external-beam radiation therapy machine. The part of the tomotherapy machine that delivers radiation for both imaging and treatment can rotate completely around the patient in the same manner as a normal CT scanner. Tomotherapy machines can capture CT images of the patient's tumor immediately before treatment sessions, to allow for very precise tumor targeting and sparing of normal tissue.

Stereotactic radiosurgery (SRS) can deliver one or more high doses of radiation to a small tumor. SRS uses extremely accurate image-guided tumor targeting and patient positioning. Therefore, a high dose of radiation can be given without excess damage to normal tissue. SRS can be used to treat small tumors with well-defined edges. It is most commonly used in the treatment of brain or spinal tumors and brain metastases from other cancer types. For the treatment of some brain metastases, patients may receive radiation therapy to the entire brain (called whole-brain radiation therapy) in addition to SRS. SRS requires the use of a head frame or other device to immobilize the patient during treatment to ensure that the high dose of radiation is delivered accurately.

Stereotactic body radiation therapy (SBRT) delivers radiation therapy in fewer sessions, using smaller radiation fields and higher doses than 3D-CRT in most cases. SBRT may treat tumors that lie outside the brain and spinal cord. Because these tumors are more likely to move with the normal motion of the body, and therefore cannot be targeted as accurately as tumors within the brain or spine, SBRT is usually given in more than one dose. SBRT can be used to treat small, isolated tumors, including cancers in the lung and liver. SBRT systems may be known by their brand names, such as the CyberKnife®.

In proton therapy, external-beam radiation therapy may be delivered by proton. Protons are a type of charged particle. Proton beams differ from photon beams mainly in the way they deposit energy in living tissue. Whereas photons deposit energy in small packets all along their path through tissue, protons deposit much of their energy at the end of their path (called the Bragg peak) and deposit less energy along the way. Use of protons may reduce the exposure of normal tissue to radiation, possibly allowing the delivery of higher doses of radiation to a tumor.

Other charged particle beams such as electron beams may be used to irradiate superficial tumors, such as skin cancer or tumors near the surface of the body, but they cannot travel very far through tissue.

Internal radiation therapy (brachytherapy) is radiation delivered from radiation sources (radioactive materials) placed inside or on the body. Several brachytherapy techniques are used in cancer treatment. Interstitial brachytherapy may use a radiation source placed within tumor tissue, such as within a prostate tumor. Intracavitary brachytherapy may use a source placed within a surgical cavity or a body cavity, such as the chest cavity, near a tumor. Episcleral brachytherapy, which may be used to treat melanoma inside the eye, may use a source that is attached to the eye. In brachytherapy, radioactive isotopes can be sealed in tiny pellets or "seeds." These seeds may be placed in patients using delivery devices, such as needles, catheters, or some other type of carrier. As the isotopes decay naturally, they give off radiation that may damage nearby cancer cells. Brachytherapy may be able to deliver higher doses of radiation to some cancers than external-beam radiation therapy while causing less damage to normal tissue.

Brachytherapy can be given as a low-dose-rate or a high-dose-rate treatment. In low-dose-rate treatment, cancer cells receive continuous low-dose radiation from the source over a period of several days. In high-dose-rate treatment, a robotic machine attached to delivery tubes placed inside the body may guide one or more radioactive sources into or near a tumor, and then removes the sources at the end of each treatment session. High-dose-rate treatment can be given in one or more treatment sessions. An example of a high-dose-rate treatment is the MammoSite® system. Bracytherapy may be used to treat patients with breast cancer who have undergone breast-conserving surgery.

The placement of brachytherapy sources can be temporary or permanent. For permanent brachytherapy, the sources may be surgically sealed within the body and left there, even after all of the radiation has been given off. In some instances, the remaining material (in which the radioactive isotopes were sealed) does not cause any discomfort or harm to the patient. Permanent brachytherapy is a type of low-dose-rate brachytherapy. For temporary brachytherapy, tubes (catheters) or other carriers are used to deliver the radiation sources, and both the carriers and the radiation sources are removed after treatment. Temporary brachytherapy can be either low-dose-rate or high-dose-rate treatment. Brachytherapy may be used alone or in addition to external-beam radiation therapy to provide a "boost" of radiation to a tumor while sparing surrounding normal tissue.

In systemic radiation therapy, a patient may swallow or receive an injection of a radioactive substance, such as radioactive iodine or a radioactive substance bound to a monoclonal antibody. Radioactive iodine (131I) is a type of systemic radiation therapy commonly used to help treat cancer, such as thyroid cancer. Thyroid cells naturally take up radioactive iodine. For systemic radiation therapy for some other types of cancer, a monoclonal antibody may help target the radioactive substance to the right place. The antibody joined to the radioactive substance travels through the blood, locating and killing tumor cells. For example, the drug ibritumomab tiuxetan (Zevalin®) may be used for the treatment of certain types of B-cell non-Hodgkin lymphoma (NHL). The antibody part of this drug recognizes and binds to a protein found on the surface of B lymphocytes. The combination drug regimen of tositumomab and iodine I 131 tositumomab (Bexxar®) may be used for the treatment of certain types of cancer, such as NHL. In this regimen, nonradioactive tositumomab antibodies may be given to patients first, followed by treatment with tositumomab antibodies that have 131I attached. Tositumomab may recognize and bind to the same protein on B lymphocytes as ibritumomab. The nonradioactive form of the antibody may help protect normal B lymphocytes from being damaged by radiation from 131I.

Some systemic radiation therapy drugs relieve pain from cancer that has spread to the bone (bone metastases). This is a type of palliative radiation therapy. The radioactive drugs samarium-153-lexidronam (Quadramet®) and strontium-89 chloride (Metastron®) are examples of radiopharmaceuticals may be used to treat pain from bone metastases.

Biological therapy (sometimes called immunotherapy, biotherapy, or biological response modifier (BRM) therapy) uses the body's immune system, either directly or indirectly, to fight cancer or to lessen the side effects that may be caused by some cancer treatments. Biological therapies include interferons, interleukins, colony-stimulating factors, monoclonal antibodies, vaccines, gene therapy, and nonspecific immunomodulating agents.

Interferons (IFNs) are types of cytokines that occur naturally in the body. Interferon alpha, interferon beta, and interferon gamma are examples of interferons that may be used in cancer treatment.

Like interferons, interleukins (ILs) are cytokines that occur naturally in the body and can be made in the laboratory. Many interleukins have been identified for the treatment of cancer. For example, interleukin-2 (IL-2 or aldesleukin), interleukin 7, and interleukin 12 have may be used as an anti-cancer treatment. IL-2 may stimulate the growth and activity of many immune cells, such as lymphocytes, that can destroy cancer cells. Interleukins may be used to treat a number of cancers, including leukemia, lymphoma, and brain, colorectal, ovarian, breast, kidney and prostate cancers.

Colony-stimulating factors (CSFs) (sometimes called hematopoietic growth factors) may also be used for the treatment of cancer. Some examples of CSFs include, but are not limited to, G-CSF (filgrastim) and GM-CSF (sargramostim). CSFs may promote the division of bone marrow stem cells and their development into white blood cells, platelets, and red blood cells. Bone marrow is critical to the body's immune system because it is the source of all blood cells. Because anticancer drugs can damage the body's ability to make white blood cells, red blood cells, and platelets, stimulation of the immune system by CSFs may benefit patients undergoing other anti-cancer treatment, thus CSFs may be combined with other anti-cancer therapies, such as chemotherapy. CSFs may be used to treat a large variety of cancers, including lymphoma, leukemia, multiple myeloma, melanoma, and cancers of the brain, lung, esophagus, breast, uterus, ovary, prostate, kidney, colon, and rectum.

Another type of biological therapy includes monoclonal antibodies (MOABs or MoABs). These antibodies may be produced by a single type of cell and may be specific for a particular antigen. To create MOABs, a human cancer cells may be injected into mice. In response, the mouse immune system can make antibodies against these cancer cells. The mouse plasma cells that produce antibodies may be isolated and fused with laboratory-grown cells to create "hybrid" cells called hybridomas. Hybridomas can indefinitely produce large quantities of these pure antibodies, or MOABs. MOABs may be used in cancer treatment in a number of ways. For instance, MOABs that react with specific types of cancer may enhance a patient's immune response to the cancer. MOABs can be programmed to act against cell growth factors, thus interfering with the growth of cancer cells.

MOABs may be linked to other anti-cancer therapies such as chemotherapeutics, radioisotopes (radioactive substances), other biological therapies, or other toxins. When the antibodies latch onto cancer cells, they deliver these anti-cancer therapies directly to the tumor, helping to destroy it. MOABs carrying radioisotopes may also prove useful in diagnosing certain cancers, such as colorectal, ovarian, and prostate.

Rituxan® (rituximab) and Herceptin® (trastuzumab) are examples of MOABs that may be used as a biological therapy. Rituxan may be used for the treatment of non-Hodgkin lymphoma. Herceptin can be used to treat metastatic breast cancer in patients with tumors that produce excess amounts of a protein called HER2. Alternatively, MOABs may be used to treat lymphoma, leukemia, melanoma, and cancers of the brain, breast, lung, kidney, colon, rectum, ovary, prostate, and other areas.

Cancer vaccines are another form of biological therapy. Cancer vaccines may be designed to encourage the patient's immune system to recognize cancer cells. Cancer vaccines may be designed to treat existing cancers (therapeutic vaccines) or to prevent the development of cancer (prophylactic vaccines). Therapeutic vaccines may be injected in a person after cancer is diagnosed. These vaccines may stop the growth of existing tumors, prevent cancer from recurring, or eliminate cancer cells not killed by prior treatments. Cancer vaccines given when the tumor is small may be able to eradicate the cancer. On the other hand, prophylactic vaccines are given to healthy individuals before cancer develops. These vaccines are designed to stimulate the immune system to attack viruses that can cause cancer. By targeting these cancer-causing viruses, development of certain cancers may be prevented. For example, cervarix and gardasil are vaccines to treat human papilloma virus and may prevent cervical cancer. Therapeutic vaccines may be used to treat melanoma, lymphoma, leukemia, and cancers of the brain, breast, lung, kidney, ovary, prostate, pancreas, colon, and rectum. Cancer vaccines can be used in combination with other anti-cancer therapies.

Gene therapy is another example of a biological therapy. Gene therapy may involve introducing genetic material into a person's cells to fight disease. Gene therapy methods may improve a patient's immune response to cancer. For example, a gene may be inserted into an immune cell to enhance its ability to recognize and attack cancer cells. In another approach, cancer cells may be injected with genes that cause the cancer cells to produce cytokines and stimulate the immune system.

In some instances, biological therapy includes nonspecific immunomodulating agents. Nonspecific immunomodulating agents are substances that stimulate or indirectly augment the immune system. Often, these agents target key immune system cells and may cause secondary responses such as increased production of cytokines and immunoglobulins. Two nonspecific immunomodulating agents used in cancer treatment are *bacillus* Calmette-Guerin (BCG) and levamisole. BCG may be used in the treatment of superficial bladder cancer following surgery. BCG may work by stimulating an inflammatory, and possibly an immune, response. A solution of BCG may be instilled in the bladder. Levamisole is sometimes used along with fluorouracil (5-FU) chemotherapy in the treatment of stage III (Dukes' C) colon cancer following surgery. Levamisole may act to restore depressed immune function.

Photodynamic therapy (PDT) is an anti-cancer treatment that may use a drug, called a photosensitizer or photosensitizing agent, and a particular type of light. When photosensitizers are exposed to a specific wavelength of light, they may produce a form of oxygen that kills nearby cells. A photosensitizer may be activated by light of a specific wavelength. This wavelength determines how far the light can travel into the body. Thus, photosensitizers and wavelengths of light may be used to treat different areas of the body with PDT.

In the first step of PDT for cancer treatment, a photosensitizing agent may be injected into the bloodstream. The agent may be absorbed by cells all over the body but may stay in cancer cells longer than it does in normal cells. Approximately 24 to 72 hours after injection, when most of the agent has left normal cells but remains in cancer cells, the tumor can be exposed to light. The photosensitizer in the tumor can absorb the light and produces an active form of oxygen that destroys nearby cancer cells. In addition to directly killing cancer cells, PDT may shrink or destroy tumors in two other ways. The photosensitizer can damage blood vessels in the tumor, thereby preventing the cancer from receiving necessary nutrients. PDT may also activate the immune system to attack the tumor cells.

The light used for PDT can come from a laser or other sources. Laser light can be directed through fiber optic cables (thin fibers that transmit light) to deliver light to areas inside the body. For example, a fiber optic cable can be inserted through an endoscope (a thin, lighted tube used to look at tissues inside the body) into the lungs or esophagus to treat cancer in these organs. Other light sources include light-emitting diodes (LEDs), which may be used for surface tumors, such as skin cancer. PDT is usually performed as an outpatient procedure. PDT may also be repeated and may be used with other therapies, such as surgery, radiation, or chemotherapy.

Extracorporeal photophoresis (ECP) is a type of PDT in which a machine may be used to collect the patient's blood cells. The patient's blood cells may be treated outside the body with a photosensitizing agent, exposed to light, and then returned to the patient. ECP may be used to help lessen the severity of skin symptoms of cutaneous T-cell lymphoma that has not responded to other therapies. ECP may be used to treat other blood cancers, and may also help reduce rejection after transplants.

Additionally, photosensitizing agent, such as porfimer sodium or Photofrin®, may be used in PDT to treat or relieve the symptoms of esophageal cancer and non-small cell lung cancer. Porfimer sodium may relieve symptoms of esophageal cancer when the cancer obstructs the esophagus or when the cancer cannot be satisfactorily treated with laser therapy alone. Porfimer sodium may be used to treat non-small cell lung cancer in patients for whom the usual treatments are not appropriate, and to relieve symptoms in patients with non-small cell lung cancer that obstructs the airways. Porfimer sodium may also be used for the treatment of precancerous lesions in patients with Barrett esophagus, a condition that can lead to esophageal cancer.

Laser therapy may use high-intensity light to treat cancer and other illnesses. Lasers can be used to shrink or destroy tumors or precancerous growths. Lasers are most commonly used to treat superficial cancers (cancers on the surface of the body or the lining of internal organs) such as basal cell skin cancer and the very early stages of some cancers, such as cervical, penile, vaginal, vulvar, and non-small cell lung cancer.

Lasers may also be used to relieve certain symptoms of cancer, such as bleeding or obstruction. For example, lasers can be used to shrink or destroy a tumor that is blocking a patient's trachea (windpipe) or esophagus. Lasers also can be used to remove colon polyps or tumors that are blocking the colon or stomach.

Laser therapy is often given through a flexible endoscope (a thin, lighted tube used to look at tissues inside the body). The endoscope is fitted with optical fibers (thin fibers that transmit light). It is inserted through an opening in the body, such as the mouth, nose, anus, or vagina. Laser light is then precisely aimed to cut or destroy a tumor.

Laser-induced interstitial thermotherapy (LITT), or interstitial laser photocoagulation, also uses lasers to treat some cancers. LITT is similar to a cancer treatment called hyperthermia, which uses heat to shrink tumors by damaging or killing cancer cells. During LITT, an optical fiber is inserted into a tumor. Laser light at the tip of the fiber raises the temperature of the tumor cells and damages or destroys them. LITT is sometimes used to shrink tumors in the liver.

Laser therapy can be used alone, but most often it is combined with other treatments, such as surgery, chemotherapy, or radiation therapy. In addition, lasers can seal nerve endings to reduce pain after surgery and seal lymph vessels to reduce swelling and limit the spread of tumor cells.

Lasers used to treat cancer may include carbon dioxide (CO2) lasers, argon lasers, and neodymium:yttrium-aluminum-garnet (Nd:YAG) lasers. Each of these can shrink or destroy tumors and can be used with endoscopes. CO2 and argon lasers can cut the skin's surface without going into deeper layers. Thus, they can be used to remove superficial cancers, such as skin cancer. In contrast, the Nd:YAG laser is more commonly applied through an endoscope to treat internal organs, such as the uterus, esophagus, and colon. Nd:YAG laser light can also travel through optical fibers into specific areas of the body during LITT. Argon lasers are often used to activate the drugs used in PDT.

For patients with high test scores consistent with systemic disease outcome after prostatectomy, additional treatment modalities such as adjuvant chemotherapy (e.g., docetaxel, mitoxantrone and prednisone), systemic radiation therapy (e.g., samarium or strontium) and/or anti-androgen therapy (e.g., surgical castration, finasteride, dutasteride) can be designated. Such patients would likely be treated immediately with anti-androgen therapy alone or in combination with radiation therapy in order to eliminate presumed micro-metastatic disease, which cannot be detected clinically but can be revealed by the target sequence expression signature.

Such patients can also be more closely monitored for signs of disease progression. For patients with intermediate test scores consistent with biochemical recurrence only (BCR-only or elevated PSA that does not rapidly become manifested as systemic disease only localized adjuvant therapy (e.g., radiation therapy of the prostate bed) or short course of anti-androgen therapy would likely be administered. For patients with low scores or scores consistent with no evidence of disease (NED) adjuvant therapy would not likely be recommended by their physicians in order to avoid treatment-related side effects such as metabolic syndrome (e.g., hypertension, diabetes and/or weight gain), osteoporosis, proctitis, incontinence or impotence. Patients with samples consistent with NED could be designated for watchful waiting, or for no treatment. Patients with test scores that do not correlate with systemic disease but who have successive PSA increases could be designated for watchful waiting, increased monitoring, or lower dose or shorter duration anti-androgen therapy.

Target sequences can be grouped so that information obtained about the set of target sequences in the group can be used to make or assist in making a clinically relevant judgment such as a diagnosis, prognosis, or treatment choice.

A patient report is also provided comprising a representation of measured expression levels of a plurality of target sequences in a biological sample from the patient, wherein the representation comprises expression levels of target sequences corresponding to any one, two, three, four, five, six, eight, ten, twenty, thirty, forty, fifty or more of the target sequences corresponding to a target selected from Table 1 or SEQ ID NOs: 1-1815, the subsets described herein, or a combination thereof. In some embodiments, the representation of the measured expression level(s) may take the form of a linear or nonlinear combination of expression levels of the target sequences of interest. The patient report may be provided in a machine (e.g., a computer) readable format and/or in a hard (paper) copy. The report can also include standard measurements of expression levels of said plurality of target sequences from one or more sets of patients with known disease status and/or outcome. The report can be used to inform the patient and/or treating physician of the expression levels of the expressed target sequences, the likely medical diagnosis and/or implications, and optionally may recommend a treatment modality for the patient.

Also provided are representations of the gene expression profiles useful for treating, diagnosing, prognosticating, and otherwise assessing disease. In some embodiments, these profile representations are reduced to a medium that can be automatically read by a machine such as computer readable media (magnetic, optical, and the like). The articles can also include instructions for assessing the gene expression profiles in such media. For example, the articles may comprise a readable storage form having computer instructions for comparing gene expression profiles of the portfolios of genes described above. The articles may also have gene expression profiles digitally recorded therein so that they may be compared with gene expression data from patient samples. Alternatively, the profiles can be recorded in different representational format. A graphical recordation is one such format. Clustering algorithms can assist in the visualization of such data.

Cancer Aggressiveness Prediction

In some embodiments, the methods and genomic classifiers of the present invention are useful for predicting aggressive prostate cancer. In some embodiments, the methods and genomic classifiers of the present invention are used to predict patient outcomes such as biochemical recurrence (BCR), metastasis (MET) and prostate cancer death (PCSM) after radical prostatectomy. In other embodiments, the methods and genomic classifiers of the present invention are used to predict patient outcomes such as distant metastasis-free survival (DMFS), biochemical recurrence-free survival (bRFS), prostate cancer specific survival (PCSS), and overall survival (OS).

Metastasis Prediction

In some embodiments, the methods and genomic classifiers of the present invention are useful for predicting prostate cancer metastasis following radical prostatectomy. In other embodiments, the methods and genomic classifiers of the present invention are useful for determining a course of treatment following radical prostatectomy.

The following examples are provided to further illustrate the advantages and features of the present invention, but are not intended to limit the scope of the invention. While they are typical of those that might be used, other procedures, methodologies, or techniques known to those skilled in the art may alternatively be used.

EXAMPLES

Example 1: A Genomic Classifier to Predict Aggressive Prostate Cancer in Humans A genomic classifier to predict aggressive prostate cancer in human subjects was developed as follows. To build, validate and evaluate the novel genomic model, a total of 9,901 genome-wide expression profiles from assays of biopsy and radical prostatectomy (RP) tumor tissue specimens. This included genome-wide expression, treatment and outcomes data from 1,261 prostate cancer patients treated with RP in seven retrospective institutional cohorts. A second set of de-identified, and anonymized prospective RP cases with basic demographic and pathological data from clinical use of the Decipher RP test (n=6,739) was also part of this cohort. Finally, the third set of patient data included 1,694 prospective biopsy expression profiles with basic clinical data and 253 retrospective biopsy profiles with detailed clinical data at biopsy and pathological data at RP.

The retrospective RP data from 1,261 patients, as well as a randomly selected sample of 2,041 patients, which represents 30% of the prospectively collected RP samples, were used as a development cohort for the novel genomic model. The remaining 70% (n=4,698) of the prospectively collected RP samples, as well as 1,694 prospectively collected biopsy samples and 253 retrospectively collected biopsy samples (with known pathological variables at RP) were used as validation cohorts for the novel genomic model.

Affymetrix Human Exon 1.0 ST microarray (Affymetrix, Santa Clara, Calif.) data were obtained from the formalin-fixed paraffin-embedded biopsy and RP specimens described above. Microarray processing was performed in a CLIA-certified clinical operations laboratory (GenomeDx Biosciences, Inc, San Diego, Calif.). Microarrays were normalized using Single Channel Array Normalization. (Piccolo et al. Genomics. 2012; 100(6):337-344.)

The first step in the model development was to assign a metastasis score to a large prospective cohort of 1,539 patients into high metastatic risk and low metastatic risk using the validated Decipher signature (DV1). Next, these patients were grouped into high aggressiveness category (high DV1 and GS≥8) and low aggressiveness category (low DV1 and GS≥7). To select gene features for the novel genomics classifier (DV2), we processed a retrospective cohort of 545 patients treated with RP, who had long-term follow-up and clinical recurrence outcomes (metastasis vs. no metastasis) with an additional 400 prospective patients, for whom the outcome of interest was low aggressive disease (LAD) vs high aggressive disease (HAD). We selected genes that were associated with HAD, and/or metastasis (FDR adjusted p-value 0.05). From this process, a total of 172 genes were selected to train the DV2 model. Next, we trained DV2 on a total of 1,539 prospective samples (HAD: 269, LAD: 1,270) using a GLMNET model with Elasticnet mixing parameters 0.5 and the 172 filtered genes. Model optimization and performance evaluation on training data was determined using 10-fold cross validation. DV2 generates scores from between 0 and 1, where patients with higher score will have higher probability of metastasis.

Statistical Analysis

All statistical analyses were conducted using R version 3.3.2 and all tests of significance were two-sided at the 0.05 level. The primary endpoint of the analysis is high stage disease, which is defined as pathological stage T3b or above or node positive at RP. The secondary endpoint is high grade disease, which is defined as pathological Gleason Grade Group 4 to 5. Analysis were performed in both prospective and retrospective biopsy sets. Age, pretreatment PSA (log 2 transformed) and percent positive cores were modeled as continuous variables, and clinical stage, clinical Gleason Scores were treated as categorical variables. NCCN risk category was calculated using clinical stage, clinical Gleason and pretreatment PSA. The association between the genomic models and clinical pathological features were evacuated using Spearman's rank correlation. The performance of clinical model, DV1 and DV2 were compared using area under ROC curves, univariable and multivariable logistic regression models. Firth's penalized likelihood method was used in the retrospective biopsy set to adjust for rare event.

Results

In the retrospective RP data set (n=545) 812 genes were differentially expressed between tumors of patients with metastasis compared to those without after a median follow up 17 years. We used about 30% (n=2,041) of the prospective RP data set to select genes and train the DV2 model. Using the composite endpoint, we identified 1,584 differentially expressed genes comparing tumors with high and low genomic-pathologic scores. We identified 172 genes from the intersection of these two selection steps. A subset of 1,539 prospective RP patient data were then used to train the final DV2 model, again using the genomic-pathologic endpoint in a generalized linear model (GLMnet). After training the GLMnet, the final DV2 model was comprised of 60 genes with non-zero weights (Table 1). In the training data set, DV2 achieved a 10-fold cross-validated AUC of 0.92 to predict high tumor genomic-pathologic score.

TABLE 1

| Gene Targets |
|---|
| AC020571.3 |
| ANO7 |
| ARL6IP1P2 |
| ASPN |
| AZGP1 |
| AZGP1P1 |
| DEGS1 |
| ERO1LB |
| FBXL8 |
| FMO5 |
| FTH1P2 |
| FTH1P8 |
| GLB1L2 |
| GLB1L3 |
| GLYATL1P3 |
| GMNN |
| HIF3A |

TABLE 1-continued

| Gene Targets |
|---|
| INHBA |
| KIAA1210 |
| KRT15 |
| LIPH |
| LPAR3 |
| LPGAT1 |
| MIR4435-1HG |
| MKI67 |
| MLLT11 |
| MYBPC1 |
| NADK2 |
| NR4A1 |
| NUSAP1 |
| OR51A6P |
| PABPC1 |
| PART1 |
| PCAT14 |
| PGM5P4-AS1 |
| PICK1 |
| PTTG1 |
| R3HDM1 |
| RNA5SP121 |
| RP11-121G22.3 |
| RP11-159H20.3 |
| RP11-755O11.2 |
| RP11-770G2.5 |
| RP11-923I11.3 |
| RP13-753N3.3 |
| RPL31P57 |
| SCIN |
| SESN3 |
| SETP14 |
| SLC22A3 |
| SMC4 |
| TIPARP |
| TMEM100 |
| TNFRSF19 |
| TOP2A |
| TPX2 |
| TRIQK |
| VBP1 |
| WFDC2 |
| XPO6 |

Figure 1B:
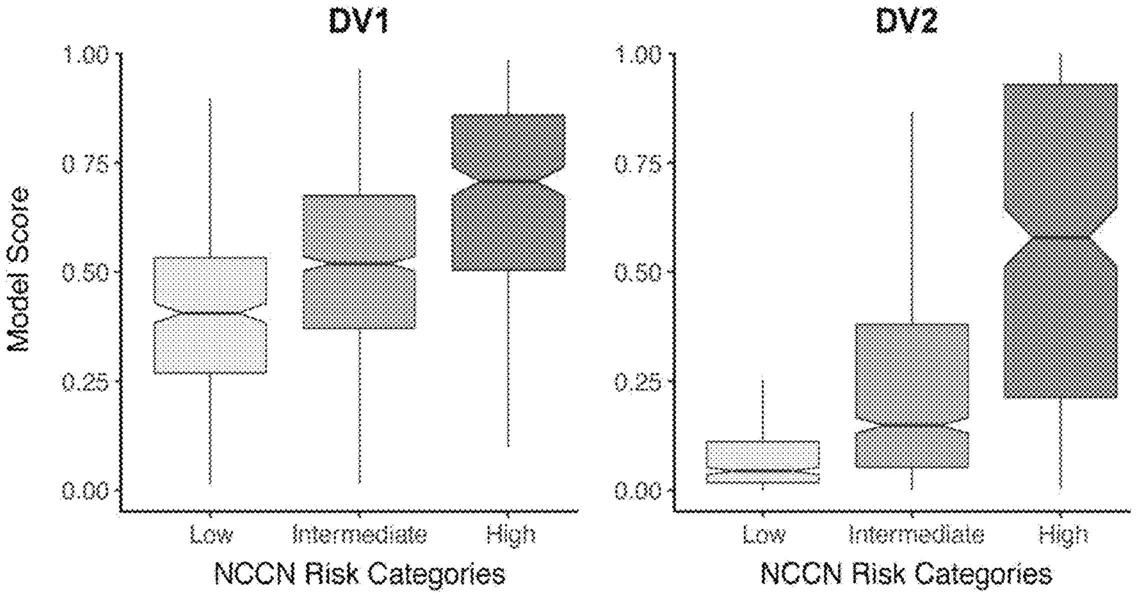
Figure 2A:
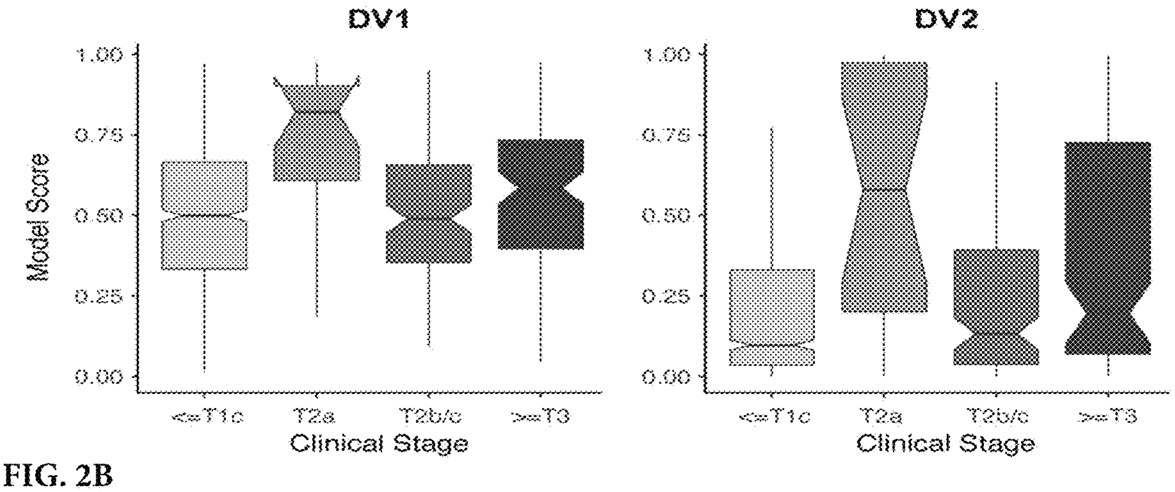
FIGS. 2A-C set forth data showing correlation of genomic classifiers with diagnostic PSA, clinical stage and percentage of positive cores.
Figure 2B:
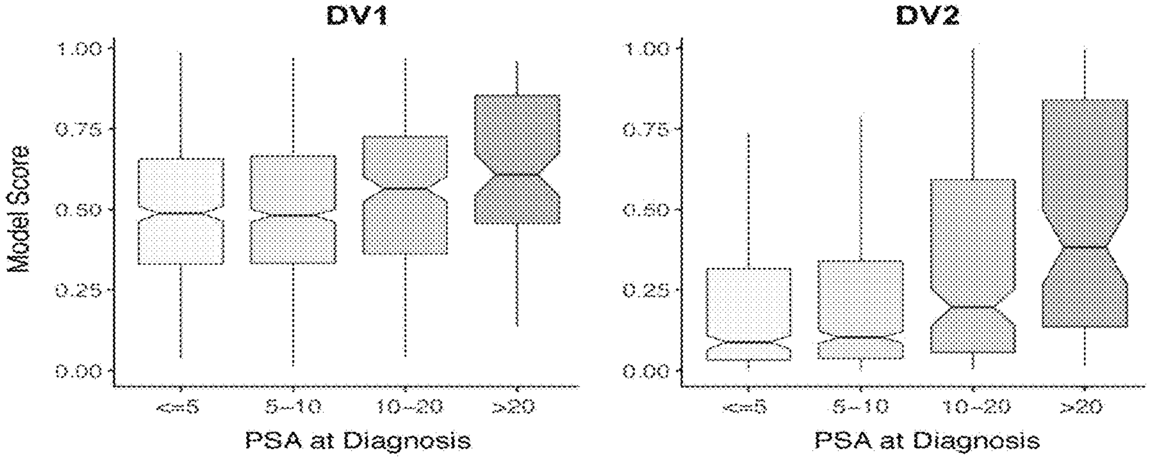
Figure 2C:
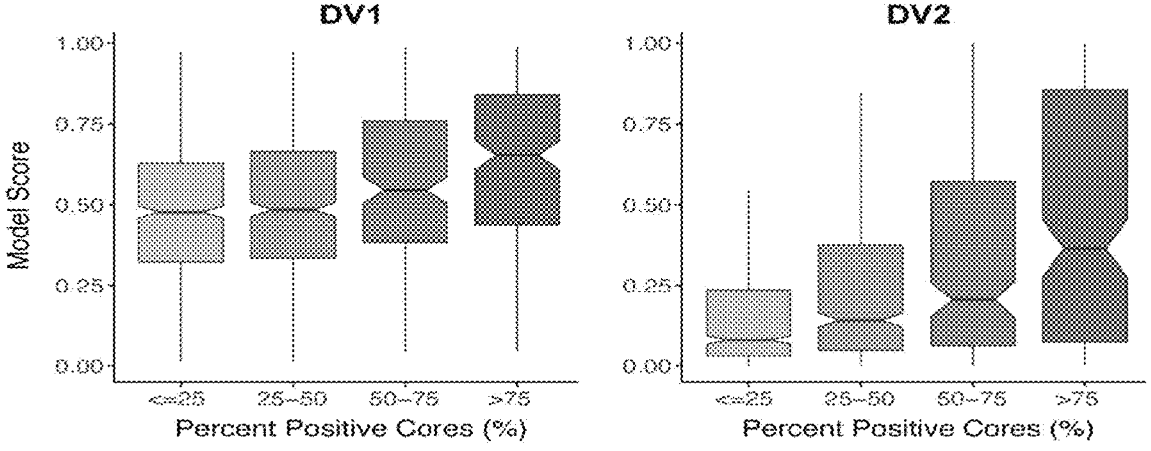
Figure 3A:
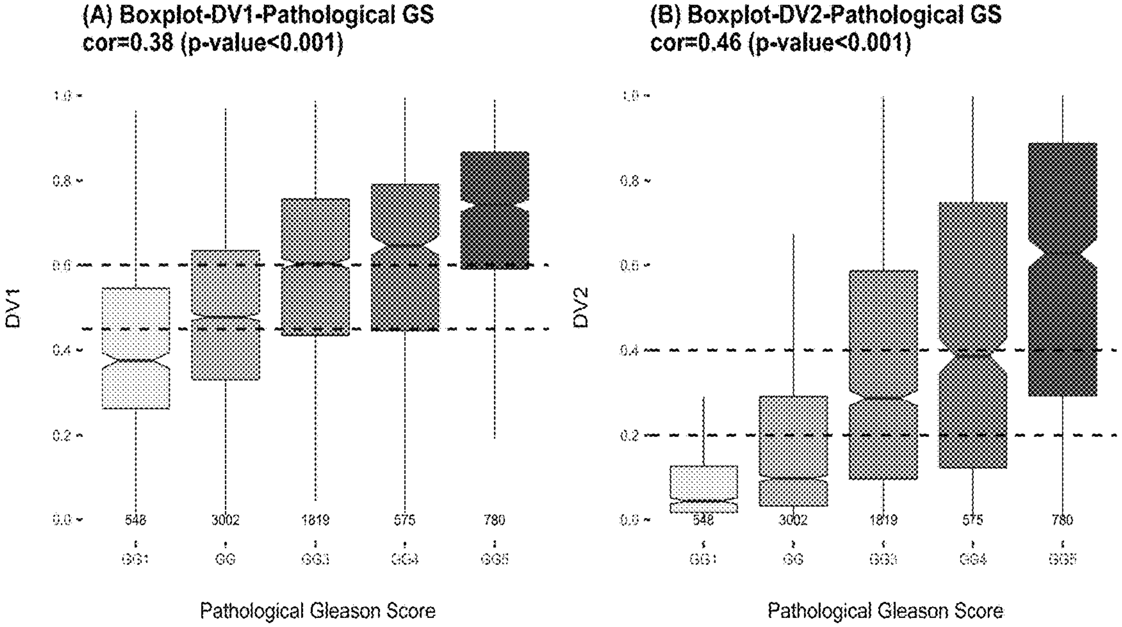
FIGS. 3A-B set forth data showing correlation of genomic classifier with pathological tumor grade and stage.
Figure 3B:
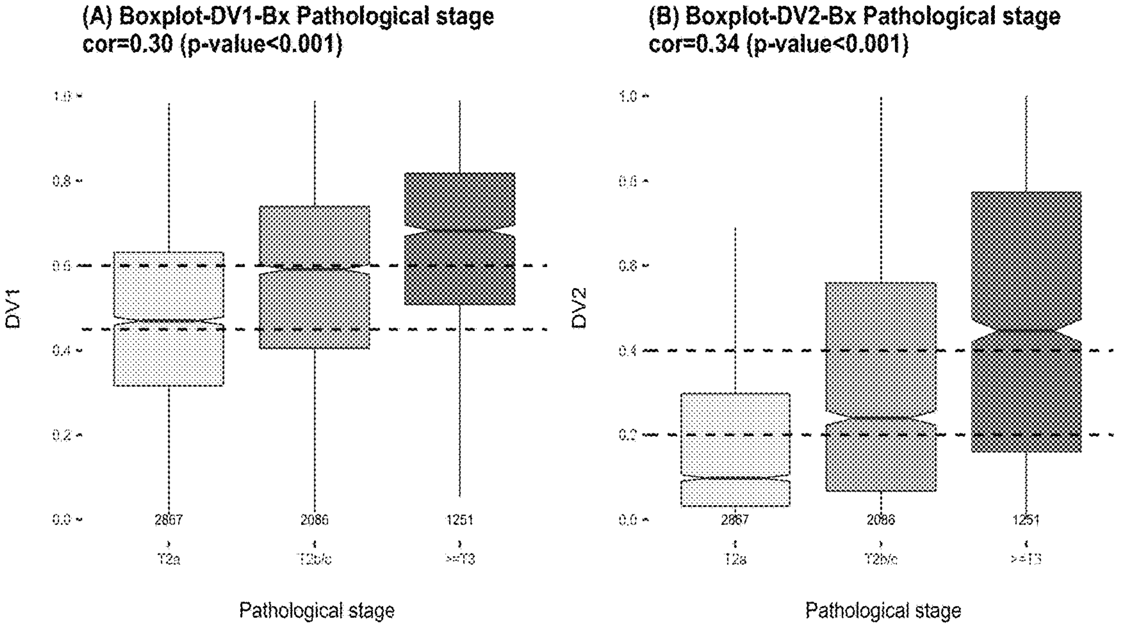
Figure 4:
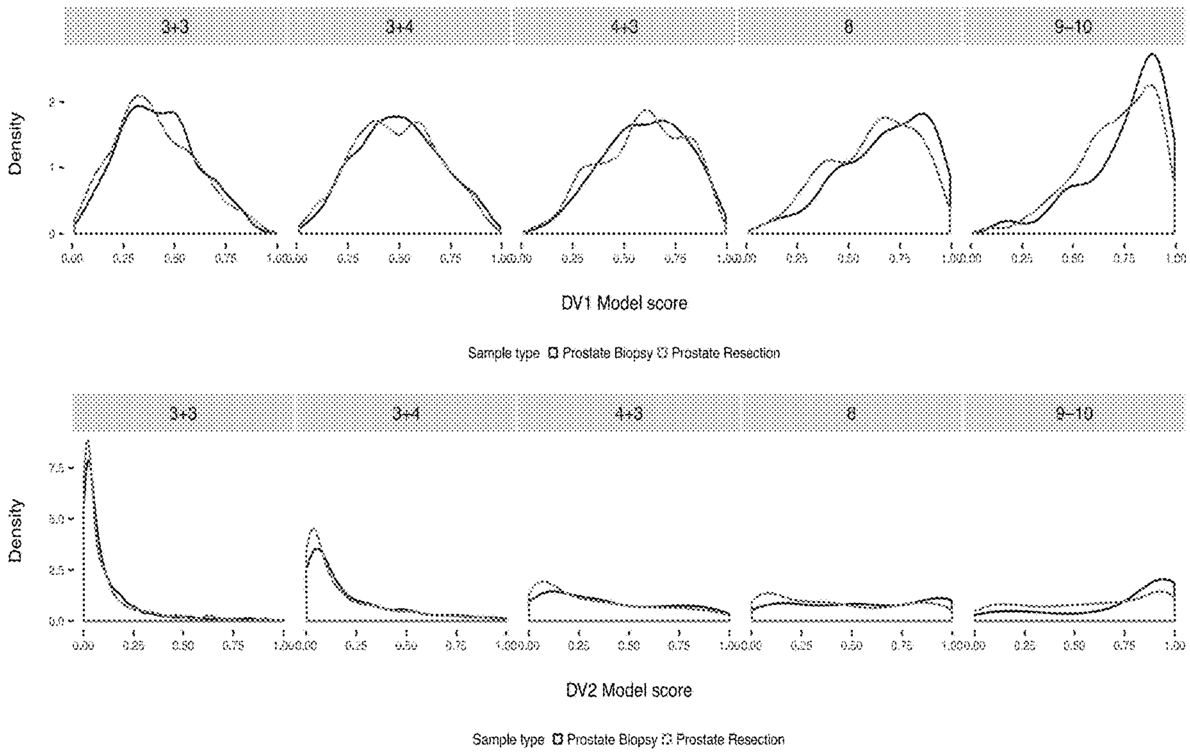
FIG. 4 sets forth data showing genomic classifier correlation with prospective RP and biopsy tumor specimens across tumor Grade Groups.

Correlation of Model Scores with Clinical Features of Prostate Cancer Tumors Sampled at Diagnosis and after RP We first evaluated DV1 and DV2 in a prospective data set of 1,694 tumor expression profiles obtained from Decipher biopsy testing, which is representative of the spectrum of non-metastatic, localized disease observed in contemporary practice (Table 2). As depicted in FIGS. 1A and 1B, both models positively correlated with biopsy Grade Groups ($p<0.001$) and NCCN risk categories ($p<0.001$) as well as diagnostic PSA, clinical stage and percentage of positive cores ($p<0.001$) (FIGS. 2A-C). Similarly, in the remaining prospective RP data set not used for DV2 training (n=6,739) model scores were positively correlated (Spearman's rank correlation, $p<0.001$) with pathological tumor grade and stage (FIG. 3A-B). Expectedly, the model scores in prospective RP and biopsy tumor specimens showed highly concordant distributions across the tumor Grade Groups (FIG. 4).

TABLE 2

| Prospective cohort for testing DV1 and DV2. | |
|---|---|
| Variables | Prospective Biopsy |
| Total | 1694 |
| **Age** | |
| Median (Q1, Q3) | 67 (61, 72) |
| **PSA** | |
| ≤5 | 451 (26.6) |
| 5-10 | 663 (39.1) |
| 10-20 | 219 (12.9) |
| >20 | 93 (5.5) |
| Unknown | 268 (15.8) |
| **Clinical Gleason Score** | |
| ≤3 + 3 | 659 (38.9) |
| 3 + 4 | 569 (33.6) |
| 4 + 3 | 232 (13.7) |
| 8 | 141 (8.3) |
| 9-10 | 93 (5.5) |
| Unknown | |
| **Clinical stage** | |
| ≤T1c | 898 (53.0) |
| T2a | 123 (7.3) |
| T2b/c | 121 (7.1) |
| ≥T3 | 18 (1.1) |
| Unknown | 534 (31.5) |
| **NCCN risk categories** | |
| Low | 340 (20.1) |
| Intermediate | 856 (50.5) |
| High | 288 (17.0) |
| Unknown | 210 (12.4) |
| **Pathological Gleason Score** | |
| ≤3 + 3 | |
| 3 + 4 | |
| 4 + 3 | |
| 8 | |
| 9-10 | |
| Unknown | 1694 (100.0) |
| **Pathological stage** | |
| pT2 | |
| pT3a | |
| pT3b | |
| pT4 | |
| Unknown | 1694 (100.0) |
| **Surgical Margin** | |
| Negative | |
| Positive | |
| Unknown | 1694 (100.0) |
| **Extracapsular Extension** | |
| Absent | |
| Present | |
| Unknown | 1694 (100.0) |
| **Seminal Vesicle Invasion** | |
| Absent | |
| Present | |
| Unknown | 1694 (100.0) |
| **Lymph Node Involvement** | |
| Absent | |
| Present | |
| Unknown | 1694 (100.0) |
| **Adverse Pathology (pT3b+/LNI+)** | |
| 0 | |
| 1 | |
| Unknown | 1694 (100.0) |

Figure 5:
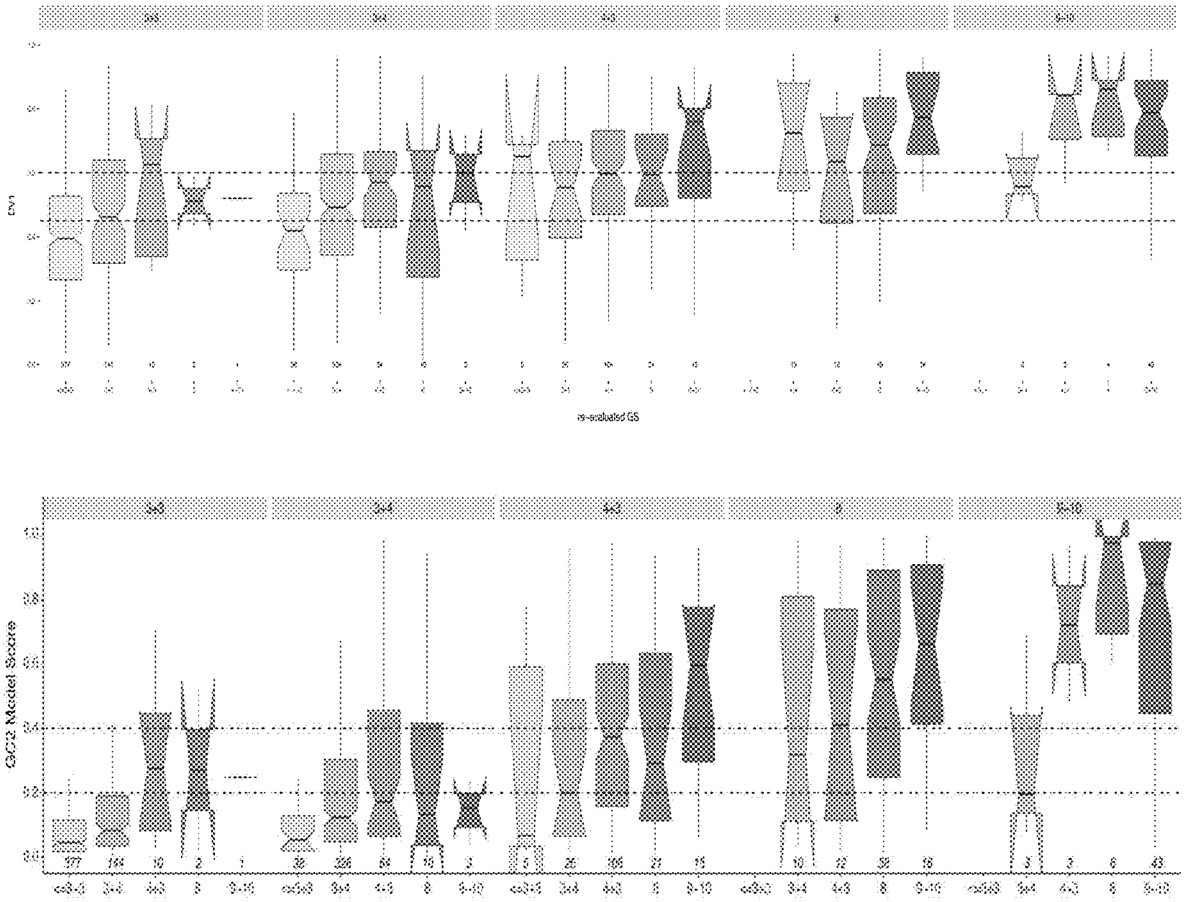
FIG. 5 sets forth data showing the distribution of genomic classifier scores among cases where tumor grading changed.
Figure 6A:
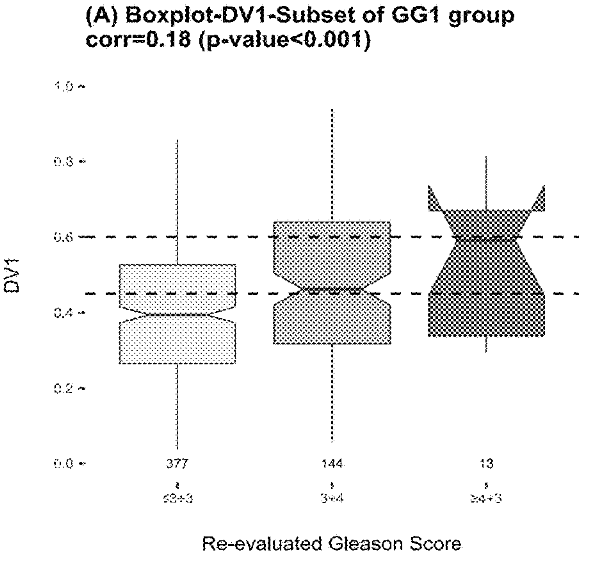
FIGS. 6A-C set forth data showing correlation of genomic classifiers with Gleason scores after pathological re-review in 1,694 biopsy samples.
Figure 6B:
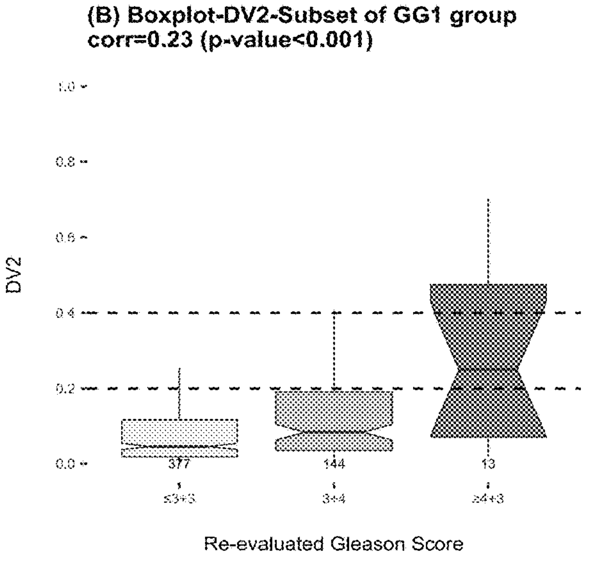
Figure 6C:
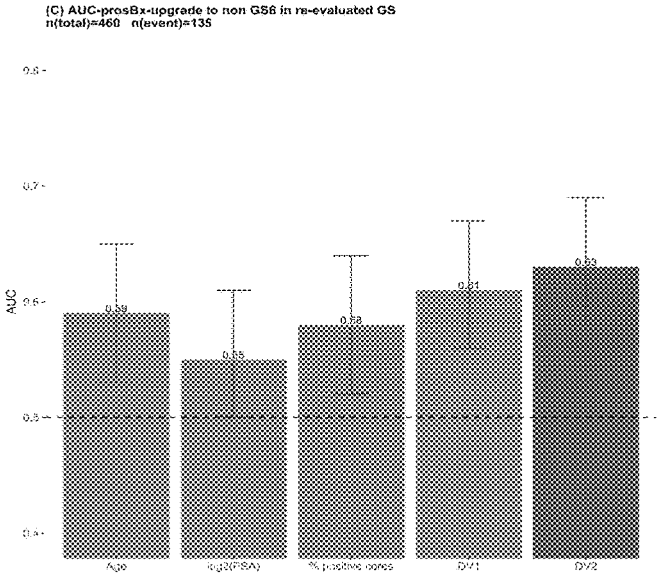

Genomic Classifier Scores Predict Presence of Higher-Grade Disease Upon Pathological Re-Review In the prospective cohort, independent pathological review was performed in order to select tumor tissue among the prostate needle biopsy cores submitted for the Decipher genome-wide expression assay. We evaluated the distribution of DV1 and DV2 scores among cases where tumor grading changed (FIG. 5). This analysis showed both genomic models were not only positively correlated ($p<0.001$) with independent histological review, but both DV1 and DV2 assigned higher scores to patients who were upgraded and lower scores to those were downgraded upon re-review The clinical impact was particularly pronounced in tumors from patients submitted for testing with an initial diagnosis of Grade Group 1 (Gleason 3+3) disease and available independent histological review. Of this subset (n=534), upgrading was observed in 157 (29%) of cases, including 13 that were upgraded to primary pattern 4 or higher (Grade Group 3-5). When these cases were assessed by DV1 and DV2, we found the DV1 model showed median scores of 0.39, 0.46, 0.59 in GG1, GG2, and GG3-5 patients, respectively (FIG. 6A). The median scores for the DV2 model in GG1, GG2, and GG3-5 patients were 0.05, 0.08 and 0.25 (FIG. 6B). The corresponding AUCs for predicting any upgrade among the Grade Group 1 tumors were 0.61 and 0.63 for DV1 and DV2; compared to 0.59, 0.55 and 0.58 for age, PSA and percent positive cores, respectively (FIG. 6C). In MVA analyses adjusting for clinical risk factors for up-grading, each 0.1 change in DV1 and DV2 scores were associated with 29% and 30% increased odds of up-grading on re-review (Table 3). Similarly, among patients initially diagnosed with Gleason 3+4 disease, both models were significant predictors of up-grading to 4+3 or above in both UVA and MVA analyses (data not shown).

TABLE 3

Logistic regression model for predicting upgrade to GG2-GG5 in prospective biopsy GG1 subset

| | | UVA | | | MVA | | |
|---|---|---|---|---|---|---|---|
| Models | variables | OR | CI | P-value | OR | CI | P-value |
| (A) DV1 | Age | 1.04 | (1.02-1.07) | 0.002 | 1.04 | (1.01-1.07) | 0.005 |
| | log(pre-op PSA) | 1.24 | (0.98-1.58) | 0.07 | 1.13 | (0.88-1.45) | 0.332 |
| | % positive cores | 1.01 | (1-1.02) | 0.026 | 1.01 | (1-1.02) | 0.019 |
| | DV1 * | 1.27 | (1.14-1.42) | <0.001 | 1.29 | (1.15-1.45) | <0.001 |

TABLE 3-continued

Logistic regression model for predicting upgrade to GG2-GG5 in prospective biopsy GG1 subset

| | | UVA | | | MVA | | |
|---|---|---|---|---|---|---|---|
| Models | variables | OR | CI | P-value | OR | CI | P-value |
| (B) DV2 | Age | 1.04 | (1.02-1.07) | 0.002 | 1.03 | (1-1.06) | 0.024 |
| | log(pre-op PSA) | 1.24 | (0.98-1.58) | 0.07 | 1.13 | (0.88-1.44) | 0.347 |
| | % positive cores | 1.01 | (1-1.02) | 0.026 | 1.01 | (1-1.02) | 0.03 |
| | DV2 * | 1.33 | (1.17-1.52) | <0.001 | 1.31 | (1.15-1.49) | <0.001 |

* per 0.1 increment of the model scores

Prediction of Higher Stage Disease at RP and Metastasis Post RP from Analysis of Diagnostic Biopsy Specimens Next, we evaluated the performance of the classifiers in a retrospective multi-institutional cohort of 253 men with Decipher biopsy data who were treated with RP and had detailed clinical and pathological data available for analysis. Demographic and clinical characteristics of this patient cohort is provided in Table 2. The median patient age at RP was 63 years (interquartile range [IQR] 57-68) with a median pre-treatment PSA of 6.60 ng/mL (IQR 4.75-11.95). At initial diagnostic biopsy, 56% of patients had Grade Group 1 and 33% clinical stage T1 disease. Accordingly, pre-treatment NCCN risk groupings classified 42% and 28% of patients as harboring low- and intermediate-risk disease, respectively. Pathological analysis of the RP specimens revealed, only 29% remained with Grade Group 1 disease and due to up-grading, 38% had Grade Group ≥3 (i.e., Gleason score 4+3 or greater) disease in the prostatectomy. Similarly, tumor pathological staging showed that 46% had extra-prostatic extension, 14% had seminal vesicle invasion and 19% had lymph node involvement. The composite end-point of high-stage disease, defined as the presence of seminal vesicle invasion or lymph node involvement was present in 21% of patients. With a median follow up post diagnosis of 7.85 years, 27 patients developed metastasis and 10 died of prostate cancer.

TABLE 4

Patient Characteristics

| Variables | Study Cohort |
|---|---|
| No. patients (%) | 253 (100.0) |
| Age at RP | |
| Median (Q1, Q3) | 62.6 (57.2, 68) |
| Pre-Operative PSA | |
| Median (Q1, Q3) | 6.6 (4.75, 12) |
| Biopsy Grade Groups | |
| Grade Group 1 | 141 (55.7) |
| Grade Group 2 | 38 (15.0) |

TABLE 4-continued

Patient Characteristics

| Variables | Study Cohort |
|---|---|
| Grade Group 3 | 27 (10.7) |
| Grade Group 4 | 31 (12.3) |
| Grade Group 5 | 16 (6.3) |
| Clinical Stage | |
| T1 | 142 (56.1) |
| T2 | 81 (32.0) |
| T3 or higher | 10 (4.0) |
| Unknown | 20 (7.9) |
| NCCN Risk Groups | |
| Low | 90 (35.6) |
| Intermediate Favorable | 29 (11.5) |
| Intermediate Unfavorable | 39 (15.4) |
| High | 72 (28.5) |
| Unknown | 23 (9.1) |
| Follow up time for Censored Patients (years) | |
| Median (Q1, Q3) | 7.85 (5.48, 10.9) |

Figure 7A:
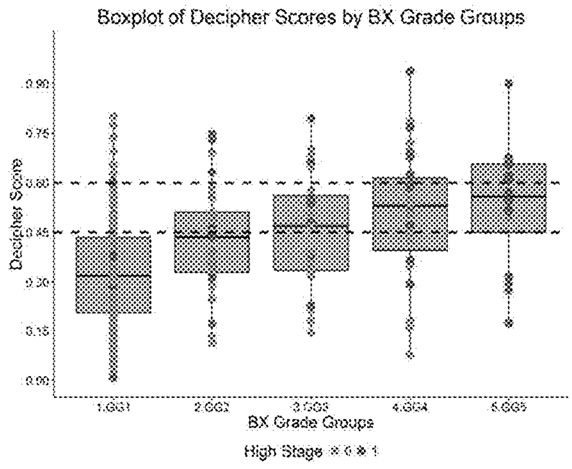
FIGS. 7A-B set forth data showing genomic classifier scores for composite endpoint: High Stage Disease (LNI or pT3b) for biopsy samples.
Figure 7B:
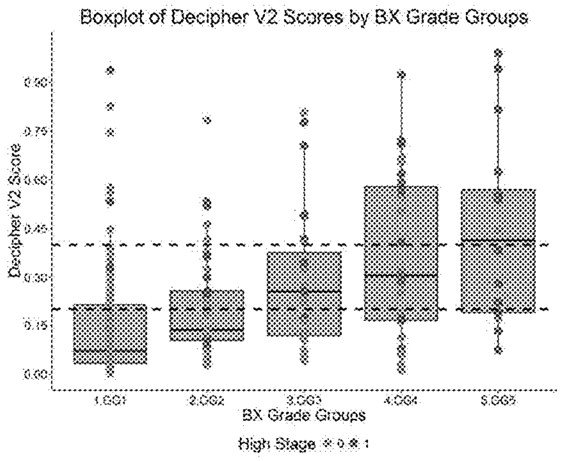
Figure 8:
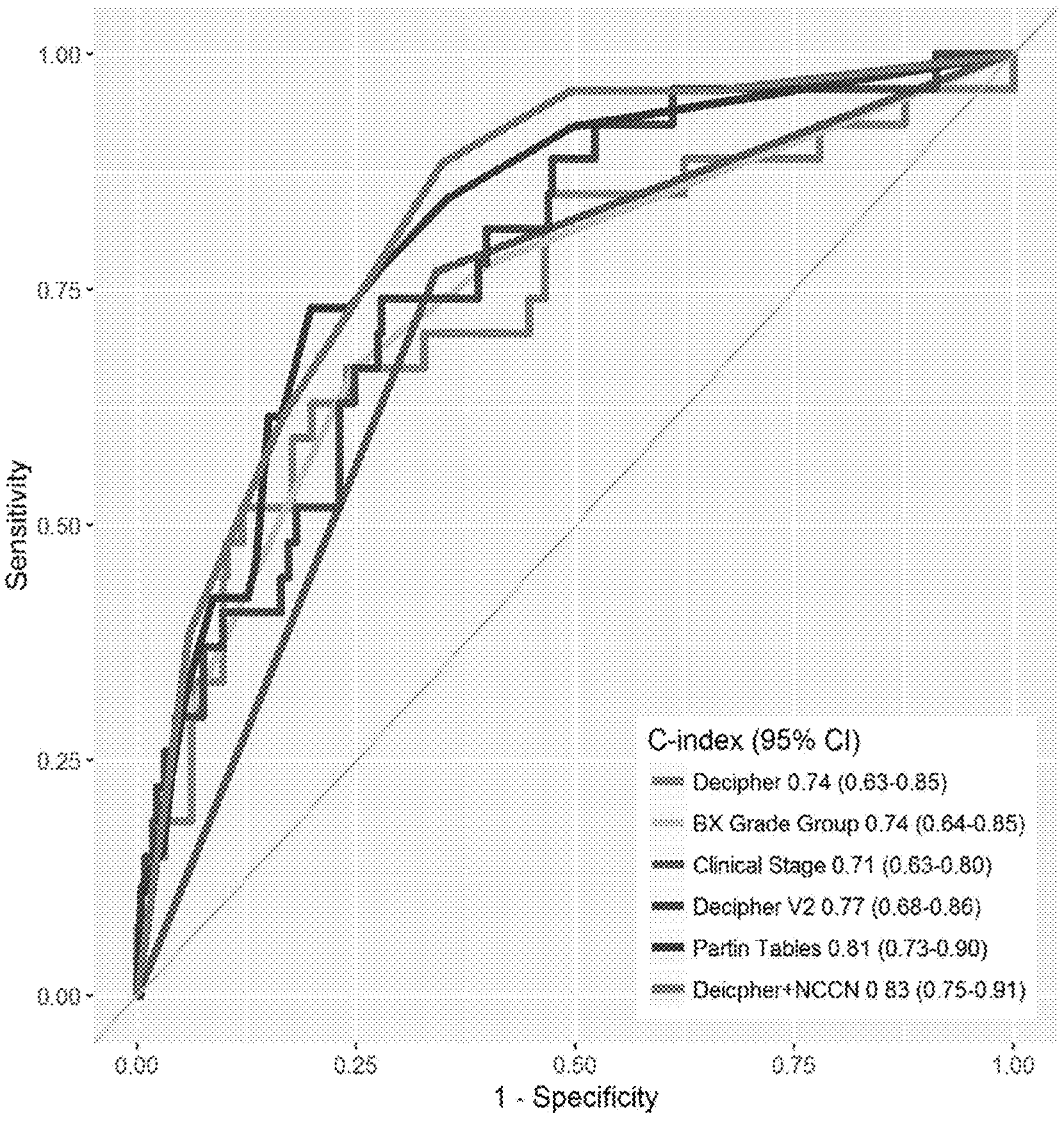
FIG. 8 sets forth data showing AUC for predicting LNI for various genomic classifiers.

We next assessed the ability of the genomic classifiers to predict the presence of lymph node involvement (LNI) upon final pathology at RP. As observed in the prospective cohorts, in the retrospective biopsy specimens both models had higher scores on average to predict patients with higher grade and stage disease ($p<0.001$) (FIGS. 7A-B). The AUC for predicting lymph node involvement (LNI) was 0.74 and 0.77 for DV1 and DV2 models respectively (FIG. 8). Similar results were obtained for the high-grade, extra-prostatic extension, seminal vesicle invasion (SVI) and a composite end-point (SVI or LNI). Using logistic regression, we found that every 0.1 increase in DV1 and DV2 model scores were associated with 18% and 40% increased odds of lymph node involvement at RP in MVA (Table 5). These data support the observation that there are many clinically lower grade patients at diagnosis that harbor high clinical-genomic risk disease which can be detected using the genomic classifiers described herein.

TABLE 5

Lymph Node Invasion. UVA/MVA Tables

| | | UVA | | | MVA | | |
|---|---|---|---|---|---|---|---|
| model | variable | OR | CI | p | OR | CI | p |
| Model 1 | BX Grade Group 2 (ref: Grade Group 1) | 1.99 | 0.45-8.74 | 0.363 | 0.82 | 0.17-4.00 | 0.805 |
| | BX Grade Group 3 (ref: Grade Group 1) | 5.27 | 1.41-9.75 | 0.014 | 2.53 | 0.60-10.65 | 0.206 |

TABLE 5-continued

Lymph Node Invasion. UVA/MVA Tables

| | | UVA | | | MVA | | |
|---|---|---|---|---|---|---|---|
| model | variable | OR | CI | p | OR | CI | p |
| | BX Grade Group 4 (ref: Grade Group 1) | 5.57 | 1.57-19.69 | 0.008 | 1.53 | 0.36-6.50 | 0.566 |
| | BX Grade Group 5 (ref: Grade Group 1) | 18.04 | 4.76-68.43 | <0.001 | 6.88 | 1.62-29.18 | 0.009 |
| | Clinical Stage ≥ T2 (ref: Clinical Stage < T2a) | 6.38 | 2.45-16.61 | <0.001 | 4.52 | 1.55-13.16 | 0.006 |
| | Decipher* | 1.66 | 1.30-2.12 | <0.001 | 1.43 | 1.10-1.88 | 0.009 |
| Model 2 | BX Grade Group 2 (ref: Grade Group 1) | 1.99 | 0.45-8.74 | 0.363 | 1.01 | 0.21-4.87 | 0.986 |
| | BX Grade Group 3 (ref: Grade Group 1) | 5.27 | 1.41-19.75 | 0.014 | 2.71 | 0.64-11.43 | 0.174 |
| | BX Grade Group 4 (ref: Grade Group 1) | 5.57 | 1.57-19.69 | 0.008 | 1.73 | 0.41-7.24 | 0.451 |
| | BX Grade Group 5 (ref: Grade Group 1) | 18.04 | 4.76-68.43 | <0.001 | 6.62 | 1.55-28.22 | 0.011 |
| | Clinical Stage ≥ T2 (ref: Clinical Stage < T2a) | 6.38 | 2.45-16.61 | <0.001 | 3.98 | 1.35-11.75 | 0.012 |
| | Decipher V2* | 1.48 | 1.26-1.75 | <0.001 | 1.28 | 1.06-1.54 | 0.010 |
| Model 3 | Partin Table | 1.09 | 1.05-1.13 | <0.001 | 1.08 | 1.04-1.13 | <0.001 |
| | Decipher* | 1.66 | 1.30-2.12 | <0.001 | 1.57 | 1.22-2.04 | 0.001 |
| Model 4 | Partin Table | 1.09 | 1.05-1.13 | <0.001 | 1.08 | 1.04-1.12 | <0.001 |
| | Decipher V2* | 1.48 | 1.26-1.75 | <0.001 | 1.42 | 1.19-1.69 | <0.001 |
| Model 5 | Decipher + NCCN Low | Reference | Reference | 1 | | — | |
| | Decipher + NCCN Intermediate | 13.84 | 1.71-111.72 | 0.014 | | | |
| | Decipher + NCCN High | 48.47 | 6.20-379.22 | <0.001 | | | |
| Model 6 | Decipher + NCCN | 2.37 | 1.68-3.33 | <0.001 | | — | |

*Decipher and Decipher V2 reported per 0.1 unit increase

Prediction of Future Metastasis

Finally, we evaluated the models for their ability to prognosticate the development of postoperative metastasis and BCR. Both models were significant predictors of distant metastasis. The addition of the genomic classifier models to clinical risk factors increased the AUC for predicting metastasis for DV1 and DV2 respectively. Similar results were observed for the prostate-cancer specific mortality endpoint. Multivariable analysis further demonstrated that the prognostic information in the GC models is independent of clinical risk factors.

These results showed that genomic classifiers of the present invention are useful for predicting presence of higher-grade disease in prostate cancer subjects. These results further showed that genomic classifiers of the present invention are useful for predicting metastasis in prostate cancer subjects. These results suggested that the methods and markers of the present invention would be useful for diagnosing, prognosing, determining the progression of cancer, or predicting benefit from therapy in a subject having prostate cancer. The results showed that the subtyping methods of the present invention may be used to determine a treatment for a subject with prostate cancer.

TABLE 6

Univariate Analysis of Target Genes

| | coef | exp. coef. | se. coef. | z | Pr . . . z . . . |
|---|---|---|---|---|---|
| AC020571.3 | −1.018756 | 0.361043799 | 0.375053027 | −2.716298565 | 0.006601635 |
| ANO7 | −2.728934592 | 0.065288812 | 0.407289095 | −6.700239767 | 2.08078E−11 |
| ARL6IP1P2 | 0.211639304 | 1.235702092 | 0.157938082 | 1.340014397 | 0.180240664 |
| ASPN | 0.734576998 | 2.084600016 | 0.289962212 | 2.533354234 | 0.011297672 |
| AZGP1 | −1.081098477 | 0.339222692 | 0.227282585 | −4.756626977 | 1.96854E−06 |
| AZGP1P1 | −1.259174028 | 0.283888413 | 0.447362548 | −2.814661249 | 0.004882867 |
| DEGS1 | 0.815286842 | 2.259823792 | 0.272577955 | 2.99102267 | 0.002780449 |
| ERO1LB | 1.958519505 | 7.088824322 | 0.431696059 | 4.536801915 | 5.71137E−06 |
| FBXL8 | −1.902271331 | 0.149229285 | 0.527510253 | −3.606131483 | 0.000310796 |
| FMO5 | −1.562260035 | 0.209661693 | 0.801119597 | −1.950095892 | 0.051164691 |
| FTH1P2 | 0.940180631 | 2.560443872 | 0.276199928 | 3.403985792 | 0.000664102 |
| FTH1P8 | 0.197938579 | 1.218887527 | 0.207877904 | 0.952186721 | 0.341002294 |
| GLB1L2 | −4.026340996 | 0.017839485 | 0.847895107 | −4.748631004 | 2.04798E−06 |
| GLB1L3 | −5.550073036 | 0.003887173 | 1.064791391 | −5.212357164 | 1.86456E−07 |
| GLYATL1P3 | −0.620320485 | 0.537772062 | 0.23410423 | −2.649761971 | 0.00805485 |
| GMNN | 2.092700107 | 8.106774799 | 0.551073019 | 3.797500574 | 0.000146162 |
| HIF3A | 0.252313025 | 1.286998838 | 1.03815061 | 0.243040868 | 0.807973738 |
| INHBA | 2.684983887 | 14.65796519 | 0.765096464 | 3.509340344 | 0.00044922 |
| KIAA1210 | −1.02505771 | 0.35877576 | 0.853948067 | −1.200374764 | 0.229993825 |
| KRT15 | −1.670025537 | 0.188242258 | 0.626029324 | −2.66764746 | 0.007638436 |
| LIPH | −3.364385361 | 0.034583266 | 0.944887437 | −3.56062027 | 0.00036998 |
| LPAR3 | −0.844270997 | 0.429870621 | 0.436019683 | −1.936313953 | 0.052829261 |

TABLE 6-continued

Univariate Analysis of Target Genes

| | coef | exp. coef. | se. coef. | z | Pr . . . z . . . |
|---|---|---|---|---|---|
| LPGAT1 | 1.220418809 | 3.388606616 | 0.389461365 | 3.133606872 | 0.00172672 |
| MIR4435-1HG | −0.367725003 | 0.692307538 | 0.604570586 | −0.608241637 | 0.543027223 |
| MKI67 | 6.792362118 | 891.0157626 | 0.946815078 | 7.173905732 | 7.28861E−13 |
| MLLT11 | 0.81044494 | 2.248908393 | 0.732562253 | 1.106315452 | 0.268590006 |
| MYBPC1 | −1.152171977 | 0.315949788 | 0.249798588 | −4.612403886 | 3.98039E−06 |
| NADK2 | 0.470137995 | 1.600215 | 0.636159807 | 0.739024991 | 0.459891822 |
| NR4A1 | −1.596285011 | 0.202647956 | 0.265223126 | −6.01864941 | 1.75878E−09 |
| NUSAP1 | 4.415561211 | 82.72825585 | 0.707849482 | 6.237994554 | 4.43216E−10 |
| OR51A6P | −1.959242252 | 0.140965197 | 0.66373524 | −2.951843046 | 0.003158834 |
| PABPC1 | 0.755077881 | 2.127777231 | 0.278842085 | 2.707905018 | 0.00677094 |
| PART1 | −2.421642916 | 0.088775647 | 0.651032126 | −3.71969803 | 0.000199461 |
| PCAT14 | −0.397683215 | 0.671874834 | 0.089040775 | −4.466304519 | 7.95823E−06 |
| PGM5P4-AS1 | −1.064105371 | 0.345036396 | 0.529431364 | −2.009902402 | 0.044441519 |
| PICK1 | −3.052693795 | 0.047231521 | 0.94395319 | −3.233946162 | 0.001220925 |
| PTTG1 | 5.054760024 | 156.7669056 | 0.720961903 | 7.011133323 | 2.364E−12 |
| R3HDM1 | 1.124121147 | 3.077510979 | 0.688704174 | 1.632226417 | 0.102631798 |
| RNA5SP121 | −0.159834272 | 0.852285025 | 0.28514785 | −0.560531219 | 0.575117152 |
| RP11-121G22.3 | 0.54826177 | 1.730242842 | 0.289930617 | 1.891010254 | 0.058622975 |
| RP11-159H20.3 | 1.086933391 | 2.965167109 | 0.387286134 | 2.80653836 | 0.005007695 |
| RP11-755O11.2 | −2.21597345 | 0.10904731 | 0.708352751 | −3.128347348 | 0.001757923 |
| RP11-770G2.5 | 0.656284161 | 1.927616298 | 0.511472642 | 1.283126615 | 0.199447721 |
| RP11-923I11.3 | 0.012186678 | 1.012261238 | 0.387323413 | 0.031463831 | 0.974899637 |
| RP13-753N3.3 | 0.391755198 | 1.479575464 | 0.350940795 | 1.116299967 | 0.264293756 |
| RPL31P57 | −0.723295796 | 0.485150661 | 0.142803819 | −5.064961152 | 4.08484E−07 |
| SCIN | −3.777998567 | 0.022868415 | 1.097206642 | −3.443288093 | 0.000574687 |
| SESN3 | 0.677784496 | 1.969509438 | 0.24823972 | 2.730362794 | 0.006326466 |
| SETP14 | 0.630624885 | 1.878784237 | 0.289203892 | 2.180554631 | 0.029216374 |
| SLC22A3 | −2.210758134 | 0.109617512 | 0.47027084 | −4.701031715 | 2.5885E−06 |
| SMC4 | 5.768903761 | 320.1865391 | 0.88769243 | 6.498764174 | 8.09824E−11 |
| TIPARP | −2.217536636 | 0.108876982 | 0.550632508 | −4.027253394 | 5.64322E−05 |
| TMEM100 | −2.882377174 | 0.056001479 | 1.005740682 | −2.86592481 | 0.00415793 |
| TNFRSF19 | −2.416480569 | 0.089235122 | 0.696215197 | −3.470881677 | 0.000518753 |
| TOP2A | 4.112985372 | 61.12893806 | 0.454912893 | 9.041259181 | 0 |
| TPX2 | 5.182498017 | 178.1272206 | 0.647974958 | 7.997991208 | 1.22125E−15 |
| TRIQK | 1.167161854 | 3.212861116 | 0.384612581 | 3.034642943 | 0.002408206 |
| VBP1 | 0.783207999 | 2.188481664 | 0.471928306 | 1.659591065 | 0.096996747 |
| WFDC2 | −1.140244348 | 0.319740884 | 0.746624189 | −1.527199849 | 0.126711324 |
| XPO6 | 0.374919547 | 1.454874361 | 0.425155032 | 0.881841962 | 0.377862276 |

TABLE 7

Target Sequences

| SEQ ID NO. | Gene | Affy Probeset ID | Sequence |
|---|---|---|---|
| 1 | MLLT11 | 2358694 | TCGCCAGGCATTTCGGGGCAAAACGAAGCGGAGCCCCCCAAA CCCCCAGACCTAACCAAGTTCAGAGATTCGCAGAAGCACGCC CCCCACCCCAAATTTATTGTGCTCTACCCAAAATGGAATAGGA CTAGGTTTATTTACCCATTGTGAGGGTAGAGAGGCGAGTCTGG AGGAGCAGGGATTGGGAGAAGGGGTGGAAAAATACTCTGATT CTTAAAAATACTTTGTAACCTAAAGTCCTTAAATTGTGGAAGAA AGGAATACTCCTCCTTTCCATTGTAGTCTAGAGTTAAGATTTCA AATCCATAAATTAGAGGACCTAAAATTAGAGGGCAATTAACTG CTCATTCATTGGGCCCCCAGTCAGCACGGGGGTGCTGGAAGA GATCGGGAATAATAGCGCAGACCAATGAGCCTAGGGAGATGC TTTCATCGTCTCTCCTTCCCTCAAGTGTTCTGGAACCTATCATT TGAATTAGCCGAGTCAGGCAGGAGGGGGCGGGGAATCCTTC CGCCCTTCTTAGGAGGGGCTGCATTGCAGGGGGAGAGTGAA CTGACAGACTCAGTCACTGAAGAGGGAAAAGGAGTGAGAAGA CAAAGCCGTCAAAGCCCCAACAGCTTTGTATTTCTCCAGCCCG GCGCAGA |
| 2 | MLLT11 | 2358695 | GGGACCCTGTGAGTAGCCAGTACAGTTC |
| 3 | MLLT11 | 2358696 | AGAACTGGATCTGTCGGAGCTGGAAGGCCTGGGTCTGTCAGA TACAGCCACCTACAAGGTCAAAGACAGCAGCGTTGGCAAAAT GATCGGGCAAGCA |
| 4 | MLLT11 | 2358697 | GTGATGGCCTCCTTGAGTACAGCACCTTCAAC |
| 5 | MLLT11 | 2358698 | TGGAGAGCTCCCATTGCCAGCATCCA |

TABLE 7-continued

Target Sequences

| SEQ ID NO. | Gene | Affy Probeset ID | Sequence |
|---|---|---|---|
| 6 | MLLT11 | 2358699 | TCAAGCAATGGAGTACTGGGTCACAGGGATTCCTCCTTTCCCC CCCAAATATTAACTCCAGAAACTAGGCCTGACTGGGGACACCT GAGAGTAGTATAGTAGTGCAAAATGGAAGACTGATTTTTGACT CTATTATAATCAGCTTCAGAGATTCCTTAAACCTTCCTAATTTC CTGCTCCAGGGCAGTAAACACAAATATTTCTTCAAGGGGTGAT GAAAACCTCGGAAGTTTTAATTTGAGGTTATCTGCTACGAAAC AGTATTTCTAAAAGGCTAAAGTGATAAGTCTCTTGCTTTTTTTT GATCCTGCTCTTATATTCTTTTTTTTCCTCAGAGAAATCAGGAG GGTAGTTAGAGGTATAAAACAGGAGGAAATATTATGGAAAATG AAAATAGGGAAAATAATTGAATCATTTTAGAAGTAGCTAATTTC TTTTCTCAAAAGAGTGTCCCTTCTTCACACCTACTCACTTTACA ACTTTGCTCCTAACTGTGGGTTGAAAACTCTAGCTAAAGAAAG TTATCAAATCTTAACATGCATTCCTACTATTATGATAGTTTTTAA GGTTTCAATTCAATCTTCTGAACGGCATAAGTCCTATTTTA |
| 7 | DEGS1 | 2382361 | GGGAGCGCGCCCAGCATCGCTTGGGCCTCCTCCACCCGCTC AGGAGGGGAAACAGGAGAGCCGGGAGCACAACAGCCTCGCG CGCCCGCCGCCGCCTCAGCCTTAGGGGAGGCCACTACGCCT CTGGTTACATTTCTTG |
| 8 | DEGS1 | 2382362 | TAGTCAGGACAGGATAAACAGTCGCTATATTAAGACCATGTAC GTGTCCCTAGACCTAGTTCT |
| 9 | DEGS1 | 2382363 | TCCGCCCACGCCTCCGTCTCCTCCGCGCTCCGCCACAGCCG GCCGACACCACACCAGCCGGGGAGCCGCCG |
| 10 | DEGS1 | 2382364 | CTAGTCTGCAAGCCACCGCTGTCGCC |
| 11 | DEGS1 | 2382365 | GACTTCGAGTGGGTCTACACCGACCAGCCGCA |
| 12 | DEGS1 | 2382366 | GTGAGGGCCAGCGGGCGCCCCGTTAT |
| 13 | DEGS1 | 2382367 | GGGCCCTGCGCGGTCGTGGGCGCCGGAGGCCC |
| 14 | DEGS1 | 2382368 | CGGAGCCGCGCAGCTCCGACCCTTCCGCGAAGAGGCGCAGG CGCGTCCCCGAGCGCGGGAGTCCCCGCCAGGCCCACGCCG GCCGGTTGGGGCGAAGGGTGTCCCCGGCTGTGCCAGCCTTG AGTAGATCTTTTCGCTAGAAGATTCCTGTGCCCTCAGGTGGGC GCCCTTTCCTCTCACCACTCCCTCTCCTCCGGAGCGGGCC |
| 15 | DEGS1 | 2382369 | TTGGGGCTGCCTGAGTGCTAGGCAGGGTGTGGTCCTGGGCAT CCTTGGGCCTACCAGCGAGCCCT |
| 16 | DEGS1 | 2382370 | GGTCTCAGATGATGCGCCTGCCATGGCCTCCCAAAGTCCTGG GATTACAGGCGTGAGCCACCCTGCCAGGCCACATATGATATA TTTTATCAATGCCTTATCTACATGTTACATAGGAATAATCTAGC GTCCTACCTGTGTAAAAACCAACTCTGGAATACTGAAACTGAG CTACT |
| 17 | DEGS1 | 2382371 | TTGATGAAACCTGATCCCAATTTGATATGGATTAT |
| 18 | DEGS1 | 2382372 | TCTGGAAGTTATCAATACCGTGGCACAGGTCACTTTTGACATT TTAATTTATTACTTTTTGGGAATTAAATCCTTAGTCTACATGTTG GCAGCATCTTTACTTGGCCTGGGTTTG |
| 19 | DEGS1 | 2382373 | TGGCCAGGCTAGTATTTTGTCAGTCCAAGCAGTTCATTAAAAA AAAAAAAAACAAAAAGAGCAAGAATATAAATACTGCATCTTCCA GCCTACTTTTACAAAGGGTTCACTCTTGGGTCCTTAAGCTTAG TGGT |
| 20 | DEGS1 | 2382374 | CTGGAGTTTCCTGGATGGGTGCAGT |
| 21 | DEGS1 | 2382375 | GCTGAATACTATGACAACCTCCCTCACTACAATTCCTGGATAA AAGTACTGTATGATTTTGTGATGGATGATACAATAAGTCCCTAC TCAAGAATGAAGAGGCACCAAAA |
| 22 | DEGS1 | 2382376 | ATATCATTAGTGCCAAAGGGATTCTTCTC |
| 23 | DEGS1 | 2382377 | AAGAGCTCGGTGATACCAAGAAGTGAATCTGGCTTTTAAACAG TCAGCCTGACTCTGTACTGCTCAGTTTCACTCACAGGAAACTT GTGACTTGTGTATTATCGTCATTGAGGATGTTTCACTCATGTCT GTCATTTTATAAGCATATCATTTAAAAAGCTTCTAAAAAGCTATT TCGCCAGGCACGG |

TABLE 7-continued

Target Sequences

| SEQ ID NO. | Gene | Affy Probeset ID | Sequence |
|---|---|---|---|
| 24 | DEGS1 | 2382378 | AAGCTATTTCTAGTTTATTTCACTATAAAGTTTTGCTTTATTAAA AAGCTAATAAACAGCTATTAATCAC |
| 25 | DEGS1 | 2382379 | CTATATAATATGGTAACTTGGGTACCGGGGGAACTTTAAAATTT CATCTCAAAAATAATTTTTAAAAAGCCTGAGGTATGATATAGCA TAAAAGATTGAGATGAAAATATATTTCCCTGTAAGCTGAATTAC TCATTTAAAAATTTTAACTTCTATATGGGACCCGAATTA |
| 26 | DEGS1 | 2382380 | CTGCTGAATCCTGTACAGCCTTACTCATAAATAA |
| 27 | FTH1P2 | 2384397 | ACTTTGCCAAATACTTTCTTCACCAATCTCATGAGGAGAGGGA ACATGCTGAGAAACTG |
| 28 | FTH1P2 | 2384398 | GAAAAAAGTGTGAATCAGTCACTAC |
| 29 | FTH1P2 | 2384399 | TACCTGAATAAGCAGGTGAAAGCCATCAAAGAAT |
| 30 | FTH1P2 | 2384400 | TCTGGCTCGGCGGAATACCTCTTAGACAAGCA |
| 31 | LPAR3 | 2420617 | TTCACGGGCCACCTAGACTTTCCAGTCTAGGACTAGAGCTGTA GCAATGATCTGTTGTGCTGTACAAGAAAAGAGAAAGAGGTGTT CATTTGAGAACAGATGTTTTTATACATCAGAGTAAAAGCTGTAT TGAAGAGCAGGCTGAATCCCTTCCATATAGAATGAAATATGAG CTTGACCCCAGTCCTTATCTTCAGTTACCTCCATACCAACTGG TGGCATGTTGGATTTAGCATGTAGAATAATTTCCCATCTCTTAT TTTTCCCAAGGTTAATGGCATCCTTCTGGTACCTGGCTTACAT GTGAACTGAATTT |
| 32 | LPAR3 | 2420618 | TATATATATTCCTGTTTTTACTGATTTTTATTGATTTTGTTCAAA |
| 33 | LPAR3 | 2420619 | TTACCTGTCTCTAACAAAGCCCATGTACAGTGTTATTTGAGGTC TCCATTAATCACTGCTAGATTTCTTTAAAAAATTTTTTTTCATAG TTTAAAAGCATGGGCAGTAAAGAGAGGACCTGCTGCATTTAGA GAAAGCACAGAAACGGGAGAGGTTCGGCGGGTCCCTGCTTGT CCTATGAACTGCTCAGAGCTCCTGTCAGTCCAGCTGGGCCTT CTGGGTTCTGGCACCATTTCGTAGCCATTCTCTTT |
| 34 | LPAR3 | 2420620 | CAGTCTGCAATAAAAGCACTTCCTAA |
| 35 | LPAR3 | 2420621 | GGTTCTGCTCCTCGACGGCCTGAACTGCAGGCAGTGTGGCGT GCAGCATGTGAAAAGGTGGTTCCTGCTGCTGGCGCTGCTCAA CTCCGTCGTGAACCCCATCATCTACTCCTACAAGGACGAGGA CATGTATGGCACCATGAAGAAGATGATCTGCTGCTTCTCTCAG GAGAACCCAGAGAGGCGTCCCTCTCGCATCCCCTCCACAGTC CTCAGCAGGAGTGACACAGGCAGCCAGTACATAGAGGATA |
| 36 | LPAR3 | 2420622 | ATGGGAGAGCTCCAGTGGAGAAGGC |
| 37 | LPAR3 | 2420623 | ATGGTGGATCGGCAGTACAGCACTGTTAGCGCAG |
| 38 | LPAR3 | 2420624 | TCCATGCCAAATGTGATCTTGAACTTGA |
| 39 | LPAR3 | 2420625 | TCAGCGTCAGGGAAACCTGGCAGCAGTTAATGAGGCCTGGCC ATGGCTGTAGGCCAGGTTGGGAATCAGGAAGGGTAGATGCAT CCTC |
| 40 | LPAR3 | 2420626 | ACTGGGAGAACTAGTGAAGATGCTGAGGTGACACAGCAGACC CAGGTTGTTCTGGAGGCTCTACCTGAGTTTGCATGCAGCTTAG AAACTAAAACTGTGTCTTCTCAGTTGCATGGAGTGGACTCTCA GAAGGACATAGAGATTGTC |
| 41 | LPAR3 | 2420627 | GACTCCTTATCACCAGGCTCGAGCACTAGCAGGAGGGACACT GGTGCTACGTGGCAGAGACCTTCTTCCAGTTATCTTAGCAACT GGTGGATCCCAGGGACTCCCCTTAGAGTTTCTACATTATTGGG CTTTCAGAACTGGACTCACCAATGAGTCAGGGAGACAGTGTTC CTGCTCTCTATCTGTGCTGAGTCTGCCTATCTGGGCCCATGAC AAGGCTTATGATA |
| 42 | LPAR3 | 2420628 | ATGCAGGCCCAATTAAATAGGCCTGTGGCCAGTCTTCAGCCC ACAGCTGAACTGCCTCATCTGGCAAGAAAGAGCCCATGTAGG ATCTTGAGTGT |

TABLE 7-continued

| Target Sequences | | | |
|---|---|---|---|
| SEQ ID NO. | Gene | Affy Probeset ID | Sequence |
| 43 | LPAR3 | 2420629 | TGTGGCGGAAAGATCCCATTACCTCAAAGAATCAATACTGTTG AGAGATTTGACCAAGTTCACTTTGTAAATTACTGCAGCATTGTG GCTGCAGCTCTGGACCTTCTAGTTCCTGCTTCTTCTAGTGGGT CCCAACTTCTTGC |
| 44 | LPAR3 | 2420630 | TTGTTTTCAGGGCAGGCCGTCAATCGGTGGGTGCAAAAATGC AGTTGCCACTCAGTTGCTGCCCCTACGCTGCTGTTTGACA |
| 45 | LPAR3 | 2420631 | GAAGGCAAAGTAGCAGTAAGCAACGAAACGATAGCTCAAGTT CTCATGCTAGGAGGAAATGGGTGA |
| 46 | LPAR3 | 2420632 | ATACAGCATGATAGAGACAAGGATTCCAAAATCCTAGGTGGAG AGAACAGGACCCTTTGTGAGACAGTCATGGTCACA |
| 47 | LPAR3 | 2420633 | CCTCATCATGGTTGTGGTGTACCTGCGGATCTACGTGTACGTC AAGAGGAAAACCAACGTCTTGTCTCCGCATACAAGTGGGTCC ATCAGCCGCCGGAGGACACCCATGAAGCTAATG |
| 48 | LPAR3 | 2420634 | ACACTGCTCATTTTGCTTGTCTGGGCCATCGCCATTTTTATGG GGGCGGTCCCCACACTGGGCTGGAATTGCCTCTGCAACATCT CTGCCTGCTCTTCCCTGGCCCCCATTTACAGCAGGAGTTACCT TGTTTTCTG |
| 49 | LPAR3 | 2420635 | TTCTAATTCTCTGGTCATCGCGGCAGTGATCAAAAACAGAAAA TTTCATTTCCCCTTCTACTACCTGTTGGCTAATTTAGCTGCTGC CGATTTCTTCGCTGGAATTGCCTATGTATTCCTGATGTTTAACA CAGGCCCAGTTTCAAAAACTTTGACTGTCAACCGCTGGTTTCT CCGTCAGGGGCTTCTGGACAGTAGCTTGACTGCTTCCCTCAC CAACTTGCTGGTTATCGCCGTGGAGAGGCACATGTCAATCATG AGGATGCGGGTCCATA |
| 50 | LPAR3 | 2420636 | ATGGACAATAAATTCTTAAGCAACAAAAGAAAATACTGGGTCA CAAGCAACTGGGTAGCTCTGATGGA |
| 51 | LPAR3 | 2420637 | AGGAACTAGTTATCCTGTGGAGATCTGGACGTCTAACTATTTG GACAACACTTACATTGATTGTCACTATCATATAACTAAGAAAAT AGGTCATTTTGGCAAAAATTTTTTCTTTGTCTTTAGAATTTGAAA CTTTGAGGTTTTGATTTAATTACATATGACACTCCTCTTGTCTA AACCTTTCAATTGCATTTATCAACTACCACTCTTTTTTTTTTTAT CAGATCAGACCTATTTTAGATATCTTGCTGTTCTGCAAGATATT TGTTAGAACAGGCCTGCATATGTTTTCTATGAATGGAGACTGA ATTTAAAACATTAAAGTATGAGATTGTTTTTCATGTGTGTTCAC CGGAATCTGTTTAAGAAACTACAGCATGTTAACTCTCCATCTCA TTTTTCAGAAACACACGTGCACAGTGGAAGAAATGCACACACA GCATTGTAGCCAGGC |
| 52 | LPAR3 | 2420638 | GGGCTCGGCGGCGCGGGTGAACGTGAGCG |
| 53 | LPAR3 | 2420639 | CTGGAGAGGAGGCGCTCCGCCCGCCCGCCGCGTCCTCCGCT GCTTCTCCCGCGCCCGGCTGGAGCCCGGCGCCCGGTCGCCCC GTCGCGCTCGACCCCGAGGGCATGCGGCA |
| 54 | FMO5 | 2433231 | TTGGCAGTGCAATCAGCCTTTGCTAATGGGACTATTCCTTTTAA TCTGGTAGCTGCAGCTTCATACTCAGGAGCAAGTCTCTTG |
| 55 | FMO5 | 2433233 | GTCTGAGAAATTGTCCCGGAATAAAGGGGCCTAAGGAGACAT AACATCTAAATGTAATGTAGTATCCTGGATGGACTCCTGCAAC AGAAAAAGAACTTTAAGTAAAAATTAAGGGAATATTAATAAAGT ATGCATTTTGGTTAATAATGTATCAATATTGGTTTATTAGTTGTG ACAAATGTACCAGAGGAATGTAAAATGTCAACAATAAAGGAAA TTGGATGTGGGGTACATGAGAATGCTGTACTATTTTTGCAACT TTTCTTAAATCTAAAACTCTTATAAAATTTAAAAATAAAAAGAAA TGTGGAGTTATTATTATTATTTTTTGGCTCAGGATTTGACCCAG AGCTATGGTCTGGCAGA |
| 56 | FMO5 | 2433234 | CCAGTTTTTCTCATGTCGTAAAGTGTAGTTCTGAAAAACAGAG CAAATGAAATGCAAAGCAGGTACTTGGGTTTACATCCCAGTGC CACTGATGATTCTGTTTTCTCATCTGTGGAAGTTTCACTGTTCT TGTTTCATGGAGAAATTAACTAAGTGTCAGCTGTCAGGCACAC TGAACTCAGGTGATGTTCATTAATAGCTGTTGTACAATATGTTT GTATTTGGATTGCTGCTTATTACTTAACAACAGGATAAACCTGA ACAATGGAAAAGACCAACATTAGAGAGTATTATCTTTCCAAATA CACACACCTGTAAGAGAACTGGAAATGTGAGAACTACAACTTC TTCTTATTTAAACATTTGAACAATTGCCGGCCCTTTCACCGAAT |

TABLE 7-continued

| Target Sequences | | | |
|---|---|---|---|
| SEQ ID NO. | Gene | Affy Probeset ID | Sequence |
| | | | TTACCTGTGGAATGCCTTTTGAGAGTTAGAGAACTGAGAACTG<br>GTATTACTTTTCAGGTCTTTTGCTTTCCCTAATCCTTGTGATAC<br>TGGAGATTTATCATCTATTAAAATGGACCTAGTATTTTTAAATCT<br>GCATATCAAAAGCAAATTGAATGTCTCTTGCTTCCTTTTAATTT<br>CTTTTAACATATAAATTTCTCTTTTAGCATGTAAATTTGTTGAAT<br>TAACAGCCCTTTGATAATATAATTCCTAGTTATCAGCAATAAGT<br>ACACCAGTTTCTTTTTTAAATTAGGAGTATGTAATTCTAAATTAA<br>TTGATTCTCTCATTGTACATATTATATGCAAGGTTACAAAAAAA<br>AATCAATGGTTAATGATTTTTTAGCTCAACCAAGCTAAAAGATG<br>TGAACAAGAAATTGAACTCAAAACAACTTAAGATACAAAGCTCT<br>TGTTACTGATAATGTCTAATAATATTCATCAATTTACCATATCTT<br>GCTCTTATATTAAAATGTTCTATCATTTTCCTAATTATTTTAAAG<br>TCGATTACAAAAATATATATATATTCTTGTAGTGCCAGAAAATT<br>GAATACATTAATAAATGGGGTAGAATAGATGAATCTCCCATGA<br>AGAAGAATTCCAAATAATTTATGAACTCTGCCCTCAAGGATATG<br>GAGCAGAACTTCCTACTTCTCTAGTGTGAGCTGAATAGTGACT<br>TCCTTCCAAAAATTACATATGGAAAGGGGGAAAATAACTTTGTA<br>GTGGAGAAATCTGATAAACACTATCTCGGCTAGGTTATCAAGA |
| 57 | FMO5 | 2433235 | TCCTTGTGGTAATCCCTAGACTGGGAGCTCAGGTACTCTTTTA<br>GTCATCTTTGTATGTCTTTAGCAGAGTTCTTGACATGTGGTAG<br>GTGCTTAATAAATGTTTGTTGTTTATCAAATTTTATGGTAGGGA<br>GAGTAAGTCAGCATCGGTATAAAATCGCTTACTCCACGTAACT<br>CTTCTTCTGATAGGG |
| 58 | FMO5 | 2433236 | TCTTTGCTATAATTATAGCTTACTTCTAG |
| 59 | FMO5 | 2433237 | GTAGTTCTATGACTTCAACAATGACAATAG |
| 60 | FMO5 | 2433238 | GCCAACGCCATACCATTCAGGGAGACTACATAGATACCATGG<br>AAGAGCTTGCTGATTTGGTGGGGGTCAGGCCCAATCTGCTGT<br>CTCTGGCCTTCACTGACCCCAAGCTGGCATTACACTTATTACT<br>GGGACCCTGCACTCCAATCCACTATCGTGTACAGGGCCCTGG<br>AAAGTGGGATGGGGCTCGAAAAGCTATCCTCA |
| 61 | FMO5 | 2433239 | GATGGCAGAAATATCTAAAGCTCAAGAGGAAATTG |
| 62 | FMO5 | 2433240 | GTCTAAAGACATTGCCCTCACAGAGTGA |
| 63 | FMO5 | 2433241 | TTCACGGAGACAGCTGCCATATTTGAGGATGGCTCCAGGGAG<br>GATGACATTGATGCTGTTATCTTTGCCACAGGCTATAGCTTTG<br>ACTTTCCGTTTCTGGAAGATTCCGTCAAAGTGGTCAAAAACAA<br>GATATCCCTGTATAAAAAGGTCTTCCCTCCTAACCTGGAAAGG<br>CCAACTCTTGCAATCATAGGCTTGATTCAGCCCTTAGGAGCCA<br>TTATGCCCATT |
| 64 | FMO5 | 2433242 | AAACTATTGACCTGTGGCCTTATCATATCACACACAGAATATTA<br>TTGTTACTTGAGAAATCATATATGCACTCCTCAAACAACACTCT<br>TCCTTCACTCCTCCAACACTCTCCCTTTCAGTGCATCCAGGGT<br>CCAACTTCAGATCTGATCTTGATCTGTGCCAACCTAGTATAAAT<br>TAGACCTTTTCCAAACTTCATGCATAGACCAAGGGGAAGATTA |
| 65 | FMO5 | 2433243 | TGGGAGTGCAGGGATAGTGGCCAAAGCACAAGAATAAGGACT<br>CTTCACACTGGCTAATAGTAAAGCCACCTCTACCCATACATTA<br>AGAA |
| 66 | FMO5 | 2433244 | TCGTGTAGGGGACTACGGATATCCTGCTGATGTGTTGTTCTCT<br>TCTCGACTTACACATTTTATATGGAAGATCTGTGGCCAATCATT<br>A |
| 67 | FMO5 | 2433245 | TTCAAAGGGCAGTACTTCCACAGTCGAGACTATAAGAACCCAG<br>AGGGATTCACTGGAAAGAGAGTCATTATAATTGGCATTGGGAA<br>TTCTGGAGGGGATCTGGCTGTAGAGATTAGCCAAACAGCCAA<br>GC |
| 68 | FMO5 | 2433246 | ATGAATGTCTTTGATGGAGTCATGGTTTGCACTGGCCATCACA<br>CCAATGCTCATCTACCTCTGGA |

TABLE 7-continued

Target Sequences

| SEQ ID NO. | Gene | Affy Probeset ID | Sequence |
|---|---|---|---|
| 69 | FMO5 | 2433247 | AAGGTCTCAGGACATATAGGGGTCAGGAGAAGAATAGGCATT TAGTGCATGGAGTGTCATAAAAGCACAGGAGAAGCCCAGGCT TTACTCAGGTGTTACAGTGCCTTAGGACCTGGACCAAGAGAC CTAGTGACTTGCACTTTTCTAGAAGAGGAGGGTACATTAGCCT GCCAACACTATGTTATTTTTTTCTGTCTTGTGGAAATTTTCTCAT TCTGACTACAGCCCCAAACAGTTCTTATTTGTGGAGTATGAAA ATCAAATATCCCTGCATGGGTCCTATTATGTGATA |
| 70 | FMO5 | 2433248 | GAAAAGGAGCCCTATAGCTCAGTCACTTAT |
| 71 | FMO5 | 2433249 | TGGGCCCGTAGAAGCACATAGTGTTTCCTTAACCTAAGTAGGG TAACCCATATTTATTATTTTTTATAAAGCTAAAAATCATAACACT ATCCTGTTTCACAGCCTCTTTCTTTATAGTTCTTTGTAAAATGG GTATTTATGGGAGCCAAAGGGAGATTCATTTATATAAAATGAG AGCCACTGAGGTGTTTTTCTACCCTA |
| 72 | FMO5 | 2433250 | TGCACATGTATTTATCCTACCCAGGCAAAAACTCCATTCTTTGT CCTCCTTTGCTCCTCAAAAATATTCAAGGGACAGTCTCTCTTTC ATATATTTTGGCTGCAGATACAGGAAGCCACCTGGCAGAGTGT TTTCATTACCTTCATTTCACATTATTTGATTGCAATAAACAGATG AAGGGAAATGTTTTCCCCATTACAGAAGGGAACTGATAGGTAT GGGAACTTTAAAACTCTCTGGTTCCACAACTTGTCCATTACTG CTTAGCCCTTTTGTACTTTCTGAAGTACTTTCCAATATATTTGTT TACATGAACATCATAAAAACCCAGTAAAGTATAGCTCTTGGGT AGTTAACTCTGGTGTAGAGGGGAGAACATGGAATTGCAGAATA AAAACCTGAATTCTGGTGCTTGCCCTACCACTAACTAACTTAG ATGTTAGACAAGCAATTTCCTCAATTTCAATTTTTAAAAATTTTC TTGTTTGTAAAACAAGATGATTGTACCAGATCACTTCTGTGGTT CCTTCCTGCTCTAAAGTATTCTAGGACTTTTCTATAATTTCTGA TCACGACCATAAAAGAATTTTATGGTCAGATATTTCTGACAGCT GGCAAAAAGCCCAAACCTTCTGCCTTCTGATCATCCTGCTAAG |
| 73 | FMO5 | 2433251 | AATTGTGTGGGTATCTTTGTGTTTGAAGTTGTTTGCCAA |
| 74 | FMO5 | 2433252 | AGGAAGGGCCAGTATTTACAAATCAGTGATCATCAATACTTCT AAAGAGATGATGTGCTTCAGTGACTATCCAATCCCAGATCATT ATCCCAACTTCATGCATAATGCCCAGGTCCTGGAGTATTTCAG GATGTATGCCAAAGAATTTGACCTTCTAAAGTATATTCGATTTA |
| 75 | FMO5 | 2433253 | GAGCGGGCTCTCTTCCATCAAGTGCTGCGTAGAAGAAGGCTT GGAACCTGTCTGCTTTGAAAGGACTGATGACATCGGAG |
| 76 | FMO5 | 2433254 | GCGACACTAACAGGTGAAGATCTCGGGAGACC |
| 77 | FMO5 | 2433255 | TGAGATCCGGTACCGCAGCAGAGCACTCTCAGCTCTGGGTCT TGCAGGCGCAGGGCTCCCCCATGCCAGCAGAAAGATTTCCTC TGGTGAAGAGGACCGTCGAATCTGTCCTCCTCAAGACACCTCT TGTACAGAATTTATTCGAATGCCACGGCCAAGGTCTTCCTTGA AA |
| 78 | FMO5 | 2433256 | AGCCCACGTTTTATTCCCATCGAGGGAGGGAGAATGGGTGCC GCTGAGTGGGCGGGGGAGTGGTCCCTGAAAGGAGGTGGAGT GCTACAGCCCCTCCCCGTTGGCTCTCGCTGTTTGTCCGTTGTT GGTTTATACTAATTTGACAACAGCCGCCTGTTGAGTCTCCTCC AGATCGCAGCTGAAGGATCTGTTGAGCGCTTCAGGAAAGGC |
| 79 | FMO5 | 2433257 | TCCGCCCACGGCAGGAGCGAAGGAAGGCCCTGGCGCGGGC GGGTAAACTGCCCACCGGGCGGCCCACCCGCTGCGCCCCCG GCCCGCAAGAGGCAGTCCCAATAGGTTGGCCCGCCTGGCCG AAGTCCGCCCGGAGCCCGCTCACCTGTCAGCC |
| 80 | FMO5 | 2433259 | CTGTCCTTGGTGTATAATTCCTACAACTGGAACTGTTTGTGCAT CTTACTTAAATTTATCAGTTAATATTAGGTATTATGAGTTCCCCT TGGCCTTAACCCCTACTCTTATCAAAGAAACATGTTTAGAAAAT GAAGCTTATCTTCCACAGGACTTTAGGCATAAAATGTGATTA |
| 81 | FMO5 | 2433261 | GCTGGTGAAAAGGAGTAGGTTTGGA |
| 82 | FMO5 | 2433263 | GTAGTAGTATTCTAAGAATCGCGTGATGTTTTCTTA |
| 83 | FMO5 | 2433264 | AATGTTGGATTAGATACTGAGGCTGTAGTCCCTGCTGTAACGG ACATGTTGGAAGCTGGTGTTCTAGATACTTACCTGGGAAAACA CTGGTCTATCAAACTCGCTGCTAATGCTGCAGTCACTGTACTT AGAGTGGGTCAGGTAATC |

TABLE 7-continued

| Target Sequences | | | |
|---|---|---|---|
| SEQ ID NO. | Gene | Affy Probeset ID | Sequence |
| 84 | FMO5 | 2433265 | GAAGTAATCTCTAAACTTTATGCAG |
| 85 | FMO5 | 2433266 | ACTGGCAGAAATACTCTGGAGAAAACTCTGG |
| 86 | FMO5 | 2433267 | AGAAGTTTGCTGAGGCGTTTGAAGCTATTCCC |
| 87 | FMO5 | 2433268 | ATATGATGTTAGTGAAGCTAAACTCAAAATGGGATGTCTGAAG<br>ACTCTGTAAAACAGT |
| 88 | FMO5 | 2433269 | AAATAGCAGTGTACTCTTGTCCTTTTGATGGCATGATAACAGA<br>AACTAAG |
| 89 | FMO5 | 2433271 | GAGATACTCAGGTGGTGGTTTTTAAGCATGAAAAGGAAGATGG<br>CATCATTTCTACCATAGTACTTCAGGGCTCTACAGACAATCTGA<br>TGGATGACATAGAAAGGGCAGTAGATGATGGTGTTAATACTTT<br>CAAAGTTCTTACAAGGGATAAACGTCTTGTACCCGGAGGTGGA<br>GCAACAGAAATTGAATTAGCCAAACAGATCACATCA |
| 90 | FMO5 | 2433273 | AATGAAGTATTTCTGGCCAAGCTTATTGTTCAGGCATGCGTAT<br>CTATTTTTCCTGATTCTGGCCATTTCAAAGTTGATAACATCAGA<br>GTTTGTAAAATTCT |
| 91 | FMO5 | 2433275 | GTACAGCATATGGACGAAATGGAATGA |
| 92 | FMO5 | 2433277 | AATTCTCTCTTTGACATGGGCTTTCTTTTTAAGAACCCAAGGCA<br>TTGTTTTGTAGAGAGTCTCTAAATTTAGACTTGCATAATTTTTTT<br>CCTTTATTATATTCAGGTTAAATGTTTTTGACACATATACTACAT<br>AGGACATGTTGATCTTAGTGGGTCACATCAAGAACCACATTAT<br>GTCAGTTTATCTCACAGTAATAATGCTAAATTTGACCACTTAGA<br>TAAGGTGGTATAGATACCATCAAGTTTCTCCACTATAAAGATAT<br>TTTTTCCCGTTGAAGTTAATCAGTGGGGTGA |
| 93 | FMO5 | 2433279 | CACAGTGAGGAGGTCTATGCAAACCTACCCCAAAGGCTGAGG<br>AAGCTGAGAGGCTGAAGAAAGAAGCTGACAGATTCAGTTTCTT<br>AGAAACATTTCATAGGGACTTATGAACAGAAGCCATGTCTGTC<br>TCAGGCAGTGGTGAGACAAGATGGTAGATCCCCATACCATTAT<br>CTCCTGACCCAGGGATGATATACCACAGGGGAGGGGCACACA<br>TACTTCAGAGCGAATGGGTAGGAGTTTGCCCTAAGGGTGGGA<br>TTTACAGTAAGTACATACTATTAAACAACAGATTAACTGGAAAT<br>CTCAGAGGTATTCCCGAAACCAGGGTTGATCAGAAGTCA |
| 94 | FMO5 | 2433281 | CAGTTCTTTTTGCATGATACCCAACAACAAA |
| 95 | FMO5 | 2433283 | GGACCCATGGCGAGAGCCATCTTTAATATCATTGGCTTGTCAA<br>ATGGGCAGTTCTAAGGGAGCTTGGCCTTACCTGCTCTGGGGA<br>ATTGCAGGTTGCCACATAACA |
| 96 | FMO5 | 2433285 | CCCAACAGAGAATAGGGATACCTGCACATAGCCCTTCAGTGC<br>CAGTGGCAAATATAGGGCTTCGTTTCATTACCTCAGTTGGCAA<br>CATGGTGATTGGTGCTAATA |
| 97 | FMO5 | 2433287 | TTCATTCTAGTATATAAAAAAGCAAATGACTGGGTGCAATGGC<br>T |
| 98 | FMO5 | 2433289 | CCAGGTATGCTGTAGAATATCCCTCAGTTGGGATTTATCTTATT<br>TTTTTCTCATGGTTAAATTGGGGTTATGACTTTTGGGGAGGAAT<br>ATTATAAGGTGCCATTCTCCTCACCTCCCATCAAGGGTACATA<br>CTATCCACATTATACCCACTGTTTTTTTTTTTTTTTTTGGAAACT<br>TAAAACTCATTTTATGTTATTATAAGTAAGAAATTAGCATTCAAT<br>ATATGCCACAATATATCTTTGTTGAAGTGTAAGTTTGTTCCACT<br>TTTCTATTTTTCATTTTCCAACTTTTATTTTAGGTTCGGGGGTAC<br>ATATGAAAGTTTGTTACAAGGATAAATTGTATGGGGCTGGTAT<br>AACTGCTAGCCATATGCAGAAGATTGACACTGGATCCCTTCCT<br>TTTGCCATATATG |
| 99 | FMO5 | 2433291 | AGCTCGATGGGATCCGCATCGTGTGCAATCACCACCAGCTGA<br>GTCTTCTTGTTCTCCACCAAGGTGGTGATTGTGTTAACCCCTG<br>CTGGAAAGACGGGTGGTGTCTCGATGGGGGTATCCCCTTTGC<br>TAGCAGCTTTCTTCTCAGTCCAGGACAACAGTCTCTGCTTCTT<br>CTCTTGTTTTGTCTCTGGTCTGTGCTTGTGGGCCCGCGTAAGC<br>AGTCAGTAGCTGTT |

TABLE 7-continued

Target Sequences

| SEQ ID NO. | Gene | Affy Probeset ID | Sequence |
|---|---|---|---|
| 100 | FMO5 | 2433293 | CGTCTGATTGCCTGAACTGCCCGTCAAGGAGGTGGCATGTGT TCATCATTCATTTATTATTTAATCAACATCGACTATCATGTGTCA GACACTCCGCTGGGCCCTGGGGGTTCTAGAAGTAAGACTTGT TCCGTGCCCTCCAGTGATTCACGATAAGATCAAACTGTTCTTG TTCGGTTTACCTAGTGATAAATTGATTTAGTCCCTGAAATCCCT TTCTTACTGCCTGTGACCTGTAGGCCAAAATTGGGAACCTCTG AATAGTAGTAAATTAAAATCACCAAAGACGTCATTGTGGCAGT GGGTATCTC |
| 101 | LPGAT1 | 2454486 | GACCACTGGGTCTTGGGAATCAGTAGGGGCTGTATCCAGCAC ACCACTGCCCCATCCTTTTTTTCTTAACTATTAGTGTTGAATAA ACTTCTCATAGTTAATCTACTTGCTGAACTCAGGAAATTCCTAT CACTGACCCTGGCCAGGGCTTTAAAGGGTAGGAAAAGCATTA ATGTCAGTCCTACACAGCGAACTTTTGATTTAGAAGAATGTGA CAGAAAGAAAACATTTACTGAAATACATGGGAAGCTTGCATAT TTCTAAAGTTGTCTTTATACTTTTCATTTCTCAAAGCTAAGTAAA CTGTGGTATAGGCATCTCTAAGATGTTAGCATTTAAAACATCAA TTGTTTTATTGATGTTTAAACAATTGTTTAAATCCCACTGAAAAA TTTAAATATTAAAATATCTTGCACAGTCTACCAAATGAGTTAAAT CGTTACAGTCGTGTCTACCTCTTATTTTTCTATCTGTATTTAGG CTGCTGTTTTGGTGAGATTCTAATTTCTTTTTCCCCTGGAACTA CTTTCTGTGGAAGACAAGGAACAGACTGGGGACAGAGGCCTG AAAACAAATTGGAAGCACTCAGAGATCTATTGCTGACCAGCCC TATTCCTCATGAGTTG |
| 102 | LPGAT1 | 2454487 | CTCCAGGGTGACAAATGCCAATAGATATGTGAGTTAATTTTTTT AAATATCTCCGTGAGTTGTAAATAGATGTGTATTTGATCTGCCC TATCCTTCTTTGATTCTTTAACATGTTCTCTCTCTTCTGTTTGCA AAATATGTTTGAAAGCATTGGTAGTGCTTTCCTTATCAGTAACT GGAGTTCTCCTGCTTGCACTAGAGAAGGTAAAGAGAGAATCA GTATTCTTATATGGCAATCTGGGGAAGCAGCAATATGCCACTG TACAAAACTGAAGAAAAGTTCCTAATTTGTACTTTGTGAAGGGA GATGAAAGGACGTTTAAAGTATATATATTTTGTCAAGAGGAAA GAAGATAAAACTATGCCAGTTTTATATCAATAGCTTGTAGAAGC TCAGCTCTTCTTGGTCTTGGCTAGACTGCCTAGATTCCCACAG CAGACAAGGTTGAGAATCCATTGCTGGAATCTTGGTATTGATG AGTTACAGTGATGGAACATGTGCTTGGCCACAGGCAGGTCCA GTCACTGCAAAAGTGACCAAGCCAGCAGGTCACCCTTAACTTC AGAAACAATTATTGGTGGTGAACTGTACTTAAATTGCAGAGAA ACCTGTAAGTAATGGAAGGTAAAGAAAAATTACAGAATGGAAA ATAATATTTTGGGCAAGCAAACAAATTCACTGAGAATTCCAAAA GTATATTAAAAAAGAAGATAGCTATGAGTTCAGATCTATCTTAT TGGTCTTTAATATTACAACCAATCCTTAACTTTCCACTATAAAG GAAGGATTACTAGATTGATTACTTTCTGGATAGATAATCTGGTA ATAAATGATAGGTAAATCAAAAATTACTTTTATTTAGGAGTTTG AATTCTTACTCTCATCAGACATTTTTTTTCTAGGGACGCTTACT AATTAAATGATTTAAGTTGTTTCTTAGGGGTTTTTTGCCTATATA TTTATGACTGTGTTAATGAGTAGTGAAATGATGCGGAAAGACA GCTATCAGGAAGAGGAAATACAGAAGCCTGAATAATCTATGGG TTAGAAAAGCATCCCTGAATAATCAAAAATTGGCAGTATTGGC ATTGTTCTCAAGCCTTTTTATGAAAATGAAATCTGAAATCACCA AATGTAAACCTGGGAACATTATTCTAGTGTTGCTGTCTTGGATT CATGTTAAGAAGCGTCTTCATTCTTTGCTCATGTTGCCCACTTC TTGTGGATTTGTCTGAGTGTTTTTTGACAATCACTTCCTTAAAG ACTCTTCTGAACTAGTTGGACCTGGTTAATC |
| 103 | LPGAT1 | 2454488 | GGTCACCGTAGGAGTTCAGACTTTCTTTCATAAGTGTGCATTA TTTTACATGTGCAAATCAGAATATATTTAAAAAAAAGCAAAAGA AATTCAATGGATGGATTAATATTTATCCCCCTTTGGGATATTTT AAAATCTACTAAAATGAGGATTAGTAATATAATGACCTGCTAAT ATATTTTAAGAACATGTTTTAAAAAGATACACTCTATCACATATT TAAGCAAACATCACATTTGGAGAAGAGGAAATCATAAAATCAT CCTAGAAGACTATCTGAGAGAAATTCTGTTGCCACCAGTTATA CTTGACAATTTAGTTGAAGCTCAGAAAGTTATATTCATCCCTCT TAGCTGTAGTCTATATTAGGGCAGTTCTCTAGAACGCCCACAT TTCCACCAACTCAGTAAACTTGAGGGGAGCTGGTTGGCACCT CGTGAAGAACTCTTTCCCTGTCGTTTGCAGTAACAAACTCCAG TCTGTTGCAGTAACAAACTCCAGTCTGTTGCAGTAACAAACTC TAGAATATTGACATTCTCTGTGGGGGAAAAGCAGTGTCCACTG GACCCCTTCTGGTACTGGATGTGTTCTTTACAAAGGCTAGCTC AGTCCAACACTGTGTTTACATACACTCGTGCTTTTCCTTATCTG ACTTCTCATTTTGTATCAGAGGCATATCATAAATTGATAATTTTG CAAAATGCACTTTTTTGAGATGCAGATATAGCAAAGGATTAGTA ATATAGCCTGAAAACAAATGGGAGCATAGCAGTGTGTGAGGTT |

TABLE 7-continued

Target Sequences

| SEQ ID NO. | Gene | Affy Probeset ID | Sequence |
|---|---|---|---|
| | | | CTCGAGAACTGTCTTGTCTCTGTGTGTTTATTTGCCTGCCAGT GCTCTCCAGCGCCATCCTGCCCTGGACACCACCCTGACGTGA TGCCTCTATTGCAGCTCAGAGGCTTTATTTTTTCCATTTTGACA TTGGCACTAAATGCATTTGGGGATGGTTAAAACAAATTACTATA GAACATTTAAATGATCAGTTTAAGGGGAAATAGGCTAGTTTATA GAAAAATAAGAGCTAGTGGCTTATAATGGTGACAGGTTCTCAT GTGGCACCCCTAGGACCTGTGCAGACAGTAGTCTGTTGAATC ATTACATCAAGGAGCTGCCCCTGTCAGGGTGAGTGTAATTAG GAACGATACCAGCACATAAGGCTCCCCCCAATCTCTTCCAGTT GCTTTTTCTTTTTTCTTTTTTTTTTAGACAGGTCTTACTCTGTCA CCCAGGCTGTAGTGCAGTGGCATAATCTCAGCTCACTGCAGT CTCTGCCTCCCGGGTTCGAGCGATTCTCCTGCCTCAGCCTCC CGAGTAGCTGGGACTACAGGCACCCACCATCATGCTTGGCTA ATTTTTGTATTTTTAGTAGAGATGGGGTTTCACCATGTTGGCCA GGCTGGCCTCGAACTCCTGACCTCAGGTGATCTGCCCACCTC GGCTTCCTAAAGTGCTGGGATTGCAGGCGTGAGCCACCACGC CCGGCCTCCAGTTGCTTTTGAAGAGGGTAAAGTCAAGTTTCTA TTTCTAGAAAACATTTTTTAGAAATTTGTTGCGATGTTTGTACAA TTTACCTCATAAGAGAACCACACCCTTCTCCAAAAGTGCTGGT ACTGCATCAGTGAGATGAGTAGGGTTTTTGTTTGGGATTGTAA GACTATTAAGATCCTAGTAAGTCAGTGGTAGTTTACTGTGATGT GAGCATTGTAGATTCCCCCGTTGTCACTAATCACACAACAATTT TGAGAAGTAGGCTATAAAACAAAAAAAGGTTGCTGTTTTCTATT TTTAAATAAACCAAAAAAAAACAGAAAAGATGTGAATTTTCCCC AGTTATGTGGGAAAGGTAAAGCAACACCAAATAAAAGCCCACA GCAGCTTCATCTTTACGATAACTCAGTGCATATGTGAAAGAGA ATGATGCATTAACTGAAATACCTCATTGAATATTATACTACTAC TGGTAAAATGCAGAAGACAGTGTTAATGTGTTTGGTTTGGGGA CTGGTTGTTATAAAATGCAATTTTTTTTTAAATCTAAGCATTTCA TTATGTGTTCTACAGTGTCGGTGAATAAATGAAACCAATCTCAA TTTAGAGGTATGGATGATGACAGAAAGCCCAATAGAAGCTTAA TGATGCTTCTGTTTGAGGCCCAGCAAGCACCACTAAATTACTG GATGAAATGAAATTGTTCACTTGAGGGATTAGTCAACCATCTG GGGGAGAAGTTGCTCACTGTCAAATACAGCATGCACGGTCCT AGCTGATAGACCTTTTCCTCATTGCTACAGCAAGCCACAGGGT AGAGTGACCAGTTCTCCTATCCAAAAATAAATGCGAACATGCA TACATAAATGTGGCTGAGGGCCACTTTTGCCATCACTGTGC |
| 104 | LPGAT1 | 2454489 | GTACAACATCATTCAGTATTTTTACCATTGCCTGTTTT |
| 105 | LPGAT1 | 2454490 | GACCCTCAGCAACTTGTGGATATTTCTCATACAGTCTTTTGCAT TTTTGTCAGGCTATATGTG |
| 106 | LPGAT1 | 2454491 | TTCCAATTAAAGATGTACCCCTGGAGACTGATGACCTTACCAC TTGGCTCTATCAG |
| 107 | LPGAT1 | 2454492 | CTAATGGACCTGAACTCTTGAAAGATAAAGACTAAAGCAAACA CAAGAAGGTGACATGGAGGACCAGACTATACAGGGCAAGGTC TGCTTCTAGAATTCCTAATAGTACATGGGGGTTCATTAACCTTT TTCTCTCCTCTTGTGAATGTTTAAAAATTTCCATTATAATTTAAA AAACTTATTATAAACATAAGATATTGTAGCAATAATACAATAATA GCATACTATAAAAAAGACTGAGAACAATAGGAGCTCTTTA |
| 108 | LPGAT1 | 2454493 | CAAGGTCACGCAACTGGCAAGTGGTAGAGTCAGGATTCAACC CCAGGCAGTCTGCCCAATAGCTTTTTTTTTTTTTGAGACAGAAT TTTACTCTTGTTGCCCAGGCTGGAGTACAGTGGTACGATCTCG GCTCACTGCAACCTCCGCCTTCCAGTTTCAAGCTATTCTGCCT CAGCCTCCCGAGTAGCTAGGATTACAGGCACCTGCCACCACA TCTGGCTAATTTTTGTATTTTTAGTAGAGACGAGGTTTCACCAT GTTGGCCAGGCTGGTCTCGAGCTCCTGACCTCGTGATCTGCC CACCTCAGCCTCCCAAAGTCCTGGGATTACAGGTGTGAGCCA CCGCACCTGGCGTGATAGTTTGTATGCTTAATCACTAGGCCAC ACTG |
| 109 | LPGAT1 | 2454494 | GAGGAGATGTAAGCCTAGCATTATATG |
| 110 | LPGAT1 | 2454495 | GGCCCTAATTGGTTATGAGCCCATTGCTACACCCCAATACTTG TCATGAAGAGAATGATATATGATGACAGGTCTGACATGGGTTT TTAATGAGAAGGGTGCCAAGACTACCAGAATTGGCTGAGTGAT AATAGATTGGCAGACATTTGCTTGGGATAAATTTATTTTGTTTT TTAAAGAAAAGCTAGATAATCCTTTCCCTTGGTGAGAGGATTC CTGC |

TABLE 7-continued

Target Sequences

| SEQ ID NO. | Gene | Affy Probeset ID | Sequence |
|---|---|---|---|
| 111 | LPGAT1 | 2454496 | TGTTTGTCAGCTCACATTTTGGAGTCTTGACGTAAAAATTCAAA TGCTCCAACTCCAGTATAGGGGGTGCCAGCTGCTAAGTATTAT TTTACATTTTTTTGAAAGTGTAATTTCATCTAGTGCTTTTAAAT CTGACTATGGATTTTGGTAGTATATTCTCTATTTAAGAGCACAT TCTGAATTACTGATAATAAGAATGTTCATTTCTTGAAAATTAGG AGCTAGTTTTTCATTTGGGTAGCTATTGGTATTGTAAAGGTTTA TTTCTGGTGTATATGTATTTACTTATTTAAATCCCACAAGCACT CCTCTGATTTGATTTCAAGAGGACTGGTATTCAATGTATTTAAT CCTTTGCCATATTAGGGGATTAGTCATTTTAATATTTTAATCCTA TGGTGACCAATCAGAGTAATA |
| 112 | LPGAT1 | 2454497 | GCCTTTTAGCCTTACTATGTTTCCATGTGAAAGACCTCAACCC GTGGCAACTACCAAGGACA |
| 113 | LPGAT1 | 2454498 | ACAGCAAATCAAAAGGCCTCCAGTGGATAATAGATACAACGAT AGCTTATCCCAAAGCTGAACCTATAGATATTCA |
| 114 | LPGAT1 | 2454499 | CAGAGATCGAAAATGGATTGTTTTGTTTCCAGAAGGGGGCTTC CTCAGGAAGAGGCGAGAAACAAGTCAGGCATTTGCCAAGAAA AATAACTTGCCATTTCTTACAAATGTTACTCTGCCAAGGTCTGG GGCAACAAAA |
| 115 | LPGAT1 | 2454500 | TCTTGAGAACTTAATAGCTATCTTAATCATAATCAGTTCACTTC AGCAAACTGACTAACAAAATGTCTTACATGTTTTGCATTTGGGA TACATTTGATCTAAAGACTGAAAGCATACTAATTATTTTGAGGA GTTTCTGTAATTTTGTTGGCTG |
| 116 | LPGAT1 | 2454501 | GAGAAGGCAGCGGAACCAACAATTAGAAAGCTTAGCAGTCTC AGGGATCCGAAAAGCTAGCTGAGCACCTTACCTCATTTCCAGC TTTAGGAAATAATTGAATTTACAGTGTAGTGTAACAGTTGATTC TAATGATGATCATCAGGCATCAAGAAGAGGGGC |
| 117 | LPGAT1 | 2454502 | GATGTGGTTGATGGATCATATTTTT |
| 118 | LPGAT1 | 2454503 | TTCTCTATGCTGATAGGCAGTCTGCACTAAGTTGAGCATAAAT ATGGTGACCTCCTGGGAGCAGTGAACAACTAGGTCACACAAG AAGGGTGAACC |
| 119 | LPGAT1 | 2454504 | CGAGGCCATCCAGGACAACAGGGTGAA |
| 120 | LPGAT1 | 2454505 | GCAACAGGAGATGTGTGCACACTGAT |
| 121 | LPGAT1 | 2454506 | ACACAGTAGGCATAGGGCTCTTTTAGTTACTAGTGATTCCAAA AGTGACTTTAATCCCATTACTCAGGATCTCTATGGTACTGTCAA TTAGATCTTCCTCATTTTTGCAACATGTTTACGTAGCATTAATG ATATTATTGTTTCATAAGTGAGAAAATGAAGACACAGAAGGATA AAATAGTTTGTTGCATCAGCTTGCGGGCATAATAAGCAACCTT TCTTCTCTCTGTTAATTCTGTTTTGTAGGCCAGTATAATGGCTT TAGTGTCACTGTTGTTAAGGAGTTTTTGATGGGTTGTTTCTATT TTCTTTTTGAGATGTGAACTGTCCAGATTAATTCTAATCTATAA CTTTTGGGAAAAGTATATTGATATACATGTTAGAATGTGTGTGT GTATGTGTGTGTGTTGTGTGTATGTAGTAGATGATAACCTTTAG CTTTGGTTTTCAATAAGAATTTTAAAATTTATTACAATTAGAAAA TTTTTCCTCCAGTTTTTATTCAGTTGTCCTTTTTCCCTTTGGAAA TAGTGGACCTGACCCAATTCTTTTTTGAGAATTCATTTCATAGA GCAGCGTGTTAGAATATTTTTGTTCTTCTAATCAAGTGCAGTGT AAGAACTGTAGACATCCATAATTTCTTTTCTATCCCTTGGTTAA GATATTAGCTTTATTACTATATTTACTGGTCCTGGAATAGCAAG GCATAATCTGAGGAGCATAGCTACTTCATCTGTGTAATAAATT GCTCTTTCACTACAAACATTTTAATACTGATTTTGTTGGTCATTT AACTTTCTAATAGTGGTCCTTAAATTATGCTCTAAAAGAAGAAT ACCATATATATTGGAAATTAAATTTGTTGTTGAATAAAATTAGAA TTATTATAAAATTCAACACGACCTTATTGCTACCTCAGGA |
| 122 | LPGAT1 | 2454507 | CCTACTTCCTAACTATGTAAGTTTGAAAACAGTGCTTAACCTTT TGTGCCTCATTTTCCTCATTTGCATATTGGGGATGATACTATCT GCATATTTGGAATTTTGTGAAGATTAAATCAGAAAATAATGTAA ATTATTTTCTATTACTAAGTACTAGTGCATGGCACATAATAAAC ATTCCATAAATGTTAGCTATTAAGATTATTATTTATATATCTATTT AATAATATCTGCTACTATTATTATTTTAGTTATGTAACCCCTCCA AAAGCTACCTCTTGAGCCTTGCTTTCTCAAATTTTAACCTCTTA AAATTTAAGAGTCAAAGGGACACTGACCATGATTTCCTAGTGT GTACAATG |

TABLE 7-continued

Target Sequences

| SEQ ID NO. | Gene | Affy Probeset ID | Sequence |
|---|---|---|---|
| 123 | LPGAT1 | 2454508 | CCTTGTTTCAAGCTGGAAGTGGGGATAACATAGAGCCCTTCAC ACATCTGCTTTTCTCATCCCCTTCAACTGTCTGTTCTTGTTTTA AGAGTGAGAGATTAAAATGTTGATTTGTAGCCAAGCAAGTGGC TGTGGCTTATCAACATTGAGCCTCACTGTAGGGTAATCTTATT GGAATATTTCACTGGGGAACCCCAAATGTCAGTATTTTTAGGT CTTTCCTCTTGAGGTGATCAAATTCCCTA |
| 124 | LPGAT1 | 2454509 | GGTGAAGTGTCCAAGTCTTTTCTTAATTTTTTTAATTGGGTAGT TTGTTCTCTTAATGCTGAGTTTTGAGAGGTTTTTTTTTTTTTTT GAGACGGAGTTTCGCCCTTGTTGCGCAGACTGGAGTGCAATG GCGTGATCTCAGCTCACTGCAATTTCCACAACCCTGCCCGGG TTCAAGTGATTCTCCTGCCTCAGCCTCCTGAGTAGCTGGGATT ACAGGCATGTGCCACCACACCCGGCTAATTTTGTATTTTTAGT AGAGACGGGGTTTCTCCATGTTGGTCAGGCTGGTCTCGAACT CCCGACCTCAAGTGATCTGCCTGCCTTGGCCTCCCAAAGTGC TGGGATTACAGGCGTGAGTTTTCTATATACTTGGGATATAAAC CCTTTGTTGGATATGTGATTGCATATTATTTTCTCTCATTTTATT CTCTTAACAGTGTCTTTTCCTCATTAAAATGTTTACATTTTGATA AAGTCTAATTTATTGATTTTTTTAAAAAAAATTGGGCAGCCCCCA AGCCAGAATAGGTTGAGAGAGACTCCCCAGTTCATTGATGTTA TTTTCTTTTATGGCTTGTGTTTTTCATGTCATGTCTAAGAGTACT TTGCCCA |
| 125 | LPGAT1 | 2454510 | GGTCTGATTTGTTACCTGATGCTCACAGAGTACT |
| 126 | LPGAT1 | 2454511 | TTTCTTTAGTAGGAAGTGCTGTACAGATATCTCACGTTGAGGA AATGCTTTATATTGCCTTTGTCTTAATATTTCAAGGGCAAACCA AAAGAGATACTAGCTTAACTAATGATCCACTTCTGCATGCTTTA TTTGGATCTAGGATAAATCAGTACCCCACCCCCCGGAGTTTAA GTGATGATTGGTA |
| 127 | LPGAT1 | 2454512 | CATTTTATCCACACACGCAAGAGAAG |
| 128 | LPGAT1 | 2454513 | GTAAGAGTGAGAACACTTTTCTTTAA |
| 129 | LPGAT1 | 2454514 | AGGTTTGCCTTCATGGTCGTCAACAACCTGGTTGCTATTCCAT CCTACATCTGCTATGTAATTATACTTCAGCCCCTTCGAGTGCT GGACAGTAAGCGGTTCTGGTATATCGAAGGAATCATGTATAAA TGGCTTTTAGGAATGGTAGCTTCCTGGGGATGGTATGCTGGAT ATAC |
| 130 | LPGAT1 | 2454515 | CCTTGCCCTCTGGTCGGAAATCTCATTCTCTTCATCCCCAGTT CCTTGGCTTTTACCTCTTTCTGGCTTTTGCTCCCTTCCCCCTAC TCCTGTCCTTCCTCTTTTTCGCATTATAACCCCCTACTTTCTTC CTCTCACCTTGTAAGCTTTTTTTCTAGGCCCCCCATTTTTTTTC TTAAAAAAAAAAGGGAAACAAAAACCCTATTGCTACAAATGAG AATTTTGAGGGTAACTCTTCGCTAGAGCCAGAGACCTTTTAAA GGAATGCATCGGTGTGCAGGAATCGTGGTGGTGAGGAGACTG AGGTCCTCAGTATCTGGGAAATCTTATTGAGGGGACCCTGTTT CGGTCATGTCACTTGTGTCTTCAGTTTGGAGATCCTGAGGTTG TCTGAAGCGAGTGGATCTATTTTTCTAAGTCCAATAGACGACC GCAGTGAGACACGGTGCGGGGACGGCCACCGATTACTGAAT GGGAATTGTGTTATCATTTGCTAAATATATTGTGACATACTTCG TGCCTCGGTGAACAGCTC |
| 131 | LPGAT1 | 2454516 | CAGCCGCGAGGGGAGTAGGGCGCCAGCGCGCCCGCTCGCG CAGCGCCTCGGGCCGCTTGGGCCGCCACCGCGTCCATGACC GCGACCCCTCGGCGGG |
| 132 | LPGAT1 | 2454517 | CCTTGGGGACCGAGTCTCGGCGCCGCCGGGGAACGGGCGC GGGCCGCGCCACAGCCGGAGCGGGGCAGGGCCCCGCCACC GCCTTCTTCCGCCGGCCCCGCCGCCGGCCATGCATTCTTCCG GCTCCTCT |
| 133 | LPGAT1 | 2454524 | TGAGGCCAGTAAGCCCAAGAACTTAAATGAACATTCTTATACT TTAGTTTGCATTCTCAGAGCTGGGGAACTGTCTGTAGGCACAG AAGATGGAAAAGGGATTTTCTGGTCTGTTTCTGACTTTAAGTTA CACATTTTAAAAAGTACTCTGAAGACACTGGGGTTTGTTCATCC CCGGCTTGCTACTAAAGTAGTAATG |
| 134 | LPGAT1 | 2454525 | TGCCAAAGGAATTCTGCTCAGCAGATTAAGTATGTTCATGTTTT AGAATAAAAATTGCCAAAACTTTGTTGAGAAACCACTTATGAG GAAACCTTAAATACTAATTAGGAAGCTAAAAATTGAATATTGGT ATATTGGTATAGAATGAATATATATATATATATATATCTTTTTCC |

TABLE 7-continued

| Target Sequences | | | |
|---|---|---|---|
| SEQ ID NO. | Gene | Affy Probeset ID | Sequence |
| | | | AAATTATGACATTCCGTGTAATATGAGTGAATTACTCAGCTCTG CTGATGAGGACTTATGTTG |
| 135 | ERO1LB | 2462330 | CTATGCAATCCTCGAACTCAGTGTGCTTTTCCCTGACAGGATA TATAAAAAGGTAGATTAGGTCAACCCTCCTTTAAGCTTACTCTC CCCTCACCTTTTCTTTTCACTGTATATAAACGGTACTTTCTGTG ATTCATACCAACAGAGGACTTTCTGTGATTCATACCAACAGTC CTAAACTGTCATTTTCTAAATCTGGGATTTAAAATCTTTAGACA ATATTTAAAATCTTGATTTTTTTTAAATGTCAGCAGATACAATTT GGAAGATTGCATCTGTGTAGAAGTAATGCAGGTACAAGATCTA GAGTTTTTCCTTAGACTCTTTAGTCTTTTCTGAATTAAAGAATAA GTGCTCTTAAATCCATATTTATCCTGTCAAAGTCTGAAATGTG TTCATTGATGATTTGGTGACATCTAAAAAATTGTATTTAGTTGG CTTGGCTCACCCCTCTTAAAAATACTTAGCCATCTCTTGGTGG GATGTGGTGGGGGTATTAAGGTCTCAGAGTTATTTATTTTCTC ACCTAATTTCAAACCTTTATAAACTTGGGGTTTTGTTGTTGATG GTGGTAGTATTTTTTGTTAAGTTGTTTAAAAGGCTGACTTGATT GGAGCCTCCTCTACTTTTTCTTGAGGGTTGCAAGTATTGTATG GTGGGGGAGGGGGGCCTTAAGGCAAACTGTCTAAAAAGTGAC TATCCAATTAATTTAACTAGTAAATTAGTAAGAATTATTCTTAGT ATTCACTCAGAGTTTAAGATGTGAAAAATCTGCACTTTGTTTAT CACTCTAAATGTAAAGAACTTTTTGATAGTGTTATTTCACCACT CCCTCAGTTAAAGGCTATTATTTAAACTGTTTACTGGAGAAAAT CCTCGCTCATGTCCATTTATTGTTTTTTTCTGTACTGTGATTTGT TTCAAGCTTAGGAAAACTAGTATATTAGAGTATGTTCTAGGAAA TTAAAAGATCTGGTTAGAGTAAAAAGTTCTTTTTAAGGTTCTTA ACTAATTTTTTCACAACTAAGAAAATAAATGAAGTATTCTTAGG CTGAAATTCATCTTATTTTATCATAAATTAGATTGTAGGGGCAG CCTACATTTTTGTGTATGTGTTTTTATTTCTTAAATGATTGTGTG AGCCTGGTGACATTTTATGGTTCTTGTGATCTAAACTGTTTTTC CAATTCACATCTTTTGTCGTGAAGTGATATTATACTAGAGTACT GTTTGCATTGTAAAAATGCTTTGCTGGTGCTCTGGCATTTTGTC TTTATCTCATCACCTAATTTAAAAACCCAGCACTTGATAATATA ACTGACAGAAATGATTGTACCCACTGATGAAGTAATGAAAATG AAGAAAAGGAAAATATTCCTTCCTTCAATGGCGTAAGTTTATTT TTTACTTAAGTGGCATCTATGTAAGTTAGACAAACTATATATTA AAATTGGTAAACTTTGAATGTTTCTCCTGTTTTGATTCTTAGATT ATGAGGAGGATCAGACAGAATAAGACTCCACACTTTTGAAATT TGATAAGTCAAAACGTTTTATTTTGACATTTTTAACATTGTGAAT TATTCGATATTTGTAATCTCTGTATGTATATGAAACTCTGCCAT GTTTTTCAACTTTGCCTATGTGCCACTGTA |
| 136 | ERO1LB | 2462331 | CTAGGGAACAAATGTTGCTCAGGGCTGGTGTCAGTGAGAAAA ATTTATCAATGCTTTTTAATGTGTTTTTACCCTTGCCTCACTGTG TGTGTGTCACTTTCTATAATATAAAGAAATACTATAATATTTCTA GAATCTGGAACTGTCACCATGATGAATGGCCCTTTCAATGCAT AGTTACAGAAATTCCTGAAGATTCCCCAGGACTTCAATTTCATT GGTTTTTATTTGCAGTTTTTAGTTGCTGTAATTGTTGCTGTTTC CAGTCTAAAGGACCTC |
| 137 | ERO1LB | 2462332 | AGAGACATAAAGTGACTGTGGAAAGCCTTTTAATTATGGACAT TCATCAGAAAGACACTAATCTGACTTCAAGAATTCTGAACTATT AA |
| 138 | ERO1LB | 2462333 | TTTAAAGTCTTATTACAACACAGTA |
| 139 | ERO1LB | 2462334 | GTACTAACTTAGAGAGGCCTTAATGCTGACAAGTCAGTTTCTC TACAGGTCATAGGAAAAACTAAGTTTCCAATTGCCAGTGTTTTT CAGTTTGCTGCCTTAATTTTGTAAGGGAGATATTCTTCTAATAT TCTTTTTGCTTGGCTATAACTTGTTCAACTACAATAGCAGGAGT AAGGAATGTGTGATTGAGAAGGTGATAAAAGAAAATTAAAACC TTCATCTGCTCCTTATTTTTCTTAAATTTTCATTACTATTTTTTTC TTTTCTCACCTTTTTCCTGCACTATGCTCTTTATTTCTGAAGCTC AGAGGTCATTTTTCTTTCACTCATTTCTACATGATTTACTTCTGT ATAGAGACATATAATTTGCTTGCTTGTTTATATCACCAGTGG |
| 140 | ERO1LB | 2462335 | AGGAACTGCCCTGAAGATATTATTCTCTGAAAAAGAAATCCAA AAGCTTCCAGAGAATAGTCCATCTAAAGGCTTCCAACTCACCC GACAGGAAATAGTTGCTCT |
| 141 | ERO1LB | 2462336 | TGTGTCTATGTTTCTATTGATACAATACCAGATTCATTTGTGAA GTTGGTGGTCATTACGAACCGAGTATATCCGTATTTTACATATG |
| 142 | ERO1LB | 2462337 | ACATTTCAAGAATATCTCCCGTATAATGGACTGTGTTG |

TABLE 7-continued

Target Sequences

| SEQ ID NO. | Gene | Affy Probeset ID | Sequence |
|---|---|---|---|
| 143 | ERO1LB | 2462338 | GTCCTTTCCCATGCACTTTGATGAGAAATCCATGTTTGCAGGTGACAAAAAAGGGGCCAAG |
| 144 | ERO1LB | 2462339 | TTTATACTTGATTGAGCTTCGAGCTTTGTCAAAGGTGGCTCCATATTTTGAGCGCTCAATTGTCGATCTTTACACTGGAAATGCAGAAGAAGATGCTGACACAAAAACTCTTCTAC |
| 145 | ERO1LB | 2462340 | GGAGAAAAGAGTCTTCTATAAGCTTATATCGGGACTTCATGCTAGCATCAATTTACATCTATGCGCAAATTATCTTTTGG |
| 146 | ERO1LB | 2462341 | TGTCATATACTTTTAGGGAGGAAGCTACAAAATAAAATTCAATTTCTTTTGGTCCCCATCCATGACAATTTGAATATTCTAGCAAGAATTCCCAATTAGGGAACGAGAACTCAAAAGAATTATTTTTTCTAGTTAGAGGCCACGTGCTTC |
| 147 | ERO1LB | 2462342 | AGCATATTTTTGTAAGGTCTAGGATTT |
| 148 | ERO1LB | 2462343 | GAGAATCATTCTACACATGGCTAGAAG |
| 149 | ERO1LB | 2462344 | AGAGGCCATATTTTTTAGTACGTTGGGTACTAGACTTTTCCTGTTGGCACTTGAGGTGTTTTGAATCACAAGTGATATAATGATAAATGATCCTTACTATATGTTGAATGAATTAATTTGTTAGACGTTTTCATTTTTGTACAAAGTATGAAGACTCTCAGGAGGCAAAGTAATTCCCCACCGTCTAGTTTATCCCTAGACTCCTTACTCAGCTCATCTGAGTGTTCGGTTTTTC |
| 150 | ERO1LB | 2462345 | TTTGTTTGTTTCAAGTGTGGAGGAAATTTTTTGTAACAATCAGAATTTGATTTTTCCTTTATGGAATTCAAAAGAAAGTATTCCTG |
| 151 | ERO1LB | 2462346 | CCTGGCCAAAATGTGCAAATCTTATACTCTTTGACCTGTATTCTGATTAAGAGGACTCATTTGCAGGGCGTCTACTCAGTGACCAAGGTTTGTGATATAATTAATAGTTTAACAGTTTTAATCTCAAAAAATAGTATTGGGATCTGAGCTATGTAAGACATTT |
| 152 | ERO1LB | 2462347 | GCCTCGATCTGTTTATCGTCCTTTAAATCCTCTGGCGCCTAGCCGA |
| 153 | ERO1LB | 2462348 | AAGAAGGAACGACTGATAGAGGGTCGGGAGAGGCCGGGTGCTGTGGCTCACGCCTGTAATCCCAGCACTTTGGGAGGCCAAGGTGGGTGGATCATCTGAGGTCAGGAGTTCAAGACCAGCCTGGCCAACATGGTGAAACCCCGTGTCAACTAAAAATACAAAAAAATTAGCCGGGCATGATGGCAGGTGCCTGTAATCCCAGCTACTTGGGAGGCTGAGGCAGGAGAATCACTTGAACCCGGGAGGCAGAGGTTACAATGAGCAGAGATTGCGCCACTGTACTCCAGCCTGGGTGACTAAGTGAAACTCTGTCTCAAAAAAAAAAGAGGGTGGGGAGGGGAGTATTTGTTTCTATTGGAATAAAATTATACACTATAAAAGTTAAAACATTCTATGTTTGGGTATTATGCTTTCTTT |
| 154 | ERO1LB | 2462349 | GCTGCTCAGTATGTAGACCTATTGCTGAACCCAGAGCGTTACACTGGCTATAAAGGGACCTCTGCATGGAGAGTGTGGAACAGCATCTATGAA |
| 155 | ERO1LB | 2462350 | CCTGCACAACAAAGTAAGACCACTTTTCTTAAAAAAGAACAATGAAAAACCTGATATAATTGATTTTCCTCTTGTGATTTTTTAGCTCCCTTAAAGTATATTTTAAATCATCATGGTTTAATATCTGAATCATGGTTTTTCTTCTTTATTGGTTATTTGGTTGGTTTTCTTGGGAAAAGAGGTTGGTACTAGTCCAATTTGCACGTTTGTAGAGGATTCTA |
| 156 | ERO1LB | 2462351 | CTGGGGAGGACTCTAATTCGACTTCTCCACAGCCCTTTTTCCA |
| 157 | ERO1LB | 2462352 | CAAAGAAGCTTTCATTGACTGGGCAAGATATGATGATTCACGGGATCACTTTTGTGAACT |
| 158 | ERO1LB | 2462353 | TGCTACTAGTAGTGTATCAGTTATCTGTTCTACAACTTCTCCAGTGATTGGTACTATGATTTTTAAACAGCTTTACTTTGAGGTATAATGAAATATGATACACTGCATATAAAGTATACAGTTTGATGTTTTGACATGTGTCCACCCATATAACATCATCACAATTAAGATACCATAGGTTGGGTG |
| 159 | ERO1LB | 2462354 | ATGATCTAGGGACTAGGCTTAAGTCATTGGAAGATTTTGGGGTAAATTGCCAGTTTATATTCTTTGTCATTTTTTTCTCCATTGGGTTGGATTTTAAAATTATTACTGATTTGTAAGCATTCTTTATATAATG |

TABLE 7-continued

| Target Sequences | | | |
|---|---|---|---|
| SEQ ID NO. | Gene | Affy Probeset ID | Sequence |
| | | | TGATAATTCTTTGTTGGCTGTGTTGTTAGGATTTGTCCTTTAATTTTGCATATAGTTTTTTGTTGTTGAACAGAAATTATTCTTTAAACTTAAAAAATTTAAGTATAATACACATATGGTGGAATAGAAAATTCTTAAGTGTAAAGGTCAATGTAACTTTACAAAGTGAACCCAACTCTATAGCCACCATCCAGAGCATTATACTTGCTGTCCAGATTACCATGTGTACTTTCCTAGTCATTATCACCTTCCAAAGTTAACCGTGATTTTGAGATACTGACAGAGATTAGTTTAACTGTTTATAAATAGAATGATATAGAACATATTCTGTTGTATCTGGCTTCTTTTTGTTAACATGTGTCTGAGATTCATTCATGTTTTTGGGCATAGTAATGTTTAATTCTTTTTTATTGGCACATAGTATTCTATAGTAAGAATGTGCCATGTTTCCATTCTGCTCTTGATAGCTTATGCTTTGGGGCCATTTC |
| 160 | ERO1LB | 2462355 | GAGCAAGCTAATAAACTGGGAGCAAT |
| 161 | ERO1LB | 2462356 | TTCCGGTTGGAATAAAAGCTGGGCATTCTAATAAG |
| 162 | ERO1LB | 2462357 | ATGTTCCAGCTACATGCACTTCTCCCATTGGTAAACCCTAGATTAGATTGGTAAACTCTAGGTTAATCGTGTGGGCCAAAAAAAGCTTTCTAGTAATCCAAAATTGCCTACACTTTGTTAGAGCAGAAG |
| 163 | ERO1LB | 2462358 | TAATCTGAAGCGACCTTGTCCTTTCTGGGCAGAAGATGGCCACTGTTCAATAAAAGACTGTCATGTGGAGCCCTGTCCA |
| 164 | ERO1LB | 2462359 | GGTTGCATACTGAGCACTACTTTAGCAAGCCTGGCCAGGAATGGTCTCTCTGCTTAGGTGTGATATGTGAGAGAGACTTGAATGCGGCGAAAGAGTGAGCCGTCATAAGATCTGGAGGA |
| 165 | ERO1LB | 2462360 | ATGAGAAGTGCTGTCCCTTCCATTCGTGGTGGCAG |
| 166 | ERO1LB | 2462361 | GCAGCCTCAGTGGAAACCTCAGGTAAGCCTGTGGGGAATTCTTAAGATGGAATAACCCTTCCGAGTTAGTCGTCCCCATTTGGCACGAGAGGTATAGGCCTTTATATCTCTCCATCAGTTGGTCATTGGATGAAGGCCACCAGAGGAAATAAGGATCCAATCTTGGGTAAGGTGGTTCTTTTCACCCAAGCTTGTCTACCTGCAGCATTTCCACAACTGAGGTAATTACATCCCCTTTATTCCTGAAGGGTGATCTGAGTAGTATGTTACAGTGTCTACCACAGTCCACTCGTTGCACCATGTATTTC |
| 167 | ERO1LB | 2462362 | TCCTACCTAATGTGAAAGAGCCATGAGAAGGTTTGGGGAAAGAACATGCCAGGGAAAAGATGTAGAATACCAAGTAAATGGTCTTGAGATAGAAATAAGCTTGGTGTGTTGAATAGGCAGAAAGCTGGTATAGCTGGAGTGAACGAGAGGGAGAGTTGGAAATATAGGTAGGCACCAGATTTAAAAAACAGTAGGACCGTATTGACCATGTAAGGATGCTGGATTTTATTTTAAGCAGGATAAGAAACTACTGAAGGGATTTTTGTGCAAAAAAGACTGTAAGGGTAGAAGACAAGAAATAGAGGAACCATTTAGGAGACTCTTGTGTTAGTTCAGATAAAAACAATACAGATTTGCAATAGAATGCTGCAGCTGAAAAATGTAGAAAATGATCAAATTAGGGTTGTACACAAAAGGCAACACCAGCAAGCTTTTCTGATGAATTGAGTGTGACGTATGATATAGAAATGAAATCAAGGATGATGCCTAAGTTTTGAGTGCACATATACAAGCACAAATGTACATATATGTAAAATCATGACCAAATAGATTTTATTCCAAGAATGCAAGGATGATTCTTGCATTGATGTTGATAATCATCAAAATTCAATATGTGCTCCTGATTTTTAAAATAATAAGAATGATGTATATTTCTTAACATGATGATTTCAGTCCTAACATCAGCATAGCTAACACGTCTTGCATATGGGGAAACACTAGAGGAATTCTCACTTAGGTCAGGAACCAAGACAAGGATACCCACTATCTGCATTAACTG |
| 168 | ERO1LB | 2462363 | GGAACCACTGGGATTTTGTATCAAATTAACTATTTTCCCATATTTTCCAAACTTTATGTAAGAGTTATATTTCTGTCCAGGTACGGTCATATGACCTGTTGGACCAAAAGAAGGAAGGACACCTTGGTTGACAGTCTCATTTGCATGAGTAAAAGTGGAGTCATTGTTTCCCAAAGGGAAATTAGGGACTGTTACAAAAGAAGGAATAATGGAACTTGGATAGGCAAAAGTGACAATGTGGTTCTTGGCTACTCAACAATC |
| 169 | ERO1LB | 2462364 | CCGTTCCTGAAGTACTGCAATACCAGGTCGATGCGAGGAGTGGATGGAGCAAGCTCCTATTCCATCTCCCTACTCCAAAAATCCATGTAATATATTGTTCTCGGGTAGAGGACATATCAGGTATTAACAGATACTTCACTTGATCTTAGCCAAAAGGCCGAGAAGCCATTGGAGAGACAGGTGCTTCTTTAAATTTCCACCACTAAATCTATAAATCTAAGTGCATTTGTAGCTGCTTTCTCTTGTTTCTTTTCTACCATAACATTGAACTATATGAAATTTTTACTTTTATATTTCAAAAATGG |

TABLE 7-continued

| Target Sequences | | | |
|---|---|---|---|
| SEQ ID NO. | Gene | Affy Probeset ID | Sequence |
| | | | TTGAACATGCCAGTTTCATATTGCTCAATGTAATACAGTGGGG GAAGTGTTTCTTGTATCAAAAACCATCTCTTCACAAGTGGTCCA GTTCACA |
| 170 | ERO1LB | 2462365 | GTTCTGGATGATTGCTTGTGTGATATTGACAGCATCGATAACTT CAATACCTACAAAATCTTCCCCAAAATAAAAAAATTGCAAGAGA GAGACTATTTTCGTTATTACAAG |
| 171 | ERO1LB | 2462366 | CTGAGCTGTGTCTGCCAAGTGGCATCGCCAG |
| 172 | ERO1LB | 2462367 | CTGACCGTCCAGTGCGGGAAACATCTGCGAACCGCCCGCAG GGTGGGGGGACGGCGACACTCCGGGTAATGGCAGTCAAAAG AGGAAGATGGTGACGGTCCCCCTGAGCTGTTTTCGTTTTTTCC TCTCGGATGTGTTAAGCGGCTGGGAGTGTGGCGGGAGATGG GACGGGCATGAACCACCTCGGCTGTCTTGCGAAGGGAGCGA GCGCCCAGAGAAACGGTGACGTCCTT |
| 173 | ERO1LB | 2462368 | ATGAGCCAAGGGGTCCGCCGGGCAGGCGCTGGGCAGGGGG TAGCGGCCGCGGTGCAGCTGCTGGTCACCCTGAGCTTCCTGC GGAGCGTCGTCGAGGCGCAG |
| 174 | MIR4435-1HG | 2492489 | TGTCAACTCTGTGTTGGAGCCAGTAGGGAGCTCTGTGGGTCC TCGAGCAGGAAAATCCCATGGCTTAAGCAGTGTTTCAGGAAG ACTGGGATGTTAGGCTCCGGAGCTCTGAGCAAGTCAGATGGG ACTGGGAGTCATAAGAAGGCTTGACTGTGGCTAGTGATAACC A |
| 175 | MIR4435-1HG | 2492490 | GTGAGGACCTCTGATGGACCAGGAAATTGGAATTCTGCCTGG GAGGCAAGCCCATGGAGGCCCTGATCTGCTTGGACAGAGAGT AGCTCCCTTCACCTGTAAAATGAGAGTGAACGAGCTGGTG |
| 176 | MIR4435-1HG | 2492491 | TCACAGCATTCCTGTAAAAGGTATGAGGTTCGCCCTGATTGGA CCAGCCGAGGTCACATGCCTACACATGAGCCAATCACAGTGG ATAAAGGACTG |
| 177 | MIR4435-1HG | 2492498 | AAATTGACATTCCAGACAAGCGGTGCCTGAGCCCGTG |
| 178 | MIR4435-1HG | 2492499 | TGTGAAGACTGGACTTAAACAGCTACACCACCAGAAGCCGAG AGAG |
| 179 | MIR4435-1HG | 2492501 | AGATGCTAATCCAGCGTGCGTCCTGACAGAGGTTGAAGGGGG CTTCTCAAGTCCCAGGTCCAGCTTGGTGTGGTTCAGCTACTCA AGAGACATCTGCTGCTAATGGATGAGCAGTCAACCTGGACGC AGG |
| 180 | MIR4435-1HG | 2492502 | CAAAAGGAAGGTGTCGGCAAGATCGTTTTTTTCTGAGAGC |
| 181 | MIR4435-1HG | 2492506 | TGAAACAGGAAGCTCTATGACACACTTGATCGAAT |
| 182 | MIR4435-1HG | 2492507 | CACCTCTACCTGTTGCCCGCCGATCACAGCCGGAATGCAGCT GAAAGATTCCCTGGGGCCTGGTT |
| 183 | MIR4435-1HG | 2492508 | TATTTTGGTCATGGGCTGGTCTGGTCGGTTTCCCATTTGTCTG GCCAGTCTCTATGTGTCTTAATCCCTTGTCCTTCATTAA |
| 184 | MIR4435-1HG | 2492509 | AAAGGCTGCAGTCACCAGCATCTTTTCCAACCTTAATGAACTG TATCCTCAAAAGAACACTATCAGACTG |
| 185 | MIR4435-1HG | 2492510 | GCTCTGCCGACTTCCAGTTCTGGAACAAGATGGTTAAACTCAT TTTTCCCTGCTCTGCTCCTCTAAATACAACTAAGTACCTTGGAA ACTATTCAGCAGACAATGATAAAGGGCTCTGAAAGCTAGAAGA AAAGGTGTACTTGCAAGAAACCTCAGGACT |
| 186 | MIR4435-1HG | 2492516 | GCTTCTGCAGTTTGCCTTGGAGTCTGGGCTGT |
| 187 | MIR4435-1HG | 2492517 | TAAGAATGTAGATGCCGGTTGCACCTTCTGTTGTCTTGGAAGA GACTGCAGTGCTTGGCTGGAAAATAAGCTGCTCGGGACTCCT CTGAGA |

TABLE 7-continued

Target Sequences

| SEQ ID NO. | Gene | Affy Probeset ID | Sequence |
|---|---|---|---|
| 188 | MIR4435-1HG | 2492518 | CCTACCCATGAGGAACAAGCCTGTGGGGGGACTGATATTATC ACTTCTGTCATCAAGAAATAAGGCCGCAGGCATCCCTGAATAT AGAGCATTTATTAATCGAACTGTGAAAATGAAACACAGACAGT GATGACAGCTGGAAGTTGGCCAATGTCCTGTTGTCATATTGCC CTCAGCCTAGGGACTGGCCTGTGGCTCACTGACCCTGTCTCC CACTCTCCACCTCTCATCAGCAACTGGACCTGGTGCACCTGGT CTACCTCATGTCCAGTGTTTTCCGCAGTACCTGACTGGTATCC CCACCCTTGGTTGTTGTGTGGTGAGCTCGTCCCTATGTTGGCA AGTTACTTAATTCCTAGGTGTCCCGCCTTCCTCACTGTAAAA |
| 189 | MIR4435-1HG | 2492530 | CCCTGGCATCATATTGGGACTTGTTAAGGGCTGAATTGTGTCC CATCCCAAATTCGTATGGTGCCACCCCAACTCCAGTACCTTGG AATGTGACCGTATTTGGAGAAAGGGTCTCTGAAGAGGTAATTA AGGTAAAATGAGGTCATATGGGTGGCCTCTAATTCAATATGAC |
| 190 | MIR4435-1HG | 2492538 | TTGCTGATATACTTACAAACTGGTAAACAATGCTCTTTAATCAA CAATTCATAATCTGGGTCAGCGATTTTTATCTCCATATTTGCTC ATACTGTATGACATCAATATTTTATATTGGCTTGCCCATAACTT A |
| 191 | MIR4435-1HG | 2492544 | GCCAGTTCGCCTTTCGCTTTCTAAAATCATCTTGCTGGAGAGA ACGGTTATCAAATCCCATCCACTGCCCATGTAAAATAAATACC ATTCAGAAAAGCGTGGCATGGATGGCCATACTTCTGATGGGTT TATAACTGTAGATTGCATACGATCCCAACGTGAAGCCTGAAAT ACGACATTCAACGTCAGGCTTATTCCAGGCTACTGCTGTGGCT ACTTTTGTAATTCAACCAGTGGGGCGTTTTAGGCTAACGTATAT TGCCTCTAAGCTGATAAGCATTTTCCTGATCCCAGGCCCCTTC TAAAATTGAACACACACGTTCAGCTGGGGACACCTA |
| 192 | MIR4435-1HG | 2492546 | TCAGTTTTGTGCTTACAGTCCCGCA |
| 193 | MIR4435-1HG | 2492548 | TGGGAGGCCAAGGTGGGCGGATCATGAGCTCAGGGGTTCAA GACCAGCCTGGCCAACGTAGTGAAACCCCGTCTCTACTAAAA ACAAAAAAATTAGCTGGGCATGGTGGCGCACACCTGTAGTCC CAGCTACTCGGGAGGCTGAGGCAGGAGAATTGCTTGAACCTG GGAGGCAGAGGTTGCAGTGAGCTGAGATCGCTCCACTGCACT CCGGTTTGGGC |
| 194 | MIR4435-1HG | 2492552 | CTGGGGACACTATGGCCCCATCCTAGCCTGGTG |
| 195 | MIR4435-1HG | 2492554 | GAAAAGATTTTTATTCGTGTCTACATCAGTGTGAAAGGCTTCAT CCTGG |
| 196 | MIR4435-1HG | 2492556 | TGGACTTCTCTTTAGCTGGGGTGGTGGCTGCTGGAGAGGGCC CTGCTTGCTCATCTCTGCCAGCTTCCCAGTCCCTGCAACCAGC AGTGGCCAGCCTCTGGCCACCCCCATGAAAGCACATAAAAGG GTTGGGGA |
| 197 | MIR4435-1HG | 2492558 | GGGAACAAAATGTCTGCTCAAACCATGACAAAATTGGCCACAA TTTGCCGATTGGGCTGATAACAAAAG |
| 198 | MIR4435-1HG | 2492568 | AGGTCGAGGCACTGTCCTAGCTTGTGACCTGCTCCCATACCTA TTTTCTCAGGGTGGAAGCAGACGCTCCAACTCCCACA |
| 199 | MIR4435-1HG | 2492569 | AGACCCAAAGCCTGTAGGAAGTATAGCAGGCCTCACCCAATA CCCTGCAGTT |
| 200 | MIR4435-1HG | 2492571 | CCTCAAGAGAACATGGAGTCCTTTG |
| 201 | MIR4435-1HG | 2492573 | TCAGTGGCCTCCGAGTAACCCACCTGCTCCAGTCTGCAGATTT CCATCTCACTGAC |
| 202 | MIR4435-1HG | 2492575 | CAAAGGCTTCTCTTGCTGGCTGAGAATTGTTGGGGAGCTCCCT GCCCACGGAGGGC |
| 203 | MIR4435-1HG | 2492577 | GGGTTCCTGTCGGAATCTTGGAGCTCATCCCCCAAACTTGAGA TT |

TABLE 7-continued

Target Sequences

| SEQ ID NO. | Gene | Affy Probeset ID | Sequence |
|---|---|---|---|
| 204 | MIR4435-1HG | 2492581 | AAATGCTTAGGGAGACAGTTCACAGATATATATGTACTTCACA GGGCACAATTTAATCCATAAATCAATCATGGATCACTGCTAAA GAAAACAAAATATGCTGCCACTAATTTGCCACCACCCTGTGAG CATGATTGGATGATGTTTA |
| 205 | MIR4435-1HG | 2492583 | AGGCAGCCTTTTCTGTCACAACACAACGCTGAGCCGGCAGCC TGGCTCTGTCAGGATCTGGGGCTCCAGCGCCCGAGAAGCCCA GCCTCGCCGGCGGCCAAGTTCACCGCGAGGCC |
| 206 | MIR4435-1HG | 2492584 | CCGAGGAGGCGGAGCATGGAACTCGACAGTTAAAACATTTAA GAGA |
| 207 | MIR4435-1HG | 2492590 | TGGCAGCTCCATCTACACAGTGTCGGGCTAGGCATGGGAGCA TTCTGGGCCAGGAGAAAGGGGATTGGATCCTGGATGGTGGGA ACCGCAGGTGTCCCCCTCCACGTGCCTGGGTCCAAGACTGCT CTGCTCTGGACCTTCTACGCCTTCAGAGGTACAAGTTGCAGTG CTACCCTTGCTGAACCTACAACCCTGTTCAAGTGACAACTTCT CTGAGTCTCATACGAGGATATTGAAAGAACCTTCTGCACAGGG CTGTTGTGAGGATTAACCGTAATAATACAAGAATATCTGGCAC TTGCATTCAGCAACTCACCGCTTACTTGTTCAACCAGGTAAAA AGGTTCTGATCCCAGTGTTGCAGGACAGAAAGACCTCCCCCT CTGTAGCTGCAGATGTGACCCAGCACAGAAAAAATGGCAGGT GAAAGACAGGCAGGAAGAGCAACTAAGAAGGTGGGAGGCAC CTCCATAAGATGCCTGAGGCCATGGGGATGACCGTTCACAGA GCTAGTCCCTCGAGCAATGTGTTA |
| 208 | MIR4435-1HG | 2492591 | TGTGGCTCCAAGTTCCGTAGGACTCACTAGTCTTTTTTTCCCTA GAGGGTCTTGCCATTGAGAGGCAGGTGATGTGCTGTTTCAGA AAACAAAATTGGGACATGTCCTGATATGACATCCATCAAATATA TACAGATAGGTGTCACAGCCCCCGAAAAAGCTTATCTCTTCTA GGCCACACATAGCTATTTCCTCCAACTGTGTCAGACATTACAA AGTTTCTAGCAATCAAAACAAGTCAAATGCCATTCTCAGGACC CGTTGGAGGATTTTTTGCTTTGTTTTGGCTTTGTACGGTATCCA TACCATTTTCCAAATTCTTTTGTCCTTACATATTTTGTTTTTCTTA AAAAAAAAAAAAATCACCTATAATCCCATCACCAGACAAAACCAC TAGAAAGAAACCAACATTTTAGCCATGTTTTTCTGTATATAAAA AAAGTGTGTGTGGAATTTTTCATAACAATATTGGGACCATGAC ATCTATCACATTTTTTATTAGGAAATGGCCTTCAACAATATGCA TTTAACAATATGCTTGATGTCTGTGTAATATTTCATCTAACAAAT ATATCATGATTTATTTAAGTATTCCCTGATTGCTTGCTTCTAACT AGAAAAAACAATTTTTCTAAGTGTCACCACTGGGTTAGAGTAAT CTCAGCCAATCCTCCTAATAGCACTGTGAGACCAGAGTTATGA TAATCTTCAGTTAATGGACAAGGGACATGATGGTGTGGAAGGA TAAATAAACTACCCAAAGACAACTAGCTAGTGAGACCAGCATG GACAGTCAAGCCCAGTGCATGTAATCTGTGCTCCCCTGCACT GTTGCTCATATACTTGGACCCTTGC |
| 209 | MIR4435-1HG | 2492593 | CAACCCAGGGTCCTTGCAGAGAGATTGATCTGCCAGCAGTGG CATCAGCAGCAATAGTAGCAGCAGCAAAGCCCTGGACAGTCC TGGCCCCCAGTCCACAACTTAGACACAGCACATGGCCTAATTC ACCCACAGAAGCAGCCACTGTGAAGCCCTGTGTCTCCCCAGA CTCCATCCAGTGGCATAAGGAGACCCAGGCCCTGCAGCTTCC TCCCCATCATGGAAGGCTGTCCATCTA |
| 210 | MIR4435-1HG | 2492595 | ACTTAAAATAGGAGTGAGGTGAGAGGGGCAGCTGGGCTCATG GACGTCAAGTGGACAGTTTCTCAGCTGGTATTTCCTATATTTC CTGTTTTGGACAGCAGGTTCCTGCCCTTCTAAGCTGGGGGTA GGGGTGAGGGAGTGTATGTTAAAAAGCTCTGTGGACTTGCT |
| 211 | MIR4435-1HG | 2492597 | GGTATTACCTGATCCCAACTTGGCACCAAAAGACAGCCAACAT AGACTCATTCCTCCTGCTTCCTGGTGAGCCTGGTATTCTCCTC CACTTCCACTGACAGACATGTAGGGTGACTGGGTGGTATCAA CAATAGGAACCACATCATAACAGGCAGCCTAGTTTGGGAAGC ACTCTTGGTCTCCGTAGGCCTGAGACTCCTTTTGCCCATCTAG AGG |

TABLE 7-continued

Target Sequences

| SEQ ID NO. | Gene | Affy Probeset ID | Sequence |
|---|---|---|---|
| 212 | MIR4435-1HG | 2492601 | AGACTGACCCTACAATAAATGCTTAAGAGAGTCCTACATCTGGAAGCAAAAGGGCTATATTCACCATCATGAAAACCCTAAAGTATAAAACTCATTGGTAAAGCAGACACACAAATAAGAAAGAGAATGGAACCACATGTTATCATTACAGAAAACCACCAAACTGCAAAGATAAACAAAGGAAAGAAAGAAAGAAAGAAAGGAAGGAAGAAAGGAAGGAAGAAAAAGGATTATTTAAAATTATCAGAAAACAATTGAAATGACAGGAATAAGACCTCACCTATCAATAACAACTTTTTAAATGGCTTAAATTTCCCAGTTAAAAGATATAGACTGGCTGAATGGATTTTAAAAGTGACCTAACTCTATGCTA |
| 213 | MIR4435-1HG | 2492603 | AGAAGCTTGTTTTGAGCTCATTCAATATGCATCAGGTGGCGGTAACATCTGGAG |
| 214 | MIR4435-1HG | 2492605 | AGGGTGCTGGTTCTGAGCCAACTTTGCATGGAAGGCCCAGCAGACCACGCTCATTACTTACAGCCAGCATCATCGGGGAACTCCGGCACAGA |
| 215 | MIR4435-1HG | 2492607 | GCGGCCCTAGTCCACTCTCATGATGCCTCCATTAATCCCCCGGTCAGGGACCTTCCAGCCCTGCCCACAGCAGTCGATGCCTTCAGTGCATCTCAGTCTTCCACCC |
| 216 | MIR4435-1HG | 2492609 | TCAGGTCATCCGCTCCATGGAGGTCCCCGTTCCTACCTTGGCCTTGCCTTTCCCCCTGCATGTAACCTTGGTGAACTTTTCACAAGAGTCTGCGCAGTCT |
| 217 | MIR4435-1HG | 2492610 | TAAGCAGATTAATGCCGAGGAAAAGCCTTGGTGA |
| 218 | MIR4435-1HG | 2492612 | CCCGTGGAGAGAGCCCCGCTGGTGAGGAAGCACGGGGACCCTGCTGCAGGGCTGGTGGAGGGCTCCTTCTGCAGACTTCTGAGCTTGGAGCACAGATGGG |
| 219 | MIR4435-1HG | 2492614 | CTGGCTCCTGCACTACTATGGCCTTTTGGCTC |
| 220 | MIR4435-1HG | 2492616 | TTCCAAGGTCTCACAAGAGTTTGCCTCCTCTCATTGCCATGTGAAGACCTCTGTGGGGGAACAATGCATGGGTTCTTGGGGTATTATAGGGGACTACAGAGAAGTGTCACCTCCACCCAACAGCCTGATTCAGTCTACTCCTCAGGAGGAACACAAAGTGGTCTCTCTAGTGCCATGAAACCCCAAAAAGTGTCAACCAGTATTAAAGGCCTGCCTGATATACAACCCTCGA |
| 221 | MIR4435-1HG | 2492618 | ATGAAGCTAGGCCCCCCTGTCCTGACAGCTTTCCACCCCTTCCCTGCCCCTCTCACCCTGCTTTCCAGGGGCAATGCACCTCCCCACTTCT |
| 222 | MIR4435-1HG | 2492620 | CCAGACACCACTGGCCTACATCAAACTCCAGGCCACAGATGGAAATAGGACTGAGATCCCTGGACCTGGG |
| 223 | MIR4435-1HG | 2492621 | AGATCAGGTGGATTGAGGATGTCACTGCCATCCCCTCCAAAAGCACCTGCAGGAAGGGGGTTGCCATGGTCACCATCTGTGAACAGGACTCCTCAAAATGTTT |
| 224 | MIR4435-1HG | 2492622 | TCAAGGTGGCCTTGCGCTTCACCGAGGAGGTGTCATTACCAAACGTGCTGGACATTGGCTACCTACGGAAGAAAGATTAA |
| 225 | MIR4435-1HG | 2492624 | CCTTCCTACCTGGTAGTAGCACTGACATCCTCTTCATCCACTGGAAGCTTCCAGATCCTGGCCCCCACAACCCATTCTCTCCCCATAGGGCTTCCACAGAAACACAACGTGTACTGTGTGCCAAATGACT |
| 226 | MIR4435-1HG | 2492626 | TTATACATGGCCTCACTGTTGGGGAGGCAGTAGGGAGTGTTGGAGACCAGGGTCAGGACTAGGGCTAGGGCAAGGCTAGGAAGGTGCCCAGGATGCATGTTTTAAG |
| 227 | MIR4435-1HG | 2492628 | TAAGAAAAGGATCGTGGTGGTAGCAGGAAATAAGACAGAAATTTTCCATGGGGGCTCCAGGTCTGAA |
| 228 | MIR4435-1HG | 2492636 | GTCTTTTCTTGAACAGGAACTTGCATACTCAAAAACAACA |
| 229 | MIR4435-1HG | 2492638 | GATCCCGTGGAAACACAGCACCGGAGGATATGGGATAAGAGACAACAGAGAGGAGTGGTGCTTCCTGAATTTAGGAAACATAGCTGCTACTTTGGGCCCTCTAGATACTTGAAAGAA |

TABLE 7-continued

| Target Sequences | | | |
|---|---|---|---|
| SEQ ID NO. | Gene | Affy Probeset ID | Sequence |
| 230 | MIR4435-1HG | 2492639 | AGGGAAGCCAGGTTGTTCATGGACATTCAGTGGAAGAATTAAGGCAATTAAATGTTAAGTTTTGCAGGGCTGGTCGACAAGAGAA |
| 231 | MIR4435-1HG | 2492640 | GTGTGTATTCTCCATTGGTCACAATGCAC |
| 232 | MIR4435-1HG | 2492642 | GACAAGAATAACTCCCCACTGGGACTGGAGGAGAGGAAGGCACATGGGGGCCCTTGGCAGGGTGG |
| 233 | MIR4435-1HG | 2492643 | TCAGTCACGTCTGCGCCAGAGCTTTGATGACCCACCTGTCAGCCACACTAAGGGCCCTGCCATGAATAAGGCCTCCGTCACTGAGGATCCTGTACCCCTCTGCCATAAACTCAGTGACCTGACTG |
| 234 | MIR4435-1HG | 2492645 | GAACTCCCACTGTATAATTGCTAAACACAATGACAGCTATAATTGAGGCACTGAAGGAAGGTCAGGGGAGCCCAGGAGGGCGGGGCTGCTGCTGCCTGCTGAGCTGGGAGGGTTGGTGGCACCCCTTGCCCTGGGTTGCCATAGCAGATATCATAATCAATTACGGCCGTCTTTCATGAGGAACCTGGATCTTTCCCAAGGAATC |
| 235 | R3HDM1 | 2507381 | AGGGGCGGGATTCTGCCAGCCGCGGCTGCCGCTGGAGCCGGTGTCCGGGCTGGTGATGGGGTTAATTCCCTTTCGTAAGACTCTTACTTGC |
| 236 | R3HDM1 | 2507382 | CTGCCTCCGCGGCTGCTCTTGCAGCCCCAGGGACTCGGGAGCCAGCCACAGCAGGCCTGCCAAGAGCGTGGTACTGCTCTCTCGTGTGGCTGGCGCCGGTGCCCCGGGCTCCCCCGGCCGCCCCACGGCCGCATCCCCTGGCCTTGCACCAAGAGAATTTTCAGCTTCGACCGGTTGG |
| 237 | R3HDM1 | 2507383 | CCCGGGATCAGATTTACACACGTTTTGATTCCTGAGCCTTAGGCTGCCAACAAATCTTTGTGGGCTTTGAAGTTTTTTGGTGTTTTGTTTTCTTTTGTTGCTGTGACTAGGTGCAAAGGGTG |
| 238 | R3HDM1 | 2507384 | TTGGGTTCTGAGGAAACATCTGAGTTTTGATCATTTCTTCAGGGTTTGAGAAGACTATGGTGGCTTAATGATCTTCTGTATTCCATAACTAGTACACCTAGTTACAGAATTGACATAGATACATTCAGGTCCTGGAGGAAATTTGTGGTATCTATTAAAAAAATGAAAATTGCCAGTCATGTAGTAGTCACC |
| 239 | R3HDM1 | 2507385 | TATTATGCAGAAGATGTGCATTGCCATGCCTTGCAAGTAATAGGGTTTTTTTTCTTCTTTTTTGAACTGGTACTTTAATATACCTAATTACATCCATTTGAGTTAGTATTAAGTTTTAATTTCTCAGAAATAAAGTAGTGAAAATTGGTAGCAGTTTTGTTTTTCCCATTCTTGAGAATATTACAGTGATAAACAAGGCTTGATAGGTTTGTAAAATACTATTGCTATTTGAATTAAAAAATTTCACTATTGACTTTCCATATTCTATTGTAAATAAGTTGGGGAATTAGTGTGTCAAGGGGGTGTGGTAACAAATGGTAATGTAATTTTCAAATTGCTATTGCAGCACCAAACCACAGA |
| 240 | R3HDM1 | 2507386 | TGAGACGTTAGCATCAACATGACTGTATATCATTTCCAGAATTTAATTCAATTAGTTATTGGCTGAGGGATGAAATAGAGATGAAACTAAATCCTGGCCTCAAACTAGTTTTGTACCTTATTTTCCAGCAATTTGGTTTTTTTATATCTAGATTTTATCTTTACTATTTTCCCTCATCTTACCCATTCTTAGTCTCCATACACACCTATTAACTTTAATTTCCTTTTCTGAGAATTTTGAAAGCCCTATAGTTTATGATCTTTTTTCCCTCTTTGCCTTGTGAATTTTATATTTGTGAGTTTTTTCCAAATTTCTACCTGTCAGCTCACTTCTTTAGGCAAGGTGTAAGGTTTTTGAGCCCCCTTATTTCATTTTTTATTTTTTTAAGAGACAGGGATTCACCCTGTCACCCAGACTGGAGTGCAGCGACAGGATCATAGCTCACCACAGCCTTGAACTCTGAGGCTCAAGGGAGCTTCCCATCTTATGCTCCCAAGTA |
| 241 | R3HDM1 | 2507387 | GTGTGCAGTGGACCGGTGAACATCACCACCTGAGCTCTGCCTCCTGTCAGATCAGCGGTGGCATTAGATTCTCATAGGATTGCAAACCTTACTGTGAACTGCGCATGCAAGGGATCTGGGTTGCGTGCTTCTTATGAGAATCTAATGCCTGATGATCTGAGGTAGAACAGTTTCATCCCATAACCATCCTCCTCACCGCCTGCACCATCTGGGGAAAAATTATTTTCCACCAAACAGGTCCCTGGTGCCAAAAAGGTTGGGGACTGCTGCTCTTAGGACAGAAAGAAAGAAGTTCCATAACTAGAGTAAAATATCACCTTACAGTATGAGGTAGCTTA |
| 242 | R3HDM1 | 2507388 | GCAATCAGAACACCTACAGCATTTATCAACTAAGTTCACTGTCTTATATGGGTGTGATTTGTGGTCCCCTAAAACAATTACAGTGGT |

TABLE 7-continued

Target Sequences

| SEQ ID NO. | Gene | Affy Probeset ID | Sequence |
|---|---|---|---|
| | | | AAAGATCACTGATTGCAGATCACCATCACCAGACATAATAATGAAAGAGTTTGAAATATTGCAAGAATTACCAAACTATTACACAGAGACATGAAGTGAGCACATGTTGGGAAAATGGTACTGATCGATATGCTTGACTCAAGAGTTGCCACAAA |
| 243 | R3HDM1 | 2507389 | AAGTGATAGGATTGTTGCCCACCCAGGACGTTATGGATTCACTCAGCATTCATTCATGAAATATTCGTTGATAATTTACTATGTGCCGTGTACTGCCTATATAAAGCAGAGAGTACTTGCCCTTATGGATTTTATTTTCTAGTGAGTGAGACAAA |
| 244 | R3HDM1 | 2507390 | AGAAACTAAATCACTGCCTTGTACAATAAAAAGCTCTATGTTGGGGTGATCAGACCCAACACCAGGTCATGGGGGCGATGAGTCCGGTGGAGTCAAAGGAATGAGAAAAAGACAGTTTGAGAGAGAAAGTGGGACCGGGGAGCCTACGCTATTTATTG |
| 245 | R3HDM1 | 2507391 | TGAAAATTGGGCCTTAAGCACATAAAAAGTTTTAAGTTCATACAGAGAAATAAGCTCACGCCTGTAATCCCAACACTTTGGGAGGCCAAGGTGGGTGGATCACCTGAGGTTTCTCAACCTCGAGACCAGCC |
| 246 | R3HDM1 | 2507392 | GCACTTCTCTGACTATAGTTTTTATATGACTTTGACTCTCAGAACCCTGGTAATTTTTTACGTAGTCTCCAGAAATAACATAAAATAACTTAGATGTTGGCAAGTGTGGAGAAAGGAGCCCAAAATGTAATGCAAGCACTAACAGATGAAC |
| 247 | R3HDM1 | 2507393 | ATGCCTTGGTCGTTTTGTGTCCCTGGGCTGTTGGCAGTGTGACTCTGCTACAGAATACCACTTGGGGAGATCAGCTTACTCAGTACAGGGTG |
| 248 | R3HDM1 | 2507394 | CAGATCTTTCTTCACATCGTGCAGGTAACGTATGAGCATTGTCTGATGGATCCTTACAACATTCCTGTATGCTTTTGGAAAGTATGATCTTTGTTTAACAAAATGGGAAACAGAGGCACATGCTATACCCAGCTATCACAGAAAACAATAGTTAGAATCCAGAAAACATACTCATCTGGTTTAGTGTGTTGCCCA |
| 249 | R3HDM1 | 2507395 | AGCAGGCACTCCCAATGCCAGACTAATCAGCTGG |
| 250 | R3HDM1 | 2507396 | GAGCTCTATAGAGGAGCAATGCAGAGCATCAGTTTACAGGTACTATGGAA |
| 251 | R3HDM1 | 2507397 | AATCTTGCCATACTTGCACAGCTGACCAAC |
| 252 | R3HDM1 | 2507398 | ATTCAACTGCTAGAGAATGTGAAGTTTCACATTTTAAGCCATCAAAGAACCATTGG |
| 253 | R3HDM1 | 2507399 | TGTGCCAAAACAGTCCTGAATGTTCGTGTTGGCCTTAATGAACCACCCCTTAGTGACTCAGTCACCATTCTCCACAAGCCCTACAGCCATCCCGG |
| 254 | R3HDM1 | 2507400 | CCTCAGCTGCAAACTATGTAATACTGCTTTTATGGGGATTAAATGAATTAATACACTTAAAGCATTGGGAGTAGTGCTTAGTAAATAATAAATAACTCTTTAAGGGTTTGCTGTTAATATTACCAGTTTCACAGCACATATTGCAATCAGTTATTATCTTGTATATTTTGTCTCTGCACTAGAATGTAAGCATTTTAGGTTCTAGGATCCCATCTGCTTGGTTCACTCATGTATCCCTATTACCTAGAACAGTGCTCTGTACATAGTATCCAGTCTG |
| 255 | R3HDM1 | 2507401 | GCGCCCAGCCTAATACTAAGCTTCTAATCTTAA |
| 256 | R3HDM1 | 2507402 | GTCCATTCCAGTCCGGGAATCTACAGTGGTGACAAGGACATGGGACTCCTCCTGCCAGATTACAGATGGTTCACTACAGTTGACATCCTGGCTGACAACTGTGAAAAAGAACCTTGGATTATTTTATTTTATTTTTGTGGGACACCACAATCCCAAATCC |
| 257 | R3HDM1 | 2507403 | GCTTCAAGCTCCCTGTAGAATTCGAAAATAAC |
| 258 | R3HDM1 | 2507404 | GATGTCTGATACTGTTACTGTAAAAGAT |
| 259 | R3HDM1 | 2507405 | AAGTGAAAGATACAACCAGAGTTGAAAATCTTATCAAATCAGAAAACTATGGGAAGATTTTGGTAGAGAAGAATGAACATTGTATTGAGAACAATATAGATTTGCAG |
| 260 | R3HDM1 | 2507406 | TCATACAAAACTCACTTCTCAAAATTC |

TABLE 7-continued

| Target Sequences | | | |
|---|---|---|---|
| SEQ ID NO. | Gene | Affy Probeset ID | Sequence |
| 261 | R3HDM1 | 2507407 | TCAGTCAGGAAACGAAGCAAGGCTTGGGCTGAGTGAATTTTCT ATTCTACAGGGTATCCAAAGAGGTCCTTTGTTGGCATTTAACA GGCCGGTGGACTTGGTCTGGAGCATCCCGGATTGCTTCTCGC ACCTGTCTGG |
| 262 | R3HDM1 | 2507408 | CAACAAGGTGGGTCCAAAGTAGTCAGACTTCTTATGTGGCAG CTCAGGGGTCCCAGAGAGAATGTTCCAAGAAAGCCAAGCAAA GCTGCAAGGTTTCTTTTGACATAGGCCCAGAAGTTCCAGAACG TTACTTCAGCTATC |
| 263 | R3HDM1 | 2507409 | CATAGCGACTGTAACGATTTGGAAGGAGGGA |
| 264 | R3HDM1 | 2507410 | CAATGCCACGCTTCTTCGACAATGAAGGCAGTACATAA |
| 265 | R3HDM1 | 2507411 | AATCTTAGCTATTTCCTGTTTGTCAAACAAAGATTAAAAGCATG TATGTGGCAAAGCGTGGTGGCTCCTGCCAGCACTTTGGGATG CCGAGGCAGGAGGTTTACCTGAGCCCAGGACTTTGAGACCAG CCTGGACAACACACGAAGACTTTGTCTCTACAAAAATAAAAAT AAAAAAATTATTCATGCGTCACGGTACATACCTGTA |
| 266 | R3HDM1 | 2507412 | CGGCCATTGCAGTCATTTGGACAGAC |
| 267 | R3HDM1 | 2507413 | CAAGCTCAAAGTTAAAGCTAGTTCGGAGCCTTGCAGTGTGTGA AGAATCTCCACCACCCCCTGCACCAGAGATATCACAGGAGAA CCA |
| 268 | R3HDM1 | 2507414 | TGAGTGTAAGGAAGTTGCCAGTGTCTTTGGTAAACAAGACAGA GAGTGCAAAAAGCAAGTGTTTGTCATCCTAGTAAAAACTGCCA GTGTGCATCATTTACCCTATATTATGAACACAAATTTTAACTGG TATGATGAATTAAGAAGA |
| 269 | R3HDM1 | 2507415 | AATTCAGATCCAGTTAACACAATCATTTGAGAAAGAAGAGAAG CCCTCAAAAGATGAAGCAGAAAAAGAAAAGGCCAGTGATAAGT TGCCCAGAAAA |
| 270 | R3HDM1 | 2507416 | ATTCCAGTCAAGAATACACTGATTCAACTGGCATAGATCTACAT GAATTTTTAGTA |
| 271 | R3HDM1 | 2507417 | CCTCTATAGATGCAAACGTTTTTAAGTTATCCACATAGACATTT TTTAACTGTACGGTTTAATGGTTTTTAGTATATTCAATATACAGA TAGGAGCACTATCACCACAGTTATAGAACTTTTTCATTGCCCCA AAAGAAACCCCATACATTGTAGCTATTCCTATGCTAATAATAAT AGTAATACTGATATTGGATGATCCCAACCCTAATCTGTTTTCTG TTTCTGTAGATTTCCCTGTTCTGGACATCTCATATGAATGAAAT TATATAATGTATGGTCGTTCATGACTGGCTTTTA |
| 272 | R3HDM1 | 2507418 | ACAGTTTTGTGAGTTCAGGTCAGGAGATGAGGCTGGAGCTGG ATGAAGACCAGCTCATGCCTGCCTTGTACATATGTTTAGTTCTA AGAACAGTAAGAAACCCATGACAGATTTAACAAAGGGAGTGAT GTGTGATCACATATGTGTTCTTAAAAGATTGTTATGCATGTTTC ATGTAGAATAGATTAGGGAAGATCAGGGAAGATACAGGGAGA CAATATACTCCTGCTGTAGTAGTCAAGCCAGAAATCCTGTTGC CTGGATCCAGGGTTGTGGCAGTAGAAAAATA |
| 273 | R3HDM1 | 2507419 | CTGATGTGTAGACTTTCAGGTGACCAAAGCAGGGGCTACCAG TTCTTCTATTGAAATTGAGAATAATCTGCATAGTGTTTATTTTAG GGAATCATTAACCTCTTGGCCTCGTTTTCTTGATCTGTAAACTT TGGAAGACAAAACTGAATGATTTGTAAAGCTGCTTTTAGCTTTA AGTTTCTGTAAGTTACATTTTTTTTTTCACATGTATATGAAATTT CCAATTAGCACAGGAAAATTCTAGAGCCATGTTATGGGTGTGT GAGCAGGGAGGTCCTTTGGGGAGTGATACCATTAATTTGTTGC AGCTAAGAGAACTAAATAAGACCCTAGTGATCTAAAGGAGCAC ATACAGGTACTCCCTAGAGTCCTTATTTATTTTATATGTTGGAG GTTTTTGGTTCACTTAGATTTTTATGGGAAAATTTAAAAATATAT AATGGCAGTTTATAGAATGGGTTGAAATATCCTCTTCTTCTAAA TTAGCGATATAATTAATACTTCTCTGCCATAGTCCCATCTACAT ACTAGTATTAGATTCCCATAGAAGTATTCCTGTTGTTACTGGCA TTGCATGTTCTTTAGAATACTGTTTCTATGGAGTTCAGCATGAT AACAAAGTCCTGAGCCTAACTAAAGATGTCTGT |
| 274 | R3HDM1 | 2507420 | ATGCTGCTGAAATTGGAACAAGAAATTTTAGATTTCATTGGTAA TA |

TABLE 7-continued

Target Sequences

| SEQ ID NO. | Gene | Affy Probeset ID | Sequence |
|---|---|---|---|
| 275 | R3HDM1 | 2507421 | GACATCTTACCATAGGATGCTATTACACAGAGTAGCCGCTTAC TTTGGATTAGACCACAATGTTGAT |
| 276 | R3HDM1 | 2507422 | TGGGAAGTCTGTCATAGTAAACAAAACTAGCAA |
| 277 | R3HDM1 | 2507423 | CTCCAGCCTTGAATCAGTGGTGTTATGGATGTCAACAACCCAG TGTCCACTGGGGTGTCTCAATGGAGCGGGAAGTTGGCGATTA CAGGGCAGTAAATTCAGGCATCTATAA |
| 278 | R3HDM1 | 2507424 | AACCTTGTGTTTGTCCTCTAGATCACAGTGGAACTTGCAACATT TCTGTGGAAGAAAGATGAGTCCACTATAAAATGTATTGCTAAG ATTTCATAATCGTTACTTTAGGTCACAACTTTGACTTCTATAAAA GAACATCTCTTTTCTAACCTGTTCCAGTTAATGTTAGCAAACCT GTGCCCTACTGTAATTTAAAATTAATGGATGCACTTTGAAGTAG TCTGTAAGTTTTTAGCTAATTGAATGACAAAATATTTTATTACTT TCAGGTATAACACCAAACTAGGTACCATAGGAGTAGCATAAGA TACGGCACTGCACTTTCCTTGTCCCAGCATTTTTTCGTAGGTTT AGACGAGGCAGTACAGGCTTTGGGTCTAACTGACCTGAGCTC CAACTATGGCTTAATCATATGCCTGCCTTTGACCTTGCATATTT GCTTAAGCCATTTGAACCTCGGTTTG |
| 279 | R3HDM1 | 2507425 | AAGGATGATAAAGGTGAAGACTTTCAGAAACGTTATATCCTCA AGAGAGATAACTC |
| 280 | R3HDM1 | 2507426 | CTAGAACAATTGTAGGATTTGTATAGGTGCAAGACATACTATA CCAGTAGTTCATTTGCCTAAAA |
| 281 | R3HDM1 | 2507427 | GAGAATACGTTTGAAAGATGACAGAAGAAGCAAATCTATAGAA GAAAGAGAAGAAGAGTACCAGAGAGCCAGAGACCGAATATTT TCCCAAGA |
| 282 | R3HDM1 | 2507428 | TTACGTTGTAGGGTCTCAGTCTCCCTTTTATCTATTGATCACAT TTATTTTTAATCACATTTGTTGCACATAAGGTCATCTTTTAGAAA TATTGAGATCAGTTTTGCTTGTGTTATTAATAGTTTATAAAATAC TACATTGCAGTAGTTATATAAAATTTTACAAAAGTTGGAAGCAG GTAGACTACAGGAGTCATTAAAAGAATGTTCTCCAGTCTATATA GTTTGTGTGATTTTTTTTCCCCAGACTTGTGACAGACTTGAGAT TTTTATTAATAGAAATTGCTCCACTGTCTACAAAATCATATACTC TAGATGCTACTTGTTAGTTGACTTTCTTTGACAAATAATTTATTT CTTCTTTTGAAATAAAGCTAATTGATTTTGTAGGTTAATATCTGT TTTCTTCTTCATAAGTGATTATATAAGATAGGCTTTCTAAATGG CTAATTATTTTATGCATATATGCCAGAAGAGAATCAATTTGTTTT TTGTCAACATCTACTAAGCATCTGTCCTGTAATATGTGTTA |
| 283 | R3HDM1 | 2507429 | CCTGTGTTCCCAAGAGAATTACATTATTGACAA |
| 284 | R3HDM1 | 2507430 | ATGCCAGTAGTACCCAGCAGAGGCGCCAGATATTTAG |
| 285 | R3HDM1 | 2507431 | TGAAGTACTCGGAACCACGACCCTGGAGCAGCACAGATTCAG ACAGCTCTCTTCGAAACCTGAAACCTGCTGTAACCAAAGCCAG CAGCTTCAGTGGAATCTCAGTCCTGACAAGAG |
| 286 | R3HDM1 | 2507432 | GCAAAAGCATAGGCAGGCTTTCAAAA |
| 287 | R3HDM1 | 2507433 | TCCGGAGCACTTAAGGGGTAATATGTTTCTTGACATGAGGATT CACTCTCTGTCCTGGACACAGATTTACAACCATCAATTACCATA AAAATTCTTCTCTATTGTGACATAAACTTAATTAGGTAGGTTCA ATGAAACATTATCTCTTGATTGAATGCCCATAGGTAATTGGAAA TTCTTTATTACTTATTCGTAGTTGGTAGAAGGCATGGTTTCTCA CCTAGGATTATTTA |
| 288 | R3HDM1 | 2507434 | AATCAGCTGGGCGTAATAGCACGTGTCTGTAG |
| 289 | R3HDM1 | 2507435 | TAGGGTCATCTACAGGCTCTCTTTCTCACATCCAGCAGCCTCT TCCAGGTACAGCTCTCAGCCAGTCTTCTCATGGCGCACCTGTC GTCTATCCAACTGTCAGCACTCATAGTTCTCTTTCCTTTGATGG TGGCCTAAATGGGCAAGTCGCATCTCCTAGCACTAGCTTCTTT TTGCTTCCCTTGGAAGCGGCAGGCATAC |
| 290 | R3HDM1 | 2507436 | TGATCTCTGGTTTTTGACAACAGTATTACAATACATTTAACTTTT TTAAGATGACCCTTAAATTACATTTGACCGCCTTCACCCAAATC TGCTCCACCAATTTTTTCTCCAAATTATTTAGCAGTCAACAAAT ACCCAGGACAACTTGTTTTAGTTATCTATAACTGTCACACAAA TTATCAGTATACTAATTGATTAAAATAATTTTACTTTAGAGTACT |

TABLE 7-continued

Target Sequences

| SEQ ID NO. | Gene | Affy Probeset ID | Sequence |
|---|---|---|---|
| | | | TTTTCTGCTTGATAGCTATAGACTAGTATAGTCTTCTCTCCCAAATA |
| 291 | R3HDM1 | 2507437 | ATGGGAGTCCAGTTGTGTATAATCCTCCTATGACTCAACAACCAGTTAGATCCCAAGTGCCTGGACCTCCA |
| 292 | R3HDM1 | 2507438 | AACAACCAGCAGCTAATCACATTTTCTCACAG |
| 293 | R3HDM1 | 2507439 | GTTGACTTGCCTTTACATATTTGGGACTAAATTCGCTAATTATAATTGAGATAGCCTAAGTATCTCTTAGAACTTTAATATTCTGCCACTAGTGATATTCCACTCACTACTCATAGGAAAAGAGATAACTTCAAAGGTTTTTCCCCTGATAAATACTGAAAATATGTTGGAAAGAAGGGAATTGTTTTAATCATATGAGCCTGTCTGGTGAGTATTTTATCCCTATTTCACAACAGCAAGAAATGGACAACAGGAGAAATAAAAACAAAACTGTGATTGTTCATTGGCCCAATGAGCAAAGTGAGTTGTTTTAAGATTCCACAGATTAAGCAGTTAGAAGAAACTGAGATAGGCTGCTCAGGTTCTGCAAGGTACTCTTC |
| 294 | R3HDM1 | 2507440 | GAAGAAGTATGATGATAAACTTGAACTG |
| 295 | R3HDM1 | 2507441 | TTGTGGTAAAAGTGCAACTCAAATCATTATTATCTATCTATGATGTCATAGACAAACAATGTCTATCTTAGTTGACATAGAAGTTCTCTATTTAAATTATTGCCTGAACAATCTTAATTCCATTAGTTTATCTAACATTTTTAAAGTATTGTCTCTGAAGACAACATGCAGAGATATTGTTCAGAAGGAGATGCATGAATATACATTTTAACTAAGAGTTTTCATCAAGTGAGATTCCCTGGGTTCCTCATCTACTTGCTTATGTGGCTGTCTACAAGTCACTTAATT |
| 296 | R3HDM1 | 2507442 | TCTGCAGTCCTCTTCACAGCCTGTTCAGTACTCTACAGCCCCTTACCCATCCCCGTTCCTGCCAGTCTCACCCACC |
| 297 | R3HDM1 | 2507443 | GATAACCTAGGGTCTCAGTTTAGCCACATGAGTCTTGCTCGCCAGCCATCTGCTGATGGTTCTGACCCTCATGCCGCCATGTTCCAGTCCACTGTGGTTCTT |
| 298 | R3HDM1 | 2507444 | GTTATATCATGACAGCAGCCCCTCCACCACATCCTCCTCCACCGCCACCACCACCACCTCCTCCTCCTCCCCTACCACCTGGGCAGCCAG |
| 299 | R3HDM1 | 2507445 | CCTACTGCTGGATATCCTGCCTCTGGTCATC |
| 300 | R3HDM1 | 2507446 | ATGGTTATTAGTTGGGTTCTGCCTCTTTATACAGTGATTGGAGTGTCATTAGACCCTTTAAATTTAATATATTTTTGACATGGTATGCCATGTCATACCAGATTCAGGTATGCCACATTGCTATTTTTTTATTTGCCCTATCTGTATTTTATTCTACTTTCCTGCATTTTATATTATTTGAACTTTTTTTTTTTATAATATTGAATGCTTTACGAATTTCCGTGTC |
| 301 | R3HDM1 | 2507447 | TAGCCTTAAGGTAATATAAGCCATATTTTAAATAATTTCATGCATGATGTAAAGTTTTGACTGTAACCTGTCACATGAGGTCAGGTGTGGAGTTTCTTTTTGAGTACTGACATGACATGATGCTTTTGGCATCATGTTGGTACTCAGAAAGTTAAAGATTTTGGAGCATTTCAGATTTTGGACATTTGGATTTTTAAAATACTCGCCCAGGCTCA |
| 302 | R3HDM1 | 2507448 | ATGCCAGCCTGTTATTGCGCTCCAG |
| 303 | R3HDM1 | 2507449 | GCCACTATCACTCCAGCCAACCTCAGTATCGCCCAGTCCCTTCTGTTCATTACAATTCACATCTAAACCAACCA |
| 304 | R3HDM1 | 2507450 | GTCTCTCAGGATCTCGAATATGTTCATACATATGAGTTTGCAAACCAATGAGATTAAAAGAGTGAGCAAATCTTAGCATCCTCTGGAAAATACCACAGTGTCACGTCTACATGCTAAAGGGTTGGGAGCTGTACTGGGAATATCTTAAGCAGTTTGTTAAGTGGCTGCCATCTCTTACTGCCATTGAGATTGAAACTGTCTTTGCAGCCTGATAAATCACCTATGG |
| 305 | R3HDM1 | 2507451 | AAACAATTTTGATCTCAGTGTATAAAACTATCTTATTGATTTTTTAATGAACTCATTTCTCTGTATGCTTCT |
| 306 | R3HDM1 | 2507452 | TCAGCCTTTTATAACTCTAGGAGTT |
| 307 | R3HDM1 | 2507453 | AAGTTTGTAGCTTCACCATATACATTTAATATTTTGCAATAATTGGCCTTGTTC |

TABLE 7-continued

| Target Sequences | | | |
|---|---|---|---|
| SEQ ID NO. | Gene | Affy Probeset ID | Sequence |
| 308 | R3HDM1 | 2507454 | AGCTGTTGGATTCGGGGCCGTAGCACTGTCTGAGAGGTTTAC ATTTCTCACAGTG |
| 309 | R3HDM1 | 2507455 | AGCATGACATCAAACGGACCTAATACACCTAAATGCATTTGAA GCTACTTGGTCTCGGTTCTTACCAACGATATAATTTAATTTTTTT TTCCAAACGATGATGTTGTTGCATACCTGTGGAAAGCAAAATG ATTCTGTGAAACTATACTTTTAGTTTTGCAACCATTTGATAACTT CAAAGATTATCAATGTATTATATCTTTAGTCTTAGCTTTCCAGAT AACCCAGA |
| 310 | R3HDM1 | 2507456 | TAACCTGCCGCCACTGAAATCTGGAGCCAAATATATCTGGTAA GTACCCACAGATTTCCTTGAGTTGTATAGACTCTTCCATGGAAT AGTTCTTTAAATAGCTGTGAGCAATAAACTCTGTGTGACTGTTT TTGTTAGAATTGGTTTTTGTATATGTATATGTTTATTTCAGGCAC AGGAGTGAGAGAAGAGGGGATGAGAGATGAGAAGGGATAATC AAGTGTGATGGCAATTGCATCTCCTTCCAAATACACCCATGGG GCTGGCTTTAGTTGAACTTGCCCACCTACTAAAATAG |
| 311 | R3HDM1 | 2507457 | TCGCCCATAAAACGTAGCAGCTCTCCTTGCACAAAATGTGTCC AGGTTAAAGCTGGCACTGCCCTGCTGAGTAAAGTCTGACTTCT TGGCAAAGCAGCCTGACTTTGTGGAGAAGACAGCCAGTATCT ATGAAAACTCTGCTAGACTAATCTTGTATAGACTCATCTGGAAT GTGGCAACAGACTTTTTGAGCAAAAGCAGCCTCCGAGGCAAA ACAGCAAAACTAAAGCCCAAAGGGAACATTGGAGATTCACTTG GAAATACTCAGGCTGAGAGACAGAACTGTGGGATGTGGAACC TGAAATAGTGTCACTATTTGAGCCAGTTCTTCTCCTTCCCAATT GTCTTTTGTTATGTTTTAATATTTTTAGAGATGGAGTCTCACTGT TTTGCCTAGACTGGAGTGCAGTGGCCCTTCCTAATTGTTTAAT ACAATTTATGCGTATAATCTAATTATAGTAAGGCAAGGAAGTGT AACTTTGAAATACATCAGTAGTAAACCACGCATCTTGCGGGTA GTGGACAAACCA |
| 312 | R3HDM1 | 2507458 | GCCTGAGCGATAGAGACTGCATCTGAAAACAAACAAACAAAAA GAATAAGATACCATTGGAAATTTACTCATGCAGCTTTCATGAT |
| 313 | R3HDM1 | 2507459 | ATGAATTCAGAGCAGGATTTAACTCATTGTACCATTACAG |
| 314 | R3HDM1 | 2507460 | TACCAAGGAATAGTTGGAGTTCAGCAACCCCAGAGTCAGAGC CTAGTCAGTGGCCAACCCAACAGCATTGGAAATCAGATTCAAG GAGTGGTCATCCC |
| 315 | R3HDM1 | 2507461 | CCATCAGACTTATCAACAGCCTGTTATGTTCCCTAATCAGTCTA ATCAAGGATCTATGCCCACAACAGGAATGCCTGTTTACTATAG TGTCATTCCACCTGGTCAACAA |
| 316 | R3HDM1 | 2507462 | AGTCTTTGGAATTACCCGCAGCTTGGACCCAAATGAGGCAGAT AAACTTGAAATAAGGTAGATGTAAGCTGACAGTAGTGATTGGT CACCATGTGACAAACTAGCATTGATCTGTTCCAAGTATAGAGT ACCAATGTGAGAAATTGAATGAGTTGTACGTGAAGCAGGGAAT GTGTATTCTGTCAGACTCATCTTGGTACATTTTGGA |
| 317 | R3HDM1 | 2507463 | CAGGGTCTTGATCCATACAGTCTTACTATGTTTTAGATGCTAAA TGGACTCTAGTAGCCTTCATTTTATTACAAGATTATAAGGAATA AGATTCCTATAAGAACACAAAGTGAGTCTTTGTTTTGAAAAATG TCTTACTTAGCTTGGGTTGCTTAGCAAAATTGTTTTCTTACAGA GGTTCCTTGTGTAGAAAGGTAGAATTTGAATTATTATGTCTACT TTCAGCTCATCCTTTCAGTTCACTGAGGCAACTTTGTGTTTGGA TTGGATTGTGTTGTTACTTATCATTATGAAGATTGAGCACAGCC TGATACAAGTCAACATATACTGTCACTTTAAGCGAGCAAAGTA CTAGTCAGGGACACTAATTTTACAACAACTCATGAGATTTTTCT CAGTCCTTAGTGTGGAGAGAAAATTAGTTTGATACCAGCAGCC TTCAAAAGTGGGCAAGTGAGTTGGATATCTTCAAAATGCTCTC ATTTTTACCGGTTCTTCTCCTATTTTCCCTTTCATTTTCACTATT TTTATCTTGAAATTCAAAACGATAATACCTTTGTCTTTGATCTAT ATTCTCAAAGGGGTAGCATACAGACAGGAACTTGAAAAGACTA TAGCCTTTTTTTAAGAACCTTTAAAAAATGTTTCACAGAATCTTT ATGAAATTATGAAAAAGAAAACCTACTTTTAAGTCTTTTTCCCTT TTTTCTGTCCACAGTCTGTTTTTCCTCATTTTTGTATCCTAGTAT TTCTCTAGTGTCCCTTTTGTCCTACTTGTGATACCTCTCTTG |
| 318 | R3HDM1 | 2507464 | TTTTGGGTGGCAGATAACATTTTACTTAATTGGGGTTCAAAGTT AGTGTTCTTTGTCATCAAGTTGATTTCAGATGTTCATCTGTAAA AACCATTCTTAGCTTGGAGGCAATACAGAAGCAAGCAGTGGTC TGGGTTTTGCCTATAGGCCATAGTTTGCCAACTCCTGTACTAG |

TABLE 7-continued

Target Sequences

| SEQ ID NO. | Gene | Affy Probeset ID | Sequence |
|---|---|---|---|
| | | | ATGGTTGATAGCCAGCAAAAAAAAAAGACAAAGAGGCAGTGG<br>TCACAAATGAAGACCAACAACTTAGGAAAAAGGAGTGTGGAAG<br>CCAACATACAAGGAGATTT |
| 319 | R3HDM1 | 2507465 | TCAGCCGACTTAGAAGCAATACAAGCCAGAAGACAGTGGAGC<br>AACATCTTTATTTGAAGAAGTGAAAGAAAGAAAACTTGCATTCT<br>ATACCTGTAAAAATATTTTTCAGAAACAGAGATTTCAAACACAC<br>AAAAGCTGAATTAATTGCCAGCCACCTCGCACTGTGAGAACTG<br>TTAAAGGAAGTTT |
| 320 | R3HDM1 | 2507466 | AGGCAACTTTGGTGAGGCTTTATGGTGTGCATATACATAAAAC<br>TCTTTAAATTATATACTTTATGTGTGGTTTATTTTCTATAAATTAT<br>ACCTCAGTAAAACTATAAAATAATCTGAGTCTTAAATTTTTTCTT<br>AGAGACTGGTTCTTGCTGTCATTTAGGCTGGAATGCAGTGGTG<br>TGATCCTGACTCACTGAGGCCTCAACCTCCTGGGCTCAAGCA<br>ATCCTCCTGCGTCAGCCTCCCAAGTAGCTGGGACTACAGGTG<br>CACGCCACCACACCTGGCTAATTTTTTAATTTTTTTTAAAGATA<br>GGATCTCACTGTATTACCCTGCTGGTGTCGAACTTTTGGGCTC<br>AAGCAATCCTCCCACCTCAGTCTCCCAAACTGCTGGGTTTACA<br>GATGTGAGCCACCTTGCCTAGCCTTCTTTTCTAATAGTTTAAAC<br>AAAGACTAGTTTTGGATAAAGTGAAAAGAAATACTGTAAAACTA<br>ACAAATTATTAAAAACAAGAGTAAGAATTTGTGAGGTTAAGATA<br>GGCCACAGGGCATTTAATGGAGGAATAAAGGTAGACTTGAAC<br>TAACTGTAAAACCTGTTACAGAGTCATATTGAAATGTTAAAATT<br>TAATCAAAAGTGTTTTTTTCAAAAAGCAAATGACTAAAAACTCC<br>TTTCAGCCAGAGGTGAGAGATCGGGGGGAAACAAAAAAACAA<br>TAAAAAGAAAGTCCAAATACCTATGTTGCACCAGCCTGACCAA<br>CATAGTGAAGCCCCACCTTTACTAAAAATACAAGAAATTAGCT<br>GGAAGTGGTGGCATACTCCTGTAATCCCAACAAAATACATGTA<br>AAACCTTTATGCCCAAAACCATCTTGTGATGTGGAAGATTTGTA<br>CTCCCTATGGTTTATATCTTAGAACAGATGTCAGAAAACTACAG<br>CCCACAATCAAAGAATGGTTTTTAAATTTGTAAAGGATTATTAT<br>TTTTTAACTCCTAAGTGACCATGTGTTACTCAGAGTTAAAATAT<br>ATACTAGCTGGCTCTTGCAGAAAAAGTTTACCAGCATCTGCCT<br>TAAAAAAACCTTGGCAGATAGGTATCAGAGACATGTTTATGAA<br>TGTTTGTAGCAACAATGTTTAGCCTAATACTGGAAGTAATCCAA<br>ATAAAATGGAATAGAATGTGTAAGTATATTTTGATGTATTCATTT<br>CAGACACTACTATACAACAAAGAAAATTACTAAAGTACAACTAC<br>TTGTATCCAATTGGTTGAGTCTCACAGA |
| 321 | R3HDM1 | 2507467 | GTTGGACAAAGTGGGTCACGCCTGT |
| 322 | R3HDM1 | 2507468 | AGGCAGGGATGCTTCTAAGATACTAGCAATGTTCTGTTTCCCA<br>ATCTGAATGAAGTTACATAGATAATTATTTTGTTATTATACTTAA<br>TTTAAACTGTAATATATTTCTAAGCACTCTATATTCGTCTGTTCT<br>CGCATTGCTATAAAGAAATGCCTGAGACTGAGTAATCTATAAA<br>GAAAAGAGGTTTAATTGGCTCACAGCTCCGCAGGCTGCATAG<br>GAAGCATAGTGGCTTCTAGGGAGGCCTCGGGAAACTTCAATT<br>ATGGCAGAAGGCAAGAGGGAAGCAGGCACGTCTTACATGGCT<br>GGAGCCCGAGGAAGAGAAGAGTGGGGGAGCACCACACACT<br>TTTTAAAGAACCAGATCTCATGAGAACTCACTGTACAGTACCA<br>AGGGGGAATGGTGCTAAACCATTAGAAACCACCTCCATGATC<br>CAGTCACCTCCCAGCAGGCCCCACCTCCAGCGTTGGGGATTA<br>CATTGTGAATGAGATTTAGGTGGAGACACACATCCAAACAATA<br>TTACACTCAGATAGATAGATAGATAGATAGATAGATAGATAGAT<br>AGATAGATAGATAGATAGATAGATAGATAAGATAGATAAGATA<br>GATTGATTAGATAGATTAGATAGATAGATAGATAGATAGATAGA<br>TTAGATATTCCAAACCCCAAAAAATAGCAAAATCATTCGAAGAG<br>AGGCCTAAATATATAGAAGACTTTAGGAGAAAAAAAGCTAACA<br>GAATGGGAGGAGAGGAATTGAAGACAATAAATAGAGACAGCC<br>TTTGAAGAGAATTGCTTTCATAAGGATAAGCGTTGAATTGGATT<br>CGTATATGGAGAGGATGAAGTCAAGACAGAGGATCCTTTTTTG<br>ATTGAAAGATAGATGCATGTGTTTGTATGCTGAAGGGAAAGGC<br>TTAGTAGATACAGAAGATTTGCCTCTGCAAGGGACAAGAGAGA<br>GAGTTGTAAGGTCCCCAGGGAGGGTGAGAGCCACCACAAAAA<br>TGGAAGCGGGTTAGCCTTAGATAACAGTGCAGAGGATTTCAT<br>GGGCAGTAAACGAGGACAAGGAGAGTATAAGGATACAGATAT<br>GGGTAGATGGATAGATATGGCAGCAAGAGAAATTCTCTTCTGA<br>TTGCTTTGCTTTTCTCAGTGAATTAGTCAAGATATCAAGTACAT<br>TATCAGAGTAGAAGAATGTTCTAAAGTTTTGTAAATGTAGAAAT<br>CCATTACAGCTATATTAAGACTAATATTCAAAGGAAAGAAGCAA<br>GATACAGGGGAAATGTGACAAGTATGCCTAATAAAAGCTTATT<br>ATATAGAACATTTTTATCACTTCTCTATGTTCTAAGATGGTAACA<br>GTGAGACTACAAGTAAATAATCCATAGAGATAAATTGTTACTCG |

TABLE 7-continued

| Target Sequences | | | |
|---|---|---|---|
| SEQ ID NO. | Gene | Affy Probeset ID | Sequence |
| | | | AAGAAAACTGATAGTAAGTTTTCACATGGGAAAATGTTGTCTTA CCAGCAATCCAAAAAATGAGAATTAAGGCAACTTGAACACAAA AAGTAGGCTAAAACATATAGTTAGCAATACTGTGCATAGAGAC GTTTAAACATTACTGGTTGCTAGGCATATCAAGCCCATTTTTCT ATAAATCAGTCGGGATATTTAACAAAATGCAAAATTGCTGTACT TTTAAATTCTACCTCTAAAATTTTATCACAAAGATAATCCACCC CAGAATTTAAATTGTGGCTAAACAAATTATAACAGTGCTATTAT TAACATAAGAATCCAAATAAAAAGATGCAAAAAAAAAAACATGG AGTAACCTGGTAACCTTTGAATAGTTTAAATTTTCTTCTCCATTT ATTTTTCTGCTAGGCTGATTAAGTTTAGCTTAAGTCATAGTGAG ATTTACTTAGTTGTCACAGACCGTTTCTCAGATAGTGGGACCA GTGAGTTTTAAAGGTGTTTGTTCTGTGTTAATTGCTCCAGTATC TTCAATTCAGAAGAATAAATGTTTGATATTCAGGCTGCTATAGT TCACAAATGGATTTTATTGATGACTTACAGCATTTTAAGTGAAT AGAGCACATGTCTATTAAGTAATATTATTAAGTTCAGGAAGCTT GCTTAACTGCCATTGACAATAAGATGTAGGGTGGTTTAAAAAG GCAGAAAACCAAATGACTTAACACACCTTGACAACTGTTCATA AATTTTCAAAGACATCGCTTCTAGTAGTCACTAAAAGCTGTAGT AGATGTATGACTTGCTTTTCAAATGAATCAATTATTGCTTGAGA AGAATACACTTGTTCCTATTCTCCCATCTAAAAAATAATTTGAA ATAGCAGCCATGAAATATTTACAAAAACATAAAGAGAAAAGAC ACATGATGGCAGTTTATTTTCATGTGGAATTTCCCATGCTATTA ATTTTCCTAAGTCTCGACCTTTTGTGGGTGA |
| 323 | R3HDM1 | 2507469 | CAGGAGCATCAGAGACATCTTTGTG |
| 324 | R3HDM1 | 2507470 | GGTATATATACCCTCACCACAAAAAATATATATAAAATGGAAAT TACTATGACTTTGAGAAAGCTTATGAGGCAGAAAGTTGGTGTT TTCTTCCAGAGACTACAAGCCTAGTTGAGCATCTGACCTGCAA ATGAATTGGTTATT |
| 325 | R3HDM1 | 2507471 | TCTTCAGTAGGTTACCTGCAACATCCAGGATCAGAACAAGTAC AATTTCCTCGAACCACTTCACCATGCAGTTCCCAGCAGCTTCA AGGCCACCAATGT |
| 326 | R3HDM1 | 2507472 | TGATGATGCAGCTCAGTGTACCAAACAATCCACAATCTTGTGC CCACTCACCCCCGCAGTGGAAACAAAACAAATATTACTGTGAT CACCAGAG |
| 327 | R3HDM1 | 2507473 | TGATACCTGATACCAGTGGGACATTTTACTTGACAAATTGGCC CTGTTACTTGAATAGATGGCATTTTGAAATAGGAGCTTGGTCT GTTATACATTAAAAGAGACTCAAGAGGTATAATATCAGATATAA TGTATGGATCTTATTTGGATATTGAATGATCAAAAGACATTTTTT AAGGCCAGGCGCAGTGGCTCATGCCTGTAATCCCAGCACTTT GGGAAGCTAAGGCAGACCTGGAACGCAGGAGTTCGAGACCA GCCTGGGTAACATGGTGAAACCCTGTCTCTATAAAAAATACAA AAAATTATTCGGCCATGGCAGTGTGCA |
| 328 | R3HDM1 | 2507474 | GGCCATCTTGGCTATGCCAGAAAGTAAGGAAGGGATGGAAGA AAAATAGGGACGTCTTGAAGAATACAGGATCAGGAGTGGAGG TTTGGGGCATAAAACAATGATAGAAATGAATGATCATCCATAG AATAAAATAAGAATTCATGAGTCCATACTGATAAAAATCAATAA ATGGAAAATGAAACTGTCTTACCTTAGTGTAATATAAAGTGATA AATGTAGAATCGTGAAATTAAAAGATCACCACCAAGAAAACCA TCAGGCAAGAGTCACCACTAGAGGCTACAAAA |
| 329 | R3HDM1 | 2507475 | AGCCCTCAACTCAGTAGCCCCATTATTTCACCAGCTCAGTCGC CAGCACCAGCTCAGCTGTCCACCCTGAAAACTGTACGTCCCT CTGGACCACCACTTTCCATCATGCCCCAATTTTCTAGAC |
| 330 | R3HDM1 | 2507476 | GAGATTCCAGGTATCCATTACTTGGCCAGCCACTGCAGTACAA TCCTCCTGCTGTTCTGCACGGACACATT |
| 331 | R3HDM1 | 2507477 | AAGACAACTAACCTCCTAGGCTTTGTTGCAGAACATCATAGCT CCCTCAGAGT |
| 332 | R3HDM1 | 2507478 | TGAAGGACAGGAATGCCACTGCCACAGGCAGAATCCAGAAGG CCTGGGACTGATTTTCTTCTGCCAGAGTGCAAAACCCAAACTA |
| 333 | R3HDM1 | 2507479 | CATTATTAACGTTGTTTCTCAACTATTTGTGGGTTTTCAG |
| 334 | R3HDM1 | 2507480 | GAAGGAGACAAGCTAAAAAAGCTGCATCCA |

TABLE 7-continued

Target Sequences

| SEQ ID NO. | Gene | Affy Probeset ID | Sequence |
|---|---|---|---|
| 335 | R3HDM1 | 2507481 | GAAGGTCTTGGAAATTACTGAACTACCAGATGGAATAACTCGC ATGGAAGCTGAAAAGCTTTTTGGGGAACTCTTTAAAATTGGCG CCAAGATCCGGTGGCTCCGGGACCCCCAGTCCCAACCACGTC GTCACCCCCTCTGCTGTGGCAGTGGGGACAACACTGCCAACC CTGAACGCTCTAAACCCAGTGACTTG |
| 336 | R3HDM1 | 2507482 | GACTCCTAGGATGTGTGTTCATGGCATTATAGCTTTTGAAGAA AGGCCAGTGATCCAGCAAAGGGGGAAAAATATGCATTTCACC CCACATGACTAGGAATCCACATCAGAATGATACAGAGTTAGCA GGTTTTTCTAAGGAAATGCCATTCAAATGCCTCCTAACTTTTAT AGTTATTTTGTTTTATATTTCTAAATTCTTGTATCAGATCCAAAG CTCTATTGTACAGCAAATTATTCTTCAAAATGATTATAACCAGTT GCACCCTGTATTTCTTTTTGCAGCCAGCACAATGTGACCCAAC TTAAAATTTGGGGGAAAAAGAATGCAGGAGTGAAATAACCAAG TCAAAACCATGTACTATCTCCTTGGGGGTTAGGGATGCTAAGA AGAGCCCACAAATAGAGGATTACTCTTCCCCTGAATCTCTAAA CTCAGAAACAATTACCAAAAAATACATAACTCTTCCTTGTAGGG CCCTTTCCTTATTCATTTAGGTAGTGTGAACATTAAGTATAAAA TAAATTATGTTCTTAATGCCTCTTAAACCACTTACATTCAAAGG GGAACAGAAATCATTCTAAGCAGGAAAATACTTCCACTTTTTTT TTTTCAAGTATCTCTCTAATAACTAAATGCCACTTATTTGCATTC TCCTTGTGGATTTTTTGTCACCTAAGGAAATGCATTTGATGAGT GCTGGAAACTTCTTAAGTGCTTTACAGTTTGTTTTCATTGTTTG CAGCGGATCACTGGACATCAAAGATTCATTGCACTTATGAACA AGGAACCTTCTTTTCAATTTCTGTGTAATTTGCAAGGCTGTACA ATGTGTGCTGATGCAAGCC |
| 337 | R3HDM1 | 2507483 | TCAGTTCAAGAGAATAAATGTTTAC |
| 338 | R3HDM1 | 2507485 | ATCTTCACTGCTGTTCAACATTATAATGGAGGTATTAACCAATA TAGTTAGATACATCGATTTAAGGCATAAGAATGGGTAAAGAAG AAAGACTATCTCTGCAGATTATATGATAACGGGTTGAGCATCC CTAATCTGAAAGGCTCCAAAATTCAAAACTTTTTAAGCAGTCAC ACGATGCACAAAGTAAA |
| 339 | R3HDM1 | 2507486 | AGGTACAGTAGTTTCTTGTTGGAATAA |
| 340 | R3HDM1 | 2507488 | TTGTTGAGAAAAGGTTACCCTCTGACAC |
| 341 | R3HDM1 | 2507489 | GCCTAGACAACATAATGAGATTCCATCTCTATAAAAAAATTAAA AATTAGCCAGGTGTGGTGGTATACACCTGTAGCGCT |
| 342 | R3HDM1 | 2507491 | TGACTCTCCGGGTCACGACGTTAACCAAAAAATAAGACAAAAA GAGAATATATTCTATATGATTCTAATTATATGAAATCCAGCTGC AGACAAACTAATCTGTTATGTTAAAAATCAGATAGTAGTAGAGA TGGGGTGTGGAACTGACTGGGAAGGGACTGGAGGGAACTCTT CCAGGGATGGAAATGTTCTTTAAGGGGGTGGGGGAACAGGGT ATGGTTACACGGACTTTTACAGTTGTTAGAATTCATCAGATTCA ACACTTAGAATGTTTATTTTATTGATTGTATTGTATGTTAATTAT ATCTCAATTTCCTTAAAAACTTACACACACACATATGCATGAGT CAGCCCACACATGTAGAAGA |
| 343 | R3HDM1 | 2507492 | ACAGTCTGGTATGAATGCCGCAGGAGGAACACCTAGCCCAGC CTATTAGGAGGGGTCTTTGTACTGCTGACTATAATCTTATCTC |
| 344 | AC020571.3 | 2521178 | AAGGCAACTGGTCTGATTTTTCAGGTAAGAACATATGAGAGGC AGGCTGAGACCAATTTTCTACCAGGCCAGCTAATTCATCACAA TGACAAGCTATGGGTCATATGCTTTCAGGAACCAGACACTGGA ACATGTCGTCTGATGTAC |
| 345 | AC020571.3 | 2521179 | GAATCCAATGGGGAGTAAGAGAAAGTCCCTTTTCAAGGAGCT |
| 346 | AC020571.3 | 2521180 | CATGTGTTCGGAGACAACCAGAAGCAGCAATGCTCAAAACCA CAAAACTCTGGATTGCCGACTCTGCACATCCTGGTTCCTCTAG ATACAGTTCAGTGGCACATTCACAAATAAACGTTTTCAAAAACT GCCCTCAGGCAGTTCTAGAGAAATGCTTTGACTTGCCTAATGG TATAATGTCAAGAAAGGAAGACGAGCACTGATCATTCATACTC ATTATTACAGTCACAGGGCACTGTCTGACTTGACAGATACAGC CGAGCAGTTAAAAGGTTATGGGAATTTAAGTCCATTATGGTCA TACGATTCTTATGGACCCAGAGATATGAAATTAATCAGCCACA TGTGTAGGGACAAAGTT |
| 347 | ANO7 | 2536218 | CCCGTTTTGCCAGCCCAAGACTAGGAGCCACGGCACCTGTCC T |

TABLE 7-continued

| Target Sequences | | | |
|---|---|---|---|
| SEQ ID NO. | Gene | Affy Probeset ID | Sequence |
| 348 | ANO7 | 2536219 | CGGGCACTCACTGGATGGACAGACAGACGCCTGCTGTGCCA GGCCTGCCAGACGCTCCCGCCCCGGCACTGGTTTCTTCCTGG AGCTCGTGGCTGGCTAGGGGGTTCTCCATGTGCTCATGGCCA GGAGAGTCTGCCGAGCCAGCCCAGCCCCATTCTACTCCGAGT CGAGTCTGTA |
| 349 | ANO7 | 2536220 | ATGCTGCGGCGACGGGCCCAGGAAGAGGACAGCACCGTCCT GATCGATGTGAGCCCCCCTGAGGCAGAGAAGAGGGGCTCTTA CGGGAGCACAGCCCACG |
| 350 | ANO7 | 2536221 | CCAGGTGGACAGCAAGCGGCCGCCTGCAGAGCTGGGAGTCC TGCCAAGCCCCGGATC |
| 351 | ANO7 | 2536222 | CTGAAGCTAGACAGGCAGCAGGACAGTGCCGCCCGGGACAG AACAGACATGCACAGGACCTGGCGGGAGACTTTTCTGGATAA TCTTCGTGCGGCTGG |
| 352 | ANO7 | 2536223 | TGACCCATGACCTTGCCGCATGAGGCCTGAGGGCATGGTGTC CAGAGTCCCAGAGCAGATCAGGCCCCAAAGTCCTGCTGGACC CCCCAGCCACCGTGAGCTCCTCCGTGTGGCTAGGGAGCTGCT GTCCAGAGGCGGAGGTAAACATTGATCCCTCCTGCACACTCA GCTCTCTCATGGAAGTCGGAGCCCTCAGGGTCACCTGAAAAC TCT |
| 353 | ANO7 | 2536224 | TTGCCATTCACCTGTCCCGTCTCCAACATTAAAGCTT |
| 354 | ANO7 | 2536225 | TGTCGAGGCCCGGTTGGCTTTCAGAGGCGTATCCATGGGAGT AGGTGTCATGTATCAAATAGGAGATTCAAAGTCAGCTGTTACC ACGGCTACAGAAATGCCAGTCTTTTCCTAAGAGTGCGAA |
| 355 | ANO7 | 2536226 | AGGACGGGAACACCACAGTGCACTACGCCCTCCTCAGCGCCT CCTGGGCTGTGCTCTGCTACTACGCCGAAGACCTGCGCCTGA AGC |
| 356 | ANO7 | 2536227 | AGTTACCCAACCAGGCCTCCAACTGGTCGGCCGGCCTGCTGG CATGGCTGGGCATCCCCAACGTCCTGCTGGAGGTTGTGCCAG ACGTACCCCCCGAGTACTACTCCTGCCGGTTCAGA |
| 357 | ANO7 | 2536228 | CTTCCTCGGGAGTGACAACCAGGACACCTTCTTCACAAG |
| 358 | ANO7 | 2536229 | TATGGCCACGAGAAGAAAAACCTGCTTGGGATCCACCAGCTG CTGGCAGAGGGTGTCCTCAGTGC |
| 359 | ANO7 | 2536230 | TTCAAGACGCCCCCAGAGGGCCCGCAG |
| 360 | ANO7 | 2536231 | GCTCCACGCCTCAACCAGCGCCAAGTCCTTTTCCAGCACTGG GCGCGCTGGGGCAAGTGGAACAAGTACCAGCCCCTGGACCA CGTGCGCAGGTACTTCGGGGAGAAGGTGGCCCTCTACTTCGC CTG |
| 361 | ANO7 | 2536232 | CTTCCTGGTGTTCTCAGACATACCC |
| 362 | ANO7 | 2536233 | GGCAGCAAGGACAGCTTCGAGATGTGCCCACTTTGCCTCGAC TGCCCTTTCTGGCTG |
| 363 | ANO7 | 2536234 | CCGGCTGTTCGACCACGGCGGCACCGTGTT |
| 364 | ANO7 | 2536235 | CTGCTGGAGTACTGGAAGCGGAAGAGCGCCACGCTGGCCTA CCGCTGGGACTGCTCTGACTACGAG |
| 365 | ANO7 | 2536236 | CGAACCCCATCACGGGTGAGGACGAGCCCTACTTCCCTGAGA GGAGCCGCGCGCGCCGCATGCTGGCCGGCTCTGTGGTGATC GTGGT |
| 366 | ANO7 | 2536237 | TGTGCCTCGTGTCTATCATCCTGTACCGTGCCATCATGGCCAT CGTGGTGTCCAGGTCGGGCAACACCCTTCTCGCAG |
| 367 | ANO7 | 2536238 | CATCGCCAGCCTCACGGGGTCTGTAGTGAACCTCGTCTTCAT CCTCATCCTCTCCAAGATCTATGTATCCCTGGCCCACG |
| 368 | ANO7 | 2536239 | GCCAGAACGTGACTTTCTCACTCACTGACACACATGGCCCTCA TTTCTATT |

TABLE 7-continued

| Target Sequences | | | |
|---|---|---|---|
| SEQ ID NO. | Gene | Affy Probeset ID | Sequence |
| 369 | ANO7 | 2536240 | AAATGCACCGCACCCAGACCAAGTTCGAGGACGCCTTCACCC TCAAGGTGTTCATCTTCCAGTTCGTCAACTTCTACTCCTCACCC GTCTACATTG |
| 370 | ANO7 | 2536241 | CCAGGCAACTACCACACCTTGTTTGGAGTCCGCAATGAGGAG |
| 371 | ANO7 | 2536242 | TCTTCCATTCGAGCTTTGATTTGCAGCAATTCCTCCCACCACC GGCTATTTCCATCGCCCAGCCAGGG |
| 372 | ANO7 | 2536243 | TGGAGGCTGCCTGATCGAGCTGGCACAGGAGCTCCTGGTCAT CATGGTGGGCAAGCAGGTCATCAACAACATGCAGGAGGTCCT CATCC |
| 373 | ANO7 | 2536244 | TGGTGGCAGAAGTTCCGGCTTCGCTCCAAGAAGAGGAAGGCG GGAGCTTCTGCAGGGGCTAGCCAGGGGCCC |
| 374 | ANO7 | 2536245 | TGTGAGGGTCTGTTTGACGAGTACCTGGAAATGG |
| 375 | ANO7 | 2536246 | GAGCAGGTTTCTGCCCCAACGCCTGCCCTGAGTTAGTTCCTG AGCTCACCGAGCCGGAGAAGGCCCGTGACCAGCCAGAAGCA CGGAGCGCAGGGC |
| 376 | ANO7 | 2536247 | TGAGGGCGGACGGTGGCGGAGAGCCCGGCCGTGACCC |
| 377 | ANO7 | 2536248 | CTGCAGTTCGGCTTCGTCACCATCTTCGTGGCCGCCTGTCCG CTCGCGCCGCTCTTCGCCCTGCTCAACAACTGGGTGGAGATC CGCTTGGACGCGCGCAAGTTCGTCTGCGAGTACCGGCGCCC GGTGGCCGAGCGCGCCCAGGACATCGGCATCTGGTTCCACAT CCTGGCGGGCCTCACGCACCTGGCGGTCATCAGCAA |
| 378 | ANO7 | 2536249 | CTTCTCGTCCGACTTCCTGCCGCGCGCCTACTACCGGTGGAC CCGCGCCCACGACCTGCGCGGCTTCCTCAACTTCACGCTGGC GCGAGCCCCGTCCTCCTTCGCCGCCGCGCACAACCGCACGT GCA |
| 379 | ANO7 | 2536250 | AGAGTATCCTGTTTGGGAAGAATTCCCATTTCAGGCACCCTCG ATGAAGAGCCAGGCCAGGAACATGGGATGAGAGAGCGAAATG GTGGAAAAAGGGGAGATAGGCTAATTCCAGA |
| 380 | ANO7 | 2536251 | CCTGGCTGCGCGCACTGAGTCCTGTGTCTGCTG |
| 381 | ANO7 | 2536252 | GTATCGGGCTTTCCGGGATGACGATGGACATTATTCCCAGAC CTACTGGA |
| 382 | ANO7 | 2536253 | TCCCATCCATGGCATGAGGCCCCGACCCTGTGCTTTGCCTAAT TCGAGCACGTG |
| 383 | ANO7 | 2536254 | TTGGTCAAATCAGAGCTCTTCTCTGCACCTGCGTTTTCCCTGC CTGGCCTCATCCCTGGGTTGTGGTGTGGACATTGTGGGTGTC TCCACAGGAGCCCCAGGGCCACGAAAGCTGGGGTGGC |
| 384 | ANO7 | 2536255 | CTGGCCCTGTGAAGGCCACTCTGGGCGTTTGGGTG |
| 385 | ANO7 | 2536256 | ATGTGGTTTTCTCCGTTGGCCGCCTCCTGGACCTCCTGGTGC CTGACATCCCAGAGTCTGTGGAGATCAAAGTGAAGCGGGAGT ACTACCTGGCTAAGCAGGCACTGGCTGA |
| 386 | ANO7 | 2536257 | TGAACTGTACAGCCCAGTCTCGGCCCTCCCCCCAGCCCTCTC CCTATCCTTGTCAGTGGCTGCTCTACCTCCGGACACTGAGTCA CAT |
| 387 | ANO7 | 2536258 | ACGGAACAAAGGATGAGCAGCCCGAGGG |
| 388 | ANO7 | 2536259 | CGTGCACTCCCTGAGGTCACAGGGCCCTGCCCAGCCGCCCA CTGTGCCTCGTGGCCATGGCCTGCTCCTGGCCCTAGTCTGAC TTGTCCCTGC |
| 389 | ANO7 | 2536260 | GCTCCCACTGGACACCCTTCACGGTTCCCAAGGCCAGCCAGC TGCAGCAGTGACGCCTGGAAGGACATCTGGTGGTCCTTAGGG GAGTGGCCCCTCCTGAGCCCTGCGAGCAGCGTCCTTTTCCTC TTC |

TABLE 7-continued

Target Sequences

| SEQ ID NO. | Gene | Affy Probeset ID | Sequence |
|---|---|---|---|
| 390 | ANO7 | 2536261 | TGTGTGAACCGCTGGCTGCTGTTGTGCCTCATCTCTGGGCACATTGCCTGCTTCCCCCCAGCGCCGGCTTCTCTCCTCAGAGCGCCTGTCACTCCATCCC |
| 391 | ANO7 | 2536262 | TTCGAATGTTTCAGAGCGCAGGGCCGTTCTCCCTCGTGTCCTCTGGACCCACCCGCCCCTTCCTGCCCTGTTTGCGCAGGGACATCACCCACATGCCCCAGCTCTCGGACCCTGCAGCTCTGTGTCCCAGGCCACAGCAAAGGTCTGTTGAACCCCTCCCTCCATTCCCAGTTATCTGGGTCCTCTGGATTCTTCTGTTTCTTGAATCAGGCTCTGCTTTCCCCCTAGCCACTACAGGCAGCCTCTGACAGTGCCGCTTTACTTGCATTCTGCAGCAATTACATGTGTCCTTTTGATCCTTGCCCAACTTCCCTCCCTCTCCCAGCTCCTGGCCCCTGGCCCAGGGCCCCTCTTGCTGTTTTTACCTCTGTTCCTTGGGGCCTAGTACCCAGCAAGCACCCAAATGGGGGAGGTTTTGGGATGAGAGGAGGAAACGTGTATACCTGTAACATCTGGTGGCTCTTCCCCCAGAAGTTTGTGTTCATACATAATTGTTTTCCACGCTGGATCATAATGTGACGTGCAGTTCTGCCCTGTGCTGGGGAGCCACATGAAGCTTCCCCTGGCTAACTTGCTACCCCGCAGCAATCCCAGTGTGGCCGTCTGCTTGCTAAAAAATG |
| 392 | FTH1P2 | 2545844 | TCACTACTGGAACTGCACAAACTGGCCACTGACAAAAATGACCC |
| 393 | MIR4435-1HG | 2570866 | GGAAGTCCAGCCTTACCAACTTGTGAACCTTGTCTGAAGGGAGCCAGGGCCTGCCAATGGAACCACCTCCAGGAGCTGCAACTGCTGTTGTCATTAATACCATTGTGTCTATTTTTTGAGAGAGATAAACTTTTCATGGTGTTACATTTTGGAAAAAAAAAAAAAAAGACTAGGTGAACAGTCAGGTAGGAAAGCAGCATAACAGTCCCTTAAATTCTGATCATGTAGGACATTCTTCTTTGCCCTGGGCCTGGGAAAATGCAGCATGTTCCAGAGCAAAAGTCCTAATGAGGGGAACTAAACCAGTGGGACCCAAACCAATGTCCTGGCTCACTGAGGACCCGTTAGAACCAAATCTCTGGGTGTGGACAGGCTCCCATACTTTTCAAAAATTCCCCTGATGACTAATGAACAACCAGAGGTAAGAACCAGTGGCCCAGAGGAATAACCAGCCCAGCTGTTGTACGAGCTCGCTAAGCTGGCTCAGGTCAATGTTGAATTCTCTGCTAGGCAGCTCCTCATAAGAACTGGCAGAGATGGTTCTTACACAACAACAGGTGACAACTCCAGACTCTGCCGGAAGTTCCAGGATCTGGGTTCCCGGACAATGCATGACAC |
| 394 | MIR4435-1HG | 2570867 | GGTTATCTTTCCTCCACTCGAGGGATTGAAGCTAGGCTGTCCCACGGCACCGGGCTCGTGGC |
| 395 | MIR4435-1HG | 2570868 | CAAAGCCACGCATGCAGAGAGGTTACCAGTGTCCATCCAGACGCCCACTTCACAGACAGGTAGCCAAGCGCCAGAGCCCGGCTATTGTAGCCCTAAGTG |
| 396 | MIR4435-1HG | 2570869 | ACATTCTGGATGAAAGAAACTACTCAAAAAGAATGTTTACTGTATGATTCCATTTTTATGTTTAAGAACAGGTAAAATTAACCTGTGATGACAGACATCAGAGTCATGGTTACTCCTGAGGAGAGGGGTTTACTAGATGGGACA |
| 397 | MIR4435-1HG | 2570870 | CCTCTCAGATCACCCAGGAATTCTACTCCTAGGTTTTTCTCAAGGAGAAGTTAAGTGCAAATATCCATCAAAATGCTCATAAATTTTATTTGTAATAGCTAAAAACAAGACACAACTCAAATACCTATTAAATGTTTATCTAGACACAATCCAAATGTAATACAGTCATGCTCTGCACAATCATGGTCCCATGAAATTATAATGGAAGGAAAAATTCCTATCACCCAAGTGCACACTGTTTATAAAGTCCACAGCGGTGT |
| 398 | MIR4435-1HG | 2570871 | GCACAAATGGTATTCTGTATCTGAAAATTGTTTGGATTAACTTTTGATTCTTGCCTGGTTAAAGAATTACAATTCTTACCTCAGATCATGCTTAAACTATC |
| 399 | MIR4435-1HG | 2570872 | TCTGGAAATGTAACTACTATAATGGACCTTACAAATGCACAAATGGGGCCGGGT |
| 400 | MIR4435-1HG | 2570873 | GCGAGTGTTCTCATTGCATTCGTGACCCCATTGATCTTGCAACAGCCCCATGCATCAGTTATTGCCATTATACCATTTTACCGATAAGGAAACTGTGGCAGGGAGGGGTCAAGCACCTTGGGTATTTGACAGCAAAACCAAGGCTTGGTGGTATCATAAAACTTCCAAGTAGTAATTCACAAAGGTGACTGGGAAATGGAAGTGACCAGAAATCTTTGCACTATGAGGACAAGTTCATGACCCTGATACATTCTTGTCCAGGTAGTATAGCTCCAGA |

TABLE 7-continued

Target Sequences

| SEQ ID NO. | Gene | Affy Probeset ID | Sequence |
|---|---|---|---|
| 401 | MIR4435-1HG | 2570874 | CTACTGCATTTCTGTCACTCGCTGAAAAGGACACTCTGTCAGA AAATCTTCTAGCAAACTTCAAAGGGCAAAATCACCCCTTGTTA CTGATAAAGCCCAGAGAGCTTCAGCAGCTAACATTCCCTGGA CAGGGCACAGCAAGGATTTGAACCTAGGTCAGTCTGGCCAGA ACACCCACAAGCTTTCCTTAACTCAGTGTGCTATCTCCCCACG ACTAGGTCACTACTGCTTTATAATCACCTTTGTAGCCACCAGT GGATTTTGCTCATCAGTATTTTTCAGGCAATTGATACTTTAGAT ATTCAGCTGCAAGACGTATGCAGTTTTCATTGACATCTTTTGGA GAAACTGACAAACCTGGACTTGACTTAATGCCTTTGGAACCTT CCAAGATGTTATATAACTCTAGATAGAAGGCTGGGCCTCCATG ATGTCAGGAATGTTGCATTCTTATTTCCCCATAGATAAACCCAT TTGTCCACAAAGTCAAGGAGTCAGGCAGAGGCCCTTGCCATG GGGCTTTTTAGGATAAAGCAACAAGCCTGGACTTTGCTCTACA ACAGGGTTTTGCATAGGGAGTGGTATGACCAGATCCCTCAAG AA |
| 402 | MIR4435-1HG | 2570875 | GGTGGGATCACTCAGATTCTACAGATATTAAAAGGATAATAAG GAAGTATTGTAAACTTTTATGCCTATAAATTTTAAAACTTAGATA AAATGGATAAATTCCTGGCAAGGCACAATCTACCAGAGCCCAC TCAAAAAGAAAGAAAGAACCCAGACAATCCTCTATTTACGGAA TAAATTGAATGTTTAGTTTAAAATGTATGCATGAAGAAAATTCC CGGTTGACATGGCTTCACTAGTG |
| 403 | MIR4435-1HG | 2570876 | CAATAATATAAAGGTCAGAAGGGGAGAAATGGAAGTATCCTGT TGTAAGTTTCTTATGCTATACGCGAACTGGTATAATATCATTTG AAGGTAGGCTATAATAAGTTAAAGATGTGTTCTGTTAATCCTAA GAAATATGAAAATAACACAATAACAAAGAGTTACAGCAAATAAG ACAACAAAAGAGATAAAGTTGGATCATAAAAATA |
| 404 | MIR4435-1HG | 2570877 | CAAAGGTTTCTGCTCAAGGGTTTCTGCTGCAGTAATTTGTGAT TCTAAGTATTTTCTTGTCAGTCTTTCCAATTTAAGGGGCAGTAA ACCTCACTTCTCTGATGGATCTAAGAGTTGTTAATTAATCAGTT TGTTCAGCCTTTTATTTGTTGTTAGGATGTAGTGACAACTTCCA AGCTCCTTACGTACTGGATTGCAAACCAGAAGTCAAACTATTC CTTAGAAATGAAGGGGAAGTAAAGTCATTTTCAGATGACAGGA TACTAAAAGAATATGTCACCAGAAGACTTGCCCTTAAGGAATG ACTAAAGCA |
| 405 | MIR4435-1HG | 2570878 | GCCACTGCTTTGCTGAGTCATTCTACTATGCAGCCCCTCAGAC ACAAAGCCCGGCGGCCACCTGCCCACAGAGGCACAGAGGGC CAGCCAACTGCAAGCACGGAACTTCAGGATCTTGCTTTTCGG GTTATTTTCACTACTGTAATTTTTTTGTCCTTAGGTAAAAAGGAT AATAATTGTGGAAAATTATGTCCTTAGGTTAAAAAGATCCTGGA TCATGCCAGATATTAAAATATGGATAAAATTGGCATGATCTTGG AATCTGAACAGAAAAGAAGCTGCTTTTAGCTGTTTTCAACTGTT TTTAGCTTTTCTGTCTAAACAGCTGTTTA |
| 406 | MIR4435-1HG | 2570879 | CTTAGCTGACATTACTTTGATCATGAACTTTGTTGCCT |
| 407 | MIR4435-1HG | 2570880 | TCGCTGGGGTATGACCATTCCCCTGGCCTTCCTATCTTCCCAT CTATGCCCAACATGGCTGCCAAGGGGATCTGTCCTAAATGCA AAGTTAGCCATGCCTGCCC |
| 408 | MIR4435-1HG | 2570881 | GGGGAGGATAAAATTTGGAGCAAGATTCTCAAGGAAGCAACA AGATCCTAAG |
| 409 | MIR4435-1HG | 2570882 | TCTTGGACGAGCCTGAGGATGTCTACAAGTGGAAGAA |
| 410 | MIR4435-1HG | 2570883 | TGGAGGAGGATCCAAGGCTCAGAAAGAGAAGGAG |
| 411 | MIR4435-1HG | 2570884 | TGCCTATTGTTCTGGATCATTTTGAGAAAAAAAAAGAGATACCT TGAAGAAAGATGAAGACAAAATATGGAAGGGTGCTGAATTTAC AAAAAGCCTAAGGGGAAAAAACTCAAATGTCCCTCAGGAGTG GAATGAGTAAACAAATCATGGCGTGTTCACACAATGGAATGCT ACCTACCAATAAAAAGGAATGAACTGCGGATGCACACAGAAAC ATGGGTGAATCCACTAGGCATCATGTTG |
| 412 | MIR4435-1HG | 2570885 | CAGCCATTTGCAGAGCATTGGAGTAAGTTTTACCTTCATCCCT TAGATGTGAATTTGTTATCCTCACTGTGACAATCCCCTTATCACA TGGCTTTTAGAAGGATTCTCAAAAAGCTAGACTCTCACATTCAA CTTTGCAATTGCCTGGCTGGGTGTTACGTTTCTTTGCCTCCTA |

TABLE 7-continued

Target Sequences

| SEQ ID NO. | Gene | Affy Probeset ID | Sequence |
|---|---|---|---|
| | | | TTAGAGACCCTATCAGCATCTAAAACTAGCGTTGTTTGAGGAT GTTGGAGCCAACGGTTCTTTGCCAGATAGAACTTTGTGTGTCC AAATAAATGGTTCAAAATCATCAAGCAAATAAATACCCTGGAAT AAGAGAAGCCTCATGAGGATTTGACTCCAAATTGACTTCCTCT GTTCTGCAGTAAGAAGTTAGGAATTAAACCAAACCTTGCCTGA GGTTCAGGTATACTCAAAAGCAATGAGGTGTGGCTCAGGTGT GCGCTGGCAAGGTCACTGTGAAGTTCAGCCAGAGGCTTTGCA AGCCTGGGCCTGAGAAGCCAGACCTCTTAGATCCAGAAGGGC CAATGGAGCTGGGCTGGCCTGCTGCCACTCACAGGCAGAGA CTCTGCCAGCAGAAGGGACTCTGCTGTCAGAGCTGGAGGGCA GCGGACCACATGGCTGAGGCCCAACCACAGGTCTCCTGACTC AAAACCTCTTCCCAGGGCTTGTCCTCCTCCCTAAATATATGTG CCCCAAATTGTCACCAGATCTCGGGAAAGCACTGGCTTT |
| 413 | MIR4435-1HG | 2570886 | GAGGTAGACACTATTCCCAGCTGGATACTCTCAATGTTGAGGA TATAGATGCACAAACCAATGCAGGGAGGCCTCCAGGAGCCAC TGGAGAAGAAATCTTCAGATCCTACCAGGCCCATAGCTGTTGC CTTTGTGGGCTCCTGGGTTAATTTCCACACATCAGTGGCCCAC CTTATGATATCCTCCCTGCATGCCACACTCCCGGCCATGCTCT GTGGACAGCCATTATTTCCAGTAATTGCTAATGGGAGCCAGTC TCCAAAGAGTAATGAATCAGAGGTGTTCCTTGGAATGTGTTAC ACTAGGACTTCGCCGATCTCACAGGCTCCTTTCCAGATGAGCT GACTGTAATCTCTGGGAAGCTGGATCTGGAGGAACAATGGGA TGGGATTTGCGGTGACCCTTCCTGCCCTTCTTGAGCAGCTTGT GAACCAGAAGATGTGCCTGGAGAGAAAGCCTCATTTGGGGAA GTGCAGTAGTC |
| 414 | MIR4435-1HG | 2570887 | CAGATCTCAGCTGCCGAGTGGAAACCCCATTCTCACACCATA GCTATGGGACTGGGGGAAAGGGGAGGAAATAACTAAAGAGTA AGGAATTGGGGGAGGCTTTGAGGTTTGGATGTGACAGGTAGT TTGCATGTAGTTGGAATGCAGTAACATTGGTCCACAAGGTT |
| 415 | MIR4435-1HG | 2570888 | GAGCACGTGATCACTTCTCACAACTAATGGAGCCAAGATTCTG TCCTTATGGCTCCAGAGACCTCTTTTTTTTCCCACTGTACCACA ACACTCACCAGGACTGGAGTGCCACCTATGACCTCATTGCATA ATGGATGGCTTGTCCTCA |
| 416 | MIR4435-1HG | 2570889 | TTAAAGATCTGTAGGCTTACTAGCCATGACAATGATGACAATA ATGATGATGAAAATGACATCATCATTACCAATAGCTACTGCCAT CTATTGATCCCATAACATGTGATCATATC |
| 417 | MIR4435-1HG | 2570890 | AGTCATGTAGTTTGAGCACTCCAGATTTATTTTCCTAATTCAAG ATTGTTATAGATACGCTAGATTCTTTGCATGTCTATATAAATTTT AGAATCAATTTGTAAATTTCTACAACAGATTCCTGCTAGCATTA TTACTGGGATTGCAATAACTCTACAGATCAATTTGTGGAGAAC TGACATCTCAACAACATTGAGTCTTCCAATCTGCAAACATGATA CTGTGTGTGTGTGTGTGTGTGTGTGTGTGTGTGTGTGTGTGTG TCTTCTTTAATTTCTTTCAATAATTGTTTAGTTTTCAACATAGAG ATCTTGTCCATCTTTTGTTGTTTATTCATGAGTATTTTATGCTTT TTGAAGATACTGTAAATAAAATTGTTTTTCTAATTTCATTTCCCA AATTCTTGCTGCTGATATATAAAAGTATAATTGATATTTTAATAT TAACCTTGTATCCTGTGACCTTGTTCAATTGATGTA |
| 418 | MIR4435-1HG | 2570891 | GCTCAGTTTGCTTATCCGTTCTCCTGTTGATGAACATCTGATGT TTGCAGTTCTCCTCTCCGTGAGTCTTCTTGTAAACATAATTTTC ATTTCTCTTGGGAAAAACCCTAGGAGTGGTACTGCTGGGTCAA GGGGGTAGGTGTTTGTATAGCTTTATAAGAAGTTACCACATCC TTACTAATATTTGGTGATAGCTATTCTTTAAGTTAAAAGTGTAG AGGCATCTCGTTGTGGTTTTAATTTTTATCTCCCAAATGAGTAA TGATAAGTGTCTCTTCATATACCGAATGGCTA |
| 419 | MIR4435-1HG | 2570892 | CTTGCAGGCCCTGTGAACATATATACTTCCTGGTGGGAAGAGC AAGGGAGCCTCTGGTGGAAAGCAGCCCCAGGGTCCAAGAAC CACACAGCCCTGCATTAGGGCCCCCAGGGAGGGAGAAGACC AAGGTCATGCTTTTGAACCTGGATGCCAGAAGAGAACAGCTGT GGGGAAAAGCATGCCTGGAACCAAGAAAAACATGTTTACCAG GGGCCATTCCTCACACCAGCTGCAGGCAGGGTCAGGAAAGC CACAGGCTGCACTGTAGTTGCAACCTTGCATGCGGACGCAAG GCTCAGAATGTTCCTCAAAGATCCTAAAATGTTCCCAGAGTCA GGCTGAGTCCATTCA |
| 420 | MIR4435-1HG | 2570893 | CACTACAACTGGCTGTCGGTCTCCC |

TABLE 7-continued

Target Sequences

| SEQ ID NO. | Gene | Affy Probeset ID | Sequence |
|---|---|---|---|
| 421 | MIR4435-1HG | 2570894 | ATGTGATGGCCAAGGGAGCTTCATCAATCATGGCATCTCAAGGGAGCTGGAGCAGATGAGGAGGAGATGGAGGTCCCAGGAAGGGCTGTGATCTGCCTGGGGTCCCACAATGGGAAAC |
| 422 | MIR4435-1HG | 2570895 | CTCACACAGGCAGTTAGCCAAGGCCTGATATGCAGAAAGTGC |
| 423 | MIR4435-1HG | 2570896 | ACCCAGGGAGGATAGCACATGTCTTCGGCTACACTGGTGAAGGCATCGTGCCTGCTCCACAG |
| 424 | MIR4435-1HG | 2570897 | TGCAGCTGATACCCAGGATGTATTATTATTACTGTGACACAGTGAATCTAAAAGAGG |
| 425 | MIR4435-1HG | 2570898 | CTCAAGGGAGATTGTATGAGACTCCTATAGGGTAGAACCTACTCTGAAAGAACTCACCTCAATTAAGCTTGATTGGAGTAAAAGCCAAGGCTAGACACCTAAGCTTC |
| 426 | MIR4435-1HG | 2570899 | CTCAGAAACCTGTAGATCTCTATGA |
| 427 | MIR4435-1HG | 2570900 | CCCTAATGACTAATTGTTTTGAGCA |
| 428 | MIR4435-1HG | 2570901 | TCCCTCATAATGTCTGCTCTGTGTCACTATGTACCCTCCCCTGTCCTCCATTCCCCACACCAAGAGTATTATGAGTATTAAATGCCACGTGGGCAGGTTCCCCAGGCAATGAGGGGGTGGGCCTGTCAAATGCAGGCCATGCAGAATGCCGCAGGGCGGGAGACGGGTGAGCCAAGGGAGCCGAGAGTTCCAGATAACAGAGTGCACAGCAAATGCCATGGCCCGCGTCCAGCAACCAGGAGAAACAGAACTGCTGAGCTCAGAATAGGCCAAGGCCGC |
| 429 | MIR4435-1HG | 2570902 | GAACTCCCACTGTATAATTGCTAAACACAATGACAGCTATAATTGAGGCACTGAAGGAAGGTCAGGGGAGCCCAGGAGGGCGGGGCTGCTGCTGCCTGCTGAGCTGGGAGGGTTGGTGGCACCCCTTGCCCTGGGTTGCCATAGCAGATATCATAATCAATTACGGCCGTCTTTCATGAGGAACCTGGATCTTTCCCAAGGAATC |
| 430 | MIR4435-1HG | 2570903 | CTGCAGGCTGGAGGCTTAGCCACTTCTCAGGAGGAGCCTAGAAAGGATATTGGTCGCCCAGCTGCTGAACCTGCCCCAGCATCCTTGAGGGTCTTGAAAATCTATTTTATGCTGGGCACCTG |
| 431 | MIR4435-1HG | 2570904 | ATGCACTATGTAGCCCATGAGAAGGAGACCAACTCCGAGGAGCTGAGAGTGAGAGGAGACTGCATTCTCAGACACAATTGTCCAGACACTTCCTTTAAAAACTACACGCCAATGCCCAATAATGCT |
| 432 | MIR4435-1HG | 2570905 | CGGGACACATATGGGAATACAATTACAGCAAAGCCGGCAAGGCTCAGTGAGGGGCAGAGGGCCTGGCCACATGAGGAGCCAGTGCTGTGGGCAGGCCCGGGTCTGAGTGCTGGCTGTGTGTCCTGCACAACCACATCTCCCAGAGTGCATTCGTCACCATCCACTCCAGATGCCCCTTGAACAAATGAATTTCACAGTTGCAAAAGGCTGAAAAATGCTCTGTGACCTGGCACCCCCTTGGGGAACCACAGTGCATTAAAGGCTCT |
| 433 | MIR4435-1HG | 2570906 | TTGTGATTTTCGTTCCTGAATTCATAGAG |
| 434 | MIR4435-1HG | 2570907 | GGTGCCCTGCAATGTTAAGCAAAAAAAAAAAAAAAAAAAAAGACTTTGGAAATAGAGTTATGGAGCCAGGATGGGTCTTGAGTTAGCCTCACTCTTTATTTCTTTATTCAAGGAATGGTTGTTCAGGGCCAGCGGCTCAGCCCTGGGAGCACTGACTGCTTCAAGACACAGACTCCTCTGGGATGCCAGGCAGAGTCTGCTCCTGAAGGCAGACTCCACTCTTCATGGGG |
| 435 | MIR4435-1HG | 2570908 | CCTCACCTTTGCAGGAGACTCTCAATTTCTCAGTCCACATCAGCTCTCAGACCACCAAAGCAAGGGTTATTTTTCTAAAAGACATTTGTTCCCATTGCTCCTCTGACTAAAGTTCCTACTATGGGACATTTGCCCTTGGCACTCAAGGACCTTGCAATCAGGCTGAGAACCTCAGGTTCTCAAACTCAAGACCATGGGGAATGTAATAGGTGAATCAGGCAGGTGAAGTCCAGGACTC |
| 436 | MIR4435-1HG | 2570909 | CAGGATGACTCAGAACCCGCGTATGAATGCTGTCTATTCATGGGTCCAGGCTTTTGTTAAAGTCTGGGCCTGCA |

TABLE 7-continued

Target Sequences

| SEQ ID NO. | Gene | Affy Probeset ID | Sequence |
|---|---|---|---|
| 437 | MIR4435-1HG | 2570910 | TGTTGAGTGCTAGCTGTTGTTGAGTGCTTGTCCTGCCTGGGCC CTGTTTTTAGCCTTTGATGTACATTTCTCCATTTAACTTCCACAA TAGCCCTATTAGGCAGCTAGTATTATT |
| 438 | MIR4435-1HG | 2570911 | CAGGGCTTCCTTCAACTCAGGGTTC |
| 439 | MIR4435-1HG | 2570912 | CCCGTGGAGAGAGCCCCGCTGGTGAGGAAGCACGGGGACCC TGCTGCAGGGCTGGTGGAGGGCTCCTTCTGTAGACTTCTGAG CTTGGAGCACAGATGGG |
| 440 | MIR4435-1HG | 2570913 | TCAGGTCATCCGCTCCATGGAGGTCCCCGTTCCTACCTTGGC CTTGCCTTTCCCCCTGCATGTAACCTTGGTGAACTTTTCACAA GAGTCTGCGCAGTCTTCTTGTAAGCAGATTAATGCCGAGGAAA AGCCTTGGTG |
| 441 | MIR4435-1HG | 2570914 | TTCTCTCCCGACAGGAGCGGCCAGGACAGGGAGCAGAAGGT GACTGCTGTGCTGCCTGGAGCTCTTCTGTCCGGAGGTTTAGT |
| 442 | MIR4435-1HG | 2570915 | ACTCCGTACAGAGAGCGTTCCAGCC |
| 443 | MIR4435-1HG | 2570916 | AGAATCAGTTGTCTCCCAGGCGGGG |
| 444 | MIR4435-1HG | 2570917 | ACAAGGGCGGTGCATCAAGACCACA |
| 445 | MIR4435-1HG | 2570918 | CGGCCCCCAGATATCTGAGGAAGGCTGAGC |
| 446 | MIR4435-1HG | 2570919 | AGACTGACCCTACAATAAATGCTTAAGAGAGTCCTACATCTGG AAGCAAAAGGGCTATATTCACCATCATGAAAACCCAAAAGTAT AAAACTCATTGGTAAAGCAGACACACAAATAAGAAAGAGAATG GAACCACATGTTATCATTACAGAAAACCACCAAACTGCAAAGA TAAACAAAGGAAAGAAAGAAAGAAAGGAAGGAAGAAAGGAAG GAAGAAAAAGGATTATTTAAAATTATCAGAAAACAATTAAAATG ACAGGAATAAGACCTCACCTATCAATAACAACTTTTTTAAATGG CTTAAATTTCCCAGTTAAAAGATATAGACTGGCTGAATGGATTT TAAAAGTGACCTAACTCTATGCTA |
| 447 | MIR4435-1HG | 2570920 | GGTATTACCTGATCCCAACTTGGCACCAAAAGACAGCCAACAT AGACTCATTCCTCCTGCTTCCTGGTGAGCCTGGTATTCTCCTC CACTTCCACTGACAGACATGTAGGGTGACTGGGTGGTATCAA CAATAGGAACCACATCATAACAGGCAGCCTAGTTTGGGAAGC ACTCTTGGTCTCCGTAGGCCTGAGACTCCTTTTGCCCATCTAG AGG |
| 448 | MIR4435-1HG | 2570921 | ACTTAAAATAGGAGTGAGGTGAGAGGGGCAGCTGGGCTCATG GACGTCAAGTGGACAGTTTCTCAGCTGGTATTTCCTATATTTC CTGTTTTGGACAGCAGGTTCCTGCCCTTCTAAGCTGGGGGTA GGGGTGAGGGAGTGTATGTTAAAAAGCTCTGTGGACTTGCT |
| 449 | MIR4435-1HG | 2570922 | GAGCCCTTGTTCAGTGATCCTATGACTTGTCAGCTCAGTGAAT TGCTCTGACTCTTACTGCTTTCATTTATGAAATGGAGACAATAA CCCCTCTCTCATAGGAAGGGTAAGACCAGAAGAGCCTACACT ATGGTTGGAATAATATTTGTATACAGTGATCAAGAGAATGTTCT CTGAAACCAGACTCTCTTTAAATCTTACCTCTATCACTTATTAG TTATATGGCTAGCTGTTAAATGAGGTCAAAAGAGTGTGTTCTTC ATAAAACTATACAGAAGATTAAATTAATTAAAACATGTACAGTC CTTTTAAAAAAGATCAAGTGAAACAGCATACATGAAAGTGCTTT CAGCACGCTGAGAATAACAATAGCAATGGCTAGAGATTATGGA GCACTCCCCACTGCCAGCACCAGGGGAACTTTGTACCTACAA CTTTTTACTTAGTCCACATAACCATGAATTCGTCTCATTTATGTA GACCGGGAAACA |
| 450 | MIR4435-1HG | 2570923 | CAACCCAGGGTCCTTGCAGAGAGATTGATCTGCCAGCAGTGG CATCAGCAGCAATAGTAGCAGCAGCAAAGCCCTGGACAGTCC TGGCCCCCAGTCCACAACTTAGACACAGCACATGGCCTAATTC ACCCACAGAAGCAGCCACTGTGAAGCCCTGTGTCTCCCCAGA CTCCATCCAGTGGCATAAGGAGACCCAGGCCCTGCAGCTTCC TCCCCATCATGGAAGGCTGTCCATCTA |

TABLE 7-continued

| Target Sequences | | | |
|---|---|---|---|
| SEQ ID NO. | Gene | Affy Probeset ID | Sequence |
| 451 | MIR4435-1HG | 2570924 | TTCTTTTTGTCTCCCATATACGCTG |
| 452 | MIR4435-1HG | 2570925 | GCTCTGCCGACTTCCAGTTCTGGAACAAGATGGTTAAACTCATTTTTCCCTGCTCTGCTCCTCTAAATACAACTAAGTACCTTGGAAACTATTCAGCAGACAATGATAAAGGGCTCTGAAAGCTAGAAGAAAAGGTGTACTTGCAAGAAACCTCAGGACT |
| 453 | MIR4435-1HG | 2570926 | GACATAGAATCAACCAAAATGGCCATCAGTGATAGACTGGATAAAGAAAATGTGGTACATATACACCATGGAATACTATGCAGCCGTAGAAAGAAACGAGATCATGTCCGTTGCAGGGACATGGATGGAGCTGGAAGCCATTATCCTCAGAAAACTAACCCAGGAACAGAAAAGCAAACACCACATGTTCTCACTCATAAGTGGGAGCTGAAGACTGAGAACACATGGAACCAGGGAGAGGAACAACACACACTGAGGCCTGCCACTGCAGGTGGGGGTTCAGGGGAGGGAGAGCATCAGGAAAATAGCTAATGCATGTCAGGCTTAATAAGTAGGTGATTGGCTGATAGGTGCAGCAAACTGCCATGGCACACGTTTACCTATGTAACAAACCTACAAATACTACACATGTA |
| 454 | MIR4435-1HG | 2570927 | TGTCTTGCTGGCCTGAAATCGAGTACGCAGCCCGGGGTGATCAGGGTCTCCCGGCCCGGATGTGTGAGACTTGCTTCCCCTGGGCAATAGGCGATACGATGCTTTAGGAGGAAGGTGTCTCTCCCTCCTAAGCCCCGGAGGGGAGAACTTCCAAAGACAGAAAACCACAGGCTTCCTGGCACAGAGCTTTCCCTTTATCAGCTAAAGCAGAATCTTTTCTGGCCTTAACCTGGCCCCTTCCTCTAACTGCAGGCAGAGAGGCAGACAGAAAAGCACTTGCTGAAACACAAAGTTTTGTTCTGTCCTCAACGAACTGTCTAGAGCTGATTGCTGATAGTCGTGGTGCATTATGCCTTCCTGGTTTTCATTTAATTGGGCACCACGCTGCCTTTCAAGACGCCTTAAAGGAACCAACAACCAAATCCAAGAGAGCTGGACAGACCATTGAACACACAGTAGGCTGTGTCTCGTGGCTTTCGTTGTCTGGTGCCTCAAAGAAAACACCAGAAAGATTGTTTCTAAGCTAGAGCCACCCCAGATTGCTTAAAGTGCAAAGCTCACTGCTGTTGGGGGTACCCTTGTGAGACACTGGAAAGCTGGTTTTACCGTGGCCCTATGAA |
| 455 | MIR4435-1HG | 2570928 | CCGAGGAGGCGGAGCATGGAACTCGACAGTTAAAACATTTAAGAGA |
| 456 | MIR4435-1HG | 2570929 | AGGCAGCCTTTTCTGTCACAACACAACGCTGAGCCGGCAGCCTGGCTCTGTCAGGATCTGGGGCTCCCGCGCCCGAGAAGCCCAGCCTCGCCGGCGGCCAAGTTCACCGCGAGGCC |
| 457 | MIR4435-1HG | 2570930 | GACTCTGAAACTACCCGGCTCTGCAGAAGCACGCTGGGCCCAGGGGCTTCTAGACTGACAGC |
| 458 | MIR4435-1HG | 2570931 | AAAGGCTGCAGTCACCAGCATCTTTTCCAACCTTAATGAACTGTATCCTCAAAAGAACACTATCAGACTG |
| 459 | MIR4435-1HG | 2570932 | GAAAATTCCTATCCCACCAGCAAATCAGCCCG |
| 460 | MIR4435-1HG | 2570933 | CTCCCAGATAAAGAGATCAACACGGGACAG |
| 461 | MIR4435-1HG | 2570934 | GGGTTCCTGTCGGAATCTTGGAGCTCATCCCCCAAACTTGAGATT |
| 462 | MIR4435-1HG | 2570935 | CAAAGGCTTCTCTTGCTGGCTGAGAATTGTTGGGGAGCTCCCTGCCCACGGAGGGC |
| 463 | MIR4435-1HG | 2570936 | AAACTTTAAGGAAGACAACTGTGCATTCTC |
| 464 | MIR4435-1HG | 2570937 | TGGAACATACGTTCTTGTGAACATAGAGAGTGGCATTTTCTTATGTCGATGTAATGTGAACAACTCCTGGTCACC |
| 465 | MIR4435-1HG | 2570938 | TTGGTACATGCCAGCACGGTCTGTG |
| 466 | MIR4435-1HG | 2570939 | GATTCACTGTGCGAGGACCCACCTGACACC |
| 467 | MIR4435-1HG | 2570940 | GTAAGGTGACCAATGGCTGGCTGAAG |

TABLE 7-continued

Target Sequences

| SEQ ID NO. | Gene | Affy Probeset ID | Sequence |
|---|---|---|---|
| 468 | MIR4435-1HG | 2570941 | TCCGAGCTGTCACGTGGTTTATACA |
| 469 | MIR4435-1HG | 2570942 | TCAGGTTTGCTGGGAGGAATCCAGAA |
| 470 | MIR4435-1HG | 2570943 | CCACTCTAGGCAGGACTTTCATATCCTTTATCTAACTGTCACATGATGGGGTGACATGTTGATCCCCCCACAGCCTGGATGATAGAAATATTTGTGGTTTGATATGCGTCAGCGCTTATGACTTTGGCATA |
| 471 | MIR4435-1HG | 2570944 | GGTCATATTTCACGTCTGCCCTGTA |
| 472 | MIR4435-1HG | 2570945 | TGCTTTACAAACACTGACTCCTCAACACACGGTCATCTCTAAAAGAAAGGGTGTTTGGCAGTTCCTCGACAGTTCTGGAAAGGCTGCCTTACTAGAAGCAGAGTCA |
| 473 | MIR4435-1HG | 2570946 | TATTTTGGTCATGGGCTGGTCTGGTCGGTTTCCCATTTGTCTGGCCAGTCTCTGTGTGTCTTAATCCCTTGTCCTTCATTAA |
| 474 | MIR4435-1HG | 2570947 | CACCTCTACCTGTTGCCCGCCGATCACAGCCGGAATGCAGCTGAAAGATTCCCTGGGGCCTGGTT |
| 475 | MIR4435-1HG | 2570948 | TGACAGACACTGAAAATCACGACTCATCCCCCTC |
| 476 | MIR4435-1HG | 2570949 | TGAAACAGGAAGCTCTATGACACACTTGATCGAAT |
| 477 | MIR4435-1HG | 2570950 | AGCGGCAGAGCAGTTATTAACAGAATCACAGTCTTTCTGGAGCTGCTGTCAGTCCTGTGCTGTCCTCAGGGCCTTTGCTTGGTCAGGGGCCCCACTTCTTATCCACCCTTCCCTCTACCTCACCGAGGCTGCTAGGCCCAGGTGTATTGTGATTATTTGATGCACCTGGGAGGCCATGTCTCCCGGGGAGTCTCAGGACCTCATTGGGCTGGAATTCCACGGGGATCTCTCATTGGGTCTCTTTGGGCCTTTGGAGAGGGGAGTGCAGGGCACCACCTGGGCGAACACCTGTGCCATCCTGTAAGTCCTTGTGTGACTCTTCATCCAAGTCAACAGGGGC |
| 478 | MIR4435-1HG | 2570951 | CGTGGACCCGGCTATGTCTGACTTTGTGCTG |
| 479 | MIR4435-1HG | 2570952 | GGGAACAAAATGTCTGCTCAAACCATGACAAAATTGGCCACAATTTGCCGATTGGGCTGATAACAAAAG |
| 480 | MIR4435-1HG | 2570953 | GTGTGTACTAATCACTCAGACAGTG |
| 481 | MIR4435-1HG | 2570954 | GAAAAGATTTTTATTCGTGTCTACATCAGTGTGAAAGGCTTCATCCTG |
| 482 | MIR4435-1HG | 2570955 | CTGGGGACACTATGGCCCCATCCTAGCCTGGTG |
| 483 | MIR4435-1HG | 2570956 | TGGGAGGCCAAGGTGGGCGGATCATGAGCTCAGGGGTTCAAGACCAGCCTGGCCAACGTAGTGAAACCCCGTCTCTACTAAAAACAAAAAAAATTAGCTGGGCATGGTGGCGCACACCTGTAGTCCCAGCTACTCGGGAGGCTGAGGCAGGAGAATTGCTTGAACCTGGGAGGCAGAGGTTGCAGTGAGCTGAGATCGCTCCACTGCACTCCGGTTTGGGC |
| 484 | MIR4435-1HG | 2570957 | TTGCTGATATACTTACAAACTGGTAAACAATGCTCTTTAATCAACAATTCATAATCTGGGTCAGCGATTTTTATCTCCATATTTGCTCATACTGTATGACATCAATATTTTATATTGGCTTGCCCATAACTTA |
| 485 | MIR4435-1HG | 2570958 | CTGTGCCAGTCAAGCCTGGCCTGTGGCTGTGACACCTGCATTACCCCAGATGGTTGCCTGACCTAGGCCTGTCCTTCTATCTGCTTTGTTTTTATGTTGATTACTAGGTGAAGCACAGTGTTAAAAACGGGAAGAAAAGGCTAGGAATGCAGTTATGGGAGTGTGAGGCTGGGTTGGAATAGGTGGGAGAAAGTCCAGGGCTGAGTGTGTGGACCCTGCTCTAGGGATCTGACCGGCTCAAGCTCCCAGGCCATTAAACAAAGTTG |

TABLE 7-continued

Target Sequences

| SEQ ID NO. | Gene | Affy Probeset ID | Sequence |
|---|---|---|---|
| 486 | MIR4435-1HG | 2570959 | CTGTTGCCATTTGAACAAGTTGTTAAGAAAATCTGCCATGTTTTGCTCTTTTTTAAAAGGAATGACTTTAATAACCATAGCAACACTTACTCAGTTTTGTGATCCACTCCAAGATTATGGGAGCAAGAACAGATACTCCTGAAAGCAACCCTCACCTCCTCCCCCGCCCCCTGCCCTCAGCAAGTCCTGGCCTGTGTGAACTGAAGGGTTTGGAAGCTCTGGTTTCTAGGAGTGCCCAGAAGCTAGAAAGACTAGGGTGTACTAGTTATTGAGGGGCAGTTGTC |
| 487 | MIR4435-1HG | 2570960 | AAAGGCATTTCTGATTTAATTAAGAGTTG |
| 488 | MIR4435-1HG | 2570961 | ATGAAGGAGGAGTCGTCTACACTTGTAAAAA |
| 489 | MIR4435-1HG | 2570962 | TCCTTGAGTTAAAGAAATTTGTGTC |
| 490 | MIR4435-1HG | 2570963 | TAATCCAGTGCTCAACATATTTTTGTTGAATAAAAGCACAAAGAGATTCATGAGAAGAGGGAAATGTTGCATACTTAGGGTAGGAGCAAACCACAGAGGTCTTTCTCAGCCTGGGCAAAGAATGTCAACTCTGTGTTGGAGCCAGTAGGGAGCTCTGTGGGTCCTCGAGCAGGAAAATCCCATGGCTTAAGCAGTGTTTCAGGAAGACTGGGATGTTAGGCTCCAGAGCTCTGAGCAAGTCAGATGGGACTGGGAGTCATAAGAAGGCTTGACTGTGGCTAGTGATAACCAATGAGCACTGGAAACATGGAGGGGAATCTTTCCTCCCTTTTATATCAGGGTTCTCTCCTAGAGGAGCAGGTGAGGACCTCTGATGGACCAGGAAATTGGAATTCTGCCTGGGAGGCAAGCCCATGGAGGCCCTGATCTGCTTGGACAGAGAGTAGCTCCCTTCACCTGTAAAATGAGAGTGAACGAGCTGGTGTCTAAGGAATTCAGAATCCCCCCCCTGGAGTTCCACAGGGTATGTGGGATTTTAGGGGGACCAGGGTGTCCCCAGTGCAAGAAGGAGGCTCCCACCAAGGGGCTGCAGCACTGCAGATAACCCCCAGGGGTATGAAAAGAGGCTGAACTGGGGGCCTCCACAGTCAGAATCCATCCATTGACCCAGGATG |
| 491 | MIR4435-1HG | 2570964 | CCCTGGCATCATATTGGGACTTGTTAAGGGCTGAATTGTGTCCCATCCCAAATTTGTATGGTGCCACCCCAACTCCAGTACCTTGGAATGTGACCGTATTTGGAGAAAGGGTCTCTGAAGAGGTAATTAAGGTAAAATGAGGTCATATGGGTGGCCTCTAATTCAATATGAC |
| 492 | MIR4435-1HG | 2570965 | TTTCCATTTCCTAGTAGGGCCAGTC |
| 493 | MIR4435-1HG | 2570966 | TATGTGCATTAGTTTGCTTGGACTGCTATAACGAAATACTACTTGGTG |
| 494 | MIR4435-1HG | 2570967 | GAGCTTTTAGAGAATATGGGCCAGAAACAGGAAGGAGTCAGGACCTGATAACGGGAACCAGCGGACAGTGAACGCAGTG |
| 495 | MIR4435-1HG | 2570968 | GTGAATACAATATTCTCCTTTTGTTTTCACTTTTCCTAAAAGTTAAATCAAGGTTCAAAAGAAAATCGAGG |
| 496 | MIR4435-1HG | 2570969 | AGATGCTAATCCAGCGTGCGTCCTGGCAGAGGTTGAAGGGGGCTCCTCAAGTCCCAGGTCCAGCTTGGTGTGGTTCAGCTACTCGAGAGACATCTGCTGCTAATGGATGAGCAGTCAACCTGGACGCAGG |
| 497 | MIR4435-1HG | 2570970 | TGTGAAGACTGGACTTAAACAGCTACACCACCAGAAGCCGAGAGAG |
| 498 | MIR4435-1HG | 2570971 | AAATTGACATTCCAGACAAGCGGTGCCTGAGCCCGTG |
| 499 | MIR4435-1HG | 2570972 | CTTAGTCGTGTGTACATCATTGGGAATGGAGGGAAATAAATGACTGGATGGTCGCTGCTTTTTAA |
| 500 | MIR4435-1HG | 2570974 | AATCCCATGGTCTTCAATTTGGTCATTTAAAAATAATCTACAAGGTATACTGTTTTT |
| 501 | MIR4435-1HG | 2570975 | CACCACTCTATTTAACAGTGCTGGAAATATTAGCCAGCAAAACAGATAAAGAAAAATAAATAAATGGCATAGACTGGAAAGATTCATAGTTGGCACAATTATGTATATATAAAATCCTCAGGAATGTACACTTTACATACTAGAATTTAAAAGTAAGTTTAGCAACTGTGTTAGTTCGTTTTCATGCTGCTGATAAAGACATACCTGAGACTGGACAA |

TABLE 7-continued

Target Sequences

| SEQ ID NO. | Gene | Affy Probeset ID | Sequence |
|---|---|---|---|
| | | | TTTACAAAAGAAAGGTTTATTGGACCTATAGTTCCACATGTCTG<br>GGGAGGCCTCACAATCATGGCGGCAGGCAAGGAGGGGCAAG<br>TCACATCTTATGTGGATGGCAACAGGCAAAGAGAGAGCTTGT<br>GCAGGGAAACTCCTGTTTTTAAAACCACCAGATCTCATGACAC<br>CCATTCACTGTCAGGAGAACAGCATGGGAAAGACCCACCCCC<br>ATGATTCAATTGTCTCCCACAAGGCCCCTCCCATACCACATGG<br>GAATTATGGGAGCTACAAGATGAGATTTGGGTGGGGACACAG<br>AGCCAAACCACATCAGCAACATGTCAGAACACAGAAAAAATGT<br>AAAATATCACTGTATTTCTATGTACTAGTAGTGAACTGTCAGAT<br>GTTAAAATTCAATTGCTTAGAATGGCATCAAAAATATGAAATAC<br>TGGCCAGGCGTTATGGCTCTTGCCTGTACTCCCATTGCTTTGG<br>AAGGCTGAGGCGGGTGGATACCTTTGAGGCCAGGAGTTCAAG<br>ACCATCCTGAGCAACAGGGCAAAACCTTGTCTCTACTAAAAAT<br>ACAAAAAATTAGCTGGGCATGGTGGCCTGTACCTATAATCCCA<br>GCTACTTGGGAGGCTGAGACACAACAATCACTTGAACCTGGG<br>ATGCAGAGGTTGCAGGGAGCTGAGATTGAACCACTGTACTCC<br>AGCCTGGGGAACAAACTGAGACTCTGTCTCAAAAAAAAAGAAA<br>GAAATACTTATGGGTAAATCTGACAAAATAAGTGTAAGACCTG<br>TACACTAAAAACTACAAAACATTGCTGAAATAAATTAAAGAAGA<br>CCTAAATAATCGGAGAGATATACTTTGTTTAAAGGTCAGAAGT<br>CTCAGTATTGCTAAAATGAGAACTCTTCCCAATGCAGTGCTAA<br>TCAAATTTCTAGCAGGCTTTTTGTAGAAATTGAAAAGCAGATTT<br>GAAATTCATATGGAAGTGCGAACAAAACC |
| 502 | MIR4435-1HG | 2570977 | CCACCATGTGATACCACTACATGTATTTTAGAATTGCTAAAATT<br>AAGAAGACTGACCATATGGGGTGAGGATATGGAGGAAATGAA<br>ATTCTCATACAATGCTATTGGTAATGTAAAATCAAACTACCACT<br>TTGGA |
| 503 | MIR4435-1HG | 2570979 | GCTTGAACCAGGAAACTGGATATCATCTTAA |
| 504 | MIR4435-1HG | 2570980 | ATGTTTGGGAACCCAACAATTAATGCAG |
| 505 | MIR4435-1HG | 2570982 | CCCGAATGTATCTCCCAGATGTCCAGAATACGCCATCTGCAAA<br>ACTGAACTCATCCTCTTTCCCCAGAATGTATCTCCCGGATGTC<br>GAGAATACGCCATCTGCAAAACTGAACTCGTCCTCTTTCCCCC<br>GAATGTATCTCCCAGATGTCCAGAATACGCCATCTGCAAAACT<br>GAACTCGTCCTCTTTCCCCCGAATGTATCATCTCCCAGATGTC<br>CAGAATACGCCATCTGCAAAACTGAACTCATCCTCTTTCCCCA<br>GAATGTATCTCGCGGATGTCCAGAATACGCCATCTGCAAAACT<br>GAACTCGTCCTCTTTCCCCCGAATGTATCTCCCGGATGTCCAG<br>AATACGCCATCTGCAAAACTGAACTCGTCCTCTTTCCCCAGAA<br>TGTATCTCCCGGATGTCCAGAATACGCCATCTGCAAAACTGAA<br>CTCGTCCTCTTTCCCCCGAATGTATCTCCCGGATGTCCAGAAT<br>ACACCATCTGCAAAACTGAACTCGTCCTCTTTCCCCCGAATGT<br>ATCTCCCGGATGTCCAGAATACGCCATCTGCAAAACTGAACTC<br>GTCCTCTTTCCCCCGAATGTATCTCCCGGATGTCCAGAATACG<br>CCATCTGCAAAACTGAACTCGTCCTCTTTCCCCCGAATGTATC<br>TCCCGGATGTCCAGAATACGCCATCTGCAAAACTGAACTCGTC<br>CTGTTTCCCCCGAATGTATCTCCCGGATGTCCAGAATACGCCA<br>TCTGCAAAACTGAACTCGTCCTCTTTCCCCAGAATGTATCTCC<br>CGGATGTCCAGAATACTCCATCTGCAAAACTGAACTCATCCTC<br>TTTCCCCCGAATGTATCTCCCGGATGTCCAGAATACGCCATCT<br>GCAAAACTGAACTCGTCCTCTTTCCCCCGAATGTATCTCCCGG<br>ATGTACAGAATACGCCATCTGCAAAACTGAACTCGTCCTCTTT<br>CCCCCGAATGTATCTCCCGGATGTCCAGAATACGCCATCTGCA<br>AAACTGAACTCGTCCTCTTTCCCCAGAATGTATCTCCCGGATG<br>TCCAGAATACGCCATCTGCAAAACTGAACTCGTCCTCTTTCCC<br>CCGAATGTATCTCCCGGATGTCCAGAATACGCCATCTGCAAAA<br>CTGAACTCGTCCTCTTTCCCCCGAATGTATCTCCCGGATGTCC<br>AGAATACGCCATCTGCAAAACTGAACTCGTCCTGTTTCCCCCG<br>AATGTATCTCCCGGATGTCCAGAATACGCCATCTGCAAAACTG<br>AACTCGTCCTCTTTCCCCAGAATGTATCTCCCGGATGTCCAGA<br>ATACTCCATCTGCAAAACTGAACTCGTCCTCTTTCCCCCGAAT<br>GTATCTCCCGGATGTCCAGAATACTCCATCTGCAAAACTGAAC<br>TCGTCCTCTTTCCCCAGAATGTATCTCCCGGATGTCCAGAATA<br>CGCCATCTGCAAAACTGAACTCGTCCTCTTTCTCCCGAATGTA<br>TCTCCCGGATGTCCAGAATACGCCATCTGCAAAACTGAACTCG<br>TCCTCTTTCCCCCGAATGTATCTCCCGGATGTCCAGAATACGC<br>CATCTGCAAAACTGAACTCGTCCTCTTTCCCCCGAATGTATCT<br>CCCGGATGTCCAGAATACGCCATCGGCAAAACTGAACTCGTC<br>CTCTTTCCCCAGAATGTATCTCCCGGATGTCCAGAATATGCCA |

TABLE 7-continued

| Target Sequences | | | |
|---|---|---|---|
| SEQ ID NO. | Gene | Affy Probeset ID | Sequence |
| | | | TCTGCAAAACTGAACTCGTCCTCTTTCCCCCGAATGTATCTCC CGGATGTCCAGAATACGCCATCGGCAAAACTGAACTCG |
| 506 | MIR4435-1HG | 2570984 | ATGTCCAGAATACGCCATCTGCAAAACTGAACTCGTCCTCTTT CC |
| 507 | MIR4435-1HG | 2570986 | AAAGAGATTCTCACTTAGAGACATCATAAGGAAACTACTGAAA ACTAGGAACAAAGGAATTATCTTCAAAGCAGCAATGAAAAATG ACATTATTTATAAAATTACAATTATTTAAAGGGTTGTAGATTTCT CATCAGAAACCATAGAGGCCAGGCCGGGCGCTGTGGCTCAC GCTGTAATCCCAGCACTTTGGGAGGCCGAGGTGGGCAGATCA CTTGAGGTCAGGAGTTCAGGACCAGCCTGGGCGAAACCTGG GCAAAACCCTGTCTCAACTAAAAAATAAGAAACTTAGCCAGAC GCAGTGGTGTGTGTCTGTAGTCCCCGCTACTCAGGAGGCTGA GGCAGGAGAATCGCTTGAACCTGGGAGGCAGAGGTTGCAGT GAGCCGAGATCACACCACTGCACTCCAGCCCGGGCGACAGA GCATAGAAGCCAGAATGCAATTGAACAACATTTC |
| 508 | MIR4435-1HG | 2570988 | TCAGTCACGTCTGCGCCAGAGCTTTGATGACCCACCTGTCAG CCACACTAAGGGCCCTGCCATGAATAAGGCCTCCGTCACTGA GGATCCTGTACCCCTCTGCCATAAACTCAGTGACCTGACTG |
| 509 | MIR4435-1HG | 2570989 | CCCACATTCAAAAGGCTTGCCCGAGAGGCCT |
| 510 | MIR4435-1HG | 2570991 | TCAAGGTGGCCTTGCGCTTCACCGAGGAGGTGTCATTACCAA ACGTGCTGGACATTGGCTACCTACGGAAGAAAGATTAA |
| 511 | MIR4435-1HG | 2570992 | CCAGACACCACTGGCCTACATCAAACTCCAGGCCACAGATGG AAATAGGACTGAGATCCCTGGACCTGGG |
| 512 | MIR4435-1HG | 2570993 | ATGAAGCTAGGCCCCCCTGTCCTGACAGCTTTCCACCCCTTCC CTGCCCCTCTCACCCTGCTTTCCAGGGGCAATGCACCTCCCC ACTTCT |
| 513 | MIR4435-1HG | 2570995 | TGTATTTGGCATCTACCATATCTTTGCATC |
| 514 | MIR4435-1HG | 2570997 | CACACATAACTCTGGGCGTAAAGTGAGTAAAAATATGAGACTT AGAAGAATATTTCATCATGGTATGCTGATTGGGGATTTCACTTA CTGA |
| 515 | MIR4435-1HG | 2570998 | TCACTACGATTATCTGAATCTCATA |
| 516 | MIR4435-1HG | 2571000 | TCACCCTTGACATCCGCAGAATCCACCCTCCT |
| 517 | MIR4435-1HG | 2571001 | AGTCCTGGGGAACTCTCATCTGGAAAAAGGCGCTCATGACAG GTGGTGCCAACCTTCCACGGATGCTTTTCAGCA |
| 518 | MIR4435-1HG | 2571019 | TTCAGCGCCGAATTGATGAGGACAC |
| 519 | MIR4435-1HG | 2571021 | ATGGAGAAACAGGCGGCCCAGCCAGGCCCTTTCACTGCCCGT GATGGA |
| 520 | MIR4435-1HG | 2571023 | TCCACCAGACTGATGACACTTATTCCACTTGGTTCCCAGAACT AAGAG |
| 521 | MIR4435-1HG | 2571025 | GGGCATTTGGACTCTAACCGGGACAACCTAGTGGCCGGGCAG GGGATGCAGGCACCACAGGTCACAGTAGTTTGCTACGAGTGT CAGCTTTT |
| 522 | MIR4435-1HG | 2571027 | CCTGTGGGAATCCATAAAGAATTGATTCTCATCCCCCAGAAGT GAGATCCCGCTTGTGTCATCA |
| 523 | MIR4435-1HG | 2571029 | CTGGTGCACCTGGTCTACCTCATGTCCAGTGTTT |
| 524 | MIR4435-1HG | 2571031 | TCCTGCAGTTCCAATGTGAGCAGCAGTTGTTTCCAAGGCTAAC AATTTCACGCCAACTAGAAGCCTCCACAAGTCAGGTGCCAGG CATTTCTAAGCCAGTAGAGCAGCTCCGCTTGTTTCTC |

TABLE 7-continued

Target Sequences

| SEQ ID NO. | Gene | Affy Probeset ID | Sequence |
|---|---|---|---|
| 525 | MIR4435-1HG | 2571033 | CTTGGCTGGTGGATCTCGGGTTAAAATCGACTTAGGATGCCCCCCTTAT |
| 526 | MIR4435-1HG | 2571035 | GCTTCTGCAGTTTGCCTTGGAGTCTGGGCTGT |
| 527 | PGM5P4-AS1 | 2571794 | TGAATTTATATTACCGAGTGGAGGGTCACATG |
| 528 | PGM5P4-AS1 | 2571795 | AGTAAATCCATTTGCTGATTGCAATA |
| 529 | PGM5P4-AS1 | 2571796 | CTCTTGTGTAAAAATCTAACTCATCTCGCTGAATTTCCTGATTTAAAAGTCTAATTCATTTCACCAAA |
| 530 | PGM5P4-AS1 | 2571797 | CCAGACGTACAGAGGCTGGGAGCCATTGTGGTGTGCTATATTGATGACGGCAGCAGTGGG |
| 531 | PGM5P4-AS1 | 2571798 | TTGTGTATCTGCGTTCCTTTCAACAAGTGTGACTTCCTCAATGGCATCATTCGTGAGCGTAACACAGAGCTCAGC |
| 532 | PGM5P4-AS1 | 2571799 | GAGCTGAAATCGACCAGGGGGTTCTTATCCAACAG |
| 533 | PGM5P4-AS1 | 2571800 | GCCTACCTAAAATATTGAATGCTGTTAATAAATCTCCTGAGGCCAGCATAAGAAGGTGATGGGCAAAACTAAT |
| 534 | PGM5P4-AS1 | 2571801 | CTTAGAGGGCCCCACAGTTGTTTGCTG |
| 535 | PGM5P4-AS1 | 2571802 | TGGTTACAATGGTACTTTCAGCCTGTCCGAATTATGTATTGCCCCTCCCCTTTTTATTAATAACATTGAAGTGTGATGGGACAACCACTGAAGCCGTCAGTTGAAACCTGCTGGGACTTTTTAGCCATTCTCTTCAACATAAAGAATGGGTGTTTTTGGAGGGGGTGAGAGGAATGGGGAAATGTTGTCAAAGAGTACAATGTTTTAGTTGAGACAGGAAGAATATATTTTGTTGAGATCTACAGCACAGCATG |
| 536 | PGM5P4-AS1 | 2571803 | TGTGCTAGGTTTCTTTGCATGTACC |
| 537 | PGM5P4-AS1 | 2571804 | AGCCTCCTCCAAAACAGCACACTTTCCG |
| 538 | PGM5P4-AS1 | 2571805 | TTTCTCCCGCCCACCTTCTCCGCTGCCAGACCGCCCGAGCTGCCCTCAGTTTCTCCCCAAGTTGGACTCACTTTCGGGGTGTCCCACAAGCCCGATCCCAGAGCCTGCT |
| 539 | PGM5P4-AS1 | 2571806 | CGACCTCGACGGCCGTCCTGCCGAAGTACCTGCCGTCGCTGCCCACCCCCGTGGTGCGGCCCTGACGGTCGCGCAGGTCGACGGACGACAGCGCGCTCCGGATGAAGTTGGGCGGGTAGCT |
| 540 | FTH1P2 | 2590365 | AGACTGTGATGACTGGGAGAGCGGGCTGAATGCGATGGAGTGTGCATTACATTTGGA |
| 541 | RNA5SP121 | 2602465 | CATAGTACTCTGAACATGCCCGATTTCATCTGT |
| 542 | FTH1P2 | 2629711 | TGACAAAAATGACCCCCATTTGTGTGACTTCATTGAG |
| 543 | SETP14 | 2648928 | ATGAAACAGACAGACTTAATGAACAAGCCAGTGAGGAGATTTTGAAAGTAGAACAGAAATATAACAAACTCCGCCAACCATTTTTTCAGAAGAGGTCAGAATTGATCGCCAAAATCCCAAATTTTTGGGTAACAACATTTGTCAGCCATC |
| 544 | SETP14 | 2648929 | TTTGACGAAACGTTCAAGTCAAACACAGA |
| 545 | SETP14 | 2648930 | GAGGTCATCAAAGATGATATCTGGCCAAACCCATTACA |
| 546 | TIPARP | 2649130 | GCGTACAAGGCCCACGAAATAGTCGGCCGCCGCAG |
| 547 | TIPARP | 2649131 | ATAAGTCCACCGCACAGAACTCGCGCGCCTCCCCTCGAACGAACGCGCACGCGCGCGCAGGGGGCGGGTCTTCTTCCCGACACCCACTGA |

TABLE 7-continued

| Target Sequences | | | |
|---|---|---|---|
| SEQ ID NO. | Gene | Affy Probeset ID | Sequence |
| 548 | TIPARP | 2649132 | CTCCGCCTCCGCGACGGGCCGTCGGGAGGAGGCGACCGGAA GCCACTTAAAGCAGAGATCGAGGTGACAGGCGAGCTGGCTG GACTCGGA |
| 549 | TIPARP | 2649133 | CGCGGTCGAGGCTTTCTGCGTTCGCGGCGGCGGAATGGCCC |
| 550 | TIPARP | 2649134 | TCTGTGGTCCCTAGACGTCGGCTCCCGCCCTCGGCGCTGATC TCCGGCGCGGGCACTGCTTTCCACTCGGCTCCTGTCGTCCGT TCTCTCAGG |
| 551 | TIPARP | 2649135 | GGGCGCGTCTATGCGGCCTCCCCCGCGGGCCGACCCCGGGT GCTCTGAGGCGCCTAGGAGC |
| 552 | TIPARP | 2649136 | GGCACGGCAGCTACGGGAGCCTTCCGGCTACCCCGCGTTTC GGGCTGCAG |
| 553 | TIPARP | 2649137 | CATTAACTTTGAGAGCGCACAAGTCTTCGTCTTCCTCCCCGCC GCCGCGGGAAGCGCTCGCCGCCTTTCCCCCGCGCTTCGCGG CTCAGTTCTGCGAGCCCCCAAGACCCGTTGGACGCTCCTCGG G |
| 554 | TIPARP | 2649138 | CTCAGCTGCACTGCGCGGAGTTGGCGCGGCCCGGGACCAGG AGCTGAGCAAACCGCCGCGGCCAACAGGAGGCGTCACTCGG ACCCGGGCTCGGCGCCGGGGTGTCGCGCGGCGGCGGGCGG GCAGGCTTTGGAGCGGCAGTTTTTTCGGAAAGTGC |
| 555 | TIPARP | 2649139 | ATGATCATCTTCCTTCCTTTCCTCGTAG |
| 556 | TIPARP | 2649140 | GATTTTTAGACTCTGAGGAGCAGTTGGAGCTAATCCACATT |
| 557 | TIPARP | 2649141 | CAGACTGTGTAGTGCAGCCTCCCTCTCCTCCTGATGACTTTTC ATGCCAAATGAGACTCTCTGAGAAGATCACTCCATTGAAGACT TGTTTTAAGAAAAAGGATCAGAAAAGATTGGGAACTGGAACCC TGAGGTCTTTGAGGCCAATATTAAACACTCTTCTAGAATCTGG CTCACTTGATGGGGTTTTTAGATCTAGGAACCAGAGTACAGAT GA |
| 558 | TIPARP | 2649142 | GGGGACCAGATACCGGAAGCCCATCCTTCCACTGAAGCTCCA GAACGAGTGGTTCCAATCCAAGATCACAGCTTTCCATCAGAAA CCCTCAGTGGGACGGTGGCAGATTCCACACCAGCTCACTTCC AGACTGATCTTTTGCACCCAGTTTCAAGTGATGTTCCTACTAGT CCTGACTG |
| 559 | TIPARP | 2649143 | GTATTTATAACAACTTGTAGAACTGTTG |
| 560 | TIPARP | 2649144 | AAAACTTTGCAGAACAGCGGCTCCCACTTCACCTTCATGAAGC AAATTTCCAGTCTGCTGAGTACTTCAG |
| 561 | TIPARP | 2649145 | AAGTTGACTTGTGGTCATTGCAACCTGGTTTT |
| 562 | TIPARP | 2649146 | ATAACGGCATGTTGAGCCTTGCTGAGAGATTCACAAACAAGCT GGAGCAGCCCAGGTTCACATGGTTACCACATTATTTGGCTAAA GCTATTAATCTCTGTGGTCAGGCCTGTAAAGCTGGTCTATCTG TGCAGATTGCGCATAACCAGGAAGT |
| 563 | TIPARP | 2649147 | GCCTTCTATCCCAGCTGTTCTTACAGAAATTAAGTTTCACTTTC TCATCAGGCTATGGTTGAGAAGTATGTCTCATTTATAGTGCCTT CTGTGATCTTAGGACATGTGACTA |
| 564 | TIPARP | 2649148 | TGTGATTTCAGACAGCATCCTTCTCACTAACTTGCTGCCTTCTT GGAATAAGAATTTCCAAGATGTCTCAGGAGGTACCAAGGGAG CAGCAACAAGGCCTAATGATCACTTCTTCAAGAATTTATCCCA AGAAATGCATTGTATCTTAAGTTGGGGAACACTTTTACCTACTC AAAAATCTTTTGAGGTATTCAGATAAATCCATGATCTGAGTTTT ATGTTAATAGTTTTACAGTGTCATAGTGTGGTAATTAAGTGTAG AATTTTAACCTCTGAGGCTGGGCGCAGTGGCTCACGCCTGTA ATCTTAGCTTTTTGGAAGGCTGAGGCAGAAGAATTGCTTGAGA CCAGCCCAGGCAACATGGCGAAACCTTGTCTCTACAGAAAAAT ACAAAAATTAGCTGAGTGTGGTGGATCATGCCTATAGTCACAG CTACTGGGGATGCTGAGGTGGGAGGGTAGTTTAAGCAAGGGA GTTTGAGGTGGCAGTGAGCCTAGTTGGCACTATT |
| 565 | TIPARP | 2649149 | GGACAAGAATTTTGGGCAGATTTGAATGCC |

TABLE 7-continued

| Target Sequences | | | |
|---|---|---|---|
| SEQ ID NO. | Gene | Affy Probeset ID | Sequence |
| 566 | TIPARP | 2649150 | TTTGACCAACTACGAAGGCTGTCCACACCACCCTCTAGCAATG TCAACTCTATTTACCACACAGTCTGGAAATTCTTCTGTAGGGAC CACTTTGGATG |
| 567 | TIPARP | 2649151 | TGTCATTCGATTGATTGAAGAAGCCAACTCTCGGGGTCTGAAA GAGGTTCGATTTATGATGTGGAATAACCACTACATCCTCCACA AT |
| 568 | TIPARP | 2649152 | GGTGGGGTTCCCACACAAGCTCCTCCACCTCTTGAAGCAACTT CATCATCACAAATTATCTGCCCAGATGGGGTCACTTCAGCAAA CTTTTACCCTGAAACTTGGGTTTATATGCATCCATCTCAGGACT TCATCCAAGTCCCTGTTTCTGCAGAGGATA |
| 569 | TIPARP | 2649153 | ATGAAAAGTTCAAGACGGCCGGGCGCAGTGGCTCAAGCCTGT AATCCCAGCACTTTGGGAGGCCGAGGCGGGCAGATTACGAG GTCAGGAGATCGAGACCATCCTAGCTAACACGGTGAAACCCC GTCTCTACTAAAAATAGAAAAAATTAGCTGGGCGTGGTGGCGG GCACCTGTAGTCCCAGCTACTCGGGAGGCTGAGGCAGGAGA ATGGTGTGAACCTGGGAGGCGGAGCTTGCAGTGAGCCGAGA TTGCGCCACTGCACTCCAGCCTGGGCGACAGAGCCAGACTCC GTCTCAAAAAAAAAAAAAAAAAAGTTCAAGAATCAAGAGAGCTT TATTGTAGCCAGTGTCAAATGAGGAACATAATAGTAAACATTTG CACAGAATTTATGTTC |
| 570 | TIPARP | 2649154 | CAGGAAAATGTTTGGCCGTGACAGGATAATAAATG |
| 571 | TIPARP | 2649155 | GACCCTCGAGTCTGTGGAAAGCATGC |
| 572 | TIPARP | 2649156 | TCCAAAGGAGTCCACTTCATGTTTCTGGCCAAAGTGCTGACGG GCAGATACACAATGGGCAGTCATGGCATGAGAAGGCCCCCGC CAGTCAATCCTGGCAGTGTCACCAGTGACCTTTATGACTCTTG TG |
| 573 | TIPARP | 2649157 | TACCCTTATTTTGTTATCCAATATGAAGAA |
| 574 | TIPARP | 2649158 | GCTTGGGCCTGGTAGAAGTTTGACCAAATGGAATGGAGGCTG TGAGCAATGTGAGGATTCTATTTATTTATTTACGTTTGATAAAA CTTACTGGAACTAGTACTACCATGCGTATTCCCTGTCCAAAGC ATCACTGCTTTGGTATAGTATAAGTTCATGAAATTCTGGTGGGT AGAAAGAAATTTTTATTTCTATCAGCAGTACTAAAATGTATCAG CCAACCAGAGAACATCAGTGACTTTAACTTCTGCAGAGTTTGC CCCAGAATTCAGAGTTCTATTTAGAGGAAGTTAAAACAACAAC AAAAAACAACCATTTGAAAAATTTTTGTCACCAGCAAAACTTTT CACTAATTAGTGATATGAAATGTGATTTTTGTGTTGTTAAACTT CAGCTTTGGAAAACTCAGTCTCTTTCATTATCATCCATTCCAAT TTGAAGGAGTTGGGCAGCTAATTTGGTTAAAGGCAGTCTTGAG GGTTAGAAGTATTACTTCCTTTTCGGGTTCCAGACCTAGCTTG |
| 575 | TIPARP | 2649159 | AAACTTGGAAATTGTGCCAGTGGTCCAGCTGGAGCACAACGT TTGGTGA |
| 576 | TIPARP | 2649160 | TCAGAGAGGTAGCAACTAGGTAAACTCCTTATAAAAAGCAAAT ACCTGGATTTACAAAAGTGAAAGTAGTTGTTCACAAAAGAATTC GCCATGGAATTCTTTCAGTTACCAAGCTCTCCTGGTAATGTTT GTGGTTATATCATTTACACAAAACTTTTCAGGAACTTCTGTGTT GTTTAAGCAAGATGTATCTGTACTGATGTCTCAGTGAATCAGT CTGTTTATTAAGCACTTATCAGGGCTTCCACACACTTATTTATT |
| 577 | SMC4 | 2650205 | ATGCGCAGGAGCGACAATAAGATGGCG |
| 578 | SMC4 | 2650206 | GCCATTTTCGAGTGAAGGACCCGGAGCCGAAACA |
| 579 | SMC4 | 2650207 | GTGGGTACTACACAACCGTCTCCAGCCTTGGTCTGA |
| 580 | SMC4 | 2650208 | GCCAGCGTCCGACTTGAAGTTGCTAGTGGTTAGTCCCAGCCT TCGCCCTTCGCGGTCCGACCGCTGAGAGGAGGGAGACTTCGT TATGCCCCGGGCCGTCAACGGCGCCAGGAGCTAAAGGGCGG GCAGACGAAAGCGGGCGGCGAGTCGCCAGTTAGTCTTCACC GCTCTGGAGAGAGTTGCTAGCCACGGGATCCTGACCCGGACA CGAACTCGTTTCTCCACGTCGGTGCGCGCTTGCATCCCTGGC CCCGAAAGCGTGGGAATGTCCGGAAATGCTGGCGTATGGGA GTTCCTTA |
| 581 | SMC4 | 2650209 | GCACGTCTAGATTTTCCCACTTACATAG |

TABLE 7-continued

Target Sequences

| SEQ ID NO. | Gene | Affy Probeset ID | Sequence |
|---|---|---|---|
| 582 | SMC4 | 2650210 | AGTCCTGCCTTCTTGCCACTCGTGTCTTTCGATGGCTCCCTTC CCGAAGTCCCGCTGCCTCTAAGCGGAGTGTTAAGCGGGGCTC TCGGAAGCCGGTGGACCGAGATTT |
| 583 | SMC4 | 2650211 | GGCGGGCGCGGTGTAGCGGCCCGCGGGCTGACTTGCTCCCG GCTGTCCC |
| 584 | SMC4 | 2650212 | ATGCCCCGTAAAGGCACCCAGCCCTC |
| 585 | SMC4 | 2650213 | CCCTGACGGCGCCAGCAGCGACGCGGAGCCTGAGCCGCCGT CCGGCCGCACGGAGA |
| 586 | SMC4 | 2650214 | CCTCCGTGGTGTTAGATTGCCGTTAAAGAGAAGACGATAATTT ATTTGAAGCCACTGTAGCTTTTGTGAGTCCAGGAGTTGGGTGA CATTATTAAACCCTCGTGGCAGTGTCGCTGAAGTTCATGAGTT TCCAAAATGAAGGTTCCAGGTGCTCAGCGGTACGGAGAATTG CATCTA |
| 587 | SMC4 | 2650215 | TGAGGAACTTGATAATAGAAGTTTAGAAGAG |
| 588 | SMC4 | 2650216 | CCAGAACTTCAAATCCTATGCTGGGGAGAAA |
| 589 | SMC4 | 2650217 | CGCTTTTCCTGTATTATCGGGCCAAATGGCAGTGGCAAATCCA ATGTTATTGATTCTATGCTTTTTGTGTTTGGCTATCGAGCACAA AAAATAAGATCTAAAAAACTCTCAGTATTAATACATAATTCTGAT GAACACAAGGACATTCAGAGTTGTACA |
| 590 | SMC4 | 2650218 | TTGAGAAAGGGACCAAAACAGCATGGAAAAGTATCAATTCTTT GCTAAGTTGGGTTATTAATGAGAACTACTGGCAGTTTGTGTGC ATGTTCAATTGAAGTTTTTAATCCATAGAATTAGTTTCAGTATGA AATGAGTGAATTTTGAAGTAGGCCTATGACTTAATACCAACAAT T |
| 591 | SMC4 | 2650219 | AAGGGGATGATTATGAAGTCATTCCTAACAGTAATTTCTATGTA TCC |
| 592 | SMC4 | 2650220 | AACGGCCTGCAGAGATAATACTTCTGTCTATCACATAAGTGGA AAGAAAAAGACATTTAAGGATGTTGGAAATCTTCTTCGAAGCC ATGGAATTGACTTGGACCATAATAGATTTTTA |
| 593 | SMC4 | 2650221 | CTGTAGCAGCACATCATGGTTTACATGCTACAGTCAAGATGCG AATCATTATTTGCTGCTCTAGAAATTTAAGGAA |
| 594 | SMC4 | 2650222 | GTAAATATTGGCGTAGTGAAATATATATTAAACACCAATATTAC TGTGCTGCTTTAGTG |
| 595 | SMC4 | 2650223 | GTGTTTGATTTACCTAAGCACCTAGTTAATTTAATCTTTGTAAC ACTTTGGATGGTTAACTTAACCTTTACTCAAGTTGGTTTTTGTT TTGTTGAAAATGACTTACTTGGTGGAACCACTACTACTGAAAG AACGAAACTTTGATATTACATTGTTAAGTATCAGAGCTGTTACA GAGCAAGTCCTTTTAAAGAGATGTAAAAATTAAGTACCTGTGC CAAACTGATTTTTATTAGAAACCCTGTTTTCTTTAAGTAAAAGTA TATTCTACCAGCATGGCTTGG |
| 596 | SMC4 | 2650224 | TATCCACAACTAGGGTGAAGGTGGTGGAGAGCAGCAAGGAAG CTACCTCTAACCAACCAGAA |
| 597 | SMC4 | 2650225 | CTCAAAGAGTGGTATAACTGGATCATAATATCCTTGTTTGCCAC TCAAGAAAGTGTTCCATAACTTAAGATAACAGTGGTGGGAAAA ATCATTTAAGACCTTGTTTCATATGCTTTAAGATACAAGAAATA GAGATAACACTGGGAACATATGAAACTTTGTCAGCATCAGATA ATAGTGTTGTAGCGACTTGAAACATTTTTTGTCTGTGATTGTGC CAGTCACTATTTGTGACTTGGATTGAACCTTGATATGACTTTAA ATTCAGGTTGATGTTTTAAAATTATTTCTGAAATATATTGAGCTT ATTGCCCTAAATTAAAACTATATTCTGTAATTTTACATGAGTTAT GTAAGTTTTCTGAAGAAATAAGGAGGAATCCTTTAGGCACAGA CTGTCAATCTACAGATT |
| 598 | SMC4 | 2650226 | ACTCTTGGCTTTATTATTTAACTGCTCCCAATTCTCACTTAAGA TTGATTTAGCTAAACATACAC |
| 599 | SMC4 | 2650227 | GAACAAATTGCTATGATGAAACCAA |

TABLE 7-continued

Target Sequences

| SEQ ID NO. | Gene | Affy Probeset ID | Sequence |
|---|---|---|---|
| 600 | SMC4 | 2650228 | AGATATAATTGGTTGTGGACGGCTAAATGAACCTATTAAAGTC TTGTGTCGGAGAGTT |
| 601 | SMC4 | 2650229 | GGAGAGAAAAACATAGCTATCGAATTTCTTACCTTGGAAA |
| 602 | SMC4 | 2650230 | GTAAGTGCCTTGATTGATATTACCAATTTTTATATTAGTTTTTAA CCATTAAGTCAAAGCCCTTCTCT |
| 603 | SMC4 | 2650231 | AAGGAATTATGTGGTGAACTTATCCAATGTGAGGACTATCTGG CTGTGACACCTGTCATCCCGTTGATCACCAGGGTTGAATTTAT TAAA |
| 604 | SMC4 | 2650232 | TTATGAGTTGCAGAAACGAATTGCTGAAATGGAAACTCAAAAG GAAAAAATTCATGAAGATACCAAAGAAATTAATG |
| 605 | SMC4 | 2650233 | GATAATTGTATTACATGTGTATTTATATATAAAGTTACTTCTAGC ACATTGTGAGTGTAAGACATTTGCCAGCATATCAAGTGGTG |
| 606 | SMC4 | 2650234 | CCCTAGTGGCGTAGCACAGTAACAAACAATAAGCATTTGGCTT CACAGTTTAATCTTTTAGTAGTCCACAAATCTGATAGAGGGATA GGATTTGGGTTTTTCTAGATAGATTTTTAAGGGTTTTATCATGT CCCTACTTGATGCCATTTTTCAATGACACTAGTATCTCTAATTA TTTTTAAATAAAAAAATTTGTATAGTAAGTTTATTGTATAGTAAC TTGTAAGTATATTCGTAAAAGGTAAAACCAAAATTTTACTCCTA TGGTAAAATTTTTATATACCTAGACATTGTAGTCACTGGAAAAT GTGTTATTTTCCCTCCAACTTAGAAAGGCAAAATAGCTGTCATA ATCAAAAATACAGGTGCTTCTTCAACTATGGGGAGAGGGATCA TCTTGGAATAAGGAGAGTTTAGGATCCTGCCTTATTAAGAGC CTGGACATA |
| 607 | SMC4 | 2650235 | ATTACAAAATTTATTGAGGAGAATAAAGAAAAATTTACACAGCT AGATTTGGAAGATGTTCAAGTTAGAGAAAAGTTAAAACATGCC ACGAGTAAAGCC |
| 608 | SMC4 | 2650236 | TCCGTGTAGTCAGAGCATATTTATAGCTAAAGAAGAATAATTAC AACCTGAAATCAGGAGAGAAGGATGACAGACCTGAGGCCCTG CCAGAGACAGTTTTCCTTCATAAGAGGTCAGGTGTTTGTAGAA GTAGTTTTACTATTAGATTGAGAGAATATAGAAATTACAGTGAA TAGTCGGGAAAATACTTGTTAAAGCTAGCTAATTTAACTCTGAT TATAAAGAAAAGAAGAACTAGAGGACCCTGAGAAATGCCTTTA AATA |
| 609 | SMC4 | 2650237 | GCCAAGAGTAACAATATCATTAATGAAACAACAACCAGAAACA ATGCCCTCGAGAAGGAAAAAGAGAAAGAAGAAAAAAAATTAAA GGAAGTTATGGATAGCCTTAAACAGGAAA |
| 610 | SMC4 | 2650238 | TGAAACCTGAACTGGTAAGTTTGGACTTTTAATGTCCAACATTC CTAAAACTAGTCAACCTAGACTTAGATGACTATTCTTTTAATTC CTGCTGA |
| 611 | SMC4 | 2650239 | GTCAATGGATAATGCAGTAGCTTTCATGATGGGATACTTCATA GTTAGTGGATTTTCACTGTTTGCTTATTTAATATATATTGAGTAC TCATGTGCCCTGCACCCCATGTTAATGACAAAGCTAGGCCTCA AATGTCTTTATTCCTCAGCGTAATGATCGATCTCACAAAGCTCT TGTGAAATCAGTTGGGAAAAGACTATGTACAGTGAATATTGAC AACTAGGCAAAAACTGAATCTAGTCCACTTGTGAGAA |
| 612 | SMC4 | 2650240 | AAGCACGTTCAAAGATGGATGTAGCCCAGTCAGAACTTGATAT CTATCTCAGTCGTCATAATACTGCAGTGTCTCAATTAACTAAGG CTAAGGAAGCTCTAATTGCAGC |
| 613 | SMC4 | 2650241 | AAAGAATGAGGTCAGCATTTCAGTATTCCATATGTGAACTGAG ACTATCAAGAAACTATATTATCCCCAGAAGCACCATATAGTAAG TAAATCACCACCACCACCCCACTGTAGAAATAATTTAAACAAAA GAAAGTTTGTGTTTCTTTAAATCTTAAGTATAGACAATTTAAAG ATAAATAAAAAACAAGTGTATATGTATTTATATAATGAATATACA AACAACTATCTTAATGTGTTTTGGGTTTTGAATTTATGGATGTA GTTTCTTTGCTTGCATTCCAAAATGTTATAAACTAACTAAGATG TATAGCTTATCGGTGCCTGTCCCCCATCCTTGAGTGAATTAGA TGTCTAAGGAATTTCGTAAACTTTAATCTCCAAAGATCTCCAAA ACCTCAGTA |
| 614 | SMC4 | 2650242 | AAGAGCTCATTAGCAATGAATCGAAGTAGGGGGAAAGTCCTT GATGCAATAATTCAAGAA |

TABLE 7-continued

| SEQ ID NO. | Gene | Affy Probeset ID | Sequence |
|---|---|---|---|
| | | | Target Sequences |
| 615 | SMC4 | 2650243 | TGACAACCATATTTCAAGTGTCACTGTATATAAAATAAGATTCA TTTTGTTTGTTTTAAGGCACATTTATTTTTAAACATTTTGCCCTT ACAGTTTCTTGTTTACTTAGCTTTAGATAAATACAATTATTTCAT ACATATCAAGAAAAAATACTAGTAATGTCACACAAAC |
| 616 | SMC4 | 2650244 | GGGGACTTAGGAGCCATTGATGAAAAATACGACGTGGCTATAT CATCCTGTTGTCATGCACTGGACTACATTGTTGTTGATTCTATT GATATAGCCCAAGAATGTG |
| 617 | SMC4 | 2650245 | GGCTGTATGGGCGAAAAAGATGACCGAAATTCAAACTCCTGAA AATACTCCTCGTTTATTTGATTTAGTAAAAGTAAAAGATGAGAA AATTCGCCAAGCTTTTTATTTTGCTTTACGAGATACCTTAGTAG CTGACAACTTGGATCAAGCCACAAGAGTAGCATATCAAAAAGA TAGAAGATGGAGAGTGGTAACTTTACAGGGACAAATCA |
| 618 | SMC4 | 2650246 | GAAGAATGGGTTCCTCACTTGTTAT |
| 619 | SMC4 | 2650247 | CAGTTGCAAAACGACTCTAAAAAAGCAATGCAAATCCA |
| 620 | SMC4 | 2650248 | GTGAACGAGAAATGAGGAACACACTAGAAAAATTTACTGCAAG CATCCAG |
| 621 | SMC4 | 2650249 | GGAACTTGAAGCTAATGTACTTGCTACAGCCC |
| 622 | SMC4 | 2650250 | TACTGGCCAGGCTTTGTTTTAGGTCCTACTGATAGAGCAGTAA ACAAAAATAAAGTCTCTTCCCAGGGAGCACACATGTAAGATGG CACATATTTGAGTGGAGGCCCAAAGAAAGTATGAGTGCTAACC CATGTATGTTTGAGAAAAAAGCATTCCAAGAAGAGTATAAAGG AGCAAATACAAAGGCTGAAGCAGGAGTATGCTGGGAACACAA ACCATTGTGGCTGGAATAAAGGACGGAAGAACCCAGATTCTCT GAGGCCTTCACCCACACTCCCCTTTCCCTGCAAGCACCCACA ACAATGGCTTTGATGGTACCTGATGGTCAATTGAGAAGCCAAA ATGTATATCTGTGCTATTAATGGCAACATTTTCATGGAGAGACT GCAAGAGTCTATATGTGTTTCATCCTTATTTGAAAAGGAATCCT TGACTTTGTTAGGAGCTCTATATATCTCCTCTCATAGAAATGCC ATATATTATCAGGAGACTGTTAATATCTCATGTGGAGGACCCA TTTGTGCAAGCATA |
| 623 | SMC4 | 2650251 | ACTTTTACTCTTCGTTGTCACAGGAAGGAACGCTAATTCATCTT ATATCCTCCACTTTGTTTTAATGTGGAGAACTGCGAAGTTATGT TAGCAGAAGAAAATAACCACAATTTCTTCATTGTGGGCAAGTT AATATTGAGTTAGGCACATAGTGTATCTAAGGCTAAAAATCATT ATGAACTCAGTAGTCAAGGAAGTGCCCTAAGAAAAAGTTGTAA AGATATTTTAAAAGAAGCTGAGAACATGAAGCCATTAAGAAAT GGTGTGTTTACAGCCGAGCTAGTGTGTTTAACTTT |
| 624 | SMC4 | 2650252 | GCTGAGGTTAAACGCTTACACAATACCATCGTAGAAATCAATA ATCATAAACTCAAGGCCCAACAAGACAAACTTGATAAAATAAAT AAGCAATTAGATGAATGTGCTTCTGCTATTACTAAAGCCCAAG TAGCAATCAAGACT |
| 625 | SMC4 | 2650253 | GTAGAGTATGCATGTTACCCTAACTTGTTTTCCCTTTCCCTGCC TTCACATTGGAAAGGGGGTTACTATGTAATGTTCCATAAAATGT TTCTCTTACTGTTAATTTATTGAACCTGTCTGACACATTACCTAA TGGGACTTCCATGACGGAAAACCTATAATGAACATTTATCCTAT GGCCAATTAAAAAGGCTGGTAAACAGGTATGCCATA |
| 626 | SMC4 | 2650254 | TGTCTTGCGTACAGAGAAAGAAATAAAAGATACTGAGAAAGAG GTGGATGACCTAACAGCAGAGCTGAAAAGTCTTGAGGACAAA GCAGCAGAGGTCGTAAAGAA |
| 627 | SMC4 | 2650255 | TCCAGAAAGAACATCGCAATCTGCTTCAAGAATTAAAAGTTATT CAAGAAAATGAACATGCTCTTCAAAAAGATGCACTTAGTATTAA GTTGAAACTTGAACAAATAGATGGTCACATTGCTGAACATAA |
| 628 | SMC4 | 2650256 | AAGAGATTTCGGTTCTAAGCCCAGAGGATCTTGAAGCGATCAA GAATCCAGATTCTATAACAAATCAAATTGCACTTTTGGAAGCCC GGTGTCATGAAATGAAACCAAACCTCGGTGCCATCGCAGAGT ATAAAAAGAA |

TABLE 7-continued

Target Sequences

| SEQ ID NO. | Gene | Affy Probeset ID | Sequence |
|---|---|---|---|
| 629 | SMC4 | 2650257 | ATTTTCCCTATCATAATCTTTTCACAG |
| 630 | SMC4 | 2650258 | TATGAAGATCTTCGGAAACAAAGGCTTAATGAATTTATGGCAG GTTTTTATATAATAACAAATAAATTAAAGGAAAATTACCAAATGC TTACTTTGGGAGGGGACGCCGAACTCGAGCTTGTAGACAGCT TGGATCCTTTCTCT |
| 631 | SMC4 | 2650259 | GTTCATTGGCTTTAGTATTTGCTCTTCACCACTACAAGCCCACT CCCCTTTACTTCATGGATGAGA |
| 632 | SMC4 | 2650260 | GTGATTTACCTGTTATTACTTAATGT |
| 633 | SMC4 | 2650261 | GCACAGTTCATAATAATTTCTCTTCGAAATAATATGTTTGAGAT TTCGGATAGACTTATTGGAATTTACAAGACATACAACATAACAA AAAGTGTTGCTGTAAATCCAAAAGAAATTGCATCTAAGGGACT TTGT |
| 634 | SMC4 | 2650262 | TTCAAGTTGATTCAGTGTATTACTGATTTTTTTCTATTTGTAAAG GATTATGAGTTGTATAAAATACATACTCCCTAAACTAGA |
| 635 | SMC4 | 2650263 | CAAGGTTGTGCTATCAAGGCTCAGCATACCTTCGTGGGCCTTT GATTTACCAACACTGGAAATGCCTGCCAACTAATCTTGGATAG ATTCTTTAAGGCATTCCACTTAGCTTGCCAGTTGA |
| 636 | SMC4 | 2650264 | GCCTAGGCTATCTCGTAAGTTGAAAAATATCCCACTATAGTTG CTTCATGAGTATGAAGTAAGATGGCCTCTGATTTACACTGGTT CAATTTACAAATTTTCAACTTTATGATAGGTTTATCCGGGTACT AAATGCATTTCAACTTGATAGTTTCAACTTATGATAGGTTTACC AGGATGTAGTCCCACTGTTGAGGAGCATCTATTTAGGGGTTAA TTACTTTAGTAATAAGTGGAAAGTAAGATACCTTGAGTAATGTT TGCCTATAAAATTGTCAGCGTATTTTTACACTATTGGCTCAAGA ATGTTATAATGCTAAGGGACATAAGTTGGCAACCACTTGGTTTT TGGAAGGACTTTCGGTATTGTATTAGAAGTCTGCCCTAGCTGT TAAATTTCTGG |
| 637 | SMC4 | 2650266 | GATGTAACTATTTTGCTTTGTAAATATCCTGCCTTTAA |
| 638 | SMC4 | 2650267 | TGTTTCTTAATAGCTGTACTCTATCTCTTCAGTAAGTAATTTGC CAGGAGAAATACAATGTTTTTAAGGAATATTTTTGTCAGCGTAA ACTGTTAAACACTGAATCCCAACTTTTAGCTATCTGAAAAATGT ATACTTAAATAATACATTATGGCCATTTGACTCAAATGTAAGTT |
| 639 | LIPH | 2708858 | TCTCTTTCCTGGTAAGCAGGGAGTCAAAACAATAGCAAGAAAA TGCCAGAAATAGAATTTCTACTACTTTGTAAACTCTAGGCTCGT GGGTCTCCTAGCTCTCAGTACCTGGCTCACTGTAGGATGGGT AGATGGGTGAATGAATGGATAAAGAAAGGAAGTTTGTTCACCG GAGAGGAGATGAATTTCAGTAAGTTTCATGTAACAGTGATCAG GAGAAATA |
| 640 | LIPH | 2708859 | GGCTGTCACCTATTTTGCCAACACGTGAATTCAAAACATGAAC CGGTTTGCTTTTGGAGAATCTGAAGACTCCAGTTTGAGGAATC CTTTGCTTCCCTGGAGGTAGATGCTGTCTGCAAATCTAGAATG ACAGCAGGAGTCCAGTCAAGAGGTCCTGTCAGGCCAAGGCCA GAAAGAAGGGAGGACAATCCCTGGGGCCAGATGCCCAGTGT GAGGGGAGGCATGATCTGTCCCATGGCTGTGGCCACTGCAG GAAGGTCTGTGAAAAGGAGGTGACAGGCCCAGTCACCTCCTC TTCACCCAAGTGATTGCTCCTTCAACTGCTATCTGTGAAAATAG CCTTTGTTATGAAGAAATTGACTCTCTCTCTCTTTTTTTTTTTTT GGAGTTGCCTAGGCTGGAGTGCAATGGTACGATCTCAGCTCA CTGCAACCTCCACCTCCCAGGTTCAATTGATTCTCCTGCCTCA GCCTCCTGAGTAGCTGGGATTACAGGCATGTGCCACCACACC CGGCTAATTTTTGTATTTTTATTAGAGACAGGGTTTCACCACGT TAGCCAGGCTCGTCTCGAACTCCTGTCCTCAGGTGACTACCC GTCTCGGCCTCCCAAAGTGCTGGGATTACAGGCATGAGCCAC CACACCCGGCCAAAAATGGATTCTCTATG |
| 641 | LIPH | 2708860 | CTGCTGGGACTAGATAGTGGATGAAGAAAGAAGGACGAGGAA GCCGTGGGGCAGCCTCTTCACATGGGGACAGGGGATGGAGC ATGAGGCAAGGGAAGGAAAAGCAGAGCTTATTTTTCACCTAAG GTGGAGAAGGATCACTTTACAGGCAACGCTCATTTTAAGCAAC C |
| 642 | LIPH | 2708861 | TCGGGCTGTTTGCTCAGGGAAGGCAAGAAAGCCACGTGCTGG CCCTCTGCCTT |

TABLE 7-continued

| Target Sequences | | | |
|---|---|---|---|
| SEQ ID NO. | Gene | Affy Probeset ID | Sequence |
| 643 | LIPH | 2708862 | CAAGGCTTTTTTCAGTAGCGTCCTATGGATGTCACATTGTACAT CAAACAACCTTGTGATTATAAAACGATCCTGGGAAGGAGCCCC TAACTAGGGCAAGTCAGAAATAGCCAGGCTCGCAGCAGCGCA GCGCTGTGTCTGCTGTGTCCTGGGGCCTCCCTTGTTCCGACC TGTCAATTCTGCTGCCTGTCACGCGGGTGGTTCTGCCCATCG CGGCTGCGGGTCAAGCATCTTCAAGGGAAGGACGGACTGGA GGCCTCACCGTGGACTCAACTCTGCATTC |
| 644 | LIPH | 2708863 | GCCTCAGCTGTGTCGGTATGATCTTGTCCTGATGGAAAACGTT GAAACAGTCTTCCAACCTATTCTTTGCCCAGAGTTGCA |
| 645 | LIPH | 2708864 | CTCTAATAGGCCCAAGGTACAAGCTCAGGATTCTCCGAATGAA GTTAAGGTCCCTTGCCCATCC |
| 646 | LIPH | 2708865 | TCAGAAATATCACCAAGTGAGTCTACTTGCAAGATTTAATCAAG ATCTGGATAAAGTG |
| 647 | LIPH | 2708866 | CTTTGTGGATATTATAACATGGAACAAGAATGTAAGAAGAGGG GACATTACCATCAAATTGAGAGA |
| 648 | LIPH | 2708867 | TATTATGCTGATAATTGGAAAGACCATCTAAGGGGGAAAGATC CTCCAATGACGAAGGCATTCTTTGAC |
| 649 | LIPH | 2708868 | ACCACCAGAGGTCTGTATACCTGTACCTGTCTTCCCTGAGAGA GAGCTGCACCATCACTGCGTATCCCTGTGACTCCTACCAGGAT TATAGGAATGGCAAGTGTGTCAGCTGCGGCACGTCACAAAAA |
| 650 | LIPH | 2708869 | CTGGGCTACAAGGAGCCATTAGGAAACATAGACTTCTACCCAA ATGGAGGATTGGATCAACCTGGCTGCCC |
| 651 | LIPH | 2708870 | CTGCACCCGACCTATATATACATTTCTAGGTCCTCATTTTCTAG AAGTAGTTCCAATCTTTTTACCATCCTAGCTCTCAAATATTTAAA GATTTTATCTACTAAGTAAACATTCATTTTTTCCTGTATCCTATT TATTAGTTATACAAATGCAAATAGAGGCTCAGAAGCACCAGGC AATTAAAGGGTTGCAGC |
| 652 | LIPH | 2708871 | CCTGCAGGCCCTTTATTCAACGGGAAACCTCACCAAGACAGAT TAGATCCCAGTGATGCGCAGTTTGTTGATGTCATCCATTCCGA CACTGATG |
| 653 | LIPH | 2708872 | TGATGACATTTACATGATCGGAGTAAGTCTAGGAGCCCACATA TCTGGGTTTGTTGGAGAGATGTACGATGGAT |
| 654 | LIPH | 2708873 | TTACAATGATGGACCTCTTGAAATTCCA |
| 655 | LIPH | 2708874 | AGGCTGATGCTCTACACAAGGAAAAACCTGACCTGCGCACAA ACCATCAACTCCTCAGCTTTTGGGAACTTGAATGTGACCAAGA AAACCACCTTCATTGTCCATGGATTCAGGCCAACAGGCTCCCC TCCTGTTTGGATGGATGACTTAGTAAAGGGTTTGCTCTCTGTT GAAGACATGAACGTAGTTGTTGTTGATTGGAATCGAGGAGCTA CAACTTTAATATATACCCATGCCTCTAGTAAGACCAGA |
| 656 | LIPH | 2708875 | TATTCATCAGTTTGTTGTGCTTGTCAAGA |
| 657 | LIPH | 2708876 | CTCACTGTGAGCAAAATCCCACAGTGGAAACTCTTAAGCCTCT GCGAAGTAAATCATTCTTGTGAATGTGACACACGATCTC |
| 658 | PART1 | 2811146 | TGCAATGTCAGCTATTTAGGACAGAAACATCCAAGGCCGTGTC AGAACTCAATTACGACTACATATGCATTA |
| 659 | PART1 | 2811147 | ACGCCAACTATAGGACTCGTGCTTCTCGTACGCTGGGCTATAA TCTATGAAACTGAGCTCCAG |
| 660 | PART1 | 2811148 | CCTCATAACAAGTCTAACTGGCTCTGGAAA |
| 661 | PART1 | 2811149 | ACAGATGAGATATTCTACACATTAATCTACTTATCTGGAATCAC TTT |
| 662 | PART1 | 2811150 | CACAGCTTCCTTGTCGGAGGGGAAAAGGACAGGTGATCTGGG GAAAACGCAGCTACACCTGGAGCAAGGTCTCTTCCCGGCTTG GCAATCTCAGCTGTGCCGGCGCTAC |

TABLE 7-continued

Target Sequences

| SEQ ID NO. | Gene | Affy Probeset ID | Sequence |
|---|---|---|---|
| 663 | PART1 | 2811151 | CTGCTGCCTTCGGTGACTATATGAGAATGGAAACTTCTAAGGA AGCCAGGTTGTTAGAATTGTTACCCCCTTTACTCAGAGATAAC ATAGATTATCCAGGCTGA |
| 664 | PART1 | 2811152 | AATTTTCAACACAGACTCCCTGCTTCTCA |
| 665 | PART1 | 2811153 | TGTTCAAATCTCCATTTGTTGACAGACAAAGCCAACAATACTCT AAACTGAGGCCTGCAAGTCATTTCATT |
| 666 | PART1 | 2811154 | TTCACCTCCTACAACTCCGAAGAAAACCCTTACTGTCCAAGAC CGTCACCAGCAACCATCCGCAGTCATTCAAGTGGAAGCTTTCA CAGCTTTTGTACATTCTCTGTGTCAATATACAACTGAGTTACAG ACTGTCCC |
| 667 | PART1 | 2811155 | CATCAGGACTTGTATTAGCAGGTTCTGGCTAGAGAGACTATCT CCTGTCATCACGATCAATTAATGTTTTCTGGTGATCACATCAGG CCCTATCTAAGAAGCTCATGGTATACAAGGGTCACCCAAATAG CTGAGTGCAGTCCTTGCTCATATTTCCTTCATCTTAACCCCGC AAACAAGAATTAAGATGATCCCAATAAAAGAAAAATTGCTCAG GAAACTGAACCTTTTTCTGAACCAAGCACTGTCAGCAAATCTC AGGTATTAGAGCAACTATGGTTGATTGAAAAGTGTCTCAAAAT CTGGGCCAAGAATGATTGCTAGGTCCATAAGCTAATTTGTCTG GCCTTGCCATTTACGTAAGCC |
| 668 | PART1 | 2811156 | TGGGATGGCCGTTCAGGAAATCTTCTGTTTGCTTTGCACGCTC CTGAGTATAGGACAAAGCGCTGTTGTTTAAGAACATAAATAAC AAAAGCTTTGTTCTTCCAAACCGAGAGGGAAACTGTAGATCTA TCCAAAATGACTTGGTCTTAAACTGCCTAAGGATGACAAGAAT GAAATATTATTTTAGGCTGCCCATCAGCATCCGTCTCTCAATCT CCTGTCTTGGCTTCAGAAAACAATGACTCAATATGGTCTTTTTC TGACACATTGCAGCCTTAGGA |
| 669 | PART1 | 2811157 | TGCTCTTCTTGGTCCCACTCAAATGGGAAGTTCTGCTCGAGGC CAGAAATAGAAAACAGGAAGTCAACAGAACTGATTTTCCTAAC TGCCCAAATGCAAATCACCACACTCCGTTATGGATGAGAATT |
| 670 | PART1 | 2811158 | TTGCCCTCACATACACATAAGTTTGTCATTGTTCTTCAGTTCTT TGGGTAATCTCTTCCTAGAAACTGCATCTAACAAATAGACCAC ATCCCCAAATTCCATCATGTCCAAAAAGAAGCACGGTATTTCC ATCAACACCCCAGCTGCCATCACCAAGCCAACTCGCCTGACTT CCATTCACTTACTAGCAAACATTTACCAAGTATCTGCCATGTTC ATTTTGTCAATGAGAATGACATGGGACTTGTTCCTCTAGGAGA TCACAGTCTA |
| 671 | PART1 | 2811159 | CCTGCTGCCCAATAACCTGATGTTGTCACTCTCATATTTAAAAC CCATAAGTGCTGCCGGGAGCGGTGGCTCACGCCTGTAATCCC AGCACTTTGGGAGGCCGAGGCGGGCGGATCACAAGGTCAAG AGATCGAGACCATCCTGGCCAACGTGGTGAAGCCCAGCCTCT ACTAAAAATACAAAAATTAGCTGGGCGGGGTGGCACACACCT GTAGTCCCAGCTACTTGGCAGGCTGAGGCAGGAGAATTGCTT GAACCCGGAGGCAGAGGTTGCAGTGAGCCGAGATTGCACTAC TGCACTCCAGACTGGTGACGGAGCGAGACGCTGTCAAAAAAA CAAAACAAAACAAAAAACATATCAATGCTGATGAACCAAGTGC AAAGCCCTGAGCTTGGCCAGGCAACATAGCCTGGAAACCTGA CTTTTAATCCTTACTTTGCTCTATTCCCCAACATACACACACT TCATACACCACACCTAAAAGAGACTTCCCACAGTTTTCCAAAA ATGACTCACATTTATATTTCCTGTTTTTCCCTTTGCCCACCCTG CCCTCTCTCCCTCTGCCTTCATTTTTTAATTAACCTCTGGAAC TCAGGTGCTCCTGCTCCAAGGTTTAGGTCAAAAGTTACCTCCT CCATGAAGCTTTCTCTCATTCTCCCACAATGTGTGAAAGCCCC ATTCTCAGATTTGCTTAGTTGTGCATTTGTATATTCTACCTTGC ACTACAGTCATTTGTATATTTATCTTATGGTTTCTGTGCCTTAG GAAAGGTACACTGTCTTAATCATCTTTGTTCAATACAGTGCCTA GCAGAGTGCCTCAAGTATAATATGTGCTCAATAAATAATAGAT GCATTTTTCCATGCATATTTTCTACTATATCGAAGTGGAAAATA TATCCATGTGATATAGTGAAAAATATCTCATGAAGAGAGATACA GTGAGGAAAATATCTCATGAAGACCAAAAAGCAGAAATCCAAG TTTTTTCTTTTCATTACTATCATCAGTGATTATTAATTTTATGTGT CAACTTGGTTGGGCTTAGGGATGCTCAGATAGCTGGTAAAATA TTATTTCTGGATGTGTCTCTCAGGGTGTTTCTGGGGGAAATTA GCATTTGAATCAGTAGACTAAATAAAGAAAATCTGCCCTCACA AATGTGAGCCAGCATCATCCAATTTATTGACAGTTTAGATACAA CAATAAGGCAGAAGAAGGTGAACTCTCTTTCCTTGAGCTGGGA CATCCATCTTCTCCTGCTCTGACATTGGAGTTTCTAGTTCTTGG |

TABLE 7-continued

| Target Sequences | | | |
|---|---|---|---|
| SEQ ID NO. | Gene | Affy Probeset ID | Sequence |
| | | | GACTTCAGATTCTCCCCTGAAGTTTCTCAGGCCTTTTGGCATC AGACTGGAAGTTATGCCATTGGCTCCCCTGGTTCTCAGACCTT TGGACTCAGACTGAATTATACCACTGGCTTTCCTGGTTCTCCA GCTTCAAGATGACATATTGTGAGACTTTTCAACCTCCATAATTG CATGAGCCAATTTCCACAATATATCTCCTCTTATGTATCTATAT ATTTCCTATTGGTTTTGTTTCTCTACAGAATCCTAATAGATCATC TAATTGTTTATCTAACAAGTATTTTCCTCCCTAGACAATATGTTG GGCACTAGGGACACAAAAATAAAAACACAGACATCTGCACTCA ATAAACTTACATTCAATATCAGAGAGATTGGCACAGAATACAAA TAAAATGAGATACATGCAAAATAATATGAATTGCAAAATTACGG CAATTCACCACCAACTAGGTGTGTGACCGTGGGAAAATCACAC TGTGAGCTAAATATTAGCAAGTTTAAAATGCAAAATCAGAGGC AGTCTATGAATTGGACTTTGCTAATGGCCTCCTTTGCTGATGG ATGGCACATTGGTGTTAGAAAGTGCTTATTTTTGCAAAGGTCC ATTATTGATGCTTTAATTCTAAGGAAATTATGTAGGCAGAAACT AAAGAAAGGTTAAAAAAACAGCAGCTAAAATTGATACTTAGAC AATAAAAAACTAATTATAAGTGATTTATCAGCACCACTAGATAA CTACATTGGTGAAATTTAAGGCCATGAAATGCAGGACAAGCCT CGTAGGAAGCAAGGTCCCAGTGGATGAGATGCTGTCCTCTGG GCTCCTAACCTTCCACCACTAGTATTCACCATATCTGATTGGAA ATGTGTGCATGTGAGTCGGCCTCCCCTCTATGATGTGAGTAG GGACCTATTTTTGCTCATCTCTGTATCCTCTACACACGATGCTT GG |
| 672 | PART1 | 2811160 | GGAGCTAAAAGAAGAAATAGTCAAAATTTTCTAAATGAG |
| 673 | PART1 | 2811161 | CTGCCTTGTACTTCATGCAGGTTGAACAGAAATGTTTTCTGAG CATGTATTGTTACAGCCCTCTGAGATGGTATAAAAGAATGAAA GAAGACACGACCTGCCTTCCAGGAGTTTCACA |
| 674 | PART1 | 2811162 | AGGGAAAAGCATTTCTAATGGAGGAGATGGCTGTGGAGAGGA GAGG |
| 675 | PART1 | 2811163 | ACCTTCCACCCTTTCACTATGAAGGACCCTCACCA |
| 676 | PART1 | 2811164 | AGATTGCATATGTATTGGGAAGCTCCTGGG |
| 677 | PART1 | 2811165 | TCCACTTTCCTGTGAGGTCAAATGCGGTAAAGGGATGCTCCAA CCCTACCCTCCATGTACCTGCCTTTCCTGTGATTCCGAAGAAG GGGTGG |
| 678 | PART1 | 2811166 | CTATTAATTAATCCAGAGAAGTGTGTTGCTATAAAATATTCTGT GAAGCATTTTCACTTATT |
| 679 | PART1 | 2811167 | TTTGAAGAACTAGAGAAAATCATCAT |
| 680 | PART1 | 2811168 | GGGATTTGCTGGCATTGATTTCCCAGGATGGCAAAGTGCTAAG AACTAAACCTTTAAAGCTAACAAAATGTACTGATGTCTTTGCAA AGTATCCAAGACCAACAAGAAAGTAATTTCCCACCTCACCCTA CCACCACCCAGAAAAGGAGCACAGAGATGGGGAAGAGAGTG GCTGCATCTGGCATCCAGCCAGAGGAGTCCGTGCAGGGATTC T |
| 681 | PART1 | 2811169 | GATGATGCAGCTCCCTCAAGTATCACATGAAGATAGTGG |
| 682 | PART1 | 2811170 | CAGCAATGTATGAGGTCCAAGGACCAGGACCAAAGGGAAAAA CAGCCATCTCACCAGACACCTGCCTACGACCAGATGCGTCAT CTCCAATATTAGCTAACTCCCTGGAACCTGGACTCA |
| 683 | PART1 | 2811171 | GGCCTCTCAATCAATTACAAAACTGAGAATTCTGACAGTTTTGT GTATTTCCTCTTTGCATGTGATGTATATGTGTGTATTTGTATATA TTAACCATTTTCCTTTTTCTCTCTTCATTATTTTATGAAAGTTGT TGAATATAAACTCTACAATTTAGCCTTTAGGTAAGAGAATATTC AGTGGGACTTTGATTTGAGGAGTATTTAAGACAGCCAGATGAG ACTACGATAACTGTTGGAACTGTGTGTCTCCTCATTTGGGGAA AGGGGTGAGAACTCTGCATTTCTCTGAAGAACAGAGTTGACTT TGTGTTATACAGAGTTCAAATATATATATAAAATGGTGCATGTG GAAGCTAAGAAGCCAAAGGAGTTCACCAAGACAGTTATCAATA TATTGCCTCTCCGCTCCAAATCCACCCTTCTTTGCCCTGTTCC ACGATACTAATCTGGCTCCTCGGTCAGCCAGTGCAATGTCATC TGTTGCTGGTAGAGTGTA |
| 684 | PTTG1 | 2838202 | TTAAACCAGGAGTGCGCCGCGTCCGTTCACCGCGGCCTCAGA TGAATGCGGCTGTTAAGACCTGC |

TABLE 7-continued

| Target Sequences | | | |
|---|---|---|---|
| SEQ ID NO. | Gene | Affy Probeset ID | Sequence |
| 685 | PTTG1 | 2838203 | GGCTTAGATGGCTCCGAGCCCGTTTGAGCGTGGTCTCGGACT GCTAACTGGACCAACGGCAACTGTCTGATGAGTGCCAGCCCC AAACCGCGCGCTGCTCGGGACCTTAGAGCCTCTG |
| 686 | PTTG1 | 2838204 | TGTTCCGCTGTTTAGCTCTTGTTTTTTGTGTGGACACTCCTAGG ATAGAAAGTTTGGTATGTTGCTATACCTTTGCTTC |
| 687 | PTTG1 | 2838205 | GCACCCGTGTGGTTGCTAAGGATGGGC |
| 688 | PTTG1 | 2838206 | TATACAAGGCTGCAGTCGGATACACTGGTATTGTGGACGTGG CCTGGAGCTGGACGAGACATTTAGTGTACTTTTTGGGCAATTG GAGTCGTTTGTTATTGGTCCTTTTTCATTTTTAATATCTTAATGA GATGATTTAAGGAAGTTACTGAATCTCTGCTATTAGGCCTATC |
| 689 | PTTG1 | 2838207 | GATCTCAAGTTTCAACACCACGTTTTGGCAAAACGTTCGATGC CCCACCAGCC |
| 690 | PTTG1 | 2838208 | GTAAGTGTTGGCTATAAAGACACTGTTTAAACACTTAAGCACTT TTGACTCTTAAAATGACTATTGGCATCATCCTACGTAGCTTTCT TC |
| 691 | PTTG1 | 2838209 | CTGCCTCAGATGATGCCTATCCAGAAATAGAAAAATTCTTTCC CTTCAATCCTCTAG |
| 692 | PTTG1 | 2838210 | ATGAGACTGTCTGAATCTGGGTTGCTTTGGACAAGTGTACTTG TTGATGGAATTATTTGCAAGGTATCATCTTAGGTCAGGAGGGG AATAGGAACAAAGATGTAGAAGACATTGTTCCTGTCTGTAAAA GCTTATCACCTAGAGGAGGTAAGATGTATTCATGAACATTGAA TAAGTCCCATTGTGGACAGTCTTTCTCACAAGGCTT |
| 693 | PTTG1 | 2838211 | CTGAAGAGCACCAGATTGCGCACCTCCCCTTGAGTGGAGTGC CTCTCATGATCCTTGACGAGGAGAGAGA |
| 694 | PTTG1 | 2838212 | CTGTTGCAGTCTCCTTCAAGCATTCTGTCGACCCTGGATGTTG AATTGCCACCTGTTTGCTGTGACATAGATAT |
| 695 | PTTG1 | 2838213 | TCTTAGTGCTTCAGAGTTTGTGTGTATTTGT |
| 696 | NADK2 | 2853389 | TTATTCTGTGCCCTGTTGACTTCATTCACTGTTAACATTTGACA TAGAATGATTAGTTATTAAATCAGGGTGAAGTGCTTACCTGGT CAGTGTAGGCTCTTCAGATAATTTTGACTTAATATTTTTGATAC TCCTTGTGCATTTACATTC |
| 697 | NADK2 | 2853390 | TCTTAAAGTATCTGCGTAGACATTCATAGCAAAGAATTTATGAC ATATCAGATAGAAATACATTAAAATGTAGTGTTTTCCCAGAGAT TGATCTGGCTTTTTTTTTTTGATATACATAAGATACCACTTTATA AAGAAGCTCCATACTATAGAACCTCCCCTAACAGGCTTAAAAT ACCTTCTTTTTTTTTTTTTTTTTTTTTGAGAACGGAGTCTTGCTT TGTCACCCAGGCTGGACTGCAGTGGCATGATCTCGGCTCTGC AACCTCCATCTCCCAGGTTCAAGCGATTCTCCTGCCTCAGCCT CCCAAGTAGCTGGGATTACAGGCAGGCACCACTATGCCTGGC TAATTTTTTGTATTTTTAGTAGATATGGGGATTCACCATGTTGG TCAGGCTGGTCTCGAACTCCTGACCTTGTGATCTGCCTGCCTC GGCCTCCCAGTATTGGGATTACAGGCATGAGCCACCATGCCC GGCCTTAAAATGCCTTCTTAAAGGAAAAATGCCAACTCCATCC TTAATCTCAAGGAAATCTGATTGTCCAAATAGATCTGTTAATAT GTAACATATTAATAGGTAACTTGCTGTGTAAAATTATAAGCCAT ATTTTAAAAGGTTTTAAAAATACTTATTGTGCTCCATTTGTGATA TAATTTCTAACATTTCTGCTCTGTGATGGGGGTTTATTTGTAAG AATAAGAGGCAAAGGAATGTTAGCATAGCAAAAATGTGTTTGA ATGAGTTAACCTTTTAATCGCAACCCTATGTGA |
| 698 | NADK2 | 2853391 | TGCCAAAAGATCCTGTCGTTGCATAATCAAACAGTTGGTATTCT CGTGCCGTTGTTCAAAGTCATGTGTTTCTTTCATTTGGTGCTGA AAATTTCTGTTCAATCATTGACAAATATTTATTGAACACCCACT CTGTGCCATGTAAAACTATGTCAGGTGCTGGATATGTTGATGA ATGAAACAGACTCTATCCTTATACAATTTGAGTCTTGTGGGCTC AGAAGTAAATTCTGTGAAAGCTGGACGGATAGTCGAATTGAGT GCTCTTA |
| 699 | NADK2 | 2853392 | CCTCCTAATTGTGGGATTGTCAGAACTGAACACATATCATTTGA TTAGTGCATATTTTTTATAGTACCTGAAAACCAAGATTTTGAAA AAATTTTCAAGACAGAGAATTTTGATAAATCCTGACATTGACCT |

TABLE 7-continued

Target Sequences

| SEQ ID NO. | Gene | Affy Probeset ID | Sequence |
|---|---|---|---|
| | | | AATTGACATAGGTAAATATGTTTGTATATGTGCTAATAATTTTCT AATTTCGGAACACGATGATGTTATGACTATTGATT |
| 700 | NADK2 | 2853393 | CTACCAGTCGTAAAGTGACATTTTTTGGTTATTGTTGAGACTGC TTGCCCGTGGGCTCAGAAGTGAGATTTGCATTATTCTTCTGTT GGATTCTGATAGAAAAAAAGACATTCACTGTATAAGAAAATGG ATGGACTGAACCAATTAGAATTGATACCAGTGAAATTTTTATAT TGCTTACAATTGGTAACCAAGAGTGCTGATA |
| 701 | NADK2 | 2853394 | TGTTCGTTCTCGTTGTTGGGATGCCTGTATGGTTGTGGATGGA GGAACTTCTTTTGAGTTTAATGATGGTGCAATTGCTTCGATGAT GATCAATAAAGAAGATGAGCTTCGAACTGTGCTTCTTG |
| 702 | NADK2 | 2853395 | TCACTGCTCTACAGTCCGGAAGAACCAAAAATACTTTTCAGTA TTCGAGAACCAATAGCAAATAGAGTTTTCTCAAGCAGTCGTCA GCGTTGTTTCTCCTCAAA |
| 703 | NADK2 | 2853396 | GAGAATTAGTGCTGTTAGAGAAAGAATACTTATGAAGAAATCT G |
| 704 | NADK2 | 2853397 | GAAATTTGAGTCTTCCATTGAACAGAGAATTGGTAGAGAAA |
| 705 | NADK2 | 2853398 | CATTCAATATTAACAGGGTTGCAACT |
| 706 | NADK2 | 2853399 | ATGAGATTTCAGTTGATGATGGTCCATGGGAAAAACAGAAGAG TTCAGGGCTCAATTTGTGTACTGGAACAGGATCAAAGGCCT |
| 707 | NADK2 | 2853400 | AATGTCTTATTCTTGGGCTGTAGCAGTGGACAATTTAAGAAGA AGTATACCCACTCTAAAGG |
| 708 | NADK2 | 2853401 | GCTGAGAGCTAGCTTTGCTTTATAATTTTGTACTTACTAAAAAA TTAAATAACTTATAAATGGAGGAAAACTTGGATCAGTTGATAGA TTTTGGGGGAGTTAGTGAAATTTCTTGAGGGGATTTTCAATCG AATGCTTTTATTTTCTGTGGCAGTAATGATCTGGTTGGTTTATC TCATAAATAACTGATGCTGCTGCTTTTTGTGTTCTTTGATGTCT CACCTTATGTTTTTACTAAGTAAGGACAGCAATGGATTGGCTTC TGATGC |
| 709 | NADK2 | 2853402 | CCCAACTTCTGCCAGTGAGAGCACTAAATGAAGTCTTCATTGG GGAGAGTCTGTCATCCAG |
| 710 | NADK2 | 2853403 | CATTTGCTGCTTAAATCCAAAATAGTTCTCTT |
| 711 | NADK2 | 2853404 | TGGAACTGGAGAACACACTTTTTTAGCTCATCACATGGCTTTT GGCAGAAGGCTTCAGTTCCTCACCATGTTGGTCTCTCCAAAGG GTTGTTCATGTTATCTCTTCCTC |
| 712 | NADK2 | 2853405 | TGGAGGCAGAGAATCAGGTTATACCTTGAAGGGACTGGCATA AACCCTGTACCTGTGGACCTTCACGAGCAGCAGCTAAGCTTG AATCAGCACAATAGAGC |
| 713 | NADK2 | 2853406 | GCTATATCTAGCTCAGTATCTTGGACTTTATGGGTTCTTGATAG AGTTTGACTTAATTTAAGTTACTTGGGAGATTTTGTACAAGCAC ATTAGGTGTTTCCGTTATAATTGAAAAGAGAATAAATATTCAAA TCTGTCATTGATAAGGAAGCTATAGG |
| 714 | NADK2 | 2853407 | AGGGTCATTTATGCCTGCCCGTTCGATATACACATTCCTTTCC AGAAGCCTTACAGAAGTTCTATCGTGGTGAGTTCA |
| 715 | NADK2 | 2853408 | GCTGCTGGCAGCGAGTAAAGTCTTGGACAGACTTAAACCAGT TATAGGGGTAAACACTGATCCAGA |
| 716 | NADK2 | 2853409 | GGAATTGAGGTTCGTCTAGTAAAGAGGAGAGAATATGATGAAG AGACTGTTCGATGGGCAGATGCTGTCATAGCTGCAGGAG |
| 717 | NADK2 | 2853410 | TACAGTGGACTTCTTGAACGACATCATATTCACACCAAAAATG |
| 718 | NADK2 | 2853411 | AAGCAAATCCAAGTGGAACAAAGGTCATCTAACCGCCTCTACA AGTATTAGTTTATCTTTGGTCATCAAGTAGCCATATGCAGTGTG TTAAAAAGTCATCAAGGCTGAGGCA |

TABLE 7-continued

Target Sequences

| SEQ ID NO. | Gene | Affy Probeset ID | Sequence |
|---|---|---|---|
| 719 | NADK2 | 2853412 | ATTAACACTAATGATTTTGAGCCATAAGATTATATTTGA |
| 720 | NADK2 | 2853413 | GAGGCTTTTGGCTAGGCATTAAATTTTGGCACAGGCTGTCTAA TCTATTATAGTATATCTTGGTAAGTTAACATCTATTAATTAATTT TCACAATAGCCAAATGCTTCCTCAGCTTCTCTTTTGTGAGAACA TAACGAAAATTACAAAGCAAGGACAAAACTATTTAAAAACTCTT AACCCAGTATTCGTAGGCAA |
| 721 | NADK2 | 2853414 | ATGTATCTTATTTTCCTGGGGCTTGCCGAGAGCCAG |
| 722 | NADK2 | 2853415 | CATCTCAAGCCAAAGTTCCCTAACAGTCAACGC |
| 723 | NADK2 | 2853416 | CCCATTGATTGACCAGTGACTTATTTTGTGATATCAGATTTCTG GTCAAACATTTTACCTCTACTGTCTCATGACCTTTCAAAGGCCA GTAAAACTATTATTACAATTTACTTGCATCATTAAGAGATGTAG CTGTTGGCAAATGTGCAATTGCTATTAACAGGGTCCTTGACAC AAATTAGAACTCTAGATGAAACAAAACTGACTTGGAAAGGATTT TGACACCAGAAACATACCTCATTGGTCAAAAAAAGGTTTTATTT AAAGCTCTTTTTCACCTGTCACCAGGGATGGGGAACTGAATAA GGAAAAAAAATTTTAATGTAGAACAAATAAGAAGTCAGCAGTTT CTGCCCTCCTCTCCATCATTCCAGGTCTCACAACTCGGCAACC CTTTTACTGG |
| 724 | NADK2 | 2853417 | GAAAAGGAGAGTGCCCGGTGCTACCATGA |
| 725 | NADK2 | 2853418 | GTACGTTATTAAGGAGAAATGTCAGGACAAGGGGCTGGTATA CTGGGTAGTGTGTGAA |
| 726 | NADK2 | 2853419 | GCCTTTTCCTTGCTGGAACGTGGTCGTTGGACACTACGAGCTT GTTTTAAAAGCACAGGTCTTTGGTGCTAAGAAGGAAA |
| 727 | NADK2 | 2853420 | ACTGCGAGGCCTAGGGCACTCCGGAAAGTCCTTCAGC |
| 728 | NADK2 | 2853421 | CGAGCAGCAGCGGTACCGTTACGCGGAGCTCTCG |
| 729 | NADK2 | 2853422 | GGCCCACGATGACTTGCTACCGAGGCTTCTTGCTGGGCAGCT GTTGTCGCGTGG |
| 730 | NADK2 | 2853423 | CCGGCGGTAGGGAGCTGAGGCAAGGGGCCCGAGCCCAAG |
| 731 | NADK2 | 2853424 | CCACTAGCTGGGGCCTCCATTTCTTCCCCGCCCACCTTTCTCC CGCGTGGGGTCTCCCGTTTCCCAATCGCCACGCTTTCCCCGC CTTCGTCAACGCCTGGGTACGTCCCCCTAGCCGCGTGGGCCA CGCACGTCCTGGCACTTAACCTCTGCCCGTCCGGCGCGAAG |
| 732 | RPL31P57 | 2858553 | AAAGAGCTCCGGAAACTTGCCCTGAAGGAGATGGGAACTCCA GATGCACACTTTGATACCAGGCTCAACAAAGCTGTCTGGGCC AAAGGAATAAGCAACGTCTCATACTGTATCCATGTTCGGTTGT CCAG |
| 733 | GMNN | 2898603 | TCAGTTGGTCACGTGGTTGTTCGGAGCGGGCGAGCGGAGTTA GCAGGGCTTTACTGCAGAGCGCGCCGGGCACTCCAGCGACC GTGGGGATCAG |
| 734 | GMNN | 2898604 | CTGTGGCCTTTTGCGAGGTGCTGCAGCCATAGCTACGTGCGT TCGCTACGAGGATTGAGCGTCTCCACCCA |
| 735 | GMNN | 2898605 | AGGCGCACAGCCTCTAGACGACTCGCTTTCCCTCCGGCCAAC CTCTGAAGCCGCGTCCTACTTTGACAGCTGCAGGGCCGC |
| 736 | GMNN | 2898606 | GTTGGGAGGTGAGTCGAGGGACTGCCCCATTGGCTG |
| 737 | GMNN | 2898607 | ACTGCCCGCCCCCTAGCCTGGCGCTGGGCCTCCGGGACAAG TTGGCTGGGTCCGGGCTTGGGGACTGCA |
| 738 | GMNN | 2898608 | TTGCCTCGACCTTCCAGCACTTTGGTGATCATGCAGGTGATCC GCCTGCCTCGACCTCCCAAAGTGCTGGGATTACAGATGTGAG CCACCACGCCCGGCCTTTCCTAAGCTTTTTTGTTTGCACATGT GTGTGCACGCGCCAGGACACAAGGTAAAATGTATTAATGTTAG AAGCCACTGCACTGAGTAAAGGCATGGCCACAAAAATTAGGG ACATCTATCGACGAGGCACAGGCGCAGACACGGCAGGGGCC AATGGGTAGTGGGCAGTGGGCAGTGGGCAGTGGAGCAGCAG TTCAGATGCTGAGTTTGGCCCAGTGGTCTAGTCAACCGCATTA CATA |

TABLE 7-continued

Target Sequences

| SEQ ID NO. | Gene | Affy Probeset ID | Sequence |
|---|---|---|---|
| 739 | GMNN | 2898609 | CAGGAAAGTTAAGATGCTGCTCTTTAGGATGGACCTGGGCATA CCCTAGTATCTGTTTATTTTGCTTTTTCTGGTGACTATTTAATCC AGGACAATATGTTTAGAAATTTTAAACCAGTTTTAGAAATTGGT TTAAAATACATTAATTTCATTTTTTCAGCTATAATTATTATGTGT GTATATATGTAAAATATAGATATCAAGAGTCATTAACTTTAGTC ACCTTAGTC |
| 740 | GMNN | 2898610 | TCTTCTGTGCTTCACCATCTACATA |
| 741 | GMNN | 2898611 | ATGAAGCAGAAACAAGAAGAAATCAAAGAGA |
| 742 | GMNN | 2898612 | TGTAGAAAGCATGGGGCTAAAAGTATTTTGACATAATTTATCCA AATTTAGCCTGGCTATAATTTCTGTAAGCCTTGAGTTAGTCAGA GGATGAGTAACAATAGAGAACATTTTTAAAAAACTAATTACGGT TGAATATTAAGTCTGACCCAA |
| 743 | GMNN | 2898613 | GCACTGACATTTTAGCCACCTTCTAATGAATGGGCTTGAAGCA GAACTGCTTCTACTATCAGGTAATGGTTGAGGGGGGATGTCTA TTACACATGTACTTTGTTTTGTGTAAAGTATGTTCTGGAAAGTT ACATTCTTTTGGTGAGTACATGTAAGTATTTGAGGGATATTCAT GATTTAAGGAGGCCTGAAATGAATCTTTTTGATTAGGGAAAGA AATATTTTGCAGTGTAAATGATTAACCATTTCTTCCAGTTTACCT GTTTGGTGAGTTCATACCATAAATGTTACGATGTTTGGTTTTAT AAAAGAGTACCTGTAAGTTTTTAGTTTCTGTGTGGAAGATTTTT TCAGAGAGAATACAGATAGCCTTCTTGTATTAGAATTTTGTCAT ATGTGGTTTGAAACTGTTCATTGGAGCTGAGGAATTTTGTTAC GTTTGTTTTAACTAGATATGATTAACAAAATGACCATAGCAAGA GCATGCATTGAAATGAGAGAAGTTACGTGTGTTTGTGTCTAGT TTGGGTAATATGATTCATTCTTAAGAATTCTTCAAACTTTATTAT AATTTTTGGAAATAACAAGTTTGTCAGTTGATTAAACCAGTGTC TTGTTCATAGGCGACCTTACGCAATTATATAGCA |
| 744 | GMNN | 2898614 | AATAGTTCTGTCCCAAGAAGAACTCTGAAG |
| 745 | GMNN | 2898615 | CTGCATCTGGATCTCTTGTTGGAAGAGAAA |
| 746 | GMNN | 2898616 | TTCAGCTAAGCTCTTGACCCCAGTCTAATCCAAAATAATTGTTG CAAATAAAATTCCTAAAATGTTACTATATGTTTTGGTAGAATTTT TAATTGTATAACTTTTTTAAAGATCCAGAGATGTGAAAAAGTTA GATATGCGTACTCTTTTT |
| 747 | GMNN | 2898617 | TGACCACTTAACATCTACAACTTCCAGCCCTGGGGTTATTGTC CCAGAATCTAGTGAAAATAAAAATCTTGGAGGAGTCACCCAGG AGTCATTTGATCTTA |
| 748 | GMNN | 2898618 | TTATGAATTCTGCCAATTACTGTAA |
| 749 | GMNN | 2898619 | TGCTGAAGGTCACAGTAACATTTGGACTCATTTTGAATTGCCTT GAAGACAGGAAGAAGAGAAATAGATGGTAGGATTTTTATTAGG CAAAATTAGGAAAGGTTGACTGGATAGAAATAAAGCAGCTCTT TAAAAATATTGTAGATTGAAGAGCAGGATTTGTGACACTCATAT CTGATTAGG |
| 750 | GMNN | 2898620 | GTGGAACACATTATCCTTGTAACCCTCTGCGATACATG |
| 751 | GMNN | 2898621 | TAAAATAACTGCGAAGAAATCCCAAACTTTATTACATTTGTTGT TTGAACTTTATTATATTTGTTGACAGTGGTATTA |
| 752 | GMNN | 2898622 | AGAAAAACGGAGAAAGGCGCTGTATGAAGCACTTAAGGA |
| 753 | GMNN | 2898623 | GAATCCCGTTGTGTTGAGAGTCAATTCTATGCTGCATGTCCTC CATGTTATATACTTGGAG |
| 754 | GMNN | 2898624 | AAAGGACAATGAAATTGCCCGCCTGAAAAAGGAGAAT |
| 755 | GMNN | 2898625 | TGAATGGTGAACCTCTGGATAATTTTGAATCACTGGATAATCA GGAATTTGATTCTGAAGAAGAAACTGTTGAGGATTCTCTAGTG GAAGACTCAGAAATTGGCACGTGTGCTGAAGGAACTGTATCTT CCTCTACGGATGCAAAGCCATGTA |
| 756 | GMNN | 2898626 | TGCCGAAGTTTACCTCCACTAGTTCTTTGTAGCAGAGTACATA ACTACATAATGCCAACTCTGGAATCAAATTTCCTTGTTTGAATC CTGGGACCCTATTGCATTAAAGTA |

TABLE 7-continued

Target Sequences

| SEQ ID NO. | Gene | Affy Probeset ID | Sequence |
|---|---|---|---|
| 757 | GMNN | 2898627 | GTGAATAGGATTTTCTCAGTTGTCAGCCATGACTTATGTTTATT ACTAAA |
| 758 | GMNN | 2898628 | TTGTGTATAACTTAGAATAATGAAATATAAGGAGTATGTGTAGA AA |
| 759 | SLC22A3 | 2934522 | GGCTGCGGCCGGCACAGCGCCAGGGCGAGTGAGGCGGGTG GCGCGGGGGAGGCGGCGGAGTAAAGAGAGGCCGCCGGCTG GGTCCGCGGGTCACTCCGAGGCGCGG |
| 760 | SLC22A3 | 2934523 | CTCCTTCGACGAGGCGCTGCAGCGGGTGGGCGAGTTCGGGC GCTTCCAGAGGCGCGTGTTTTTGCTGCTGTGCCTGACGGGCG TCACCTTCGCCTTCCTCTTCGTCGGCGTGGTCTTCCTGGGCAC GCAGCCCGACCACTACTGGTGCCGCGGGCCAA |
| 761 | SLC22A3 | 2934524 | CGGCCAACGACAGCGCCTCCGCCACTAGCGCTCTCAGCTGC GCGGACCCACTCGCCGCCTTCCCCAACCGCTCGGCTCCCCTT GTGCCGTGCCGCGGCGGCTGGCGCTACGCCCAGGCCCACTC CACCATCGTCAGCGA |
| 762 | SLC22A3 | 2934525 | GAAGCCGGCGGGAGAGGACGATGCTGGCTCCCAGGCGGACA AGCCGCGTGTGA |
| 763 | SLC22A3 | 2934526 | TTCCGGATTCGCTTATGGTCTCCAGGGTCAAAGGAAAGGGCG AACCAACGTTTGAAGGCAGCAGCAGCTTTTTTCCAGTTGCCCA AATGGTTACTCAAAATGCAAGGGGACA |
| 764 | SLC22A3 | 2934527 | GTGCACGAGAACGTCCCATCCAGGGACCCACGGATACTTCGT TCCTGCCAGGGTCTCCTTTGGGCCGACAGAGTTGTCTCTAATT GAGTGCAGGCAGCCCCGGAGCCCGCCGAGAGCTGAGGCTGG GCTGGGCTCCCGGGGACTCGGGCAGCTATTTCAGGCAGACG C |
| 765 | SLC22A3 | 2934528 | GAGGGAAGTGACCTGGAAGCGGAGCAGAGGTCGCAGCTGGC CCCTGCTGGGCCTAGTCTCGCTTCTGTCGTG |
| 766 | SLC22A3 | 2934529 | GCGTGTGCCCAGCTTAGATCCACCTGCAGCTGGCTCTGAACG CTGGATG |
| 767 | SLC22A3 | 2934530 | GCTCAGTGTCTTCCGCTGCTGTCTC |
| 768 | SLC22A3 | 2934531 | GTGGTGTTCTTGTCATCCTGGAAGCCCTGCCTTGGGCCATGC CTGAAATGCACTAA |
| 769 | SLC22A3 | 2934532 | TGACTCATGCGCATGGCATCAAGGCAGCCATGCCCAGGCCCA GCTCTTACCTCTGGGGAAGATAGACAGCTGACAGGTCAGGAC ACAGACTTTGGTGGCAACTGCCCGAGCACCCACATAGCAAGT TGCCGAGGCCAGGGGCATGCAGAGCCAGGAAAACCTGGGAA GATGCATAAACAGGCCCAGCC |
| 770 | SLC22A3 | 2934533 | CTGACACCTTGCGTGGGAGACACTAACAGGGAGAAGAGCTGA GCCTCCCCCAGCCTTCTGACCTACAGCACCATGTGATCATGAA TATGTGTTATTCTAAGCCACTAAGTTGGTGGTAATTTGTTATAT AGCAATAGAAAACAGATGCATTAAGTTTGTCTACAATGCCCAT GCCTGCAGTCATATTCTTTGGCTTCCTAGAAGGTGACCAGC |
| 771 | SLC22A3 | 2934534 | CCACTGATTTCATGACCTAACTAGAAAAACTTAGACTCGCTTTT GGCCATGGAGACATACATTTCCAACAAAATTTTACTTCTGCATA ATAATTATTTCTTAAAATTTATTACATCTTATTTTTTTATCAATTA TGATCTAAAGATAATTGTAATTATAACCCAAGCAGAAAAAATCC AATATTTAGAGACTTATTGCCACAGGAAAATTTTAAAAATTAAA TGTCAATTTATATATGTAACTTATTGTACATAGAAGTATGGTGA CAAAACCTATAAAATATTTTCTACACGAAATACATTACATTAGA ATAAAAGTCTGTGGAAATGAAAATAAGAGCTCAAAGAGAAAAA AATTGATGTCAAATTTCAGACTATTAAAGAACAGTCTGTTTATA GCAATTGGACACCTGATAGCATATAATATTC |
| 772 | SLC22A3 | 2934535 | TGTCTGTGTCAATGCGTGGATGCTGGACCTCACCCAAGCCAT CCTGAACCTCGGCTTCCTGACTGGAGCATTCACCTTAGGCTAT GCAGCAGACAG |
| 773 | SLC22A3 | 2934536 | CCAAGTGCGTAGTATCCCAAGTATGTAAAACTGGTTCAGCATT CTAAAGTCAATTAATGTCATCCATCAATCACATCGACAAACTAA |

TABLE 7-continued

| SEQ ID NO. | Gene | Affy Probeset ID | Sequence |
|---|---|---|---|
| | | | GGAAGAAAAAATGACATGATCATATCAATAGATACAGACAAAG TATTTGTCAAAATCCAACATCTATATATGACAAAAGCTCTCAGT AAACTAGAAATATAGGGGAACTTCCTCAACTTGATAAGGAATG TCTATTAAAAAAACTACAGTTAACATCATACTTAATGACGATAA ACTGTACAGAAGCTTTCTCACTAAGATCAGAAACAAGCCAAAT ATGTCATCTCTAATAACTTCTTTTCAATGCCATGCTAGAAGCCC TCGCTAATACAATAAATAAGACAAGTAAAGAAAATAACAGGTAT ACTGATTGGAAAGGAAGAAATAAAAACTGTCTTTGTTCACAGA TGTCATGATTGTCTATGTAGAAAATCAAAAGAATTAACAACAAC AACAACCAAAAAAAAAAACTCCTGAAACTAATAAGTGAGTATAG TGAAGTTGCAGGGTACAAGGCTAATACACAAAAGTCAACTGCT TTCCTATGTACCAACAATGAACAAGTAGGATTTGAATTTAAACA CATAATGCCATTTACATTAGCACCACAAGAATACACAACACTTA GATATAAATCTAACAACATATGTACAAGATTTATGTGAGGAAAA GTGCAAAACTCTAATGAAAGAAATTAGAGATGATCTAAATAAAT GGAGAGATATTCAACATTCATGGATAGGAAGACTCAATATTGT CAAGATGTCAGTTCTTCCCAACTTGATGTATATATTCAATACAA TACTAATCAAAATCCTACAGAGTTATTTTGTGGATATTGACAAA CTAGTTCTAAAGTTTATATGTAGAGACAAAAGACCCAGAATAG CCAACGCAGTACTGAAGGAGAAGAACAAAGCCAGAGGACTGG CACTACTTAACGT |
| 774 | SLC22A3 | 2934537 | ATCCTGCCTTGGTGTTGGCGTCACTGGGGTTGTGGTGGCCTT TGCACCAAACTTCCCTGTGTTTGTGATCTTCCGCTTCCTGCAA GGTG |
| 775 | SLC22A3 | 2934538 | TGACAGAAATAGTAGGTTCGAAACAAAGGAGGATTGTGGGAAT CGTGATTCAAATGTTCTTTACCCTTGGAATCATAATTCTCCCTG GAATTGCCTACTTCATCCCCAACTGGCAAGGAATCCAGTTAGC CATCACGCTGC |
| 776 | SLC22A3 | 2934539 | CCCGTTGGCTGATTACTCGGAAGAAAGGAGATAAAGCATTACA GATCCTGAGACGCATTGCTAAGTGCAATGGGAAATACCTCTCA TCAAATTACTC |
| 777 | SLC22A3 | 2934540 | GGAAAAATCATAGGACATATTAAAGAAGAAATGATTATGAAGC TCTATTAG |
| 778 | SLC22A3 | 2934541 | CGGAGAAGGTTAGAATGGATTTGAAAGAATGTGGTTGGATTCA AAGAAGCCCTAGGAGACCCAACAAGTCAGCATTTTTCTCTTGT GAAAAGAACCACCTGCCAACCCCAGCCTGTTCCATTGCTGAC ATCAGAGG |
| 779 | SLC22A3 | 2934542 | CATTTGCCAAGGTTTCTGGCTGGCCTCTGGCTTTGTTGAAGAG ATAGCTAGCACTAGCAGGGAGAAA |
| 780 | SLC22A3 | 2934543 | AGGCTCTCTGAACATACAAACAGTATAACTGTTGTTCACTAAAT GGAAAAATCCCAAAATCAAAAACCAATGCAAAACAGTGAAGTG GCTTGAGCTCCTAGGAGGTTAGGTAGAAATTAAAGAGAATCAG TGGATGGGTAGAATTTTAAGCAGTAGGTAGTTACCCAATGTAG AACGAGGATTAGCTTAGACACCTAGTCTGG |
| 781 | SLC22A3 | 2934544 | CTGCCCATTCCTCCCGTTTTTGTATGGGATATACTCATAGAGA ATA |
| 782 | SLC22A3 | 2934545 | GATGAATGGTGCCAATTCTACCAGCAAAGCCTTCATCTT |
| 783 | SLC22A3 | 2934546 | TGTCATTCAACACCGAAAGATATTGAGGGGAGGATGTTCTCCT ACACCTTTAATTGAAATGGAAATTCAATTTAAAGGTGCTTTAAA GAATGAGATTGCAGCCTTGGAGCAGGCTAGGCAGACTTGTGG GATGCCTCATCAGA |
| 784 | SLC22A3 | 2934547 | ACCTGGTTCTTCATCTGGTCCTGAGTCCTTGCCCATTCTACTG TGGCTCTGGCCCTGCTTCATTCCTGCCTGATTCATCCTCAGAA GGCAGGTTTCTGTCCTGTCCCTACACATC |
| 785 | SLC22A3 | 2934548 | AATTACTGTGCTTCTCGACTGTGGATAAATGAGAAAATACTCCT CTCTGTGAACGCGCTCCTTCGTGGAGACAGTAATGAGTACAA CTTCCAGAGCTCTGCGCAGCCAGCAACCCTGGCAGGAGTCCC TGTGTTATTCATAACCCAGAGCTGTGTTGCCATGGCAGTACTG CTTGCTAGACCTTGGACCCA |
| 786 | SLC22A3 | 2934549 | GTGTGCTACTGGCTTATGGCTGATACGTAAGAGAATCTCATCT ATCTCTAAATGTTCTGCCTTAAGCCGCACAAAGGA |

TABLE 7-continued

| Target Sequences | | | |
|---|---|---|---|
| SEQ ID NO. | Gene | Affy Probeset ID | Sequence |
| 787 | SLC22A3 | 2934550 | TGTGCAGAAAATATTCTGCAAATCAAGAACCAGAAAA |
| 788 | SLC22A3 | 2934551 | AAATGGAGGAAATTCCGAGATGACAGTGGTTTTGGTTCT |
| 789 | SLC22A3 | 2934552 | GCTCTTTGAGAATGTAGTCGGGACTTGCCCCAGTCACCCTTGC CCTGAGAACTCAGTGACTGGGGCTAATGTCACCCTGGCTGTC C |
| 790 | SLC22A3 | 2934553 | GGAGACACCTACCAGGAATCTAGTGGGACAAGGTTTCAGGGA TCCTGGAATCCTGCCCACACCCAACAGCTGGAACAGTTCCCT CAGCTGGCGAGTGGACAGGTGGTCT |
| 791 | SLC22A3 | 2934554 | GATGTTAAAGACCATGTTCCCATAGAAATAATTCCCAAAGCATT CAGAAGACTGAGAAGAAGTGATGATAAGAATTGTTCTGGGCA GGAGTGT |
| 792 | SLC22A3 | 2934555 | TTTCAAAAATTGCCGAAGTACTACAG |
| 793 | SLC22A3 | 2934556 | ACTAACCTCTGCAGTTTAACCTTGAGCGATACCTTTTCCCATGA ATAG |
| 794 | SLC22A3 | 2934557 | AGAGTGTCGATACTAGGCAACAAGCCTCTGAACAGATAGTGTT ACCCGGAACATCACCCTTTTCTCCCTTTGCTTCAAATCAAAACC AGCATCCCCCATTTAGACAGCATAAAAGGTATG |
| 795 | SLC22A3 | 2934558 | CTTCACTGAGACACAAGGAAACTTTTGGGGATCATGGAAAGG GTCCGTACCACGGTTGTGGTGGTGGTTATAAGACTATATATTT GTCAAAAGTCTTCAAAGTGTGCACTTAGAATTGCTGAAGTTTAT TGTACATAAATTACATGTAAATATCATAAAGTGCATGTAAATGG T |
| 796 | SLC22A3 | 2934559 | CAGATGAGGAAGTTAGTAATCCATCCTTTTTAGATCTGGTGAG AACTCCCCAAATGAGGAAATGCACACTTATTCTTATG |
| 797 | SLC22A3 | 2934560 | CGCAGTGGTGTATCAAGGACTTGTCATGCGCCTGGGAATTATA GGGGGCAACCTCTATATAGACTTTTTCATCTCGGGCGTGGTG GAACTGCCAGGAGCTCTCTTGATCTTACTAACCATTGAGCGCC TTGGACGACGCCTCCCCTTTGCGGCAAGCAATATAGTGGCAG GGGTGGCATGCCTTGTCACTGCGTTCTTACCA |
| 798 | SLC22A3 | 2934561 | TATTTGGTAAATTCAGAATTGTACCCAACAACATTACG |
| 799 | SLC22A3 | 2934562 | GTTTCGCTCTGTTCAGGTCTGTGTGATTTTGGGGGAATCATAG CCCCATTTCTGCTCTTTCGGCTAGCAGCCGTGTGGCTAGAACT ACCTCTGATCATCTTT |
| 800 | SLC22A3 | 2934563 | TTCTTAAGAGCCTTCATCTACATTCTTTGTACTAAAAGAGACCT ATAATAATTGTTAGGTTCAATAATGATAATGATAGTCATTTATCT TATTATAATAACTATTTCATTGATAATTATGATATTAATTTCATCT TATTATAATAACTATTTCAGTTTTGAGAGCCAATTCAGTTATAAT GAATGGTTTTAATTTACTTTATATTAAAGGGTGCTGATAAATAAT GTTCAATTAGCATTCTTTGGGTTCTGAGTTAAATGCTGTGA |
| 801 | SLC22A3 | 2934564 | CAGAAAGTGCTACTGTCCAGCAAAGACAGAGTAGTCCAGGAG ACAAGACAC |
| 802 | SLC22A3 | 2934565 | ATGACCTTCAGGACTGCAGCCCACAGCCCAGTGGCAGGCAG GCGGGGCCTGAGACTGCGAGGGGAGACAGCCGAATTTCTAA AAACTCAGCGACAACAGAATGTGATAACTGCT |
| 803 | SLC22A3 | 2934566 | TTCAAAGCAAGAGGATGCCGCATCCTCAAGCACCTGGTGCTA GAGGATGGAGTGCAGTTGTGAGCTGGGCCTGAAGAGAGGTG GTGCCAGGGCAGGGCAGGGACTGGATCCGGAAGGGCCTCAA GGACATGCCAAGGCTTTGCTCTTTATACACACAGCAGTGGAAA GTGACTGGACAGTTTCACCCTGAGGTGGACAGAGCTGGCCTT GCATTGTAGAAACACAGATATGCAAGTGGGTTGGAAGGACCC CCCAGCATCGTCCCTCTGATGGTAGATATGCAA |
| 804 | SLC22A3 | 2934567 | TTTGTAAGCCAGTCATCAAGCACAGATATCATCAAAAAGTAAA GAATATGAAATATATGAGAAATAGAGGCAATAAATGCCCAACA CTCATCAGTCCCTAATTCAGCTACTACACCTTCAGTATTACCTG TGCTCCTGAGATTGTGTCTGCTGCATCTTTATGGTGGAAGCCC CATTGATGGGGCTCCTGCATCACTTCCCAGTGGCCCAGGCAG |

TABLE 7-continued

| Target Sequences | | | |
|---|---|---|---|
| SEQ ID NO. | Gene | Affy Probeset ID | Sequence |
| | | | GGATGTTGTGTCAGTAGCCTGAAGGGCCCACAGTGGGAGCAT TTAAACCATGCACATTGGCAGATGCTGCCAATCAGGGCTTGAT TGCCCAAAGAGGGTTGTTAGGCATTTACCAGC |
| 805 | SLC22A3 | 2934568 | ACTGGAGGAAGGGTTGATCCCTACAGTGAGGAGCCCAAAGAG ACAGGCCTAGGAGAAGGCTGGTCCCGGAGTAGACACCAGGA CAAGCTTTCCACTGTAAG |
| 806 | SLC22A3 | 2934569 | AGGGGCAGGTAAGTGAGAGTGTCAGTGAGCGGGCGCAGAGG GGACTCCC |
| 807 | SLC22A3 | 2934570 | TGGACCCTAAGAAGGAACTCAGTCA |
| 808 | SLC22A3 | 2934571 | TATACAGGGGCCGTGGTGCTACTCAGGGTTTGAGGAAGGGAG AGAACCTTTGAAGCTGTGGTAAGGGAGAGCTGGGGCATTGAT CTGGGATGCAGAGGTTGCTGTGGTTGAGAGCTACTCCAGTGA GCAACATGATGGCTTCAGAGTGAGCAGGCCCCATGGGAGAG GGCCCAGCTGTGTCTTCCTGGAGCGGTAACACCTT |
| 809 | SLC22A3 | 2934572 | GTATCCTGGCATCCATCTGTGGTGGCCTTGTGATGCTTTTGCC TGAAACCAAGGGTATTGCCTTGCCAGAGACAGTG |
| 810 | SLC22A3 | 2934573 | GTACTGTACAAAATTCAATGCACCCTAA |
| 811 | SLC22A3 | 2934574 | CCCTCCAGAGCTAGATAAGAGTATGCATTGTTTTTTTTAATGTG GTTGTGAAGAGAGAAGCATTTTCACATAAGGTGCTAAGACTCA GAAGTGATCTAAAGGCAGGAACTGCTGATGTGGGAAAGTGGA AATTGCTGGGACATACAGCAGCAGGGGATTAACAGTGTGGCT TACTCTACAGAGTGAGGATGCGTCAGGTCTGTCTAGATGGAAT GGCATAGGCAGGTTTTCAAGACTGACTACAAAGTGAAATGTCA CTGAACAACATGTTATAGTATTTATAAAAAACTAAAACCAAAGG TGTTTTCTCTCTGCAGCTGGATAGGAAGACAGATGACACACAG ATGATAGATAATAGGTAGATGATAGATAATAGGTAGATGGATG ATAGATAGATATAATAGATGATAATCATAGATAGATAAGTGATA GTAGATAAATGATAAATAATAGATGATAGATGATAGATAGATAC AGATAGATAAATAGACAGGTAGATGATAGGTAATGTCTGGATA GATAGGTGGATAGATAAATAGATAATAGATGATAGATAATAAAC ATTAGTAGGAAGATAGAGAGATTGAGTTTTGGAGGGGGGTGT TTAAATAGGGTATAAGTAAAACTAATACCCAGCCAATATATTAA CATGAGGAGTAATGTCAAGAAAAATTCACATTACACAAATTCTT TCTAATTGTTTGAAATTTTTTCATTAAAACATAGAGATATGAATA TGAGAATGTATAGTACAAGATGTAAAATATTAATATGTGCCCTC TGTGGACACAAATGGGCTGGGAAGAGGGGTAGGGAAGGGAG GACCATCACTTTCTTGCCAGAGACTTCCATACTGTTTGATTTTC TTTAAAAATTAGAACACGTAGTCTTGTGTTGCTTGTGTAGTTTT AAAAAATGATGTAACAGCTAATTTAACAACTAAAAAGCAATCTT AATAATGACTTAGGAATTAAGAACATGGAGCTCTAAATATTTTT AATATATAAAAAATCCTGAGGAACAGCTTTCTTCCCTTTGATTC TATTCCACTGACTGCCTTCTGTTTACACAATGAGAGTGATGCTT TCATTCTTTATCCCCAAACCAATCAGGATCAGATTTGCAAACTC ATCAGGAAAAAATGGAAGAAAAGGGAGTCCTCTGAAATCAAGA CTTTTCTACTGCTTCAGTAACATTAAAAATAAACAGCTAGGAGA GGTTTTTTTGTTTTTGTTTTTGTTTGTTTTTGGCTTGGGGAGTG TGGGTGGAAGGGGGTTGTCTAAATGGTGTGCAAGGAAAATCA ATACCCAACTAACATATAAACATGAAGGATTATACCAGCAAAAA TTTAAGGTACCCAGATTCTTTCTAATTTTTTTCTGTTTATAATTT TTCATAATGAAAAGTTGGGTACATTAATTAATTATACCTAGTCT CTATACATGAAAAAAAATATAGTAGAAGTATGGTTTACAGTGCT ACAATTTAAGCACATTAATTGTGATCCATGGTTATTTACTCTAC AAAAATTACTTAGTGCTAAATTACTAAAACTTGCTAGCATTTCC CTTTTAAAAATCACACTGGATTATTTTATCGTTTCTGCTGGTTTT TGTTCATGTTAACAGCTCATTTCCAAATATATGTTAATTCAGTA GAAGTTCATAAAGAACTTAAATGCTATAATGCTAACAAACCCCT GTATCAGAGGAACCAGCCCCCAATATTTCAGCATAGGTTCTAT TTTCCATAAGTGTTGGCCAGCTGAGAAATAAAAAGAGTACAAA GAGAGGAATTTTACAGCTGGGCCGCTGGGGGTGACATCACAT ATCGGTAGGACTGTGATGCCCACCTGAGCCTTAAAGCCAGCA AGTTTTTATTAAGGGTTTCAAAAGGGGAGGGGGTGTAAGAACA GGGAGTAGGTACAAAGATCACATGCTTCAAAGGGCAAAAAGG AGAACAAAGATCACAAGGCAAAGGGCAAAAACAAACATCACAA GACAAAGAGCAAAAGCAGAATGACTGAAAAGGGTCTATGTTCA GCGGTGCATGTATTGTCTTGATAAACATCTTAAACAACAGAAA ACAGGGTTCTAGAGCAGAGAACTGGTCTGACCTCAAATTTACC AGGGCGGGGTTTCCCAATCCTAGTAAGCCTGAGGGTACTGCA |

TABLE 7-continued

| Target Sequences | | | |
|---|---|---|---|
| SEQ ID NO. | Gene | Affy Probeset ID | Sequence |
| | | | GGAGGCCAGGGTGTATTTCAGTCCTTATCTCAACCGCATAAGG CAGACTCTCCCAGTGCGACTGTTTATAGACCTCCCCCTAGGAA CGCATTCCTTTCCCAGGGTCTTAATTATTAATATTCCTTGCTAG GAAAAGACTTCAGCAATATCTTCCCTACTTGCACATCCATTTAT AGGCTCTCTGCAAGAAGAAAAATATGGCTGTATTCTGCCCGAT CCCACAAGCAGTCAGACCTTA |
| 812 | SLC22A3 | 2934575 | CCACATTCCTGTAAATGTGGCAGGAATAAGAAAACCCCAGTTT CCCGCTCTCACCTTTGA |
| 813 | SLC22A3 | 2934576 | TGTGCCTTGCAGAGATGCACGTGTG |
| 814 | SLC22A3 | 2934577 | ATCTGGTCAAGGGACTAAGCTCCTAGCTGACCATTCATTCTGA AGATTGCATGGAGGATGAACATCTGGGAATCCTGTTAATGAGA AGGCTGAATCACAGGCACCTGGGCCAAAGGGTGTGAGCATTC ATGTTCTCTGCTCACCTTGGTTTCCGCACACCTTCGCAATGTG AACAGGTCAGGAGTCCCTCCCGTCCACCTCCTCTGTAACAGC TGGGGTTCCAGGCATGGTTTAGGCCCTGTTCCAGCAATAAGA ACCAATCTGCTGTACAATCTGAGGACTTGGCTCTGTTATTTACA AAATGATGCTGTGGTTCTGAGATTATTTGGGACATTTTTGGCTC TCCTTTAGTGGACACCTAGAGCCACAGATTCCCTTCTTTACTAA ACAAATCCCATGGATTCTGATTTCTGGGTCTTAGGATTTTAAAA GTGAAGGGATATTTTTCTTATATTTGTGAGTTCAGTTCCGATGG TGCCCGTGGTCAAAAGCGAAAA |
| 815 | SLC22A3 | 2934580 | ATTGCTGACTCATGGCTGTATCTGGCCTAATATTGTTCTGGTTA ATCCATCTCTGACTCATGGCCATATCTGGCCTAATATTGTTCTG GT |
| 816 | SLC22A3 | 2934582 | GTGGGTTCTTGTGACTGTACCATTCA |
| 817 | SLC22A3 | 2934584 | GCAAACAGCAATTAATTAGCTAATAGAACAACAAAAGGCCCCA TATCCTGTAGCCAATTGAAGATCTGAGTTTAATCAGACCAGTG CTTCAAAATGGGTAGAGCCTTG |
| 818 | SLC22A3 | 2934585 | CTGTCCTTTGCATGTGAGTTTCTGCTGGATCCTTTCAT |
| 819 | SLC22A3 | 2934586 | TGCTGGCTACAATTTGGAACTGTGCAGTTTAAATATTTATTTAT TTTGTTTTGTTTTTACTCTTTCTAATTTGGATATTAGGTTTTGCT TCATCTGTGTTTTTTTTCTCTTACTCAGTCAATAACCATATCTCC AAACTAAATTAACGTTACTAAAGTGGGGAATTTCCCCTTCCTAT ATTCTCATAAGTGATTGAGCATCTGTCCTCATATAGGACTTGCT GCCTTGGAGGGGAGGGGCCAGACCTGGGAAAAAGAGGAGCC ATGAATAACTCTGCTTCCTACATTTGGCTTCTTCTCTTCCTCCA TATCCATGATTTATATATGTGAAGGAAGAACAAGAAATAACTTA ATAGGCCATTTGTCAATGAGAGTACAGTGTAGGAAGGGTGGA AAGTGAATATAAAATCTAGATTGGGGCTTCTGGTTTCCTGTTCA GCCTATAAGGAGCTTAGAATTTGCCACTCAGTCTTGACAACAA GTAAAATGCTGAACAAACTGAAAAATCAATAATTCTTCTCAGAT CCATAAGAGAAGTGAGATTACAGGGCAAACTACTACCTTCAGC ATCACCCCGCACCCCCAACCCCACTAAATAGAAAGACAGGAG AATACAGAGAATCATAACACAGGCGCAGAAACCTCCTTGAGAG AGCCAGGGTAGATAAACATGAACTGTAATTGATGAATTCCTGG AGGATCACTGTGGATGACCTGAAGGATTAAAAACTCTAGAGG GACTCACTCAAAGGAGGGCCCAAGCTTTTGTGATTTTTTTTTTT TTTTTTTTTTTTTTTGCCACCTGAAGCTCTACAAGGTTCCAAAG GTGAATATTAAGGAAAATCCCTCATGCTCTGGCAGCCAGAGG GGAAAAGGAACAATTTTGAAATATGCCAGAATATCGTTCTTAAC AATGTCTGCCCTCAGGAGAAGATGTTTAACCAGAGCCTAATCT TCTGGGGTTTTCTGAGAGCCTCATTGATCTGGGGGAAGGGAA ATACCAACTCCAGCCCCTTCTAGCCTTCCAAGTGGAGAAAGAG AAACACCAAATTCTAGCCTCCTCTAGCTTTCAACTTGGAAGAA GGGAAATACCCAGCTCCAGCCCCCTCTAGCCTTTCTCCCCTA GTTCAGAGGAGAGGGATAGAGAAGCATTTGTGAAGTTCACCG TTTAGAGACATAGGTTC |
| 820 | SLC22A3 | 2934587 | ATTAATGGCAGACACCACAGATCCAGGAAACTCAAAGGAAATC AAGCAAGATAAACATAAAAAAGTATACCTAGTTATATCGTAGTC AAACTACAGAAAGCCAAAGATAAAGGAAAAATTCTGAAAGAAG AGTGGGGGGATAATGTCTTACTATAGTAAAAGAGCAATGATAA AAATTACACCCTACTTCTTTTCAGAAACCAGGTAAGCAAGAAG AAAGTGGAATACTTAAAGTGTCAAGAAAAAAAATCCAATCTAGA ATTCTATACTGTGCAAAGTTATCATTTAAAAGTGAAGGAGAAAT AAAGACTTTGTTAGACAAAAATTGAGGGAATTTGATGCCTTGTA |

TABLE 7-continued

| Target Sequences | | | |
|---|---|---|---|
| SEQ ID NO. | Gene | Affy Probeset ID | Sequence |
| | | | ATAAATGTTAAAAGAAATTATTTAGAGAGAATGAAAATGATCTAGGTTAGAAATCCAGATCTACATAAA |
| 821 | SLC22A3 | 2934588 | AGGTACTCATACTACTCATGAAGTGATACAGTGTTATTT |
| 822 | SCIN | 2990412 | CATATGGAGACCTTTTCCCTACAAAACACTTTTTTGAGAATTAGCAAAGCATGGTGG |
| 823 | SCIN | 2990413 | TGGATGACTATTTGGGTGGCAAGCCAGTGCAGAATAGAGAACTTCAAGGATATGAGTCTAATGACTTTGTTAGCTATTTCAAAGGCGGTCTG |
| 824 | SCIN | 2990414 | CCCTCCACACGTGTTCAGTTAAAGTGTGAGGAATACCCTCCCCAGACAAACATCACAGATTTCCGAAATCAAACACGCTCCAGCAAGTGTTCTGCACACCCCACTG |
| 825 | SCIN | 2990415 | GGCGTGGCATCTGGATTAAATCATGTTCTTACGAACGACCTGACAGCCAAGAGGCTCCTACATGTGAAGGGTCGTAGAGTGGTGAGAGCCACAGAAGTTCCCCTTAGCTGGGACAGTTTCAACAAGGGTGACTGCTTCATCATTGACC |
| 826 | SCIN | 2990416 | AAGCTTTTTCATTTATTCGTCCAGCAGCATCT |
| 827 | SCIN | 2990417 | GTTAGTATAGAAACAGCACTCCTCTTCTAAAAAGATAC |
| 828 | SCIN | 2990418 | GGTGTGGTTCCTCGTGCAACAAATATGAACGTCTGAAGGCAAACCAGGTAGCTACTGGCATTCGGTACAATGAAAGGAAAGGAAGGTCTGAACTAATTGTCGTGGA |
| 829 | SCIN | 2990419 | TGGCTTCCATATGGAATGCCGAGTATGTCAGCCTG |
| 830 | SCIN | 2990420 | TCTTAGGGGAAAAGCCAGAGCTTCCAGATGGAGGTGATGATGATGACATTATAGCAGACATAAGTAACAGGAAA |
| 831 | SCIN | 2990421 | GGGCTGCCAAACAAATTTTCGTATGGAAA |
| 832 | SCIN | 2990422 | GTAAAGATGCTAATCCCCAAGAGAGGAAGGCTGCAATGAAGACAGCTGAAGAATTTCTACAGCAAATGAATTATTCCAAGA |
| 833 | SCIN | 2990423 | CCAGAAGGAGGTGAAACACCAATCTTCAAACAG |
| 834 | SCIN | 2990424 | GCTTCGGGAAAGTTTATGTCACAGAGAAAGTGGCTCAAATAAAACAAATTCCCTTTGATGCCTCAAAATTACACAGTTCTCCGCAGATGGCAGCCCAGCACAATATGGTGGATGATGGTTC |
| 835 | SCIN | 2990425 | CGTGTAGAAAACAATGGTAGGATCCAAGTTGACCAAAACTCATATGGTGAATTCTATGGTGGTGACTGCTACATCATACTCTACACCTATCCCAGAGG |
| 836 | SCIN | 2990426 | TGCGTTCCTGACTGTTCAGTTGGATCGGTCCCTTGGAGGACA |
| 837 | SCIN | 2990427 | GGCAAAGAGCCTGTTCACCTACTGAGTTTGTTCAAAGACAAACCGCTCATTATTTACAAGAATGGAACATCAAAGAAAGGAGGTCAGGCACCTGCTCCCCCTACACGCCTCTTTCAAGTCCGGAGAAACCTGGCATCTATCACCAGA |
| 838 | SCIN | 2990428 | TCCTGAAACTGCCACAAAATAGTGGCTACATCTGGGTAGGAAAAGGTGCTAGCCAGGAGGAGGAGAAAGGAGCAGAGTATGTAGCAAGTGTCCTAAAGTGCAAAACCTTAAGGATCCAAGA |
| 839 | SCIN | 2990429 | AAAAAGACTACCAGACCTCACCACTACTGGAAACCCAGGCTGAAGACCATCCACCTCGGCTTTACGGCTGCTCTAA |
| 840 | SCIN | 2990430 | AAGAGATTCCAGGAGAGTTCACCCAGGATGATTTAGCTGAAGATGAT |
| 841 | SCIN | 2990431 | ATTTATTTGGATTGGCAAAGATGCTAATGAAGTTGAGAAA |
| 842 | SCIN | 2990432 | GTAAGCTCAATCGATGGACCATTATAGCAGTAACCGGGCACCATTATGACCGAGTGTCTGGCTTGCTCTTTGCCACCATGTCTTACAAAAATAC |
| 843 | SCIN | 2990433 | GAGGACACCAATTGTCATCATAAAACAGGGCCATGAGCC |

TABLE 7-continued

| Target Sequences | | | |
|---|---|---|---|
| SEQ ID NO. | Gene | Affy Probeset ID | Sequence |
| 844 | SCIN | 2990434 | ACAAGGCAGTTATCTCATTGCTGTTTTGGGAGAGGAACGGGA AAAGCTTTTTGCTTATTTGTCTTTTGAAAATTAAGGCTGGGCGC GGTGGCTCACACCTGTAATCCCAGCACTTTGAGAGGATGAGG TAGGCGGATCACTGGGGTCAGGATTTCGAGACCAGCCTGGCC AACATGGCGAAACCTCGCCTCTACTAAAAATACAAAAAAATTA GCTGCGCGTGGTGGTGCACGCCTGTAGTCCCTGCTACTTGGA AGGCTGAGACAGGAAAATTGCTTGAACCCAGGAGGCTGAGGT TGCAGTGAGCCAGGATTGCGCCACCACACTCCAGCCTGGGCA ACAGAGACTCTGTCTCAAAAAAAAAAAAAAAAAAAATTAACCTC AACCAAACGCCTATTTTTTAATGCTTAGTTTTGGCTTGAAATTC TTCTTCACCTGGAGTTTTCTTACGTTAATACATTAAAATAACCT GAAGGAAACTTTCGTTATGGGCCAATATTAGCTCTTATGGAAA CTGATTTATATCTTTTTTATGACCTTTCAAAAGTAAAATACTATG CATAATCTAGAAAGATTTGTCAGATAGGAAATTTTATAATGCAT TAGCCATTAGTCAGAGTTGTTTTTTAACATGCCAGAGAAAAAGT TGTAATGCCTTGGAAGTTATTCTCTTTTCTATAGATTGTGTTCA AAAGATGTGTATACTTGCAATAAGGTTTATGTTAAGGTGGCTTT AACAATTGGTTGCTA |
| 845 | SCIN | 2990435 | GAATTGTATTGTTATCCACTTAGATACATGTACATGTACAGTAC ATGTTTAATA |
| 846 | SCIN | 2990449 | AAACACTATAAAGTGGCGGCGAATAAGGTTCCTCCTGCTGCTC TCGGTTTAGTCCAAGATCAGCGATATCACGCGTCCCCCGGAG CATCGCGTGCAGGA |
| 847 | SCIN | 2990450 | CCGACGCACCAAGGCCGGCGAGGGGAGGGCGTAG |
| 848 | SCIN | 2990451 | TTATTTGTTGCTTTCGGGCACTGGCTTATTTTCTCTATGATTGC GGGAATTATTGTTCTGGGCTTCTTTAAAACAG |
| 849 | SCIN | 2990452 | GATTCTACCCGCACCATGCTGCTTGTGGGTCTGGTAGACAAAA ACTCCGCTTCATTCGGAAGCTGGCGTCCTCAG |
| 850 | SCIN | 2990453 | CTACATCTACATCTTTATGGTATTCTCA |
| 851 | SCIN | 2990454 | TTAGGGTTCGGATCCCAAATCGGCAGAAGAATGACA |
| 852 | SCIN | 2990456 | GCGGGAGCTATACCACGAAGAGTTCGCCCGGGCGGGCAAGC AGGCGGGGCTGCAGGTCTGGAGGATTGAGAAGCTGGAGCTG GTGCCCGTGCCCCAGAGCGCTCACGGCGACTTCTACGTCGG GGATGCCTACCTGGTGCTGCACACGGCCAAGACGAGCCGAG GCTTCACCTACC |
| 853 | SCIN | 2990458 | GTTCTACTGTTGTATAGTGCTATGTGGTGAATACAGTTAACAAT AATTTATTGTATATTTTTTCAAAGCTAGAAAAGGATTTCGAGTG TTCCCAGTACAAATAAGTGATAACTATTTGAGGTGATTGATGTG CTAATTACTCTGATTTGATCATTACACACTTTATACTTGTATCAA AATATCACTCTGTAGCCAATAAATATGTACA |
| 854 | SCIN | 2990459 | TTTGTTAGCCATTAAAGCAGTTTGAACTTATCCTACCCATCCTC TTTTCCATCCCTCAGGAGTAGGGGACATATATGTAATATTGTA GCCTGGGGGTGGGGAGTGAGGATGAGGATGGATGTGTGAGT CTGGTTTGTACTCATCAGTCCTCACTAATCTATAACCTTCGTTG AGGTGTAGTCATTCCATTAATTCTTGAGCTTTCGGCTTTGGCCT CTGTTC |
| 855 | SCIN | 2990460 | AGCCACTACTGCATTCTTCTCAGGAACTCTGCTTTGTTTTTCCC AGACTACCCTAGAATTGTGGGACACGGTATCCTCATCGTACCA GTGCCCCTTGGCCCAGTGGCTTGGATGCTACCCTCAGTCATTT CTGCTCTAATGCTTAGGCTCATGGAGGGGTGTAGGACAAATC AATTGGAAGGGAAGTGTGCTGGGCTCTTCTCAAAGATTGATTG CTTTGGGTTAGATTTCCTACTTTTTTCAGTCTTCTTTTTTACTTT TTGAACCAGACAAACTAGTCTTACACCACCTCACATTCTTGCCT ACTCTGTGTTTCCTGCAAGATACACTCCAGCCCCTAAGACCCA CACCGTACTGCTTAAGATG |
| 856 | SCIN | 2990462 | AGCTGCTGTCCCTTAGTATTGAATATCTCTATTTTCTTTTAATCA TAGAATTCACTGATATTTTAGCAGATAATGTGGCCGTCCAGGC AGGCATGAGATTTCTCAGCCTTACTTCAACTTGATTATGACCAT GTGACCCAATTCTGACATTTGCCTAAAGGAAAATTTACCTAAAA AGGCGTTTTCTTGCTATGGCA |

TABLE 7-continued

| Target Sequences | | | |
|---|---|---|---|
| SEQ ID NO. | Gene | Affy Probeset ID | Sequence |
| 857 | SCIN | 2990463 | TTCTGAATGCATCACGGCAAAGATGCATGTACTCATGAAGCAT AAAATTAAAAATATGATACATTCACTACATGAAAATATGATATAC GGTTTTTCTTCAGTATCCGCGGGAGATTGGCTCGAGGAACCC CATGGATACCAACATCCTTGAATGCTCAAGTCCCTTATATAAAA CGGCATAGTATTTGCATAAAACCTATACCATTCTCCTG |
| 858 | AZGP1P1 | 3015108 | ATGGTGTCTGTCCTGCTGTCTCTGCTGCTGCTTCTGGGTCCTG CTGTCCTCCAGGAGACCCGAGATG |
| 859 | AZGP1P1 | 3015110 | TCATGCCTTGCAGGAAAGGTTTGGTTGTGAGATCCAGAATAAC AGAAGCACTGGAGCATTCTGGAAGA |
| 860 | AZGP1P1 | 3015111 | AGATGTTCTTCACGGTGGAAACGGCACTTACCTGACCTGGTTG TTGGTGCATGTGCCC |
| 861 | INHBA | 3047577 | GAGGCAGCCCTTTCTTATGCAGAAAATACAATACGCACTGCAT GAGAAGCTTGAGAGTGGATTCTAATCCAGGTCTGTCGACCTTG GATATCATGCATGTGGGAAGGTGGGTGTGGTGAGAAAAGTTT TAAGGCAAGAGTAGATGGCCATGTTCAACTTTACAAAATTTCTT GGAAAACTGGCAGTATTTTGAACTGCATCTTCTTTGGTACCGG AACCTGCAGAAACAGTGTGAGAAATTAAGTCCTGGTTCACTGC GCAGTAGCAAAGATGGTC |
| 862 | INHBA | 3047578 | CTTTTACTCTGAACTAGGTGGGCGCATTTCAAAAATTCGGATG GGAAAAAGCCTGGAAATTCCAGTGAATATTCAGCAAGGCCCTC TTTCATTGTACAGGGATCAAATTTCCTCCTCTTTTTTGTGCCCC CTCCCACTTCTACAAGTTATCCCCTGTGGGGAAAACAGGATGA TAATCAAAACTCTGGGCTGATGTTTTTCCAACTTAGTGTCTATT GGAATCAATCTTAAATCAGAAGCTTTTTCAGAAAAATAATATTT AGGCCAGAATTAGAGTTGAGTGTATTTTTTAAAAATGATTAAGG CTTGGTTGTGAGAAATATTACCTGTACCAGCTGGGAAAAATAA TGTCATCACTAACTAAAAGATAATTAATTTGAGAGAAAGTGTTA AGAGAGGGAGAGTAAGGAAGAGAACAGTTAAGAGGAGGCAG AGGTGAGGGCAGTAGTAAAAATCTCTAAAATTTTAATTTACAGC CAAAATTCTTCATGTGTAAATTTGTATTGATTCAGATGCAGAAA TGAAAAAAAAACACCTTTGTTTTATAAATATCAAAGTACATGCT TAAAGCCAAGTTTTTATCTAGTTTATTCTAGTACTTAGCTTGCC TGGAATA |
| 863 | INHBA | 3047582 | TGGAAAAAATCCTTAGCCAGGGCTCAGAGATGAAGCAGTGAA AGAGACAGGAATTGGGAGGGAAAGGGAGAATGGTGTACCCTT TATTTCTTCTGAAATCACACTGATGACATCAGTTGTTTAAACGG GGTATTGTCCTTTCCCCCCTTGAGGTTCCCTTGTGAGCCTTGA ATCAACCAATCTAGTCTGCAGTAGTGTGGACTAGAACAACCCA AATAGCATCTAGAAAGCCATGAGTTTGAAAGGGCCCATCACAG GCACTTTCCTA |
| 864 | INHBA | 3047583 | TATCATGCCAACTACTGCGAGGGTGAGTGCCCGAGCCATATA GCAGGCACGTCCGGGTCCTCACTGTCCTTCCACTCAACAGTC ATCAACCACTACCGCATGCGGGGCCATAGCCCCTTTGCCAAC CTCAAATCGTGCTGTGTGCCCACCAAGCTGAGACCCATG |
| 865 | INHBA | 3047584 | GGAAAAGGAGCAGTCGCACAGACCTTTCCTC |
| 866 | INHBA | 3047585 | GTGAGCAGTGCCAGGAGAGTGGCGCCAGCTTG |
| 867 | INHBA | 3047586 | TTGCTCTCTGAAAAAGTAGTAGACGCTCGGAAGAGCACCTGG CATGTCTTCCCTGTCTCCAGCAGCATCCAGCGGTTGCTGGAC CAGGGCAAGAGCTCCCTGGACGTTCGGAT |
| 868 | INHBA | 3047587 | AGACGCTGCACTTCGAGATTTCCAAGGAAGGCAGTGACCTGT CAGTGGTGGAGCGTGCAGAAGTCTGGCTCTTCCTAAAAGTCC CCAAGGCCAACAGGACCAGGACCAAAGTCACCATCCGCCTCT TCCAGCAGCAGAAGCACCCGCAGGGCAGCTTGGACACAGGG GAAG |
| 869 | INHBA | 3047588 | GGCTGTCATTTGTTGACCCCTATTCAAGAGGGTCTGTCACAGA AGACTCCTGCTTGCCTGAAATTTACGAGTGCATGTAAATG |
| 870 | INHBA | 3047589 | CTGGAACTGAGTGGTTGCTAAATTCAACTGCCCTGACAATGTG GGGATTTCCTGTCCATTAGCAGCGATTGCTATTTGACATATGTT TCTGGTGCCCATTAATCTGCCCTGTAATGGGTCAGAGGCAAAA ATGGGGGATTCAGAGGTACTAGGTGGCTCTCTTAATTTAATAG AACTCAATGCTAAGGACGCCTCTATTTGTTAATAAGTAATCAAG |

TABLE 7-continued

| Target Sequences | | | |
|---|---|---|---|
| SEQ ID NO. | Gene | Affy Probeset ID | Sequence |
| | | | TCATTGGCTACTTTCTGCTAAACACTAGACTATGATAGTGACCT TAGACCCCGGGCATTCTAAACCAGGCTGGCA |
| 871 | INHBA | 3047590 | CAGATTTGTGCATGGGATACATGTACAGCAGACAGTTGTAAGG AGGTCCACGGTCATGGAAAAGA |
| 872 | INHBA | 3047591 | GCTGGATTTCCGTTAACTATAGAAATCCAGGCAGGGAGATCCT CCCAGGGAGTTGCAA |
| 873 | INHBA | 3047592 | AGAACTTGAAACTGTGCCTAAAATTTATAG |
| 874 | INHBA | 3047593 | GCCCTTGCCTCAGTGAATTTACCACTATCATAATCACAGTGTG CAGAGTGTGTTAAATTAAGAACAGAATCCACAGTACGCAATGC |
| 875 | INHBA | 3047594 | ATGAGGTCGGAGTCAGAGGAACTCCCCTTACCAC |
| 876 | INHBA | 3047595 | CTCCAGGCTAGTTATCCAAGGCTTGGGAGGTTTCCCTCGGCC TTCTCCTAAGGCCTTGGCAGGACCCTGCCACCCTAAAATCAAC TGCTGATTGCCTTTTTAGATTTAAATGATTAAGCTCTGCTTATG GGAATCTTCTTCTCTTTTATTTTGTTAAGAAACAAACAACAACA ACAAAACCCACACCAATTCTTAGCAAAGGGGAATATCGAATTC AGATTTTGAAAAAATAAGTCATCATGCTTCCTAAAATAAGACAG CTTCTCCCTCTAACTGCTCTCTCTGCTCTGGTATTCTATCTA |
| 877 | INHBA | 3047596 | AGGATGTACCCAACTCTCAGCCAGAGATGGTGGAGGCCGTCA AGAAGCACATTTTAAACATGCTGCACTTGAAGAAGAGACCCGA TGTCACCCAGCCGGTACCCAAGGCGGCGCTTCTGAACGCGAT CAGAAAGCTTCATGTGGGCAAAGTCGGGGAGAACGGGTATGT GGAGATAGAGGATGACATTGGAAGGAGGGCAGAAATGAATGA ACTTATGGAGCAGACCTCGGAGATCATCACGTTTGCCGAGTC A |
| 878 | INHBA | 3047597 | TGCTTTGGCTGAGAGGATTTCTGTTGGCAAGTTGCTGG |
| 879 | INHBA | 3047598 | CACACAAAAAAACCTGCGCGTGAGGGGGGAGGAAAAGCAGG GCCTTTTAAAAAGGCAATCACAACAACTTTTGCTGCCA |
| 880 | INHBA | 3047599 | CCTTCTCTCTTACTCGGAGACAGTCAGAACTCTCCTCCCTGAC AGCCACAAACC |
| 881 | INHBA | 3047600 | GTGCCAATACCATGAAGAGGAGCTCAGACAGCTCTTACCACAT GATACAAGAGCCGGCTGGTGGAAGAGT |
| 882 | INHBA | 3047602 | TTGGGGCATCTTGAAAGTGTCACTGCAGTATAGCAATCTCTCT CAGGTAATATAGAGATAAAGGGAATATAATAAATTGACCTGTTA TTTATTATCTTTTTCATACCTAGGACATTCCGAGGCTTAATATAT TTCTGAAGCCTACAGCCCTGATAAACATCAATCCCACGTCAGT TTCCAGCAGTCTCATCTCCCCACACCCTTCTGCAATGAAAGCT AATGTAAAAGAAAGAAATATGCACTGCTTAATAAGTCAGAATAC AATAGAACTTGTAAAATGTACCTGCATATAAGGTAGACATTAG GAAGACTTGAATCTCTCTCTTCCCCCTGTTCTCCTGAGCATTAT GGCAACAGCATTT |
| 883 | INHBA | 3047604 | ATGCCTTTAGGGGTTACACGCTCTCTTCCGTGAATAATGGGGA AGAGCGGCCACAAGAGGGCGCGTTCCAAAGACTTTTGCTCCT TGTCAGTGTATCCAGGGAAAGGCAGTTGCGCGTACTGGAAGC CCCTGTCTGTAGCGCCCTAATCTTGGTGATTATCAGTTACCGC CTGCTC |
| 884 | INHBA | 3047606 | GAGGGTTGCTTCCTGTCTTTGTATACCAACCTCCACACATGAT GGATTCAATGACAGCTCGTATCCAGTTGCCTTTAACCATGTCA TATGACTAAGTATACCTATGCCTTTGACCACTTTTAACCGCACT ACCGTTACTAGCAATATGCCCCTCTTTCTGACTTACTGGACTT G |
| 885 | INHBA | 3047608 | ACCAGGGCATCTTTCCGGGGGTGCAGATAGCCTGCTGGCTGT GTGGCTTCCCCTTGCAGGAGAAGCCCTGGTGTCCTACAAGCT TCCCAGTTTGGCTCTCTCAC |
| 886 | INHBA | 3047610 | AGTGACAGTCATTTTTACCTTTAGAAAATGTCTATAAGTGCACA GGCACCACATTCAAGACAGGGAAGAGCTACTTTGGGGGACAG TTGTCATTGAACCAGCAGTTACTT |

TABLE 7-continued

Target Sequences

| SEQ ID NO. | Gene | Affy Probeset ID | Sequence |
|---|---|---|---|
| 887 | INHBA | 3047612 | AGCCGGAGGAAAGCCGCGGCATTTTCGGGTGCTAGGGGAGC AGA |
| 888 | INHBA | 3047613 | ATTAGGTGATGGTAGCGGACTAGCCGACGGAGGGCAGGCAG GGGAGGGGGAGAGGACTTTACAGAAAAGGAATTCTCGGTCGA GCTCTGCCTGGAGATGACTGGCTTACACTTACTAAACCCAGCG GGTCA |
| 889 | INHBA | 3047615 | ATTGATGTTTCTGGAGCTGAAACCCCAAAGGTGTTAGGTTACT TGTAACAGAAAAAGTCTTACAAATAGTTGTTTTGGAAAAGGGG ACAGTATATATAATTCAGAAAGCATTGTTAACCTGTGCAAACTG TAATTATAACTTAGTGTCACAATTTTCTTGCCCTCTTCCCCTTG CACTCAGATCTTATCTTGTAGTAATGATATTTATTAACTCTTTCC ACCTAAACTGCATTGCTTGACTGTAATGCTATGAACACACTAG GTG |
| 890 | AZGP1 | 3063591 | CACAGTCAATGGATCCACAAGGCCTGAGGAGCAGTGTGGGG GGACAGACAGGAGGTGGATTTGGAGACCGAAGACTGGGATG CCTGTCTTGAGTAGACTTGGACCCAAAAAATCATCTCACCTTG AGCCCA |
| 891 | AZGP1 | 3063592 | AGCCCCTCGTGGTGCCCTGGGAGGCCAGCTA |
| 892 | AZGP1 | 3063593 | TCTTCACAATGGAAATGGCACTTACCAGTCCTGGGTGG |
| 893 | AZGP1 | 3063594 | GGCAAGAGGGAAAGCGTCAGCCTTCCCTGATATTCTGGAAAG TCTCCCGGGGCTGGGGGTGGGCAGGTACAGAGCTTCGAGCT CTGCTGATCGCTGACATCCAGGG |
| 894 | AZGP1 | 3063595 | AGGGTAACACTGTCTGTAAGAGGCAGAGCTGGGACTCAAATT CCAGATTTCAGATTCCAAATCCCATCGTTTTTTATCTCTACAAT GATGCCTCCCATCTGGGTGGTGGAGAGAAGGGAGGCGTGTA AAATGTCAGCCCCAGAAGGACAAGAGCAAGCCAGTGTGAGCG GAATTGATGGCTGCAAGCTGAGACTTGGATTGGAGACGTAGT GAGACTCAGGATTGTGCAGTGCTGCAGGGAAGTGGTTGCTGG ATAGAGGCATGGGCTGAACCAAGCAGCTGGACTGAGACTGGG GGACAGAACTCCAAAGCCCACTGAGATGTGGGAAAACATGGA GAAGCACACGGAGCATTCACAACTTATTGCCGTCAGAGTC |
| 895 | AZGP1 | 3063596 | GAGCCCAGAATAAAAGACGATCTCAGGCTAGGAGCTCAGGCA ACATCTTAGTCCGGTCTCATCTGTTCCTGGATGTCCCTCAGAC CCCCAGCTTTCATCTTTTAGGATTTATTCCTTCCCTGGGATAAT ATAATTTGTGGTCCAAAAAGAACATCATCAAAATTTCAGGCAGA ATGGGCCAGGAAG |
| 896 | AZGP1 | 3063597 | CCAGTCTACGTGCAGCGGGCCAAGGCTTACCTGGAGGA |
| 897 | AZGP1 | 3063598 | TGAGATCGAGAATAACAGAAGCAGCGGAGCATTCTGGAAATAT TACTAT |
| 898 | AZGP1 | 3063599 | GATTTCGCCATATCACCCTGGCTGGTCTGGAACCCCTGGGCT CAAGCGATCCACTCGCTTCAGCTTCTCAAAGTGCTGGGATTAC AGGCATGAGCCACAGCGCCCAGGCTGTAGCTCTCTTAAGGAG GAACATATCTCATCTGAGACAAACCTGAAATGCCAAACCAAAC TGAGTTAGCCCCTCTCTGTCTGTTGTATATATTGGAGTAATAAC CTATTTGTCTTGATAAAGGGATTGCATGCTTGAATTGCAAAAAC CTTTATTTCTTTTGGGTTGCCCAATGTGCAAGACTAAGAGT |
| 899 | AZGP1 | 3063600 | CATACGATGCAGACCCAGGAAGGGCCACCTGCGCTATGGTCA GAGGA |
| 900 | AZGP1 | 3063601 | GGAGACCCTGAAAGACATCGTGGAGTATTACAACG |
| 901 | AZGP1 | 3063602 | ACACTGGGCTGTCCAAGCATGTTGAAGACGTCCCCGCGTTTC AGGCCCTTGGCTCACTCAATGACCTCCAGTTCTTTAGATACAA CAGTAAAGACAGGAAGTC |
| 902 | AZGP1 | 3063603 | TGCTGCTTCTGGGTCCTGCTGTCCCCCAGGAGAACCAAGAT |
| 903 | AZGP1 | 3063604 | CCCGTCCTGGCACTCCCATTGGCCTGTAGATTCACCTCCCCT GGGCAGGGCCCCAGGACCCAGGATAATATCTGTGCCTC |
| 904 | TRIQK | 3144581 | GAGTCTGTCACAGTTTCTTTGTGTAA |

TABLE 7-continued

| Target Sequences | | | |
|---|---|---|---|
| SEQ ID NO. | Gene | Affy Probeset ID | Sequence |
| 905 | TRIQK | 3144582 | GCCGGTGTTATTTACTAGATTCTTCCCTTTGAACTCACAGACTC AAGAGACAGACCAAGAGTTCTTATATACTCACCACAGCGGACC AATCCAAGTGGCATTTTTAGGAAAGGTTGCAGCATTTAATGCC ATGTGGTATGTCTGTTCGTCAAGTGGGTGGCAAGGGAATATCC AAGCTGGCATTTTGGATATGATGGGCCTTTTACTTTCCTGAGT GACATGCCACATGTCAAGAAATACTGCTCCCCACCCCCCCACT CCCATCACATTTACGTGAACAATTTTCATTTAGTTATTTCCCGT TCCATATGGTGTTAAAACAGTCGTATTAAATAAAGATTATTTCT AGTTTTCAGTGGTAATTTAAATGAGAGGATATGTAATAATTGCT TATTAGATACTTATCCAAATGAAATATAACAGAGTTTACAGTAC TTAAAATGGCTGGTTATGGTCTTGGAAATGTTTGAAAATTCATT ATCCTGAAAAAAACTTTACCATTCTGTTTTACCCTTGAGGTATT TTTTGGGGAAAAATGTTTTTGATAACTATTAATCTAAATATAGTA TAATTATAGGCAAATTTCACTGCCTAGTTTTATTGATATCCTGA GTCTACAGCTAGTCCATTCGTATGACTGATTGATTTATGATAGC TCCAGAGAACCATAAATTTCAAAGGCTAAACTCTCTGATTTTAG TAAATAGTAGGTAAAGTGACACAATATATGTTTACACAACACTG TTTTCATGAAATGCAAACTTTGCAAAACTCACATTAACTGGGAA GCAGCCAACCCTCTGTAGAGAAATCCCAGATTGGGAGTCTGG TTTGAATCTTTGAAGACAGAAAGGTGATATCCGGCCTGCTGTT TTAAAGGGACCACACTTTTGAATACCTACTGGTGTTTGGCAGA AATCTGAGACTGGCACCAGACACAAATTTTAGACATGGGTATC TTCCCTCCAGTA |
| 906 | TRIQK | 3144583 | TGCTTTGACAGCCACCCTATACATGGTACATTTAGATGAAATG GGAACCAGATCCTAAATTTTTCAAATGTCATTGCCAATTTATGT GTATAATTCCATCACTTCCTGATGAGTAAGTCTATTTTTGTTCT ATATACATCATAAGTTAGTATATATTCTTATTTACAGAAACATGC TCAAATCACATTCAGAAAGAACAAAAAGTCATGGGAAATTTTTT ATTTTACAACAAAGCCCTGCTTTCTTTCTGGACGTATTTTACAT CATTAGAGAGACTATCTGCACATACATCTACCATAATCTTTTTC CTTCTTTGCCAACTGTTCAGTGCACATGTGCTGCATCAGAAAT GGCACCTGGATGACAGAAGCTCAAAGAGTCACATATGTCTCTA AAATAGAGTTCTTTTCCTCTTGGGCTGTCTGAACTGGTGTAAAT AGAAGCTCAGTTGATCTTGGTTTTAATTAACTTATTACTCTATTA ATATAACCTTGGAATTCTATTCTAATTATGTTGTTCTGGCTGCT TGTAGTATCAGTTCGCCCCTCTTGTTAGGGAGATATGTAACAA TCTGTCATTTAATTGAGCAGTCTTTTTCACATAACAGTAATAGC AAAAATCCTACCTACTCAGAATCATCTTCTTAGGTTGTCTCCTA AATCTGAACAATACAGTTGTTTTATAAAATTACATTTTGTCTCTT GAGATTTAATCAATTAGAACTCTTTAGGGAGAAAATAAATAATA GAAGAAAATATATGCCTCATATTTCATATGTAATTATCTGTTGAT ATAATTTTTCAATGTATTTTGTATTTGTGGGAGCATAATGACCT GTACATTC |
| 907 | TRIQK | 3144584 | CTCACCACGGATGTTGACCCTGATCTGGACCAAGA |
| 908 | TRIQK | 3144585 | GAAGTTGGCCTTGTACTTGCAGCTATATTGGCACTACTACTGG CTTTCTAT |
| 909 | TRIQK | 3144586 | GCCAAGGTATTACTACCAAGCTGTAACAGCTGTTGAACTGCCA GATGATATATTTGGTTGTCTTCCAGAATTTGCTATTATGATCAC GAAACACTGCCTTCTTTTCGCTCCTGATTG |
| 910 | TRIQK | 3144587 | TTTACGAGCAACCAAATTAAAAGCAG |
| 911 | TRIQK | 3144588 | AAAGGAGGCATTACAAGTGATATTTCAGAAATAAAAAATACAA GCTACTTTGGGTAACTGAATGCCAATAAATTAGTTAACCTAGA GGAAATGGATAAATTCCTAGACTCATACAACTCACTAAGATTG AACCATG |
| 912 | TRIQK | 3144589 | ACCTGATGAGCAAAATGGCTGAACAGAATCCTCTAGCGATCAT CCCCCCACAGGAACACCAAACTGAACAACTATTCACACAAAAC AAGCACCTTCATAAGAAGCAAAAAACAGGTGAACCGGTACCTG GCTTTAACATCGTATTAAGGAAAGAGGCACTGAAGAGGATTTG AAAGACAATCTTGAGTCACCTATACCACCCCTTTCCCGTACTT CACCTTTGGCCATGTGGTGTTAAGAGACAATCTGTGCACTTGC ATGAGGGAGAGTGCAGTGATTGTGGGAATTTGCCTTGGAACT CAGTGCTGCCCTGTCACAGTGGAAAGCCACACAGGGAAGAAC TTAGCTGGTGCCCACA |
| 913 | TRIQK | 3144590 | CCTCCTAACTATGCATGTACCTTTCACATTTTATTGCAAAACTA TTAGGCTATAATAAGAACATGCATCAAGCAGGGACACCAATAT CTTGCCTGGCATTTAATTATCAAAAACACCTGTGCTACAATAGT |

TABLE 7-continued

Target Sequences

| SEQ ID NO. | Gene | Affy Probeset ID | Sequence |
|---|---|---|---|
| | | | ATATTCACGTGTATAATTCTTTATATGTAGACATTTAAGTGCTTG AATTATTTAAAAAATCTACTGTCTGGATAAAACTTCCATA |
| 914 | TRIQK | 3144591 | GCTACTATAAAACTTCCTGTTGATCAGTACAGAAAACAA |
| 915 | TRIQK | 3144592 | TTGCTTGTGACATGACTAGTTCTTGTCTGACTTCATCTTCATCT TGTAATGCCTTACTAGAAGGAATGAGGAACAACTTGCAGACAC CAGTTTGAAGAATACTTACGACTGTAACATTGTATTCTATGAAT AATGACATATTGTAATTGAGGCTAGGAAATAGAGTCTGTGCTA GGAAGAAAAGGAGAATATGAATGTGGTAATCAGGTTGTACTCT CTGCTGCAATA |
| 916 | TRIQK | 3144593 | AAACAAGTTGGTTGGATAGCTGTCCTCCATGCAGTCATTCATG ATCCAGGCTGTCATCATCTTCATCACTCATGTTCAGAGTTACC CTAGAGGTCATCTCCATTTCATCCAGATAAATGAGTATGCAAG GAACGTTTTTA |
| 917 | TRIQK | 3144594 | CTGCTGGGATGTTGGCTTAAATGACTAGAAAGGAATTGGGGG AAGCATAATGAGTAACCATTTTGGCAGATAGCCTCAGTGATTT GCTTTAAGAAAAAATTAAGCATAGTCTGTAAAGGCAAAAAACAA AACTAAATTGAAAAGGGAATAATATCTTGAGTGTTTATTCATTT AATCCAACTTCTCTCCTAAAATGGAGTGGTATCTTCCCTAGCC ACACACA |
| 918 | TRIQK | 3144595 | GCTAATGTCTCCCTGGATTTCTTGGGAGTTTGCTATCTAACCAT CAAAGCAATAGAAATGAATGATGATTACTGCAAGGCTTTGAAG AACAAAGAAAAGTCAGAACATTTTAAAGGTTCTACATGTCTGA GTC |
| 919 | TRIQK | 3144596 | ATGGGGACTCCTCCATTTACCAAGGCTACAGCTGACTCCTGGA GAGGCCTGAGTACTCATTGCAGTTT |
| 920 | TRIQK | 3144597 | CCTTTTGTTTGATTAAGCTCTTAGCGTGCAGTG |
| 921 | TRIQK | 3144598 | CAGTCTGAAGGTTTGTCGGGTAATAGTCAAGTGGATATGAAAC TGCCCTTTGTGAACCTCAG |
| 922 | TRIQK | 3144599 | GGGAAGCAACGTCAATCAGTGGTACTGGAAAATGAGT |
| 923 | TRIQK | 3144600 | TTGGTGTTTGCCTCATTTGAGCCTGGTTTGAACAGTTGGCCAC CTTTGGCCAAAACTCAGTGATTGGCACAAAAGTCGGTTGCAGT CTGTTTACACATGGAAAGGTTACAGTTTACTGTGCACAGAGAA ACCATTAGGTCACATTTAGAATATATAAGGAGGCAGCATTGGG CTAAACTTGACAATTGCTTATT |
| 924 | TRIQK | 3144601 | CGATTAGAGATTAAGTTGCCAGCTTTAAAAATGGGGACTAGTG TGTAAGCCTTTTGTATGTACATATGTACATGCACTAAGTATGTA AATACATACATATTGTGAGACTAGGTTCTCACAGTAAATATCTG ATAAAAATCCCTGGGGGAGGGGAAAAGGAACCATTTTGAAATA CACCACAGCACTCTGTTCTTAAAAAGGTCTCTCCTCAAGAGAA ACTAGTGTATATAAAAAACTTACTTTCTAAATGTAACTGTTACTC TACTAATCCAGAGTTTCAAACATGTGTGAACAATAAGATAGCAT ACATAATTTGGCATTTTAAAAGTTATCCAAAGATACTTTTGTAG AAGCCACTTAGC |
| 925 | TRIQK | 3144602 | TTTTCTGGCAATGAACCTGGGTTCCAAGCATAGGTTTTTCTTAT GGAAGGCAGTTTTACAATAAGGAAATGTTTTTACTTGTATTTAT TTTGTGATATTTCAGCAAATCCAAATAAATGTAGTAACATTTATA AAGCTATACATTTATAACTGATTTATTTGTTAAATATTTAGTATT ATCAATTGTCTGTTAAAGATTTGTTGCTACATTAAATGCTTGGT CTGTCTTGATGTTCAGTACATTATTATACTTTGGTATATTGCAAT ATTTTGATAATTATGTATTGGTTTTAGTCACTGTTCCTGCATATT AAGTAATAAACAGATTAATATCATCATAAAATATCATTTACTCAG CAATATTTCTTAGTAAATTGATACATCCATTTTTCTTATGTATTG TGGAGAGAGGAAATATGACATAAAATGGAAGAATATGGGCCTC TGTTTATCTCTGACCTCATCGCTTACTGTTCTTTCCCACTCCTC ACTCTACTCAAAGCCTTTAAATAGCTCTCCATTTTACTCAACAT CAAATCTAAATAAAGCTCTTAAACTGGTCTAAATGTCTCTACAG TACTTGAACCTTTGTTATTTCTCTAATTTCATCTTCAACTCTGCT CATCGTTATTCTCTTGCCCTGGGCATACTGCCTCCCTTTTTGTT CTCTGAACGTGCCAGGCATTTT |

TABLE 7-continued

Target Sequences

| SEQ ID NO. | Gene | Affy Probeset ID | Sequence |
|---|---|---|---|
| 926 | TRIQK | 3144603 | CAGGAATGCAAGCACTGCTACCTAACTAAAGACCTTGGCTTTG GAAACATCTTACCCCTTGGCAGCTCTCCAGAGTTTAGACTTGG CAGCATCAAAGAC |
| 927 | TRIQK | 3144604 | TCTTCCAACGTCAAAGCCAGCAACATTGCAGCAATCTGACTTA TTTTGTTGTCATGTCTCCTGACCACATCTGGAAGGGTTATCTAC TTTTGAAGACACATCCAGATAATTCAGGACAATCTGTCCATTTT GAGGTTCTTC |
| 928 | TRIQK | 3144605 | GGAGCTTGGTGTATTCCTGAATCCATCAGATGTTGGTGTCCGC GTGGATGACTAGGAAAAGGGGATTGGAGATTAGGTTTCTTCTA CTTGGAGTTCTCTGCTGCTTGTTTGAGCTTAATAAGCCTCCTG AAGAAGTTGAAGCAATTTATTGCTAGAGGAGCCCCAATGTATA ATCTCCCTTTCATTCTCTACTGTGGAGAGGTGTGCTAAACCTG TAGAGCTGTTTTTGCTTCACTCGGCTCATACTTAATG |
| 929 | TRIQK | 3144606 | CCGGGAATGAAAGCGGGCGCACCTCTTTAGCGAGCCCTAAAG CGTTTGGGAGACGATCGTTCCGTCCCTGGGAGCGGCACTTGG TGGGGCTGGGCGGAGGGAGGCTCTGCAAGAGAAACCCGGAG TCCG |
| 930 | TRIQK | 3144607 | CCTGAGTGACAGAACCGTGGACAGCAACATTTCCCACAGGAC ACGAAGTTTGTCGGCCCTTGCCTTGGCAG |
| 931 | TRIQK | 3144608 | GATGTCCAGCAGCTAGTAGATGTAGAAGTGCTGTTTGTTACTG GGTATGTCCTTGCTGTCAGGGAAGTGCACCTGTTTCAG |
| 932 | TRIQK | 3144609 | GCTAAAACTGGTAAGGTGCCCATGGGTTCCATGGAACCTCCA CATCCATTTACAAAGCCCTCTAGGAAGACTGGGCTAGTTGCTT TCTTCAGCTTCAGTATTATGG |
| 933 | TRIQK | 3144610 | ATACACCTTAAGCAACCAGGTATCCTTGATTGTGGGAGTTCCT TGGAACATGAGCAGA |
| 934 | TRIQK | 3144611 | TAACCTGGACTTTCATAAAACTGGCATATCTTCTGTTTTACATG GAAAATTATTTTATCTTAAGTTTCCATTTAGTTGATTAAAAATAG GGTTATGAATGTTAAATAAGTGATGATTTATTGCAAAGGAAATA TGTTTCGAAAGGTCGAATA |
| 935 | TRIQK | 3144612 | GAGTCCCCTGGTCTTTACATATTAAAAATATTAGGCTGTCCTG GAAATGTTGTCTTATTTGTCTGACTTCACCACTAAAGTATGAGT CCCTTAAGGTTGTCATTTCATTTTTGTAGTCCTTATGCCTAAAA TAGCAACA |
| 936 | TRIQK | 3144613 | TATCCTGCTGGTGAGTTTGGGAAAAGGAATTGGATCGGGGCA TGCAGCGTCTCCTTATCTGCAAACAGGCCTGCCGGTGGGAAT CATGGTACTGTTCCCCAGCAACACAACATTAATTTCAGAGGGA GATGCTCTGCCACTACAGGAGTG |
| 937 | PABPC1 | 3146782 | TGACACCGCCATGAAAACGATCAGCACCGTCGAATCCTCACG CCCCACTCAAGTTCCTTGATTGCTTCAATAATGTCCTCCGTAG CAAAAGGATCTAGTTCAAAATCGGGAGTTACATTTCATTGTCAT GCCTAAAACGTAAGAATTGCTCATTCACTTTGGAGCAGTTCTT CAGTCTATCCTTGATTTTCATGACCTTGACACTTTTGAACATTA TAGACCAGTTATTCAATAGAATATCTTTCAATCTGGGTTTGTCC GATACCTCTTTATTATTAGATTGAAATGATACATTTTGGTGGAA CTATCACAGAATTGACATTGCATTCTTCTCATTACATCCTGTCT GGTGGCCTG |
| 938 | PABPC1 | 3146783 | AAAGGAATCCTAGTGACGAGTTGTCTTGAAAGAGAAGAAAAAA AGTTAAAAAACAGAAGAAAAAGGAGATCTTTAACCGTGCTGGG TATAAAATTCTAAGTCAGGATACTTTTCTTCCTTTGAGCATCTTT GACTGCCTGGGGAATATCAGACATTCTTTTAGTGGCCTTGTGA TCATTTTGCTGAGCTTGTTCATATTCCTGTTC |
| 939 | PABPC1 | 3146784 | GCATCAAACTGAACCGCGACTTGTCCAAAGTCACATAGTAAGT GGAGGTGGAACTGGGCTTTAAATCCAAGCCTACATACAGACTA GAGTTCACACTTTTAGGCTTGGCATAAACTGCCTATAAACTATA AAAAAGTAAAACTCCATAAAATCTCAGGTACTTGGACTACCTTC AGTCTGA |

TABLE 7-continued

Target Sequences

| SEQ ID NO. | Gene | Affy Probeset ID | Sequence |
|---|---|---|---|
| 940 | PABPC1 | 3146785 | AGTATGGGTGACTATTCTTTACAAATCCATTTGTGATGCAGTG GTAATTTGGTGGCACTGCAATTATGGCCAGCAATGAAGATTAT AAAATAATTGCCTGAGGAACCAAGCTCATGTGCACTAAAAAGA AGCAGG |
| 941 | PABPC1 | 3146786 | CTGCACTTGGCCCTACACCGATGAATTTTT |
| 942 | PABPC1 | 3146787 | TGCTGAGCCGACATAAGAATCTTTTATGAAAAATGTACTGTTAA GTTCAGGGGGTCTATTGGTTTTATGTAAAAGGCACAAGACAAT TCCTGTAGTGCATTTTATGAGTTAAGGTTTCCATACGGATTATT GAAACAATTTGTTACATGTATTTGTTACATGATCTTAATATTTCA TGTACAAGACTGACACCCATCCACTTTTGAAGATAAGCCAGTT TATGGGGTTTTTTTTTTTGCGGGTAGAGGTTGGGTCTCCCTAT TTTGTCCAGGCTGGTCTCGAATTCCTGGGCTCAAGCATAAGCA TAAGGC |
| 943 | PABPC1 | 3146788 | CCTTATGTACCGAGCAAATGCCAGGTCTAGCAAACATAATGCT AGTCCTAGATTACTTATTGATTTAAAAACAAAAAAACACAAAAA AATAGTAAAATATAAAAACAAATTAATGTTTTATAGACCCTGGG AAAAAGAATTTTCAGCAAAGTACAAAAATTTAAAGCATTCCTTT CTTTAATTTTGTAATTCTTTACTGTGGAATAGCTCAGAA |
| 944 | PABPC1 | 3146789 | TGATCAGGGACCATGAAAAGAAACTTGTGCTTCACCGAAGAAA AATATCTAAACATCGAAAAACTTAAATATTATGG |
| 945 | PABPC1 | 3146790 | CAACCTGGAGTGCATTGACGCGATCTCGGCTCACTGCAACCT CCACCTCCCAGGTTCAAGCAATTCTCCTGCCTCGGCCTCCCG AGCAGCTGGGATTAACAGGCCCATGCCTGCCACCGTGCCCAG CTAATTTTTGTATTTTTACTAGACTTGGGGTTTTGCCATGTTGG CCAGGCTGGTCTGGAACTTCTGACCTCAAGTGATCCGCCCAC CTCGGCCTCCCAAAGTCTTGAAATTACAGGCGTGAGCCACTG CGCCCTGCCAGATTTTGTATAGTAATATATATATAAAATGACCT GTCACAGGTTGGCTTTCATAGTTTTACCTTTCCTTTTTGGGTGG TGCCCTTGGGTCTCTACTACTGTCTTTCATCACTCCCAAGAAAT TGAGTAGTGCAGCCAGGATCAGGACCAGGGATTGGCAAATGT TTTTTGTAAAGGGCCAGATAGGAAATATTTTGGGCTTTGAGGA CTGTGTTATCTCTGAAATGATCTTGTTCCAGTGTTACCATGTCA AGAC |
| 946 | PABPC1 | 3146791 | ATGAAGCTGTAGCTGTACTACAAGCCCACCAAGCTAAAGAGG CTGCCCAGAAAGCAGTTAACAGTGCCACCGGTGTTCCAACTG TTT |
| 947 | PABPC1 | 3146792 | GTACAGTTGTAAAGTCTGCATAATAACCTGTGGCGCTATTTATC CCCATTTTATAGATAGGTAAACTGAAACAGGCTGAATAATTTGC CAAATGCTCACACAGCTCTTAAGTGGCAGAGCCTGGCTTCAAA TCCCATCAGCTCCAACAGCCATACTCTCAACTGCTGCTGCTTT CTCTAGTGGAGAAAGAGAAATATTTTTCGAGTGTGGGGAGGA CAAGGAAAGAGTAGTGCAGGGGAGCGATTCATAATTCT |
| 948 | PABPC1 | 3146793 | GCCATGCACCCTACTCTTGCTGGTA |
| 949 | PABPC1 | 3146794 | TCCTCAAGAGCAAAAGCAAATGTTG |
| 950 | PABPC1 | 3146795 | AATGGGTCCACGTCCTGCAGCTGCA |
| 951 | PABPC1 | 3146797 | TGCAAACCTCAGATCGAAGAAGACAGCATAAACACTTTTCACT CAGTAAGTTTTCCCAGTTAATGTA |
| 952 | PABPC1 | 3146798 | TCAGGTATATTTATAAGTGTGGGCGGCAAACCACCC |
| 953 | PABPC1 | 3146799 | AACCGTGCTGCATACTATCCTCCTA |
| 954 | PABPC1 | 3146800 | CAACCAGAACCATGAAGGTTTTCGTATTTGGTCATT |
| 955 | PABPC1 | 3146802 | TTATGATGGAGGGTGGTCGCAGCAAA |
| 956 | PABPC1 | 3146803 | CTGACCTGGCTAGGGTAATGCATATGTGTAGTTTGCCCTTAAT AATTGGGTATTAAGGAAAAATTGTGAACTCAATGGGTAAATAC AAGATGATTAAGCATTAACAGGGTTTAGTTATTTGATTCAGTGA TTTATAATTGTCTAA |
| 957 | PABPC1 | 3146804 | GGAGTACGATAGAATTTATTCCTGAATGTTTTTGTCTTCAGTGT GTTCCCTGGATATTGTTTAAATTGAGTGTTGTGCATCAGCATAT |

TABLE 7-continued

| Target Sequences | | | |
|---|---|---|---|
| SEQ ID NO. | Gene | Affy Probeset ID | Sequence |
| | | | TTTGAATGTATGAAGCATGCATGTTTTTCTGTTTCTTGAGACAG GATCTCATTATGTTGCCCAGGTTGGAGTGCAGGGGCATGCCA CAATCACAGCTCACTGCAGCCTCAGCCTTTCCTGGGCTTAAGC CAAGCTTGTCCAACCCGCTGCTTGCAGGCCACATGCGGCCCA AGAATGCTTTTA |
| 958 | PABPC1 | 3146805 | GATGATGGTATTGATGATGAACGTCTCCGGAAAGAGTTTTCTC CAT |
| 959 | PABPC1 | 3146806 | TTATGTTGGTCGAGCTCAGAAAAAGGTGGAACGGCAGACGGA ACTTAAGCGCAAATTTGAACAGATGAAACAAGATAGGATCACC AGAT |
| 960 | PABPC1 | 3146808 | TGCCTTGGCCCATACATCTTCTAAATTTCTGTAATCAAATGTGA TTTTTAACCTTTTCTGCCCCACTTGCCTGAGATACCACCCGCC TCAGTTACCTGTCTCTCCTACTTTAGAGGGAGTTAGGGGAAAA CATGTCTTCAGAAATAAATGCTTCCTCTTCCAGGTAGTTCACCT GTGTCTTTAAAAAGAATTTTTTTCCCTGTCTTTCAAATTCCTGT ATTACCTATGTCTTACCAAAGAGTCCAACTATGTATTCCTTCCA CTCCTGTTGAAAGTCGGGTAGGCCAAGGCTTAATAAATACTTG TTTCTTAATTGATACAAAGAAAATCAAATTGGTCTTAGCACAAT AGCTCATGCCTGTAACCCTAGCGCTTGGGGAGGTCAAAGAGG GAAGATACTTGAAGCCACAAGTTTTAGACTAGCCCGG |
| 961 | PABPC1 | 3146809 | TTTGTTGGACGATTTAAGTCTCGTAAAGAACGAGAAGCTGAAC TTGGAGCTAGGGCAAAAGAATTCACCAATG |
| 962 | PABPC1 | 3146810 | TTAGAGTACACGATTGGGAAGTTTAAATTTTTATTCTAGGAGAT GGCAAAGAAAGCGCAAGCGCCACTTTAAAATGACGATGAAAG CTTTTTAATTTGATAGAGGTCTTTTTATTGGCATGGTACACATG CACTTCCACTCATTTGTATTGATGGGAGTGATCCCTTTAACCCT AGGTTAGCTAGAGAAGA |
| 963 | PABPC1 | 3146811 | GTTATAAATATCTAGCTAATCATATTTTGAATCTTATTTTTAATA ATTCCAAATCCATTCATTTTAAGTTAATATTTGTCAGGGAGAAG TTAGATGCACATAAGATAAAAGAATAAAAACATTTTAAAGATGA ATAACAAAAATTCATGTAGTTGTACTGGAGTGAAAATTAATAAG CTAATCTTGATTTTTACAATTGAATTTTCTACACAGTAAGTGTAA CATACA |
| 964 | PABPC1 | 3146812 | TGAAAATGGTTCCAAGGGCTATGGATTTGTACACTTTGAGACG CAGGAAGCAGCTGA |
| 965 | PABPC1 | 3146813 | GCTACATTTAGTTTAGTGCTTGAAATAGGAACTGTGCAGTAAT GGATATCTTTATTTCACAAATATCCAGGTTAGATGGCTAACAGA TTGTCTCTCAACA |
| 966 | PABPC1 | 3146815 | GGAGCGTGCTTTGGACACCATGAATTTTG |
| 967 | PABPC1 | 3146816 | TTTAGGAAATGGACTAGTTTTCATATAATATTGTTAGTTATTAGC AATGAAATGACCAATTTTAGCAAGTAGTTGGGAAGAAGTTAAA ATATTTAAATCTATAAACTACTTCCAGCTTGTAGATAAATCTGTT GCGTAATGTC |
| 968 | PABPC1 | 3146817 | AGGCAGGATGTATCAATGCATGTCAGATGGGGGTAGATAACTT TGGGGCAGGTTATCACAACCTAAGAGTTGGTGGAGAAAACAT GGGAATGAATTCTAGAGACCACAAAATGAAAACTTGAAAGTGT TACTCTTTCTCAGCTTAACGTTTTTAAATCCAAAAAACAATTTTT ACATTTCTTGGGATTCGAAGAGTTGAACTTCAGGTTGCCGTGG TTACAGTGTACAGTATATATTATCAGTCTGTACCAGTAGACCAG TACCCTAACTACTGAAAAGAATATGGCAGTTTTCCATTTGTCTA GTTTCTGTATGTACAATTTACTATCCAATTAATTACTTAAGTGGA TTTCTTGTTCTTTTTTAAAAACTTATTGCTACATTGATAGGCAGA ATAGCTTCTGAAAGTGACCAGTTTTCAATTTCATAGGAAGAGG TGACTCATTGAAAAATAGCTCAAGCAAAGTCAGCTAAAAAAAA AAAAAAACTAGGGAAGCTGAGTAGGTGTGGTCAATTGATAATG AGCTAACAGCTGATTATCACTATATTCTAGAAACTGGAACTTTC ATTTATAAAAAAAGAGGTGGCCGGAAAATTCATCCTGTC |
| 969 | PABPC1 | 3146818 | TGTGGCAGCCGACCACTTTGAAGGCCAGTTTTCTCAGGCAACT TAGACCATTTTTAGTCAAATTTTATCTTAGATTCACAGTACTGG TGGTTTTCGAGTATATTATGTTACCTTCTGAAATAGTTCCTGTC GTTTTGAGGGGCTTTTCTTTATAAAATAGTCAACTTTGGCTATA AAATGTTACTTTAGTGTAATTCCAACTGGACCAGTCTTATCTGT |

TABLE 7-continued

| Target Sequences | | | |
|---|---|---|---|
| SEQ ID NO. | Gene | Affy Probeset ID | Sequence |
| | | | AGCATGCAAGAAGTTCAAGTTTCTCTTTTATTTTTAAAAGTGGC CCATGATACCTGTAAATC |
| 970 | PABPC1 | 3146819 | CTACGAGAAGTTCAGCCCGGCCGGGCCCATCCTCTCCATCCG GGTCTGCAGGGACATGATCACCCGCCGCTCCTTGGGCTACGC GTATGTGAACTTCCAGCAGC |
| 971 | PABPC1 | 3146820 | GTCGCGGCCTGTGGCCCTGCGGGCAGC |
| 972 | PABPC1 | 3146821 | CCCGGCACTCGCTCTCCTCCTCTCACGGAAAG |
| 973 | PABPC1 | 3146822 | GATTTTTGTCCCTCTGCGCTTGCTCCCCGCTCCCCT |
| 974 | PABPC1 | 3146823 | TCGCTCCCCGCCGGCAGCCGGCAGCCAGCGGCAGTGGATCG ACCCC |
| 975 | PABPC1 | 3146824 | CCAAGAAGGAACCAAGAGACCGAGGCCTTCCCGCTGCCCGG ACCCGACACCGCCACC |
| 976 | PABPC1 | 3146825 | GCTGGCTCCATCTACGCACGTTTCGGAAACCGGGCCCGGAGG GGACCACGCCCGCTCACCCGTGCCCGGCGTCCCCCGGAGCT GGGGCTAGAGGAGCCGGGCCGGCCGCAGCGGGAAGAGGCC ACAGGCGGCCGCGCACGTGGGGGGTGGTTAGCGCGGAGGA ACCCGGAAGCCCTTTGCACCGCCCACCGCCGCGGTGACGGG TTAACGCTCCTCCTGGTGGAGGCAGGGGCGGGCGGGGCGGA AGGCGGGGACGCCTCAGCCAACACCCCCGAGGACCGCCCGC GAGCCGTCCTCCCCACCCCCACGGACGCGACGCAGCGCGGG CTCCGCTTCCCCGGCCGCGGCGCCTGCGCAAAAGCCCCGCC CCTTCGCCCGAGCCCCACCCCCACACCGCAGCCTCCACCGC CGCCACCTCTCCCTTCCTCTCTGCTCTTTCCTCCTGTTTTCTCT TCCCTCCTCCCCCTGGCCTCCGCGTCTCCTCCTACTCCGGCG CTGACGCTCGCGTAGGGGCCCTGGCGTCAGACGCGCGGGGG CGGGGCGAGTGCGGCGCGGGGTATAAGTAGAGGGTGCAGGA GGCGGTGCTTCCCCTTCTCCCCGGCGGTTAGTGCTGAGAGTG CGGAGTGTGTGCTCCGGGCTCGGAACACACATTTATT |
| 977 | PABPC1 | 3146826 | AGGCACCGCTTCTGCGGCCGACGCGCGTGGCGGCGGTGCCG GCTGGGACTCGTAGTGCGGTCCGG |
| 978 | PGM5P4-AS1 | 3159288 | ACTATGTTGTGAGCCTGCGAAAGAAGTTTGTGTG |
| 979 | PGM5P4-AS1 | 3159289 | ATGGAAAACTGGGAGCCGCCTTGGAATCTACAGGGCCGG |
| 980 | PGM5P4-AS1 | 3159291 | CGACCTCGACGGCCGTCCTGCCGAAGAACCTGCCGTCGCTG CCCGCCCCCGTGGTGCGGCCCTGACGGTCGCGCAGGCCGAC GGACGACAGCGCGCTCCGGATGAAGTTGGGCGGGTAGCT |
| 981 | PGM5P4-AS1 | 3159293 | AGCCTCCTCCAAAACAGCACACTTTCCG |
| 982 | PGM5P4-AS1 | 3159294 | TGGTTACAATGGTACTTTCAGCCTGTCCGAATTATGTATTGCC CCTCCCCTTTTTATTAATAACATTGAAGTGTGATGGGACAACCA CTGAAGCCGTCAGTTGAAACCTGCTGGGACTTTTTAGCCATTC TCTTCAACATAAAGAATGGGTGTTTTTGGAGGGGGTGAGAGG AATGGGGAAATGTTGTCAAAGAGTACAACGTTTTAGTTGAGAC AGGAAGAATATATTTTGTTGAGATCTACAGCACAGCATG |
| 983 | PGM5P4-AS1 | 3159295 | GCCTACCTAAAATATTGAATGCTGTTAATAAATCTCCTGAGGC CAGCATAAGAAGGTGATGGGCAAAACTAAT |
| 984 | PGM5P4-AS1 | 3159296 | TTGTGTATCTGCGTTCCTTTCAACAAGTGTGACTTCCTCCATG GCATCATTCGTGAGCGTAACACAGAGCTCAGC |
| 985 | PGM5P4-AS1 | 3159297 | GCTCTGAGAGGCTCTTCCTAATAGAACTGCTGCTTCAGTTTAG CTTGAAAAAGCCCACACCCAGTTCCTAATGACAAACATCTGAA CACCGGGTCTTCCCACGAGCAAGACCATGCTATGCCTCCTGC TCGCTCTGTTCTATAAGCAACCCACAGATTGCTCCCTGTGAAG A |
| 986 | PGM5P4-AS1 | 3159298 | AGTAAATCCATTTGCTGATTGCAATA |

TABLE 7-continued

Target Sequences

| SEQ ID NO. | Gene | Affy Probeset ID | Sequence |
|---|---|---|---|
| 987 | PGM5P4-AS1 | 3173158 | ACTATGTTGTGAGCCTGCGAAAGAAGTTTGTGTG |
| 988 | PGM5P4-AS1 | 3173159 | TGGTTACAATGGTACTTTCAGCCTGTCCGAATTATGTATTGCC CCTCCCCTTTTTATTAATAACATTGAAGTGTGATGGGAAAACCA CTGAAGCCGTCAGTTGAAACCTGCTGGGACTTTTTAGCCATTC TCTTCAACATAAAGAATGGGTGTTTTTGGAGGGGGTGAGAGG AATGGGGAAATGTTGTCAAAGAGTACAGTGTTTTAGTTGAGAC AGGAAGAATATATTTTGTTGAGATCTACAGCACAGCATG |
| 989 | RP11-159H20.3 | 3175548 | CCTCAATGGGAACCCTGGTGCAGAA |
| 990 | RP11-159H20.3 | 3175571 | GTGCGGGGTGGTGGCACTGTCAGCAGGGACCACTGGGAAGT TGAGGATGAGGACATCAAAAATAAC |
| 991 | RP11-159H20.3 | 3175573 | AAAGGTTACCAGTTCACCAACTGTGCTTTACGGTGAAAAACA |
| 992 | RP11-159H20.3 | 3175574 | CCACCATGACAGATGACCTGGCAGGTTATG |
| 993 | SETP14 | 3190668 | AGAACAGCAAGAAGCGATTGAACACATTGATGA |
| 994 | SETP14 | 3190670 | ATATAACAAACTCCGCCAACCATTTTTTCAGAAGAGGTCAGAA TTGATCGCCAAAATCCCAAATTTTTG |
| 995 | SETP14 | 3190675 | AGTGGTGATCCATCTTCGAAGTCCACCGAAATCAAATGGA |
| 996 | SETP14 | 3190678 | AGAGAGCTTCTTTACCTGGTTTACTGACCATTCTGATGCAGGT GCTGATGAGTTAGGAGAGGTCATCAAAGATGATATTTGGCCAA ACCCATTACAGTACTACT |
| 997 | PGM5P4-AS1 | 3208467 | GGGAGCAGCATTCCACCAGACCCTGATTTAGCAAGATATTTCC GTATCATTCCCCCAACCAGCTGGAA |
| 998 | PGM5P4-AS1 | 3208469 | CCAGACGTACAGAGGCTGGGAGCCATTGTGGTGTGCTATATT GATGACGGCAGCAGTGGG |
| 999 | PGM5P4-AS1 | 3208471 | TTGTGTATCTGCGTTCCTTTCAACAAGTGTGACTTCCTCAATGG CATCATTCGTGAGCGTAACACAGAGCTCAGC |
| 1000 | PGM5P4-AS1 | 3208473 | CTTAGAGGGCCCCACAGTTGTTTGCTG |
| 1001 | PGM5P4-AS1 | 3208475 | TGGTTACAATGGTACTTTCAGCCTGTCCGAATTATGTATTGCC CCTCCCCTTTTTATTAATAACATTGAAGTGTGATGGGACAACCA CTGAAGCCGTCTGTTGAAACCTGCTGGGACTTTTTAGCCATTC TCTTCAACATAAAGAATGGGTGTTTTTGGAGGGGGTGAGAGG AATGGGGAAATGTTGTCAAAGAGTACAATGTTTTAGTTGAGAC AGGAGGAATATATTTTGTTGAGATCTACAGCACAGCATG |
| 1002 | PGM5P4-AS1 | 3208476 | AGCCTCCTCCAAAACAGCACACTTTCCG |
| 1003 | PGM5P4-AS1 | 3208477 | AAAAATGAGCAGGTGCGGGATGTGCGCAGAGTCGGAGAAGA GTCCAGGGCGCCCGGAGTGGCTCCAGGAACGACGGAAAC |
| 1004 | PGM5P4-AS1 | 3208478 | ACTATGTTGTGAGCCTGCGAAAGAAGTTTGTGTG |
| 1005 | ASPN | 3214846 | TCATGTCTTAGAGCCCGTCTTTATGTTTAAAACTAATTTCTTAAA ATAAAGCCTTCAGTAAATGTTCATTACCAACTTGATAAATGCTA CTCATAAGAGCTGGTTTGGGGCTATAGCATATGCTTTTTTTTTT TTAATTATTACCTGATTTAAAAATCTCTGTAAAAACGTGTAGTGT TTCATAAAATCTGTAACTCGCATTTTAATGATCCGCTATTATAA GCTTTTAATAGCATGAAAATTGTTAGGCTATATAACATTGCCAC TTCAACTCTAAGGAATATTTTTGAGATATCCCTTTGGAAGACCT TGCTTGGAAGAGCCTGGACACTAACAATTCTACACCAAATTGT CTCTTCAAATACGTATGGACTGGATAACTCTGAGAA |

TABLE 7-continued

Target Sequences

| SEQ ID NO. | Gene | Affy Probeset ID | Sequence |
|---|---|---|---|
| 1006 | ASPN | 3214847 | CTAATTCAATTGCAAGAGTGGGAGTAAATGACTTCTGTCCAAC AGTGCCAAAGATGAAGAAATCTTTATACAGTGCAATAAGTTTAT TCAACAACCCGGTGAAATACTGGGAAATGCAACCTGCAACATT TCGTTGTGTTTTGAGCAGAATGAGCGTTCAGCTTGGGAAC |
| 1007 | ASPN | 3214848 | TGACAACTCTTAACTGGCTGGAAGGGGCCACAGATTCCTTGG AGAATCTAATAAAGATTTAGATCTTCCCAAGAACAAAAGTTTTC ATCTTCCAAGGAGCTTGAGAACAAAACTGGGCAACAAGCCACT CTGCCTCTTCTCTTTTTCTTTCCGGTGTATCTTTAAACAAGTTT CGTTCACTGTACTCCTTTGAGATACAAACCATCAAAATGAATGT AATATAGGCAGGTGCTAATCTCAAGATCACAACTTTTGCTTTGA CTTTTCCAAATGCTGCATTTGGATGTCTGTTTAGCCAGTGACTA CAACTTGAGTCCGTCCTCTCTCAAGCTGCCCCATCCCTGATGT CATTTCTGCTTAATTTGCTCCACAACTCTGCTTCCAGCTTCTGG TCTCTCTTAAATC |
| 1008 | ASPN | 3214849 | ACATTCTACTTGTGTTCAGTAGATATTGGTATTTTTCTTCAGTTT TTATAACACACTTTAGCACACCTCAAGCAAAGACCAAGTAAGC AGCAAGGGTGATTCAAACATAATGACTCTCCAGGTTGCATGAG GTG |
| 1009 | ASPN | 3214850 | ATCACAGATATCGAAAATGGGAGTCTTGCTAACATACCACGTG TGAGAGAAATACATTTGGAAAACAATAAACTAAAAAAAATCCCT TCAGGATTACCAGAGTTGAAATACCTCCAG |
| 1010 | ASPN | 3214851 | TAGGACAGGCTTATATTCTAACTAGTTTGCGGTGTTTTCAGCTA ACTCTATCACACCTAACCATCTGTGTAAGACTTGATGCATT |
| 1011 | ASPN | 3214852 | GCTTACCACCAACTTTATTGGAGCTTCACTTAGATTATAATAAA ATTTCAACAGTGGAACTTGAGGAT |
| 1012 | ASPN | 3214853 | GATAAATGATATCACATGGAAGCTGTCAGCCAAATCCACAAAA GGAGTGTCTCAAACAAATTAATATGGAAATAAATCAAAAGAAG AGGGAGAAAAAAGGAGGGAGTATGTTGTACATTAAGAGAGATT TCAAGAGCGATAAGAACCAAATGTATTCTGTAAACTTCATTTAA TCCTAACTTGAACAAATCAACTGTAAAATGACGTATTTGAGA |
| 1013 | ASPN | 3214854 | CCGGTACAAAAGTGTGCTAACATTTGTCAGCAGTTACTGAGCT TCTGCCAAATTCACACCTCTGCTCGTTTTATCCTAGAGGCTAC ACTTCAATCTTCTCTCTGGTTACCCACCTTCCCCATTTCCTAAG GGACACAACAGTTCCCTCAACTTCTACAAGTCCTCTCCCAGAG ATTA |
| 1014 | ASPN | 3214855 | CCCAGGCATTTAGCCACAGTTTGAGGTGAAGCCTATGAGCCC AGACTGGGCAGCCCCTGGCTCTGGCAGGAATGGACATGCCAT TCAAGGCAAGGCATTTTGTACCCAGCTTCTTCCCAGGTGTACT GTGAAGACTAATGGGCCAATACACAGAAAGGTCTGAGGACAA CATCCAGCACGTAGGAAGTGACCACCTGTGACATAATCATTAC CAAGATGAGCACTGTGCTCTTTATCATGGCTTTGTGTGACCCA AGGCTAGCACCTCAAGTAGAATGCTCCTTAAGTCTGCCAGATG ACCAGTGTTCTAACCCATTACTTCCAAGCTCCCTGTCTGATGA TTAGCTGCATA |
| 1015 | ASPN | 3214856 | TAATAATGGGATAGAGCCAGGGGCATTTGAAGGGGTGACGGT GTTCCATATCAGAATTGCAGAAGCAAAACTGACCTCAGTTCCT A |
| 1016 | ASPN | 3214857 | CCTGAACAACAACAAGCTAACGAAGATTCACCCAAAAGCCTTT CTAACCACAAAGAAGTTGCGAAGGCTGTATCTGTCCCACAATC AACTAAGTGAAATACCACTTAATCTTCCCAAATCATTAGCAGAA CTC |
| 1017 | ASPN | 3214858 | AATACTGGTAAATCAAATCCACTTCC |
| 1018 | ASPN | 3214859 | ATTCCATTTGATACTCGAATGCTTGATC |
| 1019 | ASPN | 3214860 | ATGGGTCTTAAGCTTTACCTGTGGAATTCTCATGAGAAAGAGA TTAAGATGCAAGTACTGTTTGAGAAAACTTGTTCATGTAGAAC GACTGTGGA |
| 1020 | ASPN | 3214861 | TGCTATTCTGACAATTTAAAGGATGGAAAAAGTCTCATTGAAAT TTCAAAAATAATCTGAGTGTATAAGTTTTTTTCATTTAAGTTTTT AGGTGGAAAGTACAGCAAACCCCAAAGTACATCCAAACTTATT TTTAAAATTAAGAAAATCAAAGGAAAACTAAGGGAATGTTGTCC |

TABLE 7-continued

| Target Sequences | | | |
|---|---|---|---|
| SEQ ID NO. | Gene | Affy Probeset ID | Sequence |
| | | | ATAGAACATTTCCTTCTCTTCCCCAGTTAAATCAAAGCATTTAA TTTTAATTCCCTTCAGAGAGAATGGACATCACATGCAGTTCTAT CTCAGGGTGCTAGCAGGTTGAGACTGTACTTTTCAGTAAAACT CCATGATAACAAAATAAGCTGCATGTCTAGAACAATGAAATGA GTTATAGAAAGCTTGTGAAATCTCTAATCTA |
| 1021 | ASPN | 3214862 | TTTGATCTGTTTCCAATGTGTCCATTTGGATGTCAGTGCTATTC ACGAGTTGTACATTGC |
| 1022 | ASPN | 3214863 | TGTGCTCCTATTATTCCTGGCTTTGTGCTCTGCCAAACCCTTCT TTAGCCCTTCACACATCGCACTGAAGAATATGATGCTGAAGGA TATGG |
| 1023 | ASPN | 3214864 | TCCTAGACTGGTCTTCTACACTAAGACACC |
| 1024 | ASPN | 3214865 | GAAGTTTGGGGATATCACAGCTATATTAAATGAAACAGTAAATA TATTTTTCAATATTTAAAATATTTTCTAATGTGTATTTAAAATGTG TGAATTACTGAAATGTCAATTTTACTTATACATTTGAATATTCAT TTTTTTCCTTGATAAATGTCTTCCTTATTATAATGAAATGGCACT GAAAAGTTCAAATGGAAATCTATTCAATTCCAAGAAAGAATACT TATCAGCAATAGTTTAGCTAGCACTATATTCAATATGAAAGATT AGGAAATTTTCACAGCATGTATACAGTCAGAATTTAACACTTTC AAAGATTTCCTTTGTCTACTCCCAAAGTAAATTTCTGATTAAATT TTAGATTAAAAAATTTAAGCAATGTATTCAATATTCTACTCCCTA GTAATCTAAATAGCGCACAGCATTCTTTCATGTTAATCTATTCA GAGGTGTGGCACCCAGGAAACA |
| 1025 | ASPN | 3214866 | TGGACTAATCTGTGGGAGCAGTTTATTCCAGTATCACCCAGGG TGCAGCCACACCAGGACTGTGTTGAAGGGTGTTTTTTTTCTTT TAAATGTAATACCTCCTCATCTTTTCTTCTTACACAGTGTCTGA GAACATTTACATTATAGATAAGTAGTACATGGTGGATAACTTCT ACTTTTAGGAGGACTACTCTCTTC |
| 1026 | ARL6IP1P2 | 3242825 | GGAAACGCCTCTTCACACTAAAGGAAGAA |
| 1027 | ARL6IP1P2 | 3242826 | TGACTTCCTTACTATTGCTTCCTGGACTAA |
| 1028 | MKI67 | 3312496 | ACTCGTGAGCACATCTTTAGGGACCAAGAGTGACTTTCTGTAA GGAGTGACTCGTGGCTTGCCTTGGTCTCTTGGGAATACTTTTC TAACTAGGGTTGCTCTCACCTGAGACATTCTCCACCCGCGGAA TCTCAGGGTCCCAGGCTGTGGGCCATCACGACCTCAAACTGG CTCCTAATCTCCAGCTTTCCTGTCATTGAAAGCTTCGGAAGTTT ACTGGCTCTGCTCCCGCCTGTTTTCTTTCTGACTCTATCTGGC AGCCCGATGCCACCCAGTACAGGAAGTGACACCAGTACTCTG TAAAGCATCATCATCCTTGGAGAGACTGAGCACTCAGCACCTT CAGCCACGATTTCAGGATCGCTTCCTTGTGAGCCGCTGCCTC CGAAATCTCCTTTGAAGCCCAGACATCTTTCTCCAGCTTCAGA CTTGTAGATATAACTCGTTCATCTTCATTTACTTTCCACTTTGC CCCCTGTCCTCTCTGTGTTCCCCAAATCAGAGAATAGCCCGCC ATCCCCCAGGTCACCTGTCTGGATTCCTCCCCATTCACCCACC TTGCCAGGTGCAGGTGAGGATGGTGCACCAGACAGGGTAGCT GTCCCCCAAAATGTGCCCTGTGCGGGCAGTGCCCTGTCTCCA CGTTTGTTTCCCCAGTGTCTGGCGGGGAGCCAGGTGACATCA TAAATACTTGCTGAATGAATGCAGAAATCAGCGGTACTGACTT GTACTATATTGGCTGCCATGATAGGGTTCTCACAGCGTCATCC ATGATCGTAAGGGAGAATGACATTCTGCTTGAGGGAGGGAAT AGAAAGGGGCAGGGAGGGGACATCTGAGGGCTTCACAGGGC TGCAAAGGGTACAGGGATTGCACCAGGGCAGAACAGGGGAG GGTGTTCAAGGAAGAGTGGCTCTTAGCAGAGGCACTTTGGAA GGTGTGAGGCATAAATGCTTCCTTCTACGTAGGCCAACCTCAA AACTTTCAGTAGGAATGTTGCTATGATCAAGTTGTTCTAACACT TTAGACTTAGTAGTAATTATGAACCTCACATAGAAAAATTTCAT CCAGCCATATGCCTGTGGAGTGGAATATTCTGTTTAGTAGAAA AATCCTTTAGAGTTCAGCTCTAACCAGAAATCTTGCTGAAGTAT GTCAGCACCTTTTCTCACCCTGGTAAGTACAGTATTTCAAGAG CACGCTAAGGGTGGTTTTCATTTTACAGGGCTGTTGATGATGG GTTAAAAATGTTCATTTAAGGGCTACCCCCGTGTTTAATAGATG AACACCACTTCTACACAACCCTCCTTGGTACTGGGGGAGGGA GAGATCTGACAAATACTGCCCATTCCCCTAGGCTGACTGGATT TGAGAACA |
| 1029 | MKI67 | 3312497 | ATGAGCGCACGGATGAATGGAGCTTACAAGATCTGTCTTTCCA ATGGCCGGGGGCATTTGGTCCCCAAATTAAGGCTATTGGACA TCTGCACAGGACAGTCCTATTTTTGATGTC |

TABLE 7-continued

| Target Sequences | | | |
|---|---|---|---|
| SEQ ID NO. | Gene | Affy Probeset ID | Sequence |
| 1030 | MKI67 | 3312498 | AGGAACAACTATCCTCGTCTGTCCCAACACTGAGCAGGCACT CGGTAAAC |
| 1031 | MKI67 | 3312499 | ATTTGCTGGGTCTGAATCGGCTTCATAAACTCCACTGGGAGCA CTGCTGGGCTCCTGGACTGAGAATAGTTGAACACCGGGGGCT TTGTGAAGGAGTCTGGGCCAAGGTTTGCCCTCAGCTTTGCAG AATGAAGCCTTGAGGTCTGTCACCACCCACAGCCACCCTACA GCAGCCTTAACTGTGACACTTGCCACACTGTGTCGTCGTTTGT TTGCCTATGTCCTCC |
| 1032 | MKI67 | 3312500 | GGACAATGTGTGTGTCAAGAAAATAAGAACCAGAAGTCATAGG GACAGTGAAGATATTTG |
| 1033 | MKI67 | 3312501 | GTTCAGCAAACGAAACTCATGTAGCAATAACCTCTTCAGATAC AGAATTCTGGCAAGTACAGCTGTCCAGACAGACCCTCTTCGG CACAAACTAGGAAGCTTCAACTG |
| 1034 | MKI67 | 3312502 | CAGAAGAGTGCGAAGGTTCTCATGCAGAATCAGAAAGGGAAA GGAGAAGCAGGAAATTCAGACTCCATGTGCCTGAGATCAAGA AAGACAAAAAGCCAGCCTGCAGCAAGCACTTTGGAGAGCAAA TCTGTGCAGAGAGTAACGCGGAGTGTCAA |
| 1035 | MKI67 | 3312503 | GAGCCCGGAAACCCATACCTAGAGACAAAG |
| 1036 | MKI67 | 3312504 | TATCCCTGCGCTCCAGACGCCAAAAT |
| 1037 | MKI67 | 3312505 | GAGCAAAGTACCAAGGCATTACCTTGA |
| 1038 | MKI67 | 3312506 | AAGAGGCTGCGCTGCATGCCAGCACCAGAGGAAATTGTGGAG GAGCTGCCAGCCAGCAAGAAGCAGAGGGTTGCTCCCAGGGC AAGAGGCAAATCATCCGAACCCGTGGTCATCATGAAGAGAAG TTTGAGGACTTCTGCAAAAAGAATTGAACCTGCGGAAGAGCTG AACAGCAACGACATGAAAACCAACAAAGAGGAACACAAATTAC AAGACTCGGTCCCTG |
| 1039 | MKI67 | 3312507 | CCCGTGCTCTAGAAGACCTGGTTGACTTCAAAGAGCTCTTCTC AGCACCAGGTCACACTGAAGAGTCAATGACTATTGACAAAAAC ACAAAAATTCCCTGCAAATCTCCCCCACCAGAACTAACAGACA CTGCCACGAGCACAAAGAGATGCCCCAAGACACGTCCCAGGA AAGAAGTAAAAGAGGAGCTCTCAGCAGTTGAGAGGCTCACGC AAACATCAGGGCAAAGCACACACACACACAAAGAACCAGCAA GCGGTGATGAGGGCATCAAAGTATTGAAGCAACGTGCAAAGA AGAAACCAAACCCAGTAGAAGAGGAACCCAGCAGGAGAAGGC CAAGAGCACCTAAGGAAAAGGCCCAACCCCTGGAAGACCTGG CCGGCTTCACAGAGCTCTCTGAAACATCAGGTCACACTCAGG AATCACTGACTGCTGGCAAAGCCACTAAAATACCCTGCGAATC TCCCCCACTAGAAGTGGTAGACACCACAGCAAGCACAAAGAG GCATCTCAGGACACGTGTGCAGAAGGTACAAGTAAAAGAAGA GCCTTCAGCAGTCAAGTTCACACAAACATCAGGGGAAACCAC GGATGCAGACAAAGAACCAGCAGGTGAAGATAAAGGCATCAA AGCATTGAAGGAATCTGCAAAACAGACACCGGCTCCAGCAGC AAGTGTAACTGGCAGCAGGAGACGGCCAAGAGCACCCAGGG AAAGTGCCCAAGCCATAGAAGACCTAGCTGGCTTCAAAGACC CAGCAGCAGGTCACACTGAAGAATCAATGACTGATGACAAAAC CACTAAAATACCCTGCAAATCATCACCAGAACTAGAAGACACC GCAACAAGCTCAAAGAGACGGCCCAGGACACGTGCCCAGAAA GTAGAAGTGAAGGAGGAGCTGTTAGCAGTTGGCAAGCTCACA CAAACCTCAGGGGAGACCACGCACACCGACAAAGAGCCGGTA GGTGAGGGCAAAGGCACGAAAGCATTTAAGCAACCTGCAAAG CGGAAGCTGGACGCAGAAGATGTAATTGGCAGCAGGAGACAG CCAAGAGCACCTAAGGAAAAGGCCCAACCCCTGGAAGATCTG GCCAGCTTCCAAGAGCTCTCTCAAACACCAGGCCACACTGAG GAACTGGCAAATGGTGCTGCTGATAGCTTTACAAGCGCTCCAA AGCAAACACCTGACAGTGGAAAACCTCTAAAAATATCCAGAAG AGTTCTTCGGGCCCCTAAAGTAGAACCCGTGGGAGACGTGGT AAGCACCAGAGACCCTGTA |
| 1040 | MKI67 | 3312508 | GGAGAACTCTTAGCGTGCAGGAATCTAATGCCATCAGCAGGC AAAGCCATGCACACGCCTAAACCATCAGTAGGTGAAGAGAAA GACATCATCATATTTGTGGGAACTCCAGTGCAGAAACTGGACC TGACAGAGAACTTAACCGGCAGCAAGAGACGGCCACAAACTC CTAAGGAAGAGGCCCAGGCTCTGGAAGACCTGACTGGCTTTA AAGAGCTCTTCCAGACCCCTGGTCATACTGAAGAAGCAGTGG |

TABLE 7-continued

Target Sequences

| SEQ ID NO. | Gene | Affy Probeset ID | Sequence |
|---|---|---|---|
| | | | CTGCTGGCAAAACTACTAAAATGCCCTGCGAATCTTCTCCACC |
| | | | AGAATCAGCAGACACCCCAACAAGCACAAGAAGGCAGCCCAA |
| | | | GACACCTTTGGAGAAAAGGGACGTACAGAAGGAGCTCTCAGC |
| | | | CCTGAAGAAGCTCACACAGACATCAGGGGAAACCACACACAC |
| | | | AGATAAAGTACCAGGAGGTGAGGATAAAAGCATCAACGCGTTT |
| | | | AGGGAAACTGCAAAACAGAAACTGGACCCAGCAGCAAGTGTA |
| | | | ACTGGTAGCAAGAGGCACCCAAAAACTAAGGAAAAGGCCCAA |
| | | | CCCCTAGAAGACCTGGCTGGCTTGAAAGAGCTCTTCCAGACA |
| | | | CCAGTATGCACTGACAAGCCCACGACTCACGAGAAAACTACC |
| | | | AAAATAGCCTGCAGATCACAACCAGACCCAGTGGACACACCA |
| | | | ACAAGCTCCAAGCCACAGTCCAAGAGAAGTCTCAGGAAAGTG |
| | | | GACGTAGAAGAAGAATTCTTCGCACTCAGGAAACGAACACCAT |
| | | | CAGCAGGCAAAGCCATGCACACACCCAAACCAGCAGTAAGTG |
| | | | GTGAGAAAAACATCTACGCATTTATGGGAACTCCAGTGCAGAA |
| | | | ACTGGACCTGACAGAGAACTTAACTGGCAGCAAGAGACGGCT |
| | | | ACAAACTCCTAAGGAAAAGGCCCAGGCTCTAGAAGACCTGGC |
| | | | TGGCTTTAAAGAGCTCTTCCAGACACGAGGTCACACTGAGGA |
| | | | ATCAATGACTAACGATAAAACTGCCAAAGTAGCCTGCAAATCT |
| | | | TCACAACCAGACCCAGACAAAAACCCAGCAAGCTCCAAGCGA |
| | | | CGGCTCAAGACATCCCTGGGGAAAGTGGGCGTGAAAGAAGA |
| | | | GCTCCTAGCAGTTGGCAAGCTCACACAGACATCAGGAGAGAC |
| | | | TACACACACACACACAGAGCCAACAGGAGATGGTAAGAGCAT |
| | | | GAAAGCATTTATGGAGTCTCCAAAGCAGATCTTAGACTCAGCA |
| | | | GCAAGTCTAACTGGCAGCAAGAGGCAGCTGAGAACTCCTAAG |
| | | | GGAAAGTCTGAAGTCCCTGAAGACCTGGCCGGCTTCATCGAG |
| | | | CTCTTCCAGACACCAAGTCACACTAAGGAATCAATGACTAACG |
| | | | AAAAAACTACCAAAGTATCCTACAGAGCTTCACAGCCAGACCT |
| | | | AGTGGACACCCCAACAAGCTCCAAGCCACAGCCCAAGAGAAG |
| | | | TCTCAGGAAAGCAGACACTGAAGAAGAATTTTTAGCATTTAGG |
| | | | AAACAAACGCCATCAGCAGGCAAAGCCATGCACACACCCAAA |
| | | | CCAGCAGTAGGTGAAGAGAAAGACATCAACACGTTTTTGGGA |
| | | | ACTCCAGTGCAGAAACTGGACCAGCCAGGAAATTTACCTGGC |
| | | | AGCAATAGACGGCTACAAACTCGTAAGGAAAAGGCCCAGGCT |
| | | | CTAGAAGAACTGACTGGCTTCAGAGAGCTTTTCCAGACACCAT |
| | | | GCACTGATAACCCCACGACTGATGAGAAAACTACCAAAAAAAT |
| | | | ACTCTGCAAATCTCCGCAATCAGACCCAGCGGACACCCCAAC |
| | | | AAACACAAAGCAACGGCCCAAGAGAAGCCTCAAGAAAGCAGA |
| | | | CGTAGAGGAAGAATTTTTAGCATTCAGGAAACTAACACCATCA |
| | | | GCAGGCAAAGCCATGCACACGCCTAAAGCAGCAGTAGGTGAA |
| | | | GAGAAAGACATCAACACATTTGTGGGGACTCCAGTGGAGAAA |
| | | | CTGGACCTGCTAGGAAATTTACCTGGCAGCAAGAGACGGCCA |
| | | | CAAACTCCTAAAGAAAAGGCCAAGGCTCTAGAAGATCTGGCT |
| | | | GGCTTCAAAGAGCTCTTCCAGACACCAGGTCACACTGAGGAA |
| | | | TCAATGACCGATGACAAAATCACAGAAGTATCCTGCAAATCTC |
| | | | CACAACCAGACCCAGTCAAAACCCCAACAAGCTCCAAGCAAC |
| | | | GACTCAAGATATCCTTGGGGAAAGTAGGTGTGAAAGAAGAGG |
| | | | TCCTACCAGTCGGCAAGCTCACACAGACGTCAGGGAAGACCA |
| | | | CACAGACACACAGAGAGACAGCAGGAGATGGAAAGAGCATCA |
| | | | AAGCGTTTAAGGAATCTGCAAAGCAGATGCTGGACCCAGCAA |
| | | | ACTATGGAACTGGGATGGAGAGGTGGCCAAGAACACCTAAGG |
| | | | AAGAGGCCCAATCACTAGAAGACCTGGCCGGCTTCAAAGAGC |
| | | | TCTTCCAGACACCAGACCACACTGAGGAATCAACAACTGATGA |
| | | | CAAAACTACCAAAATAGCCTGCAAATCTCCACCACCAGAATCA |
| | | | ATGGACACTCCAACAAGCACAAGGAGGCGGCCCAAAACACCT |
| | | | TTGGGGAAAAGGGATATAGTGGAAGAGCTCTCAGCCCTGAAG |
| | | | CAGCTCACACAGACCACACACACAGACAAAGTACCAGGAGAT |
| | | | GAGGATAAAGGCATCAACGTGTTCAGGGAAACTGCAAAACAG |
| | | | AAACTGGACCCAGCAGCAAGTGTAACTGGTAGCAAGAGGCAG |
| | | | CCAAGAACTCCTAAGGGAAAAGCCCAACCCCTAGAAGACTTG |
| | | | GCTGGCTTGAAAGAGCTCTTCCAGACACCAATATGCACTGACA |
| | | | AGCCCACGACTCATGAGAAAACTACCAAAATAGCCTGCAGATC |
| | | | TCCACAACCAGACCCAGTGGGTACCCCAACAATCTTCAAGCC |
| | | | ACAGTCCAAGAGAAGTCTCAGGAAAGCAGACGTAGAGGAAGA |
| | | | ATCCTTAGCACTCAGGAAACGAACACCATCAGTAGGGAAAGCT |
| | | | ATGGACACACCCAAACCAGCAGGAGGTGATGAGAAAGACATG |
| | | | AAAGCATTTATGGGAACTCCAGTGCAGAAATTGGACCTGCCAG |
| | | | GAAATTTACCTGGCAGCAAAAGATGGCCACAAACTCCTAAGGA |
| | | | AAAGGCCCAGGCTCTAGAAGACCTGGCTGGCTTCAAAGAGCT |
| | | | CTTCCAGACACCAGGCACTGACAAGCCCACGACTGATGAGAA |
| | | | AACTACCAAAATAGCCTGCAAATCTCCACAACCAGACCCAGTG |
| | | | GACACCCCAGCAAGCACAAAGCAACGGCCCAAGAGAAACCTC |
| | | | AGGAAAGCAGACGTAGAGGAAGAATTTTTAGCACTCAGGAAA |
| | | | CGAACACCATCAGCAGGCAAAGCCATGGACACACCAAAACCA |
| | | | GCAGTAAGTGATGAGAAAAATATCAACACATTTGTGGAAACTC |

TABLE 7-continued

| Target Sequences | | | |
|---|---|---|---|
| SEQ ID NO. | Gene | Affy Probeset ID | Sequence |
| | | | CAGTGCAGAAACTGGACCTGCTAGGAAATTTACCTGGCAGCA AGAGACAGCCACAGACTCCTAAGGAAAAGGCTGAGGCTCTAG AGGACCTGGTTGGCTTCAAAGAA |
| 1041 | MKI67 | 3312509 | AACAACAGTTGAAGGCATCCCTGGGGAAAGTAGGTGTGAAAG AAGAGCTCCTAGCAGTCGGCAAGTTCACACGGACGTCAGGGG AGACCACGCACACGCACAGAGAGCCAGCAGGAGATGGCAAG AGCATCAGAACGTTTAAGGAGTCTCCAAAGCAGATCCTGGAC CCAGCAGCCCGTGTAACTGGAATGAAGAAGTGGCCAAGAACG CCTAAGGAAGAGGCCCAGTCACTAGAAGACCTGGCTGGCTTC AAAGAGCTCTTCCAGACACCAGGTCCCTCTGAGGAATCAATGA CTGATGAGAAAACTACCAAAATAGCCTGCAAATCTCCACCACC AGAATCAGTGGACACTCCAACAAGCACAAAGCAATGGCCTAA GAGAAGTCTC |
| 1042 | MKI67 | 3312510 | TGCAAACAGGTCAGGAAGGTCTACAGAGTTCAGGAATATACA GAAGCTACCTGTGGAAAGTAAGAGTGAAGAAACAAATACAGAA ATTGTTGAGTGCATCCTAAAAAGAGGTCAGAAGGCAACACTAC TACAACAAAGGAGAGAAGGAGAGATGAAGGAAATAGAAAGAC CTTTTGAGACATATAAGGAAAATATTGAATTAAAAGAAAACGAT GAAAAGATGAAAGCAATGAAGAGATCAAGAACTTGGGGGCAG AAATGTGCACCAATGTCTGACCTGACAGACCTCAAGAGCTTGC CTGATACAGAACTCATGAAAGACACGGCACGTGGC |
| 1043 | MKI67 | 3312511 | CCCAGTGAAGGAGCAACCGCAGTTGACAAGCACATGTCACAT CGCTATTTCAAATTCAGAGA |
| 1044 | MKI67 | 3312512 | TGGCCTCTAGATCCTAGCAGGGAGGCCTATGGGTCTCAGGAG CCCGTCACCAGCCTCCGTGCTCCAGAGCTCACGTGTGGGGTC TTGTTAGGAGGACCCAGA |
| 1045 | MKI67 | 3312513 | TAAAAACGTAGTCTTAGATCTTATAAATCTTTTGACTCTACTGTT TTTTACTGTGTTAATGTTTGTTTTGCTAACTTTGTTTATCTGCTG |
| 1046 | MKI67 | 3312514 | CGCAAACTCTCCTTGTACCATAATAATAGGGAAAGCTCATACT GAAAAAGTACATGTGCCTGCTCGACCCTACAGAGTGCTCAA |
| 1047 | MKI67 | 3312515 | AGCCTGTGGGCGAAGTTCACAGTCAA |
| 1048 | MKI67 | 3312516 | CATGGGCAGATGTAGTAAAACTTGGTGCAAAACAAACACAAAC TAAAGTCATAAAACATGGTCCTCAAAGGTC |
| 1049 | MKI67 | 3312517 | AAGAGAGTGTCTATCAGCCGAAGTCAACATGATATTTTACAGA TGATATGTTCCAAAAGAAGAAGTGGTGCTTCGGAAGCAAAT |
| 1050 | MKI67 | 3312518 | AAACAAGAGTCAGGTTCAGAAATCCATGTGGAAGTGAAGGCA CAAAGCTTGGTTATAAGCCCTCCAGCTCCTAGTCCTAGGAAAA CTCCAGTTGCCAGTGATCAACGCCGTAGGTC |
| 1051 | MKI67 | 3312519 | CCTTTGAAAAGAAGGCGTGTGTCCTTTGGTGGGCACCTAAGA CCTGAACTATTTGATGAAAACTTGCCTCCTAATACGCCTCTCAA AAGGGGAGAAGCCCCAACCAAAAGAAAGTCTCTGGTAATGCA CACTCC |
| 1052 | MKI67 | 3312520 | GGACAGATGTGCTCTGGGTTACCTGGTCTTAGTTCAGTTGATA TCAACAACTTTGGTGATTCCATT |
| 1053 | MKI67 | 3312521 | TTGAGAGGAAGATCCAAAAGGATTCCCTCAG |
| 1054 | MKI67 | 3312522 | GAAGCTTTCAACTAGAAATCGAACACCAGCTAAAGTTGAAGAT GCAGCTGACTCTGCCACTAAGCCAGAAAATCTCTCTTCCAAAA CCAGAGGAAGTATTCCTACAGATGTGGAAGTTCTGCCTACGG AAACTGAAATTCACAATGAGC |
| 1055 | MKI67 | 3312523 | CCAGCGTTAAATTAGTGAGCCGTTATGGAGAATTGAAGTCTGT TCCCACTACACAATGTCTTGACAATAGCAAAAAAAATGAATCTC CCTTTTGGAAGCTTTATGAGTCAGTGAAGAAAGAGTTGGATGT AAAATCACAAAAAGAAAATGTCCTACAGTATTGTAGAAAATCTG GATTACAAACTGATTACGCAACAGAGAAAGAAAGTGCTGATGG TTTACAGGGGGAGACCCAACTGTTGGTCTCGCGTAAGTCAAG ACCAAAATCTGGTGGGAGCGGCCACGCTGTGGCAGAGCCTG CTTCACCTGAACAAGAGCTTGACCAGAACAAGGGGAAGGGAA GAGACGTGGAGTCTGTTCAGACTCCCAGCAAGGCTGTGGGCG CCAGCTTTCCTCTCTATGAGCCGGCTAAAATG |

TABLE 7-continued

Target Sequences

| SEQ ID NO. | Gene | Affy Probeset ID | Sequence |
|---|---|---|---|
| 1056 | MKI67 | 3312524 | AGCCAGCACGTCGTGTCTCAAGATCTAGCTTCT |
| 1057 | MKI67 | 3312525 | GGCTCTCAGATCCACCCTAAGTATCCACCAGCCAAGAGGGCG CACATGCCAAGTGGAGCCTCAGTTCATCGACAGGTCCTATGG CCCATTTATGAGAAAACTGATGACGCAGTCAGTAGTTCTGA |
| 1058 | MKI67 | 3312526 | TTCAGAATGGAAGGAAGTCAACTGAATTTC |
| 1059 | MKI67 | 3312527 | CCAACACAAGTAAATGGGTCTGTTATTGATGAGCCTGTACGGC TAAAACATGGAGATGTAATAACTATTATTGATCGTTCCTTCAG |
| 1060 | MKI67 | 3312528 | TGTGACATCCGTATCCAGCTTCCTGTTGTGTCAAAACAACATT |
| 1061 | MKI67 | 3312529 | GGCTCCTTGTGGCAATAGGAAAATGGGACAGAAAGTCTTCCT GCCTGGAATTCGAGAACGTTTCCTCTTATATTGCTGTCCTGTTT GGTGG |
| 1062 | MKI67 | 3312530 | CCTGAGCCTCAGCACCTGCTTGTTTGGAAG |
| 1063 | MKI67 | 3312531 | CCCACGAGACGCCTGGTTACTATCAA |
| 1064 | MKI67 | 3312532 | TTTGCTTCTGGCCTTCCCCTACGGATTATACCTGGCCTTCCCC TACGGATTATACTCAACTTACTGTTTAGA |
| 1065 | MKI67 | 3312533 | GACTCGGTGGGAGCCGCTAGAGCCGGGCGCCCGGGGACGTA GCCTGTAGGGCCACCGGGTCCCCGTCAGAGGCGGCGGCGG GAGCAGCGGGGACTGCAGGCCGGGGTGCAGCGAACGCGAC CCCGCGGGCTGCGGCCCGGTGTGTGCGGAGCGTGGCGGGC GCAGCTTACCGGGCGGAGGTGAGCGCGGCGCCGGCTCCTCC TGCGGCGGACTTTGGGTGCGACTTGACGAGCGGTGGTTCGAC AAGTGGCCTTGCGGGCCGGAT |
| 1066 | GLYATL1P3 | 3331888 | ATGGCTCTCTGTTTCACATCAATCACGGGAACCCCTTCAACAT GGAAGTGTTGGTGGACTCCTGGCCCGAGTATCAGATGGTTAT TATCCGACCTC |
| 1067 | GLYATL1P3 | 3331891 | TGCGTTACATCAAGCGCTGCCTAGGAGCCCTGCCAGCAGCCT GTATGCTGGGCCCAGAGGGGGTCCCGGTCTCATGGGTAACCA TGGACCCTTCTTGTGAAATAGGAATGGGCTACAGTGTGGAAAA ATACCGAAGGAGAGGCAATGGGACACGGCTGATCATGCGATG CATGAAGTATCTGTGTCAGAAGAATATTCCATTTTACGGCTCTG TGCTGGAAGAAAATCAAGGCGTCATCAGAAAGACTAGTGCACT AGGTTTCCTTGAGGCCTCC |
| 1068 | GLB1L3 | 3357343 | ATGGACGATCTAGGAAACTTTCAGGGAGCTAAGGTGTCGGAG AGCAAAGTATCCTT |
| 1069 | GLB1L3 | 3357345 | GTCCCGCTACTTCGTCACCAAAGCGCCCGCCGCGCTCGCATC TGCTGTGAGGCTGTGCTCGGGCCGCTCCCGCCGAGGGAACG GCCCTCCCAAGGCTCTGCGCCCCAATTCTCGCTCGTTTGCCA AGA |
| 1070 | GLB1L3 | 3357347 | TGTCGACCCAGGTTAGGAAGCCCGAGGTCGGGGCGTTACCC CAAGGGCCCTCCCGCTTCCCCTCCGAGGGCAGAGAGGCGTC CGCGCCCGGACGCACTGCGGGAACACCTGGAGCGCCGGCG GAGCTCGGCTGTCCCCGCGGGAGGGAGCCCGACGCGCATCC TTGGGACCCGGACCCGGCGCCCGCGCCTCGGGACGGATTTC TGCCTCGGCTGCAGGCGCAGCGCGCAGACCTGAGCCT |
| 1071 | GLB1L3 | 3357348 | CCTGGAAGAGAATGGCGGGCATCTTTTTCCTGCCATTTATCTC ATCAGGTTTTGCTCCTCGGTTTAAGCAGGAAGAGAACTTCATG CTTGGAAGAGCGCATCCG |
| 1072 | GLB1L3 | 3357349 | GCTGAAGAATCGATCTGTGGGACTTGGAACTGAAAGCACAGG TCGGGGTAAGCCCCACTTCACACTGGAGGGCCACAAGTTCCT GATCTTCGGGGGCTCCATCCACTATTTCCGGGTGCCCAGGGA GTACTGGAGGGACCGCCTGCTGAAGCTGAAGGCCTGTGGCTT CAATACTGTCAC |
| 1073 | GLB1L3 | 3357350 | ATGTTCCGTGGAACCTGCATGAGCCAGAAAGAGGCAAATTTG ACTTCTCTGGGAACCTGGACCTGG |
| 1074 | GLB1L3 | 3357351 | GCTACTGGGGGTGGATTAGCAACCAAA |

TABLE 7-continued

| Target Sequences | | | |
|---|---|---|---|
| SEQ ID NO. | Gene | Affy Probeset ID | Sequence |
| 1075 | GLB1L3 | 3357352 | CCCGATGGGGCTGTGCAGAGGCTCTGAGGCTGGGAGCAGCT CAGGCCACCGACCTG |
| 1076 | GLB1L3 | 3357353 | CCTCATCCTGGGCCGTCGTGGGAGGGGCTGACGATGTGGAC CTCCCTAG |
| 1077 | GLB1L3 | 3357354 | CCTTCGTCCTGATGGCCGCAGAGATCGGGCTGTGGGTGATTC TGCGTCCAGGCCGCTACATCTGCAGTGAGATGGACCTCGGGG GCTTGCCC |
| 1078 | GLB1L3 | 3357355 | CTGGCTCCTGCAAGACCCCCGGTTACTGTTGAGGACAACCAA CAAGAGCTTCATTGAAGCAGTTGAGA |
| 1079 | GLB1L3 | 3357356 | GCGCCCAACAGCATTGCCTTTTTTATGGTGTACCCAGACCTCA TGCACTTGATAAGAAACGCCTTCATTTTTACCATGGCAACCTA GAGCACACAGTCA |
| 1080 | GLB1L3 | 3357357 | AGAAGCACAAATGCCGTTCACAGGCACATGTATGCAACGAGG AAAGCTAATTTACAGGCATCCCATTGAACTGTGGGAAATGCTA GGAAACTTTT |
| 1081 | GLB1L3 | 3357358 | TAAGTGAAATGTAATGCCCCATACCTCGCATACCTTGCACTAA TTT |
| 1082 | GLB1L3 | 3357359 | TCATCGCGGTGCAAGTGGAGAATGAGTATGGCTCATTCA |
| 1083 | GLB1L3 | 3357360 | AGAAGAGGGATTGTGGAGCTTCTCTTGACCTCTGATG |
| 1084 | GLB1L3 | 3357361 | GTGAGAAACATGTGCTGAGTGGCCACAC |
| 1085 | GLB1L3 | 3357362 | AGCCAGCCCGTGTAAATCTTGAACACACTGCAGAGAAAACCAA GTGCATCTCGATACCTCCCTTTCCCGTGTCCACTGGGATGGAT CCTGGAGTTCGATGTTACAATAAATGAGGACTCAAGGTTAAGG CTCAGGGCCACTCACAGCTCCCTATCTTGGCCTTGCTCCTGC CGTCTTTAAACACAGCAGCACTGGAGCTCCTCTGTTCTCAGGA CGCCTTTCCATCTCCCATAGTTTTTCTGTGGCAAGAAATCTGC ATTGGTGCTGCGCCTGGCTTGGGATCAGGGCCATCTCCACTA ACTTGGGAAA |
| 1086 | GLB1L3 | 3357363 | TGTTGGCCGCCATCAATTTGCAAAAACTTCACCAGGATACTTT CAATCAGCTTCATA |
| 1087 | GLB1L3 | 3357364 | CTGGTATTCCGTGAAAACAGGTTTGACAAGAAGACCGCAGGTT TTCACC |
| 1088 | GLB1L3 | 3357365 | GGAGGAGGGAACCCTGCTTGTGTCACCTCCGCTTGTGGATCA CGTCATGGAGATGAGTGGG |
| 1089 | GLB1L3 | 3357366 | ATACTGTCTTGGAGATCAGCCTGCCTTTCATTCTGCTAGGCCA TGTGGGATTTTGTGTTCCCCTCGTCTGGAGTTAGGCTGGTTGT GGGGTTTGTTGTTGCTGTGTTATCCTTTGTGCATCATGGGCTT CAAATGTTTCTGGTGGTACCTTGTGTCAAGGGCAAGTGCTGGT TTGGCAGAGGTTGTTTTCTCTGTGTCTGCATTCCCCTCTGAGT CTCGCCTTTGCATTGAGTCCCACAGAGAATCTGTTGCTTGCGG ATCTCTCAGCTATAGTATG |
| 1090 | GLB1L3 | 3357367 | CTCTCAGATGCCTCACAAGCAGCAAC |
| 1091 | GLB1L3 | 3357368 | CCATAATTTTGTCCTTCTAAGCTTCTGATGCACTGAATTATGTA AAGTGCATTCCCTTCACCAGCTTGTGCACCCTATTCTGTAACT GATA |
| 1092 | GLB1L3 | 3357369 | CCTTCTGATTATGGAATACTGGGTCGGCTGGTTCGACAGATGG GGAGATAAGCACCATGTTAAAGATG |
| 1093 | GLB1L3 | 3357370 | ACATGCTGTGTCTGAATTCATCAAATATGAGATCTCCT |
| 1094 | GLB1L3 | 3357371 | CTTTGGTTTCATGAACGGGGCCACATATTTCGGGAAGCACTCG GGCATTGTCAC |
| 1095 | GLB1L3 | 3357372 | GTCGCTGGTGTAGTAGCCTCTCCAGC |
| 1096 | GLB1L3 | 3357373 | GAGGCTCCGGAAGCCTGTTCTGGCACCACTGGGTTCTTGA |

TABLE 7-continued

| SEQ ID NO. | Gene | Affy Probeset ID | Sequence |
|---|---|---|---|
| | | | Target Sequences |
| 1097 | GLB1L3 | 3357374 | CCCAACAGGCTGTCATTGCAGTAGACAGGGCTTTCCGGGACT TAGAGCTCCGCTTCACACATCTGGTATACTGCCCTGTTGGCTT GAACCTCTGAAGAGAGGCAGGGTAGGAACGGTGACTGCTGTA AAGGCACAGACCTGCACGGCCGGGCGATACAGACTGAGCAA AGAAAAGAGTACCCGTTGAAGGGGTGTCCACTCTTTTGGCTTC CCTGGGCCACACTGGAAGAAGAAGAATTGTCTTGGGCCACAC ATGAAATACACTAACACTAATGATAGCTGATGAGCTTAAAAAAA AAACACAAAATGTTTTAAGAAAGTTTATGAATTTGTGTTGGGCT GCATTCAAAGCCATCCTGGGCCGCCTGTAGCCCATGAGCTGT GGGTTGAACAAGTTTGCATTAGAAAGTGAAGAAGTGGGGGCA AGCCCAGTGTCATGGCTTGACACTGGAAGCCAGTGGAAGGTG CCCAGGAAGAGTTGTGGGGAATGTCCTTAGACTGGCATC |
| 1098 | GLB1L3 | 3357375 | GCAGTGCTCACGGAGGCTGGAGATTACACA |
| 1099 | GLB1L3 | 3357376 | GTACTCAGCACCCATTTAACTTACGGGCCAGCCCTCCTCAT |
| 1100 | GLB1L3 | 3357377 | TGTGGGCAGCAGTTACACCAAGCTCCTGAGAACAAGGGCAAC CTTAACTTCGAACCCTGGGGTTAAAATCTGTGTGATTTTTTAAA ATCAGGGTTTCTAAGCATTTTATAAGCCTCAGTTTCTTCACTGA AGCATAAAGATAGTAACCTTGGTCTCCTGTGATGACTGCGAAG ATTGAGTTACTCTTTGTAAAGCTCTTATACCATGGATGACATAG TA |
| 1101 | GLB1L3 | 3357378 | AAGGCTGTGTATCCCCCCGTGAGACCGTCGCTGTACCTCCCG CTGTGGGACGCCCTATCCTACTTAA |
| 1102 | GLB1L3 | 3357379 | GACTGTGTGGTCCTTACGGAATCCACGTAGGAAAAGCTGCTG AGCTGGAATCGGGAGACTAGCTTCTGCCCGTGCTTCACCAGC AGCTGGGCCTGAACTTCCTGGGTCACTGCTCCCCCTTTTCCAT CAGCCTTCCTGTCCTATTTTGAAGAAAGGTGAAAGCTGTTTGG AACTGAAACTGTAGCCCTTGGATTCACATTGGTTTTACCTCTG CTATCACTATTTTAGAGAAAAGGTAGTGACTGGTACACTAAAG AAACTACATTTATTTAATGTAACTAAATTTAATTTAATGAAATAA ACATTTGCTTGGTGCCTCATTCATTGCTAGACTTCAACTATTTT AGAATACAATTTATTTACTCTTTTTTTTTCTTGAGACAGGGTCTT GCTTGGTGGCTGTGGCTGGAATGCGGTGGCACAATCATGGCT CACTGCAGCCTTGAACTCCTGGGCTGAAGCAATCCTCCGGCC TCAGCCTCTTGAGTAGCTGGGATTACAGGAGGGCACCACCAC GCCCAGCTACATTTTTAAGTTTTTTGTAGATGTGGGTCTCACTA TGTTGCCCAGGCTGCTCTCAAACTCCTGGCCTCAAGTGATGCA CCTGCTGCGGCCTCCCAAAGTGCTGGGATTACAGGCGTGAGC CCCTGCGCCCCATCCATTTCCTCTGTTAATCAGTTCTTAGGATT ATAACGATTGCTCCCTCATCACCATGCCCTGCATTTCCCTGAG TTTCCTTCCTGGGCAGTGGAGACGTAAGCACAGAGCAGTGTC ACATGGCATCTGTTTC |
| 1103 | GLB1L3 | 3357380 | CCAGTCAGGTCGCGTCAGCCCGTCAAC |
| 1104 | GLB1L3 | 3357381 | GCGGCCAGTCCTACGGGCTTGTCCTGTATGAGAAGTCCATCT GCTCCGGAGGCCGCCTCCGTGCCCACGCTCATGACGTGGCA CA |
| 1105 | GLB1L3 | 3357382 | GTTTTTGGATGAGACAATGATAGGGATTCTGAATGAGAATAAT AAGGACCTGCACATTCCTGAACTCA |
| 1106 | GLB1L3 | 3357383 | CCTGGTGGAGAATCAAGGACGAGTCAATTTTTCATGGCAAATA CAGA |
| 1107 | GLB1L3 | 3357384 | TGTCAGCATCAATAACTCTTCCCTGGAGGGCTTTACCATCTATT CCCTG |
| 1108 | GLB1L3 | 3357385 | CAGGGCCCGGCCTTCTACTGTGGGA |
| 1109 | GLB1L3 | 3357386 | TTATGGATTTGTGTTCATCAATGGACGTAACCTTGGGCGATATT GGAATATTGGGCCTCAGAAAACACTGTACCTTCCTGGAGTTTG GCTTCATCCAGAAGACAATGAG |
| 1110 | GLB1L3 | 3357387 | AAGATGATGAGTGGCTCAGATATCAAATCTACAG |
| 1111 | GLB1L3 | 3357388 | CCACTCCCGGCCGTGAACATATTTTTTGGGTTGCTGGAGTTCA TCTATAAGTCATTTTTGAGGAATAAGATTTATGTTAAGACTATC AAACACAGTGTTGCCTACAATAGCAAAAATGTGAAAATAACAA |

TABLE 7-continued

| Target Sequences | | | |
|---|---|---|---|
| SEQ ID NO. | Gene | Affy Probeset ID | Sequence |
| | | | CAACAACAAAACAGCAGAGGAATTGTTATGTATTTTGTAGTCTA TCTATATGATGCCTATTTTTAGGCTTTAAAAAGTCTTCAAAATCT TTAATGACTGATTTATCTAGTTAAATGCTTAATCCTTAGCAGGC TCTTATTCTTTAATTAAACGTGCCTTTGAGTAGATGTG |
| 1112 | GLB1L3 | 3357392 | GGTCACCGAAGCTTCTCTGAAAATGTGACATCTCTGAGGAAG GTGGAACATTAATCATCTCTAGCAGTGCATAGGCCCTCTCTAT GGCATTGTCAACTAAGCACTAATAATAGTCAGGGGACAACATG CAGCGATAGCCAAGAGCATGGATCTTGGAGCCAAAGAGATCA GGTTTTAATCTCAGCTCTGCAGCGCTAGCCATGCGCTAGCTTC ATGCAGGCTTCCTTCA |
| 1113 | GLB1L3 | 3357393 | CCACTATCACCACCATCACCATCAA |
| 1114 | GLB1L3 | 3357395 | TGAGATCTCATAAACTTTCAGATCAAAAT |
| 1115 | GLB1L2 | 3357398 | AGCCGCGAGCCCCAGCCAATGAGCGCCGGCGGGCCGGTTGC CCAGGCGACCAGTGCGCGGCTCCGCCCCCCGCGGCGAGGCT CCCGCGCGCGGCTGAGTGCGGACTGGAGTGGGAACCCGGGT CCCCGCGCTTAGAGAACACG |
| 1116 | GLB1L2 | 3357399 | CACGTGGAGCCTCCGGCGGAGGCCGGCCCGCACGCTGGGA CTCCTGCTGCTGGTCGTCTTGGGCTTCCTGGT |
| 1117 | GLB1L2 | 3357400 | CCCTCCAGCCGTCAGAGCCCTCTCAGACGCACCCCATCGCGG CCCCGTCCCCACTGCTCCGCGGAGAGCTC |
| 1118 | GLB1L2 | 3357401 | CCTCTGGGAGGCGCCTTATTCCGCAG |
| 1119 | GLB1L2 | 3357402 | TGACCCTATCTTTCAGGTCAGCACTTTCCATATTCAAAACCTCC AGTGGGAAGCCGACCGGCAGTATCGAATGAACTGA |
| 1120 | GLB1L2 | 3357403 | CAGGTAGAACAGAAGCTCAAGGAGCTCTGA |
| 1121 | GLB1L2 | 3357404 | CGGCGGTCATCGTACTCCGGATGTTCACGGCACTCCGGATGT TCTGCTGTGCCCGGTTGCATGGATCCTGGCCTATCTGTGTCTG GTCATACTCTGCATGGCA |
| 1122 | GLB1L2 | 3357405 | TGCCGAGAGGCGCTTTCTCGCGGACCGGAGCCTTCGACGGC C |
| 1123 | GLB1L2 | 3357406 | TGAAGACCTGGAATCGGGTGGATGGGTGGACGCCGCCAACG CAGAC |
| 1124 | GLB1L2 | 3357407 | TCTCTGCTCCTGCGGTCGGGCGGCTGCGACCGTGCCGGGGC TCGGAGGTACCGTGTGAAGTCGCTGTCGCGCGTGGCCGC |
| 1125 | GLB1L2 | 3357408 | CCTCCATGCCGAGTGCTGTGCTTGCTGCCGGCTGCAGCCTC |
| 1126 | GLB1L2 | 3357409 | GGCGGAGGGGAGCTTTTCCCAGCCACCTGGACGCAGGCGCC CTCGAGAGAGAAATGCCGAGGACCTGCGAAGGGGCGAGGAA GCCGATCTCTCTGCGGCCCGGAG |
| 1127 | GLB1L2 | 3357410 | TCCCTCTGCGGCTCCGCCATCGACAGCTGGGGCTGCAGGCC AAGGGCTGGAACTTCATGCTGGAGGATTCCACCTTCTGGATCT TCGGGGGCTCCATCCACTATTTCCGTGTGCCCAGGGAGTACT GGAGGGACCGCCTGCTGAAGATGAAGGCCTGTGGCTTGAACA CCCTCACCA |
| 1128 | GLB1L3 | 3357411 | ATGTTCCGTGGAACCTGCATGAGCCAGAAAGAGGCAAATTTG ACTTCTCTGGGAACCTGGACCTGG |
| 1129 | GLB1L2 | 3357412 | CACCGACCTGGTGTGGGAGTCCCCG |
| 1130 | GLB1L3 | 3357413 | CCTCATCCTGGGCCGTCGTGGGAGGGGCTGACGATGTGGAC CTCCCTAG |
| 1131 | GLB1L3 | 3357414 | CCTTCGTCCTGATGGCCGCAGAGATCGGGCTGTGGGTGATTC TGCGTCCAGGCCCCTACATCTGCAGTGAGATGGACCTCGGGG GCTTGCCC |
| 1132 | GLB1L2 | 3357415 | GGCAAAAAGCTCACAGACATAGGTCTGGTTTGTTTCTGTGTTC CAGTTCCCATTCTGTACTGAATTGTGTTCCAGTTCCCATTCTGT ACTGAATTTCCTTTTCAGGAAAAGCAGCACCCAGAGGGGATC |

TABLE 7-continued

| Target Sequences | | | |
|---|---|---|---|
| SEQ ID NO. | Gene | Affy Probeset ID | Sequence |
| | | | GCTTTCAGTGATGCTGCAGTGAGTGCCCTCACGTAGCCATGC ATG |
| 1133 | GLB1L2 | 3357416 | GGGGCATAGCTTCTGTCTCCACTACCCAGGGCCACTTCTCAG GCACTGATCCATCCAGCC |
| 1134 | GLB1L2 | 3357417 | CCTGACCCTGTTTAGGACTTCCAGACCAGGGCAAGAGGAGCC TCAGAGCCTTTTGTTAGAAAATATGTGTCTTCTCAGAACCTGAA GTGAGAAGGAAGAGCCCTGACTCCAGCTTTGGAACCAATCCA CGCTGCTGTGTTCCTCTGGGGAGTTTGGGATCATAGCAACAG GGTGGAGGGAGAATTCAACTCTTGCTCACCTGCTGCTCTGGG CTGTGCGCCACTGATGCCAAGGCGTTAGCCACGTTGGCAAGG ATGGGGACTGCCTCCTGCTCAGCCCCTCGCAGTCTCTGTCAG GCTTGTTTTTTGGGGTGACGCTAGAAGGTTGTGTCTCCTCCTT CCACAGCCTCAGTGATTCCTAACCCTTTTGACTTCACTTTTTGA AATGGGATCACAGAGCAAGTTGTTGAAAACTAGGCCTGGAGT CCTGTGAAAAGCTTTTC |
| 1135 | GLB1L2 | 3357418 | GGACAACTTACAAGGGCTTCACCGAAGCAGTGGACCTTTATTT TGACCACCTG |
| 1136 | GLB1L2 | 3357419 | ACAAGCGTGGGGGACCTATCATTGCCGTGCAGGTGGAGAATG AATATGGTTCCTATAATAAAGACCCCGCATACATGCCCTACGT CAAGAAG |
| 1137 | GLB1L2 | 3357420 | ACCGTGGCATTGTGGAACTGCTCCTGACTTCAGACAACAAGG ATGGGCTGAGCAAGGGGATTGTCCA |
| 1138 | GLB1L2 | 3357421 | GTAACTGCACTTGTGTTGGGCCGTGGGGGCTGGCGGCGGCC CTGGGCTGGCTGTGCACGCTCCCGCTGTGGG |
| 1139 | GLB1L2 | 3357422 | TGTTCTCAGCATATCAGCCTCCGTGTGCCTCTGAAAATGTCGT CCAGATTACCCTATCCTGCTGAACGCCAGGCATCTCTGTCACA CTCAGAGTGAAGCGCAGGTTCTGGGAATGACCTCGAAAGGCC TCTCCACTTGGCCTCCAGGACCTAGCTGAGCTCACCTCCTGCT CCTTCCCTTTGCTCACACCGTTTCACCCTCTTTACTGTTCCTCC AACATCCAGATCCCCAGCCTGGGGGGCTTTGCTCTTCTTCCA GAGAGCTACATGGCTGTTCTCCGAAGTTAGCGAGGCTTTCTGT AGCACCACACTTG |
| 1140 | GLB1L2 | 3357423 | GTAGTTTATTTATGTCATTCATCTGTTTCACCCAGCAGTACTCT TGGCGGGGCTT |
| 1141 | GLB1L2 | 3357424 | AGCAGCGCCTAGCTGGCACCCAGGGAGTGAAGGTCCATGAAT GGCGAGGAAAAGGCTTTTGTCCCCAGGCAGAGTCAGTCAAGG ACCCAGACCTCGTGTCTCCGGCATGGGGAGGACCAGCAGTG ATCCCCACGGCT |
| 1142 | GLB1L2 | 3357425 | CTCCCGGTTTCAGGCCTTGCAAGGAAGCCCGGGAGCCGCCA CTGCTTTTCCCTGTGGCCCTCCCACCTCCAGGCACCCACCTG CGTGCCCCTGTTGCCACCTGCTGCCCGGAATAACTTCTTTTTT TTTTTTTTAATTAAAAAAATTAAATGGTCTAAAAGTGAAATAATC GAAAATGTTGGTAGAGAAATACAGTGTTGCCTACTCTTCGTTA CATTCTCCAGAAATGACCATTTTCAACTCTTTGACTTTTTCTTTG GATATTTTCCTTCTTATTTCCAAATACTGTGAACATACAGCCCT GCATCGTTTGCTTTAAAAGTTCTGCCTATTGGCCGGGCAGTGG CTCAGGCCTGTCATCCCAGCGCTGTGGGAGGCCGAGGCGGG CGGATCATGAGGTCAGGAGATCGAGACCAGCCTGCCCAACAT GGCGAAACCCTGTCTCTACTGAAAATACAAAAAATTAGCCGGG TGTGGTGGCGGGCACCTGTAGTCCCAGCTACTCGGGAGCTGA GGCAGGAGAATCCGTGAACCCGGGTGGCGGAGTTTGCAGTG AGCCGAGATTGCACCACTGCACTCCAGCCTGGACGACAGAGC AAGACTCCGTCTCAAAAAAAAAACAAAAAACAAAAAACATTATC CGAGCGTGGTGGCGGGTGCCTGTAATCCCAGCTACTTGGGAG GCTGAGGCAGGAGAATTGCTTGAATGTGAGAGGCAGAGGTTG CAGTGAGCCCCGATGGTACCCCTGCACTCTAGCCTGGGTGAC AAGAGCAAAACTCCGTTAAAAAAAAAAATTCTGCCTATTGACTT CTTGTTCCAGTAGGTGATGAGTGTTCTTTCCTGCCAGCATGGC TGTTCAGCCCTGATAGGCGCCAGCGTGGGCCTCGCGGATGTG TATGACAACG |
| 1143 | GLB1L2 | 3357426 | CTGCTTGGCTGCATCCCGCGTGGAATCCTGCTTCCTGGAGTT CCAGGAAACAGGATGTTTCTTGGTGCTCCGTGGCTTCCCG |

TABLE 7-continued

Target Sequences

| SEQ ID NO. | Gene | Affy Probeset ID | Sequence |
|---|---|---|---|
| 1144 | GLB1L2 | 3357427 | ACTCCGGCTCCCGAGCGTTTCCTGGGTCTTCTTCCTCCTCGC CCCCGGCCAAGTTCCTCAGGGAGCCCGCCCTCCCCTTCTCGT GCTGCTGCGCATCCGGGGAGCGGCCCAGTTAC |
| 1145 | GLB1L2 | 3357428 | CAGCTCGGGCCCAGGGTTCTCAGGCAGG |
| 1146 | GLB1L2 | 3357429 | TCTTGGCCACCATCAACTTGCAGTCAACACACGAGCTGCAGCT ACTGACCACCTTTCTCTTCAACGTCCAG |
| 1147 | GLB1L2 | 3357430 | CTGCTCAGCGGCCTATGGGAATTCTGAATGCCTGTCAGCGTG CTCAGCTTCCCCAGCGCAGGGAGCTGGACTCAGGGCTGATG GCCTCTGGCCCCCCGCCCATGCCACTGTGTGCCTGCAAGGCC CGCTGCCCAGAAACACCTCTGAGGGCTGCTGTGTAGGCTGAT GCAGTGTGGACATCACCCACTGCCCTGAGAGAGGGGCCCTTT TGGTGCACTCCTAGAGGACTCGACTTTTGTGGCCTCAACTAGC TCCAGACTTGCTCCCAGGGATTGAGGGGGGAAGGAAAAACTT CCCTGTCCTATACTACACAGGCATCCGACCTTAACCTGTGAGG |
| 1148 | GLB1L2 | 3357431 | CTCTGGGCTTCTGCAAACGTGGCAGAGTGGAGCATGGTCCCA GGAATGATCTTGGCCTCCTTGGG |
| 1149 | GLB1L2 | 3357432 | CAGAACCTGCACCATGAATAGCTGTGC |
| 1150 | GLB1L2 | 3357433 | AACTGGTGTGCAGGCGAATTTGGCCCTCACCTATGCCC |
| 1151 | GLB1L2 | 3357434 | ACTGGACGGGGTGGTTTGACTCGTGGGGAGGCCCTCACAATA TCTTGGATTCTTCT |
| 1152 | GLB1L2 | 3357435 | GTTTTGAAAACCGTGTCTGCCATTGTGGACGCCGGCTCCTCCA TCAACCTCTACATGTTCCACGGAGGCACCAACTTTGGCTTCAT GAATGGAGCCATGCACTTC |
| 1153 | GLB1L2 | 3357436 | CTTCGTGTCTTTGGCAATAGAGTACCT |
| 1154 | GLB1L2 | 3357437 | CAGTCATGTTACACTCCCAGAGGAGGGA |
| 1155 | GLB1L2 | 3357438 | ATGCTGTGCTGACAGAAGCCGGCGATTACACGGCCAAGTACA TGAAGCTTCGAGACTTCTTCGGCTCCATCTC |
| 1156 | GLB1L2 | 3357439 | TCTCAGACCCCTAAAGAGTTACTTCCTTACTGTCCCACCTCGA CCCCAGTTGATCTGCGTGCAAGAATATCCTAGACA |
| 1157 | GLB1L2 | 3357440 | ACCTTCTTCCCAAGATGCCGTATGAGCCCTTAACGCCA |
| 1158 | GLB1L2 | 3357441 | CTCTGTGGGACGCCCTCAAGTACCTG |
| 1159 | GLB1L2 | 3357442 | GTGAGTGCTGTGGGCAGTCATCGGGAG |
| 1160 | GLB1L2 | 3357443 | AACCTGCCAGTCAATGGGGGAAATGGACAGTCCTTCGGGTAC ATTCTCTATGAGACCAGCATCACCTCGTCTGGCATCCTCAGTG GCCACGTGCATGATCGG |
| 1161 | GLB1L2 | 3357444 | GTAGGAGCTTCTCTTCTAAATTCCTGTGACCTTCTG |
| 1162 | GLB1L2 | 3357445 | GTGTTTGTGAACACAGTATCCATAGGATTCTTGGACTACAAGA CAACGAAGATTGCTGTCCC |
| 1163 | GLB1L2 | 3357446 | GGTTACACCGTGCTGAGGATCTTGGTGGAGAATCGTGGGCGA GTCAACTATGGGGAGAATATTGATGACCAGCGCAAA |
| 1164 | GLB1L2 | 3357447 | AATCTAGCTAAATGTGGGTGGTTTCA |
| 1165 | GLB1L2 | 3357448 | TTAATTGGAAATCTCTATCTGAATGATTCACCCCTGAAAAACT |
| 1166 | GLB1L2 | 3357449 | CTGGCCCGCACCCAGGTGTGAACGCCTCCAGGGGCCAG |
| 1167 | GLB1L2 | 3357450 | GTTCGGCCTGGACAAATGGAGTTCCCTCCCAGAAA |
| 1168 | GLB1L2 | 3357451 | ATGAACACCCTTCCCCTCTGTTTCAA |
| 1169 | GLB1L2 | 3357452 | TGGCCAGAACCTTGGACGTTACTGGAACATTGGACCCCAGAA GACGCTTTACCTCCCAGG |

TABLE 7-continued

| Target Sequences | | | |
|---|---|---|---|
| SEQ ID NO. | Gene | Affy Probeset ID | Sequence |
| 1170 | GLB1L2 | 3357453 | CCTGTTCCCCATGACGCCCTGCCCACCTGCCGTCCCAGGGAG CCTTCG |
| 1171 | GLB1L2 | 3357454 | GACAGACGTCAGCTGCCCTCCCAGCCGGGCCCTCTCTCCACA |
| 1172 | GLB1L2 | 3357455 | TCATCGTTTTTGAGGAGACGATGGCGGGCCCTGCATTACAGTT CACGGAAACCCCCCACCTGGGCAGGAACCAGTACATTAA |
| 1173 | GLB1L2 | 3357456 | TGCCAGTGGGAGACTGCCGCCTCCTCTTGACCTGAAGCCTGG TGGCTGCTGCCCCACCCCTCACTGCAAAAGCATCTCCTTAAGT AGCAACCTCAGGGACTGGGGGCTACAGTCTGCCC |
| 1174 | GLB1L2 | 3357457 | CCCTGCTCTTGTGCCGAGGCTGTCGGGCTGTCTCTAGGGTGG GAGCAGCTAATCAGATCGCCCAGCCTTTG |
| 1175 | GLB1L2 | 3357458 | AAAAGTGCTGAAACGTGCCCTTGCACTGGACGTCACAGCCCT GCGAGCATCTGCTGGACTCAGGCGTGCTCTTTGCTGGTTCCT GGGAGGCTTGGCCACATCCCTCATGGCCCCATTTTATCCCCG AAATCCTGGGTGTGTCACCAGTGTAGAGGGTGGGGAAGGGGT GTCTCACCTGAGCTGACTTTGTTCTTCCTTCACAACCTTCTGA GCCTTCTTTGGGATTCTGGAAGGAACTCGGCGTGAGAAACAT GTGACTT |
| 1176 | GLB1L2 | 3357459 | GAAATCCTCACCCTGCGTCTTCCCAAGTTAGCAGGTGTCTCTG |
| 1177 | GLB1L2 | 3357460 | GTGAGTCCTGGCAGAAGCCATGGCCCAT |
| 1178 | GLB1L2 | 3357461 | CCCAGCTCACATGTGAGTCCTGGCAGAAGCCATGGCCCATGT CTGCACATCCAGGGAGGA |
| 1179 | GLB1L2 | 3357462 | GTGAGTCCTGGCAGAAGCCATGGCCCAT |
| 1180 | GLB1L2 | 3357463 | TCTGCACATCCAGGGAGGAGGACAGAAGGCCCAGCTCAC |
| 1181 | GLB1L2 | 3357464 | GTGAGTCCTGGCAGAAGCCATGGCCCAT |
| 1182 | GLB1L2 | 3357465 | TCTGCACATCCAGGGAGGAGGACAGAAGGCCCAGCTCACA |
| 1183 | GLB1L2 | 3357466 | AGAGCAGCCCTCCTTCGAAGTGTGTCCAAGTCCGCATTTGAG CCTTGTTCTGGGGCCCAGCCCAACACCTGGCTTGGGCTCACT GTCCTGAGTTGCAGTAAAGCTATAACCTTGA |
| 1184 | GLB1L2 | 3357467 | AGCTGTGTATGAGCTGGTTCCGTCAGAAAGTGATGGAATGGA AGGGAACCTTCCTGCAAATCCTCCTGTAAGGTGGAGAAGCCC CTTGGATCACACTTCCACGCAGACCTG |
| 1185 | GLB1L2 | 3357468 | AGCAGGCTGAGCAACGCTTGTTCCGCCTGGTGGAGAGTTCGT TCTTCTTGGGCCCGGGGAGCTGCATGTCAGGGTGTTGCTGCT TCGCTCAAGGGTCACTTATCACGGAGGCCTCTGTGGTCACCC TACAGAGCACTGAC |
| 1186 | OR51A6P | 3360298 | TGATGTTTTCTTGCTAGTGCCACCTCTTATGAATCCCATTGTAT ATTGTG |
| 1187 | OR51A6P | 3360299 | CTTCTATGCGCCCGTCATTGCTTTGGCAT |
| 1188 | OR51A6P | 3360300 | AAGCTGGCCTGCTCCGACAACACTGTCAACTTCTTCTATGGTT TCTTTCTTGCCCTCTGTATGATGTCAGAAAGTGTGTTCATTACT GTGTCTTATGTGCTCATCCTGAAGACGATCATGGGAATTGGAT CCCATAGGGAGCGGCTCA |
| 1189 | OR51A6P | 3360301 | TGCTGTTAGTACTCCCATTTCCTTTCACTCTTACAAGGTTGACA TATTGTAGGAAAAGCCTACTCTCTCATTCCTATTGTCTCCATCA G |
| 1190 | OR51A6P | 3360302 | TTTTGACCGGTTTTGGCCATATGCCACCCTCTGAGGTACATAT CTGAGGTACTGGTGAGCTGTATCCTCACCAGTGCCAGAGTTG CCAAAATG |
| 1191 | OR51A6P | 3360303 | TGGAGCATGCCCATATATGGATATCTGTCCCCATCTGCCTCAT GTACTTGGTAGCCATCCTAGGCAATTGCACAATCCTCTTTGTT ATCAGGACTGAGCCCTCACTCCATGCACCCATGTACTATTTCC TTTCCATGTTGGCTGTCTCTGATCTGGGCCTGTCCCTCTCCTA CCTACCCACTATGCTGAGGATCTTTGTATTCAATGCCACAGGA |

TABLE 7-continued

| SEQ ID NO. | Gene | Affy Probeset ID | Sequence |
|---|---|---|---|
| | | | ATCTCCTCAAATGCTCGCTTTGCTCAAGAATTCTTTATTCATGG ATTCACAGATATGGAGTCCTCAGTG |
| 1192 | FTH1P2 | 3375656 | AAGCTGCAGAACCAACGAGGTGGCCGAATCTTCCTTCAG |
| 1193 | RP11-770G2.5 | 3377879 | AGGTGCTGGTCATCATTCTGTCCCATTTTTTGCCACTGTGCTA AGGCTTTTGACTCAACCAAGAAAAGGGCCGGTCTTCCAGCCT GGCCCTGCAAGAGTGTCCTAGTGCTTCAGGTAGTGGATGGGC ATCGTCATTCGTCCCACCTTCCTGCCCCCTAAAGCCCCAGGA GGACACACTCTCAGCATCAGGCCAGCTCTCCGGGTCACTGGG GCTTGGCTCAACAGGATGTGCAGGGCAGAGCCGGGAGGGAA GAGCAGAAGATGCCATGGGCTGTTCGCAGGAGCAGCCGTCC AGGGCGCCGCTGGAGGAAGATCTTCTAGTGGCTGTCTCAGCA CGTACAAAGAA |
| 1194 | RP11-770G2.5 | 3377880 | CAGAGCTTCATGACGGCCTCGGATTGGCAGTCAACCCAGGGA TACAGAAATGTAAACAAAAACAGAGCTTCCAGATAACATTACT GTGTGCTATGTGACTTTCAGAATACAGCAGCGTCCCAGACACT CTAAAGTCAAGTGAAACAAGAGATTTTAGAATCAATCTATACAC ATTTCAGAGGGCAGTCCAGG |
| 1195 | SESN3 | 3387255 | TCTTCTCTCCAGCTAGGTGCACTTGAGGTTGTTCATAAATGTAA AATTATGTCAGGTTTCTAACATGGGACACTGCACACAGTTGTC TGACCTGATGAACCATCCCATTTGAAAGTATAGATTATTATTAT TTCTTGTAGTATTTGGTTGTTTTCCATCTCATTCATGAACAACT CAACCTGATAGTAGTATCCAATAAATGCCTTTCAGGGCTCAGG AATGAATTGACATCCTAGTTAAGAAATGAGACTTAATAATGGAG ACTGAATGAGGCGGTTTGTATTAAATTATATGCCATGAAGTGTT CATTTTAGCTTTAACCTAATTATGACTGTACCACCATGAAGTAC AGAATGAAAAATTATATATATGGGGGGGAAACAGAATGAATAT CTGATTCTTTTGAATGCTTGTGGAAATCTTTGAGATCGTGCAG GGCATACCACAAAATAGCCTTTAGAACAGATACCCAATTTTAC AGTTCATAGGACAACATCAAACATTAGTAAGTCTAAATAAGATG AATAGAATTTTTGTTATGTAAATTTTGCTAGAACAGTCTATTTTC TTGCACCCCTCAAGTTAACCTCTTAAAAAAATGAATGTATAATT TCTACCGAAAGAATATCAGAGAGAATCTCTCTGGCCTATAGTG TTAAAATATTGTTCACAAATCCTGATTAGTTAAGTGCATACATT ATGAAACTTACAGAATAAAACTTATTATACATCTCTTTCTTAAAT TAATATCTTTACACATTTTCAACTGGCTCCCCAAGTCTGATAAG GAAGGATTAAAAGAAAAAAGAAATGTATTAGTTGGGTGGCCAA GGAGTTTCCTTTGTAATGTTGAGAGACTTCCGCTTTCTGAATTT CGCTGGTTCTCTAAGGTAAAAGAGTTAAATAGTACCCTTGTTC ACCAAGGAAAGTGATCCAAACTATATATCTAGTGCAGATATTTC CTTTGCATTATTTAGTCTTCTCTGGAGAGAAAATACAGTTTCCC CTTCCTCTTTCTCTTCACATTTACTCTTTTCAACCCAAAATAAGA GACATAGAAAGCAAACCACAGCCAGTTTGGCATCTTCTCAGTG CTACTAGTA |
| 1196 | SESN3 | 3387256 | TGACTTGTAACCCTTCAGTGGAATGGGAAATTTCTG |
| 1197 | SESN3 | 3387257 | TGGCTTAGTTAGCAGACCTAGAATCTGCCCAGGTGAGACCTA GAACAAAAATAGCTGGGGTGAAATGGATAAGAGAGGTAGAGG TATATGTCAAGGCAGAGCCCTATGAGGAAGGAAGAGTTTTCAA AGAATATGAGGAACATAGTGCTGAGAGTGTGGCTGCCTTCAG CACCGTACACCTAATCTAGAGAAAATATTTCCCATGTGGGAGG TCCTGTCTGCATTCAGTCCACCCTTTTCTGCCTGCTTCTTCCTC CAAGTGCCTCAACCTCTACATGCTCACTCTCCTCCCCCTTCCCT CAGCCCATCTTGGTCTAAGCAGCTTTCACAATCCAAACCAAAC ATCACCAGCCACCCGCTGATAAGTCACCAGCATTTACTTTCCT GAGTTACTTTTTCTCCATTCATTGAGACTATGGATTCATCCCAA CTCCTTCTAAATCCCTCAACCATCCAGCTATATTTTGGCTAACC TTTGCCCTAGACACTCTACCAGATGTTAATGCAGTATCAAGTG TAAATTGTGTCACCCTATTCTGTTCTACCCTTTTCCCTGCTGCC GAAATATCTTGCTCTCCTCTACCTCATCCCCAAAGAGCCTATAA ATTCAGAGTATCCAACCTTTTCATGGATTCACTCACTGTTGTTC A |
| 1198 | SESN3 | 3387258 | CGCTGTTGAACCAAGCTGCTCACTGGACACATATTTGTGTCCC CAGGAGATTATTTGTCAGGCACTGTTTTTTATTTGTTTGTTTGT TCATTTATTGTTGTTTTACTGCTATTGGCGATAACATGAAATGT GATACAGCTATTGCCCATAATTTAATGTGAAATTAATCATGATG AATTCTATAGCATGCTACTGAAATGCCAAATTCAGCTATTTTCT TTCTCTTCTAAAATGGAAGTTTCAGTTTTCCATATCAGATGTAT ATAAGTGGAATTATAACACAATCCTATCACTGACAGTAATCCTC |

TABLE 7-continued

| Target Sequences | | | |
|---|---|---|---|
| SEQ ID NO. | Gene | Affy Probeset ID | Sequence |
| | | | AGTCACCTTAAATAATCAGTGCTCACAGTGCTGCTTACAGTTC ATTTAGTTGGCACATATAAACCTGTACCCACACAAGACTGACC AAAAATTTTCTTTGCACATTTTTCCTTTCTCATAGTTTTTTTCTAT ATTTCGTTAAGCAAAGGAAGGTTAATATGCCTATTTTTCCTGTT AGGCTTTTAGAAATTATTTTCCATGACTTTTGTTCTTATAATAGG TTAGACAGTTTATTTTTCAAAGGTAAAAATTGTGTTTCTATGCAT TAATGTGATTGAACTACAAAAACAGAGTGCAATATGTTCAAAAA ATACTCAACTAAACTTTCCCCCTGTCATATCACTGCAAAAGTGT CCTTTTAAACAGAGCCATAAAGAAATTTTTTTCAAATTTCTTTAT TGCACAGGCTTTTTTCAGTTTTACCTTTCTGGGATTGAACAATG TTCCTTTCATAATGCCAAAGCATTCCCTTCCCCAGAAAAATCTC CTTGGACAACTGGTTTAAAAACGTTATTAAGTCATAGGGGAGG AATAAGCGGCCAAAAAGTCACATTTTTGCATTGGTTTACGTTG CTTGATTAGACTATCTTCAGAGAGCACATTATGTGTTTATAGCT TTAATTTGTATTATGTCAATGAACCAGTGAAGTGCCTAAAGAGA TGCTTACAACTATCCAGTAGGACACAACTGCACTGCTTTTTAAA CACTTTTTGGTTAGTTAAGGGTGACTTGAATTGTACACATACAT GCTAATTTTTGAAAACTTATCCATTTTTCATAGTAAATAATATAG ATAAAATTTTCTGTTAGAGTTCCCGCAAATATTTCATTTTAGACT TACTTGTGATATAAGATTTAACTTTTCTTTTGTGAAAGAATCGT GAACTAGTGTTTCATGAAATCATTTTCCTCTTCCATTTATCATC CTCCTCTGGTACAATATATTGGGTTGCTTTCTTTTAGATTTTGT TCCAGATAGGAAAACAAATATGACTGTATACTTATTAACATAAG GTAGTTCTGCATTTTTGGATTCCAGGATCCTGTTTGAAATCTTC CATGTGAGGAAAAAATTACTAATATTTTTAAAGACAGGGTGGTT TATTTAAAGAGATTATTCAGAGAACTTGTGCCATATCTCGTCTG TTTTATTGCATATGCCATATGTTAACTTTTATTCAATATTACATT ATGTAGATATGTAATACAAAGAAAATATTTAGGAGAATGGCAAA ACACAAATGGCAACATAAATGTCCATTTGACTTACCTAACTTCA CAACTTTCAAGTTGAGGATGTCATTTATTCTTGAATTTGTTTTTT TACTAGATGCTTTCAATTAATAGCCCTATATTTTTGTGCAGGCG AACTGTATAACAGGATAAAAAATGATTTGTATGTATTGAAAAGG AGGAGAAATTCTCACAGAACACCATATGAGCTTTAGACCAAAA GGGGAAACAAGGTTTAAGTAACTAAAATGGCCACTTAGTTTGT GTTTATTTTTTTCCCTGGAAATGTAAGTAGTTGGAGTTTAGGCT ATGGAAATATTAGTGCCTTTAATAGATCTCTTTCCTTGCAAAGT TTCTTTTTAGCTCAGCATTGATCTATCTTATCAATAGGAAAATAA GTTGACTTGGAACTATAAACAAAAACAACACCATATATTTATGA ACCTCAGTGAACCAGCCTAGAAAAATTGACTTCTGCAGGTGCT AAAGCACCTACTAATACGCAGCATGCACAGCATTTCAGGTTGT GAATACCATTTTACAACGAGTTTGCTGTTAACTCTCTTTATCCA ATGCAAACTTGAAATTCTGATGCGGTTTTCCAGGGTGGTATTTT TTCAGAGTATTGAATTTACTATTTAGTAATTTATAGTATAGCTTT TTATATTAAAATGTGATATTTTTAAAAGAGATATCTGGTTCAATT GGTATAATGACGTGATTATGCAATATGCTGATCTACACCTTGC GCTCACATTGTGCCAAACTTAAATGTGCAAGTGTACGTGAGAA AAGCACATGTGAATGTGAATTCTTTAATTCTTTGCTTATTATGTT AAAATTAGTCTTCATAGTCCACTGATGTGTATGCTTGAATAATG TCTATTTACTTTGGAATTTCAAGATTTCCAGCTTCAATGGTAATT TATAATTTCTCAGATCACCTTAAGAAATATTGAGATACTCTCCC ACCTGAAAATAATCTGTTCTTTAACCCACCTGACTATGGGAGT AGCCAGGCAGGTGCCTCACTGGCTTCTTCAGACGAGGCTTCC TCAGGTGGATATATGACTATTAGGGGAAAAGAGGCTTTTGAGA CAGCTTATTACCTCCTTCCCCTTTTTGAACTAAGTACATTGTCT CAGTCCCAGTATGAATTTGTCCCATTTGGGGTATTTTTAAAATA AAAGATGGCTAACATGGAATCTGGGGCATAGCCTTGGCCTTTA ATTATGGTTGTAAGCCCAAATAATGGCAGAGAAACACAGGGCT GTTTTTACAACAGAAAACTCAATATAAGTTTTATATAAGAATCCT ATAAAATTTGAACCAGAGCTCCTATTTAGTTGTTATAATGTCTC CTAAAGATCTTAAATGCTTCTAAAAGCTAATTATTATTCCAGAG CAACTTTTTCCTTTTCCCCCTTATAAAGTTTTTTTTTAAATCCAA AATCTTAGATTTCTGTGCCACAGCAAAATAAAATGATCAACAAT TAAAGATCTGTACTTAAAATAGTACACCATTTTTAGTGGAGGGA GGGTGCATGCCTATATGATGGTAAGATTCTTTTGAACTCTAAG GACAATTCCTCATGGAAAAAATAAATTTCAGTGCATATTATAAA AATGATTTGCACTGTGTTAGCAAAATAAGGTGTTTTAGGTTGTA TTTTAAAGACAATTCTAAATCATTTCTCTGGAAAGCAAGACCTT AAATTCTTCTCTTTAATAGAACTGCTTTTATGCAAAGAGATGGT CTTAACATGGACTAAACAGTACATAACAATAATGTTTGTTATGT AAATAGTATATCACATTTGCTTAGTAGCACAATTCAACAGCAGG CTGAAAGTCGTGGCTCCTCTGCTCAGATTGAGTTTTAAGTTAC CTAATTTATGTAATCAGAATCTATTCTAGGTGGCCGTCAACGTA AACTGTGTTTC |

TABLE 7-continued

Target Sequences

| SEQ ID NO. | Gene | Affy Probeset ID | Sequence |
|---|---|---|---|
| 1199 | SESN3 | 3387260 | CTAGTGTCAAAGTTTAGCCGTTTGTTTTTTTTTTTTTGTTTTTTG CGGCTGTAATGTGCAATGATGTGTTTTATTTTCCTTGATGCTTA ACATTACTAACAATTGCAAAAATAATACTGAGGAGCACTACTTT GCATTGTTTGTAGTTGGAGTTTTGGATACTGATCATAAATCATG AATCTGGCGTATTAATGCTTAAC |
| 1200 | SESN3 | 3387261 | TACTTTTAATGGAAGCACGAATGCAAGCTGAACTTCTTTATGCT CTTCGTGCCATAACTCGGCATTTGACCT |
| 1201 | SESN3 | 3387262 | TATGGCTTCAGTACCTAACAGATTTTTTGAAGTCTTAGAGCCAC TCACATCAGGTAAATACCCATTTTACATCCAGCATTTCCCCTTG ATGGGTCTTTATCCCATATTTATATGTTTGCTCTAGATTTTCTTC CTTTTCTAGATTGTATCTAGAAATTCTCTTTACTCTTCAGGAGA ATATATCCAACCACATATCCAACTGGTATAAATATATCAAAAGA ATATAATATTAAAACATATTTTTATAGTAAATTTTGAAAACTTGT GGATACCCATTTTAACTTATCAGCCGAGATGTAACCCCGAAAG AAATGTTCTGCAGAATTTTATCTGAAAGACTCTAGGGAAGCTAT GTATGTCTA |
| 1202 | SESN3 | 3387263 | GTACGTGTTTCAGTATTAAGCATTATACCATAG |
| 1203 | SESN3 | 3387264 | GAAGCCTGAAGGTTTACATTAAGACAGTGACCTGCTATCCTGA GAGAACTACAAAACGCATGTATGATAGTTACTGGCGGCAGTTC AAACACTCAGAAAA |
| 1204 | SESN3 | 3387265 | GGTTCTCCCTGGTGAACAGACTTTATTCTGACATTGGACATCT TCTTGATGAAAAGTTTCGGATGGTCTACAATCTCACATATAACA CTATGGCCACCCATGAGGATGTTGACACAACCATGCTGCGCA GAGCTTTATTTAACTAT |
| 1205 | SESN3 | 3387266 | TGACATGATTATAACATCTGATGTCTCTCGATATATTGAAGACC CTGGTTTTGGGTATGAAGACTTTGCCAGACGAGGAGAAGAGC ATTTGCCAACATTCCGAGCTCAG |
| 1206 | SESN3 | 3387267 | CAGTGGTGTTAGTAAGATACAGTTAATTTATTTCTTAAATGGAT ATTTCTTCCTGTATTAATGAAACAAAAAATAGATAGTAAGTGTG TAGTATAGTACTTGGTATATGGTAAGTACTCAGTAAACACCGT CTCTTTTCTTTATATGTAATGAAGTTTGTTAAGAATTTTAATAAG ATTTATCTGAAATTGGGTAACCGGAGCACTTAATCTTTCCTG |
| 1207 | SESN3 | 3387268 | TTGACCAGCGTTATAAAGTATTCCAGATTCTATGTAAGGATTCT AAGAATAGTTTTTCAAGTCTTTTGAAGAAAATAAATGTTTAAAG TATTCTACAGGGGTCATATTCTGTAGCTTGGTAACAGGGTTAA CTAGCTTTTACTGTTTTTTGTATTTTCAGTTACGCATTCCATTAC TGCAACAGAATGTTTCCCGTATTATGTCAGTAACTACTTCTTAG GGGCAGAATAATGCAGATAATGAACAAAATACTATTTCTTTTGA GTACAGACTTTGAAATATTTGTTTAGATAGAATTAAAGCTAGAG TTTTAGATTTAATAATCAGAATGCTAATTTTAACTTCTTAAGATA AATTTAGGAAAAAAGTATTTGTGGATTGAGGGACCTTTGTACAT TTC |
| 1208 | SESN3 | 3387269 | TTTCAGTCTCTACCTTCTTGGAACTTTAAGCTGGGACTACAGC CTTCAAAAGTGAATTTTGACTAGAAAGTCTTGGACCTTAGCCA A |
| 1209 | SESN3 | 3387270 | CTCTTCTATCTTACCCTCATGCTATTGCTTTCCCTCAGGCTGGT TCATCCTTGAATGTATTTCAGATTGAGTTGAGAGAAACTTTCAG CTTTGTAGTTCATACTCTATCCTGGATA |
| 1210 | SESN3 | 3387271 | GGATTCTCTAAGTGAGCTAGAGGCCTTAATGGAAAGGATGAAA AGACTTCAAGAAGAAAGGGAAGATGAAGAGGCGTCTCAAGAA GAAATGAGCACTCGTTTTGAAAAGGAGAAGA |
| 1211 | SESN3 | 3387272 | TGGTCTCTGCCTGAACTGGTACATGCTGTGGTCCTCCTGGCA CATTATCATGCTTTGGCAAGCTTTGTTTTTGGTAGTGGTATCAA TCCAGAGAGAGATCCAGAAATCTCCAATGGATTCAGGCTAATA TCAGTCAACAATTTCTGCGTTTGTGATCTTGCTAATGACAACAA CATAGAGAATGCATCTCTTTCAGGCAGCAACTTTG |
| 1212 | SESN3 | 3387273 | TTTTAAAGACTGGAGGTATTGCTGAGTGGTTGAATGGTTTGGA ATATGTGCCACAAAGACTGAAAAATCTTAATGAAATTAATAAGC TGCTAGCACATCGACCTTGGCTGATCACAAAAGAGCACA |

TABLE 7-continued

| Target Sequences | | | |
|---|---|---|---|
| SEQ ID NO. | Gene | Affy Probeset ID | Sequence |
| 1213 | SESN3 | 3387274 | GTGCTTATTTTCCTATGTTCACATAACACCTTCCTCACTTATTCT TTCTCCCTTCCAAAATAGGCATGTGTCCTTGTGTGTGTATAGA GCTAAGTATAATTTATGGACATAAGAACTGAAGAAGCCTATGG CCTTTTGGATACCAAGTGTCTTGGGTATATTTGGA |
| 1214 | SESN3 | 3387275 | GAATACTCTACATCCGGTCGTCTGGACAACATCACACAGGTCA TGAGTTTACACACTCAGTACCTGGAGTCTTTCTTGCGGAGCCA GTTTTACATGTTGCGCA |
| 1215 | SESN3 | 3387276 | TCTGTTTCCAGTATGAGCAACTGCATAATTTCAGTGTCTGTTAA TATCAAATGAATATTCATTTGCTTCAATAGTGGCATAATTTATT |
| 1216 | SESN3 | 3387277 | GACAAGAGGACCAAGTGCCTTTATTCCAGA |
| 1217 | SESN3 | 3387278 | AGTGAGCGTGCCCTTGATACTTTTCTGGGGACTGTAATGTAAG CAGAAATTGAGACAAGGGTCCTTGGAACTGGCTGATAGTTTTT TTTCTTCCTAATTTGCCCAAATAGGACAAATAGGTTGATTGGTT CAGAGCATTTCTGCAATTACACTAAAATGCTTGGTTCTGGGATT GAGTAGGTGTGACCATCAAATGAATAACTCTGTGGAGCAGTCA TTTAACATTTCAAAAAGTTATAAAAATGTCTGAAAATGCAATTTT AAAAAAGCAAAACCAAATGAGTCCAGAGCAGCACTGTCCGGT AGAACTGTCTGCAGTGGAAGATGGAAATGTCTGCGCTGTCCT GTAGAGTACACGTGGTCCTATG |
| 1218 | SESN3 | 3387279 | CGGAGAAGAGCTAGCGAGTTCTCTAGATAAAAAAGATTCAGGA GGCAGTTGCATGGGTTGCTCATTTTCGTATCCTGTGCCCTTAT TTTTTCCTTCATCTGCTCCATCGTCTTCCCTACAATATAGTCAC CATAACAAATTTGAGTAGAATTTTGTTTTGTGTAAAGAATATGG TAGCCATAGAAGAGAACATTGA |
| 1219 | SESN3 | 3387280 | TAAAAAGTAGTAATGTTGGCCGCGCGTGGT |
| 1220 | SESN3 | 3387281 | CCATTATCTAGGTTGCACATTTGTGAAAGCATCAGTATATGATG CGTTCCATGGTTGGGATCTAATGATACCCAGATCAAGCCATGA CATAACTAGTGCAGTGTGCAAGATTCAAGCCCTATTC |
| 1221 | SESN3 | 3387282 | AGGTGGTACCTGATGCAGGAATATGTGAGTGTTGGTGTTGGA GAGTGTTGTGAGAGGAAGATTATTCAGCAGAAACAAACCCTTC CTCTGATGAGCAGAAGTGGTGGAT |
| 1222 | SESN3 | 3387283 | TGGCGAGATGTGGTTCTGCTATTTATTTTAAGTTAGAACTCTTA TTCTGAGAGTTTTCCATAGAAACACAGTAAGATATGTGGTTAA GTTCCAGAGTACTGTTAATATTACAGGTATGTTCAGGCATTTGT TAATTAGCCTAGAAACCTAACCACTGGGTATAACGTTTCCAGA GGAACATATATCCTGAAATTCAAGTAACCGCTTCACTAGAGAC TGTCTTTCCTAACTTGTTTACTCAGCATTAAAAAGGTAATGATT TTGGCAAAAAAAAAAATATTTTTCAATATGTTTACTCCAAGGAT GTGCTTGTCGGTTGTGCTGTGTCTAATAGGAAAACTGTGTTAA TGAAGTTCCATCCAATATTTAGGTAGGAGTTGAATGAAGAAAG AGATAAAGTTGGGTAATAATAAGCAGGGTGTTGGGACAACTGA TGGCCAATATCAAACTGGCTTATCCTTGTTCACTTTGTA |
| 1223 | SESN3 | 3387284 | AAAGATCACATTTACCTCATGGGTAACTAAAGCTGGGTTTTGT GGAAGATCATTGTAATTATCTGAAACTGTGACTCTTACTTCCTT TTTTTTTTGGAGTCTCACTCTGTCACCCAGGCTGGAGTGCAGT GGCGCCATCTTGGCTCAGTGAAACCACCGCCTCCCGGGTTCA AGCGATTCTCCTGCCTCAGCCTCCTAAGTAGCTGGGATTACAA GCACCCACCACCATACCCAGCTAATTTTTTATATTTTTTGTAGA GACGGGGTTTCACCATGTTGGCCACGCTGGCTTCGAACTCCT GACCTCAAGTGATCTGCCTGCCTTGGCCTCCCAAAGTGCTAG GATTAAAGGCACGAGCCACCCAGCCCGGCTGTGACTCTTACT TTCAAAACACATTTTATAATATCTATAATGACAATAGCTTCTACT GAATACTACTTATGTGCTAAGCATTTAAACTCTACATATGTTAT CACATTCAAGCATCACAATTAACCTGCGATGAATTATTACTCAC AGTTTATGGATAAAGAAACTAGGGCTCACAGGGC |
| 1224 | SESN3 | 3387285 | TGTGCAGGTCTTGAATTACAATTTGTTCTGCTATCTTTGTACAG ATATTTGAATTTTTTTTTGTTACTGTGTCATGTATGAGAAAGATT GTCATTGATTGTGAAGGAACTGGCTTTTTAAAAAGAATTCCTTC CATATTTACTTAAGTTAAATGTTTACTTGTGAGAACACAAATTTA TTGTTATCAGTAGTTGTAACTTTATTACTAAAATACTTGAAAGTT GCTTGGTATATTTATATGCTTTATAGTTCAGGTTCAATAGAAGA TTTAATTTGTAAAAAGTGTTCTGCTGCTTC |

TABLE 7-continued

Target Sequences

| SEQ ID NO. | Gene | Affy Probeset ID | Sequence |
|---|---|---|---|
| 1225 | SESN3 | 3387286 | GTCGGCCGCCGCCAACTACCTGCTCTGTACCAACTGCCGGAA AGTGCTGCGGAAG |
| 1226 | SESN3 | 3387287 | CCCTCCGCCCGCTCTCGCCTCGGCG |
| 1227 | SESN3 | 3387288 | CGTCTCCGCCGTCGCTGGGGCAGCTGCCGCGGTGGTCGCCT CTGGCAGTGCCGCTAGCTTTCAGGCAGTCGCCTCTCCTCCCG ACATCCCGCCTTGA |
| 1228 | SESN3 | 3387289 | GCCAGTAGGCGATGCAAGTTATCTCTGGGGCCCGGAGGACAC GAGTGAGGACCGGGCACCAATCAGGTTCTCGCTCTGCGCCG GCCTTTGTTCTCACTCGGGAGCAGGTTGCGGGCGTCTAGCAT CGGGAACCCGCATTCGACTCGGACGCGCATTGCTA |
| 1229 | NR4A1 | 3415226 | CAGGAGGGCCCCCTGCGCTAATCTGCCCTGGCAGCAGCGAG CTGGCACGCCCTGGGTGCATCATCCGGTGTGCTCT |
| 1230 | NR4A1 | 3415228 | GACCCGCCGGGCCAGATCCCATCTCTGGCGACGCGGAGAAA AATCTGGAAGCCGTCGTCGGA |
| 1231 | NR4A1 | 3415230 | CCGCGCGGCCGGAACTGCGGGCGGGG |
| 1232 | NR4A1 | 3415231 | GGCGCCCCTGCGGTGCAGAGCAGCTCAGGGCCGGCTGGTGC GCGACCCCGGAAAGCGGG |
| 1233 | NR4A1 | 3415232 | AGTCCAATAGCCAGTGAAGGCCTGGTCCTGCCCT |
| 1234 | NR4A1 | 3415233 | GCCTCCACCATGGACAGAGGCCAGGCCCTGC |
| 1235 | NR4A1 | 3415234 | GCCCTGAAGGCAGACGGGATAATGTGGTTGGCCAAGGCCTGT TGGTCCATCCAGAGTG |
| 1236 | NR4A1 | 3415235 | CCCAGGGTCACGCTCATGCTGGGGCTCCCGTCAGCTGACTAT TTTG |
| 1237 | NR4A1 | 3415236 | GTCAGGTCCAGTCAAGAGGGCCCAAAGTG |
| 1238 | NR4A1 | 3415237 | CCAACCAATCTTGGGATTCTCCCTTCGTGCGGTTGTCTGGGAC CTTTTTCCAGGGTCAAAGCAGATCGTGAGGAGGAAGC |
| 1239 | NR4A1 | 3415238 | ATTTGGATGTGGAGCCTCTCCTTTCCATTGTGAACTGAATTCTA CCAGCACTGGGCCTGGTGATGTCTGCATTAGGCAGATGAGGA AGCAGTCTTGGAGAGGACAAGGGACTGGCCTCAGGTCACACA TCAGGCTTGCTAGCTCCTGGACAAAGATGCCTCTGATAGCTCT TCCATA |
| 1240 | NR4A1 | 3415239 | CCTGCCCTGGGCTACTTACTACTGAGGATGCACAAAGGATCTT CCCACCACGGACTAGGAGACAGTGCCCTTGTCCTCATGTTGTT CACATACTGGTCGGTGAGGGATGGGTCTGAGTACATGATAAA TCCCTGGGCCCCATAAGATTTGACTAGGAGGGGTAAGGGCCT GGTGAACTGCTCAGAAAATAAACTGTGTTGTCAGCAGGAGGA CCCCTTTCTACTATGAGATATTGCATTCCCTGCTAATCATACTT GTGCTCTATCTGTTGATAGAACAAATACATAATGAGAAACAGC CACTGTGCTTTCAGAAGAACACACTTGAAAGAATTTGTTCTCAA TAAATTACATCTGCATCTGGATCCATATGAAGAAATACGTTCCT CTCATTCAGGCGTGGCTATTT |
| 1241 | NR4A1 | 3415240 | ATGGCCAAAGCTCGACGGGCGGCCTGCGTCAGTGGCGC |
| 1242 | NR4A1 | 3415241 | GGCTCGGCCGGGGAGTCCCAGTGGCGGAGGCTACGAAACTT GGGGGAGTGCACAGAAGAACTTCGGGAGCGCACGC |
| 1243 | NR4A1 | 3415242 | GACCAGGGACCAGGCTGAGACTCGGGGCGCCAGTCCGGGCA GGGGCA |
| 1244 | NR4A1 | 3415243 | TTCCCTTCGGGGAACGTGCATCTGTTTTTAGGAGCGGTGCATG AAGGAGATGGGTGTACGCGCGGGCAGAGAGGATGTTGTAGG GCCGGCATGC |
| 1245 | NR4A1 | 3415244 | TGTTGGAGTCTTGGGGCGGTGCTGCCTAGAGGATACCTCCCA ACCATTCCAGCTCCAGATGCTGATCATCCCTATG |
| 1246 | NR4A1 | 3415245 | TGAGGCTTGTTCAGCAGAACAGGTGCAAGCCACATTGTTGCC AAGACCTGCCTGAAGCCGGATTCTCC |

TABLE 7-continued

| Target Sequences | | | |
|---|---|---|---|
| SEQ ID NO. | Gene | Affy Probeset ID | Sequence |
| 1247 | NR4A1 | 3415246 | TGTCCTAGTGCAGGCAGATGTGGCCACCCTCACCTCTCGCAG GGTGCTGCATGCCTG |
| 1248 | NR4A1 | 3415247 | GTACTGTTGTCCATTCTCCTGAGAGTCCAGGGGGCTGTGGTC TCCTTCCTCCCCCCTTGCCCTGTCCCCAGCAAATGGCCTTTAA AGGTCTGGAGCCAGGTTACCGATGAGGAGGCCTAGGTTCCCT TCCTCTTTGCTTCTGGGAGCATCTCGAGCAGTGCAGAGTGGC TTCCCAGCCCCAGATGGCAGGATTGGGGTGGGTTTGGGATCT GCTGCCTTTGCTCAGTGTGCAGGGTTGGGGTGGAAATGGGGG ACAGGCTAGGGCCTCTGCATTAGGCTGCCTTCTTAGGCAGGT GGGCTTTCACTTCCAGCTCCTCTTCCATTTTCACGATGTCCTTC TTCCTAGGCACTGCGAGGGGAGGAGAAAAGGGGCTTTGCAGA GGCCTGGGAGTATTCCCAGGAAGTGCCTGGTTGGCGAAACAA CCAGGGAGCTGCTCCTGGGAGCTGGGCTGAGGCTTTGCTGG GCTGCCTCTCCCACTCACCCTTCTCCCGGCCCCCACCATGCC TTCCCCATGGGGAGGGGCAGGGGGCTGGAGGAACACAGCT TCCCCCTGTTCTAGCAGAGAAATGCTGGCTGTATGCCTCCCCT AGGGTTCCCAGGCTGACTAGGGTGTGGCTGGCCTTCTGATGG AGCCCACTCATGCTGGGCCGCTGCCCAGGGGCTTTGTGGCAC CTAGGTCGAGATGGTACTCAGGCCAGGGGTCAGGATTCCTGG GTGCTCTGGTCCCGGTGCCTCTGTCTCATCTTTAGGCTGGGAT TCCTGC |
| 1249 | NR4A1 | 3415248 | TCCAAGCCCAATATGGGACACCAGCACCGAGT |
| 1250 | NR4A1 | 3415249 | GACCACCTGGCAAGCGACCCCCTGACCCCT |
| 1251 | NR4A1 | 3415250 | CCAGCTTCAGCACCTTCATGGACGGCTACACAGGAGAG |
| 1252 | NR4A1 | 3415251 | CTCGGCCTCCTCCACATCCTCGTCCTCAGCCACCTC |
| 1253 | NR4A1 | 3415252 | GACTTCCAGGTGTACGGCTGCTACCCCGGCCCCCTGAGCGG CCCAGTGGATGAG |
| 1254 | NR4A1 | 3415253 | GGCTCCTTCGGCCACTTCTCGCCCAGCCAGACTTACGAAGGC CTGCGGGCATGGACAGAGCAGCTGC |
| 1255 | NR4A1 | 3415254 | AGAGAGCTATTCCATGCCTACGGCCTTCCCAGGTTTGGCACC CACTTCTCCACACCTTGAGGGCTCGGGGATACTGGATACACC CGTGACCTCAACCAAGGCCCGGAGCGGGGCCCCAGGTGGAA GTGAAGGCCGCTGTGCTGTGTGTGGGGACAACGCTTCATGCC AGCATTATGGTGTCCGCACATG |
| 1256 | NR4A1 | 3415255 | CGCGCAGCCCCAGGTGGGGCCTTTTGTTGGAAATGGAGAGA GGCTGGCCTCATCCCATTGGGACCTGTGGTCTCCC |
| 1257 | NR4A1 | 3415256 | GAAGCTTTCATTTGCCGGGACACTCGGGCCCATGGGATTGCA CAGAGCTGGAGGGAGGGGTGAGATAGGGGCAGATAGGAGCT GCAGGGGTGCCTGGCGAGCCTCTGGTTTTCCTCTGCTCCTCT GCCTGTCCTCTCCCAACTCAAGGTTCTAGTGGGAAGGGGTGC CCCCAGGCTCTCATGTTCCTGGCGTGAGATGAAAGGATCCCT GCGGAGGGTTTGGTTCTTGAGGGCTGGGGGTGGACTTGGGA ACAGGCTGTGTGTTTGTCCCAGCGATGGTGCCTGCTTAGCTTC CCGTCCCCACCCCCCAGCCCCTTGGCCCTCTCCTGTCTGCCC TAGGGAGAAGGCAGGTGGACAAGGGCCCATGAAAAAATACAG GTGTCTAGACTGCCAGGGAGACCCTGGCCCCCAGTAGTGTGT CCTGGGGACTTCCTCAGAGCGAGAAACCTCCCCCAATGTCTT CAAGACTTTTCTCTCCCCCCGCCCAACCCCGTCTCTCCCTCCC TTGCCACCCAAATGTTAGAAAAATAGCTGTGAACAGAGAGCGC TTTTGTCTGCAATGGCAGCAGGATCTGGACGGTCCCCTCCCC TAAGTTCCCCCCTCCCCACCCCACACTCTGACAGCTTGTTCCG TGTTGCCC |
| 1258 | NR4A1 | 3415257 | GCACAGTGCAGAAAAACGCCAAGTACATCTGCCTGGCTAACA AGGACTGCCCTGTGGACAAGAGGCGGCGAAACCGCTGCCAG TTCTGCCGCTT |

TABLE 7-continued

Target Sequences

| SEQ ID NO. | Gene | Affy Probeset ID | Sequence |
|---|---|---|---|
| 1259 | NR4A1 | 3415258 | CCCAGCGGGGCAAGGGTAGGCTTGAGTGGAGTGGGACCAGC AGGGCCCCCAGGCTTCTGCCCTGGAGGACCCAGAGGAGGGC ACGTCTTATTTCCACCCCACCTCTGAACCCCAGGCCTTGGAGG GAGGCAGCCTACACCTGCCTGGATTGTGAGGGTGGTGGCAG GGGGAGGTTCCTATAGGGTACCTTGGATCTCAGGGACTCTGG GTCCTAGGGACTCGGTGGGGCGCGTCTCAGCAGTGGTGTGC ACGGCTTGGGCTGAGAGGCC |
| 1260 | NR4A1 | 3415259 | TTGTCCGAACAGACAGCCTGAAGGGGCGGCGGGGCCGGCTA CCTTCAAAACCCAAGCAGCCCCCAGATGCCTCCCCTGCCAAT CTCCTCACTTCCCTGGTCCGTGCACACCTGGACTCAGGG |
| 1261 | NR4A1 | 3415260 | CCCAGCACTGCCAAACTGGACTACTCCAAG |
| 1262 | NR4A1 | 3415261 | CTTTGTGCGTGTTAGGAGAGCTACCCCCTCTGGAAGGACTGA ATGAGAAAGGAGGTTTAAAAAAGAAAGAAAGAAAAGCGACTCC CTCCAGTTCGACAGATCAAAGAGAGGATCCCCCTCTCGGCTG ACCAGATGGGAAAATGCACCCCCTCAGGCAGGTGGCCAATTA GAA |
| 1263 | NR4A1 | 3415262 | GGGATGTACAGCAGTTCTACGACCTGCTCTCCGGTTCTCTGG A |
| 1264 | NR4A1 | 3415263 | GTCATCCGCAAGTGGGCGGAGAAGATCCCTGGCTTTGCTGAG CTGTCACCGGCTGACCAGGACCTGTTGCTGGAGTCGGCCTTC CTGGAGCTCTTCATCCTCCGCCT |
| 1265 | NR4A1 | 3415264 | CTTTCCCTGATACACCTGCCTGTGAACCACCCTGATCGCTCTT CGTGCC |
| 1266 | NR4A1 | 3415265 | CTAAGCCAGGCGAGGGCAAGCTCATCTTCTGCTCAGGCCTGG TGCTACACCGGCTGCAGTGTGCCCGTGGCTTCGGGGACTGGA TTGACAGTATCCTGGCCTTCTCAAGGTCCCTGCACAGCTTGCT TG |
| 1267 | NR4A1 | 3415266 | TCAGATGTACAGCTAATCCTGTACCCTTCC |
| 1268 | NR4A1 | 3415267 | ACCGGCATGGGCTGCAGGAGCCGCGGCGGGTGGAGGAGCT G |
| 1269 | NR4A1 | 3415268 | GAACCGCATCGCCAGCTGCCTGAAGGAGCACGTGGCAGCTG TGGCGGGCGAGCCCCAGCCAGCCAGCTGCCTGTCACGTCTG TTGGGCAAACTGCCCGAGCTGCGGACCCTGTGCACCCAGGG CCTGCAGCGCATCTTCTACCTCAAGCTGGAGGACTTGGTGCC CCCTCCACCCATCATTGACAAGATCTTC |
| 1270 | NR4A1 | 3415269 | TGCACATGCGCACTCTCATATGCCACCCCATGTGCCTTTAGTC CACGGACCCCCAGAGCACC |
| 1271 | NR4A1 | 3415270 | CTGGGCTTGAGCTGCAGAATGACTCCACCTTCTCACCTGCTCC AGGAGGTTTGCAGG |
| 1272 | NR4A1 | 3415271 | GGGTGACCCCACGATTTGTCTTATCCCCCCCAGCCTGGCCCC GGCCTTTATGTTTTTGTAAGATAAACCGTTTTTAACACATAGC GCCGTGCTGTAAATAAGCCCAGTG |
| 1273 | NR4A1 | 3415272 | ACCCTCCTTCCACATGTACATAAACTGTCACTCTAGGAAGAAG ACAAATGACAGATTCTGACATTTATATTTGTGTATTTTCCTGGA TTTATAGTATGTGACTTTTCTGATTAATATATTTA |
| 1274 | RP11-121G22.3 | 3424282 | GTGTAAAAGTGTGAGACAACACATTTCTGTTGTTTAAGACACA CAATCTGTGGTACTTTGATACAGCAGCCCTGACAAACTAATAC ATGGGGTGTCTCATTGTAGTTTTAATCAGTAACACCCATTATGA ACTGAAAACGTCTGCTACTT |
| 1275 | RP11-121G22.3 | 3424283 | CAAGAGGTGACCATCAGCAAGCCCAGGAGAGAGGCCTCAGAA GAAACCAGACCTGCTGATTCCTTGATCTTG |
| 1276 | RP11-121G22.3 | 3424284 | CAACTTGAATGCTTCCTGATTAAATATATACAGGAGTGATTTCA GAGGAATTT |
| 1277 | RP11-121G22.3 | 3424285 | CCATTAAGACTAACCGTTTTTGCTGGAGCTGCAAGATTTTCCAT TTCTTCATGAGTCACCCAAACGTTGCCTGAAGGCTAGTG |

TABLE 7-continued

Target Sequences

| SEQ ID NO. | Gene | Affy Probeset ID | Sequence |
|---|---|---|---|
| 1278 | RP11-121G22.3 | 3424286 | GTGGCTCTTGAACAACACAGGTTTGAACTGCATCATTCCACTTATACACAG |
| 1279 | RP11-121G22.3 | 3424287 | ACTCCTGAGACAACATGACCAATCTCTCCC |
| 1280 | RP11-121G22.3 | 3424288 | CGTACTTTCAACATAAAGACGACGAGGATAAAGGCATTTATGATGAACTACTTCCACATA |
| 1281 | RP11-121G22.3 | 3424289 | GCTTACTTTATTGTACGAATGGAGCATATATGTGTACATATAAAACACATAATACATGCTTATCAACTATTTGTGTTATCAGTAAGGCTTCCAGTCAACAGTAGGCTCTTAGTAGTTAAGTCTTGGGAGAGCCAAAAATTCTAGCTGATTTTTTGACTGTGTGTGGGGGGTCAGCACCCTTAACTCCTATCTTATTCAAGGGGCTATTGTATTCTAAATTGTCTTTTAGCTTGAGTCATAATCCAGGTATAGTG |
| 1282 | RP11-121G22.3 | 3424290 | GCAAAATACAGTGCCAAGAGCTCTGGACCACAAATCAGAAGACCTGAGCCCTAATTCCTTTCCA |
| 1283 | RP11-121G22.3 | 3424291 | TTTGTTCGTCGCTTGCCAAAATAGCAGCGAACTCTCTGTCAAACTGCAACTCATTTTATCGGAGCAAAAACT |
| 1284 | RP11-121G22.3 | 3424292 | GAAGCAGCTGATCGCTAATATCTGATGGCTAATATGCTAAATTTCCCTGTC |
| 1285 | RP11-121G22.3 | 3424293 | GAGGCAGTGCAGCTTGTGTTACAACTCAAAAGAGTAATACTCTGAAAAAAGAAAAAAAAAGATGGCGCTGAAAATAAACATGTTCAGCAGCCATTGTGATTCAACTTACCCAGATGTGCTTTTCATGAGATGGAGAAGGACGGATGGAAAAGAAAAGCACACAAATGTTAATGGATACAGTTCAATCCAAAGAAAACCATGGAATAAAACAAGAGCATTATTTAAGATGTGAGAAAGCTCAGGTATGAGAAAGACATGGTGCCATTTTGTATTTCATCATGACACACATACTCACTGCGTCGAAAAGCATAGTCA |
| 1286 | MYBPC1 | 3428597 | GCGAATGCAACTTTGACCCTAAGAAATCCTTTATGCAGGTGGAGACACAGCTTCTTCAACCAATGAAAGAAATAATATCTGGCTTCTTGAATAGTTTCATGGTGCCACCAACAAAAACTATCATAGACCAACAATGGCAAGATGGCATCGGCAAGAATGAGCTG |
| 1287 | MYBPC1 | 3428598 | CCAGAATCTCATCGTGCAGGCTACAAATAGCAGCTGCAGCTGCAGACCAAGGGCTGGCCTTTACATGTCCATGGTGCAAAAGGACTCCTG |
| 1288 | MYBPC1 | 3428599 | CAACTGCTTGTCACACCGACCTGCACCATCTCTCGCCTGCCTGTGGGGTTTCTGTCAACTAGTCGTGGAGGGAAG |
| 1289 | MYBPC1 | 3428600 | ATGCCAGAACCCACTAAGAAAGAGG |
| 1290 | MYBPC1 | 3428601 | AGTATCCCCGAATCAAACATGAATGTTGAAGTCAACTACCCAGACTGAAG |
| 1291 | MYBPC1 | 3428602 | TACACACTAACTTTAATTTGGAATACAGTAAATATTGTATTAGTGTGTCATATATTTACTGAATTAAAAATTAAAATTGGTTGGGCATGGTGGCTCATGCCTATAAACTCAGCACTCAGGGAAGCAGAGGCAGGTGGATCACCTGAGGTCAGGAGTTTGAGACCAGCCTGGCCAACATGGTGAAACCTTGTCTCTACTAAAAATACAAAAAATTAGCTGAGCGTGGTGGTGGACCCGTGTAATT |
| 1292 | MYBPC1 | 3428603 | TGCCAGGGGACGGTTATGGATTTCTTGGCAGCAAGGAGAAGCGGCTTTTGTGCAGGGAGGAACAGCCTGCCAGTCAACTATATTTATGGAGCACCTGCTGTGTGGAATCTGAAAAGGAGAAGGAGAAGGGCCTTGTCCTCAAGAAGCTTGTGATCAAAGGGAGAAGAAAAGTCCCCATCTACTGT |
| 1293 | MYBPC1 | 3428604 | TGAACAACGGCTTTGAATGCGAACCTGGGGAGTGTAGACCTAACCAAATAATAAT |
| 1294 | MYBPC1 | 3428605 | ATTTGGCACGGGAAATGCTATGCTCTTTGTTCATGTGGATGCCTTTACCTACTTGGAAATAGTATGTTCTTTAACAGAAGTTTCTTTGTCAGACTTCATAGCCAGACTGCTCTGTAATAACCAGA |

TABLE 7-continued

| Target Sequences | | | |
|---|---|---|---|
| SEQ ID NO. | Gene | Affy Probeset ID | Sequence |
| 1295 | MYBPC1 | 3428606 | AAAATGAAGTGCCAGCCCCAGCCCCACCCC |
| 1296 | MYBPC1 | 3428607 | CACTCACACACGTTTGGGCTGCAAATACAGAGGGTCCATCCC AGCATGATTTGGCCTCCACGGGTGCTGTGAGCTGTGAGCTTT AACCTAACTCCTACTGAGAAGTTGGATGGTGACCATTGTGATA AGTTGAGAATAATAAAAATAATACACTGTGTTTATATAATCCTC TTGTGTTAATCTAATTTGGATGGCACTTCATATATATTAGGGGG ACAATTCTTATGAAACCTTTCAAATTATGTAAAAGTTATTATGTC CGCATTTTACAGTGTGGAGGCTGAGCCTCCATCCAAGGGGCT GAAGAATTTGTGAGGCTTTTTCCTATATAGTGAAGGTCAAACA AACCCACATCTTCTTTATGAGAGTGGGGAGTGGATCCATCTCT ACCCTG |
| 1297 | MYBPC1 | 3428608 | CTGGCAACAGGAAATGAGTACAGAGATCCAGTGAGACCCTT |
| 1298 | MYBPC1 | 3428609 | AAAAATATGCTTGTACTTTCTACACAG |
| 1299 | MYBPC1 | 3428610 | AGAGAAGGAGGCCGGAACTACACCAGCAAAAG |
| 1300 | MYBPC1 | 3428611 | TCTGCAAGTCCCAATCAGTATAATGACAAATGGTGCATTGCTA AGTTTCCATTACATGTATTTCTAAAAGAAAAACAACAATGATAA AAATATCACAAGCACTTGTTGAGATGCCAGCAAATTAATTGGT AGTTTCCAAGTTTCGACATGCATGCTA |
| 1301 | MYBPC1 | 3428612 | GACACTACTGTTGGGTGATCTAGACGAAGACTATTTCATGATA CTCTGAAGCGCTGCATTCATATGTATTCCTTCATGGTCTAAAAC AACTGTGCATGTCCTCCAAATAGTCTTAACATTTAGTAGACTTT GAAACTACTCACCTATCAAATTTTTGCTTAAAAAACAGATTGCC GGCCAGG |
| 1302 | MYBPC1 | 3428613 | GCACAATGTTGTGGAATGTGAATGCATGCATATTAGTTCAGGA GAAAAAATTCAAAATGAACTAAGTTTGGGAG |
| 1303 | MYBPC1 | 3428614 | TGCTAACAGGAAACAATACCGACGTTCTTTTTCTTATAGCATTT GTATTATAAAAAGCACAAAGCTCCAGCCCACTGAA |
| 1304 | MYBPC1 | 3428615 | ATGAAGTCTTTTCTCCTTGACTTTTTACTCCTATTTCTTG |
| 1305 | MYBPC1 | 3428616 | GAAGAGGAAGTCTCCCCGCCTAGCGCCTTGCCT |
| 1306 | MYBPC1 | 3428617 | GCTTTCATACTTGGAGCTCTACTGATTTTCCATCCAAGCCAACT TGTAGGGTTTTTTCCTTCCTATCACCAGAGGAGACAGGGTTTA GGGGAATCCAAGAAGGTTGAAGTCAGCACT |
| 1307 | MYBPC1 | 3428618 | TTTGGGTAGTCGGGCCCTGGAGAGAAAAGATTCAG |
| 1308 | MYBPC1 | 3428619 | GAGCTCATTTCTTGAAGCTGTATTGATTCTAATCCTTGTCTTAT TCAGATTGTAGTTTTTACGGCAATCTTTCATTACGTTTCCTCTT ACAAGAAAACTAATGTATTGAGAAACAATTAATTTTGCATGATA CACACGCATTCAAGGATCTAGCCAAAAATACCACAGGTTTGTT CTATCATTTTTA |
| 1309 | MYBPC1 | 3428620 | ACTGGCCACCATTGTTTACCTGTTAGGGGACAGGCAAGATGG GGAAGCAAAGGAATTATTGCCATCAAAGAGAGAATAACAGCTT ACCTGGAAAGTTCCACTATTTCTAAGAATTACATAATGTTCATT TGCCCCATCATGGAAGAGATACCCCTGTAAGAATGGGAATCT GTTCCCCTCTACTGATGGCTGCTGGGGGCAGAAAGAATGATG TTGTATTTATCTAGGTTTATTAGACAAAGAAAAGCTACAGCGTT GGTGAGAACAACAAATCCAGGTAAGACTGCCTAAGAAGAGCC TGGCCCTGAAATAATCCTTTT |
| 1310 | MYBPC1 | 3428621 | TGGACCCTTGTCGAAACTCCTCCTGGGGAGGAACAAGCCAAG CAGAATGCCAACTCCCAGCTGTCCATCT |
| 1311 | MYBPC1 | 3428622 | AGCAAAACAAATGACGCTTGTTAAAGAGCAAGCTGAATCCCTT ATGCTTCTTCTAG |
| 1312 | MYBPC1 | 3428623 | ATCACCTTCATAGCCAAAGTCAAGGCTGAAGATCTTCTGAGAA AACCCACTATCAAATGGTTCAAAGGAAAATGGATGGACCTGGC CAGCAAAGCCGGGAAGCACCTTCAG |
| 1313 | MYBPC1 | 3428624 | CATTTGAGATGCAGATCATCAAGGCCAAAGATAACTTTGCAGG AAATTACAGATGCGAGGTCACCTATAAGGATAAGTTTGACAGC TG |

TABLE 7-continued

| SEQ ID NO. | Gene | Affy Probeset ID | Sequence |
|---|---|---|---|
| | | | Target Sequences |
| 1314 | MYBPC1 | 3428625 | TCTACTGGGACTACTCCAAACATTGACATCAG |
| 1315 | MYBPC1 | 3428626 | AGGATGCAGGAGAACTTGACTTTAGTGGTCT |
| 1316 | MYBPC1 | 3428627 | AGTGAGACATTGTGGCCTGGAAGTCTTTCAGACACCCACTCA GAGAAGTCAAGTTTAAAGTGGATGTTCTTCAGAGAATTTTTCAT TTCTGAAAATGTGTTTTGCTTATAGAATATAACAGAGTTGACTA GAAAGAGAGAAACAACTGCATACTAATCTTTTAAAGCCTTTAAC AGTTGCTTTTAAACTTTCTTTTTAAATGTTTCATGACTCTTCACC TATTTTTTTTTAAATGGGGACGAAGAGATATGAAAACTGAGACA TAAGACAAATACCTAGAAACCTCTAAGACTGCACATATGATTTG GTAGAAGTCTGAAGGTATACACATTGTAAGAGGCAGACCTA |
| 1317 | MYBPC1 | 3428628 | ATAGATACACTTTTGTGGGAGGAAAAATAGTGGTAAAAACATG GACTGGAGTCTCAGCTCTACCATTTACTAATTATGTGACTTTGG TCAAATATTTGACCCCTCTGAGACTTGGATTTCACATCTGGAAA TGTGAAGAATAAACACTACTTAATAGAATTATTGTGCAAATTAA ATTAAGTGTAAAAAGCTTGGTTCACAGTAGGTGGCAAATAAAT ATGTACTTCCTCTAAGGAAATGTGTCATTTTCTCTAACATAGTT TATATTCATAAGGAGACAACA |
| 1318 | MYBPC1 | 3428629 | CTCTGTACAACGAAAGATCTTCCTGCTCTGAACAAAGCCAGCT TACTTCAAATAGACATTAGCTAAATCAGATTAAATCTTTTGGGC AGCATCCTGTTATAGGAATTGACCTGTATAAATACTTGTAAGTT GTACTCTACATAAAATTTCTATAACTGTTATACTCTTCACTAGG ATCACCAAGTTATTGAAATTTTGATGTAGATGAAAATACAGTGA GTATTATACAGGTCTATCCCGAGGCTTGGAAAAGAATCAGAAG TGCCTACAGAAATTTGGCTTTTTCTCCTCACTGTAACTTAACAT AGCCATGCAGACAGGGTCATGTGCAGCCACCATGGTA |
| 1319 | MYBPC1 | 3428630 | CAGTGAGTACGAGAAGATCGCCTTCCAGTATGGAATCACCGA CCTGCGCGGCATGCTCAAGCGACTCAAGCGCATGCGCAGA |
| 1320 | MYBPC1 | 3428631 | CTTGATCCTGCATATCAGGTTGACAAAGGAGGCAGAGTGAGG TTTGTTGTGGAGCTGGCAGATCCAAAGTTGGAGGTGAAATGGT ATAAAAATGGTCAAGAAATTCGACCCAGTACCAA |
| 1321 | MYBPC1 | 3428632 | TACATCTTTGAACACAAAGGATGCCAGAGAATCCTGTTTATCA ATAACTGTCAGATGACAGATGATTCAGAGTATTATGTGACAGC CGGTGATGAGAAATGTTCCACTGAGCTCTTCGTAAG |
| 1322 | MYBPC1 | 3428633 | TGGTCACCAGGAGCTGTTGGCTTCTTCTCCCAGGGATAATGAT CAAAGTGA |
| 1323 | MYBPC1 | 3428634 | AGCCTCCAATTATGGTGACCAAACAGCTGGAAGATACAACTGC TTATTGTGGGGAGAGAGTGGAATTAGAATGTGAGGTGTCTGAA GATGA |
| 1324 | MYBPC1 | 3428635 | TCCCTGGTCCAAAATCAAGATACCGAATTAGAGTTGAGGGTAA AAAACACATCTTGATCATAGAGGGAGCAACAAAGGCTGATGCT GCAGAATATTCAGTAATGACAACAGGAGGACAATCATCTGCTA AACTTAGTG |
| 1325 | MYBPC1 | 3428636 | TGACACCTCTGACTGATCAGACTGTAAATCTTGGA |
| 1326 | MYBPC1 | 3428637 | CCTGTTCAGGAGAGTGACCGTCTAAAGGTGGTTCACAAG |
| 1327 | MYBPC1 | 3428638 | TCCACAAGTTAGTGATAGCCAATGCCCTCACTGAAGATGAAGG TGATTATGTATTTGCACCTGATGCCTACAATGTTACTCTGC |
| 1328 | MYBPC1 | 3428639 | AGGAAACAAGCTTCGTCTTGAGATCCCCCATCAGCGGAGAACC ACCTCCTAAAGCCATGTGGAGCCGGGGA |
| 1329 | MYBPC1 | 3428640 | GGCAGTGGCCGGATAAGAACAGAATCTTACCCTGATAGCAGC ACTCTGGTCATTGATATAGCTGAAAGAGATGACTCTGGTGTTT ACCACATCAATCTGAAAAACGAAGCTGGAGAGGCACATGCAA GCATCAAGGTTA |
| 1330 | MYBPC1 | 3428641 | CTGATCCTCCAGTGGCACCGACTGTGACAGAGGTGGGAGATG ACTGGTGTATCATGAACTGGGAGCCTCCTGCCTACGACGGAG GCTCTCCAATCCTAG |

TABLE 7-continued

Target Sequences

| SEQ ID NO. | Gene | Affy Probeset ID | Sequence |
|---|---|---|---|
| 1331 | MYBPC1 | 3428642 | AAGAAACAAAGCTCCAGGTGGATGAGGCTGAATTTTGATCTCTGCAAAGAAACAACTTTTGAGCCCAAGAAGATGATTGAAGGTGTGGCCTATGAGGTCCGCATCTTTGCAGTCAATGCCATTGGCATCTCCAAGCCCAGTATGCCCTCCAGG |
| 1332 | MYBPC1 | 3428643 | CCTCCTACTCTTCTGACTGTGGACTCTGTCACTGACACGACTGTCACGATGAGGTGGCGCCCCCCAGACCACATTGGTGCAGCAGGTTTAGATGGCTATGTGCTAGAGTATTGCTTTGA |
| 1333 | MYBPC1 | 3428644 | GTGCCTCAGGTCAGAAGCCACAGTCTGCACAGAGCAGGCTGTGCTCTCCTGAGGAACCCCCCTAACACCGTTTGGTCTCTTCCGTCACTGCTCTGAGGACAAATCTCTTTGCACACTTTGCATACTTTACTAACAGAGAATGCTGACTGCTGATACGATATTATTC |
| 1334 | MYBPC1 | 3428645 | GTACATCAGCAAAACAGTCTGATGAA |
| 1335 | MYBPC1 | 3428646 | TCTGATTGACAAGACGAAGTTCACCATCACAGGTCTGCCAAC |
| 1336 | MYBPC1 | 3428647 | TGCGTGTGAAGGCTGTTAATGCAGCTGGTGCCAGCGAGCCCAAGTACTATTCTCAGCCCATTCTCGTGAAGGAAATCATAG |
| 1337 | MYBPC1 | 3428648 | ACCTCCAAAGATTCGCATTCCAAGACACCTGAAGCAAACCTATATCCGCAGAGTTGGAGAAGCTGTCAATCTGGTTATACCTTTCCAG |
| 1338 | MYBPC1 | 3428649 | AATAAAACCAGAAGTGGCAACAAGGCAG |
| 1339 | MYBPC1 | 3428650 | ATAAACATTCGCAACTCTGAGACTGATACAATCATATTTATTAGAAAAGCAGAGAGGAGCCACTCTGGGAAATATGATCTGCAAGTCAAAGTGGACAAATTCGTGGAGACCGCATC |
| 1340 | MYBPC1 | 3428651 | CCAAATTGTGAAGATTGAGGATGTCTGGGGAGAAAATGTCGCTCTCACATGGACTCCACCAAAGGATGATGGAAATGCTGCTATCACAGGCTATACCATTCA |
| 1341 | MYBPC1 | 3428652 | CTTTCTCTGGTTCATCAGTAGCAAAAGG |
| 1342 | MYBPC1 | 3428653 | CCAACTGGGGCTATGGAGAAGTGATGTGGCAGAGCAGAAAGGAAAAGACCTGTGGAGCCACAGAGCTGGTCTTAAACCCCAGCATTGCTACTTAAGACCACATGTATAAGGACCACACGTGACCACAATCACT |
| 1343 | MYBPC1 | 3428654 | GGTTTACTGTCATTGAGCATTATCATCGAACCAGTGCCACCATTACTGAATTGGTCATAGGGAATGAATATTACTTCCGGGTCTTTTCTGAAAACATGTGTGGCCTCAGTGAGGATGCCACCATGACTAAAGAGAGTGCAGTGATCGCCAGG |
| 1344 | MYBPC1 | 3428655 | TCAGAGGCACCCATGTTTACTCAGCCTTTGGTTAACACCTATGCCATAGCTGGTTACAATGCCACCCTAAACTGCAGTGTG |
| 1345 | MYBPC1 | 3428656 | GTACCATGTTCTTCTATCACATCAGTTAAAGTCCCTGTCTTGTA |
| 1346 | MYBPC1 | 3428657 | CACTACACTGTCTGCGATAGGTTAAAGTAAACAACAATTACACTACACTGTAAGACAGAATATGAATGTGCTTTGATAAGGGTACAGTGTGCTAAGAAGGGAGCTATCATATCCAGTTGAAGAGATTAGAAAGGTTTCAAGGTTTCATGTTTGCATTTGAAAAGAACAACGAATTAATGAATATCGCCCATAGAGATGTACATATCCCTGGGTGCAAGACAGAAAGTACCCTAGAATTGGGAAAATTTATGAACTTCTTTTTTTCCTGTATATACCTTGATCAGAAATAGGGAAGTCGTC |
| 1347 | MYBPC1 | 3428658 | CACTGGCTTTGATGGTCTATTAATATGCCAATTACAGATATGTTTTGACCTAAGTTTCTTCA |
| 1348 | MYBPC1 | 3428659 | GGATGATCCAAGATACAGGATGTTCAGCAACCAGGGAGTCTGTACCCTGGAAATTCGCAAGCCCAGCCCCTATGATGGAGGCACTTACTGCTGCAAAGCAGTCAATGACCTT |
| 1349 | MYBPC1 | 3428660 | GCCTTACTATTGAGATAACCCTTACAAATTTAAACATTTTTAGCTGCTTTATTGGCTTTAAATGATTAAGTTCATAATTGCAAGTCATCTGGTTTCTAAACTGCTAGCCTTATTAGTTCCAAAGTATTGTTGATGCTTTTG |
| 1350 | MYBPC1 | 3428661 | TATATCAAGGAGTAAATACCCCTGGACAACCAGTCTTCCTGGAG |

TABLE 7-continued

| Target Sequences | | | |
|---|---|---|---|
| SEQ ID NO. | Gene | Affy Probeset ID | Sequence |
| 1351 | MYBPC1 | 3428662 | TTATATCCCACTGGATATTCTACTTTCCGTTCCATTCCTCTTAC ATGAAAATGCACCTTGCATGTAAAGCTTGACTTTCTCATTTGCT TTTAATTGTACCCCTTAGCAGCTCATGGCATACAGTGCTTATG CCATGAACAAGGAAGGCCAAATTATTCAAGGATATTAAG |
| 1352 | MYBPC1 | 3428663 | TGTACACTAACACTTTGTCTATTGTCTATGTTTTTCTTTTGTTGA AAAACACGATATATATATGTTGTAGGGTTTTGGTTTTTGTATTT GTTTTAAGCTAATGGTTTGGAAGCTCTT |
| 1353 | MYBPC1 | 3428664 | GTCATAAGCCATACCAAGCCTGTGGAGTATGGCATGATTTTCA TTACATAATCCAATGAAAATAGACTTATTTTAAATCCCTAACTTT GTAGTTTTAATTTGTATTTCACTATCTTGAAATTAACAGCTAGTA CTTATCCATCACAGCAGTCTCCTACTGACATGAAGCAAGTTGT TGAATGCAGTAGAGCATGAATGAAAGCATTTAATGTAGACAAA AATGGGTGATACCCAAGCATTCTGAATTATTTGCATCAAGGAA TGGACATGTACATAAGTGGCATCATTTCTACCAATATGTGACTT GAGTTGTTTTTTTAAAAAAAGGAGAATGACTTTCTCAAATTTGC ATTAAAGAAGTTTTTAAGAATGTTCAAATGGCATGCTGCTTTGT CTGGACGTGAATTTATTAGCAAGTAGTAAAGCACTTCACTAAA GGACCATGAATTTTTGTGGTTTCATGGATTCTCTCTTGAAGGG TACTTTTATTTTTTTAATATAATTCAGAAACTCAGAAGGTAGGTA TGAAATATTGGTAGGTGTTTCTCGCACCTTCAGAAAGTATTGG ACCGGTCTTATTATTATAATTTTAACAAAATATTTCCAATTTTTG TGCTTTTGACATGCATAAATGACCAAAGTTAAAGGGAGTAGTT TTTATCTTTTCTAATGTGCTTGAATCGAAACTCTCTGTGCCTAA TTAAAAAGAACATTAACAAACTGGAAGCAGATCTTCCCACTGA TCCATAATGTGGTATGCATTTATTCTGCTGTTCAGTCAGAACAT TTAAATCATCTATGAGGAATCACAAAACCTCTCAAAGAGCAATA AATACTTTCCAACCACTTGGGAATTTAAATGAAGATTGAACAAT AGTAGGGGAAAAACTGCTGTGGTTCTACTGGGAAC |
| 1354 | MYBPC1 | 3428665 | AGACTCCTCTTGCAAGGCGTACCTCCAAACATAATTGATTCGT ATCTGCGAGACTTACACTCAAGCAATC |
| 1355 | MYBPC1 | 3428666 | TGGCTACTGTCTCTCTGCACTCTGCTGCTTTGAAATCTGGTTG AAATGAGAAAAAGCATTTTCTGTTTTCCCACCAGGCCCCCAAG TGTGGTCTTTTTCTTTCCTCCTAATGTTGAAGAGA |
| 1356 | RP11-923I11.3 | 3454981 | GGCTGCGCTGCTCTTTGATTGGCTTCGTTAATATTTGGCAAAG CATTGCCACTTACCCACTCAGCGAAGATGCACAAAAACGTCAT CACTGATTCTTTCAGTTCGATGCCTGTTAACTGCGGGTGTAAA CTGCTGGTGATGGTGTCATTTACTACCAAAGAAGTGTGGAGCA GGATGGGTGAGAGAGTGAGTGAGTGAGCAGGTGGAAGGACA GTGGGTGAAGGATAAAAAGGTGGGAAACATTTTTTTTTTAAAA AGTGAAACTTCAAATACAGCGGAGGTGGCTTCTTTCCTATGAG GCTGGCTGATGGGTGCCAGATACCAAGGCCCATGTGTTACTG AGGAGACAGCCTGCTGGGCTGGGGTCAGGAGCTAGCGGAGG GAAACGGTTAGATCTCAGAAAAATCTCATCACTATGCCCTAGT AGCTTAATGACATCACTAGCATGAGCACATGGTGTACTTGGCG GGATCTT |
| 1357 | RP11-755O11.2 | 3468066 | TCACCGGCTGTCACATAATACTCTGAATCATCTGTCATCTGAC AGTTATTGATAAACAGGATTCTCTGGCATCCTTTGTG |
| 1358 | RP11-755O11.2 | 3468067 | ACCAGAAGACTCATTAGGATCCATAATAGCTGCCAGTGTAGAG GAGCCTCAGTTACTTTCACTTTGATCATTATCCCTGGGAGAAG AAGCCAACAGCTCCTGGTGACCACAATAAGAGATTTC |
| 1359 | RP11-755O11.2 | 3468068 | TGTGTGAAACAAGGATTATCCAGTAAAATCTGTTGGGTTTCAA AGCTATAACTAGAATAATTATTTTTGCAAGATAGTGCTTGGCTT GAGTCAAAACATGAGGCATTTGTACTCAACAGGTTCTCTTTCT CCC |
| 1360 | RP11-755O11.2 | 3468069 | GAGCCACCTGCTCGCACTCAAGATGAATCAGGTGCAACTGCT AAGAGTGGATATTACCCCCATGTAGGCTCTTGAAGCACATTAG TAAGAATATCATTTAATGCATTTTAAAGATAACTATGATTCTCTA TTAGAATGAACAATCTACACTGTACCAATTACTACAAATCCTGC TGTGTAATTTACTGTACCTTTCAACATAACATTTCATTTTAAGAT TTAAAATTTCTAGTTTTTAATTTTAAGATTACTCACAAGGAACCT G |
| 1361 | RP11-755O11.2 | 3468070 | TAAGCCACACCCATTTACATCTGAGGTCACAACTACTCATCAG ATTTGAATAATCCTCTTTCTACTGCTTCACAACAGTTCACAAG CCACAACA |

TABLE 7-continued

Target Sequences

| SEQ ID NO. | Gene | Affy Probeset ID | Sequence |
|---|---|---|---|
| 1362 | RP11-755O11.2 | 3468071 | TCTGTTCTTATCCGGCCACTGCCTTCCATAATAGCCTAAGAAGTGG |
| 1363 | RP11-755O11.2 | 3468072 | CTTGACATGTCAGCTTGATTCTAGAAGTGCGTTTACCTGGAGGACTTACCCACAACTTTAACCTTGATGCTTGCATGTGCCTCTCCAGCTTCGTTTTTCAGATTGATGTGGTAAACACCAGAGTCATCTCTTTCAGCTATATCA |
| 1364 | TNFRSF19 | 3481420 | CACTGATCAGATTACAGGCATTTCATCTCCCTGCTCGTCTGCCTTTGATCTGCATGGTTAATTTTATTTTCCTGGATTTGAAGTTTCGTCTGGGCTTGTGCTGA |
| 1365 | TNFRSF19 | 3481421 | GTAAGTACTGCAAAGAGCTCAGCATGTTGCAG |
| 1366 | TNFRSF19 | 3481422 | ACACTCAAATGAGGGAAAGTGGGAACTATAGTGTTTGTTCCCTCAGCATCTGAGGGGGACTGCTTTCAGGACACCCTCTTGGATACCAAAATCTGCAAATGCTCAAGTCCCTTACAAAAAATGGTATAAATTTGCATATGCTCTG |
| 1367 | TNFRSF19 | 3481423 | CGTTGCCGGGCTACGGGAGAGCGCGGAGCCCTGCGCTGGGAGGTGCACGGTGTGCACGCTGGACTGGACCCCCATGCAACCCCGCGCCCTGCGCCTTAACCAGGACTGCTCCGCGCGCCC |
| 1368 | TNFRSF19 | 3481424 | GGGTTATCTTCTAGTCCACATGTCACATAATATGTACCTTTATTTACCTTTTAAACTGAAGTTTTAAAACCTGGGTTTTAAAAAGAGAACAACTACCCATCAGCAATTACAGAAGACAAAGGAACTTGTGTGTCTGAAGACTGAGTGTTATTTAGCAGCTCTTTGGTCAGCTTGGATTGGTCACATATGTGGAAACTGGGAAATAATAGGGGCTACTTACACTGGAGAAGAACACTACAAATGGTGTAAAGAGTGGTTTTGGAATGTATCCAGACTTCCTTCTAAAATAAAAATTTAAACAGCTGTGTTTGAGAGATGGGTATGCACAATTCTTGTAAGAAAGACTGTGTAGATGTTTGAGGTCCCCTTAGTCCCTGATGCTACCATTGTTCC |
| 1369 | TNFRSF19 | 3481425 | TTGTCTGTATTAGAGCACTACCTTCAAGAAATGGGGTTCTGACCTGGATTTGTGCTACCACAGTGACTTGCATT |
| 1370 | TNFRSF19 | 3481426 | AACTCTCCAACAATAAATACATTTGATAAGAAAG |
| 1371 | TNFRSF19 | 3481427 | TAAAAGTGCTACTAGAACAAGAGAA |
| 1372 | TNFRSF19 | 3481428 | GTGGAGAAGGTTTGTACAGAATTATATGCATCAAAAACAATGTCC |
| 1373 | TNFRSF19 | 3481429 | AGACTGTAGACAGCAAGAATTCAGGGATCGGTCTGGAAACTGTGTTCC |
| 1374 | TNFRSF19 | 3481430 | TAGCTCAGCAGATCCAACTCCCATGG |
| 1375 | TNFRSF19 | 3481431 | CCCAGCCTCCCGATTGGGAGACACCTCCCAGCAGGGGTCGCCAGACACCTCATACAGGAGAGCTCTGGCTGGCATCTGGTGGGTGCCCCTTTGGGACGAAGCTTCCAGAGGAAGGAACAGGCAGCAGTCTTTGCTGTTCTGCAGCCTCTGCCAATGATACCCAGGCAAACAGGGTCTGGAGTGGACCTCCAACAAACTCCAGCAGACCTGAAGCAAAGGGCCTGACTGTTTGTAGGAA |
| 1376 | TNFRSF19 | 3481432 | GTCTTCTCAAGGATTCGGGGAAGTACTGCGTACTTCCTTCAAGCTTTTAAG |
| 1377 | TNFRSF19 | 3481433 | ATGTGGCTTCGGCTATGGGGAGGATGCACAGTGTGTGACGTGCCGGCTGCACA |
| 1378 | TNFRSF19 | 3481434 | GCAAGCCCTGTCTGGACTGCGCAGTGGTGAACCGCTTTCAGAAGGCAAATTGTTCAGCCACCAGTGATGCCATCTGCGGGGACTGCTTGCCAG |
| 1379 | TNFRSF19 | 3481435 | TTATAGGAAGACGAAACTTGTCGGCTTTCAAGACATGGAGTGTGTGCCTTGTG |
| 1380 | TNFRSF19 | 3481436 | ACGCAACACAGGCAGAGCCAAGGGGACGCCTGGCCTTTTGA |
| 1381 | TNFRSF19 | 3481437 | GTACCTGCCTGCTAAGGAACAGACCCACCTGCCTGCTGTGGTTGTATTGCCAGAAGTGTTGGATTCACATCTTGGCTGCGCTTTG |

TABLE 7-continued

| SEQ ID NO. | Gene | Affy Probeset ID | Sequence |
|---|---|---|---|
| Target Sequences | | | |
| | | | TACTGATGGTGTAACCTTGGGCAAATAGTCTCCCCTCTTTGAA CCTCTGTTTACTCTGGAAAATGCCCAAGTCTGCAGATTTTGGA TAGAACTAAATGAACTAGTAGTCCAGCAACATGATA |
| 1382 | TNFRSF19 | 3481438 | TCGGCCATACCCTGACCCAGATGTGTTCTTTGGAGGGTCTGCT GCTTTGGAGTTGTCCTGGACGGGGAGGATCTCATGGTGCATC TGGCTCTGATGTTTGTCTTCTGGGGCTTCACCTCCCCTGGTGG GTGAGCACTGAAGGGTACCGGAAAGTGGGTTCCATGGAGTTT TGTGCCTGA |
| 1383 | TNFRSF19 | 3481439 | GCAGCTCAGATGGGGGCCAGGTGCTGTGGCTCACGCCTGTAA TCTTACTACTTTGGGAGGCTGAGGTGGGAGGATCACTTGAGC CCAGGAGTTCAAGACCAGCCTGGGCAACATAGTGAGACACCA TATTCACAAAAAATAA |
| 1384 | TNFRSF19 | 3481440 | CCTCTGCATGATGAGCCCACAAAGCCAGTGCCTAAAGGACTA ATTAAGGGCTCCATTTACTGA |
| 1385 | TNFRSF19 | 3481441 | TGGTATTTATGGTAATTAACATACAAAACAGCTGTACTTACAAT CCGGCAAGTGCCAAAGAGG |
| 1386 | TNFRSF19 | 3481442 | GTCAGGCCCCCTGGAAGATTTGGCCAGCAGGGCAGTGGTCTG CGTGCCC |
| 1387 | TNFRSF19 | 3481443 | CCGGCCCTGGAGGGAGCGGGCGACA |
| 1388 | TNFRSF19 | 3481444 | TCCCTAAGTGAAGCTGACCCACACATAACCCACACCC |
| 1389 | TNFRSF19 | 3481445 | GTGGCTTCTTGCTGGACCTAGCTTAACGACGAGCCTG |
| 1390 | TNFRSF19 | 3481446 | TCCAACTCCTACCTTGGGAGAGAATGACAGTGAACCAAACAAG TAAAGTAT |
| 1391 | TNFRSF19 | 3481447 | GGAGAGCACAGCCAGGCCACAGTGGCC |
| 1392 | TNFRSF19 | 3481448 | CAGCAGATCTATTGGAGTGTGCCTGGCAGCTGGTTCTGCAGG AGCTCACCTGCCCTAATAGAATGTTCAGGCCCTTCTG |
| 1393 | TNFRSF19 | 3481449 | ATGCAGTCACCTCCACAGAATGCCCCCCGCCCCTGCCCCAGG ACACCCAGACGTTGCTCAGCATGCTTACTGCCCCCACGTCTG ATCACAGTGGCCCGTCATGCAGACACCAAGACCAATGGGAAG GCGGAGGACCCCGAACATCTCTGTG |
| 1394 | TNFRSF19 | 3481450 | GGTGCCTGCCAGCTTCGCCATAAACACTGCATCTGCAGTTGTT CAGAGCATGCTGACCCCATTCC |
| 1395 | TNFRSF19 | 3481451 | GTGCCAGCAAGGTCAACCTCGTGAAGATCGCGTCCACGGCCT CCAGCCCACGGGACACGGCGCTGGCTGCCGTTATCTGCAGC GCTCTGGCCA |
| 1396 | TNFRSF19 | 3481452 | GTAAGAGACAGTTTATGGAGAAGAAACCCAGCT |
| 1397 | TNFRSF19 | 3481453 | GTAAGTTTTGAGCTCATTACATTTCTTAGCATTTAGGGGAAGG GCATTTATTACTATTGTCGTGCAAGTGTTCCACAAGAGACTTG GCTGAGACAAGCACCAGTGAGTTGTGAAAGAACGCA |
| 1398 | TNFRSF19 | 3481454 | AGCTTTGTAAGGAGACTTACAAGGCTGTGATGTCCCTGCGCCA CTAGGCAAAAATAAA |
| 1399 | TNFRSF19 | 3481455 | GGTCTCTGCGGTCACAGGACATTCAGTACAACGGCTCTGAGC TGTCGTGTTTTGACAGACCTCAGCTCCACGAATATGCCCACAG A |
| 1400 | TNFRSF19 | 3481456 | TGCGCTTGCTCCCATCCATGTGCTGTGAGGAGGCCTGCAGCC CCAACCCGGCGACTCTTGGTTGTGGGGTGCATTCTGCAGCCA GTCTTCAGGCAA |
| 1401 | TNFRSF19 | 3481457 | GGAGATGGTGCCGACTTTCTTCGGATCCCTCACGCAGTCCAT CTGTGGCGAGTTTTCAGA |

TABLE 7-continued

Target Sequences

| SEQ ID NO. | Gene | Affy Probeset ID | Sequence |
|---|---|---|---|
| 1402 | TNFRSF19 | 3481458 | AGCTCAACGTCTTTGGATTCAAATAGCAGTCAAGATTTGGTTG GTGGGGCTGTTCCAGTCCAGTCTCATTCTGAAAACTTTACAGC AGCTACTGATTTATCTAGATATAACAACACACTGGTAGAATCAG CATCAACTCAGGATGCACTAACTATGAGAAGCCAGCTAGATCA GGAGAGTGGTGCTGTCATCCACCCAGCCA |
| 1403 | TNFRSF19 | 3481459 | GTAAGGCAGCGACTGGGTTCCCTGTGA |
| 1404 | TNFRSF19 | 3481460 | TGACTTACAGTAGATCAGAACTCTGTTCCCAGCATAAGATTTG GGGGAACCTGATGAGTTTTTTTTTTGCATCTTTAATAATTTCTT GTATGTTGTAGAGTATGTTTTAAAATAAATTTCAAGTATTTTTTT AAAAAACTAACACAGCTAATATATAAGAGCAAAGTGGACAGCT GCATTCTTTTATTCCTCTTTGTAAGTACAACCACTTAGCACAGC |
| 1405 | TNFRSF19 | 3481461 | ATGTCATTCTGTATCCTGGCCTGATTATATCAGAGAC |
| 1406 | TNFRSF19 | 3481462 | GAACTTTTAGGGGATTCTATAGACAAAACATTTTTTAGCTTTGG AGGGAAAAAATTGGTTTCATTCTCAAAACGGGGGAATGGAGAA GTAAGAGAAGGGAGACGAGTGAATGAAGGAAAAACAAATTAG GCAGTTAACACATACAAAGTATCTACCTCTGAGCTCTGCCTGG AGTTAGGAAAGGCTGTTCACTGATCTTGTTCTTTTGAGCCATC CA |
| 1407 | TNFRSF19 | 3481463 | GCCTCTCTTGTTAGGAGATCATCTGAAGAACTAGGGTTACGGT GCTGCCAGCTGACTAATGACTGTTTTTCAGTTTTGTCAGGAAA CAGAATTACCACTCACCTTAATTTTGTAGCTTGTACCCAAGTTT GTGATGTCAATTGCCAAGACTAAGGAATGAAACGTCTTCATAC GAGGTCATCCCGGAGCCAACTCATTGCCTGCTTT |
| 1408 | TNFRSF19 | 3481464 | TTGTCGTGCTCCTTCCAATTGTGTAAGATTAGTTAGCACATCAT CTCCTACTTTAGCCATCCGGTGTTGGATTTAAGAGGACGGTGC TTCTTTCTATTAAAGTGCTCCATCCCCTACCATCTACACATTAG CATTGTCTCTAGAGCTAAGACAGAAATTAACCCCGTTCAGTCA CAAAGCAGGGAATGGTTCATTTACTCTTAATCTTTATGCCCTG GAGAAGACCTACTTGAACAGGGCATATTTTTTAGACTTCTGAA CATCAGTATGTTCGAGGGTACTATGATATTTTGGTTTGGAATTG CCCTGCCCAAGTCACTGTCTTTTAACTTTTAAACTGAATATTAA AATGTATCTGTCTTTCCTAGTATGTTTTTATCTTCTCATGTATTA TCCATGGTTTTCTCTGTTTGTGACAGATTAGTAAAATTTAATGA GCCCTCTTTCTTGTGGCCGTTTCTCCATAGTTTTAGGTTTTGAT ATGTGTTTACTAGCTTGCCTGTGTCTGGTACATCTCATGACCT CAATTCCCTCACCTGAAATAGGAAATGAGAATGTTTCATTGTA GCCCCAAGCGGTCATGTCAACCTAGTGCCTAGTCATAATTAAT TGACTTTTCCTGTATTACTTCTTTTTTTAAGTATAAACCAATGAT CCTTTGGTAGTCAAGAACTCTTAGGAACATTGCCTTTTGGACA TGTAAAATATTTAGGATTTGACCACACAATGGCTATGAAAATGC AAGTAGTTTCCTCGCGTGACCTCACCATGATTCACATACGTGC CACTGTTTGAAATCTGGTCTGTTTGCATTTCTGTTATGACAGAG AGATGATGTTTGCATTTCTGTTATGACAGAGAGATGATGAAAG TAGGCAGGGCTGTGTTCCTTTGTGTAGCCTGTATATATTTTCC ATATGTAGAGCCCTGATTAACTTCAAGGACAAACACTGGCTGG AGAAAGCCAGACTGATGGGAATGAGACTTTGGCCAAAAATCC CAAAACATCATTTTCAATCAGTAGAGAAGTGCTTAGGGTTGAA AATTGATTTCATTTGCTACTGAATTTGGTAAATCCTGGGTAACT TTTATCAAGATGAAGACATTTTACCCTACCTACTCTAGAAATAT ACAACAATGTTATATTTTACACTCCTTGGAAACATTTGAGGAAA AAAATGCAATTTGCACTTCACTTTGTTGGAATATCCCATAGCAC TCAATAAACTCAGCTGCTAGAGTGCCGATGTCA |
| 1409 | LPGAT1 | 3512095 | GACCTTTCTTTGTGTTATCTGCATGTTGTAACGTGTGATAAGAA TGAATGTAAAGGCTGTGGCAACTGTAATTAATTTTTGTAAAGG GCTGGTCACACGTGGATCTGGTTTATGAATG |
| 1410 | DEGS1 | 3579471 | GACTTCGAGTGGGTCTACACCGACCAGCCGCA |
| 1411 | NUSAP1 | 3590391 | CAGGGATTTGAACCGCGCTGACGAAGTTTGGTGATCCATCTTC CGAGTATCGCCGGGATTTCGAATCGCG |
| 1412 | NUSAP1 | 3590392 | CTGGACTCCCTCAAGTACAGTGACCTGCAGAACTTAGCCAAG AGTCTGGGTCTC |

TABLE 7-continued

| Target Sequences | | | |
|---|---|---|---|
| SEQ ID NO. | Gene | Affy Probeset ID | Sequence |
| 1413 | NUSAP1 | 3590393 | TTAAAAGCCTTGAAAGGCTACATTAAACATGAGGCAAGAAAAG |
| 1414 | NUSAP1 | 3590394 | TCTTGTGATGAGACTGAGATACAGATCAGCAACCAGGAAGAA GCTGAGAGACAGCCACTTGGCCATGTCACCAAAACAAGGAGA AGGTGCAAGACTGTCCGTGTGGACCCTGACTCACAG |
| 1415 | NUSAP1 | 3590395 | AACTGAAAATAAACCACCTATGCCAAAATTGGCATACTTTTATG GAGATTTCTTTT |
| 1416 | NUSAP1 | 3590396 | AAATAAGTAATCCCACTGAATTCCAG |
| 1417 | NUSAP1 | 3590397 | TCAGAGCTACTGCAAAAGTTCCTTCTCCACCAGACGAGCACCA AGAAGCT |
| 1418 | NUSAP1 | 3590398 | ACAGAGATTCAAAGGTACCTTCAGAA |
| 1419 | NUSAP1 | 3590399 | CCATTGATCAATATATTGAGAGAAA |
| 1420 | NUSAP1 | 3590400 | CAGCCCATCAATAAGGGAGGGGTCAG |
| 1421 | NUSAP1 | 3590401 | TGTGGCTTCTACTCCCATCAGCCAACGACGCTCGCAAGGCCG GTCTTGTGGCCCTGCAAGTCAGAGTACCTTGGGTCTG |
| 1422 | NUSAP1 | 3590402 | CTAAAGATAATGAGCATAAGCGTTCACTGACCAAGACTCCAGC CAGAAAGTCTGCACATGTGACCGTGTCTG |
| 1423 | NUSAP1 | 3590403 | TGCTTGGGACACACAAATTAAAGACCATCACGGGGAATTCTGC |
| 1424 | NUSAP1 | 3590404 | CCCATTCAAGTTGACAACTGAGGCAACGCAGACTCCAGTCTC CAATAAGAAACCAGTGTTTGATCTTAAAGCAAGTTTGTCTCGTC CC |
| 1425 | NUSAP1 | 3590405 | ACCATGGGGGCAATCTAAAGAAAATAATTATCTAAATCAACAT GTCAACAGAATTA |
| 1426 | NUSAP1 | 3590406 | AGCAACGGAAGAAACGCGAGCAAGAACGAAAGGAGAAGAAAG CAAAGGTTTTGGGAATGCGAAGGGGCCTCATTTTGGCTGAAG AT |
| 1427 | NUSAP1 | 3590407 | CCCACTTTAGTCACGAGATCTTTTTCTGCTAACTGTTCATAGTC TGTGTAGTGTCCATGGGTTCTTCATGTGCTATGATCTCTGAAA AGACGTTATCACCTTAAAGCTCAAATTCTTTGGGATGGTTTTTA CTTAAGTCCATTAACAATTCAGGTTTCTAACGAGACCCATCCTA AAATTCTGTTTCTAGATTTTTAATGTCAAGTTCCCAAGTTCCCC CTGCTGGTTCTAATATTAACAGAACTGCAGTCTTCTGCTAGCC AATAGCATTTACCTGATGGCAGCTAGTTATGCAAGCTTCAGGA GAATTTGAACAATAACAAGAATAGGGTAAGCTGGGATAGAAAG GCCACCTCTTCACTCTCTATAGAATATAGTAACCTTTATGAAAC GGGGCCATATAGTTTGGTTATGACATCAATATTTTACCTAGGT GAAATTGTTTAGGCTTATGTACCTTCGTTCAAATA |
| 1428 | NUSAP1 | 3590408 | TACATAGCCCTATCGAAATGCGAGGATTAATGCTTTAATGCTTT TAGAGACAGGGTCTCACTGTGTTGCCCAGGCTGGTCTCAAAC TCCACCAAATGTACTTCTTATTCATTTTATGGAAAAGACTAGGC TTTGCTTAGTATCATGTCCATGTTTCCTTCACCTCAGTGGAGCT TCTGAGTTTTA |
| 1429 | NUSAP1 | 3590410 | ATGGCCGCTTCAGACCCACAGCAAAGATTTTTGATAAGGCATG ACTCCTAAACGGATGAATGAGTGCCCCATTAGAGCCAAGATTC TTTTAT |
| 1430 | NUSAP1 | 3590411 | CTTGAATCCGTGAGGCAGATGTAGTGAGCAGAG |
| 1431 | NUSAP1 | 3590413 | TAGCCAAAGTCTAAGCAGAAGCCCCTGCGACCATTCCAACACT GACAGAACATTCCTCTGCCTTGTTTTACGGATACATTGGGGAA ACTTAAGGATGAGAACTTTAGAAATGGTATTTCTTGGAAACCC ACTTGCTTGTAAATCAGTGGT |

TABLE 7-continued

| Target Sequences | | | |
|---|---|---|---|
| SEQ ID NO. | Gene | Affy Probeset ID | Sequence |
| 1432 | NUSAP1 | 3590415 | TGGTATCTGGTGTTAAGGCAGTGCCGAATGGAGGGCAGGAAA CACATTTTTAAATATTTATGGATTTATGTATTTTTCTCATAAAGA CAGGGTCTCCCTATGATTCCCAGGCTCTCCTTGAACGCCTAG GCTCAAGTGATCCTCCCACCTCAGCCTCCCAAAGTGCTGGGA TTACAGGTGTGAGCCACCAGATTATATTTATTTCTATTCGCTGT ATTTAATTCTTAACCCCATGTTTATTTTACATAACTTCCCTATTT CTCAAAAAGAATTTAAGGCCTATTCTCAAAATAATG |
| 1433 | NUSAP1 | 3590417 | TTATGAACCATTAAGACAAATTAGACCAGGCATG |
| 1434 | NUSAP1 | 3590419 | CCCAGGGCACCTACATATCCAGATAGACATAAATTCCTCACTC CTAAGAAAACCAGGCTTACAAGGCGTCAAGGCCCTATAAAGA GGAAAAACCCAGGACGGTCCTTAGAGGCTTCCTTCAGCATGA AAACCAAGTTAAAGCCAGAGCTCATCCTGGGTTGCAGCAAGT CATGGTTGGGCCCA |
| 1435 | FBXL8 | 3665216 | GCTGCTTCCCGTCCGCTGTCCTCTGC |
| 1436 | FBXL8 | 3665217 | GGGCAAAGCCCATCTGGTCCGCCGAGCAG |
| 1437 | FBXL8 | 3665218 | ACAGCTGCCAGACTTCGGTAAATCAAGGGGGCGCCCCCTGGA GACCAGAATTTTCTGGTACCCCTGGGGATCCGGCTTCAAGATC GCTGCTACCAGTGGGCACTCAAAACGGGGTGCCCATGGGTCC CAGGTACAAGCCCGGCCGAACGTATCTGAAGCCCCAGGAAAC ACGTGGCACAAATTCCGGGAGAAACTGTTAGCCCGGAAGATA |
| 1438 | FBXL8 | 3665219 | AGCATTTGTACACCTAAGCTCGGTCTTCCTGCAACACTTTGCG CCTTCCCGACCTCAGAGACGTCCGTCTC |
| 1439 | FBXL8 | 3665220 | AGCTATTGGGAGTGGCGGATCCTCCCACCCC |
| 1440 | FBXL8 | 3665221 | TGGCACTCATCTTCCGCCACCTGTCCCTGAGAGACCGTGCTG CCGCCGCCAGGGTCTGCAGGGCCTGGGCCGCCGCTGCTACC TGCAGCGCCGTGTGG |
| 1441 | FBXL8 | 3665222 | ACTTCCCACGGGTCACTCAGCTAGGGAATGGCAGAGGCAGAA TTCGAACCTAGCAGTCCGGAGGCCATGCCAAGACTCCTTAGA GACAGCTGAGAAAGCCCAGTTCCTAAAATATCATTGGCTCTCC ATGTCCAGGTTTCATCCTGTGGCAGACGCCACTGAAATCTTCT AAAAGGATAGGATGCGAGTTCCCTCCTTTGGGGCAACA |
| 1442 | FBXL8 | 3665223 | AGGCCTTTTCTGCACGGCTCTAACC |
| 1443 | FBXL8 | 3665224 | AGTGCCGCGGAGAAAAACCGCTCTTCGACGCGGGCCGCGAC GTCCTGGAGGCTGTGCACGCTGTATGCGGGGCGGCCAGCCA GCTACGCCACCTCGACCTGCGGCGCTTGTCCTTCACACTGGA CGACGCGCTGGTGCTGCAGGCGGCGCGCAGCTGTCCCGAGC TCCACAGCCTTTTTCTGGACAACAGTACCCTAGTGGGCAGCGT GGGTCCCGGCTCAGTGCTCGAGCTACTGGAGGCCTGCCCGC GCCTGCGCGCTCTCGGCCTGCACCTAGCCAGTTTGTCGCACG CCATCCTCGAAGCA |
| 1444 | FBXL8 | 3665225 | GCGCCCCGAGTGCTAGTGCCTTCTTTTGGGATTGTTGCCCCC CGGGTCTTTACCGAGTTGGGAACTGTGATGGCATCGGGACCA GTCCTGGGCGCCCTGAGACCACTCGCTGCTCT |
| 1445 | FBXL8 | 3665226 | ACACTGCCCCCCTCTCTTGCCTCCA |
| 1446 | FBXL8 | 3665227 | GTGAGTGTGAAATAAACAAATCCTGCAGTG |
| 1447 | ARL6IP1P2 | 3683039 | TGACTTCCTTACTATTGCTTCCTGGACTAA |
| 1448 | XPO6 | 3686340 | ATGGGCCTTGGTCACACTCCTTGGCTTCTCCCACCGCAAGCA ACGCTGCCTGCCTCTGCCGCTCCTCCACATCTTGCCGCTGCC CAGCAGAGCTGGCTTCTGGGTCCACCTGAGCACTGGACGGTG CTCCCAGGGCGTTGGAGCAGGCGGAGGGGTGTGTGGCCAGG TACTAGGAGGCACCAGGAAATCCCGCGGGGTGGCCCATGCA GACCAGGCGCACGTGGCTCATGGGGCAGAATTGCCAAGGAC AGCTCACGACAGTGCCACCTT |
| 1449 | XPO6 | 3686341 | AATGTGCACAGGCTGGTCAACGACCTGCGCTACTACAGACTC TGCAACGACAGCCTGC |

TABLE 7-continued

Target Sequences

| SEQ ID NO. | Gene | Affy Probeset ID | Sequence |
|---|---|---|---|
| 1450 | XPO6 | 3686342 | TTAGTCTCAGCCATGGAGGTCCCGAGTTCCTGGCTCTGCAGC CCCTCCATTTGTCTTGGCATCTTTGTTCATACCCAGGACCCTG CCGTTCTCCCTCCTGGGTGATGAGCCCCGGTGGGGCCAGCAT TGGAGTGTGCCCAGGCTTGCATTCAGGCTGAGATGGTTGGTG CTTGGGAGCTGCACTTCTGGGTCCCCAGGGTTAGAGGTGGGA CCCAGGTTCCCCGGCTGTCTTGGGCTCTTTCCAGACCAGCCC CAGCTCAGCTTGGGCTGAGTTGCTGCCAGGTCCTGGGAGGAG CCCTCCTAGTACTCACCCTCTTGTCCCACTGCTGCCACCTGTG CAGGGACTGTCAGGTGGGCTGTCCCCACCCGTGCAGCACCTC GGTGGGAGCTGGGTGCTGCTGGCTCTTGGTGTCCATGAGGC CATCTTGTTGGAGCCTGACAGTGCCTGGGACCTCCTTCCCCAT GGGGCTCACCTGTTCTCTTCTTCCTGTGTCAGGTGACCAGGC CTCTCTCTTGCCTGATAGGAACTTCTGGGAACTTTTCCTTGTAC CGTTTTATACTTGATGAAATTAGGAAAAGAAATCGCTTTCTCCC TGGTCCTCTTGGGGTTCTTGACCTGAGTCCTCTGTGAAGCAGC TTGTCCACGGCTCCACCGTAGTGCTCAGATGCACACACTGCT CTCACTGGTGCAAACCTGGCCGCCTGCTTTCCTCATTTGCCAC GTGTGGCAGGGAAGCTTTTGCTTAGACTCATCCTGTTCTCCTT TGTCTTGGGGTCTTCCTTTTCTTGGGACTTGTTCTCTCCTAAGC CTCTTCCAGTTCACTTCAGCCCCTGGATATGTTTTTTCCTTTTT CTAGAGGCCAGATCCTAATACTTAATGATCAGCTTCTAACGAC ATCAATATCAGTCAACTTTTTGATTTAAAGCTGTGGTTTCAAAA TCTAGTTATAGGCCAGGCGCGGTGTCTCACACCTGTAATCTCA GCACTTTGGGAGGCCAAGGCGGGCGGATCACTTGAGGTTAG GGGGTTTGAGACCAGCCTGGCCAACATGGCGAAACCCTGTCT CTACTAAAAATAAAAAAAATTAGTCAGGTGTGGTGGCACACGC CTGTAATCCCAGCTGCTTGGGAGGCTGAGGCACAAGAATCTC TTGAACCCGGGAGGCAGAGGTTGCAGTGAGCGGAGGTTGTG CCACTGCACTCCAGCCTGGGCGGCAGAGTGGGACTTTGTCTC AAAAAAAAAAATCTAGTTATATCAGAAGCACCTGGGGTACTTAT TAAAAATGGAGAAACAGACTTCTGTGTTCTACCCAGGAAATTC TGGTTTGGCATTTGGGAGCCACTGATTTAAAAGACATCCCTTA GTTGGTTTTTTGAGGGTAAAATAAAAGAATCACCACCTTCCATT CAGTCACGCACTGTGTGTTTGAAGCCAGCTGCTTCTCAAGCCC CGGGCCAGGAACTGGGGCACCAGTCCCAGCCTTCACCAAGT CTTTCATGGTAGACAGGCCAATACAGCACCCTCTGTGGACCA CATAGTGCCAAGCATGTGACATGTCTTGGCTCGAGTAAGCCTT CTAACAAGCCTCTGAAGTGTGGGTCCTGTTACTCCCCCATTTC ACAGATGGTGGGGGCTCAGAAGGTGAGCAGTTCACAGAACTT GGAAGTGGTAGAGCTGCGAAGCAGGAGGCAGACCTGGGTGT TCTGGCCCCAGAGCCTGCACACACTCCCCAGAAGCAGATTGC TCAGGACAGAGGCGCTGAGCTGGCTGCTGGGGCCAGGAAAT AGGAGGCATCTGTGCAGACTTTGGGAAGAGGCAGGCTTTGAA TGGAGTTCTGGAAGAGGAATAGTGGTTGGGCAGGAAAATGAA CTTGGTCCTGCTCATGGCTCTGCTGGGGCTTGCTGGGCCTGT TTGAGTCCTCACCGGGACCTACACTGAAAAAAAAAGCAGGGT CTCACCGTGTGCATGATGGCGGAGGTCAGGGCCTCACTTCTG GCCCAGGGCCTTCCATGGCCCACGCTGCGCCCAGTGGGACA GGCCTTGGGACTGTGTTTGCTGCTGCTCGGGTGGCTCTCGAG GGGCAGGGGCGGCCTGGAGCCCCGTGGGTAAAGGTTCTGCA GACATTGCTCGGTGTGCGCGTCACCTCAAGGGGCCATGGTGA AGAAGAGGGCTGTCACCACAGCCATGTCTGCGTTTGAGGGGC CGGACTCAGGAGCAAGTGTGCTGGTCTCTTCAGTGTGAGCTG GGGCCAGCTTCTTCATGGTGCAGCGCTTTGGTCTTTCTGTCCT TAGACTAGTGGTTCTGGTAGGGCTTGGTGGCAGCCTTGTGGT GAGGACTCAGTGAGTTGATGTCTGTATGTTGATTGCAGCAGTG TCTGGCACCCGAGAGGCCCTAGGGACGTATTCCTCTTG |
| 1451 | XPO6 | 3686343 | AGGTCCTGGTCCACAAGTCCCATGATCTTCTGCAGGAGGAGA TTGGCATCGCCATCTACAACATGGCCTCAGTCGACTTTGATGG CTTCTTTGCCGCCTTCCTCCCAGAGTTCCTGACCAGCTGTGAT GGTGTGGATGCCAACCAGAAAAGTGTGCTGGGG |
| 1452 | XPO6 | 3686344 | GTCCTTTCTCCAGCCCGACATCCACCTTTTTAAACAAAATCTCT TCTACTTGGAGACTCTCAACACCAAGCAGA |
| 1453 | XPO6 | 3686345 | ACAGGACTGAGCTTCTGTGCCTGGACTGAACTAGTAACTTTTA CACCCAGGAATTCCAAAGCAGTTTAAAAATACTTTGCTTAGCC CCCAGGCAGAGGCTTAACCTCCAGG |
| 1454 | XPO6 | 3686346 | GCCGAGCTGTTTGAGCTCCTTTTCCGGACGCTCCATCACAACT GGAGGTACTTCTTCAAGTCCACCGTGCTGGCCAGTG |

TABLE 7-continued

Target Sequences

| SEQ ID NO. | Gene | Affy Probeset ID | Sequence |
|---|---|---|---|
| 1455 | XPO6 | 3686347 | GAGCAGTTAGCCGAGAGCATCCTCCACGAGGGCAGCACAGGCTGCCGGGTGGTGGAGAAGTTTCTGAAGATCCTGCAGGTGGTGGTCCAGGAGCCAGGCCAGGTGTTCAAGCCCTTCCTCCCCAGCATCATCGCCCTGTGCATGGAGCA |
| 1456 | XPO6 | 3686348 | ACTGATGAGATGCTGAGCTTCTTCCTCACTCTGTTTCGAGGCCTTAGAGTACAGATGGGTGTGCCTTTCACTGAGCAAATCATACAGACTTTC |
| 1457 | XPO6 | 3686349 | ACCAGACACTCAGCGTCTTAGAAGATATTGTGGAGAATATCTCGGGGGAGTCCACCAAGTCTCGACAGATTTGCTACCAGTCGCTGCAGGAATC |
| 1458 | XPO6 | 3686350 | CATTTTTGAAGCGTCCAGGCCTGTTTTCTTGTCATATGTCTCCTAGTCTTGTTTTGCCTGATTGTTTCCATAGGTTGTGGTGTAGTGGTGCATGTTCGTGTTCGCATTTCCTCTTGCATTGCTTCTGTTTGTCCCATCCTTGGTGATGCTCAGTCTGGATGCCTGTTGGGAGTAGGGCCTGCCAGTCTGTCCATTGGGAAGGTGCTTGGCAGGTGTAATTGCTCAGGACTGTAGAGAAAGTGGGCGAGGTCAAGAGTTGGACTTGGGTCTGAATGGCTCCAGCTC |
| 1459 | XPO6 | 3686351 | AGCAGTGGCCCGTGCGCTCCATCAACCACGCCAGCCTCATCTCTGCACTCTCCCGGGACTATCGCAACCTGAAGC |
| 1460 | XPO6 | 3686352 | CCAGGTGTTGGTGTGCCGAGCCCTCTCTAACATCTTGCTGCTTCCGTGGCCAAACCTTC |
| 1461 | XPO6 | 3686353 | AGCTGCTGCTATCTGCGTGCCACTTACTGGTCTCACTGGCCACCACCGTGCGGCCCGTCTTTCTGATCAGCATCCCTGCAGTGCAGAAAGTATTCAACAGAATCACTGATGCCTCTGCCCTGCGACTTGTCGATAA |
| 1462 | XPO6 | 3686354 | GGGCAAAATGCTATGAAACGGCACCGCATGCTCCAGAGAAATATTTCATGAAAGGAAGTCAATCGATGCAGCAAACTTCATTGTTGTCTTATTTTAAGTAATTGCCACAGCCACCCCAACTTTGAGCAACCACCACCCTGTTCAGTCAGCAGCAGTCACTTTCAAGGAAGACCCTTCACCAGCAAAAAGATTACCGCTCTGAAGGCTCAGATGATTGTTAGCATTTTTAGCAATAAACTACTTTTTAACTAAGATATGTACATTGTTTTCTTAGACATAATGCTTATTGCACACTTTATAGACTATAGTGTAAACAAAACATATGCATTGGGAAACAAAAAAATTAGTGTGCCTTGCGTTATTGCATAATTTGCTTTATTGTGGTGGTCTGGAGCTGAACCTGCAGTATCTCTGAGGTATGCCTGTATATCCTTCCAGACTTTTTTCTCTTTTTATGTAATAAGTAATAACTAAGTTTGTAGATAGCTGGAGATA |
| 1463 | XPO6 | 3686355 | GTTGTAGCCTACATGCATTCAGATACAACTTTACTTTTTTAGTTATCTGAGTTCCACATGAATACATGCTCACTG |
| 1464 | XPO6 | 3686356 | GGCTTACTCTCACTGGTTAGCACAGTATTGCAGTGAAGTTCACCGGCAGAACACGCAGCAGTTCGTGACACTCATCTCTACTACCATGGATGCAATCACAC |
| 1465 | XPO6 | 3686357 | GAGGACCTTTTGCAGATCCAGATCTTAATTTTTTTAAAAGCATGTCCTACAATCTGGATTTGTCTAATTATTTCCATTATATTAGATTCAGTTTAAACATTTTTAGCAAGGTTACTACATAGGCAATGATGTGCCTTTCCTCTTGCATCATGTCAGAAGGCTCTTAATATCAA |
| 1466 | XPO6 | 3686358 | TTTCAGCCTTGAGGAGCTCTACAGATGTGCTAGATTGACTGAAATTCTTACTCCTAAGGCTGACTTTGATGTCCTTTCTCTT |
| 1467 | XPO6 | 3686359 | TCAAAGTCACTCTGTACGGATCTCAGATAAAATTGTACAACATTGAAACTGCTGTGCCATCAGTATTGAAACC |
| 1468 | XPO6 | 3686360 | GATATATCTTATCTGTTCAGTTGGCGGGGCGCA |
| 1469 | XPO6 | 3686361 | AACATCACGGCGGAGAACGACTGCCGGCGGCTGCACTGCTCCCTGAGAGACTTGAGCTCCCTGCTGCAGGCCGTGGGCCGCCTGGCCGAGTACTTTATCGGGGA |
| 1470 | XPO6 | 3686362 | TTTGAAGAAGTTGTGTTGAAAAGTAAGGAAATTTCAGA |
| 1471 | XPO6 | 3686363 | GCCTGTGTAAATGGGCGCCAGCCGCGATTCTTGTCTACTCCTGGTGCTGTGACCGTGTATGACAATGGGATGCACATTTTGGCCAGC |

TABLE 7-continued

Target Sequences

| SEQ ID NO. | Gene | Affy Probeset ID | Sequence |
|---|---|---|---|
| 1472 | XPO6 | 3686364 | CTTCTTATGGGATCTGTCCCGGCTCTG |
| 1473 | XPO6 | 3686365 | TTTAAAGGCTTATGATGAAAAGCTGTGGGGGAG |
| 1474 | XPO6 | 3686366 | TGTTCTTCAGGACAATTTAGAAGTTTATTTGGGATTACAACAGT TTATAGTCACTTCAGGGTCAG |
| 1475 | XPO6 | 3686368 | TCCTGCTCACAGAGGTGTTGAATCGAATCCAGTTCAGATACAA CCAAGCCCAGCTG |
| 1476 | XPO6 | 3686369 | TTGTTTGGATATCTGGACGCTGTTTTTGGACTATCT |
| 1477 | XPO6 | 3686371 | GTGGTTAATGGAATGAAGGGTTGCCTGTCCTGTAG |
| 1478 | XPO6 | 3686372 | AGCCTTCTAGACTTGCCAGATTGAAATGACACAGTGATCTGCC CATCAACTTTTTATCATTTCCCTTCACTTTAATTGGGTCACAAC ACAAATGACTTAGAAAATGTGAGCGCACTAGATTATAAGAAGC CTTAGCAGACAGTGTCTGAGGATTAAAGTTGC |
| 1479 | XPO6 | 3686373 | CAGGAGCAACATGGGACATTTTATTTCCGGGCCAGTTTTGCTT TTCTGAGTAGTAGTTTTCTCTGCTTTTATTATTTCACATATCTCT GTTTTGAAAAATAGCTTTTGCAGTAATGAGCTTCAGAATTGCTT TTAGCCATTATTTCATTTTCAGCTAAGGCCTAGTATGTCTTTAC CTT |
| 1480 | XPO6 | 3686374 | AAAACCGTGATGTTTGCTCTGTATAAGAACACAATCTGATATG GTAATATGTTCTTAAAAATTATTTGGTGATAGCTTTCCATATGAA TTCAAAGGCATCATTATTCACACTTTCATATTCTTTCTGTCTGT GGTTAAGAAAGGCTGTATTACCTTTTTTTTAATGATCTGTGTGT CTCATGTCTATCTCTTCATATGTTAATTTAAAAATCTAGCTGCTT GTATCAACTATCAAATATCAGTTGTTTTGACTTTAATCATAATGT AGTCACAGACAACTTTGTTGTGGCTTCCATTTGGATGGTATAG AAATGTCATTATGGATTGTCTATGTACTGATGTTGTTACGTGTA ACTTTTGTGCTCTTGGTTTTACATTTTAATCCTGTGCTTCCTATT GCCCTGTGAAAGCTGAGAGGTGCCTGGGAGCAGAAAGGTGA CATAAATAATGCTGTGTGCTTGCTTCCTGGCTCTGGGTCCCCT ACCACTAATTCTAAACAGCTCAGTCCATTCTCAGTTGTTTAGGA GCTGCTAACCAGATCCTTGGCTTCTCTTTCCCTCTACTGCCTTT TCCCCTAACTTTCTACTGTTCATTAGCACCTGTACCAGAAGG |
| 1481 | XPO6 | 3686375 | TTGTTATTGTCCTCTCAAGTGGAGCCTACAATGACCTACTTTTT TTTTTTTTTAAAAGCACTCTAAAAGACGACTCCATCACAGTACT CTGAGGCAGGGTTTCATGATTTATGTCTCTTGCAGATGAGGTC ATTTATGTATCTTACAACTGCTGCTGTATGAAAACAGGAGGGA ATTTGGAAACTTATATTATGAACAATCAGATTGACGGTTTAGGG ACTTTC |
| 1482 | XPO6 | 3686376 | GAGACTGCTGCTCCTGCGTAGCCAAGAACAGG |
| 1483 | XPO6 | 3686377 | ACAGAAAGGTAGGTGTGTGCCAGTAAGTCTGAGATTAGCTGG AAGGGCTTGGGTGGTTAAGGGAAGTGACTGAGTTTGAAAAAT GCTTGTGCCTTGTGTAGGTTTGTTGTCTT |
| 1484 | XPO6 | 3686378 | TGCTGTGCTGCATGGCATCTGTAATCCTCTTT |
| 1485 | XPO6 | 3686379 | ATCAATGAACTCATGTCCAAGAACTGTGT |
| 1486 | XPO6 | 3686380 | AGCTAGCGCACCCTCTTAATTCCTACGTCTGTTTAGTCTTGAG TCTCTATGTAATTTGATGCCAGTGTGTCCTTTTGCTACAGCTTC TCCATTCCTTAATTCTTTATTTTGATTTATCTCTTTATCTGTGTG GTTTCTTTGTCTGTTATCCTCCTTGAGAA |
| 1487 | XPO6 | 3686381 | GGAGGGTTGAAGTGGGAGAATGGCTT |
| 1488 | XPO6 | 3686383 | GTCTTTTCTGTTTGATGAGAGCCTCATGACAAGGTGTAAAGGG TAAGAATAAACAGAAAGCAAACCACAACATGAGACAGGAAGGT AGGAGGAGAGGGGAGTGCCCTGGGTGACTGGGGTGGCTGCT GTGTGCTGCTGTGATACCTGTTTGCTAGGGAGACATGTATGCA ATGCCTGGCCGTGAGGCCCTGAGGGTGCCGGGAGCCTGGGC TTGCTACTTGAGGGAATCTTGTAGTGAAAAGAAGTTTTTATCTC TAACTCCTTTATCCAGGCTTCTTCTTGGATGTCTAGGAACTTTC TTTATATCTCCAGTTTAGTGCTTGGCATGTGGTGGGCACTTAA AGTTGGCTGAAAGAACCATTGATTTAAAGTAAACTTGGGTTAG TGCAATGGCTC |

TABLE 7-continued

| Target Sequences | | | |
|---|---|---|---|
| SEQ ID NO. | Gene | Affy Probeset ID | Sequence |
| 1489 | XPO6 | 3686385 | TAGACCATCTCTGGATTACTTCTAATA |
| 1490 | XPO6 | 3686386 | ATGGAAATCCGTAGCTGTCTGCCCAAACTCCTTTTGGCTCACC ATAAAACCTTACCTTACTTTATCCGGAACAAGCTCTGCA |
| 1491 | XPO6 | 3686390 | GCCTCTCTCAGGGCATTGGAAAGTCTGATGACAGAATTTTTTC ACGATTGTACAA |
| 1492 | XPO6 | 3686391 | GAGTGATTTATCTGATTGGTACACCAGGGA |
| 1493 | XPO6 | 3686392 | TCTCAAGCTTCATCCGTGTGGTGGCGTGTGTCAGAGCTTCCTT C |
| 1494 | XPO6 | 3686393 | AGTGGAGTCATGAAGTATTTGGCCTGTTGTGACTGCCTTATTT CACA |
| 1495 | XPO6 | 3686394 | GGCCTGTCAGCCTCCGCCCGTTCAGCCTCGGGGCCGGGGCC GCCGCCACCTCTGCCCGCGGAGGCCGGGGAGCCCCTGCCTG GGCCCGCAGCCTCCCCCGCGGGGGTCGGGCCCGGGCGGGG GTCCCGAGCAGCTGCCCTCCTCGCCGGCATCCGAGCCTCATT TCCTGCTTTTTCAGTTTCCTTGGGGAGGGGCGGGTGGGTCTG GATGAATTGTCTCGGGGTCCCCCGATGAGGCGACCCGGGCG GCCCTGCCCTTTTTAGAGGGTCCCCTCGGGGCCCGGTGGGG AAGGGGTTGTCTTTGCATGGGTGGGGGACTTCCCGAGTCTGC CGGGACCATGACCTGAACTGTGCGAGCGGGACGTGTCCGAA GCCCAAGA |
| 1496 | XPO6 | 3686396 | TGCTTTGTGATAGGGAGAGTTATTTCTAAGGGAAAGGAATGTA CCCTGTATTTCTTTCTTTTTCTTTTTTTTTTTTTTTTTTTTTGAGA CAGAGTCTTGCTCTCTTGCCCAGGCTGGAATACAGTGGGGTG ATCTTGGCTCACTGCAACCTTTGCCTCCTGGGTTCAAGTGATC CTCCTGCCTCAGCCTCCTGAGTAGCTGGGACTATAGGCGCCT GCCACCACACCCGGCTAATTTTTGTATTTTTAGTAGAGATGGA GTTTCACCATGTTGGCCAGGTTGGTCTCGAACTGCTGACCTCA AGTGATAAAGTGCTGGGATTACAGGCATGAGCCACCACGCCC AGCCCGTACCCTGTATTTCTTGAAGTGAAGAATATAAAGTCTG TA |
| 1497 | XPO6 | 3686397 | TCACAGCTCATAGTGACCTCGATCTCCTGGTC |
| 1498 | XPO6 | 3686399 | TGCAGAGATTACCTATGTTACAGGCTTAAATTATAGATGTGAA GATGGTAAAGGGAGACACTATTTTAATCAAAAGCTTCCTGGGT ACAAAGCTAATGAGAGGAAAAATTATACATTTTATCAAGCTCTT TTTCAAGTAAAGAATAGCTTTCTTTTTTCATCTGGCTTCTTGCC TGACCTTCTCCCCTTCCCCTAAATGGTGAGAGGAAGGAGAGC TTGCAGATAGATTTTCCATATCGTAGGGGATTTTTATATCTGGG AAGCACAGCATTTCATATTTATAGGAGGGTGTATATTGCCAAAT GGGATATTTGGCATTACGAGTCATTTCCAGCTGAGAGAGTAAG GATGCA |
| 1499 | XPO6 | 3686401 | TCCCTGGCGTTCTGTCCAATACACTTGCCTTCAATCCAAGTTG AGGACGGTTATGGTAACCCTCTCCAAGGCTCTCTTAAGTGGG CGTCAGGGAAGCCCACTGGAGACAGGAAAGACCAAGAGGGT TGGGAGTCTAAGTGAACCTATTCCTGGGTTGGTTAGTGGTGC GTCCTGTGACAAGAAGAGAGGGACCTTGAGACGGAGAGTCAC AGGCCTGATGATAGCAGGTAAGGTGGAGCCACAGTTCCACCG CTGGGATTGGTCCCTTTGATGAAGAACAGAACGTTTCCTGGCT ACATTTGAAGTATAATTATTTGTAACAAAAGATGGATTTGGAAG AGAGCACTTTTAGGTGAAGGGCTTCTGGAGGTTTAAAAAGGCT AATTGTCCACTGTTCTCCACCACCTCCCGCTTTCAACCCCTTC AGTATTGACTCCTTTAACCTCATGTAGCTTTCGTGACTTTGAAA CACCATGTAGTAGAAGGAGCCAGAC |
| 1500 | XPO6 | 3686403 | TAAATTTTAGCCTTTCTGGTAGATGTGTAGCACTATCTTATTTTA AATTTGTATTTTCCTGATAACTAATGAGGCTGAACACTTATTTAT AGGCTTTTTGAATA |
| 1501 | XPO6 | 3686405 | GGATGTAACTGCTAGGCCACCTTCAGTTCTTTGAAGTTAGGGA CCGTCTTACTCATCATTGTATCCCAGGGGCTTAATTTAAGCAAT ATCAGTTACTTAGTGAGTATTGAATTCTCATTTCTCCAACAAAT AGCTGAGTTGCTTAGTCACTCCAGAATTAAAGCTAGGTTTAGA ATAATTGGAGCGGTGTGATGGCATGTGCCTATAGTCTCAGCTT CTCAGGAGGCTGAAGTGGGGAGGATCGCCTGAGCCCAGGGG |

TABLE 7-continued

| SEQ ID NO. | Gene | Affy Probeset ID | Sequence |
|---|---|---|---|
| | | | TTTGAGGCTGCAGTGAGCTGTGATTGTTCCACTGCACTCCAGT CTGGGGTGATACAGCAACACTCTG |
| 1502 | XPO6 | 3686407 | CTCCCACATGACTATGGTACAGTTACCATCTTCGGTTAATAGA ACATTGATTCAGTACTTTGATCTAACCTACTACCACCTGTATTC CAGTTTTGTCAATTGGCTCAGTCATGCCTTTCATAGCATTTTTT CCCTCCAGTCCAGGATCAATCTGTGGTCAGGTGTAGCATTTAC TT |
| 1503 | XPO6 | 3686409 | TGCAGCATGCTTTTATAGTGGTTCGTCAGTTTCATACTCATTCA TTACCTGATG |
| 1504 | XPO6 | 3686411 | ATGGTGTGTGTGAAGACATGGAACTGTTATGTGGAGAGAAA |
| 1505 | RP13-753N3.3 | 3716787 | ACAGTTGGTGTTACGTTAGAGCTAATAATTATACTTTAGCACGT TAACCTCAGAATTCTAAGGCTGAGAGTCAAACACTGCTAATTC ATAGAAGGCAATAGCTTGTAATAATGAATCATAAAGCTCTTCTA CTCTTTGTAGTTCAGTAGATAAAAACATCTGTCTGTAGTGAACT ATTTTATCTGATGGGAAGAACACCCGAGGATCCGCCTTCAGTA TAGAATCGAAGAGAAACTGCTTCACTAGCTCTTTTCCACTAGT CCGGGAGTCACCAATCATCA |
| 1506 | TOP2A | 3756154 | TGAAATTGAATTAAGTTTAAGGCTGGGTG |
| 1507 | TOP2A | 3756155 | GGCTGTTCCAAAACAGTAAGTTATCTCTATTGATTGT |
| 1508 | TOP2A | 3756156 | GGAACTAAGCATGGTGGGAAATGTTCCTGCT |
| 1509 | TOP2A | 3756194 | CTGGATTGCAGAAGACTCGGGGACAACATTTGATCCAAGATCT TAAATGTTATATTGATAACCATGCTCAGCAATGAGCTATTAGAT TCATTTTGGGAAATCTCCATAATTTCAATTTGTAAACTTTGTTAA GACCTGTCTACATTGTTATATGTG |
| 1510 | TOP2A | 3756195 | AGTGACCATCTCATGGGCATTGTTTTCTTCTCTGCTTTGTCTGT GTTTTGAGTCTGCTTTCTTTTGTCTTTAAAACCTGATTTTTAAGT TCTTCTGAACTGTAGAAATAGCTATCTGATCACTTCAGCGTAAA GCAGTGTGTTTATTAACCATCCACTAAGCTAAAACTAGAGCAG TTTGATTTAAAAGTGTCACTCTTCCTCCTTTTCTACTTTCAGTAG ATATGAGATAGAGCATAATTATCTGTTTTATCTTAGTTTTATACA TAATTTACCATCAGATAGAACTTTATGGTTCTAGTACAGATACT CTACTACACTCAGCCTCTTATGTGCCAAGTTTTTCTTTAAGCAA TGAGAAATTGCTCATGTTCTTCATCTTCTCAAATCATCAGAGGC CGAAGAAAAACACTTTGGCTGTGTCTATAACTTG |
| 1511 | TOP2A | 3756196 | CAAGGGGGAGAGTGATGACTTCCATATGGACTTTGACTCAGC TGTGGCTCCTCGGGCAAAATCTGTACGGGCAAAGAAACCTAT A |
| 1512 | TOP2A | 3756197 | CTGGTGTCTCTCAAAAGCCTGATCCTGCCAAAACCAAGAATCG CCGCAAAAGGAAGCCATCCACTTCTGATGATTCTGACTCTAAT TTTGAGAAAATTGTTTCGAAAGCAGTCACAAGCAAG |
| 1513 | TOP2A | 3756198 | AGTTCCTAAAAAGAATGTGACAGTGAAGAA |
| 1514 | TOP2A | 3756199 | GGCAGTGTACCACTGTCTTCAAGCCCTCCTGCTACACATTTCC CAG |
| 1515 | TOP2A | 3756200 | TTAGTAACAAAGAACTGAAACCACAGAAAAGTGTCGTGTCAG |
| 1516 | TOP2A | 3756201 | TGATGAAGATTTTGTCCCATCAGAT |
| 1517 | TOP2A | 3756202 | ACAAACTACATTGGCATTTAAGCCAATCAAAAAAGGAAAGAAG AGAAATCCCTGGTCTGATTCAGAATCAGATAGGAGCAGTGAC GAAAGTAATTTTGATGTCCCTCCACGAGA |
| 1518 | TOP2A | 3756203 | AAAATACTGAAGGAAGCCCTCAAGAAGATGGTGTGGAACTAG AAGGCCTAAAACAAAGATTAG |
| 1519 | TOP2A | 3756204 | AACAAGATGAACAAGTCGGACTTCCTGGGAAAGGGGGGAAGG CCAAGGGGAAAAAAACACAAATGGCTGAAGTTTTGCCTTCTCC GCGTGGTCAAAGAGTCATTCCACGAATAACCATAGAAATGAA |
| 1520 | TOP2A | 3756205 | GAACAAGAGCTGGACACATTAAAAAGAAAGAGTCCATCAGATT TGTGGAAAG |

TABLE 7-continued

| Target Sequences | | | |
|---|---|---|---|
| SEQ ID NO. | Gene | Affy Probeset ID | Sequence |
| 1521 | TOP2A | 3756206 | TGACTCCGTAACAGATTCTGGACCAACCTTCAACTATCTTCTTGATATGCCCCTTTGGTATTTAACC |
| 1522 | TOP2A | 3756207 | AATGAAGAGAGTGACAACGAAAAGGAAA |
| 1523 | TOP2A | 3756208 | ATTAATTAAAGTTCTGATTCAGAGGGGATATGATTCGGATCCTGTGAAGGC |
| 1524 | TOP2A | 3756209 | GCTTTTTGACCACGTAGGCTGTTTAAAGAAATATGACACGGTGTTGGATATTCTAAGAGACTTTTTTGAACTCAGACTTAAATATTATGGATTAAGAAAAGAATGGCTCCTAGGAATGCTTGGTGCTGAATCTGCTAAACTGAATAATCAGGCTCGCTTTATCTTAGAGA |
| 1525 | TOP2A | 3756210 | CCTCCTCTCATAACAGACTATAGGGAATACCATACAGATACCACTGTGAAATTTGTTGTGAAGATGACTGAAGAAAAACTGGCAGAGGCAGAGAGAGTTGGACTACACAAAGTCTTCAAACTCCAAACTAG |
| 1526 | TOP2A | 3756211 | TCAAGGGTACTATTGAAGAACTGGCTCCAAATCAATATGTGATTAGTGGTGAAGTAGCTATTCTTAATTCTACAACCATTGAAATCTCAGAGCTTCCCGTCAGAACATGGA |
| 1527 | TOP2A | 3756212 | GGCTCGATTGTTATTTCCACCAAAAGATGATCACACGTTGAAGTTTTTATATGATGACAACCAGCGTGTTGAGCCTGAATGGTACATTCCTATTATTCCCATGGTGCTGATAAATGGTGCTGAAGGAATCGGTACTGGGTGGTCCTGCAAAATCCCCAACTTTGATGTGCGTGAAATTG |
| 1528 | TOP2A | 3756213 | GACCATTATCAATTTGGCTCAGAATTTTGTGGGTAGCAATAATCTAAACCTCTTGCAGCCCATTGGTCAGTTTGGTACCAGGCTACATGGTGGCAAGGATTCTGCTAGTCCACGATA |
| 1529 | TOP2A | 3756214 | TGTTTACTTGCTTCAAACGGAATGACAAGCGAGAAGTAAAGGTTGCCCAATTAGCTG |
| 1530 | TOP2A | 3756215 | TCTGACATATAATGACTTCATCAACAAGGAACTTATCTTGTTCTCAAATTCTGATAACGAGAGATCTATCCCTTCTATGGTGGATG |
| 1531 | TOP2A | 3756216 | AACAGATAGATGATCGAAAGGAATGGTTAACTAATTTCATGGAGGATAGAAGACAACGAAAGTTACTTGGGCTTCCTG |
| 1532 | TOP2A | 3756217 | CCAGCACATCAAAGGAAGCTAAAGAATACTTTGCAGATATGAAAAGACATCGTATCCAGTTCAAATATTCTGGT |
| 1533 | TOP2A | 3756218 | GAAGAGTGGAAGAGTTCTACTCCAAAT |
| 1534 | TOP2A | 3756219 | TGGCCCTCTCTTCTGCGACATCGTTTTCTGGAGGAATT |
| 1535 | TOP2A | 3756220 | AATATCATCAAGATTGTGGGTCTTCAGTACAAGAAAAACTATGAAGATGAAGATTCATTGAAGACGCTTCGTTATGGGAA |
| 1536 | TOP2A | 3756221 | TGGGAGAGACAAATATGGGGTTTTCCCTCTTAGAGGAAAAATACTCAATGTTCGAGAAGCTTCTCATAAGCAG |
| 1537 | TOP2A | 3756222 | CTCCACTGAGTGTACGCTTATCCTGACTGAGGGAGATTCAGCCAAAACTTTGGCT |
| 1538 | TOP2A | 3756223 | CATTGGCTGTGGTATTGTAGAAAGCATACTAAACTGGGTGAAGTTTAAGGCCCAAGTCCAGTTAAACAAGAAGTGTTCAGCTGTAAAACATAATAGAATCAAGGGAATTCCCAAACTCGA |
| 1539 | TOP2A | 3756224 | TGTAAATGCCTTAATTGAAAACCCAACCTTTGACTCTCAGACAAAAGAAAACATGACTTTACAACCCAAGAG |
| 1540 | TOP2A | 3756225 | GCTGATCAGATTGTGACTAAACTTGTTGATGTTGTGAAGAAGAAGAACAAGGGTGGTGTTGCAGTAAAAGCACATCAG |
| 1541 | TOP2A | 3756226 | AAAGGATTTCGTAGTTATGTGGACATGTATTTGAAGGACAAGTTGGATGAAACTGGTAACTCCTTGAAAGTAATACATGAACAAGTAAACCACAGGTGGGAAGTGTGTTTAACTATGAGTGAAAAAGGCTTTCAGCAAATTAGCTTTGTC |

TABLE 7-continued

| SEQ ID NO. | Gene | Affy Probeset ID | Sequence |
|---|---|---|---|
| Target Sequences | | | |
| 1542 | TOP2A | 3756227 | TATACATGTATCACCTTTCAGCCTGATTTGTCTAAGTTTAAAAT GCAAAGCCTGGACAAAGATATTGTTGCACTAATGGTCAGAAGA GCATATGATATTGCTGGATCCACCAAAGATGTC |
| 1543 | TOP2A | 3756228 | TGGCTATGGAGCCAAATTGTGTAACATATTCAGTACCAAATTTA C |
| 1544 | TOP2A | 3756229 | TGAAAAGATGTATGTCCCAGCTCTCATATTTGGACAGCTCCTA ACTTCTAGTAACTATG |
| 1545 | TOP2A | 3756230 | TAATGCTGCGGACAACAAACAAAGGGACCCAAAAATGTCTTGT ATTAGAGTCACAATTGATCC |
| 1546 | TOP2A | 3756231 | CAAATGTGGGTTTACGATGAAGATGTTGGCATTAACTATAGGG AAGTCACTTTTGTTCCTGGTTTGTACA |
| 1547 | TOP2A | 3756232 | GAACATATTTTGCTCCGCCCAGACACCTACATTGGTTCTGTGG AATTAGTGACCCAG |
| 1548 | TOP2A | 3756233 | CCTGTAAATGAAAATATGCAAGTCAACAAAATAAAG |
| 1549 | TOP2A | 3756234 | GTTCTTGAGCCCCTTCACGACCGTCACC |
| 1550 | TOP2A | 3756235 | TTCAAGTGGAGCTCTCCTAACCGACGCGCGTCTGTGGAGAAG CGGCTTGGTCGGGGGTGGTCTCGTGGGGTCCTGCCTGTTTAG TCGCTTTCAG |
| 1551 | TOP2A | 3756237 | TTAAATAGGAATTCATACCAGGGACAAAGCAG |
| 1552 | TOP2A | 3756239 | GGTCACTTATACACGCATTTCTTTAAAATATCTGATTAGGTATT TATAGTTTGAAAGAGATGATGTTTCCTTGACTGAGCATCTTGAG AAATCAAGATTTAGTTGACAATTAGACATGAGGAGAATAGAGA GCTAGAAGACCTTGCATAAACTGATTGACCAAGAGAATAGATA CACTAATCATGTCTACAGGAACAGAAAATAAAAGAGACAGAGA AGAGATAATAAATCTGATGGTAAAAAAAAAAAAAGGCAGGAAG ATTACGAATGGCTTCTACTCTCTGGGTGTGGTGGCGCATGCCT GTAATCTCAGCACTTGAGCTGGGGAGGTCAAGGCTGCAGTGA GCCTAGGTAGTGCCACTGCACTCCAGCCTGGACACAAGAGTG AGAGAGACCCTGTCTCCAAAAAAAAAATGATTTGATCATATATGA TTTGACTGCCCCCTTGTGGTAATTTACATTTGTCAATGGTTTAG GGAGACTTGCCTGTATACCGGGATATACAAATTTATGCAAGCA CGAAGACAGTTTA |
| 1553 | TOP2A | 3756241 | ATCGGCCCGTTTCCTATTATGGAAGATTTAGGTCATTTCCATGT TATAAATAATATTGAGGTGATTATTTTGGAGTATAAAACAAGAA TGTTTATATTATGATCTATTACCTAACAAATAATTTTGCTCATTA TATAGTAAATTGTGTTTTATCACAAGGCTATAAACAGCATGTTC |
| 1554 | TOP2A | 3756243 | GCTCATTTGTATTCTAGATTTCTGATAGATCCCTTCTTCCCTAA TATGATCCCTAATATGAATCTTC |
| 1555 | TOP2A | 3756245 | AAATAAAGCATGAGTACATTTTTAGTGGCTTAATATCAACTTCT ATTGCAG |
| 1556 | TOP2A | 3756247 | CTTAAATTATTAATCATGATTTATCTTTACATATATGTGTTCTTAT TGT |
| 1557 | KRT15 | 3757079 | TTGCATGCGCTCTATTCCCCCTCTGCCTCTCCCCACCTTCTTT GGAGCAAGGAGATGCAGCTGTATTGTGTAACAAGCTCATTTGT ACAGTGT |
| 1558 | KRT15 | 3757080 | GTGTCTATTGCAGGAGAAACGTCCCTTGCCACTCCCCACTCTC ATCAGGCCAAGTGGAGGACTGGCCAGAGGGCCTGCACATGC AAACTCCAGTCCCTGCCTTCAGAGAGCTGAAAAGGGTCCCTC GGT |
| 1559 | KRT15 | 3757081 | GTGGTTTCTTCCCACAAGAGAGAAATCTAA |
| 1560 | KRT15 | 3757082 | CAATTTCCACATCAATGTAGAAGAGTCAGTGGA |
| 1561 | KRT15 | 3757083 | TTGAGTAGGCTTCATTCAGGGCATGTCTCTCCCCCAGGCCCC ATCTTCATACACTTCCGCTAAGATGCCCACAATTCATCCCCCTT CATGTGCAGCTTGAAAAACCCTGACATTGTTGCTCCCTGCCGG GCATACCTGCCATTGCCACTGCCCATCTCTGTGATGAGGAATT |

TABLE 7-continued

Target Sequences

| SEQ ID NO. | Gene | Affy Probeset ID | Sequence |
|---|---|---|---|
| | | | CAACACCAGATCTCTGGCAGCTCTTGAGGGATTGGCCAGTGG CCATTCTCAGGGGTGCTGTCTAGTTTTCC |
| 1562 | KRT15 | 3757084 | GATGGCTGGCATTGCCATCAGGGAAG |
| 1563 | KRT15 | 3757085 | AGGATCTGGACTCCTCACTCTGGTCCTTGGCTGTTACCTGGGA CAGGTCACTTCCTCTCTCTGGATCCGTGTTTCTTCTGTAAATGA TAGAGGCTGGGCTAGTGGTAGTTAAGATCTAGTGCTCATTCCA TTCTCTGCATGAGATAGATGGGTATTCTTGTAGTTCAGAATCTT GACCAGCTCAGTGGCTCATGCCTGTAATCCCAGCACTTTGGG AGTCCAAGGCGGGTGGATCACTTGAGGTCAGGAGTTCGAGAC CAGCATGGCCAATATGGTGAAACCCCGTCTCTACTAAAAATAC AAAAATTAGCTGGGCGTGGTGGCGGGTGCCTGTAATCCCAGC TACTCGGGAGGCTGAGGCACAAGAATCACTTGAACCCGGGAG GCGGAGGTTTCAGTGGGCTGAGATCGTGCCACTGCACTCCAG CCTGGGCGACAGAGTGAGATTCCGTCTCAAAAAACAAAACAAA ACAAAACAAAATCTGTCTACTTGGGGATAGCAGGCCTGGATG GGCTAGCAGGATGTCCCACCCCTAGAGGAGTCAGATGTGTGG GTGGTGGTGGTGTAGGGTCTGAAGAACACTGCATAGCTATCT ACATGAGCTTCCCTTACGGACACTTGAGCTTGTGCCCTTTGCT TAAATC |
| 1564 | KRT15 | 3757086 | AGAGTGCCGCTATGCCACGCAGCTGCAGCAGATCCAGGGGC TCATTGGTGGCCTGGAGGCCCAGCTGAGTGAGCTCCGATGCG AGATGGAGGCTCAGAACCAGGAGTACAAGATGCTGCTTGACA TAAAGACACGGCTGG |
| 1565 | KRT15 | 3757087 | CCTGATGTGTCTATGCATCTGTCACTCCCCCA |
| 1566 | KRT15 | 3757088 | AGAGGTGGCCTCCAACACAGAAATGATCCAGACCAGCAAGAC GGAGATCACAGACCTGAGACGCACGATGCAGGAGCTG |
| 1567 | KRT15 | 3757089 | CTGGCCGGCCAGGTCAATGTGGAGATGGACGCAGCACCGGG TGTGGACCTGACCCGTGTGCTGGCAGAGATGAGGGAGCAGTA CGAGGCCATGGCGGAGAAGAACCGCCGGGATGTCGAGGCCT |
| 1568 | KRT15 | 3757090 | GTGAGAGCTGGCCCCCATCACCCCTGA |
| 1569 | KRT15 | 3757091 | TGACATCAACGGCTTGCGCCGAGTCCTGGATGAGC |
| 1570 | KRT15 | 3757092 | CTCCTCTTCCTGCATTGCCCACTTTACTTGGCCTTCTCCTGGC TCTGACTCAGGCAGCCAAGACCCCTCCCACTTCC |
| 1571 | KRT15 | 3757093 | ACCATCGACAACTCCCGGGTCATCCTGGAGATCG |
| 1572 | KRT15 | 3757094 | GTTCTGTAGATCCATGGCTGTGTCCAAGGTGTGCAGGAGGCA GTGACCATGAGTTGTCCACAGTGGGGCTGGTGGAGTGTCTCT GAGAGAGCTATTGTCAGAGCTGGCTGCACCCCACTGCCCCAC TCTCCTGGGCAACCAATTCCCACAGGCAATACTGCCTCCTTGG TCTTTCGTGCCCTGGAGA |
| 1573 | KRT15 | 3757095 | GTGAGTCCTCGGATGTCAAAGAGAGG |
| 1574 | KRT15 | 3757096 | CAACCAGCCCAGAATGCGACTACAGCCAATACT |
| 1575 | KRT15 | 3757098 | CTCTGGCAATGAGAAAATTACCATGC |
| 1576 | KRT15 | 3757099 | GTTTGTCTCTTCAGGGTCAGGAGGAGGATATGGGGGTGGCAT GAGGGTCTGTGGCTTTGGTGGAGGGGCTGGTAGTGTTTTC |
| 1577 | KRT15 | 3757100 | GGTGGAAGCCGAAGTATCTCAGCTTCTTCTGC |
| 1578 | KRT15 | 3757101 | GAGGTCCCACAACACCCTCTGAAGGGTATATAAGGAGCCCCA GCGTGCAGCCTGGCCTGGTACCTCCTGCCAGCATCTCTTGGG TTTGCTGAGAACTCACGGGCTCCAGCTACCTG |
| 1579 | KRT15 | 3757102 | GATCGGCCAGTGGACTCCCAAACTAAGAACACGGAGCTGTCC TCTTGGGGAGAGGCTCAGGGCTCGGGGAAGTGAAGTCCAGC TGAGGGCACAGTTGGCCTGAGCTGCTCTCAGTACAGGCAGAG GCCTTGGTAGCTGTGCTGTGATGAGAGTTCGCTCCCTGCTGC TCTCTTCTGGCATGGAGAGATGAACCTGTAATCCAAGTGTTAA AACCGTGCCCTG |

TABLE 7-continued

| Target Sequences | | | |
|---|---|---|---|
| SEQ ID NO. | Gene | Affy Probeset ID | Sequence |
| 1580 | KRT15 | 3757103 | CCCAGCCTTATCAGCGGAGGTTTGCCCCAACACATCCCAGAA ACGAGCAAAGGTTCAGCGCCGTGCAGTTGGCAGGTGTCGGG ATCATCAGTCATCCCCTTGTCAGTCCCAAGCCTGCTGGGCTTT TGTGAGGGTGCCAGGAACACAGGCTGGAGGATGGCAGGAGG GGAGTAGAGGTGGGAGGAGGGGAGTCCATCTGCAGCACCAG GTAAGGGGATGGATGCTGGCTCCTCTGGTCACCTCAGCTGGA ACACTACTCAAGGTC |
| 1581 | KRT15 | 3757104 | GACAGAGCTTTATCTTCGCAAGGCCATCCCACCTGGTGCTAAT GAGGAGGCTCCGGGCCCCACCCAGATCTGGAGCTCACAGTA GCGGTTTGGACTGAAACCAGGGATTTGTGCGTGGGGCAGTGA GGGGGGCAGCTGCCGCCCCTGGCCTGGGCCTGAGAGTATAG AGAAAGCCACCTCGAGGGGCTGCTGGAGGAGAGTCAGGTGC AGAAGGGGATCTGGCTGGGGTCCAGCCCTTCCTCACCCTGGG GTGAAAGGCGAGTAATTGTTCTTGAGTTAATTGCTGGGGCCAC AATGTCTGCAGAGGCTTTTAATGAGCTCTGGATGATCTGAGTT TGATTATTTTTCTTTCGGAGGAAAAGACAATACCCTCCCACCCA TGAGACAATACCACACTGTCTGTGCCCAGCATTGGAGGCCAG GCTCACTGCGAAGATGGATGAGAAGGAACCCACCCCCAGCCT TGCTGGCTGGCAGTTCCCCTTGCCAGCCCAGCTCAGATGCAG GAATTTGGGGTCTGCAGGAAGGACTCTTTCCCTGTGCCCTGTT TGGTTGAGGGTGTGAGGACCTGTTTGAGTCCTGGCTTTGCCC CTTACCAGTGGTGCCACCTGGCACAAGTTGCTTCACCTCTCCA AGTTTCAATTTCATTCTTTCTGAATCTTGGGTGGGGGTCACCCT CTGTTGTGAGGATGAGAGGAGGTGATGGATGCAAAAGTGCTT TGTAAATCACAAAGTGCAGGGTAGAAGTAAAGGATTATGCTAT TATAGCAAAATAAGAACCTAAGAACAACCTGCGTTGCCCCATA GGAGCTGGCTATGGAAGGTCGATGCCGTTGAGCCTAAGAACA TGCTCAGGCTCACAGGGCATGTTCTGATGCCCAACGACAAAG CCCCTCCTGGTGAGGGCACTCAGGCGCAGGTGCCGGTCATG CACCCTGGCCCCTGCATGTCTGGCACCTGGGTGGGGATCCAG GAGGGGGCAGGATGGGGGCTCTTGGGCCACAGGGCTTCCCT GGAAGTGAGAGTTGAGAGCGCCCCTTGCCACAGGGAAACAGA GACTTAAAAAGGTAAATGTCCACAGTCTTACCATGGTAATTGG TAGGGTCAGGATTTGAACCCAGGCCTCACAGTCTTACCATGAT AATTGATAAAGCCAGGATTCAAACCCGGGCCTGAGGGACTCC AGAGCCCTGTCCACTTCACCATGCTGCAACCTGGGCTAGGAA TCCTCCTCCTGAGTTTCTGTAAGCCCTGGGGCCAGGTCCAGA GGGCTGAGCCACACCTCCAAGTGGCACTGCCCACAGGTATCA GGTGTCCCTGGAAAGGTGTCCCTGAGCTGGTGGCAGAGAAAA GGGCTCTCCTGAGTGTTCAACTC |
| 1582 | KRT15 | 3757105 | GCAGGCCCAACCCTATGAGTGATGGGGGCAAGTGAGGGACA CTAGTTCCACGCCCGCATGCTGCCAAATGTACTCAGCACCCT GCTAAGGAGGCTGGAGACCCCATCACGGCCATGGCAATCCC GAAGGAGGAGCTGTTTCAAGGTTGGTTATGAACATGTAACCCC AGAGCCCCGCTGCTGTAGCCTGGACTGGGACCCCCTTCTGCC CCCTCCCTAGCTGTCCTGTTCTGGCCTCCAGCACCCACAAAC CACCACCCCCAACTTAACTTCTCAGGAAGCCTTGGAGCTGGA GGGAGAGGCCTGGCTGCACCCCCAGCTGGGACTGCCCAGAG GCGCTTGTCCCTGCCCATGAAAGCCTCCCTTGTCACAGCTGA AACCTTCCCTCTGCCTCAGGGGCCCCTGGAATGTGGCTGCGG GGCGGGGTCTGGGCCCACACAGGTGGGGCAGGTGACTGTCA GGTCTCAGGCCTGAGTGTCAGGAATGAAGCCTGCCTTTGTGT GTGCACAGTGCAGGGTGGGGCTGGACTGGGGACACTTTTCTG TCTCAGCCTGGAGACCTGGGATAGGAGGGAGAGGGGAGTGG GGAAGTTGAGGGGAGTGCCTTTACATCCTGCTGGTCATCGTG GCCACTTCAGTCTGTTGAGCATTTCCTGTGAGTCATCTTGCTC CAACTGAGAGTCAGGCTGAGCTGGAGTTATTTCCATTTTCCTG ATTGGTAGACTAAGGCTCA |
| 1583 | TMEM100 | 3763391 | CGTCTTTGGTCAGGAACTTTATAATGTGCTAT |
| 1584 | TMEM100 | 3763392 | TTGCAGTTCCAAATTGCCATCTTCCCTTGTCTCATTTGCAAGTT CTCAATTGTATTTCTCTCAAATGGACAGGTTCCTTCTTTACTGG AGGATTTTTGTTTTTATCATATTGGTTTTTCATTACTTCTGAATA GTCTTAATTACGTTTACTAAATTCTAAAGGATTTCTGTGCTATTA TAATTAGG |

TABLE 7-continued

Target Sequences

| SEQ ID NO. | Gene | Affy Probeset ID | Sequence |
|---|---|---|---|
| 1585 | TMEM100 | 3763393 | ACCCTAAGGGCTACTTCTGAGACTGAAAAATCAGCTTTCTATTT ACATGAAACACTTTGGGGGTCATGGGAGTGCACAGCATTAGA CAGTATTTGGTTCACCCTGTAAAGTAGCCAAGAAAAGATGAGA AAAATCAAGATAGGCCTGGCACACTAGACATTTGCCTCCAAAA GAAATAACCTACAGTCTTAAGATGTATCATAAAAATGTTCTGCC AAGGATCTAAATTACCTTGGGTTTCGCATATGTCTATGA |
| 1586 | TMEM100 | 3763394 | GTTGTGATCACCACAGTCCCTCTGGTCAGTGAGATTCAGTTGA TGGCTGCTACAGGGGGTACCGAGCTCTCCTGCTACCGCTGCA TCATCCCCTTTGCTGTGGTTGTCTTCATCGCCGGCATCGTGGT CACCGCGGTGGCTTACAGCTTCAATTCCCATGGGTC |
| 1587 | TMEM100 | 3763395 | TGGTGAGACTGTCCAGATCTAGTCTGTAAACCCAGCTTAGAAG CACT |
| 1588 | TMEM100 | 3763396 | TTGGAAGATATTGTTACACTTCAGACCACAAATCCCCACCTCA TT |
| 1589 | TMEM100 | 3763397 | AATTTGGGGACAGATCTTGATTTTCAGGTTAGCTCAATCTCAG CTTTGG |
| 1590 | TMEM100 | 3763398 | AGAAGTTGGACGAAGAGGCTCAGGCGTTGCTGTTTCTTGTCTT CCAAGTCAAGTGGTTACTCTGGTAATG |
| 1591 | TMEM100 | 3763399 | ATCCCAAACCAGAGCAGACCCTATAGTAAAGTATTTTTACATCT TTTCCTTTCCCCAGAAGAGATCCCTAACCTATTGTTTTAT |
| 1592 | TMEM100 | 3763400 | GTTTGCACCTTTAGCTTTGGTAACAGGAAAGCATGCTTTTCAA CAGAATAAGGTGATATTCAGAGCTTCAGTGCAGTTATTGGGCT ATCTTGCAGGCAAAGTGGTACTAGAAAATAGAGGGGAATTGC CCTCAAGGGCC |
| 1593 | TMEM100 | 3763401 | ATGCTCCTCTTACCAAGCCTGCAACTTAAAACCTATGGTTTAAA CTGTGCTTTCAATTATCTGGAGGAGGCCAGCACTGATGAGCC CATCCTGAGCCAGTCATTTTAAGGCCAGTGCTACCTAACTGAG ACAAGGCTAATCTGGTC |
| 1594 | TMEM100 | 3763402 | CAGTTTATTATGGTATTGGACACCCCATGCTCCTTACTGCATTG GCTTTGGGTAAGAAGGAGTGAAAATTAGTGTGCGAACCTGAAA ACCTAGAATTTCTGATTGGGACTGA |
| 1595 | RPL31P57 | 3766793 | AAAATCTACAGTCGGTGTGAATGTGAACTAA |
| 1596 | RPL31P57 | 3766795 | AAAGAGCTCCGGAAACTTGCCCTGAAGGAGATGGGAACTCCA GATGCACACTTTGATACCAGGCTCAACAAAGCTGTCTGGGCC AAAGGAATAAGCAACGTCTCATACTGTATCCATGTTCGGTTGT CCAG |
| 1597 | HIF3A | 3836706 | ATGGCGCTGGGGCTGCAGCGCGCAAG |
| 1598 | HIF3A | 3836707 | GGGGTTTTATCTGGCCATGTTCCCATGGGACCCTGGAAAATGT TCTAGGTCCTCAGCTTTCC |
| 1599 | HIF3A | 3836708 | ATCTCACCGCCGTGCGCACCCACTCGTAACTCGCACCCGGGT CCTGGCTGCACCGCATCCCCTCCTGCACCCCCTGGATGGCCC TTCAGCCAACGGGGGCCTG |
| 1600 | HIF3A | 3836709 | CAAGGATGCTCTTGGGAAGTCCCTGGTGG |
| 1601 | HIF3A | 3836710 | GTACGGCTTGCAGCCCAGAGTGCCCAGTGAG |
| 1602 | HIF3A | 3836711 | TCAAGATGAGGAGCCAGTAGTGAGG |
| 1603 | HIF3A | 3836712 | CGCCACAGAGAGGAGCGAGGCGCCAGAGGCACC |
| 1604 | HIF3A | 3836713 | GTCGACCACGGAGCTGCGCAAGGAAAAGTCCC |
| 1605 | HIF3A | 3836714 | TGCTGTACCAGCTGGCTCACACGCTGCCCTTCGCCCGCGGCG TCAGCGCCCACCTGGACAAGGC |
| 1606 | HIF3A | 3836715 | ATGCGCCTCACCATCAGCTACCTGCGCATGCACCGCCTCTGC GCCG |
| 1607 | HIF3A | 3836716 | GGAATCCAGGCCACTAGGATGTACCCCCACTTCCTTGG |

TABLE 7-continued

Target Sequences

| SEQ ID NO. | Gene | Affy Probeset ID | Sequence |
|---|---|---|---|
| 1608 | HIF3A | 3836717 | ACCACTGGATGCCTGCTACCTGAAGGCCCTGGAGGGCTTCGT CATGGTGCTCACCGCCGAGGGAGACATGGCTTACCTGTCGGA GAATGTCAGCAA |
| 1609 | HIF3A | 3836718 | TTGGTATCTGTTCCTTTTCTCTGCCTCGTTACCCCACTCCTGGT A |
| 1610 | HIF3A | 3836719 | CTGGAGCTCATTGGACACAGCATCTTTGATTTCATCCACCCCT GTGAC |
| 1611 | HIF3A | 3836720 | GAGCTTCAGGACGCCCTGACCCCCCAGC |
| 1612 | HIF3A | 3836721 | GAGGCCCCCACGGAGCGGTGCTTCTCCTTGCGC |
| 1613 | HIF3A | 3836722 | ATGAAGAGTACACTCACCAGCCGCGGGCGCACCCTCAACCTC AAGGCGGCCACCTGG |
| 1614 | HIF3A | 3836723 | TGCTGAACTGCTCTGGACATATGAGGGCCTACAAGCCACCTG CGCAGACTTCTCCAGCTGGGAGCCCTGACTCAGAGCCCCCGC TGCAGTGCCTGGTGCTCATCTGCGAAGCCATCCCCCACCCAG GCAGCCTGGAGCCCCCACTGGGCCGAGGGGCCTTCCTCA |
| 1615 | HIF3A | 3836724 | CGCCACAGCCTGGACATGAAGTTCACCTACTGTGACGACAG |
| 1616 | HIF3A | 3836725 | AAGTGGCTGGCTATAGTCCCGATGACCTGATCGGCTGTTCCG CCTACGAGTACATCCACGCGCTGGACTCCGATG |
| 1617 | HIF3A | 3836726 | GTGCGAAGCCAGCTGCCACATGGCCCCCAGCTGACACCAGG ACCCCCCAG |
| 1618 | HIF3A | 3836727 | CCCAGGATGCACTGCCTCCCCACCTCAACACCAGCTCCCTGC TCCCCAAGCCCCAAGGAACTGTCTCCTTCCTTGCCCCCTCATA CCCAGTCCCCAGATATTTCTCTCCC |
| 1619 | HIF3A | 3836728 | CAGTAACAGGGCAGTATCGCTTCCTGGCCCGGAGTGGTGGCT ACCTGTGGACCCAGACCCAGGCCACAGTGGTGTCAGGGGGA CGGGGCCCCCAGTCGGAGAGTATCGTCTGTGTCCATTTTTTA |
| 1620 | HIF3A | 3836729 | TGGGCCTGATCTGCATGTGTGGACAGGTGTGTGTGTGTGT GTGTGTGTGCGTATGAGCATGCATGTGTATCATGCATAAGTGT ATGTGAGGGAGTGTGCACGTGTACACATATGAGGAATGTGTG TCACCATGTAAATGCCGGTGTGTGTGTCTGCATGGACACAGGT ATGTGTATGGGTGTGTAGACTGTTAATTTTTTTTTTTTTTTTTTT TTTTTTTTTTGCGTGAACCTCTGCTTAAGTG |
| 1621 | HIF3A | 3836730 | GCAAAGTGGTTAGGACCCATTCTCAAAAAAAAAAAAAAAAAA AACCTGAAAACAGACCAAAAAAAAAAACCACACACACGCAAAG ATAGATGGTTTGCATATGGTAAATTCTCTTTATGGTACACAGTT CTGTGAATTTTTGACACACGCATGCAGTTG |
| 1622 | HIF3A | 3836731 | TGCACCCGGCCCATGTTGTGGTTTATATCAGTAGTTCCTTTGT AAATAGTGAACAGTATTCCATGGTATGAATAGAGCACAGGTTT TTTTTTTATCCATTCACCAGTTAGAAGACATTGGGCTGTTTCCA AGTTTGGGTGATTACAAAAAAACAGCTACTGTAAACATTCTCAT ACAAGATTTTATGAGATCACATGTTTTCATTTCTCTTGGGTAAA CAGCTAGGATTGGAATGGATGGGTTATATAGTAAGTGTATATT TAATCTAAGAAACTGCCATGGCTGGGCACAGTGGCTCACGCC TGTAATCCCAGCACTTTGGGAAGCCAAGGAAGGAGGATGACT AGAGCCTCTGAGGTGAAGACCAGCCTGGGCAAAGTGGTTAAG ACTCAACCGC |
| 1623 | HIF3A | 3836732 | GACAGAGTTTTGCCCTTGTCACTCAG |
| 1624 | HIF3A | 3836733 | TGAAACCCTTATAGGAGACAAATAAATGTGGGCAATTATTTTCT GCAAAATGCCCTCCAAGCCCCTGGGCGCCATTGCCTTCTGTA ATAGGACATCACC |
| 1625 | HIF3A | 3836734 | AAGAGACCGGAGTGGTGCTGTCCCTGGAGCAAACGGAGCAA CACTCTCGCAGACCCATTCAGCGGGGCGCCCCCTCTCAGAAG GACA |
| 1626 | HIF3A | 3836735 | CCCGGATCCTTGCCTTCCTGCACCCGCCTTCCCTGAGCGAGG CTGCCCTGGCCGCTGACCCCCGCCGTTTCTGCAGCCCTGACC |

TABLE 7-continued

| Target Sequences | | | |
|---|---|---|---|
| SEQ ID NO. | Gene | Affy Probeset ID | Sequence |
| | | | TCCGTCGCCTCCTGGGACCCATCCTGGATGGGGCTTCAGTAG CAGCC |
| 1627 | HIF3A | 3836736 | TGCTCTCCTAATAATGCAACAATCGTCAACACAGAAGAAGACT TCTGTGACCAAATGTGGGCAGTTTTTCCCACACACCAAGCAGC GGACACCAGCTGGGTGTCCTCCAATTCAATTCCGGCATCATCT A |
| 1628 | HIF3A | 3836737 | CCAGATGAACTACCTGTGGGCACCGAGAATGTGCACAGACTC TTCACCTCCGGGAAAGACACTGAGG |
| 1629 | HIF3A | 3836738 | CAAACTCTCAGTCAGGGCTACAGTCATCTGGGGTTAGAGGGT TTTCTTCCAAGCTCACACACATGAGGTTGTTGGCAGGCCTCAA TCCCTCACTTTGCTTTGGCTGGAGGCCTCAGTTCCTCATCACG TGAACCTCTACATAGACTCCCTAAGTGTCCTCACAACATGGCA GTTGGCTTCCCTAAGGCAAA |
| 1630 | HIF3A | 3836739 | CCAGCTCAACGCCAGCGAGCAGCTACCCAGGGCCTACCACA GACCTCTGGGGGCTGTCCCCCGGCCCCGTGCTCGGAGCTTC CATG |
| 1631 | HIF3A | 3836740 | CCAGAGCTCAGAGGACGAGGACGAGGGAGTGGAGCTGCTGG GA |
| 1632 | HIF3A | 3836741 | CAGCCCAGAACACGAAAACTTTCTGCTC |
| 1633 | HIF3A | 3836742 | GGGATTCTCTGGCCCTCATTACCTAGCTGGCTTAAACCTACTG TTTTATA |
| 1634 | HIF3A | 3836743 | CTGGTTGAGGGTCATACAGAAAGTCAGTGGGCCAGCTGAGAC TAAAGCCTGATCT |
| 1635 | HIF3A | 3836744 | GTCCTCGGGCGAAGGAAGAAGGAGAAGGGGGATGAGGCCCT GGAGGAACACAA |
| 1636 | HIF3A | 3836745 | AGTTTCCTTCTGACAGGAGGACCAGCCCCAGG |
| 1637 | HIF3A | 3836746 | AGCACCCCACTCCTGAACCTGAATGAGCCCCTGG |
| 1638 | HIF3A | 3836747 | AAGTGTAACGGGGAAATAATGCATGCAAGGAAAAAGGTTTGG AGTAGGGGGATTTCAGTTTTAAACAGTATGATCAGGGTGGTTT CATTGAGAAGGT |
| 1639 | HIF3A | 3836748 | AGTGCGCTTCATTACGTCTGGCTAATTTTTTAATTTCTGTAGAG AAAGAGGTCTTGCTATGTTGCTCAGGCTGGTCTCAAACTCCTG GGCTCAAGTGATCCTCCTGCCTCAGCCTTCCAAAGTGCTGAG ATTGTGCCTGGCTGTCTCTGTCTTCTTTGGGGAAAAGCAAGGC CAATGTAGCTGAAGCAGAGAGGAGAGAAAGGTGAGGGCTGAC TGCATGGAGCCTCTGTGGGGCATTGTGATGGCTTTGAAGTCA CCTTGCTTGAGGAGGCTGCCTCAGGGCCTTTGCATATCCTGAT CCTTCTGCCTGGCATACTTTTCCCTCTGTTCTTTGCCATGTTAC CACATCCTTTAGATCTCAAACCAAATATTACTCCTTACACAAAG CCCTGCCTAACTTCATACGCTCATGGTTTATAACACTCCATAAT TACACAGGCCTTTGTGTCATAATTTGATGACTGTCTGTCTTCTC CTTTGGGTATGAGACCTTCAAGGGCAGGGGCCAGGGCTGTCT GGGTCCCTGCTGTTCTCTTCTTTGTGCACATGGGTGGGCGGT GGCTAAGCACAGAGGAAGTTCTCAGCACATATTTGTGAATGAG GAGCTAAGATTCACGCACTCGCACTGTGCCTAGCTTTGTGCTA AATCCTCTATGCACCTGATCCAATTGGCGCTTCTCACTGGAGT GTCGGTCCCATA |
| 1640 | HIF3A | 3836749 | GTTTTCACTTTGTCACCCAGTCTGG |
| 1641 | HIF3A | 3836750 | ACCACCACGCCCGACAGTAAATATGTTTTGAA |
| 1642 | HIF3A | 3836751 | CACAGCAAGTAAATAGCAATGCCTGGATTCAAACTAGGGCAG CATCTGACTCTGGACTCGGGTTCTTCACCGCAGCCCTGAACA CCCCAGAGAGGTTCAGAGAGCAGAACGTGCCCAAGACGTCAC TGCCGTTTGAATCCAGACAGGCTTGCCTCACCACCCAGG |
| 1643 | HIF3A | 3836752 | CTCACTGCTCTCTCCGTACTCAGACGAGGAC |
| 1644 | HIF3A | 3836753 | TGGTCTCAGCTCAGTGACCTCTGGGAGGTGGTCCCTGGCCCC CTCCTCCTTCTCTCAGGATTTCTCTTGGGGTTCTCAATACTTGG |

TABLE 7-continued

| Target Sequences | | | |
|---|---|---|---|
| SEQ ID NO. | Gene | Affy Probeset ID | Sequence |
| | | | TTACCTCATTATCCCTTTCTCTGCCTCTCTTGGCTTTATTTTGG GGAATCAGGGGTGAGGAGGGTTGGGGGGGTCATATCTGTGTT TCCAGGTTCTGGGGAGAACAATGATCCACGGGTCAACGTGAT CACATTTC |
| 1645 | HIF3A | 3836754 | CCAGTGACTTCCGATTGAGGCCAAAGACCCCAAGCTGCCCGC CAGCTCTGACTGCCCCTTGCGCTCTGGGCTTCCTGCCGCCCC CAGCTTTGCCTGGACACTGA |
| 1646 | HIF3A | 3836755 | TGACCTGCACTGGTTCTAGACCACACAACCTCCAATGTGGTCT GCTTTAGATCACCTTCTTCTTCTTCCTTCTTCCTCTTCCTCTTC CTCCTGCTCCTCTTCCTCTTCTTCTTCTTTTTTTTTTTTGACAGA GTCTTGCTCTGTCACCCAGGCTGGAGTGCAGTGGCGCGATTT CAGCTTACTGCAGCCTCCGCGCCCTGGGTTCAAGTGATTCTC CTGCCTCAACTTCCCAAATAGCCGGGACTACGGGCATGTGCC ACATTGCCCGGCTAATTTTTGTATTTTTAGTAGAGATGGGGTTT CACCACGTTGTCCAGTCTGGTCTCGAACTCCTGACCTCAAGTG CTCCACCTGCCTCAGCCTTCCAAAGTGCTGGGATTACAGGCG TGAGCCACTGCACCCGGCTAGAACTCACTTTCTCCAAATCCCT CTGCTTCGAATTTCACCGTCTTCAGCTCTTTCTAGTTCTGGGC CTCACCAGCCTCTCATTCTGCCTGTTTTCAAACCTTACGATCC CCAAAAATTGTCTGGTTCTGGGCCTCTA |
| 1647 | HIF3A | 3836756 | CCGGTTCCAGATCTTATATTCAGTGATTTCCTCTGGTTCTGGA CCCCACAACTCCAAGCTTCCTATTGGTTCCAGTTCTCCTGATC GGTAATACATTTGGTTCCAAATCCAGACCTCTTAATCTCTCTCT TTTTTTTTTTTTTTTTTGAGACAGAGTCCCACTCTGTCACCCA GGCTGGAGTACAGTGGCTCAATCTCGGCTCACTGCAGCCTCC ACCTCCTGGGTTCAAGCAATTCTTGGGCCTCAGCCTCCCAAAT AGCTGGGATTACAGGCATGTGCCACCACGCCCAGCTAAGTTT TATATTTTTAGTAGAGACAGTGTTTCACCATGTTGGCCAGGCT GGTCTTGAACTCCCGACCTCAACTGATCCACCCGCCTCAGCC TCCCAAAGTGCTGAAATTACAGGAGTGAGCCTGGCCAGACTT CTTAATTTCTAAATCACTTTTGTTTTAGACCTTATGAGGCTCAG CTTATTCTTCTGCAGTTCTCTATAACCAAGACTCATTTTCTCTC ATCAAAAACAAGTACAGAGAGTTTGATGTGTTTATCTCTTTTTT CTTCCTCTTCTTTTTTTTTTTTTTCTTTTTTGAGATGGAGTCTCT CTCTGTTGCCCAGGCTGGAGTATAATGGTGCCATCTAGGCTCA CTGCAACCTCCGCCTCCTGATTCAAGTGATTCTCCTGCCTCAG CCTCCTAAATTGGTGGGATTACAGGAGCCCACCACCACATCC GGCTACCTTTGTGTATTTTTTAGTAGAGACGGGGTTTTGCCAA GTTGGAGGGGCTGGTCTTGAACTCTTGACCTCAGATGATCCA CCCGCCTCAGCCTCCCAAAGTGCTGGGATTACAGGCATAAGC CACCGTGCCCGACCCTGTCCTTATCTTATAATAACCAGTTCTT CTAGAACCAGACGATGCTCTAGTTCTCCTAGATTCTGAACCTC ATGACCTGTACCACTCACTAGTTCCAGACTACACAACTTCTAG AAGGTGCCACCTCCAGGGTCCTGATTCAAGATCTGGTGATCT GCTGTTTCTCTGGTTCTAGAACTGACTTACAAGTGCCTTCTGAT TCTAGACCTCATTCCGTAAGTTCCCTTG |
| 1648 | HIF3A | 3836757 | CCCAGCCTCCTAAATCTATTCTGGGCTTCCC |
| 1649 | HIF3A | 3836758 | CACTGAACTTACCCAATTCCTTCTTTCAGTCTTAAGTTTTCCCA TTCTAAACCCCTACCCTCTAGGCTGTGCTGCTCCTGGACTTCA TGCCTCTCCATTCTCATTGCCTACAATCTCTGTGCCCCAGAAC CCCCTCCACTTCCCACCCCAGCCCTCCAGACATGCACTTACCT TGACTTTACCCCACATGTTTGGGGCACCTGGGGC |
| 1650 | HIF3A | 3836759 | AGCTGTCTGCCACCATCTATGTGCCTCCCTTACCCCCCAGCTT TCTTTCTACAGATGGTGCTACTCTTGGTCTCCCACAGGAAAAG GCCTCCCCCCTTCTTAGCCCCATTTACCCCGTTTGTGGAAGGC ACTGCTCGCTCTGTTTTGTCAGAGAGTGGCCTATCCAGATTGG TGCTA |
| 1651 | TPX2 | 3881448 | TCCTCCCGGAGTTTGGAACGGCTGAAGTTCACCTTCCAGCCC CTAGCGCCGTTCGCGCCGCTAGGCCTGGCTTCTGAGGCGGTT GCGGTGCTCGGTCGCCGCCTAGGCGGGGCAGGGTGCGAGCA GGGGCTTCGGGCCACGCTTCTCTTGGCGACAGGATTTTGCTG TGAAGTCCGTCCGGGAAACGGAGGAAAAAAAGAGTTGCGGGA GGCTGTCGGCTAATAAC |

TABLE 7-continued

| Target Sequences | | | |
|---|---|---|---|
| SEQ ID NO. | Gene | Affy Probeset ID | Sequence |
| 1652 | TPX2 | 3881449 | ATGCCCTCAGGAAGTGTGGCGTTTGATGGAGGAAAACAGA |
| 1653 | TPX2 | 3881450 | TGAGGGAGTTCAAGAGCCAGTTTGTGTTTCTGTGCTTCACAAA GCCACCCTTGTCTAATTCTTGA |
| 1654 | TPX2 | 3881451 | TGATACATATTTGCCAGACTTCAAGATTTCAGAAAAGGGGTGA AAGAGAAGATTGCAACTTTGAGTCAGACCTGTAGGCCTGATAG ACTGATTAAACC |
| 1655 | TPX2 | 3881452 | GAGTGTGCACTTCAGTGGCGTGATC |
| 1656 | TPX2 | 3881453 | CATTTGGGTAAGTTAATAGTCAATTTATAGGCCACGTAAATGG GAAGGATTATTTCCTTAAATCAAGAGATTAGACAATCATTGCTT GTCATGAATATTTAATAAAAATTTGAGAAAGCTCAGTTTCTTTT GGGCTGCAAACATAGATCTAGGGAAATAAATACTGCTTAACTA TTTTGTTG |
| 1657 | TPX2 | 3881454 | AAGGTGACCTGCTGAGAAAAGTGGTACAAATACTGGGAAAAA CCTGCTCTTCTGC |
| 1658 | TPX2 | 3881455 | CACAAGTTAAAAGCTCTTATTCCTATGATGCCCCCTCGGATTTC ATCAATTTTTCATCCTTGGATGATGAAGGAGATACTCAAAACAT AGATT |
| 1659 | TPX2 | 3881456 | TACTGGTAGGGAGCTTTAGTTTGCATTTTAAATGCGTGATAGT GATTTGTTTTGCTTCCTTGCTGATCAGACAATGATGATCTTCCC TTTTCACAG |
| 1660 | TPX2 | 3881457 | GGAACTGGAGGGCTTTTTCAGGGCAAAACTCCTTTGAGAAAG GCTAATCTTCAGCAAGCTATTGTCACACCTTTGAAAC |
| 1661 | TPX2 | 3881458 | GACAACACTTACTACAAAGAGGCAGAAAAAGAAAATCTTGTGG AACAATCCATTCCGTCAAATGCTTGTTCTTCCCTGGAAGTTGA GGCAGCCATATCAAGAAAA |
| 1662 | TPX2 | 3881459 | CAAGAGATGTGCCACTCCTGTAATCATCGATGAAAT |
| 1663 | TPX2 | 3881460 | CCTTGTATACCACTTGTAAGTTTCTTTTCTGAATTTACACTTTAG ATTGAATAGATTAAAATTAAAAATGGTACATCTGTAATATGTTT GGTGTACCTCAA |
| 1664 | TPX2 | 3881461 | TCCATATGCAGTAGATTTGGGGAGGAGGGTACAGGCTATGCT TCAGGGAATTGAAAAC |
| 1665 | TPX2 | 3881462 | AGAAGGCAGTGCTCATCAAGATACTGCTGAAAAGAATGCATCT TCCCCAGAGAAAGCCAAGGGTAGACATACTGTGCCTTGTATG CCACCTG |
| 1666 | TPX2 | 3881463 | GAGAAGAGTATGAAAATGCAGCAAGAGGTGG |
| 1667 | TPX2 | 3881464 | ATCAGTGAGCCAGGTCACCAAATCAGTTGACTTCCACTTCCGC ACAGATGAGCGAATCAAACAACATCCTAAGAACCAGGAGGAAT ATAAGGAAGTGAACTTTACATCTGAACTACGAAAGCATCCTTC |
| 1668 | TPX2 | 3881465 | GGTTGGGGCAGACCAGTCAAATCTCATGCAGTTTTGTTACCAG AGCACCAACAAAATCAGTAATAATCGTTAAGTAAAAATGCTAGT ACTAATAATCTCCACTTGCATTTGTAGTCAGTATCATCATTTTTT GAAATTAGTTATTTGCATTCTTAAACCCTGAGGTTATGCTTCTT TCTTTGAGATACAGGTCCTTGAAGGGTTTTGCTTCCAATTAGA GACCAGTTTTATCAAAATTACTGGTCCAAGGAATAGGAATAGG CTTCTTCATCAGTCTC |
| 1669 | TPX2 | 3881466 | CTCTGTGCCGAATATGTGGCTTATGGTAGATGTGAGCTCTTCC GTGACATTTCATT |
| 1670 | TPX2 | 3881467 | GCCCGAGTGACTAAGGGATGTACCATTGTTAAGCCTTTCAACC TGTCCCAAGGAAAGAAAAGAACATTTGATGAAACAGTTTCTAC ATATGTGCCCCTTGCACAGCAAGTTGAAGACTTCC |
| 1671 | TPX2 | 3881468 | ATGGCTCACTTCAGTGTCCAACTCCTGGGCT |
| 1672 | TPX2 | 3881469 | TGAATCACCACTTACAAGTAAACTGGGTCTTGCGGATCTAGAT GAACATCTGTC |

TABLE 7-continued

| Target Sequences | | | |
|---|---|---|---|
| SEQ ID NO. | Gene | Affy Probeset ID | Sequence |
| 1673 | TPX2 | 3881470 | CTGTTACCCTCCAAATCTTCTGTGACCAAGATTTGCAGAGACC CACAGACTCCTGTACTGCAAACCAAACACCGTGCACGGGCTG TGACCTGCAAAAGTACAGCAGAGCTGGAGGCTGAGGAGCTCG AGAAATTGCAACA |
| 1674 | TPX2 | 3881471 | GTAAGTCCCACTGGCAGTATCTGAG |
| 1675 | TPX2 | 3881472 | CTTGATCCCAGAATACTTGAAGGTGGGCCCATCTTGCCCAAGA AACCACCTGTGAAACCACCCACCGAGCCTATTGGCTTTGATTT GGAAATTGAGAAAAGAATCCAGGAGCGAGAATCAAAGAAGAA AACAGAGGATGAACACTTTGAATTTCATTCCAGACCTTGCCCT ACTAAGATTTTG |
| 1676 | TPX2 | 3881473 | CACCTGTTTCAGATGAGGTAACCGAGGCACACAGAGGTTATG TAGTATTCCTAGAGCACTCAGCTAGTACATGGTGGAGCAAGTA AGAGTTCAGACACTCTAGCTACAGAGTCTGTGATCCTAATACC TCATTATATGCCTCTCCATTACATGATAGAATTTTGACTTGCAG AAATGCAAATGGACTGGATTGGCAGAACATTCCAGGCAGTAG GAATTACATGATAAAAAGCCTGACGGTGGGAAACAAGAAGCTT CTACTGGGAGCTGTTAGTGGGTCAGTTAAGCTGGAGAAAAGT TTATCAAGAGCCACTGGAAACTGTTTCAGAGAAGTGAGTTGTA GTTTGATAATAGGCTCACAACCACAAGTTTAGAGAAAATGTGC AATCAGGAAGCAAGGCTACAGTCAGAGAATAAGCAATGGAGT TAAGCACCTGCATAAATGCGAAAGCGGCTTTTAGTTACATTTC AGTG |
| 1677 | TPX2 | 3881474 | ACAGGGACCGTGTGTATCTATATTATTCACTCTGTATCCCTAG CCCCTAGCATAGTGACCACCACAGCACAAGCACTCTGATATC GGATAACTGAGTGAGTAATAGTAGAAGCTGACATGCACCTAGA CACTAGGAATTCAAAGATGGTATAAGACACGGCCCTTGTCCTC AAAGCTTTCATAGTCTGGTAGAGCATATAGATGTGTAAATGAG TAAATATGGTAATATTAACCAACATATGTTCATTGAACAGTTAC TACGGGGTCTTCTA |
| 1678 | TPX2 | 3881475 | AGTGGAGATCATTTTGTGATATCTAATTGAGTTGCTTACTCCTT TCAG |
| 1679 | TPX2 | 3881476 | TGTTCCTGAAAAGAAGGTACTTCCAATCACC |
| 1680 | TPX2 | 3881477 | CATTGAAGAACAGAATTCGAATGCCCACCAAAGA |
| 1681 | TPX2 | 3881478 | GACGAACCGGTAGTGATAAAAGCTCAACCTGTGCCACATTATG GGGTGCCTTTTAAGCCCCAAATCCCAGAGGCAAGAACTGTGG AAATATGCCCTTTCTCGTTTGATTCTCGAGACAAAGAACGTCA GTTA |
| 1682 | TPX2 | 3881479 | GTGCCCAAGTTCAAGGCACTTCCCTTGCCTCATTTTGACACCA TTAACCTGCCAGAGAAGAAGGTAAAGAATGTGACCCAGATTGA ACCTTTCTGCTTGGAGACTGACAG |
| 1683 | TPX2 | 3881480 | GTAGGGGATGGGGAGAGCAGCCAAAATGTTAATTGCTTG |
| 1684 | TPX2 | 3881481 | TTGGAGGTGGGAAGAATACTTTATAGGTGATACTGTATAGTTC CTAATGAATCATGTGTGAAGGCAGAAAATGTCTAGTTGTTTATT TTTATGATATAAAGATAGGTCTTAAAAGTACCTTTAAAATTTTTT GTTTTTTTTAATTGACAAATAATAGTTGTACATATTCTTGGGGTA CATAGTGATGTTTCAATATGTATAATGTGTAATGATCTGATCAG GGTAATTAGCATATCCATAATCTCAAACATTTATCATTTCTTTGT GTTTGGAATCTTTTTTTTTTTAATTTAAAAGTAAACTTTAGCACA CCAACATG |
| 1685 | TPX2 | 3881482 | CTTGTTTCAAGGCTCGTCCAAACACCGTCATCTCTCAGGAG |
| 1686 | TPX2 | 3881483 | TTCAGGAACCTTTTCAGCTGGCTACTGAGAAGAGAGCCAAAGA GCGGCAGGAGCTGGAGAAGAGAATGGCTGAGGTAGAAGCCC AGAAAGCCCAGCAGTTGGAGGAGGCCAGACTACAGGAGGAA GAG |
| 1687 | TPX2 | 3881484 | TGGGAGCATGAGCACTGACGAACACAAACATGCCTCTG |
| 1688 | TPX2 | 3881485 | AACCATGATGCCTTTCCTAGGACTGTTTTTTATTTATTTGTTTAT TTTATTTATGTAACTTATTATTTCCTCTGGGGTTAAGAAGCACC ACTGAGTTTTGTAATTAGACAAGAATACATAGCGAAGGACATG GGAATTAAATGGCAACTGTATTTTTGTTTTAATACTGAGCCCAA |

TABLE 7-continued

Target Sequences

| SEQ ID NO. | Gene | Affy Probeset ID | Sequence |
|---|---|---|---|
| | | | ACTCCTTGGAGTTACAGTGTTCGTCGCTCCAGGTAATCCTCTA CTAACATAATTATTTAGATGTTGGTTATCCAAAAAGAAACCTGA ACTCCACATTAAGGACCAATCTGCTAGGAGGGC |
| 1689 | TPX2 | 3881486 | TGTACTCTGGGAAATTCTTAGCTTGTAACTTCTCTGCTATACTT GAGTACAGCCCTATTATACCCTAGTAAATCACACAGGACATAG GTTTGGCATTCTTTAGTGAAAGCTGAGGGACTTGAGGAGACTG TGGCCTAAAGGAAAGCTGGGGGACCCAATAGAGACCTGAATA GAAACCCTTTTGGGCTCCAAAGCACATACACTTTTCCATCATA CCGTGTTGCCCCCCAGGCCCCACTCCCCACACCTGAAACTAG TGACTGGGACCTGTA |
| 1690 | TPX2 | 3881487 | GTGCATAAGGCAAATCCAATACGCAAGTACCAGGGTCTGGAG ATAAAGTCAAGTGACCAGCCTCTGACTGTG |
| 1691 | TPX2 | 3881488 | CCAAATTCTCCACTCGATTCCACTGCTAA |
| 1692 | TPX2 | 3881489 | TCAGCTGTGAGCTGCGGATACCGCCCGGCAATGGGACCTGCT CTTAACCTCAAACCTAGGACCGTCTTGCTTTGTCATTGGGCAT GGAGAGAACCCATTTCTCCAGACTTTTACCTACCCGTGCCTGA GA |
| 1693 | TPX2 | 3881490 | CAGAAAATAAAGATAGTTAAATCCT |
| 1694 | TPX2 | 3881491 | GTCCTCTTCTCTGCATACCGTGAATTTATAGTTAAGGATCCCTT TGCTGTGAGGGTAGAAAACCTCACCAACTGCACCAGTGAGGA AGAAGACTGCGTGGATTCATGGGGAGCCTCACAGCAGCCACG CAGCAGGCTCTGGGTGGGGCTGCCGTTAAGGCACGTTCTTTC |
| 1695 | TPX2 | 3881492 | GGAACCGTGCAGTGTGCATTTTAAGACC |
| 1696 | TPX2 | 3881493 | TGGCCTGGAATAAATACGTTTTGTC |
| 1697 | TPX2 | 3881499 | ATGGAGTTTCACCATTTTGGCCAGGCTGGTCTCGAACTCCTGA CCTCAGGTGATCTACCTGCCTCGGCCTCTGAAA |
| 1698 | TPX2 | 3881500 | GTGCTCTGAAACCTACTTTGCCTGATATTAATATAGCCACTCTA GTTTTCTTTTGATTGGTTTTAGCATGGTATGTCTATATTTAAAGT GCATTTTTTTGTAGACAGCATATAATTGGGTCTTGCTTTATTATT TAATATTATTGTTGCTGCATTTTAATTGGAATAAATGCATCTATT TTAGCCTTGACATGCTATGCTATTATTTTGTGTGTGCGTGTGAG TCTCTCTGCCCCAAAAATATTTCTTTAGGAGATGAACCAAATGA TTGTTCTCTGAAATGAATAATGCCTAAACTATGTTTTCATGGCC TATCTTTTCTTCCCTGTCATCTTGTTGCAGTTTAATTCCTTTATC AGGAGTCAGTTCATATGCTATGTGATTAAGTGCTGTTTCTTCCA TG |
| 1699 | WFDC2 | 3886939 | TAAATCCCCGCACCTGAGCATCGGCTCACA |
| 1700 | WFDC2 | 3886940 | ATGCCTGCTTGTCGCCTAGGCCCGCTAGCCGCCGCCCTCC |
| 1701 | WFDC2 | 3886941 | CTGCTGCTGTTCGGCTTCACCCTAGTCTCAG |
| 1702 | WFDC2 | 3886942 | CCAGGCTGACCAGAACTGCACGCAAGAGTGCGTCTCGGACAG CGAATGCGCCGACAACCTCAAGTGCTGCAGCGCGGGCTGTG CCACCTTCT |
| 1703 | WFDC2 | 3886943 | GGCGGGGCCGCGCTGGGCTGGGAGGAG |
| 1704 | WFDC2 | 3886944 | GCAGTTTCCTTCTCGAACCGGCCGAAGCCTGCCCTGCGGGAA AGCCCGGAGCCTGGGGCGCTCACCTCTCCTCTTGGAGTCCCT CCCTGGGGGCCTCCCCCAGCCCTGGGGAAAGACTGGGAGAG CCTGGCCTGGCAAGATTTTCCCCAATTCCTCTGTCCAGGCGG AAAGGAACTTTACAGATTTAGGAAAATGCCCCGCTCATCTTAA AGATGTGTAAGGGAGCATCGGTGAGAAAAAAATGTTCTTGCCC AAGGTCACACCGCCATCCCATGGCTGCTGGAGTCATAGTGAG GGTTCA |
| 1705 | WFDC2 | 3886945 | CTGGACACTGTATCGCCCTTCGTCGTCTTTCAGTCAATCTCTT CCACTCTAAGGATTGAGTGAGCGCGAGCTGGGGACTCTCTCA AAG |
| 1706 | WFDC2 | 3886946 | GCAGTCTCCACCAGGCTATCAGAACAGGGGGTGGCTTAAAC |

TABLE 7-continued

Target Sequences

| SEQ ID NO. | Gene | Affy Probeset ID | Sequence |
|---|---|---|---|
| 1707 | WFDC2 | 3886947 | CTTTATCCAGAATACAGCCCCTGTGACTTTT |
| 1708 | WFDC2 | 3886948 | TACGGTGACCCAAGACACCGATCAGCAGGGAGGTG |
| 1709 | WFDC2 | 3886949 | AGATTTGGAGAGAAAGCAGGCAGCAGCCAGATGAGAGAGGTG GAGGAGCAAAGGAGGGAGTCTTTGCTGTTTGATGGATGA |
| 1710 | WFDC2 | 3886950 | ATCAGGTGGCTGTAGATGTGTAGTGT |
| 1711 | WFDC2 | 3886951 | GTATCTGCTCCAGAGTGCACTATTCCTCACGGCACAGTCCCTC ATGGCTTCCCTTGGCTAGGGGAGGGAGTTCCCTGACCTCTTG TGCTTCCCAGGTGAGATGATGCCCTACCCTACTTCTGCTCGCC |
| 1712 | WFDC2 | 3886952 | AACCATGATGTACCTCAGTTGATGAATGGATTTGGCTGGGCCT GGCTCCCCTCTATCTAACCTGGGAAGTGGAGTGTGATTGTGT GTGTGTTTGTTAGTGGAAGGACGTGTGGTTTCTCTCTGCATGG ATGAATGAGTGTATTTGGAGGGTCATGGTGCTGAGAGACTGC AACTGGGATTCGGTCTGTGGGTATGAGTGAAGATTATAAGTGT GTAACCCCTCACATGTGTACTGTACTTTACACTTTAAGTGGCA GCATAGTGCTTAACCATGGCAGCAGCAGTTAACACATAGACTC TGCAGCTAGATTTCTTGGGGTTC |
| 1713 | WFDC2 | 3886953 | TTAGGGGCTTGATACCTGGCATGTAATAAGAGCTAATTAAGTG TTCACTGTTATAATTTCTCATAACTACAGAGTAGT |
| 1714 | WFDC2 | 3886954 | TGGCACCTAAAGACACGGAGGCTCTGGGAGATTTCTGGCCCT AGGCCACGAAGGCCCACTTGGGACTCAAGCT |
| 1715 | WFDC2 | 3886955 | GGTCCTGTGATTCCATTTGGGAGCAGGAGGAGGGATTTGCAG |
| 1716 | WFDC2 | 3886956 | CTCAGGTGCCCAAGATGGACTCAGGCAGGCAGCTCTGCTGTA TGTGAAGCCCAGTGAGG |
| 1717 | WFDC2 | 3886957 | ATGCTGCAGGTACAAGTTAATCTCCCTGTATCGCCTCTGCCCA CTTACCCT |
| 1718 | WFDC2 | 3886958 | GTGAACATTAACTTTCCCCAGCTCGGCCTCTGTCGGGACCAGT GCCAGGTGGACAGCCAGTGTCCTGGCCAGATGAAATGCTGCC GCAATGGCTGTGGGAAGGTGT |
| 1719 | WFDC2 | 3886959 | GCCTAGTCTAATGGATATTGTTGTTGATGGTATTGTTATAATTT TCT |
| 1720 | WFDC2 | 3886960 | CCACCACCAGGCTGAGCAGTGAGGAGAGAAAGTTTCTGCCTG GCCCTGCATCTGGTTCCAGCCCACCTGC |
| 1721 | WFDC2 | 3886961 | CCCTCTTGGGCTGACCACAGCTTCTCCC |
| 1722 | FMO5 | 3928073 | GTGGGAAGAAAGACTGGGATGATGACCAAAA |
| 1723 | FMO5 | 3928077 | GAAAACTCTGGAGTTAAGGCCAATGAAGTAATCTCTAAACTTT ATGCAGTAC |
| 1724 | FMO5 | 3928078 | AATTGAATTAGCCAAACAGATCACATCA |
| 1725 | FMO5 | 3928079 | GGCTCTACAGACAATCTGATGGATGA |
| 1726 | FMO5 | 3928081 | GAGATACTCAGGTGGTGGTTTTTAA |
| 1727 | FMO5 | 3928085 | CTATTGCTGATACTGGTGCAAATGTCGTAGTAACAGGTGGCAA AGTGGCAGACATGGCTCTTCATTA |
| 1728 | FMO5 | 3928087 | AAATAGCAGTGTACTCTTGTCCTTTTGATGGCATGATAACAGA AACTAAG |
| 1729 | FMO5 | 3928089 | GTTGATAACATCAGAGTTTGTAAAATTCT |
| 1730 | FMO5 | 3928093 | CCTGGAATTAGCTGAAGAACTTCTGA |
| 1731 | FMO5 | 3928097 | AGAAGAGGCTGTGTATAGAAACATACAAGCTTGCAAGGAGCTT GCCCAAACCACTCGTACAGCATATGGAC |
| 1732 | PCAT14 | 3939348 | GGTGAAGGGACTCTCGAGTGTGGTCATTGA |

TABLE 7-continued

Target Sequences

| SEQ ID NO. | Gene | Affy Probeset ID | Sequence |
|---|---|---|---|
| 1733 | PCAT14 | 3939349 | AAGGCCTCCGTCTCCTGCATGTCCTT |
| 1734 | PCAT14 | 3939350 | GGTACTCTACAGTGTGGTCATTGAGGACAAGTTGACGAGAGA GTCCCAAGTACGTCCACGGTCAGC |
| 1735 | PCAT14 | 3939351 | CAGCAAGGAACGGAAAGTTCACATTGTAAATATGTAGCAGAGT CTGTAATGGCTCAGTCAACGCAAAATGTTGACTACAGTCAATT ACAGGAGATAATATACCCTGAATCATCAAAATTGGGGGAAGGA GGTCCAGAATCATTGGGGCCATCAGAGCCTAAACCACGATC |
| 1736 | PCAT14 | 3939352 | CTACAATGAACTCACTGGAGATGCAAAGAAAAGTGTGGAGATG GAGACACCCCAATCGACTCGCCAG |
| 1737 | PCAT14 | 3939353 | CAGGAACGGAGACAATCGTGAAAGCTGCTGATAGCCTCACAA ATCTTAAGCCAGTCACTTGGGTTAAAAGCATCAGAAGTTTCAC TATTGTAAATTTCATA |
| 1738 | PCAT14 | 3939354 | ATGGGCCATAGTGACGATGGTGGTTTTGTCAAAAAGAAAAGG GGGGGATATGTAAGGAAAAGAGAGATCAGACTTTCACTGTGT CTATGTAGAAAAGGAAGACATAAGAAACTCCATTTTGATCTGTA CTAAGAAAAATTGTTTTGCCTTGAGATGCTGTTAATCTGTAACT TTAGCCCCAACCCTGTGCTCACGGAAACATGTGCTGTAAGGTT TAAGGGATC |
| 1739 | PCAT14 | 3939356 | ATTTTAGGCGCTGGACTTGGGTTCGGGGCACCTGGCCTTTCC TTGTGTATTTCTCCTACTGTCTGCCTAACTATTTAATACAATAAA AGAAAACCAGCCCCTGGTTCTTGTGGTGTTTCCACCCTCCCG GGTCCCCGCTGGCTGCCTGGCTTCCTCCCGCAGCTCCTGCTG TGTGTGTATGTGTGTGTGTGTGCACATCTGTGGGGCGTATGTG TGTTCGTCTTTGTAATTGAGGCTGCAGAGTGGAGAGAGCAGG GGTTTTCTCTGGGGACCCAGAGAGAAGGAGGCGTTTTCACCA CAGC |
| 1740 | PCAT14 | 3939358 | CCTTTGAGGGAGATCAAGTCTAAATTTGAAGGGAGTCCAAATT CATACTGGGGTAATTTATTCAGATTATAAAGGGGGAATTCAGT TAGTGATCAGCTCCACTGTTCCCCGGAGTGCCAATCCAGGTG ATAGAATTGCTCAATTACTGCTTTTGCCTTATGTTAAAATTGGG GAAAACAAAAAGGAAAGAACAGGAGGGTTTGGAAGTACCAAC CCTGCAGGAAAAGCTGCTTATTGGGCTAATCAGGTCTCAGAG GATAGACCCGTGTGTACAGTCACTATTCAGGGAAAGAGTTTGA AGGATTAGTGGATACCCAGGCTGATGTTTCTGTCATCGGCATA GGTACTGCCTCAG |
| 1741 | PCAT14 | 3939360 | CAGATGGCGTATAATGCCGTAATTCAACCCATGGGGGCTCTC CCACCCCGGTTGCCCTCTCCAGCCATGGTCCCCTTTAATTATA ATTGATCTGAAGGATTGCTTTTTTACCATTCCTCTGGCAAAACA GGATTTTGAAAAATTTGCTTTTACCACACCAGCCTAAATAATAA AGAACCAGCCACCAGGTTTCAGTGGAAAGTATTGCCTCAGGG AATGCTTAATAGTTCAACTATTTGTCAGCTCAAGCTCTGCAACC AGTTAGAGACAAGTTTTCAGACTGTTACATCGTTCACTATGTTG ATATTTTGTGTGCTGCAGAAACGAGAGACAAATTAATTGACCG TTACACATTTCTGCAGACAGAGGTTGCCAACGCGGGACTGAC AATAACA |
| 1742 | PCAT14 | 3939362 | GGTTGCCGTCATTACAGTGTTAACAAGATTTTAATCAGTCTATT AACATTGTATCAGATTCTGCATATGTAGTACAGGCTACAAAGG ATATTGAGAGAGCCCTAATCAAATACATTATGGATGATCAGTTA AACCCGCTGTTTAATTTGTTACAACAAAATGTAAGAAAAAGAAA TTTCCCATTTTATATTACTCATATTCGAGCACACACTAATTTACC AGGGCCTTTAACTAAAGCAAATGAACAAGCTGACTTGCTAGTA TCATCTGCATTCATGGAAGCACAAGAACTTCATGCCTTGACTC ATGTAAATGCAATAGGATTAAAAAATAAATTTGATATCACATGG AAACAGACAAAAAAATATTGTACAACATTGCACCCAGTGTCAGA TTCTACACCTGGCCACTC |
| 1743 | PCAT14 | 3939364 | AGGTCAGGCCGGTTCTTTGCTCTGAACCCTGTTTTCTGTTAAG ATGTTTATCAAGACAATACATGCACCGCTGAACATAGACCCTT ATCAGGAGTTTCTGATTTTGCTCTGGTCCTGTTTCTTCAGAAGC |
| 1744 | PICK1 | 3945181 | ATGCTGCCGGATGAGGTGGATGCCTGGCTGTGGCTCTGGGA GAGCCAACCTCCCCCAGGGAACCCACTTTACACAATAGCAGT GGCAGCAGAGGCTGGCGAGGAGACAAGATTCGGACTCTGGG GAGCACTGATAGCATTTCCCGAGCCTCA |

TABLE 7-continued

Target Sequences

| SEQ ID NO. | Gene | Affy Probeset ID | Sequence |
|---|---|---|---|
| 1745 | PICK1 | 3945182 | ACGCTGTCAGCCTGTCCAGACCGTTCCTCTGTTTTCGCTTGTT<br>CCTACTAACAGCGAGCTTCCGCCAATACTTGTTCTCGTTCTTG<br>GTTCCGAGCGTCCCGGGAGCCGGGAAGGGAAGGATTGTCTG<br>CAGGGATTGGAGCAAATATCCAGTGGGGGGAAAGCCGGGAC<br>TTCCGCGTCTTGCCGGAAGTGACGTGACAATCGCGGCCA |
| 1746 | PICK1 | 3945183 | TGGCCGGGACCCGGCTGTGGGACCAACGCTTCCG |
| 1747 | PICK1 | 3945184 | ACTCTGGGATCTGAGCCTATCGCCCTGGCCTGGAGC |
| 1748 | PICK1 | 3945185 | TTGGGTTCCTTAAATCCTATGCTCCTTTCT |
| 1749 | PICK1 | 3945186 | CCCTACCGAGCTGGGCAGTTAGCCAGCCCACTCCAACT |
| 1750 | PICK1 | 3945187 | CAGACTTGGATTATGACATCGAAGAGGATAAACT |
| 1751 | PICK1 | 3945188 | AAGGATGCTCAGAACCTGATCGGGATCAGCATTGGAGGAGGG<br>GCCCAGTACTGTCCCTGCCTCTATATCGT |
| 1752 | PICK1 | 3945189 | AGCAGCCTTGGACGGCACAGTGGCAGCTGGCGATGAGATCA<br>CCGGTGTCAATGGCAGGTCAATCAAAGGGAAAACTAAGGTGG<br>AGGTGGCGAAGATGATTCAGGA |
| 1753 | PICK1 | 3945190 | CAGAGCAGGTGTCCAGAGGCAGCAACACATGTTTCTGAGA |
| 1754 | PICK1 | 3945191 | GAGGTGACCATCCACTACAACAAGCTGCAGGCGGACCCCAAG<br>CAGGGCATGTCCCTGGACATT |
| 1755 | PICK1 | 3945192 | GCCCAAAGGAGAAGTGCCACAGCCAGCCCTGCCCTCCCCTTT<br>ATGACAGGAGAATCCAGAGTTACATGGCTGTGGGCTCTGACC<br>TCTGACCAAGCAAATCTGAAAGGCCTGGGAGGCCTCCCGGTG<br>CTCTCCCTGCATCTGTTCTTGTACTCTGTC |
| 1756 | PICK1 | 3945193 | TGTTGAAGAAAGTCAAGCACCGGCTGGTGGAGAACATGAGTT<br>CAGGGACCGCAGATGCTCTGGGCCTGAGCCGGGCCATCCTG<br>TGCAA |
| 1757 | PICK1 | 3945194 | CTCTGCCCGTGGAACTGAGAAGTCACCATCTCTGTACCCCCA<br>GAGGCCTCTCCAGCTCCCGGAGGGTCCACAGCTGTCAGCTG<br>GGCTGTCTTAGCCAGTGCCCCTCAGGTCACAGATGGGAAAAT<br>AGACTTAGTGTGGGGAGGTGCCTCTGCCCCTGCCCTCAGCCC<br>CTTACCCCTCACCCCAGCACTCTCGCGGCCCACCTCCTGCCT<br>CCTTTGTCCAGGAGGTGGTGCTGCTGCCCTTGCCTCTGCAGG<br>TCCTCCCTTCGTGGTGGCTGCGCAGGCGAGGGGGGAGGCGT<br>GTACATGCACATTTACACACGCATGCACACATGCGCACACACT<br>TTCCCTCCCTGGGGTGGCCAGCGAAACACTCAGTCCCCCTCC<br>TACCGTCGCCAGTCCGAGTTTAAAAATAGCAGCAGCTCTGCA<br>GTGTGCCTGTGGGGTAGATATAAATACTTCTAGAAATTGTAGG<br>CTCAGCTGGGCACACTGGGCTTTATTGGCTAA |
| 1758 | PICK1 | 3945195 | CTTGTCAAGAGGCTAGAGGAGCTGGAGCGGACCGCTGAGCTA<br>TACAAAG |
| 1759 | PICK1 | 3945196 | TACGGGCCTTTTATGAGCTGTCGCAGACTCACCGGG |
| 1760 | PICK1 | 3945197 | CCTGCGGGAACATCTAGATCAGCTGGTCTCTTAAGGGCCGC<br>AACGATGAACAGGCCCCACCCTGTCTCCTCACACTGCCACTG<br>GCAGTACACAAGGCCCTTGCTTATTTATATTTCTGACAACCTGT<br>AACTCTGGGCAGGCCGACTGCAGCTGACCCCAGCTACTGCAG<br>AAAATGAAGCCCAGACAAAGGAGAGGGCCACACTGCTCCCAA<br>GTGGTGGAGCTGTTGTTCCAATCCAGGTGTCTAGACTCGGAC<br>CAGTGTTCTGCCTCA |
| 1761 | PICK1 | 3945198 | CAATCCAGTTTCCTCCAGGTGTAGACTCAGCTCCTTCAGGGG<br>GTTTAGACCAGCTCTCTTGGAGGTGTAGCCCCTGTGCAGACAT<br>TGGCTTCCAGCCTGCCAGGCCCCCTGCCCTGCTTCTCCCCAA<br>CAAACCCCTGGCTTCTCTTAGGGGGCCAAGTAGGGGCAGCCT<br>TCAAGGCAAACTTGTCCTGCA |
| 1762 | PICK1 | 3945199 | TTTGGGGACGTGTTCTCCGTGATCGGGGTGCGGGAGCCCCA<br>GCCAGCTGCGAGCGAGGCTTTTGTGAAGTTCGCCGATGCCCA<br>CCGCAGCATCGAGAAGTTCGGCATTCGGCTTCTGAAAACCA |

TABLE 7-continued

Target Sequences

| SEQ ID NO. | Gene | Affy Probeset ID | Sequence |
|---|---|---|---|
| 1763 | PICK1 | 3945200 | ACTGAGTCACAGCTTGCCCTAGGCCTGGCACTAGTCTTCTCAT CCTTGAGAGGGACAAGGCATCAGGGAGCACCATCTGGCTCTG ATAGTCGAGTCCACCAACAAGGGTGACGCATCAGTGCCATTC ATTG |
| 1764 | PICK1 | 3945201 | GACGGATCTGAACACGTACCTCAACAAAGCCATCCCGGACAC TCGCCTCACCATCAAGAAGTACCTGGACGTGAAGTTTGAGTAC CTG |
| 1765 | PICK1 | 3945202 | CTGCTGCGCCTGCACAAAGAAGCATCTG |
| 1766 | PICK1 | 3945203 | GGACTCCCTGAACACCTGCGCCAGCCTCTCCTGCTGCGTGTG GGTGATGGGGGTGGAGCTGGGGACCTGGGGTGGGGGTAGTA GCCACTCTGACAGCCT |
| 1767 | PICK1 | 3945204 | GATGGATGACGAGGAATACAGCTGCATT |
| 1768 | PICK1 | 3945205 | CTGGACTCTCGTTCCTGGAGATTTAGGGCCATCTTCCCAGTCC CGCTCGCTGGGCCTCGGGGTGCTGGGCACCCGGCCGGGAAC CACTCCCTCAGTCTGGGGGACTCTTGGAGGGAAATCGGATTT TCTTCACTCCTATGAGGCGCTTTTAAGTGTTTGATTTTTCTGCT GTCGGGATCCATTTCGTGGCCAGTGTTCATTGAATGTGGCAGA GGTTTGGGTTTGGTTTTTTCCTCTCTTCAAAGCTATCACTGAGT GCTTCTGAGAAACACTGAAGTCTCAGAAATGAGGTCTCAGGAA TGAAGAACAGCCGTGGCTTTGAAAGCACA |
| 1769 | PICK1 | 3945206 | GGCGAGCCCCTTTACCGGGTGAGCACCGGCAACTATGAGTAC CGCCTGATCCTGCGCTGCCGCCAGGAGGCGCGCGCCCGCTT CTCCCAGATGCGCAAGGATG |
| 1770 | PICK1 | 3945207 | GCCTCGTGTCCACCATGTCCAAGTACTACAACGACTGCTACGC AGTGCTGCGGGATGCCGACGTCTTCCCCATCGA |
| 1771 | PICK1 | 3945208 | GTAGACCTGGCGCACACCACATTGGCCTATGGCCTCAACCAG G |
| 1772 | PICK1 | 3945209 | GTTCACAGATGGGGAGGAGGAGGAGGA |
| 1773 | PICK1 | 3945210 | TGGGGAGCCGTCCAGGGATACACGAGGGGCTGCTGGGC |
| 1774 | PICK1 | 3945211 | GTGCCCCGCGGCTGTGGTGCCGGGGGCAGG |
| 1775 | PICK1 | 3945212 | GCGACGCATAAAGGCCTGCTGGCTTGGGGCGCCTGCCTCCCT GCTCCTCTGTCCTCGCACAGCGAACCTGGGCTCCTGCCCAGG ACAGGCACCAGGGTCATGGCCTGGGACCTGGACACTGGCCC CTCCACCCTCCCTCCCCTCCCGGCTCCCCGGCCAGAGGGAG AGCTTGGTCTCTGGACCTGCCTTAGGAAGGAGAGGGAGGGCA GGAAGGAAAAGAAAGGACTTGGAGGTGGCAGGAGTCCGAGC CCTGCTCCTTGTGGGCGCTCACACTGCCCCCGGAGCCTGCTG GGAGTGGGGCCAGCCGTGGACAGCTGAGGTTGGGGTCAATG CCTCCTGGGCACCCTTGCCTCGCCCCAGACCGGCCCGTCCA GTCCCCATCACACCTCGGCGGCCTTTATTTA |
| 1776 | PICK1 | 3945213 | TGGGTTCTGGGCCTGTATCGAATAAACACAAACCTG |
| 1777 | FTH1P8 | 3994182 | CTCAGAGGCGGCCATCAACCGCCAGATCAA |
| 1778 | FTH1P8 | 3994183 | GTCTTACTACTTTGACCACGATGATGTGGCTTTGAAGAACTTT GCCAAATACTTTCTTCACCAATCTCATGAGGAGAGGGAACATG CTGAGGAACTGATGAAG |
| 1779 | FTH1P8 | 3994184 | CTGGGAGCGGGCTGAATGAGATGGAG |
| 1780 | VBP1 | 3996816 | CGCAGCCAATCAGCACCTAGAGGTTGGGCTACTTTCGGCCAA AGGAGAACGGGGACTTGTGGGGGACGCTCCCTGCGCACCAA TGAATGTGCATGGAGATGGAGAGGCGGGCCTGCAAGTGCGA ACAAGCCAATC |
| 1781 | VBP1 | 3996817 | CGGCCGTTAAGGACAGTTGTGGCAAAGGAGAAATGGCCACAG GGAATGGGCGGCGGCTCCACCTGGGGATTCCTGAGGCCGTG TTT |
| 1782 | VBP1 | 3996818 | TGGCCTCTAAATAGACCAGGGTCTGAATCCTGGCTCTGCTTCC CAGTTGCTGCTTAACCTTAAGCATATTATTTTACCACTTTGAGC |

TABLE 7-continued

| SEQ ID NO. | Gene | Affy Probeset ID | Sequence |
|---|---|---|---|
| | | | TTGAGTTTCTTTAACTGAAATAGGGATGACAATACTTAGAGAGT TGTTATGGGAAACAGAGAACATGCTTGCAGTATTGCAGTGTAG TAGGTGTCGAATAGGTATTAATATTCATGATGATAGGAAGCAA TATACCATAGTGGTTAGAAGTCAGACCCAGTCCATTCCCCAAC CCCGCTGAGGCAGTAATTTGTTTTC |
| 1783 | VBP1 | 3996819 | CAGTATTAAAGAAGCTGGATGAACAGTACCAGAAGTATAAGTT TATGGAACTCAACCTTGCTCAAAAGAAA |
| 1784 | VBP1 | 3996820 | GCTAAAAGGTCAGATTCCTGAAATTAAACAGACTTTGGAAATT CTAAAATACATGCAGAAGAAAA |
| 1785 | VBP1 | 3996821 | GAGTCCACCAACTCAATGGAGACCAGATTCTTGCTGGCAGATA ACCTGTATTGCAAAGCTTCAGTTCCTCCTACCGATAAAATGTGT CTG |
| 1786 | VBP1 | 3996822 | TGCATATGTTCTTCCTGTCCTTACACATTCTTTATAAGGTTGTT CCCACATTGTTGGAGCACAGAGCCATTATATACTGTTTGCTCT CTCTCTTTCTCTCTCTCATCTTTCATTTATCCTAGTTCTTCGTGT AAATATTG |
| 1787 | VBP1 | 3996823 | TTGATGAAGCTCAGGCATTGTTGGAAAAGAATTTATCGACTGC CACAAAGAATCTTGATTCCCTGGAGGAAGACCTTGACTTTCTT CGAGATCAATTTACTACCACAGA |
| 1788 | VBP1 | 3996824 | TCATCTGACGGGTAGTGTGGAAACTTCATCCAGCTATGAGATG ACGAGGGCCTAGGACGGGTGGCTTGTGGAAAGGAAAAGATAT TAAACGTGTGAGAAAAAAACAGGATCCAGTGACTTAGATGGGT ACAGGAGCCAAAAGTGAGGAAATCCTCTAAGATGAGTCCTACA AGCTTAGTTAAATGCCATTTGTTATTGCTAGTACTGC |
| 1789 | VBP1 | 3996825 | ATATGGCCAGGGTTTATAATTGGGATGTAAAAAGAAGAAACAA GGATGACTCTACCAAGAACAAA |
| 1790 | VBP1 | 3996826 | TATGGAAGCTGAATGCCGGACGCTAGCACAGTTTACTTTTTCC CTTTCTAATCGGCTGATGTTACTCTCACTTGATGTGGTTAAACC ATTTTAGAGGTAGAGAAGACAGACAGTTTGAATATTTGTAAACT TGTTTTTCTTTGGTATATTTAGGACTTAGTGGTCCTCTGTTGCT ATTGTCTTCTATAAGTGGAGTTTCATGACTTACTGCTTAACGAA TAACTAACTACTATGATATTCTGGACATTTTAGGAAATGGTAAT TTGCCTTGCTACACATTAAGAGGG |
| 1791 | VBP1 | 3996827 | GCCTAAGGTGATTTTGTAGTTCTTAACAGTTCTCCAGAGCATCT TGAACAGGAATATTAAGATAAATGTGAATCTGCAATGGCTGAA AAGAGTTGTGAGCTTTTTTATTCATGATAAAACCTTATAGGAAT AGTATAAAAAATCCCTGTGGAAAGCTACTAGTACATTGACCAG CGCTGGGTGATACAGATTCT |
| 1792 | KIAA1210 | 4019318 | GCTCTAAGCTTTGCAAGGGATCCTAAAAGAGGCGGTGGAAGT GAAAATTCTGGGTCTCCAAGAAAAATTTCTGCACAGCCAGTTCT CCAATCAGCCTATCACCCCTTGAAACATCTTCCCTGTGTCCCT GGGGGCCCCTGATGCTTTCTCCTTGGGTGATAGTAACATGCA GAGCACTTACACAAAGCTCCCTCTTTGGACATACCCCACGTCG ACCTGTCACAGGCCTGGCTGTAGCGAGCACCTCCCTATGACG CAGAATGCTTCTTGGGAATTATCTTACTCCTCTGGAGGGTTAG TCCATCAATGTTTTGCTTCTTGTCCCAATACTACTGTGACCCTC TCTGATCGCACAGAAATCACTGCCTATCACATATATCCTGTTAA GCACTGAAGACCCTATTGAAATTAGAGTTCTACAGATGCCAAA AGCTGTACTTTCCATCAGGCAGATGGCAAGCTTACTGCCTTGA TGCACATCTGGAGCCACTGGAGCTCCTTCCTCTCTGGTTCCAG CATTAAGGTGGAGAACTCCATGTAGCTTCTTGTCCTTTCCCCT CAGCTGTCTTTGCTTCACAAGGTTTTAGCCCAAAGCAAGAGTG CAATCCCAAAGCCACAGAGAAATGAACTTTCCGCTACCTGGAA GCTTTAAGTGAGTAAATCAGCTTTTCCCCTCTCATTCCTAGAG GCACACACCTCAAAAGTTACTAGGCTGGAGAGACCCTACCTTC CAGTGACCCACTCATCCCCCAGCCACGGAGAAGAGGGAAGAC CAAAAAGGGAGAGTGAGAAAGAGGATGAGAGGGATGGTCAG CTGTGAGGGGAGGGGGCAAGTGGCCCAGCAAATGTTGATGC CTCCCTTCCCATCTTGCCACACGGTCTTTTTCTTTTGTAGCACA GCCTCCATTAATAACTCCTCGGCTGAGGATGAAGATGTAGGCA |

TABLE 7-continued

Target Sequences

| SEQ ID NO. | Gene | Affy Probeset ID | Sequence |
|---|---|---|---|
| | | | CCTTTACCCCCAGAGCCAGTTCCTTAATTGGCTGGCTTTCTGA GATGCAGACCACCCTAGAATCTCATCTAGGTTCACTAGAAGTT AGTTAAATCTTCCTTTCTCTGTCTTTCTCTTCATTCCATCCCCC AAACCCACCAAACACTAAGGGAGAGCTCCCTTTGGATGTCTG GGCAGTAAACCTAGCTCATT |
| 1793 | KIAA1210 | 4019319 | AGAAACCAAACGATCTTCAACTCTCCCAGCCAAGTTCCAGAAC CCAGTTGAGCCAATTGAGCCTGTCTGGTTCTCACTGGCCAGG AAGAAAGCCAAAGCATGGAGCCACATGGCA |
| 1794 | KIAA1210 | 4019320 | GATCAGAGGAAACCTGAAAGGAGGAAACATTATATGGCATTCC ATAAACAACATACCCAATATCGCTGGGGTTCCTTATTGCTTGT GTGTTATTTGCTGTGGTTCC |
| 1795 | KIAA1210 | 4019321 | CCAGTGTCCATAAACAGGAGAAGACAGCACAGATGAAGCCAC CTAAGCCTACAAAATCAG |
| 1796 | KIAA1210 | 4019322 | CCTGCTGGTCAACAGTCAGATTATGCTGTCTCAGAGCCGGTTT GGATAACTATGGCAAAGCAGAAGCAGAAGAGTTTCAAGGCCC ACATTTCTGTGAAAGAGCTGAAAACTAAGAGCAATGCTGGAGC CGATGCTGAGACTAAGGAGCCTA |
| 1797 | KIAA1210 | 4019323 | TCCAGATGGCAAGCAGATATCAAGTGGA |
| 1798 | KIAA1210 | 4019324 | TTTGGAGTTCGACTGAAAAGAGCCCCTCCCTCGCAGAAGTATA AGAGTGAGAAACAAGATAACTTCACCCAGCTTGCTTCAGTGCC CTCGGGCCCAATTTCATCCTCTGTAGGCAGGGGACATAAAATC AGAAGCACTTC |
| 1799 | KIAA1210 | 4019325 | TCCTCAAATTTCGAGCGGGCTGCTATTGAGGCAGACATTTCTG GGAGTCCATTGCCTCCCCAATATGCTACCCAGTTCTTAAAGAG GTCTAAAGTTCAGGAAATGACCTCACGACTAGAGAAAATGGCT GTTGAAGGCACTTCTAACAAATCACCGATTCCCAGGCGTCCGA CCCAGTCATTCGTGAAATTTATGGCACAGCAAATCTTTTCAGA GAGCTCTGCTCTTAAGAGGGGCAGTGATGTGGCACCTCTGCC TCCCAATCTTCCTTCCAAATCTTTATCAAAGCCTGAAGTCAAGC ACCAAGTTTTCTCAGATTCAGGGAGTGCTAATCCTAAGGGAGG CATTTCTTCAAAGATGCTACCTATGAAGCACCCTTTACAGTCCT TGGGGAGGCCTGAAGACCCACAGAAAGTTTTCTCTTATTCAGA GAGAGCTCCTGGGAAGTGCAGCAGTTTTAAAGAGCAGCTGTC TCCCAGGCAGCTTTCCCAGGCCTTGAGGAAACCTGAGTATGA GCAAAAAGTCTCCCCTGTTTCTGCCAGTTCTCCTAAAGAGTGG AGGAATTCTAAAAAGCAGCTGCCTCCCAAACATTCTTCCCAAG CCTCAGATAGGTCTAAATTCCAGCCACAGATGTCATCAAAGGG CCCAGTGAATGTACCTGTAAAGCAGAGCAGCGGTGAGAAGCA CCTGCCTTCAAGTAGTCCTTTCCAGCAACAGGTTCATTCAAGT TCTGTGAATGCTGCTGCTAGGCGATCTGTTTTTGA |
| 1800 | KIAA1210 | 4019326 | GGCTATCCAATGTCAGCAGCATATGGAAGAAGATGGAGAAGA AAAGGAGCAAGTGTTTCAGGATTGAGTGGGTGTGAATTCAAAG GAAGAAGCCTTAAACAATCCAGTGAAGGGTATGGCCTGGGCG ATAGAGCTGGGTCTTCACCTACCAATAAGACTGCCAGGAATGT CCCTTTCTCGCACTTGTCCTTAG |
| 1801 | KIAA1210 | 4019327 | TGGAGCATAGTCAGCTATTATCAGCGCTGTATGCTGGATATGA AACTACTGGATGGAGCTAAGGATGCAGCAGATAGTGAGGGAA GAAAGGCACAAGGGGCCCTTCCAT |
| 1802 | KIAA1210 | 4019328 | TGTTGGCTCCAGTTGATGGCAAGCTGATTTCTAGCAGTATTTG ATAAAAAAATTCCAGTTCCTCAAATTAAGTTGAATAGTTATGTT ACGTTTTTGCCACAAAGGATTTCACATGTGGGTCCAAAGACAG GACATTCCTAAACACGTTT |
| 1803 | KIAA1210 | 4019329 | AACCTTCCATTGGTTTCTGAAGAAGAAAAGAGCATAACCAAAC CAAAAGAAATCAACGAAAAGAAGCTGGGA |
| 1804 | KIAA1210 | 4019330 | CCTTCCAGTGTGGTTCAGTCATTTCCAGGGTATTTTAGAGGGA TCCCTGCAGTGTGTCACTCAGACATTAGAA |
| 1805 | KIAA1210 | 4019331 | CACAGTCCTTGACTGCATTTGCCACACTTGCCTCTACCAGTAG CACCCAGCTGCCCATTGGTTTCAGCACCCCAGCCACCACCCA GGGCTGTTTGGATTCTTCAGCTGCTCGCCACAAAATGACTT |
| 1806 | KIAA1210 | 4019332 | GGTTACAGGCTCCATCACTATCCCACTGGAG |

TABLE 7-continued

| Target Sequences | | | |
|---|---|---|---|
| SEQ ID NO. | Gene | Affy Probeset ID | Sequence |
| 1807 | KIAA1210 | 4019333 | ATCCCACCTGTTATCCAACCTGAAATAATTTCTAAGAACTTGGT AGAAATCTCTCTCGATGATGAGTCACCTAAGAATCCACAAAAG AAGGCTTTACCACATAAGAGTTTGACAGCG |
| 1808 | KIAA1210 | 4019334 | TTCTAATGGATTAAGTGACATTCAGAACAACGAGGAGATTGTT AAAGAAGAA |
| 1809 | KIAA1210 | 4019335 | CTCTGCCTAAACCTAGGAGTAAGGTTCCTGGAGTTGTGTCTGG AGCCATGTCAGGAGCTGTGCTTCAAAATGTGCCTACAAGTGCA GTCTGGGTT |
| 1810 | KIAA1210 | 4019336 | TTCCTTCTATGGATCCCCAGAGAGG |
| 1811 | KIAA1210 | 4019337 | GCAGCATGGGGAGCAAAGCCCTATCCCATGATAGCATCTTCA TGTTGGGTCCTGAGCCTGAAAGATCA |
| 1812 | KIAA1210 | 4019338 | AAAGAAGCCGAAGATACCCAGGAAGAAGAA |
| 1813 | KIAA1210 | 4019339 | CCTACAATGGCTGAATCACTAAGTGAAATTTCTGACAGTCTGG ATGT |
| 1814 | KIAA1210 | 4019340 | ATGCCCTGTACCCAAGGTGATTTACAGCAGGGTTTCCTTAAAG CTAGGTATTTGGAGCCCTCACCTCCCAGGAGTCACCTGGAAG GTTCTGGACTTGCAGGTCCCT |
| 1815 | KIAA1210 | 4019341 | TGATTGCTGGTAATCTTGGGGATCTGGCCAGGATAGTGGGCC CCTCACATCATGCTAGTCAGCTTCTCCTACTCCAAG |

Example 2: Validation of a Genomic Classifier to Predict Aggressive Prostate Cancer in Humans The genomic classifiers described in Example 1 above were further validated as follows. Expression profiles from assays of biopsy and radical prostatectomy (RP) tumor tissue specimens from multiple patient cohorts were analyzed. This included genome-wide expression, treatment and outcomes data from prostate cancer patients treated with RP retrospective institutional cohorts and pathological data from clinical use of the Decipher RP test.

Prediction of Future Metastasis

RP clinical validation of the genomic classifiers (DV1 and DV2) ability to prognosticate the development of postoperative metastasis at 5 years and 10 years was determined. As shown in Table 8 below, genomic classifiers DV1 and DV2 were prognostic for 5-year metastasis and 10-year metastasis. Similar results were observed for prostate-cancer specific mortality end-point (See Table 9). Multivariable analysis further demonstrated that the prognostic information in the GC models is independent of clinical risk factors.

TABLE 8

| Metastasis Endpoint for Genomic Classifiers | | | | | | | | | |
|---|---|---|---|---|---|---|---|---|---|
| | | MVA HR | 5 year AUC | Cumulative Incidence of Metastasis @ 5 year - Risk Group | | | Cumulative Incidence of Metastasis @ 10 year - Risk Group | | |
| Dataset | Classifier | (95% CI) | (95% CI) | Low | Int | High | Low | Int | High |
| Decipher Meta RP (n = 855) (Spratt JCO 2017) | Dv1 | 1.20 (1.09-1.33) | 0.72 (0.66-0.78) | 2.4 | 5.8 | 15.2 | 5.5 | 15.0 | 26.7 |
| | Dv2 | 1.33 (1.18-1.49) | 0.79 (0.73-0.84) | 1.5 | 6.8 | 15.2 | 3.9 | 12.0 | 31.4 |
| | Dv1 + CC | — | 0.78 (0.72-0.85) | — | — | — | — | — | — |
| | Dv2 + CC | — | 0.82 (0.77-0.86) | — | — | — | — | — | — |
| CCF RP (n = 179) (Klein EU 2015) | Dv1 | 1.28 (1.12-1.47) | 0.78 (0.67-0.88) | 5.1 | 4.8 | 17.5 | 15.4 | 38.0 | 60.1 |
| | Dv2 | 1.27 (1.09-1.48) | 0.75 (0.62-0.87) | 4.2 | 4.5 | 20.6 | 11.2 | 42.5 | 67.5 |
| | Dv1 + CC | — | 0.76 (0.62-0.91) | — | — | — | — | — | — |
| | Dv2 + CC | — | 0.74 (0.61-0.87) | — | — | — | — | — | — |

TABLE 8-continued

| Metastasis Endpoint for Genomic Classifiers | | | | | | | | | |
|---|---|---|---|---|---|---|---|---|---|
| | | MVA HR | 5 year AUC | Cumulative Incidence of Metastasis @ 5 year - Risk Group | | | Cumulative Incidence of Metastasis @ 10 year - Risk Group | | |
| Dataset | Classifier | (95% CI) | (95% CI) | Low | Int | High | Low | Int | High |
| Leuven RP (n = 61) | Dv1 | 1.26 (1.07-1.49) | 0.71 (0.50-0.87) | 13.3 | 7.1 | 34.5 | 41.5 | 22.1 | 56.1 |
| | Dv2 | 1.20 (1.03-1.41) | 0.74 (0.53-0.89) | 14.3 | 18.8 | 29.2 | 29.4 | 45.5 | 51.3 |
| | Dv1 + CC | — | 0.78 (0.64-0.95) | — | — | — | — | — | — |
| | Dv2 + CC | — | 0.76 (0.61-0.97) | — | — | — | — | — | — |

TABLE 9

| PCSM Endpoint for Genomic Classifiers | | | |
|---|---|---|---|
| Dataset | Classifier | OR (95% CI) | AUC (95% CI) |
| Decipher PCSM | Dv1 | 1.48 (1.33-1.64) | 0.73 (0.67-0.78) |
| [All patients] | Dv2 | 1.47 (1.36-1.58) | 0.79 (0.74-0.84) |
| (n = 561) | Dv1 + CC | 1.31 (1.17-1.46) | 0.80 (0.75-0.83) |
| (Karnes EU 2017) | Dv2 + CC | 1.33 (1.23-1.45) | 0.82 (0.79-0.86) |
| Decipher PCSM | Dv1 | 1.37 (1.21-1.54) | 0.69 (0.62-0.76) |
| [High Risk: | Dv2 | 1.35 (1.24-1.48) | 0.73 (0.67-0.79) |
| PSA >20 or RP | Dv1 + CC | 1.29 (1.14-1.46) | 0.72 (0.68-0.77) |
| Gleason >8 or RP | Dv2 + CC | 1.30 (1.18-1.43) | 0.75 (0.71-0.79) |
| Stage pT3b/N1] | | | |
| (n = 323) | | | |
| Decipher PCSM | Dv1 | 1.35 (1.18-1.53) | 0.69 (0.62-0.77) |
| [BCR patients] | Dv2 | 1.34 (1.22-1.49) | 0.74 (0.67-0.81) |
| (n = 212) | Dv1 + CC | 1.25 (1.09-1.43) | 0.75 (0.70-0.80) |
| | Dv2 + CC | 1.26 (1.14-1.41) | 0.77 (0.72-0.82) |

Treatment Guidance

Treatment guidance, including adjuvant radiotherapy and salvage radiotherapy from Decipher RP testing was determined. Table 10 shows treatment guidance data for the metastasis endpoint for genomic classifiers.

TABLE 10

| Treatment Guidance - Metastasis Endpoint for Genomic Classifiers | | | | | | | |
|---|---|---|---|---|---|---|---|
| | | | | Cumulative Incidence of Metastasis @ 5 year | | Cumulative Incidence of Metastasis @ 10 year | |
| Dataset | Classifier | MVA HR (95% CI) | 5 year AUC (95% CI) | Adjuvant RT | Salvage RT | Adjuvant RT | Salvage RT |
| ART vs SRT | Dv1 Low | — | — | 0 | 6.0 | 9.4 | 10.7 |
| guidance | Dv1 High | — | — | 7.5 | 23.3 | 7.5 | 31.3 |
| (n = 188) | Dv2 Low | — | — | 0 | 3.6 | 0 | 7.7 |
| (Den JCO 2015) | Dv2 High | — | — | 6.6 | 25.1 | 17.2 | 34.4 |
| SRT intensification | Dv1 | 1.3 (1.09-1.6) | 0.81 (0.7-0.9) | — | — | — | — |
| (n = 170) (Freedland | Dv2 | 1.68 (1.32-2.3) | 0.86 (0.73-0.95) | — | — | — | — |
| EU 2016) | Dv1 + CC | — | 0.8 (0.7-0.9) | — | — | — | — |
| | Dv2 + CC | — | 0.88 (0.81-0.94) | — | — | — | — |

These results showed that genomic classifiers of the present invention are useful for predicting presence of higher-grade disease in prostate cancer subjects. These results further showed that genomic classifiers of the present invention are useful for predicting metastasis in prostate cancer subjects. These results suggested that the methods and markers of the present invention would be useful for diagnosing, prognosing, determining the progression of cancer, or predicting benefit from therapy in a subject having prostate cancer. The results showed that the subtyping methods of the present invention may be used to determine a treatment for a subject with prostate cancer.

Although the disclosure has been described with reference to the above examples, it will be understood that modifications and variations are encompassed within the spirit and scope of the disclosure. Accordingly, the disclosure is limited only by the following claims.

What is claimed is:

1. A method for treating prostate cancer in a subject comprising:

a) obtaining or having obtained an expression level in the sample from the subject with prostate cancer for a plurality of targets comprising SMC4, PABPC1, TRIQK, TIPARP, and AZGP1;

b) subtyping the prostate cancer as metastatic based at least on the expression level of the plurality of targets; and c) administering a treatment selected from adjuvant chemotherapy, systemic radiation therapy, and/or anti-androgen therapy to the subject when the subtyping of step b) indicates that the prostate cancer is metastatic.

2. The method of claim 1, wherein the plurality of targets comprise DNA and/or RNA.

3. The method of claim 1, wherein the biological sample is a urine sample, a blood sample or a prostate tumor sample.

* * * * *

SEQUENCE LISTING

<160> NUMBER OF SEQ ID NOS: 1815

<210> SEQ ID NO 1
<211> LENGTH: 645
<212> TYPE: DNA
<213> ORGANISM: Homo sapiens

<400> SEQUENCE: 1
tcgccaggca tttcggggca aaacgaagcg gagcccccca aaccccccaga cctaaccaag 60 ttcagagatt cgcagaagca cgcccccccac ccccaaattta ttgtgctcta cccaaaatgg 120
aataggacta ggtttattta cccattgtga gggtagagag gcgagtctgg aggagcaggg 180
attgggagaa ggggtggaaa aatactctga ttcttaaaaa tactttgtaa cctaaagtcc 240
ttaaattgtg gaagaaagga atactcctcc tttccattgt agtctagagt taagatttca 300
aatccataaa ttagaggacc taaaattaga gggcaattaa ctgctcattc attgggcccc 360
cagtcagcac gggggtgctg gaagagatcg ggaataatag cgcagaccaa tgagcctagg 420
gagatgcttt catcgtctct ccttccctca agtgttctgg aacctatcat ttgaattagc 480
cgagtcaggc aggagggggc ggggaatcct tccgcccttc ttaggagggg ctgcattgca 540
gggggagagt gaactgacag actcagtcac tgaagaggga aaaggagtga gaagacaaag 600
ccgtcaaagc cccaacagct ttgtatttct ccagcccggc gcaga 645

<210> SEQ ID NO 2
<211> LENGTH: 28
<212> TYPE: DNA
<213> ORGANISM: Homo sapiens

<400> SEQUENCE: 2
gggaccctgt gagtagccag tacagttc 28

<210> SEQ ID NO 3
<211> LENGTH: 97
<212> TYPE: DNA
<213> ORGANISM: Homo sapiens

<400> SEQUENCE: 3
agaactggat ctgtcggagc tggaaggcct gggtctgtca gatacagcca cctacaaggt 60
caaagacagc agcgttggca aaatgatcgg gcaagca 97

<210> SEQ ID NO 4
<211> LENGTH: 32
<212> TYPE: DNA
<213> ORGANISM: Homo sapiens

<400> SEQUENCE: 4
gtgatggcct ccttgagtac agcaccttca ac 32

<210> SEQ ID NO 5
<211> LENGTH: 26
<212> TYPE: DNA
<213> ORGANISM: Homo sapiens

<400> SEQUENCE: 5
tggagagctc ccattgccag catcca 26

<210> SEQ ID NO 6
<211> LENGTH: 607
<212> TYPE: DNA
<213> ORGANISM: Homo sapiens

<400> SEQUENCE: 6
tcaagcaatg gagtactggg tcacagggat tcctcctttc ccccccaaat attaactcca 60
gaaactaggc ctgactgggg acacctgaga gtagtatagt agtgcaaaat ggaagactga 120
tttttgactc tattataatc agcttcagag attccttaaa ccttcctaat ttcctgctcc 180
agggcagtaa acacaaatat ttcttcaagg ggtgatgaaa acctcggaag ttttaatttg 240
aggttatctg ctacgaaaca gtatttctaa aaggctaaag tgataagtct cttgcttttt 300
tttgatcctg ctcttatatt cttttttttc ctcagagaaa tcaggagggt agttagaggt 360
ataaaacagg aggaaatatt atggaaaatg aaaataggga aaataattga atcattttag 420
aagtagctaa tttcttttct caaaagagtg tcccttcttc acacctactc actttacaac 480
tttgctccta actgtgggtt gaaaactcta gctaaagaaa gttatcaaat cttaacatgc 540
attcctacta ttatgatagt ttttaaggtt tcaattcaat cttctgaacg gcataagtcc 600
tattta 607

<210> SEQ ID NO 7
<211> LENGTH: 139
<212> TYPE: DNA
<213> ORGANISM: Homo sapiens

<400> SEQUENCE: 7
gggagcgcgc ccagcatcgc ttgggcctcc tccacccgct caggagggga aacaggagag 60
ccgggagcac aacagcctcg cgcgcccgcc gccgcctcag ccttagggga ggccactacg 120
cctctggtta catttcttg 139

<210> SEQ ID NO 8
<211> LENGTH: 63
<212> TYPE: DNA
<213> ORGANISM: Homo sapiens

<400> SEQUENCE: 8
tagtcaggac aggataaaca gtcgctatat taagaccatg tacgtgtccc tagacctagt 60
tct 63

<210> SEQ ID NO 9
<211> LENGTH: 71
<212> TYPE: DNA
<213> ORGANISM: Homo sapiens

<400> SEQUENCE: 9
tccgcccacg cctccgtctc ctccgcgctc cgccacagcc ggccgacacc acaccagccg 60
gggagccgcc g 71

<210> SEQ ID NO 10
<211> LENGTH: 26
<212> TYPE: DNA
<213> ORGANISM: Homo sapiens

<400> SEQUENCE: 10
ctagtctgca agccaccgct gtcgcc 26

<210> SEQ ID NO 11
<211> LENGTH: 32
<212> TYPE: DNA
<213> ORGANISM: Homo sapiens

<400> SEQUENCE: 11
gacttcgagt gggtctacac cgaccagccg ca 32

<210> SEQ ID NO 12
<211> LENGTH: 26
<212> TYPE: DNA
<213> ORGANISM: Homo sapiens

<400> SEQUENCE: 12
gtgagggcca gcgggcgccc cgttat 26

<210> SEQ ID NO 13
<211> LENGTH: 32
<212> TYPE: DNA
<213> ORGANISM: Homo sapiens

<400> SEQUENCE: 13
gggccctgcg cggtcgtggg cgccggaggc cc 32

<210> SEQ ID NO 14
<211> LENGTH: 205
<212> TYPE: DNA
<213> ORGANISM: Homo sapiens

<400> SEQUENCE: 14
cggagccgcg cagctccgac ccttccgcga agaggcgcag gcgcgtcccc gagcgcggga 60
gtccccgcca ggcccacgcc ggccggttgg ggcgaagggt gtccccggct gtgccagcct 120
tgagtagatc ttttcgctag aagattcctg tgccctcagg tgggcgccct ttcctctcac 180
cactccctct cctccggagc gggcc 205

<210> SEQ ID NO 15
<211> LENGTH: 65
<212> TYPE: DNA
<213> ORGANISM: Homo sapiens

<400> SEQUENCE: 15
ttggggctgc ctgagtgcta ggcagggtgt ggtcctgggc atccttgggc ctaccagcga 60
gccct 65

<210> SEQ ID NO 16
<211> LENGTH: 176
<212> TYPE: DNA
<213> ORGANISM: Homo sapiens

<400> SEQUENCE: 16
ggtctcagat gatgcgcctg ccatggcctc ccaaagtcct gggattacag gcgtgagcca 60
ccctgccagg ccacatatga tatattttat caatgcctta tctacatgtt acataggaat 120
aatctagcgt cctacctgtg taaaaaccaa ctctggaata ctgaaactga gctact 176

<210> SEQ ID NO 17
<211> LENGTH: 35
<212> TYPE: DNA
<213> ORGANISM: Homo sapiens

<400> SEQUENCE: 17
ttgatgaaac ctgatcccaa tttgatatgg attat 35

<210> SEQ ID NO 18
<211> LENGTH: 115

<212> TYPE: DNA
<213> ORGANISM: Homo sapiens

<400> SEQUENCE: 18
tctggaagtt atcaataccg tggcacaggt cacttttgac attttaattt attacttttt 60
gggaattaaa tccttagtct acatgttggc agcatcttta cttggcctgg gtttg 115

<210> SEQ ID NO 19
<211> LENGTH: 134
<212> TYPE: DNA
<213> ORGANISM: Homo sapiens

<400> SEQUENCE: 19
tggccaggct agtattttgt cagtccaagc agttcattaa aaaaaaaaaa aacaaaaaga 60
gcaagaatat aaatactgca tcttccagcc tacttttaca aagggttcac tcttgggtcc 120
ttaagcttag tggt 134

<210> SEQ ID NO 20
<211> LENGTH: 25
<212> TYPE: DNA
<213> ORGANISM: Homo sapiens

<400> SEQUENCE: 20
ctggagtttc ctggatgggt gcagt 25

<210> SEQ ID NO 21
<211> LENGTH: 110
<212> TYPE: DNA
<213> ORGANISM: Homo sapiens

<400> SEQUENCE: 21
gctgaatact atgacaacct ccctcactac aattcctgga taaaagtact gtatgatttt 60
gtgatggatg atacaataag tccctactca agaatgaaga ggcaccaaaa 110

<210> SEQ ID NO 22
<211> LENGTH: 29
<212> TYPE: DNA
<213> ORGANISM: Homo sapiens

<400> SEQUENCE: 22
atatcattag tgccaaaggg attcttctc 29

<210> SEQ ID NO 23
<211> LENGTH: 188
<212> TYPE: DNA
<213> ORGANISM: Homo sapiens

<400> SEQUENCE: 23
aagagctcgg tgataccaag aagtgaatct ggcttttaaa cagtcagcct gactctgtac 60
tgctcagttt cactcacagg aaacttgtga cttgtgtatt atcgtcattg aggatgtttc 120
actcatgtct gtcattttat aagcatatca tttaaaaagc ttctaaaaag ctatttcgcc 180
aggcacgg 188

<210> SEQ ID NO 24
<211> LENGTH: 70
<212> TYPE: DNA
<213> ORGANISM: Homo sapiens

<400> SEQUENCE: 24
aagctatttc tagtttattt cactataaag ttttgcttta ttaaaaagct aataaacagc 60
tattaatcac 70

<210> SEQ ID NO 25
<211> LENGTH: 171
<212> TYPE: DNA
<213> ORGANISM: Homo sapiens

<400> SEQUENCE: 25
ctatataata tggtaacttg ggtaccgggg gaactttaaa atttcatctc aaaaataatt 60
tttaaaaagc ctgaggtatg atatagcata aaagattgag atgaaaatat atttccctgt 120
aagctgaatt actcatttaa aaattttaac ttctatatgg gacccgaatt a 171

<210> SEQ ID NO 26
<211> LENGTH: 34
<212> TYPE: DNA
<213> ORGANISM: Homo sapiens

<400> SEQUENCE: 26
ctgctgaatc ctgtacagcc ttactcataa ataa 34

<210> SEQ ID NO 27
<211> LENGTH: 59
<212> TYPE: DNA
<213> ORGANISM: Homo sapiens

<400> SEQUENCE: 27
actttgccaa atactttctt caccaatctc atgaggagag ggaacatgct gagaaactg 59

<210> SEQ ID NO 28
<211> LENGTH: 25
<212> TYPE: DNA
<213> ORGANISM: Homo sapiens

<400> SEQUENCE: 28
gaaaaaagtg tgaatcagtc actac 25

<210> SEQ ID NO 29
<211> LENGTH: 34
<212> TYPE: DNA
<213> ORGANISM: Homo sapiens

<400> SEQUENCE: 29
tacctgaata agcaggtgaa agccatcaaa gaat 34

<210> SEQ ID NO 30
<211> LENGTH: 32
<212> TYPE: DNA
<213> ORGANISM: Homo sapiens

<400> SEQUENCE: 30
tctggctcgg cggaatacct cttagacaag ca 32

<210> SEQ ID NO 31
<211> LENGTH: 316
<212> TYPE: DNA
<213> ORGANISM: Homo sapiens

<400> SEQUENCE: 31
ttcacgggcc acctagactt tccagtctag gactagagct gtagcaatga tctgttgtgc 60
tgtacaagaa aagagaaaga ggtgttcatt tgagaacaga tgtttttata catcagagta 120
aaagctgtat tgaagagcag gctgaatccc ttccatatag aatgaaatat gagcttgacc 180
ccagtcctta tcttcagtta cctccatacc aactggtggc atgttggatt tagcatgtag 240
aataatttcc catctcttat ttttcccaag gttaatggca tccttctggt acctggctta 300
catgtgaact gaattt 316

<210> SEQ ID NO 32
<211> LENGTH: 45
<212> TYPE: DNA
<213> ORGANISM: Homo sapiens

<400> SEQUENCE: 32
tatatatatt cctgttttta ctgattttta ttgattttgt tcaaa 45

<210> SEQ ID NO 33
<211> LENGTH: 251
<212> TYPE: DNA
<213> ORGANISM: Homo sapiens

<400> SEQUENCE: 33
ttacctgtct ctaacaaagc ccatgtacag tgttatttga ggtctccatt aatcactgct 60
agatttcttt aaaaaatttt ttttcatagt ttaaaagcat gggcagtaaa gagaggacct 120
gctgcattta gagaaagcac agaaacggga gaggttcggc gggtccctgc ttgtcctatg 180
aactgctcag agctcctgtc agtccagctg ggccttctgg gttctggcac catttcgtag 240
ccattctctt t 251

<210> SEQ ID NO 34
<211> LENGTH: 26
<212> TYPE: DNA
<213> ORGANISM: Homo sapiens

<400> SEQUENCE: 34
cagtctgcaa taaaagcact tcctaa 26

<210> SEQ ID NO 35
<211> LENGTH: 251
<212> TYPE: DNA
<213> ORGANISM: Homo sapiens

<400> SEQUENCE: 35
ggttctgctc ctcgacggcc tgaactgcag gcagtgtggc gtgcagcatg tgaaaaggtg 60
gttcctgctg ctggcgctgc tcaactccgt cgtgaacccc atcatctact cctacaagga 120
cgaggacatg tatggcacca tgaagaagat gatctgctgc ttctctcagg agaacccaga 180
gaggcgtccc tctcgcatcc cctccacagt cctcagcagg agtgacacag gcagccagta 240
catagaggat a 251

<210> SEQ ID NO 36
<211> LENGTH: 25
<212> TYPE: DNA
<213> ORGANISM: Homo sapiens

<400> SEQUENCE: 36
atgggagagc tccagtggag aaggc 25

<210> SEQ ID NO 37
<211> LENGTH: 34
<212> TYPE: DNA

<213> ORGANISM: Homo sapiens

<400> SEQUENCE: 37
atggtggatc ggcagtacag cactgttagc gcag 34

<210> SEQ ID NO 38
<211> LENGTH: 28
<212> TYPE: DNA
<213> ORGANISM: Homo sapiens

<400> SEQUENCE: 38
tccatgccaa atgtgatctt gaacttga 28

<210> SEQ ID NO 39
<211> LENGTH: 88
<212> TYPE: DNA
<213> ORGANISM: Homo sapiens

<400> SEQUENCE: 39
tcagcgtcag ggaaacctgg cagcagttaa tgaggcctgg ccatggctgt aggccaggtt 60
gggaatcagg aagggtagat gcatcctc 88

<210> SEQ ID NO 40
<211> LENGTH: 147
<212> TYPE: DNA
<213> ORGANISM: Homo sapiens

<400> SEQUENCE: 40
actgggagaa ctagtgaaga tgctgaggtg acacagcaga cccaggttgt tctggaggct 60
ctacctgagt ttgcatgcag cttagaaact aaaactgtgt cttctcagtt gcatggagtg 120
gactctcaga aggacataga gattgtc 147

<210> SEQ ID NO 41
<211> LENGTH: 227
<212> TYPE: DNA
<213> ORGANISM: Homo sapiens

<400> SEQUENCE: 41
gactccttat caccaggctc gagcactagc aggagggaca ctggtgctac gtggcagaga 60
ccttcttcca gttatcttag caactggtgg atcccaggga ctccccttag agtttctaca 120
ttattgggct ttcagaactg gactcaccaa tgagtcaggg agacagtgtt cctgctctct 180
atctgtgctg agtctgccta tctgggccca tgacaaggct tatgata 227

<210> SEQ ID NO 42
<211> LENGTH: 95
<212> TYPE: DNA
<213> ORGANISM: Homo sapiens

<400> SEQUENCE: 42
atgcaggccc aattaaatag gcctgtggcc agtcttcagc ccacagctga actgcctcat 60
ctggcaagaa agagcccatg taggatcttg agtgt 95

<210> SEQ ID NO 43
<211> LENGTH: 143
<212> TYPE: DNA
<213> ORGANISM: Homo sapiens

<400> SEQUENCE: 43
tgtggcggaa agatcccatt acctcaaaga atcaatactg ttgagagatt tgaccaagtt 60
cactttgtaa attactgcag cattgtggct gcagctctgg accttctagt tcctgcttct 120
tctagtgggt cccaacttct tgc 143

<210> SEQ ID NO 44
<211> LENGTH: 82
<212> TYPE: DNA
<213> ORGANISM: Homo sapiens

<400> SEQUENCE: 44
ttgttttcag ggcaggccgt caatcggtgg gtgcaaaaat gcagttgcca ctcagttgct 60
gcccctacgc tgctgtttga ca 82

<210> SEQ ID NO 45
<211> LENGTH: 66
<212> TYPE: DNA
<213> ORGANISM: Homo sapiens

<400> SEQUENCE: 45
gaaggcaaag tagcagtaag caacgaaacg atagctcaag ttctcatgct aggaggaaat 60
gggtga 66

<210> SEQ ID NO 46
<211> LENGTH: 78
<212> TYPE: DNA
<213> ORGANISM: Homo sapiens

<400> SEQUENCE: 46
atacagcatg atagagacaa ggattccaaa atcctaggtg gagagaacag gaccctttgt 60
gagacagtca tggtcaca 78

<210> SEQ ID NO 47
<211> LENGTH: 118
<212> TYPE: DNA
<213> ORGANISM: Homo sapiens

<400> SEQUENCE: 47
cctcatcatg gttgtggtgt acctgcggat ctacgtgtac gtcaagagga aaaccaacgt 60
cttgtctccg catacaagtg ggtccatcag ccgccggagg acacccatga agctaatg 118

<210> SEQ ID NO 48
<211> LENGTH: 137
<212> TYPE: DNA
<213> ORGANISM: Homo sapiens

<400> SEQUENCE: 48
acactgctca ttttgcttgt ctgggccatc gccattttta tgggggcggt ccccacactg 60
ggctggaatt gcctctgcaa catctctgcc tgctcttccc tggcccccat ttacagcagg 120
agttaccttg ttttctg 137

<210> SEQ ID NO 49
<211> LENGTH: 275
<212> TYPE: DNA
<213> ORGANISM: Homo sapiens

<400> SEQUENCE: 49
ttctaattct ctggtcatcg cggcagtgat caaaaacaga aaatttcatt tccccttcta 60
ctacctgttg gctaatttag ctgctgccga tttcttcgct ggaattgcct atgtattcct 120

-continued

```
gatgtttaac acaggcccag tttcaaaaac tttgactgtc aaccgctggt ttctccgtca    180

ggggcttctg gacagtagct tgactgcttc cctcaccaac ttgctggtta tcgccgtgga    240

gaggcacatg tcaatcatga ggatgcgggt ccata                               275


<210> SEQ ID NO 50
<211> LENGTH: 68
<212> TYPE: DNA
<213> ORGANISM: Homo sapiens

<400> SEQUENCE: 50

atggacaata aattcttaag caacaaaaga aaatactggg tcacaagcaa ctgggtagct     60

ctgatgga                                                              68


<210> SEQ ID NO 51
<211> LENGTH: 454
<212> TYPE: DNA
<213> ORGANISM: Homo sapiens

<400> SEQUENCE: 51

aggaactagt tatcctgtgg agatctggac gtctaactat ttggacaaca cttacattga     60

ttgtcactat catataacta agaaaatagg tcattttggc aaaaattttt tctttgtctt    120

tagaatttga aactttgagg ttttgattta attacatatg acactcctct tgtctaaacc    180

tttcaattgc atttatcaac taccactctt ttttttttta tcagatcaga cctattttag    240

atatcttgct gttctgcaag atatttgtta gaacaggcct gcatatgttt tctatgaatg    300

gagactgaat ttaaaacatt aaagtatgag attgtttttc atgtgtgttc accggaatct    360

gtttaagaaa ctacagcatg ttaactctcc atctcatttt tcagaaacac acgtgcacag    420

tggaagaaat gcacacacag cattgtagcc aggc                                454


<210> SEQ ID NO 52
<211> LENGTH: 29
<212> TYPE: DNA
<213> ORGANISM: Homo sapiens

<400> SEQUENCE: 52

gggctcggcg gcgcgggtga acgtgagcg                                       29


<210> SEQ ID NO 53
<211> LENGTH: 111
<212> TYPE: DNA
<213> ORGANISM: Homo sapiens

<400> SEQUENCE: 53

ctggagagga ggcgctccgc ccgcccgccg cgtcctccgc tgcttctccg cgcccggctg     60

gagcccggcg cccggtcgcc ccgtcgcgct cgaccccgag ggcatgcggc a             111


<210> SEQ ID NO 54
<211> LENGTH: 84
<212> TYPE: DNA
<213> ORGANISM: Homo sapiens

<400> SEQUENCE: 54

ttggcagtgc aatcagcctt tgctaatggg actattcctt ttaatctggt agctgcagct     60

tcatactcag gagcaagtct cttg                                            84


<210> SEQ ID NO 55
<211> LENGTH: 366
```

<212> TYPE: DNA
<213> ORGANISM: Homo sapiens

<400> SEQUENCE: 55
gtctgagaaa ttgtcccgga ataaaggggc ctaaggagac ataacatcta aatgtaatgt 60
agtatcctgg atggactcct gcaacagaaa aagaacttta agtaaaaatt aagggaatat 120
taataaagta tgcattttgg ttaataatgt atcaatattg gtttattagt tgtgacaaat 180
gtaccagagg aatgtaaaat gtcaacaata aaggaaattg gatgtggggt acatgagaat 240
gctgtactat ttttgcaact tttcttaaat ctaaaactct tataaaattt aaaaataaaa 300
agaaatgtgg agttattatt attatttttt ggctcaggat ttgacccaga gctatggtct 360
ggcaga 366

<210> SEQ ID NO 56
<211> LENGTH: 1185
<212> TYPE: DNA
<213> ORGANISM: Homo sapiens

<400> SEQUENCE: 56
ccagtttttc tcatgtcgta aagtgtagtt ctgaaaaaca gagcaaatga aatgcaaagc 60
aggtacttgg gtttacatcc cagtgccact gatgattctg ttttctcatc tgtggaagtt 120
tcactgttct tgtttcatgg agaaattaac taagtgtcag ctgtcaggca cactgaactc 180
aggtgatgtt cattaatagc tgttgtacaa tatgtttgta tttggattgc tgcttattac 240
ttaacaacag gataaacctg aacaatggaa aagaccaaca ttagagagta ttatctttcc 300
aaatacacac acctgtaaga gaactggaaa tgtgagaact acaacttctt cttatttaaa 360
catttgaaca attgccggcc ctttcaccga atttacctgt ggaatgcctt ttgagagtta 420
gagaactgag aactggtatt acttttcagg tcttttgctt tccctaatcc ttgtgatact 480
ggagatttat catctattaa aatggaccta gtatttttaa atctgcatat caaaagcaaa 540
ttgaatgtct cttgcttcct tttaatttct tttaacatat aaatttctct tttagcatgt 600
aaatttgttg aattaacagc cctttgataa tataattcct agttatcagc aataagtaca 660
ccagtttctt ttttaaatta ggagtatgta attctaaatt aattgattct ctcattgtac 720
atattatatg caaggttaca aaaaaaaatc aatggttaat gattttttag ctcaaccaag 780
ctaaaagatg tgaacaagaa attgaactca aaacaactta agatacaaag ctcttgttac 840
tgataatgtc taataatatt catcaattta ccatatcttg ctcttatatt aaaatgttct 900
atcattttcc taattatttt aaagtcgatt acaaaaatat atatatattc ttgtagtgcc 960
agaaaattga atacattaat aaatggggta gaatagatga atctcccatg aagaagaatt 1020
ccaaataatt tatgaactct gccctcaagg atatggagca gaacttccta cttctctagt 1080
gtgagctgaa tagtgacttc cttccaaaaa ttacatatgg aaagggggaa aataactttg 1140
tagtggagaa atctgataaa cactatctcg gctaggttat caaga 1185

<210> SEQ ID NO 57
<211> LENGTH: 188
<212> TYPE: DNA
<213> ORGANISM: Homo sapiens

<400> SEQUENCE: 57
tccttgtggt aatccctaga ctgggagctc aggtactctt ttagtcatct ttgtatgtct 60
ttagcagagt tcttgacatg tggtaggtgc ttaataaatg tttgttgttt atcaaatttt 120

-continued atggtaggga gagtaagtca gcatcggtat aaaatcgctt actccacgta actcttcttc 180
tgataggg 188

<210> SEQ ID NO 58
<211> LENGTH: 29
<212> TYPE: DNA
<213> ORGANISM: Homo sapiens

<400> SEQUENCE: 58
tctttgctat aattatagct tacttctag 29

<210> SEQ ID NO 59
<211> LENGTH: 30
<212> TYPE: DNA
<213> ORGANISM: Homo sapiens

<400> SEQUENCE: 59
gtagttctat gacttcaaca atgacaatag 30

<210> SEQ ID NO 60
<211> LENGTH: 201
<212> TYPE: DNA
<213> ORGANISM: Homo sapiens

<400> SEQUENCE: 60
gccaacgcca taccattcag ggagactaca tagataccat ggaagagctt gctgatttgg 60
tgggggtcag gcccaatctg ctgtctctgg ccttcactga ccccaagctg gcattacact 120
tattactggg accctgcact ccaatccact atcgtgtaca gggccctgga aagtgggatg 180
gggctcgaaa agctatcctc a 201

<210> SEQ ID NO 61
<211> LENGTH: 35
<212> TYPE: DNA
<213> ORGANISM: Homo sapiens

<400> SEQUENCE: 61
gatggcagaa atatctaaag ctcaagagga aattg 35

<210> SEQ ID NO 62
<211> LENGTH: 28
<212> TYPE: DNA
<213> ORGANISM: Homo sapiens

<400> SEQUENCE: 62
gtctaaagac attgccctca cagagtga 28

<210> SEQ ID NO 63
<211> LENGTH: 225
<212> TYPE: DNA
<213> ORGANISM: Homo sapiens

<400> SEQUENCE: 63
ttcacggaga cagctgccat atttgaggat ggctccaggg aggatgacat tgatgctgtt 60
atctttgcca caggctatag ctttgacttt ccgtttctgg aagattccgt caaagtggtc 120
aaaaacaaga tatccctgta taaaaaggtc ttccctccta acctggaaag gccaactctt 180
gcaatcatag gcttgattca gcccttagga gccattatgc ccatt 225

<210> SEQ ID NO 64
<211> LENGTH: 218

<212> TYPE: DNA
<213> ORGANISM: Homo sapiens

<400> SEQUENCE: 64
aaactattga cctgtggcct tatcatatca cacacagaat attattgtta cttgagaaat 60
catatatgca ctcctcaaac aacactcttc cttcactcct ccaacactct ccctttcagt 120
gcatccaggg tccaacttca gatctgatct tgatctgtgc caacctagta taaattagac 180
cttttccaaa cttcatgcat agaccaaggg gaagatta 218

<210> SEQ ID NO 65
<211> LENGTH: 89
<212> TYPE: DNA
<213> ORGANISM: Homo sapiens

<400> SEQUENCE: 65
tgggagtgca gggatagtgg ccaaagcaca agaataagga ctcttcacac tggctaatag 60
taaagccacc tctacccata cattaagaa 89

<210> SEQ ID NO 66
<211> LENGTH: 88
<212> TYPE: DNA
<213> ORGANISM: Homo sapiens

<400> SEQUENCE: 66
tcgtgtaggg gactacggat atcctgctga tgtgttgttc tcttctcgac ttacacattt 60
tatatggaag atctgtggcc aatcatta 88

<210> SEQ ID NO 67
<211> LENGTH: 130
<212> TYPE: DNA
<213> ORGANISM: Homo sapiens

<400> SEQUENCE: 67
ttcaaagggc agtacttcca cagtcgagac tataagaacc cagagggatt cactggaaag 60
agagtcatta taattggcat tgggaattct ggaggggatc tggctgtaga gattagccaa 120
acagccaagc 130

<210> SEQ ID NO 68
<211> LENGTH: 65
<212> TYPE: DNA
<213> ORGANISM: Homo sapiens

<400> SEQUENCE: 68
atgaatgtct ttgatggagt catggtttgc actggccatc acaccaatgc tcatctacct 60
ctgga 65

<210> SEQ ID NO 69
<211> LENGTH: 292
<212> TYPE: DNA
<213> ORGANISM: Homo sapiens

<400> SEQUENCE: 69
aaggtctcag gacatatagg ggtcaggaga agaataggca tttagtgcat ggagtgtcat 60
aaaagcacag gagaagccca ggctttactc aggtgttaca gtgccttagg acctggacca 120
agagacctag tgacttgcac ttttctagaa gaggagggta cattagcctg ccaacactat 180
gttatttttt tctgtcttgt ggaaattttc tcattctgac tacagcccca aacagttctt 240
atttgtggag tatgaaaatc aaatatccct gcatgggtcc tattatgtga ta 292

<210> SEQ ID NO 70
<211> LENGTH: 30
<212> TYPE: DNA
<213> ORGANISM: Homo sapiens

<400> SEQUENCE: 70
gaaaaggagc cctatagctc agtcacttat 30

<210> SEQ ID NO 71
<211> LENGTH: 201
<212> TYPE: DNA
<213> ORGANISM: Homo sapiens

<400> SEQUENCE: 71
tgggcccgta gaagcacata gtgtttcctt aacctaagta gggtaaccca tatttattat 60
tttttataaa gctaaaaatc ataacactat cctgtttcac agcctctttc tttatagttc 120
tttgtaaaat gggtatttat gggagccaaa gggagattca tttatataaa atgagagcca 180
ctgaggtgtt tttctaccct a 201

<210> SEQ ID NO 72
<211> LENGTH: 656
<212> TYPE: DNA
<213> ORGANISM: Homo sapiens

<400> SEQUENCE: 72
tgcacatgta tttatcctac ccaggcaaaa actccattct ttgtcctcct ttgctcctca 60
aaaatattca agggacagtc tctctttcat atattttggc tgcagataca ggaagccacc 120
tggcagagtg ttttcattac cttcatttca cattatttga ttgcaataaa cagatgaagg 180
gaaatgtttt ccccattaca gaagggaact gataggtatg ggaactttaa aactctctgg 240
ttccacaact tgtccattac tgcttagccc ttttgtactt tctgaagtac tttccaatat 300
atttgtttac atgaacatca taaaaaccca gtaaagtata gctcttgggt agttaactct 360
ggtgtagagg ggagaacatg gaattgcaga ataaaaacct gaattctggt gcttgcccta 420
ccactaacta acttagatgt tagacaagca atttcctcaa tttcaatttt taaaaatttt 480
cttgtttgta aaacaagatg attgtaccag atcacttctg tggttccttc ctgctctaaa 540
gtattctagg acttttctat aatttctgat cacgaccata aaagaatttt atggtcagat 600
atttctgaca gctggcaaaa agcccaaacc ttctgccttc tgatcatcct gctaag 656

<210> SEQ ID NO 73
<211> LENGTH: 39
<212> TYPE: DNA
<213> ORGANISM: Homo sapiens

<400> SEQUENCE: 73
aattgtgtgg gtatctttgt gtttgaagtt gtttgccaa 39

<210> SEQ ID NO 74
<211> LENGTH: 173
<212> TYPE: DNA
<213> ORGANISM: Homo sapiens

<400> SEQUENCE: 74
aggaagggcc agtatttaca aatcagtgat catcaatact tctaaagaga tgatgtgctt 60
cagtgactat ccaatcccag atcattatcc caacttcatg cataatgccc aggtcctgga 120
gtatttcagg atgtatgcca aagaatttga ccttctaaag tatattcgat tta 173

<210> SEQ ID NO 75
<211> LENGTH: 80
<212> TYPE: DNA
<213> ORGANISM: Homo sapiens

<400> SEQUENCE: 75
gagcgggctc tcttccatca agtgctgcgt agaagaaggc ttggaacctg tctgctttga 60
aaggactgat gacatcggag 80

<210> SEQ ID NO 76
<211> LENGTH: 32
<212> TYPE: DNA
<213> ORGANISM: Homo sapiens

<400> SEQUENCE: 76
gcgacactaa caggtgaaga tctcgggaga cc 32

<210> SEQ ID NO 77
<211> LENGTH: 172
<212> TYPE: DNA
<213> ORGANISM: Homo sapiens

<400> SEQUENCE: 77
tgagatccgg taccgcagca gagcactctc agctctgggt cttgcaggcg cagggctccc 60
ccatgccagc agaaagattt cctctggtga agaggaccgt cgaatctgtc ctcctcaaga 120
cacctcttgt acagaattta ttcgaatgcc acggccaagg tcttccttga aa 172

<210> SEQ ID NO 78
<211> LENGTH: 210
<212> TYPE: DNA
<213> ORGANISM: Homo sapiens

<400> SEQUENCE: 78
agcccacgtt ttattcccat cgagggaggg agaatgggtg ccgctgagtg ggcgggggag 60
tggtccctga aaggaggtgg agtgctacag cccctccccg ttggctctcg ctgtttgtcc 120
gttgttggtt tatactaatt tgacaacagc cgcctgttga gtctcctcca gatcgcagct 180
gaaggatctg ttgagcgctt caggaaaggc 210

<210> SEQ ID NO 79
<211> LENGTH: 154
<212> TYPE: DNA
<213> ORGANISM: Homo sapiens

<400> SEQUENCE: 79
tccgcccacg gcaggagcga aggaaggccc tggcgcgggc gggtaaactg cccaccgggc 60
ggcccacccg ctgcgccccc ggcccgcaag aggcagtccc aataggttgg cccgcctggc 120
cgaagtccgc ccggagcccg ctcacctgtc agcc 154

<210> SEQ ID NO 80
<211> LENGTH: 175
<212> TYPE: DNA
<213> ORGANISM: Homo sapiens

<400> SEQUENCE: 80
ctgtccttgg tgtataattc ctacaactgg aactgtttgt gcatcttact taaatttatc 60
agttaatatt aggtattatg agttcccctt ggccttaacc cctactctta tcaaagaaac 120
atgtttagaa aatgaagctt atcttccaca ggactttagg cataaaatgt gatta 175

<210> SEQ ID NO 81
<211> LENGTH: 25
<212> TYPE: DNA
<213> ORGANISM: Homo sapiens

<400> SEQUENCE: 81
gctggtgaaa aggagtaggt ttgga 25

<210> SEQ ID NO 82
<211> LENGTH: 36
<212> TYPE: DNA
<213> ORGANISM: Homo sapiens

<400> SEQUENCE: 82
gtagtagtat tctaagaatc gcgtgatgtt ttctta 36

<210> SEQ ID NO 83
<211> LENGTH: 147
<212> TYPE: DNA
<213> ORGANISM: Homo sapiens

<400> SEQUENCE: 83
aatgttggat tagatactga ggctgtagtc cctgctgtaa cggacatgtt ggaagctggt 60
gttctagata cttacctggg aaaacactgg tctatcaaac tcgctgctaa tgctgcagtc 120
actgtactta gagtgggtca ggtaatc 147

<210> SEQ ID NO 84
<211> LENGTH: 25
<212> TYPE: DNA
<213> ORGANISM: Homo sapiens

<400> SEQUENCE: 84
gaagtaatct ctaaacttta tgcag 25

<210> SEQ ID NO 85
<211> LENGTH: 31
<212> TYPE: DNA
<213> ORGANISM: Homo sapiens

<400> SEQUENCE: 85
actggcagaa atactctgga gaaaactctg g 31

<210> SEQ ID NO 86
<211> LENGTH: 32
<212> TYPE: DNA
<213> ORGANISM: Homo sapiens

<400> SEQUENCE: 86
agaagtttgc tgaggcgttt gaagctattc cc 32

<210> SEQ ID NO 87
<211> LENGTH: 58
<212> TYPE: DNA
<213> ORGANISM: Homo sapiens

<400> SEQUENCE: 87
atatgatgtt agtgaagcta aactcaaaat gggatgtctg aagactctgt aaaacagt 58

-continued

<210> SEQ ID NO 88
<211> LENGTH: 50
<212> TYPE: DNA
<213> ORGANISM: Homo sapiens

<400> SEQUENCE: 88
aaatagcagt gtactcttgt ccttttgatg gcatgataac agaaactaag 50

<210> SEQ ID NO 89
<211> LENGTH: 209
<212> TYPE: DNA
<213> ORGANISM: Homo sapiens

<400> SEQUENCE: 89
gagatactca ggtggtggtt tttaagcatg aaaaggaaga tggcatcatt tctaccatag 60
tacttcaggg ctctacagac aatctgatgg atgacataga aagggcagta gatgatggtg 120
ttaatacttt caaagttctt acaagggata aacgtcttgt acccggaggt ggagcaacag 180
aaattgaatt agccaaacag atcacatca 209

<210> SEQ ID NO 90
<211> LENGTH: 101
<212> TYPE: DNA
<213> ORGANISM: Homo sapiens

<400> SEQUENCE: 90
aatgaagtat ttctggccaa gcttattgtt caggcatgcg tatctatttt tcctgattct 60
ggccatttca aagttgataa catcagagtt tgtaaaattc t 101

<210> SEQ ID NO 91
<211> LENGTH: 27
<212> TYPE: DNA
<213> ORGANISM: Homo sapiens

<400> SEQUENCE: 91
gtacagcata tggacgaaat ggaatga 27

<210> SEQ ID NO 92
<211> LENGTH: 296
<212> TYPE: DNA
<213> ORGANISM: Homo sapiens

<400> SEQUENCE: 92
aattctctct ttgacatggg ctttcttttt aagaacccaa ggcattgttt tgtagagagt 60
ctctaaattt agacttgcat aattttttttc ctttattata ttcaggttaa atgtttttga 120
cacatatact acataggaca tgttgatctt agtgggtcac atcaagaacc acattatgtc 180
agtttatctc acagtaataa tgctaaattt gaccacttag ataaggtggt atagatacca 240
tcaagtttct ccactataaa gatatttttt cccgttgaag ttaatcagtg gggtga 296

<210> SEQ ID NO 93
<211> LENGTH: 338
<212> TYPE: DNA
<213> ORGANISM: Homo sapiens

<400> SEQUENCE: 93
cacagtgagg aggtctatgc aaacctaccc caaaggctga ggaagctgag aggctgaaga 60
aagaagctga cagattcagt ttcttagaaa catttcatag ggacttatga acagaagcca 120
tgtctgtctc aggcagtggt gagacaagat ggtagatccc cataccatta tctcctgacc 180

-continued

```
cagggatgat ataccacagg ggaggggcac acatacttca gagcgaatgg gtaggagttt    240

gccctaaggg tgggatttac agtaagtaca tactattaaa caacagatta actggaaatc    300

tcagaggtat tcccgaaacc agggttgatc agaagtca                            338


<210> SEQ ID NO 94
<211> LENGTH: 31
<212> TYPE: DNA
<213> ORGANISM: Homo sapiens

<400> SEQUENCE: 94

cagttctttt tgcatgatac ccaacaacaa a                                    31


<210> SEQ ID NO 95
<211> LENGTH: 106
<212> TYPE: DNA
<213> ORGANISM: Homo sapiens

<400> SEQUENCE: 95

ggacccatgg cgagagccat ctttaatatc attggcttgt caaatgggca gttctaaggg     60

agcttggcct tacctgctct ggggaattgc aggttgccac ataaca                   106


<210> SEQ ID NO 96
<211> LENGTH: 105
<212> TYPE: DNA
<213> ORGANISM: Homo sapiens

<400> SEQUENCE: 96

cccaacagag aatagggata cctgcacata gcccttcagt gccagtggca aatatagggc     60

ttcgtttcat tacctcagtt ggcaacatgg tgattggtgc taata                    105


<210> SEQ ID NO 97
<211> LENGTH: 44
<212> TYPE: DNA
<213> ORGANISM: Homo sapiens

<400> SEQUENCE: 97

ttcattctag tatataaaaa agcaaatgac tgggtgcaat ggct                      44


<210> SEQ ID NO 98
<211> LENGTH: 409
<212> TYPE: DNA
<213> ORGANISM: Homo sapiens

<400> SEQUENCE: 98

ccaggtatgc tgtagaatat ccctcagttg ggatttatct tatttttttc tcatggttaa     60

attggggtta tgacttttgg ggaggaatat tataaggtgc cattctcctc acctcccatc    120

aagggtacat actatccaca ttatacccac tgtttttttt tttttttttg gaaacttaaa    180

actcatttta tgttattata agtaagaaat tagcattcaa tatatgccac aatatatctt    240

tgttgaagtg taagtttgtt ccacttttct atttttcatt ttccaacttt tattttaggt    300

tcgggggtac atatgaaagt ttgttacaag gataaattgt atggggctgg tataactgct    360

agccatatgc agaagattga cactggatcc cttccttttg ccatatatg                409


<210> SEQ ID NO 99
<211> LENGTH: 227
<212> TYPE: DNA
<213> ORGANISM: Homo sapiens

<400> SEQUENCE: 99
```

agctcgatgg gatccgcatc gtgtgcaatc accaccagct gagtcttctt gttctccacc 60
aaggtggtga ttgtgttaac ccctgctgga aagacgggtg gtgtctcgat gggggtatcc 120
cctttgctag cagctttctt ctcagtccag gacaacagtc tctgcttctt ctcttgtttt 180
gtctctggtc tgtgcttgtg ggcccgcgta agcagtcagt agctgtt 227

<210> SEQ ID NO 100
<211> LENGTH: 311
<212> TYPE: DNA
<213> ORGANISM: Homo sapiens

<400> SEQUENCE: 100
cgtctgattg cctgaactgc ccgtcaagga ggtggcatgt gttcatcatt catttattat 60
ttaatcaaca tcgactatca tgtgtcagac actccgctgg gccctggggg ttctagaagt 120
aagacttgtt ccgtgccctc cagtgattca cgataagatc aaactgttct tgttcggttt 180
acctagtgat aaattgattt agtccctgaa atccctttct tactgcctgt gacctgtagg 240
ccaaaattgg gaacctctga atagtagtaa attaaaatca ccaaagacgt cattgtggca 300
gtgggtatct c 311

<210> SEQ ID NO 101
<211> LENGTH: 626
<212> TYPE: DNA
<213> ORGANISM: Homo sapiens

<400> SEQUENCE: 101
gaccactggg tcttgggaat cagtaggggc tgtatccagc acaccactgc cccatccttt 60
ttttcttaac tattagtgtt gaataaactt ctcatagtta atctacttgc tgaactcagg 120
aaattcctat cactgaccct ggccagggct ttaaagggta ggaaaagcat taatgtcagt 180
cctacacagc gaacttttga tttagaagaa tgtgacagaa agaaaacatt tactgaaata 240
catgggaagc ttgcatattt ctaaagttgt ctttatactt ttcatttctc aaagctaagt 300
aaactgtggt ataggcatct ctaagatgtt agcatttaaa acatcaattg ttttattgat 360
gtttaaacaa ttgtttaaat cccactgaaa aatttaaata ttaaaatatc ttgcacagtc 420
taccaaatga gttaaatcgt tacagtcgtg tctacctctt atttttctat ctgtatttag 480
gctgctgttt tggtgagatt ctaatttctt tttcccctgg aactactttc tgtggaagac 540
aaggaacaga ctggggacag aggcctgaaa acaaattgga agcactcaga gatctattgc 600
tgaccagccc tattcctcat gagttg 626

<210> SEQ ID NO 102
<211> LENGTH: 1295
<212> TYPE: DNA
<213> ORGANISM: Homo sapiens

<400> SEQUENCE: 102
ctccagggtg acaaatgcca atagatatgt gagttaattt ttttaaatat ctccgtgagt 60
tgtaaataga tgtgtatttg atctgcccta tccttctttg attctttaac atgttctctc 120
tcttctgttt gcaaaatatg tttgaaagca ttggtagtgc tttccttatc agtaactgga 180
gttctcctgc ttgcactaga gaaggtaaag agagaatcag tattcttata tggcaatctg 240
gggaagcagc aatatgccac tgtacaaaac tgaagaaaag ttcctaattt gtactttgtg 300
aagggagatg aaaggacgtt taaagtatat atattttgtc aagaggaaag aagataaaac 360

```
tatgccagtt ttatatcaat agcttgtaga agctcagctc ttcttggtct tggctagact    420

gcctagattc ccacagcaga caaggttgag aatccattgc tggaatcttg gtattgatga    480

gttacagtga tggaacatgt gcttggccac aggcaggtcc agtcactgca aaagtgacca    540

agccagcagg tcacccttaa cttcagaaac aattattggt ggtgaactgt acttaaattg    600

cagagaaacc tgtaagtaat ggaaggtaaa gaaaaattac agaatggaaa ataatatttt    660

gggcaagcaa acaaattcac tgagaattcc aaaagtatat taaaaaagaa gatagctatg    720

agttcagatc tatcttattg gtctttaata ttacaaccaa tccttaactt tccactataa    780

aggaaggatt actagattga ttactttctg gatagataat ctggtaataa atgataggta    840

aatcaaaaat tacttttatt taggagtttg aattcttact ctcatcagac atttttttc    900

tagggacgct tactaattaa atgatttaag ttgtttctta ggggttttt gcctatatat    960

ttatgactgt gttaatgagt agtgaaatga tgcggaaaga cagctatcag gaagaggaaa   1020

tacagaagcc tgaataatct atgggttaga aaagcatccc tgaataatca aaaattggca   1080

gtattggcat tgttctcaag ccttttttatg aaaatgaaat ctgaaatcac caaatgtaaa   1140

cctgggaaca ttattctagt gttgctgtct tggattcatg ttaagaagcg tcttcattct   1200

ttgctcatgt tgcccacttc ttgtggattt gtctgagtgt tttttgacaa tcacttcctt   1260

aaagactctt ctgaactagt tggacctggt taatc                               1295
```

<210> SEQ ID NO 103
<211> LENGTH: 2379
<212> TYPE: DNA
<213> ORGANISM: Homo sapiens

<400> SEQUENCE: 103

```
ggtcaccgta ggagttcaga ctttctttca taagtgtgca ttattttaca tgtgcaaatc     60

agaatatatt taaaaaaaag caaaagaaat tcaatggatg gattaatatt tatcccccctt   120

tgggatattt taaaatctac taaaatgagg attagtaata taatgacctg ctaatatatt    180

ttaagaacat gttttaaaaa gatacactct atcacatatt taagcaaaca tcacatttgg    240

agaagaggaa atcataaaat catcctagaa gactatctga gagaaattct gttgccacca    300

gttatacttg acaatttagt tgaagctcag aaagttatat tcatccctct tagctgtagt    360

ctatattagg gcagttctct agaacgccca catttccacc aactcagtaa acttgagggg    420

agctggttgg cacctcgtga agaactcttt ccctgtcgtt tgcagtaaca aactccagtc    480

tgttgcagta acaaactcca gtctgttgca gtaacaaact ctagaatatt gacattctct    540

gtgggggaaa agcagtgtcc actggacccc ttctggtact ggatgtgttc tttacaaagg    600

ctagctcagt ccaacactgt gtttacatac actcgtgctt ttccttatct gacttctcat    660

tttgtatcag aggcatatca taaattgata attttgcaaa atgcactttt ttgagatgca    720

gatatagcaa aggattagta atatagcctg aaaacaaatg ggagcatagc agtgtgtgag    780

gttctcgaga actgtcttgt ctctgtgtgt ttatttgcct gccagtgctc tccagcgcca    840

tcctgccctg gacaccaccc tgacgtgatg cctctattgc agctcagagg ctttattttt    900

tccattttga cattggcact aaatgcattt ggggatggtt aaaacaaatt actatagaac    960

atttaaatga tcagtttaag gggaaatagg ctagtttata gaaaaataag agctagtggc   1020

ttataatggt gacaggttct catgtggcac ccctaggacc tgtgcagaca gtagtctgtt   1080

gaatcattac atcaaggagc tgcccctgtc agggtgagtg taattaggaa cgataccagc   1140

acataaggct ccccccaatc tcttccagtt gctttttctt ttttcttttt tttttagaca   1200
```

ggtcttactc tgtcacccag gctgtagtgc agtggcataa tctcagctca ctgcagtctc 1260
tgcctcccgg gttcgagcga ttctcctgcc tcagcctccc gagtagctgg gactacaggc 1320
acccaccatc atgcttggct aatttttgta tttttagtag agatggggtt tcaccatgtt 1380
ggccaggctg gcctcgaact cctgacctca ggtgatctgc ccacctcggc ttcctaaagt 1440
gctgggattg caggcgtgag ccaccacgcc cggcctccag ttgcttttga agagggtaaa 1500
gtcaagtttc tatttctaga aaacattttt tagaaatttg ttgcgatgtt tgtacaattt 1560
acctcataag agaaccacac ccttctccaa aagtgctggt actgcatcag tgagatgagt 1620
agggtttttg tttgggattg taagactatt aagatcctag taagtcagtg gtagtttact 1680
gtgatgtgag cattgtagat tcccccgttg tcactaatca cacaacaatt ttgagaagta 1740
ggctataaaa caaaaaaagg ttgctgtttt ctatttttaa ataaaccaaa aaaaaacaga 1800
aaagatgtga attttcccca gttatgtggg aaaggtaaag caacaccaaa taaaagccca 1860
cagcagcttc atctttacga taactcagtg catatgtgaa agagaatgat gcattaactg 1920
aaatacctca ttgaatatta tactactact ggtaaaatgc agaagacagt gttaatgtgt 1980
ttggtttggg gactggttgt tataaaatgc aatttttttt taaatctaag catttcatta 2040
tgtgttctac agtgtcggtg aataaatgaa accaatctca atttagaggt atggatgatg 2100
acagaaagcc caatagaagc ttaatgatgc ttctgtttga ggcccagcaa gcaccactaa 2160
attactggat gaaatgaaat tgttcacttg agggattagt caaccatctg ggggagaagt 2220
tgctcactgt caaatacagc atgcacggtc ctagctgata gaccttttcc tcattgctac 2280
agcaagccac agggtagagt gaccagttct cctatccaaa aataaatgcg aacatgcata 2340
cataaatgtg gctgagggcc acttttgcca tcactgtgc 2379

<210> SEQ ID NO 104
<211> LENGTH: 38
<212> TYPE: DNA
<213> ORGANISM: Homo sapiens

<400> SEQUENCE: 104
gtacaacatc attcagtatt tttaccattg cctgtttt 38

<210> SEQ ID NO 105
<211> LENGTH: 63
<212> TYPE: DNA
<213> ORGANISM: Homo sapiens

<400> SEQUENCE: 105
gaccctcagc aacttgtgga tatttctcat acagtctttt gcatttttgt caggctatat 60
gtg 63

<210> SEQ ID NO 106
<211> LENGTH: 56
<212> TYPE: DNA
<213> ORGANISM: Homo sapiens

<400> SEQUENCE: 106
ttccaattaa agatgtaccc ctggagactg atgaccttac cacttggctc tatcag 56

<210> SEQ ID NO 107
<211> LENGTH: 259
<212> TYPE: DNA
<213> ORGANISM: Homo sapiens

<400> SEQUENCE: 107
ctaatggacc tgaactcttg aaagataaag actaaagcaa acacaagaag gtgacatgga 60
ggaccagact atacagggca aggtctgctt ctagaattcc taatagtaca tgggggttca 120
ttaacctttt tctctcctct tgtgaatgtt taaaaatttc cattataatt taaaaaactt 180
attataaaca taagatattg tagcaataat acaataatag catactataa aaaagactga 240
gaacaatagg agctcttta 259

<210> SEQ ID NO 108
<211> LENGTH: 389
<212> TYPE: DNA
<213> ORGANISM: Homo sapiens

<400> SEQUENCE: 108
caaggtcacg caactggcaa gtggtagagt caggattcaa ccccaggcag tctgcccaat 60
agcttttttt ttttttgaga cagaatttta ctcttgttgc ccaggctgga gtacagtggt 120
acgatctcgg ctcactgcaa cctccgcctt ccagtttcaa gctattctgc ctcagcctcc 180
cgagtagcta ggattacagg cacctgccac cacatctggc taatttttgt atttttagta 240
gagacgaggt ttcaccatgt tggccaggct ggtctcgagc tcctgacctc gtgatctgcc 300
cacctcagcc tcccaaagtc ctgggattac aggtgtgagc caccgcacct ggcgtgatag 360
tttgtatgct taatcactag gccacactg 389

<210> SEQ ID NO 109
<211> LENGTH: 27
<212> TYPE: DNA
<213> ORGANISM: Homo sapiens

<400> SEQUENCE: 109
gaggagatgt aagcctagca ttatatg 27

<210> SEQ ID NO 110
<211> LENGTH: 220
<212> TYPE: DNA
<213> ORGANISM: Homo sapiens

<400> SEQUENCE: 110
ggccctaatt ggttatgagc ccattgctac accccaatac ttgtcatgaa gagaatgata 60
tatgatgaca ggtctgacat gggtttttaa tgagaagggt gccaagacta ccagaattgg 120
ctgagtgata atagattggc agacatttgc ttgggataaa tttattttgt tttttaaaga 180
aaagctagat aatcctttcc cttggtgaga ggattcctgc 220

<210> SEQ ID NO 111
<211> LENGTH: 418
<212> TYPE: DNA
<213> ORGANISM: Homo sapiens

<400> SEQUENCE: 111
tgtttgtcag ctcacatttt ggagtcttga cgtaaaaatt caaatgctcc aactccagta 60
tagggggtgc cagctgctaa gtattatttt acattttttt tgaaagtgta atttcatcta 120
gtgcttttaa atctgactat ggattttggt agtatattct ctatttaaga gcacattctg 180
aattactgat aataagaatg ttcatttctt gaaaattagg agctagtttt tcatttgggt 240
agctattggt attgtaaagg tttatttctg gtgtatatgt atttacttat ttaaatccca 300
caagcactcc tctgatttga tttcaagagg actggtattc aatgtattta atcctttgcc 360

-continued atattagggg attagtcatt ttaatatttt aatcctatgg tgaccaatca gagtaata 418

<210> SEQ ID NO 112
<211> LENGTH: 62
<212> TYPE: DNA
<213> ORGANISM: Homo sapiens

<400> SEQUENCE: 112
gccttttagc cttactatgt ttccatgtga aagacctcaa cccgtggcaa ctaccaagga 60
ca 62

<210> SEQ ID NO 113
<211> LENGTH: 76
<212> TYPE: DNA
<213> ORGANISM: Homo sapiens

<400> SEQUENCE: 113
acagcaaatc aaaaggcctc cagtggataa tagatacaac gatagcttat cccaaagctg 60
aacctataga tattca 76

<210> SEQ ID NO 114
<211> LENGTH: 139
<212> TYPE: DNA
<213> ORGANISM: Homo sapiens

<400> SEQUENCE: 114
cagagatcga aaatggattg ttttgtttcc agaaggggc ttcctcagga agaggcgaga 60
aacaagtcag gcatttgcca agaaaaataa cttgccattt cttacaaatg ttactctgcc 120
aaggtctggg gcaacaaaa 139

<210> SEQ ID NO 115
<211> LENGTH: 154
<212> TYPE: DNA
<213> ORGANISM: Homo sapiens

<400> SEQUENCE: 115
tcttgagaac ttaatagcta tcttaatcat aatcagttca cttcagcaaa ctgactaaca 60
aaatgtctta catgttttgc atttgggata catttgatct aaagactgaa agcatactaa 120
ttattttgag gagtttctgt aattttgttg gctg 154

<210> SEQ ID NO 116
<211> LENGTH: 162
<212> TYPE: DNA
<213> ORGANISM: Homo sapiens

<400> SEQUENCE: 116
gagaaggcag cggaaccaac aattagaaag cttagcagtc tcagggatcc gaaaagctag 60
ctgagcacct tacctcattt ccagctttag gaaataattg aatttacagt gtagtgtaac 120
agttgattct aatgatgatc atcaggcatc aagaagaggg gc 162

<210> SEQ ID NO 117
<211> LENGTH: 25
<212> TYPE: DNA
<213> ORGANISM: Homo sapiens

<400> SEQUENCE: 117
gatgtggttg atggatcata ttttt 25

<210> SEQ ID NO 118
<211> LENGTH: 96
<212> TYPE: DNA
<213> ORGANISM: Homo sapiens

<400> SEQUENCE: 118
ttctctatgc tgataggcag tctgcactaa gttgagcata aatatggtga cctcctggga 60
gcagtgaaca actaggtcac acaagaaggg tgaacc 96

<210> SEQ ID NO 119
<211> LENGTH: 27
<212> TYPE: DNA
<213> ORGANISM: Homo sapiens

<400> SEQUENCE: 119
cgaggccatc caggacaaca gggtgaa 27

<210> SEQ ID NO 120
<211> LENGTH: 26
<212> TYPE: DNA
<213> ORGANISM: Homo sapiens

<400> SEQUENCE: 120
gcaacaggag atgtgtgcac actgat 26

<210> SEQ ID NO 121
<211> LENGTH: 921
<212> TYPE: DNA
<213> ORGANISM: Homo sapiens

<400> SEQUENCE: 121
acacagtagg catagggctc ttttagttac tagtgattcc aaaagtgact ttaatcccat 60
tactcaggat ctctatggta ctgtcaatta gatcttcctc atttttgcaa catgtttacg 120
tagcattaat gatattattg tttcataagt gagaaaatga agacacagaa ggataaaata 180
gtttgttgca tcagcttgcg ggcataataa gcaacctttc ttctctctgt taattctgtt 240
ttgtaggcca gtataatggc tttagtgtca ctgttgttaa ggagtttttg atgggttgtt 300
tctattttct ttttgagatg tgaactgtcc agattaattc taatctataa cttttgggaa 360
aagtatattg atatacatgt tagaatgtgt gtgtgtatgt gtgtgtgttg tgtgtatgta 420
gtagatgata acctttagct ttggttttca ataagaattt taaaatttat tacaattaga 480
aaatttttcc tccagttttt attcagttgt ccttttttccc tttggaaata gtggacctga 540
cccaattctt ttttgagaat tcatttcata gagcagcgtg ttagaatatt tttgttcttc 600
taatcaagtg cagtgtaaga actgtagaca tccataattt cttttctatc ccttggttaa 660
gatattagct ttattactat atttactggt cctggaatag caaggcataa tctgaggagc 720
atagctactt catctgtgta ataaattgct ctttcactac aaacatttta atactgattt 780
tgttggtcat ttaactttct aatagtggtc cttaaattat gctctaaaag aagaatacca 840
tatatattgg aaattaaatt tgttgttgaa taaaattaga attattataa aattcaacac 900
gaccttattg ctacctcagg a 921

<210> SEQ ID NO 122
<211> LENGTH: 362
<212> TYPE: DNA
<213> ORGANISM: Homo sapiens

<400> SEQUENCE: 122
cctacttcct aactatgtaa gtttgaaaac agtgcttaac cttttgtgcc tcattttcct 60
catttgcata ttggggatga tactatctgc atatttggaa ttttgtgaag attaaatcag 120
aaaataatgt aaattatttt ctattactaa gtactagtgc atggcacata ataaacattc 180
cataaatgtt agctattaag attattattt atatatctat ttaataatat ctgctactat 240
tattatttta gttatgtaac ccctccaaaa gctacctctt gagccttgct ttctcaaatt 300
ttaacctctt aaaatttaag agtcaaaggg acactgacca tgatttccta gtgtgtacaa 360
tg 362

<210> SEQ ID NO 123
<211> LENGTH: 245
<212> TYPE: DNA
<213> ORGANISM: Homo sapiens

<400> SEQUENCE: 123
ccttgtttca agctggaagt ggggataaca tagagccctt cacacatctg cttttctcat 60
ccccttcaac tgtctgttct tgttttaaga gtgagagatt aaaatgttga tttgtagcca 120
agcaagtggc tgtggcttat caacattgag cctcactgta gggtaatctt attggaatat 180
ttcactgggg aaccccaaat gtcagtattt ttaggtcttt cctcttgagg tgatcaaatt 240
cccta 245

<210> SEQ ID NO 124
<211> LENGTH: 615
<212> TYPE: DNA
<213> ORGANISM: Homo sapiens

<400> SEQUENCE: 124
ggtgaagtgt ccaagtcttt tcttaatttt tttaattggg tagtttgttc tcttaatgct 60
gagttttgag aggttttttt tttttttttg agacggagtt tcgcccttgt tgcgcagact 120
ggagtgcaat ggcgtgatct cagctcactg caatttccac aaccctgccc gggttcaagt 180
gattctcctg cctcagcctc ctgagtagct gggattacag gcatgtgcca ccacacccgg 240
ctaattttgt atttttagta gagacggggt ttctccatgt tggtcaggct ggtctcgaac 300
tcccgacctc aagtgatctg cctgccttgg cctcccaaag tgctgggatt acaggcgtga 360
gttttctata tacttgggat ataaaccctt tgttggatat gtgattgcat attattttct 420
ctcattttat tctcttaaca gtgtcttttc ctcattaaaa tgtttacatt ttgataaagt 480
ctaatttatt gatttttttta aaaaaattgg gcagccccca agccagaata ggttgagaga 540
gactccccag ttcattgatg ttattttctt ttatggcttg tgtttttcat gtcatgtcta 600
agagtacttt gccca 615

<210> SEQ ID NO 125
<211> LENGTH: 34
<212> TYPE: DNA
<213> ORGANISM: Homo sapiens

<400> SEQUENCE: 125
ggtctgattt gttacctgat gctcacagag tact 34

<210> SEQ ID NO 126
<211> LENGTH: 187
<212> TYPE: DNA
<213> ORGANISM: Homo sapiens

<400> SEQUENCE: 126
tttctttagt aggaagtgct gtacagatat ctcacgttga ggaaatgctt tatattgcct 60
ttgtcttaat atttcaaggg caaaccaaaa gagatactag cttaactaat gatccacttc 120
tgcatgcttt atttggatct aggataaatc agtaccccac cccccggagt ttaagtgatg 180
attggta 187

<210> SEQ ID NO 127
<211> LENGTH: 26
<212> TYPE: DNA
<213> ORGANISM: Homo sapiens

<400> SEQUENCE: 127
cattttatcc acacacgcaa gagaag 26

<210> SEQ ID NO 128
<211> LENGTH: 26
<212> TYPE: DNA
<213> ORGANISM: Homo sapiens

<400> SEQUENCE: 128
gtaagagtga gaacactttt ctttaa 26

<210> SEQ ID NO 129
<211> LENGTH: 176
<212> TYPE: DNA
<213> ORGANISM: Homo sapiens

<400> SEQUENCE: 129
aggtttgcct tcatggtcgt caacaacctg gttgctattc catcctacat ctgctatgta 60
attatacttc agccccttcg agtgctggac agtaagcggt tctggtatat cgaaggaatc 120
atgtataaat ggcttttagg aatggtagct tcctggggat ggtatgctgg atatac 176

<210> SEQ ID NO 130
<211> LENGTH: 535
<212> TYPE: DNA
<213> ORGANISM: Homo sapiens

<400> SEQUENCE: 130
ccttgccctc tggtcggaaa tctcattctc ttcatcccca gttccttggc ttttacctct 60
ttctggcttt tgctcccttc cccctactcc tgtccttcct ctttttcgca ttataacccc 120
ctactttctt cctctcacct tgtaagcttt ttttctaggc cccccatttt ttttcttaaa 180
aaaaaaaggg aaacaaaaac cctattgcta caaatgagaa ttttgagggt aactcttcgc 240
tagagccaga gacctttttaa aggaatgcat cggtgtgcag gaatcgtggt ggtgaggaga 300
ctgaggtcct cagtatctgg gaaatcttat tgaggggacc ctgtttcggt catgtcactt 360
gtgtcttcag tttggagatc ctgaggttgt ctgaagcgag tggatctatt tttctaagtc 420
caatagacga ccgcagtgag acacggtgcg gggacggcca ccgattactg aatgggaatt 480
gtgttatcat ttgctaaata tattgtgaca tacttcgtgc ctcggtgaac agctc 535

<210> SEQ ID NO 131
<211> LENGTH: 97
<212> TYPE: DNA
<213> ORGANISM: Homo sapiens

<400> SEQUENCE: 131
cagccgcgag gggagtaggg cgccagcgcg cccgctcgcg cagcgcctcg ggccgcttgg 60
gccgccaccg cgtccatgac cgcgacccct cggcggg 97

<210> SEQ ID NO 132
<211> LENGTH: 130
<212> TYPE: DNA
<213> ORGANISM: Homo sapiens

<400> SEQUENCE: 132
ccttggggac cgagtctcgg cgccgccggg gaacgggcgc gggccgcgcc acagccggag 60
cggggcaggg ccccgccacc gccttcttcc gccggccccg ccgccggcca tgcattcttc 120
cggctcctct 130

<210> SEQ ID NO 133
<211> LENGTH: 199
<212> TYPE: DNA
<213> ORGANISM: Homo sapiens

<400> SEQUENCE: 133
tgaggccagt aagcccaaga acttaaatga acattcttat actttagttt gcattctcag 60
agctggggaa ctgtctgtag gcacagaaga tggaaaaggg attttctggt ctgtttctga 120
ctttaagtta cacattttaa aaagtactct gaagacactg ggtttgttc atccccggct 180 tgctactaaa gtagtaatg 199

<210> SEQ ID NO 134
<211> LENGTH: 239
<212> TYPE: DNA
<213> ORGANISM: Homo sapiens

<400> SEQUENCE: 134
tgccaaagga attctgctca gcagattaag tatgttcatg ttttagaata aaaattgcca 60
aaactttgtt gagaaaccac ttatgaggaa accttaaata ctaattagga agctaaaaat 120
tgaatattgg tatattggta tagaatgaat atatatatat atatatatct ttttccaaat 180
tatgacattc cgtgtaatat gagtgaatta ctcagctctg ctgatgagga cttatgttg 239

<210> SEQ ID NO 135
<211> LENGTH: 1655
<212> TYPE: DNA
<213> ORGANISM: Homo sapiens

<400> SEQUENCE: 135
ctatgcaatc ctcgaactca gtgtgctttt ccctgacagg atatataaaa aggtagatta 60
ggtcaaccct cctttaagct tactctcccc tcaccttttc ttttcactgt atataaacgg 120
tactttctgt gattcatacc aacagaggac tttctgtgat tcataccaac agtcctaaac 180
tgtcattttc taaatctggg atttaaaatc tttagacaat atttaaaatc ttgatttttt 240
ttaaatgtca gcagatacaa tttggaagat tgcatctgtg tagaagtaat gcaggtacaa 300
gatctagagt ttttccttag actctttagt cttttctgaa ttaaagaata agtgctctta 360
aatccatatt ttatcctgtc aaagtctgaa atgtgttcat tgatgatttg gtgacatcta 420
aaaaattgta tttagttggc ttggctcacc cctcttaaaa atacttagcc atctcttggt 480
gggatgtggt gggggtatta aggtctcaga gttatttatt ttctcaccta atttcaaacc 540
tttataaact tggggttttg ttgttgatgg tggtagtatt ttttgttaag ttgtttaaaa 600
ggctgacttg attggagcct cctctacttt ttcttgaggg ttgcaagtat tgtatggtgg 660

-continued

```
gggaggggggg ccttaaggca aactgtctaa aaagtgacta tccaattaat ttaactagta    720

aattagtaag aattattctt agtattcact cagagtttaa gatgtgaaaa atctgcactt    780

tgtttatcac tctaaatgta aagaactttt tgatagtgtt atttcaccac tccctcagtt    840

aaaggctatt atttaaactg tttactggag aaaatcctcg ctcatgtcca tttattgttt    900

ttttctgtac tgtgatttgt ttcaagctta ggaaaactag tatattagag tatgttctag    960

gaaattaaaa gatctggtta gagtaaaaag ttctttttaa ggttcttaac taattttttc   1020

acaactaaga aaataaatga agtattctta ggctgaaatt catcttattt tatcataaat   1080

tagattgtag gggcagccta catttttgtg tatgtgtttt tatttcttaa atgattgtgt   1140

gagcctggtg acattttatg gttcttgtga tctaaactgt ttttccaatt cacatctttt   1200

gtcgtgaagt gatattatac tagagtactg tttgcattgt aaaaatgctt tgctggtgct   1260

ctggcatttt gtctttatct catcacctaa tttaaaaacc cagcacttga taatataact   1320

gacagaaatg attgtaccca ctgatgaagt aatgaaaatg aagaaaagga aaatattcct   1380

tccttcaatg gcgtaagttt attttttact taagtggcat ctatgtaagt tagacaaact   1440

atatattaaa attggtaaac tttgaatgtt tctcctgttt tgattcttag attatgagga   1500

ggatcagaca gaataagact ccacactttt gaaatttgat aagtcaaaac gttttatttt   1560

gacattttta acattgtgaa ttattcgata tttgtaatct ctgtatgtat atgaaactct   1620

gccatgtttt tcaactttgc ctatgtgcca ctgta                              1655
```

<210> SEQ ID NO 136
<211> LENGTH: 279
<212> TYPE: DNA
<213> ORGANISM: Homo sapiens

<400> SEQUENCE: 136

```
ctagggaaca aatgttgctc agggctggtg tcagtgagaa aaatttatca atgcttttta     60

atgtgttttt acccttgcct cactgtgtgt gtgtcacttt ctataatata aagaaatact    120

ataatatttc tagaatctgg aactgtcacc atgatgaatg gccctttcaa tgcatagtta    180

cagaaattcc tgaagattcc ccaggacttc aatttcattg gtttttattt gcagttttta    240

gttgctgtaa ttgttgctgt ttccagtcta aaggacctc                          279
```

<210> SEQ ID NO 137
<211> LENGTH: 89
<212> TYPE: DNA
<213> ORGANISM: Homo sapiens

<400> SEQUENCE: 137

```
agagacataa agtgactgtg gaaagccttt taattatgga cattcatcag aaagacacta     60

atctgacttc aagaattctg aactattaa                                      89
```

<210> SEQ ID NO 138
<211> LENGTH: 25
<212> TYPE: DNA
<213> ORGANISM: Homo sapiens

<400> SEQUENCE: 138

```
tttaaagtct tattacaaca cagta                                          25
```

<210> SEQ ID NO 139
<211> LENGTH: 396
<212> TYPE: DNA
<213> ORGANISM: Homo sapiens

<400> SEQUENCE: 139
gtactaactt agagaggcct taatgctgac aagtcagttt ctctacaggt cataggaaaa 60
actaagtttc caattgccag tgtttttcag tttgctgcct taattttgta agggagatat 120
tcttctaata ttctttttgc ttggctataa cttgttcaac tacaatagca ggagtaagga 180
atgtgtgatt gagaaggtga taaaagaaaa ttaaaacctt catctgctcc ttatttttct 240
taaattttca ttactatttt tttcttttct cacctttttc ctgcactatg ctctttattt 300
ctgaagctca gaggtcattt ttctttcact catttctaca tgatttactt ctgtatagag 360
acatataatt tgcttgcttg tttatatcac cagtgg 396

<210> SEQ ID NO 140
<211> LENGTH: 105
<212> TYPE: DNA
<213> ORGANISM: Homo sapiens

<400> SEQUENCE: 140
aggaactgcc ctgaagatat tattctctga aaaagaaatc caaaagcttc cagagaatag 60
tccatctaaa ggcttccaac tcacccgaca ggaaatagtt gctct 105

<210> SEQ ID NO 141
<211> LENGTH: 88
<212> TYPE: DNA
<213> ORGANISM: Homo sapiens

<400> SEQUENCE: 141
tgtgtctatg tttctattga tacaatacca gattcatttg tgaagttggt ggtcattacg 60
aaccgagtat atccgtattt tacatatg 88

<210> SEQ ID NO 142
<211> LENGTH: 38
<212> TYPE: DNA
<213> ORGANISM: Homo sapiens

<400> SEQUENCE: 142
acatttcaag aatatctccc gtataatgga ctgtgttg 38

<210> SEQ ID NO 143
<211> LENGTH: 61
<212> TYPE: DNA
<213> ORGANISM: Homo sapiens

<400> SEQUENCE: 143
gtcctttccc atgcactttg atgagaaatc catgtttgca ggtgacaaaa aaggggccaa 60
g 61

<210> SEQ ID NO 144
<211> LENGTH: 116
<212> TYPE: DNA
<213> ORGANISM: Homo sapiens

<400> SEQUENCE: 144
tttatacttg attgagcttc gagctttgtc aaaggtggct ccatattttg agcgctcaat 60
tgtcgatctt tacactggaa atgcagaaga agatgctgac acaaaaactc ttctac 116

<210> SEQ ID NO 145
<211> LENGTH: 80
<212> TYPE: DNA

<213> ORGANISM: Homo sapiens

<400> SEQUENCE: 145
ggagaaaaga gtcttctata agcttatatc gggacttcat gctagcatca atttacatct 60
atgcgcaaat tatcttttgg 80

<210> SEQ ID NO 146
<211> LENGTH: 150
<212> TYPE: DNA
<213> ORGANISM: Homo sapiens

<400> SEQUENCE: 146
tgtcatatac ttttagggag gaagctacaa aataaaattc aatttctttt ggtccccatc 60
catgacaatt tgaatattct agcaagaatt cccaattagg gaacgagaac tcaaaagaat 120
tattttttct agttagaggc cacgtgcttc 150

<210> SEQ ID NO 147
<211> LENGTH: 27
<212> TYPE: DNA
<213> ORGANISM: Homo sapiens

<400> SEQUENCE: 147
agcatatttt tgtaaggtct aggattt 27

<210> SEQ ID NO 148
<211> LENGTH: 27
<212> TYPE: DNA
<213> ORGANISM: Homo sapiens

<400> SEQUENCE: 148
gagaatcatt ctacacatgg ctagaag 27

<210> SEQ ID NO 149
<211> LENGTH: 235
<212> TYPE: DNA
<213> ORGANISM: Homo sapiens

<400> SEQUENCE: 149
agaggccata ttttttagta cgttgggtac tagacttttc ctgttggcac ttgaggtgtt 60
ttgaatcaca agtgatataa tgataaatga tccttactat atgttgaatg aattaatttg 120
ttagacgttt tcatttttgt acaaagtatg aagactctca ggaggcaaag taattcccca 180
ccgtctagtt tatccctaga ctccttactc agctcatctg agtgttcggt ttttc 235

<210> SEQ ID NO 150
<211> LENGTH: 86
<212> TYPE: DNA
<213> ORGANISM: Homo sapiens

<400> SEQUENCE: 150
tttgtttgtt tcaagtgtgg aggaaatttt ttgtaacaat cagaatttga tttttccttt 60
atggaattca aaagaaagta ttcctg 86

<210> SEQ ID NO 151
<211> LENGTH: 163
<212> TYPE: DNA
<213> ORGANISM: Homo sapiens

<400> SEQUENCE: 151
cctggccaaa atgtgcaaat cttatactct ttgacctgta ttctgattaa gaggactcat 60
ttgcagggcg tctactcagt gaccaaggtt tgtgatataa ttaatagttt aacagtttta 120
atctcaaaaa atagtattgg gatctgagct atgtaagaca ttt 163

<210> SEQ ID NO 152
<211> LENGTH: 46
<212> TYPE: DNA
<213> ORGANISM: Homo sapiens

<400> SEQUENCE: 152
gcctcgatct gtttatcgtc ctttaaatcc tctggcgcct agccga 46

<210> SEQ ID NO 153
<211> LENGTH: 417
<212> TYPE: DNA
<213> ORGANISM: Homo sapiens

<400> SEQUENCE: 153
aagaaggaac gactgataga gggtcgggag aggccgggtg ctgtggctca cgcctgtaat 60
cccagcactt tgggaggcca aggtgggtgg atcatctgag gtcaggagtt caagaccagc 120
ctggccaaca tggtgaaacc ccgtgtcaac taaaaataca aaaaaattag ccgggcatga 180
tggcaggtgc ctgtaatccc agctacttgg gaggctgagg caggagaatc acttgaaccc 240
gggaggcaga ggttacaatg agcagagatt gcgccactgt actccagcct gggtgactaa 300
gtgaaactct gtctcaaaaa aaaaagaggg tggggagggg agtatttgtt tctattggaa 360
taaaattata cactataaaa gttaaaacat tctatgtttg ggtattatgc tttcttt 417

<210> SEQ ID NO 154
<211> LENGTH: 93
<212> TYPE: DNA
<213> ORGANISM: Homo sapiens

<400> SEQUENCE: 154
gctgctcagt atgtagacct attgctgaac ccagagcgtt acactggcta taaagggacc 60
tctgcatgga gagtgtggaa cagcatctat gaa 93

<210> SEQ ID NO 155
<211> LENGTH: 221
<212> TYPE: DNA
<213> ORGANISM: Homo sapiens

<400> SEQUENCE: 155
cctgcacaac aaagtaagac cacttttctt aaaaaagaac aatgaaaaac ctgatataat 60
tgattttcct cttgtgattt tttagctccc ttaaagtata ttttaaatca tcatggttta 120
atatctgaat catggttttt cttctttatt ggttatttgg ttggttttct tgggaaaaga 180
ggttggtact agtccaattt gcacgtttgt agaggattct a 221

<210> SEQ ID NO 156
<211> LENGTH: 43
<212> TYPE: DNA
<213> ORGANISM: Homo sapiens

<400> SEQUENCE: 156
ctggggagga ctctaattcg acttctccac agcccttttt cca 43

<210> SEQ ID NO 157
<211> LENGTH: 60
<212> TYPE: DNA

<213> ORGANISM: Homo sapiens

<400> SEQUENCE: 157
caaagaagct ttcattgact gggcaagata tgatgattca cgggatcact tttgtgaact 60

<210> SEQ ID NO 158
<211> LENGTH: 186
<212> TYPE: DNA
<213> ORGANISM: Homo sapiens

<400> SEQUENCE: 158
tgctactagt agtgtatcag ttatctgttc tacaacttct ccagtgattg gtactatgat 60
ttttaaacag ctttactttg aggtataatg aaatatgata cactgcatat aaagtataca 120
gtttgatgtt ttgacatgtg tccacccata taacatcatc acaattaaga taccataggt 180
tgggtg 186

<210> SEQ ID NO 159
<211> LENGTH: 622
<212> TYPE: DNA
<213> ORGANISM: Homo sapiens

<400> SEQUENCE: 159
atgatctagg gactaggctt aagtcattgg aagattttgg ggtaaattgc cagtttatat 60
tctttgtcat ttttttctcc attgggttgg attttaaaat tattactgat ttgtaagcat 120
tctttatata atgtgataat tctttgttgg ctgtgttgtt aggatttgtc ctttaatttt 180
gcatatagtt ttttgttgtt gaacagaaat tattctttaa acttaaaaaa tttaagtata 240
atacacatat ggtggaatag aaaattctta agtgtaaagg tcaatgtaac tttacaaagt 300
gaacccaact ctatagccac catccagagc attatacttg ctgtccagat taccatgtgt 360
actttcctag tcattatcac cttccaaagt taaccgtgat tttgagatac tgacagagat 420
tagttttaac tgtttataaa tagaatgata tagaacatat tctgttgtat ctggcttctt 480
tttgttaaca tgtgtctgag attcattcat gtttttgggc atagtaatgt ttaattcttt 540
tttattggca catagtattc tatagtaaga atgtgccatg tttccattct gctcttgata 600
gcttatgctt tggggccatt tc 622

<210> SEQ ID NO 160
<211> LENGTH: 26
<212> TYPE: DNA
<213> ORGANISM: Homo sapiens

<400> SEQUENCE: 160
gagcaagcta ataaactggg agcaat 26

<210> SEQ ID NO 161
<211> LENGTH: 35
<212> TYPE: DNA
<213> ORGANISM: Homo sapiens

<400> SEQUENCE: 161
ttccggttgg aataaaagct gggcattcta ataag 35

<210> SEQ ID NO 162
<211> LENGTH: 129
<212> TYPE: DNA
<213> ORGANISM: Homo sapiens

<400> SEQUENCE: 162
atgttccagc tacatgcact tctcccattg gtaaacccta gattagattg gtaaactcta 60
ggttaatcgt gtgggccaaa aaaagctttc tagtaatcca aaattgccta cactttgtta 120
gagcagaag 129

<210> SEQ ID NO 163
<211> LENGTH: 79
<212> TYPE: DNA
<213> ORGANISM: Homo sapiens

<400> SEQUENCE: 163
taatctgaag cgaccttgtc ctttctgggc agaagatggc cactgttcaa taaaagactg 60
tcatgtggag ccctgtcca 79

<210> SEQ ID NO 164
<211> LENGTH: 119
<212> TYPE: DNA
<213> ORGANISM: Homo sapiens

<400> SEQUENCE: 164
ggttgcatac tgagcactac tttagcaagc ctggccagga atggtctctc tgcttaggtg 60
tgatatgtga gagagacttg aatgcggcga aagagtgagc cgtcataaga tctggagga 119

<210> SEQ ID NO 165
<211> LENGTH: 35
<212> TYPE: DNA
<213> ORGANISM: Homo sapiens

<400> SEQUENCE: 165
atgagaagtg ctgtcccttc cattcgtggt ggcag 35

<210> SEQ ID NO 166
<211> LENGTH: 308
<212> TYPE: DNA
<213> ORGANISM: Homo sapiens

<400> SEQUENCE: 166
gcagcctcag tggaaacctc aggtaagcct gtggggaatt cttaagatgg aataaccctt 60
ccgagttagt cgtccccatt tggcacgaga ggtataggcc tttatatctc tccatcagtt 120
ggtcattgga tgaaggccac cagaggaaat aaggatccaa tcttgggtaa ggtggttctt 180
ttcacccaag cttgtctacc tgcagcattt ccacaactga ggtaattaca tccccttat 240 tcctgaaggg tgatctgagt agtatgttac agtgtctacc acagtccact cgttgcacca 300
tgtatttc 308

<210> SEQ ID NO 167
<211> LENGTH: 778
<212> TYPE: DNA
<213> ORGANISM: Homo sapiens

<400> SEQUENCE: 167
tcctacctaa tgtgaaagag ccatgagaag gtttggggaa agaacatgcc agggaaaaga 60
tgtagaatac caagtaaatg gtcttgagat agaaataagc ttggtgtgtt gaataggcag 120
aaagctggta tagctggagt gaacgagagg gagagttgga aatataggta ggcaccagat 180
ttaaaaaaca gtaggaccgt attgaccatg taaggatgct ggattttatt ttaagcagga 240
taagaaacta ctgaagggat ttttgtgcaa aaaagactgt aagggtagaa gacaagaaat 300

```
agaggaacca tttaggagac tcttgtgtta gttcagataa aaacaataca gatttgcaat    360

agaatgctgc agctgaaaaa tgtagaaaat gatcaaatta gggttgtaca caaaaggcaa    420

caccagcaag cttttctgat gaattgagtg tgacgtatga tatagaaatg aaatcaagga    480

tgatgcctaa gttttgagtg cacatataca agcacaaatg tacatatatg taaaatcatg    540

accaaataga ttttattcca agaatgcaag gatgattctt gcattgatgt tgataatcat    600

caaaattcaa tatgtgctcc tgattttttaa aataataaga atgatgtata tttcttaaca   660

tgatgatttc agtcctaaca tcagcatagc taacacgtct tgcatatggg gaaacactag    720

aggaattctc acttaggtca ggaaccaaga caaggatacc cactatctgc attaactg      778
```

<210> SEQ ID NO 168
<211> LENGTH: 261
<212> TYPE: DNA
<213> ORGANISM: Homo sapiens

<400> SEQUENCE: 168

```
ggaaccactg ggattttgta tcaaattaac tattttccca tattttccaa actttatgta     60

agagttatat ttctgtccag gtacggtcat atgacctgtt ggaccaaaag aaggaaggac    120

accttggttg acagtctcat ttgcatgagt aaaagtggag tcattgtttc ccaaagggaa    180

attagggact gttacaaaag aaggaataat ggaacttgga taggcaaaag tgacaatgtg    240

gttcttggct actcaacaat c                                              261
```

<210> SEQ ID NO 169
<211> LENGTH: 399
<212> TYPE: DNA
<213> ORGANISM: Homo sapiens

<400> SEQUENCE: 169

```
ccgttcctga agtactgcaa taccaggtcg atgcgaggag tggatggagc aagctcctat     60

tccatctccc tactccaaaa atccatgtaa tatattgttc tcgggtagag gacatatcag    120

gtattaacag atacttcact tgatcttagc caaaaggccg agaagccatt ggagagacag    180

gtgcttcttt aaatttccac cactaaatct ataaatctaa gtgcatttgt agctgctttc    240

tcttgtttct tttctaccat aacattgaac tatatgaaat ttttactttt atatttcaaa    300

aatggttgaa catgccagtt tcatattgct caatgtaata cagtggggga agtgtttctt    360

gtatcaaaaa ccatctcttc acaagtggtc cagttcaca                           399
```

<210> SEQ ID NO 170
<211> LENGTH: 111
<212> TYPE: DNA
<213> ORGANISM: Homo sapiens

<400> SEQUENCE: 170

```
gttctggatg attgcttgtg tgatattgac agcatcgata acttcaatac ctacaaaatc     60

ttccccaaaa taaaaaaatt gcaagagaga gactattttc gttattacaa g             111
```

<210> SEQ ID NO 171
<211> LENGTH: 31
<212> TYPE: DNA
<213> ORGANISM: Homo sapiens

<400> SEQUENCE: 171

```
ctgagctgtg tctgccaagt ggcatcgcca g                                    31
```

<210> SEQ ID NO 172
<211> LENGTH: 233
<212> TYPE: DNA
<213> ORGANISM: Homo sapiens

<400> SEQUENCE: 172
ctgaccgtcc agtgcgggaa acatctgcga accgcccgca gggtgggggg acggcgacac 60
tccgggtaat ggcagtcaaa agaggaagat ggtgacggtc cccctgagct gttttcgttt 120
tttcctctcg gatgtgttaa gcggctggga gtgtggcggg agatgggacg ggcatgaacc 180
acctcggctg tcttgcgaag ggagcgagcg cccagagaaa cggtgacgtc ctt 233

<210> SEQ ID NO 173
<211> LENGTH: 102
<212> TYPE: DNA
<213> ORGANISM: Homo sapiens

<400> SEQUENCE: 173
atgagccaag gggtccgccg ggcaggcgct gggcaggggg tagcggccgc ggtgcagctg 60
ctggtcaccc tgagcttcct gcggagcgtc gtcgaggcgc ag 102

<210> SEQ ID NO 174
<211> LENGTH: 169
<212> TYPE: DNA
<213> ORGANISM: Homo sapiens

<400> SEQUENCE: 174
tgtcaactct gtgttggagc cagtagggag ctctgtgggt cctcgagcag gaaaatccca 60
tggcttaagc agtgtttcag gaagactggg atgttaggct ccggagctct gagcaagtca 120
gatgggactg ggagtcataa gaaggcttga ctgtggctag tgataacca 169

<210> SEQ ID NO 175
<211> LENGTH: 124
<212> TYPE: DNA
<213> ORGANISM: Homo sapiens

<400> SEQUENCE: 175
gtgaggacct ctgatggacc aggaaattgg aattctgcct gggaggcaag cccatggagg 60
ccctgatctg cttggacaga gagtagctcc cttcacctgt aaaatgagag tgaacgagct 120
ggtg 124

<210> SEQ ID NO 176
<211> LENGTH: 96
<212> TYPE: DNA
<213> ORGANISM: Homo sapiens

<400> SEQUENCE: 176
tcacagcatt cctgtaaaag gtatgaggtt cgccctgatt ggaccagccg aggtcacatg 60
cctacacatg agccaatcac agtggataaa ggactg 96

<210> SEQ ID NO 177
<211> LENGTH: 37
<212> TYPE: DNA
<213> ORGANISM: Homo sapiens

<400> SEQUENCE: 177
aaattgacat tccagacaag cggtgcctga gcccgtg 37

<210> SEQ ID NO 178

<211> LENGTH: 46
<212> TYPE: DNA
<213> ORGANISM: Homo sapiens

<400> SEQUENCE: 178
tgtgaagact ggacttaaac agctacacca ccagaagccg agagag 46

<210> SEQ ID NO 179
<211> LENGTH: 130
<212> TYPE: DNA
<213> ORGANISM: Homo sapiens

<400> SEQUENCE: 179
agatgctaat ccagcgtgcg tcctgacaga ggttgaaggg ggcttctcaa gtcccaggtc 60
cagcttggtg tggttcagct actcaagaga catctgctgc taatggatga gcagtcaacc 120
tggacgcagg 130

<210> SEQ ID NO 180
<211> LENGTH: 40
<212> TYPE: DNA
<213> ORGANISM: Homo sapiens

<400> SEQUENCE: 180
caaaaggaag gtgtcggcaa gatcgttttt ttctgagagc 40

<210> SEQ ID NO 181
<211> LENGTH: 35
<212> TYPE: DNA
<213> ORGANISM: Homo sapiens

<400> SEQUENCE: 181
tgaaacagga agctctatga cacacttgat cgaat 35

<210> SEQ ID NO 182
<211> LENGTH: 65
<212> TYPE: DNA
<213> ORGANISM: Homo sapiens

<400> SEQUENCE: 182
cacctctacc tgttgcccgc cgatcacagc cggaatgcag ctgaaagatt ccctggggcc 60
tggtt 65

<210> SEQ ID NO 183
<211> LENGTH: 82
<212> TYPE: DNA
<213> ORGANISM: Homo sapiens

<400> SEQUENCE: 183
tattttggtc atgggctggt ctggtcggtt tcccatttgt ctggccagtc tctatgtgtc 60
ttaatccctt gtccttcatt aa 82

<210> SEQ ID NO 184
<211> LENGTH: 70
<212> TYPE: DNA
<213> ORGANISM: Homo sapiens

<400> SEQUENCE: 184
aaaggctgca gtcaccagca tcttttccaa ccttaatgaa ctgtatcctc aaaagaacac 60
tatcagactg 70

<210> SEQ ID NO 185
<211> LENGTH: 160
<212> TYPE: DNA
<213> ORGANISM: Homo sapiens

<400> SEQUENCE: 185
gctctgccga cttccagttc tggaacaaga tggttaaact catttttccc tgctctgctc 60
ctctaaatac aactaagtac cttggaaact attcagcaga caatgataaa gggctctgaa 120
agctagaaga aaaggtgtac ttgcaagaaa cctcaggact 160

<210> SEQ ID NO 186
<211> LENGTH: 32
<212> TYPE: DNA
<213> ORGANISM: Homo sapiens

<400> SEQUENCE: 186
gcttctgcag tttgccttgg agtctgggct gt 32

<210> SEQ ID NO 187
<211> LENGTH: 91
<212> TYPE: DNA
<213> ORGANISM: Homo sapiens

<400> SEQUENCE: 187
taagaatgta gatgccggtt gcaccttctg ttgtcttgga agagactgca gtgcttggct 60
ggaaaataag ctgctcggga ctcctctgag a 91

<210> SEQ ID NO 188
<211> LENGTH: 384
<212> TYPE: DNA
<213> ORGANISM: Homo sapiens

<400> SEQUENCE: 188
cctacccatg aggaacaagc ctgtgggggg actgatatta tcacttctgt catcaagaaa 60
taaggccgca ggcatccctg aatatagagc atttattaat cgaactgtga aaatgaaaca 120
cagacagtga tgacagctgg aagttggcca atgtcctgtt gtcatattgc cctcagccta 180
gggactggcc tgtggctcac tgaccctgtc tcccactctc cacctctcat cagcaactgg 240
acctggtgca cctggtctac ctcatgtcca gtgttttccg cagtacctga ctggtatccc 300
cacccttggt tgttgtgtgg tgagctcgtc cctatgttgg caagttactt aattcctagg 360
tgtcccgcct tcctcactgt aaaa 384

<210> SEQ ID NO 189
<211> LENGTH: 172
<212> TYPE: DNA
<213> ORGANISM: Homo sapiens

<400> SEQUENCE: 189
ccctggcatc atattgggac ttgttaaggg ctgaattgtg tcccatccca aattcgtatg 60
gtgccacccc aactccagta ccttggaatg tgaccgtatt tggagaaagg gtctctgaag 120
aggtaattaa ggtaaaatga ggtcatatgg gtggcctcta attcaatatg ac 172

<210> SEQ ID NO 190
<211> LENGTH: 133
<212> TYPE: DNA
<213> ORGANISM: Homo sapiens

<400> SEQUENCE: 190
ttgctgatat acttacaaac tggtaaacaa tgctctttaa tcaacaattc ataatctggg 60
tcagcgattt ttatctccat atttgctcat actgtatgac atcaatattt tatattggct 120
tgcccataac tta 133

<210> SEQ ID NO 191
<211> LENGTH: 338
<212> TYPE: DNA
<213> ORGANISM: Homo sapiens

<400> SEQUENCE: 191
gccagttcgc ctttcgcttt ctaaaatcat cttgctggag agaacggtta tcaaatccca 60
tccactgccc atgtaaaata aataccattc agaaaagcgt ggcatggatg gccatacttc 120
tgatgggttt ataactgtag attgcatacg atcccaacgt gaagcctgaa atacgacatt 180
caacgtcagg cttattccag gctactgctg tggctacttt tgtaattcaa ccagtggggc 240
gttttaggct aacgtatatt gcctctaagc tgataagcat tttcctgatc ccaggcccct 300
tctaaaattg aacacacacg ttcagctggg gacaccta 338

<210> SEQ ID NO 192
<211> LENGTH: 25
<212> TYPE: DNA
<213> ORGANISM: Homo sapiens

<400> SEQUENCE: 192
tcagttttgt gcttacagtc ccgca 25

<210> SEQ ID NO 193
<211> LENGTH: 220
<212> TYPE: DNA
<213> ORGANISM: Homo sapiens

<400> SEQUENCE: 193
tgggaggcca aggtgggcgg atcatgagct caggggttca agaccagcct ggccaacgta 60
gtgaaacccc gtctctacta aaaacaaaaa aattagctgg gcatggtggc gcacacctgt 120
agtcccagct actcgggagg ctgaggcagg agaattgctt gaacctggga ggcagaggtt 180
gcagtgagct gagatcgctc cactgcactc cggtttgggc 220

<210> SEQ ID NO 194
<211> LENGTH: 33
<212> TYPE: DNA
<213> ORGANISM: Homo sapiens

<400> SEQUENCE: 194
ctggggacac tatggcccca tcctagcctg gtg 33

<210> SEQ ID NO 195
<211> LENGTH: 49
<212> TYPE: DNA
<213> ORGANISM: Homo sapiens

<400> SEQUENCE: 195
gaaaagattt ttattcgtgt ctacatcagt gtgaaaggct tcatcctgg 49

<210> SEQ ID NO 196
<211> LENGTH: 135
<212> TYPE: DNA
<213> ORGANISM: Homo sapiens

<400> SEQUENCE: 196
tggacttctc tttagctggg gtggtggctg ctggagaggg ccctgcttgc tcatctctgc 60
cagcttccca gtccctgcaa ccagcagtgg ccagcctctg gccaccccca tgaaagcaca 120
taaaagggtt gggga 135

<210> SEQ ID NO 197
<211> LENGTH: 69
<212> TYPE: DNA
<213> ORGANISM: Homo sapiens

<400> SEQUENCE: 197
gggaacaaaa tgtctgctca aaccatgaca aaattggcca caatttgccg attgggctga 60
taacaaaag 69

<210> SEQ ID NO 198
<211> LENGTH: 80
<212> TYPE: DNA
<213> ORGANISM: Homo sapiens

<400> SEQUENCE: 198
aggtcgaggc actgtcctag cttgtgacct gctcccatac ctattttctc agggtggaag 60
cagacgctcc aactcccaca 80

<210> SEQ ID NO 199
<211> LENGTH: 52
<212> TYPE: DNA
<213> ORGANISM: Homo sapiens

<400> SEQUENCE: 199
agacccaaag cctgtaggaa gtatagcagg cctcacccaa taccctgcag tt 52

<210> SEQ ID NO 200
<211> LENGTH: 25
<212> TYPE: DNA
<213> ORGANISM: Homo sapiens

<400> SEQUENCE: 200
cctcaagaga acatggagtc ctttg 25

<210> SEQ ID NO 201
<211> LENGTH: 56
<212> TYPE: DNA
<213> ORGANISM: Homo sapiens

<400> SEQUENCE: 201
tcagtggcct ccgagtaacc cacctgctcc agtctgcaga tttccatctc actgac 56

<210> SEQ ID NO 202
<211> LENGTH: 56
<212> TYPE: DNA
<213> ORGANISM: Homo sapiens

<400> SEQUENCE: 202
caaaggcttc tcttgctggc tgagaattgt tggggagctc cctgcccacg gagggc 56

<210> SEQ ID NO 203
<211> LENGTH: 45
<212> TYPE: DNA
<213> ORGANISM: Homo sapiens

<400> SEQUENCE: 203

```
gggttcctgt cggaatcttg gagctcatcc cccaaacttg agatt          45
```

<210> SEQ ID NO 204
<211> LENGTH: 148
<212> TYPE: DNA
<213> ORGANISM: Homo sapiens

<400> SEQUENCE: 204

```
aaatgcttag ggagacagtt cacagatata tatgtacttc acagggcaca atttaatcca   60
taaatcaatc atggatcact gctaaagaaa acaaaatatg ctgccactaa tttgccacca  120
ccctgtgagc atgattggat gatgttta                                     148
```

<210> SEQ ID NO 205
<211> LENGTH: 116
<212> TYPE: DNA
<213> ORGANISM: Homo sapiens

<400> SEQUENCE: 205

```
aggcagcctt ttctgtcaca acacaacgct gagccggcag cctggctctg tcaggatctg   60
gggctccagc gcccgagaag cccagcctcg ccggcggcca agttcaccgc gaggcc      116
```

<210> SEQ ID NO 206
<211> LENGTH: 46
<212> TYPE: DNA
<213> ORGANISM: Homo sapiens

<400> SEQUENCE: 206

```
ccgaggaggc ggagcatgga actcgacagt taaaacattt aagaga                  46
```

<210> SEQ ID NO 207
<211> LENGTH: 532
<212> TYPE: DNA
<213> ORGANISM: Homo sapiens

<400> SEQUENCE: 207

```
tggcagctcc atctacacag tgtcgggcta ggcatgggag cattctgggc caggagaaag   60
gggattggat cctggatggt gggaaccgca ggtgtccccc tccacgtgcc tgggtccaag  120
actgctctgc tctggacctt ctacgccttc agaggtacaa gttgcagtgc tacccttgct  180
gaacctacaa ccctgttcaa gtgacaactt ctctgagtct catacgagga tattgaaaga  240
accttctgca cagggctgtt gtgaggatta accgtaataa tacaagaata tctggcactt  300
gcattcagca actcaccgct tacttgttca accaggtaaa aaggttctga tcccagtgtt  360
gcaggacaga aagacctccc cctctgtagc tgcagatgtg acccagcaca gaaaaaatgg  420
caggtgaaag acaggcagga agagcaacta agaaggtggg aggcacctcc ataagatgcc  480
tgaggccatg gggatgaccg ttcacagagc tagtccctcg agcaatgtgt ta          532
```

<210> SEQ ID NO 208
<211> LENGTH: 854
<212> TYPE: DNA
<213> ORGANISM: Homo sapiens

<400> SEQUENCE: 208

```
tgtggctcca agttccgtag gactcactag tctttttttc cctagagggt cttgccattg   60
agaggcaggt gatgtgctgt ttcagaaaac aaaattggga catgtcctga tatgacatcc  120
atcaaatata tacagatagg tgtcacagcc cccgaaaaag cttatctctt ctaggccaca  180
catagctatt tcctccaact gtgtcagaca ttacaaagtt tctagcaatc aaaacaagtc  240
```

aaatgccatt ctcaggaccc gttggaggat tttttgcttt gttttggctt tgtacggtat 300
ccataccatt ttccaaattc ttttgtcctt acatattttg tttttcttaa aaaaaaaaaa 360
atcacctata atcccatcac cagacaaaac cactagaaag aaaccaacat tttagccatg 420
tttttctgta tataaaaaaa gtgtgtgtgg aatttttcat aacaatattg ggaccatgac 480
atctatcaca ttttttatta ggaaatggcc ttcaacaata tgcatttaac aatatgcttg 540
atgtctgtgt aatatttcat ctaacaaata tatcatgatt tatttaagta ttccctgatt 600
gcttgcttct aactagaaaa aacaattttt ctaagtgtca ccactgggtt agagtaatct 660
cagccaatcc tcctaatagc actgtgagac cagagttatg ataatcttca gttaatggac 720
aagggacatg atggtgtgga aggataaata aactacccaa agacaactag ctagtgagac 780
cagcatggac agtcaagccc agtgcatgta atctgtgctc ccctgcactg ttgctcatat 840
acttggaccc ttgc 854

<210> SEQ ID NO 209
<211> LENGTH: 238
<212> TYPE: DNA
<213> ORGANISM: Homo sapiens

<400> SEQUENCE: 209
caacccaggg tccttgcaga gagattgatc tgccagcagt ggcatcagca gcaatagtag 60
cagcagcaaa gccctggaca gtcctggccc ccagtccaca acttagacac agcacatggc 120
ctaattcacc cacagaagca gccactgtga agccctgtgt ctccccagac tccatccagt 180
ggcataagga gacccaggcc ctgcagcttc ctccccatca tggaaggctg tccatcta 238

<210> SEQ ID NO 210
<211> LENGTH: 168
<212> TYPE: DNA
<213> ORGANISM: Homo sapiens

<400> SEQUENCE: 210
acttaaaata ggagtgaggt gagaggggca gctgggctca tggacgtcaa gtggacagtt 60
tctcagctgg tatttcctat atttcctgtt ttggacagca ggttcctgcc cttctaagct 120
gggggtaggg gtgagggagt gtatgttaaa aagctctgtg gacttgct 168

<210> SEQ ID NO 211
<211> LENGTH: 216
<212> TYPE: DNA
<213> ORGANISM: Homo sapiens

<400> SEQUENCE: 211
ggtattacct gatcccaact tggcaccaaa agacagccaa catagactca ttcctcctgc 60
ttcctggtga gcctggtatt ctcctccact tccactgaca gacatgtagg gtgactgggt 120
ggtatcaaca ataggaacca catcataaca ggcagcctag tttgggaagc actcttggtc 180
tccgtaggcc tgagactcct tttgcccatc tagagg 216

<210> SEQ ID NO 212
<211> LENGTH: 374
<212> TYPE: DNA
<213> ORGANISM: Homo sapiens

<400> SEQUENCE: 212
agactgaccc tacaataaat gcttaagaga gtcctacatc tggaagcaaa agggctatat 60

-continued tcaccatcat gaaaacccta aagtataaaa ctcattggta aagcagacac acaaataaga 120
aagagaatgg aaccacatgt tatcattaca gaaaaccacc aaactgcaaa gataaacaaa 180
ggaaagaaag aaagaaagaa aggaaggaag aaaggaagga agaaaaagga ttatttaaaa 240
ttatcagaaa acaattgaaa tgacaggaat aagacctcac ctatcaataa caactttttt 300
aaatggctta aatttcccag ttaaaagata tagactggct gaatggattt taaaagtgac 360
ctaactctat gcta 374

<210> SEQ ID NO 213
<211> LENGTH: 54
<212> TYPE: DNA
<213> ORGANISM: Homo sapiens

<400> SEQUENCE: 213
agaagcttgt tttgagctca ttcaatatgc atcaggtggc ggtaacatct ggag 54

<210> SEQ ID NO 214
<211> LENGTH: 92
<212> TYPE: DNA
<213> ORGANISM: Homo sapiens

<400> SEQUENCE: 214
agggtgctgg ttctgagcca actttgcatg gaaggcccag cagaccacgc tcattactta 60
cagccagcat catcggggaa ctccggcaca ga 92

<210> SEQ ID NO 215
<211> LENGTH: 106
<212> TYPE: DNA
<213> ORGANISM: Homo sapiens

<400> SEQUENCE: 215
gcggccctag tccactctca tgatgcctcc attaatcccc cggtcaggga ccttccagcc 60
ctgcccacag cagtcgatgc cttcagtgca tctcagtctt ccaccc 106

<210> SEQ ID NO 216
<211> LENGTH: 100
<212> TYPE: DNA
<213> ORGANISM: Homo sapiens

<400> SEQUENCE: 216
tcaggtcatc cgctccatgg aggtccccgt tcctaccttg gccttgcctt tccccctgca 60
tgtaaccttg gtgaactttt cacaagagtc tgcgcagtct 100

<210> SEQ ID NO 217
<211> LENGTH: 34
<212> TYPE: DNA
<213> ORGANISM: Homo sapiens

<400> SEQUENCE: 217
taagcagatt aatgccgagg aaaagccttg gtga 34

<210> SEQ ID NO 218
<211> LENGTH: 100
<212> TYPE: DNA
<213> ORGANISM: Homo sapiens

<400> SEQUENCE: 218
cccgtggaga gagccccgct ggtgaggaag cacggggacc ctgctgcagg gctggtggag 60
ggctccttct gcagacttct gagcttggag cacagatggg 100

<210> SEQ ID NO 219
<211> LENGTH: 32
<212> TYPE: DNA
<213> ORGANISM: Homo sapiens

<400> SEQUENCE: 219
ctggctcctg cactactatg gccttttggc tc 32

<210> SEQ ID NO 220
<211> LENGTH: 232
<212> TYPE: DNA
<213> ORGANISM: Homo sapiens

<400> SEQUENCE: 220
ttccaaggtc tcacaagagt ttgcctcctc tcattgccat gtgaagacct ctgtggggga 60
acaatgcatg ggttcttggg gtattatagg ggactacaga gaagtgtcac ctccacccaa 120
cagcctgatt cagtctactc ctcaggagga acacaaagtg gtctctctag tgccatgaaa 180
ccccaaaaag tgtcaaccag tattaaaggc ctgcctgata tacaaccctc ga 232

<210> SEQ ID NO 221
<211> LENGTH: 91
<212> TYPE: DNA
<213> ORGANISM: Homo sapiens

<400> SEQUENCE: 221
atgaagctag gcccccctgt cctgacagct ttccacccct tccctgcccc tctcaccctg 60
ctttccaggg gcaatgcacc tccccacttc t 91

<210> SEQ ID NO 222
<211> LENGTH: 70
<212> TYPE: DNA
<213> ORGANISM: Homo sapiens

<400> SEQUENCE: 222
ccagacacca ctggcctaca tcaaactcca ggccacagat ggaaatagga ctgagatccc 60
tggacctggg 70

<210> SEQ ID NO 223
<211> LENGTH: 103
<212> TYPE: DNA
<213> ORGANISM: Homo sapiens

<400> SEQUENCE: 223
agatcaggtg gattgaggat gtcactgcca tcccctccaa aagcacctgc aggaaggggg 60
ttgccatggt caccatctgt gaacaggact cctcaaaatg ttt 103

<210> SEQ ID NO 224
<211> LENGTH: 80
<212> TYPE: DNA
<213> ORGANISM: Homo sapiens

<400> SEQUENCE: 224
tcaaggtggc cttgcgcttc accgaggagg tgtcattacc aaacgtgctg gacattggct 60
acctacggaa gaaagattaa 80

<210> SEQ ID NO 225
<211> LENGTH: 130
<212> TYPE: DNA

<213> ORGANISM: Homo sapiens

<400> SEQUENCE: 225
ccttcctacc tggtagtagc actgacatcc tcttcatcca ctggaagctt ccagatcctg 60
gcccccacaa cccattctct ccccataggg cttccacaga aacacaacgt gtactgtgtg 120
ccaaatgact 130

<210> SEQ ID NO 226
<211> LENGTH: 106
<212> TYPE: DNA
<213> ORGANISM: Homo sapiens

<400> SEQUENCE: 226
ttatacatgg cctcactgtt ggggaggcag tagggagtgt tggagaccag ggtcaggact 60
agggctaggg caaggctagg aaggtgccca ggatgcatgt tttaag 106

<210> SEQ ID NO 227
<211> LENGTH: 67
<212> TYPE: DNA
<213> ORGANISM: Homo sapiens

<400> SEQUENCE: 227
taagaaaagg atcgtggtgg tagcaggaaa taagacagaa attttccatg gggctccag 60 gtctgaa 67

<210> SEQ ID NO 228
<211> LENGTH: 40
<212> TYPE: DNA
<213> ORGANISM: Homo sapiens

<400> SEQUENCE: 228
gtcttttctt gaacaggaac ttgcatactc aaaaacaaca 40

<210> SEQ ID NO 229
<211> LENGTH: 117
<212> TYPE: DNA
<213> ORGANISM: Homo sapiens

<400> SEQUENCE: 229
gatcccgtgg aaacacagca ccggaggata tgggataaga gacaacagag aggagtggtg 60
cttcctgaat ttaggaaaca tagctgctac tttgggccct ctagatactt gaaagaa 117

<210> SEQ ID NO 230
<211> LENGTH: 85
<212> TYPE: DNA
<213> ORGANISM: Homo sapiens

<400> SEQUENCE: 230
agggaagcca ggttgttcat ggacattcag tggaagaatt aaggcaatta aatgttaagt 60
tttgcagggc tggtcgacaa gagaa 85

<210> SEQ ID NO 231
<211> LENGTH: 29
<212> TYPE: DNA
<213> ORGANISM: Homo sapiens

<400> SEQUENCE: 231
gtgtgtattc tccattggtc acaatgcac 29

<210> SEQ ID NO 232
<211> LENGTH: 65
<212> TYPE: DNA
<213> ORGANISM: Homo sapiens

<400> SEQUENCE: 232
gacaagaata actccccact gggactggag gagaggaagg cacatggggg cccttggcag 60
ggtgg 65

<210> SEQ ID NO 233
<211> LENGTH: 125
<212> TYPE: DNA
<213> ORGANISM: Homo sapiens

<400> SEQUENCE: 233
tcagtcacgt ctgcgccaga gctttgatga cccacctgtc agccacacta agggccctgc 60
catgaataag gcctccgtca ctgaggatcc tgtacccctc tgccataaac tcagtgacct 120
gactg 125

<210> SEQ ID NO 234
<211> LENGTH: 205
<212> TYPE: DNA
<213> ORGANISM: Homo sapiens

<400> SEQUENCE: 234
gaactcccac tgtataattg ctaaacacaa tgacagctat aattgaggca ctgaaggaag 60
gtcaggggag cccaggaggg cggggctgct gctgcctgct gagctgggag ggttggtggc 120
accccttgcc ctgggttgcc atagcagata tcataatcaa ttacggccgt ctttcatgag 180
gaacctggat ctttcccaag gaatc 205

<210> SEQ ID NO 235
<211> LENGTH: 91
<212> TYPE: DNA
<213> ORGANISM: Homo sapiens

<400> SEQUENCE: 235
aggggcggga ttctgccagc cgcggctgcc gctggagccg gtgtccgggc tggtgatggg 60
gttaattccc tttcgtaaga ctcttacttg c 91

<210> SEQ ID NO 236
<211> LENGTH: 178
<212> TYPE: DNA
<213> ORGANISM: Homo sapiens

<400> SEQUENCE: 236
ctgcctccgc ggctgctctt gcagccccag ggactcggga gccagccaca gcaggcctgc 60
caagagcgtg gtactgctct ctcgtgtggc tggcgccggt gccccgggct cccccggccg 120
ccccacggcc gcatcccctg gccttgcacc aagagaattt tcagcttcga ccggttgg 178

<210> SEQ ID NO 237
<211> LENGTH: 122
<212> TYPE: DNA
<213> ORGANISM: Homo sapiens

<400> SEQUENCE: 237
cccgggatca gatttacaca cgttttgatt cctgagcctt aggctgccaa caaatctttg 60
tgggctttga agttttttgg tgttttgttt tcttttgttg ctgtgactag gtgcaaaggg 120
tg 122

<210> SEQ ID NO 238
<211> LENGTH: 192
<212> TYPE: DNA
<213> ORGANISM: Homo sapiens

<400> SEQUENCE: 238
ttgggttctg aggaaacatc tgagttttga tcatttcttc agggtttgag aagactatgg 60
tggcttaatg atcttctgta ttccataact agtacaccta gttacagaat tgacatagat 120
acattcaggt cctggaggaa atttgtggta tctattaaaa aaatgaaaat tgccagtcat 180
gtagtagtca cc 192

<210> SEQ ID NO 239
<211> LENGTH: 360
<212> TYPE: DNA
<213> ORGANISM: Homo sapiens

<400> SEQUENCE: 239
tattatgcag aagatgtgca ttgccatgcc ttgcaagtaa tagggttttt tttcttcttt 60
tttgaactgg tactttaata tacctaatta catccatttg agttagtatt aagttttaat 120
ttctcagaaa taaagtagtg aaaattggta gcagttttgt ttttcccatt cttgagaata 180
ttacagtgat aaacaaggct tgataggttt gtaaaatact attgctattt gaattaaaaa 240
atttcactat tgactttcca tattctattg taaataagtt ggggaattag tgtgtcaagg 300
gggtgtggta acaaatggta atgtaatttt caaattgcta ttgcagcacc aaaccacaga 360

<210> SEQ ID NO 240
<211> LENGTH: 499
<212> TYPE: DNA
<213> ORGANISM: Homo sapiens

<400> SEQUENCE: 240
tgagacgtta gcatcaacat gactgtatat catttccaga atttaattca attagttatt 60
ggctgaggga tgaaatagag atgaaactaa atcctggcct caaactagtt ttgtacctta 120
ttttccagca atttggtttt tttatatcta gattttatct ttactatttt ccctcatctt 180
acccattctt agtctccata cacacctatt aactttaatt tccttttctg agaattttga 240
aagccctata gtttatgatc ttttttccct ctttgccttg tgaattttat atttgtgagt 300
tttttccaaa tttctacctg tcagctcact tctttaggca aggtgtaagg tttttgagcc 360
cccttatttc attttttatt tttttaagag acagggattc accctgtcac ccagactgga 420
gtgcagcgac aggatcatag ctcaccacag ccttgaactc tgaggctcaa gggagcttcc 480
catcttatgc tcccaagta 499

<210> SEQ ID NO 241
<211> LENGTH: 338
<212> TYPE: DNA
<213> ORGANISM: Homo sapiens

<400> SEQUENCE: 241
gtgtgcagtg gaccggtgaa catcaccacc tgagctctgc ctcctgtcag atcagcggtg 60
gcattagatt ctcataggat tgcaaacctt actgtgaact gcgcatgcaa gggatctggg 120
ttgcgtgctt cttatgagaa tctaatgcct gatgatctga ggtagaacag tttcatccca 180
taaccatcct cctcaccgcc tgcaccatct ggggaaaaat tattttccac caaacaggtc 240
cctggtgcca aaaaggttgg ggactgctgc tcttaggaca gaaagaaaga agttccataa 300
ctagagtaaa atatcacctt acagtatgag gtagctta 338

<210> SEQ ID NO 242
<211> LENGTH: 242
<212> TYPE: DNA
<213> ORGANISM: Homo sapiens

<400> SEQUENCE: 242
gcaatcagaa cacctacagc atttatcaac taagttcact gtcttatatg ggtgtgattt 60
gtggtcccct aaaacaatta cagtggtaaa gatcactgat tgcagatcac catcaccaga 120
cataataatg aaagagtttg aaatattgca agaattacca aactattaca cagagacatg 180
aagtgagcac atgttgggaa aatggtactg atcgatatgc ttgactcaag agttgccaca 240
aa 242

<210> SEQ ID NO 243
<211> LENGTH: 155
<212> TYPE: DNA
<213> ORGANISM: Homo sapiens

<400> SEQUENCE: 243
aagtgatagg attgttgccc acccaggacg ttatggattc actcagcatt cattcatgaa 60
atattcgttg ataatttact atgtgccgtg tactgcctat ataaagcaga gagtacttgc 120
ccttatggat tttattttct agtgagtgag acaaa 155

<210> SEQ ID NO 244
<211> LENGTH: 158
<212> TYPE: DNA
<213> ORGANISM: Homo sapiens

<400> SEQUENCE: 244
agaaactaaa tcactgcctt gtacaataaa aagctctatg ttggggtgat cagacccaac 60
accaggtcat gggggcgatg agtccggtgg agtcaaagga atgagaaaaa gacagtttga 120
gagagaaagt gggaccgggg agcctacgct atttattg 158

<210> SEQ ID NO 245
<211> LENGTH: 131
<212> TYPE: DNA
<213> ORGANISM: Homo sapiens

<400> SEQUENCE: 245
tgaaaattgg gccttaagca cataaaaagt tttaagttca tacagagaaa taagctcacg 60
cctgtaatcc caacactttg ggaggccaag gtgggtggat cacctgaggt ttctcaacct 120
cgagaccagc c 131

<210> SEQ ID NO 246
<211> LENGTH: 152
<212> TYPE: DNA
<213> ORGANISM: Homo sapiens

<400> SEQUENCE: 246
gcacttctct gactatagtt ttttatatga ctttgactct cagaaccctg gtaatttttt 60
acgtagtctc cagaaataac ataaaataac ttagatgttg gcaagtgtgg agaaaggagc 120
ccaaaatgta atgcaagcac taacagatga ac 152

<210> SEQ ID NO 247
<211> LENGTH: 92
<212> TYPE: DNA
<213> ORGANISM: Homo sapiens

<400> SEQUENCE: 247
atgccttggt cgttttgtgt ccctgggctg ttggcagtgt gactctgcta cagaatacca 60
cttggggaga tcagcttact cagtacaggg tg 92

<210> SEQ ID NO 248
<211> LENGTH: 195
<212> TYPE: DNA
<213> ORGANISM: Homo sapiens

<400> SEQUENCE: 248
cagatctttc ttcacatcgt gcaggtaacg tatgagcatt gtctgatgga tccttacaac 60
attcctgtat gcttttggaa agtatgatct ttgtttaaca aaatgggaaa cagaggcaca 120
tgctataccc agctatcaca gaaaacaata gttagaatcc agaaaacata ctcatctggt 180
ttagtgtgtt gccca 195

<210> SEQ ID NO 249
<211> LENGTH: 34
<212> TYPE: DNA
<213> ORGANISM: Homo sapiens

<400> SEQUENCE: 249
agcaggcact cccaatgcca gactaatcag ctgg 34

<210> SEQ ID NO 250
<211> LENGTH: 50
<212> TYPE: DNA
<213> ORGANISM: Homo sapiens

<400> SEQUENCE: 250
gagctctata gaggagcaat gcagagcatc agtttacagg tactatggaa 50

<210> SEQ ID NO 251
<211> LENGTH: 30
<212> TYPE: DNA
<213> ORGANISM: Homo sapiens

<400> SEQUENCE: 251
aatcttgcca tacttgcaca gctgaccaac 30

<210> SEQ ID NO 252
<211> LENGTH: 56
<212> TYPE: DNA
<213> ORGANISM: Homo sapiens

<400> SEQUENCE: 252
attcaactgc tagagaatgt gaagtttcac attttaagcc atcaaagaac cattgg 56

<210> SEQ ID NO 253
<211> LENGTH: 95
<212> TYPE: DNA
<213> ORGANISM: Homo sapiens

<400> SEQUENCE: 253
tgtgccaaaa cagtcctgaa tgttcgtgtt ggccttaatg aaccacccct tagtgactca 60
gtcaccattc tccacaagcc ctacagccat cccgg 95

<210> SEQ ID NO 254
<211> LENGTH: 277
<212> TYPE: DNA
<213> ORGANISM: Homo sapiens

<400> SEQUENCE: 254
cctcagctgc aaactatgta atactgcttt tatggggatt aaatgaatta atacacttaa 60
agcattggga gtagtgctta gtaaataata aataactctt taagggtttg ctgttaatat 120
taccagtttc acagcacata ttgcaatcag ttattatctt gtatattttg tctctgcact 180
agaatgtaag cattttaggt tctaggatcc catctgcttg gttcactcat gtatccctat 240
tacctagaac agtgctctgt acatagtatc cagtctg 277

<210> SEQ ID NO 255
<211> LENGTH: 33
<212> TYPE: DNA
<213> ORGANISM: Homo sapiens

<400> SEQUENCE: 255
gcgcccagcc taatactaag cttctaatct taa 33

<210> SEQ ID NO 256
<211> LENGTH: 160
<212> TYPE: DNA
<213> ORGANISM: Homo sapiens

<400> SEQUENCE: 256
gtccattcca gtccgggaat ctacagtggt gacaaggaca tgggactcct cctgccagat 60
tacagatggt tcactacagt tgacatcctg gctgacaact gtgaaaaaga accttggatt 120
attttatttt atttttgtgg gacaccacaa tcccaaatcc 160

<210> SEQ ID NO 257
<211> LENGTH: 32
<212> TYPE: DNA
<213> ORGANISM: Homo sapiens

<400> SEQUENCE: 257
gcttcaagct ccctgtagaa ttcgaaaata ac 32

<210> SEQ ID NO 258
<211> LENGTH: 28
<212> TYPE: DNA
<213> ORGANISM: Homo sapiens

<400> SEQUENCE: 258
gatgtctgat actgttactg taaaagat 28

<210> SEQ ID NO 259
<211> LENGTH: 107
<212> TYPE: DNA
<213> ORGANISM: Homo sapiens

<400> SEQUENCE: 259
aagtgaaaga tacaaccaga gttgaaaatc ttatcaaatc agaaaactat gggaagattt 60
tggtagagaa gaatgaacat tgtattgaga acaatataga tttgcag 107

<210> SEQ ID NO 260
<211> LENGTH: 27
<212> TYPE: DNA

<213> ORGANISM: Homo sapiens

<400> SEQUENCE: 260
tcatacaaaa ctcacttctc aaaattc 27

<210> SEQ ID NO 261
<211> LENGTH: 138
<212> TYPE: DNA
<213> ORGANISM: Homo sapiens

<400> SEQUENCE: 261
tcagtcagga aacgaagcaa ggcttgggct gagtgaattt tctattctac agggtatcca 60
aagaggtcct ttgttggcat ttaacaggcc ggtggacttg gtctggagca tcccggattg 120
cttctcgcac ctgtctgg 138

<210> SEQ ID NO 262
<211> LENGTH: 141
<212> TYPE: DNA
<213> ORGANISM: Homo sapiens

<400> SEQUENCE: 262
caacaaggtg ggtccaaagt agtcagactt cttatgtggc agctcagggg tcccagagag 60
aatgttccaa gaaagccaag caaagctgca aggtttcttt tgacataggc ccagaagttc 120
cagaacgtta cttcagctat c 141

<210> SEQ ID NO 263
<211> LENGTH: 31
<212> TYPE: DNA
<213> ORGANISM: Homo sapiens

<400> SEQUENCE: 263
catagcgact gtaacgattt ggaaggaggg a 31

<210> SEQ ID NO 264
<211> LENGTH: 38
<212> TYPE: DNA
<213> ORGANISM: Homo sapiens

<400> SEQUENCE: 264
caatgccacg cttcttcgac aatgaaggca gtacataa 38

<210> SEQ ID NO 265
<211> LENGTH: 207
<212> TYPE: DNA
<213> ORGANISM: Homo sapiens

<400> SEQUENCE: 265
aatcttagct atttcctgtt tgtcaaacaa agattaaaag catgtatgtg gcaaagcgtg 60
gtggctcctg ccagcacttt gggatgccga ggcaggaggt ttacctgagc ccaggacttt 120
gagaccagcc tggacaacac acgaagactt tgtctctaca aaaataaaaa taaaaaaatt 180
attcatgcgt cacggtacat acctgta 207

<210> SEQ ID NO 266
<211> LENGTH: 26
<212> TYPE: DNA
<213> ORGANISM: Homo sapiens

<400> SEQUENCE: 266
cggccattgc agtcatttgg acagac 26

<210> SEQ ID NO 267
<211> LENGTH: 88
<212> TYPE: DNA
<213> ORGANISM: Homo sapiens

<400> SEQUENCE: 267
caagctcaaa gttaaagcta gttcggagcc ttgcagtgtg tgaagaatct ccaccacccc    60
ctgcaccaga gatatcacag gagaacca                                       88

<210> SEQ ID NO 268
<211> LENGTH: 148
<212> TYPE: DNA
<213> ORGANISM: Homo sapiens

<400> SEQUENCE: 268
tgagtgtaag gaagttgcca gtgtctttgg taaacaagac agagagtgca aaaagcaagt    60
gtttgtcatc ctagtaaaaa ctgccagtgt gcatcattta ccctatatta tgaacacaaa   120
ttttaactgg tatgatgaat taagaaga                                      148

<210> SEQ ID NO 269
<211> LENGTH: 97
<212> TYPE: DNA
<213> ORGANISM: Homo sapiens

<400> SEQUENCE: 269
aattcagatc cagttaacac aatcatttga gaaagaagag aagccctcaa aagatgaagc    60
agaaaaagaa aaggccagtg ataagttgcc cagaaaa                             97

<210> SEQ ID NO 270
<211> LENGTH: 56
<212> TYPE: DNA
<213> ORGANISM: Homo sapiens

<400> SEQUENCE: 270
attccagtca agaatacact gattcaactg gcatagatct acatgaattt ttagta        56

<210> SEQ ID NO 271
<211> LENGTH: 299
<212> TYPE: DNA
<213> ORGANISM: Homo sapiens

<400> SEQUENCE: 271
cctctataga tgcaaacgtt tttaagttat ccacatagac attttttaac tgtacggttt    60
aatggttttt agtatattca atatacagat aggagcacta tcaccacagt tatagaactt   120
tttcattgcc ccaaaagaaa ccccatacat tgtagctatt cctatgctaa taataatagt   180
aatactgata ttggatgatc ccaaccctaa tctgttttct gtttctgtag atttccctgt   240
tctggacatc tcatatgaat gaaattatat aatgtatggt cgttcatgac tggctttta    299

<210> SEQ ID NO 272
<211> LENGTH: 289
<212> TYPE: DNA
<213> ORGANISM: Homo sapiens

<400> SEQUENCE: 272
acagttttgt gagttcaggt caggagatga ggctggagct ggatgaagac cagctcatgc    60
ctgccttgta catatgttta gttctaagaa cagtaagaaa cccatgacag atttaacaaa   120
gggagtgatg tgtgatcaca tatgtgttct taaaagattg ttatgcatgt ttcatgtaga 180
atagattagg gaagatcagg gaagatacag ggagacaata tactcctgct gtagtagtca 240
agccagaaat cctgttgcct ggatccaggg ttgtggcagt agaaaaata 289

<210> SEQ ID NO 273
<211> LENGTH: 647
<212> TYPE: DNA
<213> ORGANISM: Homo sapiens

<400> SEQUENCE: 273
ctgatgtgta gactttcagg tgaccaaagc aggggctacc agttcttcta ttgaaattga 60
gaataatctg catagtgttt attttaggga atcattaacc tcttggcctc gttttcttga 120
tctgtaaact ttggaagaca aaactgaatg atttgtaaag ctgcttttag ctttaagttt 180
ctgtaagtta cattttttttt ttcacatgta tatgaaattt ccaattagca caggaaaatt 240
ctagagccat gttatgggtg tgtgagcagg gaggtccttt ggggagtgat accattaatt 300
tgttgcagct aagagaacta aataagaccc tagtgatcta aaggagcaca tacaggtact 360
ccctagagtc cttatttatt ttatatgttg gaggtttttg gttcacttag atttttatgg 420
gaaaatttaa aaatatataa tggcagttta tagaatgggt tgaaatatcc tcttcttcta 480
aattagcgat ataattaata cttctctgcc atagtcccat ctacatacta gtattagatt 540
cccatagaag tattcctgtt gttactggca ttgcatgttc tttagaatac tgtttctatg 600
gagttcagca tgataacaaa gtcctgagcc taactaaaga tgtctgt 647

<210> SEQ ID NO 274
<211> LENGTH: 46
<212> TYPE: DNA
<213> ORGANISM: Homo sapiens

<400> SEQUENCE: 274
atgctgctga aattggaaca agaaatttta gatttcattg gtaata 46

<210> SEQ ID NO 275
<211> LENGTH: 67
<212> TYPE: DNA
<213> ORGANISM: Homo sapiens

<400> SEQUENCE: 275
gacatcttac cataggatgc tattacacag agtagccgct tactttggat tagaccacaa 60
tgttgat 67

<210> SEQ ID NO 276
<211> LENGTH: 33
<212> TYPE: DNA
<213> ORGANISM: Homo sapiens

<400> SEQUENCE: 276
tgggaagtct gtcatagtaa acaaaactag caa 33

<210> SEQ ID NO 277
<211> LENGTH: 112
<212> TYPE: DNA
<213> ORGANISM: Homo sapiens

<400> SEQUENCE: 277
ctccagcctt gaatcagtgg tgttatggat gtcaacaacc cagtgtccac tggggtgtct 60
caatggagcg ggaagttggc gattacaggg cagtaaattc aggcatctat aa 112

<210> SEQ ID NO 278
<211> LENGTH: 464
<212> TYPE: DNA
<213> ORGANISM: Homo sapiens

<400> SEQUENCE: 278
aaccttgtgt ttgtcctcta gatcacagtg gaacttgcaa catttctgtg gaagaaagat 60
gagtccacta taaaatgtat tgctaagatt tcataatcgt tactttaggt cacaactttg 120
acttctataa aagaacatct cttttctaac ctgttccagt taatgttagc aaacctgtgc 180
cctactgtaa tttaaaatta atggatgcac tttgaagtag tctgtaagtt tttagctaat 240
tgaatgacaa aatattttat tactttcagg tataacacca aactaggtac cataggagta 300
gcataagata cggcactgca ctttccttgt cccagcattt tttcgtaggt ttagacgagg 360
cagtacaggc tttgggtcta actgacctga gctccaacta tggcttaatc atatgcctgc 420
ctttgacctt gcatatttgc ttaagccatt tgaacctcgg tttg 464

<210> SEQ ID NO 279
<211> LENGTH: 56
<212> TYPE: DNA
<213> ORGANISM: Homo sapiens

<400> SEQUENCE: 279
aaggatgata aaggtgaaga ctttcagaaa cgttatatcc tcaagagaga taactc 56

<210> SEQ ID NO 280
<211> LENGTH: 65
<212> TYPE: DNA
<213> ORGANISM: Homo sapiens

<400> SEQUENCE: 280
ctagaacaat tgtaggattt gtataggtgc aagacatact ataccagtag ttcatttgcc 60
taaaa 65

<210> SEQ ID NO 281
<211> LENGTH: 93
<212> TYPE: DNA
<213> ORGANISM: Homo sapiens

<400> SEQUENCE: 281
gagaatacgt ttgaaagatg acagaagaag caaatctata gaagaaagag aagaagagta 60
ccagagagcc agagaccgaa tattttccca aga 93

<210> SEQ ID NO 282
<211> LENGTH: 531
<212> TYPE: DNA
<213> ORGANISM: Homo sapiens

<400> SEQUENCE: 282
ttacgttgta gggtctcagt ctccctttta tctattgatc acatttattt ttaatcacat 60
ttgttgcaca taaggtcatc ttttagaaat attgagatca gttttgcttg tgttattaat 120
agtttataaa atactacatt gcagtagtta tataaaattt tacaaaagtt ggaagcaggt 180
agactacagg agtcattaaa agaatgttct ccagtctata tagtttgtgt gatttttttt 240
ccccagactt gtgacagact tgagattttt attaatagaa attgctccac tgtctacaaa 300
atcatatact ctagatgcta cttgttagtt gactttcttt gacaaataat ttatttcttc 360

-continued

```
ttttgaaata aagctaattg attttgtagg ttaatatctg ttttcttctt cataagtgat    420

tatataagat aggctttcta aatggctaat tattttatgc atatatgcca gaagagaatc    480

aatttgtttt ttgtcaacat ctactaagca tctgtcctgt aatatgtgtt a             531


<210> SEQ ID NO 283
<211> LENGTH: 33
<212> TYPE: DNA
<213> ORGANISM: Homo sapiens

<400> SEQUENCE: 283

cctgtgttcc caagagaatt acattattga caa                                  33


<210> SEQ ID NO 284
<211> LENGTH: 37
<212> TYPE: DNA
<213> ORGANISM: Homo sapiens

<400> SEQUENCE: 284

atgccagtag tacccagcag aggcgccaga tatttag                              37


<210> SEQ ID NO 285
<211> LENGTH: 117
<212> TYPE: DNA
<213> ORGANISM: Homo sapiens

<400> SEQUENCE: 285

tgaagtactc ggaaccacga ccctggagca gcacagattc agacagctct cttcgaaacc     60

tgaaacctgc tgtaaccaaa gccagcagct tcagtggaat ctcagtcctg acaagag       117


<210> SEQ ID NO 286
<211> LENGTH: 26
<212> TYPE: DNA
<213> ORGANISM: Homo sapiens

<400> SEQUENCE: 286

gcaaaagcat aggcaggctt tcaaaa                                          26


<210> SEQ ID NO 287
<211> LENGTH: 233
<212> TYPE: DNA
<213> ORGANISM: Homo sapiens

<400> SEQUENCE: 287

tccggagcac ttaaggggta atatgtttct tgacatgagg attcactctc tgtcctggac     60

acagatttac aaccatcaat taccataaaa attcttctct attgtgacat aaacttaatt    120

aggtaggttc aatgaaacat tatctcttga ttgaatgccc ataggtaatt ggaaattctt    180

tattacttat tcgtagttgg tagaaggcat ggtttctcac ctaggattat tta           233


<210> SEQ ID NO 288
<211> LENGTH: 32
<212> TYPE: DNA
<213> ORGANISM: Homo sapiens

<400> SEQUENCE: 288

aatcagctgg gcgtaatagc acgtgtctgt ag                                   32


<210> SEQ ID NO 289
<211> LENGTH: 201
<212> TYPE: DNA
<213> ORGANISM: Homo sapiens
```

<400> SEQUENCE: 289
tagggtcatc tacaggctct ctttctcaca tccagcagcc tcttccaggt acagctctca 60
gccagtcttc tcatggcgca cctgtcgtct atccaactgt cagcactcat agttctcttt 120
cctttgatgg tggcctaaat gggcaagtcg catctcctag cactagcttc tttttgcttc 180
ccttggaagc ggcaggcata c 201

<210> SEQ ID NO 290
<211> LENGTH: 269
<212> TYPE: DNA
<213> ORGANISM: Homo sapiens

<400> SEQUENCE: 290
tgatctctgg tttttgacaa cagtattaca atacatttaa cttttttaag atgaccctta 60
aattacattt gaccgccttc acccaaatct gctccaccaa ttttttctcc aaattattta 120
gcagtcaaca aatacccagg acaacttgtt tttagttatc tataactgtc acacaaatta 180
tcagtatact aattgattaa aataatttta ctttagagta ctttttctgc ttgatagcta 240
tagactagta tagtcttctc tcccaaata 269

<210> SEQ ID NO 291
<211> LENGTH: 71
<212> TYPE: DNA
<213> ORGANISM: Homo sapiens

<400> SEQUENCE: 291
atgggagtcc agttgtgtat aatcctccta tgactcaaca accagttaga tcccaagtgc 60
ctggacctcc a 71

<210> SEQ ID NO 292
<211> LENGTH: 32
<212> TYPE: DNA
<213> ORGANISM: Homo sapiens

<400> SEQUENCE: 292
aacaaccagc agctaatcac attttctcac ag 32

<210> SEQ ID NO 293
<211> LENGTH: 380
<212> TYPE: DNA
<213> ORGANISM: Homo sapiens

<400> SEQUENCE: 293
gttgacttgc ctttacatat ttgggactaa attcgctaat tataattgag atagcctaag 60
tatctcttag aactttaata ttctgccact agtgatattc cactcactac tcataggaaa 120
agagataact tcaaaggttt ttcccctgat aaatactgaa aatatgttgg aaagaaggga 180
attgttttaa tcatatgagc ctgtctggtg agtattttat ccctatttca caacagcaag 240
aaatggacaa caggagaaat aaaaacaaaa ctgtgattgt tcattggccc aatgagcaaa 300
gtgagttgtt ttaagattcc acagattaag cagttagaag aaactgagat aggctgctca 360
ggttctgcaa ggtactcttc 380

<210> SEQ ID NO 294
<211> LENGTH: 28
<212> TYPE: DNA
<213> ORGANISM: Homo sapiens

<400> SEQUENCE: 294
gaagaagtat gatgataaac ttgaactg 28

<210> SEQ ID NO 295
<211> LENGTH: 288
<212> TYPE: DNA
<213> ORGANISM: Homo sapiens

<400> SEQUENCE: 295
ttgtggtaaa agtgcaactc aaatcattat tatctatcta tgatgtcata gacaaacaat 60
gtctatctta gttgacatag aagttctcta tttaaattat tgcctgaaca atcttaattc 120
cattagttta tctaacattt ttaaagtatt gtctctgaag acaacatgca gagatattgt 180
tcagaaggag atgcatgaat atacatttta actaagagtt ttcatcaagt gagattccct 240
gggttcctca tctacttgct tatgtggctg tctacaagtc acttaatt 288

<210> SEQ ID NO 296
<211> LENGTH: 76
<212> TYPE: DNA
<213> ORGANISM: Homo sapiens

<400> SEQUENCE: 296
tctgcagtcc tcttcacagc ctgttcagta ctctacagcc ccttacccat ccccgttcct 60
gccagtctca cccacc 76

<210> SEQ ID NO 297
<211> LENGTH: 102
<212> TYPE: DNA
<213> ORGANISM: Homo sapiens

<400> SEQUENCE: 297
gataacctag ggtctcagtt tagccacatg agtcttgctc gccagccatc tgctgatggt 60
tctgaccctc atgccgccat gttccagtcc actgtggttc tt 102

<210> SEQ ID NO 298
<211> LENGTH: 90
<212> TYPE: DNA
<213> ORGANISM: Homo sapiens

<400> SEQUENCE: 298
gttatatcat gacagcagcc cctccaccac atcctcctcc accgccacca ccaccacctc 60
ctcctcctcc cctaccacct gggcagccag 90

<210> SEQ ID NO 299
<211> LENGTH: 31
<212> TYPE: DNA
<213> ORGANISM: Homo sapiens

<400> SEQUENCE: 299
cctactgctg gatatcctgc ctctggtcat c 31

<210> SEQ ID NO 300
<211> LENGTH: 226
<212> TYPE: DNA
<213> ORGANISM: Homo sapiens

<400> SEQUENCE: 300
atggttatta gttgggttct gcctctttat acagtgattg gagtgtcatt agaccccttta 60 aatttaatat atttttgaca tggtatgcca tgtcatacca gattcaggta tgccacattg 120
ctattttttt atttgcccta tctgtatttt attctacttt cctgcatttt atattatttg 180
aacttttttt ttttataata ttgaatgctt tacgaatttc cgtgtc 226

<210> SEQ ID NO 301
<211> LENGTH: 215
<212> TYPE: DNA
<213> ORGANISM: Homo sapiens

<400> SEQUENCE: 301
tagccttaag gtaatataag ccatatttta aataatttca tgcatgatgt aaagttttga 60
ctgtaacctg tcacatgagg tcaggtgtgg agtttctttt tgagtactga catgacatga 120
tgcttttggc atcatgttgg tactcagaaa gttaaagatt ttggagcatt tcagattttg 180
gacatttgga tttttaaaat actcgcccag gctca 215

<210> SEQ ID NO 302
<211> LENGTH: 25
<212> TYPE: DNA
<213> ORGANISM: Homo sapiens

<400> SEQUENCE: 302
atgccagcct gttattgcgc tccag 25

<210> SEQ ID NO 303
<211> LENGTH: 74
<212> TYPE: DNA
<213> ORGANISM: Homo sapiens

<400> SEQUENCE: 303
gccactatca ctccagccaa cctcagtatc gcccagtccc ttctgttcat tacaattcac 60
atctaaacca acca 74

<210> SEQ ID NO 304
<211> LENGTH: 226
<212> TYPE: DNA
<213> ORGANISM: Homo sapiens

<400> SEQUENCE: 304
gtctctcagg atctcgaata tgttcataca tatgagtttg caaaccaatg agattaaaag 60
agtgagcaaa tcttagcatc ctctggaaaa taccacagtg tcacgtctac atgctaaagg 120
gttgggagct gtactgggaa tatcttaagc agtttgttaa gtggctgcca tctcttactg 180
ccattgagat tgaaactgtc tttgcagcct gataaatcac ctatgg 226

<210> SEQ ID NO 305
<211> LENGTH: 72
<212> TYPE: DNA
<213> ORGANISM: Homo sapiens

<400> SEQUENCE: 305
aaacaatttt gatctcagtg tataaaacta tcttattgat tttttaatga actcatttct 60
ctgtatgctt ct 72

<210> SEQ ID NO 306
<211> LENGTH: 25
<212> TYPE: DNA
<213> ORGANISM: Homo sapiens

<400> SEQUENCE: 306
tcagcctttt ataactctag gagtt 25

<210> SEQ ID NO 307
<211> LENGTH: 54
<212> TYPE: DNA
<213> ORGANISM: Homo sapiens

<400> SEQUENCE: 307
aagtttgtag cttcaccata tacatttaat attttgcaat aattggcctt gttc 54

<210> SEQ ID NO 308
<211> LENGTH: 55
<212> TYPE: DNA
<213> ORGANISM: Homo sapiens

<400> SEQUENCE: 308
agctgttgga ttcggggccg tagcactgtc tgagaggttt acatttctca cagtg 55

<210> SEQ ID NO 309
<211> LENGTH: 229
<212> TYPE: DNA
<213> ORGANISM: Homo sapiens

<400> SEQUENCE: 309
agcatgacat caaacggacc taatacacct aaatgcattt gaagctactt ggtctcggtt 60
cttaccaacg atataattta attttttttt ccaaacgatg atgttgttgc atacctgtgg 120
aaagcaaaat gattctgtga aactatactt ttagttttgc aaccatttga taacttcaaa 180
gattatcaat gtattatatc tttagtctta gctttccaga taacccaga 229

<210> SEQ ID NO 310
<211> LENGTH: 298
<212> TYPE: DNA
<213> ORGANISM: Homo sapiens

<400> SEQUENCE: 310
taacctgccg ccactgaaat ctggagccaa atatatctgg taagtaccca cagatttcct 60
tgagttgtat agactcttcc atggaatagt tctttaaata gctgtgagca ataaactctg 120
tgtgactgtt tttgttagaa ttggtttttg tatatgtata tgtttatttc aggcacagga 180
gtgagagaag aggggatgag agatgagaag ggataatcaa gtgtgatggc aattgcatct 240
ccttccaaat acacccatgg ggctggcttt agttgaactt gcccacctac taaaatag 298

<210> SEQ ID NO 311
<211> LENGTH: 530
<212> TYPE: DNA
<213> ORGANISM: Homo sapiens

<400> SEQUENCE: 311
tcgcccataa aacgtagcag ctctccttgc acaaaatgtg tccaggttaa agctggcact 60
gccctgctga gtaaagtctg acttcttggc aaagcagcct gactttgtgg agaagacagc 120
cagtatctat gaaaactctg ctagactaat cttgtataga ctcatctgga atgtggcaac 180
agactttttg agcaaaagca gcctccgagg caaaacagca aaactaaagc ccaaagggaa 240
cattggagat tcacttggaa atactcaggc tgagagacag aactgtggga tgtggaacct 300
gaaatagtgt cactatttga gccagttctt ctccttccca attgtctttt gttatgtttt 360
aatattttta gagatggagt ctcactgttt tgcctagact ggagtgcagt ggcccttcct 420
aattgtttaa tacaatttat gcgtataatc taattatagt aaggcaagga agtgtaactt 480
tgaaatacat cagtagtaaa ccacgcatct tgcgggtagt ggacaaacca 530

<210> SEQ ID NO 312
<211> LENGTH: 86
<212> TYPE: DNA
<213> ORGANISM: Homo sapiens

<400> SEQUENCE: 312
gcctgagcga tagagactgc atctgaaaac aaacaaacaa aaagaataag ataccattgg 60
aaatttactc atgcagcttt catgat 86

<210> SEQ ID NO 313
<211> LENGTH: 40
<212> TYPE: DNA
<213> ORGANISM: Homo sapiens

<400> SEQUENCE: 313
atgaattcag agcaggattt aactcattgt accattacag 40

<210> SEQ ID NO 314
<211> LENGTH: 98
<212> TYPE: DNA
<213> ORGANISM: Homo sapiens

<400> SEQUENCE: 314
taccaaggaa tagttggagt tcagcaaccc cagagtcaga gcctagtcag tggccaaccc 60
aacagcattg gaaatcagat tcaaggagtg gtcatccc 98

<210> SEQ ID NO 315
<211> LENGTH: 109
<212> TYPE: DNA
<213> ORGANISM: Homo sapiens

<400> SEQUENCE: 315
ccatcagact tatcaacagc ctgttatgtt ccctaatcag tctaatcaag gatctatgcc 60
cacaacagga atgcctgttt actatagtgt cattccacct ggtcaacaa 109

<210> SEQ ID NO 316
<211> LENGTH: 208
<212> TYPE: DNA
<213> ORGANISM: Homo sapiens

<400> SEQUENCE: 316
agtctttgga attacccgca gcttggaccc aaatgaggca gataaacttg aaataaggta 60
gatgtaagct gacagtagtg attggtcacc atgtgacaaa ctagcattga tctgttccaa 120
gtatagagta ccaatgtgag aaattgaatg agttgtacgt gaagcaggga atgtgtattc 180
tgtcagactc atcttggtac attttgga 208

<210> SEQ ID NO 317
<211> LENGTH: 791
<212> TYPE: DNA
<213> ORGANISM: Homo sapiens

<400> SEQUENCE: 317
cagggtcttg atccatacag tcttactatg ttttagatgc taaatggact ctagtagcct 60
tcattttatt acaagattat aaggaataag attcctataa gaacacaaag tgagtctttg 120
ttttgaaaaa tgtcttactt agcttgggtt gcttagcaaa attgttttct tacagaggtt 180

```
ccttgtgtag aaaggtagaa tttgaattat tatgtctact ttcagctcat cctttcagtt    240

cactgaggca actttgtgtt tggattggat tgtgttgtta cttatcatta tgaagattga    300

gcacagcctg atacaagtca acatatactg tcactttaag cgagcaaagt actagtcagg    360

gacactaatt ttacaacaac tcatgagatt tttctcagtc cttagtgtgg agagaaaatt    420

agtttgatac cagcagcctt caaaagtggg caagtgagtt ggatatcttc aaaatgctct    480

catttttacc ggttcttctc ctattttccc tttcattttc actattttta tcttgaaatt    540

caaaacgata atacctttgt ctttgatcta tattctcaaa ggggtagcat acagacagga    600

acttgaaaag actatagcct ttttttaaga acctttaaaa aatgtttcac agaatcttta    660

tgaaattatg aaaaagaaaa cctactttta agtctttttc cctttttttct gtccacagtc   720

tgtttttcct catttttgta tcctagtatt tctctagtgt ccctttttgtc ctacttgtga   780

tacctctctt g                                                          791


<210> SEQ ID NO 318
<211> LENGTH: 278
<212> TYPE: DNA
<213> ORGANISM: Homo sapiens

<400> SEQUENCE: 318

ttttgggtgg cagataacat tttacttaat tggggttcaa agttagtgtt ctttgtcatc     60

aagttgattt cagatgttca tctgtaaaaa ccattcttag cttggaggca atacagaagc    120

aagcagtggt ctgggttttg cctataggcc atagtttgcc aactcctgta ctagatggtt    180

gatagccagc aaaaaaaaaa gacaaagagg cagtggtcac aaatgaagac caacaactta    240

ggaaaaagga gtgtggaagc caacatacaa ggagattt                            278


<210> SEQ ID NO 319
<211> LENGTH: 186
<212> TYPE: DNA
<213> ORGANISM: Homo sapiens

<400> SEQUENCE: 319

tcagccgact tagaagcaat acaagccaga agacagtgga gcaacatctt tatttgaaga     60

agtgaaagaa agaaaacttg cattctatac ctgtaaaaat atttttcaga aacagagatt    120

tcaaacacac aaaagctgaa ttaattgcca gccacctcgc actgtgagaa ctgttaaagg    180

aagttt                                                               186


<210> SEQ ID NO 320
<211> LENGTH: 1247
<212> TYPE: DNA
<213> ORGANISM: Homo sapiens

<400> SEQUENCE: 320

aggcaacttt ggtgaggctt tatggtgtgc atatacataa aactctttaa attatatact     60

ttatgtgtgg tttattttct ataaattata cctcagtaaa actataaaat aatctgagtc    120

ttaaattttt tcttagagac tggttcttgc tgtcatttag gctggaatgc agtggtgtga    180

tcctgactca ctgaggcctc aacctcctgg gctcaagcaa tcctcctgcg tcagcctccc    240

aagtagctgg gactacaggt gcacgccacc acacctggct aattttttaa ttttttttaa    300

agataggatc tcactgtatt accctgctgg tgtcgaactt ttgggctcaa gcaatcctcc    360

cacctcagtc tcccaaactg ctgggtttac agatgtgagc caccttgcct agccttcttt    420

tctaatagtt taaacaaaga ctagttttgg ataaagtgaa aagaaatact gtaaaactaa    480
```

caaattatta aaaacaagag taagaatttg tgaggttaag ataggccaca gggcatttaa 540
tggaggaata aaggtagact tgaactaact gtaaaacctg ttacagagtc atattgaaat 600
gttaaaattt aatcaaaagt gtttttttca aaaagcaaat gactaaaaac tcctttcagc 660
cagaggtgag agatcggggg gaaacaaaaa aacaataaaa agaaagtcca aatacctatg 720
ttgcaccagc ctgaccaaca tagtgaagcc ccacctttac taaaaataca agaaattagc 780
tggaagtggt ggcatactcc tgtaatccca acaaaataca tgtaaaacct ttatgcccaa 840
aaccatcttg tgatgtggaa gatttgtact ccctatggtt tatatcttag aacagatgtc 900
agaaaactac agcccacaat caaagaatgg tttttaaatt tgtaaaggat tattattttt 960
taactcctaa gtgaccatgt gttactcaga gttaaaatat atactagctg gctcttgcag 1020
aaaaagttta ccagcatctg ccttaaaaaa accttggcag ataggtatca gagacatgtt 1080
tatgaatgtt tgtagcaaca atgtttagcc taatactgga agtaatccaa ataaaatgga 1140
atagaatgtg taagtatatt ttgatgtatt catttcagac actactatac aacaaagaaa 1200
attactaaag tacaactact tgtatccaat tggttgagtc tcacaga 1247

<210> SEQ ID NO 321
<211> LENGTH: 25
<212> TYPE: DNA
<213> ORGANISM: Homo sapiens

<400> SEQUENCE: 321
gttggacaaa gtgggtcacg cctgt 25

<210> SEQ ID NO 322
<211> LENGTH: 2373
<212> TYPE: DNA
<213> ORGANISM: Homo sapiens

<400> SEQUENCE: 322
aggcagggat gcttctaaga tactagcaat gttctgtttc ccaatctgaa tgaagttaca 60
tagataatta ttttgttatt atacttaatt taaactgtaa tatatttcta agcactctat 120
attcgtctgt tctcgcattg ctataaagaa atgcctgaga ctgagtaatc tataaagaaa 180
agaggtttaa ttggctcaca gctccgcagg ctgcatagga agcatagtgg cttctaggga 240
ggcctcggga aacttcaatt atggcagaag gcaagaggga agcaggcacg tcttacatgg 300
ctggagcccg aggaagagaa gagtgggggg agcaccacac actttttaaa gaaccagatc 360
tcatgagaac tcactgtaca gtaccaaggg ggaatggtgc taaaccatta gaaaccacct 420
ccatgatcca gtcacctccc agcaggcccc acctccagcg ttggggatta cattgtgaat 480
gagatttagg tggagacaca catccaaaca atattacact cagatagata gatagataga 540
tagatagata gatagataga tagatagata gatagataga tagataagat agataagata 600
gattgattag atagattaga tagatagata gatagataga tagattagat attccaaacc 660
ccaaaaaata gcaaaatcat tcgaagagag gcctaaatat atagaagact ttaggagaaa 720
aaaagctaac agaatgggag gagaggaatt gaagacaata aatagagaca gcctttgaag 780
agaattgctt tcataaggat aagcgttgaa ttggattcgt atatggagag gatgaagtca 840
agacagagga tcctttttg attgaaagat agatgcatgt gtttgtatgc tgaagggaaa 900
ggcttagtag atacagaaga tttgcctctg caagggacaa gagagagagt tgtaaggtcc 960
ccagggaggg tgagagccac cacaaaaatg gaagcgggtt agccttagat aacagtgcag 1020
aggatttcat gggcagtaaa cgaggacaag gagagtataa ggatacagat atgggtagat 1080
ggatagatat ggcagcaaga gaaattctct tctgattgct ttgcttttct cagtgaatta 1140
gtcaagatat caagtacatt atcagagtag aagaatgttc taaagttttg taaatgtaga 1200
aatccattac agctatatta agactaatat tcaaaggaaa gaagcaagat acaggggaaa 1260
tgtgacaagt atgcctaata aaagcttatt atatagaaca tttttatcac ttctctatgt 1320
tctaagatgg taacagtgag actacaagta aataatccat agagataaat tgttactcga 1380
agaaaactga tagtaagttt tcacatggga aaatgttgtc ttaccagcaa tccaaaaaat 1440
gagaattaag gcaacttgaa cacaaaaagt aggctaaaac atatagttag caatactgtg 1500
catagagacg tttaaacatt actggttgct aggcatatca agcccatttt tctataaatc 1560
agtcgggata tttaacaaaa tgcaaaattg ctgtactttt aaattctacc tctaaaattt 1620
tatcacaaag ataatccacc ccagaattta aattgtggct aaacaaatta taacagtgct 1680
attattaaca taagaatcca aataaaaaga tgcaaaaaaa aaaacatgga gtaacctggt 1740
aacctttgaa tagtttaaat tttcttctcc atttattttt ctgctaggct gattaagttt 1800
agcttaagtc atagtgagat ttacttagtt gtcacagacc gtttctcaga tagtgggacc 1860
agtgagtttt aaaggtgttt gttctgtgtt aattgctcca gtatcttcaa ttcagaagaa 1920
taaatgtttg atattcaggc tgctatagtt cacaaatgga ttttattgat gacttacagc 1980
attttaagtg aatagagcac atgtctatta agtaatatta ttaagttcag gaagcttgct 2040
taactgccat tgacaataag atgtagggtg gtttaaaaag gcagaaaacc aaatgactta 2100
acacaccttg acaactgttc ataaattttc aaagacatcg cttctagtag tcactaaaag 2160
ctgtagtaga tgtatgactt gcttttcaaa tgaatcaatt attgcttgag aagaatacac 2220
ttgttcctat tctcccatct aaaaaataat ttgaaatagc agccatgaaa tatttacaaa 2280
aacataaaga gaaaagacac atgatggcag tttattttca tgtggaattt cccatgctat 2340
taattttcct aagtctcgac cttttgtggg tga 2373

<210> SEQ ID NO 323
<211> LENGTH: 25
<212> TYPE: DNA
<213> ORGANISM: Homo sapiens

<400> SEQUENCE: 323
caggagcatc agagacatct ttgtg 25

<210> SEQ ID NO 324
<211> LENGTH: 144
<212> TYPE: DNA
<213> ORGANISM: Homo sapiens

<400> SEQUENCE: 324
ggtatatata ccctcaccac aaaaaatata tataaaatgg aaattactat gactttgaga 60
aagcttatga ggcagaaagt tggtgttttc ttccagagac tacaagccta gttgagcatc 120
tgacctgcaa atgaattggt tatt 144

<210> SEQ ID NO 325
<211> LENGTH: 99
<212> TYPE: DNA
<213> ORGANISM: Homo sapiens

<400> SEQUENCE: 325
tcttcagtag gttacctgca acatccagga tcagaacaag tacaatttcc tcgaaccact 60

-continued

```
tcaccatgca gttcccagca gcttcaaggc caccaatgt                           99


<210> SEQ ID NO 326
<211> LENGTH: 94
<212> TYPE: DNA
<213> ORGANISM: Homo sapiens

<400> SEQUENCE: 326

tgatgatgca gctcagtgta ccaaacaatc cacaatcttg tgcccactca cccccgcagt     60

ggaaacaaaa caaatattac tgtgatcacc agag                                 94


<210> SEQ ID NO 327
<211> LENGTH: 328
<212> TYPE: DNA
<213> ORGANISM: Homo sapiens

<400> SEQUENCE: 327

tgatacctga taccagtggg acattttact tgacaaattg gccctgttac ttgaatagat     60

ggcattttga aataggagct tggtctgtta tacattaaaa gagactcaag aggtataata    120

tcagatataa tgtatggatc ttatttggat attgaatgat caaaagacat tttttaaggc    180

caggcgcagt ggctcatgcc tgtaatccca gcactttggg aagctaaggc agacctggaa    240

cgcaggagtt cgagaccagc ctgggtaaca tggtgaaacc ctgtctctat aaaaaataca    300

aaaaattatt cggccatggc agtgtgca                                       328


<210> SEQ ID NO 328
<211> LENGTH: 290
<212> TYPE: DNA
<213> ORGANISM: Homo sapiens

<400> SEQUENCE: 328

ggccatcttg gctatgccag aaagtaagga agggatggaa gaaaaatagg gacgtcttga     60

agaatacagg atcaggagtg gaggtttggg gcataaaaca atgatagaaa tgaatgatca    120

tccatagaat aaaataagaa ttcatgagtc catactgata aaaatcaata aatggaaaat    180

gaaactgtct taccttagtg taatataaag tgataaatgt agaatcgtga aattaaaaga    240

tcaccaccaa gaaaaccatc aggcaagagt caccactaga ggctacaaaa               290


<210> SEQ ID NO 329
<211> LENGTH: 124
<212> TYPE: DNA
<213> ORGANISM: Homo sapiens

<400> SEQUENCE: 329

agccctcaac tcagtagccc cattatttca ccagctcagt cgccagcacc agctcagctg     60

tccaccctga aaactgtacg tccctctgga ccaccacttt ccatcatgcc ccaattttct    120

agac                                                                 124


<210> SEQ ID NO 330
<211> LENGTH: 71
<212> TYPE: DNA
<213> ORGANISM: Homo sapiens

<400> SEQUENCE: 330

gagattccag gtatccatta cttggccagc cactgcagta caatcctcct gctgttctgc     60

acggacacat t                                                          71
```

<210> SEQ ID NO 331
<211> LENGTH: 53
<212> TYPE: DNA
<213> ORGANISM: Homo sapiens

<400> SEQUENCE: 331
aagacaacta acctcctagg ctttgttgca gaacatcata gctccctcag agt 53

<210> SEQ ID NO 332
<211> LENGTH: 85
<212> TYPE: DNA
<213> ORGANISM: Homo sapiens

<400> SEQUENCE: 332
tgaaggacag gaatgccact gccacaggca gaatccagaa ggcctgggac tgattttctt 60
ctgccagagt gcaaaaccca aacta 85

<210> SEQ ID NO 333
<211> LENGTH: 40
<212> TYPE: DNA
<213> ORGANISM: Homo sapiens

<400> SEQUENCE: 333
cattattaac gttgtttctc aactatttgt gggttttcag 40

<210> SEQ ID NO 334
<211> LENGTH: 30
<212> TYPE: DNA
<213> ORGANISM: Homo sapiens

<400> SEQUENCE: 334
gaaggagaca agctaaaaaa gctgcatcca 30

<210> SEQ ID NO 335
<211> LENGTH: 196
<212> TYPE: DNA
<213> ORGANISM: Homo sapiens

<400> SEQUENCE: 335
gaaggtcttg gaaattactg aactaccaga tggaataact cgcatggaag ctgaaaagct 60
ttttggggaa ctctttaaaa ttggcgccaa gatccggtgg ctccgggacc cccagtccca 120
accacgtcgt cacccccctct gctgtggcag tggggacaac actgccaacc ctgaacgctc 180
taaacccagt gacttg 196

<210> SEQ ID NO 336
<211> LENGTH: 849
<212> TYPE: DNA
<213> ORGANISM: Homo sapiens

<400> SEQUENCE: 336
gactcctagg atgtgtgttc atggcattat agcttttgaa gaaaggccag tgatccagca 60
aagggggaaa aatatgcatt tcaccccaca tgactaggaa tccacatcag aatgatacag 120
agttagcagg tttttctaag gaaatgccat tcaaatgcct cctaactttt atagttattt 180
tgttttatat ttctaaattc ttgtatcaga tccaaagctc tattgtacag caaattattc 240
ttcaaaatga ttataaccag ttgcaccctg tatttctttt tgcagccagc acaatgtgac 300
ccaacttaaa atttgggga aaaagaatgc aggagtgaaa taaccaagtc aaaaccatgt 360
actatctcct tgggggttag ggatgctaag aagagcccac aaatagagga ttactcttcc 420
cctgaatctc taaactcaga aacaattacc aaaaaataca taactcttcc ttgtagggcc 480
ctttccttat tcatttaggt agtgtgaaca ttaagtataa aataaattat gttcttaatg 540
cctcttaaac cacttacatt caaaggggaa cagaaatcat tctaagcagg aaaatacttc 600
cacttttttt ttttcaagta tctctctaat aactaaatgc cacttatttg cattctcctt 660
gtggattttt tgtcacctaa ggaaatgcat ttgatgagtg ctggaaactt cttaagtgct 720
ttacagtttg ttttcattgt ttgcagcgga tcactggaca tcaaagattc attgcactta 780
tgaacaagga accttctttt caatttctgt gtaatttgca aggctgtaca atgtgtgctg 840
atgcaagcc 849

<210> SEQ ID NO 337
<211> LENGTH: 25
<212> TYPE: DNA
<213> ORGANISM: Homo sapiens

<400> SEQUENCE: 337
tcagttcaag agaataaatg tttac 25

<210> SEQ ID NO 338
<211> LENGTH: 191
<212> TYPE: DNA
<213> ORGANISM: Homo sapiens

<400> SEQUENCE: 338
atcttcactg ctgttcaaca ttataatgga ggtattaacc aatatagtta gatacatcga 60
tttaaggcat aagaatgggt aaagaagaaa gactatctct gcagattata tgataacggg 120
ttgagcatcc ctaatctgaa aggctccaaa attcaaaact ttttaagcag tcacacgatg 180
cacaaagtaa a 191

<210> SEQ ID NO 339
<211> LENGTH: 27
<212> TYPE: DNA
<213> ORGANISM: Homo sapiens

<400> SEQUENCE: 339
aggtacagta gtttcttgtt ggaataa 27

<210> SEQ ID NO 340
<211> LENGTH: 28
<212> TYPE: DNA
<213> ORGANISM: Homo sapiens

<400> SEQUENCE: 340
ttgttgagaa aaggttaccc tctgacac 28

<210> SEQ ID NO 341
<211> LENGTH: 80
<212> TYPE: DNA
<213> ORGANISM: Homo sapiens

<400> SEQUENCE: 341
gcctagacaa cataatgaga ttccatctct ataaaaaaat taaaaattag ccaggtgtgg 60
tggtatacac ctgtagcgct 80

<210> SEQ ID NO 342
<211> LENGTH: 368
<212> TYPE: DNA

<213> ORGANISM: Homo sapiens

<400> SEQUENCE: 342
tgactctccg ggtcacgacg ttaaccaaaa aataagacaa aaagagaata tattctatat 60
gattctaatt atatgaaatc cagctgcaga caaactaatc tgttatgtta aaaatcagat 120
agtagtagag atggggtgtg gaactgactg ggaagggact ggagggaact cttccaggga 180
tggaaatgtt ctttaagggg gtgggggaac agggtatggt tacacggact tttacagttg 240
ttagaattca tcagattcaa cacttagaat gtttatttta ttgattgtat tgtatgttaa 300
ttatatctca atttccttaa aaacttacac acacacatat gcatgagtca gcccacacat 360
gtagaaga 368

<210> SEQ ID NO 343
<211> LENGTH: 85
<212> TYPE: DNA
<213> ORGANISM: Homo sapiens

<400> SEQUENCE: 343
acagtctggt atgaatgccg caggaggaac acctagccca gcctattagg aggggtcttt 60
gtactgctga ctataatctt atctc 85

<210> SEQ ID NO 344
<211> LENGTH: 147
<212> TYPE: DNA
<213> ORGANISM: Homo sapiens

<400> SEQUENCE: 344
aaggcaactg gtctgatttt tcaggtaaga acatatgaga ggcaggctga gaccaatttt 60
ctaccaggcc agctaattca tcacaatgac aagctatggg tcatatgctt tcaggaacca 120
gacactggaa catgtcgtct gatgtac 147

<210> SEQ ID NO 345
<211> LENGTH: 42
<212> TYPE: DNA
<213> ORGANISM: Homo sapiens

<400> SEQUENCE: 345
gaatccaatg ggagtaaga gaaagtccct tttcaaggag ct 42

<210> SEQ ID NO 346
<211> LENGTH: 361
<212> TYPE: DNA
<213> ORGANISM: Homo sapiens

<400> SEQUENCE: 346
catgtgttcg gagacaacca gaagcagcaa tgctcaaaac cacaaaactc tggattgccg 60
actctgcaca tcctggttcc tctagataca gttcagtggc acattcacaa ataaacgttt 120
tcaaaaactg ccctcaggca gttctagaga aatgctttga cttgcctaat ggtataatgt 180
caagaaagga agacgagcac tgatcattca tactcattat tacagtcaca gggcactgtc 240
tgacttgaca gatacagccg agcagttaaa aggttatggg aatttaagtc cattatggtc 300
atacgattct tatggaccca gagatatgaa attaatcagc cacatgtgta gggacaaagt 360
t 361

<210> SEQ ID NO 347
<211> LENGTH: 43

<212> TYPE: DNA
<213> ORGANISM: Homo sapiens

<400> SEQUENCE: 347
cccgttttgc cagcccaaga ctaggagcca cggcacctgt cct 43

<210> SEQ ID NO 348
<211> LENGTH: 177
<212> TYPE: DNA
<213> ORGANISM: Homo sapiens

<400> SEQUENCE: 348
cgggcactca ctggatggac agacagacgc ctgctgtgcc aggcctgcca gacgctcccg 60
ccccggcact ggtttcttcc tggagctcgt ggctggctag ggggttctcc atgtgctcat 120
ggccaggaga gtctgccgag ccagcccagc cccattctac tccgagtcga gtctgta 177

<210> SEQ ID NO 349
<211> LENGTH: 100
<212> TYPE: DNA
<213> ORGANISM: Homo sapiens

<400> SEQUENCE: 349
atgctgcggc gacgggccca ggaagaggac agcaccgtcc tgatcgatgt gagcccccct 60
gaggcagaga agaggggctc ttacgggagc acagcccacg 100

<210> SEQ ID NO 350
<211> LENGTH: 57
<212> TYPE: DNA
<213> ORGANISM: Homo sapiens

<400> SEQUENCE: 350
ccaggtggac agcaagcggc cgcctgcaga gctgggagtc ctgccaagcc ccggatc 57

<210> SEQ ID NO 351
<211> LENGTH: 98
<212> TYPE: DNA
<213> ORGANISM: Homo sapiens

<400> SEQUENCE: 351
ctgaagctag acaggcagca ggacagtgcc gcccgggaca gaacagacat gcacaggacc 60
tggcgggaga cttttctgga taatcttcgt gcggctgg 98

<210> SEQ ID NO 352
<211> LENGTH: 213
<212> TYPE: DNA
<213> ORGANISM: Homo sapiens

<400> SEQUENCE: 352
tgacccatga ccttgccgca tgaggcctga gggcatggtg tccagagtcc cagagcagat 60
caggccccaa agtcctgctg gaccccccag ccaccgtgag ctcctccgtg tggctaggga 120
gctgctgtcc agaggcggag gtaaacattg atccctcctg cacactcagc tctctcatgg 180
aagtcggagc cctcagggtc acctgaaaac tct 213

<210> SEQ ID NO 353
<211> LENGTH: 37
<212> TYPE: DNA
<213> ORGANISM: Homo sapiens

<400> SEQUENCE: 353

-continued ttgccattca cctgtcccgt ctccaacatt aaagctt 37

<210> SEQ ID NO 354
<211> LENGTH: 124
<212> TYPE: DNA
<213> ORGANISM: Homo sapiens

<400> SEQUENCE: 354
tgtcgaggcc cggttggctt tcagaggcgt atccatggga gtaggtgtca tgtatcaaat 60
aggagattca aagtcagctg ttaccacggc tacagaaatg ccagtctttt cctaagagtg 120
cgaa 124

<210> SEQ ID NO 355
<211> LENGTH: 87
<212> TYPE: DNA
<213> ORGANISM: Homo sapiens

<400> SEQUENCE: 355
aggacgggaa caccacagtg cactacgccc tcctcagcgc ctcctgggct gtgctctgct 60
actacgccga agacctgcgc ctgaagc 87

<210> SEQ ID NO 356
<211> LENGTH: 119
<212> TYPE: DNA
<213> ORGANISM: Homo sapiens

<400> SEQUENCE: 356
agttacccaa ccaggcctcc aactggtcgg ccggcctgct ggcatggctg ggcatcccca 60
acgtcctgct ggaggttgtg ccagacgtac cccccgagta ctactcctgc cggttcaga 119

<210> SEQ ID NO 357
<211> LENGTH: 39
<212> TYPE: DNA
<213> ORGANISM: Homo sapiens

<400> SEQUENCE: 357
cttcctcggg agtgacaacc aggacacctt cttcacaag 39

<210> SEQ ID NO 358
<211> LENGTH: 65
<212> TYPE: DNA
<213> ORGANISM: Homo sapiens

<400> SEQUENCE: 358
tatggccacg agaagaaaaa cctgcttggg atccaccagc tgctggcaga gggtgtcctc 60
agtgc 65

<210> SEQ ID NO 359
<211> LENGTH: 27
<212> TYPE: DNA
<213> ORGANISM: Homo sapiens

<400> SEQUENCE: 359
ttcaagacgc ccccagaggg cccgcag 27

<210> SEQ ID NO 360
<211> LENGTH: 128
<212> TYPE: DNA
<213> ORGANISM: Homo sapiens

<400> SEQUENCE: 360

```
gctccacgcc tcaaccagcg ccaagtcctt ttccagcact gggcgcgctg gggcaagtgg    60

aacaagtacc agcccctgga ccacgtgcgc aggtacttcg gggagaaggt ggccctctac   120

ttcgcctg                                                            128

<210> SEQ ID NO 361
<211> LENGTH: 25
<212> TYPE: DNA
<213> ORGANISM: Homo sapiens

<400> SEQUENCE: 361

cttcctggtg ttctcagaca taccc                                          25

<210> SEQ ID NO 362
<211> LENGTH: 57
<212> TYPE: DNA
<213> ORGANISM: Homo sapiens

<400> SEQUENCE: 362

ggcagcaagg acagcttcga gatgtgccca ctttgcctcg actgcccttt ctggctg       57

<210> SEQ ID NO 363
<211> LENGTH: 30
<212> TYPE: DNA
<213> ORGANISM: Homo sapiens

<400> SEQUENCE: 363

ccggctgttc gaccacggcg gcaccgtgtt                                     30

<210> SEQ ID NO 364
<211> LENGTH: 66
<212> TYPE: DNA
<213> ORGANISM: Homo sapiens

<400> SEQUENCE: 364

ctgctggagt actggaagcg gaagagcgcc acgctggcct accgctggga ctgctctgac   60

tacgag                                                               66

<210> SEQ ID NO 365
<211> LENGTH: 88
<212> TYPE: DNA
<213> ORGANISM: Homo sapiens

<400> SEQUENCE: 365

cgaaccccat cacgggtgag gacgagccct acttccctga gaggagccgc gcgcgccgca   60

tgctggccgg ctctgtggtg atcgtggt                                       88

<210> SEQ ID NO 366
<211> LENGTH: 78
<212> TYPE: DNA
<213> ORGANISM: Homo sapiens

<400> SEQUENCE: 366

tgtgcctcgt gtctatcatc ctgtaccgtg ccatcatggc catcgtggtg tccaggtcgg   60

gcaacaccct tctcgcag                                                  78

<210> SEQ ID NO 367
<211> LENGTH: 80
<212> TYPE: DNA
<213> ORGANISM: Homo sapiens
```

<400> SEQUENCE: 367
catcgccagc ctcacggggt ctgtagtgaa cctcgtcttc atcctcatcc tctccaagat 60
ctatgtatcc ctggcccacg 80

<210> SEQ ID NO 368
<211> LENGTH: 51
<212> TYPE: DNA
<213> ORGANISM: Homo sapiens

<400> SEQUENCE: 368
gccagaacgt gactttctca ctcactgaca cacatggccc tcatttctat t 51

<210> SEQ ID NO 369
<211> LENGTH: 96
<212> TYPE: DNA
<213> ORGANISM: Homo sapiens

<400> SEQUENCE: 369
aaatgcaccg cacccagacc aagttcgagg acgccttcac cctcaaggtg ttcatcttcc 60
agttcgtcaa cttctactcc tcacccgtct acattg 96

<210> SEQ ID NO 370
<211> LENGTH: 42
<212> TYPE: DNA
<213> ORGANISM: Homo sapiens

<400> SEQUENCE: 370
ccaggcaact accacacctt gtttggagtc cgcaatgagg ag 42

<210> SEQ ID NO 371
<211> LENGTH: 68
<212> TYPE: DNA
<213> ORGANISM: Homo sapiens

<400> SEQUENCE: 371
tcttccattc gagctttgat ttgcagcaat tcctcccacc accggctatt tccatcgccc 60
agccaggg 68

<210> SEQ ID NO 372
<211> LENGTH: 89
<212> TYPE: DNA
<213> ORGANISM: Homo sapiens

<400> SEQUENCE: 372
tggaggctgc ctgatcgagc tggcacagga gctcctggtc atcatggtgg gcaagcaggt 60
catcaacaac atgcaggagg tcctcatcc 89

<210> SEQ ID NO 373
<211> LENGTH: 72
<212> TYPE: DNA
<213> ORGANISM: Homo sapiens

<400> SEQUENCE: 373
tggtggcaga agttccggct tcgctccaag aagaggaagg cgggagcttc tgcaggggct 60
agccaggggc cc 72

<210> SEQ ID NO 374
<211> LENGTH: 34
<212> TYPE: DNA
<213> ORGANISM: Homo sapiens

<400> SEQUENCE: 374
tgtgagggtc tgtttgacga gtacctggaa atgg 34

<210> SEQ ID NO 375
<211> LENGTH: 96
<212> TYPE: DNA
<213> ORGANISM: Homo sapiens

<400> SEQUENCE: 375
gagcaggttt ctgccccaac gcctgccctg agttagttcc tgagctcacc gagccggaga 60
aggcccgtga ccagccagaa gcacggagcg cagggc 96

<210> SEQ ID NO 376
<211> LENGTH: 37
<212> TYPE: DNA
<213> ORGANISM: Homo sapiens

<400> SEQUENCE: 376
tgagggcgga cggtggcgga gagcccggcc gtgaccc 37

<210> SEQ ID NO 377
<211> LENGTH: 203
<212> TYPE: DNA
<213> ORGANISM: Homo sapiens

<400> SEQUENCE: 377
ctgcagttcg gcttcgtcac catcttcgtg gccgcctgtc cgctcgcgcc gctcttcgcc 60
ctgctcaaca actgggtgga gatccgcttg gacgcgcgca agttcgtctg cgagtaccgg 120
cgcccggtgg ccgagcgcgc ccaggacatc ggcatctggt tccacatcct ggcgggcctc 180
acgcacctgg cggtcatcag caa 203

<210> SEQ ID NO 378
<211> LENGTH: 128
<212> TYPE: DNA
<213> ORGANISM: Homo sapiens

<400> SEQUENCE: 378
cttctcgtcc gacttcctgc cgcgcgccta ctaccggtgg acccgcgccc acgacctgcg 60
cggcttcctc aacttcacgc tggcgcgagc cccgtcctcc ttcgccgccg cgcacaaccg 120
cacgtgca 128

<210> SEQ ID NO 379
<211> LENGTH: 116
<212> TYPE: DNA
<213> ORGANISM: Homo sapiens

<400> SEQUENCE: 379
agagtatcct gtttgggaag aattcccatt tcaggcaccc tcgatgaaga gccaggccag 60
gaacatggga tgagagagcg aaatggtgga aaaaggggag ataggctaat tccaga 116

<210> SEQ ID NO 380
<211> LENGTH: 33
<212> TYPE: DNA
<213> ORGANISM: Homo sapiens

<400> SEQUENCE: 380
cctggctgcg cgcactgagt cctgtgtctg ctg 33

<210> SEQ ID NO 381
<211> LENGTH: 50
<212> TYPE: DNA
<213> ORGANISM: Homo sapiens

<400> SEQUENCE: 381
gtatcgggct ttccgggatg acgatggaca ttattcccag acctactgga 50

<210> SEQ ID NO 382
<211> LENGTH: 54
<212> TYPE: DNA
<213> ORGANISM: Homo sapiens

<400> SEQUENCE: 382
tcccatccat ggcatgaggc cccgaccctg tgctttgcct aattcgagca cgtg 54

<210> SEQ ID NO 383
<211> LENGTH: 122
<212> TYPE: DNA
<213> ORGANISM: Homo sapiens

<400> SEQUENCE: 383
ttggtcaaat cagagctctt ctctgcacct gcgttttccc tgcctggcct catccctggg 60
ttgtggtgtg gacattgtgg gtgtctccac aggagcccca gggccacgaa agctggggtg 120
gc 122

<210> SEQ ID NO 384
<211> LENGTH: 35
<212> TYPE: DNA
<213> ORGANISM: Homo sapiens

<400> SEQUENCE: 384
ctggccctgt gaaggccact ctgggcgttt gggtg 35

<210> SEQ ID NO 385
<211> LENGTH: 112
<212> TYPE: DNA
<213> ORGANISM: Homo sapiens

<400> SEQUENCE: 385
atgtggtttt ctccgttggc cgcctcctgg acctcctggt gcctgacatc ccagagtctg 60
tggagatcaa agtgaagcgg gagtactacc tggctaagca ggcactggct ga 112

<210> SEQ ID NO 386
<211> LENGTH: 88
<212> TYPE: DNA
<213> ORGANISM: Homo sapiens

<400> SEQUENCE: 386
tgaactgtac agcccagtct cggccctccc cccagccctc tccctatcct tgtcagtggc 60
tgctctacct ccggacactg agtcacat 88

<210> SEQ ID NO 387
<211> LENGTH: 28
<212> TYPE: DNA
<213> ORGANISM: Homo sapiens

<400> SEQUENCE: 387
acggaacaaa ggatgagcag cccgaggg 28

<210> SEQ ID NO 388
<211> LENGTH: 93
<212> TYPE: DNA
<213> ORGANISM: Homo sapiens

<400> SEQUENCE: 388
cgtgcactcc ctgaggtcac agggccctgc ccagccgccc actgtgcctc gtggccatgg 60
cctgctcctg gccctagtct gacttgtccc tgc 93

<210> SEQ ID NO 389
<211> LENGTH: 129
<212> TYPE: DNA
<213> ORGANISM: Homo sapiens

<400> SEQUENCE: 389
gctcccactg gacacccttc acggttccca aggccagcca gctgcagcag tgacgcctgg 60
aaggacatct ggtggtcctt aggggagtgg cccctcctga gccctgcgag cagcgtcctt 120
ttcctcttc 129

<210> SEQ ID NO 390
<211> LENGTH: 100
<212> TYPE: DNA
<213> ORGANISM: Homo sapiens

<400> SEQUENCE: 390
tgtgtgaacc gctggctgct gttgtgcctc atctctgggc acattgcctg cttcccccca 60
gcgccggctt ctctcctcag agcgcctgtc actccatccc 100

<210> SEQ ID NO 391
<211> LENGTH: 620
<212> TYPE: DNA
<213> ORGANISM: Homo sapiens

<400> SEQUENCE: 391
ttcgaatgtt tcagagcgca gggccgttct ccctcgtgtc ctctggaccc acccgcccct 60
tcctgccctg tttgcgcagg gacatcaccc acatgcccca gctctcggac cctgcagctc 120
tgtgtcccag gccacagcaa aggtctgttg aacccctccc tccattccca gttatctggg 180
tcctctggat tcttctgttt cttgaatcag gctctgcttt ccccctagcc actacaggca 240
gcctctgaca gtgccgcttt acttgcattc tgcagcaatt acatgtgtcc ttttgatcct 300
tgcccaactt ccctccctct cccagctcct ggcccctggc ccagggcccc tcttgctgtt 360
tttacctctg ttccttgggg cctagtaccc agcaagcacc caaatggggg aggttttggg 420
atgagaggag gaaacgtgta tacctgtaac atctggtggc tcttccccca gaagtttgtg 480
ttcatacata attgttttcc acgctggatc ataatgtgac gtgcagttct gccctgtgct 540
ggggagccac atgaagcttc ccctggctaa cttgctaccc cgcagcaatc ccagtgtggc 600
cgtctgcttg ctaaaaaatg 620

<210> SEQ ID NO 392
<211> LENGTH: 44
<212> TYPE: DNA
<213> ORGANISM: Homo sapiens

<400> SEQUENCE: 392
tcactactgg aactgcacaa actggccact gacaaaaatg accc 44

<210> SEQ ID NO 393

<211> LENGTH: 617
<212> TYPE: DNA
<213> ORGANISM: Homo sapiens

<400> SEQUENCE: 393
ggaagtccag ccttaccaac ttgtgaacct tgtctgaagg gagccagggc ctgccaatgg 60
aaccacctcc aggagctgca actgctgttg tcattaatac cattgtgtct attttttgag 120
agagataaac ttttcatggt gttacatttt ggaaaaaaaa aaaaaagact aggtgaacag 180
tcaggtagga aagcagcata acagtccctt aaattctgat catgtaggac attcttcttt 240
gccctgggcc tgggaaaatg cagcatgttc cagagcaaaa gtcctaatga ggggaactaa 300
accagtggga cccaaaccaa tgtcctggct cactgaggac ccgttagaac caaatctctg 360
ggtgtggaca ggctcccata cttttcaaaa attcccctga tgactaatga acaaccagag 420
gtaagaacca gtggcccaga ggaataacca gcccagctgt tgtacgagct cgctaagctg 480
gctcaggtca atgttgaatt ctctgctagg cagctcctca taagaactgg cagagatggt 540
tcttacacaa caacaggtga caactccaga ctctgccgga agttccagga tctgggttcc 600
cggacaatgc atgacac 617

<210> SEQ ID NO 394
<211> LENGTH: 62
<212> TYPE: DNA
<213> ORGANISM: Homo sapiens

<400> SEQUENCE: 394
ggttatcttt cctccactcg agggattgaa gctaggctgt cccacggcac cgggctcgtg 60
gc 62

<210> SEQ ID NO 395
<211> LENGTH: 99
<212> TYPE: DNA
<213> ORGANISM: Homo sapiens

<400> SEQUENCE: 395
caaagccacg catgcagaga ggttaccagt gtccatccag acgcccactt cacagacagg 60
tagccaagcg ccagagcccg gctattgtag ccctaagtg 99

<210> SEQ ID NO 396
<211> LENGTH: 144
<212> TYPE: DNA
<213> ORGANISM: Homo sapiens

<400> SEQUENCE: 396
acattctgga tgaaagaaac tactcaaaaa gaatgtttac tgtatgattc catttttatg 60
tttaagaaca ggtaaaatta acctgtgatg acagacatca gagtcatggt tactcctgag 120
gagaggggtt tactagatgg gaca 144

<210> SEQ ID NO 397
<211> LENGTH: 260
<212> TYPE: DNA
<213> ORGANISM: Homo sapiens

<400> SEQUENCE: 397
cctctcagat cacccaggaa ttctactcct aggtttttct caaggagaag ttaagtgcaa 60
atatccatca aaatgctcat aaattttatt tgtaatagct aaaaacaaga cacaactcaa 120
atacctatta aatgtttatc tagacacaat ccaaatgtaa tacagtcatg ctctgcacaa 180
tcatggtccc atgaaattat aatggaagga aaaattccta tcacccaagt gcacactgtt 240
tataaagtcc acagcggtgt 260

<210> SEQ ID NO 398
<211> LENGTH: 101
<212> TYPE: DNA
<213> ORGANISM: Homo sapiens

<400> SEQUENCE: 398
gcacaaatgg tattctgtat ctgaaaattg tttggattaa cttttgattc ttgcctggtt 60
aaagaattac aattcttacc tcagatcatg cttaaactat c 101

<210> SEQ ID NO 399
<211> LENGTH: 54
<212> TYPE: DNA
<213> ORGANISM: Homo sapiens

<400> SEQUENCE: 399
tctggaaatg taactactat aatggacctt acaaatgcac aaatggggcc gggt 54

<210> SEQ ID NO 400
<211> LENGTH: 277
<212> TYPE: DNA
<213> ORGANISM: Homo sapiens

<400> SEQUENCE: 400
gcgagtgttc tcattgcatt cgtgacccca ttgatcttgc aacagcccca tgcatcagtt 60
attgccatta taccatttta ccgataagga aactgtggca gggaggggtc aagcaccttg 120
ggtatttgac agcaaaacca aggcttggtg gtatcataaa acttccaagt agtaattcac 180
aaaggtgact gggaaatgga agtgaccaga aatctttgca ctatgaggac aagttcatga 240
ccctgataca ttcttgtcca ggtagtatag ctccaga 277

<210> SEQ ID NO 401
<211> LENGTH: 603
<212> TYPE: DNA
<213> ORGANISM: Homo sapiens

<400> SEQUENCE: 401
ctactgcatt tctgtcactc gctgaaaagg acactctgtc agaaaatctt ctagcaaact 60
tcaaagggca aaatcacccc ttgttactga taaagcccag agagcttcag cagctaacat 120
tccctggaca gggcacagca aggatttgaa cctaggtcag tctggccaga acacccacaa 180
gctttcctta actcagtgtg ctatctcccc acgactaggt cactactgct ttataatcac 240
ctttgtagcc accagtggat tttgctcatc agtatttttc aggcaattga tactttagat 300
attcagctgc aagacgtatg cagttttcat tgacatcttt tggagaaact gacaaacctg 360
gacttgactt aatgcctttg gaaccttcca agatgttata taactctaga tagaaggctg 420
ggcctccatg atgtcaggaa tgttgcattc ttatttcccc atagataaac ccatttgtcc 480
acaaagtcaa ggagtcaggc agaggccctt gccatggggc tttttaggat aaagcaacaa 540
gcctggactt tgctctacaa cagggttttg catagggagt ggtatgacca gatccctcaa 600
gaa 603

<210> SEQ ID NO 402
<211> LENGTH: 241
<212> TYPE: DNA

<213> ORGANISM: Homo sapiens

<400> SEQUENCE: 402
ggtgggatca ctcagattct acagatatta aaaggataat aaggaagtat tgtaaacttt 60
tatgcctata aattttaaaa cttagataaa atggataaat tcctggcaag gcacaatcta 120
ccagagccca ctcaaaaaga aagaaagaac ccagacaatc ctctatttac ggaataaatt 180
gaatgtttag tttaaaatgt atgcatgaag aaaattcccg gttgacatgg cttcactagt 240
g 241

<210> SEQ ID NO 403
<211> LENGTH: 209
<212> TYPE: DNA
<213> ORGANISM: Homo sapiens

<400> SEQUENCE: 403
caataatata aaggtcagaa ggggagaaat ggaagtatcc tgttgtaagt ttcttatgct 60
atacgcgaac tggtataata tcatttgaag gtaggctata ataagttaaa gatgtgttct 120
gttaatccta agaaatatga aaataacaca ataacaaaga gttacagcaa ataagacaac 180
aaaagagata aagttggatc ataaaaata 209

<210> SEQ ID NO 404
<211> LENGTH: 313
<212> TYPE: DNA
<213> ORGANISM: Homo sapiens

<400> SEQUENCE: 404
caaaggtttc tgctcaaggg tttctgctgc agtaatttgt gattctaagt attttcttgt 60
cagtctttcc aatttaaggg gcagtaaacc tcacttctct gatggatcta agagttgtta 120
attaatcagt ttgttcagcc ttttatttgt tgttaggatg tagtgacaac ttccaagctc 180
cttacgtact ggattgcaaa ccagaagtca aactattcct tagaaatgaa ggggaagtaa 240
agtcattttc agatgacagg atactaaaag aatatgtcac cagaagactt gcccttaagg 300
aatgactaaa gca 313

<210> SEQ ID NO 405
<211> LENGTH: 332
<212> TYPE: DNA
<213> ORGANISM: Homo sapiens

<400> SEQUENCE: 405
gccactgctt tgctgagtca ttctactatg cagcccctca gacacaaagc ccggcggcca 60
cctgcccaca gaggcacaga gggccagcca actgcaagca cggaacttca ggatcttgct 120
tttcgggtta ttttcactac tgtaattttt ttgtccttag gtaaaaagga taataattgt 180
ggaaaattat gtccttaggt taaaaagatc ctggatcatg ccagatatta aaatatggat 240
aaaattggca tgatcttgga atctgaacag aaaagaagct gcttttagct gttttcaact 300
gtttttagct tttctgtcta aacagctgtt ta 332

<210> SEQ ID NO 406
<211> LENGTH: 38
<212> TYPE: DNA
<213> ORGANISM: Homo sapiens

<400> SEQUENCE: 406
cttagctgac attactttga tcatgaactt tgttgcct 38

<210> SEQ ID NO 407
<211> LENGTH: 104
<212> TYPE: DNA
<213> ORGANISM: Homo sapiens

<400> SEQUENCE: 407
tcgctggggt atgaccattc ccctggcctt cctatcttcc catctatgcc caacatggct 60
gccaagggga tctgtcctaa atgcaaagtt agccatgcct gccc 104

<210> SEQ ID NO 408
<211> LENGTH: 52
<212> TYPE: DNA
<213> ORGANISM: Homo sapiens

<400> SEQUENCE: 408
ggggaggata aaatttggag caagattctc aaggaagcaa caagatccta ag 52

<210> SEQ ID NO 409
<211> LENGTH: 37
<212> TYPE: DNA
<213> ORGANISM: Homo sapiens

<400> SEQUENCE: 409
tcttggacga gcctgaggat gtctacaagt ggaagaa 37

<210> SEQ ID NO 410
<211> LENGTH: 34
<212> TYPE: DNA
<213> ORGANISM: Homo sapiens

<400> SEQUENCE: 410
tggaggagga tccaaggctc agaaagagaa ggag 34

<210> SEQ ID NO 411
<211> LENGTH: 243
<212> TYPE: DNA
<213> ORGANISM: Homo sapiens

<400> SEQUENCE: 411
tgcctattgt tctggatcat tttgagaaaa aaaaagagat accttgaaga aagatgaaga 60
caaaatatgg aagggtgctg aatttacaaa aagcctaagg ggaaaaaact caaatgtccc 120
tcaggagtgg aatgagtaaa caaatcatgg cgtgttcaca caatggaatg ctacctacca 180
ataaaaagga atgaactgcg gatgcacaca gaaacatggg tgaatccact aggcatcatg 240
ttg 243

<210> SEQ ID NO 412
<211> LENGTH: 723
<212> TYPE: DNA
<213> ORGANISM: Homo sapiens

<400> SEQUENCE: 412
cagccatttg cagagcattg gagtaagttt taccttcatc ccttagatgt gaatttgtta 60
tcctcactgt gacaatccct tatcacatgg cttttagaag gattctcaaa aagctagact 120
ctcacattca actttgcaat tgcctggctg ggtgttacgt ttctttgcct cctattagag 180
accctatcag catctaaaac tagcgttgtt tgaggatgtt ggagccaacg gttctttgcc 240
agatagaact ttgtgtgtcc aaataaatgg ttcaaaatca tcaagcaaat aaataccctg 300

-continued gaataagaga agcctcatga ggatttgact ccaaattgac ttcctctgtt ctgcagtaag 360
aagttaggaa ttaaaccaaa ccttgcctga ggttcaggta tactcaaaag caatgaggtg 420
tggctcaggt gtgcgctggc aaggtcactg tgaagttcag ccagaggctt tgcaagcctg 480
ggcctgagaa gccagacctc ttagatccag aagggccaat ggagctgggc tggcctgctg 540
ccactcacag gcagagactc tgccagcaga agggactctg ctgtcagagc tggagggcag 600
cggaccacat ggctgaggcc caaccacagg tctcctgact caaaacctct tcccagggct 660
tgtcctcctc cctaaatata tgtgccccaa attgtcacca gatctcggga aagcactggc 720
ttt 723

<210> SEQ ID NO 413
<211> LENGTH: 481
<212> TYPE: DNA
<213> ORGANISM: Homo sapiens

<400> SEQUENCE: 413
gaggtagaca ctattcccag ctggatactc tcaatgttga ggatatagat gcacaaacca 60
atgcagggag gcctccagga gccactggag aagaaatctt cagatcctac caggcccata 120
gctgttgcct ttgtgggctc ctgggttaat ttccacacat cagtggccca ccttatgata 180
tcctccctgc atgccacact cccggccatg ctctgtggac agccattatt tccagtaatt 240
gctaatggga gccagtctcc aaagagtaat gaatcagagg tgttccttgg aatgtgttac 300
actaggactt cgccgatctc acaggctcct ttccagatga gctgactgta atctctggga 360
agctggatct ggaggaacaa tgggatggga tttgcggtga cccttcctgc ccttcttgag 420
cagcttgtga accagaagat gtgcctggag agaaagcctc atttggggaa gtgcagtagt 480
c 481

<210> SEQ ID NO 414
<211> LENGTH: 167
<212> TYPE: DNA
<213> ORGANISM: Homo sapiens

<400> SEQUENCE: 414
cagatctcag ctgccgagtg gaaaccccat tctcacacca tagctatggg actgggggaa 60
aggggaggaa ataactaaag agtaaggaat tgggggaggc tttgaggttt ggatgtgaca 120
ggtagtttgc atgtagttgg aatgcagtaa cattggtcca caaggtt 167

<210> SEQ ID NO 415
<211> LENGTH: 148
<212> TYPE: DNA
<213> ORGANISM: Homo sapiens

<400> SEQUENCE: 415
gagcacgtga tcacttctca caactaatgg agccaagatt ctgtccttat ggctccagag 60
acctcttttt tttcccactg taccacaaca ctcaccagga ctggagtgcc acctatgacc 120
tcattgcata atggatggct tgtcctca 148

<210> SEQ ID NO 416
<211> LENGTH: 116
<212> TYPE: DNA
<213> ORGANISM: Homo sapiens

<400> SEQUENCE: 416
ttaaagatct gtaggcttac tagccatgac aatgatgaca ataatgatga tgaaaatgac 60
atcatcatta ccaatagcta ctgccatcta ttgatcccat aacatgtgat catatc 116

<210> SEQ ID NO 417
<211> LENGTH: 479
<212> TYPE: DNA
<213> ORGANISM: Homo sapiens

<400> SEQUENCE: 417
agtcatgtag tttgagcact ccagatttat tttcctaatt caagattgtt atagatacgc 60
tagattcttt gcatgtctat ataaatttta gaatcaattt gtaaatttct acaacagatt 120
cctgctagca ttattactgg gattgcaata actctacaga tcaatttgtg gagaactgac 180
atctcaacaa cattgagtct tccaatctgc aaacatgata ctgtgtgtgt gtgtgtgtgt 240
gtgtgtgtgt gtgtgtgtgt gtgtcttctt taatttcttt caataattgt ttagttttca 300
acatagagat cttgtccatc ttttgttgtt tattcatgag tattttatgc tttttgaaga 360
tactgtaaat aaaattgttt ttctaatttc atttcccaaa ttcttgctgc tgatatataa 420
aagtataatt gatattttaa tattaacctt gtatcctgtg accttgttca attgatgta 479

<210> SEQ ID NO 418
<211> LENGTH: 294
<212> TYPE: DNA
<213> ORGANISM: Homo sapiens

<400> SEQUENCE: 418
gctcagtttg cttatccgtt ctcctgttga tgaacatctg atgtttgcag ttctcctctc 60
cgtgagtctt cttgtaaaca taattttcat ttctcttggg aaaaacccta ggagtggtac 120
tgctgggtca agggggtagg tgtttgtata gctttataag aagttaccac atccttacta 180
atatttggtg atagctattc tttaagttaa aagtgtagag gcatctcgtt gtggttttaa 240
tttttatctc ccaaatgagt aatgataagt gtctcttcat ataccgaatg gcta 294

<210> SEQ ID NO 419
<211> LENGTH: 351
<212> TYPE: DNA
<213> ORGANISM: Homo sapiens

<400> SEQUENCE: 419
cttgcaggcc ctgtgaacat atatacttcc tggtgggaag agcaagggag cctctggtgg 60
aaagcagccc cagggtccaa gaaccacaca gccctgcatt agggccccca gggagggaga 120
agaccaaggt catgcttttg aacctggatg ccagaagaga acagctgtgg ggaaaagcat 180
gcctggaacc aagaaaaaca tgtttaccag gggccattcc tcacaccagc tgcaggcagg 240
gtcaggaaag ccacaggctg cactgtagtt gcaaccttgc atgcggacgc aaggctcaga 300
atgttcctca aagatcctaa aatgttccca gagtcaggct gagtccattc a 351

<210> SEQ ID NO 420
<211> LENGTH: 25
<212> TYPE: DNA
<213> ORGANISM: Homo sapiens

<400> SEQUENCE: 420
cactacaact ggctgtcggt ctccc 25

<210> SEQ ID NO 421
<211> LENGTH: 118
<212> TYPE: DNA

<213> ORGANISM: Homo sapiens

<400> SEQUENCE: 421
atgtgatggc caagggagct tcatcaatca tggcatctca agggagctgg agcagatgag 60
gaggagatgg aggtcccagg aagggctgtg atctgcctgg ggtcccacaa tgggaaac 118

<210> SEQ ID NO 422
<211> LENGTH: 42
<212> TYPE: DNA
<213> ORGANISM: Homo sapiens

<400> SEQUENCE: 422
ctcacacagg cagttagcca aggcctgata tgcagaaagt gc 42

<210> SEQ ID NO 423
<211> LENGTH: 62
<212> TYPE: DNA
<213> ORGANISM: Homo sapiens

<400> SEQUENCE: 423
acccagggag gatagcacat gtcttcggct acactggtga aggcatcgtg cctgctccac 60
ag 62

<210> SEQ ID NO 424
<211> LENGTH: 57
<212> TYPE: DNA
<213> ORGANISM: Homo sapiens

<400> SEQUENCE: 424
tgcagctgat acccaggatg tattattatt actgtgacac agtgaatcta aaagagg 57

<210> SEQ ID NO 425
<211> LENGTH: 107
<212> TYPE: DNA
<213> ORGANISM: Homo sapiens

<400> SEQUENCE: 425
ctcaagggag attgtatgag actcctatag ggtagaacct actctgaaag aactcacctc 60
aattaagctt gattggagta aaagccaagg ctagacacct aagcttc 107

<210> SEQ ID NO 426
<211> LENGTH: 25
<212> TYPE: DNA
<213> ORGANISM: Homo sapiens

<400> SEQUENCE: 426
ctcagaaacc tgtagatctc tatga 25

<210> SEQ ID NO 427
<211> LENGTH: 25
<212> TYPE: DNA
<213> ORGANISM: Homo sapiens

<400> SEQUENCE: 427
ccctaatgac taattgtttt gagca 25

<210> SEQ ID NO 428
<211> LENGTH: 279
<212> TYPE: DNA
<213> ORGANISM: Homo sapiens

<400> SEQUENCE: 428

```
tccctcataa tgtctgctct gtgtcactat gtaccctccc ctgtcctcca ttccccacac    60

caagagtatt atgagtatta aatgccacgt gggcaggttc cccaggcaat gaggggtgg    120

gcctgtcaaa tgcaggccat gcagaatgcc gcagggcggg agacgggtga gccaagggag   180

ccgagagttc cagataacag agtgcacagc aaatgccatg gcccgcgtcc agcaaccagg   240

agaaacagaa ctgctgagct cagaataggc caaggccgc                         279

<210> SEQ ID NO 429
<211> LENGTH: 205
<212> TYPE: DNA
<213> ORGANISM: Homo sapiens

<400> SEQUENCE: 429

gaactcccac tgtataattg ctaaacacaa tgacagctat aattgaggca ctgaaggaag    60

gtcaggggag cccaggaggg cggggctgct gctgcctgct gagctgggag ggttggtggc   120

accccttgcc ctgggttgcc atagcagata tcataatcaa ttacggccgt ctttcatgag   180

gaacctggat ctttcccaag gaatc                                        205

<210> SEQ ID NO 430
<211> LENGTH: 122
<212> TYPE: DNA
<213> ORGANISM: Homo sapiens

<400> SEQUENCE: 430

ctgcaggctg gaggcttagc cacttctcag gaggagccta gaaaggatat tggtcgccca    60

gctgctgaac ctgccccagc atccttgagg gtcttgaaaa tctattttat gctgggcacc   120

tg                                                                 122

<210> SEQ ID NO 431
<211> LENGTH: 126
<212> TYPE: DNA
<213> ORGANISM: Homo sapiens

<400> SEQUENCE: 431

atgcactatg tagcccatga gaaggagacc aactccgagg agctgagagt gagaggagac    60

tgcattctca gacacaattg tccagacact tcctttaaaa actacacgcc aatgcccaat   120

aatgct                                                             126

<210> SEQ ID NO 432
<211> LENGTH: 266
<212> TYPE: DNA
<213> ORGANISM: Homo sapiens

<400> SEQUENCE: 432

cgggacacat atgggaatac aattacagca aagccggcaa ggctcagtga ggggcagagg    60

gcctggccac atgaggagcc agtgctgtgg gcaggcccgg gtctgagtgc tggctgtgtg   120

tcctgcacaa ccacatctcc cagagtgcat tcgtcaccat ccactccaga tgccccttga   180

acaaatgaat ttcacagttg caaaaggctg aaaaatgctc tgtgacctgg cacccccttg   240

gggaaccaca gtgcattaaa ggctct                                       266

<210> SEQ ID NO 433
<211> LENGTH: 29
<212> TYPE: DNA
<213> ORGANISM: Homo sapiens
```

<400> SEQUENCE: 433
ttgtgatttt cgttcctgaa ttcatagag 29

<210> SEQ ID NO 434
<211> LENGTH: 231
<212> TYPE: DNA
<213> ORGANISM: Homo sapiens

<400> SEQUENCE: 434
ggtgccctgc aatgttaagc aaaaaaaaaa aaaaaaaaaa aagactttgg aaatagagtt 60
atggagccag gatgggtctt gagttagcct cactctttat ttctttattc aaggaatggt 120
tgttcagggc cagcggctca gccctgggag cactgactgc ttcaagacac agactcctct 180
gggatgccag gcagagtctg ctcctgaagg cagactccac tcttcatggg g 231

<210> SEQ ID NO 435
<211> LENGTH: 238
<212> TYPE: DNA
<213> ORGANISM: Homo sapiens

<400> SEQUENCE: 435
cctcaccttt gcaggagact ctcaatttct cagtccacat cagctctcag accaccaaag 60
caagggttat ttttctaaaa gacatttgtt cccattgctc ctctgactaa agttcctact 120
atgggacatt tgcccttggc actcaaggac cttgcaatca ggctgagaac ctcaggttct 180
caaactcaag accatgggga atgtaatagg tgaatcaggc aggtgaagtc caggactc 238

<210> SEQ ID NO 436
<211> LENGTH: 74
<212> TYPE: DNA
<213> ORGANISM: Homo sapiens

<400> SEQUENCE: 436
caggatgact cagaacccgc gtatgaatgc tgtctattca tgggtccagg cttttgttaa 60
agtctgggcc tgca 74

<210> SEQ ID NO 437
<211> LENGTH: 115
<212> TYPE: DNA
<213> ORGANISM: Homo sapiens

<400> SEQUENCE: 437
tgttgagtgc tagctgttgt tgagtgcttg tcctgcctgg gccctgtttt tagcctttga 60
tgtacatttc tccatttaac ttccacaata gccctattag gcagctagta ttatt 115

<210> SEQ ID NO 438
<211> LENGTH: 25
<212> TYPE: DNA
<213> ORGANISM: Homo sapiens

<400> SEQUENCE: 438
cagggcttcc ttcaactcag ggttc 25

<210> SEQ ID NO 439
<211> LENGTH: 100
<212> TYPE: DNA
<213> ORGANISM: Homo sapiens

<400> SEQUENCE: 439
cccgtggaga gagccccgct ggtgaggaag cacggggacc ctgctgcagg gctggtggag 60
ggctccttct gtagacttct gagcttggag cacagatggg 100

<210> SEQ ID NO 440
<211> LENGTH: 138
<212> TYPE: DNA
<213> ORGANISM: Homo sapiens

<400> SEQUENCE: 440
tcaggtcatc cgctccatgg aggtccccgt tcctaccttg gccttgcctt tccccctgca 60
tgtaaccttg gtgaactttt cacaagagtc tgcgcagtct tcttgtaagc agattaatgc 120
cgaggaaaag ccttggtg 138

<210> SEQ ID NO 441
<211> LENGTH: 83
<212> TYPE: DNA
<213> ORGANISM: Homo sapiens

<400> SEQUENCE: 441
ttctctcccg acaggagcgg ccaggacagg gagcagaagg tgactgctgt gctgcctgga 60
gctcttctgt ccggaggttt agt 83

<210> SEQ ID NO 442
<211> LENGTH: 25
<212> TYPE: DNA
<213> ORGANISM: Homo sapiens

<400> SEQUENCE: 442
actccgtaca gagagcgttc cagcc 25

<210> SEQ ID NO 443
<211> LENGTH: 25
<212> TYPE: DNA
<213> ORGANISM: Homo sapiens

<400> SEQUENCE: 443
agaatcagtt gtctcccagg cgggg 25

<210> SEQ ID NO 444
<211> LENGTH: 25
<212> TYPE: DNA
<213> ORGANISM: Homo sapiens

<400> SEQUENCE: 444
acaagggcgg tgcatcaaga ccaca 25

<210> SEQ ID NO 445
<211> LENGTH: 30
<212> TYPE: DNA
<213> ORGANISM: Homo sapiens

<400> SEQUENCE: 445
cggcccccag atatctgagg aaggctgagc 30

<210> SEQ ID NO 446
<211> LENGTH: 370
<212> TYPE: DNA
<213> ORGANISM: Homo sapiens

<400> SEQUENCE: 446
agactgaccc tacaataaat gcttaagaga gtcctacatc tggaagcaaa agggctatat 60

-continued

```
tcaccatcat gaaaacccaa aagtataaaa ctcattggta aagcagacac acaaataaga    120

aagagaatgg aaccacatgt tatcattaca gaaaaccacc aaactgcaaa gataaacaaa    180

ggaaagaaag aaagaaagga aggaagaaag gaaggaagaa aaaggattat ttaaaattat    240

cagaaaacaa ttaaaatgac aggaataaga cctcacctat caataacaac tttttaaat     300

ggcttaaatt tcccagttaa aagatataga ctggctgaat ggattttaaa agtgacctaa    360

ctctatgcta                                                           370
```

<210> SEQ ID NO 447
<211> LENGTH: 216
<212> TYPE: DNA
<213> ORGANISM: Homo sapiens

<400> SEQUENCE: 447

```
ggtattacct gatcccaact tggcaccaaa agacagccaa catagactca ttcctcctgc     60

ttcctggtga gcctggtatt ctcctccact tccactgaca gacatgtagg gtgactgggt    120

ggtatcaaca ataggaacca catcataaca ggcagcctag tttgggaagc actcttggtc    180

tccgtaggcc tgagactcct tttgcccatc tagagg                              216
```

<210> SEQ ID NO 448
<211> LENGTH: 168
<212> TYPE: DNA
<213> ORGANISM: Homo sapiens

<400> SEQUENCE: 448

```
acttaaaata ggagtgaggt gagaggggca gctgggctca tggacgtcaa gtggacagtt     60

tctcagctgg tatttcctat atttcctgtt ttggacagca ggttcctgcc cttctaagct    120

gggggtaggg gtgagggagt gtatgttaaa aagctctgtg gacttgct                 168
```

<210> SEQ ID NO 449
<211> LENGTH: 491
<212> TYPE: DNA
<213> ORGANISM: Homo sapiens

<400> SEQUENCE: 449

```
gagcccttgt tcagtgatcc tatgacttgt cagctcagtg aattgctctg actcttactg     60

ctttcattta tgaaatggag acaataaccc ctctctcata ggaagggtaa gaccagaaga    120

gcctacacta tggttggaat aatatttgta tacagtgatc aagagaatgt tctctgaaac    180

cagactctct ttaaatctta cctctatcac ttattagtta tatggctagc tgttaaatga    240

ggtcaaaaga gtgtgttctt cataaaacta tacagaagat taaattaatt aaaacatgta    300

cagtcctttt aaaaaagatc aagtgaaaca gcatacatga aagtgctttc agcacgctga    360

gaataacaat agcaatggct agagattatg gagcactccc cactgccagc accaggggaa    420

ctttgtacct acaacttttt acttagtcca cataaccatg aattcgtctc atttatgtag    480

accgggaaac a                                                         491
```

<210> SEQ ID NO 450
<211> LENGTH: 238
<212> TYPE: DNA
<213> ORGANISM: Homo sapiens

<400> SEQUENCE: 450

```
caacccaggg tccttgcaga gagattgatc tgccagcagt ggcatcagca gcaatagtag     60

cagcagcaaa gccctggaca gtcctggccc ccagtccaca acttagacac agcacatggc    120
```

ctaattcacc cacagaagca gccactgtga agccctgtgt ctccccagac tccatccagt 180
ggcataagga gacccaggcc ctgcagcttc ctccccatca tggaaggctg tccatcta 238

<210> SEQ ID NO 451
<211> LENGTH: 25
<212> TYPE: DNA
<213> ORGANISM: Homo sapiens

<400> SEQUENCE: 451
ttctttttgt ctcccatata cgctg 25

<210> SEQ ID NO 452
<211> LENGTH: 160
<212> TYPE: DNA
<213> ORGANISM: Homo sapiens

<400> SEQUENCE: 452
gctctgccga cttccagttc tggaacaaga tggttaaact catttttccc tgctctgctc 60
ctctaaatac aactaagtac cttggaaact attcagcaga caatgataaa gggctctgaa 120
agctagaaga aaaggtgtac ttgcaagaaa cctcaggact 160

<210> SEQ ID NO 453
<211> LENGTH: 413
<212> TYPE: DNA
<213> ORGANISM: Homo sapiens

<400> SEQUENCE: 453
gacatagaat caaccaaaat ggccatcagt gatagactgg ataaagaaaa tgtggtacat 60
atacaccatg gaatactatg cagccgtaga aagaaacgag atcatgtccg ttgcagggac 120
atggatggag ctggaagcca ttatcctcag aaaactaacc caggaacaga aaagcaaaca 180
ccacatgttc tcactcataa gtgggagctg aagactgaga acacatggaa ccagggagag 240
gaacaacaca cactgaggcc tgccactgca ggtgggggtt caggggaggg agagcatcag 300
gaaaatagct aatgcatgtc aggcttaata agtaggtgat tggctgatag gtgcagcaaa 360
ctgccatggc acacgtttac ctatgtaaca aacctacaaa tactacacat gta 413

<210> SEQ ID NO 454
<211> LENGTH: 620
<212> TYPE: DNA
<213> ORGANISM: Homo sapiens

<400> SEQUENCE: 454
tgtcttgctg gcctgaaatc gagtacgcag cccggggtga tcagggtctc ccggcccgga 60
tgtgtgagac ttgcttcccc tgggcaatag gcgatacgat gctttaggag gaaggtgtct 120
ctccctccta agccccggag gggagaactt ccaaagacag aaaaccacag gcttcctggc 180
acagagcttt ccctttatca gctaaagcag aatcttttct ggccttaacc tggccccttc 240
ctctaactgc aggcagagag gcagacagaa aagcacttgc tgaaacacaa agttttgttc 300
tgtcctcaac gaactgtcta gagctgattg ctgatagtcg tggtgcatta tgccttcctg 360
gttttcattt aattgggcac cacgctgcct ttcaagacgc cttaaaggaa ccaacaacca 420
aatccaagag agctggacag accattgaac acacagtagg ctgtgtctcg tggctttcgt 480
tgtctggtgc ctcaaagaaa acaccagaaa gattgtttct aagctagagc caccccagat 540
tgcttaaagt gcaaagctca ctgctgttgg gggtaccctt gtgagacact ggaaagctgg 600
ttttaccgtg gccctatgaa 620

<210> SEQ ID NO 455
<211> LENGTH: 46
<212> TYPE: DNA
<213> ORGANISM: Homo sapiens

<400> SEQUENCE: 455
ccgaggaggc ggagcatgga actcgacagt taaaacattt aagaga 46

<210> SEQ ID NO 456
<211> LENGTH: 116
<212> TYPE: DNA
<213> ORGANISM: Homo sapiens

<400> SEQUENCE: 456
aggcagcctt ttctgtcaca acacaacgct gagccggcag cctggctctg tcaggatctg 60
gggctcccgc gcccgagaag cccagcctcg ccggcggcca agttcaccgc gaggcc 116

<210> SEQ ID NO 457
<211> LENGTH: 62
<212> TYPE: DNA
<213> ORGANISM: Homo sapiens

<400> SEQUENCE: 457
gactctgaaa ctacccggct ctgcagaagc acgctgggcc caggggcttc tagactgaca 60
gc 62

<210> SEQ ID NO 458
<211> LENGTH: 70
<212> TYPE: DNA
<213> ORGANISM: Homo sapiens

<400> SEQUENCE: 458
aaaggctgca gtcaccagca tcttttccaa ccttaatgaa ctgtatcctc aaaagaacac 60
tatcagactg 70

<210> SEQ ID NO 459
<211> LENGTH: 32
<212> TYPE: DNA
<213> ORGANISM: Homo sapiens

<400> SEQUENCE: 459
gaaaattcct atcccaccag caaatcagcc cg 32

<210> SEQ ID NO 460
<211> LENGTH: 30
<212> TYPE: DNA
<213> ORGANISM: Homo sapiens

<400> SEQUENCE: 460
ctcccagata aagagatcaa cacgggacag 30

<210> SEQ ID NO 461
<211> LENGTH: 45
<212> TYPE: DNA
<213> ORGANISM: Homo sapiens

<400> SEQUENCE: 461
gggttcctgt cggaatcttg gagctcatcc cccaaacttg agatt 45

<210> SEQ ID NO 462
<211> LENGTH: 56
<212> TYPE: DNA
<213> ORGANISM: Homo sapiens

<400> SEQUENCE: 462
caaaggcttc tcttgctggc tgagaattgt tggggagctc cctgcccacg gagggc 56

<210> SEQ ID NO 463
<211> LENGTH: 30
<212> TYPE: DNA
<213> ORGANISM: Homo sapiens

<400> SEQUENCE: 463
aaactttaag gaagacaact gtgcattctc 30

<210> SEQ ID NO 464
<211> LENGTH: 75
<212> TYPE: DNA
<213> ORGANISM: Homo sapiens

<400> SEQUENCE: 464
tggaacatac gttcttgtga acatagagag tggcattttc ttatgtcgat gtaatgtgaa 60
caactcctgg tcacc 75

<210> SEQ ID NO 465
<211> LENGTH: 25
<212> TYPE: DNA
<213> ORGANISM: Homo sapiens

<400> SEQUENCE: 465
ttggtacatg ccagcacggt ctgtg 25

<210> SEQ ID NO 466
<211> LENGTH: 30
<212> TYPE: DNA
<213> ORGANISM: Homo sapiens

<400> SEQUENCE: 466
gattcactgt gcgaggaccc acctgacacc 30

<210> SEQ ID NO 467
<211> LENGTH: 26
<212> TYPE: DNA
<213> ORGANISM: Homo sapiens

<400> SEQUENCE: 467
gtaaggtgac caatggctgg ctgaag 26

<210> SEQ ID NO 468
<211> LENGTH: 25
<212> TYPE: DNA
<213> ORGANISM: Homo sapiens

<400> SEQUENCE: 468
tccgagctgt cacgtggttt ataca 25

<210> SEQ ID NO 469
<211> LENGTH: 26
<212> TYPE: DNA
<213> ORGANISM: Homo sapiens

<400> SEQUENCE: 469

```
tcaggtttgc tgggaggaat ccagaa                                           26
```

<210> SEQ ID NO 470
<211> LENGTH: 131
<212> TYPE: DNA
<213> ORGANISM: Homo sapiens

<400> SEQUENCE: 470

```
ccactctagg caggactttc atatccttta tctaactgtc acatgatggg gtgacatgtt     60

gatcccccca cagcctggat gatagaaata tttgtggttt gatatgcgtc agcgcttatg    120

actttggcat a                                                         131
```

<210> SEQ ID NO 471
<211> LENGTH: 25
<212> TYPE: DNA
<213> ORGANISM: Homo sapiens

<400> SEQUENCE: 471

```
ggtcatattt cacgtctgcc ctgta                                           25
```

<210> SEQ ID NO 472
<211> LENGTH: 106
<212> TYPE: DNA
<213> ORGANISM: Homo sapiens

<400> SEQUENCE: 472

```
tgctttacaa acactgactc ctcaacacac ggtcatctct aaaagaaagg gtgtttggca     60

gttcctcgac agttctggaa aggctgcctt actagaagca gagtca                   106
```

<210> SEQ ID NO 473
<211> LENGTH: 82
<212> TYPE: DNA
<213> ORGANISM: Homo sapiens

<400> SEQUENCE: 473

```
tattttggtc atgggctggt ctggtcggtt tcccatttgt ctggccagtc tctgtgtgtc     60

ttaatccctt gtccttcatt aa                                              82
```

<210> SEQ ID NO 474
<211> LENGTH: 65
<212> TYPE: DNA
<213> ORGANISM: Homo sapiens

<400> SEQUENCE: 474

```
cacctctacc tgttgcccgc cgatcacagc cggaatgcag ctgaaagatt ccctggggcc     60

tggtt                                                                 65
```

<210> SEQ ID NO 475
<211> LENGTH: 34
<212> TYPE: DNA
<213> ORGANISM: Homo sapiens

<400> SEQUENCE: 475

```
tgacagacac tgaaaatcac gactcatccc cctc                                 34
```

<210> SEQ ID NO 476
<211> LENGTH: 35
<212> TYPE: DNA
<213> ORGANISM: Homo sapiens

<400> SEQUENCE: 476
tgaaacagga agctctatga cacacttgat cgaat 35

<210> SEQ ID NO 477
<211> LENGTH: 340
<212> TYPE: DNA
<213> ORGANISM: Homo sapiens

<400> SEQUENCE: 477
agcggcagag cagttattaa cagaatcaca gtctttctgg agctgctgtc agtcctgtgc 60
tgtcctcagg gcctttgctt ggtcaggggc cccacttctt atccaccctt ccctctacct 120
caccgaggct gctaggccca ggtgtattgt gattatttga tgcacctggg aggccatgtc 180
tcccggggag tctcaggacc tcattgggct ggaattccac ggggatctct cattgggtct 240
ctttgggcct ttggagaggg gagtgcaggg caccacctgg gcgaacacct gtgccatcct 300
gtaagtcctt gtgtgactct tcatccaagt caacaggggc 340

<210> SEQ ID NO 478
<211> LENGTH: 31
<212> TYPE: DNA
<213> ORGANISM: Homo sapiens

<400> SEQUENCE: 478
cgtggacccg gctatgtctg actttgtgct g 31

<210> SEQ ID NO 479
<211> LENGTH: 69
<212> TYPE: DNA
<213> ORGANISM: Homo sapiens

<400> SEQUENCE: 479
gggaacaaaa tgtctgctca aaccatgaca aaattggcca caatttgccg attgggctga 60
taacaaaag 69

<210> SEQ ID NO 480
<211> LENGTH: 25
<212> TYPE: DNA
<213> ORGANISM: Homo sapiens

<400> SEQUENCE: 480
gtgtgtacta atcactcaga cagtg 25

<210> SEQ ID NO 481
<211> LENGTH: 48
<212> TYPE: DNA
<213> ORGANISM: Homo sapiens

<400> SEQUENCE: 481
gaaaagattt ttattcgtgt ctacatcagt gtgaaaggct tcatcctg 48

<210> SEQ ID NO 482
<211> LENGTH: 33
<212> TYPE: DNA
<213> ORGANISM: Homo sapiens

<400> SEQUENCE: 482
ctggggacac tatggcccca tcctagcctg gtg 33

<210> SEQ ID NO 483
<211> LENGTH: 220
<212> TYPE: DNA

<213> ORGANISM: Homo sapiens

<400> SEQUENCE: 483
tgggaggcca aggtgggcgg atcatgagct caggggttca agaccagcct ggccaacgta 60
gtgaaacccc gtctctacta aaaacaaaaa aattagctgg gcatggtggc gcacacctgt 120
agtcccagct actcgggagg ctgaggcagg agaattgctt gaacctggga ggcagaggtt 180
gcagtgagct gagatcgctc cactgcactc cggtttgggc 220

<210> SEQ ID NO 484
<211> LENGTH: 133
<212> TYPE: DNA
<213> ORGANISM: Homo sapiens

<400> SEQUENCE: 484
ttgctgatat acttacaaac tggtaaacaa tgctctttaa tcaacaattc ataatctggg 60
tcagcgattt ttatctccat atttgctcat actgtatgac atcaatattt tatattggct 120
tgcccataac tta 133

<210> SEQ ID NO 485
<211> LENGTH: 266
<212> TYPE: DNA
<213> ORGANISM: Homo sapiens

<400> SEQUENCE: 485
ctgtgccagt caagcctggc ctgtggctgt gacacctgca ttaccccaga tggttgcctg 60
acctaggcct gtccttctat ctgctttgtt tttatgttga ttactaggtg aagcacagtg 120
ttaaaaacgg gaagaaaagg ctaggaatgc agttatggga gtgtgaggct gggttggaat 180
aggtgggaga aagtccaggg ctgagtgtgt ggaccctgct ctagggatct gaccggctca 240
agctcccagg ccattaaaca aagttg 266

<210> SEQ ID NO 486
<211> LENGTH: 284
<212> TYPE: DNA
<213> ORGANISM: Homo sapiens

<400> SEQUENCE: 486
ctgttgccat ttgaacaagt tgttaagaaa atctgccatg ttttgctctt ttttaaaagg 60
aatgacttta ataaccatag caacacttac tcagttttgt gatccactcc aagattatgg 120
gagcaagaac agatactcct gaaagcaacc ctcacctcct cccccgcccc ctgccctcag 180
caagtcctgg cctgtgtgaa ctgaagggtt tggaagctct ggtttctagg agtgcccaga 240
agctagaaag actagggtgt actagttatt gaggggcagt tgtc 284

<210> SEQ ID NO 487
<211> LENGTH: 29
<212> TYPE: DNA
<213> ORGANISM: Homo sapiens

<400> SEQUENCE: 487
aaaggcattt ctgatttaat taagagttg 29

<210> SEQ ID NO 488
<211> LENGTH: 31
<212> TYPE: DNA
<213> ORGANISM: Homo sapiens

<400> SEQUENCE: 488
atgaaggagg agtcgtctac acttgtaaaa a 31

<210> SEQ ID NO 489
<211> LENGTH: 25
<212> TYPE: DNA
<213> ORGANISM: Homo sapiens

<400> SEQUENCE: 489
tccttgagtt aaagaaattt gtgtc 25

<210> SEQ ID NO 490
<211> LENGTH: 674
<212> TYPE: DNA
<213> ORGANISM: Homo sapiens

<400> SEQUENCE: 490
taatccagtg ctcaacatat ttttgttgaa taaaagcaca aagagattca tgagaagagg 60
gaaatgttgc atacttaggg taggagcaaa ccacagaggt ctttctcagc ctgggcaaag 120
aatgtcaact ctgtgttgga gccagtaggg agctctgtgg gtcctcgagc aggaaaatcc 180
catggcttaa gcagtgtttc aggaagactg ggatgttagg ctccagagct ctgagcaagt 240
cagatgggac tgggagtcat aagaaggctt gactgtggct agtgataacc aatgagcact 300
ggaaacatgg aggggaatct ttcctccctt ttatatcagg gttctctcct agaggagcag 360
gtgaggacct ctgatggacc aggaaattgg aattctgcct gggaggcaag cccatggagg 420
ccctgatctg cttggacaga gagtagctcc cttcacctgt aaaatgagag tgaacgagct 480
ggtgtctaag gaattcagaa tccccccct ggagttccac agggtatgtg ggattttagg 540
gggaccaggg tgtccccagt gcaagaagga ggctcccacc aaggggctgc agcactgcag 600
ataaccccca ggggtatgaa aagaggctga actgggggcc tccacagtca gaatccatcc 660
attgacccag gatg 674

<210> SEQ ID NO 491
<211> LENGTH: 172
<212> TYPE: DNA
<213> ORGANISM: Homo sapiens

<400> SEQUENCE: 491
ccctggcatc atattgggac ttgttaaggg ctgaattgtg tcccatccca aatttgtatg 60
gtgccacccc aactccagta ccttggaatg tgaccgtatt tggagaaagg gtctctgaag 120
aggtaattaa ggtaaaatga ggtcatatgg gtggcctcta attcaatatg ac 172

<210> SEQ ID NO 492
<211> LENGTH: 25
<212> TYPE: DNA
<213> ORGANISM: Homo sapiens

<400> SEQUENCE: 492
tttccatttc ctagtagggc cagtc 25

<210> SEQ ID NO 493
<211> LENGTH: 48
<212> TYPE: DNA
<213> ORGANISM: Homo sapiens

<400> SEQUENCE: 493
tatgtgcatt agtttgcttg gactgctata acgaaatact acttggtg 48

<210> SEQ ID NO 494
<211> LENGTH: 79
<212> TYPE: DNA
<213> ORGANISM: Homo sapiens

<400> SEQUENCE: 494
gagcttttag agaatatggg ccagaaacag gaaggagtca ggacctgata acgggaacca 60
gcggacagtg aacgcagtg 79

<210> SEQ ID NO 495
<211> LENGTH: 71
<212> TYPE: DNA
<213> ORGANISM: Homo sapiens

<400> SEQUENCE: 495
gtgaatacaa tattctcctt ttgttttcac ttttcctaaa agttaaatca aggttcaaaa 60
gaaaatcgag g 71

<210> SEQ ID NO 496
<211> LENGTH: 130
<212> TYPE: DNA
<213> ORGANISM: Homo sapiens

<400> SEQUENCE: 496
agatgctaat ccagcgtgcg tcctggcaga ggttgaaggg ggctcctcaa gtcccaggtc 60
cagcttggtg tggttcagct actcgagaga catctgctgc taatggatga gcagtcaacc 120
tggacgcagg 130

<210> SEQ ID NO 497
<211> LENGTH: 46
<212> TYPE: DNA
<213> ORGANISM: Homo sapiens

<400> SEQUENCE: 497
tgtgaagact ggacttaaac agctacacca ccagaagccg agagag 46

<210> SEQ ID NO 498
<211> LENGTH: 37
<212> TYPE: DNA
<213> ORGANISM: Homo sapiens

<400> SEQUENCE: 498
aaattgacat tccagacaag cggtgcctga gcccgtg 37

<210> SEQ ID NO 499
<211> LENGTH: 65
<212> TYPE: DNA
<213> ORGANISM: Homo sapiens

<400> SEQUENCE: 499
cttagtcgtg tgtacatcat tgggaatgga gggaaataaa tgactggatg gtcgctgctt 60
tttaa 65

<210> SEQ ID NO 500
<211> LENGTH: 57
<212> TYPE: DNA
<213> ORGANISM: Homo sapiens

<400> SEQUENCE: 500
aatcccatgg tcttcaattt ggtcatttaa aaataatcta caaggtatac tgttttt 57

<210> SEQ ID NO 501
<211> LENGTH: 1190
<212> TYPE: DNA
<213> ORGANISM: Homo sapiens

<400> SEQUENCE: 501
caccactcta tttaacagtg ctggaaatat tagccagcaa aacagataaa gaaaaataaa 60
taaatggcat agactggaaa gattcatagt tggcacaatt atgtatatat aaaatcctca 120
ggaatgtaca ctttacatac tagaatttaa aagtaagttt agcaactgtg ttagttcgtt 180
ttcatgctgc tgataaagac atacctgaga ctggacaatt tacaaaagaa aggtttattg 240
gacctatagt tccacatgtc tggggaggcc tcacaatcat ggcggcaggc aaggaggggc 300
aagtcacatc ttatgtggat ggcaacaggc aaagagagag cttgtgcagg gaaactcctg 360
tttttaaaac caccagatct catgacaccc attcactgtc aggagaacag catgggaaag 420
acccaccccc atgattcaat tgtctcccac aaggcccctc ccataccaca tgggaattat 480
gggagctaca agatgagatt tgggtgggga cacagagcca aaccacatca gcaacatgtc 540
agaacacaga aaaaatgtaa aatatcactg tatttctatg tactagtagt gaactgtcag 600
atgttaaaat tcaattgctt agaatggcat caaaaatatg aaatactggc caggcgttat 660
ggctcttgcc tgtactccca ttgctttgga aggctgaggc gggtggatac ctttgaggcc 720
aggagttcaa gaccatcctg agcaacaggg caaaaccttg tctctactaa aaatacaaaa 780
aattagctgg gcatggtggc ctgtacctat aatcccagct acttgggagg ctgagacaca 840
acaatcactt gaacctggga tgcagaggtt gcagggagct gagattgaac cactgtactc 900
cagcctgggg aacaaactga gactctgtct caaaaaaaaa gaaagaaata cttatgggta 960
aatctgacaa aataagtgta agacctgtac actaaaaact acaaaacatt gctgaaataa 1020
attaaagaag acctaaataa tcggagagat atactttgtt taaaggtcag aagtctcagt 1080
attgctaaaa tgagaactct tcccaatgca gtgctaatca aatttctagc aggctttttg 1140
tagaaattga aaagcagatt tgaaattcat atggaagtgc gaacaaaacc 1190

<210> SEQ ID NO 502
<211> LENGTH: 135
<212> TYPE: DNA
<213> ORGANISM: Homo sapiens

<400> SEQUENCE: 502
ccaccatgtg ataccactac atgtatttta gaattgctaa aattaagaag actgaccata 60
tggggtgagg atatggagga aatgaaattc tcatacaatg ctattggtaa tgtaaaatca 120
aactaccact ttgga 135

<210> SEQ ID NO 503
<211> LENGTH: 31
<212> TYPE: DNA
<213> ORGANISM: Homo sapiens

<400> SEQUENCE: 503
gcttgaacca ggaaactgga tatcatctta a 31

<210> SEQ ID NO 504
<211> LENGTH: 28
<212> TYPE: DNA
<213> ORGANISM: Homo sapiens

<400> SEQUENCE: 504
atgtttggga acccaacaat taatgcag 28

<210> SEQ ID NO 505
<211> LENGTH: 1757
<212> TYPE: DNA
<213> ORGANISM: Homo sapiens

<400> SEQUENCE: 505
cccgaatgta tctcccagat gtccagaata cgccatctgc aaaactgaac tcatcctctt 60
tccccagaat gtatctcccg gatgtcgaga atacgccatc tgcaaaactg aactcgtcct 120
ctttcccccg aatgtatctc ccagatgtcc agaatacgcc atctgcaaaa ctgaactcgt 180
cctctttccc ccgaatgtat catctcccag atgtccagaa tacgccatct gcaaaactga 240
actcatcctc tttccccaga atgtatctcg cggatgtcca gaatacgcca tctgcaaaac 300
tgaactcgtc ctctttcccc cgaatgtatc tcccggatgt ccagaatacg ccatctgcaa 360
aactgaactc gtcctctttc cccagaatgt atctcccgga tgtccagaat acgccatctg 420
caaaactgaa ctcgtcctct ttcccccgaa tgtatctccc ggatgtccag aatacaccat 480
ctgcaaaact gaactcgtcc tctttccccc gaatgtatct cccggatgtc cagaatacgc 540
catctgcaaa actgaactcg tcctctttcc cccgaatgta tctcccggat gtccagaata 600
cgccatctgc aaaactgaac tcgtcctctt tcccccgaat gtatctcccg gatgtccaga 660
atacgccatc tgcaaaactg aactcgtcct gtttcccccg aatgtatctc ccggatgtcc 720
agaatacgcc atctgcaaaa ctgaactcgt cctctttccc cagaatgtat ctcccggatg 780
tccagaatac tccatctgca aaactgaact catcctcttt cccccgaatg tatctcccgg 840
atgtccagaa tacgccatct gcaaaactga actcgtcctc tttcccccga atgtatctcc 900
cggatgtaca gaatacgcca tctgcaaaac tgaactcgtc ctctttcccc cgaatgtatc 960
tcccggatgt ccagaatacg ccatctgcaa aactgaactc gtcctctttc cccagaatgt 1020
atctcccgga tgtccagaat acgccatctg caaaactgaa ctcgtcctct ttcccccgaa 1080
tgtatctccc ggatgtccag aatacgccat ctgcaaaact gaactcgtcc tctttccccc 1140
gaatgtatct cccggatgtc cagaatacgc catctgcaaa actgaactcg tcctgtttcc 1200
cccgaatgta tctcccggat gtccagaata cgccatctgc aaaactgaac tcgtcctctt 1260
tccccagaat gtatctcccg gatgtccaga atactccatc tgcaaaactg aactcgtcct 1320
ctttcccccg aatgtatctc ccggatgtcc agaatactcc atctgcaaaa ctgaactcgt 1380
cctctttccc cagaatgtat ctcccggatg tccagaatac gccatctgca aaactgaact 1440
cgtcctcttt ctcccgaatg tatctcccgg atgtccagaa tacgccatct gcaaaactga 1500
actcgtcctc tttcccccga atgtatctcc cggatgtcca gaatacgcca tctgcaaaac 1560
tgaactcgtc ctctttcccc cgaatgtatc tcccggatgt ccagaatacg ccatcggcaa 1620
aactgaactc gtcctctttc cccagaatgt atctcccgga tgtccagaat atgccatctg 1680
caaaactgaa ctcgtcctct ttcccccgaa tgtatctccc ggatgtccag aatacgccat 1740
cggcaaaact gaactcg 1757

<210> SEQ ID NO 506
<211> LENGTH: 45
<212> TYPE: DNA
<213> ORGANISM: Homo sapiens

<400> SEQUENCE: 506
atgtccagaa tacgccatct gcaaaactga actcgtcctc tttcc 45

<210> SEQ ID NO 507
<211> LENGTH: 456
<212> TYPE: DNA
<213> ORGANISM: Homo sapiens

<400> SEQUENCE: 507
aaagagattc tcacttagag acatcataag gaaactactg aaaactagga acaaaggaat 60
tatcttcaaa gcagcaatga aaaatgacat tatttataaa attacaatta tttaaagggt 120
tgtagatttc tcatcagaaa ccatagaggc caggccgggc gctgtggctc acgctgtaat 180
cccagcactt tgggaggccg aggtgggcag atcacttgag gtcaggagtt caggaccagc 240
ctgggcgaaa cctgggcaaa accctgtctc aactaaaaaa taagaaactt agccagacgc 300
agtggtgtgt gtctgtagtc cccgctactc aggaggctga ggcaggagaa tcgcttgaac 360
ctgggaggca gaggttgcag tgagccgaga tcacaccact gcactccagc ccgggcgaca 420
gagcatagaa gccagaatgc aattgaacaa catttc 456

<210> SEQ ID NO 508
<211> LENGTH: 125
<212> TYPE: DNA
<213> ORGANISM: Homo sapiens

<400> SEQUENCE: 508
tcagtcacgt ctgcgccaga gctttgatga cccacctgtc agccacacta agggccctgc 60
catgaataag gcctccgtca ctgaggatcc tgtacccctc tgccataaac tcagtgacct 120
gactg 125

<210> SEQ ID NO 509
<211> LENGTH: 31
<212> TYPE: DNA
<213> ORGANISM: Homo sapiens

<400> SEQUENCE: 509
cccacattca aaaggcttgc ccgagaggcc t 31

<210> SEQ ID NO 510
<211> LENGTH: 80
<212> TYPE: DNA
<213> ORGANISM: Homo sapiens

<400> SEQUENCE: 510
tcaaggtggc cttgcgcttc accgaggagg tgtcattacc aaacgtgctg gacattggct 60
acctacggaa gaaagattaa 80

<210> SEQ ID NO 511
<211> LENGTH: 70
<212> TYPE: DNA
<213> ORGANISM: Homo sapiens

<400> SEQUENCE: 511
ccagacacca ctggcctaca tcaaactcca ggccacagat ggaaatagga ctgagatccc 60
tggacctggg 70

<210> SEQ ID NO 512
<211> LENGTH: 91
<212> TYPE: DNA

<213> ORGANISM: Homo sapiens

<400> SEQUENCE: 512
atgaagctag gcccccctgt cctgacagct ttccacccct tccctgcccc tctcaccctg 60
ctttccaggg gcaatgcacc tccccacttc t 91

<210> SEQ ID NO 513
<211> LENGTH: 30
<212> TYPE: DNA
<213> ORGANISM: Homo sapiens

<400> SEQUENCE: 513
tgtatttggc atctaccata tctttgcatc 30

<210> SEQ ID NO 514
<211> LENGTH: 91
<212> TYPE: DNA
<213> ORGANISM: Homo sapiens

<400> SEQUENCE: 514
cacacataac tctgggcgta aagtgagtaa aaatatgaga cttagaagaa tatttcatca 60
tggtatgctg attggggatt tcacttactg a 91

<210> SEQ ID NO 515
<211> LENGTH: 25
<212> TYPE: DNA
<213> ORGANISM: Homo sapiens

<400> SEQUENCE: 515
tcactacgat tatctgaatc tcata 25

<210> SEQ ID NO 516
<211> LENGTH: 32
<212> TYPE: DNA
<213> ORGANISM: Homo sapiens

<400> SEQUENCE: 516
tcacccttga catccgcaga atccaccctc ct 32

<210> SEQ ID NO 517
<211> LENGTH: 75
<212> TYPE: DNA
<213> ORGANISM: Homo sapiens

<400> SEQUENCE: 517
agtcctgggg aactctcatc tggaaaaagg cgctcatgac aggtggtgcc aaccttccac 60
ggatgctttt cagca 75

<210> SEQ ID NO 518
<211> LENGTH: 25
<212> TYPE: DNA
<213> ORGANISM: Homo sapiens

<400> SEQUENCE: 518
ttcagcgccg aattgatgag gacac 25

<210> SEQ ID NO 519
<211> LENGTH: 48
<212> TYPE: DNA
<213> ORGANISM: Homo sapiens

<400> SEQUENCE: 519

```
atggagaaac aggcggccca gccaggccct ttcactgccc gtgatgga          48
```

<210> SEQ ID NO 520
<211> LENGTH: 48
<212> TYPE: DNA
<213> ORGANISM: Homo sapiens

<400> SEQUENCE: 520

```
tccaccagac tgatgacact tattccactt ggttcccaga actaagag          48
```

<210> SEQ ID NO 521
<211> LENGTH: 92
<212> TYPE: DNA
<213> ORGANISM: Homo sapiens

<400> SEQUENCE: 521

```
gggcatttgg actctaaccg ggacaaccta gtggccgggc aggggatgca ggcaccacag    60

gtcacagtag tttgctacga gtgtcagctt tt                                  92
```

<210> SEQ ID NO 522
<211> LENGTH: 64
<212> TYPE: DNA
<213> ORGANISM: Homo sapiens

<400> SEQUENCE: 522

```
cctgtgggaa tccataaaga attgattctc atcccccaga agtgagatcc cgcttgtgtc    60

atca                                                                64
```

<210> SEQ ID NO 523
<211> LENGTH: 34
<212> TYPE: DNA
<213> ORGANISM: Homo sapiens

<400> SEQUENCE: 523

```
ctggtgcacc tggtctacct catgtccagt gttt                                34
```

<210> SEQ ID NO 524
<211> LENGTH: 122
<212> TYPE: DNA
<213> ORGANISM: Homo sapiens

<400> SEQUENCE: 524

```
tcctgcagtt ccaatgtgag cagcagttgt ttccaaggct aacaatttca cgccaactag    60

aagcctccac aagtcaggtg ccaggcattt ctaagccagt agagcagctc cgcttgtttc   120

tc                                                                 122
```

<210> SEQ ID NO 525
<211> LENGTH: 49
<212> TYPE: DNA
<213> ORGANISM: Homo sapiens

<400> SEQUENCE: 525

```
cttggctggt ggatctcggg ttaaaatcga cttaggatgc cccccttat              49
```

<210> SEQ ID NO 526
<211> LENGTH: 32
<212> TYPE: DNA
<213> ORGANISM: Homo sapiens

<400> SEQUENCE: 526
gcttctgcag tttgccttgg agtctgggct gt 32

<210> SEQ ID NO 527
<211> LENGTH: 32
<212> TYPE: DNA
<213> ORGANISM: Homo sapiens

<400> SEQUENCE: 527
tgaatttata ttaccgagtg gagggtcaca tg 32

<210> SEQ ID NO 528
<211> LENGTH: 26
<212> TYPE: DNA
<213> ORGANISM: Homo sapiens

<400> SEQUENCE: 528
agtaaatcca tttgctgatt gcaata 26

<210> SEQ ID NO 529
<211> LENGTH: 68
<212> TYPE: DNA
<213> ORGANISM: Homo sapiens

<400> SEQUENCE: 529
ctcttgtgta aaaatctaac tcatctcgct gaatttcctg atttaaaagt ctaattcatt 60
tcaccaaa 68

<210> SEQ ID NO 530
<211> LENGTH: 60
<212> TYPE: DNA
<213> ORGANISM: Homo sapiens

<400> SEQUENCE: 530
ccagacgtac agaggctggg agccattgtg gtgtgctata ttgatgacgg cagcagtggg 60

<210> SEQ ID NO 531
<211> LENGTH: 75
<212> TYPE: DNA
<213> ORGANISM: Homo sapiens

<400> SEQUENCE: 531
ttgtgtatct gcgttccttt caacaagtgt gacttcctca atggcatcat tcgtgagcgt 60
aacacagagc tcagc 75

<210> SEQ ID NO 532
<211> LENGTH: 35
<212> TYPE: DNA
<213> ORGANISM: Homo sapiens

<400> SEQUENCE: 532
gagctgaaat cgaccagggg gttcttatcc aacag 35

<210> SEQ ID NO 533
<211> LENGTH: 73
<212> TYPE: DNA
<213> ORGANISM: Homo sapiens

<400> SEQUENCE: 533
gcctacctaa aatattgaat gctgttaata aatctcctga ggccagcata agaaggtgat 60
gggcaaaact aat 73

<210> SEQ ID NO 534
<211> LENGTH: 27
<212> TYPE: DNA
<213> ORGANISM: Homo sapiens

<400> SEQUENCE: 534
cttagagggc cccacagttg tttgctg 27

<210> SEQ ID NO 535
<211> LENGTH: 254
<212> TYPE: DNA
<213> ORGANISM: Homo sapiens

<400> SEQUENCE: 535
tggttacaat ggtactttca gcctgtccga attatgtatt gcccctcccc tttttattaa 60
taacattgaa gtgtgatggg acaaccactg aagccgtcag ttgaaacctg ctgggacttt 120
ttagccattc tcttcaacat aaagaatggg tgtttttgga gggggtgaga ggaatgggga 180
aatgttgtca aagagtacaa tgttttagtt gagacaggaa gaatatattt tgttgagatc 240
tacagcacag catg 254

<210> SEQ ID NO 536
<211> LENGTH: 25
<212> TYPE: DNA
<213> ORGANISM: Homo sapiens

<400> SEQUENCE: 536
tgtgctaggt ttctttgcat gtacc 25

<210> SEQ ID NO 537
<211> LENGTH: 28
<212> TYPE: DNA
<213> ORGANISM: Homo sapiens

<400> SEQUENCE: 537
agcctcctcc aaaacagcac actttccg 28

<210> SEQ ID NO 538
<211> LENGTH: 109
<212> TYPE: DNA
<213> ORGANISM: Homo sapiens

<400> SEQUENCE: 538
tttctcccgc ccaccttctc cgctgccaga ccgcccgagc tgccctcagt ttctccccaa 60
gttggactca ctttcggggt gtcccacaag cccgatccca gagcctgct 109

<210> SEQ ID NO 539
<211> LENGTH: 121
<212> TYPE: DNA
<213> ORGANISM: Homo sapiens

<400> SEQUENCE: 539
cgacctcgac ggccgtcctg ccgaagtacc tgccgtcgct gcccaccccc gtggtgcggc 60
cctgacggtc gcgcaggtcg acggacgaca gcgcgctccg gatgaagttg ggcgggtagc 120
t 121

<210> SEQ ID NO 540
<211> LENGTH: 57
<212> TYPE: DNA
<213> ORGANISM: Homo sapiens

<400> SEQUENCE: 540
agactgtgat gactgggaga gcgggctgaa tgcgatggag tgtgcattac atttgga 57

<210> SEQ ID NO 541
<211> LENGTH: 33
<212> TYPE: DNA
<213> ORGANISM: Homo sapiens

<400> SEQUENCE: 541
catagtactc tgaacatgcc cgatttcatc tgt 33

<210> SEQ ID NO 542
<211> LENGTH: 37
<212> TYPE: DNA
<213> ORGANISM: Homo sapiens

<400> SEQUENCE: 542
tgacaaaaat gacccccatt tgtgtgactt cattgag 37

<210> SEQ ID NO 543
<211> LENGTH: 150
<212> TYPE: DNA
<213> ORGANISM: Homo sapiens

<400> SEQUENCE: 543
atgaaacaga cagacttaat gaacaagcca gtgaggagat tttgaaagta gaacagaaat 60
ataacaaact ccgccaacca ttttttcaga agaggtcaga attgatcgcc aaaatcccaa 120
atttttgggt aacaacattt gtcagccatc 150

<210> SEQ ID NO 544
<211> LENGTH: 29
<212> TYPE: DNA
<213> ORGANISM: Homo sapiens

<400> SEQUENCE: 544
tttgacgaaa cgttcaagtc aaacacaga 29

<210> SEQ ID NO 545
<211> LENGTH: 38
<212> TYPE: DNA
<213> ORGANISM: Homo sapiens

<400> SEQUENCE: 545
gaggtcatca aagatgatat ctggccaaac ccattaca 38

<210> SEQ ID NO 546
<211> LENGTH: 35
<212> TYPE: DNA
<213> ORGANISM: Homo sapiens

<400> SEQUENCE: 546
gcgtacaagg cccacgaaat agtcggccgc cgcag 35

<210> SEQ ID NO 547
<211> LENGTH: 90
<212> TYPE: DNA
<213> ORGANISM: Homo sapiens

<400> SEQUENCE: 547
ataagtccac cgcacagaac tcgcgcgcct cccctcgaac gaacgcgcac gcgcgcgcag 60
ggggcgggtc ttcttcccga cacccactga 90

<210> SEQ ID NO 548
<211> LENGTH: 90
<212> TYPE: DNA
<213> ORGANISM: Homo sapiens

<400> SEQUENCE: 548
ctccgcctcc gcgacgggcc gtcgggagga ggcgaccgga agccacttaa agcagagatc 60
gaggtgacag gcgagctggc tggactcgga 90

<210> SEQ ID NO 549
<211> LENGTH: 41
<212> TYPE: DNA
<213> ORGANISM: Homo sapiens

<400> SEQUENCE: 549
cgcggtcgag gctttctgcg ttcgcggcgg cggaatggcc c 41

<210> SEQ ID NO 550
<211> LENGTH: 93
<212> TYPE: DNA
<213> ORGANISM: Homo sapiens

<400> SEQUENCE: 550
tctgtggtcc ctagacgtcg gctcccgccc tcggcgctga tctccggcgc gggcactgct 60
ttccactcgg ctcctgtcgt ccgttctctc agg 93

<210> SEQ ID NO 551
<211> LENGTH: 61
<212> TYPE: DNA
<213> ORGANISM: Homo sapiens

<400> SEQUENCE: 551
gggcgcgtct atgcggcctc ccccgcgggc cgaccccggg tgctctgagg cgcctaggag 60
c 61

<210> SEQ ID NO 552
<211> LENGTH: 50
<212> TYPE: DNA
<213> ORGANISM: Homo sapiens

<400> SEQUENCE: 552
ggcacggcag ctacgggagc cttccggcta ccccgcgttt cgggctgcag 50

<210> SEQ ID NO 553
<211> LENGTH: 127
<212> TYPE: DNA
<213> ORGANISM: Homo sapiens

<400> SEQUENCE: 553
cattaacttt gagagcgcac aagtcttcgt cttcctcccc gccgccgcgg gaagcgctcg 60
ccgcctttcc cccgcgcttc gcggctcagt tctgcgagcc cccaagaccc gttggacgct 120
cctcggg 127

<210> SEQ ID NO 554
<211> LENGTH: 157
<212> TYPE: DNA
<213> ORGANISM: Homo sapiens

<400> SEQUENCE: 554
ctcagctgca ctgcgcggag ttggcgcggc ccgggaccag gagctgagca aaccgccgcg 60
gccaacagga ggcgtcactc ggacccgggc tcggcgccgg ggtgtcgcgc ggcggcgggc 120
gggcaggctt tggagcggca gttttttcgg aaagtgc 157

<210> SEQ ID NO 555
<211> LENGTH: 28
<212> TYPE: DNA
<213> ORGANISM: Homo sapiens

<400> SEQUENCE: 555
atgatcatct tccttccttt cctcgtag 28

<210> SEQ ID NO 556
<211> LENGTH: 41
<212> TYPE: DNA
<213> ORGANISM: Homo sapiens

<400> SEQUENCE: 556
gatttttaga ctctgaggag cagttggagc taatccacat t 41

<210> SEQ ID NO 557
<211> LENGTH: 217
<212> TYPE: DNA
<213> ORGANISM: Homo sapiens

<400> SEQUENCE: 557
cagactgtgt agtgcagcct ccctctcctc ctgatgactt ttcatgccaa atgagactct 60
ctgagaagat cactccattg aagacttgtt ttaagaaaaa ggatcagaaa agattgggaa 120
ctggaaccct gaggtctttg aggccaatat taaacactct tctagaatct ggctcacttg 180
atggggtttt tagatctagg aaccagagta cagatga 217

<210> SEQ ID NO 558
<211> LENGTH: 179
<212> TYPE: DNA
<213> ORGANISM: Homo sapiens

<400> SEQUENCE: 558
ggggaccaga taccggaagc ccatccttcc actgaagctc cagaacgagt ggttccaatc 60
caagatcaca gctttccatc agaaaccctc agtgggacgg tggcagattc cacaccagct 120
cacttccaga ctgatctttt gcacccagtt tcaagtgatg ttcctactag tcctgactg 179

<210> SEQ ID NO 559
<211> LENGTH: 28
<212> TYPE: DNA
<213> ORGANISM: Homo sapiens

<400> SEQUENCE: 559
gtatttataa caacttgtag aactgttg 28

<210> SEQ ID NO 560
<211> LENGTH: 70
<212> TYPE: DNA
<213> ORGANISM: Homo sapiens

<400> SEQUENCE: 560
aaaactttgc agaacagcgg ctcccacttc accttcatga agcaaatttc cagtctgctg 60
agtacttcag 70

-continued

<210> SEQ ID NO 561
<211> LENGTH: 32
<212> TYPE: DNA
<213> ORGANISM: Homo sapiens

<400> SEQUENCE: 561
aagttgactt gtggtcattg caacctggtt tt 32

<210> SEQ ID NO 562
<211> LENGTH: 154
<212> TYPE: DNA
<213> ORGANISM: Homo sapiens

<400> SEQUENCE: 562
ataacggcat gttgagcctt gctgagagat tcacaaacaa gctggagcag cccaggttca 60
catggttacc acattatttg gctaaagcta ttaatctctg tggtcaggcc tgtaaagctg 120
gtctatctgt gcagattgcg cataaccagg aagt 154

<210> SEQ ID NO 563
<211> LENGTH: 112
<212> TYPE: DNA
<213> ORGANISM: Homo sapiens

<400> SEQUENCE: 563
gccttctatc ccagctgttc ttacagaaat taagtttcac tttctcatca ggctatggtt 60
gagaagtatg tctcatttat agtgccttct gtgatcttag gacatgtgac ta 112

<210> SEQ ID NO 564
<211> LENGTH: 508
<212> TYPE: DNA
<213> ORGANISM: Homo sapiens

<400> SEQUENCE: 564
tgtgatttca gacagcatcc ttctcactaa cttgctgcct tcttggaata agaatttcca 60
agatgtctca ggaggtacca agggagcagc aacaaggcct aatgatcact tcttcaagaa 120
tttatcccaa gaaatgcatt gtatcttaag ttggggaaca cttttaccta ctcaaaaatc 180
ttttgaggta ttcagataaa tccatgatct gagttttatg ttaatagttt tacagtgtca 240
tagtgtggta attaagtgta gaattttaac ctctgaggct gggcgcagtg gctcacgcct 300
gtaatcttag ctttttggaa ggctgaggca gaagaattgc ttgagaccag cccaggcaac 360
atggcgaaac cttgtctcta cagaaaaata caaaaattag ctgagtgtgg tggatcatgc 420
ctatagtcac agctactggg gatgctgagg tgggagggta gtttaagcaa gggagtttga 480
ggtggcagtg agcctagttg gcactatt 508

<210> SEQ ID NO 565
<211> LENGTH: 30
<212> TYPE: DNA
<213> ORGANISM: Homo sapiens

<400> SEQUENCE: 565
ggacaagaat tttgggcaga tttgaatgcc 30

<210> SEQ ID NO 566
<211> LENGTH: 98
<212> TYPE: DNA
<213> ORGANISM: Homo sapiens

<400> SEQUENCE: 566
tttgaccaac tacgaaggct gtccacacca ccctctagca atgtcaactc tatttaccac 60
acagtctgga aattcttctg tagggaccac tttggatg 98

<210> SEQ ID NO 567
<211> LENGTH: 88
<212> TYPE: DNA
<213> ORGANISM: Homo sapiens

<400> SEQUENCE: 567
tgtcattcga ttgattgaag aagccaactc tcggggtctg aaagaggttc gatttatgat 60
gtggaataac cactacatcc tccacaat 88

<210> SEQ ID NO 568
<211> LENGTH: 160
<212> TYPE: DNA
<213> ORGANISM: Homo sapiens

<400> SEQUENCE: 568
ggtggggttc ccacacaagc tcctccacct cttgaagcaa cttcatcatc acaaattatc 60
tgcccagatg gggtcacttc agcaaacttt taccctgaaa cttgggttta tatgcatcca 120
tctcaggact tcatccaagt ccctgtttct gcagaggata 160

<210> SEQ ID NO 569
<211> LENGTH: 396
<212> TYPE: DNA
<213> ORGANISM: Homo sapiens

<400> SEQUENCE: 569
atgaaaagtt caagacggcc gggcgcagtg gctcaagcct gtaatcccag cactttggga 60
ggccgaggcg ggcagattac gaggtcagga gatcgagacc atcctagcta acacggtgaa 120
accccgtctc tactaaaaat agaaaaaatt agctgggcgt ggtggcgggc acctgtagtc 180
ccagctactc gggaggctga ggcaggagaa tggtgtgaac ctgggaggcg gagcttgcag 240
tgagccgaga ttgcgccact gcactccagc ctgggcgaca gagccagact ccgtctcaaa 300
aaaaaaaaaa aaaaagttca agaatcaaga gagctttatt gtagccagtg tcaaatgagg 360
aacataatag taaacatttg cacagaattt atgttc 396

<210> SEQ ID NO 570
<211> LENGTH: 35
<212> TYPE: DNA
<213> ORGANISM: Homo sapiens

<400> SEQUENCE: 570
caggaaaatg tttggccgtg acaggataat aaatg 35

<210> SEQ ID NO 571
<211> LENGTH: 26
<212> TYPE: DNA
<213> ORGANISM: Homo sapiens

<400> SEQUENCE: 571
gaccctcgag tctgtggaaa gcatgc 26

<210> SEQ ID NO 572
<211> LENGTH: 130
<212> TYPE: DNA
<213> ORGANISM: Homo sapiens

<400> SEQUENCE: 572
tccaaaggag tccacttcat gtttctggcc aaagtgctga cgggcagata cacaatgggc 60
agtcatggca tgagaaggcc cccgccagtc aatcctggca gtgtcaccag tgacctttat 120
gactcttgtg 130

<210> SEQ ID NO 573
<211> LENGTH: 30
<212> TYPE: DNA
<213> ORGANISM: Homo sapiens

<400> SEQUENCE: 573
tacccttatt ttgttatcca atatgaagaa 30

<210> SEQ ID NO 574
<211> LENGTH: 521
<212> TYPE: DNA
<213> ORGANISM: Homo sapiens

<400> SEQUENCE: 574
gcttgggcct ggtagaagtt tgaccaaatg gaatggaggc tgtgagcaat gtgaggattc 60
tatttattta tttacgtttg ataaaactta ctggaactag tactaccatg cgtattccct 120
gtccaaagca tcactgcttt ggtatagtat aagttcatga aattctggtg ggtagaaaga 180
aatttttatt tctatcagca gtactaaaat gtatcagcca accagagaac atcagtgact 240
ttaacttctg cagagtttgc cccagaattc agagttctat ttagaggaag ttaaaacaac 300
aacaaaaaac aaccatttga aaaatttttg tcaccagcaa aacttttcac taattagtga 360
tatgaaatgt gatttttgtg ttgttaaact tcagctttgg aaaactcagt ctctttcatt 420
atcatccatt ccaatttgaa ggagttgggc agctaatttg gttaaaggca gtcttgaggg 480
ttagaagtat tacttccttt tcgggttcca gacctagctt g 521

<210> SEQ ID NO 575
<211> LENGTH: 49
<212> TYPE: DNA
<213> ORGANISM: Homo sapiens

<400> SEQUENCE: 575
aaacttggaa attgtgccag tggtccagct ggagcacaac gtttggtga 49

<210> SEQ ID NO 576
<211> LENGTH: 261
<212> TYPE: DNA
<213> ORGANISM: Homo sapiens

<400> SEQUENCE: 576
tcagagaggt agcaactagg taaactcctt ataaaaagca aatacctgga tttacaaaag 60
tgaaagtagt tgttcacaaa agaattcgcc atggaattct ttcagttacc aagctctcct 120
ggtaatgttt gtggttatat catttacaca aaacttttca ggaacttctg tgttgtttaa 180
gcaagatgta tctgtactga tgtctcagtg aatcagtctg tttattaagc acttatcagg 240
gcttccacac acttatttat t 261

<210> SEQ ID NO 577
<211> LENGTH: 27
<212> TYPE: DNA
<213> ORGANISM: Homo sapiens

<400> SEQUENCE: 577

-continued atgcgcagga gcgacaataa gatggcg 27

<210> SEQ ID NO 578
<211> LENGTH: 34
<212> TYPE: DNA
<213> ORGANISM: Homo sapiens

<400> SEQUENCE: 578
gccattttcg agtgaaggac ccggagccga aaca 34

<210> SEQ ID NO 579
<211> LENGTH: 36
<212> TYPE: DNA
<213> ORGANISM: Homo sapiens

<400> SEQUENCE: 579
gtgggtacta cacaaccgtc tccagccttg gtctga 36

<210> SEQ ID NO 580
<211> LENGTH: 299
<212> TYPE: DNA
<213> ORGANISM: Homo sapiens

<400> SEQUENCE: 580
gccagcgtcc gacttgaagt tgctagtggt tagtcccagc cttcgccctt cgcggtccga 60
ccgctgagag gagggagact tcgttatgcc ccgggccgtc aacggcgcca ggagctaaag 120
ggcgggcaga cgaaagcggg cggcgagtcg ccagttagtc ttcaccgctc tggagagagt 180
tgctagccac gggatcctga cccggacacg aactcgtttc tccacgtcgg tgcgcgcttg 240
catccctggc cccgaaagcg tgggaatgtc cggaaatgct ggcgtatggg agttcctta 299

<210> SEQ ID NO 581
<211> LENGTH: 28
<212> TYPE: DNA
<213> ORGANISM: Homo sapiens

<400> SEQUENCE: 581
gcacgtctag attttcccac ttacatag 28

<210> SEQ ID NO 582
<211> LENGTH: 109
<212> TYPE: DNA
<213> ORGANISM: Homo sapiens

<400> SEQUENCE: 582
agtcctgcct tcttgccact cgtgtctttc gatggctccc ttcccgaagt cccgctgcct 60
ctaagcggag tgttaagcgg ggctctcgga agccggtgga ccgagattt 109

<210> SEQ ID NO 583
<211> LENGTH: 49
<212> TYPE: DNA
<213> ORGANISM: Homo sapiens

<400> SEQUENCE: 583
ggcgggcgcg gtgtagcggc ccgcgggctg acttgctccc ggctgtccc 49

<210> SEQ ID NO 584
<211> LENGTH: 26
<212> TYPE: DNA
<213> ORGANISM: Homo sapiens

<400> SEQUENCE: 584
atgccccgta aaggcaccca gccctc 26

<210> SEQ ID NO 585
<211> LENGTH: 56
<212> TYPE: DNA
<213> ORGANISM: Homo sapiens

<400> SEQUENCE: 585
ccctgacggc gccagcagcg acgcggagcc tgagccgccg tccggccgca cggaga 56

<210> SEQ ID NO 586
<211> LENGTH: 177
<212> TYPE: DNA
<213> ORGANISM: Homo sapiens

<400> SEQUENCE: 586
cctccgtggt gttagattgc cgttaaagag aagacgataa tttatttgaa gccactgtag 60
cttttgtgag tccaggagtt gggtgacatt attaaaccct cgtggcagtg tcgctgaagt 120
tcatgagttt ccaaaatgaa ggttccaggt gctcagcggt acggagaatt gcatcta 177

<210> SEQ ID NO 587
<211> LENGTH: 31
<212> TYPE: DNA
<213> ORGANISM: Homo sapiens

<400> SEQUENCE: 587
tgaggaactt gataatagaa gtttagaaga g 31

<210> SEQ ID NO 588
<211> LENGTH: 31
<212> TYPE: DNA
<213> ORGANISM: Homo sapiens

<400> SEQUENCE: 588
ccagaacttc aaatcctatg ctggggagaa a 31

<210> SEQ ID NO 589
<211> LENGTH: 159
<212> TYPE: DNA
<213> ORGANISM: Homo sapiens

<400> SEQUENCE: 589
cgcttttcct gtattatcgg gccaaatggc agtggcaaat ccaatgttat tgattctatg 60
ctttttgtgt ttggctatcg agcacaaaaa ataagatcta aaaaactctc agtattaata 120
cataattctg atgaacacaa ggacattcag agttgtaca 159

<210> SEQ ID NO 590
<211> LENGTH: 176
<212> TYPE: DNA
<213> ORGANISM: Homo sapiens

<400> SEQUENCE: 590
ttgagaaagg gaccaaaaca gcatggaaaa gtatcaattc tttgctaagt tgggttatta 60
atgagaacta ctggcagttt gtgtgcatgt tcaattgaag tttttaatcc atagaattag 120
tttcagtatg aaatgagtga attttgaagt aggcctatga cttaatacca acaatt 176

<210> SEQ ID NO 591
<211> LENGTH: 47
<212> TYPE: DNA

<213> ORGANISM: Homo sapiens

<400> SEQUENCE: 591
aaggggatga ttatgaagtc attcctaaca gtaatttcta tgtatcc 47

<210> SEQ ID NO 592
<211> LENGTH: 118
<212> TYPE: DNA
<213> ORGANISM: Homo sapiens

<400> SEQUENCE: 592
aacggcctgc agagataata cttctgtcta tcacataagt ggaaagaaaa agacatttaa 60
ggatgttgga aatcttcttc gaagccatgg aattgacttg gaccataata gattttta 118

<210> SEQ ID NO 593
<211> LENGTH: 76
<212> TYPE: DNA
<213> ORGANISM: Homo sapiens

<400> SEQUENCE: 593
ctgtagcagc acatcatggt ttacatgcta cagtcaagat gcgaatcatt atttgctgct 60
ctagaaattt aaggaa 76

<210> SEQ ID NO 594
<211> LENGTH: 59
<212> TYPE: DNA
<213> ORGANISM: Homo sapiens

<400> SEQUENCE: 594
gtaaatattg gcgtagtgaa atatatatta aacaccaata ttactgtgct gctttagtg 59

<210> SEQ ID NO 595
<211> LENGTH: 284
<212> TYPE: DNA
<213> ORGANISM: Homo sapiens

<400> SEQUENCE: 595
gtgtttgatt tacctaagca cctagttaat ttaatctttg taacactttg gatggttaac 60
ttaaccttta ctcaagttgg tttttgtttt gttgaaaatg acttacttgg tggaaccact 120
actactgaaa gaacgaaact ttgatattac attgttaagt atcagagctg ttacagagca 180
agtcctttta aagagatgta aaaattaagt acctgtgcca aactgatttt tattagaaac 240
cctgttttct ttaagtaaaa gtatattcta ccagcatggc ttgg 284

<210> SEQ ID NO 596
<211> LENGTH: 62
<212> TYPE: DNA
<213> ORGANISM: Homo sapiens

<400> SEQUENCE: 596
tatccacaac tagggtgaag gtggtggaga gcagcaagga agctacctct aaccaaccag 60
aa 62

<210> SEQ ID NO 597
<211> LENGTH: 412
<212> TYPE: DNA
<213> ORGANISM: Homo sapiens

<400> SEQUENCE: 597
ctcaaagagt ggtataactg gatcataata tccttgtttg ccactcaaga aagtgttcca 60

-continued taacttaaga taacagtggt gggaaaaatc atttaagacc ttgtttcata tgctttaaga 120
tacaagaaat agagataaca ctgggaacat atgaaacttt gtcagcatca gataatagtg 180
ttgtagcgac ttgaaacatt ttttgtctgt gattgtgcca gtcactattt gtgacttgga 240
ttgaaccttg atatgacttt aaattcaggt tgatgtttta aaattatttc tgaaatatat 300
tgagcttatt gccctaaatt aaaactatat tctgtaattt tacatgagtt atgtaagttt 360
tctgaagaaa taaggaggaa tcctttaggc acagactgtc aatctacaga tt 412

<210> SEQ ID NO 598
<211> LENGTH: 65
<212> TYPE: DNA
<213> ORGANISM: Homo sapiens

<400> SEQUENCE: 598
actcttggct ttattattta actgctccca attctcactt aagattgatt tagctaaaca 60
tacac 65

<210> SEQ ID NO 599
<211> LENGTH: 25
<212> TYPE: DNA
<213> ORGANISM: Homo sapiens

<400> SEQUENCE: 599
gaacaaattg ctatgatgaa accaa 25

<210> SEQ ID NO 600
<211> LENGTH: 58
<212> TYPE: DNA
<213> ORGANISM: Homo sapiens

<400> SEQUENCE: 600
agatataatt ggttgtggac ggctaaatga acctattaaa gtcttgtgtc ggagagtt 58

<210> SEQ ID NO 601
<211> LENGTH: 40
<212> TYPE: DNA
<213> ORGANISM: Homo sapiens

<400> SEQUENCE: 601
ggagagaaaa acatagctat cgaatttctt accttggaaa 40

<210> SEQ ID NO 602
<211> LENGTH: 68
<212> TYPE: DNA
<213> ORGANISM: Homo sapiens

<400> SEQUENCE: 602
gtaagtgcct tgattgatat taccaatttt tatattagtt tttaaccatt aagtcaaagc 60
ccttctct 68

<210> SEQ ID NO 603
<211> LENGTH: 90
<212> TYPE: DNA
<213> ORGANISM: Homo sapiens

<400> SEQUENCE: 603
aaggaattat gtggtgaact tatccaatgt gaggactatc tggctgtgac acctgtcatc 60
ccgttgatca ccagggttga atttattaaa 90

<210> SEQ ID NO 604
<211> LENGTH: 77
<212> TYPE: DNA
<213> ORGANISM: Homo sapiens

<400> SEQUENCE: 604
ttatgagttg cagaaacgaa ttgctgaaat ggaaactcaa aaggaaaaaa ttcatgaaga 60
taccaaagaa attaatg 77

<210> SEQ ID NO 605
<211> LENGTH: 86
<212> TYPE: DNA
<213> ORGANISM: Homo sapiens

<400> SEQUENCE: 605
gataattgta ttacatgtgt atttatatat aaagttactt ctagcacatt gtgagtgtaa 60
gacatttgcc agcatatcaa gtggtg 86

<210> SEQ ID NO 606
<211> LENGTH: 447
<212> TYPE: DNA
<213> ORGANISM: Homo sapiens

<400> SEQUENCE: 606
ccctagtggc gtagcacagt aacaaacaat aagcatttgg cttcacagtt taatctttta 60
gtagtccaca aatctgatag agggatagga tttgggtttt tctagataga tttttaaggg 120
ttttatcatg tccctacttg atgccatttt tcaatgacac tagtatctct aattattttt 180
aaataaaaaa atttgtatag taagtttatt gtatagtaac ttgtaagtat attcgtaaaa 240
ggtaaaacca aaattttact cctatggtaa aatttttata tacctagaca ttgtagtcac 300
tggaaaatgt gttattttcc ctccaactta gaaaggcaaa atagctgtca taatcaaaaa 360
tacaggtgct tcttcaacta tggggagagg gatcatcttg gaataaggag agttttagga 420
tcctgcctta ttaagagcct ggacata 447

<210> SEQ ID NO 607
<211> LENGTH: 99
<212> TYPE: DNA
<213> ORGANISM: Homo sapiens

<400> SEQUENCE: 607
attacaaaat ttattgagga gaataaagaa aaatttacac agctagattt ggaagatgtt 60
caagttagag aaaagttaaa acatgccacg agtaaagcc 99

<210> SEQ ID NO 608
<211> LENGTH: 264
<212> TYPE: DNA
<213> ORGANISM: Homo sapiens

<400> SEQUENCE: 608
tccgtgtagt cagagcatat ttatagctaa agaagaataa ttacaacctg aaatcaggag 60
agaaggatga cagacctgag gccctgccag agacagtttt ccttcataag aggtcaggtg 120
tttgtagaag tagttttact attagattga gagaatatag aaattacagt gaatagtcgg 180
gaaaatactt gttaaagcta gctaatttaa ctctgattat aaagaaaaga agaactagag 240
gaccctgaga aatgccttta aata 264

<210> SEQ ID NO 609
<211> LENGTH: 115
<212> TYPE: DNA
<213> ORGANISM: Homo sapiens

<400> SEQUENCE: 609
gccaagagta acaatatcat taatgaaaca acaaccagaa acaatgccct cgagaaggaa 60
aaagagaaag aagaaaaaaa attaaaggaa gttatggata gccttaaaca ggaaa 115

<210> SEQ ID NO 610
<211> LENGTH: 95
<212> TYPE: DNA
<213> ORGANISM: Homo sapiens

<400> SEQUENCE: 610
tgaaacctga actggtaagt ttggactttt aatgtccaac attcctaaaa ctagtcaacc 60
tagacttaga tgactattct tttaattcct gctga 95

<210> SEQ ID NO 611
<211> LENGTH: 255
<212> TYPE: DNA
<213> ORGANISM: Homo sapiens

<400> SEQUENCE: 611
gtcaatggat aatgcagtag ctttcatgat gggatacttc atagttagtg gattttcact 60
gtttgcttat ttaatatata ttgagtactc atgtgccctg caccccatgt taatgacaaa 120
gctaggcctc aaatgtcttt attcctcagc gtaatgatcg atctcacaaa gctcttgtga 180
aatcagttgg gaaaagacta tgtacagtga atattgacaa ctaggcaaaa actgaatcta 240
gtccacttgt gagaa 255

<210> SEQ ID NO 612
<211> LENGTH: 109
<212> TYPE: DNA
<213> ORGANISM: Homo sapiens

<400> SEQUENCE: 612
aagcacgttc aaagatggat gtagcccagt cagaacttga tatctatctc agtcgtcata 60
atactgcagt gtctcaatta actaaggcta aggaagctct aattgcagc 109

<210> SEQ ID NO 613
<211> LENGTH: 404
<212> TYPE: DNA
<213> ORGANISM: Homo sapiens

<400> SEQUENCE: 613
aaagaatgag gtcagcattt cagtattcca tatgtgaact gagactatca agaaactata 60
ttatccccag aagcaccata tagtaagtaa atcaccacca ccaccccact gtagaaataa 120
tttaaacaaa agaaagtttg tgtttcttta aatcttaagt atagacaatt taaagataaa 180
taaaaaacaa gtgtatatgt atttatataa tgaatataca aacaactatc ttaatgtgtt 240
ttgggttttg aatttatgga tgtagtttct ttgcttgcat tccaaaatgt tataaactaa 300
ctaagatgta tagcttatcg gtgcctgtcc cccatccttg agtgaattag atgtctaagg 360
aatttcgtaa actttaatct ccaaagatct ccaaaacctc agta 404

<210> SEQ ID NO 614
<211> LENGTH: 60
<212> TYPE: DNA

<213> ORGANISM: Homo sapiens

<400> SEQUENCE: 614
aagagctcat tagcaatgaa tcgaagtagg gggaaagtcc ttgatgcaat aattcaagaa 60

<210> SEQ ID NO 615
<211> LENGTH: 170
<212> TYPE: DNA
<213> ORGANISM: Homo sapiens

<400> SEQUENCE: 615
tgacaaccat atttcaagtg tcactgtata taaaataaga ttcattttgt ttgttttaag 60
gcacatttat ttttaaacat tttgccctta cagtttcttg tttacttagc tttagataaa 120
tacaattatt tcatacatat caagaaaaat actagtaatg tcacacaaac 170

<210> SEQ ID NO 616
<211> LENGTH: 106
<212> TYPE: DNA
<213> ORGANISM: Homo sapiens

<400> SEQUENCE: 616
ggggacttag gagccattga tgaaaaatac gacgtggcta tatcatcctg ttgtcatgca 60
ctggactaca ttgttgttga ttctattgat atagcccaag aatgtg 106

<210> SEQ ID NO 617
<211> LENGTH: 212
<212> TYPE: DNA
<213> ORGANISM: Homo sapiens

<400> SEQUENCE: 617
ggctgtatgg gcgaaaaaga tgaccgaaat tcaaactcct gaaaatactc ctcgtttatt 60
tgatttagta aaagtaaaag atgagaaaat tcgccaagct ttttattttg ctttacgaga 120
taccttagta gctgacaact tggatcaagc cacaagagta gcatatcaaa aagatagaag 180
atggagagtg gtaactttac agggacaaat ca 212

<210> SEQ ID NO 618
<211> LENGTH: 25
<212> TYPE: DNA
<213> ORGANISM: Homo sapiens

<400> SEQUENCE: 618
gaagaatggg ttcctcactt gttat 25

<210> SEQ ID NO 619
<211> LENGTH: 38
<212> TYPE: DNA
<213> ORGANISM: Homo sapiens

<400> SEQUENCE: 619
cagttgcaaa acgactctaa aaaagcaatg caaatcca 38

<210> SEQ ID NO 620
<211> LENGTH: 50
<212> TYPE: DNA
<213> ORGANISM: Homo sapiens

<400> SEQUENCE: 620
gtgaacgaga aatgaggaac acactagaaa aatttactgc aagcatccag 50

-continued

<210> SEQ ID NO 621
<211> LENGTH: 32
<212> TYPE: DNA
<213> ORGANISM: Homo sapiens

<400> SEQUENCE: 621
ggaacttgaa gctaatgtac ttgctacagc cc 32

<210> SEQ ID NO 622
<211> LENGTH: 531
<212> TYPE: DNA
<213> ORGANISM: Homo sapiens

<400> SEQUENCE: 622
tactggccag gctttgtttt aggtcctact gatagagcag taaacaaaaa taaagtctct 60
tcccagggag cacacatgta agatggcaca tatttgagtg gaggcccaaa gaaagtatga 120
gtgctaaccc atgtatgttt gagaaaaaag cattccaaga agagtataaa ggagcaaata 180
caaaggctga agcaggagta tgctgggaac acaaaccatt gtggctggaa taaaggacgg 240
aagaacccag attctctgag gccttcaccc acactcccct ttccctgcaa gcacccacaa 300
caatggcttt gatggtacct gatggtcaat tgagaagcca aaatgtatat ctgtgctatt 360
aatggcaaca ttttcatgga gagactgcaa gagtctatat gtgtttcatc cttatttgaa 420
aaggaatcct tgactttgtt aggagctcta tatatctcct ctcatagaaa tgccatatat 480
tatcaggaga ctgttaatat ctcatgtgga ggacccattt gtgcaagcat a 531

<210> SEQ ID NO 623
<211> LENGTH: 296
<212> TYPE: DNA
<213> ORGANISM: Homo sapiens

<400> SEQUENCE: 623
acttttactc ttcgttgtca caggaaggaa cgctaattca tcttatatcc tccactttgt 60
tttaatgtgg agaactgcga agttatgtta gcagaagaaa ataaccacaa tttcttcatt 120
gtgggcaagt taatattgag ttaggcacat agtgtatcta aggctaaaaa tcattatgaa 180
ctcagtagtc aaggaagtgc cctaagaaaa agttgtaaag atattttaaa agaagctgag 240
aacatgaagc cattaagaaa tggtgtgttt acagccgagc tagtgtgttt aacttt 296

<210> SEQ ID NO 624
<211> LENGTH: 144
<212> TYPE: DNA
<213> ORGANISM: Homo sapiens

<400> SEQUENCE: 624
gctgaggtta aacgcttaca caataccatc gtagaaatca ataatcataa actcaaggcc 60
caacaagaca aacttgataa aataaataag caattagatg aatgtgcttc tgctattact 120
aaagcccaag tagcaatcaa gact 144

<210> SEQ ID NO 625
<211> LENGTH: 213
<212> TYPE: DNA
<213> ORGANISM: Homo sapiens

<400> SEQUENCE: 625
gtagagtatg catgttaccc taacttgttt tccctttccc tgccttcaca ttggaaaggg 60
ggttactatg taatgttcca taaaatgttt ctcttactgt taatttattg aacctgtctg 120
acacattacc taatgggact tccatgacgg aaaacctata atgaacattt atcctatggc 180
caattaaaaa ggctggtaaa caggtatgcc ata 213

<210> SEQ ID NO 626
<211> LENGTH: 105
<212> TYPE: DNA
<213> ORGANISM: Homo sapiens

<400> SEQUENCE: 626
tgtcttgcgt acagagaaag aaataaaaga tactgagaaa gaggtggatg acctaacagc 60
agagctgaaa agtcttgagg acaaagcagc agaggtcgta aagaa 105

<210> SEQ ID NO 627
<211> LENGTH: 130
<212> TYPE: DNA
<213> ORGANISM: Homo sapiens

<400> SEQUENCE: 627
tccagaaaga acatcgcaat ctgcttcaag aattaaaagt tattcaagaa aatgaacatg 60
ctcttcaaaa agatgcactt agtattaagt tgaaacttga acaaatagat ggtcacattg 120
ctgaacataa 130

<210> SEQ ID NO 628
<211> LENGTH: 139
<212> TYPE: DNA
<213> ORGANISM: Homo sapiens

<400> SEQUENCE: 628
aagagatttc ggttctaagc ccagaggatc ttgaagcgat caagaatcca gattctataa 60
caaatcaaat tgcacttttg gaagcccggt gtcatgaaat gaaaccaaac ctcggtgcca 120
tcgcagagta taaaaagaa 139

<210> SEQ ID NO 629
<211> LENGTH: 27
<212> TYPE: DNA
<213> ORGANISM: Homo sapiens

<400> SEQUENCE: 629
attttcccta tcataatctt ttcacag 27

<210> SEQ ID NO 630
<211> LENGTH: 144
<212> TYPE: DNA
<213> ORGANISM: Homo sapiens

<400> SEQUENCE: 630
tatgaagatc ttcggaaaca aaggcttaat gaatttatgg caggttttta tataataaca 60
aataaattaa aggaaaatta ccaaatgctt actttgggag gggacgccga actcgagctt 120
gtagacagct tggatccttt ctct 144

<210> SEQ ID NO 631
<211> LENGTH: 66
<212> TYPE: DNA
<213> ORGANISM: Homo sapiens

<400> SEQUENCE: 631
gttcattggc tttagtattt gctcttcacc actacaagcc cactcccctt tacttcatgg 60
atgaga 66

<210> SEQ ID NO 632
<211> LENGTH: 26
<212> TYPE: DNA
<213> ORGANISM: Homo sapiens

<400> SEQUENCE: 632
gtgatttacc tgttattact taatgt 26

<210> SEQ ID NO 633
<211> LENGTH: 135
<212> TYPE: DNA
<213> ORGANISM: Homo sapiens

<400> SEQUENCE: 633
gcacagttca taataatttc tcttcgaaat aatatgtttg agatttcgga tagacttatt 60
ggaatttaca agacatacaa cataacaaaa agtgttgctg taaatccaaa agaaattgca 120
tctaagggac tttgt 135

<210> SEQ ID NO 634
<211> LENGTH: 84
<212> TYPE: DNA
<213> ORGANISM: Homo sapiens

<400> SEQUENCE: 634
ttcaagttga ttcagtgtat tactgatttt tttctatttg taaaggatta tgagttgtat 60
aaaatacata ctccctaaac taga 84

<210> SEQ ID NO 635
<211> LENGTH: 121
<212> TYPE: DNA
<213> ORGANISM: Homo sapiens

<400> SEQUENCE: 635
caaggttgtg ctatcaaggc tcagcatacc ttcgtgggcc tttgatttac caacactgga 60
aatgcctgcc aactaatctt ggatagattc tttaaggcat tccacttagc ttgccagttg 120
a 121

<210> SEQ ID NO 636
<211> LENGTH: 403
<212> TYPE: DNA
<213> ORGANISM: Homo sapiens

<400> SEQUENCE: 636
gcctaggcta tctcgtaagt tgaaaaatat cccactatag ttgcttcatg agtatgaagt 60
aagatggcct ctgatttaca ctggttcaat ttacaaattt tcaactttat gataggttta 120
tccgggtact aaatgcattt caacttgata gtttcaactt atgataggtt taccaggatg 180
tagtcccact gttgaggagc atctatttag gggttaatta ctttagtaat aagtggaaag 240
taagatacct tgagtaatgt ttgcctataa aattgtcagc gtatttttac actattggct 300
caagaatgtt ataatgctaa gggacataag ttggcaacca cttggttttt ggaaggactt 360
tcggtattgt attagaagtc tgccctagct gttaaatttc tgg 403

<210> SEQ ID NO 637
<211> LENGTH: 38
<212> TYPE: DNA
<213> ORGANISM: Homo sapiens

<400> SEQUENCE: 637
gatgtaacta ttttgctttg taaatatcct gcctttaa 38

<210> SEQ ID NO 638
<211> LENGTH: 176
<212> TYPE: DNA
<213> ORGANISM: Homo sapiens

<400> SEQUENCE: 638
tgtttcttaa tagctgtact ctatctcttc agtaagtaat ttgccaggag aaatacaatg 60
tttttaagga atatttttgt cagcgtaaac tgttaaacac tgaatcccaa cttttagcta 120
tctgaaaaat gtatacttaa ataatacatt atggccattt gactcaaatg taagtt 176

<210> SEQ ID NO 639
<211> LENGTH: 223
<212> TYPE: DNA
<213> ORGANISM: Homo sapiens

<400> SEQUENCE: 639
tctctttcct ggtaagcagg gagtcaaaac aatagcaaga aaatgccaga aatagaattt 60
ctactacttt gtaaactcta ggctcgtggg tctcctagct ctcagtacct ggctcactgt 120
aggatgggta gatgggtgaa tgaatggata aagaaaggaa gtttgttcac cggagaggag 180
atgaatttca gtaagtttca tgtaacagtg atcaggagaa ata 223

<210> SEQ ID NO 640
<211> LENGTH: 668
<212> TYPE: DNA
<213> ORGANISM: Homo sapiens

<400> SEQUENCE: 640
ggctgtcacc tattttgcca acacgtgaat tcaaaacatg aaccggtttg cttttggaga 60
atctgaagac tccagtttga ggaatccttt gcttccctgg aggtagatgc tgtctgcaaa 120
tctagaatga cagcaggagt ccagtcaaga ggtcctgtca ggccaaggcc agaaagaagg 180
gaggacaatc cctggggcca gatgcccagt gtgaggggag gcatgatctg tcccatggct 240
gtggccactg caggaaggtc tgtgaaaagg aggtgacagg cccagtcacc tcctcttcac 300
ccaagtgatt gctccttcaa ctgctatctg tgaaaatagc ctttgttatg aagaaattga 360
ctctctctct cttttttttt ttttggagtt gcctaggctg gagtgcaatg gtacgatctc 420
agctcactgc aacctccacc tcccaggttc aattgattct cctgcctcag cctcctgagt 480
agctgggatt acaggcatgt gccaccacac ccggctaatt tttgtatttt tattagagac 540
agggtttcac cacgttagcc aggctcgtct cgaactcctg tcctcaggtg actacccgtc 600
tcggcctccc aaagtgctgg gattacaggc atgagccacc acacccggcc aaaaatggat 660
tctctatg 668

<210> SEQ ID NO 641
<211> LENGTH: 170
<212> TYPE: DNA
<213> ORGANISM: Homo sapiens

<400> SEQUENCE: 641
ctgctgggac tagatagtgg atgaagaaag aaggacgagg aagccgtggg gcagcctctt 60
cacatgggga caggggatgg agcatgaggc aagggaagga aaagcagagc ttatttttca 120
cctaaggtgg agaaggatca ctttacaggc aacgctcatt ttaagcaacc 170

<210> SEQ ID NO 642
<211> LENGTH: 53
<212> TYPE: DNA
<213> ORGANISM: Homo sapiens

<400> SEQUENCE: 642
tcgggctgtt tgctcaggga aggcaagaaa gccacgtgct ggccctctgc ctt 53

<210> SEQ ID NO 643
<211> LENGTH: 283
<212> TYPE: DNA
<213> ORGANISM: Homo sapiens

<400> SEQUENCE: 643
caaggctttt ttcagtagcg tcctatggat gtcacattgt acatcaaaca accttgtgat 60
tataaaacga tcctgggaag gagcccctaa ctagggcaag tcagaaatag ccaggctcgc 120
agcagcgcag cgctgtgtct gctgtgtcct ggggcctccc ttgttccgac ctgtcaattc 180
tgctgcctgt cacgcgggtg gttctgccca tcgcggctgc gggtcaagca tcttcaaggg 240
aaggacggac tggaggcctc accgtggact caactctgca ttc 283

<210> SEQ ID NO 644
<211> LENGTH: 81
<212> TYPE: DNA
<213> ORGANISM: Homo sapiens

<400> SEQUENCE: 644
gcctcagctg tgtcggtatg atcttgtcct gatggaaaac gttgaaacag tcttccaacc 60
tattctttgc ccagagttgc a 81

<210> SEQ ID NO 645
<211> LENGTH: 64
<212> TYPE: DNA
<213> ORGANISM: Homo sapiens

<400> SEQUENCE: 645
ctctaatagg cccaaggtac aagctcagga ttctccgaat gaagttaagg tcccttgccc 60
atcc 64

<210> SEQ ID NO 646
<211> LENGTH: 58
<212> TYPE: DNA
<213> ORGANISM: Homo sapiens

<400> SEQUENCE: 646
tcagaaatat caccaagtga gtctacttgc aagatttaat caagatctgg ataaagtg 58

<210> SEQ ID NO 647
<211> LENGTH: 66
<212> TYPE: DNA
<213> ORGANISM: Homo sapiens

<400> SEQUENCE: 647
ctttgtggat attataacat ggaacaagaa tgtaagaaga ggggacatta ccatcaaatt 60
gagaga 66

<210> SEQ ID NO 648
<211> LENGTH: 69
<212> TYPE: DNA

<213> ORGANISM: Homo sapiens

<400> SEQUENCE: 648
tattatgctg ataattggaa agaccatcta agggggaaag atcctccaat gacgaaggca 60
ttctttgac 69

<210> SEQ ID NO 649
<211> LENGTH: 128
<212> TYPE: DNA
<213> ORGANISM: Homo sapiens

<400> SEQUENCE: 649
accaccagag gtctgtatac ctgtacctgt cttccctgag agagagctgc accatcactg 60
cgtatccctg tgactcctac caggattata ggaatggcaa gtgtgtcagc tgcggcacgt 120
cacaaaaa 128

<210> SEQ ID NO 650
<211> LENGTH: 71
<212> TYPE: DNA
<213> ORGANISM: Homo sapiens

<400> SEQUENCE: 650
ctgggctaca aggagccatt aggaaacata gacttctacc caaatggagg attggatcaa 60
cctggctgcc c 71

<210> SEQ ID NO 651
<211> LENGTH: 194
<212> TYPE: DNA
<213> ORGANISM: Homo sapiens

<400> SEQUENCE: 651
ctgcacccga cctatatata catttctagg tcctcatttt ctagaagtag ttccaatctt 60
tttaccatcc tagctctcaa atatttaaag attttatcta ctaagtaaac attcattttt 120
tcctgtatcc tatttattag ttatacaaat gcaaatagag gctcagaagc accaggcaat 180
taaagggttg cagc 194

<210> SEQ ID NO 652
<211> LENGTH: 94
<212> TYPE: DNA
<213> ORGANISM: Homo sapiens

<400> SEQUENCE: 652
cctgcaggcc ctttattcaa cgggaaacct caccaagaca gattagatcc cagtgatgcg 60
cagtttgttg atgtcatcca ttccgacact gatg 94

<210> SEQ ID NO 653
<211> LENGTH: 74
<212> TYPE: DNA
<213> ORGANISM: Homo sapiens

<400> SEQUENCE: 653
tgatgacatt tacatgatcg gagtaagtct aggagcccac atatctgggt ttgttggaga 60
gatgtacgat ggat 74

<210> SEQ ID NO 654
<211> LENGTH: 28
<212> TYPE: DNA
<213> ORGANISM: Homo sapiens

<400> SEQUENCE: 654
ttacaatgat ggacctcttg aaattcca 28

<210> SEQ ID NO 655
<211> LENGTH: 252
<212> TYPE: DNA
<213> ORGANISM: Homo sapiens

<400> SEQUENCE: 655
aggctgatgc tctacacaag gaaaaacctg acctgcgcac aaaccatcaa ctcctcagct 60
tttgggaact tgaatgtgac caagaaaacc accttcattg tccatggatt caggccaaca 120
ggctcccctc ctgtttggat ggatgactta gtaaagggtt tgctctctgt tgaagacatg 180
aacgtagttg ttgttgattg gaatcgagga gctacaactt taatatatac ccatgcctct 240
agtaagacca ga 252

<210> SEQ ID NO 656
<211> LENGTH: 29
<212> TYPE: DNA
<213> ORGANISM: Homo sapiens

<400> SEQUENCE: 656
tattcatcag tttgttgtgc ttgtcaaga 29

<210> SEQ ID NO 657
<211> LENGTH: 82
<212> TYPE: DNA
<213> ORGANISM: Homo sapiens

<400> SEQUENCE: 657
ctcactgtga gcaaaatccc acagtggaaa ctcttaagcc tctgcgaagt aaatcattct 60
tgtgaatgtg acacacgatc tc 82

<210> SEQ ID NO 658
<211> LENGTH: 72
<212> TYPE: DNA
<213> ORGANISM: Homo sapiens

<400> SEQUENCE: 658
tgcaatgtca gctatttagg acagaaacat ccaaggccgt gtcagaactc aattacgact 60
acatatgcat ta 72

<210> SEQ ID NO 659
<211> LENGTH: 63
<212> TYPE: DNA
<213> ORGANISM: Homo sapiens

<400> SEQUENCE: 659
acgccaacta taggactcgt gcttctcgta cgctgggcta taatctatga aactgagctc 60
cag 63

<210> SEQ ID NO 660
<211> LENGTH: 30
<212> TYPE: DNA
<213> ORGANISM: Homo sapiens

<400> SEQUENCE: 660
cctcataaca agtctaactg gctctggaaa 30

<210> SEQ ID NO 661
<211> LENGTH: 47
<212> TYPE: DNA
<213> ORGANISM: Homo sapiens

<400> SEQUENCE: 661
acagatgaga tattctacac attaatctac ttatctggaa tcacttt 47

<210> SEQ ID NO 662
<211> LENGTH: 109
<212> TYPE: DNA
<213> ORGANISM: Homo sapiens

<400> SEQUENCE: 662
cacagcttcc ttgtcggagg ggaaaaggac aggtgatctg gggaaaacgc agctacacct 60
ggagcaaggt ctcttcccgg cttggcaatc tcagctgtgc cggcgctac 109

<210> SEQ ID NO 663
<211> LENGTH: 104
<212> TYPE: DNA
<213> ORGANISM: Homo sapiens

<400> SEQUENCE: 663
ctgctgcctt cggtgactat atgagaatgg aaacttctaa ggaagccagg ttgttagaat 60 tgttacccc tttactcaga gataacatag attatccagg ctga 104

<210> SEQ ID NO 664
<211> LENGTH: 29
<212> TYPE: DNA
<213> ORGANISM: Homo sapiens

<400> SEQUENCE: 664
aattttcaac acagactccc tgcttctca 29

<210> SEQ ID NO 665
<211> LENGTH: 71
<212> TYPE: DNA
<213> ORGANISM: Homo sapiens

<400> SEQUENCE: 665
tgttcaaatc tccatttgtt gacagacaaa gccaacaata ctctaaactg aggcctgcaa 60
gtcatttcat t 71

<210> SEQ ID NO 666
<211> LENGTH: 138
<212> TYPE: DNA
<213> ORGANISM: Homo sapiens

<400> SEQUENCE: 666
ttcacctcct acaactccga agaaaaccct tactgtccaa gaccgtcacc agcaaccatc 60
cgcagtcatt caagtggaag ctttcacagc ttttgtacat tctctgtgtc aatatacaac 120
tgagttacag actgtccc 138

<210> SEQ ID NO 667
<211> LENGTH: 366
<212> TYPE: DNA
<213> ORGANISM: Homo sapiens

<400> SEQUENCE: 667
catcaggact tgtattagca ggttctggct agagagacta tctcctgtca tcacgatcaa 60
ttaatgtttt ctggtgatca catcaggccc tatctaagaa gctcatggta tacaagggtc 120
acccaaatag ctgagtgcag tccttgctca tatttccttc atcttaaccc cgcaaacaag 180
aattaagatg atcccaataa aagaaaaatt gctcaggaaa ctgaaccttt ttctgaacca 240
agcactgtca gcaaatctca ggtattagag caactatggt tgattgaaaa gtgtctcaaa 300
atctgggcca agaatgattg ctaggtccat aagctaattt gtctggcctt gccatttacg 360
taagcc 366

<210> SEQ ID NO 668
<211> LENGTH: 281
<212> TYPE: DNA
<213> ORGANISM: Homo sapiens

<400> SEQUENCE: 668
tgggatggcc gttcaggaaa tcttctgttt gctttgcacg ctcctgagta taggacaaag 60
cgctgttgtt taagaacata aataacaaaa gctttgttct tccaaaccga gagggaaact 120
gtagatctat ccaaaatgac ttggtcttaa actgcctaag gatgacaaga atgaaatatt 180
attttaggct gcccatcagc atccgtctct caatctcctg tcttggcttc agaaaacaat 240
gactcaatat ggtctttttc tgacacattg cagccttagg a 281

<210> SEQ ID NO 669
<211> LENGTH: 128
<212> TYPE: DNA
<213> ORGANISM: Homo sapiens

<400> SEQUENCE: 669
tgctcttctt ggtcccactc aaatgggaag ttctgctcga ggccagaaat agaaaacagg 60
aagtcaacag aactgatttt cctaactgcc caaatgcaaa tcaccacact ccgttatgga 120
tgagaatt 128

<210> SEQ ID NO 670
<211> LENGTH: 270
<212> TYPE: DNA
<213> ORGANISM: Homo sapiens

<400> SEQUENCE: 670
ttgccctcac atacacataa gtttgtcatt gttcttcagt tctttgggta atctcttcct 60
agaaactgca tctaacaaat agaccacatc cccaaattcc atcatgtcca aaaagaagca 120
cggtatttcc atcaacaccc cagctgccat caccaagcca actcgcctga cttccattca 180
cttactagca aacatttacc aagtatctgc catgttcatt ttgtcaatga gaatgacatg 240
ggacttgttc ctctaggaga tcacagtcta 270

<210> SEQ ID NO 671
<211> LENGTH: 2253
<212> TYPE: DNA
<213> ORGANISM: Homo sapiens

<400> SEQUENCE: 671
cctgctgccc aataacctga tgttgtcact ctcatattta aaacccataa gtgctgccgg 60
gagcggtggc tcacgcctgt aatcccagca ctttgggagg ccgaggcggg cggatcacaa 120
ggtcaagaga tcgagaccat cctggccaac gtggtgaagc ccagcctcta ctaaaaatac 180
aaaaattagc tgggcggggt ggcacacacc tgtagtccca gctacttggc aggctgaggc 240

-continued aggagaattg cttgaacccg gaggcagagg ttgcagtgag ccgagattgc actactgcac 300
tccagactgg tgacggagcg agacgctgtc aaaaaaacaa aacaaaacaa aaaacatatc 360
aatgctgatg aaccaagtgc aaagccctga gcttggccag gcaacatagc ctggaaacct 420
gacttttaat ccttactttg ctctattccc ccaacataca cacacttcat acaccacacc 480
taaaagagac ttcccacagt tttccaaaaa tgactcacat ttatatttcc tgtttttccc 540
tttgcccacc ctgccctctc tccctctgcc ttcatttttt taattaacct ctggaactca 600
ggtgctcctg ctccaaggtt taggtcaaaa gttacctcct ccatgaagct ttctctcatt 660
ctcccacaat gtgtgaaagc cccattctca gatttgctta gttgtgcatt tgtatattct 720
accttgcact acagtcattt gtatatttat cttatggttt ctgtgcctta ggaaaggtac 780
actgtcttaa tcatctttgt tcaatacagt gcctagcaga gtgcctcaag tataatatgt 840
gctcaataaa taatagatgc atttttccat gcatattttc tactatatcg aagtggaaaa 900
tatatccatg tgatatagtg aaaaatatct catgaagaga gatacagtga ggaaaatatc 960
tcatgaagac caaaaagcag aaatccaagt tttttctttt cattactatc atcagtgatt 1020
attaatttta tgtgtcaact tggttgggct tagggatgct cagatagctg gtaaaatatt 1080
atttctggat gtgtctctca gggtgtttct gggggaaatt agcatttgaa tcagtagact 1140
aaataaagaa aatctgccct cacaaatgtg agccagcatc atccaattta ttgacagttt 1200
agatacaaca ataaggcaga agaaggtgaa ctctctttcc ttgagctggg acatccatct 1260
tctcctgctc tgacattgga gtttctagtt cttgggactt cagattctcc cctgaagttt 1320
ctcaggcctt ttggcatcag actggaagtt atgccattgg ctcccctggt tctcagacct 1380
ttggactcag actgaattat accactggct ttcctggttc tccagcttca agatgacata 1440
ttgtgagact tttcaacctc cataattgca tgagccaatt tccacaatat atctcctctt 1500
atgtatctat atatttccta ttggttttgt ttctctacag aatcctaata gatcatctaa 1560
ttgtttatct aacaagtatt ttcctcccta gacaatatgt tgggcactag ggacacaaaa 1620
ataaaaacac agacatctgc actcaataaa cttacattca atatcagaga gattggcaca 1680
gaatacaaat aaaatgagat acatgcaaaa taatatgaat tgcaaaatta cggcaattca 1740
ccaccaacta ggtgtgtgac cgtgggaaaa tcacactgtg agctaaatat tagcaagttt 1800
aaaatgcaaa atcagaggca gtctatgaat tggactttgc taatggcctc ctttgctgat 1860
ggatggcaca ttggtgttag aaagtgctta tttttgcaaa ggtccattat tgatgcttta 1920
attctaagga aattatgtag gcagaaacta aagaaaggtt aaaaaaacag cagctaaaat 1980
tgatacttag acaataaaaa actaattata agtgatttat cagcaccact agataactac 2040
attggtgaaa tttaaggcca tgaaatgcag gacaagcctc gtaggaagca aggtcccagt 2100
ggatgagatg ctgtcctctg ggctcctaac cttccaccac tagtattcac catatctgat 2160
tggaaatgtg tgcatgtgag tcggcctccc ctctatgatg tgagtaggga cctatttttg 2220
ctcatctctg tatcctctac acacgatgct tgg 2253

<210> SEQ ID NO 672
<211> LENGTH: 39
<212> TYPE: DNA
<213> ORGANISM: Homo sapiens

<400> SEQUENCE: 672
ggagctaaaa gaagaaatag tcaaaatttt ctaaatgag 39

-continued

<210> SEQ ID NO 673
<211> LENGTH: 118
<212> TYPE: DNA
<213> ORGANISM: Homo sapiens

<400> SEQUENCE: 673
ctgccttgta cttcatgcag gttgaacaga aatgttttct gagcatgtat tgttacagcc 60
ctctgagatg gtataaaaga atgaaagaag acacgacctg ccttccagga gtttcaca 118

<210> SEQ ID NO 674
<211> LENGTH: 46
<212> TYPE: DNA
<213> ORGANISM: Homo sapiens

<400> SEQUENCE: 674
agggaaaagc atttctaatg gaggagatgg ctgtggagag gagagg 46

<210> SEQ ID NO 675
<211> LENGTH: 35
<212> TYPE: DNA
<213> ORGANISM: Homo sapiens

<400> SEQUENCE: 675
accttccacc ctttcactat gaaggaccct cacca 35

<210> SEQ ID NO 676
<211> LENGTH: 30
<212> TYPE: DNA
<213> ORGANISM: Homo sapiens

<400> SEQUENCE: 676
agattgcata tgtattggga agctcctggg 30

<210> SEQ ID NO 677
<211> LENGTH: 92
<212> TYPE: DNA
<213> ORGANISM: Homo sapiens

<400> SEQUENCE: 677
tccactttcc tgtgaggtca aatgcggtaa agggatgctc caaccctacc ctccatgtac 60
ctgcctttcc tgtgattccg aagaaggggt gg 92

<210> SEQ ID NO 678
<211> LENGTH: 62
<212> TYPE: DNA
<213> ORGANISM: Homo sapiens

<400> SEQUENCE: 678
ctattaatta atccagagaa gtgtgttgct ataaaatatt ctgtgaagca ttttcactta 60
tt 62

<210> SEQ ID NO 679
<211> LENGTH: 26
<212> TYPE: DNA
<213> ORGANISM: Homo sapiens

<400> SEQUENCE: 679
tttgaagaac tagagaaaat catcat 26

<210> SEQ ID NO 680
<211> LENGTH: 214
<212> TYPE: DNA

<213> ORGANISM: Homo sapiens

<400> SEQUENCE: 680
gggatttgct ggcattgatt tcccaggatg gcaaagtgct aagaactaaa cctttaaagc 60
taacaaaatg tactgatgtc tttgcaaagt atccaagacc aacaagaaag taatttccca 120
cctcacccta ccaccaccca gaaaaggagc acagagatgg ggaagagagt ggctgcatct 180
ggcatccagc cagaggagtc cgtgcaggga ttct 214

<210> SEQ ID NO 681
<211> LENGTH: 39
<212> TYPE: DNA
<213> ORGANISM: Homo sapiens

<400> SEQUENCE: 681
gatgatgcag ctccctcaag tatcacatga agatagtgg 39

<210> SEQ ID NO 682
<211> LENGTH: 120
<212> TYPE: DNA
<213> ORGANISM: Homo sapiens

<400> SEQUENCE: 682
cagcaatgta tgaggtccaa ggaccaggac caaagggaaa aacagccatc tcaccagaca 60
cctgcctacg accagatgcg tcatctccaa tattagctaa ctccctggaa cctggactca 120

<210> SEQ ID NO 683
<211> LENGTH: 498
<212> TYPE: DNA
<213> ORGANISM: Homo sapiens

<400> SEQUENCE: 683
ggcctctcaa tcaattacaa aactgagaat tctgacagtt ttgtgtattt cctctttgca 60
tgtgatgtat atgtgtgtat ttgtatatat taaccatttt cctttttctc tcttcattat 120
tttatgaaag ttgttgaata taaactctac aatttagcct ttaggtaaga gaatattcag 180
tgggactttg atttgaggag tatttaagac agccagatga gactacgata actgttggaa 240
ctgtgtgtct cctcatttgg ggaaaggggt gagaactctg catttctctg aagaacagag 300
ttgactttgt gttatacaga gttcaaatat atatataaaa tggtgcatgt ggaagctaag 360
aagccaaagg agttcaccaa gacagttatc aatatattgc ctctccgctc caaatccacc 420
cttctttgcc ctgttccacg atactaatct ggctcctcgg tcagccagtg caatgtcatc 480
tgttgctggt agagtgta 498

<210> SEQ ID NO 684
<211> LENGTH: 65
<212> TYPE: DNA
<213> ORGANISM: Homo sapiens

<400> SEQUENCE: 684
ttaaaccagg agtgcgccgc gtccgttcac cgcggcctca gatgaatgcg gctgttaaga 60
cctgc 65

<210> SEQ ID NO 685
<211> LENGTH: 118
<212> TYPE: DNA
<213> ORGANISM: Homo sapiens

<400> SEQUENCE: 685
ggcttagatg gctccgagcc cgtttgagcg tggtctcgga ctgctaactg gaccaacggc 60
aactgtctga tgagtgccag ccccaaaccg cgcgctgctc gggaccttag agcctctg 118

<210> SEQ ID NO 686
<211> LENGTH: 79
<212> TYPE: DNA
<213> ORGANISM: Homo sapiens

<400> SEQUENCE: 686
tgttccgctg tttagctctt gttttttgtg tggacactcc taggatagaa agtttggtat 60
gttgctatac ctttgcttc 79

<210> SEQ ID NO 687
<211> LENGTH: 27
<212> TYPE: DNA
<213> ORGANISM: Homo sapiens

<400> SEQUENCE: 687
gcacccgtgt ggttgctaag gatgggc 27

<210> SEQ ID NO 688
<211> LENGTH: 173
<212> TYPE: DNA
<213> ORGANISM: Homo sapiens

<400> SEQUENCE: 688
tatacaaggc tgcagtcgga tacactggta ttgtggacgt ggcctggagc tggacgagac 60
atttagtgta ctttttgggc aattggagtc gtttgttatt ggtccttttt catttttaat 120
atcttaatga gatgatttaa ggaagttact gaatctctgc tattaggcct atc 173

<210> SEQ ID NO 689
<211> LENGTH: 53
<212> TYPE: DNA
<213> ORGANISM: Homo sapiens

<400> SEQUENCE: 689
gatctcaagt ttcaacacca cgttttggca aaacgttcga tgccccacca gcc 53

<210> SEQ ID NO 690
<211> LENGTH: 90
<212> TYPE: DNA
<213> ORGANISM: Homo sapiens

<400> SEQUENCE: 690
gtaagtgttg gctataaaga cactgtttaa acacttaagc acttttgact cttaaaatga 60
ctattggcat catcctacgt agctttcttc 90

<210> SEQ ID NO 691
<211> LENGTH: 57
<212> TYPE: DNA
<213> ORGANISM: Homo sapiens

<400> SEQUENCE: 691
ctgcctcaga tgatgcctat ccagaaatag aaaaattctt tcccttcaat cctctag 57

<210> SEQ ID NO 692
<211> LENGTH: 208
<212> TYPE: DNA
<213> ORGANISM: Homo sapiens

<400> SEQUENCE: 692
atgagactgt ctgaatctgg gttgctttgg acaagtgtac ttgttgatgg aattatttgc 60
aaggtatcat cttaggtcag gaggggaata ggaacaaaga tgtagaagac attgttcctg 120
tctgtaaaag cttatcacct agaggaggta agatgtattc atgaacattg aataagtccc 180
attgtggaca gtctttctca caaggctt 208

<210> SEQ ID NO 693
<211> LENGTH: 70
<212> TYPE: DNA
<213> ORGANISM: Homo sapiens

<400> SEQUENCE: 693
ctgaagagca ccagattgcg cacctcccct tgagtggagt gcctctcatg atccttgacg 60
aggagagaga 70

<210> SEQ ID NO 694
<211> LENGTH: 74
<212> TYPE: DNA
<213> ORGANISM: Homo sapiens

<400> SEQUENCE: 694
ctgttgcagt ctccttcaag cattctgtcg accctggatg ttgaattgcc acctgtttgc 60
tgtgacatag atat 74

<210> SEQ ID NO 695
<211> LENGTH: 31
<212> TYPE: DNA
<213> ORGANISM: Homo sapiens

<400> SEQUENCE: 695
tcttagtgct tcagagtttg tgtgtatttg t 31

<210> SEQ ID NO 696
<211> LENGTH: 150
<212> TYPE: DNA
<213> ORGANISM: Homo sapiens

<400> SEQUENCE: 696
ttattctgtg ccctgttgac ttcattcact gttaacattt gacatagaat gattagttat 60
taaatcaggg tgaagtgctt acctggtcag tgtaggctct tcagataatt ttgacttaat 120
atttttgata ctccttgtgc atttacattc 150

<210> SEQ ID NO 697
<211> LENGTH: 773
<212> TYPE: DNA
<213> ORGANISM: Homo sapiens

<400> SEQUENCE: 697
tcttaaagta tctgcgtaga cattcatagc aaagaattta tgacatatca gatagaaata 60
cattaaaatg tagtgttttc ccagagattg atctggcttt tttttttga tatacataag 120 ataccacttt ataaagaagc tccatactat agaacctccc ctaacaggct taaaatacct 180
tctttttttt tttttttt tttgagaacg gagtcttgct ttgtcaccca ggctggactg 240
cagtggcatg atctcggctc tgcaacctcc atctcccagg ttcaagcgat tctcctgcct 300
cagcctccca agtagctggg attacaggca ggcaccacta tgcctggcta attttttgta 360
tttttagtag atatggggat tcaccatgtt ggtcaggctg gtctcgaact cctgaccttg 420
tgatctgcct gcctcggcct cccagtattg ggattacagg catgagccac catgcccggc 480
cttaaaatgc cttcttaaag gaaaaatgcc aactccatcc ttaatctcaa ggaaatctga 540
ttgtccaaat agatctgtta atatgtaaca tattaatagg taacttgctg tgtaaaatta 600
taagccatat tttaaaaggt tttaaaaata cttattgtgc tccatttgtg atataatttc 660
taacatttct gctctgtgat gggggtttat ttgtaagaat aagaggcaaa ggaatgttag 720
catagcaaaa atgtgtttga atgagttaac cttttaatcg caaccctatg tga 773

<210> SEQ ID NO 698
<211> LENGTH: 269
<212> TYPE: DNA
<213> ORGANISM: Homo sapiens

<400> SEQUENCE: 698
tgccaaaaga tcctgtcgtt gcataatcaa acagttggta ttctcgtgcc gttgttcaaa 60
gtcatgtgtt tctttcattt ggtgctgaaa atttctgttc aatcattgac aaatatttat 120
tgaacaccca ctctgtgcca tgtaaaacta tgtcaggtgc tggatatgtt gatgaatgaa 180
acagactcta tccttataca atttgagtct tgtgggctca gaagtaaatt ctgtgaaagc 240
tggacggata gtcgaattga gtgctctta 269

<210> SEQ ID NO 699
<211> LENGTH: 212
<212> TYPE: DNA
<213> ORGANISM: Homo sapiens

<400> SEQUENCE: 699
cctcctaatt gtgggattgt cagaactgaa cacatatcat ttgattagtg catatttttt 60
atagtacctg aaaaccaaga ttttgaaaaa attttcaaga cagagaattt tgataaatcc 120
tgacattgac ctaattgaca taggtaaata tgtttgtata tgtgctaata attttctaat 180
ttcggaacac gatgatgtta tgactattga tt 212

<210> SEQ ID NO 700
<211> LENGTH: 205
<212> TYPE: DNA
<213> ORGANISM: Homo sapiens

<400> SEQUENCE: 700
ctaccagtcg taaagtgaca ttttttggtt attgttgaga ctgcttgccc gtgggctcag 60
aagtgagatt tgcattattc ttctgttgga ttctgataga aaaaaagaca ttcactgtat 120
aagaaaatgg atggactgaa ccaattagaa ttgataccag tgaaattttt atattgctta 180
caattggtaa ccaagagtgc tgata 205

<210> SEQ ID NO 701
<211> LENGTH: 125
<212> TYPE: DNA
<213> ORGANISM: Homo sapiens

<400> SEQUENCE: 701
tgttcgttct cgttgttggg atgcctgtat ggttgtggat ggaggaactt cttttgagtt 60
taatgatggt gcaattgctt cgatgatgat caataaagaa gatgagcttc gaactgtgct 120
tcttg 125

<210> SEQ ID NO 702

<211> LENGTH: 104
<212> TYPE: DNA
<213> ORGANISM: Homo sapiens

<400> SEQUENCE: 702
tcactgctct acagtccgga agaaccaaaa atacttttca gtattcgaga accaatagca 60
aatagagttt tctcaagcag tcgtcagcgt tgtttctcct caaa 104

<210> SEQ ID NO 703
<211> LENGTH: 44
<212> TYPE: DNA
<213> ORGANISM: Homo sapiens

<400> SEQUENCE: 703
gagaattagt gctgttagag aaagaatact tatgaagaaa tctg 44

<210> SEQ ID NO 704
<211> LENGTH: 41
<212> TYPE: DNA
<213> ORGANISM: Homo sapiens

<400> SEQUENCE: 704
gaaatttgag tcttccattg aacagagaat tggtagagaa a 41

<210> SEQ ID NO 705
<211> LENGTH: 26
<212> TYPE: DNA
<213> ORGANISM: Homo sapiens

<400> SEQUENCE: 705
cattcaatat taacagggtt gcaact 26

<210> SEQ ID NO 706
<211> LENGTH: 84
<212> TYPE: DNA
<213> ORGANISM: Homo sapiens

<400> SEQUENCE: 706
atgagatttc agttgatgat ggtccatggg aaaaacagaa gagttcaggg ctcaatttgt 60
gtactggaac aggatcaaag gcct 84

<210> SEQ ID NO 707
<211> LENGTH: 62
<212> TYPE: DNA
<213> ORGANISM: Homo sapiens

<400> SEQUENCE: 707
aatgtcttat tcttgggctg tagcagtgga caatttaaga agaagtatac ccactctaaa 60
gg 62

<210> SEQ ID NO 708
<211> LENGTH: 269
<212> TYPE: DNA
<213> ORGANISM: Homo sapiens

<400> SEQUENCE: 708
gctgagagct agctttgctt tataattttg tacttactaa aaaattaaat aacttataaa 60
tggaggaaaa cttggatcag ttgatagatt ttgggggagt tagtgaaatt tcttgagggg 120
attttcaatc gaatgctttt attttctgtg gcagtaatga tctggttggt ttatctcata 180
aataactgat gctgctgctt tttgtgttct ttgatgtctc accttatgtt tttactaagt 240
aaggacagca atggattggc ttctgatgc 269

<210> SEQ ID NO 709
<211> LENGTH: 61
<212> TYPE: DNA
<213> ORGANISM: Homo sapiens

<400> SEQUENCE: 709
cccaacttct gccagtgaga gcactaaatg aagtcttcat tggggagagt ctgtcatcca 60
g 61

<210> SEQ ID NO 710
<211> LENGTH: 32
<212> TYPE: DNA
<213> ORGANISM: Homo sapiens

<400> SEQUENCE: 710
catttgctgc ttaaatccaa aatagttctc tt 32

<210> SEQ ID NO 711
<211> LENGTH: 109
<212> TYPE: DNA
<213> ORGANISM: Homo sapiens

<400> SEQUENCE: 711
tggaactgga gaacacactt ttttagctca tcacatggct tttggcagaa ggcttcagtt 60
cctcaccatg ttggtctctc caaagggttg ttcatgttat ctcttcctc 109

<210> SEQ ID NO 712
<211> LENGTH: 101
<212> TYPE: DNA
<213> ORGANISM: Homo sapiens

<400> SEQUENCE: 712
tggaggcaga gaatcaggtt ataccttgaa gggactggca taaaccctgt acctgtggac 60
cttcacgagc agcagctaag cttgaatcag cacaatagag c 101

<210> SEQ ID NO 713
<211> LENGTH: 158
<212> TYPE: DNA
<213> ORGANISM: Homo sapiens

<400> SEQUENCE: 713
gctatatcta gctcagtatc ttggacttta tgggttcttg atagagtttg acttaattta 60
agttacttgg gagattttgt acaagcacat taggtgtttc cgttataatt gaaaagagaa 120
taaatattca aatctgtcat tgataaggaa gctatagg 158

<210> SEQ ID NO 714
<211> LENGTH: 78
<212> TYPE: DNA
<213> ORGANISM: Homo sapiens

<400> SEQUENCE: 714
agggtcattt atgcctgccc gttcgatata cacattcctt tccagaagcc ttacagaagt 60
tctatcgtgg tgagttca 78

<210> SEQ ID NO 715
<211> LENGTH: 66
<212> TYPE: DNA

<213> ORGANISM: Homo sapiens

<400> SEQUENCE: 715
gctgctggca gcgagtaaag tcttggacag acttaaacca gttatagggg taaacactga 60
tccaga 66

<210> SEQ ID NO 716
<211> LENGTH: 82
<212> TYPE: DNA
<213> ORGANISM: Homo sapiens

<400> SEQUENCE: 716
ggaattgagg ttcgtctagt aaagaggaga gaatatgatg aagagactgt tcgatgggca 60
gatgctgtca tagctgcagg ag 82

<210> SEQ ID NO 717
<211> LENGTH: 43
<212> TYPE: DNA
<213> ORGANISM: Homo sapiens

<400> SEQUENCE: 717
tacagtggac ttcttgaacg acatcatatt cacaccaaaa atg 43

<210> SEQ ID NO 718
<211> LENGTH: 112
<212> TYPE: DNA
<213> ORGANISM: Homo sapiens

<400> SEQUENCE: 718
aagcaaatcc aagtggaaca aaggtcatct aaccgcctct acaagtatta gtttatcttt 60
ggtcatcaag tagccatatg cagtgtgtta aaaagtcatc aaggctgagg ca 112

<210> SEQ ID NO 719
<211> LENGTH: 39
<212> TYPE: DNA
<213> ORGANISM: Homo sapiens

<400> SEQUENCE: 719
attaacacta atgattttga gccataagat tatatttga 39

<210> SEQ ID NO 720
<211> LENGTH: 196
<212> TYPE: DNA
<213> ORGANISM: Homo sapiens

<400> SEQUENCE: 720
gaggcttttg gctaggcatt aaattttggc acaggctgtc taatctatta tagtatatct 60
tggtaagtta acatctatta attaattttc acaatagcca aatgcttcct cagcttctct 120
tttgtgagaa cataacgaaa attacaaagc aaggacaaaa ctatttaaaa actcttaacc 180
cagtattcgt aggcaa 196

<210> SEQ ID NO 721
<211> LENGTH: 36
<212> TYPE: DNA
<213> ORGANISM: Homo sapiens

<400> SEQUENCE: 721
atgtatctta ttttcctggg gcttgccgag agccag 36

<210> SEQ ID NO 722
<211> LENGTH: 33
<212> TYPE: DNA
<213> ORGANISM: Homo sapiens

<400> SEQUENCE: 722
catctcaagc caaagttccc taacagtcaa cgc 33

<210> SEQ ID NO 723
<211> LENGTH: 403
<212> TYPE: DNA
<213> ORGANISM: Homo sapiens

<400> SEQUENCE: 723
cccattgatt gaccagtgac ttattttgtg atatcagatt tctggtcaaa cattttacct 60
ctactgtctc atgacctttc aaaggccagt aaaactatta ttacaattta cttgcatcat 120
taagagatgt agctgttggc aaatgtgcaa ttgctattaa cagggtcctt gacacaaatt 180
agaactctag atgaaacaaa actgacttgg aaaggatttt gacaccagaa acatacctca 240
ttggtcaaaa aaaggtttta tttaaagctc tttttcacct gtcaccaggg atggggaact 300
gaataaggaa aaaaaatttt aatgtagaac aaataagaag tcagcagttt ctgccctcct 360
ctccatcatt ccaggtctca caactcggca accctttttac tgg 403

<210> SEQ ID NO 724
<211> LENGTH: 29
<212> TYPE: DNA
<213> ORGANISM: Homo sapiens

<400> SEQUENCE: 724
gaaaaggaga gtgcccggtg ctaccatga 29

<210> SEQ ID NO 725
<211> LENGTH: 58
<212> TYPE: DNA
<213> ORGANISM: Homo sapiens

<400> SEQUENCE: 725
gtacgttatt aaggagaaat gtcaggacaa ggggctggta tactgggtag tgtgtgaa 58

<210> SEQ ID NO 726
<211> LENGTH: 80
<212> TYPE: DNA
<213> ORGANISM: Homo sapiens

<400> SEQUENCE: 726
gccttttcct tgctggaacg tggtcgttgg acactacgag cttgttttaa aagcacaggt 60
ctttggtgct aagaaggaaa 80

<210> SEQ ID NO 727
<211> LENGTH: 37
<212> TYPE: DNA
<213> ORGANISM: Homo sapiens

<400> SEQUENCE: 727
actgcgaggc ctagggcact ccggaaagtc cttcagc 37

<210> SEQ ID NO 728
<211> LENGTH: 34
<212> TYPE: DNA
<213> ORGANISM: Homo sapiens

<400> SEQUENCE: 728
cgagcagcag cggtaccgtt acgcggagct ctcg 34

<210> SEQ ID NO 729
<211> LENGTH: 54
<212> TYPE: DNA
<213> ORGANISM: Homo sapiens

<400> SEQUENCE: 729
ggcccacgat gacttgctac cgaggcttct tgctgggcag ctgttgtcgc gtgg 54

<210> SEQ ID NO 730
<211> LENGTH: 39
<212> TYPE: DNA
<213> ORGANISM: Homo sapiens

<400> SEQUENCE: 730
ccggcggtag ggagctgagg caaggggccc gagcccaag 39

<210> SEQ ID NO 731
<211> LENGTH: 168
<212> TYPE: DNA
<213> ORGANISM: Homo sapiens

<400> SEQUENCE: 731
ccactagctg gggcctccat ttcttccccg cccacctttc tcccgcgtgg ggtctcccgt 60
ttcccaatcg ccacgctttc cccgccttcg tcaacgcctg ggtacgtccc cctagccgcg 120
tgggccacgc acgtcctggc acttaacctc tgcccgtccg gcgcgaag 168

<210> SEQ ID NO 732
<211> LENGTH: 131
<212> TYPE: DNA
<213> ORGANISM: Homo sapiens

<400> SEQUENCE: 732
aaagagctcc ggaaacttgc cctgaaggag atgggaactc cagatgcaca ctttgatacc 60
aggctcaaca aagctgtctg ggccaaagga ataagcaacg tctcatactg tatccatgtt 120
cggttgtcca g 131

<210> SEQ ID NO 733
<211> LENGTH: 94
<212> TYPE: DNA
<213> ORGANISM: Homo sapiens

<400> SEQUENCE: 733
tcagttggtc acgtggttgt tcggagcggg cgagcggagt tagcagggct ttactgcaga 60
gcgcgccggg cactccagcg accgtgggga tcag 94

<210> SEQ ID NO 734
<211> LENGTH: 71
<212> TYPE: DNA
<213> ORGANISM: Homo sapiens

<400> SEQUENCE: 734
ctgtggcctt ttgcgaggtg ctgcagccat agctacgtgc gttcgctacg aggattgagc 60
gtctccaccc a 71

<210> SEQ ID NO 735
<211> LENGTH: 81

<212> TYPE: DNA
<213> ORGANISM: Homo sapiens

<400> SEQUENCE: 735
aggcgcacag cctctagacg actcgctttc cctccggcca acctctgaag ccgcgtccta 60
ctttgacagc tgcagggccg c 81

<210> SEQ ID NO 736
<211> LENGTH: 36
<212> TYPE: DNA
<213> ORGANISM: Homo sapiens

<400> SEQUENCE: 736
gttgggaggt gagtcgaggg actgccccat tggctg 36

<210> SEQ ID NO 737
<211> LENGTH: 69
<212> TYPE: DNA
<213> ORGANISM: Homo sapiens

<400> SEQUENCE: 737
actgcccgcc ccctagcctg gcgctgggcc tccgggacaa gttggctggg tccgggcttg 60
gggactgca 69

<210> SEQ ID NO 738
<211> LENGTH: 342
<212> TYPE: DNA
<213> ORGANISM: Homo sapiens

<400> SEQUENCE: 738
ttgcctcgac cttccagcac tttggtgatc atgcaggtga tccgcctgcc tcgacctccc 60
aaagtgctgg gattacagat gtgagccacc acgcccggcc tttcctaagc ttttttgttt 120
gcacatgtgt gtgcacgcgc caggacacaa ggtaaaatgt attaatgtta gaagccactg 180
cactgagtaa aggcatggcc acaaaaatta gggacatcta tcgacgaggc acaggcgcag 240
acacggcagg ggccaatggg tagtgggcag tgggcagtgg gcagtggagc agcagttcag 300
atgctgagtt tggcccagtg gtctagtcaa ccgcattaca ta 342

<210> SEQ ID NO 739
<211> LENGTH: 230
<212> TYPE: DNA
<213> ORGANISM: Homo sapiens

<400> SEQUENCE: 739
caggaaagtt aagatgctgc tctttaggat ggacctgggc ataccctagt atctgtttat 60
tttgcttttt ctggtgacta tttaatccag gacaatatgt ttagaaattt taaaccagtt 120
ttagaaattg gtttaaaata cattaatttc attttttcag ctataattat tatgtgtgta 180
tatatgtaaa atatagatat caagagtcat taactttagt caccttagtc 230

<210> SEQ ID NO 740
<211> LENGTH: 25
<212> TYPE: DNA
<213> ORGANISM: Homo sapiens

<400> SEQUENCE: 740
tcttctgtgc ttcaccatct acata 25

<210> SEQ ID NO 741

<211> LENGTH: 31
<212> TYPE: DNA
<213> ORGANISM: Homo sapiens

<400> SEQUENCE: 741
atgaagcaga aacaagaaga aatcaaagag a 31

<210> SEQ ID NO 742
<211> LENGTH: 153
<212> TYPE: DNA
<213> ORGANISM: Homo sapiens

<400> SEQUENCE: 742
tgtagaaagc atggggctaa aagtattttg acataattta tccaaattta gcctggctat 60
aatttctgta agccttgagt tagtcagagg atgagtaaca atagagaaca tttttaaaaa 120
actaattacg gttgaatatt aagtctgacc caa 153

<210> SEQ ID NO 743
<211> LENGTH: 647
<212> TYPE: DNA
<213> ORGANISM: Homo sapiens

<400> SEQUENCE: 743
gcactgacat tttagccacc ttctaatgaa tgggcttgaa gcagaactgc ttctactatc 60
aggtaatggt tgaggggga tgtctattac acatgtactt tgttttgtgt aaagtatgtt 120
ctggaaagtt acattctttt ggtgagtaca tgtaagtatt tgagggatat tcatgattta 180
aggaggcctg aaatgaatct tttgattag ggaaagaaat attttgcagt gtaaatgatt 240
aaccatttct tccagtttac ctgtttggtg agttcatacc ataaatgtta cgatgtttgg 300
ttttataaaa gagtacctgt aagtttttag tttctgtgtg gaagattttt tcagagagaa 360
tacagatagc cttcttgtat tagaattttg tcatatgtgg tttgaaactg ttcattggag 420
ctgaggaatt ttgttacgtt tgttttaact agatatgatt aacaaaatga ccatagcaag 480
agcatgcatt gaaatgagag aagttacgtg tgtttgtgtc tagtttgggt aatatgattc 540
attcttaaga attcttcaaa ctttattata atttttggaa ataacaagtt tgtcagttga 600
ttaaaccagt gtcttgttca taggcgacct tacgcaatta tatagca 647

<210> SEQ ID NO 744
<211> LENGTH: 30
<212> TYPE: DNA
<213> ORGANISM: Homo sapiens

<400> SEQUENCE: 744
aatagttctg tcccaagaag aactctgaag 30

<210> SEQ ID NO 745
<211> LENGTH: 30
<212> TYPE: DNA
<213> ORGANISM: Homo sapiens

<400> SEQUENCE: 745
ctgcatctgg atctcttgtt ggaagagaaa 30

<210> SEQ ID NO 746
<211> LENGTH: 151
<212> TYPE: DNA
<213> ORGANISM: Homo sapiens

<400> SEQUENCE: 746

```
ttcagctaag ctcttgaccc cagtctaatc caaaataatt gttgcaaata aaattcctaa    60

aatgttacta tatgttttgg tagaattttt aattgtataa cttttttaaa gatccagaga   120

tgtgaaaaag ttagatatgc gtactctttt t                                  151
```

<210> SEQ ID NO 747
<211> LENGTH: 101
<212> TYPE: DNA
<213> ORGANISM: Homo sapiens

<400> SEQUENCE: 747

```
tgaccactta acatctacaa cttccagccc tggggttatt gtcccagaat ctagtgaaaa    60

taaaaatctt ggaggagtca cccaggagtc atttgatctt a                       101
```

<210> SEQ ID NO 748
<211> LENGTH: 25
<212> TYPE: DNA
<213> ORGANISM: Homo sapiens

<400> SEQUENCE: 748

```
ttatgaattc tgccaattac tgtaa                                          25
```

<210> SEQ ID NO 749
<211> LENGTH: 183
<212> TYPE: DNA
<213> ORGANISM: Homo sapiens

<400> SEQUENCE: 749

```
tgctgaaggt cacagtaaca tttggactca ttttgaattg ccttgaagac aggaagaaga    60

gaaatagatg gtaggatttt tattaggcaa aattaggaaa ggttgactgg atagaaataa   120

agcagctctt taaaaatatt gtagattgaa gagcaggatt tgtgacactc atatctgatt   180

agg                                                                 183
```

<210> SEQ ID NO 750
<211> LENGTH: 38
<212> TYPE: DNA
<213> ORGANISM: Homo sapiens

<400> SEQUENCE: 750

```
gtggaacaca ttatccttgt aaccctctgc gatacatg                            38
```

<210> SEQ ID NO 751
<211> LENGTH: 78
<212> TYPE: DNA
<213> ORGANISM: Homo sapiens

<400> SEQUENCE: 751

```
taaaataact gcgaagaaat cccaaacttt attacatttg ttgtttgaac tttattatat    60

ttgttgacag tggtatta                                                  78
```

<210> SEQ ID NO 752
<211> LENGTH: 39
<212> TYPE: DNA
<213> ORGANISM: Homo sapiens

<400> SEQUENCE: 752

```
agaaaaacgg agaaaggcgc tgtatgaagc acttaagga                           39
```

<210> SEQ ID NO 753

<211> LENGTH: 61
<212> TYPE: DNA
<213> ORGANISM: Homo sapiens

<400> SEQUENCE: 753
gaatcccgtt gtgttgagag tcaattctat gctgcatgtc ctccatgtta tatacttgga 60
g 61

<210> SEQ ID NO 754
<211> LENGTH: 37
<212> TYPE: DNA
<213> ORGANISM: Homo sapiens

<400> SEQUENCE: 754
aaaggacaat gaaattgccc gcctgaaaaa ggagaat 37

<210> SEQ ID NO 755
<211> LENGTH: 153
<212> TYPE: DNA
<213> ORGANISM: Homo sapiens

<400> SEQUENCE: 755
tgaatggtga acctctggat aattttgaat cactggataa tcaggaattt gattctgaag 60
aagaaactgt tgaggattct ctagtggaag actcagaaat tggcacgtgt gctgaaggaa 120
ctgtatcttc ctctacggat gcaaagccat gta 153

<210> SEQ ID NO 756
<211> LENGTH: 111
<212> TYPE: DNA
<213> ORGANISM: Homo sapiens

<400> SEQUENCE: 756
tgccgaagtt tacctccact agttctttgt agcagagtac ataactacat aatgccaact 60
ctggaatcaa atttccttgt ttgaatcctg ggaccctatt gcattaaagt a 111

<210> SEQ ID NO 757
<211> LENGTH: 50
<212> TYPE: DNA
<213> ORGANISM: Homo sapiens

<400> SEQUENCE: 757
gtgaatagga ttttctcagt tgtcagccat gacttatgtt tattactaaa 50

<210> SEQ ID NO 758
<211> LENGTH: 46
<212> TYPE: DNA
<213> ORGANISM: Homo sapiens

<400> SEQUENCE: 758
ttgtgtataa cttagaataa tgaaatataa ggagtatgtg tagaaa 46

<210> SEQ ID NO 759
<211> LENGTH: 106
<212> TYPE: DNA
<213> ORGANISM: Homo sapiens

<400> SEQUENCE: 759
ggctgcggcc ggcacagcgc cagggcgagt gaggcgggtg gcgcggggga ggcggcggag 60
taaagagagg ccgccggctg ggtccgcggg tcactccgag gcgcgg 106

<210> SEQ ID NO 760
<211> LENGTH: 158
<212> TYPE: DNA
<213> ORGANISM: Homo sapiens

<400> SEQUENCE: 760
ctccttcgac gaggcgctgc agcgggtggg cgagttcggg cgcttccaga ggcgcgtgtt 60
tttgctgctg tgcctgacgg gcgtcacctt cgccttcctc ttcgtcggcg tggtcttcct 120
gggcacgcag cccgaccact actggtgccg cgggccaa 158

<210> SEQ ID NO 761
<211> LENGTH: 139
<212> TYPE: DNA
<213> ORGANISM: Homo sapiens

<400> SEQUENCE: 761
cggccaacga cagcgcctcc gccactagcg ctctcagctg cgcggaccca ctcgccgcct 60
tccccaaccg ctcggctccc cttgtgccgt gccgcggcgg ctggcgctac gcccaggccc 120
actccaccat cgtcagcga 139

<210> SEQ ID NO 762
<211> LENGTH: 53
<212> TYPE: DNA
<213> ORGANISM: Homo sapiens

<400> SEQUENCE: 762
gaagccggcg ggagaggacg atgctggctc ccaggcggac aagccgcgtg tga 53

<210> SEQ ID NO 763
<211> LENGTH: 112
<212> TYPE: DNA
<213> ORGANISM: Homo sapiens

<400> SEQUENCE: 763
ttccggattc gcttatggtc tccagggtca aaggaaaggg cgaaccaacg tttgaaggca 60
gcagcagctt ttttccagtt gcccaaatgg ttactcaaaa tgcaagggga ca 112

<210> SEQ ID NO 764
<211> LENGTH: 168
<212> TYPE: DNA
<213> ORGANISM: Homo sapiens

<400> SEQUENCE: 764
gtgcacgaga acgtcccatc cagggaccca cggatacttc gttcctgcca gggtctcctt 60
tgggccgaca gagttgtctc taattgagtg caggcagccc cggagcccgc cgagagctga 120
ggctgggctg ggctcccggg gactcgggca gctatttcag gcagacgc 168

<210> SEQ ID NO 765
<211> LENGTH: 72
<212> TYPE: DNA
<213> ORGANISM: Homo sapiens

<400> SEQUENCE: 765
gagggaagtg acctggaagc ggagcagagg tcgcagctgg cccctgctgg gcctagtctc 60
gcttctgtcg tg 72

<210> SEQ ID NO 766
<211> LENGTH: 49
<212> TYPE: DNA

<213> ORGANISM: Homo sapiens

<400> SEQUENCE: 766
gcgtgtgccc agcttagatc cacctgcagc tggctctgaa cgctggatg 49

<210> SEQ ID NO 767
<211> LENGTH: 25
<212> TYPE: DNA
<213> ORGANISM: Homo sapiens

<400> SEQUENCE: 767
gctcagtgtc ttccgctgct gtctc 25

<210> SEQ ID NO 768
<211> LENGTH: 56
<212> TYPE: DNA
<213> ORGANISM: Homo sapiens

<400> SEQUENCE: 768
gtggtgttct tgtcatcctg gaagccctgc cttgggccat gcctgaaatg cactaa 56

<210> SEQ ID NO 769
<211> LENGTH: 188
<212> TYPE: DNA
<213> ORGANISM: Homo sapiens

<400> SEQUENCE: 769
tgactcatgc gcatggcatc aaggcagcca tgcccaggcc cagctcttac ctctggggaa 60
gatagacagc tgacaggtca ggacacagac tttggtggca actgccccgag cacccacata 120 gcaagttgcc gaggccaggg gcatgcagag ccaggaaaac ctgggaagat gcataaacag 180
gcccagcc 188

<210> SEQ ID NO 770
<211> LENGTH: 213
<212> TYPE: DNA
<213> ORGANISM: Homo sapiens

<400> SEQUENCE: 770
ctgacacctt gcgtgggaga cactaacagg gagaagagct gagcctcccc cagccttctg 60
acctacagca ccatgtgatc atgaatatgt gttattctaa gccactaagt tggtggtaat 120
ttgttatata gcaatagaaa acagatgcat taagtttgtc tacaatgccc atgcctgcag 180
tcatattctt tggcttccta gaaggtgacc agc 213

<210> SEQ ID NO 771
<211> LENGTH: 428
<212> TYPE: DNA
<213> ORGANISM: Homo sapiens

<400> SEQUENCE: 771
ccactgattt catgacctaa ctagaaaaac ttagactcgc ttttggccat ggagacatac 60
atttccaaca aaattttact tctgcataat aattatttct taaaatttat tacatcttat 120
ttttttatca attatgatct aaagataatt gtaattataa cccaagcaga aaaaatccaa 180
tatttagaga cttattgcca caggaaaatt ttaaaaatta aatgtcaatt tatatatgta 240
acttattgta catagaagta tggtgacaaa acctataaaa tattttctac acgaaataca 300
ttacattaga ataaaagtct gtggaaatga aaataagagc tcaaagagaa aaaaattgat 360
gtcaaatttc agactattaa agaacagtct gtttatagca attggacacc tgatagcata 420
taatattc 428

<210> SEQ ID NO 772
<211> LENGTH: 96
<212> TYPE: DNA
<213> ORGANISM: Homo sapiens

<400> SEQUENCE: 772
tgtctgtgtc aatgcgtgga tgctggacct cacccaagcc atcctgaacc tcggcttcct 60
gactggagca ttcaccttag gctatgcagc agacag 96

<210> SEQ ID NO 773
<211> LENGTH: 971
<212> TYPE: DNA
<213> ORGANISM: Homo sapiens

<400> SEQUENCE: 773
ccaagtgcgt agtatcccaa gtatgtaaaa ctggttcagc attctaaagt caattaatgt 60
catccatcaa tcacatcgac aaactaagga agaaaaaatg acatgatcat atcaatagat 120
acagacaaag tatttgtcaa aatccaacat ctatatatga caaaagctct cagtaaacta 180
gaaatatagg ggaacttcct caacttgata aggaatgtct attaaaaaaa ctacagttaa 240
catcatactt aatgacgata aactgtacag aagctttctc actaagatca gaaacaagcc 300
aaatatgtca tctctaataa cttcttttca atgccatgct agaagccctc gctaatacaa 360
taaataagac aagtaaagaa aataacaggt atactgattg gaaaggaaga aataaaaact 420
gtctttgttc acagatgtca tgattgtcta tgtagaaaat caaaagaatt aacaacaaca 480
acaaccaaaa aaaaaaactc ctgaaactaa taagtgagta tagtgaagtt gcagggtaca 540
aggctaatac acaaaagtca actgctttcc tatgtaccaa caatgaacaa gtaggatttg 600
aatttaaaca cataatgcca tttacattag caccacaaga atacacaaca cttagatata 660
aatctaacaa catatgtaca agatttatgt gaggaaaagt gcaaaactct aatgaaagaa 720
attagagatg atctaaataa atggagagat attcaacatt catggatagg aagactcaat 780
attgtcaaga tgtcagttct tcccaacttg atgtatatat tcaatacaat actaatcaaa 840
atcctacaga gttattttgt ggatattgac aaactagttc taaagtttat atgtagagac 900
aaaagaccca gaatagccaa cgcagtactg aaggagaaga acaaagccag aggactggca 960
ctacttaacg t 971

<210> SEQ ID NO 774
<211> LENGTH: 89
<212> TYPE: DNA
<213> ORGANISM: Homo sapiens

<400> SEQUENCE: 774
atcctgcctt ggtgttggcg tcactggggt tgtggtggcc tttgcaccaa acttccctgt 60
gtttgtgatc ttccgcttcc tgcaaggtg 89

<210> SEQ ID NO 775
<211> LENGTH: 141
<212> TYPE: DNA
<213> ORGANISM: Homo sapiens

<400> SEQUENCE: 775
tgacagaaat agtaggttcg aaacaaagga ggattgtggg aatcgtgatt caaatgttct 60
ttacccttgg aatcataatt ctccctggaa ttgcctactt catccccaac tggcaaggaa 120
tccagttagc catcacgctg c 141

<210> SEQ ID NO 776
<211> LENGTH: 97
<212> TYPE: DNA
<213> ORGANISM: Homo sapiens

<400> SEQUENCE: 776
cccgttggct gattactcgg aagaaaggag ataaagcatt acagatcctg agacgcattg 60
ctaagtgcaa tgggaaatac ctctcatcaa attactc 97

<210> SEQ ID NO 777
<211> LENGTH: 51
<212> TYPE: DNA
<213> ORGANISM: Homo sapiens

<400> SEQUENCE: 777
ggaaaaatca taggacatat taaagaagaa atgattatga agctctatta g 51

<210> SEQ ID NO 778
<211> LENGTH: 136
<212> TYPE: DNA
<213> ORGANISM: Homo sapiens

<400> SEQUENCE: 778
cggagaaggt tagaatggat ttgaaagaat gtggttggat tcaaagaagc cctaggagac 60
ccaacaagtc agcatttttc tcttgtgaaa agaaccacct gccaacccca gcctgttcca 120
ttgctgacat cagagg 136

<210> SEQ ID NO 779
<211> LENGTH: 67
<212> TYPE: DNA
<213> ORGANISM: Homo sapiens

<400> SEQUENCE: 779
catttgccaa ggtttctggc tggcctctgg ctttgttgaa gagatagcta gcactagcag 60
ggagaaa 67

<210> SEQ ID NO 780
<211> LENGTH: 203
<212> TYPE: DNA
<213> ORGANISM: Homo sapiens

<400> SEQUENCE: 780
aggctctctg aacatacaaa cagtataact gttgttcact aaatggaaaa atcccaaaat 60
caaaaaccaa tgcaaaacag tgaagtggct tgagctccta ggaggttagg tagaaattaa 120
agagaatcag tggatgggta gaattttaag cagtaggtag ttacccaatg tagaacgagg 180
attagcttag acacctagtc tgg 203

<210> SEQ ID NO 781
<211> LENGTH: 46
<212> TYPE: DNA
<213> ORGANISM: Homo sapiens

<400> SEQUENCE: 781
ctgcccattc ctcccgtttt tgtatgggat atactcatag agaata 46

<210> SEQ ID NO 782
<211> LENGTH: 39
<212> TYPE: DNA
<213> ORGANISM: Homo sapiens

<400> SEQUENCE: 782
gatgaatggt gccaattcta ccagcaaagc cttcatctt 39

<210> SEQ ID NO 783
<211> LENGTH: 143
<212> TYPE: DNA
<213> ORGANISM: Homo sapiens

<400> SEQUENCE: 783
tgtcattcaa caccgaaaga tattgagggg aggatgttct cctacacctt taattgaaat 60
ggaaattcaa tttaaaggtg ctttaaagaa tgagattgca gccttggagc aggctaggca 120
gacttgtggg atgcctcatc aga 143

<210> SEQ ID NO 784
<211> LENGTH: 115
<212> TYPE: DNA
<213> ORGANISM: Homo sapiens

<400> SEQUENCE: 784
acctggttct tcatctggtc ctgagtcctt gcccattcta ctgtggctct ggccctgctt 60
cattcctgcc tgattcatcc tcagaaggca ggtttctgtc ctgtccctac acatc 115

<210> SEQ ID NO 785
<211> LENGTH: 191
<212> TYPE: DNA
<213> ORGANISM: Homo sapiens

<400> SEQUENCE: 785
aattactgtg cttctcgact gtggataaat gagaaaatac tcctctctgt gaacgcgctc 60
cttcgtggag acagtaatga gtacaacttc cagagctctg cgcagccagc aaccctggca 120
ggagtccctg tgttattcat aacccagagc tgtgttgcca tggcagtact gcttgctaga 180
ccttggaccc a 191

<210> SEQ ID NO 786
<211> LENGTH: 78
<212> TYPE: DNA
<213> ORGANISM: Homo sapiens

<400> SEQUENCE: 786
gtgtgctact ggcttatggc tgatacgtaa gagaatctca tctatctcta aatgttctgc 60
cttaagccgc acaaagga 78

<210> SEQ ID NO 787
<211> LENGTH: 37
<212> TYPE: DNA
<213> ORGANISM: Homo sapiens

<400> SEQUENCE: 787
tgtgcagaaa atattctgca aatcaagaac cagaaaa 37

<210> SEQ ID NO 788
<211> LENGTH: 39
<212> TYPE: DNA
<213> ORGANISM: Homo sapiens

<400> SEQUENCE: 788
aaatggagga aattccgaga tgacagtggt tttggttct 39

<210> SEQ ID NO 789
<211> LENGTH: 86
<212> TYPE: DNA
<213> ORGANISM: Homo sapiens

<400> SEQUENCE: 789
gctctttgag aatgtagtcg ggacttgccc cagtcaccct tgccctgaga actcagtgac 60
tggggctaat gtcaccctgg ctgtcc 86

<210> SEQ ID NO 790
<211> LENGTH: 109
<212> TYPE: DNA
<213> ORGANISM: Homo sapiens

<400> SEQUENCE: 790
ggagacacct accaggaatc tagtgggaca aggtttcagg gatcctggaa tcctgcccac 60
acccaacagc tggaacagtt ccctcagctg gcgagtggac aggtggtct 109

<210> SEQ ID NO 791
<211> LENGTH: 93
<212> TYPE: DNA
<213> ORGANISM: Homo sapiens

<400> SEQUENCE: 791
gatgttaaag accatgttcc catagaaata attcccaaag cattcagaag actgagaaga 60
agtgatgata agaattgttc tgggcaggag tgt 93

<210> SEQ ID NO 792
<211> LENGTH: 26
<212> TYPE: DNA
<213> ORGANISM: Homo sapiens

<400> SEQUENCE: 792
tttcaaaaat tgccgaagta ctacag 26

<210> SEQ ID NO 793
<211> LENGTH: 48
<212> TYPE: DNA
<213> ORGANISM: Homo sapiens

<400> SEQUENCE: 793
actaacctct gcagtttaac cttgagcgat accttttccc atgaatag 48

<210> SEQ ID NO 794
<211> LENGTH: 120
<212> TYPE: DNA
<213> ORGANISM: Homo sapiens

<400> SEQUENCE: 794
agagtgtcga tactaggcaa caagcctctg aacagatagt gttacccgga acatcaccct 60
tttctccctt tgcttcaaat caaaaccagc atcccccatt tagacagcat aaaaggtatg 120

<210> SEQ ID NO 795
<211> LENGTH: 174
<212> TYPE: DNA
<213> ORGANISM: Homo sapiens

<400> SEQUENCE: 795
cttcactgag acacaaggaa acttttgggg atcatggaaa gggtccgtac cacggttgtg 60
gtggtggtta taagactata tatttgtcaa aagtcttcaa agtgtgcact tagaattgct 120
gaagtttatt gtacataaat tacatgtaaa tatcataaag tgcatgtaaa tggt 174

<210> SEQ ID NO 796
<211> LENGTH: 80
<212> TYPE: DNA
<213> ORGANISM: Homo sapiens

<400> SEQUENCE: 796
cagatgagga agttagtaat ccatcctttt tagatctggt gagaactccc caaatgagga 60
aatgcacact tattcttatg 80

<210> SEQ ID NO 797
<211> LENGTH: 202
<212> TYPE: DNA
<213> ORGANISM: Homo sapiens

<400> SEQUENCE: 797
cgcagtggtg tatcaaggac ttgtcatgcg cctgggaatt atagggggca acctctatat 60
agactttttc atctcgggcg tggtggaact gccaggagct ctcttgatct tactaaccat 120
tgagcgcctt ggacgacgcc tcccctttgc ggcaagcaat atagtggcag gggtggcatg 180
ccttgtcact gcgttcttac ca 202

<210> SEQ ID NO 798
<211> LENGTH: 38
<212> TYPE: DNA
<213> ORGANISM: Homo sapiens

<400> SEQUENCE: 798
tatttggtaa attcagaatt gtacccaaca acattacg 38

<210> SEQ ID NO 799
<211> LENGTH: 102
<212> TYPE: DNA
<213> ORGANISM: Homo sapiens

<400> SEQUENCE: 799
gtttcgctct gttcaggtct gtgtgatttt gggggaatca tagccccatt tctgctcttt 60
cggctagcag ccgtgtggct agaactacct ctgatcatct tt 102

<210> SEQ ID NO 800
<211> LENGTH: 266
<212> TYPE: DNA
<213> ORGANISM: Homo sapiens

<400> SEQUENCE: 800
ttcttaagag ccttcatcta cattctttgt actaaaagag acctataata attgttaggt 60
tcaataatga taatgatagt catttatctt attataataa ctatttcatt gataattatg 120
atattaattt catcttatta taataactat ttcagttttg agagccaatt cagttataat 180
gaatggtttt aatttacttt atattaaagg gtgctgataa ataatgttca attagcattc 240
tttgggttct gagttaaatg ctgtga 266

<210> SEQ ID NO 801
<211> LENGTH: 51
<212> TYPE: DNA

<213> ORGANISM: Homo sapiens

<400> SEQUENCE: 801
cagaaagtgc tactgtccag caaagacaga gtagtccagg agacaagaca c 51

<210> SEQ ID NO 802
<211> LENGTH: 114
<212> TYPE: DNA
<213> ORGANISM: Homo sapiens

<400> SEQUENCE: 802
atgaccttca ggactgcagc ccacagccca gtggcaggca ggcggggcct gagactgcga 60
ggggagacag ccgaatttct aaaaactcag cgacaacaga atgtgataac tgct 114

<210> SEQ ID NO 803
<211> LENGTH: 284
<212> TYPE: DNA
<213> ORGANISM: Homo sapiens

<400> SEQUENCE: 803
ttcaaagcaa gaggatgccg catcctcaag cacctggtgc tagaggatgg agtgcagttg 60
tgagctgggc ctgaagagag gtggtgccag ggcagggcag ggactggatc cggaagggcc 120
tcaaggacat gccaaggctt tgctctttat acacacagca gtggaaagtg actggacagt 180
ttcaccctga ggtggacaga gctggccttg cattgtagaa acacagatat gcaagtgggt 240
tggaaggacc ccccagcatc gtccctctga tggtagatat gcaa 284

<210> SEQ ID NO 804
<211> LENGTH: 332
<212> TYPE: DNA
<213> ORGANISM: Homo sapiens

<400> SEQUENCE: 804
tttgtaagcc agtcatcaag cacagatatc atcaaaaagt aaagaatatg aaatatatga 60
gaaatagagg caataaatgc ccaacactca tcagtcccta attcagctac tacaccttca 120
gtattacctg tgctcctgag attgtgtctg ctgcatcttt atggtggaag ccccattgat 180
ggggctcctg catcacttcc cagtggccca ggcagggatg ttgtgtcagt agcctgaagg 240
gcccacagtg ggagcattta aaccatgcac attggcagat gctgccaatc agggcttgat 300
tgcccaaaga gggttgttag gcatttacca gc 332

<210> SEQ ID NO 805
<211> LENGTH: 101
<212> TYPE: DNA
<213> ORGANISM: Homo sapiens

<400> SEQUENCE: 805
actggaggaa gggttgatcc ctacagtgag gagcccaaag agacaggcct aggagaaggc 60
tggtcccgga gtagacacca ggacaagctt tccactgtaa g 101

<210> SEQ ID NO 806
<211> LENGTH: 49
<212> TYPE: DNA
<213> ORGANISM: Homo sapiens

<400> SEQUENCE: 806
aggggcaggt aagtgagagt gtcagtgagc gggcgcagag gggactccc 49

<210> SEQ ID NO 807
<211> LENGTH: 25
<212> TYPE: DNA
<213> ORGANISM: Homo sapiens

<400> SEQUENCE: 807
tggaccctaa gaaggaactc agtca 25

<210> SEQ ID NO 808
<211> LENGTH: 202
<212> TYPE: DNA
<213> ORGANISM: Homo sapiens

<400> SEQUENCE: 808
tatacagggg ccgtggtgct actcagggtt tgaggaaggg agagaacctt tgaagctgtg 60
gtaagggaga gctggggcat tgatctggga tgcagaggtt gctgtggttg agagctactc 120
cagtgagcaa catgatggct tcagagtgag caggccccat gggagagggc ccagctgtgt 180
cttcctggag cggtaacacc tt 202

<210> SEQ ID NO 809
<211> LENGTH: 77
<212> TYPE: DNA
<213> ORGANISM: Homo sapiens

<400> SEQUENCE: 809
gtatcctggc atccatctgt ggtggccttg tgatgctttt gcctgaaacc aagggtattg 60
ccttgccaga gacagtg 77

<210> SEQ ID NO 810
<211> LENGTH: 28
<212> TYPE: DNA
<213> ORGANISM: Homo sapiens

<400> SEQUENCE: 810
gtactgtaca aaattcaatg caccctaa 28

<210> SEQ ID NO 811
<211> LENGTH: 2408
<212> TYPE: DNA
<213> ORGANISM: Homo sapiens

<400> SEQUENCE: 811
ccctccagag ctagataaga gtatgcattg tttttttaa tgtggttgtg aagagagaag 60
cattttcaca taaggtgcta agactcagaa gtgatctaaa ggcaggaact gctgatgtgg 120
gaaagtggaa attgctggga catacagcag caggggatta acagtgtggc ttactctaca 180
gagtgaggat gcgtcaggtc tgtctagatg gaatggcata ggcaggtttt caagactgac 240
tacaaagtga aatgtcactg aacaacatgt tatagtattt ataaaaaact aaaaccaaag 300
gtgttttctc tctgcagctg gataggaaga cagatgacac acagatgata gataataggt 360
agatgataga taataggtag atggatgata gatagatata atagatgata atcatagata 420
gataagtgat agtagataaa tgataaataa tagatgatag atgatagata gatacagata 480
gataaataga caggtagatg ataggtaatg tctggataga taggtggata gataaataga 540
taatagatga tagataataa acattagtag gaagatagag agattgagtt ttggaggggg 600
gtgtttaaat agggtataag taaaactaat acccagccaa tatattaaca tgaggagtaa 660
tgtcaagaaa aattcacatt acacaaattc tttctaattg tttgaaattt tttcattaaa 720

```
acatagagat atgaatatga gaatgtatag tacaagatgt aaaatattaa tatgtgccct    780

ctgtggacac aaatgggctg ggaagagggg tagggaaggg aggaccatca ctttcttgcc    840

agagacttcc atactgtttg attttcttta aaaattagaa cacgtagtct tgtgttgctt    900

gtgtagtttt aaaaaatgat gtaacagcta atttaacaac taaaaagcaa tcttaataat    960

gacttaggaa ttaagaacat ggagctctaa atatttttaa tatataaaaa atcctgagga   1020

acagctttct tccctttgat tctattccac tgactgcctt ctgtttacac aatgagagtg   1080

atgctttcat tctttatccc caaaccaatc aggatcagat ttgcaaactc atcaggaaaa   1140

aatggaagaa aagggagtcc tctgaaatca agacttttct actgcttcag taacattaaa   1200

aataaacagc taggagaggt ttttttgttt ttgtttttgt ttgtttttgg cttggggagt   1260

gtgggtggaa gggggttgtc taaatggtgt gcaaggaaaa tcaataccca actaacatat   1320

aaacatgaag gattatacca gcaaaaattt aaggtaccca gattctttct aatttttttc   1380

tgtttataat ttttcataat gaaaagttgg gtacattaat taattatacc tagtctctat   1440

acatgaaaaa aaatatagta gaagtatggt ttacagtgct acaatttaag cacattaatt   1500

gtgatccatg gttatttact ctacaaaaat tacttagtgc taaattacta aaacttgcta   1560

gcatttccct tttaaaaatc acactggatt attttatcgt ttctgctggt ttttgttcat   1620

gttaacagct catttccaaa tatatgttaa ttcagtagaa gttcataaag aacttaaatg   1680

ctataatgct aacaaacccc tgtatcagag gaaccagccc ccaatatttc agcataggtt   1740

ctattttcca taagtgttgg ccagctgaga aataaaaaga gtacaaagag aggaatttta   1800

cagctgggcc gctgggggtg acatcacata tcggtaggac tgtgatgccc acctgagcct   1860

taaagccagc aagtttttat taagggtttc aaaaggggag ggggtgtaag aacagggagt   1920

aggtacaaag atcacatgct tcaaagggca aaaaggagaa caaagatcac aaggcaaagg   1980

gcaaaaacaa acatcacaag acaaagagca aaagcagaat gactgaaaag ggtctatgtt   2040

cagcggtgca tgtattgtct tgataaacat cttaaacaac agaaaacagg gttctagagc   2100

agagaactgg tctgacctca aatttaccag ggcggggttt cccaatccta gtaagcctga   2160

gggtactgca ggaggccagg gtgtatttca gtccttatct caaccgcata aggcagactc   2220

tcccagtgcg actgtttata gacctccccc taggaacgca ttcctttccc agggtcttaa   2280

ttattaatat tccttgctag gaaaagactt cagcaatatc ttccctactt gcacatccat   2340

ttataggctc tctgcaagaa gaaaaatatg gctgtattct gcccgatccc acaagcagtc   2400

agacctta                                                            2408
```

<210> SEQ ID NO 812
<211> LENGTH: 60
<212> TYPE: DNA
<213> ORGANISM: Homo sapiens

<400> SEQUENCE: 812

```
ccacattcct gtaaatgtgg caggaataag aaaaccccag tttcccgctc tcacctttga     60
```

<210> SEQ ID NO 813
<211> LENGTH: 25
<212> TYPE: DNA
<213> ORGANISM: Homo sapiens

<400> SEQUENCE: 813

```
tgtgccttgc agagatgcac gtgtg                                           25
```

<210> SEQ ID NO 814
<211> LENGTH: 497
<212> TYPE: DNA
<213> ORGANISM: Homo sapiens

<400> SEQUENCE: 814
atctggtcaa gggactaagc tcctagctga ccattcattc tgaagattgc atggaggatg 60
aacatctggg aatcctgtta atgagaaggc tgaatcacag gcacctgggc caaagggtgt 120
gagcattcat gttctctgct caccttggtt tccgcacacc ttcgcaatgt gaacaggtca 180
ggagtccctc ccgtccacct cctctgtaac agctggggtt ccaggcatgg tttaggccct 240
gttccagcaa taagaaccaa tctgctgtac aatctgagga cttggctctg ttatttacaa 300
aatgatgctg tggttctgag attatttggg acatttttgg ctctccttta gtggacacct 360
agagccacag attcccttct ttactaaaca aatcccatgg attctgattt ctgggtctta 420
ggattttaaa agtgaaggga tatttttctt atatttgtga gttcagttcc gatggtgccc 480
gtggtcaaaa gcgaaaa 497

<210> SEQ ID NO 815
<211> LENGTH: 90
<212> TYPE: DNA
<213> ORGANISM: Homo sapiens

<400> SEQUENCE: 815
attgctgact catggctgta tctggcctaa tattgttctg gttaatccat ctctgactca 60
tggccatatc tggcctaata ttgttctggt 90

<210> SEQ ID NO 816
<211> LENGTH: 26
<212> TYPE: DNA
<213> ORGANISM: Homo sapiens

<400> SEQUENCE: 816
gtgggttctt gtgactgtac cattca 26

<210> SEQ ID NO 817
<211> LENGTH: 108
<212> TYPE: DNA
<213> ORGANISM: Homo sapiens

<400> SEQUENCE: 817
gcaaacagca attaattagc taatagaaca acaaaaggcc ccatatcctg tagccaattg 60
aagatctgag tttaatcaga ccagtgcttc aaaatgggta gagccttg 108

<210> SEQ ID NO 818
<211> LENGTH: 38
<212> TYPE: DNA
<213> ORGANISM: Homo sapiens

<400> SEQUENCE: 818
ctgtcctttg catgtgagtt tctgctggat cctttcat 38

<210> SEQ ID NO 819
<211> LENGTH: 1183
<212> TYPE: DNA
<213> ORGANISM: Homo sapiens

<400> SEQUENCE: 819
tgctggctac aatttggaac tgtgcagttt aaatatttat ttattttgtt ttgtttttac 60

```
tctttctaat ttggatatta ggttttgctt catctgtgtt ttttttctct tactcagtca    120

ataaccatat ctccaaacta aattaacgtt actaaagtgg ggaatttccc cttcctatat    180

tctcataagt gattgagcat ctgtcctcat ataggacttg ctgccttgga ggggaggggc    240

cagacctggg aaaaagagga gccatgaata actctgcttc ctacatttgg cttcttctct    300

tcctccatat ccatgattta tatatgtgaa ggaagaacaa gaaataactt aataggccat    360

ttgtcaatga gagtacagtg taggaagggt ggaaagtgaa tataaaatct agattggggc    420

ttctggtttc ctgttcagcc tataaggagc ttagaatttg ccactcagtc ttgacaacaa    480

gtaaaatgct gaacaaactg aaaaatcaat aattcttctc agatccataa gagaagtgag    540

attacagggc aaactactac cttcagcatc accccgcacc cccaacccca ctaaatagaa    600

agacaggaga atacagagaa tcataacaca ggcgcagaaa cctccttgag agagccaggg    660

tagataaaca tgaactgtaa ttgatgaatt cctggaggat cactgtggat gacctgaagg    720

attaaaaact ctagagggac tcactcaaag gagggcccaa gcttttgtga tttttttttt    780

tttttttttt ttttttgcca cctgaagctc tacaaggttc caaaggtgaa tattaaggaa    840

aatccctcat gctctggcag ccagagggga aaaggaacaa ttttgaaata tgccagaata    900

tcgttcttaa caatgtctgc cctcaggaga agatgtttaa ccagagccta atcttctggg    960

gttttctgag agcctcattg atctggggga agggaaatac caactccagc cccttctagc   1020

cttccaagtg gagaaagaga aacaccaaat tctagcctcc tctagctttc aacttggaag   1080

aagggaaata cccagctcca gccccctcta gcctttctcc cctagttcag aggagaggga   1140

tagagaagca tttgtgaagt tcaccgttta gagacatagg ttc                     1183
```

<210> SEQ ID NO 820
<211> LENGTH: 417
<212> TYPE: DNA
<213> ORGANISM: Homo sapiens

<400> SEQUENCE: 820

```
attaatggca gacaccacag atccaggaaa ctcaaaggaa atcaagcaag ataaacataa     60

aaaagtatac ctagttatat cgtagtcaaa ctacagaaag ccaaagataa aggaaaaatt    120

ctgaaagaag agtgggggga taatgtctta ctatagtaaa agagcaatga taaaaattac    180

accctacttc ttttcagaaa ccaggtaagc aagaagaaag tggaatactt aaagtgtcaa    240

gaaaaaaaat ccaatctaga attctatact gtgcaaagtt atcatttaaa agtgaaggag    300

aaataaagac tttgttagac aaaaattgag ggaatttgat gccttgtaat aaatgttaaa    360

agaaattatt tagagagaat gaaaatgatc taggttagaa atccagatct acataaa       417
```

<210> SEQ ID NO 821
<211> LENGTH: 39
<212> TYPE: DNA
<213> ORGANISM: Homo sapiens

<400> SEQUENCE: 821

```
aggtactcat actactcatg aagtgataca gtgttattt                            39
```

<210> SEQ ID NO 822
<211> LENGTH: 57
<212> TYPE: DNA
<213> ORGANISM: Homo sapiens

<400> SEQUENCE: 822

```
catatggaga ccttttccct acaaaacact tttttgagaa ttagcaaagc atggtgg        57
```

<210> SEQ ID NO 823
<211> LENGTH: 92
<212> TYPE: DNA
<213> ORGANISM: Homo sapiens

<400> SEQUENCE: 823
tggatgacta tttgggtggc aagccagtgc agaatagaga acttcaagga tatgagtcta 60
atgactttgt tagctatttc aaaggcggtc tg 92

<210> SEQ ID NO 824
<211> LENGTH: 106
<212> TYPE: DNA
<213> ORGANISM: Homo sapiens

<400> SEQUENCE: 824
ccctccacac gtgttcagtt aaagtgtgag gaataccctc cccagacaaa catcacagat 60
ttccgaaatc aaacacgctc cagcaagtgt tctgcacacc ccactg 106

<210> SEQ ID NO 825
<211> LENGTH: 148
<212> TYPE: DNA
<213> ORGANISM: Homo sapiens

<400> SEQUENCE: 825
ggcgtggcat ctggattaaa tcatgttctt acgaacgacc tgacagccaa gaggctccta 60
catgtgaagg gtcgtagagt ggtgagagcc acagaagttc cccttagctg ggacagtttc 120
aacaagggtg actgcttcat cattgacc 148

<210> SEQ ID NO 826
<211> LENGTH: 32
<212> TYPE: DNA
<213> ORGANISM: Homo sapiens

<400> SEQUENCE: 826 aagcttttc atttattcgt ccagcagcat ct 32

<210> SEQ ID NO 827
<211> LENGTH: 38
<212> TYPE: DNA
<213> ORGANISM: Homo sapiens

<400> SEQUENCE: 827
gttagtatag aaacagcact cctcttctaa aaagatac 38

<210> SEQ ID NO 828
<211> LENGTH: 106
<212> TYPE: DNA
<213> ORGANISM: Homo sapiens

<400> SEQUENCE: 828
ggtgtggttc ctcgtgcaac aaatatgaac gtctgaaggc aaaccaggta gctactggca 60
ttcggtacaa tgaaaggaaa ggaaggtctg aactaattgt cgtgga 106

<210> SEQ ID NO 829
<211> LENGTH: 35
<212> TYPE: DNA
<213> ORGANISM: Homo sapiens

<400> SEQUENCE: 829
tggcttccat atggaatgcc gagtatgtca gcctg 35

<210> SEQ ID NO 830
<211> LENGTH: 74
<212> TYPE: DNA
<213> ORGANISM: Homo sapiens

<400> SEQUENCE: 830
tcttagggga aaagccagag cttccagatg gaggtgatga tgatgacatt atagcagaca 60
taagtaacag gaaa 74

<210> SEQ ID NO 831
<211> LENGTH: 29
<212> TYPE: DNA
<213> ORGANISM: Homo sapiens

<400> SEQUENCE: 831
gggctgccaa acaaattttc gtatggaaa 29

<210> SEQ ID NO 832
<211> LENGTH: 81
<212> TYPE: DNA
<213> ORGANISM: Homo sapiens

<400> SEQUENCE: 832
gtaaagatgc taatccccaa gagaggaagg ctgcaatgaa gacagctgaa gaatttctac 60
agcaaatgaa ttattccaag a 81

<210> SEQ ID NO 833
<211> LENGTH: 33
<212> TYPE: DNA
<213> ORGANISM: Homo sapiens

<400> SEQUENCE: 833
ccagaaggag gtgaaacacc aatcttcaaa cag 33

<210> SEQ ID NO 834
<211> LENGTH: 121
<212> TYPE: DNA
<213> ORGANISM: Homo sapiens

<400> SEQUENCE: 834
gcttcgggaa agtttatgtc acagagaaag tggctcaaat aaaacaaatt ccctttgatg 60
cctcaaaatt acacagttct ccgcagatgg cagcccagca caatatggtg gatgatggtt 120
c 121

<210> SEQ ID NO 835
<211> LENGTH: 98
<212> TYPE: DNA
<213> ORGANISM: Homo sapiens

<400> SEQUENCE: 835
cgtgtagaaa acaatggtag gatccaagtt gaccaaaact catatggtga attctatggt 60
ggtgactgct acatcatact ctacacctat cccagagg 98

<210> SEQ ID NO 836
<211> LENGTH: 42
<212> TYPE: DNA
<213> ORGANISM: Homo sapiens

<400> SEQUENCE: 836
tgcgttcctg actgttcagt tggatcggtc ccttggagga ca 42

<210> SEQ ID NO 837
<211> LENGTH: 147
<212> TYPE: DNA
<213> ORGANISM: Homo sapiens

<400> SEQUENCE: 837
ggcaaagagc ctgttcacct actgagtttg ttcaaagaca aaccgctcat tatttacaag 60
aatggaacat caaagaaagg aggtcaggca cctgctcccc ctacacgcct ctttcaagtc 120
cggagaaacc tggcatctat caccaga 147

<210> SEQ ID NO 838
<211> LENGTH: 121
<212> TYPE: DNA
<213> ORGANISM: Homo sapiens

<400> SEQUENCE: 838
tcctgaaact gccacaaaat agtggctaca tctgggtagg aaaaggtgct agccaggagg 60
aggagaaagg agcagagtat gtagcaagtg tcctaaagtg caaaacctta aggatccaag 120
a 121

<210> SEQ ID NO 839
<211> LENGTH: 76
<212> TYPE: DNA
<213> ORGANISM: Homo sapiens

<400> SEQUENCE: 839
aaaaagacta ccagacctca ccactactgg aaacccaggc tgaagaccat ccacctcggc 60
tttacggctg ctctaa 76

<210> SEQ ID NO 840
<211> LENGTH: 47
<212> TYPE: DNA
<213> ORGANISM: Homo sapiens

<400> SEQUENCE: 840
aagagattcc aggagagttc acccaggatg atttagctga agatgat 47

<210> SEQ ID NO 841
<211> LENGTH: 40
<212> TYPE: DNA
<213> ORGANISM: Homo sapiens

<400> SEQUENCE: 841
atttatttgg attggcaaag atgctaatga agttgagaaa 40

<210> SEQ ID NO 842
<211> LENGTH: 94
<212> TYPE: DNA
<213> ORGANISM: Homo sapiens

<400> SEQUENCE: 842
gtaagctcaa tcgatggacc attatagcag taaccgggca ccattatgac cgagtgtctg 60
gcttgctctt tgccaccatg tcttacaaaa atac 94

<210> SEQ ID NO 843
<211> LENGTH: 39
<212> TYPE: DNA

<213> ORGANISM: Homo sapiens

<400> SEQUENCE: 843
gaggacacca attgtcatca taaaacaggg ccatgagcc 39

<210> SEQ ID NO 844
<211> LENGTH: 750
<212> TYPE: DNA
<213> ORGANISM: Homo sapiens

<400> SEQUENCE: 844
acaaggcagt tatctcattg ctgttttggg agaggaacgg gaaaagcttt ttgcttattt 60
gtcttttgaa aattaaggct gggcgcggtg gctcacacct gtaatcccag cactttgaga 120
ggatgaggta ggcggatcac tggggtcagg atttcgagac cagcctggcc aacatggcga 180
aacctcgcct ctactaaaaa tacaaaaaaa ttagctgcgc gtggtggtgc acgcctgtag 240
tccctgctac ttggaaggct gagacaggaa aattgcttga acccaggagg ctgaggttgc 300
agtgagccag gattgcgcca ccacactcca gcctgggcaa cagagactct gtctcaaaaa 360
aaaaaaaaaa aaaaattaac ctcaaccaaa cgcctatttt ttaatgctta gttttggctt 420
gaaattcttc ttcacctgga gttttcttac gttaatacat taaaataacc tgaaggaaac 480
tttcgttatg ggccaatatt agctcttatg gaaactgatt tatatctttt ttatgacctt 540
tcaaaagtaa aatactatgc ataatctaga aagatttgtc agataggaaa ttttataatg 600
cattagccat tagtcagagt tgttttttaa catgccagag aaaaagttgt aatgccttgg 660
aagttattct cttttctata gattgtgttc aaaagatgtg tatacttgca ataaggttta 720
tgttaaggtg gctttaacaa ttggttgcta 750

<210> SEQ ID NO 845
<211> LENGTH: 54
<212> TYPE: DNA
<213> ORGANISM: Homo sapiens

<400> SEQUENCE: 845
gaattgtatt gttatccact tagatacatg tacatgtaca gtacatgttt aata 54

<210> SEQ ID NO 846
<211> LENGTH: 99
<212> TYPE: DNA
<213> ORGANISM: Homo sapiens

<400> SEQUENCE: 846
aaacactata aagtggcggc gaataaggtt cctcctgctg ctctcggttt agtccaagat 60
cagcgatatc acgcgtcccc cggagcatcg cgtgcagga 99

<210> SEQ ID NO 847
<211> LENGTH: 34
<212> TYPE: DNA
<213> ORGANISM: Homo sapiens

<400> SEQUENCE: 847
ccgacgcacc aaggccggcg aggggagggc gtag 34

<210> SEQ ID NO 848
<211> LENGTH: 76
<212> TYPE: DNA
<213> ORGANISM: Homo sapiens

<400> SEQUENCE: 848
ttatttgttg ctttcgggca ctggcttatt ttctctatga ttgcgggaat tattgttctg 60
ggcttcttta aaacag 76

<210> SEQ ID NO 849
<211> LENGTH: 75
<212> TYPE: DNA
<213> ORGANISM: Homo sapiens

<400> SEQUENCE: 849
gattctaccc gcaccatgct gcttgtgggt ctggtagaca aaaactccgc ttcattcgga 60
agctggcgtc ctcag 75

<210> SEQ ID NO 850
<211> LENGTH: 28
<212> TYPE: DNA
<213> ORGANISM: Homo sapiens

<400> SEQUENCE: 850
ctacatctac atctttatgg tattctca 28

<210> SEQ ID NO 851
<211> LENGTH: 36
<212> TYPE: DNA
<213> ORGANISM: Homo sapiens

<400> SEQUENCE: 851
ttagggttcg gatcccaaat cggcagaaga atgaca 36

<210> SEQ ID NO 852
<211> LENGTH: 176
<212> TYPE: DNA
<213> ORGANISM: Homo sapiens

<400> SEQUENCE: 852
gcgggagcta taccacgaag agttcgcccg ggcgggcaag caggcggggc tgcaggtctg 60
gaggattgag aagctggagc tggtgcccgt gccccagagc gctcacggcg acttctacgt 120
cggggatgcc tacctggtgc tgcacacggc caagacgagc cgaggcttca cctacc 176

<210> SEQ ID NO 853
<211> LENGTH: 208
<212> TYPE: DNA
<213> ORGANISM: Homo sapiens

<400> SEQUENCE: 853
gttctactgt tgtatagtgc tatgtggtga atacagttaa caataattta ttgtatattt 60
tttcaaagct agaaaaggat ttcgagtgtt cccagtacaa ataagtgata actatttgag 120
gtgattgatg tgctaattac tctgatttga tcattacaca ctttatactt gtatcaaaat 180
atcactctgt agccaataaa tatgtaca 208

<210> SEQ ID NO 854
<211> LENGTH: 222
<212> TYPE: DNA
<213> ORGANISM: Homo sapiens

<400> SEQUENCE: 854
tttgttagcc attaaagcag tttgaactta tcctacccat cctcttttcc atccctcagg 60
agtaggggac atatatgtaa tattgtagcc tgggggtggg gagtgaggat gaggatggat 120

-continued gtgtgagtct ggtttgtact catcagtcct cactaatcta taaccttcgt tgaggtgtag 180
tcattccatt aattcttgag ctttcggctt tggcctctgt tc 222

<210> SEQ ID NO 855
<211> LENGTH: 366
<212> TYPE: DNA
<213> ORGANISM: Homo sapiens

<400> SEQUENCE: 855
agccactact gcattcttct caggaactct gctttgtttt tcccagacta ccctagaatt 60
gtgggacacg gtatcctcat cgtaccagtg ccccttggcc cagtggcttg gatgctaccc 120
tcagtcattt ctgctctaat gcttaggctc atggaggggt gtaggacaaa tcaattggaa 180
gggaagtgtg ctgggctctt ctcaaagatt gattgctttg ggttagattt cctacttttt 240
tcagtcttct tttttacttt ttgaaccaga caaactagtc ttacaccacc tcacattctt 300
gcctactctg tgtttcctgc aagatacact ccagccccta agacccacac cgtactgctt 360
aagatg 366

<210> SEQ ID NO 856
<211> LENGTH: 197
<212> TYPE: DNA
<213> ORGANISM: Homo sapiens

<400> SEQUENCE: 856
agctgctgtc ccttagtatt gaatatctct attttctttt aatcatagaa ttcactgata 60
ttttagcaga taatgtggcc gtccaggcag gcatgagatt tctcagcctt acttcaactt 120
gattatgacc atgtgaccca attctgacat ttgcctaaag gaaaatttac ctaaaaaggc 180
gttttcttgc tatggca 197

<210> SEQ ID NO 857
<211> LENGTH: 212
<212> TYPE: DNA
<213> ORGANISM: Homo sapiens

<400> SEQUENCE: 857
ttctgaatgc atcacggcaa agatgcatgt actcatgaag cataaaatta aaaatatgat 60
acattcacta catgaaaata tgatatacgg tttttcttca gtatccgcgg gagattggct 120
cgaggaaccc catggatacc aacatccttg aatgctcaag tcccttatat aaaacggcat 180
agtatttgca taaaacctat accattctcc tg 212

<210> SEQ ID NO 858
<211> LENGTH: 67
<212> TYPE: DNA
<213> ORGANISM: Homo sapiens

<400> SEQUENCE: 858
atggtgtctg tcctgctgtc tctgctgctg cttctgggtc ctgctgtcct ccaggagacc 60
cgagatg 67

<210> SEQ ID NO 859
<211> LENGTH: 68
<212> TYPE: DNA
<213> ORGANISM: Homo sapiens

<400> SEQUENCE: 859
tcatgccttg caggaaaggt ttggttgtga gatccagaat aacagaagca ctggagcatt 60
ctggaaga 68

<210> SEQ ID NO 860
<211> LENGTH: 58
<212> TYPE: DNA
<213> ORGANISM: Homo sapiens

<400> SEQUENCE: 860
agatgttctt cacggtggaa acggcactta cctgacctgg ttgttggtgc atgtgccc 58

<210> SEQ ID NO 861
<211> LENGTH: 276
<212> TYPE: DNA
<213> ORGANISM: Homo sapiens

<400> SEQUENCE: 861
gaggcagccc tttcttatgc agaaaataca atacgcactg catgagaagc ttgagagtgg 60
attctaatcc aggtctgtcg accttggata tcatgcatgt gggaaggtgg gtgtggtgag 120
aaaagtttta aggcaagagt agatggccat gttcaacttt acaaaatttc ttggaaaact 180
ggcagtattt tgaactgcat cttctttggt accggaacct gcagaaacag tgtgagaaat 240
taagtcctgg ttcactgcgc agtagcaaag atggtc 276

<210> SEQ ID NO 862
<211> LENGTH: 616
<212> TYPE: DNA
<213> ORGANISM: Homo sapiens

<400> SEQUENCE: 862
cttttactct gaactaggtg ggcgcatttc aaaaattcgg atgggaaaaa gcctggaaat 60
tccagtgaat attcagcaag gccctctttc attgtacagg gatcaaattt cctcctcttt 120
tttgtgcccc ctcccacttc tacaagttat cccctgtggg gaaaacagga tgataatcaa 180
aactctgggc tgatgttttt ccaacttagt gtctattgga atcaatctta aatcagaagc 240
tttttcagaa aaataatatt taggccagaa ttagagttga gtgtattttt taaaaatgat 300
taaggcttgg ttgtgagaaa tattacctgt accagctggg aaaaataatg tcatcactaa 360
ctaaaagata attaatttga gagaaagtgt taagagaggg agagtaagga agagaacagt 420
taagaggagg cagaggtgag ggcagtagta aaaatctcta aaattttaat ttacagccaa 480
aattcttcat gtgtaaattt gtattgattc agatgcagaa atgaaaaaaa aacacctttg 540
ttttataaat atcaaagtac atgcttaaag ccaagttttt atctagttta ttctagtact 600
tagcttgcct ggaata 616

<210> SEQ ID NO 863
<211> LENGTH: 268
<212> TYPE: DNA
<213> ORGANISM: Homo sapiens

<400> SEQUENCE: 863
tggaaaaaat ccttagccag ggctcagaga tgaagcagtg aaagagacag gaattgggag 60
ggaaagggag aatggtgtac cctttatttc ttctgaaatc acactgatga catcagttgt 120
ttaaacgggg tattgtcctt tccccccttg aggttccctt gtgagccttg aatcaaccaa 180
tctagtctgc agtagtgtgg actagaacaa cccaaatagc atctagaaag ccatgagttt 240
gaaagggccc atcacaggca ctttccta 268

-continued

<210> SEQ ID NO 864
<211> LENGTH: 165
<212> TYPE: DNA
<213> ORGANISM: Homo sapiens

<400> SEQUENCE: 864
tatcatgcca actactgcga gggtgagtgc ccgagccata tagcaggcac gtccgggtcc 60
tcactgtcct tccactcaac agtcatcaac cactaccgca tgcggggcca tagccccttt 120
gccaacctca aatcgtgctg tgtgcccacc aagctgagac ccatg 165

<210> SEQ ID NO 865
<211> LENGTH: 31
<212> TYPE: DNA
<213> ORGANISM: Homo sapiens

<400> SEQUENCE: 865
ggaaaaggag cagtcgcaca gacctttcct c 31

<210> SEQ ID NO 866
<211> LENGTH: 32
<212> TYPE: DNA
<213> ORGANISM: Homo sapiens

<400> SEQUENCE: 866
gtgagcagtg ccaggagagt ggcgccagct tg 32

<210> SEQ ID NO 867
<211> LENGTH: 113
<212> TYPE: DNA
<213> ORGANISM: Homo sapiens

<400> SEQUENCE: 867
ttgctctctg aaaaagtagt agacgctcgg aagagcacct ggcatgtctt ccctgtctcc 60
agcagcatcc agcggttgct ggaccagggc aagagctccc tggacgttcg gat 113

<210> SEQ ID NO 868
<211> LENGTH: 171
<212> TYPE: DNA
<213> ORGANISM: Homo sapiens

<400> SEQUENCE: 868
agacgctgca cttcgagatt tccaaggaag gcagtgacct gtcagtggtg gagcgtgcag 60
aagtctggct cttcctaaaa gtccccaagg ccaacaggac caggaccaaa gtcaccatcc 120
gcctcttcca gcagcagaag cacccgcagg gcagcttgga cacaggggaa g 171

<210> SEQ ID NO 869
<211> LENGTH: 83
<212> TYPE: DNA
<213> ORGANISM: Homo sapiens

<400> SEQUENCE: 869
ggctgtcatt tgttgacccc tattcaagag ggtctgtcac agaagactcc tgcttgcctg 60
aaatttacga gtgcatgtaa atg 83

<210> SEQ ID NO 870
<211> LENGTH: 292
<212> TYPE: DNA
<213> ORGANISM: Homo sapiens

<400> SEQUENCE: 870

-continued ctggaactga gtggttgcta aattcaactg ccctgacaat gtggggattt cctgtccatt 60
agcagcgatt gctatttgac atatgtttct ggtgcccatt aatctgccct gtaatgggtc 120
agaggcaaaa atgggggatt cagaggtact aggtggctct cttaatttaa tagaactcaa 180
tgctaaggac gcctctattt gttaataagt aatcaagtca ttggctactt tctgctaaac 240
actagactat gatagtgacc ttagaccccg ggcattctaa accaggctgg ca 292

<210> SEQ ID NO 871
<211> LENGTH: 65
<212> TYPE: DNA
<213> ORGANISM: Homo sapiens

<400> SEQUENCE: 871
cagatttgtg catgggatac atgtacagca gacagttgta aggaggtcca cggtcatgga 60
aaaga 65

<210> SEQ ID NO 872
<211> LENGTH: 58
<212> TYPE: DNA
<213> ORGANISM: Homo sapiens

<400> SEQUENCE: 872
gctggatttc cgttaactat agaaatccag gcagggagat cctcccaggg agttgcaa 58

<210> SEQ ID NO 873
<211> LENGTH: 30
<212> TYPE: DNA
<213> ORGANISM: Homo sapiens

<400> SEQUENCE: 873
agaacttgaa actgtgccta aaatttatag 30

<210> SEQ ID NO 874
<211> LENGTH: 86
<212> TYPE: DNA
<213> ORGANISM: Homo sapiens

<400> SEQUENCE: 874
gcccttgcct cagtgaattt accactatca taatcacagt gtgcagagtg tgttaaatta 60
agaacagaat ccacagtacg caatgc 86

<210> SEQ ID NO 875
<211> LENGTH: 34
<212> TYPE: DNA
<213> ORGANISM: Homo sapiens

<400> SEQUENCE: 875
atgaggtcgg agtcagagga actcccctta ccac 34

<210> SEQ ID NO 876
<211> LENGTH: 302
<212> TYPE: DNA
<213> ORGANISM: Homo sapiens

<400> SEQUENCE: 876
ctccaggcta gttatccaag gcttgggagg tttccctcgg ccttctccta aggccttggc 60
aggaccctgc caccctaaaa tcaactgctg attgcctttt tagatttaaa tgattaagct 120
ctgcttatgg gaatcttctt ctcttttatt ttgttaagaa acaaacaaca acaacaaaac 180

```
ccacaccaat tcttagcaaa ggggaatatc gaattcagat tttgaaaaaa taagtcatca    240

tgcttcctaa aataagacag cttctccctc taactgctct ctctgctctg gtattctatc    300

ta                                                                   302

<210> SEQ ID NO 877
<211> LENGTH: 254
<212> TYPE: DNA
<213> ORGANISM: Homo sapiens

<400> SEQUENCE: 877

aggatgtacc caactctcag ccagagatgg tggaggccgt caagaagcac attttaaaca    60

tgctgcactt gaagaagaga cccgatgtca cccagccggt acccaaggcg gcgcttctga    120

acgcgatcag aaagcttcat gtgggcaaag tcggggagaa cgggtatgtg gagatagagg    180

atgacattgg aaggagggca gaaatgaatg aacttatgga gcagacctcg gagatcatca    240

cgtttgccga gtca                                                      254

<210> SEQ ID NO 878
<211> LENGTH: 38
<212> TYPE: DNA
<213> ORGANISM: Homo sapiens

<400> SEQUENCE: 878

tgctttggct gagaggattt ctgttggcaa gttgctgg                            38

<210> SEQ ID NO 879
<211> LENGTH: 79
<212> TYPE: DNA
<213> ORGANISM: Homo sapiens

<400> SEQUENCE: 879

cacacaaaaa aacctgcgcg tgagggggga ggaaaagcag ggccttttaa aaaggcaatc    60

acaacaactt ttgctgcca                                                 79

<210> SEQ ID NO 880
<211> LENGTH: 54
<212> TYPE: DNA
<213> ORGANISM: Homo sapiens

<400> SEQUENCE: 880

ccttctctct tactcggaga cagtcagaac tctcctccct gacagccaca aacc          54

<210> SEQ ID NO 881
<211> LENGTH: 70
<212> TYPE: DNA
<213> ORGANISM: Homo sapiens

<400> SEQUENCE: 881

gtgccaatac catgaagagg agctcagaca gctcttacca catgatacaa gagccggctg    60

gtggaagagt                                                           70

<210> SEQ ID NO 882
<211> LENGTH: 362
<212> TYPE: DNA
<213> ORGANISM: Homo sapiens

<400> SEQUENCE: 882

ttggggcatc ttgaaagtgt cactgcagta tagcaatctc tctcaggtaa tatagagata    60

aagggaatat aataaattga cctgttattt attatctttt tcatacctag gacattccga    120
```

-continued

```
ggcttaatat atttctgaag cctacagccc tgataaacat caatcccacg tcagtttcca    180

gcagtctcat ctccccacac ccttctgcaa tgaaagctaa tgtaaaagaa agaaatatgc    240

actgcttaat aagtcagaat acaatagaac ttgtaaaatg tacctgcata taaggtagac    300

attaggaaga cttgaatctc tctcttcccc ctgttctcct gagcattatg gcaacagcat    360

tt                                                                   362
```

<210> SEQ ID NO 883
<211> LENGTH: 176
<212> TYPE: DNA
<213> ORGANISM: Homo sapiens

<400> SEQUENCE: 883

```
atgcctttag ggttacacgg ctctcttccg tgaataatgg ggaagagcgg ccacaagagg     60

gcgcgttcca aagacttttg ctccttgtca gtgtatccag ggaaaggcag ttgcgcgtac    120

tggaagcccc tgtctgtagc gccctaatct tggtgattat cagttaccgc ctgctc        176
```

<210> SEQ ID NO 884
<211> LENGTH: 174
<212> TYPE: DNA
<213> ORGANISM: Homo sapiens

<400> SEQUENCE: 884

```
gagggttgct tcctgtcttt gtataccaac ctccacacat gatggattca atgacagctc     60

gtatccagtt gcctttaacc atgtcatatg actaagtata cctatgcctt tgaccacttt    120

taaccgcact accgttacta gcaatatgcc cctctttctg acttactgga cttg          174
```

<210> SEQ ID NO 885
<211> LENGTH: 104
<212> TYPE: DNA
<213> ORGANISM: Homo sapiens

<400> SEQUENCE: 885

```
accagggcat ctttccgggg gtgcagatag cctgctggct gtgtggcttc cccttgcagg     60

agaagccctg gtgtcctaca agcttcccag tttggctctc tcac                     104
```

<210> SEQ ID NO 886
<211> LENGTH: 110
<212> TYPE: DNA
<213> ORGANISM: Homo sapiens

<400> SEQUENCE: 886

```
agtgacagtc atttttacct ttagaaaatg tctataagtg cacaggcacc acattcaaga     60

cagggaagag ctactttggg ggacagttgt cattgaacca gcagttactt               110
```

<210> SEQ ID NO 887
<211> LENGTH: 44
<212> TYPE: DNA
<213> ORGANISM: Homo sapiens

<400> SEQUENCE: 887

```
agccggagga aagccgcggc attttcgggt gctaggggag caga                      44
```

<210> SEQ ID NO 888
<211> LENGTH: 131
<212> TYPE: DNA
<213> ORGANISM: Homo sapiens

<400> SEQUENCE: 888
attaggtgat ggtagcggac tagccgacgg agggcaggca ggggaggggg agaggacttt 60
acagaaaagg aattctcggt cgagctctgc ctggagatga ctggcttaca cttactaaac 120
ccagcgggtc a 131

<210> SEQ ID NO 889
<211> LENGTH: 265
<212> TYPE: DNA
<213> ORGANISM: Homo sapiens

<400> SEQUENCE: 889
attgatgttt ctggagctga aaccccaaag gtgttaggtt acttgtaaca gaaaaagtct 60
tacaaatagt tgttttggaa aaggggacag tatatataat tcagaaagca ttgttaacct 120
gtgcaaactg taattataac ttagtgtcac aattttcttg ccctcttccc cttgcactca 180
gatcttatct tgtagtaatg atatttatta actctttcca cctaaactgc attgcttgac 240
tgtaatgcta tgaacacact aggtg 265

<210> SEQ ID NO 890
<211> LENGTH: 131
<212> TYPE: DNA
<213> ORGANISM: Homo sapiens

<400> SEQUENCE: 890
cacagtcaat ggatccacaa ggcctgagga gcagtgtggg gggacagaca ggaggtggat 60
ttggagaccg aagactggga tgcctgtctt gagtagactt ggacccaaaa aatcatctca 120
ccttgagccc a 131

<210> SEQ ID NO 891
<211> LENGTH: 31
<212> TYPE: DNA
<213> ORGANISM: Homo sapiens

<400> SEQUENCE: 891
agcccctcgt ggtgccctgg gaggccagct a 31

<210> SEQ ID NO 892
<211> LENGTH: 38
<212> TYPE: DNA
<213> ORGANISM: Homo sapiens

<400> SEQUENCE: 892
tcttcacaat ggaaatggca cttaccagtc ctgggtgg 38

<210> SEQ ID NO 893
<211> LENGTH: 106
<212> TYPE: DNA
<213> ORGANISM: Homo sapiens

<400> SEQUENCE: 893
ggcaagaggg aaagcgtcag ccttccctga tattctggaa agtctcccgg ggctgggggt 60
gggcaggtac agagcttcga gctctgctga tcgctgacat ccaggg 106

<210> SEQ ID NO 894
<211> LENGTH: 377
<212> TYPE: DNA
<213> ORGANISM: Homo sapiens

<400> SEQUENCE: 894
agggtaacac tgtctgtaag aggcagagct gggactcaaa ttccagattt cagattccaa 60
atcccatcgt tttttatctc tacaatgatg cctcccatct gggtggtgga gagaagggag 120
gcgtgtaaaa tgtcagcccc agaaggacaa gagcaagcca gtgtgagcgg aattgatggc 180
tgcaagctga gacttggatt ggagacgtag tgagactcag gattgtgcag tgctgcaggg 240
aagtggttgc tggatagagg catgggctga accaagcagc tggactgaga ctgggggaca 300
gaactccaaa gcccactgag atgtgggaaa acatggagaa gcacacggag cattcacaac 360
ttattgccgt cagagtc 377

<210> SEQ ID NO 895
<211> LENGTH: 186
<212> TYPE: DNA
<213> ORGANISM: Homo sapiens

<400> SEQUENCE: 895
gagcccagaa taaaagacga tctcaggcta ggagctcagg caacatctta gtccggtctc 60
atctgttcct ggatgtccct cagaccccca gctttcatct tttaggattt attccttccc 120
tgggataata taatttgtgg tccaaaaaga acatcatcaa aatttcaggc agaatgggcc 180
aggaag 186

<210> SEQ ID NO 896
<211> LENGTH: 38
<212> TYPE: DNA
<213> ORGANISM: Homo sapiens

<400> SEQUENCE: 896
ccagtctacg tgcagcgggc caaggcttac ctggagga 38

<210> SEQ ID NO 897
<211> LENGTH: 49
<212> TYPE: DNA
<213> ORGANISM: Homo sapiens

<400> SEQUENCE: 897
tgagatcgag aataacagaa gcagcggagc attctggaaa tattactat 49

<210> SEQ ID NO 898
<211> LENGTH: 299
<212> TYPE: DNA
<213> ORGANISM: Homo sapiens

<400> SEQUENCE: 898
gatttcgcca tatcaccctg gctggtctgg aacccctggg ctcaagcgat ccactcgctt 60
cagcttctca aagtgctggg attacaggca tgagccacag cgcccaggct gtagctctct 120
taaggaggaa catatctcat ctgagacaaa cctgaaatgc caaaccaaac tgagttagcc 180
cctctctgtc tgttgtatat attggagtaa taacctattt gtcttgataa agggattgca 240
tgcttgaatt gcaaaaacct ttatttcttt tgggttgccc aatgtgcaag actaagagt 299

<210> SEQ ID NO 899
<211> LENGTH: 47
<212> TYPE: DNA
<213> ORGANISM: Homo sapiens

<400> SEQUENCE: 899
catacgatgc agacccagga agggccacct gcgctatggt cagagga 47

<210> SEQ ID NO 900
<211> LENGTH: 35
<212> TYPE: DNA
<213> ORGANISM: Homo sapiens

<400> SEQUENCE: 900
ggagaccctg aaagacatcg tggagtatta caacg 35

<210> SEQ ID NO 901
<211> LENGTH: 103
<212> TYPE: DNA
<213> ORGANISM: Homo sapiens

<400> SEQUENCE: 901
acactgggct gtccaagcat gttgaagacg tccccgcgtt tcaggccctt ggctcactca 60
atgacctcca gttctttaga tacaacagta aagacaggaa gtc 103

<210> SEQ ID NO 902
<211> LENGTH: 41
<212> TYPE: DNA
<213> ORGANISM: Homo sapiens

<400> SEQUENCE: 902
tgctgcttct gggtcctgct gtcccccagg agaaccaaga t 41

<210> SEQ ID NO 903
<211> LENGTH: 80
<212> TYPE: DNA
<213> ORGANISM: Homo sapiens

<400> SEQUENCE: 903
cccgtcctgg cactcccatt ggcctgtaga ttcacctccc ctgggcaggg ccccaggacc 60
caggataata tctgtgcctc 80

<210> SEQ ID NO 904
<211> LENGTH: 26
<212> TYPE: DNA
<213> ORGANISM: Homo sapiens

<400> SEQUENCE: 904
gagtctgtca cagtttcttt gtgtaa 26

<210> SEQ ID NO 905
<211> LENGTH: 971
<212> TYPE: DNA
<213> ORGANISM: Homo sapiens

<400> SEQUENCE: 905
gccggtgtta tttactagat tcttcccttt gaactcacag actcaagaga cagaccaaga 60
gttcttatat actcaccaca gcggaccaat ccaagtggca tttttaggaa aggttgcagc 120
atttaatgcc atgtggtatg tctgttcgtc aagtgggtgg caagggaata tccaagctgg 180
cattttggat atgatgggcc ttttactttc ctgagtgaca tgccacatgt caagaaatac 240
tgctccccac ccccccactc ccatcacatt tacgtgaaca attttcattt agttatttcc 300
cgttccatat ggtgttaaaa cagtcgtatt aaataaagat tatttctagt tttcagtggt 360
aatttaaatg agaggatatg taataattgc ttattagata cttatccaaa tgaaatataa 420
cagagtttac agtacttaaa atggctggtt atggtcttgg aaatgtttga aaattcatta 480
tcctgaaaaa aactttacca ttctgtttta cccttgaggt attttttggg gaaaaatgtt 540
tttgataact attaatctaa atatagtata attataggca aatttcactg cctagtttta 600
ttgatatcct gagtctacag ctagtccatt cgtatgactg attgatttat gatagctcca 660
gagaaccata aatttcaaag gctaaactct ctgattttag taaatagtag gtaaagtgac 720
acaatatatg tttacacaac actgttttca tgaaatgcaa actttgcaaa actcacatta 780
actgggaagc agccaaccct ctgtagagaa atcccagatt gggagtctgg tttgaatctt 840
tgaagacaga aaggtgatat ccggcctgct gttttaaagg gaccacactt ttgaatacct 900
actggtgttt ggcagaaatc tgagactggc accagacaca aattttagac atgggtatct 960
tccctccagt a 971

<210> SEQ ID NO 906
<211> LENGTH: 844
<212> TYPE: DNA
<213> ORGANISM: Homo sapiens

<400> SEQUENCE: 906
tgctttgaca gccaccctat acatggtaca tttagatgaa atgggaacca gatcctaaat 60
ttttcaaatg tcattgccaa tttatgtgta taattccatc acttcctgat gagtaagtct 120
atttttgttc tatatacatc ataagttagt atatattctt atttacagaa acatgctcaa 180
atcacattca gaaagaacaa aaagtcatgg gaaatttttt attttacaac aaagccctgc 240
tttctttctg gacgtatttt acatcattag agagactatc tgcacataca tctaccataa 300
tctttttcct tctttgccaa ctgttcagtg cacatgtgct gcatcagaaa tggcacctgg 360
atgacagaag ctcaaagagt cacatatgtc tctaaaatag agttcttttc ctcttgggct 420
gtctgaactg gtgtaaatag aagctcagtt gatcttggtt ttaattaact tattactcta 480
ttaatataac cttggaattc tattctaatt atgttgttct ggctgcttgt agtatcagtt 540
cgcccctctt gttagggaga tatgtaacaa tctgtcattt aattgagcag tctttttcac 600
ataacagtaa tagcaaaaat cctacctact cagaatcatc ttcttaggtt gtctcctaaa 660
tctgaacaat acagttgttt tataaaatta cattttgtct cttgagattt aatcaattag 720
aactctttag ggagaaaata aataatagaa gaaaatatat gcctcatatt tcatatgtaa 780
ttatctgttg atataatttt tcaatgtatt ttgtatttgt gggagcataa tgacctgtac 840
attc 844

<210> SEQ ID NO 907
<211> LENGTH: 35
<212> TYPE: DNA
<213> ORGANISM: Homo sapiens

<400> SEQUENCE: 907
ctcaccacgg atgttgaccc tgatctggac caaga 35

<210> SEQ ID NO 908
<211> LENGTH: 51
<212> TYPE: DNA
<213> ORGANISM: Homo sapiens

<400> SEQUENCE: 908
gaagttggcc ttgtacttgc agctatattg gcactactac tggctttcta t 51

<210> SEQ ID NO 909
<211> LENGTH: 117
<212> TYPE: DNA

<213> ORGANISM: Homo sapiens

<400> SEQUENCE: 909
gccaaggtat tactaccaag ctgtaacagc tgttgaactg ccagatgata tatttggttg 60
tcttccagaa tttgctatta tgatcacgaa acactgcctt cttttcgctc ctgattg 117

<210> SEQ ID NO 910
<211> LENGTH: 26
<212> TYPE: DNA
<213> ORGANISM: Homo sapiens

<400> SEQUENCE: 910
tttacgagca accaaattaa aagcag 26

<210> SEQ ID NO 911
<211> LENGTH: 136
<212> TYPE: DNA
<213> ORGANISM: Homo sapiens

<400> SEQUENCE: 911
aaaggaggca ttacaagtga tatttcagaa ataaaaaata caagctactt tgggtaactg 60
aatgccaata aattagttaa cctagaggaa atggataaat tcctagactc atacaactca 120
ctaagattga accatg 136

<210> SEQ ID NO 912
<211> LENGTH: 358
<212> TYPE: DNA
<213> ORGANISM: Homo sapiens

<400> SEQUENCE: 912
acctgatgag caaaatggct gaacagaatc ctctagcgat catcccccca caggaacacc 60
aaactgaaca actattcaca caaaacaagc accttcataa gaagcaaaaa acaggtgaac 120
cggtacctgg ctttaacatc gtattaagga aagaggcact gaagaggatt tgaaagacaa 180
tcttgagtca cctataccac ccctttcccg tacttcacct ttggccatgt ggtgttaaga 240
gacaatctgt gcacttgcat gagggagagt gcagtgattg tgggaatttg ccttggaact 300
cagtgctgcc ctgtcacagt ggaaagccac acagggaaga acttagctgg tgcccaca 358

<210> SEQ ID NO 913
<211> LENGTH: 216
<212> TYPE: DNA
<213> ORGANISM: Homo sapiens

<400> SEQUENCE: 913
cctcctaact atgcatgtac ctttcacatt ttattgcaaa actattaggc tataataaga 60
acatgcatca agcagggaca ccaatatctt gcctggcatt taattatcaa aaacacctgt 120
gctacaatag tatattcacg tgtataattc tttatatgta gacatttaag tgcttgaatt 180
atttaaaaaa tctactgtct ggataaaact tccata 216

<210> SEQ ID NO 914
<211> LENGTH: 39
<212> TYPE: DNA
<213> ORGANISM: Homo sapiens

<400> SEQUENCE: 914
gctactataa aacttcctgt tgatcagtac agaaaacaa 39

<210> SEQ ID NO 915
<211> LENGTH: 228
<212> TYPE: DNA
<213> ORGANISM: Homo sapiens

<400> SEQUENCE: 915
ttgcttgtga catgactagt tcttgtctga cttcatcttc atcttgtaat gccttactag 60
aaggaatgag gaacaacttg cagacaccag tttgaagaat acttacgact gtaacattgt 120
attctatgaa taatgacata ttgtaattga ggctaggaaa tagagtctgt gctaggaaga 180
aaaggagaat atgaatgtgg taatcaggtt gtactctctg ctgcaata 228

<210> SEQ ID NO 916
<211> LENGTH: 140
<212> TYPE: DNA
<213> ORGANISM: Homo sapiens

<400> SEQUENCE: 916
aaacaagttg gttggatagc tgtcctccat gcagtcattc atgatccagg ctgtcatcat 60
cttcatcact catgttcaga gttaccctag aggtcatctc catttcatcc agataaatga 120
gtatgcaagg aacgttttta 140

<210> SEQ ID NO 917
<211> LENGTH: 223
<212> TYPE: DNA
<213> ORGANISM: Homo sapiens

<400> SEQUENCE: 917
ctgctgggat gttggcttaa atgactagaa aggaattggg ggaagcataa tgagtaacca 60
ttttggcaga tagcctcagt gatttgcttt aagaaaaaat taagcatagt ctgtaaaggc 120
aaaaaacaaa actaaattga aaagggaata atatcttgag tgtttattca tttaatccaa 180
cttctctcct aaaatggagt ggtatcttcc ctagccacac aca 223

<210> SEQ ID NO 918
<211> LENGTH: 133
<212> TYPE: DNA
<213> ORGANISM: Homo sapiens

<400> SEQUENCE: 918
gctaatgtct ccctggattt cttgggagtt tgctatctaa ccatcaaagc aatagaaatg 60
aatgatgatt actgcaaggc tttgaagaac aaagaaaagt cagaacattt taaaggttct 120
acatgtctga gtc 133

<210> SEQ ID NO 919
<211> LENGTH: 68
<212> TYPE: DNA
<213> ORGANISM: Homo sapiens

<400> SEQUENCE: 919
atggggactc ctccatttac caaggctaca gctgactcct ggagaggcct gagtactcat 60
tgcagttt 68

<210> SEQ ID NO 920
<211> LENGTH: 33
<212> TYPE: DNA
<213> ORGANISM: Homo sapiens

<400> SEQUENCE: 920

-continued cctttttgttt gattaagctc ttagcgtgca gtg 33

<210> SEQ ID NO 921
<211> LENGTH: 62
<212> TYPE: DNA
<213> ORGANISM: Homo sapiens

<400> SEQUENCE: 921
cagtctgaag gtttgtcggg taatagtcaa gtggatatga aactgccctt tgtgaacctc 60
ag 62

<210> SEQ ID NO 922
<211> LENGTH: 37
<212> TYPE: DNA
<213> ORGANISM: Homo sapiens

<400> SEQUENCE: 922
gggaagcaac gtcaatcagt ggtactggaa aatgagt 37

<210> SEQ ID NO 923
<211> LENGTH: 194
<212> TYPE: DNA
<213> ORGANISM: Homo sapiens

<400> SEQUENCE: 923
ttggtgtttg cctcatttga gcctggtttg aacagttggc cacctttggc caaaactcag 60
tgattggcac aaaagtcggt tgcagtctgt ttacacatgg aaaggttaca gtttactgtg 120
cacagagaaa ccattaggtc acatttagaa tatataagga ggcagcattg ggctaaactt 180
gacaattgct tatt 194

<210> SEQ ID NO 924
<211> LENGTH: 362
<212> TYPE: DNA
<213> ORGANISM: Homo sapiens

<400> SEQUENCE: 924
cgattagaga ttaagttgcc agctttaaaa atggggacta gtgtgtaagc cttttgtatg 60
tacatatgta catgcactaa gtatgtaaat acatacatat tgtgagacta ggttctcaca 120
gtaaatatct gataaaaatc cctgggggag gggaaaagga accattttga aatacaccac 180
agcactctgt tcttaaaaag gtctctcctc aagagaaact agtgtatata aaaaacttac 240
tttctaaatg taactgttac tctactaatc cagagtttca aacatgtgtg aacaataaga 300
tagcatacat aatttggcat tttaaaagtt atccaaagat acttttgtag aagccactta 360
gc 362

<210> SEQ ID NO 925
<211> LENGTH: 688
<212> TYPE: DNA
<213> ORGANISM: Homo sapiens

<400> SEQUENCE: 925
ttttctggca atgaacctgg gttccaagca taggtttttc ttatggaagg cagttttaca 60
ataaggaaat gtttttactt gtatttattt tgtgatattt cagcaaatcc aaataaatgt 120
agtaacattt ataaagctat acatttataa ctgatttatt tgttaaatat ttagtattat 180
caattgtctg ttaaagattt gttgctacat taaatgcttg gtctgtcttg atgttcagta 240
cattattata ctttggtata ttgcaatatt ttgataatta tgtattggtt ttagtcactg 300
ttcctgcata ttaagtaata aacagattaa tatcatcata aaatatcatt tactcagcaa 360
tatttcttag taaattgata catccatttt tcttatgtat tgtggagaga ggaaatatga 420
cataaaatgg aagaatatgg gcctctgttt atctctgacc tcatcgctta ctgttctttc 480
ccactcctca ctctactcaa agcctttaaa tagctctcca ttttactcaa catcaaatct 540
aaataaagct cttaaactgg tctaaatgtc tctacagtac ttgaaccttt gttatttctc 600
taatttcatc ttcaactctg ctcatcgtta ttctcttgcc ctgggcatac tgcctccctt 660
tttgttctct gaacgtgcca ggcatttt 688

<210> SEQ ID NO 926
<211> LENGTH: 99
<212> TYPE: DNA
<213> ORGANISM: Homo sapiens

<400> SEQUENCE: 926
caggaatgca agcactgcta cctaactaaa gaccttggct ttggaaacat cttacccctt 60
ggcagctctc cagagtttag acttggcagc atcaaagac 99

<210> SEQ ID NO 927
<211> LENGTH: 141
<212> TYPE: DNA
<213> ORGANISM: Homo sapiens

<400> SEQUENCE: 927
tcttccaacg tcaaagccag caacattgca gcaatctgac ttattttgtt gtcatgtctc 60
ctgaccacat ctggaagggt tatctacttt tgaagacaca tccagataat tcaggacaat 120
ctgtccattt tgaggttctt c 141

<210> SEQ ID NO 928
<211> LENGTH: 252
<212> TYPE: DNA
<213> ORGANISM: Homo sapiens

<400> SEQUENCE: 928
ggagcttggt gtattcctga atccatcaga tgttggtgtc cgcgtggatg actaggaaaa 60
ggggattgga gattaggttt cttctacttg gagttctctg ctgcttgttt gagcttaata 120
agcctcctga agaagttgaa gcaatttatt gctagaggag ccccaatgta taatctccct 180
ttcattctct actgtggaga ggtgtgctaa acctgtagag ctgtttttgc ttcactcggc 240
tcatacttaa tg 252

<210> SEQ ID NO 929
<211> LENGTH: 129
<212> TYPE: DNA
<213> ORGANISM: Homo sapiens

<400> SEQUENCE: 929
ccgggaatga aagcgggcgc acctctttag cgagccctaa agcgtttggg agacgatcgt 60
tccgtccctg ggagcggcac ttggtggggc tgggcggagg gaggctctgc aagagaaacc 120
cggagtccg 129

<210> SEQ ID NO 930
<211> LENGTH: 71
<212> TYPE: DNA
<213> ORGANISM: Homo sapiens

<400> SEQUENCE: 930
cctgagtgac agaaccgtgg acagcaacat ttcccacagg acacgaagtt tgtcggccct 60
tgccttggca g 71

<210> SEQ ID NO 931
<211> LENGTH: 81
<212> TYPE: DNA
<213> ORGANISM: Homo sapiens

<400> SEQUENCE: 931
gatgtccagc agctagtaga tgtagaagtg ctgtttgtta ctgggtatgt ccttgctgtc 60
agggaagtgc acctgtttca g 81

<210> SEQ ID NO 932
<211> LENGTH: 106
<212> TYPE: DNA
<213> ORGANISM: Homo sapiens

<400> SEQUENCE: 932
gctaaaactg gtaaggtgcc catgggttcc atggaacctc cacatccatt tacaaagccc 60
tctaggaaga ctgggctagt tgctttcttc agcttcagta ttatgg 106

<210> SEQ ID NO 933
<211> LENGTH: 58
<212> TYPE: DNA
<213> ORGANISM: Homo sapiens

<400> SEQUENCE: 933
atacacctta agcaaccagg tatccttgat tgtgggagtt ccttggaaca tgagcaga 58

<210> SEQ ID NO 934
<211> LENGTH: 152
<212> TYPE: DNA
<213> ORGANISM: Homo sapiens

<400> SEQUENCE: 934
taacctggac tttcataaaa ctggcatatc ttctgtttta catggaaaat tattttatct 60
taagtttcca tttagttgat taaaaatagg gttatgaatg ttaaataagt gatgatttat 120
tgcaaaggaa atatgtttcg aaaggtcgaa ta 152

<210> SEQ ID NO 935
<211> LENGTH: 139
<212> TYPE: DNA
<213> ORGANISM: Homo sapiens

<400> SEQUENCE: 935
gagtcccctg gtctttacat attaaaaata ttaggctgtc ctggaaatgt tgtcttattt 60
gtctgacttc accactaaag tatgagtccc ttaaggttgt catttcattt ttgtagtcct 120
tatgcctaaa atagcaaca 139

<210> SEQ ID NO 936
<211> LENGTH: 150
<212> TYPE: DNA
<213> ORGANISM: Homo sapiens

<400> SEQUENCE: 936
tatcctgctg gtgagtttgg gaaaaggaat tggatcgggg catgcagcgt ctccttatct 60
gcaaacaggc ctgccggtgg gaatcatggt actgttcccc agcaacacaa cattaatttc 120
agagggagat gctctgccac tacaggagtg 150

<210> SEQ ID NO 937
<211> LENGTH: 357
<212> TYPE: DNA
<213> ORGANISM: Homo sapiens

<400> SEQUENCE: 937
tgacaccgcc atgaaaacga tcagcaccgt cgaatcctca cgccccactc aagttccttg 60
attgcttcaa taatgtcctc cgtagcaaaa ggatctagtt caaaatcggg agttacattt 120
cattgtcatg cctaaaacgt aagaattgct cattcacttt ggagcagttc ttcagtctat 180
ccttgatttt catgaccttg acacttttga acattataga ccagttattc aatagaatat 240
ctttcaatct gggtttgtcc gatacctctt tattattaga ttgaaatgat acattttggt 300
ggaactatca cagaattgac attgcattct tctcattaca tcctgtctgg tggcctg 357

<210> SEQ ID NO 938
<211> LENGTH: 206
<212> TYPE: DNA
<213> ORGANISM: Homo sapiens

<400> SEQUENCE: 938
aaaggaatcc tagtgacgag ttgtcttgaa agagaagaaa aaaagttaaa aaacagaaga 60
aaaaggagat ctttaaccgt gctgggtata aaattctaag tcaggatact tttcttcctt 120
tgagcatctt tgactgcctg gggaatatca gacattcttt tagtggcctt gtgatcattt 180
tgctgagctt gttcatattc ctgttc 206

<210> SEQ ID NO 939
<211> LENGTH: 181
<212> TYPE: DNA
<213> ORGANISM: Homo sapiens

<400> SEQUENCE: 939
gcatcaaact gaaccgcgac ttgtccaaag tcacatagta agtggaggtg gaactgggct 60
ttaaatccaa gcctacatac agactagagt tcacactttt aggcttggca taaactgcct 120
ataaactata aaaaagtaaa actccataaa atctcaggta cttggactac cttcagtctg 180
a 181

<210> SEQ ID NO 940
<211> LENGTH: 135
<212> TYPE: DNA
<213> ORGANISM: Homo sapiens

<400> SEQUENCE: 940
agtatgggtg actattcttt acaaatccat ttgtgatgca gtggtaattt ggtggcactg 60
caattatggc cagcaatgaa gattataaaa taattgcctg aggaaccaag ctcatgtgca 120
ctaaaaagaa gcagg 135

<210> SEQ ID NO 941
<211> LENGTH: 30
<212> TYPE: DNA
<213> ORGANISM: Homo sapiens

<400> SEQUENCE: 941
ctgcacttgg ccctacaccg atgaattttt 30

<210> SEQ ID NO 942
<211> LENGTH: 311
<212> TYPE: DNA
<213> ORGANISM: Homo sapiens

<400> SEQUENCE: 942
tgctgagccg acataagaat cttttatgaa aaatgtactg ttaagttcag ggggtctatt 60
ggttttatgt aaaaggcaca agacaattcc tgtagtgcat tttatgagtt aaggtttcca 120
tacggattat tgaaacaatt tgttacatgt atttgttaca tgatcttaat atttcatgta 180
caagactgac acccatccac ttttgaagat aagccagttt atggggtttt ttttttgcg 240 ggtagaggtt gggtctccct attttgtcca ggctggtctc gaattcctgg gctcaagcat 300
aagcataagg c 311

<210> SEQ ID NO 943
<211> LENGTH: 214
<212> TYPE: DNA
<213> ORGANISM: Homo sapiens

<400> SEQUENCE: 943
ccttatgtac cgagcaaatg ccaggtctag caaacataat gctagtccta gattacttat 60
tgatttaaaa acaaaaaaac acaaaaaaat agtaaaatat aaaaacaaat taatgtttta 120
tagaccctgg gaaaaagaat tttcagcaaa gtacaaaaat ttaaagcatt cctttcttta 180
attttgtaat tctttactgt ggaatagctc agaa 214

<210> SEQ ID NO 944
<211> LENGTH: 77
<212> TYPE: DNA
<213> ORGANISM: Homo sapiens

<400> SEQUENCE: 944
tgatcaggga ccatgaaaag aaacttgtgc ttcaccgaag aaaaatatct aaacatcgaa 60
aaacttaaat attatgg 77

<210> SEQ ID NO 945
<211> LENGTH: 519
<212> TYPE: DNA
<213> ORGANISM: Homo sapiens

<400> SEQUENCE: 945
caacctggag tgcattgacg cgatctcggc tcactgcaac ctccacctcc caggttcaag 60
caattctcct gcctcggcct cccgagcagc tgggattaac aggcccatgc ctgccaccgt 120
gcccagctaa tttttgtatt tttactagac ttggggtttt gccatgttgg ccaggctggt 180
ctggaacttc tgacctcaag tgatccgccc acctcggcct cccaaagtct tgaaattaca 240
ggcgtgagcc actgcgccct gccagatttt gtatagtaat atatatataa aatgacctgt 300
cacaggttgg ctttcatagt tttacctttc ctttttgggt ggtgcccttg ggtctctact 360
actgtctttc atcactccca agaaattgag tagtgcagcc aggatcagga ccagggattg 420
gcaaatgttt tttgtaaagg gccagatagg aaatattttg ggctttgagg actgtgttat 480
ctctgaaatg atcttgttcc agtgttacca tgtcaagac 519

<210> SEQ ID NO 946
<211> LENGTH: 87
<212> TYPE: DNA
<213> ORGANISM: Homo sapiens

<400> SEQUENCE: 946
atgaagctgt agctgtacta caagcccacc aagctaaaga ggctgcccag aaagcagtta 60
acagtgccac cggtgttcca actgttt 87

<210> SEQ ID NO 947
<211> LENGTH: 254
<212> TYPE: DNA
<213> ORGANISM: Homo sapiens

<400> SEQUENCE: 947
gtacagttgt aaagtctgca taataacctg tggcgctatt tatccccatt ttatagatag 60
gtaaactgaa acaggctgaa taatttgcca aatgctcaca cagctcttaa gtggcagagc 120
ctggcttcaa atcccatcag ctccaacagc catactctca actgctgctg ctttctctag 180
tggagaaaga gaaatatttt tcgagtgtgg ggaggacaag gaaagagtag tgcaggggag 240
cgattcataa ttct 254

<210> SEQ ID NO 948
<211> LENGTH: 25
<212> TYPE: DNA
<213> ORGANISM: Homo sapiens

<400> SEQUENCE: 948
gccatgcacc ctactcttgc tggta 25

<210> SEQ ID NO 949
<211> LENGTH: 25
<212> TYPE: DNA
<213> ORGANISM: Homo sapiens

<400> SEQUENCE: 949
tcctcaagag caaaagcaaa tgttg 25

<210> SEQ ID NO 950
<211> LENGTH: 25
<212> TYPE: DNA
<213> ORGANISM: Homo sapiens

<400> SEQUENCE: 950
aatgggtcca cgtcctgcag ctgca 25

<210> SEQ ID NO 951
<211> LENGTH: 67
<212> TYPE: DNA
<213> ORGANISM: Homo sapiens

<400> SEQUENCE: 951
tgcaaacctc agatcgaaga agacagcata aacacttttc actcagtaag ttttcccagt 60
taatgta 67

<210> SEQ ID NO 952
<211> LENGTH: 36
<212> TYPE: DNA
<213> ORGANISM: Homo sapiens

<400> SEQUENCE: 952
tcaggtatat ttataagtgt gggcggcaaa ccaccc 36

<210> SEQ ID NO 953

<211> LENGTH: 25
<212> TYPE: DNA
<213> ORGANISM: Homo sapiens

<400> SEQUENCE: 953
aaccgtgctg catactatcc tccta 25

<210> SEQ ID NO 954
<211> LENGTH: 36
<212> TYPE: DNA
<213> ORGANISM: Homo sapiens

<400> SEQUENCE: 954
caaccagaac catgaaggtt ttcgtatttg gtcatt 36

<210> SEQ ID NO 955
<211> LENGTH: 26
<212> TYPE: DNA
<213> ORGANISM: Homo sapiens

<400> SEQUENCE: 955
ttatgatgga gggtggtcgc agcaaa 26

<210> SEQ ID NO 956
<211> LENGTH: 145
<212> TYPE: DNA
<213> ORGANISM: Homo sapiens

<400> SEQUENCE: 956
ctgacctggc tagggtaatg catatgtgta gtttgccctt aataattggg tattaaggaa 60
aaattgtgaa ctcaatgggt aaatacaaga tgattaagca ttaacagggt ttagttattt 120
gattcagtga tttataattg tctaa 145

<210> SEQ ID NO 957
<211> LENGTH: 271
<212> TYPE: DNA
<213> ORGANISM: Homo sapiens

<400> SEQUENCE: 957
ggagtacgat agaatttatt cctgaatgtt tttgtcttca gtgtgttccc tggatattgt 60
ttaaattgag tgttgtgcat cagcatattt tgaatgtatg aagcatgcat gtttttctgt 120
ttcttgagac aggatctcat tatgttgccc aggttggagt gcaggggcat gccacaatca 180
cagctcactg cagcctcagc ctttcctggg cttaagccaa gcttgtccaa cccgctgctt 240
gcaggccaca tgcggcccaa gaatgctttt a 271

<210> SEQ ID NO 958
<211> LENGTH: 46
<212> TYPE: DNA
<213> ORGANISM: Homo sapiens

<400> SEQUENCE: 958
gatgatggta ttgatgatga acgtctccgg aaagagtttt ctccat 46

<210> SEQ ID NO 959
<211> LENGTH: 89
<212> TYPE: DNA
<213> ORGANISM: Homo sapiens

<400> SEQUENCE: 959
ttatgttggt cgagctcaga aaaaggtgga acggcagacg gaacttaagc gcaaatttga 60
acagatgaaa caagatagga tcaccagat 89

<210> SEQ ID NO 960
<211> LENGTH: 429
<212> TYPE: DNA
<213> ORGANISM: Homo sapiens

<400> SEQUENCE: 960
tgccttggcc catacatctt ctaaatttct gtaatcaaat gtgattttta accttttctg 60
ccccacttgc ctgagatacc acccgcctca gttacctgtc tctcctactt tagagggagt 120
taggggaaaa catgtcttca gaaataaatg cttcctcttc caggtagttc acctgtgtct 180
ttaaaaagaa tttttttcc ctgtctttca aattcctgta ttacctatgt cttaccaaag 240
agtccaacta tgtattcctt ccactcctgt tgaaagtcgg gtaggccaag gcttaataaa 300
tacttgtttc ttaattgata caaagaaaat caaattggtc ttagcacaat agctcatgcc 360
tgtaacccta gcgcttgggg aggtcaaaga gggaagatac ttgaagccac aagttttaga 420
ctagcccgg 429

<210> SEQ ID NO 961
<211> LENGTH: 73
<212> TYPE: DNA
<213> ORGANISM: Homo sapiens

<400> SEQUENCE: 961
tttgttggac gatttaagtc tcgtaaagaa cgagaagctg aacttggagc tagggcaaaa 60
gaattcacca atg 73

<210> SEQ ID NO 962
<211> LENGTH: 191
<212> TYPE: DNA
<213> ORGANISM: Homo sapiens

<400> SEQUENCE: 962
ttagagtaca cgattgggaa gtttaaattt ttattctagg agatggcaaa gaaagcgcaa 60
gcgccacttt aaaatgacga tgaaagcttt ttaatttgat agaggtcttt ttattggcat 120
ggtacacatg cacttccact catttgtatt gatgggagtg atccctttaa ccctaggtta 180
gctagagaag a 191

<210> SEQ ID NO 963
<211> LENGTH: 228
<212> TYPE: DNA
<213> ORGANISM: Homo sapiens

<400> SEQUENCE: 963
gttataaata tctagctaat catattttga atcttatttt taataattcc aaatccattc 60
attttaagtt aatatttgtc agggagaagt tagatgcaca taagataaaa gaataaaaac 120
attttaaaga tgaataacaa aaattcatgt agttgtactg gagtgaaaat taataagcta 180
atcttgattt ttacaattga attttctaca cagtaagtgt aacataca 228

<210> SEQ ID NO 964
<211> LENGTH: 57
<212> TYPE: DNA
<213> ORGANISM: Homo sapiens

<400> SEQUENCE: 964
tgaaaatggt tccaagggct atggatttgt acactttgag acgcaggaag cagctga 57

<210> SEQ ID NO 965
<211> LENGTH: 100
<212> TYPE: DNA
<213> ORGANISM: Homo sapiens

<400> SEQUENCE: 965
gctacattta gtttagtgct tgaaatagga actgtgcagt aatggatatc tttatttcac 60
aaatatccag gttagatggc taacagattg tctctcaaca 100

<210> SEQ ID NO 966
<211> LENGTH: 29
<212> TYPE: DNA
<213> ORGANISM: Homo sapiens

<400> SEQUENCE: 966
ggagcgtgct ttggacacca tgaattttg 29

<210> SEQ ID NO 967
<211> LENGTH: 143
<212> TYPE: DNA
<213> ORGANISM: Homo sapiens

<400> SEQUENCE: 967
tttaggaaat ggactagttt tcatataata ttgttagtta ttagcaatga aatgaccaat 60
tttagcaagt agttgggaag aagttaaaat atttaaatct ataaactact tccagcttgt 120
agataaatct gttgcgtaat gtc 143

<210> SEQ ID NO 968
<211> LENGTH: 606
<212> TYPE: DNA
<213> ORGANISM: Homo sapiens

<400> SEQUENCE: 968
aggcaggatg tatcaatgca tgtcagatgg gggtagataa ctttggggca ggttatcaca 60
acctaagagt tggtggagaa aacatgggaa tgaattctag agaccacaaa atgaaaactt 120
gaaagtgtta ctctttctca gcttaacgtt tttaaatcca aaaaacaatt tttacatttc 180
ttgggattcg aagagttgaa cttcaggttg ccgtggttac agtgtacagt atatattatc 240
agtctgtacc agtagaccag taccctaact actgaaaaga atatggcagt tttccatttg 300
tctagtttct gtatgtacaa tttactatcc aattaattac ttaagtggat ttcttgttct 360
tttttaaaaa cttattgcta cattgatagg cagaatagct tctgaaagtg accagttttc 420
aatttcatag gaagaggtga ctcattgaaa aatagctcaa gcaaagtcag ctaaaaaaaa 480
aaaaaaacta gggaagctga gtaggtgtgg tcaattgata atgagctaac agctgattat 540
cactatattc tagaaactgg aactttcatt tataaaaaaa gaggtggccg gaaaattcat 600
cctgtc 606

<210> SEQ ID NO 969
<211> LENGTH: 281
<212> TYPE: DNA
<213> ORGANISM: Homo sapiens

<400> SEQUENCE: 969
tgtggcagcc gaccactttg aaggccagtt ttctcaggca acttagacca tttttagtca 60
aattttatct tagattcaca gtactggtgg ttttcgagta tattatgtta ccttctgaaa 120
tagttcctgt cgttttgagg ggcttttctt tataaaatag tcaactttgg ctataaaatg 180
ttactttagt gtaattccaa ctggaccagt cttatctgta gcatgcaaga agttcaagtt 240
tctcttttat ttttaaaagt ggcccatgat acctgtaaat c 281

<210> SEQ ID NO 970
<211> LENGTH: 104
<212> TYPE: DNA
<213> ORGANISM: Homo sapiens

<400> SEQUENCE: 970
ctacgagaag ttcagcccgg ccgggcccat cctctccatc cgggtctgca gggacatgat 60
cacccgccgc tccttgggct acgcgtatgt gaacttccag cagc 104

<210> SEQ ID NO 971
<211> LENGTH: 27
<212> TYPE: DNA
<213> ORGANISM: Homo sapiens

<400> SEQUENCE: 971
gtcgcggcct gtggccctgc gggcagc 27

<210> SEQ ID NO 972
<211> LENGTH: 32
<212> TYPE: DNA
<213> ORGANISM: Homo sapiens

<400> SEQUENCE: 972
cccggcactc gctctcctcc tctcacggaa ag 32

<210> SEQ ID NO 973
<211> LENGTH: 36
<212> TYPE: DNA
<213> ORGANISM: Homo sapiens

<400> SEQUENCE: 973
gatttttgtc cctctgcgct tgctccccgc tcccct 36

<210> SEQ ID NO 974
<211> LENGTH: 46
<212> TYPE: DNA
<213> ORGANISM: Homo sapiens

<400> SEQUENCE: 974
tcgctccccg ccggcagccg gcagccagcg gcagtggatc gacccc 46

<210> SEQ ID NO 975
<211> LENGTH: 57
<212> TYPE: DNA
<213> ORGANISM: Homo sapiens

<400> SEQUENCE: 975
ccaagaagga accaagagac cgaggccttc ccgctgcccg gacccgacac cgccacc 57

<210> SEQ ID NO 976
<211> LENGTH: 656
<212> TYPE: DNA
<213> ORGANISM: Homo sapiens

<400> SEQUENCE: 976
gctggctcca tctacgcacg tttcggaaac cgggcccgga ggggaccacg cccgctcacc 60

-continued

```
cgtgcccggc gtcccccgga gctggggcta gaggagccgg gccggccgca gcgggaagag    120

gccacaggcg gccgcgcacg tggggggtgg ttagcgcgga ggaacccgga agccctttgc    180

accgcccacc gccgcggtga cggttaacg ctcctcctgg tggaggcagg ggcgggcggg     240

gcggaaggcg gggacgcctc agccaacacc cccgaggacc gcccgcgagc cgtcctcccc    300

acccccacgg acgcgacgca gcgcgggctc cgcttccccg gccgcggcgc ctgcgcaaaa    360

gccccgcccc ttcgcccgag ccccaccccc acaccgcagc ctccaccgcc gccacctctc    420

ccttcctctc tgctctttcc tcctgttttc tcttccctcc tccccctggc ctccgcgtct    480

cctcctactc cggcgctgac gctcgcgtag gggccctggc gtcagacgcg cgggggcggg    540

gcgagtgcgg cgcggggtat aagtagaggg tgcaggaggc ggtgcttccc cttctccccg    600

gcggttagtg ctgagagtgc ggagtgtgtg ctccgggctc ggaacacaca tttatt        656
```

```
<210> SEQ ID NO 977
<211> LENGTH: 65
<212> TYPE: DNA
<213> ORGANISM: Homo sapiens

<400> SEQUENCE: 977

aggcaccgct tctgcggccg acgcgcgtgg cggcggtgcc ggctgggact cgtagtgcgg     60

tccgg                                                                 65


<210> SEQ ID NO 978
<211> LENGTH: 34
<212> TYPE: DNA
<213> ORGANISM: Homo sapiens

<400> SEQUENCE: 978

actatgttgt gagcctgcga aagaagtttg tgtg                                 34


<210> SEQ ID NO 979
<211> LENGTH: 39
<212> TYPE: DNA
<213> ORGANISM: Homo sapiens

<400> SEQUENCE: 979

atggaaaact gggagccgcc ttggaatcta cagggccgg                            39


<210> SEQ ID NO 980
<211> LENGTH: 121
<212> TYPE: DNA
<213> ORGANISM: Homo sapiens

<400> SEQUENCE: 980

cgacctcgac ggccgtcctg ccgaagaacc tgccgtcgct gcccgccccc gtggtgcggc     60

cctgacggtc gcgcaggccg acggacgaca gcgcgctccg gatgaagttg ggcgggtagc    120

t                                                                    121


<210> SEQ ID NO 981
<211> LENGTH: 28
<212> TYPE: DNA
<213> ORGANISM: Homo sapiens

<400> SEQUENCE: 981

agcctcctcc aaaacagcac actttccg                                        28


<210> SEQ ID NO 982
<211> LENGTH: 254
```

<212> TYPE: DNA
<213> ORGANISM: Homo sapiens

<400> SEQUENCE: 982
tggttacaat ggtactttca gcctgtccga attatgtatt gcccctcccc tttttattaa 60
taacattgaa gtgtgatggg acaaccactg aagccgtcag ttgaaacctg ctgggacttt 120
ttagccattc tcttcaacat aaagaatggg tgtttttgga gggggtgaga ggaatgggga 180
aatgttgtca aagagtacaa cgttttagtt gagacaggaa gaatatattt tgttgagatc 240
tacagcacag catg 254

<210> SEQ ID NO 983
<211> LENGTH: 73
<212> TYPE: DNA
<213> ORGANISM: Homo sapiens

<400> SEQUENCE: 983
gcctacctaa aatattgaat gctgttaata aatctcctga ggccagcata agaaggtgat 60
gggcaaaact aat 73

<210> SEQ ID NO 984
<211> LENGTH: 75
<212> TYPE: DNA
<213> ORGANISM: Homo sapiens

<400> SEQUENCE: 984
ttgtgtatct gcgttccttt caacaagtgt gacttcctcc atggcatcat tcgtgagcgt 60
aacacagagc tcagc 75

<210> SEQ ID NO 985
<211> LENGTH: 172
<212> TYPE: DNA
<213> ORGANISM: Homo sapiens

<400> SEQUENCE: 985
gctctgagag gctcttccta atagaactgc tgcttcagtt tagcttgaaa aagcccacac 60
ccagttccta atgacaaaca tctgaacacc gggtcttccc acgagcaaga ccatgctatg 120
cctcctgctc gctctgttct ataagcaacc cacagattgc tccctgtgaa ga 172

<210> SEQ ID NO 986
<211> LENGTH: 26
<212> TYPE: DNA
<213> ORGANISM: Homo sapiens

<400> SEQUENCE: 986
agtaaatcca tttgctgatt gcaata 26

<210> SEQ ID NO 987
<211> LENGTH: 34
<212> TYPE: DNA
<213> ORGANISM: Homo sapiens

<400> SEQUENCE: 987
actatgttgt gagcctgcga aagaagtttg tgtg 34

<210> SEQ ID NO 988
<211> LENGTH: 254
<212> TYPE: DNA
<213> ORGANISM: Homo sapiens

<400> SEQUENCE: 988
tggttacaat ggtactttca gcctgtccga attatgtatt gcccctcccc tttttattaa 60
taacattgaa gtgtgatggg aaaaccactg aagccgtcag ttgaaacctg ctgggacttt 120
ttagccattc tcttcaacat aaagaatggg tgtttttgga gggggtgaga ggaatgggga 180
aatgttgtca aagagtacag tgttttagtt gagacaggaa gaatatattt tgttgagatc 240
tacagcacag catg 254

<210> SEQ ID NO 989
<211> LENGTH: 25
<212> TYPE: DNA
<213> ORGANISM: Homo sapiens

<400> SEQUENCE: 989
cctcaatggg aaccctggtg cagaa 25

<210> SEQ ID NO 990
<211> LENGTH: 66
<212> TYPE: DNA
<213> ORGANISM: Homo sapiens

<400> SEQUENCE: 990
gtgcggggtg gtggcactgt cagcagggac cactgggaag ttgaggatga ggacatcaaa 60
aataac 66

<210> SEQ ID NO 991
<211> LENGTH: 42
<212> TYPE: DNA
<213> ORGANISM: Homo sapiens

<400> SEQUENCE: 991
aaaggttacc agttcaccaa ctgtgcttta cggtgaaaaa ca 42

<210> SEQ ID NO 992
<211> LENGTH: 30
<212> TYPE: DNA
<213> ORGANISM: Homo sapiens

<400> SEQUENCE: 992
ccaccatgac agatgacctg gcaggttatg 30

<210> SEQ ID NO 993
<211> LENGTH: 33
<212> TYPE: DNA
<213> ORGANISM: Homo sapiens

<400> SEQUENCE: 993
agaacagcaa gaagcgattg aacacattga tga 33

<210> SEQ ID NO 994
<211> LENGTH: 69
<212> TYPE: DNA
<213> ORGANISM: Homo sapiens

<400> SEQUENCE: 994
atataacaaa ctccgccaac catttttca gaagaggtca gaattgatcg ccaaaatccc 60
aaatttttg 69

<210> SEQ ID NO 995
<211> LENGTH: 40

<212> TYPE: DNA
<213> ORGANISM: Homo sapiens

<400> SEQUENCE: 995
agtggtgatc catcttcgaa gtccaccgaa atcaaatgga 40

<210> SEQ ID NO 996
<211> LENGTH: 104
<212> TYPE: DNA
<213> ORGANISM: Homo sapiens

<400> SEQUENCE: 996
agagagcttc tttacctggt ttactgacca ttctgatgca ggtgctgatg agttaggaga 60
ggtcatcaaa gatgatattt ggccaaaccc attacagtac tact 104

<210> SEQ ID NO 997
<211> LENGTH: 68
<212> TYPE: DNA
<213> ORGANISM: Homo sapiens

<400> SEQUENCE: 997
gggagcagca ttccaccaga ccctgattta gcaagatatt tccgtatcat tcccccaacc 60
agctggaa 68

<210> SEQ ID NO 998
<211> LENGTH: 60
<212> TYPE: DNA
<213> ORGANISM: Homo sapiens

<400> SEQUENCE: 998
ccagacgtac agaggctggg agccattgtg gtgtgctata ttgatgacgg cagcagtggg 60

<210> SEQ ID NO 999
<211> LENGTH: 75
<212> TYPE: DNA
<213> ORGANISM: Homo sapiens

<400> SEQUENCE: 999
ttgtgtatct gcgttccttt caacaagtgt gacttcctca atggcatcat tcgtgagcgt 60
aacacagagc tcagc 75

<210> SEQ ID NO 1000
<211> LENGTH: 27
<212> TYPE: DNA
<213> ORGANISM: Homo sapiens

<400> SEQUENCE: 1000
cttagagggc cccacagttg tttgctg 27

<210> SEQ ID NO 1001
<211> LENGTH: 254
<212> TYPE: DNA
<213> ORGANISM: Homo sapiens

<400> SEQUENCE: 1001
tggttacaat ggtactttca gcctgtccga attatgtatt gcccctcccc tttttattaa 60
taacattgaa gtgtgatggg acaaccactg aagccgtctg ttgaaacctg ctgggacttt 120
ttagccattc tcttcaacat aaagaatggg tgtttttgga gggggtgaga ggaatgggga 180
aatgttgtca aagagtacaa tgttttagtt gagacaggag gaatatattt tgttgagatc 240
tacagcacag catg 254

<210> SEQ ID NO 1002
<211> LENGTH: 28
<212> TYPE: DNA
<213> ORGANISM: Homo sapiens

<400> SEQUENCE: 1002
agcctcctcc aaaacagcac actttccg 28

<210> SEQ ID NO 1003
<211> LENGTH: 80
<212> TYPE: DNA
<213> ORGANISM: Homo sapiens

<400> SEQUENCE: 1003
aaaaatgagc aggtgcggga tgtgcgcaga gtcggagaag agtccagggc gcccggagtg 60
gctccaggaa cgacggaaac 80

<210> SEQ ID NO 1004
<211> LENGTH: 34
<212> TYPE: DNA
<213> ORGANISM: Homo sapiens

<400> SEQUENCE: 1004
actatgttgt gagcctgcga aagaagtttg tgtg 34

<210> SEQ ID NO 1005
<211> LENGTH: 389
<212> TYPE: DNA
<213> ORGANISM: Homo sapiens

<400> SEQUENCE: 1005
tcatgtctta gagcccgtct ttatgtttaa aactaatttc ttaaaataaa gccttcagta 60
aatgttcatt accaacttga taaatgctac tcataagagc tggtttgggg ctatagcata 120
tgcttttttt tttttaatta ttacctgatt taaaaatctc tgtaaaaacg tgtagtgttt 180
cataaaatct gtaactcgca ttttaatgat ccgctattat aagcttttaa tagcatgaaa 240
attgttaggc tatataacat tgccacttca actctaagga atatttttga gatatccctt 300
tggaagacct tgcttggaag agcctggaca ctaacaattc tacaccaaat tgtctcttca 360
aatacgtatg gactggataa ctctgagaa 389

<210> SEQ ID NO 1006
<211> LENGTH: 170
<212> TYPE: DNA
<213> ORGANISM: Homo sapiens

<400> SEQUENCE: 1006
ctaattcaat tgcaagagtg ggagtaaatg acttctgtcc aacagtgcca aagatgaaga 60
aatctttata cagtgcaata agtttattca acaacccggt gaaatactgg gaaatgcaac 120
ctgcaacatt tcgttgtgtt ttgagcagaa tgagcgttca gcttgggaac 170

<210> SEQ ID NO 1007
<211> LENGTH: 405
<212> TYPE: DNA
<213> ORGANISM: Homo sapiens

<400> SEQUENCE: 1007
tgacaactct taactggctg gaaggggcca cagattcctt ggagaatcta ataaagattt 60
agatcttccc aagaacaaaa gttttcatct tccaaggagc ttgagaacaa aactgggcaa 120
caagccactc tgcctcttct ctttttcttt ccggtgtatc tttaaacaag tttcgttcac 180
tgtactcctt tgagatacaa accatcaaaa tgaatgtaat ataggcaggt gctaatctca 240
agatcacaac ttttgctttg acttttccaa atgctgcatt tggatgtctg tttagccagt 300
gactacaact tgagtccgtc ctctctcaag ctgccccatc cctgatgtca tttctgctta 360
atttgctcca caactctgct tccagcttct ggtctctctt aaatc 405

<210> SEQ ID NO 1008
<211> LENGTH: 134
<212> TYPE: DNA
<213> ORGANISM: Homo sapiens

<400> SEQUENCE: 1008
acattctact tgtgttcagt agatattggt atttttcttc agtttttata acacacttta 60
gcacacctca agcaaagacc aagtaagcag caagggtgat tcaaacataa tgactctcca 120
ggttgcatga ggtg 134

<210> SEQ ID NO 1009
<211> LENGTH: 117
<212> TYPE: DNA
<213> ORGANISM: Homo sapiens

<400> SEQUENCE: 1009
atcacagata tcgaaaatgg gagtcttgct aacataccac gtgtgagaga aatacatttg 60
gaaaacaata aactaaaaaa aatcccttca ggattaccag agttgaaata cctccag 117

<210> SEQ ID NO 1010
<211> LENGTH: 85
<212> TYPE: DNA
<213> ORGANISM: Homo sapiens

<400> SEQUENCE: 1010
taggacaggc ttatattcta actagtttgc ggtgttttca gctaactcta tcacacctaa 60
ccatctgtgt aagacttgat gcatt 85

<210> SEQ ID NO 1011
<211> LENGTH: 68
<212> TYPE: DNA
<213> ORGANISM: Homo sapiens

<400> SEQUENCE: 1011
gcttaccacc aactttattg gagcttcact tagattataa taaaatttca acagtggaac 60
ttgaggat 68

<210> SEQ ID NO 1012
<211> LENGTH: 215
<212> TYPE: DNA
<213> ORGANISM: Homo sapiens

<400> SEQUENCE: 1012
gataaatgat atcacatgga agctgtcagc caaatccaca aaaggagtgt ctcaaacaaa 60
ttaatatgga aataaatcaa aagaagaggg agaaaaaagg agggagtatg ttgtacatta 120
agagagattt caagagcgat aagaaccaaa tgtattctgt aaacttcatt taatcctaac 180
ttgaacaaat caactgtaaa atgacgtatt tgaga 215

<210> SEQ ID NO 1013
<211> LENGTH: 177
<212> TYPE: DNA
<213> ORGANISM: Homo sapiens

<400> SEQUENCE: 1013
ccggtacaaa agtgtgctaa catttgtcag cagttactga gcttctgcca aattcacacc 60
tctgctcgtt ttatcctaga ggctacactt caatcttctc tctggttacc caccttcccc 120
atttcctaag ggacacaaca gttccctcaa cttctacaag tcctctccca gagatta 177

<210> SEQ ID NO 1014
<211> LENGTH: 352
<212> TYPE: DNA
<213> ORGANISM: Homo sapiens

<400> SEQUENCE: 1014
cccaggcatt tagccacagt ttgaggtgaa gcctatgagc ccagactggg cagcccctgg 60
ctctggcagg aatggacatg ccattcaagg caaggcattt tgtacccagc ttcttcccag 120
gtgtactgtg aagactaatg ggccaataca cagaaaggtc tgaggacaac atccagcacg 180
taggaagtga ccacctgtga cataatcatt accaagatga gcactgtgct ctttatcatg 240
gctttgtgtg acccaaggct agcacctcaa gtagaatgct ccttaagtct gccagatgac 300
cagtgttcta acccattact tccaagctcc ctgtctgatg attagctgca ta 352

<210> SEQ ID NO 1015
<211> LENGTH: 86
<212> TYPE: DNA
<213> ORGANISM: Homo sapiens

<400> SEQUENCE: 1015
taataatggg atagagccag gggcatttga aggggtgacg gtgttccata tcagaattgc 60
agaagcaaaa ctgacctcag ttccta 86

<210> SEQ ID NO 1016
<211> LENGTH: 133
<212> TYPE: DNA
<213> ORGANISM: Homo sapiens

<400> SEQUENCE: 1016
cctgaacaac aacaagctaa cgaagattca cccaaaagcc tttctaacca caaagaagtt 60
gcgaaggctg tatctgtccc acaatcaact aagtgaaata ccacttaatc ttcccaaatc 120
attagcagaa ctc 133

<210> SEQ ID NO 1017
<211> LENGTH: 26
<212> TYPE: DNA
<213> ORGANISM: Homo sapiens

<400> SEQUENCE: 1017
aatactggta aatcaaatcc acttcc 26

<210> SEQ ID NO 1018
<211> LENGTH: 28
<212> TYPE: DNA
<213> ORGANISM: Homo sapiens

<400> SEQUENCE: 1018
attccatttg atactcgaat gcttgatc 28

<210> SEQ ID NO 1019
<211> LENGTH: 95
<212> TYPE: DNA
<213> ORGANISM: Homo sapiens

<400> SEQUENCE: 1019
atgggtctta agctttacct gtggaattct catgagaaag agattaagat gcaagtactg 60
tttgagaaaa cttgttcatg tagaacgact gtgga 95

<210> SEQ ID NO 1020
<211> LENGTH: 381
<212> TYPE: DNA
<213> ORGANISM: Homo sapiens

<400> SEQUENCE: 1020
tgctattctg acaatttaaa ggatggaaaa agtctcattg aaatttcaaa aataatctga 60
gtgtataagt ttttttcatt taagttttta ggtggaaagt acagcaaacc ccaaagtaca 120
tccaaactta tttttaaaat taagaaaatc aaaggaaaac taagggaatg ttgtccatag 180
aacatttcct tctcttcccc agttaaatca aagcatttaa ttttaattcc cttcagagag 240
aatggacatc acatgcagtt ctatctcagg gtgctagcag gttgagactg tacttttcag 300
taaaactcca tgataacaaa ataagctgca tgtctagaac aatgaaatga gttatagaaa 360
gcttgtgaaa tctctaatct a 381

<210> SEQ ID NO 1021
<211> LENGTH: 60
<212> TYPE: DNA
<213> ORGANISM: Homo sapiens

<400> SEQUENCE: 1021
tttgatctgt ttccaatgtg tccatttgga tgtcagtgct attcacgagt tgtacattgc 60

<210> SEQ ID NO 1022
<211> LENGTH: 92
<212> TYPE: DNA
<213> ORGANISM: Homo sapiens

<400> SEQUENCE: 1022
tgtgctccta ttattcctgg ctttgtgctc tgccaaaccc ttctttagcc cttcacacat 60
cgcactgaag aatatgatgc tgaaggatat gg 92

<210> SEQ ID NO 1023
<211> LENGTH: 30
<212> TYPE: DNA
<213> ORGANISM: Homo sapiens

<400> SEQUENCE: 1023
tcctagactg gtcttctaca ctaagacacc 30

<210> SEQ ID NO 1024
<211> LENGTH: 468
<212> TYPE: DNA
<213> ORGANISM: Homo sapiens

<400> SEQUENCE: 1024
gaagtttggg gatatcacag ctatattaaa tgaaacagta aatatatttt tcaatattta 60
aaatattttc taatgtgtat ttaaaatgtg tgaattactg aaatgtcaat tttacttata 120
catttgaata ttcattttt tccttgataa atgtcttcct tattataatg aaatggcact 180
gaaaagttca aatggaaatc tattcaattc caagaaagaa tacttatcag caatagttta 240
gctagcacta tattcaatat gaaagattag gaaattttca cagcatgtat acagtcagaa 300
tttaacactt tcaaagattt cctttgtcta ctcccaaagt aaatttctga ttaaatttta 360
gattaaaaaa tttaagcaat gtattcaata ttctactccc tagtaatcta aatagcgcac 420
agcattcttt catgttaatc tattcagagg tgtggcaccc aggaaaca 468

<210> SEQ ID NO 1025
<211> LENGTH: 198
<212> TYPE: DNA
<213> ORGANISM: Homo sapiens

<400> SEQUENCE: 1025
tggactaatc tgtgggagca gtttattcca gtatcaccca gggtgcagcc acaccaggac 60
tgtgttgaag ggtgtttttt ttcttttaaa tgtaatacct cctcatcttt tcttcttaca 120
cagtgtctga gaacatttac attatagata agtagtacat ggtggataac ttctactttt 180
aggaggacta ctctcttc 198

<210> SEQ ID NO 1026
<211> LENGTH: 29
<212> TYPE: DNA
<213> ORGANISM: Homo sapiens

<400> SEQUENCE: 1026
ggaaacgcct cttcacacta aaggaagaa 29

<210> SEQ ID NO 1027
<211> LENGTH: 30
<212> TYPE: DNA
<213> ORGANISM: Homo sapiens

<400> SEQUENCE: 1027
tgacttcctt actattgctt cctggactaa 30

<210> SEQ ID NO 1028
<211> LENGTH: 1377
<212> TYPE: DNA
<213> ORGANISM: Homo sapiens

<400> SEQUENCE: 1028
actcgtgagc acatctttag ggaccaagag tgactttctg taaggagtga ctcgtggctt 60
gccttggtct cttgggaata cttttctaac tagggttgct ctcacctgag acattctcca 120
cccgcggaat ctcagggtcc caggctgtgg gccatcacga cctcaaactg gctcctaatc 180
tccagctttc ctgtcattga aagcttcgga agtttactgg ctctgctccc gcctgttttc 240
tttctgactc tatctggcag cccgatgcca cccagtacag gaagtgacac cagtactctg 300
taaagcatca tcatccttgg agagactgag cactcagcac cttcagccac gatttcagga 360
tcgcttcctt gtgagccgct gcctccgaaa tctcctttga agcccagaca tctttctcca 420
gcttcagact tgtagatata actcgttcat cttcatttac tttccacttt gccccctgtc 480
ctctctgtgt tccccaaatc agagaatagc ccgccatccc ccaggtcacc tgtctggatt 540
cctccccatt cacccacctt gccaggtgca ggtgaggatg gtgcaccaga cagggtagct 600
gtcccccaaa atgtgccctg tgcgggcagt gccctgtctc cacgtttgtt tccccagtgt 660
ctggcgggga gccaggtgac atcataaata cttgctgaat gaatgcagaa atcagcggta 720
ctgacttgta ctatattggc tgccatgata gggttctcac agcgtcatcc atgatcgtaa 780
gggagaatga cattctgctt gagggaggga atagaaaggg gcagggaggg gacatctgag 840
ggcttcacag ggctgcaaag ggtacaggga ttgcaccagg gcagaacagg ggagggtgtt 900
caaggaagag tggctcttag cagaggcact ttggaaggtg tgaggcataa atgcttcctt 960
ctacgtaggc caacctcaaa actttcagta ggaatgttgc tatgatcaag ttgttctaac 1020
actttagact tagtagtaat tatgaacctc acatagaaaa atttcatcca gccatatgcc 1080
tgtggagtgg aatattctgt ttagtagaaa aatcctttag agttcagctc taaccagaaa 1140
tcttgctgaa gtatgtcagc accttttctc accctggtaa gtacagtatt tcaagagcac 1200
gctaagggtg gttttcattt tacagggctg ttgatgatgg gttaaaaatg ttcatttaag 1260
ggctaccccc gtgtttaata gatgaacacc acttctacac aaccctcctt ggtactgggg 1320
gagggagaga tctgacaaat actgcccatt cccctaggct gactggattt gagaaca 1377

<210> SEQ ID NO 1029
<211> LENGTH: 115
<212> TYPE: DNA
<213> ORGANISM: Homo sapiens

<400> SEQUENCE: 1029
atgagcgcac ggatgaatgg agcttacaag atctgtcttt ccaatggccg ggggcatttg 60
gtccccaaat taaggctatt ggacatctgc acaggacagt cctatttttg atgtc 115

<210> SEQ ID NO 1030
<211> LENGTH: 50
<212> TYPE: DNA
<213> ORGANISM: Homo sapiens

<400> SEQUENCE: 1030
aggaacaact atcctcgtct gtcccaacac tgagcaggca ctcggtaaac 50

<210> SEQ ID NO 1031
<211> LENGTH: 227
<212> TYPE: DNA
<213> ORGANISM: Homo sapiens

<400> SEQUENCE: 1031
atttgctggg tctgaatcgg cttcataaac tccactggga gcactgctgg gctcctggac 60
tgagaatagt tgaacaccgg gggctttgtg aaggagtctg ggccaaggtt tgccctcagc 120
tttgcagaat gaagccttga ggtctgtcac cacccacagc caccctacag cagccttaac 180
tgtgacactt gccacactgt gtcgtcgttt gtttgcctat gtcctcc 227

<210> SEQ ID NO 1032
<211> LENGTH: 60
<212> TYPE: DNA
<213> ORGANISM: Homo sapiens

<400> SEQUENCE: 1032
ggacaatgtg tgtgtcaaga aaataagaac cagaagtcat agggacagtg aagatatttg 60

<210> SEQ ID NO 1033
<211> LENGTH: 108
<212> TYPE: DNA
<213> ORGANISM: Homo sapiens

<400> SEQUENCE: 1033
gttcagcaaa cgaaactcat gtagcaataa cctcttcaga tacagaattc tggcaagtac 60
agctgtccag acagaccctc ttcggcacaa actaggaagc ttcaactg 108

<210> SEQ ID NO 1034
<211> LENGTH: 155
<212> TYPE: DNA
<213> ORGANISM: Homo sapiens

<400> SEQUENCE: 1034
cagaagagtg cgaaggttct catgcagaat cagaaaggga aaggagaagc aggaaattca 60
gactccatgt gcctgagatc aagaaagaca aaaagccagc ctgcagcaag cactttggag 120
agcaaatctg tgcagagagt aacgcggagt gtcaa 155

<210> SEQ ID NO 1035
<211> LENGTH: 30
<212> TYPE: DNA
<213> ORGANISM: Homo sapiens

<400> SEQUENCE: 1035
gagcccggaa acccatacct agagacaaag 30

<210> SEQ ID NO 1036
<211> LENGTH: 26
<212> TYPE: DNA
<213> ORGANISM: Homo sapiens

<400> SEQUENCE: 1036
tatccctgcg ctccagacgc caaaat 26

<210> SEQ ID NO 1037
<211> LENGTH: 27
<212> TYPE: DNA
<213> ORGANISM: Homo sapiens

<400> SEQUENCE: 1037
gagcaaagta ccaaggcatt accttga 27

<210> SEQ ID NO 1038
<211> LENGTH: 226
<212> TYPE: DNA
<213> ORGANISM: Homo sapiens

<400> SEQUENCE: 1038
aagaggctgc gctgcatgcc agcaccagag gaaattgtgg aggagctgcc agccagcaag 60
aagcagaggg ttgctcccag ggcaagaggc aaatcatccg aacccgtggt catcatgaag 120
agaagtttga ggacttctgc aaaaagaatt gaacctgcgg aagagctgaa cagcaacgac 180
atgaaaacca acaaagagga acacaaatta caagactcgg tccctg 226

<210> SEQ ID NO 1039
<211> LENGTH: 1286
<212> TYPE: DNA
<213> ORGANISM: Homo sapiens

<400> SEQUENCE: 1039
cccgtgctct agaagacctg gttgacttca aagagctctt ctcagcacca ggtcacactg 60
aagagtcaat gactattgac aaaaacacaa aaattccctg caaatctccc ccaccagaac 120
taacagacac tgccacgagc acaaagagat gccccaagac acgtcccagg aaagaagtaa 180
aagaggagct ctcagcagtt gagaggctca cgcaaacatc agggcaaagc acacacacac 240

-continued

```
acaaagaacc agcaagcggt gatgagggca tcaaagtatt gaagcaacgt gcaaagaaga    300

aaccaaaccc agtagaagag gaacccagca ggagaaggcc aagagcacct aaggaaaagg    360

cccaacccct ggaagacctg gccggcttca cagagctctc tgaaacatca ggtcacactc    420

aggaatcact gactgctggc aaagccacta aaataccctg cgaatctccc ccactagaag    480

tggtagacac cacagcaagc acaaagaggc atctcaggac acgtgtgcag aaggtacaag    540

taaaagaaga gccttcagca gtcaagttca cacaaacatc aggggaaacc acggatgcag    600

acaaagaacc agcaggtgaa gataaaggca tcaaagcatt gaaggaatct gcaaaacaga    660

caccggctcc agcagcaagt gtaactggca gcaggagacg gccaagagca cccagggaaa    720

gtgcccaagc catagaagac ctagctggct tcaaagaccc agcagcaggt cacactgaag    780

aatcaatgac tgatgacaaa accactaaaa taccctgcaa atcatcacca gaactagaag    840

acaccgcaac aagctcaaag agacggccca ggacacgtgc ccagaaagta gaagtgaagg    900

aggagctgtt agcagttggc aagctcacac aaacctcagg ggagaccacg cacaccgaca    960

aagagccggt aggtgagggc aaaggcacga aagcatttaa gcaacctgca aagcggaagc   1020

tggacgcaga agatgtaatt ggcagcagga gacagccaag agcacctaag gaaaaggccc   1080

aacccctgga agatctggcc agcttccaag agctctctca aacaccaggc cacactgagg   1140

aactggcaaa tggtgctgct gatagcttta caagcgctcc aaagcaaaca cctgacagtg   1200

gaaaacctct aaaaatatcc agaagagttc ttcgggcccc taaagtagaa cccgtgggag   1260

acgtggtaag caccagagac cctgta                                        1286
```

```
<210> SEQ ID NO 1040
<211> LENGTH: 3489
<212> TYPE: DNA
<213> ORGANISM: Homo sapiens

<400> SEQUENCE: 1040
```

```
ggagaactct tagcgtgcag gaatctaatg ccatcagcag gcaaagccat gcacacgcct     60

aaaccatcag taggtgaaga gaaagacatc atcatatttg tgggaactcc agtgcagaaa    120

ctggacctga cagagaactt aaccggcagc aagagacggc cacaaactcc taaggaagag    180

gcccaggctc tggaagacct gactggcttt aaagagctct tccagacccc tggtcatact    240

gaagaagcag tggctgctgg caaaactact aaaatgccct gcgaatcttc tccaccagaa    300

tcagcagaca ccccaacaag cacaagaagg cagcccaaga caccttttgga gaaaagggac    360

gtacagaagg agctctcagc cctgaagaag ctcacacaga catcagggga aaccacacac    420

acagataaag taccaggagg tgaggataaa agcatcaacg cgtttaggga aactgcaaaa    480

cagaaactgg acccagcagc aagtgtaact ggtagcaaga ggcacccaaa aactaaggaa    540

aaggcccaac ccctagaaga cctggctggc ttgaaagagc tcttccagac accagtatgc    600

actgacaagc ccacgactca cgagaaaact accaaaatag cctgcagatc acaaccagac    660

ccagtggaca caccaacaag ctccaagcca cagtccaaga gaagtctcag gaaagtggac    720

gtagaagaag aattcttcgc actcaggaaa cgaacaccat cagcaggcaa agccatgcac    780

acacccaaac cagcagtaag tggtgagaaa aacatctacg catttatggg aactccagtg    840

cagaaactgg acctgacaga gaacttaact ggcagcaaga gacggctaca aactcctaag    900

gaaaaggccc aggctctaga agacctggct ggctttaaag agctcttcca gacacgaggt    960

cacactgagg aatcaatgac taacgataaa actgccaaag tagcctgcaa atcttcacaa   1020
```

-continued ccagacccag acaaaaaccc agcaagctcc aagcgacggc tcaagacatc cctggggaaa 1080
gtgggcgtga aagaagagct cctagcagtt ggcaagctca cacagacatc aggagagact 1140
acacacacac acacagagcc aacaggagat ggtaagagca tgaaagcatt tatggagtct 1200
ccaaagcaga tcttagactc agcagcaagt ctaactggca gcaagaggca gctgagaact 1260
cctaagggaa agtctgaagt ccctgaagac ctggccggct tcatcgagct cttccagaca 1320
ccaagtcaca ctaaggaatc aatgactaac gaaaaaacta ccaaagtatc ctacagagct 1380
tcacagccag acctagtgga caccccaaca agctccaagc cacagcccaa gagaagtctc 1440
aggaaagcag acactgaaga agaatttttta gcatttagga aacaaacgcc atcagcaggc 1500
aaagccatgc acacacccaa accagcagta ggtgaagaga aagacatcaa cacgtttttg 1560
ggaactccag tgcagaaact ggaccagcca ggaaatttac ctggcagcaa tagacggcta 1620
caaactcgta aggaaaaggc ccaggctcta gaagaactga ctggcttcag agagcttttc 1680
cagacaccat gcactgataa ccccacgact gatgagaaaa ctaccaaaaa aatactctgc 1740
aaatctccgc aatcagaccc agcggacacc ccaacaaaca caaagcaacg gcccaagaga 1800
agcctcaaga aagcagacgt agaggaagaa tttttagcat tcaggaaact aacaccatca 1860
gcaggcaaag ccatgcacac gcctaaagca gcagtaggtg aagagaaaga catcaacaca 1920
tttgtgggga ctccagtgga gaaactggac ctgctaggaa atttacctgg cagcaagaga 1980
cggccacaaa ctcctaaaga aaaggccaag gctctagaag atctggctgg cttcaaagag 2040
ctcttccaga caccaggtca cactgaggaa tcaatgaccg atgacaaaat cacagaagta 2100
tcctgcaaat ctccacaacc agacccagtc aaaaccccaa caagctccaa gcaacgactc 2160
aagatatcct tggggaaagt aggtgtgaaa gaagaggtcc taccagtcgg caagctcaca 2220
cagacgtcag ggaagaccac acagacacac agagagacag caggagatgg aaagagcatc 2280
aaagcgttta aggaatctgc aaagcagatg ctggacccag caaactatgg aactgggatg 2340
gagaggtggc caagaacacc taaggaagag gcccaatcac tagaagacct ggccggcttc 2400
aaagagctct tccagacacc agaccacact gaggaatcaa caactgatga caaaactacc 2460
aaaatagcct gcaaatctcc accaccagaa tcaatggaca ctccaacaag cacaaggagg 2520
cggcccaaaa cacctttggg gaaaagggat atagtggaag agctctcagc cctgaagcag 2580
ctcacacaga ccacacacac agacaaagta ccaggagatg aggataaagg catcaacgtg 2640
ttcagggaaa ctgcaaaaca gaaactggac ccagcagcaa gtgtaactgg tagcaagagg 2700
cagccaagaa ctcctaaggg aaaagcccaa cccctagaag acttggctgg cttgaaagag 2760
ctcttccaga caccaatatg cactgacaag cccacgactc atgagaaaac taccaaaata 2820
gcctgcagat ctccacaacc agacccagtg ggtaccccaa caatcttcaa gccacagtcc 2880
aagagaagtc tcaggaaagc agacgtagag gaagaatcct tagcactcag gaaacgaaca 2940
ccatcagtag ggaaagctat ggacacaccc aaaccagcag gaggtgatga gaaagacatg 3000
aaagcattta tgggaactcc agtgcagaaa ttggacctgc caggaaattt acctggcagc 3060
aaaagatggc cacaaactcc taaggaaaag gcccaggctc tagaagacct ggctggcttc 3120
aaagagctct tccagacacc aggcactgac aagcccacga ctgatgagaa aactaccaaa 3180
atagcctgca aatctccaca accagaccca gtggacaccc cagcaagcac aaagcaacgg 3240
cccaagagaa acctcaggaa agcagacgta gaggaagaat tttagcact caggaaacga 3300
acaccatcag caggcaaagc catggacaca ccaaaaccag cagtaagtga tgagaaaaat 3360
atcaacacat ttgtggaaac tccagtgcag aaactggacc tgctaggaaa tttacctggc 3420
agcaagagac agccacagac tcctaaggaa aaggctgagg ctctagagga cctggttggc 3480
ttcaaagaa 3489

<210> SEQ ID NO 1041
<211> LENGTH: 389
<212> TYPE: DNA
<213> ORGANISM: Homo sapiens

<400> SEQUENCE: 1041
aacaacagtt gaaggcatcc ctggggaaag taggtgtgaa agaagagctc ctagcagtcg 60
gcaagttcac acggacgtca ggggagacca cgcacacgca cagagagcca gcaggagatg 120
gcaagagcat cagaacgttt aaggagtctc caaagcagat cctggaccca gcagcccgtg 180
taactggaat gaagaagtgg ccaagaacgc ctaaggaaga ggcccagtca ctagaagacc 240
tggctggctt caaagagctc ttccagacac caggtccctc tgaggaatca atgactgatg 300
agaaaactac caaaatagcc tgcaaatctc caccaccaga atcagtggac actccaacaa 360
gcacaaagca atggcctaag agaagtctc 389

<210> SEQ ID NO 1042
<211> LENGTH: 334
<212> TYPE: DNA
<213> ORGANISM: Homo sapiens

<400> SEQUENCE: 1042
tgcaaacagg tcaggaaggt ctacagagtt caggaatata cagaagctac ctgtggaaag 60
taagagtgaa gaaacaaata cagaaattgt tgagtgcatc ctaaaaagag gtcagaaggc 120
aacactacta caacaaagga gagaaggaga gatgaaggaa atagaaagac cttttgagac 180
atataaggaa aatattgaat taaaagaaaa cgatgaaaag atgaaagcaa tgaagagatc 240
aagaacttgg gggcagaaat gtgcaccaat gtctgacctg acagacctca agagcttgcc 300
tgatacagaa ctcatgaaag acacggcacg tggc 334

<210> SEQ ID NO 1043
<211> LENGTH: 62
<212> TYPE: DNA
<213> ORGANISM: Homo sapiens

<400> SEQUENCE: 1043
cccagtgaag gagcaaccgc agttgacaag cacatgtcac atcgctattt caaattcaga 60
ga 62

<210> SEQ ID NO 1044
<211> LENGTH: 102
<212> TYPE: DNA
<213> ORGANISM: Homo sapiens

<400> SEQUENCE: 1044
tggcctctag atcctagcag ggaggcctat gggtctcagg agcccgtcac cagcctccgt 60
gctccagagc tcacgtgtgg ggtcttgtta ggaggaccca ga 102

<210> SEQ ID NO 1045
<211> LENGTH: 90
<212> TYPE: DNA
<213> ORGANISM: Homo sapiens

<400> SEQUENCE: 1045

-continued taaaaacgta gtcttagatc ttataaatct tttgactcta ctgtttttta ctgtgttaat 60
gtttgttttg ctaactttgt ttatctgctg 90

<210> SEQ ID NO 1046
<211> LENGTH: 84
<212> TYPE: DNA
<213> ORGANISM: Homo sapiens

<400> SEQUENCE: 1046
cgcaaactct ccttgtacca taataatagg gaaagctcat actgaaaaag tacatgtgcc 60
tgctcgaccc tacagagtgc tcaa 84

<210> SEQ ID NO 1047
<211> LENGTH: 26
<212> TYPE: DNA
<213> ORGANISM: Homo sapiens

<400> SEQUENCE: 1047
agcctgtggg cgaagttcac agtcaa 26

<210> SEQ ID NO 1048
<211> LENGTH: 73
<212> TYPE: DNA
<213> ORGANISM: Homo sapiens

<400> SEQUENCE: 1048
catgggcaga tgtagtaaaa cttggtgcaa aacaaacaca aactaaagtc ataaaacatg 60
gtcctcaaag gtc 73

<210> SEQ ID NO 1049
<211> LENGTH: 84
<212> TYPE: DNA
<213> ORGANISM: Homo sapiens

<400> SEQUENCE: 1049
aagagagtgt ctatcagccg aagtcaacat gatattttac agatgatatg ttccaaaaga 60
agaagtggtg cttcggaagc aaat 84

<210> SEQ ID NO 1050
<211> LENGTH: 116
<212> TYPE: DNA
<213> ORGANISM: Homo sapiens

<400> SEQUENCE: 1050
aaacaagagt caggttcaga aatccatgtg gaagtgaagg cacaaagctt ggttataagc 60
cctccagctc ctagtcctag gaaaactcca gttgccagtg atcaacgccg taggtc 116

<210> SEQ ID NO 1051
<211> LENGTH: 134
<212> TYPE: DNA
<213> ORGANISM: Homo sapiens

<400> SEQUENCE: 1051
cctttgaaaa gaaggcgtgt gtcctttggt gggcacctaa gacctgaact atttgatgaa 60
aacttgcctc ctaatacgcc tctcaaaagg ggagaagccc caaccaaaag aaagtctctg 120
gtaatgcaca ctcc 134

<210> SEQ ID NO 1052
<211> LENGTH: 66

<212> TYPE: DNA
<213> ORGANISM: Homo sapiens

<400> SEQUENCE: 1052
ggacagatgt gctctgggtt acctggtctt agttcagttg atatcaacaa ctttggtgat 60
tccatt 66

<210> SEQ ID NO 1053
<211> LENGTH: 31
<212> TYPE: DNA
<213> ORGANISM: Homo sapiens

<400> SEQUENCE: 1053
ttgagaggaa gatccaaaag gattccctca g 31

<210> SEQ ID NO 1054
<211> LENGTH: 149
<212> TYPE: DNA
<213> ORGANISM: Homo sapiens

<400> SEQUENCE: 1054
gaagctttca actagaaatc gaacaccagc taaagttgaa gatgcagctg actctgccac 60
taagccagaa aatctctctt ccaaaaccag aggaagtatt cctacagatg tggaagttct 120
gcctacggaa actgaaattc acaatgagc 149

<210> SEQ ID NO 1055
<211> LENGTH: 416
<212> TYPE: DNA
<213> ORGANISM: Homo sapiens

<400> SEQUENCE: 1055
ccagcgttaa attagtgagc cgttatggag aattgaagtc tgttcccact acacaatgtc 60
ttgacaatag caaaaaaaat gaatctccct tttggaagct ttatgagtca gtgaagaaag 120
agttggatgt aaaatcacaa aaagaaaatg tcctacagta ttgtagaaaa tctggattac 180
aaactgatta cgcaacagag aaagaaagtg ctgatggttt acagggggag acccaactgt 240
tggtctcgcg taagtcaaga ccaaaatctg gtgggagcgg ccacgctgtg gcagagcctg 300
cttcacctga acaagagctt gaccagaaca aggggaaggg aagagacgtg gagtctgttc 360
agactcccag caaggctgtg ggcgccagct ttcctctcta tgagccggct aaaatg 416

<210> SEQ ID NO 1056
<211> LENGTH: 33
<212> TYPE: DNA
<213> ORGANISM: Homo sapiens

<400> SEQUENCE: 1056
agccagcacg tcgtgtctca agatctagct tct 33

<210> SEQ ID NO 1057
<211> LENGTH: 125
<212> TYPE: DNA
<213> ORGANISM: Homo sapiens

<400> SEQUENCE: 1057
ggctctcaga tccaccctaa gtatccacca gccaagaggg cgcacatgcc aagtggagcc 60
tcagttcatc gacaggtcct atggcccatt tatgagaaaa ctgatgacgc agtcagtagt 120
tctga 125

<210> SEQ ID NO 1058
<211> LENGTH: 30
<212> TYPE: DNA
<213> ORGANISM: Homo sapiens

<400> SEQUENCE: 1058
ttcagaatgg aaggaagtca actgaatttc 30

<210> SEQ ID NO 1059
<211> LENGTH: 86
<212> TYPE: DNA
<213> ORGANISM: Homo sapiens

<400> SEQUENCE: 1059
ccaacacaag taaatgggtc tgttattgat gagcctgtac ggctaaaaca tggagatgta 60
ataactatta ttgatcgttc cttcag 86

<210> SEQ ID NO 1060
<211> LENGTH: 43
<212> TYPE: DNA
<213> ORGANISM: Homo sapiens

<400> SEQUENCE: 1060
tgtgacatcc gtatccagct tcctgttgtg tcaaaacaac att 43

<210> SEQ ID NO 1061
<211> LENGTH: 91
<212> TYPE: DNA
<213> ORGANISM: Homo sapiens

<400> SEQUENCE: 1061
ggctccttgt ggcaatagga aaatgggaca gaaagtcttc ctgcctggaa ttcgagaacg 60
tttcctctta tattgctgtc ctgtttggtg g 91

<210> SEQ ID NO 1062
<211> LENGTH: 30
<212> TYPE: DNA
<213> ORGANISM: Homo sapiens

<400> SEQUENCE: 1062
cctgagcctc agcacctgct tgtttggaag 30

<210> SEQ ID NO 1063
<211> LENGTH: 26
<212> TYPE: DNA
<213> ORGANISM: Homo sapiens

<400> SEQUENCE: 1063
cccacgagac gcctggttac tatcaa 26

<210> SEQ ID NO 1064
<211> LENGTH: 72
<212> TYPE: DNA
<213> ORGANISM: Homo sapiens

<400> SEQUENCE: 1064
tttgcttctg gccttcccct acggattata cctggccttc ccctacggat tatactcaac 60
ttactgttta ga 72

<210> SEQ ID NO 1065
<211> LENGTH: 265

<212> TYPE: DNA
<213> ORGANISM: Homo sapiens

<400> SEQUENCE: 1065
gactcggtgg gagccgctag agccgggcgc ccggggacgt agcctgtagg gccaccgggt 60
ccccgtcaga ggcggcggcg ggagcagcgg ggactgcagg ccggggtgca gcgaacgcga 120
ccccgcgggc tgcggcccgg tgtgtgcgga gcgtggcggg cgcagcttac cgggcggagg 180
tgagcgcggc gccggctcct cctgcggcgg actttgggtg cgacttgacg agcggtggtt 240
cgacaagtgg ccttgcgggc cggat 265

<210> SEQ ID NO 1066
<211> LENGTH: 96
<212> TYPE: DNA
<213> ORGANISM: Homo sapiens

<400> SEQUENCE: 1066
atggctctct gtttcacatc aatcacggga accccttcaa catggaagtg ttggtggact 60
cctggcccga gtatcagatg gttattatcc gacctc 96

<210> SEQ ID NO 1067
<211> LENGTH: 275
<212> TYPE: DNA
<213> ORGANISM: Homo sapiens

<400> SEQUENCE: 1067
tgcgttacat caagcgctgc ctaggagccc tgccagcagc ctgtatgctg ggcccagagg 60
gggtcccggt ctcatgggta accatggacc cttcttgtga aataggaatg ggctacagtg 120
tggaaaaata ccgaaggaga ggcaatggga cacggctgat catgcgatgc atgaagtatc 180
tgtgtcagaa gaatattcca ttttacggct ctgtgctgga agaaaatcaa ggcgtcatca 240
gaaagactag tgcactaggt ttccttgagg cctcc 275

<210> SEQ ID NO 1068
<211> LENGTH: 56
<212> TYPE: DNA
<213> ORGANISM: Homo sapiens

<400> SEQUENCE: 1068
atggacgatc taggaaactt tcagggagct aaggtgtcgg agagcaaagt atcctt 56

<210> SEQ ID NO 1069
<211> LENGTH: 128
<212> TYPE: DNA
<213> ORGANISM: Homo sapiens

<400> SEQUENCE: 1069
gtcccgctac ttcgtcacca aagcgcccgc cgcgctcgca tctgctgtga ggctgtgctc 60
gggccgctcc cgccgaggga acggccctcc caaggctctg cgccccaatt ctcgctcgtt 120
tgccaaga 128

<210> SEQ ID NO 1070
<211> LENGTH: 241
<212> TYPE: DNA
<213> ORGANISM: Homo sapiens

<400> SEQUENCE: 1070
tgtcgaccca ggttaggaag cccgaggtcg gggcgttacc ccaagggccc tcccgcttcc 60

-continued

```
cctccgaggg cagagaggcg tccgcgcccg gacgcactgc gggaacacct ggagcgccgg    120

cggagctcgg ctgtccccgc gggagggagc ccgacgcgca tccttgggac ccggacccgg    180

cgcccgcgcc tcgggacgga tttctgcctc ggctgcaggc gcagcgcgca gacctgagcc    240

t                                                                    241
```

<210> SEQ ID NO 1071
<211> LENGTH: 104
<212> TYPE: DNA
<213> ORGANISM: Homo sapiens

<400> SEQUENCE: 1071

```
cctggaagag aatggcgggc atctttttcc tgccatttat ctcatcaggt tttgctcctc     60

ggtttaagca ggaagagaac ttcatgcttg gaagagcgca tccg                     104
```

<210> SEQ ID NO 1072
<211> LENGTH: 180
<212> TYPE: DNA
<213> ORGANISM: Homo sapiens

<400> SEQUENCE: 1072

```
gctgaagaat cgatctgtgg gacttggaac tgaaagcaca ggtcggggta agccccactt     60

cacactggag ggccacaagt tcctgatctt cgggggctcc atccactatt tccgggtgcc    120

cagggagtac tggagggacc gcctgctgaa gctgaaggcc tgtggcttca atactgtcac    180
```

<210> SEQ ID NO 1073
<211> LENGTH: 66
<212> TYPE: DNA
<213> ORGANISM: Homo sapiens

<400> SEQUENCE: 1073

```
atgttccgtg gaacctgcat gagccagaaa gaggcaaatt tgacttctct gggaacctgg     60

acctgg                                                                66
```

<210> SEQ ID NO 1074
<211> LENGTH: 27
<212> TYPE: DNA
<213> ORGANISM: Homo sapiens

<400> SEQUENCE: 1074

```
gctactgggg gtggattagc aaccaaa                                         27
```

<210> SEQ ID NO 1075
<211> LENGTH: 56
<212> TYPE: DNA
<213> ORGANISM: Homo sapiens

<400> SEQUENCE: 1075

```
cccgatgggg ctgtgcagag gctctgaggc tgggagcagc tcaggccacc gacctg         56
```

<210> SEQ ID NO 1076
<211> LENGTH: 49
<212> TYPE: DNA
<213> ORGANISM: Homo sapiens

<400> SEQUENCE: 1076

```
cctcatcctg ggccgtcgtg ggaggggctg acgatgtgga cctccctag                 49
```

<210> SEQ ID NO 1077
<211> LENGTH: 92

<212> TYPE: DNA
<213> ORGANISM: Homo sapiens

<400> SEQUENCE: 1077
ccttcgtcct gatggccgca gagatcgggc tgtgggtgat tctgcgtcca ggccgctaca 60
tctgcagtga gatggacctc gggggcttgc cc 92

<210> SEQ ID NO 1078
<211> LENGTH: 68
<212> TYPE: DNA
<213> ORGANISM: Homo sapiens

<400> SEQUENCE: 1078
ctggctcctg caagaccccc ggttactgtt gaggacaacc aacaagagct tcattgaagc 60
agttgaga 68

<210> SEQ ID NO 1079
<211> LENGTH: 99
<212> TYPE: DNA
<213> ORGANISM: Homo sapiens

<400> SEQUENCE: 1079
gcgcccaaca gcattgcctt ttttatggtg tacccagacc tcatgcactt gataagaaac 60
gccttcattt ttaccatggc aacctagagc acacagtca 99

<210> SEQ ID NO 1080
<211> LENGTH: 95
<212> TYPE: DNA
<213> ORGANISM: Homo sapiens

<400> SEQUENCE: 1080
agaagcacaa atgccgttca caggcacatg tatgcaacga ggaaagctaa tttacaggca 60
tcccattgaa ctgtgggaaa tgctaggaaa ctttt 95

<210> SEQ ID NO 1081
<211> LENGTH: 46
<212> TYPE: DNA
<213> ORGANISM: Homo sapiens

<400> SEQUENCE: 1081
taagtgaaat gtaatgcccc atacctcgca taccttgcac taattt 46

<210> SEQ ID NO 1082
<211> LENGTH: 39
<212> TYPE: DNA
<213> ORGANISM: Homo sapiens

<400> SEQUENCE: 1082
tcatcgcggt gcaagtggag aatgagtatg gctcattca 39

<210> SEQ ID NO 1083
<211> LENGTH: 37
<212> TYPE: DNA
<213> ORGANISM: Homo sapiens

<400> SEQUENCE: 1083
agaagaggga ttgtggagct tctcttgacc tctgatg 37

<210> SEQ ID NO 1084
<211> LENGTH: 28
<212> TYPE: DNA

<213> ORGANISM: Homo sapiens

<400> SEQUENCE: 1084
gtgagaaaca tgtgctgagt ggccacac 28

<210> SEQ ID NO 1085
<211> LENGTH: 309
<212> TYPE: DNA
<213> ORGANISM: Homo sapiens

<400> SEQUENCE: 1085
agccagcccg tgtaaatctt gaacacactg cagagaaaac caagtgcatc tcgatacctc 60
cctttcccgt gtccactggg atggatcctg gagttcgatg ttacaataaa tgaggactca 120
aggttaaggc tcagggccac tcacagctcc ctatcttggc cttgctcctg ccgtctttaa 180
acacagcagc actggagctc ctctgttctc aggacgcctt tccatctccc atagtttttc 240
tgtggcaaga aatctgcatt ggtgctgcgc ctggcttggg atcagggcca tctccactaa 300
cttgggaaa 309

<210> SEQ ID NO 1086
<211> LENGTH: 57
<212> TYPE: DNA
<213> ORGANISM: Homo sapiens

<400> SEQUENCE: 1086
tgttggccgc catcaatttg caaaaacttc accaggatac tttcaatcag cttcata 57

<210> SEQ ID NO 1087
<211> LENGTH: 49
<212> TYPE: DNA
<213> ORGANISM: Homo sapiens

<400> SEQUENCE: 1087
ctggtattcc gtgaaaacag gtttgacaag aagaccgcag gttttcacc 49

<210> SEQ ID NO 1088
<211> LENGTH: 61
<212> TYPE: DNA
<213> ORGANISM: Homo sapiens

<400> SEQUENCE: 1088
ggaggaggga accctgcttg tgtcacctcc gcttgtggat cacgtcatgg agatgagtgg 60
g 61

<210> SEQ ID NO 1089
<211> LENGTH: 277
<212> TYPE: DNA
<213> ORGANISM: Homo sapiens

<400> SEQUENCE: 1089
atactgtctt ggagatcagc ctgcctttca ttctgctagg ccatgtggga ttttgtgttc 60
ccctcgtctg gagttaggct ggttgtgggg tttgttgttg ctgtgttatc ctttgtgcat 120
catgggcttc aaatgtttct ggtggtacct tgtgtcaagg gcaagtgctg gtttggcaga 180
ggttgttttc tctgtgtctg cattcccctc tgagtctcgc ctttgcattg agtcccacag 240
agaatctgtt gcttgcggat ctctcagcta tagtatg 277

<210> SEQ ID NO 1090
<211> LENGTH: 26

<212> TYPE: DNA
<213> ORGANISM: Homo sapiens

<400> SEQUENCE: 1090
ctctcagatg cctcacaagc agcaac 26

<210> SEQ ID NO 1091
<211> LENGTH: 91
<212> TYPE: DNA
<213> ORGANISM: Homo sapiens

<400> SEQUENCE: 1091
ccataatttt gtccttctaa gcttctgatg cactgaatta tgtaaagtgc attcccttca 60
ccagcttgtg caccctattc tgtaactgat a 91

<210> SEQ ID NO 1092
<211> LENGTH: 68
<212> TYPE: DNA
<213> ORGANISM: Homo sapiens

<400> SEQUENCE: 1092
ccttctgatt atggaatact gggtcggctg gttcgacaga tggggagata agcaccatgt 60
taaagatg 68

<210> SEQ ID NO 1093
<211> LENGTH: 38
<212> TYPE: DNA
<213> ORGANISM: Homo sapiens

<400> SEQUENCE: 1093
acatgctgtg tctgaattca tcaaatatga gatctcct 38

<210> SEQ ID NO 1094
<211> LENGTH: 54
<212> TYPE: DNA
<213> ORGANISM: Homo sapiens

<400> SEQUENCE: 1094
ctttggtttc atgaacgggg ccacatattt cgggaagcac tcgggcattg tcac 54

<210> SEQ ID NO 1095
<211> LENGTH: 26
<212> TYPE: DNA
<213> ORGANISM: Homo sapiens

<400> SEQUENCE: 1095
gtcgctggtg tagtagcctc tccagc 26

<210> SEQ ID NO 1096
<211> LENGTH: 40
<212> TYPE: DNA
<213> ORGANISM: Homo sapiens

<400> SEQUENCE: 1096
gaggctccgg aagcctgttc tggcaccact gggttcttga 40

<210> SEQ ID NO 1097
<211> LENGTH: 506
<212> TYPE: DNA
<213> ORGANISM: Homo sapiens

<400> SEQUENCE: 1097

-continued

```
cccaacaggc tgtcattgca gtagacaggg ctttccggga cttagagctc cgcttcacac     60

atctggtata ctgccctgtt ggcttgaacc tctgaagaga ggcagggtag gaacggtgac    120

tgctgtaaag gcacagacct gcacggccgg gcgatacaga ctgagcaaag aaaagagtac    180

ccgttgaagg ggtgtccact cttttggctt ccctgggcca cactggaaga agaagaattg    240

tcttgggcca cacatgaaat acactaacac taatgatagc tgatgagctt aaaaaaaaaa    300

cacaaaatgt tttaagaaag tttatgaatt tgtgttgggc tgcattcaaa gccatcctgg    360

gccgcctgta gcccatgagc tgtgggttga acaagtttgc attagaaagt gaagaagtgg    420

gggcaagccc agtgtcatgg cttgacactg gaagccagtg gaaggtgccc aggaagagtt    480

gtggggaatg tccttagact ggcatc                                          506
```

<210> SEQ ID NO 1098
<211> LENGTH: 30
<212> TYPE: DNA
<213> ORGANISM: Homo sapiens

<400> SEQUENCE: 1098

```
gcagtgctca cggaggctgg agattacaca                                       30
```

<210> SEQ ID NO 1099
<211> LENGTH: 41
<212> TYPE: DNA
<213> ORGANISM: Homo sapiens

<400> SEQUENCE: 1099

```
gtactcagca cccatttaac ttacgggcca gccctcctca t                          41
```

<210> SEQ ID NO 1100
<211> LENGTH: 219
<212> TYPE: DNA
<213> ORGANISM: Homo sapiens

<400> SEQUENCE: 1100

```
tgtgggcagc agttacacca agctcctgag aacaagggca accttaactt cgaaccctgg     60

ggttaaaatc tgtgtgattt tttaaaatca gggtttctaa gcattttata agcctcagtt    120

tcttcactga agcataaaga tagtaacctt ggtctcctgt gatgactgcg aagattgagt    180

tactctttgt aaagctctta taccatggat gacatagta                           219
```

<210> SEQ ID NO 1101
<211> LENGTH: 67
<212> TYPE: DNA
<213> ORGANISM: Homo sapiens

<400> SEQUENCE: 1101

```
aaggctgtgt atccccccgt gagaccgtcg ctgtacctcc cgctgtggga cgccctatcc     60

tacttaa                                                               67
```

<210> SEQ ID NO 1102
<211> LENGTH: 790
<212> TYPE: DNA
<213> ORGANISM: Homo sapiens

<400> SEQUENCE: 1102

```
gactgtgtgg tccttacgga atccacgtag gaaaagctgc tgagctggaa tcgggagact     60

agcttctgcc cgtgcttcac cagcagctgg gcctgaactt cctgggtcac tgctcccccct    120

tttccatcag ccttcctgtc ctattttgaa gaaaggtgaa agctgtttgg aactgaaact    180
```

gtagcccttg gattcacatt ggttttacct ctgctatcac tattttagag aaaaggtagt 240
gactggtaca ctaaagaaac tacatttatt taatgtaact aaatttaatt taatgaaata 300
aacatttgct tggtgcctca ttcattgcta gacttcaact attttagaat acaatttatt 360
tactcttttt ttttcttgag acagggtctt gcttggtggc tgtggctgga atgcggtggc 420
acaatcatgg ctcactgcag ccttgaactc ctgggctgaa gcaatcctcc ggcctcagcc 480
tcttgagtag ctgggattac aggagggcac caccacgccc agctacattt ttaagttttt 540
tgtagatgtg ggtctcacta tgttgcccag gctgctctca aactcctggc ctcaagtgat 600
gcacctgctg cggcctccca aagtgctggg attacaggcg tgagcccctg cgccccatcc 660
atttcctctg ttaatcagtt cttaggatta taacgattgc tccctcatca ccatgccctg 720
catttccctg agtttccttc ctgggcagtg gagacgtaag cacagagcag tgtcacatgg 780
catctgtttc 790

<210> SEQ ID NO 1103
<211> LENGTH: 27
<212> TYPE: DNA
<213> ORGANISM: Homo sapiens

<400> SEQUENCE: 1103
ccagtcaggt cgcgtcagcc cgtcaac 27

<210> SEQ ID NO 1104
<211> LENGTH: 85
<212> TYPE: DNA
<213> ORGANISM: Homo sapiens

<400> SEQUENCE: 1104
gcggccagtc ctacgggctt gtcctgtatg agaagtccat ctgctccgga ggccgcctcc 60
gtgcccacgc tcatgacgtg gcaca 85

<210> SEQ ID NO 1105
<211> LENGTH: 68
<212> TYPE: DNA
<213> ORGANISM: Homo sapiens

<400> SEQUENCE: 1105
gtttttggat gagacaatga tagggattct gaatgagaat aataaggacc tgcacattcc 60
tgaactca 68

<210> SEQ ID NO 1106
<211> LENGTH: 47
<212> TYPE: DNA
<213> ORGANISM: Homo sapiens

<400> SEQUENCE: 1106
cctggtggag aatcaaggac gagtcaattt ttcatggcaa atacaga 47

<210> SEQ ID NO 1107
<211> LENGTH: 49
<212> TYPE: DNA
<213> ORGANISM: Homo sapiens

<400> SEQUENCE: 1107
tgtcagcatc aataactctt ccctggaggg ctttaccatc tattccctg 49

<210> SEQ ID NO 1108

<211> LENGTH: 25
<212> TYPE: DNA
<213> ORGANISM: Homo sapiens

<400> SEQUENCE: 1108
cagggcccgg ccttctactg tggga 25

<210> SEQ ID NO 1109
<211> LENGTH: 109
<212> TYPE: DNA
<213> ORGANISM: Homo sapiens

<400> SEQUENCE: 1109
ttatggattt gtgttcatca atggacgtaa ccttgggcga tattggaata ttgggcctca 60
gaaaacactg taccttcctg gagtttggct tcatccagaa gacaatgag 109

<210> SEQ ID NO 1110
<211> LENGTH: 34
<212> TYPE: DNA
<213> ORGANISM: Homo sapiens

<400> SEQUENCE: 1110
aagatgatga gtggctcaga tatcaaatct acag 34

<210> SEQ ID NO 1111
<211> LENGTH: 301
<212> TYPE: DNA
<213> ORGANISM: Homo sapiens

<400> SEQUENCE: 1111
ccactcccgg ccgtgaacat attttttggg ttgctggagt tcatctataa gtcatttttg 60
aggaataaga tttatgttaa gactatcaaa cacagtgttg cctacaatag caaaaatgtg 120
aaaataacaa caacaacaaa acagcagagg aattgttatg tattttgtag tctatctata 180
tgatgcctat ttttaggctt taaaaagtct tcaaaatctt taatgactga tttatctagt 240
taaatgctta atccttagca ggctcttatt ctttaattaa acgtgccttt gagtagatgt 300
g 301

<210> SEQ ID NO 1112
<211> LENGTH: 229
<212> TYPE: DNA
<213> ORGANISM: Homo sapiens

<400> SEQUENCE: 1112
ggtcaccgaa gcttctctga aaatgtgaca tctctgagga aggtggaaca ttaatcatct 60
ctagcagtgc ataggccctc tctatggcat tgtcaactaa gcactaataa tagtcagggg 120
acaacatgca gcgatagcca agagcatgga tcttggagcc aaagagatca ggttttaatc 180
tcagctctgc agcgctagcc atgcgctagc ttcatgcagg cttccttca 229

<210> SEQ ID NO 1113
<211> LENGTH: 25
<212> TYPE: DNA
<213> ORGANISM: Homo sapiens

<400> SEQUENCE: 1113
ccactatcac caccatcacc atcaa 25

<210> SEQ ID NO 1114
<211> LENGTH: 29

<212> TYPE: DNA
<213> ORGANISM: Homo sapiens

<400> SEQUENCE: 1114
tgagatctca taaactttca gatcaaaat 29

<210> SEQ ID NO 1115
<211> LENGTH: 143
<212> TYPE: DNA
<213> ORGANISM: Homo sapiens

<400> SEQUENCE: 1115
agccgcgagc cccagccaat gagcgccggc gggccggttg cccaggcgac cagtgcgcgg 60
ctccgccccc cgcggcgagg ctcccgcgcg cggctgagtg cggactggag tgggaacccg 120
ggtccccgcg cttagagaac acg 143

<210> SEQ ID NO 1116
<211> LENGTH: 72
<212> TYPE: DNA
<213> ORGANISM: Homo sapiens

<400> SEQUENCE: 1116
cacgtggagc ctccggcgga ggccggcccg cacgctggga ctcctgctgc tggtcgtctt 60
gggcttcctg gt 72

<210> SEQ ID NO 1117
<211> LENGTH: 71
<212> TYPE: DNA
<213> ORGANISM: Homo sapiens

<400> SEQUENCE: 1117
ccctccagcc gtcagagccc tctcagacgc accccatcgc ggccccgtcc ccactgctcc 60
gcggagagct c 71

<210> SEQ ID NO 1118
<211> LENGTH: 26
<212> TYPE: DNA
<213> ORGANISM: Homo sapiens

<400> SEQUENCE: 1118
cctctgggag gcgccttatt ccgcag 26

<210> SEQ ID NO 1119
<211> LENGTH: 79
<212> TYPE: DNA
<213> ORGANISM: Homo sapiens

<400> SEQUENCE: 1119
tgaccctatc tttcaggtca gcactttcca tattcaaaac ctccagtggg aagccgaccg 60
gcagtatcga atgaactga 79

<210> SEQ ID NO 1120
<211> LENGTH: 30
<212> TYPE: DNA
<213> ORGANISM: Homo sapiens

<400> SEQUENCE: 1120
caggtagaac agaagctcaa ggagctctga 30

<210> SEQ ID NO 1121

<211> LENGTH: 103
<212> TYPE: DNA
<213> ORGANISM: Homo sapiens

<400> SEQUENCE: 1121
cggcggtcat cgtactccgg atgttcacgg cactccggat gttctgctgt gcccggttgc 60
atggatcctg gcctatctgt gtctggtcat actctgcatg gca 103

<210> SEQ ID NO 1122
<211> LENGTH: 42
<212> TYPE: DNA
<213> ORGANISM: Homo sapiens

<400> SEQUENCE: 1122
tgccgagagg cgctttctcg cggaccggag ccttcgacgg cc 42

<210> SEQ ID NO 1123
<211> LENGTH: 46
<212> TYPE: DNA
<213> ORGANISM: Homo sapiens

<400> SEQUENCE: 1123
tgaagacctg gaatcgggtg gatgggtgga cgccgccaac gcagac 46

<210> SEQ ID NO 1124
<211> LENGTH: 80
<212> TYPE: DNA
<213> ORGANISM: Homo sapiens

<400> SEQUENCE: 1124
tctctgctcc tgcggtcggg cggctgcgac cgtgccgggg ctcggaggta ccgtgtgaag 60
tcgctgtcgc gcgtggccgc 80

<210> SEQ ID NO 1125
<211> LENGTH: 41
<212> TYPE: DNA
<213> ORGANISM: Homo sapiens

<400> SEQUENCE: 1125
cctccatgcc gagtgctgtg cttgctgccg gctgcagcct c 41

<210> SEQ ID NO 1126
<211> LENGTH: 105
<212> TYPE: DNA
<213> ORGANISM: Homo sapiens

<400> SEQUENCE: 1126
ggcggagggg agcttttccc agccacctgg acgcaggcgc cctcgagaga gaaatgccga 60
ggacctgcga aggggcgagg aagccgatct ctctgcggcc cggag 105

<210> SEQ ID NO 1127
<211> LENGTH: 177
<212> TYPE: DNA
<213> ORGANISM: Homo sapiens

<400> SEQUENCE: 1127
tccctctgcg gctccgccat cgacagctgg ggctgcaggc caagggctgg aacttcatgc 60
tggaggattc caccttctgg atcttcgggg gctccatcca ctatttccgt gtgcccaggg 120
agtactggag ggaccgcctg ctgaagatga aggcctgtgg cttgaacacc ctcacca 177

<210> SEQ ID NO 1128
<211> LENGTH: 66
<212> TYPE: DNA
<213> ORGANISM: Homo sapiens

<400> SEQUENCE: 1128
atgttccgtg gaacctgcat gagccagaaa gaggcaaatt tgacttctct gggaacctgg 60
acctgg 66

<210> SEQ ID NO 1129
<211> LENGTH: 25
<212> TYPE: DNA
<213> ORGANISM: Homo sapiens

<400> SEQUENCE: 1129
caccgacctg gtgtgggagt ccccg 25

<210> SEQ ID NO 1130
<211> LENGTH: 49
<212> TYPE: DNA
<213> ORGANISM: Homo sapiens

<400> SEQUENCE: 1130
cctcatcctg ggccgtcgtg ggaggggctg acgatgtgga cctccctag 49

<210> SEQ ID NO 1131
<211> LENGTH: 92
<212> TYPE: DNA
<213> ORGANISM: Homo sapiens

<400> SEQUENCE: 1131
ccttcgtcct gatggccgca gagatcgggc tgtgggtgat tctgcgtcca ggcccctaca 60
tctgcagtga gatggacctc gggggcttgc cc 92

<210> SEQ ID NO 1132
<211> LENGTH: 174
<212> TYPE: DNA
<213> ORGANISM: Homo sapiens

<400> SEQUENCE: 1132
ggcaaaaagc tcacagacat aggtctggtt tgtttctgtg ttccagttcc cattctgtac 60
tgaattgtgt tccagttccc attctgtact gaatttcctt ttcaggaaaa gcagcaccca 120
gaggggatcg ctttcagtga tgctgcagtg agtgccctca cgtagccatg catg 174

<210> SEQ ID NO 1133
<211> LENGTH: 60
<212> TYPE: DNA
<213> ORGANISM: Homo sapiens

<400> SEQUENCE: 1133
ggggcatagc ttctgtctcc actacccagg gccacttctc aggcactgat ccatccagcc 60

<210> SEQ ID NO 1134
<211> LENGTH: 442
<212> TYPE: DNA
<213> ORGANISM: Homo sapiens

<400> SEQUENCE: 1134
cctgaccctg tttaggactt ccagaccagg gcaagaggag cctcagagcc ttttgttaga 60
aaatatgtgt cttctcagaa cctgaagtga gaaggaagag ccctgactcc agctttggaa 120

-continued

```
ccaatccacg ctgctgtgtt cctctgggga gtttgggatc atagcaacag ggtggaggga    180

gaattcaact cttgctcacc tgctgctctg ggctgtgcgc cactgatgcc aaggcgttag    240

ccacgttggc aaggatgggg actgcctcct gctcagcccc tcgcagtctc tgtcaggctt    300

gtttttttggg gtgacgctag aaggttgtgt ctcctccttc cacagcctca gtgattccta    360

accctttga cttcactttt tgaaatggga tcacagagca agttgttgaa aactaggcct    420

ggagtcctgt gaaaagcttt tc                                              442
```

<210> SEQ ID NO 1135
<211> LENGTH: 53
<212> TYPE: DNA
<213> ORGANISM: Homo sapiens

<400> SEQUENCE: 1135

```
ggacaactta caagggcttc accgaagcag tggaccttta ttttgaccac ctg            53
```

<210> SEQ ID NO 1136
<211> LENGTH: 92
<212> TYPE: DNA
<213> ORGANISM: Homo sapiens

<400> SEQUENCE: 1136

```
acaagcgtgg gggacctatc attgccgtgc aggtggagaa tgaatatggt tcctataata     60

aagaccccgc atacatgccc tacgtcaaga ag                                   92
```

<210> SEQ ID NO 1137
<211> LENGTH: 67
<212> TYPE: DNA
<213> ORGANISM: Homo sapiens

<400> SEQUENCE: 1137

```
accgtggcat tgtggaactg ctcctgactt cagacaacaa ggatgggctg agcaagggga     60

ttgtcca                                                               67
```

<210> SEQ ID NO 1138
<211> LENGTH: 72
<212> TYPE: DNA
<213> ORGANISM: Homo sapiens

<400> SEQUENCE: 1138

```
gtaactgcac ttgtgttggg ccgtgggggc tggcggcggc cctgggctgg ctgtgcacgc     60

tcccgctgtg gg                                                         72
```

<210> SEQ ID NO 1139
<211> LENGTH: 313
<212> TYPE: DNA
<213> ORGANISM: Homo sapiens

<400> SEQUENCE: 1139

```
tgttctcagc atatcagcct ccgtgtgcct ctgaaaatgt cgtccagatt accctatcct     60

gctgaacgcc aggcatctct gtcacactca gagtgaagcg caggttctgg gaatgacctc    120

gaaaggcctc tccacttggc ctccaggacc tagctgagct cacctcctgc tccttccctt    180

tgctcacacc gtttcaccct ctttactgtt cctccaacat ccagatcccc agcctggggg    240

gctttgctct tcttccagag agctacatgg ctgttctccg aagttagcga ggctttctgt    300

agcaccacac ttg                                                       313
```

<210> SEQ ID NO 1140
<211> LENGTH: 55
<212> TYPE: DNA
<213> ORGANISM: Homo sapiens

<400> SEQUENCE: 1140
gtagtttatt tatgtcattc atctgtttca cccagcagta ctcttggcgg ggctt 55

<210> SEQ ID NO 1141
<211> LENGTH: 137
<212> TYPE: DNA
<213> ORGANISM: Homo sapiens

<400> SEQUENCE: 1141
agcagcgcct agctggcacc cagggagtga aggtccatga atggcgagga aaaggctttt 60
gtccccaggc agagtcagtc aaggacccag acctcgtgtc tccggcatgg ggaggaccag 120
cagtgatccc cacggct 137

<210> SEQ ID NO 1142
<211> LENGTH: 906
<212> TYPE: DNA
<213> ORGANISM: Homo sapiens

<400> SEQUENCE: 1142
ctcccggttt caggccttgc aaggaagccc gggagccgcc actgcttttc cctgtggccc 60
tcccacctcc aggcacccac ctgcgtgccc ctgttgccac ctgctgcccg gaataacttc 120 ttttttttt ttttaattaa aaaaattaaa tggtctaaaa gtgaaataat cgaaaatgtt 180
ggtagagaaa tacagtgttg cctactcttc gttacattct ccagaaatga ccattttcaa 240
ctctttgact ttttctttgg atattttcct tcttatttcc aaatactgtg aacatacagc 300
cctgcatcgt ttgctttaaa agttctgcct attggccggg cagtggctca ggcctgtcat 360
cccagcgctg tgggaggccg aggcgggcgg atcatgaggt caggagatcg agaccagcct 420
gcccaacatg gcgaaaccct gtctctactg aaaatacaaa aaattagccg ggtgtggtgg 480
cgggcacctg tagtcccagc tactcgggag ctgaggcagg agaatccgtg aacccgggtg 540
gcggagtttg cagtgagccg agattgcacc actgcactcc agcctggacg acagagcaag 600
actccgtctc aaaaaaaaaa caaaaaaacaa aaaacattat ccgagcgtgg tggcgggtgc 660
ctgtaatccc agctacttgg gaggctgagg caggagaatt gcttgaatgt gagaggcaga 720
ggttgcagtg agccccgatg gtacccctgc actctagcct gggtgacaag agcaaaactc 780
cgttaaaaaa aaaaattctg cctattgact tcttgttcca gtaggtgatg agtgttcttt 840
cctgccagca tggctgttca gccctgatag gcgccagcgt gggcctcgcg gatgtgtatg 900
acaacg 906

<210> SEQ ID NO 1143
<211> LENGTH: 82
<212> TYPE: DNA
<213> ORGANISM: Homo sapiens

<400> SEQUENCE: 1143
ctgcttggct gcatcccgcg tggaatcctg cttcctggag ttccaggaaa caggatgttt 60
cttggtgctc cgtggcttcc cg 82

<210> SEQ ID NO 1144
<211> LENGTH: 116
<212> TYPE: DNA

<213> ORGANISM: Homo sapiens

<400> SEQUENCE: 1144
actccggctc ccgagcgttt cctgggtctt cttcctcctc gcccccggcc aagttcctca 60
gggagcccgc cctccccttc tcgtgctgct gcgcatccgg ggagcggccc agttac 116

<210> SEQ ID NO 1145
<211> LENGTH: 28
<212> TYPE: DNA
<213> ORGANISM: Homo sapiens

<400> SEQUENCE: 1145
cagctcgggc ccagggttct caggcagg 28

<210> SEQ ID NO 1146
<211> LENGTH: 71
<212> TYPE: DNA
<213> ORGANISM: Homo sapiens

<400> SEQUENCE: 1146
tcttggccac catcaacttg cagtcaacac acgagctgca gctactgacc acctttctct 60
tcaacgtcca g 71

<210> SEQ ID NO 1147
<211> LENGTH: 337
<212> TYPE: DNA
<213> ORGANISM: Homo sapiens

<400> SEQUENCE: 1147
ctgctcagcg gcctatggga attctgaatg cctgtcagcg tgctcagctt ccccagcgca 60
gggagctgga ctcagggctg atggcctctg gccccccgcc catgccactg tgtgcctgca 120
aggcccgctg cccagaaaca cctctgaggg ctgctgtgta ggctgatgca gtgtggacat 180
cacccactgc cctgagagag gggccctttt ggtgcactcc tagaggactc gacttttgtg 240
gcctcaacta gctccagact tgctcccagg gattgagggg ggaaggaaaa acttccctgt 300
cctatactac acaggcatcc gaccttaacc tgtgagg 337

<210> SEQ ID NO 1148
<211> LENGTH: 65
<212> TYPE: DNA
<213> ORGANISM: Homo sapiens

<400> SEQUENCE: 1148
ctctgggctt ctgcaaacgt ggcagagtgg agcatggtcc caggaatgat cttggcctcc 60
ttggg 65

<210> SEQ ID NO 1149
<211> LENGTH: 27
<212> TYPE: DNA
<213> ORGANISM: Homo sapiens

<400> SEQUENCE: 1149
cagaacctgc accatgaata gctgtgc 27

<210> SEQ ID NO 1150
<211> LENGTH: 38
<212> TYPE: DNA
<213> ORGANISM: Homo sapiens

<400> SEQUENCE: 1150
aactggtgtg caggcgaatt tggccctcac ctatgccc 38

<210> SEQ ID NO 1151
<211> LENGTH: 56
<212> TYPE: DNA
<213> ORGANISM: Homo sapiens

<400> SEQUENCE: 1151
actggacggg gtggtttgac tcgtggggag gccctcacaa tatcttggat tcttct 56

<210> SEQ ID NO 1152
<211> LENGTH: 105
<212> TYPE: DNA
<213> ORGANISM: Homo sapiens

<400> SEQUENCE: 1152
gttttgaaaa ccgtgtctgc cattgtggac gccggctcct ccatcaacct ctacatgttc 60
cacggaggca ccaactttgg cttcatgaat ggagccatgc acttc 105

<210> SEQ ID NO 1153
<211> LENGTH: 27
<212> TYPE: DNA
<213> ORGANISM: Homo sapiens

<400> SEQUENCE: 1153
cttcgtgtct ttggcaatag agtacct 27

<210> SEQ ID NO 1154
<211> LENGTH: 28
<212> TYPE: DNA
<213> ORGANISM: Homo sapiens

<400> SEQUENCE: 1154
cagtcatgtt acactcccag aggaggga 28

<210> SEQ ID NO 1155
<211> LENGTH: 73
<212> TYPE: DNA
<213> ORGANISM: Homo sapiens

<400> SEQUENCE: 1155
atgctgtgct gacagaagcc ggcgattaca cggccaagta catgaagctt cgagacttct 60
tcggctccat ctc 73

<210> SEQ ID NO 1156
<211> LENGTH: 78
<212> TYPE: DNA
<213> ORGANISM: Homo sapiens

<400> SEQUENCE: 1156
tctcagaccc ctaaagagtt acttccttac tgtcccacct cgaccccagt tgatctgcgt 60
gcaagaatat cctagaca 78

<210> SEQ ID NO 1157
<211> LENGTH: 38
<212> TYPE: DNA
<213> ORGANISM: Homo sapiens

<400> SEQUENCE: 1157
accttcttcc caagatgccg tatgagccct taacgcca 38

<210> SEQ ID NO 1158
<211> LENGTH: 26
<212> TYPE: DNA
<213> ORGANISM: Homo sapiens

<400> SEQUENCE: 1158
ctctgtggga cgccctcaag tacctg 26

<210> SEQ ID NO 1159
<211> LENGTH: 27
<212> TYPE: DNA
<213> ORGANISM: Homo sapiens

<400> SEQUENCE: 1159
gtgagtgctg tgggcagtca tcgggag 27

<210> SEQ ID NO 1160
<211> LENGTH: 102
<212> TYPE: DNA
<213> ORGANISM: Homo sapiens

<400> SEQUENCE: 1160
aacctgccag tcaatggggg aaatggacag tccttcgggt acattctcta tgagaccagc 60
atcacctcgt ctggcatcct cagtggccac gtgcatgatc gg 102

<210> SEQ ID NO 1161
<211> LENGTH: 36
<212> TYPE: DNA
<213> ORGANISM: Homo sapiens

<400> SEQUENCE: 1161
gtaggagctt ctcttctaaa ttcctgtgac cttctg 36

<210> SEQ ID NO 1162
<211> LENGTH: 62
<212> TYPE: DNA
<213> ORGANISM: Homo sapiens

<400> SEQUENCE: 1162
gtgtttgtga acacagtatc cataggattc ttggactaca agacaacgaa gattgctgtc 60
cc 62

<210> SEQ ID NO 1163
<211> LENGTH: 78
<212> TYPE: DNA
<213> ORGANISM: Homo sapiens

<400> SEQUENCE: 1163
ggttacaccg tgctgaggat cttggtggag aatcgtgggc gagtcaacta tggggagaat 60
attgatgacc agcgcaaa 78

<210> SEQ ID NO 1164
<211> LENGTH: 26
<212> TYPE: DNA
<213> ORGANISM: Homo sapiens

<400> SEQUENCE: 1164
aatctagcta aatgtgggtg gtttca 26

<210> SEQ ID NO 1165
<211> LENGTH: 43

<212> TYPE: DNA
<213> ORGANISM: Homo sapiens

<400> SEQUENCE: 1165
ttaattggaa atctctatct gaatgattca cccctgaaaa act 43

<210> SEQ ID NO 1166
<211> LENGTH: 38
<212> TYPE: DNA
<213> ORGANISM: Homo sapiens

<400> SEQUENCE: 1166
ctggcccgca cccaggtgtg aacgcctcca ggggccag 38

<210> SEQ ID NO 1167
<211> LENGTH: 35
<212> TYPE: DNA
<213> ORGANISM: Homo sapiens

<400> SEQUENCE: 1167
gttcggcctg gacaaatgga gttccctccc agaaa 35

<210> SEQ ID NO 1168
<211> LENGTH: 26
<212> TYPE: DNA
<213> ORGANISM: Homo sapiens

<400> SEQUENCE: 1168
atgaacaccc ttcccctctg tttcaa 26

<210> SEQ ID NO 1169
<211> LENGTH: 60
<212> TYPE: DNA
<213> ORGANISM: Homo sapiens

<400> SEQUENCE: 1169
tggccagaac cttggacgtt actggaacat tggaccccag aagacgcttt acctcccagg 60

<210> SEQ ID NO 1170
<211> LENGTH: 48
<212> TYPE: DNA
<213> ORGANISM: Homo sapiens

<400> SEQUENCE: 1170
cctgttcccc atgacgccct gcccacctgc cgtcccaggg agccttcg 48

<210> SEQ ID NO 1171
<211> LENGTH: 42
<212> TYPE: DNA
<213> ORGANISM: Homo sapiens

<400> SEQUENCE: 1171
gacagacgtc agctgccctc ccagccgggc cctctctcca ca 42

<210> SEQ ID NO 1172
<211> LENGTH: 82
<212> TYPE: DNA
<213> ORGANISM: Homo sapiens

<400> SEQUENCE: 1172
tcatcgtttt tgaggagacg atggcgggcc ctgcattaca gttcacggaa accccccacc 60
tgggcaggaa ccagtacatt aa 82

<210> SEQ ID NO 1173
<211> LENGTH: 119
<212> TYPE: DNA
<213> ORGANISM: Homo sapiens

<400> SEQUENCE: 1173
tgccagtggg agactgccgc ctcctcttga cctgaagcct ggtggctgct gccccacccc 60
tcactgcaaa agcatctcct taagtagcaa cctcagggac tgggggctac agtctgccc 119

<210> SEQ ID NO 1174
<211> LENGTH: 71
<212> TYPE: DNA
<213> ORGANISM: Homo sapiens

<400> SEQUENCE: 1174
ccctgctctt gtgccgaggc tgtcgggctg tctctagggt gggagcagct aatcagatcg 60
cccagccttt g 71

<210> SEQ ID NO 1175
<211> LENGTH: 260
<212> TYPE: DNA
<213> ORGANISM: Homo sapiens

<400> SEQUENCE: 1175
aaaagtgctg aaacgtgccc ttgcactgga cgtcacagcc ctgcgagcat ctgctggact 60
caggcgtgct ctttgctggt tcctgggagg cttggccaca tccctcatgg ccccatttta 120
tccccgaaat cctgggtgtg tcaccagtgt agagggtggg gaaggggtgt ctcacctgag 180
ctgactttgt tcttccttca caaccttctg agccttcttt gggattctgg aaggaactcg 240
gcgtgagaaa catgtgactt 260

<210> SEQ ID NO 1176
<211> LENGTH: 43
<212> TYPE: DNA
<213> ORGANISM: Homo sapiens

<400> SEQUENCE: 1176
gaaatcctca ccctgcgtct tcccaagtta gcaggtgtct ctg 43

<210> SEQ ID NO 1177
<211> LENGTH: 28
<212> TYPE: DNA
<213> ORGANISM: Homo sapiens

<400> SEQUENCE: 1177
gtgagtcctg gcagaagcca tggcccat 28

<210> SEQ ID NO 1178
<211> LENGTH: 60
<212> TYPE: DNA
<213> ORGANISM: Homo sapiens

<400> SEQUENCE: 1178
cccagctcac atgtgagtcc tggcagaagc catggcccat gtctgcacat ccagggagga 60

<210> SEQ ID NO 1179
<211> LENGTH: 28
<212> TYPE: DNA
<213> ORGANISM: Homo sapiens

<400> SEQUENCE: 1179
gtgagtcctg gcagaagcca tggcccat 28

<210> SEQ ID NO 1180
<211> LENGTH: 39
<212> TYPE: DNA
<213> ORGANISM: Homo sapiens

<400> SEQUENCE: 1180
tctgcacatc cagggaggag gacagaaggc ccagctcac 39

<210> SEQ ID NO 1181
<211> LENGTH: 28
<212> TYPE: DNA
<213> ORGANISM: Homo sapiens

<400> SEQUENCE: 1181
gtgagtcctg gcagaagcca tggcccat 28

<210> SEQ ID NO 1182
<211> LENGTH: 40
<212> TYPE: DNA
<213> ORGANISM: Homo sapiens

<400> SEQUENCE: 1182
tctgcacatc cagggaggag gacagaaggc ccagctcaca 40

<210> SEQ ID NO 1183
<211> LENGTH: 115
<212> TYPE: DNA
<213> ORGANISM: Homo sapiens

<400> SEQUENCE: 1183
agagcagccc tccttcgaag tgtgtccaag tccgcatttg agccttgttc tggggcccag 60
cccaacacct ggcttgggct cactgtcctg agttgcagta aagctataac cttga 115

<210> SEQ ID NO 1184
<211> LENGTH: 111
<212> TYPE: DNA
<213> ORGANISM: Homo sapiens

<400> SEQUENCE: 1184
agctgtgtat gagctggttc cgtcagaaag tgatggaatg gaagggaacc ttcctgcaaa 60
tcctcctgta aggtggagaa gccccttgga tcacacttcc acgcagacct g 111

<210> SEQ ID NO 1185
<211> LENGTH: 140
<212> TYPE: DNA
<213> ORGANISM: Homo sapiens

<400> SEQUENCE: 1185
agcaggctga gcaacgcttg ttccgcctgg tggagagttc gttcttcttg ggcccgggga 60
gctgcatgtc agggtgttgc tgcttcgctc aagggtcact tatcacggag gcctctgtgg 120
tcaccctaca gagcactgac 140

<210> SEQ ID NO 1186
<211> LENGTH: 50
<212> TYPE: DNA
<213> ORGANISM: Homo sapiens

<400> SEQUENCE: 1186
tgatgttttc ttgctagtgc cacctcttat gaatcccatt gtatattgtg 50

<210> SEQ ID NO 1187
<211> LENGTH: 29
<212> TYPE: DNA
<213> ORGANISM: Homo sapiens

<400> SEQUENCE: 1187
cttctatgcg cccgtcattg ctttggcat 29

<210> SEQ ID NO 1188
<211> LENGTH: 148
<212> TYPE: DNA
<213> ORGANISM: Homo sapiens

<400> SEQUENCE: 1188
aagctggcct gctccgacaa cactgtcaac ttcttctatg gtttctttct tgccctctgt 60
atgatgtcag aaagtgtgtt cattactgtg tcttatgtgc tcatcctgaa gacgatcatg 120
ggaattggat cccataggga gcggctca 148

<210> SEQ ID NO 1189
<211> LENGTH: 89
<212> TYPE: DNA
<213> ORGANISM: Homo sapiens

<400> SEQUENCE: 1189
tgctgttagt actcccattt cctttcactc ttacaaggtt gacatattgt aggaaaagcc 60
tactctctca ttcctattgt ctccatcag 89

<210> SEQ ID NO 1190
<211> LENGTH: 93
<212> TYPE: DNA
<213> ORGANISM: Homo sapiens

<400> SEQUENCE: 1190
ttttgaccgg ttttggccat atgccaccct ctgaggtaca tatctgaggt actggtgagc 60
tgtatcctca ccagtgccag agttgccaaa atg 93

<210> SEQ ID NO 1191
<211> LENGTH: 284
<212> TYPE: DNA
<213> ORGANISM: Homo sapiens

<400> SEQUENCE: 1191
tggagcatgc ccatatatgg atatctgtcc ccatctgcct catgtacttg gtagccatcc 60
taggcaattg cacaatcctc tttgttatca ggactgagcc ctcactccat gcacccatgt 120
actatttcct ttccatgttg gctgtctctg atctgggcct gtccctctcc tacctaccca 180
ctatgctgag gatctttgta ttcaatgcca caggaatctc ctcaaatgct cgctttgctc 240
aagaattctt tattcatgga ttcacagata tggagtcctc agtg 284

<210> SEQ ID NO 1192
<211> LENGTH: 39
<212> TYPE: DNA
<213> ORGANISM: Homo sapiens

<400> SEQUENCE: 1192
aagctgcaga accaacgagg tggccgaatc ttccttcag 39

<210> SEQ ID NO 1193
<211> LENGTH: 346
<212> TYPE: DNA
<213> ORGANISM: Homo sapiens

<400> SEQUENCE: 1193
aggtgctggt catcattctg tcccattttt tgccactgtg ctaaggcttt tgactcaacc 60
aagaaaaggg ccggtcttcc agcctggccc tgcaagagtg tcctagtgct tcaggtagtg 120
gatgggcatc gtcattcgtc ccaccttcct gccccctaaa gccccaggag gacacactct 180
cagcatcagg ccagctctcc gggtcactgg ggcttggctc aacaggatgt gcagggcaga 240
gccgggaggg aagagcagaa gatgccatgg gctgttcgca ggagcagccg tccagggcgc 300
cgctggagga agatcttcta gtggctgtct cagcacgtac aaagaa 346

<210> SEQ ID NO 1194
<211> LENGTH: 192
<212> TYPE: DNA
<213> ORGANISM: Homo sapiens

<400> SEQUENCE: 1194
cagagcttca tgacggcctc ggattggcag tcaacccagg gatacagaaa tgtaaacaaa 60
aacagagctt ccagataaca ttactgtgtg ctatgtgact ttcagaatac agcagcgtcc 120
cagacactct aaagtcaagt gaaacaagag attttagaat caatctatac acatttcaga 180
gggcagtcca gg 192

<210> SEQ ID NO 1195
<211> LENGTH: 1103
<212> TYPE: DNA
<213> ORGANISM: Homo sapiens

<400> SEQUENCE: 1195
tcttctctcc agctaggtgc acttgaggtt gttcataaat gtaaaattat gtcaggtttc 60
taacatggga cactgcacac agttgtctga cctgatgaac catcccattt gaaagtatag 120
attattatta tttcttgtag tatttggttg ttttccatct cattcatgaa caactcaacc 180
tgatagtagt atccaataaa tgcctttcag ggctcaggaa tgaattgaca tcctagttaa 240
gaaatgagac ttaataatgg agactgaatg aggcggtttg tattaaatta tatgccatga 300
agtgttcatt ttagctttaa cctaattatg actgtaccac catgaagtac agaatgaaaa 360
attatatata tggggggGaa acagaatgaa tatctgattc ttttgaatgc ttgtggaaat 420
ctttgagatc gtgcagggca taccacaaaa tagcctttag aacagatacc caattttaca 480
gttcatagga caacatcaaa cattagtaag tctaaataag atgaatagaa tttttgttat 540
gtaaattttg ctagaacagt ctattttctt gcacccctca agttaacctc ttaaaaaaat 600
gaatgtataa tttctaccga aagaatatca gagagaatct ctctggccta tagtgttaaa 660
atattgttca caaatcctga ttagttaagt gcatacatta tgaaacttac agaataaaac 720
ttattataca tctctttctt aaattaatat ctttacacat tttcaactgg ctccccaagt 780
ctgataagga aggattaaaa gaaaaaagaa atgtattagt tgggtggcca aggagtttcc 840
tttgtaatgt tgagagactt ccgctttctg aatttcgctg gttctctaag gtaaaagagt 900
taaatagtac ccttgttcac caaggaaagt gatccaaact atatatctag tgcagatatt 960
tcctttgcat tatttagtct tctctggaga gaaaatacag tttccccttc ctctttctct 1020
tcacatttac tcttttcaac ccaaaataag agacatagaa agcaaaccac agccagtttg 1080
gcatcttctc agtgctacta gta 1103

<210> SEQ ID NO 1196
<211> LENGTH: 36
<212> TYPE: DNA
<213> ORGANISM: Homo sapiens

<400> SEQUENCE: 1196
tgacttgtaa cccttcagtg gaatgggaaa tttctg 36

<210> SEQ ID NO 1197
<211> LENGTH: 649
<212> TYPE: DNA
<213> ORGANISM: Homo sapiens

<400> SEQUENCE: 1197
tggcttagtt agcagaccta gaatctgccc aggtgagacc tagaacaaaa atagctgggg 60
tgaaatggat aagagaggta gaggtatatg tcaaggcaga gccctatgag gaaggaagag 120
ttttcaaaga atatgaggaa catagtgctg agagtgtggc tgccttcagc accgtacacc 180
taatctagag aaaatatttc ccatgtggga ggtcctgtct gcattcagtc cacccttttc 240
tgcctgcttc ttcctccaag tgcctcaacc tctacatgct cactctcctc cccttccctc 300
agcccatctt ggtctaagca gctttcacaa tccaaaccaa acatcaccag ccacccgctg 360
ataagtcacc agcatttact ttcctgagtt actttttctc cattcattga gactatggat 420
tcatcccaac tccttctaaa tccctcaacc atccagctat attttggcta acctttgccc 480
tagacactct accagatgtt aatgcagtat caagtgtaaa ttgtgtcacc ctattctgtt 540
ctaccctttt ccctgctgcc gaaatatctt gctctcctct acctcatccc caaagagcct 600
ataaattcag agtatccaac cttttcatgg attcactcac tgttgttca 649

<210> SEQ ID NO 1198
<211> LENGTH: 3484
<212> TYPE: DNA
<213> ORGANISM: Homo sapiens

<400> SEQUENCE: 1198
cgctgttgaa ccaagctgct cactggacac atatttgtgt ccccaggaga ttatttgtca 60
ggcactgttt tttatttgtt tgtttgttca tttattgttg ttttactgct attggcgata 120
acatgaaatg tgatacagct attgcccata atttaatgtg aaattaatca tgatgaattc 180
tatagcatgc tactgaaatg ccaaattcag ctattttctt tctcttctaa aatggaagtt 240
tcagttttcc atatcagatg tatataagtg gaattataac acaatcctat cactgacagt 300
aatcctcagt caccttaaat aatcagtgct cacagtgctg cttacagttc atttagttgg 360
cacatataaa cctgtaccca cacaagactg accaaaaatt ttctttgcac atttttcctt 420
tctcatagtt tttttctata tttcgttaag caaaggaagg ttaatatgcc tatttttcct 480
gttaggcttt tagaaattat tttccatgac ttttgttctt ataataggtt agacagttta 540
tttttcaaag gtaaaaattg tgtttctatg cattaatgtg attgaactac aaaaacagag 600
tgcaatatgt tcaaaaaata ctcaactaaa ctttcccccct gtcatatcac tgcaaaagtg 660
tccttttaaa cagagccata aagaaatttt tttcaaattt ctttattgca caggcttttt 720
tcagttttac ctttctggga ttgaacaatg ttcctttcat aatgccaaag cattcccttc 780
cccagaaaaa tctccttgga caactggttt aaaaacgtta ttaagtcata ggggaggaat 840
aagcggccaa aaagtcacat ttttgcattg gtttacgttg cttgattaga ctatcttcag 900

-continued agagcacatt atgtgtttat agctttaatt tgtattatgt caatgaacca gtgaagtgcc 960
taaagagatg cttacaacta tccagtagga cacaactgca ctgcttttta aacacttttt 1020
ggttagttaa gggtgacttg aattgtacac atacatgcta atttttgaaa acttatccat 1080
ttttcatagt aaataatata gataaaattt tctgttagag ttcccgcaaa tatttcattt 1140
tagacttact tgtgatataa gatttaactt ttcttttgtg aaagaatcgt gaactagtgt 1200
ttcatgaaat cattttcctc ttccatttat catcctcctc tggtacaata tattgggttg 1260
ctttctttta gattttgttc cagataggaa aacaaatatg actgtatact tattaacata 1320
aggtagttct gcatttttgg attccaggat cctgtttgaa atcttccatg tgaggaaaaa 1380
attactaata tttttaaaga cagggtggtt tatttaaaga gattattcag agaacttgtg 1440
ccatatctcg tctgttttat tgcatatgcc atatgttaac ttttattcaa tattacatta 1500
tgtagatatg taatacaaag aaaatattta ggagaatggc aaaacacaaa tggcaacata 1560
aatgtccatt tgacttacct aacttcacaa ctttcaagtt gaggatgtca tttattcttg 1620
aatttgtttt tttactagat gctttcaatt aatagcccta tatttttgtg caggcgaact 1680
gtataacagg ataaaaaatg atttgtatgt attgaaaagg aggagaaatt ctcacagaac 1740
accatatgag ctttagacca aaaggggaaa caaggtttaa gtaactaaaa tggccactta 1800
gtttgtgttt attttttttcc ctggaaatgt aagtagttgg agtttaggct atggaaatat 1860
tagtgccttt aatagatctc tttccttgca aagtttcttt ttagctcagc attgatctat 1920
cttatcaata ggaaaataag ttgacttgga actataaaca aaaacaacac catatattta 1980
tgaacctcag tgaaccagcc tagaaaaatt gacttctgca ggtgctaaag cacctactaa 2040
tacgcagcat gcacagcatt tcaggttgtg aataccattt tacaacgagt ttgctgttaa 2100
ctctctttat ccaatgcaaa cttgaaattc tgatgcggtt ttccagggtg gtatttttttc 2160 agagtattga atttactatt tagtaattta tagtatagct ttttatatta aaatgtgata 2220
tttttaaaag agatatctgg ttcaattggt ataatgacgt gattatgcaa tatgctgatc 2280
tacaccttgc gctcacattg tgccaaactt aaatgtgcaa gtgtacgtga gaaaagcaca 2340
tgtgaatgtg aattctttaa ttctttgctt attatgttaa aattagtctt catagtccac 2400
tgatgtgtat gcttgaataa tgtctattta ctttggaatt tcaagatttc cagcttcaat 2460
ggtaatttat aatttctcag atcaccttaa gaaatattga gatactctcc cacctgaaaa 2520
taatctgttc tttaacccac ctgactatgg gagtagccag gcaggtgcct cactggcttc 2580
ttcagacgag gcttcctcag gtggatatat gactattagg ggaaaagagg cttttgagac 2640
agcttattac ctccttcccc tttttgaact aagtacattg tctcagtccc agtatgaatt 2700
tgtcccattt ggggtatttt taaaataaaa gatggctaac atggaatctg gggcatagcc 2760
ttggccttta attatggttg taagcccaaa taatggcaga gaaacacagg gctgttttta 2820
caacagaaaa ctcaatataa gttttatata agaatcctat aaaatttgaa ccagagctcc 2880
tatttagttg ttataatgtc tcctaaagat cttaaatgct tctaaaagct aattattatt 2940
ccagagcaac tttttccttt tcccccttat aaagtttttt tttaaatcca aaatcttaga 3000
tttctgtgcc acagcaaaat aaaatgatca acaattaaag atctgtactt aaaatagtac 3060
accattttta gtggagggag ggtgcatgcc tatatgatgg taagattctt ttgaactcta 3120
aggacaattc ctcatggaaa aaataaattt cagtgcatat tataaaaatg atttgcactg 3180
tgttagcaaa ataaggtgtt ttaggttgta ttttaaagac aattctaaat catttctctg 3240
gaaagcaaga ccttaaattc ttctctttaa tagaactgct tttatgcaaa gagatggtct 3300
taacatggac taaacagtac ataacaataa tgtttgttat gtaaatagta tatcacattt 3360
gcttagtagc acaattcaac agcaggctga aagtcgtggc tcctctgctc agattgagtt 3420
ttaagttacc taatttatgt aatcagaatc tattctaggt ggccgtcaac gtaaactgtg 3480
tttc 3484

<210> SEQ ID NO 1199
<211> LENGTH: 200
<212> TYPE: DNA
<213> ORGANISM: Homo sapiens

<400> SEQUENCE: 1199
ctagtgtcaa agtttagccg tttgtttttt ttttttgtt ttttgcggct gtaatgtgca 60
atgatgtgtt ttattttcct tgatgcttaa cattactaac aattgcaaaa ataatactga 120
ggagcactac tttgcattgt ttgtagttgg agttttggat actgatcata aatcatgaat 180
ctggcgtatt aatgcttaac 200

<210> SEQ ID NO 1200
<211> LENGTH: 72
<212> TYPE: DNA
<213> ORGANISM: Homo sapiens

<400> SEQUENCE: 1200
tacttttaat ggaagcacga atgcaagctg aacttcttta tgctcttcgt gccataactc 60
ggcatttgac ct 72

<210> SEQ ID NO 1201
<211> LENGTH: 362
<212> TYPE: DNA
<213> ORGANISM: Homo sapiens

<400> SEQUENCE: 1201
tatggcttca gtacctaaca gattttttga agtcttagag ccactcacat caggtaaata 60
cccattttac atccagcatt tccccttgat gggtctttat cccatattta tatgtttgct 120 ctagatttc ttccttttct agattgtatc tagaaattct ctttactctt caggagaata 180
tatccaacca catatccaac tggtataaat atatcaaaag aatataatat taaaacatat 240
ttttatagta aattttgaaa acttgtggat acccatttta acttatcagc cgagatgtaa 300
ccccgaaaga aatgttctgc agaattttat ctgaaagact ctagggaagc tatgtatgtc 360
ta 362

<210> SEQ ID NO 1202
<211> LENGTH: 33
<212> TYPE: DNA
<213> ORGANISM: Homo sapiens

<400> SEQUENCE: 1202
gtacgtgttt cagtattaag cattatacca tag 33

<210> SEQ ID NO 1203
<211> LENGTH: 100
<212> TYPE: DNA
<213> ORGANISM: Homo sapiens

<400> SEQUENCE: 1203
gaagcctgaa ggtttacatt aagacagtga cctgctatcc tgagagaact acaaaacgca 60
tgtatgatag ttactggcgg cagttcaaac actcagaaaa 100

<210> SEQ ID NO 1204
<211> LENGTH: 146
<212> TYPE: DNA
<213> ORGANISM: Homo sapiens

<400> SEQUENCE: 1204
ggttctccct ggtgaacaga ctttattctg acattggaca tcttcttgat gaaaagtttc 60
ggatggtcta caatctcaca tataacacta tggccaccca tgaggatgtt gacacaacca 120
tgctgcgcag agctttattt aactat 146

<210> SEQ ID NO 1205
<211> LENGTH: 109
<212> TYPE: DNA
<213> ORGANISM: Homo sapiens

<400> SEQUENCE: 1205
tgacatgatt ataacatctg atgtctctcg atatattgaa gaccctggtt ttgggtatga 60
agactttgcc agacgaggag aagagcattt gccaacattc cgagctcag 109

<210> SEQ ID NO 1206
<211> LENGTH: 218
<212> TYPE: DNA
<213> ORGANISM: Homo sapiens

<400> SEQUENCE: 1206
cagtggtgtt agtaagatac agttaattta tttcttaaat ggatatttct tcctgtatta 60
atgaaacaaa aaatagatag taagtgtgta gtatagtact tggtatatgg taagtactca 120
gtaaacaccg tctcttttct ttatatgtaa tgaagtttgt taagaatttt aataagattt 180
atctgaaatt gggtaaccgg agcacttaat ctttcctg 218

<210> SEQ ID NO 1207
<211> LENGTH: 400
<212> TYPE: DNA
<213> ORGANISM: Homo sapiens

<400> SEQUENCE: 1207
ttgaccagcg ttataaagta ttccagattc tatgtaagga ttctaagaat agtttttcaa 60
gtcttttgaa gaaaataaat gtttaaagta ttctacaggg gtcatattct gtagcttggt 120
aacagggtta actagctttt actgtttttt gtattttcag ttacgcattc cattactgca 180
acagaatgtt tcccgtatta tgtcagtaac tacttcttag gggcagaata atgcagataa 240
tgaacaaaat actatttctt ttgagtacag actttgaaat atttgtttag atagaattaa 300
agctagagtt ttagatttaa taatcagaat gctaatttta acttcttaag ataaatttag 360
gaaaaaagta tttgtggatt gagggacctt tgtacatttc 400

<210> SEQ ID NO 1208
<211> LENGTH: 87
<212> TYPE: DNA
<213> ORGANISM: Homo sapiens

<400> SEQUENCE: 1208
tttcagtctc taccttcttg gaactttaag ctgggactac agccttcaaa agtgaatttt 60
gactagaaag tcttggacct tagccaa 87

<210> SEQ ID NO 1209
<211> LENGTH: 116
<212> TYPE: DNA
<213> ORGANISM: Homo sapiens

<400> SEQUENCE: 1209
ctcttctatc ttaccctcat gctattgctt tccctcaggc tggttcatcc ttgaatgtat 60
ttcagattga gttgagagaa actttcagct ttgtagttca tactctatcc tggata 116

<210> SEQ ID NO 1210
<211> LENGTH: 116
<212> TYPE: DNA
<213> ORGANISM: Homo sapiens

<400> SEQUENCE: 1210
ggattctcta agtgagctag aggccttaat ggaaaggatg aaaagacttc aagaagaaag 60
ggaagatgaa gaggcgtctc aagaagaaat gagcactcgt tttgaaaagg agaaga 116

<210> SEQ ID NO 1211
<211> LENGTH: 208
<212> TYPE: DNA
<213> ORGANISM: Homo sapiens

<400> SEQUENCE: 1211
tggtctctgc ctgaactggt acatgctgtg gtcctcctgg cacattatca tgctttggca 60
agctttgttt ttggtagtgg tatcaatcca gagagagatc cagaaatctc caatggattc 120
aggctaatat cagtcaacaa tttctgcgtt tgtgatcttg ctaatgacaa caacatagag 180
aatgcatctc tttcaggcag caactttg 208

<210> SEQ ID NO 1212
<211> LENGTH: 126
<212> TYPE: DNA
<213> ORGANISM: Homo sapiens

<400> SEQUENCE: 1212
ttttaaagac tggaggtatt gctgagtggt tgaatggttt ggaatatgtg ccacaaagac 60
tgaaaaatct taatgaaatt aataagctgc tagcacatcg accttggctg atcacaaaag 120
agcaca 126

<210> SEQ ID NO 1213
<211> LENGTH: 166
<212> TYPE: DNA
<213> ORGANISM: Homo sapiens

<400> SEQUENCE: 1213
gtgcttattt tcctatgttc acataacacc ttcctcactt attctttctc ccttccaaaa 60
taggcatgtg tccttgtgtg tgtatagagc taagtataat ttatggacat aagaactgaa 120
gaagcctatg gccttttgga taccaagtgt cttgggtata tttgga 166

<210> SEQ ID NO 1214
<211> LENGTH: 103
<212> TYPE: DNA
<213> ORGANISM: Homo sapiens

<400> SEQUENCE: 1214
gaatactcta catccggtcg tctggacaac atcacacagg tcatgagttt acacactcag 60
tacctggagt ctttcttgcg gagccagttt tacatgttgc gca 103

<210> SEQ ID NO 1215
<211> LENGTH: 88
<212> TYPE: DNA
<213> ORGANISM: Homo sapiens

<400> SEQUENCE: 1215
tctgtttcca gtatgagcaa ctgcataatt tcagtgtctg ttaatatcaa atgaatattc 60
atttgcttca atagtggcat aatttatt 88

<210> SEQ ID NO 1216
<211> LENGTH: 30
<212> TYPE: DNA
<213> ORGANISM: Homo sapiens

<400> SEQUENCE: 1216
gacaagagga ccaagtgcct ttattccaga 30

<210> SEQ ID NO 1217
<211> LENGTH: 368
<212> TYPE: DNA
<213> ORGANISM: Homo sapiens

<400> SEQUENCE: 1217
agtgagcgtg cccttgatac ttttctgggg actgtaatgt aagcagaaat tgagacaagg 60
gtccttggaa ctggctgata gtttttttc ttcctaattt gcccaaatag gacaaatagg 120
ttgattggtt cagagcattt ctgcaattac actaaaatgc ttggttctgg gattgagtag 180
gtgtgaccat caaatgaata actctgtgga gcagtcattt aacatttcaa aaagttataa 240
aaatgtctga aaatgcaatt ttaaaaaagc aaaaccaaat gagtccagag cagcactgtc 300
cggtagaact gtctgcagtg gaagatggaa atgtctgcgc tgtcctgtag agtacacgtg 360
gtcctatg 368

<210> SEQ ID NO 1218
<211> LENGTH: 196
<212> TYPE: DNA
<213> ORGANISM: Homo sapiens

<400> SEQUENCE: 1218
cggagaagag ctagcgagtt ctctagataa aaaagattca ggaggcagtt gcatgggttg 60
ctcattttcg tatcctgtgc ccttattttt tccttcatct gctccatcgt cttccctaca 120
atatagtcac cataacaaat ttgagtagaa ttttgttttg tgtaaagaat atggtagcca 180
tagaagagaa cattga 196

<210> SEQ ID NO 1219
<211> LENGTH: 30
<212> TYPE: DNA
<213> ORGANISM: Homo sapiens

<400> SEQUENCE: 1219
taaaaagtag taatgttggc cgcgcgtggt 30

<210> SEQ ID NO 1220
<211> LENGTH: 124
<212> TYPE: DNA
<213> ORGANISM: Homo sapiens

<400> SEQUENCE: 1220
ccattatcta ggttgcacat ttgtgaaagc atcagtatat gatgcgttcc atggttggga 60
tctaatgata cccagatcaa gccatgacat aactagtgca gtgtgcaaga ttcaagccct 120
attc 124

<210> SEQ ID NO 1221
<211> LENGTH: 109
<212> TYPE: DNA
<213> ORGANISM: Homo sapiens

<400> SEQUENCE: 1221
aggtggtacc tgatgcagga atatgtgagt gttggtgttg gagagtgttg tgagaggaag 60
attattcagc agaaacaaac ccttcctctg atgagcagaa gtggtggat 109

<210> SEQ ID NO 1222
<211> LENGTH: 473
<212> TYPE: DNA
<213> ORGANISM: Homo sapiens

<400> SEQUENCE: 1222
tggcgagatg tggttctgct atttatttta agttagaact cttattctga gagttttcca 60
tagaaacaca gtaagatatg tggttaagtt ccagagtact gttaatatta caggtatgtt 120
caggcatttg ttaattagcc tagaaaccta accactgggt ataacgtttc cagaggaaca 180
tatatcctga aattcaagta accgcttcac tagagactgt ctttcctaac ttgtttactc 240
agcattaaaa aggtaatgat tttggcaaaa aaaaaaatat ttttcaatat gtttactcca 300
aggatgtgct tgtcggttgt gctgtgtcta ataggaaaac tgtgttaatg aagttccatc 360
caatatttag gtaggagttg aatgaagaaa gagataaagt tggtaataa taagcagggt 420 gttgggacaa ctgatggcca atatcaaact ggcttatcct tgttcacttt gta 473

<210> SEQ ID NO 1223
<211> LENGTH: 552
<212> TYPE: DNA
<213> ORGANISM: Homo sapiens

<400> SEQUENCE: 1223
aaagatcaca tttacctcat gggtaactaa agctgggttt tgtggaagat cattgtaatt 60
atctgaaact gtgactctta cttccttttt tttttggagt ctcactctgt cacccaggct 120
ggagtgcagt ggcgccatct tggctcagtg aaaccaccgc ctcccgggtt caagcgattc 180
tcctgcctca gcctcctaag tagctgggat tacaagcacc caccaccata cccagctaat 240
tttttatatt ttttgtagag acggggtttc accatgttgg ccacgctggc ttcgaactcc 300
tgacctcaag tgatctgcct gccttggcct cccaaagtgc taggattaaa ggcacgagcc 360
acccagcccg gctgtgactc ttactttcaa aacacatttt ataatatcta taatgacaat 420
agcttctact gaatactact tatgtgctaa gcatttaaac tctacatatg ttatcacatt 480
caagcatcac aattaacctg cgatgaatta ttactcacag tttatggata aagaaactag 540
ggctcacagg gc 552

<210> SEQ ID NO 1224
<211> LENGTH: 297
<212> TYPE: DNA
<213> ORGANISM: Homo sapiens

<400> SEQUENCE: 1224
tgtgcaggtc ttgaattaca atttgttctg ctatctttgt acagatattt gaattttttt 60
ttgttactgt gtcatgtatg agaaagattg tcattgattg tgaaggaact ggctttttaa 120
aaagaattcc ttccatattt acttaagtta aatgtttact tgtgagaaca caaatttatt 180
gttatcagta gttgtaactt tattactaaa atacttgaaa gttgcttggt atatttatat 240
gctttatagt tcaggttcaa tagaagattt aatttgtaaa aagtgttctg ctgcttc 297

<210> SEQ ID NO 1225
<211> LENGTH: 55
<212> TYPE: DNA
<213> ORGANISM: Homo sapiens

<400> SEQUENCE: 1225
gtcggccgcc gccaactacc tgctctgtac caactgccgg aaagtgctgc ggaag 55

<210> SEQ ID NO 1226
<211> LENGTH: 25
<212> TYPE: DNA
<213> ORGANISM: Homo sapiens

<400> SEQUENCE: 1226
ccctccgccc gctctcgcct cggcg 25

<210> SEQ ID NO 1227
<211> LENGTH: 97
<212> TYPE: DNA
<213> ORGANISM: Homo sapiens

<400> SEQUENCE: 1227
cgtctccgcc gtcgctgggg cagctgccgc ggtggtcgcc tctggcagtg ccgctagctt 60
tcaggcagtc gcctctcctc ccgacatccc gccttga 97

<210> SEQ ID NO 1228
<211> LENGTH: 160
<212> TYPE: DNA
<213> ORGANISM: Homo sapiens

<400> SEQUENCE: 1228
gccagtaggc gatgcaagtt atctctgggg cccggaggac acgagtgagg accgggcacc 60
aatcaggttc tcgctctgcg ccggcctttg ttctcactcg ggagcaggtt gcgggcgtct 120
agcatcggga acccgcattc gactcggacg cgcattgcta 160

<210> SEQ ID NO 1229
<211> LENGTH: 76
<212> TYPE: DNA
<213> ORGANISM: Homo sapiens

<400> SEQUENCE: 1229
caggagggcc ccctgcgcta atctgccctg gcagcagcga gctggcacgc cctgggtgca 60
tcatccggtg tgctct 76

<210> SEQ ID NO 1230
<211> LENGTH: 62
<212> TYPE: DNA
<213> ORGANISM: Homo sapiens

<400> SEQUENCE: 1230
gacccgccgg gccagatccc atctctggcg acgcggagaa aaatctggaa gccgtcgtcg 60
ga 62

<210> SEQ ID NO 1231
<211> LENGTH: 26
<212> TYPE: DNA
<213> ORGANISM: Homo sapiens

<400> SEQUENCE: 1231
ccgcgcggcc ggaactgcgg gcgggg 26

<210> SEQ ID NO 1232
<211> LENGTH: 59
<212> TYPE: DNA
<213> ORGANISM: Homo sapiens

<400> SEQUENCE: 1232
ggcgcccctg cggtgcagag cagctcaggg ccggctggtg cgcgaccccg gaaagcggg 59

<210> SEQ ID NO 1233
<211> LENGTH: 34
<212> TYPE: DNA
<213> ORGANISM: Homo sapiens

<400> SEQUENCE: 1233
agtccaatag ccagtgaagg cctggtcctg ccct 34

<210> SEQ ID NO 1234
<211> LENGTH: 31
<212> TYPE: DNA
<213> ORGANISM: Homo sapiens

<400> SEQUENCE: 1234
gcctccacca tggacagagg ccaggccctg c 31

<210> SEQ ID NO 1235
<211> LENGTH: 58
<212> TYPE: DNA
<213> ORGANISM: Homo sapiens

<400> SEQUENCE: 1235
gccctgaagg cagacgggat aatgtggttg gccaaggcct gttggtccat ccagagtg 58

<210> SEQ ID NO 1236
<211> LENGTH: 46
<212> TYPE: DNA
<213> ORGANISM: Homo sapiens

<400> SEQUENCE: 1236
cccagggtca cgctcatgct ggggctcccg tcagctgact attttg 46

<210> SEQ ID NO 1237
<211> LENGTH: 29
<212> TYPE: DNA
<213> ORGANISM: Homo sapiens

<400> SEQUENCE: 1237
gtcaggtcca gtcaagaggg cccaaagtg 29

<210> SEQ ID NO 1238
<211> LENGTH: 80
<212> TYPE: DNA
<213> ORGANISM: Homo sapiens

<400> SEQUENCE: 1238
ccaaccaatc ttgggattct cccttcgtgc ggttgtctgg gacctttttc cagggtcaaa 60
gcagatcgtg aggaggaagc 80

<210> SEQ ID NO 1239
<211> LENGTH: 177
<212> TYPE: DNA
<213> ORGANISM: Homo sapiens

<400> SEQUENCE: 1239
atttggatgt ggagcctctc ctttccattg tgaactgaat tctaccagca ctgggcctgg 60
tgatgtctgc attaggcaga tgaggaagca gtcttggaga ggacaaggga ctggcctcag 120
gtcacacatc aggcttgcta gctcctggac aaagatgcct ctgatagctc ttccata 177

<210> SEQ ID NO 1240
<211> LENGTH: 408
<212> TYPE: DNA
<213> ORGANISM: Homo sapiens

<400> SEQUENCE: 1240
cctgccctgg gctacttact actgaggatg cacaaaggat cttcccacca cggactagga 60
gacagtgccc ttgtcctcat gttgttcaca tactggtcgg tgagggatgg gtctgagtac 120
atgataaatc cctgggcccc ataagatttg actaggaggg gtaagggcct ggtgaactgc 180
tcagaaaata aactgtgttg tcagcaggag gacccctttc tactatgaga tattgcattc 240
cctgctaatc atacttgtgc tctatctgtt gatagaacaa atacataatg agaaacagcc 300
actgtgcttt cagaagaaca cacttgaaag aatttgttct caataaatta catctgcatc 360
tggatccata tgaagaaata cgttcctctc attcaggcgt ggctattt 408

<210> SEQ ID NO 1241
<211> LENGTH: 38
<212> TYPE: DNA
<213> ORGANISM: Homo sapiens

<400> SEQUENCE: 1241
atggccaaag ctcgacgggc ggcctgcgtc agtggcgc 38

<210> SEQ ID NO 1242
<211> LENGTH: 76
<212> TYPE: DNA
<213> ORGANISM: Homo sapiens

<400> SEQUENCE: 1242
ggctcggccg gggagtccca gtggcggagg ctacgaaact tgggggagtg cacagaagaa 60
cttcgggagc gcacgc 76

<210> SEQ ID NO 1243
<211> LENGTH: 47
<212> TYPE: DNA
<213> ORGANISM: Homo sapiens

<400> SEQUENCE: 1243
gaccagggac caggctgaga ctcggggcgc cagtccgggc aggggca 47

<210> SEQ ID NO 1244
<211> LENGTH: 94
<212> TYPE: DNA
<213> ORGANISM: Homo sapiens

<400> SEQUENCE: 1244

```
ttcccttcgg ggaacgtgca tctgttttta ggagcggtgc atgaaggaga tgggtgtacg    60

cgcgggcaga gaggatgttg tagggccggc atgc                               94
```

<210> SEQ ID NO 1245
<211> LENGTH: 76
<212> TYPE: DNA
<213> ORGANISM: Homo sapiens

<400> SEQUENCE: 1245

```
tgttggagtc ttggggcggt gctgcctaga ggatacctcc caaccattcc agctccagat    60

gctgatcatc cctatg                                                   76
```

<210> SEQ ID NO 1246
<211> LENGTH: 68
<212> TYPE: DNA
<213> ORGANISM: Homo sapiens

<400> SEQUENCE: 1246

```
tgaggcttgt tcagcagaac aggtgcaagc cacattgttg ccaagacctg cctgaagccg    60

gattctcc                                                            68
```

<210> SEQ ID NO 1247
<211> LENGTH: 57
<212> TYPE: DNA
<213> ORGANISM: Homo sapiens

<400> SEQUENCE: 1247

```
tgtcctagtg caggcagatg tggccaccct cacctctcgc agggtgctgc atgcctg       57
```

<210> SEQ ID NO 1248
<211> LENGTH: 765
<212> TYPE: DNA
<213> ORGANISM: Homo sapiens

<400> SEQUENCE: 1248

```
gtactgttgt ccattctcct gagagtccag ggggctgtgg tctccttcct ccccccttgc    60

cctgtcccca gcaaatggcc tttaaaggtc tggagccagg ttaccgatga ggaggcctag   120

gttcccttcc tctttgcttc tgggagcatc tcgagcagtg cagagtggct tcccagcccc   180

agatggcagg attggggtgg gtttgggatc tgctgccttt gctcagtgtg cagggttggg   240

gtggaaatgg gggacaggct agggcctctg cattaggctg ccttcttagg caggtgggct   300

ttcacttcca gctcctcttc cattttcacg atgtccttct tcctaggcac tgcgagggga   360

ggagaaaagg ggctttgcag aggcctggga gtattcccag gaagtgcctg gttggcgaaa   420

caaccaggga gctgctcctg ggagctgggc tgaggctttg ctgggctgcc tctcccactc   480

acccttctcc cggcccccac catgccttcc ccatggggga ggggcagggg gctggaggaa   540

cacagcttcc ccctgttcta gcagagaaat gctggctgta tgcctcccct agggttccca   600

ggctgactag ggtgtggctg gccttctgat ggagcccact catgctgggc cgctgcccag   660

gggctttgtg gcacctaggt cgagatggta ctcaggccag gggtcaggat tcctgggtgc   720

tctggtcccg gtgcctctgt ctcatcttta ggctgggatt cctgc                  765
```

<210> SEQ ID NO 1249
<211> LENGTH: 32
<212> TYPE: DNA
<213> ORGANISM: Homo sapiens

<400> SEQUENCE: 1249
tccaagccca atatgggaca ccagcaccga gt 32

<210> SEQ ID NO 1250
<211> LENGTH: 30
<212> TYPE: DNA
<213> ORGANISM: Homo sapiens

<400> SEQUENCE: 1250
gaccacctgg caagcgaccc cctgacccct 30

<210> SEQ ID NO 1251
<211> LENGTH: 38
<212> TYPE: DNA
<213> ORGANISM: Homo sapiens

<400> SEQUENCE: 1251
ccagcttcag caccttcatg gacggctaca caggagag 38

<210> SEQ ID NO 1252
<211> LENGTH: 36
<212> TYPE: DNA
<213> ORGANISM: Homo sapiens

<400> SEQUENCE: 1252
ctcggcctcc tccacatcct cgtcctcagc cacctc 36

<210> SEQ ID NO 1253
<211> LENGTH: 54
<212> TYPE: DNA
<213> ORGANISM: Homo sapiens

<400> SEQUENCE: 1253
gacttccagg tgtacggctg ctaccccggc cccctgagcg gcccagtgga tgag 54

<210> SEQ ID NO 1254
<211> LENGTH: 67
<212> TYPE: DNA
<213> ORGANISM: Homo sapiens

<400> SEQUENCE: 1254
ggctccttcg gccacttctc gcccagccag acttacgaag gcctgcgggc atggacagag 60
cagctgc 67

<210> SEQ ID NO 1255
<211> LENGTH: 189
<212> TYPE: DNA
<213> ORGANISM: Homo sapiens

<400> SEQUENCE: 1255
agagagctat tccatgccta cggccttccc aggtttggca cccacttctc cacaccttga 60
gggctcgggg atactggata cacccgtgac ctcaaccaag gcccggagcg gggccccagg 120
tggaagtgaa ggccgctgtg ctgtgtgtgg ggacaacgct tcatgccagc attatggtgt 180
ccgcacatg 189

<210> SEQ ID NO 1256
<211> LENGTH: 76
<212> TYPE: DNA
<213> ORGANISM: Homo sapiens

<400> SEQUENCE: 1256
cgcgcagccc caggtggggc cttttgttgg aaatggagag aggctggcct catcccattg 60
ggacctgtgg tctccc 76

<210> SEQ ID NO 1257
<211> LENGTH: 640
<212> TYPE: DNA
<213> ORGANISM: Homo sapiens

<400> SEQUENCE: 1257
gaagctttca tttgccggga cactcgggcc catgggattg cacagagctg gagggagggg 60
tgagataggg gcagatagga gctgcagggg tgcctggcga gcctctggtt ttcctctgct 120
cctctgcctg tcctctccca actcaaggtt ctagtgggaa ggggtgcccc caggctctca 180
tgttcctggc gtgagatgaa aggatccctg cggagggttt ggttcttgag ggctgggggt 240
ggacttggga acaggctgtg tgtttgtccc agcgatggtg cctgcttagc ttcccgtccc 300
caccccccag ccccttggcc ctctcctgtc tgccctaggg agaaggcagg tggacaaggg 360
cccatgaaaa aatacaggtg tctagactgc cagggagacc ctggccccca gtagtgtgtc 420
ctggggactt cctcagagcg agaaacctcc cccaatgtct tcaagacttt tctctccccc 480
cgcccaaccc cgtctctccc tcccttgcca cccaaatgtt agaaaaatag ctgtgaacag 540
agagcgcttt tgtctgcaat ggcagcagga tctggacggt cccctcccct aagttccccc 600
ctccccaccc cacactctga cagcttgttc cgtgttgccc 640

<210> SEQ ID NO 1258
<211> LENGTH: 94
<212> TYPE: DNA
<213> ORGANISM: Homo sapiens

<400> SEQUENCE: 1258
gcacagtgca gaaaaacgcc aagtacatct gcctggctaa caaggactgc cctgtggaca 60
agaggcggcg aaaccgctgc cagttctgcc gctt 94

<210> SEQ ID NO 1259
<211> LENGTH: 269
<212> TYPE: DNA
<213> ORGANISM: Homo sapiens

<400> SEQUENCE: 1259
cccagcgggg caagggtagg cttgagtgga gtgggaccag cagggccccc aggcttctgc 60
cctggaggac ccagaggagg gcacgtctta tttccacccc acctctgaac cccaggcctt 120
ggagggaggc agcctacacc tgcctggatt gtgagggtgg tggcaggggg aggttcctat 180
agggtacctt ggatctcagg gactctgggt cctagggact cggtggggcg cgtctcagca 240
gtggtgtgca cggcttgggc tgagaggcc 269

<210> SEQ ID NO 1260
<211> LENGTH: 122
<212> TYPE: DNA
<213> ORGANISM: Homo sapiens

<400> SEQUENCE: 1260
ttgtccgaac agacagcctg aaggggcggc ggggccggct accttcaaaa cccaagcagc 60
ccccagatgc ctcccctgcc aatctcctca cttccctggt ccgtgcacac ctggactcag 120
gg 122

<210> SEQ ID NO 1261
<211> LENGTH: 30
<212> TYPE: DNA
<213> ORGANISM: Homo sapiens

<400> SEQUENCE: 1261
cccagcactg ccaaactgga ctactccaag 30

<210> SEQ ID NO 1262
<211> LENGTH: 172
<212> TYPE: DNA
<213> ORGANISM: Homo sapiens

<400> SEQUENCE: 1262
ctttgtgcgt gttaggagag ctaccccctc tggaaggact gaatgagaaa ggaggtttaa 60
aaaagaaaga aagaaaagcg actccctcca gttcgacaga tcaaagagag gatccccctc 120
tcggctgacc agatgggaaa atgcaccccc tcaggcaggt ggccaattag aa 172

<210> SEQ ID NO 1263
<211> LENGTH: 43
<212> TYPE: DNA
<213> ORGANISM: Homo sapiens

<400> SEQUENCE: 1263
gggatgtaca gcagttctac gacctgctct ccggttctct gga 43

<210> SEQ ID NO 1264
<211> LENGTH: 107
<212> TYPE: DNA
<213> ORGANISM: Homo sapiens

<400> SEQUENCE: 1264
gtcatccgca agtgggcgga gaagatccct ggctttgctg agctgtcacc ggctgaccag 60
gacctgttgc tggagtcggc cttcctggag ctcttcatcc tccgcct 107

<210> SEQ ID NO 1265
<211> LENGTH: 49
<212> TYPE: DNA
<213> ORGANISM: Homo sapiens

<400> SEQUENCE: 1265
ctttccctga tacacctgcc tgtgaaccac cctgatcgct cttcgtgcc 49

<210> SEQ ID NO 1266
<211> LENGTH: 129
<212> TYPE: DNA
<213> ORGANISM: Homo sapiens

<400> SEQUENCE: 1266
ctaagccagg cgagggcaag ctcatcttct gctcaggcct ggtgctacac cggctgcagt 60
gtgcccgtgg cttcggggac tggattgaca gtatcctggc cttctcaagg tccctgcaca 120
gcttgcttg 129

<210> SEQ ID NO 1267
<211> LENGTH: 30
<212> TYPE: DNA
<213> ORGANISM: Homo sapiens

<400> SEQUENCE: 1267
tcagatgtac agctaatcct gtacccttcc 30

-continued

<210> SEQ ID NO 1268
<211> LENGTH: 41
<212> TYPE: DNA
<213> ORGANISM: Homo sapiens

<400> SEQUENCE: 1268
accggcatgg gctgcaggag ccgcggcggg tggaggagct g 41

<210> SEQ ID NO 1269
<211> LENGTH: 193
<212> TYPE: DNA
<213> ORGANISM: Homo sapiens

<400> SEQUENCE: 1269
gaaccgcatc gccagctgcc tgaaggagca cgtggcagct gtggcgggcg agccccagcc 60
agccagctgc ctgtcacgtc tgttgggcaa actgcccgag ctgcggaccc tgtgcaccca 120
gggcctgcag cgcatcttct acctcaagct ggaggacttg gtgccccctc cacccatcat 180
tgacaagatc ttc 193

<210> SEQ ID NO 1270
<211> LENGTH: 62
<212> TYPE: DNA
<213> ORGANISM: Homo sapiens

<400> SEQUENCE: 1270
tgcacatgcg cactctcata tgccacccca tgtgccttta gtccacggac ccccagagca 60
cc 62

<210> SEQ ID NO 1271
<211> LENGTH: 57
<212> TYPE: DNA
<213> ORGANISM: Homo sapiens

<400> SEQUENCE: 1271
ctgggcttga gctgcagaat gactccacct tctcacctgc tccaggaggt ttgcagg 57

<210> SEQ ID NO 1272
<211> LENGTH: 110
<212> TYPE: DNA
<213> ORGANISM: Homo sapiens

<400> SEQUENCE: 1272
gggtgacccc acgatttgtc ttatcccccc cagcctggcc ccggccttta tgttttttgt 60
aagataaacc gtttttaaca catagcgccg tgctgtaaat aagcccagtg 110

<210> SEQ ID NO 1273
<211> LENGTH: 122
<212> TYPE: DNA
<213> ORGANISM: Homo sapiens

<400> SEQUENCE: 1273
accctccttc cacatgtaca taaactgtca ctctaggaag aagacaaatg acagattctg 60
acatttatat ttgtgtattt tcctggattt atagtatgtg acttttctga ttaatatatt 120
ta 122

<210> SEQ ID NO 1274
<211> LENGTH: 150
<212> TYPE: DNA
<213> ORGANISM: Homo sapiens

<400> SEQUENCE: 1274
gtgtaaaagt gtgagacaac acatttctgt tgtttaagac acacaatctg tggtactttg 60
atacagcagc cctgacaaac taatacatgg ggtgtctcat tgtagtttta atcagtaaca 120
cccattatga actgaaaacg tctgctactt 150

<210> SEQ ID NO 1275
<211> LENGTH: 72
<212> TYPE: DNA
<213> ORGANISM: Homo sapiens

<400> SEQUENCE: 1275
caagaggtga ccatcagcaa gcccaggaga gaggcctcag aagaaaccag acctgctgat 60
tccttgatct tg 72

<210> SEQ ID NO 1276
<211> LENGTH: 53
<212> TYPE: DNA
<213> ORGANISM: Homo sapiens

<400> SEQUENCE: 1276
caacttgaat gcttcctgat taaatatata caggagtgat ttcagaggaa ttt 53

<210> SEQ ID NO 1277
<211> LENGTH: 83
<212> TYPE: DNA
<213> ORGANISM: Homo sapiens

<400> SEQUENCE: 1277
ccattaagac taaccgtttt tgctggagct gcaagatttt ccatttcttc atgagtcacc 60
caaacgttgc ctgaaggcta gtg 83

<210> SEQ ID NO 1278
<211> LENGTH: 51
<212> TYPE: DNA
<213> ORGANISM: Homo sapiens

<400> SEQUENCE: 1278
gtggctcttg aacaacacag gtttgaactg catcattcca cttatacaca g 51

<210> SEQ ID NO 1279
<211> LENGTH: 30
<212> TYPE: DNA
<213> ORGANISM: Homo sapiens

<400> SEQUENCE: 1279
actcctgaga caacatgacc aatctctccc 30

<210> SEQ ID NO 1280
<211> LENGTH: 60
<212> TYPE: DNA
<213> ORGANISM: Homo sapiens

<400> SEQUENCE: 1280
cgtactttca acataaagac gacgaggata aaggcattta tgatgaacta cttccacata 60

<210> SEQ ID NO 1281
<211> LENGTH: 254
<212> TYPE: DNA
<213> ORGANISM: Homo sapiens

<400> SEQUENCE: 1281
gcttacttta ttgtacgaat ggagcatata tgtgtacata taaaacacat aatacatgct 60
tatcaactat ttgtgttatc agtaaggctt ccagtcaaca gtaggctctt agtagttaag 120
tcttgggaga gccaaaaatt ctagctgatt ttttgactgt gtgtgggggg tcagcaccct 180
taactcctat cttattcaag gggctattgt attctaaatt gtcttttagc ttgagtcata 240
atccaggtat agtg 254

<210> SEQ ID NO 1282
<211> LENGTH: 64
<212> TYPE: DNA
<213> ORGANISM: Homo sapiens

<400> SEQUENCE: 1282
gcaaaataca gtgccaagag ctctggacca caaatcagaa gacctgagcc ctaattcctt 60
tcca 64

<210> SEQ ID NO 1283
<211> LENGTH: 72
<212> TYPE: DNA
<213> ORGANISM: Homo sapiens

<400> SEQUENCE: 1283
tttgttcgtc gcttgccaaa atagcagcga actctctgtc aaactgcaac tcattttatc 60
ggagcaaaaa ct 72

<210> SEQ ID NO 1284
<211> LENGTH: 51
<212> TYPE: DNA
<213> ORGANISM: Homo sapiens

<400> SEQUENCE: 1284
gaagcagctg atcgctaata tctgatggct aatatgctaa atttccctgt c 51

<210> SEQ ID NO 1285
<211> LENGTH: 315
<212> TYPE: DNA
<213> ORGANISM: Homo sapiens

<400> SEQUENCE: 1285
gaggcagtgc agcttgtgtt acaactcaaa agagtaatac tctgaaaaaa gaaaaaaaaa 60
gatggcgctg aaaataaaca tgttcagcag ccattgtgat tcaacttacc cagatgtgct 120
tttcatgaga tggagaagga cggatggaaa agaaaagcac acaaatgtta atggatacag 180
ttcaatccaa agaaaaccat ggaataaaac aagagcatta tttaagatgt gagaaagctc 240
aggtatgaga aagacatggt gccattttgt atttcatcat gacacacata ctcactgcgt 300
cgaaaagcat agtca 315

<210> SEQ ID NO 1286
<211> LENGTH: 164
<212> TYPE: DNA
<213> ORGANISM: Homo sapiens

<400> SEQUENCE: 1286
gcgaatgcaa ctttgaccct aagaaatcct ttatgcaggt ggagacacag cttcttcaac 60
caatgaaaga aataatatct ggcttcttga atagtttcat ggtgccacca acaaaaacta 120
tcatagacca acaatggcaa gatggcatcg gcaagaatga gctg 164

<210> SEQ ID NO 1287
<211> LENGTH: 90
<212> TYPE: DNA
<213> ORGANISM: Homo sapiens

<400> SEQUENCE: 1287
ccagaatctc atcgtgcagg ctacaaatag cagctgcagc tgcagaccaa gggctggcct 60
ttacatgtcc atggtgcaaa aggactcctg 90

<210> SEQ ID NO 1288
<211> LENGTH: 75
<212> TYPE: DNA
<213> ORGANISM: Homo sapiens

<400> SEQUENCE: 1288
caactgcttg tcacaccgac ctgcaccatc tctcgcctgc ctgtggggtt tctgtcaact 60
agtcgtggag ggaag 75

<210> SEQ ID NO 1289
<211> LENGTH: 25
<212> TYPE: DNA
<213> ORGANISM: Homo sapiens

<400> SEQUENCE: 1289
atgccagaac ccactaagaa agagg 25

<210> SEQ ID NO 1290
<211> LENGTH: 50
<212> TYPE: DNA
<213> ORGANISM: Homo sapiens

<400> SEQUENCE: 1290
agtatccccg aatcaaacat gaatgttgaa gtcaactacc cagactgaag 50

<210> SEQ ID NO 1291
<211> LENGTH: 244
<212> TYPE: DNA
<213> ORGANISM: Homo sapiens

<400> SEQUENCE: 1291
tacacactaa ctttaatttg gaatacagta aatattgtat tagtgtgtca tatatttact 60
gaattaaaaa ttaaaattgg ttgggcatgg tggctcatgc ctataaactc agcactcagg 120
gaagcagagg caggtggatc acctgaggtc aggagtttga gaccagcctg gccaacatgg 180
tgaaaccttg tctctactaa aaatacaaaa aattagctga gcgtggtggt ggacccgtgt 240
aatt 244

<210> SEQ ID NO 1292
<211> LENGTH: 185
<212> TYPE: DNA
<213> ORGANISM: Homo sapiens

<400> SEQUENCE: 1292
tgccagggga cggttatgga tttcttggca gcaaggagaa gcggcttttg tgcagggagg 60
aacagcctgc cagtcaacta tatttatgga gcacctgctg tgtggaatct gaaaaggaga 120
aggagaaggg ccttgtcctc aagaagcttg tgatcaaagg gagaagaaaa gtccccatct 180
actgt 185

<210> SEQ ID NO 1293
<211> LENGTH: 55
<212> TYPE: DNA
<213> ORGANISM: Homo sapiens

<400> SEQUENCE: 1293
tgaacaacgg ctttgaatgc gaacctgggg agtgtagacc taaccaaata ataat 55

<210> SEQ ID NO 1294
<211> LENGTH: 125
<212> TYPE: DNA
<213> ORGANISM: Homo sapiens

<400> SEQUENCE: 1294
atttggcacg ggaaatgcta tgctctttgt tcatgtggat gcctttacct acttggaaat 60
agtatgttct ttaacagaag tttctttgtc agacttcata gccagactgc tctgtaataa 120
ccaga 125

<210> SEQ ID NO 1295
<211> LENGTH: 30
<212> TYPE: DNA
<213> ORGANISM: Homo sapiens

<400> SEQUENCE: 1295
aaaatgaagt gccagcccca gccccacccc 30

<210> SEQ ID NO 1296
<211> LENGTH: 394
<212> TYPE: DNA
<213> ORGANISM: Homo sapiens

<400> SEQUENCE: 1296
cactcacaca cgtttgggct gcaaatacag agggtccatc ccagcatgat ttggcctcca 60
cgggtgctgt gagctgtgag ctttaaccta actcctactg agaagttgga tggtgaccat 120
tgtgataagt tgagaataat aaaaataata cactgtgttt atataatcct cttgtgttaa 180
tctaatttgg atggcacttc atatatatta gggggacaat tcttatgaaa cctttcaaat 240
tatgtaaaag ttattatgtc cgcattttac agtgtggagg ctgagcctcc atccaagggg 300
ctgaagaatt tgtgaggctt tttcctatat agtgaaggtc aaacaaaccc acatcttctt 360
tatgagagtg gggagtggat ccatctctac cctg 394

<210> SEQ ID NO 1297
<211> LENGTH: 41
<212> TYPE: DNA
<213> ORGANISM: Homo sapiens

<400> SEQUENCE: 1297
ctggcaacag gaaatgagta cagagatcca gtgagaccct t 41

<210> SEQ ID NO 1298
<211> LENGTH: 27
<212> TYPE: DNA
<213> ORGANISM: Homo sapiens

<400> SEQUENCE: 1298
aaaaatatgc ttgtactttc tacacag 27

<210> SEQ ID NO 1299
<211> LENGTH: 32

<212> TYPE: DNA
<213> ORGANISM: Homo sapiens

<400> SEQUENCE: 1299
agagaaggag gccggaacta caccagcaaa ag 32

<210> SEQ ID NO 1300
<211> LENGTH: 157
<212> TYPE: DNA
<213> ORGANISM: Homo sapiens

<400> SEQUENCE: 1300
tctgcaagtc ccaatcagta taatgacaaa tggtgcattg ctaagtttcc attacatgta 60
tttctaaaag aaaaacaaca atgataaaaa tatcacaagc acttgttgag atgccagcaa 120
attaattggt agtttccaag tttcgacatg catgcta 157

<210> SEQ ID NO 1301
<211> LENGTH: 182
<212> TYPE: DNA
<213> ORGANISM: Homo sapiens

<400> SEQUENCE: 1301
gacactactg ttgggtgatc tagacgaaga ctatttcatg atactctgaa gcgctgcatt 60
catatgtatt ccttcatggt ctaaaacaac tgtgcatgtc ctccaaatag tcttaacatt 120
tagtagactt tgaaactact cacctatcaa atttttgctt aaaaaacaga ttgccggcca 180
gg 182

<210> SEQ ID NO 1302
<211> LENGTH: 74
<212> TYPE: DNA
<213> ORGANISM: Homo sapiens

<400> SEQUENCE: 1302
gcacaatgtt gtggaatgtg aatgcatgca tattagttca ggagaaaaaa ttcaaaatga 60
actaagtttg ggag 74

<210> SEQ ID NO 1303
<211> LENGTH: 79
<212> TYPE: DNA
<213> ORGANISM: Homo sapiens

<400> SEQUENCE: 1303
tgctaacagg aaacaatacc gacgttcttt ttcttatagc atttgtatta taaaaagcac 60
aaagctccag cccactgaa 79

<210> SEQ ID NO 1304
<211> LENGTH: 40
<212> TYPE: DNA
<213> ORGANISM: Homo sapiens

<400> SEQUENCE: 1304
atgaagtctt ttctccttga ctttttactc ctatttcttg 40

<210> SEQ ID NO 1305
<211> LENGTH: 33
<212> TYPE: DNA
<213> ORGANISM: Homo sapiens

<400> SEQUENCE: 1305
gaagaggaag tctccccgcc tagcgccttg cct 33

<210> SEQ ID NO 1306
<211> LENGTH: 117
<212> TYPE: DNA
<213> ORGANISM: Homo sapiens

<400> SEQUENCE: 1306
gctttcatac ttggagctct actgattttc catccaagcc aacttgtagg gtttttttcct 60 tcctatcacc agaggagaca gggtttaggg gaatccaaga aggttgaagt cagcact 117

<210> SEQ ID NO 1307
<211> LENGTH: 35
<212> TYPE: DNA
<213> ORGANISM: Homo sapiens

<400> SEQUENCE: 1307
tttgggtagt cgggccctgg agagaaaaga ttcag 35

<210> SEQ ID NO 1308
<211> LENGTH: 187
<212> TYPE: DNA
<213> ORGANISM: Homo sapiens

<400> SEQUENCE: 1308
gagctcattt cttgaagctg tattgattct aatccttgtc ttattcagat tgtagttttt 60
acggcaatct ttcattacgt ttcctcttac aagaaaacta atgtattgag aaacaattaa 120
ttttgcatga tacacacgca ttcaaggatc tagccaaaaa taccacaggt ttgttctatc 180
attttta 187

<210> SEQ ID NO 1309
<211> LENGTH: 320
<212> TYPE: DNA
<213> ORGANISM: Homo sapiens

<400> SEQUENCE: 1309
actggccacc attgtttacc tgttagggga caggcaagat ggggaagcaa aggaattatt 60
gccatcaaag agagaataac agcttacctg gaaagttcca ctatttctaa gaattacata 120
atgttcattt gccccatcat ggaagagata cccctgtaag aatgggaatc tgttcccctc 180
tactgatggc tgctgggggc agaaagaatg atgttgtatt tatctaggtt tattagacaa 240
agaaaagcta cagcgttggt gagaacaaca aatccaggta agactgccta agaagagcct 300
ggccctgaaa taatcctttt 320

<210> SEQ ID NO 1310
<211> LENGTH: 70
<212> TYPE: DNA
<213> ORGANISM: Homo sapiens

<400> SEQUENCE: 1310
tggacccttg tcgaaactcc tcctggggag gaacaagcca agcagaatgc caactcccag 60
ctgtccatct 70

<210> SEQ ID NO 1311
<211> LENGTH: 56
<212> TYPE: DNA
<213> ORGANISM: Homo sapiens

<400> SEQUENCE: 1311
agcaaaacaa atgacgcttg ttaaagagca agctgaatcc cttatgcttc ttctag 56

<210> SEQ ID NO 1312
<211> LENGTH: 111
<212> TYPE: DNA
<213> ORGANISM: Homo sapiens

<400> SEQUENCE: 1312
atcaccttca tagccaaagt caaggctgaa gatcttctga gaaaacccac tatcaaatgg 60
ttcaaaggaa aatggatgga cctggccagc aaagccggga agcaccttca g 111

<210> SEQ ID NO 1313
<211> LENGTH: 88
<212> TYPE: DNA
<213> ORGANISM: Homo sapiens

<400> SEQUENCE: 1313
catttgagat gcagatcatc aaggccaaag ataactttgc aggaaattac agatgcgagg 60
tcacctataa ggataagttt gacagctg 88

<210> SEQ ID NO 1314
<211> LENGTH: 32
<212> TYPE: DNA
<213> ORGANISM: Homo sapiens

<400> SEQUENCE: 1314
tctactggga ctactccaaa cattgacatc ag 32

<210> SEQ ID NO 1315
<211> LENGTH: 31
<212> TYPE: DNA
<213> ORGANISM: Homo sapiens

<400> SEQUENCE: 1315
aggatgcagg agaacttgac tttagtggtc t 31

<210> SEQ ID NO 1316
<211> LENGTH: 348
<212> TYPE: DNA
<213> ORGANISM: Homo sapiens

<400> SEQUENCE: 1316
agtgagacat tgtggcctgg aagtctttca gacacccact cagagaagtc aagtttaaag 60
tggatgttct tcagagaatt tttcatttct gaaaatgtgt tttgcttata gaatataaca 120
gagttgacta gaaagagaga aacaactgca tactaatctt ttaaagcctt taacagttgc 180
ttttaaactt tctttttaaa tgtttcatga ctcttcacct attttttttt aaatggggac 240
gaagagatat gaaaactgag acataagaca aatacctaga aacctctaag actgcacata 300
tgatttggta gaagtctgaa ggtatacaca ttgtaagagg cagaccta 348

<210> SEQ ID NO 1317
<211> LENGTH: 283
<212> TYPE: DNA
<213> ORGANISM: Homo sapiens

<400> SEQUENCE: 1317
atagatacac ttttgtggga ggaaaaatag tggtaaaaac atggactgga gtctcagctc 60
taccatttac taattatgtg actttggtca aatatttgac ccctctgaga cttggatttc 120

-continued acatctggaa atgtgaagaa taaacactac ttaatagaat tattgtgcaa attaaattaa 180
gtgtaaaaag cttggttcac agtaggtggc aaataaatat gtacttcctc taaggaaatg 240
tgtcattttc tctaacatag tttatattca taaggagaca aca 283

<210> SEQ ID NO 1318
<211> LENGTH: 343
<212> TYPE: DNA
<213> ORGANISM: Homo sapiens

<400> SEQUENCE: 1318
ctctgtacaa cgaaagatct tcctgctctg aacaaagcca gcttacttca aatagacatt 60
agctaaatca gattaaatct tttgggcagc atcctgttat aggaattgac ctgtataaat 120
acttgtaagt tgtactctac ataaaatttc tataactgtt atactcttca ctaggatcac 180
caagttattg aaattttgat gtagatgaaa atacagtgag tattatacag gtctatcccg 240
aggcttggaa aagaatcaga agtgcctaca gaaatttggc tttttctcct cactgtaact 300
taacatagcc atgcagacag ggtcatgtgc agccaccatg gta 343

<210> SEQ ID NO 1319
<211> LENGTH: 82
<212> TYPE: DNA
<213> ORGANISM: Homo sapiens

<400> SEQUENCE: 1319
cagtgagtac gagaagatcg ccttccagta tggaatcacc gacctgcgcg gcatgctcaa 60
gcgactcaag cgcatgcgca ga 82

<210> SEQ ID NO 1320
<211> LENGTH: 119
<212> TYPE: DNA
<213> ORGANISM: Homo sapiens

<400> SEQUENCE: 1320
cttgatcctg catatcaggt tgacaaagga ggcagagtga ggtttgttgt ggagctggca 60
gatccaaagt tggaggtgaa atggtataaa aatggtcaag aaattcgacc cagtaccaa 119

<210> SEQ ID NO 1321
<211> LENGTH: 122
<212> TYPE: DNA
<213> ORGANISM: Homo sapiens

<400> SEQUENCE: 1321
tacatctttg aacacaaagg atgccagaga atcctgttta tcaataactg tcagatgaca 60
gatgattcag agtattatgt gacagccggt gatgagaaat gttccactga gctcttcgta 120
ag 122

<210> SEQ ID NO 1322
<211> LENGTH: 51
<212> TYPE: DNA
<213> ORGANISM: Homo sapiens

<400> SEQUENCE: 1322
tggtcaccag gagctgttgg cttcttctcc cagggataat gatcaaagtg a 51

<210> SEQ ID NO 1323
<211> LENGTH: 91
<212> TYPE: DNA
<213> ORGANISM: Homo sapiens

<400> SEQUENCE: 1323
agcctccaat tatggtgacc aaacagctgg aagatacaac tgcttattgt ggggagagag 60
tggaattaga atgtgaggtg tctgaagatg a 91

<210> SEQ ID NO 1324
<211> LENGTH: 138
<212> TYPE: DNA
<213> ORGANISM: Homo sapiens

<400> SEQUENCE: 1324
tccctggtcc aaaatcaaga taccgaatta gagttgaggg taaaaaacac atcttgatca 60
tagagggagc aacaaaggct gatgctgcag aatattcagt aatgacaaca ggaggacaat 120
catctgctaa acttagtg 138

<210> SEQ ID NO 1325
<211> LENGTH: 35
<212> TYPE: DNA
<213> ORGANISM: Homo sapiens

<400> SEQUENCE: 1325
tgacacctct gactgatcag actgtaaatc ttgga 35

<210> SEQ ID NO 1326
<211> LENGTH: 39
<212> TYPE: DNA
<213> ORGANISM: Homo sapiens

<400> SEQUENCE: 1326
cctgttcagg agagtgaccg tctaaaggtg gttcacaag 39

<210> SEQ ID NO 1327
<211> LENGTH: 84
<212> TYPE: DNA
<213> ORGANISM: Homo sapiens

<400> SEQUENCE: 1327
tccacaagtt agtgatagcc aatgccctca ctgaagatga aggtgattat gtatttgcac 60
ctgatgccta caatgttact ctgc 84

<210> SEQ ID NO 1328
<211> LENGTH: 70
<212> TYPE: DNA
<213> ORGANISM: Homo sapiens

<400> SEQUENCE: 1328
aggaaacaag cttcgtcttg agatccccat cagcggagaa ccacctccta aagccatgtg 60
gagccgggga 70

<210> SEQ ID NO 1329
<211> LENGTH: 139
<212> TYPE: DNA
<213> ORGANISM: Homo sapiens

<400> SEQUENCE: 1329
ggcagtggcc ggataagaac agaatcttac cctgatagca gcactctggt cattgatata 60
gctgaaagag atgactctgg tgtttaccac atcaatctga aaaacgaagc tggagaggca 120
catgcaagca tcaaggtta 139

<210> SEQ ID NO 1330
<211> LENGTH: 99
<212> TYPE: DNA
<213> ORGANISM: Homo sapiens

<400> SEQUENCE: 1330
ctgatcctcc agtggcaccg actgtgacag aggtgggaga tgactggtgt atcatgaact 60
gggagcctcc tgcctacgac ggaggctctc caatcctag 99

<210> SEQ ID NO 1331
<211> LENGTH: 153
<212> TYPE: DNA
<213> ORGANISM: Homo sapiens

<400> SEQUENCE: 1331
aagaaacaaa gctccaggtg gatgaggctg aattttgatc tctgcaaaga aacaactttt 60
gagcccaaga agatgattga aggtgtggcc tatgaggtcc gcatctttgc agtcaatgcc 120
attggcatct ccaagcccag tatgccctcc agg 153

<210> SEQ ID NO 1332
<211> LENGTH: 119
<212> TYPE: DNA
<213> ORGANISM: Homo sapiens

<400> SEQUENCE: 1332
cctcctactc ttctgactgt ggactctgtc actgacacga ctgtcacgat gaggtggcgc 60
cccccagacc acattggtgc agcaggttta gatggctatg tgctagagta ttgctttga 119

<210> SEQ ID NO 1333
<211> LENGTH: 166
<212> TYPE: DNA
<213> ORGANISM: Homo sapiens

<400> SEQUENCE: 1333
gtgcctcagg tcagaagcca cagtctgcac agagcaggct gtgctctcct gaggaacccc 60
cctaacaccg tttggtctct tccgtcactg ctctgaggac aaatctcttt gcacactttg 120
catactttac taacagagaa tgctgactgc tgatacgata ttattc 166

<210> SEQ ID NO 1334
<211> LENGTH: 26
<212> TYPE: DNA
<213> ORGANISM: Homo sapiens

<400> SEQUENCE: 1334
gtacatcagc aaaacagtct gatgaa 26

<210> SEQ ID NO 1335
<211> LENGTH: 42
<212> TYPE: DNA
<213> ORGANISM: Homo sapiens

<400> SEQUENCE: 1335
tctgattgac aagacgaagt tcaccatcac aggtctgcca ac 42

<210> SEQ ID NO 1336
<211> LENGTH: 81
<212> TYPE: DNA
<213> ORGANISM: Homo sapiens

<400> SEQUENCE: 1336
tgcgtgtgaa ggctgttaat gcagctggtg ccagcgagcc caagtactat tctcagccca 60
ttctcgtgaa ggaaatcata g 81

<210> SEQ ID NO 1337
<211> LENGTH: 88
<212> TYPE: DNA
<213> ORGANISM: Homo sapiens

<400> SEQUENCE: 1337
acctccaaag attcgcattc caagacacct gaagcaaacc tatatccgca gagttggaga 60
agctgtcaat ctggttatac ctttccag 88

<210> SEQ ID NO 1338
<211> LENGTH: 28
<212> TYPE: DNA
<213> ORGANISM: Homo sapiens

<400> SEQUENCE: 1338
aataaaacca gaagtggcaa caaggcag 28

<210> SEQ ID NO 1339
<211> LENGTH: 116
<212> TYPE: DNA
<213> ORGANISM: Homo sapiens

<400> SEQUENCE: 1339
ataaacattc gcaactctga gactgataca atcatattta ttagaaaagc agagaggagc 60
cactctggga aatatgatct gcaagtcaaa gtggacaaat tcgtggagac cgcatc 116

<210> SEQ ID NO 1340
<211> LENGTH: 102
<212> TYPE: DNA
<213> ORGANISM: Homo sapiens

<400> SEQUENCE: 1340
ccaaattgtg aagattgagg atgtctgggg agaaaatgtc gctctcacat ggactccacc 60
aaaggatgat ggaaatgctg ctatcacagg ctataccatt ca 102

<210> SEQ ID NO 1341
<211> LENGTH: 28
<212> TYPE: DNA
<213> ORGANISM: Homo sapiens

<400> SEQUENCE: 1341
ctttctctgg ttcatcagta gcaaaagg 28

<210> SEQ ID NO 1342
<211> LENGTH: 133
<212> TYPE: DNA
<213> ORGANISM: Homo sapiens

<400> SEQUENCE: 1342
ccaactgggg ctatggagaa gtgatgtggc agagcagaaa ggaaaagacc tgtggagcca 60
cagagctggt cttaaacccc agcattgcta cttaagacca catgtataag gaccacacgt 120
gaccacaatc act 133

<210> SEQ ID NO 1343
<211> LENGTH: 152
<212> TYPE: DNA

<213> ORGANISM: Homo sapiens

<400> SEQUENCE: 1343
ggtttactgt cattgagcat tatcatcgaa ccagtgccac cattactgaa ttggtcatag 60
ggaatgaata ttacttccgg gtcttttctg aaaacatgtg tggcctcagt gaggatgcca 120
ccatgactaa agagagtgca gtgatcgcca gg 152

<210> SEQ ID NO 1344
<211> LENGTH: 81
<212> TYPE: DNA
<213> ORGANISM: Homo sapiens

<400> SEQUENCE: 1344
tcagaggcac ccatgtttac tcagcctttg gttaacacct atgccatagc tggttacaat 60
gccaccctaa actgcagtgt g 81

<210> SEQ ID NO 1345
<211> LENGTH: 44
<212> TYPE: DNA
<213> ORGANISM: Homo sapiens

<400> SEQUENCE: 1345
gtaccatgtt cttctatcac atcagttaaa gtccctgtct tgta 44

<210> SEQ ID NO 1346
<211> LENGTH: 300
<212> TYPE: DNA
<213> ORGANISM: Homo sapiens

<400> SEQUENCE: 1346
cactacactg tctgcgatag gttaaagtaa acaacaatta cactacactg taagacagaa 60
tatgaatgtg ctttgataag ggtacagtgt gctaagaagg gagctatcat atccagttga 120
agagattaga aaggtttcaa ggtttcatgt ttgcatttga aaagaacaac gaattaatga 180
atatcgccca tagagatgta catatccctg ggtgcaagac agaaagtacc ctagaattgg 240
gaaaatttat gaacttcttt ttttcctgta tataccttga tcagaaatag ggaagtcgtc 300

<210> SEQ ID NO 1347
<211> LENGTH: 62
<212> TYPE: DNA
<213> ORGANISM: Homo sapiens

<400> SEQUENCE: 1347
cactggcttt gatggtctat taatatgcca attacagata tgttttgacc taagtttctt 60
ca 62

<210> SEQ ID NO 1348
<211> LENGTH: 112
<212> TYPE: DNA
<213> ORGANISM: Homo sapiens

<400> SEQUENCE: 1348
ggatgatcca agatacagga tgttcagcaa ccagggagtc tgtaccctgg aaattcgcaa 60
gcccagcccc tatgatggag gcacttactg ctgcaaagca gtcaatgacc tt 112

<210> SEQ ID NO 1349
<211> LENGTH: 141
<212> TYPE: DNA
<213> ORGANISM: Homo sapiens

<400> SEQUENCE: 1349
gccttactat tgagataacc cttacaaatt taaacatttt tagctgcttt attggcttta 60
aatgattaag ttcataattg caagtcatct ggtttctaaa ctgctagcct tattagttcc 120
aaagtattgt tgatgctttt g 141

<210> SEQ ID NO 1350
<211> LENGTH: 44
<212> TYPE: DNA
<213> ORGANISM: Homo sapiens

<400> SEQUENCE: 1350
tatatcaagg agtaaatacc cctggacaac cagtcttcct ggag 44

<210> SEQ ID NO 1351
<211> LENGTH: 170
<212> TYPE: DNA
<213> ORGANISM: Homo sapiens

<400> SEQUENCE: 1351
ttatatccca ctggatattc tactttccgt tccattcctc ttacatgaaa atgcaccttg 60
catgtaaagc ttgactttct catttgcttt taattgtacc ccttagcagc tcatggcata 120
cagtgcttat gccatgaaca aggaaggcca aattattcaa ggatattaag 170

<210> SEQ ID NO 1352
<211> LENGTH: 117
<212> TYPE: DNA
<213> ORGANISM: Homo sapiens

<400> SEQUENCE: 1352
tgtacactaa cactttgtct attgtctatg tttttctttt gttgaaaaac acgatatata 60
tatgttgtag ggttttggtt tttgtatttg ttttaagcta atggtttgga agctctt 117

<210> SEQ ID NO 1353
<211> LENGTH: 910
<212> TYPE: DNA
<213> ORGANISM: Homo sapiens

<400> SEQUENCE: 1353
gtcataagcc ataccaagcc tgtggagtat ggcatgattt tcattacata atccaatgaa 60
aatagactta ttttaaatcc ctaactttgt agttttaatt tgtatttcac tatcttgaaa 120
ttaacagcta gtacttatcc atcacagcag tctcctactg acatgaagca agttgttgaa 180
tgcagtagag catgaatgaa agcatttaat gtagacaaaa atgggtgata cccaagcatt 240
ctgaattatt tgcatcaagg aatggacatg tacataagtg gcatcatttc taccaatatg 300
tgacttgagt tgttttttta aaaaaaggag aatgactttc tcaaatttgc attaaagaag 360
tttttaagaa tgttcaaatg gcatgctgct ttgtctggac gtgaatttat tagcaagtag 420
taaagcactt cactaaagga ccatgaattt ttgtggtttc atggattctc tcttgaaggg 480
tacttttatt tttttaatat aattcagaaa ctcagaaggt aggtatgaaa tattggtagg 540
tgtttctcgc accttcagaa agtattggac cggtcttatt attataattt taacaaaata 600
tttccaattt ttgtgctttt gacatgcata aatgaccaaa gttaaaggga gtagttttta 660
tcttttctaa tgtgcttgaa tcgaaactct ctgtgcctaa ttaaaaagaa cattaacaaa 720
ctggaagcag atcttcccac tgatccataa tgtggtatgc atttattctg ctgttcagtc 780

-continued agaacattta aatcatctat gaggaatcac aaaacctctc aaagagcaat aaatactttc 840
caaccacttg ggaatttaaa tgaagattga acaatagtag gggaaaaact gctgtggttc 900
tactgggaac 910

<210> SEQ ID NO 1354
<211> LENGTH: 70
<212> TYPE: DNA
<213> ORGANISM: Homo sapiens

<400> SEQUENCE: 1354
agactcctct tgcaaggcgt acctccaaac ataattgatt cgtatctgcg agacttacac 60
tcaagcaatc 70

<210> SEQ ID NO 1355
<211> LENGTH: 121
<212> TYPE: DNA
<213> ORGANISM: Homo sapiens

<400> SEQUENCE: 1355
tggctactgt ctctctgcac tctgctgctt tgaaatctgg ttgaaatgag aaaaagcatt 60
ttctgttttc ccaccaggcc cccaagtgtg gtctttttct ttcctcctaa tgttgaagag 120
a 121

<210> SEQ ID NO 1356
<211> LENGTH: 475
<212> TYPE: DNA
<213> ORGANISM: Homo sapiens

<400> SEQUENCE: 1356
ggctgcgctg ctctttgatt ggcttcgtta atatttggca aagcattgcc acttacccac 60
tcagcgaaga tgcacaaaaa cgtcatcact gattctttca gttcgatgcc tgttaactgc 120
gggtgtaaac tgctggtgat ggtgtcattt actaccaaag aagtgtggag caggatgggt 180
gagagagtga gtgagtgagc aggtggaagg acagtgggtg aaggataaaa aggtgggaaa 240
catttttttt ttaaaaagtg aaacttcaaa tacagcggag gtggcttctt tcctatgagg 300
ctggctgatg ggtgccagat accaaggccc atgtgttact gaggagacag cctgctgggc 360
tggggtcagg agctagcgga gggaaacggt tagatctcag aaaaatctca tcactatgcc 420
ctagtagctt aatgacatca ctagcatgag cacatggtgt acttggcggg atctt 475

<210> SEQ ID NO 1357
<211> LENGTH: 80
<212> TYPE: DNA
<213> ORGANISM: Homo sapiens

<400> SEQUENCE: 1357
tcaccggctg tcacataata ctctgaatca tctgtcatct gacagttatt gataaacagg 60
attctctggc atcctttgtg 80

<210> SEQ ID NO 1358
<211> LENGTH: 123
<212> TYPE: DNA
<213> ORGANISM: Homo sapiens

<400> SEQUENCE: 1358
accagaagac tcattaggat ccataatagc tgccagtgta gaggagcctc agttactttc 60
actttgatca ttatccctgg gagaagaagc caacagctcc tggtgaccac aataagagat 120
ttc 123

<210> SEQ ID NO 1359
<211> LENGTH: 133
<212> TYPE: DNA
<213> ORGANISM: Homo sapiens

<400> SEQUENCE: 1359
tgtgtgaaac aaggattatc cagtaaaatc tgttgggttt caaagctata actagaataa 60
ttatttttgc aagatagtgc ttggcttgag tcaaaacatg aggcatttgt actcaacagg 120
ttctctttct ccc 133

<210> SEQ ID NO 1360
<211> LENGTH: 265
<212> TYPE: DNA
<213> ORGANISM: Homo sapiens

<400> SEQUENCE: 1360
gagccacctg ctcgcactca agatgaatca ggtgcaactg ctaagagtgg atattacccc 60
catgtaggct cttgaagcac attagtaaga atatcattta atgcatttta aagataacta 120
tgattctcta ttagaatgaa caatctacac tgtaccaatt actacaaatc ctgctgtgta 180
atttactgta cctttcaaca taacatttca ttttaagatt taaaatttct agtttttaat 240
tttaagatta ctcacaagga acctg 265

<210> SEQ ID NO 1361
<211> LENGTH: 95
<212> TYPE: DNA
<213> ORGANISM: Homo sapiens

<400> SEQUENCE: 1361
taagccacac ccatttacat ctgaggtcac aactactcat cagattttga ataatcctct 60
ttctactgct tcacaacagt tcacaagcca caaca 95

<210> SEQ ID NO 1362
<211> LENGTH: 46
<212> TYPE: DNA
<213> ORGANISM: Homo sapiens

<400> SEQUENCE: 1362
tctgttctta tccggccact gccttccata atagcctaag aagtgg 46

<210> SEQ ID NO 1363
<211> LENGTH: 144
<212> TYPE: DNA
<213> ORGANISM: Homo sapiens

<400> SEQUENCE: 1363
cttgacatgt cagcttgatt ctagaagtgc gtttacctgg aggacttacc cacaacttta 60
accttgatgc ttgcatgtgc ctctccagct tcgtttttca gattgatgtg gtaaacacca 120
gagtcatctc tttcagctat atca 144

<210> SEQ ID NO 1364
<211> LENGTH: 104
<212> TYPE: DNA
<213> ORGANISM: Homo sapiens

<400> SEQUENCE: 1364

-continued

```
cactgatcag attacaggca tttcatctcc ctgctcgtct gcctttgatc tgcatggtta     60

attttatttt cctggatttg aagtttcgtc tgggcttgtg ctga                     104


<210> SEQ ID NO 1365
<211> LENGTH: 32
<212> TYPE: DNA
<213> ORGANISM: Homo sapiens

<400> SEQUENCE: 1365

gtaagtactg caaagagctc agcatgttgc ag                                   32


<210> SEQ ID NO 1366
<211> LENGTH: 145
<212> TYPE: DNA
<213> ORGANISM: Homo sapiens

<400> SEQUENCE: 1366

acactcaaat gagggaaagt gggaactata gtgtttgttc cctcagcatc tgagggggac     60

tgctttcagg acaccctctt ggataccaaa atctgcaaat gctcaagtcc cttacaaaaa    120

atggtataaa tttgcatatg ctctg                                          145


<210> SEQ ID NO 1367
<211> LENGTH: 120
<212> TYPE: DNA
<213> ORGANISM: Homo sapiens

<400> SEQUENCE: 1367

cgttgccggg ctacgggaga gcgcggagcc ctgcgctggg aggtgcacgg tgtgcacgct     60

ggactggacc cccatgcaac cccgcgccct gcgccttaac caggactgct ccgcgcgccc    120


<210> SEQ ID NO 1368
<211> LENGTH: 393
<212> TYPE: DNA
<213> ORGANISM: Homo sapiens

<400> SEQUENCE: 1368

gggttatctt ctagtccaca tgtcacataa tatgtacctt tatttacctt ttaaactgaa     60

gttttaaaac ctgggtttta aaaagagaac aactacccat cagcaattac agaagacaaa    120

ggaacttgtg tgtctgaaga ctgagtgtta tttagcagct ctttggtcag cttggattgg    180

tcacatatgt ggaaactggg aaataatagg ggctacttac actggagaag aacactacaa    240

atggtgtaaa gagtggtttt ggaatgtatc cagacttcct tctaaaataa aaatttaaac    300

agctgtgttt gagagatggg tatgcacaat tcttgtaaga aagactgtgt agatgtttga    360

ggtcccctta gtccctgatg ctaccattgt tcc                                 393


<210> SEQ ID NO 1369
<211> LENGTH: 74
<212> TYPE: DNA
<213> ORGANISM: Homo sapiens

<400> SEQUENCE: 1369

ttgtctgtat tagagcacta ccttcaagaa atggggttct gacctggatt tgtgctacca     60

cagtgacttg catt                                                       74


<210> SEQ ID NO 1370
<211> LENGTH: 34
<212> TYPE: DNA
<213> ORGANISM: Homo sapiens
```

<400> SEQUENCE: 1370
aactctccaa caataaatac atttgataag aaag 34

<210> SEQ ID NO 1371
<211> LENGTH: 25
<212> TYPE: DNA
<213> ORGANISM: Homo sapiens

<400> SEQUENCE: 1371
taaaagtgct actagaacaa gagaa 25

<210> SEQ ID NO 1372
<211> LENGTH: 45
<212> TYPE: DNA
<213> ORGANISM: Homo sapiens

<400> SEQUENCE: 1372
gtggagaagg tttgtacaga attatatgca tcaaaaacaa tgtcc 45

<210> SEQ ID NO 1373
<211> LENGTH: 48
<212> TYPE: DNA
<213> ORGANISM: Homo sapiens

<400> SEQUENCE: 1373
agactgtaga cagcaagaat tcagggatcg gtctggaaac tgtgttcc 48

<210> SEQ ID NO 1374
<211> LENGTH: 26
<212> TYPE: DNA
<213> ORGANISM: Homo sapiens

<400> SEQUENCE: 1374
tagctcagca gatccaactc ccatgg 26

<210> SEQ ID NO 1375
<211> LENGTH: 238
<212> TYPE: DNA
<213> ORGANISM: Homo sapiens

<400> SEQUENCE: 1375
cccagcctcc cgattgggag acacctccca gcaggggtcg ccagacacct catacaggag 60
agctctggct ggcatctggt gggtgcccct ttgggacgaa gcttccagag gaaggaacag 120
gcagcagtct ttgctgttct gcagcctctg ccaatgatac ccaggcaaac agggtctgga 180
gtggacctcc aacaaactcc agcagacctg aagcaaaggg cctgactgtt tgtaggaa 238

<210> SEQ ID NO 1376
<211> LENGTH: 51
<212> TYPE: DNA
<213> ORGANISM: Homo sapiens

<400> SEQUENCE: 1376
gtcttctcaa ggattcgggg aagtactgcg tacttccttc aagcttttaa g 51

<210> SEQ ID NO 1377
<211> LENGTH: 53
<212> TYPE: DNA
<213> ORGANISM: Homo sapiens

<400> SEQUENCE: 1377

-continued atgtggcttc ggctatgggg aggatgcaca gtgtgtgacg tgccggctgc aca 53

<210> SEQ ID NO 1378
<211> LENGTH: 93
<212> TYPE: DNA
<213> ORGANISM: Homo sapiens

<400> SEQUENCE: 1378
gcaagccctg tctggactgc gcagtggtga accgctttca gaaggcaaat tgttcagcca 60
ccagtgatgc catctgcggg gactgcttgc cag 93

<210> SEQ ID NO 1379
<211> LENGTH: 53
<212> TYPE: DNA
<213> ORGANISM: Homo sapiens

<400> SEQUENCE: 1379
ttataggaag acgaaacttg tcggctttca agacatggag tgtgtgcctt gtg 53

<210> SEQ ID NO 1380
<211> LENGTH: 41
<212> TYPE: DNA
<213> ORGANISM: Homo sapiens

<400> SEQUENCE: 1380
acgcaacaca ggcagagcca aggggacgcc tggccttttg a 41

<210> SEQ ID NO 1381
<211> LENGTH: 207
<212> TYPE: DNA
<213> ORGANISM: Homo sapiens

<400> SEQUENCE: 1381
gtacctgcct gctaaggaac agacccacct gcctgctgtg gttgtattgc cagaagtgtt 60
ggattcacat cttggctgcg ctttgtactg atggtgtaac cttgggcaaa tagtctcccc 120
tctttgaacc tctgtttact ctggaaaatg cccaagtctg cagattttgg atagaactaa 180
atgaactagt agtccagcaa catgata 207

<210> SEQ ID NO 1382
<211> LENGTH: 179
<212> TYPE: DNA
<213> ORGANISM: Homo sapiens

<400> SEQUENCE: 1382
tcggccatac cctgacccag atgtgttctt tggagggtct gctgctttgg agttgtcctg 60
gacggggagg atctcatggt gcatctggct ctgatgtttg tcttctgggg cttcacctcc 120
cctggtgggt gagcactgaa gggtaccgga aagtgggttc catggagttt tgtgcctga 179

<210> SEQ ID NO 1383
<211> LENGTH: 142
<212> TYPE: DNA
<213> ORGANISM: Homo sapiens

<400> SEQUENCE: 1383
gcagctcaga tgggggccag gtgctgtggc tcacgcctgt aatcttacta ctttgggagg 60
ctgaggtggg aggatcactt gagcccagga gttcaagacc agcctgggca acatagtgag 120
acaccatatt cacaaaaaat aa 142

<210> SEQ ID NO 1384
<211> LENGTH: 63
<212> TYPE: DNA
<213> ORGANISM: Homo sapiens

<400> SEQUENCE: 1384
cctctgcatg atgagcccac aaagccagtg cctaaaggac taattaaggg ctccatttac 60
tga 63

<210> SEQ ID NO 1385
<211> LENGTH: 63
<212> TYPE: DNA
<213> ORGANISM: Homo sapiens

<400> SEQUENCE: 1385
tggtatttat ggtaattaac atacaaaaca gctgtactta caatccggca agtgccaaag 60
agg 63

<210> SEQ ID NO 1386
<211> LENGTH: 49
<212> TYPE: DNA
<213> ORGANISM: Homo sapiens

<400> SEQUENCE: 1386
gtcaggcccc ctggaagatt tggccagcag ggcagtggtc tgcgtgccc 49

<210> SEQ ID NO 1387
<211> LENGTH: 25
<212> TYPE: DNA
<213> ORGANISM: Homo sapiens

<400> SEQUENCE: 1387
ccggccctgg agggagcggg cgaca 25

<210> SEQ ID NO 1388
<211> LENGTH: 37
<212> TYPE: DNA
<213> ORGANISM: Homo sapiens

<400> SEQUENCE: 1388
tccctaagtg aagctgaccc acacataacc cacaccc 37

<210> SEQ ID NO 1389
<211> LENGTH: 37
<212> TYPE: DNA
<213> ORGANISM: Homo sapiens

<400> SEQUENCE: 1389
gtggcttctt gctggaccta gcttaacgac gagcctg 37

<210> SEQ ID NO 1390
<211> LENGTH: 51
<212> TYPE: DNA
<213> ORGANISM: Homo sapiens

<400> SEQUENCE: 1390
tccaactcct accttgggag agaatgacag tgaaccaaac aagtaaagta t 51

<210> SEQ ID NO 1391
<211> LENGTH: 27
<212> TYPE: DNA
<213> ORGANISM: Homo sapiens

<400> SEQUENCE: 1391
ggagagcaca gccaggccac agtggcc 27

<210> SEQ ID NO 1392
<211> LENGTH: 79
<212> TYPE: DNA
<213> ORGANISM: Homo sapiens

<400> SEQUENCE: 1392
cagcagatct attggagtgt gcctggcagc tggttctgca ggagctcacc tgccctaata 60
gaatgttcag gcccttctg 79

<210> SEQ ID NO 1393
<211> LENGTH: 151
<212> TYPE: DNA
<213> ORGANISM: Homo sapiens

<400> SEQUENCE: 1393
atgcagtcac ctccacagaa tgccccccgc ccctgcccca ggacacccag acgttgctca 60
gcatgcttac tgcccccacg tctgatcaca gtggcccgtc atgcagacac caagaccaat 120
gggaaggcgg aggaccccga acatctctgt g 151

<210> SEQ ID NO 1394
<211> LENGTH: 65
<212> TYPE: DNA
<213> ORGANISM: Homo sapiens

<400> SEQUENCE: 1394
ggtgcctgcc agcttcgcca taaacactgc atctgcagtt gttcagagca tgctgacccc 60
attcc 65

<210> SEQ ID NO 1395
<211> LENGTH: 93
<212> TYPE: DNA
<213> ORGANISM: Homo sapiens

<400> SEQUENCE: 1395
gtgccagcaa ggtcaacctc gtgaagatcg cgtccacggc ctccagccca cgggacacgg 60
cgctggctgc cgttatctgc agcgctctgg cca 93

<210> SEQ ID NO 1396
<211> LENGTH: 33
<212> TYPE: DNA
<213> ORGANISM: Homo sapiens

<400> SEQUENCE: 1396
gtaagagaca gtttatggag aagaaaccca gct 33

<210> SEQ ID NO 1397
<211> LENGTH: 122
<212> TYPE: DNA
<213> ORGANISM: Homo sapiens

<400> SEQUENCE: 1397
gtaagttttg agctcattac atttcttagc atttagggga agggcattta ttactattgt 60
cgtgcaagtg ttccacaaga gacttggctg agacaagcac cagtgagttg tgaaagaacg 120
ca 122

<210> SEQ ID NO 1398
<211> LENGTH: 58
<212> TYPE: DNA
<213> ORGANISM: Homo sapiens

<400> SEQUENCE: 1398
agctttgtaa ggagacttac aaggctgtga tgtccctgcg ccactaggca aaaataaa 58

<210> SEQ ID NO 1399
<211> LENGTH: 86
<212> TYPE: DNA
<213> ORGANISM: Homo sapiens

<400> SEQUENCE: 1399
ggtctctgcg gtcacaggac attcagtaca acggctctga gctgtcgtgt tttgacagac 60
ctcagctcca cgaatatgcc cacaga 86

<210> SEQ ID NO 1400
<211> LENGTH: 96
<212> TYPE: DNA
<213> ORGANISM: Homo sapiens

<400> SEQUENCE: 1400
tgcgcttgct cccatccatg tgctgtgagg aggcctgcag ccccaacccg gcgactcttg 60
gttgtggggt gcattctgca gccagtcttc aggcaa 96

<210> SEQ ID NO 1401
<211> LENGTH: 60
<212> TYPE: DNA
<213> ORGANISM: Homo sapiens

<400> SEQUENCE: 1401
ggagatggtg ccgactttct tcggatccct cacgcagtcc atctgtggcg agttttcaga 60

<210> SEQ ID NO 1402
<211> LENGTH: 202
<212> TYPE: DNA
<213> ORGANISM: Homo sapiens

<400> SEQUENCE: 1402
agctcaacgt ctttggattc aaatagcagt caagatttgg ttggtggggc tgttccagtc 60
cagtctcatt ctgaaaactt tacagcagct actgatttat ctagatataa caacacactg 120
gtagaatcag catcaactca ggatgcacta actatgagaa gccagctaga tcaggagagt 180
ggtgctgtca tccacccagc ca 202

<210> SEQ ID NO 1403
<211> LENGTH: 27
<212> TYPE: DNA
<213> ORGANISM: Homo sapiens

<400> SEQUENCE: 1403
gtaaggcagc gactgggttc cctgtga 27

<210> SEQ ID NO 1404
<211> LENGTH: 219
<212> TYPE: DNA
<213> ORGANISM: Homo sapiens

<400> SEQUENCE: 1404
tgacttacag tagatcagaa ctctgttccc agcataagat ttgggggaac ctgatgagtt 60

-continued tttttttgc atctttaata atttcttgta tgttgtagag tatgttttaa aataaatttc 120
aagtattttt ttaaaaaact aacacagcta atatataaga gcaaagtgga cagctgcatt 180
cttttattcc tctttgtaag tacaaccact tagcacagc 219

<210> SEQ ID NO 1405
<211> LENGTH: 37
<212> TYPE: DNA
<213> ORGANISM: Homo sapiens

<400> SEQUENCE: 1405
atgtcattct gtatcctggc ctgattatat cagagac 37

<210> SEQ ID NO 1406
<211> LENGTH: 217
<212> TYPE: DNA
<213> ORGANISM: Homo sapiens

<400> SEQUENCE: 1406
gaacttttag ggattctat agacaaaaca ttttttagct ttggagggaa aaaattggtt 60
tcattctcaa aacgggggaa tggagaagta agagaaggga gacgagtgaa tgaaggaaaa 120
acaaattagg cagttaacac atacaaagta tctacctctg agctctgcct ggagttagga 180
aaggctgttc actgatcttg ttcttttgag ccatcca 217

<210> SEQ ID NO 1407
<211> LENGTH: 207
<212> TYPE: DNA
<213> ORGANISM: Homo sapiens

<400> SEQUENCE: 1407
gcctctcttg ttaggagatc atctgaagaa ctagggttac ggtgctgcca gctgactaat 60
gactgttttt cagttttgtc aggaaacaga attaccactc accttaattt tgtagcttgt 120
acccaagttt gtgatgtcaa ttgccaagac taaggaatga aacgtcttca tacgaggtca 180
tcccggagcc aactcattgc ctgcttt 207

<210> SEQ ID NO 1408
<211> LENGTH: 1252
<212> TYPE: DNA
<213> ORGANISM: Homo sapiens

<400> SEQUENCE: 1408
ttgtcgtgct ccttccaatt gtgtaagatt agttagcaca tcatctccta ctttagccat 60
ccggtgttgg atttaagagg acggtgcttc tttctattaa agtgctccat cccctaccat 120
ctacacatta gcattgtctc tagagctaag acagaaatta accccgttca gtcacaaagc 180
agggaatggt tcatttactc ttaatcttta tgccctggag aagacctact tgaacagggc 240
atatttttta gacttctgaa catcagtatg ttcgagggta ctatgatatt ttggtttgga 300
attgccctgc ccaagtcact gtcttttaac ttttaaactg aatattaaaa tgtatctgtc 360
tttcctagta tgtttttatc ttctcatgta ttatccatgg ttttctctgt ttgtgacaga 420
ttagtaaaat ttaatgagcc ctctttcttg tggccgtttc tccatagttt taggttttga 480
tatgtgttta ctagcttgcc tgtgtctggt acatctcatg acctcaattc cctcacctga 540
aataggaaat gagaatgttt cattgtagcc ccaagcggtc atgtcaacct agtgcctagt 600
cataattaat tgacttttcc tgtattactt cttttttttaa gtataaacca atgatccttt 660
ggtagtcaag aactcttagg aacattgcct tttggacatg taaaatattt aggatttgac 720
cacacaatgg ctatgaaaat gcaagtagtt tcctcgcgtg acctcaccat gattcacata 780
cgtgccactg tttgaaatct ggtctgtttg catttctgtt atgacagaga gatgatgttt 840
gcatttctgt tatgacagag agatgatgaa agtaggcagg gctgtgttcc tttgtgtagc 900
ctgtatatat tttccatatg tagagccctg attaacttca aggacaaaca ctggctggag 960
aaagccagac tgatgggaat gagactttgg ccaaaaatcc caaaacatca ttttcaatca 1020
gtagagaagt gcttagggtt gaaaattgat ttcatttgct actgaatttg gtaaatcctg 1080
ggtaactttt atcaagatga agacatttta ccctacctac tctagaaata tacaacaatg 1140
ttatatttta cactccttgg aaacatttga ggaaaaaaat gcaatttgca cttcactttg 1200
ttggaatatc ccatagcact caataaactc agctgctaga gtgccgatgt ca 1252

<210> SEQ ID NO 1409
<211> LENGTH: 118
<212> TYPE: DNA
<213> ORGANISM: Homo sapiens

<400> SEQUENCE: 1409
gacctttctt tgtgttatct gcatgttgta acgtgtgata agaatgaatg taaaggctgt 60
ggcaactgta attaattttt gtaaagggct ggtcacacgt ggatctggtt tatgaatg 118

<210> SEQ ID NO 1410
<211> LENGTH: 32
<212> TYPE: DNA
<213> ORGANISM: Homo sapiens

<400> SEQUENCE: 1410
gacttcgagt gggtctacac cgaccagccg ca 32

<210> SEQ ID NO 1411
<211> LENGTH: 70
<212> TYPE: DNA
<213> ORGANISM: Homo sapiens

<400> SEQUENCE: 1411
cagggatttg aaccgcgctg acgaagtttg gtgatccatc ttccgagtat cgccgggatt 60
tcgaatcgcg 70

<210> SEQ ID NO 1412
<211> LENGTH: 54
<212> TYPE: DNA
<213> ORGANISM: Homo sapiens

<400> SEQUENCE: 1412
ctggactccc tcaagtacag tgacctgcag aacttagcca agagtctggg tctc 54

<210> SEQ ID NO 1413
<211> LENGTH: 43
<212> TYPE: DNA
<213> ORGANISM: Homo sapiens

<400> SEQUENCE: 1413
ttaaaagcct tgaaaggcta cattaaacat gaggcaagaa aag 43

<210> SEQ ID NO 1414
<211> LENGTH: 120
<212> TYPE: DNA
<213> ORGANISM: Homo sapiens

<400> SEQUENCE: 1414
tcttgtgatg agactgagat acagatcagc aaccaggaag aagctgagag acagccactt 60
ggccatgtca ccaaaacaag gagaaggtgc aagactgtcc gtgtggaccc tgactcacag 120

<210> SEQ ID NO 1415
<211> LENGTH: 56
<212> TYPE: DNA
<213> ORGANISM: Homo sapiens

<400> SEQUENCE: 1415
aactgaaaat aaaccaccta tgccaaaatt ggcatacttt tatggagatt tctttt 56

<210> SEQ ID NO 1416
<211> LENGTH: 26
<212> TYPE: DNA
<213> ORGANISM: Homo sapiens

<400> SEQUENCE: 1416
aaataagtaa tcccactgaa ttccag 26

<210> SEQ ID NO 1417
<211> LENGTH: 50
<212> TYPE: DNA
<213> ORGANISM: Homo sapiens

<400> SEQUENCE: 1417
tcagagctac tgcaaaagtt ccttctccac cagacgagca ccaagaagct 50

<210> SEQ ID NO 1418
<211> LENGTH: 26
<212> TYPE: DNA
<213> ORGANISM: Homo sapiens

<400> SEQUENCE: 1418
acagagattc aaaggtacct tcagaa 26

<210> SEQ ID NO 1419
<211> LENGTH: 25
<212> TYPE: DNA
<213> ORGANISM: Homo sapiens

<400> SEQUENCE: 1419
ccattgatca atatattgag agaaa 25

<210> SEQ ID NO 1420
<211> LENGTH: 26
<212> TYPE: DNA
<213> ORGANISM: Homo sapiens

<400> SEQUENCE: 1420
cagcccatca ataagggagg ggtcag 26

<210> SEQ ID NO 1421
<211> LENGTH: 79
<212> TYPE: DNA
<213> ORGANISM: Homo sapiens

<400> SEQUENCE: 1421
tgtggcttct actcccatca gccaacgacg ctcgcaaggc cggtcttgtg gccctgcaag 60
tcagagtacc ttgggtctg 79

<210> SEQ ID NO 1422
<211> LENGTH: 72
<212> TYPE: DNA
<213> ORGANISM: Homo sapiens

<400> SEQUENCE: 1422
ctaaagataa tgagcataag cgttcactga ccaagactcc agccagaaag tctgcacatg 60
tgaccgtgtc tg 72

<210> SEQ ID NO 1423
<211> LENGTH: 43
<212> TYPE: DNA
<213> ORGANISM: Homo sapiens

<400> SEQUENCE: 1423
tgcttgggac acacaaatta aagaccatca cggggaattc tgc 43

<210> SEQ ID NO 1424
<211> LENGTH: 88
<212> TYPE: DNA
<213> ORGANISM: Homo sapiens

<400> SEQUENCE: 1424
cccattcaag ttgacaactg aggcaacgca gactccagtc tccaataaga aaccagtgtt 60
tgatcttaaa gcaagtttgt ctcgtccc 88

<210> SEQ ID NO 1425
<211> LENGTH: 56
<212> TYPE: DNA
<213> ORGANISM: Homo sapiens

<400> SEQUENCE: 1425
accatggggg caatctaaag aaaataatta tctaaatcaa catgtcaaca gaatta 56

<210> SEQ ID NO 1426
<211> LENGTH: 86
<212> TYPE: DNA
<213> ORGANISM: Homo sapiens

<400> SEQUENCE: 1426
agcaacggaa gaaacgcgag caagaacgaa aggagaagaa agcaaaggtt ttgggaatgc 60
gaaggggcct cattttggct gaagat 86

<210> SEQ ID NO 1427
<211> LENGTH: 470
<212> TYPE: DNA
<213> ORGANISM: Homo sapiens

<400> SEQUENCE: 1427
cccactttag tcacgagatc tttttctgct aactgttcat agtctgtgta gtgtccatgg 60
gttcttcatg tgctatgatc tctgaaaaga cgttatcacc ttaaagctca aattctttgg 120
gatggttttt acttaagtcc attaacaatt caggtttcta acgagaccca tcctaaaatt 180
ctgtttctag atttttaatg tcaagttccc aagttccccc tgctggttct aatattaaca 240
gaactgcagt cttctgctag ccaatagcat ttacctgatg gcagctagtt atgcaagctt 300
caggagaatt tgaacaataa caagaatagg gtaagctggg atagaaaggc cacctcttca 360
ctctctatag aatatagtaa cctttatgaa acggggccat atagtttggt tatgacatca 420
atattttacc taggtgaaat tgtttaggct tatgtacctt cgttcaaata 470

<210> SEQ ID NO 1428
<211> LENGTH: 185
<212> TYPE: DNA
<213> ORGANISM: Homo sapiens

<400> SEQUENCE: 1428
tacatagccc tatcgaaatg cgaggattaa tgctttaatg cttttagaga cagggtctca 60
ctgtgttgcc caggctggtc tcaaactcca ccaaatgtac ttcttattca ttttatggaa 120
aagactaggc tttgcttagt atcatgtcca tgtttccttc acctcagtgg agcttctgag 180
tttta 185

<210> SEQ ID NO 1429
<211> LENGTH: 92
<212> TYPE: DNA
<213> ORGANISM: Homo sapiens

<400> SEQUENCE: 1429
atggccgctt cagacccaca gcaaagattt ttgataaggc atgactccta aacggatgaa 60
tgagtgcccc attagagcca agattctttt at 92

<210> SEQ ID NO 1430
<211> LENGTH: 33
<212> TYPE: DNA
<213> ORGANISM: Homo sapiens

<400> SEQUENCE: 1430
cttgaatccg tgaggcagat gtagtgagca gag 33

<210> SEQ ID NO 1431
<211> LENGTH: 150
<212> TYPE: DNA
<213> ORGANISM: Homo sapiens

<400> SEQUENCE: 1431
tagccaaagt ctaagcagaa gcccctgcga ccattccaac actgacagaa cattcctctg 60
ccttgtttta cggatacatt ggggaaactt aaggatgaga actttagaaa tggtatttct 120
tggaaaccca cttgcttgta aatcagtggt 150

<210> SEQ ID NO 1432
<211> LENGTH: 296
<212> TYPE: DNA
<213> ORGANISM: Homo sapiens

<400> SEQUENCE: 1432
tggtatctgg tgttaaggca gtgccgaatg gagggcagga aacacatttt taaatattta 60
tggatttatg tatttttctc ataaagacag ggtctcccta tgattcccag gctctccttg 120
aacgcctagg ctcaagtgat cctcccacct cagcctccca aagtgctggg attacaggtg 180
tgagccacca gattatattt atttctattc gctgtattta attcttaacc ccatgtttat 240
tttacataac ttccctattt ctcaaaaaga atttaaggcc tattctcaaa ataatg 296

<210> SEQ ID NO 1433
<211> LENGTH: 34
<212> TYPE: DNA
<213> ORGANISM: Homo sapiens

<400> SEQUENCE: 1433
ttatgaacca ttaagacaaa ttagaccagg catg 34

<210> SEQ ID NO 1434
<211> LENGTH: 183
<212> TYPE: DNA
<213> ORGANISM: Homo sapiens

<400> SEQUENCE: 1434
cccagggcac ctacatatcc agatagacat aaattcctca ctcctaagaa aaccaggctt 60
acaaggcgtc aaggccctat aaagaggaaa aacccaggac ggtccttaga ggcttccttc 120
agcatgaaaa ccaagttaaa gccagagctc atcctgggtt gcagcaagtc atggttgggc 180
cca 183

<210> SEQ ID NO 1435
<211> LENGTH: 26
<212> TYPE: DNA
<213> ORGANISM: Homo sapiens

<400> SEQUENCE: 1435
gctgcttccc gtccgctgtc ctctgc 26

<210> SEQ ID NO 1436
<211> LENGTH: 29
<212> TYPE: DNA
<213> ORGANISM: Homo sapiens

<400> SEQUENCE: 1436
gggcaaagcc catctggtcc gccgagcag 29

<210> SEQ ID NO 1437
<211> LENGTH: 211
<212> TYPE: DNA
<213> ORGANISM: Homo sapiens

<400> SEQUENCE: 1437
acagctgcca gacttcggta aatcaagggg gcgccccctg gagaccagaa ttttctggta 60
cccctgggga tccggcttca agatcgctgc taccagtggg cactcaaaac ggggtgccca 120
tgggtcccag gtacaagccc ggccgaacgt atctgaagcc ccaggaaaca cgtggcacaa 180
attccgggag aaactgttag cccggaagat a 211

<210> SEQ ID NO 1438
<211> LENGTH: 71
<212> TYPE: DNA
<213> ORGANISM: Homo sapiens

<400> SEQUENCE: 1438
agcatttgta cacctaagct cggtcttcct gcaacacttt gcgccttccc gacctcagag 60
acgtccgtct c 71

<210> SEQ ID NO 1439
<211> LENGTH: 31
<212> TYPE: DNA
<213> ORGANISM: Homo sapiens

<400> SEQUENCE: 1439
agctattggg agtggcggat cctcccaccc c 31

<210> SEQ ID NO 1440
<211> LENGTH: 98
<212> TYPE: DNA

<213> ORGANISM: Homo sapiens

<400> SEQUENCE: 1440
tggcactcat cttccgccac ctgtccctga gagaccgtgc tgccgccgcc agggtctgca 60
gggcctgggc cgccgctgct acctgcagcg ccgtgtgg 98

<210> SEQ ID NO 1441
<211> LENGTH: 208
<212> TYPE: DNA
<213> ORGANISM: Homo sapiens

<400> SEQUENCE: 1441
acttcccacg ggtcactcag ctagggaatg gcagaggcag aattcgaacc tagcagtccg 60
gaggccatgc caagactcct tagagacagc tgagaaagcc cagttcctaa aatatcattg 120
gctctccatg tccaggtttc atcctgtggc agacgccact gaaatcttct aaaaggatag 180
gatgcgagtt ccctcctttg gggcaaca 208

<210> SEQ ID NO 1442
<211> LENGTH: 25
<212> TYPE: DNA
<213> ORGANISM: Homo sapiens

<400> SEQUENCE: 1442
aggccttttc tgcacggctc taacc 25

<210> SEQ ID NO 1443
<211> LENGTH: 305
<212> TYPE: DNA
<213> ORGANISM: Homo sapiens

<400> SEQUENCE: 1443
agtgccgcgg agaaaaaccg ctcttcgacg cgggccgcga cgtcctggag gctgtgcacg 60
ctgtatgcgg ggcggccagc cagctacgcc acctcgacct gcggcgcttg tccttcacac 120
tggacgacgc gctggtgctg caggcggcgc gcagctgtcc cgagctccac agccttttc 180 tggacaacag taccctagtg ggcagcgtgg gtcccggctc agtgctcgag ctactggagg 240
cctgcccgcg cctgcgcgct ctcggcctgc acctagccag tttgtcgcac gccatcctcg 300
aagca 305

<210> SEQ ID NO 1444
<211> LENGTH: 116
<212> TYPE: DNA
<213> ORGANISM: Homo sapiens

<400> SEQUENCE: 1444
gcgccccgag tgctagtgcc ttcttttggg attgttgccc cccgggtctt taccgagttg 60
ggaactgtga tggcatcggg accagtcctg ggcgccctga gaccactcgc tgctct 116

<210> SEQ ID NO 1445
<211> LENGTH: 25
<212> TYPE: DNA
<213> ORGANISM: Homo sapiens

<400> SEQUENCE: 1445
acactgcccc cctctcttgc ctcca 25

<210> SEQ ID NO 1446
<211> LENGTH: 30

<212> TYPE: DNA
<213> ORGANISM: Homo sapiens

<400> SEQUENCE: 1446
gtgagtgtga aataaacaaa tcctgcagtg 30

<210> SEQ ID NO 1447
<211> LENGTH: 30
<212> TYPE: DNA
<213> ORGANISM: Homo sapiens

<400> SEQUENCE: 1447
tgacttcctt actattgctt cctggactaa 30

<210> SEQ ID NO 1448
<211> LENGTH: 270
<212> TYPE: DNA
<213> ORGANISM: Homo sapiens

<400> SEQUENCE: 1448
atgggccttg gtcacactcc ttggcttctc ccaccgcaag caacgctgcc tgcctctgcc 60
gctcctccac atcttgccgc tgcccagcag agctggcttc tgggtccacc tgagcactgg 120
acggtgctcc cagggcgttg gagcaggcgg aggggtgtgt ggccaggtac taggaggcac 180
caggaaatcc cgcggggtgg cccatgcaga ccaggcgcac gtggctcatg gggcagaatt 240
gccaaggaca gctcacgaca gtgccacctt 270

<210> SEQ ID NO 1449
<211> LENGTH: 58
<212> TYPE: DNA
<213> ORGANISM: Homo sapiens

<400> SEQUENCE: 1449
aatgtgcaca ggctggtcaa cgacctgcgc tactacagac tctgcaacga cagcctgc 58

<210> SEQ ID NO 1450
<211> LENGTH: 2412
<212> TYPE: DNA
<213> ORGANISM: Homo sapiens

<400> SEQUENCE: 1450
ttagtctcag ccatggaggt cccgagttcc tggctctgca gcccctccat ttgtcttggc 60
atctttgttc atacccagga ccctgccgtt ctccctcctg ggtgatgagc cccggtgggg 120
ccagcattgg agtgtgccca ggcttgcatt caggctgaga tggttggtgc ttgggagctg 180
cacttctggg tccccagggt tagaggtggg acccaggttc cccggctgtc ttgggctctt 240
tccagaccag ccccagctca gcttgggctg agttgctgcc aggtcctggg aggagccctc 300
ctagtactca ccctcttgtc ccactgctgc cacctgtgca gggactgtca ggtgggctgt 360
ccccacccgt gcagcacctc ggtgggagct gggtgctgct ggctcttggt gtccatgagg 420
ccatcttgtt ggagcctgac agtgcctggg acctccttcc ccatggggct cacctgttct 480
cttcttcctg tgtcaggtga ccaggcctct ctcttgcctg ataggaactt ctgggaactt 540
ttccttgtac cgttttatac ttgatgaaat taggaaaaga aatcgctttc tccctggtcc 600
tcttggggtt cttgacctga gtcctctgtg aagcagcttg tccacggctc caccgtagtg 660
ctcagatgca cacactgctc tcactggtgc aaacctggcc gcctgctttc ctcatttgcc 720
acgtgtggca gggaagcttt tgcttagact catcctgttc tcctttgtct tggggtcttc 780

```
cttttcttgg gacttgttct ctcctaagcc tcttccagtt cacttcagcc cctggatatg    840

tttttccctt tttctagagg ccagatccta atacttaatg atcagcttct aacgacatca    900

atatcagtca actttttgat ttaaagctgt ggtttcaaaa tctagttata ggccaggcgc    960

ggtgtctcac acctgtaatc tcagcacttt gggaggccaa ggcgggcgga tcacttgagg   1020

ttagggggtt tgagaccagc ctggccaaca tggcgaaacc ctgtctctac taaaaataaa   1080

aaaaattagt caggtgtggt ggcacacgcc tgtaatccca gctgcttggg aggctgaggc   1140

acaagaatct cttgaacccg ggaggcagag gttgcagtga gcggaggttg tgccactgca   1200

ctccagcctg ggcggcagag tgggactttg tctcaaaaaa aaaaatctag ttatatcaga   1260

agcacctggg gtacttatta aaaatggaga aacagacttc tgtgttctac ccaggaaatt   1320

ctggtttggc atttgggagc cactgattta aaagacatcc cttagttggt tttttgaggg   1380

taaaataaaa gaatcaccac cttccattca gtcacgcact gtgtgtttga agccagctgc   1440

ttctcaagcc ccgggccagg aactggggca ccagtcccag ccttcaccaa gtctttcatg   1500

gtagacaggc caatacagca ccctctgtgg accacatagt gccaagcatg tgacatgtct   1560

tggctcgagt aagccttcta acaagcctct gaagtgtggg tcctgttact cccccatttc   1620

acagatggtg ggggctcaga aggtgagcag ttcacagaac ttggaagtgg tagagctgcg   1680

aagcaggagg cagacctggg tgttctggcc ccagagcctg cacacactcc ccagaagcag   1740

attgctcagg acagaggcgc tgagctggct gctggggcca ggaaatagga ggcatctgtg   1800

cagactttgg gaagaggcag gctttgaatg gagttctgga agaggaatag tggttgggca   1860

ggaaaatgaa cttggtcctg ctcatggctc tgctggggct tgctgggcct gtttgagtcc   1920

tcaccgggac ctacactgaa aaaaaaagca gggtctcacc gtgtgcatga tggcggaggt   1980

cagggcctca cttctggccc agggccttcc atggcccacg ctgcgcccag tgggacaggc   2040

cttgggactg tgtttgctgc tgctcgggtg gctctcgagg ggcaggggcg gcctggagcc   2100

ccgtgggtaa aggttctgca gacattgctc ggtgtgcgcg tcacctcaag gggccatggt   2160

gaagaagagg gctgtcacca cagccatgtc tgcgtttgag gggccggact caggagcaag   2220

tgtgctggtc tcttcagtgt gagctggggc cagcttcttc atggtgcagc gctttggtct   2280

ttctgtcctt agactagtgg ttctggtagg gcttggtggc agccttgtgg tgaggactca   2340

gtgagttgat gtctgtatgt tgattgcagc agtgtctggc acccgagagg ccctagggac   2400

gtattcctct tg                                                       2412
```

<210> SEQ ID NO 1451
<211> LENGTH: 161
<212> TYPE: DNA
<213> ORGANISM: Homo sapiens

<400> SEQUENCE: 1451

```
aggtcctggt ccacaagtcc catgatcttc tgcaggagga gattggcatc gccatctaca     60

acatggcctc agtcgacttt gatggcttct ttgccgcctt cctcccagag ttcctgacca    120

gctgtgatgg tgtggatgcc aaccagaaaa gtgtgctggg g                        161
```

<210> SEQ ID NO 1452
<211> LENGTH: 74
<212> TYPE: DNA
<213> ORGANISM: Homo sapiens

<400> SEQUENCE: 1452

```
gtcctttctc cagcccgaca tccacctttt taaacaaaat ctcttctact tggagactct     60
```

caacaccaag caga 74

<210> SEQ ID NO 1453
<211> LENGTH: 111
<212> TYPE: DNA
<213> ORGANISM: Homo sapiens

<400> SEQUENCE: 1453
acaggactga gcttctgtgc ctggactgaa ctagtaactt ttacacccag gaattccaaa 60
gcagtttaaa aatactttgc ttagccccca ggcagaggct taacctccag g 111

<210> SEQ ID NO 1454
<211> LENGTH: 79
<212> TYPE: DNA
<213> ORGANISM: Homo sapiens

<400> SEQUENCE: 1454
gccgagctgt ttgagctcct tttccggacg ctccatcaca actggaggta cttcttcaag 60
tccaccgtgc tggccagtg 79

<210> SEQ ID NO 1455
<211> LENGTH: 149
<212> TYPE: DNA
<213> ORGANISM: Homo sapiens

<400> SEQUENCE: 1455
gagcagttag ccgagagcat cctccacgag ggcagcacag gctgccgggt ggtggagaag 60
tttctgaaga tcctgcaggt ggtggtccag gagccaggcc aggtgttcaa gcccttcctc 120
cccagcatca tcgccctgtg catggagca 149

<210> SEQ ID NO 1456
<211> LENGTH: 93
<212> TYPE: DNA
<213> ORGANISM: Homo sapiens

<400> SEQUENCE: 1456
actgatgaga tgctgagctt cttcctcact ctgtttcgag gccttagagt acagatgggt 60
gtgcctttca ctgagcaaat catacagact ttc 93

<210> SEQ ID NO 1457
<211> LENGTH: 94
<212> TYPE: DNA
<213> ORGANISM: Homo sapiens

<400> SEQUENCE: 1457
accagacact cagcgtctta gaagatattg tggagaatat ctcgggggag tccaccaagt 60
ctcgacagat ttgctaccag tcgctgcagg aatc 94

<210> SEQ ID NO 1458
<211> LENGTH: 285
<212> TYPE: DNA
<213> ORGANISM: Homo sapiens

<400> SEQUENCE: 1458
catttttgaa gcgtccaggc ctgttttctt gtcatatgtc tcctagtctt gttttgcctg 60
attgtttcca taggttgtgg tgtagtggtg catgttcgtg ttcgcatttc ctcttgcatt 120
gcttctgttt gtcccatcct tggtgatgct cagtctggat gcctgttggg agtagggcct 180

-continued

```
gccagtctgt ccattgggaa ggtgcttggc aggtgtaatt gctcaggact gtagagaaag    240

tgggcgaggt caagagttgg acttgggtct gaatggctcc agctc                    285


<210> SEQ ID NO 1459
<211> LENGTH: 75
<212> TYPE: DNA
<213> ORGANISM: Homo sapiens

<400> SEQUENCE: 1459

agcagtggcc cgtgcgctcc atcaaccacg ccagcctcat ctctgcactc tcccgggact     60

atcgcaacct gaagc                                                      75


<210> SEQ ID NO 1460
<211> LENGTH: 59
<212> TYPE: DNA
<213> ORGANISM: Homo sapiens

<400> SEQUENCE: 1460

ccaggtgttg gtgtgccgag ccctctctaa catcttgctg cttccgtggc caaaccttc      59


<210> SEQ ID NO 1461
<211> LENGTH: 136
<212> TYPE: DNA
<213> ORGANISM: Homo sapiens

<400> SEQUENCE: 1461

agctgctgct atctgcgtgc cacttactgg tctcactggc caccaccgtg cggcccgtct     60

ttctgatcag catccctgca gtgcagaaag tattcaacag aatcactgat gcctctgccc    120

tgcgacttgt cgataa                                                    136


<210> SEQ ID NO 1462
<211> LENGTH: 495
<212> TYPE: DNA
<213> ORGANISM: Homo sapiens

<400> SEQUENCE: 1462

gggcaaaatg ctatgaaacg gcaccgcatg ctccagagaa atatttcatg aaaggaagtc     60

aatcgatgca gcaaacttca ttgttgtctt attttaagta attgccacag ccaccccaac    120

tttgagcaac caccaccctg ttcagtcagc agcagtcact ttcaaggaag acccttcacc    180

agcaaaaaga ttaccgctct gaaggctcag atgattgtta gcatttttag caataaacta    240

ctttttaact aagatatgta cattgttttc ttagacataa tgcttattgc acactttata    300

gactatagtg taaacaaaac atatgcattg ggaaacaaaa aaattagtgt gccttgcgtt    360

attgcataat ttgctttatt gtggtggtct ggagctgaac ctgcagtatc tctgaggtat    420

gcctgtatat ccttccagac ttttttctct ttttatgtaa taagtaataa ctaagtttgt    480

agatagctgg agata                                                     495


<210> SEQ ID NO 1463
<211> LENGTH: 75
<212> TYPE: DNA
<213> ORGANISM: Homo sapiens

<400> SEQUENCE: 1463

gttgtagcct acatgcattc agatacaact ttactttttt agttatctga gttccacatg     60

aatacatgct cactg                                                      75
```

<210> SEQ ID NO 1464
<211> LENGTH: 101
<212> TYPE: DNA
<213> ORGANISM: Homo sapiens

<400> SEQUENCE: 1464
ggcttactct cactggttag cacagtattg cagtgaagtt caccggcaga acacgcagca 60
gttcgtgaca ctcatctcta ctaccatgga tgcaatcaca c 101

<210> SEQ ID NO 1465
<211> LENGTH: 173
<212> TYPE: DNA
<213> ORGANISM: Homo sapiens

<400> SEQUENCE: 1465
gaggaccttt tgcagatcca gatcttaatt tttttaaaag catgtcctac aatctggatt 60
tgtctaatta tttccattat attagattca gtttaaacat ttttagcaag gttactacat 120
aggcaatgat gtgcctttcc tcttgcatca tgtcagaagg ctcttaatat caa 173

<210> SEQ ID NO 1466
<211> LENGTH: 82
<212> TYPE: DNA
<213> ORGANISM: Homo sapiens

<400> SEQUENCE: 1466
tttcagcctt gaggagctct acagatgtgc tagattgact gaaattctta ctcctaaggc 60
tgactttgat gtcctttctc tt 82

<210> SEQ ID NO 1467
<211> LENGTH: 73
<212> TYPE: DNA
<213> ORGANISM: Homo sapiens

<400> SEQUENCE: 1467
tcaaagtcac tctgtacgga tctcagataa aattgtacaa cattgaaact gctgtgccat 60
cagtattgaa acc 73

<210> SEQ ID NO 1468
<211> LENGTH: 33
<212> TYPE: DNA
<213> ORGANISM: Homo sapiens

<400> SEQUENCE: 1468
gatatatctt atctgttcag ttggcggggc gca 33

<210> SEQ ID NO 1469
<211> LENGTH: 104
<212> TYPE: DNA
<213> ORGANISM: Homo sapiens

<400> SEQUENCE: 1469
aacatcacgg cggagaacga ctgccggcgg ctgcactgct ccctgagaga cttgagctcc 60
ctgctgcagg ccgtgggccg cctggccgag tactttatcg ggga 104

<210> SEQ ID NO 1470
<211> LENGTH: 38
<212> TYPE: DNA
<213> ORGANISM: Homo sapiens

<400> SEQUENCE: 1470
tttgaagaag ttgtgttgaa aagtaaggaa atttcaga 38

<210> SEQ ID NO 1471
<211> LENGTH: 87
<212> TYPE: DNA
<213> ORGANISM: Homo sapiens

<400> SEQUENCE: 1471
gcctgtgtaa atgggcgcca gccgcgattc ttgtctactc ctggtgctgt gaccgtgtat 60
gacaatggga tgcacatttt ggccagc 87

<210> SEQ ID NO 1472
<211> LENGTH: 27
<212> TYPE: DNA
<213> ORGANISM: Homo sapiens

<400> SEQUENCE: 1472
cttcttatgg gatctgtccc ggctctg 27

<210> SEQ ID NO 1473
<211> LENGTH: 33
<212> TYPE: DNA
<213> ORGANISM: Homo sapiens

<400> SEQUENCE: 1473
tttaaaggct tatgatgaaa agctgtgggg gag 33

<210> SEQ ID NO 1474
<211> LENGTH: 65
<212> TYPE: DNA
<213> ORGANISM: Homo sapiens

<400> SEQUENCE: 1474
tgttcttcag gacaatttag aagtttattt gggattacaa cagtttatag tcacttcagg 60
gtcag 65

<210> SEQ ID NO 1475
<211> LENGTH: 56
<212> TYPE: DNA
<213> ORGANISM: Homo sapiens

<400> SEQUENCE: 1475
tcctgctcac agaggtgttg aatcgaatcc agttcagata caaccaagcc cagctg 56

<210> SEQ ID NO 1476
<211> LENGTH: 36
<212> TYPE: DNA
<213> ORGANISM: Homo sapiens

<400> SEQUENCE: 1476
ttgtttggat atctggacgc tgtttttgga ctatct 36

<210> SEQ ID NO 1477
<211> LENGTH: 35
<212> TYPE: DNA
<213> ORGANISM: Homo sapiens

<400> SEQUENCE: 1477
gtggttaatg gaatgaaggg ttgcctgtcc tgtag 35

<210> SEQ ID NO 1478
<211> LENGTH: 162

<212> TYPE: DNA
<213> ORGANISM: Homo sapiens

<400> SEQUENCE: 1478
agccttctag acttgccaga ttgaaatgac acagtgatct gcccatcaac tttttatcat 60
ttcccttcac tttaattggg tcacaacaca aatgacttag aaaatgtgag cgcactagat 120
tataagaagc cttagcagac agtgtctgag gattaaagtt gc 162

<210> SEQ ID NO 1479
<211> LENGTH: 179
<212> TYPE: DNA
<213> ORGANISM: Homo sapiens

<400> SEQUENCE: 1479
caggagcaac atgggacatt ttatttccgg gccagttttg cttttctgag tagtagtttt 60
ctctgctttt attatttcac atatctctgt tttgaaaaat agcttttgca gtaatgagct 120
tcagaattgc ttttagccat tatttcattt tcagctaagg cctagtatgt ctttacctt 179

<210> SEQ ID NO 1480
<211> LENGTH: 612
<212> TYPE: DNA
<213> ORGANISM: Homo sapiens

<400> SEQUENCE: 1480
aaaaccgtga tgtttgctct gtataagaac acaatctgat atggtaatat gttcttaaaa 60
attatttggt gatagctttc catatgaatt caaaggcatc attattcaca ctttcatatt 120
ctttctgtct gtggttaaga aaggctgtat taccttttt ttaatgatct gtgtgtctca 180
tgtctatctc ttcatatgtt aatttaaaaa tctagctgct tgtatcaact atcaaatatc 240
agttgttttg actttaatca taatgtagtc acagacaact ttgttgtggc ttccatttgg 300
atggtataga aatgtcatta tggattgtct atgtactgat gttgttacgt gtaacttttg 360
tgctcttggt tttacatttt aatcctgtgc ttcctattgc cctgtgaaag ctgagaggtg 420
cctgggagca gaaaggtgac ataaataatg ctgtgtgctt gcttcctggc tctgggtccc 480
ctaccactaa ttctaaacag ctcagtccat tctcagttgt ttaggagctg ctaaccagat 540
ccttggcttc tctttccctc tactgccttt tcccctaact ttctactgtt cattagcacc 600
tgtaccagaa gg 612

<210> SEQ ID NO 1481
<211> LENGTH: 224
<212> TYPE: DNA
<213> ORGANISM: Homo sapiens

<400> SEQUENCE: 1481
ttgttattgt cctctcaagt ggagcctaca atgacctact tttttttttt tttaaaagca 60
ctctaaaaga cgactccatc acagtactct gaggcagggt ttcatgattt atgtctcttg 120
cagatgaggt catttatgta tcttacaact gctgctgtat gaaaacagga gggaatttgg 180
aaacttatat tatgaacaat cagattgacg gtttagggac tttc 224

<210> SEQ ID NO 1482
<211> LENGTH: 32
<212> TYPE: DNA
<213> ORGANISM: Homo sapiens

<400> SEQUENCE: 1482

-continued gagactgctg ctcctgcgta gccaagaaca gg 32

<210> SEQ ID NO 1483
<211> LENGTH: 113
<212> TYPE: DNA
<213> ORGANISM: Homo sapiens

<400> SEQUENCE: 1483
acagaaaggt aggtgtgtgc cagtaagtct gagattagct ggaagggctt gggtggttaa 60
gggaagtgac tgagtttgaa aaatgcttgt gccttgtgta ggtttgttgt ctt 113

<210> SEQ ID NO 1484
<211> LENGTH: 32
<212> TYPE: DNA
<213> ORGANISM: Homo sapiens

<400> SEQUENCE: 1484
tgctgtgctg catggcatct gtaatcctct tt 32

<210> SEQ ID NO 1485
<211> LENGTH: 29
<212> TYPE: DNA
<213> ORGANISM: Homo sapiens

<400> SEQUENCE: 1485
atcaatgaac tcatgtccaa gaactgtgt 29

<210> SEQ ID NO 1486
<211> LENGTH: 161
<212> TYPE: DNA
<213> ORGANISM: Homo sapiens

<400> SEQUENCE: 1486
agctagcgca ccctcttaat tcctacgtct gtttagtctt gagtctctat gtaatttgat 60
gccagtgtgt ccttttgcta cagcttctcc attccttaat tctttatttt gatttatctc 120
tttatctgtg tggtttcttt gtctgttatc ctccttgaga a 161

<210> SEQ ID NO 1487
<211> LENGTH: 26
<212> TYPE: DNA
<213> ORGANISM: Homo sapiens

<400> SEQUENCE: 1487
ggagggttga agtgggagaa tggctt 26

<210> SEQ ID NO 1488
<211> LENGTH: 396
<212> TYPE: DNA
<213> ORGANISM: Homo sapiens

<400> SEQUENCE: 1488
gtcttttctg tttgatgaga gcctcatgac aaggtgtaaa gggtaagaat aaacagaaag 60
caaaccacaa catgagacag gaaggtagga ggagagggga gtgccctggg tgactggggt 120
ggctgctgtg tgctgctgtg atacctgttt gctagggaga catgtatgca atgcctggcc 180
gtgaggccct gagggtgccg ggagcctggg cttgctactt gagggaatct tgtagtgaaa 240
agaagttttt atctctaact cctttatcca ggcttcttct tggatgtcta ggaactttct 300
ttatatctcc agtttagtgc ttggcatgtg gtgggcactt aaagttggct gaaagaacca 360
ttgatttaaa gtaaacttgg gttagtgcaa tggctc 396

<210> SEQ ID NO 1489
<211> LENGTH: 27
<212> TYPE: DNA
<213> ORGANISM: Homo sapiens

<400> SEQUENCE: 1489
tagaccatct ctggattact tctaata 27

<210> SEQ ID NO 1490
<211> LENGTH: 82
<212> TYPE: DNA
<213> ORGANISM: Homo sapiens

<400> SEQUENCE: 1490
atggaaatcc gtagctgtct gcccaaactc cttttggctc accataaaac cttaccttac 60
tttatccgga acaagctctg ca 82

<210> SEQ ID NO 1491
<211> LENGTH: 55
<212> TYPE: DNA
<213> ORGANISM: Homo sapiens

<400> SEQUENCE: 1491
gcctctctca gggcattgga aagtctgatg acagaatttt ttcacgattg tacaa 55

<210> SEQ ID NO 1492
<211> LENGTH: 30
<212> TYPE: DNA
<213> ORGANISM: Homo sapiens

<400> SEQUENCE: 1492
gagtgattta tctgattggt acaccaggga 30

<210> SEQ ID NO 1493
<211> LENGTH: 44
<212> TYPE: DNA
<213> ORGANISM: Homo sapiens

<400> SEQUENCE: 1493
tctcaagctt catccgtgtg gtggcgtgtg tcagagcttc cttc 44

<210> SEQ ID NO 1494
<211> LENGTH: 47
<212> TYPE: DNA
<213> ORGANISM: Homo sapiens

<400> SEQUENCE: 1494
agtggagtca tgaagtattt ggcctgttgt gactgcctta tttcaca 47

<210> SEQ ID NO 1495
<211> LENGTH: 379
<212> TYPE: DNA
<213> ORGANISM: Homo sapiens

<400> SEQUENCE: 1495
ggcctgtcag cctccgcccg ttcagcctcg gggccggggc cgccgccacc tctgcccgcg 60
gaggccgggg agcccctgcc tgggcccgca gcctcccccg cgggggtcgg gcccgggcgg 120
gggtcccgag cagctgccct cctcgccggc atccgagcct catttcctgc tttttcagtt 180
tccttgggga ggggcgggtg ggtctggatg aattgtctcg gggtccccccg atgaggcgac 240 ccgggcggcc ctgccctttt tagagggtcc cctcggggcc cggtggggaa ggggttgtct 300
ttgcatgggt gggggacttc ccgagtctgc cgggaccatg acctgaactg tgcgagcggg 360
acgtgtccga agcccaaga 379

<210> SEQ ID NO 1496
<211> LENGTH: 389
<212> TYPE: DNA
<213> ORGANISM: Homo sapiens

<400> SEQUENCE: 1496
tgctttgtga tagggagagt tatttctaag ggaaaggaat gtaccctgta tttctttctt 60
tttctttttt tttttttttt tttttgagac agagtcttgc tctcttgccc aggctggaat 120
acagtggggt gatcttggct cactgcaacc tttgcctcct gggttcaagt gatcctcctg 180
cctcagcctc ctgagtagct gggactatag gcgcctgcca ccacacccgg ctaatttttg 240
tatttttagt agagatggag tttcaccatg ttggccaggt tggtctcgaa ctgctgacct 300
caagtgataa agtgctggga ttacaggcat gagccaccac gcccagcccg taccctgtat 360
ttcttgaagt gaagaatata aagtctgta 389

<210> SEQ ID NO 1497
<211> LENGTH: 32
<212> TYPE: DNA
<213> ORGANISM: Homo sapiens

<400> SEQUENCE: 1497
tcacagctca tagtgacctc gatctcctgg tc 32

<210> SEQ ID NO 1498
<211> LENGTH: 353
<212> TYPE: DNA
<213> ORGANISM: Homo sapiens

<400> SEQUENCE: 1498
tgcagagatt acctatgtta caggcttaaa ttatagatgt gaagatggta aagggagaca 60
ctattttaat caaaagcttc ctgggtacaa agctaatgag aggaaaaatt atacatttta 120
tcaagctctt tttcaagtaa agaatagctt tctttttttca tctggcttct tgcctgacct 180
tctccccttc ccctaaatgg tgagaggaag gagagcttgc agatagattt tccatatcgt 240
aggggatttt tatatctggg aagcacagca tttcatattt ataggagggt gtatattgcc 300
aaatgggata tttggcatta cgagtcattt ccagctgaga gagtaaggat gca 353

<210> SEQ ID NO 1499
<211> LENGTH: 494
<212> TYPE: DNA
<213> ORGANISM: Homo sapiens

<400> SEQUENCE: 1499
tccctggcgt tctgtccaat acacttgcct tcaatccaag ttgaggacgg ttatggtaac 60
cctctccaag gctctcttaa gtgggcgtca gggaagccca ctggagacag gaaagaccaa 120
gagggttggg agtctaagtg aacctattcc tgggttggtt agtggtgcgt cctgtgacaa 180
gaagagaggg accttgagac ggagagtcac aggcctgatg atagcaggta aggtggagcc 240
acagttccac cgctgggatt ggtccctttg atgaagaaca gaacgtttcc tggctacatt 300
tgaagtataa ttatttgtaa caaaagatgg atttggaaga gagcactttt aggtgaaggg 360
cttctggagg tttaaaaagg ctaattgtcc actgttctcc accacctccc gctttcaacc 420
ccttcagtat tgactccttt aacctcatgt agctttcgtg actttgaaac accatgtagt 480
agaaggagcc agac 494

<210> SEQ ID NO 1500
<211> LENGTH: 104
<212> TYPE: DNA
<213> ORGANISM: Homo sapiens

<400> SEQUENCE: 1500
taaattttag cctttctggt agatgtgtag cactatctta ttttaaattt gtattttcct 60
gataactaat gaggctgaac acttatttat aggctttttg aata 104

<210> SEQ ID NO 1501
<211> LENGTH: 325
<212> TYPE: DNA
<213> ORGANISM: Homo sapiens

<400> SEQUENCE: 1501
ggatgtaact gctaggccac cttcagttct ttgaagttag ggaccgtctt actcatcatt 60
gtatcccagg ggcttaattt aagcaatatc agttacttag tgagtattga attctcattt 120
ctccaacaaa tagctgagtt gcttagtcac tccagaatta aagctaggtt tagaataatt 180
ggagcggtgt gatggcatgt gcctatagtc tcagcttctc aggaggctga agtggggagg 240
atcgcctgag cccaggggtt tgaggctgca gtgagctgtg attgttccac tgcactccag 300
tctggggtga tacagcaaca ctctg 325

<210> SEQ ID NO 1502
<211> LENGTH: 176
<212> TYPE: DNA
<213> ORGANISM: Homo sapiens

<400> SEQUENCE: 1502
ctcccacatg actatggtac agttaccatc ttcggttaat agaacattga ttcagtactt 60
tgatctaacc tactaccacc tgtattccag ttttgtcaat tggctcagtc atgcctttca 120
tagcattttt tccctccagt ccaggatcaa tctgtggtca ggtgtagcat ttactt 176

<210> SEQ ID NO 1503
<211> LENGTH: 54
<212> TYPE: DNA
<213> ORGANISM: Homo sapiens

<400> SEQUENCE: 1503
tgcagcatgc ttttatagtg gttcgtcagt ttcatactca ttcattacct gatg 54

<210> SEQ ID NO 1504
<211> LENGTH: 41
<212> TYPE: DNA
<213> ORGANISM: Homo sapiens

<400> SEQUENCE: 1504
atggtgtgtg tgaagacatg gaactgttat gtggagagaa a 41

<210> SEQ ID NO 1505
<211> LENGTH: 281
<212> TYPE: DNA
<213> ORGANISM: Homo sapiens

<400> SEQUENCE: 1505
acagttggtg ttacgttaga gctaataatt atactttagc acgttaacct cagaattcta 60
aggctgagag tcaaacactg ctaattcata gaaggcaata gcttgtaata atgaatcata 120
aagctcttct actctttgta gttcagtaga taaaaacatc tgtctgtagt gaactatttt 180
atctgatggg aagaacaccc gaggatccgc cttcagtata gaatcgaaga gaaactgctt 240
cactagctct tttccactag tccgggagtc accaatcatc a 281

<210> SEQ ID NO 1506
<211> LENGTH: 29
<212> TYPE: DNA
<213> ORGANISM: Homo sapiens

<400> SEQUENCE: 1506
tgaaattgaa ttaagtttaa ggctgggtg 29

<210> SEQ ID NO 1507
<211> LENGTH: 37
<212> TYPE: DNA
<213> ORGANISM: Homo sapiens

<400> SEQUENCE: 1507
ggctgttcca aaacagtaag ttatctctat tgattgt 37

<210> SEQ ID NO 1508
<211> LENGTH: 31
<212> TYPE: DNA
<213> ORGANISM: Homo sapiens

<400> SEQUENCE: 1508
ggaactaagc atggtgggaa atgttcctgc t 31

<210> SEQ ID NO 1509
<211> LENGTH: 156
<212> TYPE: DNA
<213> ORGANISM: Homo sapiens

<400> SEQUENCE: 1509
ctggattgca gaagactcgg ggacaacatt tgatccaaga tcttaaatgt tatattgata 60
accatgctca gcaatgagct attagattca ttttgggaaa tctccataat ttcaatttgt 120
aaactttgtt aagacctgtc tacattgtta tatgtg 156

<210> SEQ ID NO 1510
<211> LENGTH: 432
<212> TYPE: DNA
<213> ORGANISM: Homo sapiens

<400> SEQUENCE: 1510
agtgaccatc tcatgggcat tgttttcttc tctgctttgt ctgtgttttg agtctgcttt 60
cttttgtctt taaaacctga tttttaagtt cttctgaact gtagaaatag ctatctgatc 120
acttcagcgt aaagcagtgt gtttattaac catccactaa gctaaaacta gagcagtttg 180
atttaaaagt gtcactcttc ctccttttct actttcagta gatatgagat agagcataat 240
tatctgtttt atcttagttt tatacataat ttaccatcag atagaacttt atggttctag 300
tacagatact ctactacact cagcctctta tgtgccaagt ttttctttaa gcaatgagaa 360
attgctcatg ttcttcatct tctcaaatca tcagaggccg aagaaaaaca ctttggctgt 420
gtctataact tg 432

<210> SEQ ID NO 1511
<211> LENGTH: 85
<212> TYPE: DNA
<213> ORGANISM: Homo sapiens

<400> SEQUENCE: 1511
caagggggag agtgatgact tccatatgga ctttgactca gctgtggctc ctcgggcaaa 60
atctgtacgg gcaaagaaac ctata 85

<210> SEQ ID NO 1512
<211> LENGTH: 122
<212> TYPE: DNA
<213> ORGANISM: Homo sapiens

<400> SEQUENCE: 1512
ctggtgtctc tcaaaagcct gatcctgcca aaaccaagaa tcgccgcaaa aggaagccat 60
ccacttctga tgattctgac tctaattttg agaaaattgt ttcgaaagca gtcacaagca 120
ag 122

<210> SEQ ID NO 1513
<211> LENGTH: 30
<212> TYPE: DNA
<213> ORGANISM: Homo sapiens

<400> SEQUENCE: 1513
agttcctaaa aagaatgtga cagtgaagaa 30

<210> SEQ ID NO 1514
<211> LENGTH: 46
<212> TYPE: DNA
<213> ORGANISM: Homo sapiens

<400> SEQUENCE: 1514
ggcagtgtac cactgtcttc aagccctcct gctacacatt tcccag 46

<210> SEQ ID NO 1515
<211> LENGTH: 42
<212> TYPE: DNA
<213> ORGANISM: Homo sapiens

<400> SEQUENCE: 1515
ttagtaacaa agaactgaaa ccacagaaaa gtgtcgtgtc ag 42

<210> SEQ ID NO 1516
<211> LENGTH: 25
<212> TYPE: DNA
<213> ORGANISM: Homo sapiens

<400> SEQUENCE: 1516
tgatgaagat tttgtcccat cagat 25

<210> SEQ ID NO 1517
<211> LENGTH: 114
<212> TYPE: DNA
<213> ORGANISM: Homo sapiens

<400> SEQUENCE: 1517
acaaactaca ttggcattta agccaatcaa aaaaggaaag aagagaaatc cctggtctga 60
ttcagaatca gataggagca gtgacgaaag taattttgat gtccctccac gaga 114

<210> SEQ ID NO 1518

<211> LENGTH: 63
<212> TYPE: DNA
<213> ORGANISM: Homo sapiens

<400> SEQUENCE: 1518
aaaatactga aggaagccct caagaagatg gtgtggaact agaaggccta aaacaaagat 60
tag 63

<210> SEQ ID NO 1519
<211> LENGTH: 127
<212> TYPE: DNA
<213> ORGANISM: Homo sapiens

<400> SEQUENCE: 1519
aacaagatga acaagtcgga cttcctggga aaggggggaa ggccaagggg aaaaaaacac 60
aaatggctga agttttgcct tctccgcgtg gtcaaagagt cattccacga ataaccatag 120
aaatgaa 127

<210> SEQ ID NO 1520
<211> LENGTH: 52
<212> TYPE: DNA
<213> ORGANISM: Homo sapiens

<400> SEQUENCE: 1520
gaacaagagc tggacacatt aaaaagaaag agtccatcag atttgtggaa ag 52

<210> SEQ ID NO 1521
<211> LENGTH: 67
<212> TYPE: DNA
<213> ORGANISM: Homo sapiens

<400> SEQUENCE: 1521
tgactccgta acagattctg gaccaacctt caactatctt cttgatatgc ccctttggta 60
tttaacc 67

<210> SEQ ID NO 1522
<211> LENGTH: 28
<212> TYPE: DNA
<213> ORGANISM: Homo sapiens

<400> SEQUENCE: 1522
aatgaagaga gtgacaacga aaaggaaa 28

<210> SEQ ID NO 1523
<211> LENGTH: 51
<212> TYPE: DNA
<213> ORGANISM: Homo sapiens

<400> SEQUENCE: 1523
attaattaaa gttctgattc agaggggata tgattcggat cctgtgaagg c 51

<210> SEQ ID NO 1524
<211> LENGTH: 170
<212> TYPE: DNA
<213> ORGANISM: Homo sapiens

<400> SEQUENCE: 1524
gctttttgac cacgtaggct gtttaaagaa atatgacacg gtgttggata ttctaagaga 60 ctttttgaa ctcagactta aatattatgg attaagaaaa gaatggctcc taggaatgct 120
tggtgctgaa tctgctaaac tgaataatca ggctcgcttt atcttagaga 170

<210> SEQ ID NO 1525
<211> LENGTH: 131
<212> TYPE: DNA
<213> ORGANISM: Homo sapiens

<400> SEQUENCE: 1525
cctcctctca taacagacta tagggaatac catacagata ccactgtgaa atttgttgtg 60
aagatgactg aagaaaaact ggcagaggca gagagagttg gactacacaa agtcttcaaa 120
ctccaaacta g 131

<210> SEQ ID NO 1526
<211> LENGTH: 111
<212> TYPE: DNA
<213> ORGANISM: Homo sapiens

<400> SEQUENCE: 1526
tcaagggtac tattgaagaa ctggctccaa atcaatatgt gattagtggt gaagtagcta 60
ttcttaattc tacaaccatt gaaatctcag agcttcccgt cagaacatgg a 111

<210> SEQ ID NO 1527
<211> LENGTH: 179
<212> TYPE: DNA
<213> ORGANISM: Homo sapiens

<400> SEQUENCE: 1527
ggctcgattg ttatttccac caaaagatga tcacacgttg aagtttttat atgatgacaa 60
ccagcgtgtt gagcctgaat ggtacattcc tattattccc atggtgctga taaatggtgc 120
tgaaggaatc ggtactgggt ggtcctgcaa aatccccaac tttgatgtgc gtgaaattg 179

<210> SEQ ID NO 1528
<211> LENGTH: 117
<212> TYPE: DNA
<213> ORGANISM: Homo sapiens

<400> SEQUENCE: 1528
gaccattatc aatttggctc agaattttgt gggtagcaat aatctaaacc tcttgcagcc 60
cattggtcag tttggtacca ggctacatgg tggcaaggat tctgctagtc cacgata 117

<210> SEQ ID NO 1529
<211> LENGTH: 57
<212> TYPE: DNA
<213> ORGANISM: Homo sapiens

<400> SEQUENCE: 1529
tgtttacttg cttcaaacgg aatgacaagc gagaagtaaa ggttgcccaa ttagctg 57

<210> SEQ ID NO 1530
<211> LENGTH: 86
<212> TYPE: DNA
<213> ORGANISM: Homo sapiens

<400> SEQUENCE: 1530
tctgacatat aatgacttca tcaacaagga acttatcttg ttctcaaatt ctgataacga 60
gagatctatc ccttctatgg tggatg 86

<210> SEQ ID NO 1531
<211> LENGTH: 78
<212> TYPE: DNA

-continued

<213> ORGANISM: Homo sapiens

<400> SEQUENCE: 1531
aacagataga tgatcgaaag gaatggttaa ctaatttcat ggaggataga agacaacgaa 60
agttacttgg gcttcctg 78

<210> SEQ ID NO 1532
<211> LENGTH: 74
<212> TYPE: DNA
<213> ORGANISM: Homo sapiens

<400> SEQUENCE: 1532
ccagcacatc aaaggaagct aaagaatact ttgcagatat gaaaagacat cgtatccagt 60
tcaaatattc tggt 74

<210> SEQ ID NO 1533
<211> LENGTH: 27
<212> TYPE: DNA
<213> ORGANISM: Homo sapiens

<400> SEQUENCE: 1533
gaagagtgga agagttctac tccaaat 27

<210> SEQ ID NO 1534
<211> LENGTH: 38
<212> TYPE: DNA
<213> ORGANISM: Homo sapiens

<400> SEQUENCE: 1534
tggccctctc ttctgcgaca tcgttttctg gaggaatt 38

<210> SEQ ID NO 1535
<211> LENGTH: 80
<212> TYPE: DNA
<213> ORGANISM: Homo sapiens

<400> SEQUENCE: 1535
aatatcatca agattgtggg tcttcagtac aagaaaaact atgaagatga agattcattg 60
aagacgcttc gttatgggaa 80

<210> SEQ ID NO 1536
<211> LENGTH: 73
<212> TYPE: DNA
<213> ORGANISM: Homo sapiens

<400> SEQUENCE: 1536
tgggagagac aaatatgggg ttttccctct tagaggaaaa atactcaatg ttcgagaagc 60
ttctcataag cag 73

<210> SEQ ID NO 1537
<211> LENGTH: 55
<212> TYPE: DNA
<213> ORGANISM: Homo sapiens

<400> SEQUENCE: 1537
ctccactgag tgtacgctta tcctgactga gggagattca gccaaaactt tggct 55

<210> SEQ ID NO 1538
<211> LENGTH: 120
<212> TYPE: DNA
<213> ORGANISM: Homo sapiens

<400> SEQUENCE: 1538
cattggctgt ggtattgtag aaagcatact aaactgggtg aagtttaagg cccaagtcca 60
gttaaacaag aagtgttcag ctgtaaaaca taatagaatc aagggaattc ccaaactcga 120

<210> SEQ ID NO 1539
<211> LENGTH: 72
<212> TYPE: DNA
<213> ORGANISM: Homo sapiens

<400> SEQUENCE: 1539
tgtaaatgcc ttaattgaaa acccaacctt tgactctcag acaaaagaaa acatgacttt 60
acaacccaag ag 72

<210> SEQ ID NO 1540
<211> LENGTH: 78
<212> TYPE: DNA
<213> ORGANISM: Homo sapiens

<400> SEQUENCE: 1540
gctgatcaga ttgtgactaa acttgttgat gttgtgaaga agaagaacaa gggtggtgtt 60
gcagtaaaag cacatcag 78

<210> SEQ ID NO 1541
<211> LENGTH: 150
<212> TYPE: DNA
<213> ORGANISM: Homo sapiens

<400> SEQUENCE: 1541
aaaggatttc gtagttatgt ggacatgtat ttgaaggaca agttggatga aactggtaac 60
tccttgaaag taatacatga acaagtaaac cacaggtggg aagtgtgttt aactatgagt 120
gaaaaaggct ttcagcaaat tagctttgtc 150

<210> SEQ ID NO 1542
<211> LENGTH: 120
<212> TYPE: DNA
<213> ORGANISM: Homo sapiens

<400> SEQUENCE: 1542
tatacatgta tcacctttca gcctgatttg tctaagttta aaatgcaaag cctggacaaa 60
gatattgttg cactaatggt cagaagagca tatgatattg ctggatccac caaagatgtc 120

<210> SEQ ID NO 1543
<211> LENGTH: 45
<212> TYPE: DNA
<213> ORGANISM: Homo sapiens

<400> SEQUENCE: 1543
tggctatgga gccaaattgt gtaacatatt cagtaccaaa tttac 45

<210> SEQ ID NO 1544
<211> LENGTH: 59
<212> TYPE: DNA
<213> ORGANISM: Homo sapiens

<400> SEQUENCE: 1544
tgaaaagatg tatgtcccag ctctcatatt tggacagctc ctaacttcta gtaactatg 59

<210> SEQ ID NO 1545

-continued

<211> LENGTH: 63
<212> TYPE: DNA
<213> ORGANISM: Homo sapiens

<400> SEQUENCE: 1545
taatgctgcg gacaacaaac aaagggaccc aaaaatgtct tgtattagag tcacaattga 60
tcc 63

<210> SEQ ID NO 1546
<211> LENGTH: 70
<212> TYPE: DNA
<213> ORGANISM: Homo sapiens

<400> SEQUENCE: 1546
caaatgtggg tttacgatga agatgttggc attaactata gggaagtcac ttttgttcct 60
ggtttgtaca 70

<210> SEQ ID NO 1547
<211> LENGTH: 57
<212> TYPE: DNA
<213> ORGANISM: Homo sapiens

<400> SEQUENCE: 1547
gaacatattt tgctccgccc agacacctac attggttctg tggaattagt gacccag 57

<210> SEQ ID NO 1548
<211> LENGTH: 36
<212> TYPE: DNA
<213> ORGANISM: Homo sapiens

<400> SEQUENCE: 1548
cctgtaaatg aaaatatgca agtcaacaaa ataaag 36

<210> SEQ ID NO 1549
<211> LENGTH: 28
<212> TYPE: DNA
<213> ORGANISM: Homo sapiens

<400> SEQUENCE: 1549
gttcttgagc cccttcacga ccgtcacc 28

<210> SEQ ID NO 1550
<211> LENGTH: 94
<212> TYPE: DNA
<213> ORGANISM: Homo sapiens

<400> SEQUENCE: 1550
ttcaagtgga gctctcctaa ccgacgcgcg tctgtggaga agcggcttgg tcgggggtgg 60
tctcgtgggg tcctgcctgt ttagtcgctt tcag 94

<210> SEQ ID NO 1551
<211> LENGTH: 32
<212> TYPE: DNA
<213> ORGANISM: Homo sapiens

<400> SEQUENCE: 1551
ttaaatagga attcatacca gggacaaagc ag 32

<210> SEQ ID NO 1552
<211> LENGTH: 531
<212> TYPE: DNA
<213> ORGANISM: Homo sapiens

<400> SEQUENCE: 1552
ggtcacttat acacgcattt ctttaaaata tctgattagg tatttatagt ttgaaagaga 60
tgatgtttcc ttgactgagc atcttgagaa atcaagattt agttgacaat tagacatgag 120
gagaatagag agctagaaga ccttgcataa actgattgac caagagaata gatacactaa 180
tcatgtctac aggaacagaa aataaaagag acagagaaga gataataaat ctgatggtaa 240
aaaaaaaaaa aggcaggaag attacgaatg gcttctactc tctgggtgtg gtggcgcatg 300
cctgtaatct cagcacttga gctggggagg tcaaggctgc agtgagccta ggtagtgcca 360
ctgcactcca gcctggacac aagagtgaga gagaccctgt ctccaaaaaa aaatgatttg 420
atcatatatg atttgactgc ccccttgtgg taatttacat ttgtcaatgg tttagggaga 480
cttgcctgta taccgggata tacaaattta tgcaagcacg aagacagttt a 531

<210> SEQ ID NO 1553
<211> LENGTH: 177
<212> TYPE: DNA
<213> ORGANISM: Homo sapiens

<400> SEQUENCE: 1553
atcggcccgt ttcctattat ggaagattta ggtcatttcc atgttataaa taatattgag 60
gtgattattt tggagtataa aacaagaatg tttatattat gatctattac ctaacaaata 120
attttgctca ttatatagta aattgtgttt tatcacaagg ctataaacag catgttc 177

<210> SEQ ID NO 1554
<211> LENGTH: 67
<212> TYPE: DNA
<213> ORGANISM: Homo sapiens

<400> SEQUENCE: 1554
gctcatttgt attctagatt tctgatagat cccttcttcc ctaatatgat ccctaatatg 60
aatcttc 67

<210> SEQ ID NO 1555
<211> LENGTH: 51
<212> TYPE: DNA
<213> ORGANISM: Homo sapiens

<400> SEQUENCE: 1555
aaataaagca tgagtacatt tttagtggct taatatcaac ttctattgca g 51

<210> SEQ ID NO 1556
<211> LENGTH: 49
<212> TYPE: DNA
<213> ORGANISM: Homo sapiens

<400> SEQUENCE: 1556
cttaaattat taatcatgat ttatctttac atatatgtgt tcttattgt 49

<210> SEQ ID NO 1557
<211> LENGTH: 93
<212> TYPE: DNA
<213> ORGANISM: Homo sapiens

<400> SEQUENCE: 1557
ttgcatgcgc tctattcccc ctctgcctct ccccaccttc tttggagcaa ggagatgcag 60
ctgtattgtg taacaagctc atttgtacag tgt 93

<210> SEQ ID NO 1558
<211> LENGTH: 129
<212> TYPE: DNA
<213> ORGANISM: Homo sapiens

<400> SEQUENCE: 1558
gtgtctattg caggagaaac gtcccttgcc actccccact ctcatcaggc caagtggagg 60
actggccaga gggcctgcac atgcaaactc cagtccctgc cttcagagag ctgaaaaggg 120
tccctcggt 129

<210> SEQ ID NO 1559
<211> LENGTH: 30
<212> TYPE: DNA
<213> ORGANISM: Homo sapiens

<400> SEQUENCE: 1559
gtggtttctt cccacaagag agaaatctaa 30

<210> SEQ ID NO 1560
<211> LENGTH: 33
<212> TYPE: DNA
<213> ORGANISM: Homo sapiens

<400> SEQUENCE: 1560
caatttccac atcaatgtag aagagtcagt gga 33

<210> SEQ ID NO 1561
<211> LENGTH: 243
<212> TYPE: DNA
<213> ORGANISM: Homo sapiens

<400> SEQUENCE: 1561
ttgagtaggc ttcattcagg gcatgtctct cccccaggcc ccatcttcat acacttccgc 60
taagatgccc acaattcatc ccccttcatg tgcagcttga aaaaccctga cattgttgct 120
ccctgccggg catacctgcc attgccactg cccatctctg tgatgaggaa ttcaacacca 180
gatctctggc agctcttgag ggattggcca gtggccattc tcaggggtgc tgtctagttt 240
tcc 243

<210> SEQ ID NO 1562
<211> LENGTH: 26
<212> TYPE: DNA
<213> ORGANISM: Homo sapiens

<400> SEQUENCE: 1562
gatggctggc attgccatca gggaag 26

<210> SEQ ID NO 1563
<211> LENGTH: 645
<212> TYPE: DNA
<213> ORGANISM: Homo sapiens

<400> SEQUENCE: 1563
aggatctgga ctcctcactc tggtccttgg ctgttacctg ggacaggtca cttcctctct 60
ctggatccgt gtttcttctg taaatgatag aggctgggct agtggtagtt aagatctagt 120
gctcattcca ttctctgcat gagatagatg ggtattcttg tagttcagaa tcttgaccag 180
ctcagtggct catgcctgta atcccagcac tttgggagtc caaggcgggt ggatcacttg 240
aggtcaggag ttcgagacca gcatggccaa tatggtgaaa ccccgtctct actaaaaata 300
caaaaattag ctgggcgtgg tggcgggtgc ctgtaatccc agctactcgg gaggctgagg 360
cacaagaatc acttgaaccc gggaggcgga ggtttcagtg ggctgagatc gtgccactgc 420
actccagcct gggcgacaga gtgagattcc gtctcaaaaa acaaaacaaa acaaaacaaa 480
atctgtctac ttggggatag caggcctgga tgggctagca ggatgtccca cccctagagg 540
agtcagatgt gtgggtggtg gtggtgtagg gtctgaagaa cactgcatag ctatctacat 600
gagcttccct tacggacact tgagcttgtg ccctttgctt aaatc 645

<210> SEQ ID NO 1564
<211> LENGTH: 140
<212> TYPE: DNA
<213> ORGANISM: Homo sapiens

<400> SEQUENCE: 1564
agagtgccgc tatgccacgc agctgcagca gatccagggg ctcattggtg gcctggaggc 60
ccagctgagt gagctccgat gcgagatgga ggctcagaac caggagtaca agatgctgct 120
tgacataaag acacggctgg 140

<210> SEQ ID NO 1565
<211> LENGTH: 32
<212> TYPE: DNA
<213> ORGANISM: Homo sapiens

<400> SEQUENCE: 1565
cctgatgtgt ctatgcatct gtcactcccc ca 32

<210> SEQ ID NO 1566
<211> LENGTH: 79
<212> TYPE: DNA
<213> ORGANISM: Homo sapiens

<400> SEQUENCE: 1566
agaggtggcc tccaacacag aaatgatcca gaccagcaag acggagatca cagacctgag 60
acgcacgatg caggagctg 79

<210> SEQ ID NO 1567
<211> LENGTH: 124
<212> TYPE: DNA
<213> ORGANISM: Homo sapiens

<400> SEQUENCE: 1567
ctggccggcc aggtcaatgt ggagatggac gcagcaccgg gtgtggacct gacccgtgtg 60
ctggcagaga tgagggagca gtacgaggcc atggcggaga agaaccgccg ggatgtcgag 120
gcct 124

<210> SEQ ID NO 1568
<211> LENGTH: 27
<212> TYPE: DNA
<213> ORGANISM: Homo sapiens

<400> SEQUENCE: 1568
gtgagagctg gcccccatca cccctga 27

<210> SEQ ID NO 1569
<211> LENGTH: 35
<212> TYPE: DNA
<213> ORGANISM: Homo sapiens

<400> SEQUENCE: 1569
tgacatcaac ggcttgcgcc gagtcctgga tgagc 35

<210> SEQ ID NO 1570
<211> LENGTH: 77
<212> TYPE: DNA
<213> ORGANISM: Homo sapiens

<400> SEQUENCE: 1570
ctcctcttcc tgcattgccc actttacttg gccttctcct ggctctgact caggcagcca 60
agacccctcc cacttcc 77

<210> SEQ ID NO 1571
<211> LENGTH: 34
<212> TYPE: DNA
<213> ORGANISM: Homo sapiens

<400> SEQUENCE: 1571
accatcgaca actcccgggt catcctggag atcg 34

<210> SEQ ID NO 1572
<211> LENGTH: 187
<212> TYPE: DNA
<213> ORGANISM: Homo sapiens

<400> SEQUENCE: 1572
gttctgtaga tccatggctg tgtccaaggt gtgcaggagg cagtgaccat gagttgtcca 60
cagtggggct ggtggagtgt ctctgagaga gctattgtca gagctggctg caccccactg 120
ccccactctc ctgggcaacc aattcccaca ggcaatactg cctccttggt ctttcgtgcc 180
ctggaga 187

<210> SEQ ID NO 1573
<211> LENGTH: 26
<212> TYPE: DNA
<213> ORGANISM: Homo sapiens

<400> SEQUENCE: 1573
gtgagtcctc ggatgtcaaa gagagg 26

<210> SEQ ID NO 1574
<211> LENGTH: 33
<212> TYPE: DNA
<213> ORGANISM: Homo sapiens

<400> SEQUENCE: 1574
caaccagccc agaatgcgac tacagccaat act 33

<210> SEQ ID NO 1575
<211> LENGTH: 26
<212> TYPE: DNA
<213> ORGANISM: Homo sapiens

<400> SEQUENCE: 1575
ctctggcaat gagaaaatta ccatgc 26

<210> SEQ ID NO 1576
<211> LENGTH: 82
<212> TYPE: DNA
<213> ORGANISM: Homo sapiens

<400> SEQUENCE: 1576

-continued gtttgtctct tcagggtcag gaggaggata tgggggtggc atgagggtct gtggctttgg 60
tggaggggct ggtagtgttt tc 82

<210> SEQ ID NO 1577
<211> LENGTH: 32
<212> TYPE: DNA
<213> ORGANISM: Homo sapiens

<400> SEQUENCE: 1577
ggtggaagcc gaagtatctc agcttcttct gc 32

<210> SEQ ID NO 1578
<211> LENGTH: 116
<212> TYPE: DNA
<213> ORGANISM: Homo sapiens

<400> SEQUENCE: 1578
gaggtcccac aacaccctct gaagggtata taaggagccc cagcgtgcag cctggcctgg 60
tacctcctgc cagcatctct tgggtttgct gagaactcac gggctccagc tacctg 116

<210> SEQ ID NO 1579
<211> LENGTH: 222
<212> TYPE: DNA
<213> ORGANISM: Homo sapiens

<400> SEQUENCE: 1579
gatcggccag tggactccca aactaagaac acggagctgt cctcttgggg agaggctcag 60
ggctcgggga agtgaagtcc agctgagggc acagttggcc tgagctgctc tcagtacagg 120
cagaggcctt ggtagctgtg ctgtgatgag agttcgctcc ctgctgctct cttctggcat 180
ggagagatga acctgtaatc caagtgttaa aaccgtgccc tg 222

<210> SEQ ID NO 1580
<211> LENGTH: 265
<212> TYPE: DNA
<213> ORGANISM: Homo sapiens

<400> SEQUENCE: 1580
cccagcctta tcagcggagg tttgccccaa cacatcccag aaacgagcaa aggttcagcg 60
ccgtgcagtt ggcaggtgtc gggatcatca gtcatcccct tgtcagtccc aagcctgctg 120
ggcttttgtg agggtgccag gaacacaggc tggaggatgg caggaggggga gtagaggtgg 180 gaggagggga gtccatctgc agcaccaggt aaggggatgg atgctggctc ctctggtcac 240
ctcagctgga acactactca aggtc 265

<210> SEQ ID NO 1581
<211> LENGTH: 1375
<212> TYPE: DNA
<213> ORGANISM: Homo sapiens

<400> SEQUENCE: 1581
gacagagctt tatcttcgca aggccatccc acctggtgct aatgaggagg ctccgggccc 60
cacccagatc tggagctcac agtagcggtt tggactgaaa ccagggattt gtgcgtgggg 120
cagtgagggg ggcagctgcc gcccctggcc tgggcctgag agtatagaga aagccacctc 180
gaggggctgc tggaggagag tcaggtgcag aaggggatct ggctggggtc cagcccttcc 240
tcaccctggg gtgaaaggcg agtaattgtt cttgagttaa ttgctggggc cacaatgtct 300

-continued

```
gcagaggctt ttaatgagct ctggatgatc tgagtttgat tatttttctt tcggaggaaa    360

agacaatacc ctcccaccca tgagacaata ccacactgtc tgtgcccagc attggaggcc    420

aggctcactg cgaagatgga tgagaaggaa cccaccccca gccttgctgg ctggcagttc    480

cccttgccag cccagctcag atgcaggaat ttggggtctg caggaaggac tctttccctg    540

tgccctgttt ggttgagggt gtgaggacct gtttgagtcc tggctttgcc ccttaccagt    600

ggtgccacct ggcacaagtt gcttcacctc tccaagtttc aatttcattc tttctgaatc    660

ttgggtgggg gtcaccctct gttgtgagga tgagaggagg tgatggatgc aaaagtgctt    720

tgtaaatcac aaagtgcagg gtagaagtaa aggattatgc tattatagca aaataagaac    780

ctaagaacaa cctgcgttgc cccataggag ctggctatgg aaggtcgatg ccgttgagcc    840

taagaacatg ctcaggctca cagggcatgt tctgatgccc aacgacaaag cccctcctgg    900

tgagggcact caggcgcagg tgccggtcat gcaccctggc ccctgcatgt ctggcacctg    960

ggtggggatc caggaggggg caggatgggg gctcttgggc cacagggctt ccctggaagt   1020

gagagttgag agcgcccctt gccacaggga aacagagact taaaaaggta aatgtccaca   1080

gtcttaccat ggtaattggt agggtcagga tttgaaccca ggcctcacag tcttaccatg   1140

ataattgata aagccaggat tcaaacccgg gcctgaggga ctccagagcc ctgtccactt   1200

caccatgctg caacctgggc taggaatcct cctcctgagt ttctgtaagc cctggggcca   1260

ggtccagagg gctgagccac acctccaagt ggcactgccc acaggtatca ggtgtccctg   1320

gaaaggtgtc cctgagctgg tggcagagaa aagggctctc ctgagtgttc aactc        1375
```

<210> SEQ ID NO 1582
<211> LENGTH: 731
<212> TYPE: DNA
<213> ORGANISM: Homo sapiens

<400> SEQUENCE: 1582

```
gcaggcccaa ccctatgagt gatgggggca agtgagggac actagttcca cgcccgcatg     60

ctgccaaatg tactcagcac cctgctaagg aggctggaga ccccatcacg gccatggcaa    120

tcccgaagga ggagctgttt caaggttggt tatgaacatg taaccccaga gccccgctgc    180

tgtagcctgg actgggaccc ccttctgccc cctccctagc tgtcctgttc tggcctccag    240

cacccacaaa ccaccacccc caacttaact tctcaggaag ccttggagct ggagggagag    300

gcctggctgc acccccagct gggactgccc agaggcgctt gtccctgccc atgaaagcct    360

cccttgtcac agctgaaacc ttccctctgc ctcaggggcc cctggaatgt ggctgcgggg    420

cggggtctgg gcccacacag gtggggcagg tgactgtcag gtctcaggcc tgagtgtcag    480

gaatgaagcc tgcctttgtg tgtgcacagt gcagggtggg gctggactgg ggacactttt    540

ctgtctcagc ctggagacct gggataggag ggagagggga gtggggaagt tgaggggagt    600

gcctttacat cctgctggtc atcgtggcca cttcagtctg ttgagcattt cctgtgagtc    660

atcttgctcc aactgagagt caggctgagc tggagttatt tccattttcc tgattggtag    720

actaaggctc a                                                         731
```

<210> SEQ ID NO 1583
<211> LENGTH: 32
<212> TYPE: DNA
<213> ORGANISM: Homo sapiens

<400> SEQUENCE: 1583

```
cgtctttggt caggaacttt ataatgtgct at                                   32
```

<210> SEQ ID NO 1584
<211> LENGTH: 186
<212> TYPE: DNA
<213> ORGANISM: Homo sapiens

<400> SEQUENCE: 1584
ttgcagttcc aaattgccat cttcccttgt ctcatttgca agttctcaat tgtatttctc 60
tcaaatggac aggttccttc tttactggag gatttttgtt tttatcatat tggtttttca 120
ttacttctga atagtcttaa ttacgtttac taaattctaa aggatttctg tgctattata 180
attagg 186

<210> SEQ ID NO 1585
<211> LENGTH: 255
<212> TYPE: DNA
<213> ORGANISM: Homo sapiens

<400> SEQUENCE: 1585
accctaaggg ctacttctga gactgaaaaa tcagctttct atttacatga aacactttgg 60
gggtcatggg agtgcacagc attagacagt atttggttca ccctgtaaag tagccaagaa 120
aagatgagaa aaatcaagat aggcctggca cactagacat ttgcctccaa aagaaataac 180
ctacagtctt aagatgtatc ataaaaatgt tctgccaagg atctaaatta ccttgggttt 240
cgcatatgtc tatga 255

<210> SEQ ID NO 1586
<211> LENGTH: 164
<212> TYPE: DNA
<213> ORGANISM: Homo sapiens

<400> SEQUENCE: 1586
gttgtgatca ccacagtccc tctggtcagt gagattcagt tgatggctgc tacagggggt 60
accgagctct cctgctaccg ctgcatcatc ccctttgctg tggttgtctt catcgccggc 120
atcgtggtca ccgcggtggc ttacagcttc aattcccatg ggtc 164

<210> SEQ ID NO 1587
<211> LENGTH: 47
<212> TYPE: DNA
<213> ORGANISM: Homo sapiens

<400> SEQUENCE: 1587
tggtgagact gtccagatct agtctgtaaa cccagcttag aagcact 47

<210> SEQ ID NO 1588
<211> LENGTH: 45
<212> TYPE: DNA
<213> ORGANISM: Homo sapiens

<400> SEQUENCE: 1588
ttggaagata ttgttacact tcagaccaca aatccccacc tcatt 45

<210> SEQ ID NO 1589
<211> LENGTH: 49
<212> TYPE: DNA
<213> ORGANISM: Homo sapiens

<400> SEQUENCE: 1589
aatttgggga cagatcttga ttttcaggtt agctcaatct cagctttgg 49

<210> SEQ ID NO 1590
<211> LENGTH: 70
<212> TYPE: DNA
<213> ORGANISM: Homo sapiens

<400> SEQUENCE: 1590
agaagttgga cgaagaggct caggcgttgc tgtttcttgt cttccaagtc aagtggttac 60
tctggtaatg 70

<210> SEQ ID NO 1591
<211> LENGTH: 84
<212> TYPE: DNA
<213> ORGANISM: Homo sapiens

<400> SEQUENCE: 1591
atcccaaacc agagcagacc ctatagtaaa gtatttttac atcttttcct ttccccagaa 60
gagatcccta acctattgtt ttat 84

<210> SEQ ID NO 1592
<211> LENGTH: 139
<212> TYPE: DNA
<213> ORGANISM: Homo sapiens

<400> SEQUENCE: 1592
gtttgcacct ttagctttgg taacaggaaa gcatgctttt caacagaata aggtgatatt 60
cagagcttca gtgcagttat tggctatctt tgcaggcaaa gtggtactag aaaatagagg 120
ggaattgccc tcaagggcc 139

<210> SEQ ID NO 1593
<211> LENGTH: 146
<212> TYPE: DNA
<213> ORGANISM: Homo sapiens

<400> SEQUENCE: 1593
atgctcctct taccaagcct gcaacttaaa acctatggtt taaactgtgc tttcaattat 60
ctggaggagg ccagcactga tgagcccatc ctgagccagt cattttaagg ccagtgctac 120
ctaactgaga caaggctaat ctggtc 146

<210> SEQ ID NO 1594
<211> LENGTH: 112
<212> TYPE: DNA
<213> ORGANISM: Homo sapiens

<400> SEQUENCE: 1594
cagtttatta tggtattgga caccccatgc tccttactgc attggctttg ggtaagaagg 60
agtgaaaatt agtgtgcgaa cctgaaaacc tagaatttct gattgggact ga 112

<210> SEQ ID NO 1595
<211> LENGTH: 31
<212> TYPE: DNA
<213> ORGANISM: Homo sapiens

<400> SEQUENCE: 1595
aaaatctaca gtcggtgtga atgtgaacta a 31

<210> SEQ ID NO 1596
<211> LENGTH: 131
<212> TYPE: DNA
<213> ORGANISM: Homo sapiens

<400> SEQUENCE: 1596
aaagagctcc ggaaacttgc cctgaaggag atgggaactc cagatgcaca ctttgatacc 60
aggctcaaca aagctgtctg ggccaaagga ataagcaacg tctcatactg tatccatgtt 120
cggttgtcca g 131

<210> SEQ ID NO 1597
<211> LENGTH: 26
<212> TYPE: DNA
<213> ORGANISM: Homo sapiens

<400> SEQUENCE: 1597
atggcgctgg ggctgcagcg cgcaag 26

<210> SEQ ID NO 1598
<211> LENGTH: 62
<212> TYPE: DNA
<213> ORGANISM: Homo sapiens

<400> SEQUENCE: 1598
ggggttttat ctggccatgt tcccatggga ccctggaaaa tgttctaggt cctcagcttt 60
cc 62

<210> SEQ ID NO 1599
<211> LENGTH: 103
<212> TYPE: DNA
<213> ORGANISM: Homo sapiens

<400> SEQUENCE: 1599
atctcaccgc cgtgcgcacc cactcgtaac tcgcacccgg gtcctggctg caccgcatcc 60
cctcctgcac cccctggatg gcccttcagc caacgggggc ctg 103

<210> SEQ ID NO 1600
<211> LENGTH: 29
<212> TYPE: DNA
<213> ORGANISM: Homo sapiens

<400> SEQUENCE: 1600
caaggatgct cttgggaagt ccctggtgg 29

<210> SEQ ID NO 1601
<211> LENGTH: 31
<212> TYPE: DNA
<213> ORGANISM: Homo sapiens

<400> SEQUENCE: 1601
gtacggcttg cagcccagag tgcccagtga g 31

<210> SEQ ID NO 1602
<211> LENGTH: 25
<212> TYPE: DNA
<213> ORGANISM: Homo sapiens

<400> SEQUENCE: 1602
tcaagatgag gagccagtag tgagg 25

<210> SEQ ID NO 1603
<211> LENGTH: 33
<212> TYPE: DNA
<213> ORGANISM: Homo sapiens

<400> SEQUENCE: 1603
cgccacagag aggagcgagg cgccagaggc acc 33

<210> SEQ ID NO 1604
<211> LENGTH: 32
<212> TYPE: DNA
<213> ORGANISM: Homo sapiens

<400> SEQUENCE: 1604
gtcgaccacg gagctgcgca aggaaaagtc cc 32

<210> SEQ ID NO 1605
<211> LENGTH: 64
<212> TYPE: DNA
<213> ORGANISM: Homo sapiens

<400> SEQUENCE: 1605
tgctgtacca gctggctcac acgctgccct tcgcccgcgg cgtcagcgcc cacctggaca 60
aggc 64

<210> SEQ ID NO 1606
<211> LENGTH: 46
<212> TYPE: DNA
<213> ORGANISM: Homo sapiens

<400> SEQUENCE: 1606
atgcgcctca ccatcagcta cctgcgcatg caccgcctct gcgccg 46

<210> SEQ ID NO 1607
<211> LENGTH: 38
<212> TYPE: DNA
<213> ORGANISM: Homo sapiens

<400> SEQUENCE: 1607
ggaatccagg ccactaggat gtacccccac ttccttgg 38

<210> SEQ ID NO 1608
<211> LENGTH: 96
<212> TYPE: DNA
<213> ORGANISM: Homo sapiens

<400> SEQUENCE: 1608
accactggat gcctgctacc tgaaggccct ggagggcttc gtcatggtgc tcaccgccga 60
gggagacatg gcttacctgt cggagaatgt cagcaa 96

<210> SEQ ID NO 1609
<211> LENGTH: 45
<212> TYPE: DNA
<213> ORGANISM: Homo sapiens

<400> SEQUENCE: 1609
ttggtatctg ttccttttct ctgcctcgtt accccactcc tggta 45

<210> SEQ ID NO 1610
<211> LENGTH: 48
<212> TYPE: DNA
<213> ORGANISM: Homo sapiens

<400> SEQUENCE: 1610
ctggagctca ttggacacag catctttgat ttcatccacc cctgtgac 48

<210> SEQ ID NO 1611
<211> LENGTH: 28
<212> TYPE: DNA
<213> ORGANISM: Homo sapiens

<400> SEQUENCE: 1611
gagcttcagg acgccctgac cccccagc 28

<210> SEQ ID NO 1612
<211> LENGTH: 33
<212> TYPE: DNA
<213> ORGANISM: Homo sapiens

<400> SEQUENCE: 1612
gaggccccca cggagcggtg cttctccttg cgc 33

<210> SEQ ID NO 1613
<211> LENGTH: 57
<212> TYPE: DNA
<213> ORGANISM: Homo sapiens

<400> SEQUENCE: 1613
atgaagagta cactcaccag ccgcgggcgc accctcaacc tcaaggcggc cacctgg 57

<210> SEQ ID NO 1614
<211> LENGTH: 165
<212> TYPE: DNA
<213> ORGANISM: Homo sapiens

<400> SEQUENCE: 1614
tgctgaactg ctctggacat atgagggcct acaagccacc tgcgcagact tctccagctg 60
ggagccctga ctcagagccc ccgctgcagt gcctggtgct catctgcgaa gccatccccc 120
acccaggcag cctggagccc ccactgggcc gaggggcctt cctca 165

<210> SEQ ID NO 1615
<211> LENGTH: 41
<212> TYPE: DNA
<213> ORGANISM: Homo sapiens

<400> SEQUENCE: 1615
cgccacagcc tggacatgaa gttcacctac tgtgacgaca g 41

<210> SEQ ID NO 1616
<211> LENGTH: 75
<212> TYPE: DNA
<213> ORGANISM: Homo sapiens

<400> SEQUENCE: 1616
aagtggctgg ctatagtccc gatgacctga tcggctgttc cgcctacgag tacatccacg 60
cgctggactc cgatg 75

<210> SEQ ID NO 1617
<211> LENGTH: 50
<212> TYPE: DNA
<213> ORGANISM: Homo sapiens

<400> SEQUENCE: 1617
gtgcgaagcc agctgccaca tggcccccag ctgacaccag gaccccccag 50

<210> SEQ ID NO 1618
<211> LENGTH: 110
<212> TYPE: DNA

<213> ORGANISM: Homo sapiens

<400> SEQUENCE: 1618
cccaggatgc actgcctccc cacctcaaca ccagctccct gctccccaag ccccaaggaa 60
ctgtctcctt ccttgccccc tcatacccag tccccagata tttctctccc 110

<210> SEQ ID NO 1619
<211> LENGTH: 125
<212> TYPE: DNA
<213> ORGANISM: Homo sapiens

<400> SEQUENCE: 1619
cagtaacagg gcagtatcgc ttcctggccc ggagtggtgg ctacctgtgg acccagaccc 60
aggccacagt ggtgtcaggg ggacggggcc cccagtcgga gagtatcgtc tgtgtccatt 120
tttta 125

<210> SEQ ID NO 1620
<211> LENGTH: 246
<212> TYPE: DNA
<213> ORGANISM: Homo sapiens

<400> SEQUENCE: 1620
tgggcctgat ctgcatgtgt ggacaggtgt gtgtgtgtgt gtgtgtgtgt gcgtatgagc 60
atgcatgtgt atcatgcata agtgtatgtg agggagtgtg cacgtgtaca catatgagga 120
atgtgtgtca ccatgtaaat gccggtgtgt gtgtctgcat ggacacaggt atgtgtatgg 180
gtgtgtagac tgttaatttt tttttttttt tttttttttt tttttgcgtg aacctctgct 240
taagtg 246

<210> SEQ ID NO 1621
<211> LENGTH: 160
<212> TYPE: DNA
<213> ORGANISM: Homo sapiens

<400> SEQUENCE: 1621
gcaaagtggt taggacccat tctcaaaaaa aaaaaaaaaa aaaaacctga aaacagacca 60
aaaaaaaaaa ccacacacac gcaaagatag atggtttgca tatggtaaat tctctttatg 120
gtacacagtt ctgtgaattt ttgacacacg catgcagttg 160

<210> SEQ ID NO 1622
<211> LENGTH: 397
<212> TYPE: DNA
<213> ORGANISM: Homo sapiens

<400> SEQUENCE: 1622
tgcacccggc ccatgttgtg gtttatatca gtagttcctt tgtaaatagt gaacagtatt 60
ccatggtatg aatagagcac aggttttttt tttatccatt caccagttag aagacattgg 120
gctgtttcca agtttgggtg attacaaaaa aacagctact gtaaacattc tcatacaaga 180
ttttatgaga tcacatgttt tcatttctct tgggtaaaca gctaggattg gaatggatgg 240
gttatatagt aagtgtatat ttaatctaag aaactgccat ggctgggcac agtggctcac 300
gcctgtaatc ccagcacttt gggaagccaa ggaaggagga tgactagagc ctctgaggtg 360
aagaccagcc tgggcaaagt ggttaagact caaccgc 397

<210> SEQ ID NO 1623
<211> LENGTH: 26

<212> TYPE: DNA
<213> ORGANISM: Homo sapiens

<400> SEQUENCE: 1623
gacagagttt tgcccttgtc actcag 26

<210> SEQ ID NO 1624
<211> LENGTH: 99
<212> TYPE: DNA
<213> ORGANISM: Homo sapiens

<400> SEQUENCE: 1624
tgaaaccctt ataggagaca aataaatgtg ggcaattatt ttctgcaaaa tgccctccaa 60
gcccctgggc gccattgcct tctgtaatag gacatcacc 99

<210> SEQ ID NO 1625
<211> LENGTH: 87
<212> TYPE: DNA
<213> ORGANISM: Homo sapiens

<400> SEQUENCE: 1625
aagagaccgg agtggtgctg tccctggagc aaacggagca acactctcgc agacccattc 60
agcggggcgc cccctctcag aaggaca 87

<210> SEQ ID NO 1626
<211> LENGTH: 131
<212> TYPE: DNA
<213> ORGANISM: Homo sapiens

<400> SEQUENCE: 1626
cccggatcct tgccttcctg cacccgcctt ccctgagcga ggctgccctg gccgctgacc 60
cccgccgttt ctgcagccct gacctccgtc gcctcctggg acccatcctg gatggggctt 120
cagtagcagc c 131

<210> SEQ ID NO 1627
<211> LENGTH: 130
<212> TYPE: DNA
<213> ORGANISM: Homo sapiens

<400> SEQUENCE: 1627
tgctctccta ataatgcaac aatcgtcaac acagaagaag acttctgtga ccaaatgtgg 60
gcagtttttc ccacacacca agcagcggac accagctggg tgtcctccaa ttcaattccg 120
gcatcatcta 130

<210> SEQ ID NO 1628
<211> LENGTH: 67
<212> TYPE: DNA
<213> ORGANISM: Homo sapiens

<400> SEQUENCE: 1628
ccagatgaac tacctgtggg caccgagaat gtgcacagac tcttcacctc cgggaaagac 60
actgagg 67

<210> SEQ ID NO 1629
<211> LENGTH: 191
<212> TYPE: DNA
<213> ORGANISM: Homo sapiens

<400> SEQUENCE: 1629

-continued

```
caaactctca gtcagggcta cagtcatctg gggttagagg gttttcttcc aagctcacac     60

acatgaggtt gttggcaggc ctcaatccct cactttgctt tggctggagg cctcagttcc    120

tcatcacgtg aacctctaca tagactccct aagtgtcctc acaacatggc agttggcttc    180

cctaaggcaa a                                                          191


<210> SEQ ID NO 1630
<211> LENGTH: 86
<212> TYPE: DNA
<213> ORGANISM: Homo sapiens

<400> SEQUENCE: 1630

ccagctcaac gccagcgagc agctacccag ggcctaccac agacctctgg gggctgtccc     60

ccggccccgt gctcggagct tccatg                                          86


<210> SEQ ID NO 1631
<211> LENGTH: 43
<212> TYPE: DNA
<213> ORGANISM: Homo sapiens

<400> SEQUENCE: 1631

ccagagctca gaggacgagg acgagggagt ggagctgctg gga                       43


<210> SEQ ID NO 1632
<211> LENGTH: 28
<212> TYPE: DNA
<213> ORGANISM: Homo sapiens

<400> SEQUENCE: 1632

cagcccagaa cacgaaaact ttctgctc                                        28


<210> SEQ ID NO 1633
<211> LENGTH: 50
<212> TYPE: DNA
<213> ORGANISM: Homo sapiens

<400> SEQUENCE: 1633

gggattctct ggccctcatt acctagctgg cttaaaccta ctgttttata                50


<210> SEQ ID NO 1634
<211> LENGTH: 55
<212> TYPE: DNA
<213> ORGANISM: Homo sapiens

<400> SEQUENCE: 1634

ctggttgagg gtcatacaga aagtcagtgg gccagctgag actaaagcct gatct          55


<210> SEQ ID NO 1635
<211> LENGTH: 53
<212> TYPE: DNA
<213> ORGANISM: Homo sapiens

<400> SEQUENCE: 1635

gtcctcgggc gaaggaagaa ggagaagggg gatgaggccc tggaggaaca caa            53


<210> SEQ ID NO 1636
<211> LENGTH: 32
<212> TYPE: DNA
<213> ORGANISM: Homo sapiens

<400> SEQUENCE: 1636

agtttccttc tgacaggagg accagcccca gg                                   32
```

<210> SEQ ID NO 1637
<211> LENGTH: 34
<212> TYPE: DNA
<213> ORGANISM: Homo sapiens

<400> SEQUENCE: 1637
agcaccccac tcctgaacct gaatgagccc ctgg 34

<210> SEQ ID NO 1638
<211> LENGTH: 97
<212> TYPE: DNA
<213> ORGANISM: Homo sapiens

<400> SEQUENCE: 1638
aagtgtaacg gggaaataat gcatgcaagg aaaaaggttt ggagtagggg gatttcagtt 60
ttaaacagta tgatcagggt ggtttcattg agaaggt 97

<210> SEQ ID NO 1639
<211> LENGTH: 700
<212> TYPE: DNA
<213> ORGANISM: Homo sapiens

<400> SEQUENCE: 1639
agtgcgcttc attacgtctg gctaattttt taatttctgt agagaaagag gtcttgctat 60
gttgctcagg ctggtctcaa actcctgggc tcaagtgatc ctcctgcctc agccttccaa 120
agtgctgaga ttgtgcctgg ctgtctctgt cttctttggg gaaaagcaag gccaatgtag 180
ctgaagcaga gaggagagaa aggtgagggc tgactgcatg gagcctctgt ggggcattgt 240
gatggctttg aagtcacctt gcttgaggag gctgcctcag ggcctttgca tatcctgatc 300
cttctgcctg gcatactttt ccctctgttc tttgccatgt taccacatcc tttagatctc 360
aaaccaaata ttactcctta cacaaagccc tgcctaactt catacgctca tggtttataa 420
cactccataa ttacacaggc ctttgtgtca taatttgatg actgtctgtc ttctcctttg 480
ggtatgagac cttcaagggc aggggccagg gctgtctggg tccctgctgt tctcttcttt 540
gtgcacatgg gtgggcggtg gctaagcaca gaggaagttc tcagcacata tttgtgaatg 600
aggagctaag attcacgcac tcgcactgtg cctagctttg tgctaaatcc tctatgcacc 660
tgatccaatt ggcgcttctc actggagtgt cggtcccata 700

<210> SEQ ID NO 1640
<211> LENGTH: 25
<212> TYPE: DNA
<213> ORGANISM: Homo sapiens

<400> SEQUENCE: 1640
gttttcactt tgtcacccag tctgg 25

<210> SEQ ID NO 1641
<211> LENGTH: 32
<212> TYPE: DNA
<213> ORGANISM: Homo sapiens

<400> SEQUENCE: 1641
accaccacgc ccgacagtaa atatgttttg aa 32

<210> SEQ ID NO 1642
<211> LENGTH: 165
<212> TYPE: DNA

<213> ORGANISM: Homo sapiens

<400> SEQUENCE: 1642
cacagcaagt aaatagcaat gcctggattc aaactagggc agcatctgac tctggactcg 60
ggttcttcac cgcagccctg aacaccccag agaggttcag agagcagaac gtgcccaaga 120
cgtcactgcc gtttgaatcc agacaggctt gcctcaccac ccagg 165

<210> SEQ ID NO 1643
<211> LENGTH: 31
<212> TYPE: DNA
<213> ORGANISM: Homo sapiens

<400> SEQUENCE: 1643
ctcactgctc tctccgtact cagacgagga c 31

<210> SEQ ID NO 1644
<211> LENGTH: 222
<212> TYPE: DNA
<213> ORGANISM: Homo sapiens

<400> SEQUENCE: 1644
tggtctcagc tcagtgacct ctgggaggtg gtccctggcc ccctcctcct tctctcagga 60
tttctcttgg ggttctcaat acttggttac ctcattatcc ctttctctgc ctctcttggc 120
tttattttgg ggaatcaggg gtgaggaggg ttgggggggt catatctgtg tttccaggtt 180
ctggggagaa caatgatcca cgggtcaacg tgatcacatt tc 222

<210> SEQ ID NO 1645
<211> LENGTH: 104
<212> TYPE: DNA
<213> ORGANISM: Homo sapiens

<400> SEQUENCE: 1645
ccagtgactt ccgattgagg ccaaagaccc caagctgccc gccagctctg actgcccctt 60
gcgctctggg cttcctgccg cccccagctt tgcctggaca ctga 104

<210> SEQ ID NO 1646
<211> LENGTH: 544
<212> TYPE: DNA
<213> ORGANISM: Homo sapiens

<400> SEQUENCE: 1646
tgacctgcac tggttctaga ccacacaacc tccaatgtgg tctgctttag atcaccttct 60
tcttcttcct tcttcctctt cctcttcctc ctgctcctct tcctcttctt cttctttttt 120
ttttttgaca gagtcttgct ctgtcaccca ggctggagtg cagtggcgcg atttcagctt 180
actgcagcct ccgcgccctg ggttcaagtg attctcctgc ctcaacttcc caaatagccg 240
ggactacggg catgtgccac attgcccggc taatttttgt atttttagta gagatggggt 300
ttcaccacgt tgtccagtct ggtctcgaac tcctgacctc aagtgctcca cctgcctcag 360
ccttccaaag tgctgggatt acaggcgtga gccactgcac ccggctagaa ctcactttct 420
ccaaatccct ctgcttcgaa tttcaccgtc ttcagctctt tctagttctg ggcctcacca 480
gcctctcatt ctgcctgttt tcaaacctta cgatccccaa aaattgtctg gttctgggcc 540
tcta 544

<210> SEQ ID NO 1647
<211> LENGTH: 1103

<212> TYPE: DNA
<213> ORGANISM: Homo sapiens

<400> SEQUENCE: 1647
ccggttccag atcttatatt cagtgatttc ctctggttct ggaccccaca actccaagct 60
tcctattggt tccagttctc ctgatcggta atacatttgg ttccaaatcc agacctctta 120
atctctctct tttttttttt ttttttttga gacagagtcc cactctgtca cccaggctgg 180
agtacagtgg ctcaatctcg gctcactgca gcctccacct cctgggttca agcaattctt 240
gggcctcagc ctcccaaata gctgggatta caggcatgtg ccaccacgcc cagctaagtt 300
ttatattttt agtagagaca gtgtttcacc atgttggcca ggctggtctt gaactcccga 360
cctcaactga tccacccgcc tcagcctccc aaagtgctga aattacagga gtgagcctgg 420
ccagacttct taatttctaa atcacttttg ttttagacct tatgaggctc agcttattct 480
tctgcagttc tctataacca agactcattt tctctcatca aaaacaagta cagagagttt 540
gatgtgttta tctctttttt cttcctcttc tttttttttt ttttcttttt tgagatggag 600
tctctctctg ttgcccaggc tggagtataa tggtgccatc taggctcact gcaacctccg 660
cctcctgatt caagtgattc tcctgcctca gcctcctaaa ttggtgggat tacaggagcc 720
caccaccaca tccggctacc tttgtgtatt ttttagtaga gacggggttt tgccaagttg 780
gaggggctgg tcttgaactc ttgacctcag atgatccacc cgcctcagcc tcccaaagtg 840
ctgggattac aggcataagc caccgtgccc gaccctgtcc ttatcttata ataaccagtt 900
cttctagaac cagacgatgc tctagttctc ctagattctg aacctcatga cctgtaccac 960
tcactagttc cagactacac aacttctaga aggtgccacc tccagggtcc tgattcaaga 1020
tctggtgatc tgctgtttct ctggttctag aactgactta caagtgcctt ctgattctag 1080
acctcattcc gtaagttccc ttg 1103

<210> SEQ ID NO 1648
<211> LENGTH: 31
<212> TYPE: DNA
<213> ORGANISM: Homo sapiens

<400> SEQUENCE: 1648
cccagcctcc taaatctatt ctgggcttcc c 31

<210> SEQ ID NO 1649
<211> LENGTH: 207
<212> TYPE: DNA
<213> ORGANISM: Homo sapiens

<400> SEQUENCE: 1649
cactgaactt acccaattcc ttctttcagt cttaagtttt cccattctaa acccctaccc 60
tctaggctgt gctgctcctg gacttcatgc ctctccattc tcattgccta caatctctgt 120
gccccagaac cccctccact tcccacccca gccctccaga catgcactta ccttgacttt 180
accccacatg tttggggcac ctggggc 207

<210> SEQ ID NO 1650
<211> LENGTH: 177
<212> TYPE: DNA
<213> ORGANISM: Homo sapiens

<400> SEQUENCE: 1650
agctgtctgc caccatctat gtgcctccct taccccccag ctttctttct acagatggtg 60

-continued ctactcttgg tctcccacag gaaaaggcct ccccccttct tagccccatt taccccgttt 120
gtggaaggca ctgctcgctc tgttttgtca gagagtggcc tatccagatt ggtgcta 177

<210> SEQ ID NO 1651
<211> LENGTH: 226
<212> TYPE: DNA
<213> ORGANISM: Homo sapiens

<400> SEQUENCE: 1651
tcctcccgga gtttggaacg gctgaagttc accttccagc ccctagcgcc gttcgcgccg 60
ctaggcctgg cttctgaggc ggttgcggtg ctcggtcgcc gcctaggcgg ggcagggtgc 120
gagcaggggc ttcgggccac gcttctcttg gcgacaggat tttgctgtga agtccgtccg 180
ggaaacggag gaaaaaaaga gttgcgggag gctgtcggct aataac 226

<210> SEQ ID NO 1652
<211> LENGTH: 40
<212> TYPE: DNA
<213> ORGANISM: Homo sapiens

<400> SEQUENCE: 1652
atgccctcag gaagtgtggc gtttgatgga ggaaaacaga 40

<210> SEQ ID NO 1653
<211> LENGTH: 65
<212> TYPE: DNA
<213> ORGANISM: Homo sapiens

<400> SEQUENCE: 1653
tgagggagtt caagagccag tttgtgtttc tgtgcttcac aaagccaccc ttgtctaatt 60
cttga 65

<210> SEQ ID NO 1654
<211> LENGTH: 98
<212> TYPE: DNA
<213> ORGANISM: Homo sapiens

<400> SEQUENCE: 1654
tgatacatat ttgccagact tcaagatttc agaaaagggg tgaaagagaa gattgcaact 60
ttgagtcaga cctgtaggcc tgatagactg attaaacc 98

<210> SEQ ID NO 1655
<211> LENGTH: 25
<212> TYPE: DNA
<213> ORGANISM: Homo sapiens

<400> SEQUENCE: 1655
gagtgtgcac ttcagtggcg tgatc 25

<210> SEQ ID NO 1656
<211> LENGTH: 182
<212> TYPE: DNA
<213> ORGANISM: Homo sapiens

<400> SEQUENCE: 1656
catttgggta agttaatagt caatttatag gccacgtaaa tgggaaggat tatttcctta 60
aatcaagaga ttagacaatc attgcttgtc atgaatattt aataaaaatt tgagaaagct 120
cagtttcttt tgggctgcaa acatagatct agggaaataa atactgctta actattttgt 180
tg 182

<210> SEQ ID NO 1657
<211> LENGTH: 55
<212> TYPE: DNA
<213> ORGANISM: Homo sapiens

<400> SEQUENCE: 1657
aaggtgacct gctgagaaaa gtggtacaaa tactgggaaa aacctgctct tctgc 55

<210> SEQ ID NO 1658
<211> LENGTH: 93
<212> TYPE: DNA
<213> ORGANISM: Homo sapiens

<400> SEQUENCE: 1658
cacaagttaa aagctcttat tcctatgatg ccccctcgga tttcatcaat ttttcatcct 60
tggatgatga aggagatact caaaacatag att 93

<210> SEQ ID NO 1659
<211> LENGTH: 96
<212> TYPE: DNA
<213> ORGANISM: Homo sapiens

<400> SEQUENCE: 1659
tactggtagg gagctttagt ttgcatttta aatgcgtgat agtgatttgt tttgcttcct 60
tgctgatcag acaatgatga tcttcccttt tcacag 96

<210> SEQ ID NO 1660
<211> LENGTH: 79
<212> TYPE: DNA
<213> ORGANISM: Homo sapiens

<400> SEQUENCE: 1660
ggaactggag ggctttttca gggcaaaact cctttgagaa aggctaatct tcagcaagct 60
attgtcacac ctttgaaac 79

<210> SEQ ID NO 1661
<211> LENGTH: 105
<212> TYPE: DNA
<213> ORGANISM: Homo sapiens

<400> SEQUENCE: 1661
gacaacactt actacaaaga ggcagaaaaa gaaaatcttg tggaacaatc cattccgtca 60
aatgcttgtt cttccctgga agttgaggca gccatatcaa gaaaa 105

<210> SEQ ID NO 1662
<211> LENGTH: 36
<212> TYPE: DNA
<213> ORGANISM: Homo sapiens

<400> SEQUENCE: 1662
caagagatgt gccactcctg taatcatcga tgaaat 36

<210> SEQ ID NO 1663
<211> LENGTH: 101
<212> TYPE: DNA
<213> ORGANISM: Homo sapiens

<400> SEQUENCE: 1663
ccttgtatac cacttgtaag tttcttttct gaatttacac tttagattga atagattaaa 60
attaaaaatg gtacatctgt aatatgtttg gtgtacctca a 101

<210> SEQ ID NO 1664
<211> LENGTH: 58
<212> TYPE: DNA
<213> ORGANISM: Homo sapiens

<400> SEQUENCE: 1664
tccatatgca gtagatttgg ggaggagggt acaggctatg cttcagggaa ttgaaaac 58

<210> SEQ ID NO 1665
<211> LENGTH: 92
<212> TYPE: DNA
<213> ORGANISM: Homo sapiens

<400> SEQUENCE: 1665
agaaggcagt gctcatcaag atactgctga aaagaatgca tcttccccag agaaagccaa 60
gggtagacat actgtgcctt gtatgccacc tg 92

<210> SEQ ID NO 1666
<211> LENGTH: 31
<212> TYPE: DNA
<213> ORGANISM: Homo sapiens

<400> SEQUENCE: 1666
gagaagagta tgaaaatgca gcaagaggtg g 31

<210> SEQ ID NO 1667
<211> LENGTH: 129
<212> TYPE: DNA
<213> ORGANISM: Homo sapiens

<400> SEQUENCE: 1667
atcagtgagc caggtcacca aatcagttga cttccacttc cgcacagatg agcgaatcaa 60
acaacatcct aagaaccagg aggaatataa ggaagtgaac tttacatctg aactacgaaa 120
gcatccttc 129

<210> SEQ ID NO 1668
<211> LENGTH: 278
<212> TYPE: DNA
<213> ORGANISM: Homo sapiens

<400> SEQUENCE: 1668
ggttggggca gaccagtcaa atctcatgca gttttgttac cagagcacca acaaaatcag 60
taataatcgt taagtaaaaa tgctagtact aataatctcc acttgcattt gtagtcagta 120
tcatcatttt ttgaaattag ttatttgcat tcttaaaccc tgaggttatg cttctttctt 180
tgagatacag gtccttgaag ggttttgctt ccaattagag accagtttta tcaaaattac 240
tggtccaagg aataggaata ggcttcttca tcagtctc 278

<210> SEQ ID NO 1669
<211> LENGTH: 56
<212> TYPE: DNA
<213> ORGANISM: Homo sapiens

<400> SEQUENCE: 1669
ctctgtgccg aatatgtggc ttatggtaga tgtgagctct tccgtgacat ttcatt 56

<210> SEQ ID NO 1670
<211> LENGTH: 121

<212> TYPE: DNA
<213> ORGANISM: Homo sapiens

<400> SEQUENCE: 1670
gcccgagtga ctaagggatg taccattgtt aagcctttca acctgtccca aggaaagaaa 60
agaacatttg atgaaacagt ttctacatat gtgccccttg cacagcaagt tgaagacttc 120
c 121

<210> SEQ ID NO 1671
<211> LENGTH: 31
<212> TYPE: DNA
<213> ORGANISM: Homo sapiens

<400> SEQUENCE: 1671
atggctcact tcagtgtcca actcctgggc t 31

<210> SEQ ID NO 1672
<211> LENGTH: 54
<212> TYPE: DNA
<213> ORGANISM: Homo sapiens

<400> SEQUENCE: 1672
tgaatcacca cttacaagta aactgggtct tgcggatcta gatgaacatc tgtc 54

<210> SEQ ID NO 1673
<211> LENGTH: 140
<212> TYPE: DNA
<213> ORGANISM: Homo sapiens

<400> SEQUENCE: 1673
ctgttaccct ccaaatcttc tgtgaccaag atttgcagag acccacagac tcctgtactg 60
caaaccaaac accgtgcacg ggctgtgacc tgcaaaagta cagcagagct ggaggctgag 120
gagctcgaga aattgcaaca 140

<210> SEQ ID NO 1674
<211> LENGTH: 25
<212> TYPE: DNA
<213> ORGANISM: Homo sapiens

<400> SEQUENCE: 1674
gtaagtccca ctggcagtat ctgag 25

<210> SEQ ID NO 1675
<211> LENGTH: 183
<212> TYPE: DNA
<213> ORGANISM: Homo sapiens

<400> SEQUENCE: 1675
cttgatccca gaatacttga aggtgggccc atcttgccca agaaaccacc tgtgaaacca 60
cccaccgagc ctattggctt tgatttggaa attgagaaaa gaatccagga gcgagaatca 120
aagaagaaaa cagaggatga acactttgaa tttcattcca gaccttgccc tactaagatt 180
ttg 183

<210> SEQ ID NO 1676
<211> LENGTH: 474
<212> TYPE: DNA
<213> ORGANISM: Homo sapiens

<400> SEQUENCE: 1676

-continued cacctgtttc agatgaggta accgaggcac acagaggtta tgtagtattc ctagagcact 60
cagctagtac atggtggagc aagtaagagt tcagacactc tagctacaga gtctgtgatc 120
ctaatacctc attatatgcc tctccattac atgatagaat tttgacttgc agaaatgcaa 180
atggactgga ttggcagaac attccaggca gtaggaatta catgataaaa agcctgacgg 240
tgggaaacaa gaagcttcta ctgggagctg ttagtgggtc agttaagctg gagaaaagtt 300
tatcaagagc cactggaaac tgtttcagag aagtgagttg tagtttgata ataggctcac 360
aaccacaagt ttagagaaaa tgtgcaatca ggaagcaagg ctacagtcag agaataagca 420
atggagttaa gcacctgcat aaatgcgaaa gcggctttta gttacatttc agtg 474

<210> SEQ ID NO 1677
<211> LENGTH: 272
<212> TYPE: DNA
<213> ORGANISM: Homo sapiens

<400> SEQUENCE: 1677
acagggaccg tgtgtatcta tattattcac tctgtatccc tagcccctag catagtgacc 60
accacagcac aagcactctg atatcggata actgagtgag taatagtaga agctgacatg 120
cacctagaca ctaggaattc aaagatggta taagacacgg cccttgtcct caaagctttc 180
atagtctggt agagcatata gatgtgtaaa tgagtaaata tggtaatatt aaccaacata 240
tgttcattga acagttacta cggggtcttc ta 272

<210> SEQ ID NO 1678
<211> LENGTH: 48
<212> TYPE: DNA
<213> ORGANISM: Homo sapiens

<400> SEQUENCE: 1678
agtggagatc attttgtgat atctaattga gttgcttact cctttcag 48

<210> SEQ ID NO 1679
<211> LENGTH: 31
<212> TYPE: DNA
<213> ORGANISM: Homo sapiens

<400> SEQUENCE: 1679
tgttcctgaa aagaaggtac ttccaatcac c 31

<210> SEQ ID NO 1680
<211> LENGTH: 34
<212> TYPE: DNA
<213> ORGANISM: Homo sapiens

<400> SEQUENCE: 1680
cattgaagaa cagaattcga atgcccacca aaga 34

<210> SEQ ID NO 1681
<211> LENGTH: 132
<212> TYPE: DNA
<213> ORGANISM: Homo sapiens

<400> SEQUENCE: 1681
gacgaaccgg tagtgataaa agctcaacct gtgccacatt atggggtgcc ttttaagccc 60
caaatcccag aggcaagaac tgtggaaata tgccctttct cgtttgattc tcgagacaaa 120
gaacgtcagt ta 132

```
<210> SEQ ID NO 1682
<211> LENGTH: 110
<212> TYPE: DNA
<213> ORGANISM: Homo sapiens

<400> SEQUENCE: 1682

gtgcccaagt tcaaggcact tcccttgcct cattttgaca ccattaacct gccagagaag      60

aaggtaaaga atgtgaccca gattgaacct ttctgcttgg agactgacag                110

<210> SEQ ID NO 1683
<211> LENGTH: 39
<212> TYPE: DNA
<213> ORGANISM: Homo sapiens

<400> SEQUENCE: 1683

gtaggggatg gggagagcag ccaaaatgtt aattgcttg                             39

<210> SEQ ID NO 1684
<211> LENGTH: 319
<212> TYPE: DNA
<213> ORGANISM: Homo sapiens

<400> SEQUENCE: 1684

ttggaggtgg gaagaatact ttataggtga tactgtatag ttcctaatga atcatgtgtg      60

aaggcagaaa atgtctagtt gtttattttt atgatataaa gataggtctt aaaagtacct    120

ttaaaatttt ttgttttttt taattgacaa ataatagttg tacatattct tggggtacat    180

agtgatgttt caatatgtat aatgtgtaat gatctgatca gggtaattag catatccata    240

atctcaaaca tttatcattt ctttgtgttt ggaatctttt tttttttaat ttaaaagtaa    300

actttagcac accaacatg                                                 319

<210> SEQ ID NO 1685
<211> LENGTH: 41
<212> TYPE: DNA
<213> ORGANISM: Homo sapiens

<400> SEQUENCE: 1685

cttgtttcaa ggctcgtcca aacaccgtca tctctcagga g                         41

<210> SEQ ID NO 1686
<211> LENGTH: 128
<212> TYPE: DNA
<213> ORGANISM: Homo sapiens

<400> SEQUENCE: 1686

ttcaggaacc ttttcagctg gctactgaga agagagccaa agagcggcag gagctggaga      60

agagaatggc tgaggtagaa gcccagaaag cccagcagtt ggaggaggcc agactacagg    120

aggaagag                                                             128

<210> SEQ ID NO 1687
<211> LENGTH: 38
<212> TYPE: DNA
<213> ORGANISM: Homo sapiens

<400> SEQUENCE: 1687

tgggagcatg agcactgacg aacacaaaca tgcctctg                             38

<210> SEQ ID NO 1688
<211> LENGTH: 296
<212> TYPE: DNA
```

<213> ORGANISM: Homo sapiens

<400> SEQUENCE: 1688
aaccatgatg cctttcctag gactgttttt tatttatttg tttattttat ttatgtaact 60
tattatttcc tctggggtta agaagcacca ctgagttttg taattagaca agaatacata 120
gcgaaggaca tgggaattaa atggcaactg tatttttgtt ttaatactga gcccaaactc 180
cttggagtta cagtgttcgt cgctccaggt aatcctctac taacataatt atttagatgt 240
tggttatcca aaaagaaacc tgaactccac attaaggacc aatctgctag gagggc 296

<210> SEQ ID NO 1689
<211> LENGTH: 272
<212> TYPE: DNA
<213> ORGANISM: Homo sapiens

<400> SEQUENCE: 1689
tgtactctgg gaaattctta gcttgtaact tctctgctat acttgagtac agccctatta 60
taccctagta aatcacacag gacataggtt tggcattctt tagtgaaagc tgagggactt 120
gaggagactg tggcctaaag gaaagctggg ggacccaata gagacctgaa tagaaaccct 180
tttgggctcc aaagcacata cacttttcca tcataccgtg ttgcccccca ggccccactc 240
cccacacctg aaactagtga ctgggacctg ta 272

<210> SEQ ID NO 1690
<211> LENGTH: 72
<212> TYPE: DNA
<213> ORGANISM: Homo sapiens

<400> SEQUENCE: 1690
gtgcataagg caaatccaat acgcaagtac cagggtctgg agataaagtc aagtgaccag 60
cctctgactg tg 72

<210> SEQ ID NO 1691
<211> LENGTH: 29
<212> TYPE: DNA
<213> ORGANISM: Homo sapiens

<400> SEQUENCE: 1691
ccaaattctc cactcgattc cactgctaa 29

<210> SEQ ID NO 1692
<211> LENGTH: 130
<212> TYPE: DNA
<213> ORGANISM: Homo sapiens

<400> SEQUENCE: 1692
tcagctgtga gctgcggata ccgcccggca atgggacctg ctcttaacct caaacctagg 60
accgtcttgc tttgtcattg ggcatggaga gaacccattt ctccagactt ttacctaccc 120
gtgcctgaga 130

<210> SEQ ID NO 1693
<211> LENGTH: 25
<212> TYPE: DNA
<213> ORGANISM: Homo sapiens

<400> SEQUENCE: 1693
cagaaaataa agatagttaa atcct 25

<210> SEQ ID NO 1694
<211> LENGTH: 170
<212> TYPE: DNA
<213> ORGANISM: Homo sapiens

<400> SEQUENCE: 1694
gtcctcttct ctgcataccg tgaatttata gttaaggatc cctttgctgt gagggtagaa 60
aacctcacca actgcaccag tgaggaagaa gactgcgtgg attcatgggg agcctcacag 120
cagccacgca gcaggctctg ggtggggctg ccgttaaggc acgttctttc 170

<210> SEQ ID NO 1695
<211> LENGTH: 28
<212> TYPE: DNA
<213> ORGANISM: Homo sapiens

<400> SEQUENCE: 1695
ggaaccgtgc agtgtgcatt ttaagacc 28

<210> SEQ ID NO 1696
<211> LENGTH: 25
<212> TYPE: DNA
<213> ORGANISM: Homo sapiens

<400> SEQUENCE: 1696
tggcctggaa taaatacgtt ttgtc 25

<210> SEQ ID NO 1697
<211> LENGTH: 76
<212> TYPE: DNA
<213> ORGANISM: Homo sapiens

<400> SEQUENCE: 1697
atggagtttc accattttgg ccaggctggt ctcgaactcc tgacctcagg tgatctacct 60
gcctcggcct ctgaaa 76

<210> SEQ ID NO 1698
<211> LENGTH: 402
<212> TYPE: DNA
<213> ORGANISM: Homo sapiens

<400> SEQUENCE: 1698
gtgctctgaa acctactttg cctgatatta atatagccac tctagttttc ttttgattgg 60
ttttagcatg gtatgtctat atttaaagtg catttttttg tagacagcat ataattgggt 120
cttgctttat tatttaatat tattgttgct gcattttaat tggaataaat gcatctattt 180
tagccttgac atgctatgct attattttgt gtgtgcgtgt gagtctctct gccccaaaaa 240
tatttcttta ggagatgaac caaatgattg ttctctgaaa tgaataatgc ctaaactatg 300
ttttcatggc ctatcttttc ttccctgtca tcttgttgca gtttaattcc tttatcagga 360
gtcagttcat atgctatgtg attaagtgct gtttcttcca tg 402

<210> SEQ ID NO 1699
<211> LENGTH: 30
<212> TYPE: DNA
<213> ORGANISM: Homo sapiens

<400> SEQUENCE: 1699
taaatccccg cacctgagca tcggctcaca 30

<210> SEQ ID NO 1700

<211> LENGTH: 40
<212> TYPE: DNA
<213> ORGANISM: Homo sapiens

<400> SEQUENCE: 1700
atgcctgctt gtcgcctagg cccgctagcc gccgccctcc 40

<210> SEQ ID NO 1701
<211> LENGTH: 31
<212> TYPE: DNA
<213> ORGANISM: Homo sapiens

<400> SEQUENCE: 1701
ctgctgctgt tcggcttcac cctagtctca g 31

<210> SEQ ID NO 1702
<211> LENGTH: 92
<212> TYPE: DNA
<213> ORGANISM: Homo sapiens

<400> SEQUENCE: 1702
ccaggctgac cagaactgca cgcaagagtg cgtctcggac agcgaatgcg ccgacaacct 60
caagtgctgc agcgcgggct gtgccacctt ct 92

<210> SEQ ID NO 1703
<211> LENGTH: 27
<212> TYPE: DNA
<213> ORGANISM: Homo sapiens

<400> SEQUENCE: 1703
ggcggggccg cgctgggctg ggaggag 27

<210> SEQ ID NO 1704
<211> LENGTH: 301
<212> TYPE: DNA
<213> ORGANISM: Homo sapiens

<400> SEQUENCE: 1704
gcagtttcct tctcgaaccg gccgaagcct gccctgcggg aaagcccgga gcctggggcg 60
ctcacctctc ctcttggagt ccctccctgg gggcctcccc cagccctggg gaaagactgg 120
gagagcctgg cctggcaaga ttttccccaa ttcctctgtc caggcggaaa ggaactttac 180
agatttagga aaatgccccg ctcatcttaa agatgtgtaa gggagcatcg gtgagaaaaa 240
aatgttcttg cccaaggtca caccgccatc ccatggctgc tggagtcata gtgagggttc 300
a 301

<210> SEQ ID NO 1705
<211> LENGTH: 88
<212> TYPE: DNA
<213> ORGANISM: Homo sapiens

<400> SEQUENCE: 1705
ctggacactg tatcgccctt cgtcgtcttt cagtcaatct cttccactct aaggattgag 60
tgagcgcgag ctggggactc tctcaaag 88

<210> SEQ ID NO 1706
<211> LENGTH: 41
<212> TYPE: DNA
<213> ORGANISM: Homo sapiens

<400> SEQUENCE: 1706
gcagtctcca ccaggctatc agaacagggg gtggcttaaa c 41

<210> SEQ ID NO 1707
<211> LENGTH: 31
<212> TYPE: DNA
<213> ORGANISM: Homo sapiens

<400> SEQUENCE: 1707
ctttatccag aatacagccc ctgtgacttt t 31

<210> SEQ ID NO 1708
<211> LENGTH: 35
<212> TYPE: DNA
<213> ORGANISM: Homo sapiens

<400> SEQUENCE: 1708
tacggtgacc caagacaccg atcagcaggg aggtg 35

<210> SEQ ID NO 1709
<211> LENGTH: 81
<212> TYPE: DNA
<213> ORGANISM: Homo sapiens

<400> SEQUENCE: 1709
agatttggag agaaagcagg cagcagccag atgagagagg tggaggagca aaggagggag 60
tctttgctgt ttgatggatg a 81

<210> SEQ ID NO 1710
<211> LENGTH: 26
<212> TYPE: DNA
<213> ORGANISM: Homo sapiens

<400> SEQUENCE: 1710
atcaggtggc tgtagatgtg tagtgt 26

<210> SEQ ID NO 1711
<211> LENGTH: 128
<212> TYPE: DNA
<213> ORGANISM: Homo sapiens

<400> SEQUENCE: 1711
gtatctgctc cagagtgcac tattcctcac ggcacagtcc ctcatggctt cccttggcta 60
ggggagggag ttccctgacc tcttgtgctt cccaggtgag atgatgccct accctacttc 120
tgctcgcc 128

<210> SEQ ID NO 1712
<211> LENGTH: 322
<212> TYPE: DNA
<213> ORGANISM: Homo sapiens

<400> SEQUENCE: 1712
aaccatgatg tacctcagtt gatgaatgga tttggctggg cctggctccc ctctatctaa 60
cctgggaagt ggagtgtgat tgtgtgtgtg tttgttagtg gaaggacgtg tggtttctct 120
ctgcatggat gaatgagtgt atttggaggg tcatggtgct gagagactgc aactgggatt 180
cggtctgtgg gtatgagtga agattataag tgtgtaaccc ctcacatgtg tactgtactt 240
tacactttaa gtggcagcat agtgcttaac catggcagca gcagttaaca catagactct 300
gcagctagat ttcttggggt tc 322

<210> SEQ ID NO 1713
<211> LENGTH: 78
<212> TYPE: DNA
<213> ORGANISM: Homo sapiens

<400> SEQUENCE: 1713
ttaggggctt gatacctggc atgtaataag agctaattaa gtgttcactg ttataatttc 60
tcataactac agagtagt 78

<210> SEQ ID NO 1714
<211> LENGTH: 73
<212> TYPE: DNA
<213> ORGANISM: Homo sapiens

<400> SEQUENCE: 1714
tggcacctaa agacacggag gctctgggag atttctggcc ctaggccacg aaggcccact 60
tgggactcaa gct 73

<210> SEQ ID NO 1715
<211> LENGTH: 42
<212> TYPE: DNA
<213> ORGANISM: Homo sapiens

<400> SEQUENCE: 1715
ggtcctgtga ttccatttgg gagcaggagg agggatttgc ag 42

<210> SEQ ID NO 1716
<211> LENGTH: 59
<212> TYPE: DNA
<213> ORGANISM: Homo sapiens

<400> SEQUENCE: 1716
ctcaggtgcc caagatggac tcaggcaggc agctctgctg tatgtgaagc ccagtgagg 59

<210> SEQ ID NO 1717
<211> LENGTH: 51
<212> TYPE: DNA
<213> ORGANISM: Homo sapiens

<400> SEQUENCE: 1717
atgctgcagg tacaagttaa tctccctgta tcgcctctgc ccacttaccc t 51

<210> SEQ ID NO 1718
<211> LENGTH: 106
<212> TYPE: DNA
<213> ORGANISM: Homo sapiens

<400> SEQUENCE: 1718
gtgaacatta actttcccca gctcggcctc tgtcgggacc agtgccaggt ggacagccag 60
tgtcctggcc agatgaaatg ctgccgcaat ggctgtggga aggtgt 106

<210> SEQ ID NO 1719
<211> LENGTH: 47
<212> TYPE: DNA
<213> ORGANISM: Homo sapiens

<400> SEQUENCE: 1719
gcctagtcta atggatattg ttgttgatgg tattgttata attttct 47

<210> SEQ ID NO 1720
<211> LENGTH: 70

<212> TYPE: DNA
<213> ORGANISM: Homo sapiens

<400> SEQUENCE: 1720
ccaccaccag gctgagcagt gaggagagaa agtttctgcc tggccctgca tctggttcca 60
gcccacctgc 70

<210> SEQ ID NO 1721
<211> LENGTH: 28
<212> TYPE: DNA
<213> ORGANISM: Homo sapiens

<400> SEQUENCE: 1721
ccctcttggg ctgaccacag cttctccc 28

<210> SEQ ID NO 1722
<211> LENGTH: 31
<212> TYPE: DNA
<213> ORGANISM: Homo sapiens

<400> SEQUENCE: 1722
gtgggaagaa agactgggat gatgaccaaa a 31

<210> SEQ ID NO 1723
<211> LENGTH: 52
<212> TYPE: DNA
<213> ORGANISM: Homo sapiens

<400> SEQUENCE: 1723
gaaaactctg gagttaaggc caatgaagta atctctaaac tttatgcagt ac 52

<210> SEQ ID NO 1724
<211> LENGTH: 28
<212> TYPE: DNA
<213> ORGANISM: Homo sapiens

<400> SEQUENCE: 1724
aattgaatta gccaaacaga tcacatca 28

<210> SEQ ID NO 1725
<211> LENGTH: 26
<212> TYPE: DNA
<213> ORGANISM: Homo sapiens

<400> SEQUENCE: 1725
ggctctacag acaatctgat ggatga 26

<210> SEQ ID NO 1726
<211> LENGTH: 25
<212> TYPE: DNA
<213> ORGANISM: Homo sapiens

<400> SEQUENCE: 1726
gagatactca ggtggtggtt tttaa 25

<210> SEQ ID NO 1727
<211> LENGTH: 67
<212> TYPE: DNA
<213> ORGANISM: Homo sapiens

<400> SEQUENCE: 1727
ctattgctga tactggtgca aatgtcgtag taacaggtgg caaagtggca gacatggctc 60
ttcatta 67

<210> SEQ ID NO 1728
<211> LENGTH: 50
<212> TYPE: DNA
<213> ORGANISM: Homo sapiens

<400> SEQUENCE: 1728
aaatagcagt gtactcttgt ccttttgatg gcatgataac agaaactaag 50

<210> SEQ ID NO 1729
<211> LENGTH: 29
<212> TYPE: DNA
<213> ORGANISM: Homo sapiens

<400> SEQUENCE: 1729
gttgataaca tcagagtttg taaaattct 29

<210> SEQ ID NO 1730
<211> LENGTH: 26
<212> TYPE: DNA
<213> ORGANISM: Homo sapiens

<400> SEQUENCE: 1730
cctggaatta gctgaagaac ttctga 26

<210> SEQ ID NO 1731
<211> LENGTH: 71
<212> TYPE: DNA
<213> ORGANISM: Homo sapiens

<400> SEQUENCE: 1731
agaagaggct gtgtatagaa acatacaagc ttgcaaggag cttgcccaaa ccactcgtac 60
agcatatgga c 71

<210> SEQ ID NO 1732
<211> LENGTH: 30
<212> TYPE: DNA
<213> ORGANISM: Homo sapiens

<400> SEQUENCE: 1732
ggtgaaggga ctctcgagtg tggtcattga 30

<210> SEQ ID NO 1733
<211> LENGTH: 26
<212> TYPE: DNA
<213> ORGANISM: Homo sapiens

<400> SEQUENCE: 1733
aaggcctccg tctcctgcat gtcctt 26

<210> SEQ ID NO 1734
<211> LENGTH: 66
<212> TYPE: DNA
<213> ORGANISM: Homo sapiens

<400> SEQUENCE: 1734
ggtactctac agtgtggtca ttgaggacaa gttgacgaga gagtcccaag tacgtccacg 60
gtcagc 66

<210> SEQ ID NO 1735
<211> LENGTH: 170

<212> TYPE: DNA
<213> ORGANISM: Homo sapiens

<400> SEQUENCE: 1735
cagcaaggaa cggaaagttc acattgtaaa tatgtagcag agtctgtaat ggctcagtca 60
acgcaaaatg ttgactacag tcaattacag gagataatat accctgaatc atcaaaattg 120
ggggaaggag gtccagaatc attggggcca tcagagccta aaccacgatc 170

<210> SEQ ID NO 1736
<211> LENGTH: 67
<212> TYPE: DNA
<213> ORGANISM: Homo sapiens

<400> SEQUENCE: 1736
ctacaatgaa ctcactggag atgcaaagaa aagtgtggag atggagacac cccaatcgac 60
tcgccag 67

<210> SEQ ID NO 1737
<211> LENGTH: 101
<212> TYPE: DNA
<213> ORGANISM: Homo sapiens

<400> SEQUENCE: 1737
caggaacgga gacaatcgtg aaagctgctg atagcctcac aaatcttaag ccagtcactt 60
gggttaaaag catcagaagt ttcactattg taaatttcat a 101

<210> SEQ ID NO 1738
<211> LENGTH: 224
<212> TYPE: DNA
<213> ORGANISM: Homo sapiens

<400> SEQUENCE: 1738
atgggccata gtgacgatgg tggttttgtc aaaaagaaaa ggggggggata tgtaaggaaa 60 agagagatca gactttcact gtgtctatgt agaaaaggaa gacataagaa actccatttt 120
gatctgtact aagaaaaatt gttttgcctt gagatgctgt taatctgtaa ctttagcccc 180
aaccctgtgc tcacggaaac atgtgctgta aggtttaagg gatc 224

<210> SEQ ID NO 1739
<211> LENGTH: 302
<212> TYPE: DNA
<213> ORGANISM: Homo sapiens

<400> SEQUENCE: 1739
attttaggcg ctggacttgg gttcggggca cctggccttt ccttgtgtat ttctcctact 60
gtctgcctaa ctatttaata caataaaaga aaaccagccc ctggttcttg tggtgtttcc 120
accctcccgg gtccccgctg gctgcctggc ttcctcccgc agctcctgct gtgtgtgtat 180
gtgtgtgtgt gtgcacatct gtggggcgta tgtgtgttcg tctttgtaat tgaggctgca 240
gagtggagag agcaggggtt ttctctgggg acccagagag aaggaggcgt tttcaccaca 300
gc 302

<210> SEQ ID NO 1740
<211> LENGTH: 355
<212> TYPE: DNA
<213> ORGANISM: Homo sapiens

<400> SEQUENCE: 1740

-continued cctttgaggg agatcaagtc taaatttgaa gggagtccaa attcatactg ggtaattta 60 ttcagattat aaagggggaa ttcagttagt gatcagctcc actgttcccc ggagtgccaa 120
tccaggtgat agaattgctc aattactgct tttgccttat gttaaaattg gggaaaacaa 180
aaaggaaaga acaggagggt ttggaagtac caaccctgca ggaaaagctg cttattgggc 240
taatcaggtc tcagaggata gacccgtgtg tacagtcact attcagggaa agagtttgaa 300
ggattagtgg atacccaggc tgatgtttct gtcatcggca taggtactgc ctcag 355

<210> SEQ ID NO 1741
<211> LENGTH: 395
<212> TYPE: DNA
<213> ORGANISM: Homo sapiens

<400> SEQUENCE: 1741
cagatggcgt ataatgccgt aattcaaccc atgggggctc tcccaccccg gttgccctct 60
ccagccatgg tccccctttaa ttataattga tctgaaggat tgctttttta ccattcctct 120
ggcaaaacag gattttgaaa aatttgcttt taccacacca gcctaaataa taaagaacca 180
gccaccaggt ttcagtggaa agtattgcct cagggaatgc ttaatagttc aactatttgt 240
cagctcaagc tctgcaacca gttagagaca agttttcaga ctgttacatc gttcactatg 300
ttgatatttt gtgtgctgca gaaacgagag acaaattaat tgaccgttac acatttctgc 360
agacagaggt tgccaacgcg ggactgacaa taaca 395

<210> SEQ ID NO 1742
<211> LENGTH: 411
<212> TYPE: DNA
<213> ORGANISM: Homo sapiens

<400> SEQUENCE: 1742
ggttgccgtc attacagtgt taacaagatt ttaatcagtc tattaacatt gtatcagatt 60
ctgcatatgt agtacaggct acaaaggata ttgagagagc cctaatcaaa tacattatgg 120
atgatcagtt aaacccgctg tttaatttgt tacaacaaaa tgtaagaaaa agaaatttcc 180
cattttatat tactcatatt cgagcacaca ctaatttacc agggccttta actaaagcaa 240
atgaacaagc tgacttgcta gtatcatctg cattcatgga agcacaagaa cttcatgcct 300
tgactcatgt aaatgcaata ggattaaaaa ataaatttga tatcacatgg aaacagacaa 360
aaaatattgt acaacattgc acccagtgtc agattctaca cctggccact c 411

<210> SEQ ID NO 1743
<211> LENGTH: 130
<212> TYPE: DNA
<213> ORGANISM: Homo sapiens

<400> SEQUENCE: 1743
aggtcaggcc ggttctttgc tctgaaccct gttttctgtt aagatgttta tcaagacaat 60
acatgcaccg ctgaacatag acccttatca ggagtttctg attttgctct ggtcctgttt 120
cttcagaagc 130

<210> SEQ ID NO 1744
<211> LENGTH: 152
<212> TYPE: DNA
<213> ORGANISM: Homo sapiens

<400> SEQUENCE: 1744
atgctgccgg atgaggtgga tgcctggctg tggctctggg agagccaacc tcccccaggg 60
aacccacttt acacaatagc agtggcagca gaggctggcg aggagacaag attcggactc 120
tggggagcac tgatagcatt tcccgagcct ca 152

<210> SEQ ID NO 1745
<211> LENGTH: 207
<212> TYPE: DNA
<213> ORGANISM: Homo sapiens

<400> SEQUENCE: 1745
acgctgtcag cctgtccaga ccgttcctct gttttcgctt gttcctacta acagcgagct 60
tccgccaata cttgttctcg ttcttggttc cgagcgtccc gggagccggg aagggaagga 120
ttgtctgcag ggattggagc aaatatccag tgggggg aaa gccgggactt ccgcgtcttg 180
ccggaagtga cgtgacaatc gcggcca 207

<210> SEQ ID NO 1746
<211> LENGTH: 34
<212> TYPE: DNA
<213> ORGANISM: Homo sapiens

<400> SEQUENCE: 1746
tggccgggac ccggctgtgg gaccaacgct tccg 34

<210> SEQ ID NO 1747
<211> LENGTH: 36
<212> TYPE: DNA
<213> ORGANISM: Homo sapiens

<400> SEQUENCE: 1747
actctgggat ctgagcctat cgccctggcc tggagc 36

<210> SEQ ID NO 1748
<211> LENGTH: 30
<212> TYPE: DNA
<213> ORGANISM: Homo sapiens

<400> SEQUENCE: 1748
ttgggttcct taaatcctat gctcctttct 30

<210> SEQ ID NO 1749
<211> LENGTH: 38
<212> TYPE: DNA
<213> ORGANISM: Homo sapiens

<400> SEQUENCE: 1749
ccctaccgag ctgggcagtt agccagccca ctccaact 38

<210> SEQ ID NO 1750
<211> LENGTH: 34
<212> TYPE: DNA
<213> ORGANISM: Homo sapiens

<400> SEQUENCE: 1750
cagacttgga ttatgacatc gaagaggata aact 34

<210> SEQ ID NO 1751
<211> LENGTH: 71
<212> TYPE: DNA
<213> ORGANISM: Homo sapiens

<400> SEQUENCE: 1751
aaggatgctc agaacctgat cgggatcagc attggaggag gggcccagta ctgtccctgc 60
ctctatatcg t 71

<210> SEQ ID NO 1752
<211> LENGTH: 105
<212> TYPE: DNA
<213> ORGANISM: Homo sapiens

<400> SEQUENCE: 1752
agcagccttg gacggcacag tggcagctgg cgatgagatc accggtgtca atggcaggtc 60
aatcaaaggg aaaactaagg tggaggtggc gaagatgatt cagga 105

<210> SEQ ID NO 1753
<211> LENGTH: 40
<212> TYPE: DNA
<213> ORGANISM: Homo sapiens

<400> SEQUENCE: 1753
cagagcaggt gtccagaggc agcaacacat gtttctgaga 40

<210> SEQ ID NO 1754
<211> LENGTH: 63
<212> TYPE: DNA
<213> ORGANISM: Homo sapiens

<400> SEQUENCE: 1754
gaggtgacca tccactacaa caagctgcag gcggacccca agcagggcat gtccctggac 60
att 63

<210> SEQ ID NO 1755
<211> LENGTH: 156
<212> TYPE: DNA
<213> ORGANISM: Homo sapiens

<400> SEQUENCE: 1755
gcccaaagga gaagtgccac agccagccct gccctcccct ttatgacagg agaatccaga 60
gttacatggc tgtgggctct gacctctgac caagcaaatc tgaaaggcct gggaggcctc 120
ccggtgctct ccctgcatct gttcttgtac tctgtc 156

<210> SEQ ID NO 1756
<211> LENGTH: 88
<212> TYPE: DNA
<213> ORGANISM: Homo sapiens

<400> SEQUENCE: 1756
tgttgaagaa agtcaagcac cggctggtgg agaacatgag ttcagggacc gcagatgctc 60
tgggcctgag ccgggccatc ctgtgcaa 88

<210> SEQ ID NO 1757
<211> LENGTH: 494
<212> TYPE: DNA
<213> ORGANISM: Homo sapiens

<400> SEQUENCE: 1757
ctctgcccgt ggaactgaga agtcaccatc tctgtacccc cagaggcctc tccagctccc 60
ggagggtcca cagctgtcag ctgggctgtc ttagccagtg cccctcaggt cacagatggg 120
aaaatagact tagtgtgggg aggtgcctct gcccctgccc tcagcccctt acccctcacc 180
ccagcactct cgcggcccac ctcctgcctc ctttgtccag gaggtggtgc tgctgccctt 240
gcctctgcag gtcctccctt cgtggtggct gcgcaggcga ggggggaggc gtgtacatgc 300
acatttacac acgcatgcac acatgcgcac acactttccc tccctggggt ggccagcgaa 360
acactcagtc cccctcctac cgtcgccagt ccgagtttaa aaatagcagc agctctgcag 420
tgtgcctgtg gggtagatat aaatacttct agaaattgta ggctcagctg ggcacactgg 480
gctttattgg ctaa 494

<210> SEQ ID NO 1758
<211> LENGTH: 49
<212> TYPE: DNA
<213> ORGANISM: Homo sapiens

<400> SEQUENCE: 1758
cttgtcaaga ggctagagga gctggagcgg accgctgagc tatacaaag 49

<210> SEQ ID NO 1759
<211> LENGTH: 36
<212> TYPE: DNA
<213> ORGANISM: Homo sapiens

<400> SEQUENCE: 1759
tacgggcctt ttatgagctg tcgcagactc accggg 36

<210> SEQ ID NO 1760
<211> LENGTH: 269
<212> TYPE: DNA
<213> ORGANISM: Homo sapiens

<400> SEQUENCE: 1760
cctgcgggga acatctagat cagctggtct cttaagggcc gcaacgatga acaggcccca 60
ccctgtctcc tcacactgcc actggcagta cacaaggccc ttgcttattt atatttctga 120
caacctgtaa ctctgggcag gccgactgca gctgacccca gctactgcag aaaatgaagc 180
ccagacaaag gagagggcca cactgctccc aagtggtgga gctgttgttc caatccaggt 240
gtctagactc ggaccagtgt tctgcctca 269

<210> SEQ ID NO 1761
<211> LENGTH: 190
<212> TYPE: DNA
<213> ORGANISM: Homo sapiens

<400> SEQUENCE: 1761
caatccagtt tcctccaggt gtagactcag ctccttcagg gggtttagac cagctctctt 60
ggaggtgtag cccctgtgca gacattggct tccagcctgc caggccccct gccctgcttc 120
tccccaacaa acccctggct tctcttaggg ggccaagtag gggcagcctt caaggcaaac 180
ttgtcctgca 190

<210> SEQ ID NO 1762
<211> LENGTH: 124
<212> TYPE: DNA
<213> ORGANISM: Homo sapiens

<400> SEQUENCE: 1762
tttggggacg tgttctccgt gatcggggtg cgggagcccc agccagctgc gagcgaggct 60
tttgtgaagt tcgccgatgc ccaccgcagc atcgagaagt tcggcattcg gcttctgaaa 120
acca 124

<210> SEQ ID NO 1763
<211> LENGTH: 131
<212> TYPE: DNA
<213> ORGANISM: Homo sapiens

<400> SEQUENCE: 1763
actgagtcac agcttgccct aggcctggca ctagtcttct catccttgag agggacaagg 60
catcagggag caccatctgg ctctgatagt cgagtccacc aacaagggtg acgcatcagt 120
gccattcatt g 131

<210> SEQ ID NO 1764
<211> LENGTH: 88
<212> TYPE: DNA
<213> ORGANISM: Homo sapiens

<400> SEQUENCE: 1764
gacggatctg aacacgtacc tcaacaaagc catcccggac actcgcctca ccatcaagaa 60
gtacctggac gtgaagtttg agtacctg 88

<210> SEQ ID NO 1765
<211> LENGTH: 28
<212> TYPE: DNA
<213> ORGANISM: Homo sapiens

<400> SEQUENCE: 1765
ctgctgcgcc tgcacaaaga agcatctg 28

<210> SEQ ID NO 1766
<211> LENGTH: 99
<212> TYPE: DNA
<213> ORGANISM: Homo sapiens

<400> SEQUENCE: 1766
ggactccctg aacacctgcg ccagcctctc ctgctgcgtg tgggtgatgg gggtggagct 60
ggggacctgg ggtgggggta gtagccactc tgacagcct 99

<210> SEQ ID NO 1767
<211> LENGTH: 28
<212> TYPE: DNA
<213> ORGANISM: Homo sapiens

<400> SEQUENCE: 1767
gatggatgac gaggaataca gctgcatt 28

<210> SEQ ID NO 1768
<211> LENGTH: 329
<212> TYPE: DNA
<213> ORGANISM: Homo sapiens

<400> SEQUENCE: 1768
ctggactctc gttcctggag atttagggcc atcttcccag tcccgctcgc tgggcctcgg 60
ggtgctgggc acccggccgg gaaccactcc ctcagtctgg gggactcttg gagggaaatc 120
ggattttctt cactcctatg aggcgctttt aagtgtttga tttttctgct gtcgggatcc 180
atttcgtggc cagtgttcat tgaatgtggc agaggtttgg gtttggtttt ttcctctctt 240
caaagctatc actgagtgct tctgagaaac actgaagtct cagaaatgag gtctcaggaa 300
tgaagaacag ccgtggcttt gaaagcaca 329

<210> SEQ ID NO 1769
<211> LENGTH: 103
<212> TYPE: DNA
<213> ORGANISM: Homo sapiens

<400> SEQUENCE: 1769
ggcgagcccc tttaccgggt gagcaccggc aactatgagt accgcctgat cctgcgctgc 60
cgccaggagg cgcgcgcccg cttctcccag atgcgcaagg atg 103

<210> SEQ ID NO 1770
<211> LENGTH: 76
<212> TYPE: DNA
<213> ORGANISM: Homo sapiens

<400> SEQUENCE: 1770
gcctcgtgtc caccatgtcc aagtactaca acgactgcta cgcagtgctg cgggatgccg 60
acgtcttccc catcga 76

<210> SEQ ID NO 1771
<211> LENGTH: 43
<212> TYPE: DNA
<213> ORGANISM: Homo sapiens

<400> SEQUENCE: 1771
gtagacctgg cgcacaccac attggcctat ggcctcaacc agg 43

<210> SEQ ID NO 1772
<211> LENGTH: 27
<212> TYPE: DNA
<213> ORGANISM: Homo sapiens

<400> SEQUENCE: 1772
gttcacagat ggggaggagg aggagga 27

<210> SEQ ID NO 1773
<211> LENGTH: 38
<212> TYPE: DNA
<213> ORGANISM: Homo sapiens

<400> SEQUENCE: 1773
tggggagccg tccagggata cacgaggggc tgctgggc 38

<210> SEQ ID NO 1774
<211> LENGTH: 30
<212> TYPE: DNA
<213> ORGANISM: Homo sapiens

<400> SEQUENCE: 1774
gtgccccgcg gctgtggtgc cgggggcagg 30

<210> SEQ ID NO 1775
<211> LENGTH: 404
<212> TYPE: DNA
<213> ORGANISM: Homo sapiens

<400> SEQUENCE: 1775
gcgacgcata aaggcctgct ggcttggggc gcctgcctcc ctgctcctct gtcctcgcac 60
agcgaacctg ggctcctgcc caggacaggc accagggtca tggcctggga cctggacact 120
ggcccctcca ccctccctcc cctcccggct ccccggccag agggagagct tggtctctgg 180
acctgcctta ggaaggagag ggagggcagg aaggaaaaga aaggacttgg aggtggcagg 240

-continued

```
agtccgagcc ctgctccttg tgggcgctca cactgccccc ggagcctgct gggagtgggg    300

ccagccgtgg acagctgagg ttggggtcaa tgcctcctgg gcacccttgc ctcgccccag    360

accggcccgt ccagtcccca tcacacctcg gcggccttta ttta                     404
```

<210> SEQ ID NO 1776
<211> LENGTH: 36
<212> TYPE: DNA
<213> ORGANISM: Homo sapiens

<400> SEQUENCE: 1776

```
tgggttctgg gcctgtatcg aataaacaca aacctg                               36
```

<210> SEQ ID NO 1777
<211> LENGTH: 30
<212> TYPE: DNA
<213> ORGANISM: Homo sapiens

<400> SEQUENCE: 1777

```
ctcagaggcg gccatcaacc gccagatcaa                                      30
```

<210> SEQ ID NO 1778
<211> LENGTH: 103
<212> TYPE: DNA
<213> ORGANISM: Homo sapiens

<400> SEQUENCE: 1778

```
gtcttactac tttgaccacg atgatgtggc tttgaagaac tttgccaaat actttcttca     60

ccaatctcat gaggagaggg aacatgctga ggaactgatg aag                      103
```

<210> SEQ ID NO 1779
<211> LENGTH: 26
<212> TYPE: DNA
<213> ORGANISM: Homo sapiens

<400> SEQUENCE: 1779

```
ctgggagcgg gctgaatgag atggag                                          26
```

<210> SEQ ID NO 1780
<211> LENGTH: 135
<212> TYPE: DNA
<213> ORGANISM: Homo sapiens

<400> SEQUENCE: 1780

```
cgcagccaat cagcacctag aggttgggct actttcggcc aaaggagaac ggggacttgt     60

gggggacgct ccctgcgcac caatgaatgt gcatggagat ggagaggcgg gcctgcaagt    120

gcgaacaagc caatc                                                     135
```

<210> SEQ ID NO 1781
<211> LENGTH: 86
<212> TYPE: DNA
<213> ORGANISM: Homo sapiens

<400> SEQUENCE: 1781

```
cggccgttaa ggacagttgt ggcaaaggag aaatggccac agggaatggg cggcggctcc     60

acctggggat tcctgaggcc gtgttt                                          86
```

<210> SEQ ID NO 1782
<211> LENGTH: 285
<212> TYPE: DNA
<213> ORGANISM: Homo sapiens

<400> SEQUENCE: 1782
tggcctctaa atagaccagg gtctgaatcc tggctctgct tcccagttgc tgcttaacct 60
taagcatatt attttaccac tttgagcttg agtttcttta actgaaatag ggatgacaat 120
acttagagag ttgttatggg aaacagagaa catgcttgca gtattgcagt gtagtaggtg 180
tcgaataggt attaatattc atgatgatag gaagcaatat accatagtgg ttagaagtca 240
gacccagtcc attccccaac cccgctgagg cagtaatttg ttttc 285

<210> SEQ ID NO 1783
<211> LENGTH: 71
<212> TYPE: DNA
<213> ORGANISM: Homo sapiens

<400> SEQUENCE: 1783
cagtattaaa gaagctggat gaacagtacc agaagtataa gtttatggaa ctcaaccttg 60
ctcaaaagaa a 71

<210> SEQ ID NO 1784
<211> LENGTH: 65
<212> TYPE: DNA
<213> ORGANISM: Homo sapiens

<400> SEQUENCE: 1784
gctaaaaggt cagattcctg aaattaaaca gactttggaa attctaaaat acatgcagaa 60
gaaaa 65

<210> SEQ ID NO 1785
<211> LENGTH: 90
<212> TYPE: DNA
<213> ORGANISM: Homo sapiens

<400> SEQUENCE: 1785
gagtccacca actcaatgga gaccagattc ttgctggcag ataacctgta ttgcaaagct 60
tcagttcctc ctaccgataa aatgtgtctg 90

<210> SEQ ID NO 1786
<211> LENGTH: 140
<212> TYPE: DNA
<213> ORGANISM: Homo sapiens

<400> SEQUENCE: 1786
tgcatatgtt cttcctgtcc ttacacattc tttataaggt tgttcccaca ttgttggagc 60
acagagccat tatatactgt ttgctctctc tctttctctc tctcatcttt catttatcct 120
agttcttcgt gtaaatattg 140

<210> SEQ ID NO 1787
<211> LENGTH: 109
<212> TYPE: DNA
<213> ORGANISM: Homo sapiens

<400> SEQUENCE: 1787
ttgatgaagc tcaggcattg ttggaaaaga atttatcgac tgccacaaag aatcttgatt 60
ccctggagga agaccttgac tttcttcgag atcaatttac taccacaga 109

<210> SEQ ID NO 1788
<211> LENGTH: 208
<212> TYPE: DNA

<213> ORGANISM: Homo sapiens

<400> SEQUENCE: 1788
tcatctgacg ggtagtgtgg aaacttcatc cagctatgag atgacgaggg cctaggacgg 60
gtggcttgtg gaaaggaaaa gatattaaac gtgtgagaaa aaaacaggat ccagtgactt 120
agatgggtac aggagccaaa agtgaggaaa tcctctaaga tgagtcctac aagcttagtt 180
aaatgccatt tgttattgct agtactgc 208

<210> SEQ ID NO 1789
<211> LENGTH: 65
<212> TYPE: DNA
<213> ORGANISM: Homo sapiens

<400> SEQUENCE: 1789
atatggccag ggtttataat tgggatgtaa aaagaagaaa caaggatgac tctaccaaga 60
acaaa 65

<210> SEQ ID NO 1790
<211> LENGTH: 287
<212> TYPE: DNA
<213> ORGANISM: Homo sapiens

<400> SEQUENCE: 1790
tatggaagct gaatgccgga cgctagcaca gtttactttt tccctttcta atcggctgat 60
gttactctca cttgatgtgg ttaaaccatt ttagaggtag agaagacaga cagtttgaat 120
atttgtaaac ttgtttttct ttggtatatt taggacttag tggtcctctg ttgctattgt 180
cttctataag tggagtttca tgacttactg cttaacgaat aactaactac tatgatattc 240
tggacatttt aggaaatggt aatttgcctt gctacacatt aagaggg 287

<210> SEQ ID NO 1791
<211> LENGTH: 194
<212> TYPE: DNA
<213> ORGANISM: Homo sapiens

<400> SEQUENCE: 1791
gcctaaggtg attttgtagt tcttaacagt tctccagagc atcttgaaca ggaatattaa 60
gataaatgtg aatctgcaat ggctgaaaag agttgtgagc ttttttattc atgataaaac 120
cttataggaa tagtataaaa aatccctgtg gaaagctact agtacattga ccagcgctgg 180
gtgatacaga ttct 194

<210> SEQ ID NO 1792
<211> LENGTH: 1133
<212> TYPE: DNA
<213> ORGANISM: Homo sapiens

<400> SEQUENCE: 1792
gctctaagct ttgcaaggga tcctaaaaga ggcggtggaa gtgaaaattc tgggtctcca 60
agaaaatttc tgcacagcca gttctccaat cagcctatca ccccttgaaa catcttccct 120
gtgtccctgg gggcccctga tgctttctcc ttgggtgata gtaacatgca gagcacttac 180
acaaagctcc ctctttggac ataccccacg tcgacctgtc acaggcctgg ctgtagcgag 240
cacctcccta tgacgcagaa tgcttcttgg gaattatctt actcctctgg agggttagtc 300
catcaatgtt ttgcttcttg tcccaatact actgtgaccc tctctgatcg cacagaaatc 360
actgcctatc acatatatcc tgttaagcac tgaagaccct attgaaatta gagttctaca 420
gatgccaaaa gctgtacttt ccatcaggca gatggcaagc ttactgcctt gatgcacatc 480
tggagccact ggagctcctt cctctctggt tccagcatta aggtggagaa ctccatgtag 540
cttcttgtcc tttcccctca gctgtctttg cttcacaagg ttttagccca aagcaagagt 600
gcaatcccaa agccacagag aaatgaactt tccgctacct ggaagcttta agtgagtaaa 660
tcagcttttc ccctctcatt cctagaggca cacacctcaa aagttactag gctggagaga 720
ccctaccttc cagtgaccca ctcatccccc agccacggag aagagggaag accaaaaagg 780
gagagtgaga aagaggatga gagggatggt cagctgtgag gggagggggc aagtggccca 840
gcaaatgttg atgcctccct tcccatcttg ccacacggtc tttttctttt gtagcacagc 900
ctccattaat aactcctcgg ctgaggatga agatgtaggc acctttaccc ccagagccag 960
ttccttaatt ggctggcttt ctgagatgca gaccacccta gaatctcatc taggttcact 1020
agaagttagt taaatcttcc tttctctgtc tttctcttca ttccatcccc caaacccacc 1080
aaacactaag ggagagctcc ctttggatgt ctgggcagta aacctagctc att 1133

<210> SEQ ID NO 1793
<211> LENGTH: 115
<212> TYPE: DNA
<213> ORGANISM: Homo sapiens

<400> SEQUENCE: 1793
agaaaccaaa cgatcttcaa ctctcccagc caagttccag aacccagttg agccaattga 60
gcctgtctgg ttctcactgg ccaggaagaa agccaaagca tggagccaca tggca 115

<210> SEQ ID NO 1794
<211> LENGTH: 107
<212> TYPE: DNA
<213> ORGANISM: Homo sapiens

<400> SEQUENCE: 1794
gatcagagga aacctgaaag gaggaaacat tatatggcat tccataaaca acatacccca 60
atatcgctgg ggttccttat tgcttgtgtg ttatttgctg tggttcc 107

<210> SEQ ID NO 1795
<211> LENGTH: 60
<212> TYPE: DNA
<213> ORGANISM: Homo sapiens

<400> SEQUENCE: 1795
ccagtgtcca taaacaggag aagacagcac agatgaagcc acctaagcct acaaaatcag 60

<210> SEQ ID NO 1796
<211> LENGTH: 151
<212> TYPE: DNA
<213> ORGANISM: Homo sapiens

<400> SEQUENCE: 1796
cctgctggtc aacagtcaga ttatgctgtc tcagagccgg tttggataac tatggcaaag 60
cagaagcaga agagtttcaa ggcccacatt tctgtgaaag agctgaaaac taagagcaat 120
gctggagccg atgctgagac taaggagcct a 151

<210> SEQ ID NO 1797
<211> LENGTH: 28
<212> TYPE: DNA
<213> ORGANISM: Homo sapiens

<400> SEQUENCE: 1797
tccagatggc aagcagatat caagtgga 28

<210> SEQ ID NO 1798
<211> LENGTH: 140
<212> TYPE: DNA
<213> ORGANISM: Homo sapiens

<400> SEQUENCE: 1798
tttggagttc gactgaaaag agcccctccc tcgcagaagt ataagagtga gaaacaagat 60
aacttcaccc agcttgcttc agtgccctcg ggcccaattt catcctctgt aggcagggga 120
cataaaatca gaagcacttc 140

<210> SEQ ID NO 1799
<211> LENGTH: 764
<212> TYPE: DNA
<213> ORGANISM: Homo sapiens

<400> SEQUENCE: 1799
tcctcaaatt tcgagcgggc tgctattgag gcagacattt ctgggagtcc attgcctccc 60
caatatgcta cccagttctt aaagaggtct aaagttcagg aaatgacctc acgactagag 120
aaaatggctg ttgaaggcac ttctaacaaa tcaccgattc ccaggcgtcc gacccagtca 180
ttcgtgaaat ttatggcaca gcaaatcttt tcagagagct ctgctcttaa gaggggcagt 240
gatgtggcac ctctgcctcc caatcttcct tccaaatctt tatcaaagcc tgaagtcaag 300
caccaagttt tctcagattc agggagtgct aatcctaagg gaggcatttc ttcaaagatg 360
ctacctatga agcacccttt acagtccttg gggaggcctg aagacccaca gaaagttttc 420
tcttattcag agagagctcc tgggaagtgc agcagtttta aagagcagct gtctcccagg 480
cagctttccc aggccttgag gaaacctgag tatgagcaaa aagtctcccc tgtttctgcc 540
agttctccta aagagtggag gaattctaaa aagcagctgc ctcccaaaca ttcttcccaa 600
gcctcagata ggtctaaatt ccagccacag atgtcatcaa agggcccagt gaatgtacct 660
gtaaagcaga gcagcggtga gaagcacctg ccttcaagta gtcctttcca gcaacaggtt 720
cattcaagtt ctgtgaatgc tgctgctagg cgatctgttt ttga 764

<210> SEQ ID NO 1800
<211> LENGTH: 193
<212> TYPE: DNA
<213> ORGANISM: Homo sapiens

<400> SEQUENCE: 1800
ggctatccaa tgtcagcagc atatggaaga agatggagaa gaaaaggagc aagtgtttca 60
ggattgagtg ggtgtgaatt caaaggaaga agccttaaac aatccagtga agggtatggc 120
ctgggcgata gagctgggtc ttcacctacc aataagactg ccaggaatgt ccctttctcg 180
cacttgtcct tag 193

<210> SEQ ID NO 1801
<211> LENGTH: 109
<212> TYPE: DNA
<213> ORGANISM: Homo sapiens

<400> SEQUENCE: 1801
tggagcatag tcagctatta tcagcgctgt atgctggata tgaaactact ggatggagct 60
aaggatgcag cagatagtga gggaagaaag gcacaagggg cccttccat 109

-continued

<210> SEQ ID NO 1802
<211> LENGTH: 149
<212> TYPE: DNA
<213> ORGANISM: Homo sapiens

<400> SEQUENCE: 1802
tgttggctcc agttgatggc aagctgattt ctagcagtat ttgataaaaa aattccagtt 60
cctcaaatta agttgaatag ttatgttacg tttttgccac aaaggatttc acatgtgggt 120
ccaaagacag gacattccta aacacgttt 149

<210> SEQ ID NO 1803
<211> LENGTH: 72
<212> TYPE: DNA
<213> ORGANISM: Homo sapiens

<400> SEQUENCE: 1803
aaccttccat tggtttctga agaagaaaag agcataacca aaccaaaaga aatcaacgaa 60
aagaagctgg ga 72

<210> SEQ ID NO 1804
<211> LENGTH: 73
<212> TYPE: DNA
<213> ORGANISM: Homo sapiens

<400> SEQUENCE: 1804
ccttccagtg tggttcagtc atttccaggg tattttagag ggatccctgc agtgtgtcac 60
tcagacatta gaa 73

<210> SEQ ID NO 1805
<211> LENGTH: 126
<212> TYPE: DNA
<213> ORGANISM: Homo sapiens

<400> SEQUENCE: 1805
cacagtcctt gactgcattt gccacacttg cctctaccag tagcacccag ctgcccattg 60
gtttcagcac cccagccacc acccagggct gtttggattc ttcagctgct cgccacaaaa 120
tgactt 126

<210> SEQ ID NO 1806
<211> LENGTH: 31
<212> TYPE: DNA
<213> ORGANISM: Homo sapiens

<400> SEQUENCE: 1806
ggttacaggc tccatcacta tcccactgga g 31

<210> SEQ ID NO 1807
<211> LENGTH: 117
<212> TYPE: DNA
<213> ORGANISM: Homo sapiens

<400> SEQUENCE: 1807
atcccacctg ttatccaacc tgaaataatt tctaagaact tggtagaaat ctctctcgat 60
gatgagtcac ctaagaatcc acaaaagaag gctttaccac ataagagttt gacagcg 117

<210> SEQ ID NO 1808
<211> LENGTH: 52
<212> TYPE: DNA

<213> ORGANISM: Homo sapiens

<400> SEQUENCE: 1808
ttctaatgga ttaagtgaca ttcagaacaa cgaggagatt gttaaagaag aa 52

<210> SEQ ID NO 1809
<211> LENGTH: 95
<212> TYPE: DNA
<213> ORGANISM: Homo sapiens

<400> SEQUENCE: 1809
ctctgcctaa acctaggagt aaggttcctg gagttgtgtc tggagccatg tcaggagctg 60
tgcttcaaaa tgtgcctaca agtgcagtct gggtt 95

<210> SEQ ID NO 1810
<211> LENGTH: 25
<212> TYPE: DNA
<213> ORGANISM: Homo sapiens

<400> SEQUENCE: 1810
ttccttctat ggatccccag agagg 25

<210> SEQ ID NO 1811
<211> LENGTH: 68
<212> TYPE: DNA
<213> ORGANISM: Homo sapiens

<400> SEQUENCE: 1811
gcagcatggg gagcaaagcc ctatcccatg atagcatctt catgttgggt cctgagcctg 60
aaagatca 68

<210> SEQ ID NO 1812
<211> LENGTH: 30
<212> TYPE: DNA
<213> ORGANISM: Homo sapiens

<400> SEQUENCE: 1812
aaagaagccg aagataccca ggaagaagaa 30

<210> SEQ ID NO 1813
<211> LENGTH: 47
<212> TYPE: DNA
<213> ORGANISM: Homo sapiens

<400> SEQUENCE: 1813
cctacaatgg ctgaatcact aagtgaaatt tctgacagtc tggatgt 47

<210> SEQ ID NO 1814
<211> LENGTH: 106
<212> TYPE: DNA
<213> ORGANISM: Homo sapiens

<400> SEQUENCE: 1814
atgccctgta cccaaggtga tttacagcag ggtttcctta aagctaggta tttggagccc 60
tcacctccca ggagtcacct ggaaggttct ggacttgcag gtccct 106

<210> SEQ ID NO 1815
<211> LENGTH: 78

-continued

```
<212> TYPE: DNA
<213> ORGANISM: Homo sapiens

<400> SEQUENCE: 1815

tgattgctgg taatcttggg gatctggcca ggatagtggg cccctcacat catgctagtc      60

agcttctcct actccaag                                                    78
```